US010667808B2

(12) United States Patent

Baxter, III et al.

(10) Patent No.: US 10,667,808 B2

(45) Date of Patent: *Jun. 2, 2020

(54) STAPLE CARTRIDGE COMPRISING AN ABSORBABLE ADJUNCT

(71) Applicant: Ethicon LLC, Guaynabo, PR (US)

(72) Inventors: Chester O. Baxter, III, Loveland, OH (US); Frederick E. Shelton, IV, Hillsboro, OH (US); Jeffrey S. Swayze, West Chester, OH (US); Taylor W. Aronhalt, Loveland, OH (US); Katherine J. Schmid, Loveland, OH (US)

(73) Assignee: Ethicon LLC, Guaynabo, PR (US)

( * ) Notice: Subject to any disclaimer, the term of this patent is extended or adjusted under 35 U.S.C. 154(b) by 259 days.

This patent is subject to a terminal disclaimer.

(21) Appl. No.: 15/793,123

(22) Filed: Oct. 25, 2017

(65) Prior Publication Data

US 2018/0110516 A1 Apr. 26, 2018

Related U.S. Application Data

(63) Continuation of application No. 14/540,731, filed on Nov. 13, 2014, now Pat. No. 9,974,538, which is a (Continued)

(51) Int. Cl.

*A61B 17/064* (2006.01)
*A61B 17/072* (2006.01)
(Continued)

(52) U.S. Cl.

CPC .... *A61B 17/0643* (2013.01); *A61B 17/00491* (2013.01); *A61B 17/068* (2013.01);
(Continued)

(58) Field of Classification Search

CPC ........ A61B 17/068; A61B 17/115; A61K 9/70
(Continued)

(56) References Cited

U.S. PATENT DOCUMENTS

| | | |
|---|---|---|
| 66,052 A | 6/1867 | Smith |
| 662,587 A | 11/1900 | Blake |

(Continued)

FOREIGN PATENT DOCUMENTS

| | | |
|---|---|---|
| AU | 2011218702 B2 | 6/2013 |
| AU | 2012200178 B2 | 7/2013 |

(Continued)

OTHER PUBLICATIONS

Fast, Versatile Blackfin Processors Handle Advanced RFID Reader Applications; Analog Dialogue: vol. 40—Sep. 2006; http://www.analog.com/library/analogDialogue/archives/40-09/rfid.pdf; Wayback Machine to Feb. 15, 2012.

(Continued)

*Primary Examiner* — Nathaniel C Chukwurah

(57) ABSTRACT

A staple cartridge comprising a cartridge body, a plurality of staples, and an absorbable adjunct releasably secured to the cartridge body is disclosed. A plurality of staple cavities are defined in the cartridge body and the plurality of staples are removably positioned in the staple cavities. The absorbable adjunct comprises a first zone comprising a tissue-supporting surface, a second zone comprising a cartridge body contacting surface, and an intermediate zone position between the first zone and the second zone. The first zone comprises a first compressibility and the second zone comprises a second compressibility that is less than the first compressibility. The intermediate zone comprises a third compressibility greater than the first compressibility.

3 Claims, 327 Drawing Sheets

Related U.S. Application Data continuation of application No. 13/433,115, filed on Mar. 28, 2012, now Pat. No. 9,204,880.

(51) Int. Cl.

| | | |
|---|---|---|
| *A61B 17/115* | (2006.01) | |
| *A61B 17/068* | (2006.01) | |
| *A61B 17/10* | (2006.01) | |
| *A61B 17/00* | (2006.01) | |
| *A61B 17/29* | (2006.01) | |
| *A61B 90/00* | (2016.01) | |
| *A61B 17/32* | (2006.01) | |

(52) U.S. Cl.
CPC ........ *A61B 17/0644* (2013.01); *A61B 17/072* (2013.01); *A61B 17/07207* (2013.01); *A61B 17/07292* (2013.01); *A61B 17/105* (2013.01); *A61B 17/1155* (2013.01); *A61B 17/0682* (2013.01); *A61B 17/2909* (2013.01); *A61B 2017/00004* (2013.01); *A61B 2017/0053* (2013.01); *A61B 2017/00314* (2013.01); *A61B 2017/00327* (2013.01); *A61B 2017/00526* (2013.01); *A61B 2017/00561* (2013.01); *A61B 2017/00818* (2013.01); *A61B 2017/00862* (2013.01); *A61B 2017/00884* (2013.01); *A61B 2017/00889* (2013.01); *A61B 2017/00893* (2013.01); *A61B 2017/00898* (2013.01); *A61B 2017/00938* (2013.01); *A61B 2017/00942* (2013.01); *A61B 2017/0641* (2013.01); *A61B 2017/0725* (2013.01); *A61B 2017/07228* (2013.01); *A61B 2017/07235* (2013.01); *A61B 2017/07242* (2013.01); *A61B 2017/07257* (2013.01); *A61B 2017/07264* (2013.01); *A61B 2017/07271* (2013.01); *A61B 2017/07278* (2013.01); *A61B 2017/07285* (2013.01); *A61B 2017/2908* (2013.01); *A61B 2017/2919* (2013.01); *A61B 2017/2923* (2013.01); *A61B 2017/2927* (2013.01); *A61B 2017/2933* (2013.01); *A61B 2017/2936* (2013.01); *A61B 2017/2937* (2013.01); *A61B 2017/320052* (2013.01); *A61B 2090/0807* (2016.02)

(58) Field of Classification Search
USPC ............................................ 227/175.1–176.1
See application file for complete search history.

(56) References Cited

U.S. PATENT DOCUMENTS

| | | | |
|---|---|---|---|
| 670,748 | A | 3/1901 | Weddeler |
| 719,487 | A | 2/1903 | Minor |
| 804,229 | A | 11/1905 | Hutchinson |
| 951,393 | A | 3/1910 | Hahn |
| 1,188,721 | A | 6/1916 | Bittner |
| 1,306,107 | A | 6/1919 | Elliott |
| 1,314,601 | A | 9/1919 | McCaskey |
| 1,677,337 | A | 7/1928 | Grove |
| 1,794,907 | A | 3/1931 | Kelly |
| 1,849,427 | A | 3/1932 | Hook |
| 1,944,116 | A | 1/1934 | Stratman |
| 1,954,048 | A | 4/1934 | Jeffrey et al. |
| 2,037,727 | A | 4/1936 | La Chapelle |
| 2,132,295 | A | 10/1938 | Hawkins |
| 2,161,632 | A | 6/1939 | Nattenheimer |
| D120,434 | S | 5/1940 | Gold |
| 2,211,117 | A | 8/1940 | Hess |
| 2,214,870 | A | 9/1940 | West |
| 2,224,882 | A | 12/1940 | Peck |
| 2,318,379 | A | 5/1943 | Davis et al. |
| 2,329,440 | A | 9/1943 | La Place |
| 2,377,581 | A | 6/1945 | Shaffrey |
| 2,406,389 | A | 8/1946 | Lee |
| 2,441,096 | A | 5/1948 | Happe |
| 2,448,741 | A | 9/1948 | Scott et al. |
| 2,450,527 | A | 10/1948 | Smith |
| 2,507,872 | A | 5/1950 | Unsinger |
| 2,526,902 | A | 10/1950 | Rublee |
| 2,527,256 | A | 10/1950 | Jackson |
| 2,578,686 | A | 12/1951 | Fish |
| 2,638,901 | A | 5/1953 | Sugarbaker |
| 2,674,149 | A | 4/1954 | Benson |
| 2,701,489 | A | 2/1955 | Osborn |
| 2,711,461 | A | 6/1955 | Happe |
| 2,742,955 | A | 4/1956 | Dominguez |
| 2,804,848 | A | 9/1957 | O'Farrell et al. |
| 2,808,482 | A | 10/1957 | Zanichkowsky et al. |
| 2,853,074 | A | 9/1958 | Olson |
| 2,887,004 | A | 5/1959 | Stewart |
| 2,957,353 | A | 10/1960 | Lewis |
| 2,959,974 | A | 11/1960 | Emrick |
| 3,032,769 | A | 5/1962 | Palmer |
| 3,060,972 | A | 10/1962 | Sheldon |
| 3,075,062 | A | 1/1963 | Iaccarino |
| 3,078,465 | A | 2/1963 | Bobrov |
| 3,079,606 | A | 3/1963 | Bobrov et al. |
| 3,080,564 | A | 3/1963 | Strekopitov et al. |
| 3,166,072 | A | 1/1965 | Sullivan, Jr. |
| 3,180,236 | A | 4/1965 | Beckett |
| 3,196,869 | A | 7/1965 | Scholl |
| 3,204,731 | A | 9/1965 | Bent et al. |
| 3,266,494 | A | 8/1966 | Brownrigg et al. |
| 3,269,630 | A | 8/1966 | Fleischer |
| 3,269,631 | A | 8/1966 | Takaro |
| 3,275,211 | A | 9/1966 | Hirsch et al. |
| 3,317,103 | A | 5/1967 | Cullen et al. |
| 3,317,105 | A | 5/1967 | Astafjev et al. |
| 3,357,296 | A | 12/1967 | Lefever |
| 3,359,978 | A | 12/1967 | Smith, Jr. |
| 3,377,893 | A | 4/1968 | Shorb |
| 3,480,193 | A | 11/1969 | Ralston |
| 3,490,675 | A | 1/1970 | Green et al. |
| 3,494,533 | A | 2/1970 | Green et al. |
| 3,499,591 | A | 3/1970 | Green |
| 3,503,396 | A | 3/1970 | Pierie et al. |
| 3,509,629 | A | 5/1970 | Kidokoro |
| 3,551,987 | A | 1/1971 | Wilkinson |
| 3,568,675 | A | 3/1971 | Harvey |
| 3,572,159 | A | 3/1971 | Tschanz |
| 3,583,393 | A | 6/1971 | Takahashi |
| 3,589,589 | A | 6/1971 | Akopov |
| 3,598,943 | A | 8/1971 | Barrett |
| 3,608,549 | A | 9/1971 | Merrill |
| 3,618,842 | A | 11/1971 | Bryan |
| 3,638,652 | A | 2/1972 | Kelley |
| 3,640,317 | A | 2/1972 | Panfili |
| 3,643,851 | A | 2/1972 | Green et al. |
| 3,650,453 | A | 3/1972 | Smith, Jr. |
| 3,661,666 | A | 5/1972 | Foster et al. |
| 3,662,939 | A | 5/1972 | Bryan |
| 3,688,966 | A | 9/1972 | Perkins et al. |
| 3,695,646 | A | 10/1972 | Mommsen |
| 3,709,221 | A | 1/1973 | Riely |
| 3,717,294 | A | 2/1973 | Green |
| 3,726,755 | A | 4/1973 | Shannon |
| 3,727,904 | A | 4/1973 | Gabbey |
| 3,734,207 | A | 5/1973 | Fishbein |
| 3,740,994 | A | 6/1973 | De Carlo, Jr. |
| 3,744,495 | A | 7/1973 | Johnson |
| 3,746,002 | A | 7/1973 | Haller |
| 3,747,603 | A | 7/1973 | Adler |
| 3,747,692 | A | 7/1973 | Davidson |
| 3,751,902 | A | 8/1973 | Kingsbury et al. |
| 3,752,161 | A | 8/1973 | Bent |
| 3,799,151 | A | 3/1974 | Fukaumi et al. |
| 3,808,452 | A | 4/1974 | Hutchinson |
| 3,815,476 | A | 6/1974 | Green et al. |
| 3,819,100 | A | 6/1974 | Noiles et al. |
| 3,821,919 | A | 7/1974 | Knohl |
| 3,836,171 | A | 9/1974 | Hayashi et al. |

(56) References Cited

U.S. PATENT DOCUMENTS

| | | | |
|---|---|---|---|
| 3,837,555 | A | 9/1974 | Green |
| 3,841,474 | A | 10/1974 | Maier |
| 3,851,196 | A | 11/1974 | Hinds |
| 3,863,639 | A | 2/1975 | Kleaveland |
| 3,883,624 | A | 5/1975 | McKenzie et al. |
| 3,885,491 | A | 5/1975 | Curtis |
| 3,892,228 | A | 7/1975 | Mitsui |
| 3,894,174 | A | 7/1975 | Cartun |
| 3,902,247 | A | 9/1975 | Fleer et al. |
| 3,940,844 | A | 3/1976 | Colby et al. |
| 3,944,163 | A | 3/1976 | Hayashi et al. |
| 3,950,686 | A | 4/1976 | Randall |
| 3,952,747 | A | 4/1976 | Kimmell, Jr. |
| 3,955,581 | A | 5/1976 | Spasiano et al. |
| 3,959,879 | A | 6/1976 | Sellers |
| RE28,932 | E | 8/1976 | Noiles et al. |
| 3,972,734 | A | 8/1976 | King |
| 3,981,051 | A | 9/1976 | Brumlik |
| 4,025,216 | A | 5/1977 | Hives |
| 4,027,746 | A | 6/1977 | Kine |
| 4,034,143 | A | 7/1977 | Sweet |
| 4,038,987 | A | 8/1977 | Komiya |
| 4,054,108 | A | 10/1977 | Gill |
| 4,060,089 | A | 11/1977 | Noiles |
| 4,066,133 | A | 1/1978 | Voss |
| 4,085,337 | A | 4/1978 | Moeller |
| 4,100,820 | A | 7/1978 | Evett |
| 4,106,446 | A | 8/1978 | Yamada et al. |
| 4,106,620 | A | 8/1978 | Brimmer et al. |
| 4,108,211 | A | 8/1978 | Tanaka |
| 4,111,206 | A | 9/1978 | Vishnevsky et al. |
| 4,127,227 | A | 11/1978 | Green |
| 4,129,059 | A | 12/1978 | Van Eck |
| 4,132,146 | A | 1/1979 | Uhlig |
| 4,135,517 | A | 1/1979 | Reale |
| 4,154,122 | A | 5/1979 | Severin |
| 4,169,990 | A | 10/1979 | Lerdman |
| 4,180,285 | A | 12/1979 | Reneau |
| 4,185,701 | A | 1/1980 | Boys |
| 4,190,042 | A | 2/1980 | Sinnreich |
| 4,198,734 | A | 4/1980 | Brumlik |
| 4,198,982 | A | 4/1980 | Fortner et al. |
| 4,207,898 | A | 6/1980 | Becht |
| 4,213,562 | A | 7/1980 | Garrett et al. |
| 4,226,242 | A | 10/1980 | Jarvik |
| 4,239,431 | A | 12/1980 | Davini |
| 4,241,861 | A | 12/1980 | Fleischer |
| 4,244,372 | A | 1/1981 | Kapitanov et al. |
| 4,250,436 | A | 2/1981 | Weissman |
| 4,261,244 | A | 4/1981 | Becht et al. |
| 4,272,002 | A | 6/1981 | Moshofsky |
| 4,272,662 | A | 6/1981 | Simpson |
| 4,274,304 | A | 6/1981 | Curtiss |
| 4,274,398 | A | 6/1981 | Scott, Jr. |
| 4,275,813 | A | 6/1981 | Noiles |
| 4,278,091 | A | 7/1981 | Borzone |
| 4,289,131 | A | 9/1981 | Mueller |
| 4,289,133 | A | 9/1981 | Rothfuss |
| 4,290,542 | A | 9/1981 | Fedotov et al. |
| D261,356 | S | 10/1981 | Robinson |
| 4,293,604 | A | 10/1981 | Campbell |
| 4,296,654 | A | 10/1981 | Mercer |
| 4,296,881 | A | 10/1981 | Lee |
| 4,304,236 | A | 12/1981 | Conta et al. |
| 4,305,539 | A | 12/1981 | Korolkov et al. |
| 4,312,363 | A | 1/1982 | Rothfuss et al. |
| 4,312,685 | A | 1/1982 | Riedl |
| 4,317,451 | A | 3/1982 | Cerwin et al. |
| 4,319,576 | A | 3/1982 | Rothfuss |
| 4,321,002 | A | 3/1982 | Froehlich |
| 4,321,746 | A | 3/1982 | Grinage |
| 4,328,839 | A | 5/1982 | Lyons et al. |
| 4,331,277 | A | 5/1982 | Green |
| 4,340,331 | A | 7/1982 | Savino |
| 4,347,450 | A | 8/1982 | Colligan |
| 4,348,603 | A | 9/1982 | Huber |
| 4,349,028 | A | 9/1982 | Green |
| 4,350,151 | A | 9/1982 | Scott |
| 4,353,371 | A | 10/1982 | Cosman |
| 4,357,940 | A | 11/1982 | Muller |
| 4,361,057 | A | 11/1982 | Kochera |
| 4,366,544 | A | 12/1982 | Shima et al. |
| 4,369,013 | A | 1/1983 | Abildgaard et al. |
| 4,373,147 | A | 2/1983 | Carlson, Jr. |
| 4,376,380 | A | 3/1983 | Burgess |
| 4,379,457 | A | 4/1983 | Gravener et al. |
| 4,380,312 | A | 4/1983 | Landrus |
| 4,382,326 | A | 5/1983 | Rabuse |
| 4,383,634 | A | 5/1983 | Green |
| 4,393,728 | A | 7/1983 | Larson et al. |
| 4,394,613 | A | 7/1983 | Cole |
| 4,396,139 | A | 8/1983 | Hall et al. |
| 4,397,311 | A | 8/1983 | Kanshin et al. |
| 4,402,445 | A | 9/1983 | Green |
| 4,406,621 | A | 9/1983 | Bailey |
| 4,408,692 | A | 10/1983 | Sigel et al. |
| 4,409,057 | A | 10/1983 | Molenda et al. |
| 4,415,112 | A | 11/1983 | Green |
| 4,416,276 | A | 11/1983 | Newton et al. |
| 4,417,890 | A | 11/1983 | Dennehey et al. |
| 4,423,456 | A | 12/1983 | Zaidenweber |
| 4,428,376 | A | 1/1984 | Mericle |
| 4,429,695 | A | 2/1984 | Green |
| 4,430,997 | A | 2/1984 | DiGiovanni et al. |
| 4,434,796 | A | 3/1984 | Karapetian et al. |
| 4,438,659 | A | 3/1984 | Desplats |
| 4,442,964 | A | 4/1984 | Becht |
| 4,448,194 | A | 5/1984 | DiGiovanni et al. |
| 4,451,743 | A | 5/1984 | Suzuki et al. |
| 4,452,376 | A | 6/1984 | Klieman et al. |
| 4,454,887 | A | 6/1984 | Kruger |
| 4,461,305 | A | 7/1984 | Cibley |
| 4,467,805 | A | 8/1984 | Fukuda |
| 4,468,597 | A | 8/1984 | Baumard et al. |
| 4,469,481 | A | 9/1984 | Kobayashi |
| 4,470,414 | A | 9/1984 | Imagawa et al. |
| 4,471,780 | A | 9/1984 | Menges et al. |
| 4,471,781 | A | 9/1984 | Di Giovanni et al. |
| 4,473,077 | A | 9/1984 | Noiles et al. |
| 4,475,679 | A | 10/1984 | Fleury, Jr. |
| 4,478,220 | A | 10/1984 | Di Giovanni et al. |
| 4,480,641 | A | 11/1984 | Failla et al. |
| 4,485,816 | A | 12/1984 | Krumme |
| 4,485,817 | A | 12/1984 | Swiggett |
| 4,486,928 | A | 12/1984 | Tucker et al. |
| 4,488,523 | A | 12/1984 | Shichman |
| 4,489,875 | A | 12/1984 | Crawford et al. |
| 4,493,983 | A | 1/1985 | Taggert |
| 4,494,057 | A | 1/1985 | Hotta |
| 4,499,895 | A | 2/1985 | Takayama |
| 4,500,024 | A | 2/1985 | DiGiovanni et al. |
| D278,081 | S | 3/1985 | Green |
| 4,503,842 | A | 3/1985 | Takayama |
| 4,505,272 | A | 3/1985 | Utyamyshev et al. |
| 4,505,273 | A | 3/1985 | Braun et al. |
| 4,505,414 | A | 3/1985 | Filipi |
| 4,506,671 | A | 3/1985 | Green |
| 4,512,038 | A | 4/1985 | Alexander et al. |
| 4,520,817 | A | 6/1985 | Green |
| 4,522,327 | A | 6/1985 | Korthoff et al. |
| 4,526,174 | A | 7/1985 | Froehlich |
| 4,527,724 | A | 7/1985 | Chow et al. |
| 4,530,357 | A | 7/1985 | Pawloski et al. |
| 4,530,453 | A | 7/1985 | Green |
| 4,531,522 | A | 7/1985 | Bedi et al. |
| 4,532,927 | A | 8/1985 | Miksza, Jr. |
| 4,540,202 | A | 9/1985 | Amphoux et al. |
| 4,548,202 | A | 10/1985 | Duncan |
| 4,556,058 | A | 12/1985 | Green |
| 4,560,915 | A | 12/1985 | Soultanian |
| 4,565,109 | A | 1/1986 | Tsay |
| 4,565,189 | A | 1/1986 | Mabuchi |
| 4,566,620 | A | 1/1986 | Green et al. |
| 4,569,346 | A | 2/1986 | Poirier |

(56) References Cited

U.S. PATENT DOCUMENTS 4,569,469 A 2/1986 Mongeon et al.
4,571,213 A 2/1986 Ishimoto
4,573,468 A 3/1986 Conta et al.
4,573,469 A 3/1986 Golden et al.
4,573,622 A 3/1986 Green et al.
4,576,165 A 3/1986 Green et al.
4,576,167 A 3/1986 Noiles
4,580,712 A 4/1986 Green
4,585,153 A 4/1986 Failla et al.
4,586,501 A 5/1986 Claracq
4,586,502 A 5/1986 Bedi et al.
4,589,416 A 5/1986 Green
4,589,582 A 5/1986 Bilotti
4,589,870 A 5/1986 Citrin et al.
4,591,085 A 5/1986 Di Giovanni
RE32,214 E 7/1986 Schramm
4,597,753 A 7/1986 Turley
4,600,037 A 7/1986 Hatten
4,604,786 A 8/1986 Howie, Jr.
4,605,001 A 8/1986 Rothfuss et al.
4,605,004 A 8/1986 Di Giovanni et al.
4,606,343 A 8/1986 Conta et al.
4,607,636 A 8/1986 Kula et al.
4,607,638 A 8/1986 Crainich
4,608,981 A 9/1986 Rothfuss et al.
4,610,250 A 9/1986 Green
4,610,383 A 9/1986 Rothfuss et al.
4,612,933 A 9/1986 Brinkerhoff et al.
D286,180 S 10/1986 Korthoff
D286,442 S 10/1986 Korthoff et al.
4,617,893 A 10/1986 Donner et al.
4,617,914 A 10/1986 Ueda
4,619,262 A 10/1986 Taylor
4,619,391 A 10/1986 Sharkany et al.
D287,278 S 12/1986 Spreckelmeier
4,628,459 A 12/1986 Shinohara et al.
4,628,636 A 12/1986 Folger
4,629,107 A 12/1986 Fedotov et al.
4,632,290 A 12/1986 Green et al.
4,633,861 A 1/1987 Chow et al.
4,633,874 A 1/1987 Chow et al.
4,634,419 A 1/1987 Kreizman et al.
4,635,638 A 1/1987 Weintraub et al.
4,641,076 A 2/1987 Linden
4,642,618 A 2/1987 Johnson et al.
4,643,173 A 2/1987 Bell et al.
4,643,731 A 2/1987 Eckenhoff
4,646,722 A 3/1987 Silverstein et al.
4,646,745 A 3/1987 Noiles
4,652,820 A 3/1987 Maresca
4,654,028 A 3/1987 Suma
4,655,222 A 4/1987 Florez et al.
4,662,555 A 5/1987 Thornton
4,663,874 A 5/1987 Sano et al.
4,664,305 A 5/1987 Blake, III et al.
4,665,916 A 5/1987 Green
4,667,674 A 5/1987 Korthoff et al.
4,669,647 A 6/1987 Storace
4,671,278 A 6/1987 Chin
4,671,280 A 6/1987 Dorband et al.
4,671,445 A 6/1987 Barker et al.
4,672,964 A 6/1987 Dee et al.
4,675,944 A 6/1987 Wells
4,676,245 A 6/1987 Fukuda
4,679,460 A 7/1987 Yoshigai
4,679,719 A 7/1987 Kramer
4,684,051 A 8/1987 Akopov et al.
4,688,555 A 8/1987 Wardle
4,691,703 A 9/1987 Auth et al.
4,693,248 A 9/1987 Failla
4,698,579 A 10/1987 Richter et al.
4,700,703 A 10/1987 Resnick et al.
4,705,038 A 11/1987 Sjostrom et al.
4,708,141 A 11/1987 Inoue et al.
4,709,120 A 11/1987 Pearson
4,715,520 A 12/1987 Roehr, Jr. et al.
4,719,917 A 1/1988 Barrows et al.
4,721,099 A 1/1988 Chikama
4,724,840 A 2/1988 McVay et al.
4,727,308 A 2/1988 Huljak et al.
4,728,020 A 3/1988 Green et al.
4,728,876 A 3/1988 Mongeon et al.
4,729,260 A 3/1988 Dudden
4,730,726 A 3/1988 Holzwarth
4,741,336 A 5/1988 Failla et al.
4,743,214 A 5/1988 Tai-Cheng
4,744,363 A 5/1988 Hasson
4,747,820 A 5/1988 Hornlein et al.
4,750,902 A 6/1988 Wuchinich et al.
4,752,024 A 6/1988 Green et al.
4,754,909 A 7/1988 Barker et al.
4,761,326 A 8/1988 Barnes et al.
4,763,669 A 8/1988 Jaeger
4,767,044 A 8/1988 Green
D297,764 S 9/1988 Hunt et al.
4,773,420 A 9/1988 Green
4,777,780 A 10/1988 Holzwarth
4,781,186 A 11/1988 Simpson et al.
4,784,137 A 11/1988 Kulik et al.
4,787,387 A 11/1988 Burbank, III et al.
4,788,485 A 11/1988 Kawagishi et al.
D298,967 S 12/1988 Hunt
4,790,225 A 12/1988 Moody et al.
4,790,314 A 12/1988 Weaver
4,805,617 A 2/1989 Bedi et al.
4,805,823 A 2/1989 Rothfuss
4,807,628 A 2/1989 Peters et al.
4,809,695 A 3/1989 Gwathmey et al.
4,815,460 A 3/1989 Porat et al.
4,817,643 A 4/1989 Olson
4,817,847 A 4/1989 Redtenbacher et al.
4,819,853 A 4/1989 Green
4,821,939 A 4/1989 Green
4,827,911 A 5/1989 Broadwin et al.
4,828,542 A 5/1989 Hermann
4,828,944 A 5/1989 Yabe et al.
4,830,855 A 5/1989 Stewart
4,832,158 A 5/1989 Farrar et al.
4,833,937 A 5/1989 Nagano
4,834,720 A 5/1989 Blinkhorn
4,838,859 A 6/1989 Strassmann
4,844,068 A 7/1989 Arata et al.
4,848,637 A 7/1989 Pruitt
4,856,078 A 8/1989 Konopka
4,860,644 A 8/1989 Kohl et al.
4,862,891 A 9/1989 Smith
4,863,423 A 9/1989 Wallace
4,865,030 A 9/1989 Polyak
4,868,530 A 9/1989 Ahs
4,869,414 A 9/1989 Green et al.
4,869,415 A 9/1989 Fox
4,873,977 A 10/1989 Avant et al.
4,875,486 A 10/1989 Rapoport et al.
4,880,015 A 11/1989 Nierman
4,890,613 A 1/1990 Golden et al.
4,892,244 A 1/1990 Fox et al.
4,893,622 A 1/1990 Green et al.
4,894,051 A 1/1990 Shiber
4,896,584 A 1/1990 Stoll et al.
4,896,678 A 1/1990 Ogawa
4,900,303 A 2/1990 Lemelson
4,903,697 A 2/1990 Resnick et al.
4,909,789 A 3/1990 Taguchi et al.
4,915,100 A 4/1990 Green
4,919,679 A 4/1990 Averill et al.
4,921,479 A 5/1990 Grayzel
4,925,082 A 5/1990 Kim
4,928,699 A 5/1990 Sasai
4,930,503 A 6/1990 Pruitt
4,930,674 A 6/1990 Barak
4,931,047 A 6/1990 Broadwin et al.
4,931,737 A 6/1990 Hishiki
4,932,960 A 6/1990 Green et al.
4,933,800 A 6/1990 Yang

(56) References Cited

U.S. PATENT DOCUMENTS 4,933,843 A 6/1990 Scheller et al.
D309,350 S 7/1990 Sutherland et al.
4,938,408 A 7/1990 Bedi et al.
4,941,623 A 7/1990 Pruitt
4,943,182 A 7/1990 Hoblingre
4,944,443 A 7/1990 Oddsen et al.
4,946,067 A 8/1990 Kelsall
4,948,327 A 8/1990 Crupi, Jr.
4,949,707 A 8/1990 LeVahn et al.
4,951,860 A 8/1990 Peters et al.
4,951,861 A 8/1990 Schulze et al.
4,955,959 A 9/1990 Tompkins et al.
4,957,212 A 9/1990 Duck et al.
4,962,877 A 10/1990 Hervas
4,964,559 A 10/1990 Deniega et al.
4,964,863 A 10/1990 Kanshin et al.
4,965,709 A 10/1990 Ngo
4,973,274 A 11/1990 Hirukawa
4,973,302 A 11/1990 Armour et al.
4,978,049 A 12/1990 Green
4,978,333 A 12/1990 Broadwin et al.
4,979,952 A 12/1990 Kubota et al.
4,984,564 A 1/1991 Yuen
4,986,808 A 1/1991 Broadwin et al.
4,987,049 A 1/1991 Komamura et al.
4,988,334 A 1/1991 Hornlein et al.
4,995,877 A 2/1991 Ams et al.
4,995,959 A 2/1991 Metzner
4,996,975 A 3/1991 Nakamura
5,002,543 A 3/1991 Bradshaw et al.
5,002,553 A 3/1991 Shiber
5,005,754 A 4/1991 Van Overloop
5,009,661 A 4/1991 Michelson
5,012,411 A 4/1991 Policastro et al.
5,014,898 A 5/1991 Heidrich
5,014,899 A 5/1991 Presty et al.
5,015,227 A 5/1991 Broadwin et al.
5,018,515 A 5/1991 Gilman
5,018,657 A 5/1991 Pedlick et al.
5,024,652 A 6/1991 Dumenek et al.
5,024,671 A 6/1991 Tu et al.
5,025,559 A 6/1991 McCullough
5,027,834 A 7/1991 Pruitt
5,030,226 A 7/1991 Green et al.
5,031,814 A 7/1991 Tompkins et al.
5,035,040 A 7/1991 Kerrigan et al.
5,038,109 A 8/1991 Goble et al.
5,038,247 A 8/1991 Kelley et al.
5,040,715 A 8/1991 Green et al.
5,042,707 A 8/1991 Taheri
5,061,269 A 10/1991 Muller
5,062,491 A 11/1991 Takeshima et al.
5,062,563 A 11/1991 Green et al.
5,065,929 A 11/1991 Schulze et al.
5,071,052 A 12/1991 Rodak et al.
5,071,430 A 12/1991 de Salis et al.
5,074,454 A 12/1991 Peters
5,077,506 A 12/1991 Krause
5,079,006 A 1/1992 Urquhart
5,080,556 A 1/1992 Carreno
5,083,695 A 1/1992 Foslien et al.
5,084,057 A 1/1992 Green et al.
5,088,979 A 2/1992 Filipi et al.
5,088,997 A 2/1992 Delahuerga et al.
5,089,606 A 2/1992 Cole et al.
5,094,247 A 3/1992 Hernandez et al.
5,098,004 A 3/1992 Kerrigan
5,098,360 A 3/1992 Hirota
5,100,042 A 3/1992 Gravener et al.
5,100,420 A 3/1992 Green et al.
5,104,025 A 4/1992 Main et al.
5,104,397 A 4/1992 Vasconcelos et al.
5,104,400 A 4/1992 Berguer et al.
5,106,008 A 4/1992 Tompkins et al.
5,108,368 A 4/1992 Hammerslag et al.
5,109,722 A 5/1992 Hufnagle et al.
5,111,987 A 5/1992 Moeinzadeh et al.
5,116,349 A 5/1992 Aranyi
D327,323 S 6/1992 Hunt
5,119,009 A 6/1992 McCaleb et al.
5,122,156 A 6/1992 Granger et al.
5,124,990 A 6/1992 Williamson
5,129,570 A 7/1992 Schulze et al.
5,137,198 A 8/1992 Nobis et al.
5,139,513 A 8/1992 Segato
5,141,144 A 8/1992 Foslien et al.
5,142,932 A 9/1992 Moya et al.
5,155,941 A 10/1992 Takahashi et al.
5,156,315 A 10/1992 Green et al.
5,156,609 A 10/1992 Nakao et al.
5,156,614 A 10/1992 Green et al.
5,158,567 A 10/1992 Green
D330,699 S 11/1992 Gill
5,163,598 A 11/1992 Peters et al.
5,168,605 A 12/1992 Bartlett
5,170,925 A 12/1992 Madden et al.
5,171,247 A 12/1992 Hughett et al.
5,171,249 A 12/1992 Stefanchik et al.
5,171,253 A 12/1992 Klieman
5,173,053 A 12/1992 Swanson et al.
5,173,133 A 12/1992 Morin et al.
5,176,677 A 1/1993 Wuchinich
5,176,688 A 1/1993 Narayan et al.
5,187,422 A 2/1993 Izenbaard et al.
5,188,102 A 2/1993 Idemoto et al.
5,188,111 A 2/1993 Yates et al.
5,190,517 A 3/1993 Zieve et al.
5,190,544 A 3/1993 Chapman et al.
5,190,560 A 3/1993 Woods et al.
5,190,657 A 3/1993 Heagle et al.
5,192,288 A 3/1993 Thompson et al.
5,193,731 A 3/1993 Aranyi
5,195,505 A 3/1993 Josefsen
5,195,968 A 3/1993 Lundquist et al.
5,197,648 A 3/1993 Gingold
5,197,649 A 3/1993 Bessler et al.
5,197,966 A 3/1993 Sommerkamp
5,197,970 A 3/1993 Green et al.
5,200,280 A 4/1993 Karasa
5,201,750 A 4/1993 Hocherl et al.
5,205,459 A 4/1993 Brinkerhoff et al.
5,207,672 A 5/1993 Roth et al.
5,207,697 A 5/1993 Carusillo et al.
5,209,747 A 5/1993 Knoepfler
5,209,756 A 5/1993 Seedhom et al.
5,211,649 A 5/1993 Kohler et al.
5,211,655 A 5/1993 Hasson
5,217,457 A 6/1993 Delahuerga et al.
5,217,478 A 6/1993 Rexroth
5,219,111 A 6/1993 Bilotti et al.
5,220,269 A 6/1993 Chen et al.
5,221,036 A 6/1993 Takase
5,221,281 A 6/1993 Klicek
5,222,945 A 6/1993 Basnight
5,222,963 A 6/1993 Brinkerhoff et al.
5,222,975 A 6/1993 Crainich
5,222,976 A 6/1993 Yoon
5,223,675 A 6/1993 Taft
D338,729 S 8/1993 Sprecklemeier et al.
5,234,447 A 8/1993 Kaster et al.
5,236,269 A 8/1993 Handy
5,236,424 A 8/1993 Imran
5,236,440 A 8/1993 Hlavacek
5,239,981 A 8/1993 Anapliotis
5,240,163 A 8/1993 Stein et al.
5,242,456 A 9/1993 Nash et al.
5,242,457 A 9/1993 Akopov et al.
5,244,462 A 9/1993 Delahuerga et al.
5,246,156 A 9/1993 Rothfuss et al.
5,246,443 A 9/1993 Mai
5,253,793 A 10/1993 Green et al.
5,258,007 A 11/1993 Spetzler et al.
5,258,008 A 11/1993 Wilk
5,258,009 A 11/1993 Conners

(56) References Cited

U.S. PATENT DOCUMENTS 5,258,010 A 11/1993 Green et al.
5,258,012 A 11/1993 Luscombe et al.
5,259,366 A 11/1993 Reydel et al.
5,259,835 A 11/1993 Clark et al.
5,260,637 A 11/1993 Pizzi
5,261,135 A 11/1993 Mitchell
5,261,877 A 11/1993 Fine et al.
5,261,922 A 11/1993 Hood
5,263,629 A 11/1993 Trumbull et al.
5,263,937 A 11/1993 Shipp
5,263,973 A 11/1993 Cook
5,264,218 A 11/1993 Rogozinski
5,268,622 A 12/1993 Philipp
5,271,543 A 12/1993 Grant et al.
5,271,544 A 12/1993 Fox et al.
RE34,519 E 1/1994 Fox et al.
5,275,322 A 1/1994 Brinkerhoff et al.
5,275,323 A 1/1994 Schulze et al.
5,275,608 A 1/1994 Forman et al.
5,279,416 A 1/1994 Malec et al.
5,281,216 A 1/1994 Klicek
5,282,806 A 2/1994 Haber et al.
5,282,829 A 2/1994 Hermes
5,284,128 A 2/1994 Hart
5,285,381 A 2/1994 Iskarous et al.
5,285,945 A 2/1994 Brinkerhoff et al.
5,286,253 A 2/1994 Fucci
5,289,963 A 3/1994 McGarry et al.
5,290,271 A 3/1994 Jernberg
5,290,310 A 3/1994 Makower et al.
5,292,053 A 3/1994 Bilotti et al.
5,293,024 A 3/1994 Sugahara et al.
5,297,714 A 3/1994 Kramer
5,304,204 A 4/1994 Bregen
D347,474 S 5/1994 Olson
5,307,976 A 5/1994 Olson et al.
5,308,576 A 5/1994 Green et al.
5,309,387 A 5/1994 Mori et al.
5,309,927 A 5/1994 Welch
5,312,023 A 5/1994 Green et al.
5,312,024 A 5/1994 Grant et al.
5,312,329 A 5/1994 Beaty et al.
5,313,935 A 5/1994 Kortenbach et al.
5,313,967 A 5/1994 Lieber et al.
5,314,424 A 5/1994 Nicholas
5,314,445 A 5/1994 Heidmueller nee Degwitz et al.
5,314,466 A 5/1994 Stern et al.
5,318,221 A 6/1994 Green et al.
5,320,627 A 6/1994 Sorensen et al.
D348,930 S 7/1994 Olson
5,326,013 A 7/1994 Green et al.
5,329,923 A 7/1994 Lundquist
5,330,487 A 7/1994 Thornton et al.
5,330,502 A 7/1994 Hassler et al.
5,331,971 A 7/1994 Bales et al.
5,332,142 A 7/1994 Robinson et al.
5,333,422 A 8/1994 Warren et al.
5,333,772 A 8/1994 Rothfuss et al.
5,333,773 A 8/1994 Main et al.
5,334,183 A 8/1994 Wuchinich
5,336,130 A 8/1994 Ray
5,336,229 A 8/1994 Noda
5,336,232 A 8/1994 Green et al.
5,339,799 A 8/1994 Kami et al.
5,341,724 A 8/1994 Vatel
5,341,807 A 8/1994 Nardella
5,341,810 A 8/1994 Dardel
5,342,380 A 8/1994 Hood
5,342,381 A 8/1994 Tidemand
5,342,385 A 8/1994 Norelli et al.
5,342,395 A 8/1994 Jarrett et al.
5,342,396 A 8/1994 Cook
5,343,382 A 8/1994 Hale et al.
5,343,391 A 8/1994 Mushabac
5,344,059 A 9/1994 Green et al.
5,344,060 A 9/1994 Gravener et al.
5,344,454 A 9/1994 Clarke et al.
5,346,504 A 9/1994 Ortiz et al.
5,348,259 A 9/1994 Blanco et al.
5,350,355 A 9/1994 Sklar
5,350,388 A 9/1994 Epstein
5,350,391 A 9/1994 Iacovelli
5,350,400 A 9/1994 Esposito et al.
5,352,229 A 10/1994 Goble et al.
5,352,235 A 10/1994 Koros et al.
5,352,238 A 10/1994 Green et al.
5,354,250 A 10/1994 Christensen
5,354,303 A 10/1994 Spaeth et al.
5,356,006 A 10/1994 Alpern et al.
5,356,064 A 10/1994 Green et al.
5,358,506 A 10/1994 Green et al.
5,358,510 A 10/1994 Luscombe et al.
5,359,231 A 10/1994 Flowers et al.
D352,780 S 11/1994 Glaeser et al.
5,359,993 A 11/1994 Slater et al.
5,360,305 A 11/1994 Kerrigan
5,360,428 A 11/1994 Hutchinson, Jr.
5,361,902 A 11/1994 Abidin et al.
5,364,001 A 11/1994 Bryan
5,364,002 A 11/1994 Green et al.
5,364,003 A 11/1994 Williamson, IV
5,366,133 A 11/1994 Geiste
5,366,134 A 11/1994 Green et al.
5,366,479 A 11/1994 McGarry et al.
5,368,015 A 11/1994 Wilk
5,368,592 A 11/1994 Stern et al.
5,369,565 A 11/1994 Chen et al.
5,370,645 A 12/1994 Klicek et al.
5,372,124 A 12/1994 Takayama et al.
5,372,596 A 12/1994 Klicek et al.
5,372,602 A 12/1994 Burke
5,374,277 A 12/1994 Hassler
5,375,588 A 12/1994 Yoon
5,376,095 A 12/1994 Ortiz
5,379,933 A 1/1995 Green et al.
5,381,649 A 1/1995 Webb
5,381,782 A 1/1995 DeLaRama et al.
5,381,943 A 1/1995 Allen et al.
5,382,247 A 1/1995 Cimino et al.
5,383,460 A 1/1995 Jang et al.
5,383,880 A 1/1995 Hooven
5,383,881 A 1/1995 Green et al.
5,383,882 A 1/1995 Buess et al.
5,383,888 A 1/1995 Zvenyatsky et al.
5,383,895 A 1/1995 Holmes et al.
5,388,568 A 2/1995 van der Heide
5,389,098 A 2/1995 Tsuruta et al.
5,389,102 A 2/1995 Green et al.
5,389,104 A 2/1995 Hahnen et al.
5,391,180 A 2/1995 Tovey et al.
5,392,979 A 2/1995 Green et al.
5,395,030 A 3/1995 Kuramoto et al.
5,395,033 A 3/1995 Byrne et al.
5,395,034 A 3/1995 Allen et al.
5,395,312 A 3/1995 Desai
5,395,384 A 3/1995 Duthoit et al.
5,397,046 A 3/1995 Savage et al.
5,397,324 A 3/1995 Carroll et al.
5,400,267 A 3/1995 Denen et al.
5,403,276 A 4/1995 Schechter et al.
5,403,312 A 4/1995 Yates et al.
5,404,106 A 4/1995 Matsuda
5,404,870 A 4/1995 Brinkerhoff et al.
5,404,960 A 4/1995 Wada et al.
5,405,072 A 4/1995 Zlock et al.
5,405,073 A 4/1995 Porter
5,405,344 A 4/1995 Williamson et al.
5,405,360 A 4/1995 Tovey
5,407,293 A 4/1995 Crainich
5,408,409 A 4/1995 Glassman et al.
5,409,498 A 4/1995 Braddock et al.
5,409,703 A 4/1995 McAnalley et al.
D357,981 S 5/1995 Green et al.
5,411,481 A 5/1995 Allen et al.

(56) References Cited

U.S. PATENT DOCUMENTS 5,411,508 A 5/1995 Bessler et al.
5,413,107 A 5/1995 Oakley et al.
5,413,267 A 5/1995 Solyntjes et al.
5,413,268 A 5/1995 Green et al.
5,413,272 A 5/1995 Green et al.
5,413,573 A 5/1995 Koivukangas
5,415,334 A 5/1995 Williamson et al.
5,415,335 A 5/1995 Knodell, Jr.
5,417,203 A 5/1995 Tovey et al.
5,417,361 A 5/1995 Williamson, IV
5,419,766 A 5/1995 Chang et al.
5,421,829 A 6/1995 Olichney et al.
5,422,567 A 6/1995 Matsunaga
5,423,471 A 6/1995 Mastri et al.
5,423,809 A 6/1995 Klicek
5,423,835 A 6/1995 Green et al.
5,425,745 A 6/1995 Green et al.
5,427,298 A 6/1995 Tegtmeier
5,431,322 A 7/1995 Green et al.
5,431,323 A 7/1995 Smith et al.
5,431,654 A 7/1995 Nic
5,431,668 A 7/1995 Burbank, III et al.
5,433,721 A 7/1995 Hooven et al.
5,437,681 A 8/1995 Meade et al.
5,438,302 A 8/1995 Goble
5,438,997 A 8/1995 Sieben et al.
5,439,155 A 8/1995 Viola
5,439,156 A 8/1995 Grant et al.
5,439,479 A 8/1995 Shichman et al.
5,441,191 A 8/1995 Linden
5,441,193 A 8/1995 Gravener
5,441,483 A 8/1995 Avitall
5,441,494 A 8/1995 Ortiz
5,443,197 A 8/1995 Malis et al.
5,443,463 A 8/1995 Stern et al.
5,444,113 A 8/1995 Sinclair et al.
5,445,155 A 8/1995 Sieben
5,445,304 A 8/1995 Plyley et al.
5,445,604 A 8/1995 Lang
5,445,644 A 8/1995 Pietrafitta et al.
5,446,646 A 8/1995 Miyazaki
5,447,265 A 9/1995 Vidal et al.
5,447,417 A 9/1995 Kuhl et al.
5,447,513 A 9/1995 Davison et al.
5,449,355 A 9/1995 Rhum et al.
5,449,365 A 9/1995 Green et al.
5,449,370 A 9/1995 Vaitekunas
5,452,836 A 9/1995 Huitema et al.
5,452,837 A 9/1995 Williamson, IV et al.
5,454,378 A 10/1995 Palmer et al.
5,454,822 A 10/1995 Schob et al.
5,454,827 A 10/1995 Aust et al.
5,456,401 A 10/1995 Green et al.
5,456,917 A 10/1995 Wise et al.
5,458,279 A 10/1995 Plyley
5,458,579 A 10/1995 Chodorow et al.
5,462,215 A 10/1995 Viola et al.
5,464,013 A 11/1995 Lemelson
5,464,144 A 11/1995 Guy et al.
5,464,300 A 11/1995 Crainich
5,465,819 A 11/1995 Weilant et al.
5,465,894 A 11/1995 Clark et al.
5,465,895 A 11/1995 Knodel et al.
5,465,896 A 11/1995 Allen et al.
5,466,020 A 11/1995 Page et al.
5,467,911 A 11/1995 Tsuruta et al.
5,468,253 A 11/1995 Bezwada et al.
5,470,006 A 11/1995 Rodak
5,470,007 A 11/1995 Plyley et al.
5,470,008 A 11/1995 Rodak
5,470,009 A 11/1995 Rodak
5,470,010 A 11/1995 Rothfuss et al.
5,471,129 A 11/1995 Mann
5,472,132 A 12/1995 Savage et al.
5,472,442 A 12/1995 Klicek
5,473,204 A 12/1995 Temple
5,474,057 A 12/1995 Makower et al.
5,474,223 A 12/1995 Viola et al.
5,474,566 A 12/1995 Alesi et al.
5,474,570 A 12/1995 Kockerling et al.
5,476,206 A 12/1995 Green et al.
5,476,479 A 12/1995 Green et al.
5,476,481 A 12/1995 Schondorf
5,478,003 A 12/1995 Green et al.
5,478,354 A 12/1995 Tovey et al.
5,480,089 A 1/1996 Blewett
5,480,409 A 1/1996 Riza
5,482,197 A 1/1996 Green et al.
5,483,952 A 1/1996 Aranyi
5,484,095 A 1/1996 Green et al.
5,484,398 A 1/1996 Stoddard
5,484,451 A 1/1996 Akopov et al.
5,485,947 A 1/1996 Olson et al.
5,485,952 A 1/1996 Fontayne
5,487,499 A 1/1996 Sorrentino et al.
5,487,500 A 1/1996 Knodel et al.
5,489,058 A 2/1996 Plyley et al.
5,489,256 A 2/1996 Adair
5,489,290 A 2/1996 Furnish
5,490,819 A 2/1996 Nicholas et al.
5,492,671 A 2/1996 Krafft
5,496,312 A 3/1996 Klicek
5,496,317 A 3/1996 Goble et al.
5,497,933 A 3/1996 DeFonzo et al.
5,498,164 A 3/1996 Ward et al.
5,498,838 A 3/1996 Furman
5,501,654 A 3/1996 Failla et al.
5,503,320 A 4/1996 Webster et al.
5,503,635 A 4/1996 Sauer et al.
5,503,638 A 4/1996 Cooper et al.
5,505,363 A 4/1996 Green et al.
5,507,425 A 4/1996 Ziglioli
5,507,426 A 4/1996 Young et al.
5,509,596 A 4/1996 Green et al.
5,509,916 A 4/1996 Taylor
5,511,564 A 4/1996 Wilk
5,514,129 A 5/1996 Smith
5,514,149 A 5/1996 Green et al.
5,514,157 A 5/1996 Nicholas et al.
5,518,163 A 5/1996 Hooven
5,518,164 A 5/1996 Hooven
5,520,609 A 5/1996 Moll et al.
5,520,634 A 5/1996 Fox et al.
5,520,678 A 5/1996 Heckele et al.
5,520,700 A 5/1996 Beyar et al.
5,522,817 A 6/1996 Sander et al.
5,522,831 A 6/1996 Sleister et al.
5,527,264 A 6/1996 Moll et al.
5,527,320 A 6/1996 Carruthers et al.
5,529,235 A 6/1996 Boiarski et al.
D372,086 S 7/1996 Grasso et al.
5,531,305 A 7/1996 Roberts et al.
5,531,744 A 7/1996 Nardella et al.
5,531,856 A 7/1996 Moll et al.
5,533,521 A 7/1996 Granger
5,533,581 A 7/1996 Barth et al.
5,533,661 A 7/1996 Main et al.
5,535,934 A 7/1996 Boiarski et al.
5,535,935 A 7/1996 Vidal et al.
5,535,937 A 7/1996 Boiarski et al.
5,540,375 A 7/1996 Bolanos et al.
5,540,705 A 7/1996 Meade et al.
5,541,376 A 7/1996 Ladtkow et al.
5,541,489 A 7/1996 Dunstan
5,542,594 A 8/1996 McKean et al.
5,542,949 A 8/1996 Yoon
5,543,119 A 8/1996 Sutter et al.
5,543,695 A 8/1996 Culp et al.
5,544,802 A 8/1996 Crainich
5,547,117 A 8/1996 Hamblin et al.
5,549,583 A 8/1996 Sanford et al.
5,549,621 A 8/1996 Bessler et al.
5,549,627 A 8/1996 Kieturakis
5,549,628 A 8/1996 Cooper et al.

(56) References Cited

U.S. PATENT DOCUMENTS 5,549,637 A 8/1996 Crainich
5,551,622 A 9/1996 Yoon
5,553,624 A 9/1996 Francese et al.
5,553,675 A 9/1996 Pitzen et al.
5,553,765 A 9/1996 Knodel et al.
5,554,148 A 9/1996 Aebischer et al.
5,554,169 A 9/1996 Green et al.
5,556,020 A 9/1996 Hou
5,556,416 A 9/1996 Clark et al.
5,558,533 A 9/1996 Hashizawa et al.
5,558,665 A 9/1996 Kieturakis
5,558,671 A 9/1996 Yates
5,560,530 A 10/1996 Bolanos et al.
5,560,532 A 10/1996 DeFonzo et al.
5,561,881 A 10/1996 Klinger et al.
5,562,239 A 10/1996 Boiarski et al.
5,562,241 A 10/1996 Knodel et al.
5,562,682 A 10/1996 Oberlin et al.
5,562,690 A 10/1996 Green et al.
5,562,701 A 10/1996 Huitema et al.
5,562,702 A 10/1996 Huitema et al.
5,563,481 A 10/1996 Krause
5,564,615 A 10/1996 Bishop et al.
5,569,161 A 10/1996 Ebling et al.
5,569,270 A 10/1996 Weng
5,569,284 A 10/1996 Young et al.
5,571,090 A 11/1996 Sherts
5,571,100 A 11/1996 Goble et al.
5,571,116 A 11/1996 Bolanos et al.
5,571,285 A 11/1996 Chow et al.
5,571,488 A 11/1996 Beerstecher et al.
5,573,169 A 11/1996 Green et al.
5,573,543 A 11/1996 Akopov et al.
5,574,431 A 11/1996 McKeown et al.
5,575,054 A 11/1996 Klinzing et al.
5,575,789 A 11/1996 Bell et al.
5,575,799 A 11/1996 Bolanos et al.
5,575,803 A 11/1996 Cooper et al.
5,575,805 A 11/1996 Li
5,577,654 A 11/1996 Bishop
5,578,052 A 11/1996 Koros et al.
5,579,978 A 12/1996 Green et al.
5,580,067 A 12/1996 Hamblin et al.
5,582,611 A 12/1996 Tsuruta et al.
5,582,617 A 12/1996 Klieman et al.
5,582,907 A 12/1996 Pall
5,583,114 A 12/1996 Barrows et al.
5,584,425 A 12/1996 Savage et al.
5,586,711 A 12/1996 Plyley et al.
5,588,579 A 12/1996 Schnut et al.
5,588,580 A 12/1996 Paul et al.
5,588,581 A 12/1996 Conlon et al.
5,591,170 A 1/1997 Spievack et al.
5,591,187 A 1/1997 Dekel
5,597,107 A 1/1997 Knodel et al.
5,599,151 A 2/1997 Daum et al.
5,599,279 A 2/1997 Slotman et al.
5,599,344 A 2/1997 Paterson
5,599,350 A 2/1997 Schulze et al.
5,599,852 A 2/1997 Scopelianos et al.
5,601,224 A 2/1997 Bishop et al.
5,601,573 A 2/1997 Fogelberg et al.
5,601,604 A 2/1997 Vincent
5,602,449 A 2/1997 Krause et al.
5,603,443 A 2/1997 Clark et al.
5,605,272 A 2/1997 Witt et al.
5,605,273 A 2/1997 Hamblin et al.
5,607,094 A 3/1997 Clark et al.
5,607,095 A 3/1997 Smith et al.
5,607,433 A 3/1997 Polla et al.
5,607,450 A 3/1997 Zvenyatsky et al.
5,607,474 A 3/1997 Athanasiou et al.
5,609,285 A 3/1997 Grant et al.
5,609,601 A 3/1997 Kolesa et al.
5,611,709 A 3/1997 McAnulty
5,613,499 A 3/1997 Palmer et al.
5,613,937 A 3/1997 Garrison et al.
5,613,966 A 3/1997 Makower et al.
5,614,887 A 3/1997 Buchbinder
5,615,820 A 4/1997 Viola
5,618,294 A 4/1997 Aust et al.
5,618,303 A 4/1997 Marlow et al.
5,618,307 A 4/1997 Donlon et al.
5,619,992 A 4/1997 Guthrie et al.
5,620,289 A 4/1997 Curry
5,620,326 A 4/1997 Younker
5,620,452 A 4/1997 Yoon
5,624,398 A 4/1997 Smith et al.
5,624,452 A 4/1997 Yates
5,626,587 A 5/1997 Bishop et al.
5,626,595 A 5/1997 Sklar et al.
5,628,446 A 5/1997 Geiste et al.
5,628,743 A 5/1997 Cimino
5,628,745 A 5/1997 Bek
5,630,539 A 5/1997 Plyley et al.
5,630,540 A 5/1997 Blewett
5,630,541 A 5/1997 Williamson, IV et al.
5,630,782 A 5/1997 Adair
5,632,432 A 5/1997 Schulze et al.
5,632,433 A 5/1997 Grant et al.
5,633,374 A 5/1997 Humphrey et al.
5,634,584 A 6/1997 Okorocha et al.
5,636,779 A 6/1997 Palmer
5,636,780 A 6/1997 Green et al.
5,638,582 A 6/1997 Klatt et al.
5,639,008 A 6/1997 Gallagher et al.
D381,077 S 7/1997 Hunt
5,643,291 A 7/1997 Pier et al.
5,643,293 A 7/1997 Kogasaka et al.
5,643,294 A 7/1997 Tovey et al.
5,643,319 A 7/1997 Green et al.
5,645,209 A 7/1997 Green et al.
5,647,526 A 7/1997 Green et al.
5,647,869 A 7/1997 Goble et al.
5,649,937 A 7/1997 Bito et al.
5,649,956 A 7/1997 Jensen et al.
5,651,491 A 7/1997 Heaton et al.
5,651,762 A 7/1997 Bridges
5,651,821 A 7/1997 Uchida
5,653,373 A 8/1997 Green et al.
5,653,374 A 8/1997 Young et al.
5,653,677 A 8/1997 Okada et al.
5,653,721 A 8/1997 Knodel et al.
5,653,748 A 8/1997 Strecker
5,655,698 A 8/1997 Yoon
5,657,417 A 8/1997 Di Troia
5,657,429 A 8/1997 Wang et al.
5,657,921 A 8/1997 Young et al.
5,658,238 A 8/1997 Suzuki et al.
5,658,281 A 8/1997 Heard
5,658,298 A 8/1997 Vincent et al.
5,658,300 A 8/1997 Bito et al.
5,658,307 A 8/1997 Exconde
5,662,258 A 9/1997 Knodel et al.
5,662,260 A 9/1997 Yoon
5,662,662 A 9/1997 Bishop et al.
5,662,667 A 9/1997 Knodel
5,665,085 A 9/1997 Nardella
5,667,517 A 9/1997 Hooven
5,667,526 A 9/1997 Levin
5,667,527 A 9/1997 Cook
5,667,864 A 9/1997 Landoll
5,669,544 A 9/1997 Schulze et al.
5,669,904 A 9/1997 Platt, Jr. et al.
5,669,907 A 9/1997 Platt, Jr. et al.
5,669,918 A 9/1997 Balazs et al.
5,673,840 A 10/1997 Schulze et al.
5,673,841 A 10/1997 Schulze et al.
5,673,842 A 10/1997 Bittner et al.
5,674,286 A 10/1997 D'Alessio et al.
5,678,748 A 10/1997 Plyley et al.
5,680,981 A 10/1997 Mililli et al.
5,680,982 A 10/1997 Schulze et al.
5,680,983 A 10/1997 Plyley et al.

(56) References Cited

U.S. PATENT DOCUMENTS 5,681,341 A 10/1997 Lunsford et al.
5,683,349 A 11/1997 Makower et al.
5,685,474 A 11/1997 Seeber
5,686,090 A 11/1997 Schilder et al.
5,688,270 A 11/1997 Yates et al.
5,690,269 A 11/1997 Bolanos et al.
5,692,668 A 12/1997 Schulze et al.
5,693,020 A 12/1997 Rauh
5,693,042 A 12/1997 Boiarski et al.
5,693,051 A 12/1997 Schulze et al.
5,695,494 A 12/1997 Becker
5,695,502 A 12/1997 Pier et al.
5,695,504 A 12/1997 Gifford, III et al.
5,695,524 A 12/1997 Kelley et al.
5,697,542 A 12/1997 Knodel et al.
5,697,543 A 12/1997 Burdorff
5,697,909 A 12/1997 Eggers et al.
5,697,943 A 12/1997 Sauer et al.
5,700,270 A 12/1997 Peyser et al.
5,700,276 A 12/1997 Benecke
5,702,387 A 12/1997 Arts et al.
5,702,408 A 12/1997 Wales et al.
5,702,409 A 12/1997 Rayburn et al.
5,704,087 A 1/1998 Strub
5,704,534 A 1/1998 Huitema et al.
5,706,997 A 1/1998 Green et al.
5,706,998 A 1/1998 Plyley et al.
5,707,392 A 1/1998 Kortenbach
5,709,334 A 1/1998 Sorrentino et al.
5,709,335 A 1/1998 Heck
5,709,680 A 1/1998 Yates et al.
5,709,706 A 1/1998 Kienzle et al.
5,711,472 A 1/1998 Bryan
5,712,460 A 1/1998 Carr et al.
5,713,128 A 2/1998 Schrenk et al.
5,713,505 A 2/1998 Huitema
5,713,895 A 2/1998 Lontine et al.
5,713,896 A 2/1998 Nardella
5,713,920 A 2/1998 Bezwada et al.
5,715,604 A 2/1998 Lanzoni
5,715,987 A 2/1998 Kelley et al.
5,715,988 A 2/1998 Palmer
5,716,366 A 2/1998 Yates
5,718,359 A 2/1998 Palmer et al.
5,718,360 A 2/1998 Green et al.
5,718,548 A 2/1998 Cotellessa
5,718,714 A 2/1998 Livneh
5,720,744 A 2/1998 Eggleston et al.
D393,067 S 3/1998 Geary et al.
5,724,025 A 3/1998 Tavori
5,725,536 A 3/1998 Oberlin et al.
5,725,554 A 3/1998 Simon et al.
5,728,110 A 3/1998 Vidal et al.
5,728,113 A 3/1998 Sherts
5,728,121 A 3/1998 Bimbo et al.
5,730,758 A 3/1998 Allgeyer
5,732,821 A 3/1998 Stone et al.
5,732,871 A 3/1998 Clark et al.
5,732,872 A 3/1998 Bolduc et al.
5,733,308 A 3/1998 Daugherty et al.
5,735,445 A 4/1998 Vidal et al.
5,735,848 A 4/1998 Yates et al.
5,735,874 A 4/1998 Measamer et al.
5,738,474 A 4/1998 Blewett
5,738,629 A 4/1998 Moll et al.
5,738,648 A 4/1998 Lands et al.
5,741,271 A 4/1998 Nakao et al.
5,743,456 A 4/1998 Jones et al.
5,747,953 A 5/1998 Philipp
5,749,889 A 5/1998 Bacich et al.
5,749,893 A 5/1998 Vidal et al.
5,749,896 A 5/1998 Cook
5,749,968 A 5/1998 Melanson et al.
5,752,644 A 5/1998 Bolanos et al.
5,752,965 A 5/1998 Francis et al.
5,752,970 A 5/1998 Yoon
5,755,717 A 5/1998 Yates et al.
5,758,814 A 6/1998 Gallagher et al.
5,762,255 A 6/1998 Chrisman et al.
5,762,256 A 6/1998 Mastri et al.
5,765,565 A 6/1998 Adair
5,766,188 A 6/1998 Igaki
5,766,205 A 6/1998 Zvenyatsky et al.
5,769,303 A 6/1998 Knodel et al.
5,769,748 A 6/1998 Eyerly et al.
5,769,791 A 6/1998 Benaron et al.
5,769,892 A 6/1998 Kingwell
5,772,379 A 6/1998 Evensen
5,772,578 A 6/1998 Heimberger et al.
5,772,659 A 6/1998 Becker et al.
5,773,991 A 6/1998 Chen
5,776,130 A 7/1998 Buysse et al.
5,778,939 A 7/1998 Hok-Yin
5,779,130 A 7/1998 Alesi et al.
5,779,131 A 7/1998 Knodel et al.
5,779,132 A 7/1998 Knodel et al.
5,782,396 A 7/1998 Mastri et al.
5,782,397 A 7/1998 Koukline
5,782,748 A 7/1998 Palmer et al.
5,782,749 A 7/1998 Riza
5,782,859 A 7/1998 Nicholas et al.
5,784,934 A 7/1998 Izumisawa
5,785,232 A 7/1998 Vidal et al.
5,785,647 A 7/1998 Tompkins et al.
5,787,897 A 8/1998 Kieturakis
5,791,231 A 8/1998 Cohn et al.
5,792,135 A 8/1998 Madhani et al.
5,792,162 A 8/1998 Jolly et al.
5,792,165 A 8/1998 Klieman et al.
5,792,573 A 8/1998 Pitzen et al.
5,794,834 A 8/1998 Hamblin et al.
5,796,188 A 8/1998 Bays
5,797,536 A 8/1998 Smith et al.
5,797,537 A 8/1998 Oberlin et al.
5,797,538 A 8/1998 Heaton et al.
5,797,637 A 8/1998 Ervin
5,797,900 A 8/1998 Madhani et al.
5,797,906 A 8/1998 Rhum et al.
5,797,927 A 8/1998 Yoon
5,797,941 A 8/1998 Schulze et al.
5,797,959 A 8/1998 Castro et al.
5,799,857 A 9/1998 Robertson et al.
5,800,379 A 9/1998 Edwards
5,800,423 A 9/1998 Jensen
5,804,726 A 9/1998 Geib et al.
5,804,936 A 9/1998 Brodsky et al.
5,806,676 A 9/1998 Wasgien
5,807,376 A 9/1998 Viola et al.
5,807,378 A 9/1998 Jensen et al.
5,807,393 A 9/1998 Williamson, IV et al.
5,809,441 A 9/1998 McKee
5,810,721 A 9/1998 Mueller et al.
5,810,811 A 9/1998 Yates et al.
5,810,846 A 9/1998 Virnich et al.
5,810,855 A 9/1998 Rayburn et al.
5,812,188 A 9/1998 Adair
5,813,813 A 9/1998 Daum et al.
5,814,055 A 9/1998 Knodel et al.
5,814,057 A 9/1998 Oi et al.
5,816,471 A 10/1998 Plyley et al.
5,817,084 A 10/1998 Jensen
5,817,091 A 10/1998 Nardella et al.
5,817,093 A 10/1998 Williamson, IV et al.
5,817,109 A 10/1998 McGarry et al.
5,817,119 A 10/1998 Klieman et al.
5,820,009 A 10/1998 Melling et al.
5,823,066 A 10/1998 Huitema et al.
5,824,333 A 10/1998 Scopelianos et al.
5,826,776 A 10/1998 Schulze et al.
5,827,271 A 10/1998 Buysse et al.
5,827,298 A 10/1998 Hart et al.
5,829,662 A 11/1998 Allen et al.
5,830,598 A 11/1998 Patterson
5,833,690 A 11/1998 Yates et al.

(56) References Cited

U.S. PATENT DOCUMENTS

| | | | |
|---|---|---|---|
| 5,833,695 | A | 11/1998 | Yoon |
| 5,833,696 | A | 11/1998 | Whitfield et al. |
| 5,836,503 | A | 11/1998 | Ehrenfels et al. |
| 5,836,960 | A | 11/1998 | Kolesa et al. |
| 5,839,369 | A | 11/1998 | Chatterjee et al. |
| 5,839,639 | A | 11/1998 | Sauer et al. |
| 5,841,284 | A | 11/1998 | Takahashi |
| 5,843,021 | A | 12/1998 | Edwards et al. |
| 5,843,096 | A | 12/1998 | Igaki et al. |
| 5,843,097 | A | 12/1998 | Mayenberger et al. |
| 5,843,122 | A | 12/1998 | Riza |
| 5,843,132 | A | 12/1998 | Ilvento |
| 5,843,169 | A | 12/1998 | Taheri |
| 5,846,254 | A | 12/1998 | Schulze et al. |
| 5,847,566 | A | 12/1998 | Marritt et al. |
| 5,849,011 | A | 12/1998 | Jones et al. |
| 5,849,020 | A | 12/1998 | Long et al. |
| 5,849,023 | A | 12/1998 | Mericle |
| 5,851,179 | A | 12/1998 | Ritson et al. |
| 5,851,212 | A | 12/1998 | Zirps et al. |
| 5,853,366 | A | 12/1998 | Dowlatshahi |
| 5,855,311 | A | 1/1999 | Hamblin et al. |
| 5,855,583 | A | 1/1999 | Wang et al. |
| 5,860,581 | A | 1/1999 | Robertson et al. |
| 5,860,975 | A | 1/1999 | Goble et al. |
| 5,865,361 | A | 2/1999 | Milliman et al. |
| 5,865,638 | A | 2/1999 | Trafton |
| 5,868,361 | A | 2/1999 | Rinderer |
| 5,868,760 | A | 2/1999 | McGuckin, Jr. |
| 5,868,790 | A | 2/1999 | Vincent et al. |
| 5,871,135 | A | 2/1999 | Williamson, IV et al. |
| 5,873,885 | A | 2/1999 | Weidenbenner |
| 5,876,401 | A | 3/1999 | Schulze et al. |
| 5,878,193 | A | 3/1999 | Wang et al. |
| 5,878,607 | A | 3/1999 | Nunes et al. |
| 5,878,937 | A | 3/1999 | Green et al. |
| 5,878,938 | A | 3/1999 | Bittner et al. |
| 5,881,777 | A | 3/1999 | Bassi et al. |
| 5,891,094 | A | 4/1999 | Masterson et al. |
| 5,891,160 | A | 4/1999 | Williamson, IV et al. |
| 5,891,558 | A | 4/1999 | Bell et al. |
| 5,893,506 | A | 4/1999 | Powell |
| 5,893,835 | A | 4/1999 | Witt et al. |
| 5,893,878 | A | 4/1999 | Pierce |
| 5,894,979 | A | 4/1999 | Powell |
| 5,897,552 | A | 4/1999 | Edwards et al. |
| 5,897,562 | A | 4/1999 | Bolanos et al. |
| 5,899,824 | A | 5/1999 | Kurtz et al. |
| 5,899,914 | A | 5/1999 | Zirps et al. |
| 5,901,895 | A | 5/1999 | Heaton et al. |
| 5,902,312 | A | 5/1999 | Frater et al. |
| 5,903,117 | A | 5/1999 | Gregory |
| 5,904,647 | A | 5/1999 | Ouchi |
| 5,904,693 | A | 5/1999 | Dicesare et al. |
| 5,904,702 | A | 5/1999 | Ek et al. |
| 5,906,577 | A | 5/1999 | Beane et al. |
| 5,906,625 | A | 5/1999 | Bito et al. |
| 5,907,211 | A | 5/1999 | Hall et al. |
| 5,908,402 | A | 6/1999 | Blythe |
| 5,908,427 | A | 6/1999 | McKean et al. |
| 5,909,062 | A | 6/1999 | Krietzman |
| 5,911,353 | A | 6/1999 | Bolanos et al. |
| 5,915,616 | A | 6/1999 | Viola et al. |
| 5,916,225 | A | 6/1999 | Kugel |
| 5,918,791 | A | 7/1999 | Sorrentino et al. |
| 5,919,198 | A | 7/1999 | Graves, Jr. et al. |
| 5,921,956 | A | 7/1999 | Grinberg et al. |
| 5,924,864 | A | 7/1999 | Loge et al. |
| 5,928,137 | A | 7/1999 | Green |
| 5,928,256 | A | 7/1999 | Riza |
| 5,931,847 | A | 8/1999 | Bittner et al. |
| 5,931,853 | A | 8/1999 | McEwen et al. |
| 5,937,951 | A | 8/1999 | Izuchukwu et al. |
| 5,938,667 | A | 8/1999 | Peyser et al. |
| 5,941,442 | A | 8/1999 | Geiste et al. |
| 5,941,890 | A | 8/1999 | Voegele et al. |
| 5,944,172 | A | 8/1999 | Hannula |
| 5,944,715 | A | 8/1999 | Goble et al. |
| 5,946,978 | A | 9/1999 | Yamashita |
| 5,947,984 | A | 9/1999 | Whipple |
| 5,947,996 | A | 9/1999 | Logeman |
| 5,948,030 | A | 9/1999 | Miller et al. |
| 5,948,429 | A | 9/1999 | Bell et al. |
| 5,951,301 | A | 9/1999 | Younker |
| 5,951,516 | A | 9/1999 | Bunyan |
| 5,951,552 | A | 9/1999 | Long et al. |
| 5,951,574 | A | 9/1999 | Stefanchik et al. |
| 5,951,575 | A | 9/1999 | Bolduc et al. |
| 5,951,581 | A | 9/1999 | Saadat et al. |
| 5,954,259 | A | 9/1999 | Viola et al. |
| 5,957,831 | A | 9/1999 | Adair |
| 5,964,394 | A | 10/1999 | Robertson |
| 5,964,774 | A | 10/1999 | McKean et al. |
| 5,966,126 | A | 10/1999 | Szabo |
| 5,971,916 | A | 10/1999 | Koren |
| 5,973,221 | A | 10/1999 | Collyer et al. |
| D416,089 | S | 11/1999 | Barton et al. |
| 5,976,122 | A | 11/1999 | Madhani et al. |
| 5,977,746 | A | 11/1999 | Hershberger et al. |
| 5,980,248 | A | 11/1999 | Kusakabe et al. |
| 5,984,949 | A | 11/1999 | Levin |
| 5,988,479 | A | 11/1999 | Palmer |
| 5,990,379 | A | 11/1999 | Gregory |
| 5,993,466 | A | 11/1999 | Yoon |
| 5,997,528 | A | 12/1999 | Bisch et al. |
| 5,997,552 | A | 12/1999 | Person et al. |
| 6,001,108 | A | 12/1999 | Wang et al. |
| 6,003,517 | A | 12/1999 | Sheffield et al. |
| 6,004,319 | A | 12/1999 | Goble et al. |
| 6,004,335 | A | 12/1999 | Vaitekunas et al. |
| 6,007,521 | A | 12/1999 | Bidwell et al. |
| 6,010,054 | A | 1/2000 | Johnson et al. |
| 6,010,513 | A | 1/2000 | Tormala et al. |
| 6,010,520 | A | 1/2000 | Pattison |
| 6,012,494 | A | 1/2000 | Balazs |
| 6,013,076 | A | 1/2000 | Goble et al. |
| 6,015,406 | A | 1/2000 | Goble et al. |
| 6,015,417 | A | 1/2000 | Reynolds, Jr. |
| 6,017,322 | A | 1/2000 | Snoke et al. |
| 6,017,354 | A | 1/2000 | Culp et al. |
| 6,017,356 | A | 1/2000 | Frederick et al. |
| 6,018,227 | A | 1/2000 | Kumar et al. |
| 6,019,745 | A | 2/2000 | Gray |
| 6,022,352 | A | 2/2000 | Vandewalle |
| 6,023,641 | A | 2/2000 | Thompson |
| 6,024,708 | A | 2/2000 | Bales et al. |
| 6,024,741 | A | 2/2000 | Williamson, IV et al. |
| 6,024,748 | A | 2/2000 | Manzo et al. |
| 6,024,750 | A | 2/2000 | Mastri et al. |
| 6,024,764 | A | 2/2000 | Schroeppel |
| 6,027,501 | A | 2/2000 | Goble et al. |
| 6,030,384 | A | 2/2000 | Nezhat |
| 6,032,849 | A | 3/2000 | Mastri et al. |
| 6,033,105 | A | 3/2000 | Barker et al. |
| 6,033,378 | A | 3/2000 | Lundquist et al. |
| 6,033,399 | A | 3/2000 | Gines |
| 6,033,427 | A | 3/2000 | Lee |
| 6,036,641 | A | 3/2000 | Taylor et al. |
| 6,036,667 | A | 3/2000 | Manna et al. |
| 6,037,724 | A | 3/2000 | Buss et al. |
| 6,037,927 | A | 3/2000 | Rosenberg |
| 6,039,733 | A | 3/2000 | Buysse et al. |
| 6,039,734 | A | 3/2000 | Goble |
| 6,042,601 | A | 3/2000 | Smith |
| 6,042,607 | A | 3/2000 | Williamson, IV et al. |
| 6,043,626 | A | 3/2000 | Snyder et al. |
| 6,045,560 | A | 4/2000 | McKean et al. |
| 6,047,861 | A | 4/2000 | Vidal et al. |
| 6,049,145 | A | 4/2000 | Austin et al. |
| 6,050,172 | A | 4/2000 | Corves et al. |
| 6,050,472 | A | 4/2000 | Shibata |
| 6,050,989 | A | 4/2000 | Fox et al. |
| 6,050,990 | A | 4/2000 | Tankovich et al. |
| 6,050,996 | A | 4/2000 | Schmaltz et al. |

(56) References Cited

U.S. PATENT DOCUMENTS 6,053,390 A 4/2000 Green et al.
6,053,899 A 4/2000 Slanda et al.
6,053,922 A 4/2000 Krause et al.
6,054,142 A 4/2000 Li et al.
6,055,062 A 4/2000 Dina et al.
RE36,720 E 5/2000 Green et al.
6,056,735 A 5/2000 Okada et al.
6,056,746 A 5/2000 Goble et al.
6,059,806 A 5/2000 Hoegerle
6,062,360 A 5/2000 Shields
6,063,020 A 5/2000 Jones et al.
6,063,025 A 5/2000 Bridges et al.
6,063,050 A 5/2000 Manna et al.
6,063,095 A 5/2000 Wang et al.
6,063,097 A 5/2000 Oi et al.
6,063,098 A 5/2000 Houser et al.
6,065,679 A 5/2000 Levie et al.
6,065,919 A 5/2000 Peck
6,066,132 A 5/2000 Chen et al.
6,066,151 A 5/2000 Miyawaki et al.
6,068,627 A 5/2000 Orszulak et al.
6,071,233 A 6/2000 Ishikawa et al.
6,074,386 A 6/2000 Goble et al.
6,074,401 A 6/2000 Gardiner et al.
6,077,280 A 6/2000 Fossum
6,077,286 A 6/2000 Cuschieri et al.
6,077,290 A 6/2000 Marini
6,079,606 A 6/2000 Milliman et al.
6,080,181 A 6/2000 Jensen et al.
6,082,577 A 7/2000 Coates et al.
6,083,191 A 7/2000 Rose
6,083,223 A 7/2000 Baker
6,083,234 A 7/2000 Nicholas et al.
6,083,242 A 7/2000 Cook
6,086,544 A 7/2000 Hibner et al.
6,086,600 A 7/2000 Kortenbach
6,090,106 A 7/2000 Goble et al.
6,093,186 A 7/2000 Goble
6,099,537 A 8/2000 Sugai et al.
6,099,551 A 8/2000 Gabbay
6,102,271 A 8/2000 Longo et al.
6,104,162 A 8/2000 Sainsbury et al.
6,104,304 A 8/2000 Clark et al.
6,106,511 A 8/2000 Jensen
6,109,500 A 8/2000 Alli et al.
6,110,187 A 8/2000 Donlon
6,113,618 A 9/2000 Nic
6,117,148 A 9/2000 Ravo et al.
6,117,158 A 9/2000 Measamer et al.
6,119,913 A 9/2000 Adams et al.
6,120,433 A 9/2000 Mizuno et al.
6,120,462 A 9/2000 Hibner et al.
6,123,241 A 9/2000 Walter et al.
6,123,701 A 9/2000 Nezhat
H1904 H 10/2000 Yates et al.
6,126,058 A 10/2000 Adams et al.
6,126,359 A 10/2000 Dittrich et al.
6,126,670 A 10/2000 Walker et al.
6,131,789 A 10/2000 Schulze et al.
6,131,790 A 10/2000 Piraka
6,132,368 A 10/2000 Cooper
6,134,962 A 10/2000 Sugitani
6,139,546 A 10/2000 Koenig et al.
6,142,149 A 11/2000 Steen
6,142,933 A 11/2000 Longo et al.
6,147,135 A 11/2000 Yuan et al.
6,149,660 A 11/2000 Laufer et al.
6,151,323 A 11/2000 O'Connell et al.
6,152,935 A 11/2000 Kammerer et al.
6,155,473 A 12/2000 Tompkins et al.
6,156,056 A 12/2000 Kearns et al.
6,157,169 A 12/2000 Lee
6,159,146 A 12/2000 El Gazayerli
6,159,200 A 12/2000 Verdura et al.
6,159,224 A 12/2000 Yoon
6,162,208 A 12/2000 Hipps
6,162,220 A 12/2000 Nezhat
6,162,537 A 12/2000 Martin et al.
6,165,175 A 12/2000 Wampler et al.
6,165,184 A 12/2000 Verdura et al.
6,165,188 A 12/2000 Saadat et al.
6,167,185 A 12/2000 Smiley et al.
6,168,605 B1 1/2001 Measamer et al.
6,171,305 B1 1/2001 Sherman
6,171,316 B1 1/2001 Kovac et al.
6,171,330 B1 1/2001 Benchetrit
6,173,074 B1 1/2001 Russo
6,174,308 B1 1/2001 Goble et al.
6,174,309 B1 1/2001 Wrublewski et al.
6,174,318 B1 1/2001 Bates et al.
6,175,290 B1 1/2001 Forsythe et al.
6,179,195 B1 1/2001 Adams et al.
6,179,776 B1 1/2001 Adams et al.
6,181,105 B1 1/2001 Cutolo et al.
6,182,673 B1 2/2001 Kindermann et al.
6,185,356 B1 2/2001 Parker et al.
6,186,142 B1 2/2001 Schmidt et al.
6,187,003 B1 2/2001 Buysse et al.
6,190,386 B1 2/2001 Rydell
6,193,129 B1 2/2001 Bittner et al.
6,197,042 B1 3/2001 Ginn et al.
6,200,330 B1 3/2001 Benderev et al.
6,202,914 B1 3/2001 Geiste et al.
6,206,894 B1 3/2001 Thompson et al.
6,206,897 B1 3/2001 Jamiolkowski et al.
6,206,903 B1 3/2001 Ramans
6,206,904 B1 3/2001 Ouchi
6,209,414 B1 4/2001 Uneme
6,210,403 B1 4/2001 Klicek
6,213,999 B1 4/2001 Platt, Jr. et al.
6,214,028 B1 4/2001 Yoon et al.
6,220,368 B1 4/2001 Ark et al.
6,221,007 B1 4/2001 Green
6,221,023 B1 4/2001 Matsuba et al.
6,223,100 B1 4/2001 Green
6,223,835 B1 5/2001 Habedank et al.
6,224,617 B1 5/2001 Saadat et al.
6,228,080 B1 5/2001 Gines
6,228,081 B1 5/2001 Goble
6,228,083 B1 5/2001 Lands et al.
6,228,084 B1 5/2001 Kirwan, Jr.
6,228,089 B1 5/2001 Wahrburg
6,228,098 B1 5/2001 Kayan et al.
6,231,565 B1 5/2001 Tovey et al.
6,234,178 B1 5/2001 Goble et al.
6,237,604 B1 5/2001 Burnside et al.
6,238,384 B1 5/2001 Peer
6,241,139 B1 6/2001 Milliman et al.
6,241,140 B1 6/2001 Adams et al.
6,241,723 B1 6/2001 Heim et al.
6,245,084 B1 6/2001 Mark et al.
6,248,116 B1 6/2001 Chevillon et al.
6,248,117 B1 6/2001 Blatter
6,249,076 B1 6/2001 Madden et al.
6,249,105 B1 6/2001 Andrews et al.
6,250,532 B1 6/2001 Green et al.
6,251,485 B1 6/2001 Harris et al.
D445,745 S 7/2001 Norman
6,254,534 B1 7/2001 Butler et al.
6,254,619 B1 7/2001 Garabet et al.
6,254,642 B1 7/2001 Taylor
6,258,107 B1 7/2001 Balazs et al.
6,261,286 B1 7/2001 Goble et al.
6,261,679 B1 7/2001 Chen et al.
6,264,086 B1 7/2001 McGuckin, Jr.
6,264,087 B1 7/2001 Whitman
6,264,617 B1 7/2001 Bales et al.
6,270,508 B1 8/2001 Klieman et al.
6,270,916 B1 8/2001 Sink et al.
6,273,252 B1 8/2001 Mitchell
6,273,876 B1 8/2001 Klima et al.
6,273,897 B1 8/2001 Dalessandro et al.
6,277,114 B1 8/2001 Bullivant et al.
6,280,407 B1 8/2001 Manna et al.

(56) References Cited

U.S. PATENT DOCUMENTS 6,283,981 B1 9/2001 Beaupre
6,293,927 B1 9/2001 McGuckin, Jr.
6,293,942 B1 9/2001 Goble et al.
6,296,640 B1 10/2001 Wampler et al.
6,302,311 B1 10/2001 Adams et al.
6,302,743 B1 10/2001 Chiu et al.
6,305,891 B1 10/2001 Burlingame
6,306,134 B1 10/2001 Goble et al.
6,306,149 B1 10/2001 Meade
6,306,424 B1 10/2001 Vyakarnam et al.
6,309,397 B1 10/2001 Julian et al.
6,309,400 B2 10/2001 Beaupre
6,309,403 B1 10/2001 Minor et al.
6,312,435 B1 11/2001 Wallace et al.
6,315,184 B1 11/2001 Whitman
6,319,510 B1 11/2001 Yates
6,320,123 B1 11/2001 Reimers
6,322,494 B1 11/2001 Bullivant et al.
6,324,339 B1 11/2001 Hudson et al.
6,325,799 B1 12/2001 Goble
6,325,805 B1 12/2001 Ogilvie et al.
6,325,810 B1 12/2001 Hamilton et al.
6,328,498 B1 12/2001 Mersch
6,330,965 B1 12/2001 Milliman et al.
6,331,181 B1 12/2001 Tierney et al.
6,331,761 B1 12/2001 Kumar et al.
6,333,029 B1 12/2001 Vyakarnam et al.
6,334,860 B1 1/2002 Dorn
6,334,861 B1 1/2002 Chandler et al.
6,336,926 B1 1/2002 Goble
6,338,737 B1 1/2002 Toledano
6,343,731 B1 2/2002 Adams et al.
6,346,077 B1 2/2002 Taylor et al.
6,348,061 B1 2/2002 Whitman
D454,951 S 3/2002 Bon
6,352,503 B1 3/2002 Matsui et al.
6,352,532 B1 3/2002 Kramer et al.
6,355,699 B1 3/2002 Vyakarnam et al.
6,356,072 B1 3/2002 Chass
6,358,224 B1 3/2002 Tims et al.
6,358,263 B2 3/2002 Mark et al.
6,358,459 B1 3/2002 Ziegler et al.
6,364,877 B1 4/2002 Goble et al.
6,364,888 B1 4/2002 Niemeyer et al.
6,366,441 B1 4/2002 Ozawa et al.
6,370,981 B2 4/2002 Watarai
6,371,114 B1 4/2002 Schmidt et al.
6,373,152 B1 4/2002 Wang et al.
6,377,011 B1 4/2002 Ben-Ur
6,383,201 B1 5/2002 Dong
6,387,092 B1 5/2002 Burnside et al.
6,387,113 B1 5/2002 Hawkins et al.
6,387,114 B2 5/2002 Adams
6,391,038 B2 5/2002 Vargas et al.
6,392,854 B1 5/2002 O'Gorman
6,394,998 B1 5/2002 Wallace et al.
6,398,779 B1 6/2002 Buysse et al.
6,398,781 B1 6/2002 Goble et al.
6,398,797 B2 6/2002 Bombard et al.
6,402,766 B2 6/2002 Bowman et al.
6,406,440 B1 6/2002 Stefanchik
6,406,472 B1 6/2002 Jensen
6,409,724 B1 6/2002 Penny et al.
H2037 H 7/2002 Yates et al.
6,412,639 B1 7/2002 Hickey
6,413,274 B1 7/2002 Pedros
6,415,542 B1 7/2002 Bates et al.
6,416,486 B1 7/2002 Wampler
6,416,509 B1 7/2002 Goble et al.
6,419,695 B1 7/2002 Gabbay
6,423,079 B1 7/2002 Blake, III
6,424,885 B1 7/2002 Niemeyer et al.
RE37,814 E 8/2002 Allgeyer
6,428,070 B1 8/2002 Takanashi et al.
6,428,487 B1 8/2002 Burdorff et al.
6,429,611 B1 8/2002 Li
6,430,298 B1 8/2002 Kettl et al.
6,432,065 B1 8/2002 Burdorff et al.
6,436,097 B1 8/2002 Nardella
6,436,107 B1 8/2002 Wang et al.
6,436,110 B2 8/2002 Bowman et al.
6,436,115 B1 8/2002 Beaupre
6,436,122 B1 8/2002 Frank et al.
6,439,439 B1 8/2002 Rickard et al.
6,439,446 B1 8/2002 Perry et al.
6,440,146 B2 8/2002 Nicholas et al.
6,441,577 B2 8/2002 Blumenkranz et al.
D462,758 S 9/2002 Epstein et al.
6,443,973 B1 9/2002 Whitman
6,445,530 B1 9/2002 Baker
6,447,518 B1 9/2002 Krause et al.
6,447,523 B1 9/2002 Middleman et al.
6,447,799 B1 9/2002 Ullman
6,447,864 B2 9/2002 Johnson et al.
6,450,391 B1 9/2002 Kayan et al.
6,450,989 B2 9/2002 Dubrul et al.
6,454,781 B1 9/2002 Witt et al.
6,457,625 B1 10/2002 Tormala et al.
6,458,077 B1 10/2002 Boebel et al.
6,458,147 B1 10/2002 Cruise et al.
6,460,627 B1 10/2002 Below et al.
6,468,275 B1 10/2002 Wampler et al.
6,468,286 B2 10/2002 Mastri et al.
6,471,106 B1 10/2002 Reining
6,471,659 B2 10/2002 Eggers et al.
6,478,210 B2 11/2002 Adams et al.
6,482,200 B2 11/2002 Shippert
6,482,217 B1 11/2002 Pintor et al.
6,485,490 B2 11/2002 Wampler et al.
6,485,503 B2 11/2002 Jacobs et al.
6,485,667 B1 11/2002 Tan
6,486,286 B1 11/2002 McGall et al.
6,488,196 B1 12/2002 Fenton, Jr.
6,488,197 B1 12/2002 Whitman
6,488,659 B1 12/2002 Rosenman
6,491,201 B1 12/2002 Whitman
6,491,690 B1 12/2002 Goble et al.
6,491,701 B2 12/2002 Tierney et al.
6,491,702 B2 12/2002 Heilbrun et al.
6,492,785 B1 12/2002 Kasten et al.
6,494,882 B1 12/2002 Lebouitz et al.
6,494,885 B1 12/2002 Dhindsa
6,494,888 B1 12/2002 Laufer et al.
6,494,896 B1 12/2002 D'Alessio et al.
6,498,480 B1 12/2002 Manara
6,500,176 B1 12/2002 Truckai et al.
6,500,194 B2 12/2002 Benderev et al.
6,503,139 B2 1/2003 Coral
6,503,257 B2 1/2003 Grant et al.
6,503,259 B2 1/2003 Huxel et al.
6,505,768 B2 1/2003 Whitman
6,506,197 B1 1/2003 Rollero et al.
6,510,854 B2 1/2003 Goble
6,511,468 B1 1/2003 Cragg et al.
6,512,360 B1 1/2003 Goto et al.
6,514,252 B2 2/2003 Nezhat et al.
6,516,073 B1 2/2003 Schulz et al.
6,517,528 B1 2/2003 Pantages et al.
6,517,535 B2 2/2003 Edwards
6,517,565 B1 2/2003 Whitman et al.
6,517,566 B1 2/2003 Hovland et al.
6,520,971 B1 2/2003 Perry et al.
6,520,972 B2 2/2003 Peters
6,522,101 B2 2/2003 Malackowski
6,524,180 B1 2/2003 Simms et al.
6,525,499 B2 2/2003 Naganuma
6,527,782 B2 3/2003 Hogg et al.
6,527,785 B2 3/2003 Sancoff et al.
6,530,942 B2 3/2003 Fogarty et al.
6,532,958 B1 3/2003 Buan et al.
6,533,157 B1 3/2003 Whitman
6,533,723 B1 3/2003 Lockery et al.
6,533,784 B2 3/2003 Truckai et al.
6,535,764 B2 3/2003 Imran et al.

(56) References Cited

U.S. PATENT DOCUMENTS

| | | | |
|---|---|---|---|
| 6,539,297 | B2 | 3/2003 | Weiberle et al. |
| D473,239 | S | 4/2003 | Cockerill |
| 6,539,816 | B2 | 4/2003 | Kogiso et al. |
| 6,543,456 | B1 | 4/2003 | Freeman |
| 6,545,384 | B1 | 4/2003 | Pelrine et al. |
| 6,547,786 | B1 | 4/2003 | Goble |
| 6,550,546 | B2 | 4/2003 | Thurler et al. |
| 6,551,333 | B2 | 4/2003 | Kuhns et al. |
| 6,554,861 | B2 | 4/2003 | Knox et al. |
| 6,555,770 | B2 | 4/2003 | Kawase |
| 6,558,378 | B2 | 5/2003 | Sherman et al. |
| 6,558,379 | B1 | 5/2003 | Batchelor et al. |
| 6,558,429 | B2 | 5/2003 | Taylor |
| 6,561,187 | B2 | 5/2003 | Schmidt et al. |
| 6,565,560 | B1 | 5/2003 | Goble et al. |
| 6,566,619 | B2 | 5/2003 | Gillman et al. |
| 6,569,085 | B2 | 5/2003 | Kortenbach et al. |
| 6,569,171 | B2 | 5/2003 | DeGuillebon et al. |
| 6,578,751 | B2 | 6/2003 | Hartwick |
| 6,582,364 | B2 | 6/2003 | Butler et al. |
| 6,582,427 | B1 | 6/2003 | Goble et al. |
| 6,582,441 | B1 | 6/2003 | He et al. |
| 6,583,533 | B2 | 6/2003 | Pelrine et al. |
| 6,585,144 | B2 | 7/2003 | Adams et al. |
| 6,585,664 | B2 | 7/2003 | Burdorff et al. |
| 6,586,898 | B2 | 7/2003 | King et al. |
| 6,587,750 | B2 | 7/2003 | Gerbi et al. |
| 6,588,277 | B2 | 7/2003 | Giordano et al. |
| 6,588,643 | B2 | 7/2003 | Bolduc et al. |
| 6,588,931 | B2 | 7/2003 | Betzner et al. |
| 6,589,118 | B1 | 7/2003 | Soma et al. |
| 6,589,164 | B1 | 7/2003 | Flaherty |
| 6,592,538 | B1 | 7/2003 | Hotchkiss et al. |
| 6,592,597 | B2 | 7/2003 | Grant et al. |
| 6,594,552 | B1 | 7/2003 | Nowlin et al. |
| 6,596,296 | B1 | 7/2003 | Nelson et al. |
| 6,596,304 | B1 | 7/2003 | Bayon et al. |
| 6,596,432 | B2 | 7/2003 | Kawakami et al. |
| 6,599,295 | B1 | 7/2003 | Tornier et al. |
| 6,599,323 | B2 | 7/2003 | Melican et al. |
| D478,665 | S | 8/2003 | Isaacs et al. |
| D478,986 | S | 8/2003 | Johnston et al. |
| 6,601,749 | B2 | 8/2003 | Sullivan et al. |
| 6,602,252 | B2 | 8/2003 | Mollenauer |
| 6,602,262 | B2 | 8/2003 | Griego et al. |
| 6,603,050 | B2 | 8/2003 | Heaton |
| 6,605,078 | B2 | 8/2003 | Adams |
| 6,605,669 | B2 | 8/2003 | Awokola et al. |
| 6,605,911 | B1 | 8/2003 | Klesing |
| 6,607,475 | B2 | 8/2003 | Doyle et al. |
| 6,611,793 | B1 | 8/2003 | Burnside et al. |
| 6,613,069 | B2 | 9/2003 | Boyd et al. |
| 6,616,686 | B2 | 9/2003 | Coleman et al. |
| 6,619,529 | B2 | 9/2003 | Green et al. |
| 6,620,111 | B2 | 9/2003 | Stephens et al. |
| 6,620,161 | B2 | 9/2003 | Schulze et al. |
| 6,620,166 | B1 | 9/2003 | Wenstrom, Jr. et al. |
| 6,625,517 | B1 | 9/2003 | Bogdanov et al. |
| 6,626,834 | B2 | 9/2003 | Dunne et al. |
| H2086 | H | 10/2003 | Amsler |
| 6,629,630 | B2 | 10/2003 | Adams |
| 6,629,974 | B2 | 10/2003 | Penny et al. |
| 6,629,988 | B2 | 10/2003 | Weadock |
| 6,635,838 | B1 | 10/2003 | Kornelson |
| 6,636,412 | B2 | 10/2003 | Smith |
| 6,638,108 | B2 | 10/2003 | Tachi |
| 6,638,285 | B2 | 10/2003 | Gabbay |
| 6,638,297 | B1 | 10/2003 | Huitema |
| RE38,335 | E | 11/2003 | Aust et al. |
| 6,641,528 | B2 | 11/2003 | Torii |
| 6,644,532 | B2 | 11/2003 | Green et al. |
| 6,645,201 | B1 | 11/2003 | Utley et al. |
| 6,646,307 | B1 | 11/2003 | Yu et al. |
| 6,648,816 | B2 | 11/2003 | Irion et al. |
| 6,648,901 | B2 | 11/2003 | Fleischman et al. |
| 6,652,595 | B1 | 11/2003 | Nicolo |
| D484,243 | S | 12/2003 | Ryan et al. |
| D484,595 | S | 12/2003 | Ryan et al. |
| D484,596 | S | 12/2003 | Ryan et al. |
| 6,656,177 | B2 | 12/2003 | Truckai et al. |
| 6,656,193 | B2 | 12/2003 | Grant et al. |
| 6,659,940 | B2 | 12/2003 | Adler |
| 6,660,008 | B1 | 12/2003 | Foerster et al. |
| 6,663,623 | B1 | 12/2003 | Oyama et al. |
| 6,663,641 | B1 | 12/2003 | Kovac et al. |
| 6,666,854 | B1 | 12/2003 | Lange |
| 6,666,875 | B1 | 12/2003 | Sakurai et al. |
| 6,667,825 | B2 | 12/2003 | Lu et al. |
| 6,669,073 | B2 | 12/2003 | Milliman et al. |
| 6,670,806 | B2 | 12/2003 | Wendt et al. |
| 6,671,185 | B2 | 12/2003 | Duval |
| D484,977 | S | 1/2004 | Ryan et al. |
| 6,676,660 | B2 | 1/2004 | Wampler et al. |
| 6,677,687 | B2 | 1/2004 | Ho et al. |
| 6,679,269 | B2 | 1/2004 | Swanson |
| 6,679,410 | B2 | 1/2004 | Wursch et al. |
| 6,681,978 | B2 | 1/2004 | Geiste et al. |
| 6,681,979 | B2 | 1/2004 | Whitman |
| 6,682,527 | B2 | 1/2004 | Strul |
| 6,682,528 | B2 | 1/2004 | Frazier et al. |
| 6,682,544 | B2 | 1/2004 | Mastri et al. |
| 6,685,698 | B2 | 2/2004 | Morley et al. |
| 6,685,727 | B2 | 2/2004 | Fisher et al. |
| 6,689,153 | B1 | 2/2004 | Skiba |
| 6,692,507 | B2 | 2/2004 | Pugsley et al. |
| 6,692,692 | B2 | 2/2004 | Stetzel |
| 6,695,198 | B2 | 2/2004 | Adams et al. |
| 6,695,199 | B2 | 2/2004 | Whitman |
| 6,695,774 | B2 | 2/2004 | Hale et al. |
| 6,695,849 | B2 | 2/2004 | Michelson |
| 6,696,814 | B2 | 2/2004 | Henderson et al. |
| 6,697,048 | B2 | 2/2004 | Rosenberg et al. |
| 6,698,643 | B2 | 3/2004 | Whitman |
| 6,699,177 | B1 | 3/2004 | Wang et al. |
| 6,699,214 | B2 | 3/2004 | Gellman |
| 6,699,235 | B2 | 3/2004 | Wallace et al. |
| 6,704,210 | B1 | 3/2004 | Myers |
| 6,705,503 | B1 | 3/2004 | Pedicini et al. |
| 6,709,445 | B2 | 3/2004 | Boebel et al. |
| 6,712,773 | B1 | 3/2004 | Viola |
| 6,716,223 | B2 | 4/2004 | Leopold et al. |
| 6,716,232 | B1 | 4/2004 | Vidal et al. |
| 6,716,233 | B1 | 4/2004 | Whitman |
| 6,720,734 | B2 | 4/2004 | Norris |
| 6,722,550 | B1 | 4/2004 | Ricordi et al. |
| 6,722,552 | B2 | 4/2004 | Fenton, Jr. |
| 6,723,087 | B2 | 4/2004 | O'Neill et al. |
| 6,723,091 | B2 | 4/2004 | Goble et al. |
| 6,723,109 | B2 | 4/2004 | Solingen |
| 6,726,697 | B2 | 4/2004 | Nicholas et al. |
| 6,726,706 | B2 | 4/2004 | Dominguez |
| 6,729,119 | B2 | 5/2004 | Schnipke et al. |
| 6,731,976 | B2 | 5/2004 | Penn et al. |
| 6,736,825 | B2 | 5/2004 | Blatter et al. |
| 6,736,854 | B2 | 5/2004 | Vadurro et al. |
| 6,740,030 | B2 | 5/2004 | Martone et al. |
| 6,743,230 | B2 | 6/2004 | Lutze et al. |
| 6,744,385 | B2 | 6/2004 | Kazuya et al. |
| 6,747,121 | B2 | 6/2004 | Gogolewski |
| 6,747,300 | B2 | 6/2004 | Nadd et al. |
| 6,749,560 | B1 | 6/2004 | Konstorum et al. |
| 6,749,600 | B1 | 6/2004 | Levy |
| 6,752,768 | B2 | 6/2004 | Burdorff et al. |
| 6,752,816 | B2 | 6/2004 | Culp et al. |
| 6,754,959 | B1 | 6/2004 | Guiette, III et al. |
| 6,755,195 | B1 | 6/2004 | Lemke et al. |
| 6,755,338 | B2 | 6/2004 | Hahnen et al. |
| 6,755,843 | B2 | 6/2004 | Chung et al. |
| 6,756,705 | B2 | 6/2004 | Pulford, Jr. |
| 6,758,846 | B2 | 7/2004 | Goble et al. |
| 6,761,685 | B2 | 7/2004 | Adams et al. |
| 6,762,339 | B1 | 7/2004 | Klun et al. |
| 6,764,445 | B2 | 7/2004 | Ramans et al. |
| 6,766,957 | B2 | 7/2004 | Matsuura et al. |

(56) References Cited

U.S. PATENT DOCUMENTS 6,767,352 B2 7/2004 Field et al.
6,767,356 B2 7/2004 Kanner et al.
6,769,590 B2 8/2004 Vresh et al.
6,769,594 B2 8/2004 Orban, III
6,770,027 B2 8/2004 Banik et al.
6,770,070 B1 8/2004 Balbierz
6,770,072 B1 8/2004 Truckai et al.
6,770,078 B2 8/2004 Bonutti
6,773,409 B2 8/2004 Truckai et al.
6,773,437 B2 8/2004 Ogilvie et al.
6,773,438 B1 8/2004 Knodel et al.
6,775,575 B2 8/2004 Bommannan et al.
6,777,838 B2 8/2004 Miekka et al.
6,780,151 B2 8/2004 Grabover et al.
6,780,180 B1 8/2004 Goble et al.
6,783,524 B2 8/2004 Anderson et al.
6,786,382 B1 9/2004 Hoffman
6,786,864 B2 9/2004 Matsuura et al.
6,786,896 B1 9/2004 Madhani et al.
6,788,018 B1 9/2004 Blumenkranz
6,790,173 B2 9/2004 Saadat et al.
6,793,652 B1 9/2004 Whitman et al.
6,793,661 B2 9/2004 Hamilton et al.
6,793,663 B2 9/2004 Kneifel et al.
6,793,669 B2 9/2004 Nakamura et al.
6,796,921 B1 9/2004 Buck et al.
6,799,669 B2 10/2004 Fukumura et al.
6,802,822 B1 10/2004 Dodge
6,802,843 B2 10/2004 Truckai et al.
6,802,844 B2 10/2004 Ferree
6,805,273 B2 10/2004 Bilotti et al.
6,806,808 B1 10/2004 Watters et al.
6,808,525 B2 10/2004 Latterell et al.
6,810,359 B2 10/2004 Sakaguchi
6,814,154 B2 11/2004 Chou
6,814,741 B2 11/2004 Bowman et al.
6,817,508 B1 11/2004 Racenet et al.
6,817,509 B2 11/2004 Geiste et al.
6,817,974 B2 11/2004 Cooper et al.
6,818,018 B1 11/2004 Sawhney
6,820,791 B2 11/2004 Adams
6,821,273 B2 11/2004 Mollenauer
6,821,282 B2 11/2004 Perry et al.
6,821,284 B2 11/2004 Sturtz et al.
6,827,246 B2 12/2004 Sullivan et al.
6,827,712 B2 12/2004 Tovey et al.
6,827,725 B2 12/2004 Batchelor et al.
6,828,902 B2 12/2004 Casden
6,830,174 B2 12/2004 Hillstead et al.
6,831,629 B2 12/2004 Nishino et al.
6,832,998 B2 12/2004 Goble
6,834,001 B2 12/2004 Myono
6,835,173 B2 12/2004 Couvillon, Jr.
6,835,199 B2 12/2004 McGuckin, Jr. et al.
6,835,336 B2 12/2004 Watt
6,836,611 B2 12/2004 Popovic et al.
6,837,846 B2 1/2005 Jaffe et al.
6,837,883 B2 1/2005 Moll et al.
6,838,493 B2 1/2005 Williams et al.
6,840,423 B2 1/2005 Adams et al.
6,840,938 B1 1/2005 Morley et al.
6,841,967 B2 1/2005 Kim et al.
6,843,403 B2 1/2005 Whitman
6,843,789 B2 1/2005 Goble
6,843,793 B2 1/2005 Brock et al.
6,846,307 B2 1/2005 Whitman et al.
6,846,308 B2 1/2005 Whitman et al.
6,846,309 B2 1/2005 Whitman et al.
6,847,190 B2 1/2005 Schaefer et al.
6,849,071 B2 2/2005 Whitman et al.
6,850,817 B1 2/2005 Green
6,852,122 B2 2/2005 Rush
6,852,330 B2 2/2005 Bowman et al.
6,853,879 B2 2/2005 Sunaoshi
6,858,005 B2 2/2005 Ohline et al.
6,859,882 B2 2/2005 Fung
RE38,708 E 3/2005 Bolanos et al.
D502,994 S 3/2005 Blake, III
6,861,142 B1 3/2005 Wilkie et al.
6,861,954 B2 3/2005 Levin
6,863,668 B2 3/2005 Gillespie et al.
6,863,694 B1 3/2005 Boyce et al.
6,863,924 B2 3/2005 Ranganathan et al.
6,866,178 B2 3/2005 Adams et al.
6,866,668 B2 3/2005 Giannetti et al.
6,866,671 B2 3/2005 Tierney et al.
6,867,248 B1 3/2005 Martin et al.
6,869,430 B2 3/2005 Balbierz et al.
6,869,435 B2 3/2005 Blake, III
6,872,214 B2 3/2005 Sonnenschein et al.
6,874,669 B2 4/2005 Adams et al.
6,877,647 B2 4/2005 Green et al.
6,878,106 B1 4/2005 Herrmann
6,884,392 B2 4/2005 Malkin et al.
6,884,428 B2 4/2005 Binette et al.
6,886,730 B2 5/2005 Fujisawa et al.
6,887,710 B2 5/2005 Call et al.
6,889,116 B2 5/2005 Jinno
6,893,435 B2 5/2005 Goble
6,894,140 B2 5/2005 Roby
6,895,176 B2 5/2005 Archer et al.
6,899,538 B2 5/2005 Matoba
6,899,593 B1 5/2005 Moeller et al.
6,899,915 B2 5/2005 Yelick et al.
6,905,057 B2 6/2005 Swayze et al.
6,905,497 B2 6/2005 Truckai et al.
6,905,498 B2 6/2005 Hooven
6,908,472 B2 6/2005 Wiener et al.
6,911,033 B2 6/2005 de Guillebon et al.
6,911,916 B1 6/2005 Wang et al.
6,913,579 B2 7/2005 Truckai et al.
6,913,608 B2 7/2005 Liddicoat et al.
6,913,613 B2 7/2005 Schwarz et al.
6,921,397 B2 7/2005 Corcoran et al.
6,921,412 B1 7/2005 Black et al.
6,923,093 B2 8/2005 Ullah
6,923,803 B2 8/2005 Goble
6,923,819 B2 8/2005 Meade et al.
6,925,849 B2 8/2005 Jairam
6,926,716 B2 8/2005 Baker et al.
6,928,902 B1 8/2005 Eyssallenne
6,929,641 B2 8/2005 Goble et al.
6,929,644 B2 8/2005 Truckai et al.
6,931,830 B2 8/2005 Liao
6,932,218 B2 8/2005 Kosann et al.
6,932,810 B2 8/2005 Ryan
6,936,042 B2 8/2005 Wallace et al.
6,936,948 B2 8/2005 Bell et al.
D509,297 S 9/2005 Wells
D509,589 S 9/2005 Wells
6,938,706 B2 9/2005 Ng
6,939,358 B2 9/2005 Palacios et al.
6,942,662 B2 9/2005 Goble et al.
6,942,674 B2 9/2005 Belef et al.
6,945,444 B2 9/2005 Gresham et al.
6,945,981 B2 9/2005 Donofrio et al.
6,951,562 B2 10/2005 Zwirnmann
6,953,138 B1 10/2005 Dworak et al.
6,953,139 B2 10/2005 Milliman et al.
6,953,461 B2 10/2005 McClurken et al.
6,957,758 B2 10/2005 Aranyi
6,958,035 B2 10/2005 Friedman et al.
6,959,851 B2 11/2005 Heinrich
6,959,852 B2 11/2005 Shelton, IV et al.
6,960,107 B1 11/2005 Schaub et al.
6,960,163 B2 11/2005 Ewers et al.
6,960,220 B2 11/2005 Marino et al.
6,962,587 B2 11/2005 Johnson et al.
6,963,792 B1 11/2005 Green
6,964,363 B2 11/2005 Wales et al.
6,966,907 B2 11/2005 Goble
6,966,909 B2 11/2005 Marshall et al.
6,968,908 B2 11/2005 Tokunaga et al.
6,969,385 B2 11/2005 Moreyra

(56) References Cited

U.S. PATENT DOCUMENTS 6,969,395 B2 11/2005 Eskuri
6,971,988 B2 12/2005 Orban, III
6,972,199 B2 12/2005 Lebouitz et al.
6,974,435 B2 12/2005 Daw et al.
6,974,462 B2 12/2005 Sater
6,978,921 B2 12/2005 Shelton, IV et al.
6,978,922 B2 12/2005 Bilotti et al.
6,981,628 B2 1/2006 Wales
6,981,941 B2 1/2006 Whitman et al.
6,981,978 B2 1/2006 Gannoe
6,984,203 B2 1/2006 Tartaglia et al.
6,984,231 B2 1/2006 Goble et al.
6,986,451 B1 1/2006 Mastri et al.
6,988,649 B2 1/2006 Shelton, IV et al.
6,988,650 B2 1/2006 Schwemberger et al.
6,989,034 B2 1/2006 Hammer et al.
6,990,731 B2 1/2006 Haytayan
6,990,796 B2 1/2006 Schnipke et al.
6,993,200 B2 1/2006 Tastl et al.
6,993,413 B2 1/2006 Sunaoshi
6,994,708 B2 2/2006 Manzo
6,995,729 B2 2/2006 Govari et al.
6,996,433 B2 2/2006 Burbank et al.
6,997,931 B2 2/2006 Sauer et al.
6,997,935 B2 2/2006 Anderson et al.
6,998,736 B2 2/2006 Lee et al.
6,998,816 B2 2/2006 Wieck et al.
7,000,818 B2 2/2006 Shelton, IV et al.
7,000,819 B2 2/2006 Swayze et al.
7,000,911 B2 2/2006 McCormick et al.
7,001,380 B2 2/2006 Goble
7,001,408 B2 2/2006 Knodel et al.
7,004,174 B2 2/2006 Eggers et al.
7,007,176 B2 2/2006 Goodfellow et al.
7,008,433 B2 3/2006 Voellmicke et al.
7,008,435 B2 3/2006 Cummins
7,009,039 B2 3/2006 Yayon et al.
7,011,657 B2 3/2006 Truckai et al.
7,014,640 B2 3/2006 Kemppainen et al.
7,018,357 B2 3/2006 Emmons
7,018,390 B2 3/2006 Turovskiy et al.
7,021,669 B1 4/2006 Lindermeir et al.
7,022,131 B1 4/2006 Derowe et al.
7,023,159 B2 4/2006 Gorti et al.
7,025,064 B2 4/2006 Wang et al.
7,025,732 B2 4/2006 Thompson et al.
7,025,743 B2 4/2006 Mann et al.
7,025,774 B2 4/2006 Freeman et al.
7,025,775 B2 4/2006 Gadberry et al.
7,028,570 B2 4/2006 Ohta et al.
7,029,435 B2 4/2006 Nakao
7,029,439 B2 4/2006 Roberts et al.
7,030,904 B2 4/2006 Adair et al.
7,032,798 B2 4/2006 Whitman et al.
7,032,799 B2 4/2006 Viola et al.
7,033,356 B2 4/2006 Latterell et al.
7,035,716 B2 4/2006 Harris et al.
7,035,762 B2 4/2006 Menard et al.
7,036,680 B1 5/2006 Flannery
7,037,314 B2 5/2006 Armstrong
7,037,344 B2 5/2006 Kagan et al.
7,041,088 B2 5/2006 Nawrocki et al.
7,041,102 B2 5/2006 Truckai et al.
7,041,868 B2 5/2006 Greene et al.
7,043,852 B2 5/2006 Hayashida et al.
7,044,350 B2 5/2006 Kameyama et al.
7,044,352 B2 5/2006 Shelton, IV et al.
7,044,353 B2 5/2006 Mastri et al.
7,046,082 B2 5/2006 Komiya et al.
7,048,165 B2 5/2006 Haramiishi
7,048,687 B1 5/2006 Reuss et al.
7,048,745 B2 5/2006 Tierney et al.
7,052,454 B2 5/2006 Taylor
7,052,494 B2 5/2006 Goble et al.
7,052,499 B2 5/2006 Steger et al.
7,055,730 B2 6/2006 Ehrenfels et al.
7,055,731 B2 6/2006 Shelton, IV et al.
7,056,284 B2 6/2006 Martone et al.
7,056,330 B2 6/2006 Gayton
7,059,331 B2 6/2006 Adams et al.
7,059,508 B2 6/2006 Shelton, IV et al.
7,063,671 B2 6/2006 Couvillon, Jr.
7,063,712 B2 6/2006 Vargas et al.
7,064,509 B1 6/2006 Fu et al.
7,066,879 B2 6/2006 Fowler et al.
7,066,944 B2 6/2006 Laufer et al.
7,067,038 B2 6/2006 Trokhan et al.
7,070,083 B2 7/2006 Jankowski
7,070,559 B2 7/2006 Adams et al.
7,070,597 B2 7/2006 Truckai et al.
7,071,287 B2 7/2006 Rhine et al.
7,075,770 B1 7/2006 Smith
7,077,856 B2 7/2006 Whitman
7,080,769 B2 7/2006 Vresh et al.
7,081,114 B2 7/2006 Rashidi
7,083,073 B2 8/2006 Yoshie et al.
7,083,075 B2 8/2006 Swayze et al.
7,083,571 B2 8/2006 Wang et al.
7,083,615 B2 8/2006 Peterson et al.
7,083,619 B2 8/2006 Truckai et al.
7,083,620 B2 8/2006 Jahns et al.
7,083,626 B2 8/2006 Hart et al.
7,086,267 B2 8/2006 Dworak et al.
7,087,049 B2 8/2006 Nowlin et al.
7,087,054 B2 8/2006 Truckai et al.
7,087,071 B2 8/2006 Nicholas et al.
7,090,637 B2 8/2006 Danitz et al.
7,090,673 B2 8/2006 Dycus et al.
7,090,683 B2 8/2006 Brock et al.
7,090,684 B2 8/2006 McGuckin, Jr. et al.
7,091,191 B2 8/2006 Laredo et al.
7,091,412 B2 8/2006 Wang et al.
7,093,492 B2 8/2006 Treiber et al.
7,094,202 B2 8/2006 Nobis et al.
7,094,247 B2 8/2006 Monassevitch et al.
7,094,916 B2 8/2006 DeLuca et al.
7,096,972 B2 8/2006 Orozco, Jr.
7,097,089 B2 8/2006 Marczyk
7,097,644 B2 8/2006 Long
7,097,650 B2 8/2006 Weller et al.
7,098,794 B2 8/2006 Lindsay et al.
7,100,949 B2 9/2006 Williams et al.
7,101,187 B1 9/2006 Deconinck et al.
7,101,371 B2 9/2006 Dycus et al.
7,101,394 B2 9/2006 Hamm et al.
7,104,741 B2 9/2006 Krohn
7,108,695 B2 9/2006 Witt et al.
7,108,701 B2 9/2006 Evens et al.
7,108,709 B2 9/2006 Cummins
7,111,768 B2 9/2006 Cummins et al.
7,111,769 B2 9/2006 Wales et al.
7,112,214 B2 9/2006 Peterson et al.
RE39,358 E 10/2006 Goble
7,114,642 B2 10/2006 Whitman
7,116,100 B1 10/2006 Mock et al.
7,118,020 B2 10/2006 Lee et al.
7,118,528 B1 10/2006 Piskun
7,118,563 B2 10/2006 Weckwerth et al.
7,118,582 B1 10/2006 Wang et al.
7,119,534 B2 10/2006 Butzmann
7,121,446 B2 10/2006 Arad et al.
7,121,773 B2 10/2006 Mikiya et al.
7,122,028 B2 10/2006 Looper et al.
7,125,403 B2 10/2006 Julian et al.
7,125,409 B2 10/2006 Truckai et al.
7,126,303 B2 10/2006 Farritor et al.
7,126,879 B2 10/2006 Snyder
7,128,253 B2 10/2006 Mastri et al.
7,128,254 B2 10/2006 Shelton, IV et al.
7,128,748 B2 10/2006 Mooradian et al.
7,131,445 B2 11/2006 Amoah
7,133,601 B2 11/2006 Phillips et al.
7,134,364 B2 11/2006 Kageler et al.
7,134,587 B2 11/2006 Schwemberger et al.

(56) References Cited

U.S. PATENT DOCUMENTS 7,135,027 B2 11/2006 Delmotte
7,137,980 B2 11/2006 Buysse et al.
7,137,981 B2 11/2006 Long
7,139,016 B2 11/2006 Squilla et al.
7,140,527 B2 11/2006 Ehrenfels et al.
7,140,528 B2 11/2006 Shelton, IV
7,141,055 B2 11/2006 Abrams et al.
7,143,923 B2 12/2006 Shelton, IV et al.
7,143,924 B2 12/2006 Scirica et al.
7,143,925 B2 12/2006 Shelton, IV et al.
7,143,926 B2 12/2006 Shelton, IV et al.
7,146,191 B2 12/2006 Kerner et al.
7,147,138 B2 12/2006 Shelton, IV
7,147,139 B2 12/2006 Schwemberger et al.
7,147,140 B2 12/2006 Wukusick et al.
7,147,637 B2 12/2006 Goble
7,147,648 B2 12/2006 Lin
7,147,650 B2 12/2006 Lee
7,150,748 B2 12/2006 Ebbutt et al.
7,153,300 B2 12/2006 Goble
7,153,314 B2 12/2006 Laufer et al.
7,155,316 B2 12/2006 Sutherland et al.
7,156,863 B2 1/2007 Sonnenschein et al.
7,159,750 B2 1/2007 Racenet et al.
7,160,296 B2 1/2007 Pearson et al.
7,160,299 B2 1/2007 Baily
7,161,036 B2 1/2007 Oikawa et al.
7,161,580 B2 1/2007 Bailey et al.
7,162,758 B2 1/2007 Skinner
7,163,563 B2 1/2007 Schwartz et al.
7,166,133 B2 1/2007 Evans et al.
7,168,604 B2 1/2007 Milliman et al.
7,170,910 B2 1/2007 Chen et al.
7,171,279 B2 1/2007 Buckingham et al.
7,172,104 B2 2/2007 Scirica et al.
7,172,593 B2 2/2007 Trieu et al.
7,172,615 B2 2/2007 Morriss et al.
7,174,202 B2 2/2007 Bladen et al.
7,174,636 B2 2/2007 Lowe
7,177,533 B2 2/2007 McFarlin et al.
7,179,223 B2 2/2007 Motoki et al.
7,179,267 B2 2/2007 Nolan et al.
7,182,239 B1 2/2007 Myers
7,182,763 B2 2/2007 Nardella
7,183,737 B2 2/2007 Kitagawa
7,187,960 B2 3/2007 Abreu
7,188,758 B2 3/2007 Viola et al.
7,189,207 B2 3/2007 Viola
7,190,147 B2 3/2007 Gileff et al.
7,193,199 B2 3/2007 Jang
7,195,627 B2 3/2007 Amoah et al.
7,196,911 B2 3/2007 Takano et al.
D541,418 S 4/2007 Schechter et al.
7,199,537 B2 4/2007 Okamura et al.
7,202,576 B1 4/2007 Dechene et al.
7,202,653 B2 4/2007 Pai
7,204,404 B2 4/2007 Nguyen et al.
7,204,835 B2 4/2007 Latterell et al.
7,206,626 B2 4/2007 Quaid, III
7,207,233 B2 4/2007 Wadge
7,207,471 B2 4/2007 Heinrich et al.
7,207,472 B2 4/2007 Wukusick et al.
7,207,556 B2 4/2007 Saitoh et al.
7,208,005 B2 4/2007 Frecker et al.
7,210,609 B2 5/2007 Leiboff et al.
7,211,081 B2 5/2007 Goble
7,211,084 B2 5/2007 Goble et al.
7,211,092 B2 5/2007 Hughett
7,211,979 B2 5/2007 Khatib et al.
7,213,736 B2 5/2007 Wales et al.
7,214,224 B2 5/2007 Goble
7,215,517 B2 5/2007 Takamatsu
7,217,285 B2 5/2007 Vargas et al.
7,220,260 B2 5/2007 Fleming et al.
7,220,272 B2 5/2007 Weadock
7,225,959 B2 6/2007 Patton et al.
7,225,963 B2 6/2007 Scirica
7,225,964 B2 6/2007 Mastri et al.
7,226,450 B2 6/2007 Athanasiou et al.
7,228,505 B2 6/2007 Shimazu et al.
7,229,408 B2 6/2007 Douglas et al.
7,234,624 B2 6/2007 Gresham et al.
7,235,072 B2 6/2007 Sartor et al.
7,235,089 B1 6/2007 McGuckin, Jr.
7,235,302 B2 6/2007 Jing et al.
7,237,708 B1 7/2007 Guy et al.
7,238,195 B2 7/2007 Viola
7,238,901 B2 7/2007 Kim et al.
7,239,657 B1 7/2007 Gunnarsson
7,241,288 B2 7/2007 Braun
7,241,289 B2 7/2007 Braun
7,246,734 B2 7/2007 Shelton, IV
7,247,161 B2 7/2007 Johnston et al.
7,249,267 B2 7/2007 Chapuis
7,252,641 B2 8/2007 Thompson et al.
7,252,660 B2 8/2007 Kunz
7,255,012 B2 8/2007 Hedtke
7,255,696 B2 8/2007 Goble et al.
7,256,695 B2 8/2007 Hamel et al.
7,258,262 B2 8/2007 Mastri et al.
7,258,546 B2 8/2007 Beier et al.
7,260,431 B2 8/2007 Libbus et al.
7,265,374 B2 9/2007 Lee et al.
7,267,677 B2 9/2007 Johnson et al.
7,267,679 B2 9/2007 McGuckin, Jr. et al.
7,272,002 B2 9/2007 Drapeau
7,273,483 B2 9/2007 Wiener et al.
D552,623 S 10/2007 Vong et al.
7,275,674 B2 10/2007 Racenet et al.
7,276,044 B2 10/2007 Ferry et al.
7,276,068 B2 10/2007 Johnson et al.
7,278,562 B2 10/2007 Mastri et al.
7,278,563 B1 10/2007 Green
7,278,949 B2 10/2007 Bader
7,278,994 B2 10/2007 Goble
7,282,048 B2 10/2007 Goble et al.
7,283,096 B2 10/2007 Geisheimer et al.
7,286,850 B2 10/2007 Frielink et al.
7,287,682 B1 10/2007 Ezzat et al.
7,289,139 B2 10/2007 Amling et al.
7,293,685 B2 11/2007 Ehrenfels et al.
7,295,893 B2 11/2007 Sunaoshi
7,295,907 B2 11/2007 Lu et al.
7,296,722 B2 11/2007 Ivanko
7,296,724 B2 11/2007 Green et al.
7,297,149 B2 11/2007 Vitali et al.
7,300,373 B2 11/2007 Jinno et al.
7,300,431 B2 11/2007 Dubrovsky
7,300,450 B2 11/2007 Vleugels et al.
7,303,106 B2 12/2007 Milliman et al.
7,303,107 B2 12/2007 Milliman et al.
7,303,108 B2 12/2007 Shelton, IV
7,303,502 B2 12/2007 Thompson
7,303,556 B2 12/2007 Metzger
7,306,597 B2 12/2007 Manzo
7,308,998 B2 12/2007 Mastri et al.
7,311,238 B2 12/2007 Liu
7,313,430 B2 12/2007 Urquhart et al.
7,314,473 B2 1/2008 Jinno et al.
7,322,859 B2 1/2008 Evans
7,322,975 B2 1/2008 Goble et al.
7,322,994 B2 1/2008 Nicholas et al.
7,324,572 B2 1/2008 Chang
7,326,203 B2 2/2008 Papineau et al.
7,326,213 B2 2/2008 Benderev et al.
7,328,828 B2 2/2008 Ortiz et al.
7,328,829 B2 2/2008 Arad et al.
7,330,004 B2 2/2008 DeJonge et al.
7,331,340 B2 2/2008 Barney
7,331,343 B2 2/2008 Schmidt et al.
7,331,403 B2 2/2008 Berry et al.
7,331,406 B2 2/2008 Wottreng, Jr. et al.
7,331,969 B1 2/2008 Inganas et al.
7,334,717 B2 2/2008 Rethy et al.

(56) References Cited

U.S. PATENT DOCUMENTS 7,334,718 B2 2/2008 McAlister et al.
7,335,199 B2 2/2008 Goble et al.
7,335,401 B2 2/2008 Finke et al.
7,336,045 B2 2/2008 Clermonts
7,336,048 B2 2/2008 Lohr
7,336,184 B2 2/2008 Smith et al.
7,337,774 B2 3/2008 Webb
7,338,505 B2 3/2008 Belson
7,338,513 B2 3/2008 Lee et al.
7,341,554 B2 3/2008 Sekine et al.
7,341,555 B2 3/2008 Ootawara et al.
7,341,591 B2 3/2008 Grinberg
7,343,920 B2 3/2008 Toby et al.
7,344,532 B2 3/2008 Goble et al.
7,344,533 B2 3/2008 Pearson et al.
7,346,344 B2 3/2008 Fontaine
7,346,406 B2 3/2008 Brotto et al.
7,348,763 B1 3/2008 Reinhart et al.
7,348,875 B2 3/2008 Hughes et al.
RE40,237 E 4/2008 Bilotti et al.
7,351,258 B2 4/2008 Ricotta et al.
7,354,447 B2 4/2008 Shelton, IV et al.
7,354,502 B2 4/2008 Polat et al.
7,357,287 B2 4/2008 Shelton, IV et al.
7,357,806 B2 4/2008 Rivera et al.
7,361,168 B2 4/2008 Makower et al.
7,361,195 B2 4/2008 Schwartz et al.
7,362,062 B2 4/2008 Schneider et al.
7,364,060 B2 4/2008 Milliman
7,364,061 B2 4/2008 Swayze et al.
7,367,485 B2 5/2008 Shelton, IV et al.
7,368,124 B2 5/2008 Chun et al.
7,371,210 B2 5/2008 Brock et al.
7,371,403 B2 5/2008 McCarthy et al.
7,375,493 B2 5/2008 Calhoon et al.
7,377,918 B2 5/2008 Amoah
7,377,928 B2 5/2008 Zubik et al.
7,378,817 B2 5/2008 Calhoon et al.
RE40,388 E 6/2008 Gines
7,380,695 B2 6/2008 Doll et al.
7,380,696 B2 6/2008 Shelton, IV et al.
7,384,403 B2 6/2008 Sherman
7,384,417 B2 6/2008 Cucin
7,386,365 B2 6/2008 Nixon
7,386,730 B2 6/2008 Uchikubo
7,388,217 B2 6/2008 Buschbeck et al.
7,388,484 B2 6/2008 Hsu
7,391,173 B2 6/2008 Schena
7,394,190 B2 7/2008 Huang
7,396,356 B2 7/2008 Mollenauer
7,397,364 B2 7/2008 Govari
7,398,707 B2 7/2008 Morley et al.
7,398,907 B2 7/2008 Racenet et al.
7,398,908 B2 7/2008 Holsten et al.
7,400,107 B2 7/2008 Schneider et al.
7,400,752 B2 7/2008 Zacharias
7,401,000 B2 7/2008 Nakamura
7,401,721 B2 7/2008 Holsten et al.
7,404,449 B2 7/2008 Bermingham et al.
7,404,508 B2 7/2008 Smith et al.
7,404,509 B2 7/2008 Ortiz et al.
7,404,822 B2 7/2008 Viart et al.
7,407,074 B2 8/2008 Ortiz et al.
7,407,075 B2 8/2008 Holsten et al.
7,407,076 B2 8/2008 Racenet et al.
7,407,077 B2 8/2008 Ortiz et al.
7,407,078 B2 8/2008 Shelton, IV et al.
7,408,310 B2 8/2008 Hong et al.
7,410,085 B2 8/2008 Wolf et al.
7,410,086 B2 8/2008 Ortiz et al.
7,410,483 B2 8/2008 Danitz et al.
7,413,563 B2 8/2008 Corcoran et al.
7,416,101 B2 8/2008 Shelton, IV et al.
7,418,078 B2 8/2008 Blanz et al.
RE40,514 E 9/2008 Mastri et al.
7,419,080 B2 9/2008 Smith et al.
7,419,081 B2 9/2008 Ehrenfels et al.
7,419,321 B2 9/2008 Tereschouk
7,419,495 B2 9/2008 Menn et al.
7,422,136 B1 9/2008 Marczyk
7,422,138 B2 9/2008 Bilotti et al.
7,422,139 B2 9/2008 Shelton, IV et al.
7,424,965 B2 9/2008 Racenet et al.
7,427,607 B2 9/2008 Suzuki
D578,644 S 10/2008 Shumer et al.
7,430,772 B2 10/2008 Van Es
7,431,188 B1 10/2008 Marczyk
7,431,189 B2 10/2008 Shelton, IV et al.
7,431,230 B2 10/2008 McPherson et al.
7,431,694 B2 10/2008 Stefanchik et al.
7,431,730 B2 10/2008 Viola
7,434,715 B2 10/2008 Shelton, IV et al.
7,434,717 B2 10/2008 Shelton, IV et al.
7,435,249 B2 10/2008 Buysse et al.
7,438,209 B1 10/2008 Hess et al.
7,438,718 B2 10/2008 Milliman et al.
7,439,354 B2 10/2008 Lenges et al.
7,441,684 B2 10/2008 Shelton, IV et al.
7,441,685 B1 10/2008 Boudreaux
7,442,201 B2 10/2008 Pugsley et al.
7,443,547 B2 10/2008 Moreno et al.
7,446,131 B1 11/2008 Liu et al.
7,448,525 B2 11/2008 Shelton, IV et al.
7,450,010 B1 11/2008 Gravelle et al.
7,451,904 B2 11/2008 Shelton, IV
7,455,208 B2 11/2008 Wales et al.
7,455,676 B2 11/2008 Holsten et al.
7,455,682 B2 11/2008 Viola
D582,934 S 12/2008 Byeon
7,461,767 B2 12/2008 Viola et al.
7,462,187 B2 12/2008 Johnston et al.
7,464,845 B2 12/2008 Chou
7,464,846 B2 12/2008 Shelton, IV et al.
7,464,847 B2 12/2008 Viola et al.
7,464,848 B2 12/2008 Green et al.
7,464,849 B2 12/2008 Shelton, IV et al.
7,467,740 B2 12/2008 Shelton, IV et al.
7,467,849 B2 12/2008 Silverbrook et al.
7,472,814 B2 1/2009 Mastri et al.
7,472,815 B2 1/2009 Shelton, IV et al.
7,472,816 B2 1/2009 Holsten et al.
7,473,221 B2 1/2009 Ewers et al.
7,473,253 B2 1/2009 Dycus et al.
7,473,263 B2 1/2009 Johnston et al.
7,476,237 B2 1/2009 Taniguchi et al.
7,479,608 B2 1/2009 Smith
7,481,347 B2 1/2009 Roy
7,481,348 B2 1/2009 Marczyk
7,481,349 B2 1/2009 Holsten et al.
7,481,824 B2 1/2009 Boudreaux et al.
7,485,124 B2 2/2009 Kuhns et al.
7,485,133 B2 2/2009 Cannon et al.
7,485,142 B2 2/2009 Milo
7,487,899 B2 2/2009 Shelton, IV et al.
7,489,055 B2 2/2009 Jeong et al.
7,490,749 B2 2/2009 Schall et al.
7,491,232 B2 2/2009 Bolduc et al.
7,494,039 B2 2/2009 Racenet et al.
7,494,460 B2 2/2009 Haarstad et al.
7,494,499 B2 2/2009 Nagase et al.
7,494,501 B2 2/2009 Ahlberg et al.
7,500,979 B2 3/2009 Hueil et al.
7,501,198 B2 3/2009 Barley et al.
7,503,474 B2 3/2009 Hillstead et al.
7,506,790 B2 3/2009 Shelton, IV
7,506,791 B2 3/2009 Omaits et al.
7,507,202 B2 3/2009 Schoellhorn
7,510,107 B2 3/2009 Timm et al.
7,510,534 B2 3/2009 Burdorff et al.
7,510,566 B2 3/2009 Jacobs et al.
7,513,407 B1 4/2009 Chang
7,513,408 B2 4/2009 Shelton, IV et al.
7,517,356 B2 4/2009 Heinrich
7,524,320 B2 4/2009 Tierney et al.

(56) References Cited

U.S. PATENT DOCUMENTS 7,527,632 B2 5/2009 Houghton et al.
7,530,984 B2 5/2009 Sonnenschein et al.
7,530,985 B2 5/2009 Takemoto et al.
7,533,906 B2 5/2009 Luettgen et al.
7,534,259 B2 5/2009 Lashinski et al.
7,540,867 B2 6/2009 Jinno et al.
7,540,872 B2 6/2009 Schechter et al.
7,542,807 B2 6/2009 Bertolero et al.
7,543,730 B1 6/2009 Marczyk
7,546,939 B2 6/2009 Adams et al.
7,546,940 B2 6/2009 Milliman et al.
7,547,287 B2 6/2009 Boecker et al.
7,547,312 B2 6/2009 Bauman et al.
7,549,563 B2 6/2009 Mather et al.
7,549,564 B2 6/2009 Boudreaux
7,549,998 B2 6/2009 Braun
7,552,854 B2 6/2009 Wixey et al.
7,553,173 B2 6/2009 Kowalick
7,553,275 B2 6/2009 Padget et al.
7,554,343 B2 6/2009 Bromfield
7,556,185 B2 7/2009 Viola
7,556,186 B2 7/2009 Milliman
7,556,647 B2 7/2009 Drews et al.
7,559,449 B2 7/2009 Viola
7,559,450 B2 7/2009 Wales et al.
7,559,452 B2 7/2009 Wales et al.
7,559,937 B2 7/2009 de la Torre et al.
7,561,637 B2 7/2009 Jonsson et al.
7,562,910 B2 7/2009 Kertesz et al.
7,563,269 B2 7/2009 Hashiguchi
7,563,862 B2 7/2009 Sieg et al.
7,565,993 B2 7/2009 Milliman et al.
7,566,300 B2 7/2009 Devierre et al.
7,567,045 B2 7/2009 Fristedt
7,568,603 B2 8/2009 Shelton, IV et al.
7,568,604 B2 8/2009 Ehrenfels et al.
7,568,619 B2 8/2009 Todd et al.
7,575,144 B2 8/2009 Ortiz et al.
7,578,825 B2 8/2009 Huebner
D600,712 S 9/2009 LaManna et al.
7,583,063 B2 9/2009 Dooley
7,584,880 B2 9/2009 Racenet et al.
7,586,289 B2 9/2009 Andruk et al.
7,588,174 B2 9/2009 Holsten et al.
7,588,175 B2 9/2009 Timm et al.
7,588,176 B2 9/2009 Timm et al.
7,588,177 B2 9/2009 Racenet
7,591,783 B2 9/2009 Boulais et al.
7,591,818 B2 9/2009 Bertolero et al.
7,593,766 B2 9/2009 Faber et al.
7,595,642 B2 9/2009 Doyle
7,597,229 B2 10/2009 Boudreaux et al.
7,597,230 B2 10/2009 Racenet et al.
7,597,693 B2 10/2009 Garrison
7,597,699 B2 10/2009 Rogers
7,598,972 B2 10/2009 Tomita
7,600,663 B2 10/2009 Green
7,604,118 B2 10/2009 Iio et al.
7,604,150 B2 10/2009 Boudreaux
7,604,151 B2 10/2009 Hess et al.
7,604,668 B2 10/2009 Farnsworth et al.
7,607,557 B2 10/2009 Shelton, IV et al.
7,608,091 B2 10/2009 Goldfarb et al.
D604,325 S 11/2009 Ebeling et al.
7,611,038 B2 11/2009 Racenet et al.
7,611,474 B2 11/2009 Hibner et al.
7,615,003 B2 11/2009 Stefanchik et al.
7,615,006 B2 11/2009 Abe
7,615,067 B2 11/2009 Lee et al.
7,617,961 B2 11/2009 Viola
D605,201 S 12/2009 Lorenz et al.
D607,010 S 12/2009 Kocmick
7,624,902 B2 12/2009 Marczyk et al.
7,624,903 B2 12/2009 Green et al.
7,625,370 B2 12/2009 Hart et al.
7,630,841 B2 12/2009 Comisky et al.
7,631,793 B2 12/2009 Rethy et al.
7,631,794 B2 12/2009 Rethy et al.
7,635,074 B2 12/2009 Olson et al.
7,635,922 B2 12/2009 Becker
7,637,409 B2 12/2009 Marczyk
7,637,410 B2 12/2009 Marczyk
7,638,958 B2 12/2009 Philipp et al.
7,641,091 B2 1/2010 Olson et al.
7,641,092 B2 1/2010 Kruszynski et al.
7,641,093 B2 1/2010 Doll et al.
7,641,095 B2 1/2010 Viola
7,641,671 B2 1/2010 Crainich
7,644,783 B2 1/2010 Roberts et al.
7,644,848 B2 1/2010 Swayze et al.
7,645,230 B2 1/2010 Mikkaichi et al.
7,648,055 B2 1/2010 Marczyk
7,648,457 B2 1/2010 Stefanchik et al.
7,648,519 B2 1/2010 Lee et al.
7,650,185 B2 1/2010 Maile et al.
7,651,017 B2 1/2010 Ortiz et al.
7,651,498 B2 1/2010 Shifrin et al.
7,654,431 B2 2/2010 Hueil et al.
7,655,004 B2 2/2010 Long
7,655,288 B2 2/2010 Bauman et al.
7,655,584 B2 2/2010 Biran et al.
7,656,131 B2 2/2010 Embrey et al.
7,658,311 B2 2/2010 Boudreaux
7,658,312 B2 2/2010 Vidal et al.
7,658,705 B2 2/2010 Melvin et al.
7,659,219 B2 2/2010 Biran et al.
7,661,448 B2 2/2010 Kim et al.
7,662,161 B2 2/2010 Briganti et al.
7,665,646 B2 2/2010 Prommersberger
7,665,647 B2 2/2010 Shelton, IV et al.
7,669,746 B2 3/2010 Shelton, IV
7,669,747 B2 3/2010 Weisenburgh, II et al.
7,670,334 B2 3/2010 Hueil et al.
7,673,780 B2 3/2010 Shelton, IV et al.
7,673,781 B2 3/2010 Swayze et al.
7,673,782 B2 3/2010 Hess et al.
7,673,783 B2 3/2010 Morgan et al.
7,674,253 B2 3/2010 Fisher et al.
7,674,255 B2 3/2010 Braun
7,674,263 B2 3/2010 Ryan
7,674,270 B2 3/2010 Layer
7,682,307 B2 3/2010 Danitz et al.
7,682,367 B2 3/2010 Shah et al.
7,682,686 B2 3/2010 Curro et al.
7,686,201 B2 3/2010 Csiky
7,686,804 B2 3/2010 Johnson et al.
7,686,826 B2 3/2010 Lee et al.
7,688,028 B2 3/2010 Phillips et al.
7,691,098 B2 4/2010 Wallace et al.
7,691,103 B2 4/2010 Fernandez et al.
7,691,106 B2 4/2010 Schenberger et al.
7,694,864 B2 4/2010 Okada et al.
7,694,865 B2 4/2010 Scirica
7,695,485 B2 4/2010 Whitman et al.
7,695,493 B2 4/2010 Saadat et al.
7,699,204 B2 4/2010 Viola
7,699,835 B2 4/2010 Lee et al.
7,699,844 B2 4/2010 Utley et al.
7,699,846 B2 4/2010 Ryan
7,699,856 B2 4/2010 Van Wyk et al.
7,699,859 B2 4/2010 Bombard et al.
7,699,860 B2 4/2010 Huitema et al.
7,699,868 B2 4/2010 Frank et al.
7,703,653 B2 4/2010 Shah et al.
7,705,559 B2 4/2010 Powell et al.
7,708,180 B2 5/2010 Murray et al.
7,708,181 B2 5/2010 Cole et al.
7,708,182 B2 5/2010 Viola
7,708,758 B2 5/2010 Lee et al.
7,712,182 B2 5/2010 Zeiler et al.
7,713,190 B2 5/2010 Brock et al.
7,713,542 B2 5/2010 Xu et al.
7,714,239 B2 5/2010 Smith
7,714,334 B2 5/2010 Lin

(56) References Cited

U.S. PATENT DOCUMENTS 7,717,312 B2 5/2010 Beetel
7,717,313 B2 5/2010 Criscuolo et al.
7,717,846 B2 5/2010 Zirps et al.
7,717,873 B2 5/2010 Swick
7,717,915 B2 5/2010 Miyazawa
7,717,926 B2 5/2010 Whitfield et al.
7,718,180 B2 5/2010 Karp
7,718,556 B2 5/2010 Matsuda et al.
7,721,930 B2 5/2010 McKenna et al.
7,721,931 B2 5/2010 Shelton, IV et al.
7,721,933 B2 5/2010 Ehrenfels et al.
7,721,934 B2 5/2010 Shelton, IV et al.
7,721,936 B2 5/2010 Shalton, IV et al.
7,722,527 B2 5/2010 Bouchier et al.
7,722,607 B2 5/2010 Dumbauld et al.
7,722,610 B2 5/2010 Viola et al.
7,725,214 B2 5/2010 Diolaiti
7,726,171 B2 6/2010 Langlotz et al.
7,726,537 B2 6/2010 Olson et al.
7,726,538 B2 6/2010 Holsten et al.
7,726,539 B2 6/2010 Holsten et al.
7,727,954 B2 6/2010 McKay
7,728,553 B2 6/2010 Carrier et al.
7,729,742 B2 6/2010 Govari
7,731,072 B2 6/2010 Timm et al.
7,731,073 B2 6/2010 Wixey et al.
7,731,724 B2 6/2010 Huitema et al.
7,735,703 B2 6/2010 Morgan et al.
7,736,254 B2 6/2010 Schena
7,736,306 B2 6/2010 Brustad et al.
7,736,374 B2 6/2010 Vaughan et al.
7,738,971 B2 6/2010 Swayze et al.
7,740,159 B2 6/2010 Shelton, IV et al.
7,742,036 B2 6/2010 Grant et al.
7,743,960 B2 6/2010 Whitman et al.
7,744,624 B2 6/2010 Bettuchi
7,744,627 B2 6/2010 Orban, III et al.
7,744,628 B2 6/2010 Viola
7,747,146 B2 6/2010 Milano et al.
7,748,587 B2 7/2010 Haramiishi et al.
7,748,632 B2 7/2010 Coleman et al.
7,749,204 B2 7/2010 Dhanaraj et al.
7,751,870 B2 7/2010 Whitman
7,753,245 B2 7/2010 Boudreaux et al.
7,753,246 B2 7/2010 Scirica
7,753,904 B2 7/2010 Shelton, IV et al.
7,757,924 B2 7/2010 Gerbi et al.
7,758,594 B2 7/2010 Lamson et al.
7,758,612 B2 7/2010 Shipp
7,762,462 B2 7/2010 Gelbman
7,762,998 B2 7/2010 Birk et al.
7,766,207 B2 8/2010 Mather et al.
7,766,209 B2 8/2010 Baxter, III et al.
7,766,210 B2 8/2010 Shelton, IV et al.
7,766,821 B2 8/2010 Brunnen et al.
7,766,894 B2 8/2010 Weitzner et al.
7,770,658 B2 8/2010 Ito et al.
7,770,773 B2 8/2010 Whitman et al.
7,770,774 B2 8/2010 Mastri et al.
7,770,775 B2 8/2010 Shelton, IV et al.
7,770,776 B2 8/2010 Chen et al.
7,771,396 B2 8/2010 Stefanchik et al.
7,772,720 B2 8/2010 McGee et al.
7,772,725 B2 8/2010 Siman-Tov
7,775,972 B2 8/2010 Brock et al.
7,776,037 B2 8/2010 Odom
7,776,060 B2 8/2010 Mooradian et al.
7,776,065 B2 8/2010 Griffiths et al.
7,778,004 B2 8/2010 Nerheim et al.
7,779,737 B2 8/2010 Newman, Jr. et al.
7,780,054 B2 8/2010 Wales
7,780,055 B2 8/2010 Scirica et al.
7,780,309 B2 8/2010 McMillan et al.
7,780,663 B2 8/2010 Yates et al.
7,780,685 B2 8/2010 Hunt et al.
7,784,662 B2 8/2010 Wales et al.
7,784,663 B2 8/2010 Shelton, IV
7,787,256 B2 8/2010 Chan et al.
7,789,283 B2 9/2010 Shah
7,789,875 B2 9/2010 Brock et al.
7,789,883 B2 9/2010 Takashino et al.
7,789,889 B2 9/2010 Zubik et al.
7,793,812 B2 9/2010 Moore et al.
7,794,475 B2 9/2010 Hess et al.
7,798,386 B2 9/2010 Schall et al.
7,799,039 B2 9/2010 Shelton, IV et al.
7,799,044 B2 9/2010 Johnston et al.
7,799,965 B2 9/2010 Patel et al.
7,803,151 B2 9/2010 Whitman
7,806,871 B2 10/2010 Li et al.
7,806,891 B2 10/2010 Nowlin et al.
7,810,690 B2 10/2010 Bilotti et al.
7,810,691 B2 10/2010 Boyden et al.
7,810,692 B2 10/2010 Hall et al.
7,810,693 B2 10/2010 Broehl et al.
7,811,275 B2 10/2010 Birk et al.
7,814,816 B2 10/2010 Alberti et al.
7,815,092 B2 10/2010 Whitman et al.
7,815,565 B2 10/2010 Stefanchik et al.
7,815,662 B2 10/2010 Spivey et al.
7,819,296 B2 10/2010 Hueil et al.
7,819,297 B2 10/2010 Doll et al.
7,819,298 B2 10/2010 Hall et al.
7,819,299 B2 10/2010 Shelton, IV et al.
7,819,799 B2 10/2010 Merril et al.
7,819,884 B2 10/2010 Lee et al.
7,819,885 B2 10/2010 Cooper
7,819,886 B2 10/2010 Whitfield et al.
7,823,592 B2 11/2010 Bettuchi et al.
7,823,760 B2 11/2010 Zemlok et al.
7,824,401 B2 11/2010 Manzo et al.
7,824,422 B2 11/2010 Benchetrit
7,824,426 B2 11/2010 Racenet et al.
7,828,189 B2 11/2010 Holsten et al.
7,828,794 B2 11/2010 Sartor
7,828,808 B2 11/2010 Hinman et al.
7,831,292 B2 11/2010 Quaid et al.
7,832,408 B2 11/2010 Shelton, IV et al.
7,832,611 B2 11/2010 Boyden et al.
7,832,612 B2 11/2010 Baxter, III et al.
7,833,234 B2 11/2010 Bailly et al.
7,835,823 B2 11/2010 Sillman et al.
7,836,400 B2 11/2010 May et al.
7,837,079 B2 11/2010 Holsten et al.
7,837,080 B2 11/2010 Schwemberger
7,837,081 B2 11/2010 Holsten et al.
7,837,425 B2 11/2010 Saeki et al.
7,837,685 B2 11/2010 Weinberg et al.
7,837,687 B2 11/2010 Harp
7,837,694 B2 11/2010 Tethrake et al.
7,838,789 B2 11/2010 Stoffers et al.
7,839,109 B2 11/2010 Carmen, Jr. et al.
7,841,503 B2 11/2010 Sonnenschein et al.
7,842,025 B2 11/2010 Coleman et al.
7,842,028 B2 11/2010 Lee
7,843,158 B2 11/2010 Prisco
7,845,533 B2 12/2010 Marczyk et al.
7,845,534 B2 12/2010 Viola et al.
7,845,535 B2 12/2010 Scircia
7,845,536 B2 12/2010 Viola et al.
7,845,537 B2 12/2010 Shelton, IV et al.
7,846,085 B2 12/2010 Silverman et al.
7,846,149 B2 12/2010 Jankowski
7,848,066 B2 12/2010 Yanagishima
7,850,623 B2 12/2010 Griffin et al.
7,850,642 B2 12/2010 Moll et al.
7,850,982 B2 12/2010 Stopek et al.
7,853,813 B2 12/2010 Lee
7,854,735 B2 12/2010 Houser et al.
7,854,736 B2 12/2010 Ryan
7,857,183 B2 12/2010 Shelton, IV
7,857,184 B2 12/2010 Viola
7,857,185 B2 12/2010 Swayze et al.
7,857,186 B2 12/2010 Baxter, III et al.

(56) References Cited

U.S. PATENT DOCUMENTS 7,857,813 B2 12/2010 Schmitz et al.
7,861,906 B2 1/2011 Doll et al.
7,862,502 B2 1/2011 Pool et al.
7,862,546 B2 1/2011 Conlon et al.
7,862,579 B2 1/2011 Ortiz et al.
7,866,525 B2 1/2011 Scirica
7,866,527 B2 1/2011 Hall et al.
7,866,528 B2 1/2011 Olson et al.
7,870,989 B2 1/2011 Viola et al.
7,871,418 B2 1/2011 Thompson et al.
7,871,440 B2 1/2011 Schwartz et al.
7,875,055 B2 1/2011 Cichocki, Jr.
7,879,063 B2 2/2011 Khosravi
7,879,070 B2 2/2011 Ortiz et al.
7,883,461 B2 2/2011 Albrecht et al.
7,883,465 B2 2/2011 Donofrio et al.
7,886,951 B2 2/2011 Hessler
7,886,952 B2 2/2011 Scirica et al.
7,887,530 B2 2/2011 Zemlok et al.
7,887,535 B2 2/2011 Lands et al.
7,887,536 B2 2/2011 Johnson et al.
7,887,563 B2 2/2011 Cummins
7,891,531 B1 2/2011 Ward
7,891,532 B2 2/2011 Mastri et al.
7,892,200 B2 2/2011 Birk et al.
7,892,245 B2 2/2011 Liddicoat et al.
7,893,586 B2 2/2011 West et al.
7,896,214 B2 3/2011 Farascioni
7,896,215 B2 3/2011 Adams et al.
7,896,869 B2 3/2011 DiSilvestro et al.
7,896,877 B2 3/2011 Hall et al.
7,896,895 B2 3/2011 Boudreaux et al.
7,896,897 B2 3/2011 Gresham et al.
7,898,198 B2 3/2011 Murphree
7,900,805 B2 3/2011 Shelton, IV et al.
7,900,806 B2 3/2011 Chen et al.
7,901,381 B2 3/2011 Birk et al.
7,905,380 B2 3/2011 Shelton, IV et al.
7,905,381 B2 3/2011 Baxter, III et al.
7,905,881 B2 3/2011 Masuda et al.
7,905,889 B2 3/2011 Catanese, III et al.
7,905,890 B2 3/2011 Whitfield et al.
7,905,902 B2 3/2011 Huitema et al.
7,909,039 B2 3/2011 Hur
7,909,191 B2 3/2011 Baker et al.
7,909,220 B2 3/2011 Viola
7,909,221 B2 3/2011 Viola et al.
7,909,224 B2 3/2011 Prommersberger
7,913,891 B2 3/2011 Doll et al.
7,913,893 B2 3/2011 Mastri et al.
7,914,521 B2 3/2011 Wang et al.
7,914,543 B2 3/2011 Roth et al.
7,914,551 B2 3/2011 Ortiz et al.
7,918,230 B2 4/2011 Whitman et al.
7,918,376 B1 4/2011 Knodel et al.
7,918,377 B2 4/2011 Measamer et al.
7,918,845 B2 4/2011 Saadat et al.
7,918,848 B2 4/2011 Lau et al.
7,918,861 B2 4/2011 Brock et al.
7,918,867 B2 4/2011 Dana et al.
7,922,061 B2 4/2011 Shelton, IV et al.
7,922,063 B2 4/2011 Zemlok et al.
7,922,743 B2 4/2011 Heinrich et al.
7,923,144 B2 4/2011 Kohn et al.
7,926,691 B2 4/2011 Viola et al.
7,927,328 B2 4/2011 Orszulak et al.
7,928,281 B2 4/2011 Augustine
7,930,040 B1 4/2011 Kelsch et al.
7,930,065 B2 4/2011 Larkin et al.
7,931,660 B2 4/2011 Aranyi et al.
7,931,695 B2 4/2011 Ringeisen
7,931,877 B2 4/2011 Steffens et al.
7,934,630 B2 5/2011 Shelton, IV et al.
7,934,631 B2 5/2011 Balbierz et al.
7,934,896 B2 5/2011 Schnier
7,935,130 B2 5/2011 Williams
7,935,773 B2 5/2011 Hadba et al.
7,936,142 B2 5/2011 Otsuka et al.
7,938,307 B2 5/2011 Bettuchi
7,941,865 B2 5/2011 Seman, Jr. et al.
7,942,303 B2 5/2011 Shah
7,942,890 B2 5/2011 D'Agostino et al.
7,944,175 B2 5/2011 Mori et al.
7,945,792 B2 5/2011 Cherpantier
7,945,798 B2 5/2011 Carlson et al.
7,946,453 B2 5/2011 Voegele et al.
7,947,011 B2 5/2011 Birk et al.
7,950,560 B2 5/2011 Zemlok et al.
7,950,561 B2 5/2011 Aranyi
7,951,071 B2 5/2011 Whitman et al.
7,951,166 B2 5/2011 Orban, III et al.
7,954,682 B2 6/2011 Giordano et al.
7,954,684 B2 6/2011 Boudreaux
7,954,685 B2 6/2011 Viola
7,954,686 B2 6/2011 Baxter, III et al.
7,954,687 B2 6/2011 Zemlok et al.
7,955,253 B2 6/2011 Ewers et al.
7,955,257 B2 6/2011 Frasier et al.
7,955,322 B2 6/2011 Devengenzo et al.
7,955,327 B2 6/2011 Sartor et al.
7,955,380 B2 6/2011 Chu et al.
7,959,050 B2 6/2011 Smith et al.
7,959,051 B2 6/2011 Smith et al.
7,959,052 B2 6/2011 Sonnenschein et al.
7,963,432 B2 6/2011 Knodel et al.
7,963,433 B2 6/2011 Whitman et al.
7,963,913 B2 6/2011 Devengenzo et al.
7,963,963 B2 6/2011 Francischelli et al.
7,963,964 B2 6/2011 Santilli et al.
7,964,206 B2 6/2011 Suokas et al.
7,966,236 B2 6/2011 Noriega et al.
7,966,269 B2 6/2011 Bauer et al.
7,966,799 B2 6/2011 Morgan et al.
7,967,178 B2 6/2011 Scirica et al.
7,967,179 B2 6/2011 Olson et al.
7,967,180 B2 6/2011 Scirica
7,967,181 B2 6/2011 Viola et al.
7,967,791 B2 6/2011 Franer et al.
7,967,839 B2 6/2011 Flock et al.
7,972,298 B2 7/2011 Wallace et al.
7,972,315 B2 7/2011 Birk et al.
7,976,213 B2 7/2011 Bertolotti et al.
7,976,563 B2 7/2011 Summerer
7,979,137 B2 7/2011 Tracey et al.
7,980,443 B2 7/2011 Scheib et al.
7,981,132 B2 7/2011 Dubrul et al.
7,987,405 B2 7/2011 Turner et al.
7,988,015 B2 8/2011 Mason, II et al.
7,988,026 B2 8/2011 Knodel et al.
7,988,027 B2 8/2011 Olson et al.
7,988,028 B2 8/2011 Farascioni et al.
7,988,779 B2 8/2011 Disalvo et al.
7,992,757 B2 8/2011 Wheeler et al.
7,993,360 B2 8/2011 Hacker et al.
7,994,670 B2 8/2011 Ji
7,997,054 B2 8/2011 Bertsch et al.
7,997,468 B2 8/2011 Farascioni
7,997,469 B2 8/2011 Olson et al.
8,002,696 B2 8/2011 Suzuki
8,002,784 B2 8/2011 Jinno et al.
8,002,785 B2 8/2011 Weiss et al.
8,002,795 B2 8/2011 Beetel
8,006,365 B2 8/2011 Levin et al.
8,006,885 B2 8/2011 Marczyk
8,006,889 B2 8/2011 Adams et al.
8,007,370 B2 8/2011 Hirsch et al.
8,007,465 B2 8/2011 Birk et al.
8,007,479 B2 8/2011 Birk et al.
8,007,511 B2 8/2011 Brock et al.
8,007,513 B2 8/2011 Nalagatla et al.
8,008,598 B2 8/2011 Whitman et al.
8,011,550 B2 9/2011 Aranyi et al.
8,011,551 B2 9/2011 Marczyk et al.
8,011,553 B2 9/2011 Mastri et al.

(56) References Cited

U.S. PATENT DOCUMENTS 8,011,555 B2 9/2011 Tarinelli et al.
8,012,170 B2 9/2011 Whitman et al.
8,016,176 B2 9/2011 Kasvikis et al.
8,016,177 B2 9/2011 Bettuchi et al.
8,016,178 B2 9/2011 Olson et al.
8,016,849 B2 9/2011 Wenchell
8,016,855 B2 9/2011 Whitman et al.
8,016,858 B2 9/2011 Whitman
8,016,881 B2 9/2011 Furst
8,020,742 B2 9/2011 Marczyk
8,020,743 B2 9/2011 Shelton, IV
8,021,375 B2 9/2011 Aldrich et al.
8,025,199 B2 9/2011 Whitman et al.
8,025,896 B2 9/2011 Malaviya et al.
8,028,882 B2 10/2011 Viola
8,028,883 B2 10/2011 Stopek
8,028,884 B2 10/2011 Sniffin et al.
8,028,885 B2 10/2011 Smith et al.
8,029,510 B2 10/2011 Hoegerle
8,031,069 B2 10/2011 Cohn et al.
8,033,438 B2 10/2011 Scirica
8,033,439 B2 10/2011 Racenet et al.
8,033,440 B2 10/2011 Wenchell et al.
8,034,077 B2 10/2011 Smith et al.
8,034,337 B2 10/2011 Simard
8,034,363 B2 10/2011 Li et al.
8,035,487 B2 10/2011 Malackowski
8,037,591 B2 10/2011 Spivey et al.
8,038,045 B2 10/2011 Bettuchi et al.
8,038,046 B2 10/2011 Smith et al.
8,038,686 B2 10/2011 Huitema et al.
8,043,207 B2 10/2011 Adams
8,043,328 B2 10/2011 Hahnen et al.
8,044,536 B2 10/2011 Nguyen et al.
8,044,604 B2 10/2011 Hagino et al.
8,047,236 B2 11/2011 Perry
8,048,503 B2 11/2011 Farnsworth et al.
8,052,636 B2 11/2011 Moll et al.
8,056,787 B2 11/2011 Boudreaux et al.
8,056,788 B2 11/2011 Mastri et al.
8,056,789 B1 11/2011 White et al.
8,057,508 B2 11/2011 Shelton, IV
8,058,771 B2 11/2011 Giordano et al.
8,060,250 B2 11/2011 Reiland et al.
8,061,014 B2 11/2011 Smith et al.
8,061,576 B2 11/2011 Cappola
8,062,236 B2 11/2011 Soltz
8,062,330 B2 11/2011 Prommersberger et al.
8,063,619 B2 11/2011 Zhu et al.
8,066,158 B2 11/2011 Vogel et al.
8,066,166 B2 11/2011 Demmy et al.
8,066,167 B2 11/2011 Measamer et al.
8,066,168 B2 11/2011 Vidal et al.
8,066,720 B2 11/2011 Knodel et al.
D650,074 S 12/2011 Hunt et al.
D650,789 S 12/2011 Arnold
8,070,033 B2 12/2011 Milliman et al.
8,070,034 B1 12/2011 Knodel
8,070,035 B2 12/2011 Holsten et al.
8,070,743 B2 12/2011 Kagan et al.
8,074,858 B2 12/2011 Marczyk
8,074,861 B2 12/2011 Ehrenfels et al.
8,075,476 B2 12/2011 Vargas
8,075,571 B2 12/2011 Vitali et al.
8,079,950 B2 12/2011 Stern et al.
8,079,989 B2 12/2011 Birk et al.
8,080,004 B2 12/2011 Downey et al.
8,083,118 B2 12/2011 Milliman et al.
8,083,119 B2 12/2011 Prommersberger
8,083,120 B2 12/2011 Shelton, IV et al.
8,084,001 B2 12/2011 Burns et al.
8,084,969 B2 12/2011 David et al.
8,085,013 B2 12/2011 Wei et al.
8,087,562 B1 1/2012 Manoux et al.
8,087,563 B2 1/2012 Milliman et al.
8,089,509 B2 1/2012 Chatenever et al.
8,091,753 B2 1/2012 Viola
8,091,756 B2 1/2012 Viola
8,092,443 B2 1/2012 Bischoff
8,092,932 B2 1/2012 Phillips et al.
8,093,572 B2 1/2012 Kuduvalli
8,096,458 B2 1/2012 Hessler
8,096,459 B2 1/2012 Ortiz et al.
8,097,017 B2 1/2012 Viola
8,100,310 B2 1/2012 Zemlok
8,100,824 B2 1/2012 Hegeman et al.
8,100,872 B2 1/2012 Patel
8,102,138 B2 1/2012 Sekine et al.
8,102,278 B2 1/2012 Deck et al.
8,105,350 B2 1/2012 Lee et al.
8,107,925 B2 1/2012 Natsuno et al.
8,108,033 B2 1/2012 Drew et al.
8,108,072 B2 1/2012 Zhao et al.
8,109,426 B2 2/2012 Milliman et al.
8,110,208 B1 2/2012 Hen
8,113,405 B2 2/2012 Milliman
8,113,407 B2 2/2012 Holsten et al.
8,113,408 B2 2/2012 Wenchell et al.
8,113,410 B2 2/2012 Hall et al.
8,114,017 B2 2/2012 Bacher
8,114,100 B2 2/2012 Smith et al.
8,118,206 B2 2/2012 Zand et al.
8,118,207 B2 2/2012 Racenet et al.
8,120,301 B2 2/2012 Goldberg et al.
8,122,128 B2 2/2012 Burke, II et al.
8,123,103 B2 2/2012 Milliman
8,123,523 B2 2/2012 Carron et al.
8,123,766 B2 2/2012 Bauman et al.
8,123,767 B2 2/2012 Bauman et al.
8,125,168 B2 2/2012 Johnson et al.
8,127,975 B2 3/2012 Olson et al.
8,127,976 B2 3/2012 Scirica et al.
8,128,624 B2 3/2012 Couture et al.
8,128,643 B2 3/2012 Aranyi et al.
8,128,645 B2 3/2012 Sonnenschein et al.
8,128,662 B2 3/2012 Altarac et al.
8,132,703 B2 3/2012 Milliman et al.
8,132,705 B2 3/2012 Viola et al.
8,132,706 B2 3/2012 Marczyk et al.
8,133,500 B2 3/2012 Ringeisen et al.
8,134,306 B2 3/2012 Drader et al.
8,136,711 B2 3/2012 Beardsley et al.
8,136,712 B2 3/2012 Zingman
8,136,713 B2 3/2012 Hathaway et al.
8,137,339 B2 3/2012 Jinno et al.
8,140,417 B2 3/2012 Shibata
8,141,762 B2 3/2012 Bedi et al.
8,141,763 B2 3/2012 Milliman
8,142,200 B2 3/2012 Crunkilton et al.
8,142,425 B2 3/2012 Eggers
8,142,461 B2 3/2012 Houser et al.
8,142,515 B2 3/2012 Therin et al.
8,143,520 B2 3/2012 Cutler
8,146,790 B2 4/2012 Milliman
8,147,421 B2 4/2012 Farquhar et al.
8,147,456 B2 4/2012 Fisher et al.
8,147,485 B2 4/2012 Wham et al.
8,152,041 B2 4/2012 Kostrzewski
8,152,756 B2 4/2012 Webster et al.
8,154,239 B2 4/2012 Katsuki et al.
8,157,145 B2 4/2012 Shelton, IV et al.
8,157,148 B2 4/2012 Scirica
8,157,151 B2 4/2012 Ingmanson et al.
8,157,152 B2 4/2012 Holsten et al.
8,157,153 B2 4/2012 Shelton, IV et al.
8,157,793 B2 4/2012 Omori et al.
8,161,977 B2 4/2012 Shelton, IV et al.
8,162,138 B2 4/2012 Bettenhausen et al.
8,162,197 B2 4/2012 Mastri et al.
8,162,668 B2 4/2012 Toly
8,162,933 B2 4/2012 Francischelli et al.
8,162,965 B2 4/2012 Reschke et al.
8,167,185 B2 5/2012 Shelton, IV et al.
8,167,622 B2 5/2012 Zhou

(56) References Cited

U.S. PATENT DOCUMENTS 8,167,895 B2 5/2012 D'Agostino et al.
8,167,898 B1 5/2012 Schaller et al.
8,170,241 B2 5/2012 Roe et al.
8,172,004 B2 5/2012 Ho
8,172,120 B2 5/2012 Boyden et al.
8,172,122 B2 5/2012 Kasvikis et al.
8,172,124 B2 5/2012 Shelton, IV et al.
8,177,776 B2 5/2012 Humayun et al.
8,177,797 B2 5/2012 Shimoji et al.
8,179,705 B2 5/2012 Chapuis
8,180,458 B2 5/2012 Kane et al.
8,181,839 B2 5/2012 Beetel
8,181,840 B2 5/2012 Milliman
8,182,422 B2 5/2012 Bayer et al.
8,182,444 B2 5/2012 Uber, III et al.
8,183,807 B2 5/2012 Tsai et al.
8,186,555 B2 5/2012 Shelton, IV et al.
8,186,556 B2 5/2012 Viola
8,186,558 B2 5/2012 Sapienza
8,186,560 B2 5/2012 Hess et al.
8,191,752 B2 6/2012 Scirica
8,192,350 B2 6/2012 Ortiz et al.
8,192,460 B2 6/2012 Orban, III et al.
8,192,651 B2 6/2012 Young et al.
8,193,129 B2 6/2012 Tagawa et al.
8,196,795 B2 6/2012 Moore et al.
8,196,796 B2 6/2012 Shelton, IV et al.
8,197,501 B2 6/2012 Shadeck et al.
8,197,502 B2 6/2012 Smith et al.
8,197,837 B2 6/2012 Jamiolkowski et al.
8,201,720 B2 6/2012 Hessler
8,201,721 B2 6/2012 Zemlok et al.
8,202,549 B2 6/2012 Stucky et al.
8,205,779 B2 6/2012 Ma et al.
8,205,780 B2 6/2012 Sorrentino et al.
8,205,781 B2 6/2012 Baxter, III et al.
8,210,411 B2 7/2012 Yates et al.
8,210,414 B2 7/2012 Bettuchi et al.
8,210,415 B2 7/2012 Ward
8,210,416 B2 7/2012 Milliman et al.
8,210,721 B2 7/2012 Chen et al.
8,211,125 B2 7/2012 Spivey
8,214,019 B2 7/2012 Govari et al.
8,215,531 B2 7/2012 Shelton, IV et al.
8,215,532 B2 7/2012 Marczyk
8,215,533 B2 7/2012 Viola et al.
8,220,468 B2 7/2012 Cooper et al.
8,220,688 B2 7/2012 Laurent et al.
8,220,690 B2 7/2012 Hess et al.
8,221,402 B2 7/2012 Francischelli et al.
8,221,424 B2 7/2012 Cha
8,221,433 B2 7/2012 Lozier et al.
8,225,799 B2 7/2012 Bettuchi
8,225,979 B2 7/2012 Farascioni et al.
8,226,553 B2 7/2012 Shelton, IV et al.
8,226,635 B2 7/2012 Petrie et al.
8,226,675 B2 7/2012 Houser et al.
8,226,715 B2 7/2012 Hwang et al.
8,227,946 B2 7/2012 Kim
8,228,020 B2 7/2012 Shin et al.
8,228,048 B2 7/2012 Spencer
8,229,549 B2 7/2012 Whitman et al.
8,231,040 B2 7/2012 Zemlok et al.
8,231,042 B2 7/2012 Hessler et al.
8,231,043 B2 7/2012 Tarinelli et al.
8,235,272 B2 8/2012 Nicholas et al.
8,236,010 B2 8/2012 Ortiz et al.
8,236,011 B2 8/2012 Harris et al.
8,236,020 B2 8/2012 Smith et al.
8,237,388 B2 8/2012 Jinno et al.
8,240,537 B2 8/2012 Marczyk
8,241,271 B2 8/2012 Millman et al.
8,241,284 B2 8/2012 Dycus et al.
8,241,308 B2 8/2012 Kortenbach et al.
8,241,322 B2 8/2012 Whitman et al.
8,245,594 B2 8/2012 Rogers et al.
8,245,898 B2 8/2012 Smith et al.
8,245,899 B2 8/2012 Swensgard et al.
8,245,900 B2 8/2012 Scirica
8,245,901 B2 8/2012 Stopek
8,246,608 B2 8/2012 Omori et al.
8,246,637 B2 8/2012 Viola et al.
8,252,009 B2 8/2012 Weller et al.
8,256,654 B2 9/2012 Bettuchi et al.
8,256,655 B2 9/2012 Sniffin et al.
8,256,656 B2 9/2012 Milliman et al.
8,257,251 B2 9/2012 Shelton, IV et al.
8,257,356 B2 9/2012 Bleich et al.
8,257,386 B2 9/2012 Lee et al.
8,257,391 B2 9/2012 Orban, III et al.
8,257,634 B2 9/2012 Scirica
8,258,745 B2 9/2012 Smith et al.
8,261,958 B1 9/2012 Knodel
8,262,560 B2 9/2012 Whitman
8,262,655 B2 9/2012 Ghabrial et al.
8,267,300 B2 9/2012 Boudreaux
8,267,924 B2 9/2012 Zemlok et al.
8,267,946 B2 9/2012 Whitfield et al.
8,267,951 B2 9/2012 Whayne et al.
8,269,121 B2 9/2012 Smith
8,272,553 B2 9/2012 Mastri et al.
8,272,554 B2 9/2012 Whitman et al.
8,272,918 B2 9/2012 Lam
8,273,404 B2 9/2012 Dave et al.
8,276,801 B2 10/2012 Zemlok et al.
8,276,802 B2 10/2012 Kostrzewski
8,277,473 B2 10/2012 Sunaoshi et al.
8,281,446 B2 10/2012 Moskovich
8,281,973 B2 10/2012 Wenchell et al.
8,281,974 B2 10/2012 Hessler et al.
8,282,654 B2 10/2012 Ferrari et al.
8,285,367 B2 10/2012 Hyde et al.
8,286,723 B2 10/2012 Puzio et al.
8,286,845 B2 10/2012 Perry et al.
8,286,846 B2 10/2012 Smith et al.
8,286,847 B2 10/2012 Taylor
8,287,487 B2 10/2012 Estes
8,287,522 B2 10/2012 Moses et al.
8,287,561 B2 10/2012 Nunez et al.
8,288,984 B2 10/2012 Yang
8,289,403 B2 10/2012 Dobashi et al.
8,292,147 B2 10/2012 Viola
8,292,148 B2 10/2012 Viola
8,292,150 B2 10/2012 Bryant
8,292,151 B2 10/2012 Viola
8,292,152 B2 10/2012 Milliman et al.
8,292,155 B2 10/2012 Shelton, IV et al.
8,292,157 B2 10/2012 Smith et al.
8,292,158 B2 10/2012 Sapienza
8,292,801 B2 10/2012 Dejima et al.
8,292,888 B2 10/2012 Whitman
8,294,399 B2 10/2012 Suzuki et al.
8,298,161 B2 10/2012 Vargas
8,298,189 B2 10/2012 Fisher et al.
8,298,233 B2 10/2012 Mueller
8,298,677 B2 10/2012 Wiesner et al.
8,302,323 B2 11/2012 Fortier et al.
8,308,040 B2 11/2012 Huang et al.
8,308,041 B2 11/2012 Kostrzewski
8,308,042 B2 11/2012 Aranyi
8,308,043 B2 11/2012 Bindra et al.
8,308,046 B2 11/2012 Prommersberger
8,308,659 B2 11/2012 Scheibe et al.
8,308,725 B2 11/2012 Bell et al.
8,310,188 B2 11/2012 Nakai
8,313,496 B2 11/2012 Sauer et al.
8,313,499 B2 11/2012 Magnusson et al.
8,313,509 B2 11/2012 Kostrzewski
8,317,070 B2 11/2012 Hueil et al.
8,317,071 B1 11/2012 Knodel
8,317,074 B2 11/2012 Ortiz et al.
8,317,437 B2 11/2012 Merkley et al.
8,317,744 B2 11/2012 Kirschenman
8,317,790 B2 11/2012 Bell et al.

(56) References Cited

U.S. PATENT DOCUMENTS 8,319,002 B2 11/2012 Daniels et al.
8,322,455 B2 12/2012 Shelton, IV et al.
8,322,589 B2 12/2012 Boudreaux
8,322,590 B2 12/2012 Patel et al.
8,322,901 B2 12/2012 Michelotti
8,323,789 B2 12/2012 Rozhin et al.
8,328,061 B2 12/2012 Kasvikis
8,328,062 B2 12/2012 Viola
8,328,063 B2 12/2012 Milliman et al.
8,328,064 B2 12/2012 Racenet et al.
8,328,802 B2 12/2012 Deville et al.
8,328,823 B2 12/2012 Aranyi et al.
8,333,313 B2 12/2012 Boudreaux et al.
8,333,691 B2 12/2012 Schaaf
8,333,764 B2 12/2012 Francischelli et al.
8,333,779 B2 12/2012 Smith et al.
8,334,468 B2 12/2012 Palmer et al.
8,336,753 B2 12/2012 Olson et al.
8,336,754 B2 12/2012 Cappola et al.
8,342,377 B2 1/2013 Milliman et al.
8,342,378 B2 1/2013 Marczyk et al.
8,342,379 B2 1/2013 Whitman et al.
8,343,150 B2 1/2013 Artale
8,347,978 B2 1/2013 Forster et al.
8,348,118 B2 1/2013 Segura
8,348,123 B2 1/2013 Scirica et al.
8,348,124 B2 1/2013 Scirica
8,348,125 B2 1/2013 Viola et al.
8,348,126 B2 1/2013 Olson et al.
8,348,127 B2 1/2013 Marczyk
8,348,129 B2 1/2013 Bedi et al.
8,348,130 B2 1/2013 Shah et al.
8,348,131 B2 1/2013 Omaits et al.
8,348,837 B2 1/2013 Wenchell
8,348,959 B2 1/2013 Wolford et al.
8,348,972 B2 1/2013 Soltz et al.
8,349,987 B2 1/2013 Kapiamba et al.
8,352,004 B2 1/2013 Mannheimer et al.
8,353,437 B2 1/2013 Boudreaux
8,353,438 B2 1/2013 Baxter, III et al.
8,353,439 B2 1/2013 Baxter, III et al.
8,356,740 B1 1/2013 Knodel
8,357,144 B2 1/2013 Whitman et al.
8,357,158 B2 1/2013 McKenna et al.
8,357,161 B2 1/2013 Mueller
8,359,174 B2 1/2013 Nakashima et al.
8,360,296 B2 1/2013 Zingman
8,360,297 B2 1/2013 Shelton, IV et al.
8,360,298 B2 1/2013 Farascioni et al.
8,360,299 B2 1/2013 Zemlok et al.
8,361,501 B2 1/2013 DiTizio et al.
D676,866 S 2/2013 Chaudhri
8,365,972 B2 2/2013 Aranyi et al.
8,365,973 B1 2/2013 White et al.
8,365,975 B1 2/2013 Manoux et al.
8,365,976 B2 2/2013 Hess et al.
8,366,559 B2 2/2013 Papenfuss et al.
8,366,719 B2 2/2013 Markey et al.
8,366,787 B2 2/2013 Brown et al.
8,369,056 B2 2/2013 Senriuchi et al.
8,371,393 B2 2/2013 Higuchi et al.
8,371,491 B2 2/2013 Huitema et al.
8,371,492 B2 2/2013 Aranyi et al.
8,371,493 B2 2/2013 Aranyi et al.
8,371,494 B2 2/2013 Racenet et al.
8,372,094 B2 2/2013 Bettuchi et al.
8,376,865 B2 2/2013 Forster et al.
8,377,029 B2 2/2013 Nagao et al.
8,377,044 B2 2/2013 Coe et al.
8,382,773 B2 2/2013 Whitfield et al.
8,382,790 B2 2/2013 Uenohara et al.
D677,273 S 3/2013 Randall et al.
8,387,848 B2 3/2013 Johnson et al.
8,388,633 B2 3/2013 Rousseau et al.
8,389,588 B2 3/2013 Ringeisen et al.
8,393,513 B2 3/2013 Jankowski
8,393,514 B2 3/2013 Shelton, IV et al.
8,393,516 B2 3/2013 Kostrzewski
8,397,832 B2 3/2013 Blickle et al.
8,397,971 B2 3/2013 Yates et al.
8,397,973 B1 3/2013 Hausen
8,398,633 B2 3/2013 Mueller
8,398,669 B2 3/2013 Kim
8,398,673 B2 3/2013 Hinchliffe et al.
8,398,674 B2 3/2013 Prestel
8,400,851 B2 3/2013 Byun
8,403,138 B2 3/2013 Weisshaupt et al.
8,403,195 B2 3/2013 Beardsley et al.
8,403,196 B2 3/2013 Beardsley et al.
8,403,198 B2 3/2013 Sorrentino et al.
8,403,832 B2 3/2013 Cunningham et al.
8,403,945 B2 3/2013 Whitfield et al.
8,403,946 B2 3/2013 Whitfield et al.
8,403,950 B2 3/2013 Palmer et al.
8,408,439 B2 4/2013 Huang et al.
8,408,442 B2 4/2013 Racenet et al.
8,409,079 B2 4/2013 Okamoto et al.
8,409,174 B2 4/2013 Omori
8,409,175 B2 4/2013 Lee et al.
8,409,222 B2 4/2013 Whitfield et al.
8,409,223 B2 4/2013 Sorrentino et al.
8,411,500 B2 4/2013 Gapihan et al.
8,413,661 B2 4/2013 Rousseau et al.
8,413,870 B2 4/2013 Pastorelli et al.
8,413,871 B2 4/2013 Racenet et al.
8,413,872 B2 4/2013 Patel
8,414,577 B2 4/2013 Boudreaux et al.
8,414,598 B2 4/2013 Brock et al.
8,418,073 B2 4/2013 Mohr et al.
8,418,906 B2 4/2013 Farascioni et al.
8,418,907 B2 4/2013 Johnson et al.
8,418,908 B1 4/2013 Beardsley
8,418,909 B2 4/2013 Kostrzewski
8,419,635 B2 4/2013 Shelton, IV et al.
8,419,717 B2 4/2013 Diolaiti et al.
8,419,747 B2 4/2013 Hinman et al.
8,419,754 B2 4/2013 Laby et al.
8,423,182 B2 4/2013 Robinson et al.
8,424,737 B2 4/2013 Scirica
8,424,739 B2 4/2013 Racenet et al.
8,424,740 B2 4/2013 Shelton, IV et al.
8,424,741 B2 4/2013 McGuckin, Jr. et al.
8,425,600 B2 4/2013 Maxwell
8,427,430 B2 4/2013 Lee et al.
8,430,292 B2 4/2013 Patel et al.
8,430,892 B2 4/2013 Bindra et al.
8,430,898 B2 4/2013 Wiener et al.
8,435,257 B2 5/2013 Smith et al.
8,439,246 B1 5/2013 Knodel
8,444,036 B2 5/2013 Shelton, IV
8,444,037 B2 5/2013 Nicholas et al.
8,444,549 B2 5/2013 Viola et al.
8,449,536 B2 5/2013 Selig
8,449,560 B2 5/2013 Roth et al.
8,453,904 B2 6/2013 Eskaros et al.
8,453,906 B2 6/2013 Huang et al.
8,453,907 B2 6/2013 Laurent et al.
8,453,908 B2 6/2013 Bedi et al.
8,453,912 B2 6/2013 Mastri et al.
8,453,914 B2 6/2013 Laurent et al.
8,454,495 B2 6/2013 Kawano et al.
8,454,551 B2 6/2013 Allen et al.
8,454,628 B2 6/2013 Smith et al.
8,454,640 B2 6/2013 Johnston et al.
8,457,757 B2 6/2013 Cauller et al.
8,459,520 B2 6/2013 Giordano et al.
8,459,521 B2 6/2013 Zemlok et al.
8,459,524 B2 6/2013 Pribanic et al.
8,459,525 B2 6/2013 Yates et al.
8,464,922 B2 6/2013 Marczyk
8,464,923 B2 6/2013 Shelton, IV
8,464,924 B2 6/2013 Gresham et al.
8,464,925 B2 6/2013 Hull et al.
8,465,475 B2 6/2013 Isbell, Jr.

(56) References Cited

U.S. PATENT DOCUMENTS 8,465,502 B2 6/2013 Zergiebel
8,465,515 B2 6/2013 Drew et al.
8,469,254 B2 6/2013 Czernik et al.
8,469,946 B2 6/2013 Sugita
8,469,973 B2 6/2013 Meade et al.
8,470,355 B2 6/2013 Skalla et al.
D686,240 S 7/2013 Lin
8,474,677 B2 7/2013 Woodard, Jr. et al.
8,475,453 B2 7/2013 Marczyk et al.
8,475,454 B1 7/2013 Alshemari
8,475,474 B2 7/2013 Bombard et al.
8,479,968 B2 7/2013 Hodgkinson et al.
8,479,969 B2 7/2013 Shelton, IV
8,480,703 B2 7/2013 Nicholas et al.
8,483,509 B2 7/2013 Matsuzaka
8,485,412 B2 7/2013 Shelton, IV et al.
8,485,413 B2 7/2013 Scheib et al.
8,485,970 B2 7/2013 Widenhouse et al.
8,487,199 B2 7/2013 Palmer et al.
8,487,487 B2 7/2013 Dietz et al.
8,490,851 B2 7/2013 Blier et al.
8,490,853 B2 7/2013 Criscuolo et al.
8,491,581 B2 7/2013 Deville et al.
8,491,603 B2 7/2013 Yeung et al.
8,496,153 B2 7/2013 Demmy et al.
8,496,154 B2 7/2013 Marczyk et al.
8,496,156 B2 7/2013 Sniffin et al.
8,496,683 B2 7/2013 Prommersberger et al.
8,498,691 B2 7/2013 Moll et al.
8,499,992 B2 8/2013 Whitman et al.
8,499,993 B2 8/2013 Shelton, IV et al.
8,500,721 B2 8/2013 Jinno
8,500,762 B2 8/2013 Sholev et al.
8,502,091 B2 8/2013 Palmer et al.
8,505,799 B2 8/2013 Viola et al.
8,505,801 B2 8/2013 Ehrenfels et al.
8,506,555 B2 8/2013 Ruiz Morales
8,506,557 B2 8/2013 Zemlok et al.
8,506,580 B2 8/2013 Zergiebel et al.
8,506,581 B2 8/2013 Wingardner, III et al.
8,511,308 B2 8/2013 Hecox et al.
8,512,359 B2 8/2013 Whitman et al.
8,512,402 B2 8/2013 Marczyk et al.
8,517,239 B2 8/2013 Scheib et al.
8,517,241 B2 8/2013 Nicholas et al.
8,517,243 B2 8/2013 Giordano et al.
8,517,244 B2 8/2013 Shelton, IV et al.
8,518,024 B2 8/2013 Williams et al.
8,521,273 B2 8/2013 Kliman
8,523,042 B2 9/2013 Masiakos et al.
8,523,043 B2 9/2013 Ullrich et al.
8,523,881 B2 9/2013 Cabiri et al.
8,523,900 B2 9/2013 Jinno et al.
8,529,588 B2 9/2013 Ahlberg et al.
8,529,600 B2 9/2013 Woodard, Jr. et al.
8,529,819 B2 9/2013 Ostapoff et al.
8,532,747 B2 9/2013 Nock et al.
8,534,527 B2 9/2013 Brendel et al.
8,534,528 B2 9/2013 Shelton, IV
8,535,304 B2 9/2013 Sklar et al.
8,535,340 B2 9/2013 Allen
8,539,866 B2 9/2013 Nayak et al.
8,540,128 B2 9/2013 Shelton, IV et al.
8,540,129 B2 9/2013 Baxter, III et al.
8,540,130 B2 9/2013 Moore et al.
8,540,131 B2 9/2013 Swayze
8,540,133 B2 9/2013 Bedi et al.
8,540,733 B2 9/2013 Whitman et al.
8,540,735 B2 9/2013 Mitelberg et al.
8,550,984 B2 10/2013 Takemoto
8,551,076 B2 10/2013 Duval et al.
8,555,660 B2 10/2013 Takenaka et al.
8,556,151 B2 10/2013 Viola
8,556,918 B2 10/2013 Bauman et al.
8,556,935 B1 10/2013 Knodel et al.
8,560,147 B2 10/2013 Taylor et al.
8,561,617 B2 10/2013 Lindh et al.
8,561,870 B2 10/2013 Baxter, III et al.
8,561,871 B2 10/2013 Rajappa et al.
8,561,873 B2 10/2013 Ingmanson et al.
8,562,598 B2 10/2013 Falkenstein et al.
8,567,656 B2 10/2013 Shelton, IV et al.
8,568,416 B2 10/2013 Schmitz et al.
8,568,425 B2 10/2013 Ross et al.
D692,916 S 11/2013 Granchi et al.
8,573,459 B2 11/2013 Smith et al.
8,573,461 B2 11/2013 Shelton, IV et al.
8,573,462 B2 11/2013 Smith et al.
8,573,465 B2 11/2013 Shelton, IV
8,574,199 B2 11/2013 von Bulow et al.
8,574,263 B2 11/2013 Mueller
8,575,880 B2 11/2013 Grantz
8,575,895 B2 11/2013 Garrastacho et al.
8,579,176 B2 11/2013 Smith et al.
8,579,178 B2 11/2013 Holsten et al.
8,579,897 B2 11/2013 Vakharia et al.
8,579,937 B2 11/2013 Gresham
8,584,919 B2 11/2013 Hueil et al.
8,584,920 B2 11/2013 Hodgkinson
8,584,921 B2 11/2013 Scirica
8,585,583 B2 11/2013 Sakaguchi et al.
8,585,721 B2 11/2013 Kirsch
8,590,760 B2 11/2013 Cummins et al.
8,590,762 B2 11/2013 Hess et al.
8,590,764 B2 11/2013 Hartwick et al.
8,596,515 B2 12/2013 Okoniewski
8,597,745 B2 12/2013 Farnsworth et al.
8,599,450 B2 12/2013 Kubo et al.
8,602,287 B2 12/2013 Yates et al.
8,602,288 B2 12/2013 Shelton, IV et al.
8,603,077 B2 12/2013 Cooper et al.
8,603,089 B2 12/2013 Viola
8,603,110 B2 12/2013 Maruyama et al.
8,603,135 B2 12/2013 Mueller
8,608,043 B2 12/2013 Scirica
8,608,044 B2 12/2013 Hueil et al.
8,608,045 B2 12/2013 Smith et al.
8,608,046 B2 12/2013 Laurent et al.
8,608,745 B2 12/2013 Guzman et al.
8,613,383 B2 12/2013 Beckman et al.
8,616,427 B2 12/2013 Viola
8,616,431 B2 12/2013 Timm et al.
8,622,274 B2 1/2014 Yates et al.
8,622,275 B2 1/2014 Baxter, III et al.
8,627,993 B2 1/2014 Smith et al.
8,627,994 B2 1/2014 Zemlok et al.
8,627,995 B2 1/2014 Smith et al.
8,628,518 B2 1/2014 Blumenkranz et al.
8,628,544 B2 1/2014 Farascioni
8,628,545 B2 1/2014 Cabrera et al.
8,631,987 B2 1/2014 Shelton, IV et al.
8,631,992 B1 1/2014 Hausen et al.
8,631,993 B2 1/2014 Kostrzewski
8,632,462 B2 1/2014 Yoo et al.
8,632,525 B2 1/2014 Kerr et al.
8,632,535 B2 1/2014 Shelton, IV et al.
8,632,539 B2 1/2014 Twomey et al.
8,632,563 B2 1/2014 Nagase et al.
8,636,187 B2 1/2014 Hueil et al.
8,636,190 B2 1/2014 Zemlok et al.
8,636,191 B2 1/2014 Meagher
8,636,193 B2 1/2014 Whitman et al.
8,636,736 B2 1/2014 Yates et al.
8,636,766 B2 1/2014 Milliman et al.
8,639,936 B2 1/2014 Hu et al.
8,640,788 B2 2/2014 Dachs, II et al.
8,646,674 B2 2/2014 Schulte et al.
8,647,258 B2 2/2014 Aranyi et al.
8,652,120 B2 2/2014 Giordano et al.
8,652,151 B2 2/2014 Lehman et al.
8,657,174 B2 2/2014 Yates et al.
8,657,175 B2 2/2014 Sonnenschein et al.
8,657,176 B2 2/2014 Shelton, IV et al.
8,657,177 B2 2/2014 Scirica et al.

(56) References Cited

U.S. PATENT DOCUMENTS 8,657,178 B2 2/2014 Hueil et al.
8,657,482 B2 2/2014 Malackowski et al.
8,657,808 B2 2/2014 McPherson et al.
8,657,814 B2 2/2014 Werneth et al.
8,657,821 B2 2/2014 Palermo
D701,238 S 3/2014 Lai et al.
8,662,370 B2 3/2014 Takei
8,663,106 B2 3/2014 Stivoric et al.
8,663,192 B2 3/2014 Hester et al.
8,663,245 B2 3/2014 Francischelli et al.
8,663,262 B2 3/2014 Smith et al.
8,663,270 B2 3/2014 Donnigan et al.
8,664,792 B2 3/2014 Rebsdorf
8,668,129 B2 3/2014 Olson
8,668,130 B2 3/2014 Hess et al.
8,672,206 B2 3/2014 Aranyi et al.
8,672,207 B2 3/2014 Shelton, IV et al.
8,672,208 B2 3/2014 Hess et al.
8,672,922 B2 3/2014 Loh et al.
8,672,935 B2 3/2014 Okada et al.
8,672,951 B2 3/2014 Smith et al.
8,673,210 B2 3/2014 Deshays
8,675,820 B2 3/2014 Baic et al.
8,678,263 B2 3/2014 Viola
8,678,994 B2 3/2014 Sonnenschein et al.
8,679,093 B2 3/2014 Farra
8,679,098 B2 3/2014 Hart
8,679,137 B2 3/2014 Bauman et al.
8,679,154 B2 3/2014 Smith et al.
8,679,156 B2 3/2014 Smith et al.
8,679,454 B2 3/2014 Guire et al.
8,684,248 B2 4/2014 Milliman
8,684,249 B2 4/2014 Racenet et al.
8,684,250 B2 4/2014 Bettuchi et al.
8,684,253 B2 4/2014 Giordano et al.
8,684,962 B2 4/2014 Kirschenman et al.
8,685,004 B2 4/2014 Zemlock et al.
8,685,020 B2 4/2014 Weizman et al.
8,690,893 B2 4/2014 Deitch et al.
8,695,866 B2 4/2014 Leimbach et al.
8,696,665 B2 4/2014 Hunt et al.
8,701,958 B2 4/2014 Shelton, IV et al.
8,701,959 B2 4/2014 Shah
8,708,210 B2 4/2014 Zemlok et al.
8,708,211 B2 4/2014 Zemlok et al.
8,708,213 B2 4/2014 Shelton, IV et al.
8,714,352 B2 5/2014 Farascioni et al.
8,714,429 B2 5/2014 Demmy
8,714,430 B2 5/2014 Natarajan et al.
8,715,256 B2 5/2014 Greener
8,715,302 B2 5/2014 Ibrahim et al.
8,720,766 B2 5/2014 Hess et al.
8,721,630 B2 5/2014 Ortiz et al.
8,721,666 B2 5/2014 Schroeder et al.
8,727,197 B2 5/2014 Hess et al.
8,727,199 B2 5/2014 Wenchell
8,727,200 B2 5/2014 Roy
8,727,961 B2 5/2014 Ziv
8,728,099 B2 5/2014 Cohn et al.
8,728,119 B2 5/2014 Cummins
8,733,470 B2 5/2014 Matthias et al.
8,733,612 B2 5/2014 Ma
8,733,613 B2 5/2014 Huitema et al.
8,733,614 B2 5/2014 Ross et al.
8,734,336 B2 5/2014 Bonadio et al.
8,734,359 B2 5/2014 Ibanez et al.
8,734,478 B2 5/2014 Widenhouse et al.
8,734,831 B2 5/2014 Kim et al.
8,739,033 B2 5/2014 Rosenberg
8,739,417 B2 6/2014 Tokunaga et al.
8,740,034 B2 6/2014 Morgan et al.
8,740,037 B2 6/2014 Shelton, IV et al.
8,740,038 B2 6/2014 Shelton, IV et al.
8,740,987 B2 6/2014 Geremakis et al.
8,746,529 B2 6/2014 Shelton, IV et al.
8,746,530 B2 6/2014 Giordano et al.
8,746,533 B2 6/2014 Whitman et al.
8,746,535 B2 6/2014 Shelton, IV et al.
8,747,238 B2 6/2014 Shelton, IV et al.
8,747,441 B2 6/2014 Konieczynski et al.
8,752,264 B2 6/2014 Ackley et al.
8,752,699 B2 6/2014 Morgan et al.
8,752,747 B2 6/2014 Shelton, IV et al.
8,752,748 B2 6/2014 Whitman et al.
8,752,749 B2 6/2014 Moore et al.
8,753,664 B2 6/2014 Dao et al.
8,757,287 B2 6/2014 Mak et al.
8,757,465 B2 6/2014 Woodard, Jr. et al.
8,758,235 B2 6/2014 Jaworek
8,758,366 B2 6/2014 McLean et al.
8,758,391 B2 6/2014 Swayze et al.
8,758,438 B2 6/2014 Boyce et al.
8,763,875 B2 7/2014 Morgan et al.
8,763,877 B2 7/2014 Schall et al.
8,763,879 B2 7/2014 Shelton, IV et al.
8,764,732 B2 7/2014 Hartwell
8,770,458 B2 7/2014 Scirica
8,770,459 B2 7/2014 Racenet et al.
8,770,460 B2 7/2014 Belzer
8,771,169 B2 7/2014 Whitman et al.
8,771,260 B2 7/2014 Conlon et al.
8,777,004 B2 7/2014 Shelton, IV et al.
8,777,082 B2 7/2014 Scirica
8,777,083 B2 7/2014 Racenet et al.
8,777,898 B2 7/2014 Suon et al.
8,783,541 B2 7/2014 Shelton, IV et al.
8,783,542 B2 7/2014 Riestenberg et al.
8,783,543 B2 7/2014 Shelton, IV et al.
8,784,304 B2 7/2014 Mikkaichi et al.
8,784,404 B2 7/2014 Doyle et al.
8,784,415 B2 7/2014 Malackowski et al.
8,789,737 B2 7/2014 Hodgkinson et al.
8,789,739 B2 7/2014 Swensgard
8,789,740 B2 7/2014 Baxter, III et al.
8,789,741 B2 7/2014 Baxter, III et al.
8,790,658 B2 7/2014 Cigarini et al.
8,790,684 B2 7/2014 Dave et al.
D711,905 S 8/2014 Morrison et al.
8,794,496 B2 8/2014 Scirica
8,794,497 B2 8/2014 Zingman
8,795,276 B2 8/2014 Dietz et al.
8,795,308 B2 8/2014 Valin
8,795,324 B2 8/2014 Kawai et al.
8,796,995 B2 8/2014 Cunanan et al.
8,800,681 B2 8/2014 Rousson et al.
8,800,837 B2 8/2014 Zemlok
8,800,838 B2 8/2014 Shelton, IV
8,800,839 B2 8/2014 Beetel
8,800,840 B2 8/2014 Jankowski
8,800,841 B2 8/2014 Ellerhorst et al.
8,801,710 B2 8/2014 Ullrich et al.
8,801,734 B2 8/2014 Shelton, IV et al.
8,801,735 B2 8/2014 Shelton, IV et al.
8,801,752 B2 8/2014 Fortier et al.
8,801,801 B2 8/2014 Datta et al.
8,806,973 B2 8/2014 Ross et al.
8,807,414 B2 8/2014 Ross et al.
8,808,161 B2 8/2014 Gregg et al.
8,808,164 B2 8/2014 Hoffman et al.
8,808,274 B2 8/2014 Hartwell
8,808,294 B2 8/2014 Fox et al.
8,808,308 B2 8/2014 Boukhny et al.
8,808,311 B2 8/2014 Heinrich et al.
8,808,325 B2 8/2014 Hess et al.
8,810,197 B2 8/2014 Juergens
8,811,017 B2 8/2014 Fujii et al.
8,813,866 B2 8/2014 Suzuki
8,814,024 B2 8/2014 Woodard, Jr. et al.
8,814,025 B2 8/2014 Miller et al.
8,814,836 B2 8/2014 Ignon et al.
8,815,594 B2 8/2014 Harris et al.
8,818,523 B2 8/2014 Olson et al.
8,820,603 B2 9/2014 Shelton, IV et al.
8,820,605 B2 9/2014 Shelton, IV

(56) References Cited

U.S. PATENT DOCUMENTS

| | | | |
|---|---|---|---|
| 8,820,606 | B2 | 9/2014 | Hodgkinson |
| 8,820,607 | B2 | 9/2014 | Marczyk |
| 8,820,608 | B2 | 9/2014 | Miyamoto |
| 8,821,514 | B2 | 9/2014 | Aranyi |
| 8,822,934 | B2 | 9/2014 | Sayeh et al. |
| 8,825,164 | B2 | 9/2014 | Tweden et al. |
| 8,827,133 | B2 | 9/2014 | Shelton, IV et al. |
| 8,827,134 | B2 | 9/2014 | Viola et al. |
| 8,827,903 | B2 | 9/2014 | Shelton, IV et al. |
| 8,833,219 | B2 | 9/2014 | Pierce |
| 8,833,630 | B2 | 9/2014 | Milliman |
| 8,833,632 | B2 | 9/2014 | Swensgard |
| 8,834,353 | B2 | 9/2014 | Dejima et al. |
| 8,834,498 | B2 | 9/2014 | Byrum et al. |
| 8,834,518 | B2 | 9/2014 | Faller et al. |
| 8,840,003 | B2 | 9/2014 | Morgan et al. |
| 8,840,603 | B2 | 9/2014 | Shelton, IV et al. |
| 8,840,609 | B2 | 9/2014 | Stuebe |
| 8,840,876 | B2 | 9/2014 | Eemeta et al. |
| 8,844,789 | B2 | 9/2014 | Shelton, IV et al. |
| 8,844,790 | B2 | 9/2014 | Demmy et al. |
| 8,851,215 | B2 | 10/2014 | Goto |
| 8,851,354 | B2 | 10/2014 | Swensgard et al. |
| 8,852,174 | B2 | 10/2014 | Burbank |
| 8,852,185 | B2 | 10/2014 | Twomey |
| 8,852,199 | B2 | 10/2014 | Deslauriers et al. |
| 8,852,218 | B2 | 10/2014 | Hughett, Sr. et al. |
| 8,857,693 | B2 | 10/2014 | Schuckmann et al. |
| 8,857,694 | B2 | 10/2014 | Shelton, IV et al. |
| 8,858,538 | B2 | 10/2014 | Belson et al. |
| 8,858,571 | B2 | 10/2014 | Shelton, IV et al. |
| 8,858,590 | B2 | 10/2014 | Shelton, IV et al. |
| 8,864,007 | B2 | 10/2014 | Widenhouse et al. |
| 8,864,009 | B2 | 10/2014 | Shelton, IV et al. |
| 8,864,010 | B2 | 10/2014 | Williams |
| 8,870,050 | B2 | 10/2014 | Hodgkinson |
| 8,870,867 | B2 | 10/2014 | Walberg et al. |
| 8,870,912 | B2 | 10/2014 | Brisson et al. |
| 8,875,971 | B2 | 11/2014 | Hall et al. |
| 8,875,972 | B2 | 11/2014 | Weisenburgh, II et al. |
| 8,876,857 | B2 | 11/2014 | Burbank |
| 8,876,858 | B2 | 11/2014 | Braun |
| 8,887,979 | B2 | 11/2014 | Mastri et al. |
| 8,888,688 | B2 | 11/2014 | Julian et al. |
| 8,888,695 | B2 | 11/2014 | Piskun et al. |
| 8,888,792 | B2 | 11/2014 | Harris et al. |
| 8,888,809 | B2 | 11/2014 | Davison et al. |
| 8,893,946 | B2 | 11/2014 | Boudreaux et al. |
| 8,893,949 | B2 | 11/2014 | Shelton, IV et al. |
| 8,894,647 | B2 | 11/2014 | Beardsley et al. |
| 8,894,654 | B2 | 11/2014 | Anderson |
| 8,899,460 | B2 | 12/2014 | Wojcicki |
| 8,899,461 | B2 | 12/2014 | Farascioni |
| 8,899,462 | B2 | 12/2014 | Kostrzewski et al. |
| 8,899,463 | B2 | 12/2014 | Schall et al. |
| 8,899,464 | B2 | 12/2014 | Hueil et al. |
| 8,899,465 | B2 | 12/2014 | Shelton, IV et al. |
| 8,899,466 | B2 | 12/2014 | Baxter, III et al. |
| 8,900,267 | B2 | 12/2014 | Woolfson et al. |
| 8,905,287 | B2 | 12/2014 | Racenet et al. |
| 8,905,977 | B2 | 12/2014 | Shelton et al. |
| 8,910,846 | B2 | 12/2014 | Viola |
| 8,911,426 | B2 | 12/2014 | Coppeta et al. |
| 8,911,448 | B2 | 12/2014 | Stein |
| 8,911,460 | B2 | 12/2014 | Neurohr et al. |
| 8,911,471 | B2 | 12/2014 | Spivey et al. |
| 8,920,433 | B2 | 12/2014 | Barrier et al. |
| 8,920,435 | B2 | 12/2014 | Smith et al. |
| 8,920,438 | B2 | 12/2014 | Aranyi et al. |
| 8,920,443 | B2 | 12/2014 | Hiles et al. |
| 8,920,444 | B2 | 12/2014 | Hiles et al. |
| 8,922,163 | B2 | 12/2014 | Macdonald |
| 8,925,782 | B2 | 1/2015 | Shelton, IV |
| 8,925,783 | B2 | 1/2015 | Zemlok et al. |
| 8,925,788 | B2 | 1/2015 | Hess et al. |
| 8,926,506 | B2 | 1/2015 | Widenhouse et al. |
| 8,926,598 | B2 | 1/2015 | Mollere et al. |
| 8,931,576 | B2 | 1/2015 | Iwata |
| 8,931,679 | B2 | 1/2015 | Kostrzewski |
| 8,931,680 | B2 | 1/2015 | Milliman |
| 8,931,682 | B2 | 1/2015 | Timm et al. |
| 8,936,614 | B2 | 1/2015 | Allen, IV |
| 8,939,343 | B2 | 1/2015 | Milliman et al. |
| 8,939,344 | B2 | 1/2015 | Olson et al. |
| 8,945,163 | B2 | 2/2015 | Voegele et al. |
| 8,955,732 | B2 | 2/2015 | Zemlok et al. |
| 8,956,342 | B1 | 2/2015 | Russo et al. |
| 8,956,390 | B2 | 2/2015 | Shah et al. |
| 8,958,860 | B2 | 2/2015 | Banerjee et al. |
| 8,960,519 | B2 | 2/2015 | Whitman et al. |
| 8,960,520 | B2 | 2/2015 | McCuen |
| 8,960,521 | B2 | 2/2015 | Kostrzewski |
| 8,961,191 | B2 | 2/2015 | Hanshew |
| 8,961,504 | B2 | 2/2015 | Hoarau et al. |
| 8,963,714 | B2 | 2/2015 | Medhal et al. |
| D725,674 | S | 3/2015 | Jung et al. |
| 8,967,443 | B2 | 3/2015 | McCuen |
| 8,967,444 | B2 | 3/2015 | Beetel |
| 8,967,446 | B2 | 3/2015 | Beardsley et al. |
| 8,967,448 | B2 | 3/2015 | Carter et al. |
| 8,968,276 | B2 | 3/2015 | Zemlok et al. |
| 8,968,308 | B2 | 3/2015 | Horner et al. |
| 8,968,312 | B2 | 3/2015 | Marczyk et al. |
| 8,968,337 | B2 | 3/2015 | Whitfield et al. |
| 8,968,340 | B2 | 3/2015 | Chowaniec et al. |
| 8,968,355 | B2 | 3/2015 | Malkowski et al. |
| 8,968,358 | B2 | 3/2015 | Reschke |
| 8,970,507 | B2 | 3/2015 | Holbein et al. |
| 8,973,803 | B2 | 3/2015 | Hall et al. |
| 8,973,804 | B2 | 3/2015 | Hess et al. |
| 8,973,805 | B2 | 3/2015 | Scirica et al. |
| 8,974,440 | B2 | 3/2015 | Farritor et al. |
| 8,974,542 | B2 | 3/2015 | Fujimoto et al. |
| 8,974,932 | B2 | 3/2015 | McGahan et al. |
| 8,978,954 | B2 | 3/2015 | Shelton, IV et al. |
| 8,978,955 | B2 | 3/2015 | Aronhalt et al. |
| 8,978,956 | B2 | 3/2015 | Schall et al. |
| 8,979,843 | B2 | 3/2015 | Timm et al. |
| 8,979,890 | B2 | 3/2015 | Boudreaux |
| 8,982,195 | B2 | 3/2015 | Claus et al. |
| 8,985,429 | B2 | 3/2015 | Balek et al. |
| 8,986,302 | B2 | 3/2015 | Aldridge et al. |
| 8,989,903 | B2 | 3/2015 | Weir et al. |
| 8,991,676 | B2 | 3/2015 | Hess et al. |
| 8,991,677 | B2 | 3/2015 | Moore et al. |
| 8,991,678 | B2 | 3/2015 | Wellman et al. |
| 8,992,042 | B2 | 3/2015 | Eichenholz |
| 8,992,422 | B2 | 3/2015 | Spivey et al. |
| 8,992,565 | B2 | 3/2015 | Brisson et al. |
| 8,996,165 | B2 | 3/2015 | Wang et al. |
| 8,998,058 | B2 | 4/2015 | Moore et al. |
| 8,998,059 | B2 | 4/2015 | Smith et al. |
| 8,998,060 | B2 | 4/2015 | Bruewer et al. |
| 8,998,061 | B2 | 4/2015 | Williams et al. |
| 8,998,939 | B2 | 4/2015 | Price et al. |
| 9,000,720 | B2 | 4/2015 | Stulen et al. |
| 9,002,518 | B2 | 4/2015 | Manzo et al. |
| 9,004,339 | B1 | 4/2015 | Park |
| 9,005,230 | B2 | 4/2015 | Yates et al. |
| 9,005,238 | B2 | 4/2015 | DeSantis et al. |
| 9,005,243 | B2 | 4/2015 | Stopek et al. |
| 9,010,606 | B2 | 4/2015 | Aranyi et al. |
| 9,010,608 | B2 | 4/2015 | Casasanta, Jr. et al. |
| 9,010,611 | B2 | 4/2015 | Ross et al. |
| 9,011,437 | B2 | 4/2015 | Woodruff et al. |
| 9,011,439 | B2 | 4/2015 | Shalaby et al. |
| 9,011,471 | B2 | 4/2015 | Timm et al. |
| 9,016,539 | B2 | 4/2015 | Kostrzewski et al. |
| 9,016,540 | B2 | 4/2015 | Whitman et al. |
| 9,016,541 | B2 | 4/2015 | Viola et al. |
| 9,016,542 | B2 | 4/2015 | Shelton, IV et al. |
| 9,016,545 | B2 | 4/2015 | Aranyi et al. |
| 9,017,331 | B2 | 4/2015 | Fox |
| 9,017,355 | B2 | 4/2015 | Smith et al. |

(56) References Cited

U.S. PATENT DOCUMENTS 9,017,369 B2 4/2015 Renger et al.
9,017,371 B2 4/2015 Whitman et al.
9,021,684 B2 5/2015 Lenker et al.
9,023,014 B2 5/2015 Chowaniec et al.
9,023,069 B2 5/2015 Kasvikis et al.
9,023,071 B2 5/2015 Miller et al.
9,026,347 B2 5/2015 Gadh et al.
9,027,817 B2 5/2015 Milliman et al.
9,028,494 B2 5/2015 Shelton, IV et al.
9,028,495 B2 5/2015 Mueller et al.
9,028,510 B2 5/2015 Miyamoto et al.
9,028,519 B2 5/2015 Yates et al.
9,030,169 B2 5/2015 Christensen et al.
9,033,203 B2 5/2015 Woodard, Jr. et al.
9,033,204 B2 5/2015 Shelton, IV et al.
9,034,505 B2 5/2015 Detry et al.
9,038,881 B1 5/2015 Schaller et al.
9,039,690 B2 5/2015 Kersten et al.
9,039,694 B2 5/2015 Ross et al.
9,039,720 B2 5/2015 Madan
9,043,027 B2 5/2015 Durant et al.
9,044,227 B2 6/2015 Shelton, IV et al.
9,044,228 B2 6/2015 Woodard, Jr. et al.
9,044,229 B2 6/2015 Scheib et al.
9,044,230 B2 6/2015 Morgan et al.
9,044,241 B2 6/2015 Barner et al.
9,044,261 B2 6/2015 Houser
9,044,281 B2 6/2015 Pool et al.
9,050,083 B2 6/2015 Yates et al.
9,050,084 B2 6/2015 Schmid et al.
9,050,100 B2 6/2015 Yates et al.
9,050,120 B2 6/2015 Swarup et al.
9,050,123 B2 6/2015 Krause et al.
9,050,176 B2 6/2015 Datta et al.
9,050,192 B2 6/2015 Mansmann
9,055,941 B2 6/2015 Schmid et al.
9,055,942 B2 6/2015 Balbierz et al.
9,055,943 B2 6/2015 Zemlok et al.
9,055,944 B2 6/2015 Hodgkinson et al.
9,055,961 B2 6/2015 Manzo et al.
9,060,770 B2 6/2015 Shelton, IV et al.
9,060,776 B2 6/2015 Yates et al.
9,060,794 B2 6/2015 Kang et al.
9,060,894 B2 6/2015 Wubbeling
9,061,392 B2 6/2015 Forgues et al.
9,072,515 B2 7/2015 Hall et al.
9,072,523 B2 7/2015 Houser et al.
9,072,535 B2 7/2015 Shelton, IV et al.
9,072,536 B2 7/2015 Shelton, IV et al.
9,078,653 B2 7/2015 Leimbach et al.
9,078,654 B2 7/2015 Whitman et al.
9,084,601 B2 7/2015 Moore et al.
9,084,602 B2 7/2015 Gleiman
9,086,875 B2 7/2015 Harrat et al.
9,089,326 B2 7/2015 Krumanaker et al.
9,089,330 B2 7/2015 Widenhouse et al.
9,089,352 B2 7/2015 Jeong
9,089,360 B2 7/2015 Messerly et al.
9,091,588 B2 7/2015 Lefler
D736,792 S 8/2015 Brinda et al.
9,095,339 B2 8/2015 Moore et al.
9,095,346 B2 8/2015 Houser et al.
9,095,362 B2 8/2015 Dachs, II et al.
9,095,367 B2 8/2015 Olson et al.
9,096,033 B2 8/2015 Holop et al.
9,099,863 B2 8/2015 Smith et al.
9,099,877 B2 8/2015 Banos et al.
9,101,358 B2 8/2015 Kerr et al.
9,101,385 B2 8/2015 Shelton, IV et al.
9,101,475 B2 8/2015 Wei et al.
9,107,663 B2 8/2015 Swensgard
9,107,690 B2 8/2015 Bales, Jr. et al.
9,110,587 B2 8/2015 Kim et al.
9,113,862 B2 8/2015 Morgan et al.
9,113,864 B2 8/2015 Morgan et al.
9,113,865 B2 8/2015 Shelton, IV et al.
9,113,868 B2 8/2015 Felder et al.
9,113,873 B2 8/2015 Marczyk et al.
9,113,874 B2 8/2015 Shelton, IV et al.
9,113,876 B2 8/2015 Zemlok et al.
9,113,879 B2 8/2015 Felder et al.
9,113,880 B2 8/2015 Zemlok et al.
9,113,881 B2 8/2015 Scirica
9,113,883 B2 8/2015 Aronhalt et al.
9,113,884 B2 8/2015 Shelton, IV et al.
9,113,887 B2 8/2015 Behnke, II et al.
9,119,615 B2 9/2015 Felder et al.
9,119,657 B2 9/2015 Shelton, IV et al.
9,119,898 B2 9/2015 Bayon et al.
9,119,957 B2 9/2015 Gantz et al.
9,123,286 B2 9/2015 Park
9,124,097 B2 9/2015 Cruz
9,125,654 B2 9/2015 Aronhalt et al.
9,125,662 B2 9/2015 Shelton, IV
9,126,317 B2 9/2015 Lawton et al.
9,131,835 B2 9/2015 Widenhouse et al.
9,131,940 B2 9/2015 Huitema et al.
9,131,950 B2 9/2015 Matthew
9,131,957 B2 9/2015 Skarbnik et al.
9,138,225 B2 9/2015 Huang et al.
9,138,226 B2 9/2015 Racenet et al.
9,144,455 B2 9/2015 Kennedy et al.
D741,882 S 10/2015 Shmilov et al.
9,149,274 B2 10/2015 Spivey et al.
9,149,324 B2 10/2015 Huang et al.
9,149,325 B2 10/2015 Worrell et al.
9,153,994 B2 10/2015 Wood et al.
9,161,753 B2 10/2015 Prior
9,161,769 B2 10/2015 Stoddard et al.
9,161,803 B2 10/2015 Yates et al.
9,161,807 B2 10/2015 Garrison
9,168,038 B2 10/2015 Shelton, IV et al.
9,168,039 B1 10/2015 Knodel
9,168,042 B2 10/2015 Milliman
9,168,054 B2 10/2015 Turner et al.
9,168,144 B2 10/2015 Rivin et al.
9,179,911 B2 11/2015 Morgan et al.
9,179,912 B2 11/2015 Yates et al.
9,180,223 B2 11/2015 Yu et al.
9,182,244 B2 11/2015 Luke et al.
9,186,046 B2 11/2015 Ramamurthy et al.
9,186,137 B2 11/2015 Farascioni et al.
9,186,140 B2 11/2015 Hiles et al.
9,186,142 B2 11/2015 Fanelli et al.
9,186,143 B2 11/2015 Timm et al.
9,186,148 B2 11/2015 Felder et al.
9,186,221 B2 11/2015 Burbank
9,192,380 B2 11/2015 (Tarinelli) Racenet et al.
9,192,384 B2 11/2015 Bettuchi
9,192,430 B2 11/2015 Rachlin et al.
9,192,434 B2 11/2015 Twomey et al.
9,193,045 B2 11/2015 Saur et al.
9,197,079 B2 11/2015 Yip et al.
D744,528 S 12/2015 Agrawal
9,198,642 B2 12/2015 Storz
9,198,644 B2 12/2015 Balek et al.
9,198,661 B2 12/2015 Swensgard
9,198,662 B2 12/2015 Barton et al.
9,198,683 B2 12/2015 Friedman et al.
9,204,830 B2 12/2015 Zand et al.
9,204,877 B2 12/2015 Whitman et al.
9,204,878 B2 12/2015 Hall et al.
9,204,879 B2 12/2015 Shelton, IV
9,204,880 B2 12/2015 Baxter, III et al.
9,204,923 B2 12/2015 Manzo et al.
9,204,924 B2 12/2015 Marczyk et al.
9,211,120 B2 12/2015 Scheib et al.
9,211,121 B2 12/2015 Hall et al.
9,211,122 B2 12/2015 Hagerty et al.
9,216,013 B2 12/2015 Scirica et al.
9,216,019 B2 12/2015 Schmid et al.
9,216,020 B2 12/2015 Zhang et al.
9,216,030 B2 12/2015 Fan et al.
9,216,062 B2 12/2015 Duque et al.

(56) References Cited

U.S. PATENT DOCUMENTS 9,220,500 B2 12/2015 Swayze et al.
9,220,501 B2 12/2015 Baxter, III et al.
9,220,502 B2 12/2015 Zemlok et al.
9,220,508 B2 12/2015 Dannaher
9,220,559 B2 12/2015 Worrell et al.
9,220,570 B2 12/2015 Kim et al.
D746,854 S 1/2016 Shardlow et al.
9,226,750 B2 1/2016 Weir et al.
9,226,751 B2 1/2016 Shelton, IV et al.
9,226,754 B2 1/2016 D'Agostino et al.
9,226,761 B2 1/2016 Burbank
9,226,767 B2 1/2016 Stulen et al.
9,232,941 B2 1/2016 Mandakolathur Vasudevan et al.
9,232,945 B2 1/2016 Zingman
9,232,979 B2 1/2016 Parihar et al.
9,233,610 B2 1/2016 Kim et al.
9,237,891 B2 1/2016 Shelton, IV
9,237,892 B2 1/2016 Hodgkinson
9,237,895 B2 1/2016 McCarthy et al.
9,237,900 B2 1/2016 Boudreaux et al.
9,237,921 B2 1/2016 Messerly et al.
9,239,064 B2 1/2016 Helbig et al.
9,240,740 B2 1/2016 Zeng et al.
9,241,711 B2 1/2016 Ivanko
9,241,712 B2 1/2016 Zemlok et al.
9,241,714 B2 1/2016 Timm et al.
9,241,716 B2 1/2016 Whitman
9,241,731 B2 1/2016 Boudreaux et al.
9,244,524 B2 1/2016 Inoue et al.
D748,668 S 2/2016 Kim et al.
D749,623 S 2/2016 Gray et al.
D750,122 S 2/2016 Shardlow et al.
D750,129 S 2/2016 Kwon
9,254,131 B2 2/2016 Soltz et al.
9,259,274 B2 2/2016 Prisco
9,259,275 B2 2/2016 Burbank
9,261,172 B2 2/2016 Solomon et al.
9,265,500 B2 2/2016 Sorrentino et al.
9,265,516 B2 2/2016 Casey et al.
9,265,585 B2 2/2016 Wingardner et al.
9,271,718 B2 3/2016 Milad et al.
9,271,727 B2 3/2016 McGuckin, Jr. et al.
9,271,753 B2 3/2016 Butler et al.
9,271,799 B2 3/2016 Shelton, IV et al.
9,272,406 B2 3/2016 Aronhalt et al.
9,274,095 B2 3/2016 Humayun et al.
9,277,919 B2 3/2016 Timmer et al.
9,277,922 B2 3/2016 Carter et al.
9,282,962 B2 3/2016 Schmid et al.
9,282,963 B2 3/2016 Bryant
9,282,966 B2 3/2016 Shelton, IV et al.
9,282,974 B2 3/2016 Shelton, IV
9,283,028 B2 3/2016 Johnson
9,283,045 B2 3/2016 Rhee et al.
9,283,054 B2 3/2016 Morgan et al.
9,289,206 B2 3/2016 Hess et al.
9,289,207 B2 3/2016 Shelton, IV
9,289,210 B2 3/2016 Baxter, III et al.
9,289,211 B2 3/2016 Williams et al.
9,289,212 B2 3/2016 Shelton, IV et al.
9,289,225 B2 3/2016 Shelton, IV et al.
9,289,256 B2 3/2016 Shelton, IV et al.
9,293,757 B2 3/2016 Toussaint et al.
9,295,464 B2 3/2016 Shelton, IV et al.
9,295,465 B2 3/2016 Farascioni
9,295,466 B2 3/2016 Hodgkinson et al.
9,295,467 B2 3/2016 Scirica
9,295,468 B2 3/2016 Heinrich et al.
9,295,514 B2 3/2016 Shelton, IV et al.
9,295,522 B2 3/2016 Kostrzewski
9,295,565 B2 3/2016 McLean
9,295,784 B2 3/2016 Eggert et al.
9,301,691 B2 4/2016 Hufnagel et al.
9,301,752 B2 4/2016 Mandakolathur Vasudevan et al.
9,301,753 B2 4/2016 Aldridge et al.
9,301,755 B2 4/2016 Shelton, IV et al.
9,301,759 B2 4/2016 Spivey et al.
9,307,965 B2 4/2016 Ming et al.
9,307,986 B2 4/2016 Hall et al.
9,307,987 B2 4/2016 Swensgard et al.
9,307,988 B2 4/2016 Shelton, IV
9,307,989 B2 4/2016 Shelton, IV et al.
9,307,994 B2 4/2016 Gresham et al.
9,308,009 B2 4/2016 Madan et al.
9,308,011 B2 4/2016 Chao et al.
9,308,646 B2 4/2016 Lim et al.
9,313,915 B2 4/2016 Niu et al.
9,314,246 B2 4/2016 Shelton, IV et al.
9,314,247 B2 4/2016 Shelton, IV et al.
9,314,261 B2 4/2016 Bales, Jr. et al.
9,314,339 B2 4/2016 Mansmann
9,314,908 B2 4/2016 Tanimoto et al.
9,320,518 B2 4/2016 Henderson et al.
9,320,520 B2 4/2016 Shelton, IV et al.
9,320,521 B2 4/2016 Shelton, IV et al.
9,320,523 B2 4/2016 Shelton, IV et al.
9,325,516 B2 4/2016 Pera et al.
D755,196 S 5/2016 Meyers et al.
D756,373 S 5/2016 Raskin et al.
D756,377 S 5/2016 Connolly et al.
D757,028 S 5/2016 Goldenberg et al.
9,326,767 B2 5/2016 Koch et al.
9,326,768 B2 5/2016 Shelton, IV
9,326,769 B2 5/2016 Shelton, IV et al.
9,326,770 B2 5/2016 Shelton, IV et al.
9,326,771 B2 5/2016 Baxter, III et al.
9,326,788 B2 5/2016 Batross et al.
9,326,812 B2 5/2016 Waaler et al.
9,327,061 B2 5/2016 Govil et al.
9,331,721 B2 5/2016 Martinez Nuevo et al.
9,332,890 B2 5/2016 Ozawa
9,332,974 B2 5/2016 Henderson et al.
9,332,984 B2 5/2016 Weaner et al.
9,332,987 B2 5/2016 Leimbach et al.
9,333,040 B2 5/2016 Shellenberger et al.
9,333,082 B2 5/2016 Wei et al.
9,337,668 B2 5/2016 Yip
9,339,226 B2 5/2016 van der Walt et al.
9,345,477 B2 5/2016 Anim et al.
9,345,479 B2 5/2016 (Tarinelli) Racenet et al.
9,345,480 B2 5/2016 Hessler et al.
9,345,481 B2 5/2016 Hall et al.
9,345,503 B2 5/2016 Ishida et al.
9,351,726 B2 5/2016 Leimbach et al.
9,351,727 B2 5/2016 Leimbach et al.
9,351,728 B2 5/2016 Sniffin et al.
9,351,730 B2 5/2016 Schmid et al.
9,351,731 B2 5/2016 Carter et al.
9,351,732 B2 5/2016 Hodgkinson
D758,433 S 6/2016 Lee et al.
D759,063 S 6/2016 Chen
9,358,003 B2 6/2016 Hall et al.
9,358,005 B2 6/2016 Shelton, IV et al.
9,358,015 B2 6/2016 Sorrentino et al.
9,358,031 B2 6/2016 Manzo
9,364,217 B2 6/2016 Kostrzewski et al.
9,364,219 B2 6/2016 Olson et al.
9,364,220 B2 6/2016 Williams
9,364,226 B2 6/2016 Zemlok et al.
9,364,229 B2 6/2016 D'Agostino et al.
9,364,230 B2 6/2016 Shelton, IV et al.
9,364,231 B2 6/2016 Wenchell
9,364,233 B2 6/2016 Alexander, III et al.
9,364,279 B2 6/2016 Houser et al.
9,368,991 B2 6/2016 Qahouq
9,370,341 B2 6/2016 Ceniccola et al.
9,370,358 B2 6/2016 Shelton, IV et al.
9,370,364 B2 6/2016 Smith et al.
9,375,206 B2 6/2016 Vidal et al.
9,375,218 B2 6/2016 Wheeler et al.
9,375,230 B2 6/2016 Ross et al.
9,375,232 B2 6/2016 Hunt et al.
9,375,255 B2 6/2016 Houser et al.
D761,309 S 7/2016 Lee et al.

(56) References Cited

U.S. PATENT DOCUMENTS 9,381,058 B2 7/2016 Houser et al.
9,383,881 B2 7/2016 Day et al.
9,386,983 B2 7/2016 Swensgard et al.
9,386,984 B2 7/2016 Aronhalt et al.
9,386,985 B2 7/2016 Koch, Jr. et al.
9,386,988 B2 7/2016 Baxter, III et al.
9,387,003 B2 7/2016 Kaercher et al.
9,393,015 B2 7/2016 Laurent et al.
9,393,017 B2 7/2016 Flanagan et al.
9,393,018 B2 7/2016 Wang et al.
9,398,911 B2 7/2016 Auld
D763,277 S 8/2016 Ahmed et al.
D764,498 S 8/2016 Capela et al.
9,402,604 B2 8/2016 Williams et al.
9,402,625 B2 8/2016 Coleman et al.
9,402,626 B2 8/2016 Ortiz et al.
9,402,627 B2 8/2016 Stevenson et al.
9,402,629 B2 8/2016 Ehrenfels et al.
9,408,604 B2 8/2016 Shelton, IV et al.
9,408,606 B2 8/2016 Shelton, IV
9,408,622 B2 8/2016 Stulen et al.
9,411,370 B2 8/2016 Benni et al.
9,413,128 B2 8/2016 Tien et al.
9,414,838 B2 8/2016 Shelton, IV et al.
9,414,849 B2 8/2016 Nagashimada
9,414,880 B2 8/2016 Monson et al.
9,420,967 B2 8/2016 Zand et al.
9,421,003 B2 8/2016 Williams et al.
9,421,014 B2 8/2016 Ingmanson et al.
9,421,030 B2 8/2016 Cole et al.
9,421,060 B2 8/2016 Monson et al.
9,421,062 B2 8/2016 Houser et al.
9,427,223 B2 8/2016 Park et al.
9,427,231 B2 8/2016 Racenet et al.
D767,624 S 9/2016 Lee et al.
9,433,411 B2 9/2016 Racenet et al.
9,433,419 B2 9/2016 Gonzalez et al.
9,433,420 B2 9/2016 Hodgkinson
9,439,649 B2 9/2016 Shelton, IV et al.
9,439,650 B2 9/2016 McGuckin, Jr. et al.
9,439,651 B2 9/2016 Smith et al.
9,439,668 B2 9/2016 Timm et al.
9,445,808 B2 9/2016 Woodard, Jr. et al.
9,445,813 B2 9/2016 Shelton, IV et al.
9,445,817 B2 9/2016 Bettuchi
9,446,226 B2 9/2016 Zilberman
9,451,938 B2 9/2016 Overes et al.
9,451,958 B2 9/2016 Shelton, IV et al.
D768,152 S 10/2016 Gutierrez et al.
D768,156 S 10/2016 Frincke
D769,315 S 10/2016 Scotti
D769,930 S 10/2016 Agrawal
9,461,340 B2 10/2016 Li et al.
9,463,040 B2 10/2016 Jeong et al.
9,463,260 B2 10/2016 Stopek
9,468,438 B2 10/2016 Baber et al.
9,468,447 B2 10/2016 Aman et al.
9,470,297 B2 10/2016 Aranyi et al.
9,471,969 B2 10/2016 Zeng et al.
9,474,506 B2 10/2016 Magnin et al.
9,474,523 B2 10/2016 Meade et al.
9,474,540 B2 10/2016 Stokes et al.
9,475,180 B2 10/2016 Eshleman et al.
D770,476 S 11/2016 Jitkoff et al.
D770,515 S 11/2016 Cho et al.
D771,116 S 11/2016 Dellinger et al.
D772,905 S 11/2016 Ingenlath
9,480,476 B2 11/2016 Aldridge et al.
9,480,492 B2 11/2016 Aranyi et al.
9,483,095 B2 11/2016 Tran et al.
9,486,186 B2 11/2016 Fiebig et al.
9,486,213 B2 11/2016 Altman et al.
9,486,214 B2 11/2016 Shelton, IV
9,486,302 B2 11/2016 Boey et al.
9,488,197 B2 11/2016 Wi
9,492,146 B2 11/2016 Kostrzewski et al.
9,492,167 B2 11/2016 Shelton, IV et al.
9,492,170 B2 11/2016 Bear et al.
9,492,189 B2 11/2016 Williams et al.
9,492,192 B2 11/2016 To et al.
9,498,213 B2 11/2016 Marczyk et al.
9,498,219 B2 11/2016 Moore et al.
9,498,231 B2 11/2016 Haider et al.
9,504,455 B2 11/2016 Whitman et al.
9,504,483 B2 11/2016 Houser et al.
9,504,521 B2 11/2016 Deutmeyer et al.
D774,547 S 12/2016 Capela et al.
D775,336 S 12/2016 Shelton, IV et al.
9,510,827 B2 12/2016 Kostrzewski
9,510,828 B2 12/2016 Yates et al.
9,510,830 B2 12/2016 Shelton, IV et al.
9,510,846 B2 12/2016 Sholev et al.
9,510,895 B2 12/2016 Houser et al.
9,510,925 B2 12/2016 Hotter et al.
9,517,063 B2 12/2016 Swayze et al.
9,517,068 B2 12/2016 Shelton, IV et al.
9,517,326 B2 12/2016 Hinman et al.
9,521,996 B2 12/2016 Armstrong
9,522,029 B2 12/2016 Yates et al.
9,526,481 B2 12/2016 Storz et al.
9,526,499 B2 12/2016 Kostrzewski et al.
9,526,563 B2 12/2016 Twomey
9,526,564 B2 12/2016 Rusin
D776,683 S 1/2017 Gobinski et al.
D777,773 S 1/2017 Shi
9,532,783 B2 1/2017 Swayze et al.
9,539,726 B2 1/2017 Simaan et al.
9,545,253 B2 1/2017 Worrell et al.
9,545,258 B2 1/2017 Smith et al.
9,549,732 B2 1/2017 Yates et al.
9,549,735 B2 1/2017 Shelton, IV et al.
9,554,794 B2 1/2017 Baber et al.
9,554,796 B2 1/2017 Kostrzewski
9,554,812 B2 1/2017 Inkpen et al.
9,559,624 B2 1/2017 Philipp
9,561,013 B2 2/2017 Tsuchiya
9,561,030 B2 2/2017 Zhang et al.
9,561,031 B2 2/2017 Heinrich et al.
9,561,032 B2 2/2017 Shelton, IV et al.
9,561,038 B2 2/2017 Shelton, IV et al.
9,561,045 B2 2/2017 Hinman et al.
9,566,061 B2 2/2017 Aronhalt et al.
9,566,062 B2 2/2017 Boudreaux
9,566,065 B2 2/2017 Knodel
9,566,067 B2 2/2017 Milliman et al.
9,572,574 B2 2/2017 Shelton, IV et al.
9,572,577 B2 2/2017 Lloyd et al.
9,572,592 B2 2/2017 Price et al.
9,574,644 B2 2/2017 Parihar
9,579,088 B2 2/2017 Farritor et al.
D780,803 S 3/2017 Gill et al.
D781,879 S 3/2017 Butcher et al.
D782,530 S 3/2017 Paek et al.
9,585,550 B2 3/2017 Abel et al.
9,585,657 B2 3/2017 Shelton, IV et al.
9,585,658 B2 3/2017 Shelton, IV
9,585,659 B2 3/2017 Viola et al.
9,585,660 B2 3/2017 Laurent et al.
9,585,662 B2 3/2017 Shelton, IV et al.
9,585,663 B2 3/2017 Shelton, IV et al.
9,585,672 B2 3/2017 Bastia
9,590,433 B2 3/2017 Li
9,592,050 B2 3/2017 Schmid et al.
9,592,052 B2 3/2017 Shelton, IV
9,592,053 B2 3/2017 Shelton, IV et al.
9,592,054 B2 3/2017 Schmid et al.
9,597,073 B2 3/2017 Sorrentino et al.
9,597,075 B2 3/2017 Shelton, IV et al.
9,597,080 B2 3/2017 Milliman et al.
9,597,104 B2 3/2017 Nicholas et al.
9,597,143 B2 3/2017 Madan et al.
9,603,595 B2 3/2017 Shelton, IV et al.
9,603,598 B2 3/2017 Shelton, IV et al.
9,603,599 B2 3/2017 Miller et al.

(56) References Cited

U.S. PATENT DOCUMENTS

| | | | |
|---|---|---|---|
| 9,603,991 | B2 | 3/2017 | Shelton, IV et al. |
| D783,658 | S | 4/2017 | Hurst et al. |
| 9,610,080 | B2 | 4/2017 | Whitfield et al. |
| 9,614,258 | B2 | 4/2017 | Takahashi et al. |
| 9,615,826 | B2 | 4/2017 | Shelton, IV et al. |
| 9,622,745 | B2 | 4/2017 | Ingmanson et al. |
| 9,629,623 | B2 | 4/2017 | Lytle, IV et al. |
| 9,629,626 | B2 | 4/2017 | Soltz et al. |
| 9,629,627 | B2 | 4/2017 | Kostrzewski et al. |
| 9,629,628 | B2 | 4/2017 | Aranyi |
| 9,629,629 | B2 | 4/2017 | Leimbach et al. |
| 9,629,652 | B2 | 4/2017 | Mumaw et al. |
| 9,629,814 | B2 | 4/2017 | Widenhouse et al. |
| D786,280 | S | 5/2017 | Ma |
| D786,896 | S | 5/2017 | Kim et al. |
| D787,547 | S | 5/2017 | Basargin et al. |
| D788,123 | S | 5/2017 | Shan et al. |
| D788,140 | S | 5/2017 | Hemsley et al. |
| 9,636,111 | B2 | 5/2017 | Wenchell |
| 9,636,113 | B2 | 5/2017 | Wenchell |
| 9,636,850 | B2 | 5/2017 | Stopek (nee Prommersberger) et al. |
| 9,641,122 | B2 | 5/2017 | Romanowich et al. |
| 9,642,620 | B2 | 5/2017 | Baxter, III et al. |
| 9,649,096 | B2 | 5/2017 | Sholev |
| 9,649,110 | B2 | 5/2017 | Parihar et al. |
| 9,649,111 | B2 | 5/2017 | Shelton, IV et al. |
| 9,655,613 | B2 | 5/2017 | Schaller |
| 9,655,614 | B2 | 5/2017 | Swensgard et al. |
| 9,655,615 | B2 | 5/2017 | Knodel et al. |
| 9,655,616 | B2 | 5/2017 | Aranyi |
| 9,655,624 | B2 | 5/2017 | Shelton, IV et al. |
| 9,662,108 | B2 | 5/2017 | Williams |
| 9,662,110 | B2 | 5/2017 | Huang et al. |
| 9,662,116 | B2 | 5/2017 | Smith et al. |
| 9,662,131 | B2 | 5/2017 | Omori et al. |
| D788,792 | S | 6/2017 | Alessandri et al. |
| D789,384 | S | 6/2017 | Lin et al. |
| D790,570 | S | 6/2017 | Butcher et al. |
| 9,668,728 | B2 | 6/2017 | Williams et al. |
| 9,668,729 | B2 | 6/2017 | Williams et al. |
| 9,668,732 | B2 | 6/2017 | Patel et al. |
| 9,668,733 | B2 | 6/2017 | Williams |
| 9,668,734 | B2 | 6/2017 | Kostrzewski et al. |
| 9,675,344 | B2 | 6/2017 | Combrowski et al. |
| 9,675,351 | B2 | 6/2017 | Hodgkinson et al. |
| 9,675,354 | B2 | 6/2017 | Weir et al. |
| 9,675,355 | B2 | 6/2017 | Shelton, IV et al. |
| 9,675,372 | B2 | 6/2017 | Laurent et al. |
| 9,675,375 | B2 | 6/2017 | Houser et al. |
| 9,675,405 | B2 | 6/2017 | Trees et al. |
| 9,675,819 | B2 | 6/2017 | Dunbar et al. |
| 9,681,870 | B2 | 6/2017 | Baxter, III et al. |
| 9,681,873 | B2 | 6/2017 | Smith et al. |
| 9,681,884 | B2 | 6/2017 | Clem et al. |
| 9,687,230 | B2 | 6/2017 | Leimbach et al. |
| 9,687,231 | B2 | 6/2017 | Baxter, III et al. |
| 9,687,232 | B2 | 6/2017 | Shelton, IV et al. |
| 9,687,233 | B2 | 6/2017 | Fernandez et al. |
| 9,687,236 | B2 | 6/2017 | Leimbach et al. |
| 9,687,237 | B2 | 6/2017 | Schmid et al. |
| 9,687,253 | B2 | 6/2017 | Detry et al. |
| 9,689,466 | B2 | 6/2017 | Kanai et al. |
| 9,690,362 | B2 | 6/2017 | Leimbach et al. |
| 9,693,772 | B2 | 7/2017 | Ingmanson et al. |
| 9,693,774 | B2 | 7/2017 | Gettinger et al. |
| 9,693,777 | B2 | 7/2017 | Schellin et al. |
| 9,700,309 | B2 | 7/2017 | Jaworek et al. |
| 9,700,310 | B2 | 7/2017 | Morgan et al. |
| 9,700,312 | B2 | 7/2017 | Kostrzewski et al. |
| 9,700,317 | B2 | 7/2017 | Aronhalt et al. |
| 9,700,318 | B2 | 7/2017 | Scirica et al. |
| 9,700,319 | B2 | 7/2017 | Motooka et al. |
| 9,700,320 | B2 | 7/2017 | Dinardo et al. |
| 9,700,321 | B2 | 7/2017 | Shelton, IV et al. |
| 9,706,981 | B2 | 7/2017 | Nicholas et al. |
| 9,706,991 | B2 | 7/2017 | Hess et al. |
| 9,706,993 | B2 | 7/2017 | Hessler et al. |
| 9,707,005 | B2 | 7/2017 | Strobl et al. |
| 9,707,026 | B2 | 7/2017 | Malackowski et al. |
| 9,707,043 | B2 | 7/2017 | Bozung |
| 9,707,684 | B2 | 7/2017 | Ruiz Morales et al. |
| 9,713,468 | B2 | 7/2017 | Harris et al. |
| 9,713,470 | B2 | 7/2017 | Scirica et al. |
| 9,713,474 | B2 | 7/2017 | Lorenz |
| 9,717,497 | B2 | 8/2017 | Zerkle et al. |
| 9,717,498 | B2 | 8/2017 | Aranyi et al. |
| 9,722,236 | B2 | 8/2017 | Sathrum |
| 9,724,091 | B2 | 8/2017 | Shelton, IV et al. |
| 9,724,092 | B2 | 8/2017 | Baxter, III et al. |
| 9,724,094 | B2 | 8/2017 | Baber et al. |
| 9,724,096 | B2 | 8/2017 | Thompson et al. |
| 9,724,098 | B2 | 8/2017 | Baxter, III et al. |
| 9,724,118 | B2 | 8/2017 | Schulte et al. |
| 9,724,163 | B2 | 8/2017 | Orban |
| 9,730,692 | B2 | 8/2017 | Shelton, IV et al. |
| 9,730,695 | B2 | 8/2017 | Leimbach et al. |
| 9,730,697 | B2 | 8/2017 | Morgan et al. |
| 9,730,717 | B2 | 8/2017 | Katsuki et al. |
| 9,731,410 | B2 | 8/2017 | Hirabayashi et al. |
| 9,733,663 | B2 | 8/2017 | Leimbach et al. |
| 9,737,297 | B2 | 8/2017 | Racenet et al. |
| 9,737,301 | B2 | 8/2017 | Baber et al. |
| 9,737,302 | B2 | 8/2017 | Shelton, IV et al. |
| 9,737,303 | B2 | 8/2017 | Shelton, IV et al. |
| 9,737,365 | B2 | 8/2017 | Hegeman et al. |
| 9,743,927 | B2 | 8/2017 | Whitman |
| 9,743,928 | B2 | 8/2017 | Shelton, IV et al. |
| 9,743,929 | B2 | 8/2017 | Leimbach et al. |
| D798,319 | S | 9/2017 | Bergstrand et al. |
| 9,750,498 | B2 | 9/2017 | Timm et al. |
| 9,750,499 | B2 | 9/2017 | Leimbach et al. |
| 9,750,501 | B2 | 9/2017 | Shelton, IV et al. |
| 9,750,502 | B2 | 9/2017 | Scirica et al. |
| 9,750,639 | B2 | 9/2017 | Barnes et al. |
| 9,757,123 | B2 | 9/2017 | Giordano et al. |
| 9,757,124 | B2 | 9/2017 | Schellin et al. |
| 9,757,126 | B2 | 9/2017 | Cappola |
| 9,757,128 | B2 | 9/2017 | Baber et al. |
| 9,757,129 | B2 | 9/2017 | Williams |
| 9,757,130 | B2 | 9/2017 | Shelton, IV |
| 9,763,662 | B2 | 9/2017 | Shelton, IV et al. |
| 9,763,668 | B2 | 9/2017 | Whitfield et al. |
| 9,770,245 | B2 | 9/2017 | Swayze et al. |
| 9,770,274 | B2 | 9/2017 | Pool et al. |
| D798,886 | S | 10/2017 | Prophete et al. |
| D800,742 | S | 10/2017 | Rhodes |
| D800,744 | S | 10/2017 | Jitkoff et al. |
| D800,766 | S | 10/2017 | Park et al. |
| D800,904 | S | 10/2017 | Leimbach et al. |
| 9,775,608 | B2 | 10/2017 | Aronhalt et al. |
| 9,775,609 | B2 | 10/2017 | Shelton, IV et al. |
| 9,775,610 | B2 | 10/2017 | Nicholas et al. |
| 9,775,611 | B2 | 10/2017 | Kostrzewski |
| 9,775,613 | B2 | 10/2017 | Shelton, IV et al. |
| 9,775,614 | B2 | 10/2017 | Shelton, IV et al. |
| 9,775,618 | B2 | 10/2017 | Bettuchi et al. |
| 9,775,635 | B2 | 10/2017 | Takei |
| 9,782,169 | B2 | 10/2017 | Kimsey et al. |
| 9,782,170 | B2 | 10/2017 | Zemlok et al. |
| 9,782,180 | B2 | 10/2017 | Smith et al. |
| 9,782,193 | B2 | 10/2017 | Thistle |
| 9,782,214 | B2 | 10/2017 | Houser et al. |
| 9,788,834 | B2 | 10/2017 | Schmid et al. |
| 9,788,835 | B2 | 10/2017 | Morgan et al. |
| 9,788,836 | B2 | 10/2017 | Overmyer et al. |
| 9,788,847 | B2 | 10/2017 | Jinno |
| 9,788,851 | B2 | 10/2017 | Dannaher et al. |
| 9,788,902 | B2 | 10/2017 | Inoue et al. |
| 9,795,379 | B2 | 10/2017 | Leimbach et al. |
| 9,795,380 | B2 | 10/2017 | Shelton, IV et al. |
| 9,795,381 | B2 | 10/2017 | Shelton, IV |
| 9,795,382 | B2 | 10/2017 | Shelton, IV |
| 9,795,383 | B2 | 10/2017 | Aldridge et al. |

(56) References Cited

U.S. PATENT DOCUMENTS 9,795,384 B2 10/2017 Weaner et al.
9,797,486 B2 10/2017 Zergiebel et al.
9,801,626 B2 10/2017 Parihar et al.
9,801,627 B2 10/2017 Harris et al.
9,801,628 B2 10/2017 Harris et al.
9,801,634 B2 10/2017 Shelton, IV et al.
9,802,033 B2 10/2017 Hibner et al.
9,804,618 B2 10/2017 Leimbach et al.
D803,234 S 11/2017 Day et al.
D803,235 S 11/2017 Markson et al.
D803,850 S 11/2017 Chang et al.
9,808,244 B2 11/2017 Leimbach et al.
9,808,246 B2 11/2017 Shelton, IV et al.
9,808,247 B2 11/2017 Shelton, IV et al.
9,808,248 B2 11/2017 Hoffman
9,808,249 B2 11/2017 Shelton, IV
9,814,460 B2 11/2017 Kimsey et al.
9,814,462 B2 11/2017 Woodard, Jr. et al.
9,814,463 B2 11/2017 Williams et al.
9,814,530 B2 11/2017 Weir et al.
9,814,561 B2 11/2017 Forsell
9,820,445 B2 11/2017 Simpson et al.
9,820,737 B2 11/2017 Beardsley et al.
9,820,738 B2 11/2017 Lytle, IV et al.
9,820,741 B2 11/2017 Kostrzewski
9,820,768 B2 11/2017 Gee et al.
9,825,455 B2 11/2017 Sandhu et al.
9,826,976 B2 11/2017 Parihar et al.
9,826,977 B2 11/2017 Leimbach et al.
9,826,978 B2 11/2017 Shelton, IV et al.
9,829,698 B2 11/2017 Haraguchi et al.
D806,108 S 12/2017 Day
9,833,236 B2 12/2017 Shelton, IV et al.
9,833,238 B2 12/2017 Baxter, III et al.
9,833,239 B2 12/2017 Yates et al.
9,833,241 B2 12/2017 Huitema et al.
9,833,242 B2 12/2017 Baxter, III et al.
9,839,420 B2 12/2017 Shelton, IV et al.
9,839,421 B2 12/2017 Zerkle et al.
9,839,422 B2 12/2017 Schellin et al.
9,839,423 B2 12/2017 Vendely et al.
9,839,427 B2 12/2017 Swayze et al.
9,839,428 B2 12/2017 Baxter, III et al.
9,839,429 B2 12/2017 Weisenburgh, II et al.
9,839,480 B2 12/2017 Pribanic et al.
9,844,368 B2 12/2017 Boudreaux et al.
9,844,369 B2 12/2017 Huitema et al.
9,844,372 B2 12/2017 Shelton, IV et al.
9,844,373 B2 12/2017 Swayze et al.
9,844,374 B2 12/2017 Lytle, IV et al.
9,844,375 B2 12/2017 Overmyer et al.
9,844,376 B2 12/2017 Baxter, III et al.
9,844,379 B2 12/2017 Shelton, IV et al.
9,848,871 B2 12/2017 Harris et al.
9,848,873 B2 12/2017 Shelton, IV
9,848,875 B2 12/2017 Aronhalt et al.
9,848,877 B2 12/2017 Shelton, IV et al.
9,855,039 B2 1/2018 Racenet et al.
9,855,040 B2 1/2018 Kostrzewski
9,855,662 B2 1/2018 Ruiz Morales et al.
9,861,261 B2 1/2018 Shahinian
9,861,359 B2 1/2018 Shelton, IV et al.
9,861,361 B2 1/2018 Aronhalt et al.
9,861,362 B2 1/2018 Whitman et al.
9,861,382 B2 1/2018 Smith et al.
9,861,446 B2 1/2018 Lang
9,867,612 B2 1/2018 Parihar et al.
9,867,618 B2 1/2018 Hall et al.
9,867,620 B2 1/2018 Fischvogt et al.
9,868,198 B2 1/2018 Nicholas et al.
9,872,682 B2 1/2018 Hess et al.
9,872,683 B2 1/2018 Hopkins et al.
9,872,684 B2 1/2018 Hall et al.
9,872,722 B2 1/2018 Lech
9,877,721 B2 1/2018 Schellin et al.
9,877,723 B2 1/2018 Hall et al.
D810,099 S 2/2018 Riedel
9,883,843 B2 2/2018 Garlow
9,883,860 B2 2/2018 Leimbach
9,883,861 B2 2/2018 Shelton, IV et al.
9,884,456 B2 2/2018 Schellin et al.
9,888,919 B2 2/2018 Leimbach et al.
9,888,921 B2 2/2018 Williams et al.
9,888,924 B2 2/2018 Ebersole et al.
9,889,230 B2 2/2018 Bennett et al.
9,895,147 B2 2/2018 Shelton, IV
9,895,148 B2 2/2018 Shelton, IV et al.
9,895,813 B2 2/2018 Blumenkranz et al.
9,901,339 B2 2/2018 Farascioni
9,901,341 B2 2/2018 Kostrzewski
9,901,342 B2 2/2018 Shelton, IV et al.
9,901,344 B2 2/2018 Moore et al.
9,901,345 B2 2/2018 Moore et al.
9,901,346 B2 2/2018 Moore et al.
9,901,406 B2 2/2018 State et al.
9,901,412 B2 2/2018 Lathrop et al.
D813,899 S 3/2018 Erant et al.
9,907,456 B2 3/2018 Miyoshi
9,907,553 B2 3/2018 Cole et al.
9,907,600 B2 3/2018 Stulen et al.
9,907,620 B2 3/2018 Shelton, IV et al.
9,913,642 B2 3/2018 Leimbach et al.
9,913,644 B2 3/2018 McCuen
9,913,646 B2 3/2018 Shelton, IV
9,913,647 B2 3/2018 Weisenburgh, II et al.
9,913,648 B2 3/2018 Shelton, IV et al.
9,913,694 B2 3/2018 Brisson
9,913,733 B2 3/2018 Piron et al.
9,918,704 B2 3/2018 Shelton, IV et al.
9,918,714 B2 3/2018 Gibbons, Jr.
9,918,715 B2 3/2018 Menn
9,918,716 B2 3/2018 Baxter, III et al.
9,918,717 B2 3/2018 Czernik
9,924,941 B2 3/2018 Burbank
9,924,942 B2 3/2018 Swayze et al.
9,924,944 B2 3/2018 Shelton, IV et al.
9,924,945 B2 3/2018 Zheng et al.
9,924,946 B2 3/2018 Vendely et al.
9,924,947 B2 3/2018 Shelton, IV et al.
9,924,961 B2 3/2018 Shelton, IV et al.
9,931,106 B2 4/2018 Au et al.
9,931,116 B2 4/2018 Racenet et al.
9,931,118 B2 4/2018 Shelton, IV et al.
9,936,949 B2 4/2018 Measamer et al.
9,936,950 B2 4/2018 Shelton, IV et al.
9,936,951 B2 4/2018 Hufnagel et al.
9,936,954 B2 4/2018 Shelton, IV et al.
9,937,626 B2 4/2018 Rockrohr
9,943,309 B2 4/2018 Shelton, IV et al.
9,943,310 B2 4/2018 Harris et al.
9,943,312 B2 4/2018 Posada et al.
D819,072 S 5/2018 Clediere
9,955,954 B2 5/2018 Destoumieux et al.
9,955,965 B2 5/2018 Chen et al.
9,955,966 B2 5/2018 Zergiebel
9,962,129 B2 5/2018 Jerebko et al.
9,962,158 B2 5/2018 Hall et al.
9,962,159 B2 5/2018 Heinrich et al.
9,962,161 B2 5/2018 Scheib et al.
9,968,354 B2 5/2018 Shelton, IV et al.
9,968,355 B2 5/2018 Shelton, IV et al.
9,968,356 B2 5/2018 Shelton, IV et al.
9,968,397 B2 5/2018 Taylor et al.
9,974,529 B2 5/2018 Shelton, IV et al.
9,974,538 B2 * 5/2018 Baxter, III ....... A61B 17/07292
9,974,539 B2 5/2018 Yates et al.
9,974,541 B2 5/2018 Calderoni
9,974,542 B2 5/2018 Hodgkinson
9,980,713 B2 5/2018 Aronhalt et al.
9,980,724 B2 5/2018 Farascioni et al.
9,980,729 B2 5/2018 Moore et al.
9,980,769 B2 5/2018 Trees et al.
D819,680 S 6/2018 Nguyen
D819,682 S 6/2018 Howard et al.

(56) References Cited

U.S. PATENT DOCUMENTS

| | | | |
|---|---|---|---|
| D819,684 | S | 6/2018 | Dart |
| D820,307 | S | 6/2018 | Jian et al. |
| D820,867 | S | 6/2018 | Dickens et al. |
| 9,987,000 | B2 | 6/2018 | Shelton, IV et al. |
| 9,987,003 | B2 | 6/2018 | Timm et al. |
| 9,987,006 | B2 | 6/2018 | Morgan et al. |
| 9,987,095 | B2 | 6/2018 | Chowaniec et al. |
| 9,987,099 | B2 | 6/2018 | Chen et al. |
| 9,993,248 | B2 | 6/2018 | Shelton, IV et al. |
| 9,993,258 | B2 | 6/2018 | Shelton, IV et al. |
| 9,999,408 | B2 | 6/2018 | Boudreaux et al. |
| 9,999,423 | B2 | 6/2018 | Schuckmann et al. |
| 9,999,426 | B2 | 6/2018 | Moore et al. |
| 9,999,431 | B2 | 6/2018 | Shelton, IV et al. |
| 9,999,472 | B2 | 6/2018 | Weir et al. |
| 10,004,497 | B2 | 6/2018 | Overmyer et al. |
| 10,004,498 | B2 | 6/2018 | Morgan et al. |
| 10,004,500 | B2 | 6/2018 | Shelton, IV et al. |
| 10,004,501 | B2 | 6/2018 | Shelton, IV et al. |
| 10,004,505 | B2 | 6/2018 | Moore et al. |
| 10,004,506 | B2 | 6/2018 | Shelton, IV et al. |
| D822,206 | S | 7/2018 | Shelton, IV et al. |
| 10,010,322 | B2 | 7/2018 | Shelton, IV et al. |
| 10,010,324 | B2 | 7/2018 | Huitema et al. |
| 10,013,049 | B2 | 7/2018 | Leimbach et al. |
| 10,016,199 | B2 | 7/2018 | Baber et al. |
| 10,022,125 | B2 | 7/2018 | (Prommersberger) Stopek et al. |
| 10,024,407 | B2 | 7/2018 | Aranyi et al. |
| 10,028,742 | B2 | 7/2018 | Shelton, IV et al. |
| 10,028,743 | B2 | 7/2018 | Shelton, IV et al. |
| 10,028,744 | B2 | 7/2018 | Shelton, IV et al. |
| 10,028,761 | B2 | 7/2018 | Leimbach et al. |
| 10,029,125 | B2 | 7/2018 | Shapiro et al. |
| 10,034,344 | B2 | 7/2018 | Yoshida |
| 10,034,668 | B2 | 7/2018 | Ebner |
| D826,405 | S | 8/2018 | Shelton, IV et al. |
| 10,039,440 | B2 | 8/2018 | Fenech et al. |
| 10,039,529 | B2 | 8/2018 | Kerr et al. |
| 10,039,532 | B2 | 8/2018 | Srinivas et al. |
| 10,039,545 | B2 | 8/2018 | Sadowski et al. |
| 10,041,822 | B2 | 8/2018 | Zemlok |
| 10,045,769 | B2 | 8/2018 | Aronhalt et al. |
| 10,045,776 | B2 | 8/2018 | Shelton, IV et al. |
| 10,045,778 | B2 | 8/2018 | Yates et al. |
| 10,045,779 | B2 | 8/2018 | Savage et al. |
| 10,045,781 | B2 | 8/2018 | Cropper et al. |
| 10,052,044 | B2 | 8/2018 | Shelton, IV et al. |
| 10,052,099 | B2 | 8/2018 | Morgan et al. |
| 10,052,100 | B2 | 8/2018 | Morgan et al. |
| 10,052,102 | B2 | 8/2018 | Baxter, III et al. |
| 10,052,104 | B2 | 8/2018 | Shelton, IV et al. |
| 10,052,164 | B2 | 8/2018 | Overmyer |
| 10,058,317 | B2 | 8/2018 | Fan et al. |
| 10,058,327 | B2 | 8/2018 | Weisenburgh, II et al. |
| 10,058,395 | B2 | 8/2018 | Devengenzo et al. |
| 10,058,963 | B2 | 8/2018 | Shelton, IV et al. |
| 10,064,620 | B2 | 9/2018 | Gettinger et al. |
| 10,064,621 | B2 | 9/2018 | Kerr et al. |
| 10,064,624 | B2 | 9/2018 | Shelton, IV et al. |
| 10,064,639 | B2 | 9/2018 | Ishida et al. |
| 10,064,649 | B2 | 9/2018 | Golebieski et al. |
| 10,064,688 | B2 | 9/2018 | Shelton, IV et al. |
| 10,070,861 | B2 | 9/2018 | Spivey et al. |
| 10,070,863 | B2 | 9/2018 | Swayze et al. |
| 10,071,452 | B2 | 9/2018 | Shelton, IV et al. |
| 10,076,325 | B2 | 9/2018 | Huang et al. |
| 10,076,326 | B2 | 9/2018 | Yates et al. |
| 10,076,340 | B2 | 9/2018 | Belagali et al. |
| D831,209 | S | 10/2018 | Huitema et al. |
| D831,676 | S | 10/2018 | Park et al. |
| D832,301 | S | 10/2018 | Smith |
| 10,085,624 | B2 | 10/2018 | Isoda et al. |
| 10,085,643 | B2 | 10/2018 | Bandic et al. |
| 10,085,728 | B2 | 10/2018 | Jogasaki et al. |
| 10,085,748 | B2 | 10/2018 | Morgan et al. |
| 10,085,749 | B2 | 10/2018 | Cappola et al. |
| 10,085,751 | B2 | 10/2018 | Overmyer et al. |
| 10,085,754 | B2 | 10/2018 | Sniffin et al. |
| 10,085,806 | B2 | 10/2018 | Hagn et al. |
| 10,092,292 | B2 | 10/2018 | Boudreaux et al. |
| 10,098,635 | B2 | 10/2018 | Burbank |
| 10,098,636 | B2 | 10/2018 | Shelton, IV et al. |
| 10,098,638 | B2 | 10/2018 | Viola et al. |
| 10,098,640 | B2 | 10/2018 | Bertolero et al. |
| 10,098,642 | B2 | 10/2018 | Baxter, III et al. |
| 10,099,303 | B2 | 10/2018 | Yoshida et al. |
| 10,101,861 | B2 | 10/2018 | Kiyoto |
| 10,105,128 | B2 | 10/2018 | Cooper et al. |
| 10,105,136 | B2 | 10/2018 | Yates et al. |
| 10,105,139 | B2 | 10/2018 | Yates et al. |
| 10,105,140 | B2 | 10/2018 | Malinouskas et al. |
| 10,106,932 | B2 | 10/2018 | Anderson et al. |
| 10,111,657 | B2 | 10/2018 | McCuen |
| 10,111,679 | B2 | 10/2018 | Baber et al. |
| 10,111,698 | B2 | 10/2018 | Scheib et al. |
| 10,111,702 | B2 | 10/2018 | Kostrzewski |
| 10,117,649 | B2 | 11/2018 | Baxter, III et al. |
| 10,117,652 | B2 | 11/2018 | Schmid et al. |
| 10,117,653 | B2 | 11/2018 | Leimbach et al. |
| 10,117,654 | B2 | 11/2018 | Ingmanson et al. |
| 10,123,798 | B2 | 11/2018 | Baxter, III et al. |
| 10,124,493 | B2 | 11/2018 | Rothfuss et al. |
| 10,130,352 | B2 | 11/2018 | Widenhouse et al. |
| 10,130,359 | B2 | 11/2018 | Hess et al. |
| 10,130,361 | B2 | 11/2018 | Yates et al. |
| 10,130,363 | B2 | 11/2018 | Huitema et al. |
| 10,130,366 | B2 | 11/2018 | Shelton, IV et al. |
| 10,130,367 | B2 | 11/2018 | Cappola et al. |
| 10,130,738 | B2 | 11/2018 | Shelton, IV et al. |
| 10,130,830 | B2 | 11/2018 | Miret Carceller et al. |
| 10,133,248 | B2 | 11/2018 | Fitzsimmons et al. |
| 10,135,242 | B2 | 11/2018 | Baber et al. |
| 10,136,879 | B2 | 11/2018 | Ross et al. |
| 10,136,887 | B2 | 11/2018 | Shelton, IV et al. |
| 10,136,889 | B2 | 11/2018 | Shelton, IV et al. |
| 10,136,890 | B2 | 11/2018 | Shelton, IV et al. |
| 10,136,891 | B2 | 11/2018 | Shelton, IV et al. |
| D835,659 | S | 12/2018 | Anzures et al. |
| D836,124 | S | 12/2018 | Fan |
| 10,143,474 | B2 | 12/2018 | Bucciaglia et al. |
| 10,149,679 | B2 | 12/2018 | Shelton, IV et al. |
| 10,149,680 | B2 | 12/2018 | Parihar et al. |
| 10,149,682 | B2 | 12/2018 | Shelton, IV et al. |
| 10,149,683 | B2 | 12/2018 | Smith et al. |
| 10,149,712 | B2 | 12/2018 | Manwaring et al. |
| 10,154,841 | B2 | 12/2018 | Weaner et al. |
| 10,159,482 | B2 | 12/2018 | Swayze et al. |
| 10,159,483 | B2 | 12/2018 | Beckman et al. |
| 10,163,589 | B2 | 12/2018 | Zergiebel et al. |
| D837,244 | S | 1/2019 | Kuo et al. |
| D837,245 | S | 1/2019 | Kuo et al. |
| 10,166,025 | B2 | 1/2019 | Leimbach et al. |
| 10,166,026 | B2 | 1/2019 | Shelton, IV et al. |
| 10,172,611 | B2 | 1/2019 | Shelton, IV et al. |
| 10,172,615 | B2 | 1/2019 | Marczyk et al. |
| 10,172,616 | B2 | 1/2019 | Murray et al. |
| 10,172,617 | B2 | 1/2019 | Shelton, IV et al. |
| 10,172,619 | B2 | 1/2019 | Harris et al. |
| 10,172,620 | B2 | 1/2019 | Harris et al. |
| 10,172,636 | B2 | 1/2019 | Stulen et al. |
| 10,175,127 | B2 | 1/2019 | Collins et al. |
| 10,178,992 | B2 | 1/2019 | Wise et al. |
| 10,180,463 | B2 | 1/2019 | Beckman et al. |
| 10,182,813 | B2 | 1/2019 | Leimbach et al. |
| 10,182,815 | B2 | 1/2019 | Williams et al. |
| 10,182,816 | B2 | 1/2019 | Shelton, IV et al. |
| 10,182,818 | B2 | 1/2019 | Hensel et al. |
| 10,182,819 | B2 | 1/2019 | Shelton, IV |
| 10,188,385 | B2 | 1/2019 | Kerr et al. |
| 10,188,393 | B2 | 1/2019 | Smith et al. |
| 10,188,394 | B2 | 1/2019 | Shelton, IV et al. |
| D839,900 | S | 2/2019 | Gan |
| D841,667 | S | 2/2019 | Coren |
| 10,194,801 | B2 | 2/2019 | Elhawary et al. |

(56) References Cited

U.S. PATENT DOCUMENTS

| | | | |
|---|---|---|---|
| 10,194,904 | B2 | 2/2019 | Viola et al. |
| 10,194,907 | B2 | 2/2019 | Marczyk et al. |
| 10,194,910 | B2 | 2/2019 | Shelton, IV et al. |
| 10,194,913 | B2 | 2/2019 | Nalagatla et al. |
| 10,194,976 | B2 | 2/2019 | Boudreaux |
| 10,194,992 | B2 | 2/2019 | Robinson |
| 10,201,348 | B2 | 2/2019 | Scheib et al. |
| 10,201,349 | B2 | 2/2019 | Leimbach et al. |
| 10,201,363 | B2 | 2/2019 | Shelton, IV |
| 10,201,364 | B2 | 2/2019 | Leimbach et al. |
| 10,201,365 | B2 | 2/2019 | Boudreaux et al. |
| 10,201,381 | B2 | 2/2019 | Zergiebel et al. |
| 10,206,605 | B2 | 2/2019 | Shelton, IV et al. |
| 10,206,676 | B2 | 2/2019 | Shelton, IV |
| 10,206,677 | B2 | 2/2019 | Harris et al. |
| 10,206,678 | B2 | 2/2019 | Shelton, IV et al. |
| 10,206,748 | B2 | 2/2019 | Burbank |
| 10,210,244 | B1 | 2/2019 | Branavan et al. |
| 10,211,586 | B2 | 2/2019 | Adams et al. |
| 10,213,198 | B2 | 2/2019 | Aronhalt et al. |
| 10,213,201 | B2 | 2/2019 | Shelton, IV et al. |
| 10,213,202 | B2 | 2/2019 | Flanagan et al. |
| 10,213,203 | B2 | 2/2019 | Swayze et al. |
| 10,213,262 | B2 | 2/2019 | Shelton, IV et al. |
| D842,328 | S | 3/2019 | Jian et al. |
| 10,219,811 | B2 | 3/2019 | Haider et al. |
| 10,219,832 | B2 | 3/2019 | Bagwell et al. |
| 10,220,522 | B2 | 3/2019 | Rockrohr |
| 10,226,239 | B2 | 3/2019 | Nicholas et al. |
| 10,226,249 | B2 | 3/2019 | Jaworek et al. |
| 10,226,250 | B2 | 3/2019 | Beckman et al. |
| 10,226,251 | B2 | 3/2019 | Scheib et al. |
| 10,226,274 | B2 | 3/2019 | Worrell et al. |
| 10,231,634 | B2 | 3/2019 | Zand et al. |
| 10,231,653 | B2 | 3/2019 | Bohm et al. |
| 10,231,734 | B2 | 3/2019 | Thompson et al. |
| 10,231,794 | B2 | 3/2019 | Shelton, IV et al. |
| 10,238,385 | B2 | 3/2019 | Yates et al. |
| 10,238,386 | B2 | 3/2019 | Overmyer et al. |
| 10,238,387 | B2 | 3/2019 | Yates et al. |
| 10,238,389 | B2 | 3/2019 | Yates et al. |
| 10,238,390 | B2 | 3/2019 | Harris et al. |
| 10,238,391 | B2 | 3/2019 | Leimbach et al. |
| D844,666 | S | 4/2019 | Espeleta et al. |
| D844,667 | S | 4/2019 | Espeleta et al. |
| D845,342 | S | 4/2019 | Espeleta et al. |
| 10,245,027 | B2 | 4/2019 | Shelton, IV et al. |
| 10,245,028 | B2 | 4/2019 | Shelton, IV et al. |
| 10,245,029 | B2 | 4/2019 | Hunter et al. |
| 10,245,030 | B2 | 4/2019 | Hunter et al. |
| 10,245,032 | B2 | 4/2019 | Shelton, IV |
| 10,245,033 | B2 | 4/2019 | Overmyer et al. |
| 10,245,034 | B2 | 4/2019 | Shelton, IV et al. |
| 10,245,035 | B2 | 4/2019 | Swayze et al. |
| 10,245,058 | B2 | 4/2019 | Omori et al. |
| 10,251,648 | B2 | 4/2019 | Harris et al. |
| 10,251,649 | B2 | 4/2019 | Schellin et al. |
| 10,251,725 | B2 | 4/2019 | Valentine et al. |
| 10,258,322 | B2 | 4/2019 | Fanton et al. |
| 10,258,330 | B2 | 4/2019 | Shelton, IV et al. |
| 10,258,331 | B2 | 4/2019 | Shelton, IV et al. |
| 10,258,332 | B2 | 4/2019 | Schmid et al. |
| 10,258,333 | B2 | 4/2019 | Shelton, IV et al. |
| 10,258,336 | B2 | 4/2019 | Baxter, III et al. |
| 10,258,418 | B2 | 4/2019 | Shelton, IV et al. |
| 10,264,797 | B2 | 4/2019 | Zhang et al. |
| 10,265,065 | B2 | 4/2019 | Shelton, IV et al. |
| 10,265,067 | B2 | 4/2019 | Yates et al. |
| 10,265,068 | B2 | 4/2019 | Harris et al. |
| 10,265,072 | B2 | 4/2019 | Shelton, IV et al. |
| 10,265,073 | B2 | 4/2019 | Scheib et al. |
| 10,265,074 | B2 | 4/2019 | Shelton, IV et al. |
| 10,265,090 | B2 | 4/2019 | Ingmanson et al. |
| 10,271,844 | B2 | 4/2019 | Valentine et al. |
| 10,271,845 | B2 | 4/2019 | Shelton, IV |
| 10,271,846 | B2 | 4/2019 | Shelton, IV et al. |
| 10,271,849 | B2 | 4/2019 | Vendely et al. |
| 10,271,851 | B2 | 4/2019 | Shelton, IV et al. |
| D847,989 | S | 5/2019 | Shelton, IV et al. |
| D848,473 | S | 5/2019 | Zhu et al. |
| D849,046 | S | 5/2019 | Kuo et al. |
| 10,278,696 | B2 | 5/2019 | Gurumurthy et al. |
| 10,278,697 | B2 | 5/2019 | Shelton, IV et al. |
| 10,278,702 | B2 | 5/2019 | Shelton, IV et al. |
| 10,278,703 | B2 | 5/2019 | Nativ et al. |
| 10,278,707 | B2 | 5/2019 | Thompson et al. |
| 10,278,722 | B2 | 5/2019 | Shelton, IV et al. |
| 10,278,780 | B2 | 5/2019 | Shelton, IV |
| 10,285,694 | B2 | 5/2019 | Viola et al. |
| 10,285,695 | B2 | 5/2019 | Jaworek et al. |
| 10,285,699 | B2 | 5/2019 | Vendely et al. |
| 10,285,705 | B2 | 5/2019 | Shelton, IV et al. |
| 10,292,701 | B2 | 5/2019 | Scheib et al. |
| 10,292,704 | B2 | 5/2019 | Harris et al. |
| 10,292,707 | B2 | 5/2019 | Shelton, IV et al. |
| 10,293,100 | B2 | 5/2019 | Shelton, IV et al. |
| 10,293,553 | B2 | 5/2019 | Racenet et al. |
| 10,299,787 | B2 | 5/2019 | Shelton, IV |
| 10,299,788 | B2 | 5/2019 | Heinrich et al. |
| 10,299,792 | B2 | 5/2019 | Huitema et al. |
| 10,299,817 | B2 | 5/2019 | Shelton, IV et al. |
| 10,299,818 | B2 | 5/2019 | Riva |
| 10,299,878 | B2 | 5/2019 | Shelton, IV et al. |
| D850,617 | S | 6/2019 | Shelton, IV et al. |
| D851,676 | S | 6/2019 | Foss et al. |
| D851,762 | S | 6/2019 | Shelton, IV et al. |
| 10,307,159 | B2 | 6/2019 | Harris et al. |
| 10,307,160 | B2 | 6/2019 | Vendely et al. |
| 10,307,161 | B2 | 6/2019 | Jankowski |
| 10,307,163 | B2 | 6/2019 | Moore et al. |
| 10,307,170 | B2 | 6/2019 | Parfett et al. |
| 10,307,202 | B2 | 6/2019 | Smith et al. |
| 10,314,559 | B2 | 6/2019 | Razzaque et al. |
| 10,314,577 | B2 | 6/2019 | Laurent et al. |
| 10,314,582 | B2 | 6/2019 | Shelton, IV et al. |
| 10,314,587 | B2 | 6/2019 | Harris et al. |
| 10,314,588 | B2 | 6/2019 | Turner et al. |
| 10,314,589 | B2 | 6/2019 | Shelton, IV et al. |
| 10,314,590 | B2 | 6/2019 | Shelton, IV et al. |
| 10,315,566 | B2 | 6/2019 | Choi et al. |
| 10,321,907 | B2 | 6/2019 | Shelton, IV et al. |
| 10,321,909 | B2 | 6/2019 | Shelton, IV et al. |
| 10,321,927 | B2 | 6/2019 | Hinman |
| 10,327,743 | B2 | 6/2019 | St. Goar et al. |
| 10,327,764 | B2 | 6/2019 | Harris et al. |
| 10,327,765 | B2 | 6/2019 | Timm et al. |
| 10,327,767 | B2 | 6/2019 | Shelton, IV et al. |
| 10,327,769 | B2 | 6/2019 | Overmyer et al. |
| 10,327,776 | B2 | 6/2019 | Harris et al. |
| 10,327,777 | B2 | 6/2019 | Harris et al. |
| D854,032 | S | 7/2019 | Jones et al. |
| D854,151 | S | 7/2019 | Shelton, IV et al. |
| 10,335,144 | B2 | 7/2019 | Shelton, IV et al. |
| 10,335,145 | B2 | 7/2019 | Harris et al. |
| 10,335,147 | B2 | 7/2019 | Rector et al. |
| 10,335,148 | B2 | 7/2019 | Shelton, IV et al. |
| 10,335,149 | B2 | 7/2019 | Baxter, III et al. |
| 10,335,150 | B2 | 7/2019 | Shelton, IV |
| 10,335,151 | B2 | 7/2019 | Shelton, IV et al. |
| 10,337,148 | B2 | 7/2019 | Rouse et al. |
| 10,342,533 | B2 | 7/2019 | Shelton, IV et al. |
| 10,342,535 | B2 | 7/2019 | Scheib et al. |
| 10,342,541 | B2 | 7/2019 | Shelton, IV et al. |
| 10,342,543 | B2 | 7/2019 | Shelton, IV et al. |
| 10,342,623 | B2 | 7/2019 | Huelman et al. |
| 10,349,939 | B2 | 7/2019 | Shelton, IV et al. |
| 10,357,246 | B2 | 7/2019 | Shelton, IV et al. |
| 10,357,247 | B2 | 7/2019 | Shelton, IV et al. |
| 10,357,248 | B2 | 7/2019 | Dalessandro et al. |
| 10,357,252 | B2 | 7/2019 | Harris et al. |
| 10,363,031 | B2 | 7/2019 | Alexander, III et al. |
| 10,363,033 | B2 | 7/2019 | Timm et al. |
| 10,363,036 | B2 | 7/2019 | Yates et al. |
| 10,363,037 | B2 | 7/2019 | Aronhalt et al. |

(56) References Cited

U.S. PATENT DOCUMENTS

| | | | |
|---|---|---|---|
| 10,363,045 | B2 | 7/2019 | Whitfield et al. |
| D855,634 | S | 8/2019 | Kim |
| D856,359 | S | 8/2019 | Huang et al. |
| 10,368,838 | B2 | 8/2019 | Williams et al. |
| 10,368,861 | B2 | 8/2019 | Baxter, III et al. |
| 10,368,863 | B2 | 8/2019 | Timm et al. |
| 10,368,864 | B2 | 8/2019 | Harris et al. |
| 10,368,865 | B2 | 8/2019 | Harris et al. |
| 10,368,867 | B2 | 8/2019 | Harris et al. |
| 10,368,892 | B2 | 8/2019 | Stulen et al. |
| 10,376,262 | B2 | 8/2019 | Zemlok et al. |
| 10,376,263 | B2 | 8/2019 | Morgan et al. |
| 10,383,626 | B2 | 8/2019 | Soltz |
| 10,383,628 | B2 | 8/2019 | Kang et al. |
| 10,383,629 | B2 | 8/2019 | Ross et al. |
| 10,383,630 | B2 | 8/2019 | Shelton, IV et al. |
| 10,383,633 | B2 | 8/2019 | Shelton, IV et al. |
| 10,383,634 | B2 | 8/2019 | Shelton, IV et al. |
| 10,390,823 | B2 | 8/2019 | Shelton, IV et al. |
| 10,390,825 | B2 | 8/2019 | Shelton, IV et al. |
| 10,390,828 | B2 | 8/2019 | Vendely et al. |
| 10,390,829 | B2 | 8/2019 | Eckert et al. |
| 10,390,830 | B2 | 8/2019 | Schulz |
| 10,390,841 | B2 | 8/2019 | Shelton, IV et al. |
| 10,390,897 | B2 | 8/2019 | Kostrzewski |
| D860,219 | S | 9/2019 | Rasmussen et al. |
| 10,398,433 | B2 | 9/2019 | Boudreaux et al. |
| 10,398,434 | B2 | 9/2019 | Shelton, IV et al. |
| 10,398,436 | B2 | 9/2019 | Shelton, IV et al. |
| 10,405,854 | B2 | 9/2019 | Schmid et al. |
| 10,405,857 | B2 | 9/2019 | Shelton, IV et al. |
| 10,405,859 | B2 | 9/2019 | Harris et al. |
| 10,405,863 | B2 | 9/2019 | Wise et al. |
| 10,405,914 | B2 | 9/2019 | Manwaring et al. |
| 10,405,932 | B2 | 9/2019 | Overmyer |
| 10,413,291 | B2 | 9/2019 | Worthington et al. |
| 10,413,293 | B2 | 9/2019 | Shelton, IV et al. |
| 10,413,294 | B2 | 9/2019 | Shelton, IV et al. |
| 10,413,297 | B2 | 9/2019 | Harris et al. |
| 10,413,370 | B2 | 9/2019 | Yates et al. |
| 10,413,373 | B2 | 9/2019 | Yates et al. |
| 10,420,548 | B2 | 9/2019 | Whitman et al. |
| 10,420,549 | B2 | 9/2019 | Yates et al. |
| 10,420,550 | B2 | 9/2019 | Shelton, IV |
| 10,420,552 | B2 | 9/2019 | Shelton, IV et al. |
| 10,420,553 | B2 | 9/2019 | Shelton, IV et al. |
| 10,420,555 | B2 | 9/2019 | Shelton, IV et al. |
| 10,420,558 | B2 | 9/2019 | Nalagatla et al. |
| 10,420,559 | B2 | 9/2019 | Marczyk et al. |
| 10,420,560 | B2 | 9/2019 | Shelton, IV et al. |
| 10,420,561 | B2 | 9/2019 | Shelton, IV et al. |
| 10,420,577 | B2 | 9/2019 | Chowaniec et al. |
| D861,707 | S | 10/2019 | Yang |
| 10,426,463 | B2 | 10/2019 | Shelton, IV et al. |
| 10,426,467 | B2 | 10/2019 | Miller et al. |
| 10,426,468 | B2 | 10/2019 | Contini et al. |
| 10,426,469 | B2 | 10/2019 | Shelton, IV et al. |
| 10,426,471 | B2 | 10/2019 | Shelton, IV et al. |
| 10,426,476 | B2 | 10/2019 | Harris et al. |
| 10,426,477 | B2 | 10/2019 | Harris et al. |
| 10,426,478 | B2 | 10/2019 | Shelton, IV et al. |
| 10,426,481 | B2 | 10/2019 | Aronhalt et al. |
| 10,433,837 | B2 | 10/2019 | Worthington et al. |
| 10,433,839 | B2 | 10/2019 | Scheib et al. |
| 10,433,840 | B2 | 10/2019 | Shelton, IV et al. |
| 10,433,844 | B2 | 10/2019 | Shelton, IV et al. |
| 10,433,845 | B2 | 10/2019 | Baxter, III et al. |
| 10,433,846 | B2 | 10/2019 | Vendely et al. |
| 10,433,849 | B2 | 10/2019 | Shelton, IV et al. |
| 10,433,918 | B2 | 10/2019 | Shelton, IV et al. |
| 10,441,279 | B2 | 10/2019 | Shelton, IV et al. |
| 10,441,280 | B2 | 10/2019 | Timm et al. |
| 10,441,281 | B2 | 10/2019 | Shelton, IV et al. |
| 10,441,285 | B2 | 10/2019 | Shelton, IV et al. |
| 10,441,286 | B2 | 10/2019 | Shelton, IV et al. |
| 10,441,345 | B2 | 10/2019 | Aldridge et al. |
| 10,441,369 | B2 | 10/2019 | Shelton, IV et al. |
| 10,448,948 | B2 | 10/2019 | Shelton, IV et al. |
| 10,448,950 | B2 | 10/2019 | Shelton, IV et al. |
| 10,448,952 | B2 | 10/2019 | Shelton, IV et al. |
| 10,456,122 | B2 | 10/2019 | Koltz et al. |
| 10,456,132 | B2 | 10/2019 | Gettinger et al. |
| 10,456,133 | B2 | 10/2019 | Yates et al. |
| 10,456,137 | B2 | 10/2019 | Vendely et al. |
| 10,456,140 | B2 | 10/2019 | Shelton, IV et al. |
| 10,463,367 | B2 | 11/2019 | Kostrzewski et al. |
| 10,463,369 | B2 | 11/2019 | Shelton, IV et al. |
| 10,463,370 | B2 | 11/2019 | Yates et al. |
| 10,463,372 | B2 | 11/2019 | Shelton, IV et al. |
| 10,463,373 | B2 | 11/2019 | Mozdzierz et al. |
| 10,463,382 | B2 | 11/2019 | Ingmanson et al. |
| 10,463,383 | B2 | 11/2019 | Shelton, IV et al. |
| 10,463,384 | B2 | 11/2019 | Shelton, IV et al. |
| 10,470,762 | B2 | 11/2019 | Leimbach et al. |
| 10,470,763 | B2 | 11/2019 | Yates et al. |
| 10,470,764 | B2 | 11/2019 | Baxter, III et al. |
| 10,470,768 | B2 | 11/2019 | Harris et al. |
| 10,470,769 | B2 | 11/2019 | Shelton, IV et al. |
| 10,471,576 | B2 | 11/2019 | Totsu |
| 10,471,607 | B2 | 11/2019 | Butt et al. |
| 10,478,181 | B2 | 11/2019 | Shelton, IV et al. |
| 10,478,182 | B2 | 11/2019 | Taylor |
| 10,478,188 | B2 | 11/2019 | Harris et al. |
| 10,478,189 | B2 | 11/2019 | Bear et al. |
| 10,478,190 | B2 | 11/2019 | Miller et al. |
| 10,485,536 | B2 | 11/2019 | Ming et al. |
| 10,485,537 | B2 | 11/2019 | Yates et al. |
| 10,485,539 | B2 | 11/2019 | Shelton, IV et al. |
| 10,485,541 | B2 | 11/2019 | Shelton, IV et al. |
| 10,485,542 | B2 | 11/2019 | Shelton, IV et al. |
| 10,485,543 | B2 | 11/2019 | Shelton, IV et al. |
| 10,485,546 | B2 | 11/2019 | Shelton, IV et al. |
| 10,485,547 | B2 | 11/2019 | Shelton, IV et al. |
| D869,655 | S | 12/2019 | Shelton, IV et al. |
| 10,492,783 | B2 | 12/2019 | Shelton, IV et al. |
| 10,492,785 | B2 | 12/2019 | Overmyer et al. |
| 10,492,787 | B2 | 12/2019 | Smith et al. |
| 10,492,814 | B2 | 12/2019 | Snow et al. |
| 10,492,847 | B2 | 12/2019 | Godara et al. |
| 10,492,851 | B2 | 12/2019 | Hughett, Sr. et al. |
| 10,498,269 | B2 | 12/2019 | Zemlok et al. |
| 10,499,890 | B2 | 12/2019 | Shelton, IV et al. |
| 10,499,914 | B2 | 12/2019 | Huang et al. |
| 10,499,918 | B2 | 12/2019 | Schellin et al. |
| 10,500,309 | B2 | 12/2019 | Shah et al. |
| 2001/0000531 | A1 | 4/2001 | Casscells et al. |
| 2001/0025183 | A1 | 9/2001 | Shahidi |
| 2001/0025184 | A1 | 9/2001 | Messerly |
| 2001/0034530 | A1 | 10/2001 | Malackowski et al. |
| 2002/0014510 | A1 | 2/2002 | Richter et al. |
| 2002/0022810 | A1 | 2/2002 | Urich |
| 2002/0022836 | A1 | 2/2002 | Goble et al. |
| 2002/0022861 | A1 | 2/2002 | Jacobs et al. |
| 2002/0029032 | A1 | 3/2002 | Arkin |
| 2002/0029036 | A1 | 3/2002 | Goble et al. |
| 2002/0042620 | A1 | 4/2002 | Julian et al. |
| 2002/0087048 | A1 | 7/2002 | Brock et al. |
| 2002/0091374 | A1 | 7/2002 | Cooper |
| 2002/0095175 | A1 | 7/2002 | Brock et al. |
| 2002/0103494 | A1 | 8/2002 | Pacey |
| 2002/0116063 | A1 | 8/2002 | Giannetti et al. |
| 2002/0117534 | A1 | 8/2002 | Green et al. |
| 2002/0127265 | A1 | 9/2002 | Bowman et al. |
| 2002/0128633 | A1 | 9/2002 | Brock et al. |
| 2002/0134811 | A1 | 9/2002 | Napier et al. |
| 2002/0135474 | A1 | 9/2002 | Sylliassen |
| 2002/0143340 | A1 | 10/2002 | Kaneko |
| 2002/0151770 | A1 | 10/2002 | Noll et al. |
| 2002/0158593 | A1 | 10/2002 | Henderson et al. |
| 2002/0185514 | A1 | 12/2002 | Adams et al. |
| 2002/0188170 | A1 | 12/2002 | Santamore et al. |
| 2002/0188287 | A1 | 12/2002 | Zvuloni et al. |
| 2003/0009193 | A1 | 1/2003 | Corsaro |
| 2003/0011245 | A1 | 1/2003 | Fiebig |

(56) References Cited

U.S. PATENT DOCUMENTS

| | | | |
|---|---|---|---|
| 2003/0012805 A1 | 1/2003 | Chen et al. | |
| 2003/0040670 A1 | 2/2003 | Govari | |
| 2003/0045835 A1 | 3/2003 | Anderson et al. | |
| 2003/0066858 A1 | 4/2003 | Holgersson | |
| 2003/0078647 A1 | 4/2003 | Vallana et al. | |
| 2003/0083648 A1 | 5/2003 | Wang et al. | |
| 2003/0084983 A1 | 5/2003 | Rangachari et al. | |
| 2003/0093103 A1 | 5/2003 | Malackowski et al. | |
| 2003/0094356 A1 | 5/2003 | Waldron | |
| 2003/0096158 A1 | 5/2003 | Takano et al. | |
| 2003/0114851 A1 | 6/2003 | Truckai et al. | |
| 2003/0121586 A1 | 7/2003 | Mitra et al. | |
| 2003/0139741 A1 | 7/2003 | Goble et al. | |
| 2003/0149406 A1* | 8/2003 | Martineau ............ | A61K 9/7023 604/304 |
| 2003/0153908 A1 | 8/2003 | Goble et al. | |
| 2003/0153968 A1 | 8/2003 | Geis et al. | |
| 2003/0163085 A1 | 8/2003 | Tanner et al. | |
| 2003/0164172 A1 | 9/2003 | Chumas et al. | |
| 2003/0181900 A1 | 9/2003 | Long | |
| 2003/0190584 A1 | 10/2003 | Heasley | |
| 2003/0195387 A1 | 10/2003 | Kortenbach et al. | |
| 2003/0205029 A1 | 11/2003 | Chapolini et al. | |
| 2003/0212005 A1 | 11/2003 | Petito et al. | |
| 2003/0216732 A1 | 11/2003 | Truckai et al. | |
| 2003/0236505 A1 | 12/2003 | Bonadio et al. | |
| 2004/0006335 A1 | 1/2004 | Garrison | |
| 2004/0006340 A1 | 1/2004 | Latterell et al. | |
| 2004/0007608 A1 | 1/2004 | Ehrenfels et al. | |
| 2004/0024457 A1 | 2/2004 | Boyce et al. | |
| 2004/0028502 A1 | 2/2004 | Cummins | |
| 2004/0030333 A1 | 2/2004 | Goble | |
| 2004/0034357 A1 | 2/2004 | Beane et al. | |
| 2004/0044295 A1 | 3/2004 | Reinert et al. | |
| 2004/0044364 A1 | 3/2004 | DeVries et al. | |
| 2004/0049121 A1 | 3/2004 | Yaron | |
| 2004/0049172 A1 | 3/2004 | Root et al. | |
| 2004/0059362 A1 | 3/2004 | Knodel et al. | |
| 2004/0068161 A1 | 4/2004 | Couvillon | |
| 2004/0068224 A1 | 4/2004 | Couvillon et al. | |
| 2004/0068307 A1 | 4/2004 | Goble | |
| 2004/0070369 A1 | 4/2004 | Sakakibara | |
| 2004/0073222 A1 | 4/2004 | Koseki | |
| 2004/0078037 A1 | 4/2004 | Batchelor et al. | |
| 2004/0082952 A1 | 4/2004 | Dycus et al. | |
| 2004/0085180 A1 | 5/2004 | Juang | |
| 2004/0093024 A1 | 5/2004 | Lousararian et al. | |
| 2004/0098040 A1 | 5/2004 | Taniguchi et al. | |
| 2004/0101822 A1 | 5/2004 | Wiesner et al. | |
| 2004/0102783 A1 | 5/2004 | Sutterlin et al. | |
| 2004/0108357 A1 | 6/2004 | Milliman et al. | |
| 2004/0110439 A1 | 6/2004 | Chaikof et al. | |
| 2004/0115022 A1 | 6/2004 | Albertson et al. | |
| 2004/0116952 A1 | 6/2004 | Sakurai et al. | |
| 2004/0119185 A1 | 6/2004 | Chen | |
| 2004/0122419 A1 | 6/2004 | Neuberger | |
| 2004/0122423 A1 | 6/2004 | Dycus et al. | |
| 2004/0133095 A1 | 7/2004 | Dunki-Jacobs et al. | |
| 2004/0133189 A1 | 7/2004 | Sakurai | |
| 2004/0143297 A1 | 7/2004 | Ramsey | |
| 2004/0147909 A1 | 7/2004 | Johnston et al. | |
| 2004/0153100 A1 | 8/2004 | Ahlberg et al. | |
| 2004/0158261 A1 | 8/2004 | Vu | |
| 2004/0164123 A1 | 8/2004 | Racenet et al. | |
| 2004/0166169 A1 | 8/2004 | Malaviya et al. | |
| 2004/0167572 A1 | 8/2004 | Roth et al. | |
| 2004/0181219 A1 | 9/2004 | Goble et al. | |
| 2004/0193189 A1 | 9/2004 | Kortenbach et al. | |
| 2004/0197367 A1 | 10/2004 | Rezania et al. | |
| 2004/0199181 A1 | 10/2004 | Knodel et al. | |
| 2004/0204735 A1 | 10/2004 | Shiroff et al. | |
| 2004/0218451 A1 | 11/2004 | Said et al. | |
| 2004/0222268 A1 | 11/2004 | Bilotti et al. | |
| 2004/0225186 A1 | 11/2004 | Horne et al. | |
| 2004/0232201 A1 | 11/2004 | Wenchell et al. | |
| 2004/0236352 A1 | 11/2004 | Wang et al. | |
| 2004/0243147 A1 | 12/2004 | Lipow | |
| 2004/0243151 A1 | 12/2004 | Demmy et al. | |
| 2004/0243163 A1 | 12/2004 | Casiano et al. | |
| 2004/0247415 A1 | 12/2004 | Mangone | |
| 2004/0249366 A1 | 12/2004 | Kunz | |
| 2004/0254455 A1 | 12/2004 | Iddan | |
| 2004/0254566 A1 | 12/2004 | Plicchi et al. | |
| 2004/0254590 A1 | 12/2004 | Hoffman et al. | |
| 2004/0260315 A1 | 12/2004 | Deli et al. | |
| 2004/0267310 A1 | 12/2004 | Racenet et al. | |
| 2005/0010158 A1 | 1/2005 | Brugger et al. | |
| 2005/0010213 A1 | 1/2005 | Stad et al. | |
| 2005/0021078 A1 | 1/2005 | Vleugels et al. | |
| 2005/0032511 A1 | 2/2005 | Malone et al. | |
| 2005/0033352 A1 | 2/2005 | Zepf et al. | |
| 2005/0051163 A1 | 3/2005 | Deem et al. | |
| 2005/0054946 A1 | 3/2005 | Krzyzanowski | |
| 2005/0057225 A1 | 3/2005 | Marquet | |
| 2005/0058890 A1 | 3/2005 | Brazell et al. | |
| 2005/0059997 A1 | 3/2005 | Bauman et al. | |
| 2005/0070929 A1 | 3/2005 | Dalessandro et al. | |
| 2005/0075561 A1 | 4/2005 | Golden | |
| 2005/0080342 A1 | 4/2005 | Gilreath et al. | |
| 2005/0085693 A1 | 4/2005 | Belson et al. | |
| 2005/0090817 A1 | 4/2005 | Phan | |
| 2005/0096683 A1 | 5/2005 | Ellins et al. | |
| 2005/0116673 A1 | 6/2005 | Carl et al. | |
| 2005/0124855 A1 | 6/2005 | Jaffe et al. | |
| 2005/0125897 A1 | 6/2005 | Wyslucha et al. | |
| 2005/0130682 A1 | 6/2005 | Takara et al. | |
| 2005/0131173 A1 | 6/2005 | McDaniel et al. | |
| 2005/0131211 A1 | 6/2005 | Bayley et al. | |
| 2005/0131390 A1 | 6/2005 | Heinrich et al. | |
| 2005/0131436 A1 | 6/2005 | Johnston et al. | |
| 2005/0131457 A1 | 6/2005 | Douglas et al. | |
| 2005/0137454 A1 | 6/2005 | Saadat et al. | |
| 2005/0137455 A1 | 6/2005 | Ewers et al. | |
| 2005/0139636 A1 | 6/2005 | Schwemberger et al. | |
| 2005/0143759 A1 | 6/2005 | Kelly | |
| 2005/0143769 A1 | 6/2005 | White et al. | |
| 2005/0145671 A1 | 7/2005 | Viola | |
| 2005/0150928 A1 | 7/2005 | Kameyama et al. | |
| 2005/0154258 A1 | 7/2005 | Tartaglia et al. | |
| 2005/0154406 A1 | 7/2005 | Bombard et al. | |
| 2005/0159778 A1 | 7/2005 | Heinrich et al. | |
| 2005/0165419 A1 | 7/2005 | Sauer et al. | |
| 2005/0169974 A1 | 8/2005 | Tenerz et al. | |
| 2005/0171522 A1 | 8/2005 | Christopherson | |
| 2005/0177176 A1 | 8/2005 | Gerbi et al. | |
| 2005/0177181 A1 | 8/2005 | Kagan et al. | |
| 2005/0177249 A1 | 8/2005 | Kladakis et al. | |
| 2005/0182298 A1 | 8/2005 | Ikeda et al. | |
| 2005/0182443 A1 | 8/2005 | Jonn et al. | |
| 2005/0184121 A1 | 8/2005 | Heinrich | |
| 2005/0186240 A1 | 8/2005 | Ringeisen et al. | |
| 2005/0187545 A1 | 8/2005 | Hooven et al. | |
| 2005/0203550 A1 | 9/2005 | Laufer et al. | |
| 2005/0209614 A1 | 9/2005 | Fenter et al. | |
| 2005/0216055 A1 | 9/2005 | Scirica et al. | |
| 2005/0222587 A1 | 10/2005 | Jinno et al. | |
| 2005/0222611 A1 | 10/2005 | Weitkamp | |
| 2005/0222616 A1 | 10/2005 | Rethy et al. | |
| 2005/0222665 A1 | 10/2005 | Aranyi | |
| 2005/0228224 A1 | 10/2005 | Okada et al. | |
| 2005/0228446 A1 | 10/2005 | Mooradian et al. | |
| 2005/0230453 A1 | 10/2005 | Viola | |
| 2005/0240178 A1 | 10/2005 | Morley et al. | |
| 2005/0245965 A1 | 11/2005 | Orban, III et al. | |
| 2005/0246881 A1 | 11/2005 | Kelly et al. | |
| 2005/0251063 A1 | 11/2005 | Basude | |
| 2005/0256452 A1 | 11/2005 | DeMarchi et al. | |
| 2005/0261676 A1 | 11/2005 | Hall et al. | |
| 2005/0263563 A1 | 12/2005 | Racenet et al. | |
| 2005/0267455 A1 | 12/2005 | Eggers et al. | |
| 2005/0274034 A1 | 12/2005 | Hayashida et al. | |
| 2005/0283188 A1 | 12/2005 | Loshakove et al. | |
| 2006/0008787 A1 | 1/2006 | Hayman et al. | |
| 2006/0015009 A1 | 1/2006 | Jaffe et al. | |

(56) References Cited

U.S. PATENT DOCUMENTS

2006/0020258 A1 1/2006 Strauss et al.
2006/0020336 A1 1/2006 Liddicoat
2006/0025812 A1 2/2006 Shelton
2006/0041188 A1 2/2006 Dirusso et al.
2006/0047275 A1 3/2006 Goble
2006/0049229 A1 3/2006 Milliman et al.
2006/0052824 A1 3/2006 Ransick et al.
2006/0052825 A1 3/2006 Ransick et al.
2006/0064086 A1 3/2006 Odom
2006/0079735 A1 4/2006 Martone et al.
2006/0079879 A1 4/2006 Faller et al.
2006/0086032 A1 4/2006 Valencic et al.
2006/0087746 A1 4/2006 Lipow
2006/0089535 A1 4/2006 Raz et al.
2006/0097699 A1 5/2006 Kamenoff
2006/0100643 A1 5/2006 Laufer et al.
2006/0100649 A1 5/2006 Hart
2006/0111711 A1 5/2006 Goble
2006/0111723 A1 5/2006 Chapolini et al.
2006/0116634 A1 6/2006 Shachar
2006/0142772 A1 6/2006 Ralph et al.
2006/0154546 A1 7/2006 Murphy et al.
2006/0161050 A1 7/2006 Butler et al.
2006/0161185 A1 7/2006 Saadat et al.
2006/0167471 A1 7/2006 Phillips
2006/0173290 A1 8/2006 Lavallee et al.
2006/0173470 A1 8/2006 Oray et al.
2006/0176031 A1 8/2006 Forman et al.
2006/0178556 A1 8/2006 Hasser et al.
2006/0180633 A1 8/2006 Emmons
2006/0180634 A1 8/2006 Shelton et al.
2006/0185682 A1 8/2006 Marczyk
2006/0199999 A1 9/2006 Ikeda et al.
2006/0201989 A1 9/2006 Ojeda
2006/0206100 A1 9/2006 Eskridge et al.
2006/0217729 A1 9/2006 Eskridge et al.
2006/0235368 A1 10/2006 Oz
2006/0241666 A1 10/2006 Briggs et al.
2006/0244460 A1 11/2006 Weaver
2006/0252990 A1 11/2006 Kubach
2006/0252993 A1 11/2006 Freed et al.
2006/0258904 A1 11/2006 Stefanchik et al.
2006/0259073 A1 11/2006 Miyamoto et al.
2006/0261763 A1 11/2006 Iott et al.
2006/0263444 A1 11/2006 Ming et al.
2006/0264831 A1 11/2006 Skwarek et al.
2006/0264929 A1 11/2006 Goble et al.
2006/0271042 A1 11/2006 Latterell et al.
2006/0271102 A1 11/2006 Bosshard et al.
2006/0282064 A1 12/2006 Shimizu et al.
2006/0284730 A1 12/2006 Schmid et al.
2006/0287576 A1 12/2006 Tsuji et al.
2006/0289602 A1 12/2006 Wales et al.
2006/0291981 A1 12/2006 Viola et al.
2007/0009570 A1 1/2007 Kim et al.
2007/0010702 A1 1/2007 Wang et al.
2007/0010838 A1 1/2007 Shelton et al.
2007/0016235 A1 1/2007 Tanaka et al.
2007/0026039 A1 2/2007 Drumheller et al.
2007/0026040 A1 2/2007 Crawley et al.
2007/0027468 A1 2/2007 Wales et al.
2007/0027551 A1 2/2007 Farnsworth et al.
2007/0043387 A1 2/2007 Vargas et al.
2007/0049951 A1 3/2007 Menn
2007/0049966 A1 3/2007 Bonadio et al.
2007/0051375 A1 3/2007 Milliman
2007/0055228 A1 3/2007 Berg et al.
2007/0073341 A1 3/2007 Smith et al.
2007/0073389 A1 3/2007 Bolduc et al.
2007/0078328 A1 4/2007 Ozaki et al.
2007/0078484 A1 4/2007 Talarico et al.
2007/0084897 A1 4/2007 Shelton et al.
2007/0088376 A1 4/2007 Zacharias
2007/0090788 A1 4/2007 Hansford et al.
2007/0093869 A1 4/2007 Bloom et al.
2007/0102472 A1 5/2007 Shelton
2007/0106113 A1 5/2007 Ravo
2007/0106317 A1 5/2007 Shelton et al.
2007/0134251 A1 6/2007 Ashkenazi et al.
2007/0135686 A1 6/2007 Pruitt et al.
2007/0135803 A1 6/2007 Belson
2007/0152612 A1 7/2007 Chen et al.
2007/0155010 A1 7/2007 Farnsworth et al.
2007/0170225 A1 7/2007 Shelton et al.
2007/0173687 A1 7/2007 Shima et al.
2007/0173813 A1 7/2007 Odom
2007/0175950 A1 8/2007 Shelton et al.
2007/0175951 A1 8/2007 Shelton et al.
2007/0175955 A1 8/2007 Shelton et al.
2007/0179477 A1 8/2007 Danger
2007/0185545 A1 8/2007 Duke
2007/0187857 A1 8/2007 Riley et al.
2007/0190110 A1 8/2007 Pameijer et al.
2007/0191868 A1 8/2007 Theroux et al.
2007/0194079 A1 8/2007 Hueil et al.
2007/0194082 A1 8/2007 Morgan et al.
2007/0197954 A1 8/2007 Keenan
2007/0198039 A1 8/2007 Jones et al.
2007/0203510 A1 8/2007 Bettuchi
2007/0207010 A1 9/2007 Caspi
2007/0208359 A1 9/2007 Hoffman
2007/0208375 A1 9/2007 Nishizawa et al.
2007/0213750 A1 9/2007 Weadock
2007/0225562 A1 9/2007 Spivey et al.
2007/0233163 A1 10/2007 Bombard et al.
2007/0243227 A1 10/2007 Gertner
2007/0244471 A1 10/2007 Malackowski
2007/0246505 A1 10/2007 Pace-Floridia et al.
2007/0262592 A1 11/2007 Hwang et al.
2007/0275035 A1 11/2007 Herman et al.
2007/0276409 A1 11/2007 Ortiz et al.
2007/0279011 A1 12/2007 Jones et al.
2007/0286892 A1 12/2007 Herzberg et al.
2007/0296286 A1 12/2007 Avenell
2008/0003196 A1 1/2008 Jonn et al.
2008/0015598 A1 1/2008 Prommersberger
2008/0021486 A1 1/2008 Oyola et al.
2008/0029570 A1 2/2008 Shelton et al.
2008/0029573 A1 2/2008 Shelton et al.
2008/0029574 A1 2/2008 Shelton et al.
2008/0029575 A1 2/2008 Shelton et al.
2008/0030170 A1 2/2008 Dacquay et al.
2008/0039746 A1 2/2008 Hissong et al.
2008/0042861 A1 2/2008 Dacquay et al.
2008/0051833 A1 2/2008 Gramuglia et al.
2008/0064921 A1 3/2008 Larkin et al.
2008/0065153 A1 3/2008 Allard et al.
2008/0071328 A1 3/2008 Haubrich et al.
2008/0078802 A1 4/2008 Hess et al.
2008/0082114 A1 4/2008 McKenna et al.
2008/0082125 A1 4/2008 Murray et al.
2008/0082126 A1 4/2008 Murray et al.
2008/0083807 A1 4/2008 Beardsley et al.
2008/0085296 A1 4/2008 Powell et al.
2008/0086078 A1 4/2008 Powell et al.
2008/0091072 A1 4/2008 Omori et al.
2008/0108443 A1 5/2008 Jinno et al.
2008/0114250 A1 5/2008 Urbano et al.
2008/0125634 A1 5/2008 Ryan et al.
2008/0125749 A1 5/2008 Olson
2008/0128469 A1 6/2008 Dalessandro et al.
2008/0129253 A1 6/2008 Shiue et al.
2008/0135600 A1 6/2008 Hiranuma et al.
2008/0140115 A1 6/2008 Stopek
2008/0140159 A1 6/2008 Bornhoft et al.
2008/0154299 A1 6/2008 Livneh
2008/0154335 A1 6/2008 Thrope et al.
2008/0169328 A1 7/2008 Shelton
2008/0169332 A1 7/2008 Shelton et al.
2008/0169333 A1 7/2008 Shelton et al.
2008/0172087 A1 7/2008 Fuchs et al.
2008/0177392 A1 7/2008 Williams et al.
2008/0190989 A1 8/2008 Crews et al.
2008/0196253 A1 8/2008 Ezra et al.

(56) References Cited

U.S. PATENT DOCUMENTS

2008/0196419 A1 8/2008 Dube
2008/0197167 A1 8/2008 Viola et al.
2008/0200755 A1 8/2008 Bakos
2008/0200762 A1 8/2008 Stokes et al.
2008/0200835 A1 8/2008 Monson et al.
2008/0200911 A1 8/2008 Long
2008/0200933 A1 8/2008 Bakos et al.
2008/0200934 A1 8/2008 Fox
2008/0206186 A1 8/2008 Butler et al.
2008/0234709 A1 9/2008 Houser
2008/0242939 A1 10/2008 Johnston
2008/0249536 A1 10/2008 Stahler et al.
2008/0249608 A1 10/2008 Dave
2008/0255413 A1 10/2008 Zemlok et al.
2008/0262654 A1 10/2008 Omori et al.
2008/0269596 A1 10/2008 Revie et al.
2008/0281171 A1 11/2008 Fennell et al.
2008/0287944 A1 11/2008 Pearson et al.
2008/0293910 A1 11/2008 Kapiamba et al.
2008/0294179 A1 11/2008 Balbierz et al.
2008/0296346 A1 12/2008 Shelton, IV et al.
2008/0297287 A1 12/2008 Shachar et al.
2008/0308602 A1 12/2008 Timm et al.
2008/0308603 A1 12/2008 Shelton et al.
2008/0312686 A1 12/2008 Ellingwood
2008/0312687 A1 12/2008 Blier
2008/0315829 A1 12/2008 Jones et al.
2009/0001121 A1 1/2009 Hess et al.
2009/0001130 A1 1/2009 Hess et al.
2009/0004455 A1 1/2009 Gravagna et al.
2009/0005809 A1 1/2009 Hess et al.
2009/0012534 A1 1/2009 Madhani et al.
2009/0015195 A1 1/2009 Loth-Krausser
2009/0020958 A1 1/2009 Soul
2009/0048583 A1 2/2009 Williams et al.
2009/0048589 A1 2/2009 Takashino et al.
2009/0076506 A1 3/2009 Baker
2009/0078736 A1 3/2009 Van Lue
2009/0081313 A1 3/2009 Aghion et al.
2009/0088659 A1 4/2009 Graham et al.
2009/0090763 A1 4/2009 Zemlok et al.
2009/0099579 A1 4/2009 Nentwick et al.
2009/0099876 A1 4/2009 Whitman
2009/0112234 A1 4/2009 Crainich et al.
2009/0118762 A1 5/2009 Crainch et al.
2009/0119011 A1 5/2009 Kondo et al.
2009/0131819 A1 5/2009 Ritchie et al.
2009/0132400 A1 5/2009 Conway
2009/0143855 A1 6/2009 Weber et al.
2009/0149871 A9 6/2009 Kagan et al.
2009/0171147 A1 7/2009 Lee et al.
2009/0177226 A1 7/2009 Reinprecht et al.
2009/0181290 A1 7/2009 Baldwin et al.
2009/0188964 A1 7/2009 Orlov
2009/0192534 A1 7/2009 Ortiz et al.
2009/0198272 A1 8/2009 Kerver et al.
2009/0204108 A1 8/2009 Steffen
2009/0204109 A1 8/2009 Grove et al.
2009/0206125 A1 8/2009 Huitema et al.
2009/0206126 A1 8/2009 Huitema et al.
2009/0206131 A1 8/2009 Weisenburgh, II et al.
2009/0206133 A1 8/2009 Morgan et al.
2009/0206137 A1 8/2009 Hall et al.
2009/0206139 A1 8/2009 Hall et al.
2009/0206141 A1 8/2009 Huitema et al.
2009/0206142 A1 8/2009 Huitema et al.
2009/0221993 A1 9/2009 Sohi et al.
2009/0227834 A1 9/2009 Nakamoto et al.
2009/0234273 A1 9/2009 Intoccia et al.
2009/0242610 A1 10/2009 Shelton, IV et al.
2009/0247368 A1 10/2009 Chiang
2009/0247901 A1 10/2009 Zimmer
2009/0253959 A1 10/2009 Yoshie et al.
2009/0255974 A1 10/2009 Viola
2009/0262078 A1 10/2009 Pizzi
2009/0270895 A1 10/2009 Churchill et al.
2009/0278406 A1 11/2009 Hoffman
2009/0290016 A1 11/2009 Suda
2009/0292283 A1 11/2009 Odom
2009/0306639 A1 12/2009 Nevo et al.
2009/0308907 A1 12/2009 Nalagatla et al.
2009/0318557 A1 12/2009 Stockel
2009/0325859 A1 12/2009 Ameer et al.
2010/0005035 A1 1/2010 Carpenter et al.
2010/0012703 A1 1/2010 Calabrese et al.
2010/0015104 A1 1/2010 Fraser et al.
2010/0016888 A1 1/2010 Calabrese et al.
2010/0017715 A1 1/2010 Balassanian
2010/0023024 A1 1/2010 Zeiner et al.
2010/0030233 A1 2/2010 Whitman et al.
2010/0036370 A1 2/2010 Mirel et al.
2010/0051668 A1 3/2010 Milliman et al.
2010/0057118 A1 3/2010 Dietz et al.
2010/0065604 A1 3/2010 Weng
2010/0069942 A1 3/2010 Shelton, IV
2010/0076483 A1 3/2010 Imuta
2010/0076489 A1 3/2010 Stopek et al.
2010/0081883 A1 4/2010 Murray et al.
2010/0094340 A1 4/2010 Stopek et al.
2010/0100123 A1 4/2010 Bennett
2010/0100124 A1 4/2010 Calabrese et al.
2010/0116519 A1 5/2010 Gareis
2010/0122339 A1 5/2010 Boccacci
2010/0133317 A1 6/2010 Shelton, IV et al.
2010/0137990 A1 6/2010 Apatsidis et al.
2010/0145146 A1 6/2010 Melder
2010/0147921 A1 6/2010 Olson
2010/0147922 A1 6/2010 Olson
2010/0179022 A1 7/2010 Shirokoshi
2010/0180711 A1 7/2010 Kilibarda et al.
2010/0191262 A1 7/2010 Harris et al.
2010/0191292 A1 7/2010 DeMeo et al.
2010/0193566 A1 8/2010 Scheib et al.
2010/0204717 A1 8/2010 Knodel
2010/0204721 A1 8/2010 Young et al.
2010/0217281 A1 8/2010 Matsuoka et al.
2010/0222901 A1 9/2010 Swayze et al.
2010/0241137 A1 9/2010 Doyle et al.
2010/0249497 A1 9/2010 Peine et al.
2010/0249947 A1* 9/2010 Lesh ...................... A61L 27/16
623/23.74
2010/0256675 A1 10/2010 Romans
2010/0258327 A1 10/2010 Esenwein et al.
2010/0267662 A1 10/2010 Fielder et al.
2010/0274160 A1 10/2010 Yachi et al.
2010/0292540 A1 11/2010 Hess et al.
2010/0298636 A1 11/2010 Castro et al.
2010/0301097 A1 12/2010 Scirica et al.
2010/0310623 A1 12/2010 Laurencin et al.
2010/0312261 A1 12/2010 Suzuki et al.
2010/0318085 A1 12/2010 Austin et al.
2010/0331856 A1 12/2010 Carlson et al.
2011/0006101 A1 1/2011 Hall et al.
2011/0011916 A1 1/2011 Levine
2011/0016960 A1 1/2011 Debrailly
2011/0021871 A1 1/2011 Berkelaar
2011/0022032 A1 1/2011 Zemlok et al.
2011/0024477 A1 2/2011 Hall
2011/0024478 A1 2/2011 Shelton, IV
2011/0025311 A1 2/2011 Chauvin et al.
2011/0036891 A1 2/2011 Zemlok et al.
2011/0046667 A1 2/2011 Culligan et al.
2011/0052660 A1 3/2011 Yang et al.
2011/0060363 A1 3/2011 Hess et al.
2011/0066156 A1 3/2011 McGahan et al.
2011/0082538 A1 4/2011 Dahlgren et al.
2011/0087276 A1 4/2011 Bedi et al.
2011/0088921 A1 4/2011 Forgues et al.
2011/0091515 A1 4/2011 Zilberman et al.
2011/0095064 A1 4/2011 Taylor et al.
2011/0101069 A1 5/2011 Bombard et al.
2011/0101794 A1 5/2011 Schroeder et al.
2011/0112517 A1 5/2011 Peine et al.
2011/0112530 A1 5/2011 Keller

(56) References Cited

U.S. PATENT DOCUMENTS

2011/0114697 A1 5/2011 Baxter, III et al.
2011/0121049 A1 5/2011 Malinouskas et al.
2011/0125176 A1 5/2011 Yates et al.
2011/0127945 A1 6/2011 Yoneda
2011/0129706 A1 6/2011 Takahashi et al.
2011/0144764 A1 6/2011 Bagga et al.
2011/0147433 A1 6/2011 Shelton, IV et al.
2011/0160725 A1 6/2011 Kabaya et al.
2011/0163146 A1 7/2011 Ortiz et al.
2011/0172495 A1 7/2011 Armstrong
2011/0174861 A1 7/2011 Shelton, IV et al.
2011/0192882 A1 8/2011 Hess et al.
2011/0199225 A1 8/2011 Touchberry et al.
2011/0218400 A1 9/2011 Ma et al.
2011/0218550 A1 9/2011 Ma
2011/0225105 A1 9/2011 Scholer et al.
2011/0230713 A1 9/2011 Kleemann et al.
2011/0238044 A1 9/2011 Main et al.
2011/0241597 A1 10/2011 Zhu et al.
2011/0271186 A1 11/2011 Owens
2011/0275901 A1 11/2011 Shelton, IV
2011/0276083 A1 11/2011 Shelton, IV et al.
2011/0278343 A1 11/2011 Knodel et al.
2011/0279268 A1 11/2011 Konishi et al.
2011/0290856 A1 12/2011 Shelton, IV et al.
2011/0293690 A1 12/2011 Griffin et al.
2011/0295295 A1 12/2011 Shelton, IV et al.
2011/0313894 A1 12/2011 Dye et al.
2011/0315413 A1 12/2011 Fisher et al.
2012/0004636 A1 1/2012 Lo
2012/0007442 A1 1/2012 Rhodes et al.
2012/0016239 A1 1/2012 Barthe et al.
2012/0016413 A1 1/2012 Timm et al.
2012/0016467 A1 1/2012 Chen et al.
2012/0029272 A1 2/2012 Shelton, IV et al.
2012/0033360 A1 2/2012 Hsu
2012/0059286 A1 3/2012 Hastings et al.
2012/0064483 A1 3/2012 Lint et al.
2012/0074200 A1 3/2012 Schmid et al.
2012/0078244 A1 3/2012 Worrell et al.
2012/0080336 A1 4/2012 Shelton, IV et al.
2012/0080344 A1 4/2012 Shelton, IV
2012/0080478 A1 4/2012 Morgan et al.
2012/0080498 A1 4/2012 Shelton, IV et al.
2012/0086276 A1 4/2012 Sawyers
2012/0095458 A1 4/2012 Cybulski et al.
2012/0109186 A1 5/2012 Parrott et al.
2012/0116261 A1 5/2012 Mumaw et al.
2012/0116262 A1 5/2012 Houser et al.
2012/0116265 A1 5/2012 Houser et al.
2012/0116266 A1 5/2012 Houser et al.
2012/0118595 A1 5/2012 Pellenc
2012/0123463 A1 5/2012 Jacobs
2012/0125792 A1 5/2012 Cassivi
2012/0130217 A1 5/2012 Kauphusman et al.
2012/0132286 A1 5/2012 Lim et al.
2012/0171539 A1 7/2012 Rejman et al.
2012/0175398 A1 7/2012 Sandborn et al.
2012/0197272 A1 8/2012 Oray et al.
2012/0211542 A1 8/2012 Racenet
2012/0234895 A1 9/2012 O'Connor et al.
2012/0234897 A1 9/2012 Shelton, IV et al.
2012/0239068 A1 9/2012 Morris et al.
2012/0248169 A1 10/2012 Widenhouse et al.
2012/0251861 A1 10/2012 Liang et al.
2012/0253328 A1 10/2012 Cunningham et al.
2012/0283707 A1 11/2012 Giordano et al.
2012/0289811 A1 11/2012 Viola et al.
2012/0289979 A1 11/2012 Eskaros et al.
2012/0292367 A1 11/2012 Morgan et al.
2012/0298722 A1 11/2012 Hess et al.
2012/0303002 A1 11/2012 Chowaniec et al.
2013/0006227 A1 1/2013 Takashino
2013/0008937 A1 1/2013 Viola
2013/0012983 A1 1/2013 Kleyman
2013/0018400 A1 1/2013 Milton et al.
2013/0020375 A1 1/2013 Shelton, IV et al.
2013/0020376 A1 1/2013 Shelton, IV et al.
2013/0023861 A1 1/2013 Shelton, IV et al.
2013/0023910 A1 1/2013 Solomon et al.
2013/0026208 A1 1/2013 Shelton, IV et al.
2013/0026210 A1 1/2013 Shelton, IV et al.
2013/0030462 A1 1/2013 Keating et al.
2013/0041292 A1 2/2013 Cunningham
2013/0057162 A1 3/2013 Pollischansky
2013/0068816 A1 3/2013 Mandakolathur Vasudevan et al.
2013/0087597 A1 4/2013 Shelton, IV et al.
2013/0090534 A1 4/2013 Burns et al.
2013/0096568 A1 4/2013 Justis
2013/0098970 A1 4/2013 Racenet et al.
2013/0105552 A1 5/2013 Weir et al.
2013/0106352 A1 5/2013 Nagamine
2013/0116669 A1 5/2013 Shelton, IV et al.
2013/0123816 A1 5/2013 Hodgkinson et al.
2013/0126202 A1 5/2013 Oomori et al.
2013/0131476 A1 5/2013 Siu et al.
2013/0131651 A1 5/2013 Strobl et al.
2013/0136969 A1 5/2013 Yasui et al.
2013/0153641 A1 6/2013 Shelton, IV et al.
2013/0158390 A1 6/2013 Tan et al.
2013/0162198 A1 6/2013 Yokota et al.
2013/0169217 A1 7/2013 Watanabe et al.
2013/0172878 A1 7/2013 Smith
2013/0175317 A1 7/2013 Yates et al.
2013/0214025 A1 8/2013 Zemlok et al.
2013/0233906 A1 9/2013 Hess et al.
2013/0238021 A1 9/2013 Gross et al.
2013/0248578 A1 9/2013 Arteaga Gonzalez
2013/0253480 A1 9/2013 Kimball et al.
2013/0256373 A1 10/2013 Schmid et al.
2013/0256380 A1 10/2013 Schmid et al.
2013/0267978 A1 10/2013 Trissel
2013/0270322 A1 10/2013 Scheib et al.
2013/0277410 A1 10/2013 Fernandez et al.
2013/0306704 A1 11/2013 Balbierz et al.
2013/0317753 A1 11/2013 Kamen et al.
2013/0327552 A1 12/2013 Lovelass et al.
2013/0333910 A1 12/2013 Tanimoto et al.
2013/0334280 A1 12/2013 Krehel et al.
2013/0334283 A1 12/2013 Swayze et al.
2013/0334285 A1 12/2013 Swayze et al.
2013/0341374 A1 12/2013 Shelton, IV et al.
2014/0001231 A1 1/2014 Shelton, IV et al.
2014/0001234 A1 1/2014 Shelton, IV et al.
2014/0005640 A1 1/2014 Shelton, IV et al.
2014/0005678 A1 1/2014 Shelton, IV et al.
2014/0005702 A1 1/2014 Timm et al.
2014/0005718 A1 1/2014 Shelton, IV et al.
2014/0012299 A1 1/2014 Stoddard et al.
2014/0014705 A1 1/2014 Baxter, III
2014/0014707 A1 1/2014 Onukuri et al.
2014/0018832 A1 1/2014 Shelton, IV
2014/0039549 A1 2/2014 Belsky et al.
2014/0048580 A1 2/2014 Merchant et al.
2014/0081176 A1 3/2014 Hassan
2014/0094681 A1 4/2014 Valentine et al.
2014/0100558 A1 4/2014 Schmitz et al.
2014/0107640 A1 4/2014 Yates et al.
2014/0115229 A1 4/2014 Kothamasu et al.
2014/0131418 A1 5/2014 Kostrzewski
2014/0135832 A1 5/2014 Park et al.
2014/0151433 A1 6/2014 Shelton, IV et al.
2014/0158747 A1 6/2014 Measamer et al.
2014/0166723 A1 6/2014 Beardsley et al.
2014/0166724 A1 6/2014 Schellin et al.
2014/0166725 A1 6/2014 Schellin et al.
2014/0166726 A1 6/2014 Schellin et al.
2014/0175147 A1 6/2014 Manoux et al.
2014/0175150 A1 6/2014 Shelton, IV et al.
2014/0175152 A1 6/2014 Hess et al.
2014/0181710 A1 6/2014 Baalu et al.
2014/0188091 A1 7/2014 Vidal et al.
2014/0188159 A1 7/2014 Steege
2014/0207124 A1 7/2014 Aldridge et al.

(56) References Cited

U.S. PATENT DOCUMENTS

| | | | |
|---|---|---|---|
| 2014/0207125 | A1 | 7/2014 | Applegate et al. |
| 2014/0209658 | A1 | 7/2014 | Skalla et al. |
| 2014/0224857 | A1 | 8/2014 | Schmid |
| 2014/0228867 | A1 | 8/2014 | Thomas et al. |
| 2014/0239047 | A1 | 8/2014 | Hodgkinson et al. |
| 2014/0243865 | A1 | 8/2014 | Swayze et al. |
| 2014/0246475 | A1 | 9/2014 | Hall et al. |
| 2014/0248167 | A1 | 9/2014 | Sugimoto et al. |
| 2014/0249557 | A1 | 9/2014 | Koch et al. |
| 2014/0249573 | A1 | 9/2014 | Arav |
| 2014/0252061 | A1 | 9/2014 | Estrella et al. |
| 2014/0263541 | A1 | 9/2014 | Leimbach et al. |
| 2014/0263552 | A1 | 9/2014 | Hall et al. |
| 2014/0263558 | A1 | 9/2014 | Hausen et al. |
| 2014/0276730 | A1 | 9/2014 | Boudreaux et al. |
| 2014/0284371 | A1 | 9/2014 | Morgan et al. |
| 2014/0288460 | A1 | 9/2014 | Ouyang et al. |
| 2014/0291379 | A1 | 10/2014 | Schellin et al. |
| 2014/0291383 | A1 | 10/2014 | Spivey et al. |
| 2014/0299648 | A1 | 10/2014 | Shelton, IV et al. |
| 2014/0303645 | A1 | 10/2014 | Morgan et al. |
| 2014/0303660 | A1 | 10/2014 | Boyden et al. |
| 2014/0330161 | A1 | 11/2014 | Swayze et al. |
| 2014/0330298 | A1 | 11/2014 | Arshonsky et al. |
| 2014/0330579 | A1 | 11/2014 | Cashman et al. |
| 2014/0367445 | A1 | 12/2014 | Ingmanson et al. |
| 2014/0374130 | A1 | 12/2014 | Nakamura et al. |
| 2014/0378950 | A1 | 12/2014 | Chiu |
| 2015/0002089 | A1 | 1/2015 | Rejman et al. |
| 2015/0008248 | A1 | 1/2015 | Giordano et al. |
| 2015/0038961 | A1 | 2/2015 | Clark et al. |
| 2015/0053737 | A1 | 2/2015 | Leimbach et al. |
| 2015/0053742 | A1 | 2/2015 | Shelton, IV et al. |
| 2015/0053743 | A1 | 2/2015 | Yates et al. |
| 2015/0053746 | A1 | 2/2015 | Shelton, IV et al. |
| 2015/0053748 | A1 | 2/2015 | Yates et al. |
| 2015/0060518 | A1 | 3/2015 | Shelton, IV et al. |
| 2015/0060519 | A1 | 3/2015 | Shelton, IV et al. |
| 2015/0060520 | A1 | 3/2015 | Shelton, IV et al. |
| 2015/0060521 | A1 | 3/2015 | Weisenburgh, II et al. |
| 2015/0066000 | A1 | 3/2015 | An et al. |
| 2015/0076208 | A1 | 3/2015 | Shelton, IV |
| 2015/0076209 | A1 | 3/2015 | Shelton, IV et al. |
| 2015/0076210 | A1 | 3/2015 | Shelton, IV et al. |
| 2015/0076212 | A1 | 3/2015 | Shelton, IV |
| 2015/0080868 | A1 | 3/2015 | Kerr |
| 2015/0083781 | A1 | 3/2015 | Giordano et al. |
| 2015/0083782 | A1 | 3/2015 | Scheib et al. |
| 2015/0088547 | A1 | 3/2015 | Balram et al. |
| 2015/0090760 | A1 | 4/2015 | Giordano et al. |
| 2015/0090761 | A1 | 4/2015 | Giordano et al. |
| 2015/0090762 | A1 | 4/2015 | Giordano et al. |
| 2015/0122870 | A1 | 5/2015 | Zemlok et al. |
| 2015/0134077 | A1 | 5/2015 | Shelton, IV et al. |
| 2015/0150620 | A1 | 6/2015 | Miyamoto et al. |
| 2015/0173749 | A1 | 6/2015 | Shelton, IV et al. |
| 2015/0173756 | A1 | 6/2015 | Baxter, III et al. |
| 2015/0173789 | A1 | 6/2015 | Baxter, III et al. |
| 2015/0196295 | A1 | 7/2015 | Shelton, IV et al. |
| 2015/0196296 | A1 | 7/2015 | Swayze et al. |
| 2015/0196299 | A1 | 7/2015 | Swayze et al. |
| 2015/0201918 | A1 | 7/2015 | Kumar et al. |
| 2015/0201932 | A1 | 7/2015 | Swayze et al. |
| 2015/0201936 | A1 | 7/2015 | Swayze et al. |
| 2015/0201937 | A1 | 7/2015 | Swayze et al. |
| 2015/0201938 | A1 | 7/2015 | Swayze et al. |
| 2015/0201939 | A1 | 7/2015 | Swayze et al. |
| 2015/0201940 | A1 | 7/2015 | Swayze et al. |
| 2015/0201941 | A1 | 7/2015 | Swayze et al. |
| 2015/0222212 | A1 | 8/2015 | Iwata |
| 2015/0223868 | A1 | 8/2015 | Brandt et al. |
| 2015/0231409 | A1 | 8/2015 | Racenet et al. |
| 2015/0238118 | A1 | 8/2015 | Legassey et al. |
| 2015/0272557 | A1 | 10/2015 | Overmyer et al. |
| 2015/0272571 | A1 | 10/2015 | Leimbach et al. |
| 2015/0272580 | A1 | 10/2015 | Leimbach et al. |
| 2015/0272582 | A1 | 10/2015 | Leimbach et al. |
| 2015/0297200 | A1 | 10/2015 | Fitzsimmons et al. |
| 2015/0297222 | A1 | 10/2015 | Huitema et al. |
| 2015/0297223 | A1 | 10/2015 | Huitema et al. |
| 2015/0297225 | A1 | 10/2015 | Huitema et al. |
| 2015/0297228 | A1 | 10/2015 | Huitema et al. |
| 2015/0297229 | A1 | 10/2015 | Schellin et al. |
| 2015/0297233 | A1 | 10/2015 | Huitema et al. |
| 2015/0297234 | A1 | 10/2015 | Schellin et al. |
| 2015/0302539 | A1 | 10/2015 | Mazar et al. |
| 2015/0303417 | A1 | 10/2015 | Koeder et al. |
| 2015/0313594 | A1 | 11/2015 | Shelton, IV et al. |
| 2015/0324317 | A1 | 11/2015 | Collins et al. |
| 2015/0327864 | A1 | 11/2015 | Hodgkinson et al. |
| 2015/0336249 | A1 | 11/2015 | Iwata et al. |
| 2015/0352699 | A1 | 12/2015 | Sakai et al. |
| 2015/0366585 | A1 | 12/2015 | Lemay et al. |
| 2015/0372265 | A1 | 12/2015 | Morisaku et al. |
| 2015/0374369 | A1 | 12/2015 | Yates et al. |
| 2015/0374371 | A1 | 12/2015 | Richard et al. |
| 2015/0374372 | A1 | 12/2015 | Zergiebel et al. |
| 2015/0374378 | A1 | 12/2015 | Giordano et al. |
| 2016/0000431 | A1 | 1/2016 | Giordano et al. |
| 2016/0000437 | A1 | 1/2016 | Giordano et al. |
| 2016/0000438 | A1 | 1/2016 | Swayze et al. |
| 2016/0000442 | A1 | 1/2016 | Shelton, IV |
| 2016/0000452 | A1 | 1/2016 | Yates et al. |
| 2016/0000453 | A1 | 1/2016 | Yates et al. |
| 2016/0023342 | A1 | 1/2016 | Koenig et al. |
| 2016/0030042 | A1 | 2/2016 | Heinrich et al. |
| 2016/0058443 | A1 | 3/2016 | Yates et al. |
| 2016/0066815 | A1 | 3/2016 | Mei et al. |
| 2016/0066913 | A1 | 3/2016 | Swayze et al. |
| 2016/0069449 | A1 | 3/2016 | Kanai et al. |
| 2016/0074040 | A1 | 3/2016 | Widenhouse et al. |
| 2016/0074103 | A1 | 3/2016 | Sartor |
| 2016/0082161 | A1 | 3/2016 | Zilberman et al. |
| 2016/0089137 | A1 | 3/2016 | Hess et al. |
| 2016/0089198 | A1 | 3/2016 | Arya et al. |
| 2016/0095585 | A1 | 4/2016 | Zergiebel et al. |
| 2016/0106431 | A1 | 4/2016 | Shelton, IV et al. |
| 2016/0113653 | A1 | 4/2016 | Zingman |
| 2016/0120544 | A1 | 5/2016 | Shelton, IV et al. |
| 2016/0120545 | A1 | 5/2016 | Shelton, IV et al. |
| 2016/0135835 | A1 | 5/2016 | Onuma |
| 2016/0166248 | A1 | 6/2016 | Deville et al. |
| 2016/0166256 | A1 | 6/2016 | Baxter, III et al. |
| 2016/0174974 | A1 | 6/2016 | Schmid et al. |
| 2016/0183939 | A1 | 6/2016 | Shelton, IV et al. |
| 2016/0183943 | A1 | 6/2016 | Shelton, IV |
| 2016/0183944 | A1 | 6/2016 | Swensgard et al. |
| 2016/0192916 | A1 | 7/2016 | Shelton, IV et al. |
| 2016/0192918 | A1 | 7/2016 | Shelton, IV et al. |
| 2016/0192960 | A1 | 7/2016 | Bueno et al. |
| 2016/0192977 | A1 | 7/2016 | Manwaring et al. |
| 2016/0199063 | A1 | 7/2016 | Mandakolathur Vasudevan et al. |
| 2016/0199089 | A1 | 7/2016 | Hess et al. |
| 2016/0199956 | A1 | 7/2016 | Shelton, IV et al. |
| 2016/0206314 | A1 | 7/2016 | Scheib et al. |
| 2016/0235404 | A1 | 8/2016 | Shelton, IV |
| 2016/0235409 | A1 | 8/2016 | Shelton, IV et al. |
| 2016/0235494 | A1 | 8/2016 | Shelton, IV et al. |
| 2016/0242783 | A1 | 8/2016 | Shelton, IV et al. |
| 2016/0249910 | A1 | 9/2016 | Shelton, IV et al. |
| 2016/0249922 | A1 | 9/2016 | Morgan et al. |
| 2016/0256071 | A1 | 9/2016 | Shelton, IV et al. |
| 2016/0256154 | A1 | 9/2016 | Shelton, IV et al. |
| 2016/0256159 | A1 | 9/2016 | Pinjala et al. |
| 2016/0256160 | A1 | 9/2016 | Shelton, IV et al. |
| 2016/0256229 | A1 | 9/2016 | Morgan et al. |
| 2016/0262745 | A1 | 9/2016 | Morgan et al. |
| 2016/0262746 | A1 | 9/2016 | Shelton, IV et al. |
| 2016/0262921 | A1 | 9/2016 | Balbierz et al. |
| 2016/0270780 | A1 | 9/2016 | Hall et al. |
| 2016/0278765 | A1 | 9/2016 | Shelton, IV et al. |
| 2016/0278771 | A1 | 9/2016 | Shelton, IV et al. |
| 2016/0287279 | A1 | 10/2016 | Bovay et al. |
| 2016/0310143 | A1 | 10/2016 | Bettuchi |

(56) References Cited

U.S. PATENT DOCUMENTS

2016/0345976 A1 12/2016 Gonzalez et al.
2016/0346034 A1 12/2016 Arya et al.
2016/0354088 A1 12/2016 Cabrera et al.
2016/0367122 A1 12/2016 Ichimura et al.
2016/0374678 A1 12/2016 Becerra et al.
2017/0007236 A1 1/2017 Shelton, IV et al.
2017/0007243 A1 1/2017 Shelton, IV et al.
2017/0007244 A1 1/2017 Shelton, IV et al.
2017/0007245 A1 1/2017 Shelton, IV et al.
2017/0007248 A1 1/2017 Shelton, IV et al.
2017/0007249 A1 1/2017 Shelton, IV et al.
2017/0007250 A1 1/2017 Shelton, IV et al.
2017/0007347 A1 1/2017 Jaworek et al.
2017/0014125 A1 1/2017 Shelton, IV et al.
2017/0027572 A1 2/2017 Nalagatla et al.
2017/0027573 A1 2/2017 Nalagatla et al.
2017/0049444 A1 2/2017 Schellin et al.
2017/0049447 A1 2/2017 Barton et al.
2017/0049448 A1 2/2017 Widenhouse et al.
2017/0055986 A1 3/2017 Harris et al.
2017/0055999 A1 3/2017 Baxter, III et al.
2017/0056000 A1 3/2017 Nalagatla et al.
2017/0056002 A1 3/2017 Nalagatla et al.
2017/0056005 A1 3/2017 Shelton, IV et al.
2017/0079642 A1 3/2017 Overmyer et al.
2017/0086827 A1 3/2017 Vendely et al.
2017/0086829 A1 3/2017 Vendely et al.
2017/0086830 A1 3/2017 Yates et al.
2017/0086831 A1 3/2017 Shelton, IV et al.
2017/0086832 A1 3/2017 Harris et al.
2017/0086838 A1 3/2017 Harris et al.
2017/0086842 A1 3/2017 Shelton, IV et al.
2017/0086843 A1 3/2017 Vendely et al.
2017/0086844 A1 3/2017 Vendely et al.
2017/0105733 A1 4/2017 Scheib et al.
2017/0119388 A1 5/2017 Kostrzewski
2017/0119397 A1 5/2017 Harris et al.
2017/0143335 A1 5/2017 Gupta et al.
2017/0150965 A1 6/2017 Williams
2017/0172382 A1 6/2017 Nir et al.
2017/0172550 A1 6/2017 Mukherjee et al.
2017/0172662 A1 6/2017 Panescu et al.
2017/0172672 A1 6/2017 Bailey et al.
2017/0182211 A1 6/2017 Raxworthy et al.
2017/0196558 A1 7/2017 Morgan et al.
2017/0196561 A1 7/2017 Shelton, IV et al.
2017/0196562 A1 7/2017 Shelton, IV et al.
2017/0196637 A1 7/2017 Shelton, IV et al.
2017/0196648 A1 7/2017 Ward et al.
2017/0196649 A1 7/2017 Yates et al.
2017/0202571 A1 7/2017 Shelton, IV et al.
2017/0202596 A1 7/2017 Shelton, IV et al.
2017/0202770 A1 7/2017 Friedrich et al.
2017/0209145 A1 7/2017 Swayze et al.
2017/0209146 A1 7/2017 Yates et al.
2017/0209226 A1 7/2017 Overmyer et al.
2017/0215881 A1 8/2017 Shelton, IV et al.
2017/0215943 A1 8/2017 Allen, IV
2017/0224331 A1 8/2017 Worthington et al.
2017/0224332 A1 8/2017 Hunter et al.
2017/0224334 A1 8/2017 Worthington et al.
2017/0224335 A1 8/2017 Weaner et al.
2017/0224339 A1 8/2017 Huang et al.
2017/0231627 A1 8/2017 Shelton, IV et al.
2017/0231628 A1 8/2017 Shelton, IV et al.
2017/0238928 A1 8/2017 Morgan et al.
2017/0238929 A1 8/2017 Yates et al.
2017/0245952 A1 8/2017 Shelton, IV et al.
2017/0249431 A1 8/2017 Shelton, IV et al.
2017/0258469 A1 9/2017 Shelton, IV et al.
2017/0265774 A1 9/2017 Johnson et al.
2017/0265856 A1 9/2017 Shelton, IV et al.
2017/0281164 A1 10/2017 Harris et al.
2017/0281166 A1 10/2017 Morgan et al.
2017/0281167 A1 10/2017 Shelton, IV et al.
2017/0281169 A1 10/2017 Harris et al.
2017/0281171 A1 10/2017 Shelton, IV et al.
2017/0281173 A1 10/2017 Shelton, IV et al.
2017/0281174 A1 10/2017 Harris et al.
2017/0281183 A1 10/2017 Miller et al.
2017/0281184 A1 10/2017 Shelton, IV et al.
2017/0281186 A1 10/2017 Shelton, IV et al.
2017/0281187 A1 10/2017 Shelton, IV et al.
2017/0281189 A1 10/2017 Nalagatla et al.
2017/0290584 A1 10/2017 Jasemian et al.
2017/0290585 A1 10/2017 Shelton, IV et al.
2017/0296169 A1 10/2017 Yates et al.
2017/0296173 A1 10/2017 Shelton, IV et al.
2017/0296177 A1 10/2017 Harris et al.
2017/0296185 A1 10/2017 Swensgard et al.
2017/0296213 A1 10/2017 Swensgard et al.
2017/0311944 A1 11/2017 Morgan et al.
2017/0311949 A1 11/2017 Shelton, IV
2017/0312041 A1 11/2017 Giordano et al.
2017/0312042 A1 11/2017 Giordano et al.
2017/0319201 A1 11/2017 Morgan et al.
2017/0319207 A1 11/2017 Shelton, IV et al.
2017/0319209 A1 11/2017 Morgan et al.
2017/0325813 A1 11/2017 Aranyi et al.
2017/0333034 A1 11/2017 Morgan et al.
2017/0333035 A1 11/2017 Morgan et al.
2017/0333070 A1 11/2017 Laurent et al.
2017/0348010 A1 12/2017 Chiang
2017/0348043 A1 12/2017 Wang et al.
2017/0354413 A1 12/2017 Chen et al.
2017/0354415 A1 12/2017 Casasanta, Jr. et al.
2017/0358052 A1 12/2017 Yuan
2017/0360439 A1 12/2017 Chen et al.
2017/0360441 A1 12/2017 Sgroi
2017/0360442 A1 12/2017 Shelton, IV et al.
2017/0364183 A1 12/2017 Xiao
2017/0367695 A1 12/2017 Shelton, IV et al.
2017/0367696 A1 12/2017 Shelton, IV et al.
2017/0367697 A1 12/2017 Shelton, IV et al.
2017/0367698 A1 12/2017 Shelton, IV et al.
2017/0367699 A1 12/2017 Shelton, IV et al.
2017/0367700 A1 12/2017 Leimbach et al.
2017/0367991 A1 12/2017 Widenhouse et al.
2018/0000483 A1 1/2018 Leimbach et al.
2018/0000545 A1 1/2018 Giordano et al.
2018/0008270 A1 1/2018 Moore et al.
2018/0008271 A1 1/2018 Moore et al.
2018/0008356 A1 1/2018 Giordano et al.
2018/0008357 A1 1/2018 Giordano et al.
2018/0028184 A1 2/2018 Shelton, IV et al.
2018/0028185 A1 2/2018 Shelton, IV et al.
2018/0042611 A1 2/2018 Swayze et al.
2018/0049819 A1 2/2018 Harris et al.
2018/0049824 A1 2/2018 Harris et al.
2018/0049883 A1 2/2018 Moskowitz et al.
2018/0055513 A1 3/2018 Shelton, IV et al.
2018/0055524 A1 3/2018 Shelton, IV et al.
2018/0055525 A1 3/2018 Shelton, IV et al.
2018/0055526 A1 3/2018 Shelton, IV et al.
2018/0064437 A1 3/2018 Yates et al.
2018/0064440 A1 3/2018 Shelton, IV et al.
2018/0064441 A1 3/2018 Shelton, IV et al.
2018/0064442 A1 3/2018 Shelton, IV et al.
2018/0064443 A1 3/2018 Shelton, IV et al.
2018/0070939 A1 3/2018 Giordano et al.
2018/0070942 A1 3/2018 Shelton, IV et al.
2018/0078248 A1 3/2018 Swayze et al.
2018/0078268 A1 3/2018 Messerly et al.
2018/0085116 A1 3/2018 Yates et al.
2018/0085117 A1 3/2018 Shelton, IV et al.
2018/0103953 A1 4/2018 Shelton, IV et al.
2018/0103955 A1 4/2018 Shelton, IV et al.
2018/0110518 A1 4/2018 Overmyer et al.
2018/0110519 A1 4/2018 Lytle, IV et al.
2018/0110520 A1 4/2018 Shelton, IV et al.
2018/0110521 A1 4/2018 Shelton, IV et al.
2018/0110522 A1 4/2018 Shelton, IV et al.
2018/0110523 A1 4/2018 Shelton, IV
2018/0110574 A1 4/2018 Shelton, IV et al.

(56) References Cited

U.S. PATENT DOCUMENTS

| | | | |
|---|---|---|---|
| 2018/0110575 | A1 | 4/2018 | Shelton, IV et al. |
| 2018/0114591 | A1 | 4/2018 | Pribanic et al. |
| 2018/0116658 | A1 | 5/2018 | Aronhalt, IV et al. |
| 2018/0116662 | A1 | 5/2018 | Shelton, IV et al. |
| 2018/0116665 | A1 | 5/2018 | Hall et al. |
| 2018/0125481 | A1 | 5/2018 | Yates et al. |
| 2018/0125484 | A1 | 5/2018 | Kostrzewski |
| 2018/0125487 | A1 | 5/2018 | Beardsley |
| 2018/0125488 | A1 | 5/2018 | Morgan et al. |
| 2018/0125489 | A1 | 5/2018 | Leimbach et al. |
| 2018/0125590 | A1 | 5/2018 | Giordano et al. |
| 2018/0125594 | A1 | 5/2018 | Beardsley |
| 2018/0126504 | A1 | 5/2018 | Shelton, IV et al. |
| 2018/0132845 | A1 | 5/2018 | Schmid et al. |
| 2018/0132849 | A1 | 5/2018 | Miller et al. |
| 2018/0132850 | A1 | 5/2018 | Leimbach et al. |
| 2018/0132851 | A1 | 5/2018 | Hall et al. |
| 2018/0132926 | A1 | 5/2018 | Asher et al. |
| 2018/0132952 | A1 | 5/2018 | Spivey et al. |
| 2018/0133856 | A1 | 5/2018 | Shelton, IV et al. |
| 2018/0140299 | A1 | 5/2018 | Weaner et al. |
| 2018/0140368 | A1 | 5/2018 | Shelton, IV et al. |
| 2018/0146960 | A1 | 5/2018 | Shelton, IV et al. |
| 2018/0150153 | A1 | 5/2018 | Yoon et al. |
| 2018/0153542 | A1 | 6/2018 | Shelton, IV et al. |
| 2018/0161034 | A1 | 6/2018 | Scheib et al. |
| 2018/0168575 | A1 | 6/2018 | Simms et al. |
| 2018/0168576 | A1 | 6/2018 | Hunter et al. |
| 2018/0168577 | A1 | 6/2018 | Aronhalt et al. |
| 2018/0168578 | A1 | 6/2018 | Aronhalt et al. |
| 2018/0168579 | A1 | 6/2018 | Aronhalt et al. |
| 2018/0168580 | A1 | 6/2018 | Hunter et al. |
| 2018/0168581 | A1 | 6/2018 | Hunter et al. |
| 2018/0168582 | A1 | 6/2018 | Swayze et al. |
| 2018/0168583 | A1 | 6/2018 | Hunter et al. |
| 2018/0168584 | A1 | 6/2018 | Harris et al. |
| 2018/0168585 | A1 | 6/2018 | Shelton, IV et al. |
| 2018/0168586 | A1 | 6/2018 | Shelton, IV et al. |
| 2018/0168589 | A1 | 6/2018 | Swayze et al. |
| 2018/0168590 | A1 | 6/2018 | Overmyer et al. |
| 2018/0168591 | A1 | 6/2018 | Swayze et al. |
| 2018/0168592 | A1 | 6/2018 | Overmyer et al. |
| 2018/0168593 | A1 | 6/2018 | Overmyer et al. |
| 2018/0168594 | A1 | 6/2018 | Shelton, IV et al. |
| 2018/0168596 | A1 | 6/2018 | Beckman et al. |
| 2018/0168597 | A1 | 6/2018 | Fanelli et al. |
| 2018/0168598 | A1 | 6/2018 | Shelton, IV et al. |
| 2018/0168599 | A1 | 6/2018 | Bakos et al. |
| 2018/0168600 | A1 | 6/2018 | Shelton, IV et al. |
| 2018/0168601 | A1 | 6/2018 | Bakos et al. |
| 2018/0168602 | A1 | 6/2018 | Bakos et al. |
| 2018/0168603 | A1 | 6/2018 | Morgan et al. |
| 2018/0168604 | A1 | 6/2018 | Shelton, IV et al. |
| 2018/0168605 | A1 | 6/2018 | Baber et al. |
| 2018/0168606 | A1 | 6/2018 | Shelton, IV et al. |
| 2018/0168607 | A1 | 6/2018 | Shelton, IV et al. |
| 2018/0168608 | A1 | 6/2018 | Shelton, IV et al. |
| 2018/0168609 | A1 | 6/2018 | Fanelli et al. |
| 2018/0168610 | A1 | 6/2018 | Shelton, IV et al. |
| 2018/0168613 | A1 | 6/2018 | Shelton, IV et al. |
| 2018/0168614 | A1 | 6/2018 | Shelton, IV et al. |
| 2018/0168615 | A1 | 6/2018 | Shelton, IV et al. |
| 2018/0168616 | A1 | 6/2018 | Shelton, IV et al. |
| 2018/0168617 | A1 | 6/2018 | Shelton, IV et al. |
| 2018/0168618 | A1 | 6/2018 | Scott et al. |
| 2018/0168619 | A1 | 6/2018 | Scott et al. |
| 2018/0168621 | A1 | 6/2018 | Shelton, IV et al. |
| 2018/0168623 | A1 | 6/2018 | Simms et al. |
| 2018/0168624 | A1 | 6/2018 | Shelton, IV et al. |
| 2018/0168625 | A1 | 6/2018 | Posada et al. |
| 2018/0168626 | A1 | 6/2018 | Shelton, IV et al. |
| 2018/0168627 | A1 | 6/2018 | Weaner et al. |
| 2018/0168628 | A1 | 6/2018 | Hunter et al. |
| 2018/0168629 | A1 | 6/2018 | Shelton, IV et al. |
| 2018/0168630 | A1 | 6/2018 | Shelton, IV et al. |
| 2018/0168631 | A1 | 6/2018 | Harris et al. |
| 2018/0168632 | A1 | 6/2018 | Harris et al. |
| 2018/0168633 | A1 | 6/2018 | Shelton, IV et al. |
| 2018/0168634 | A1 | 6/2018 | Harris et al. |
| 2018/0168635 | A1 | 6/2018 | Shelton, IV et al. |
| 2018/0168636 | A1 | 6/2018 | Shelton, IV et al. |
| 2018/0168637 | A1 | 6/2018 | Harris et al. |
| 2018/0168638 | A1 | 6/2018 | Harris et al. |
| 2018/0168639 | A1 | 6/2018 | Shelton, IV et al. |
| 2018/0168640 | A1 | 6/2018 | Shelton, IV et al. |
| 2018/0168641 | A1 | 6/2018 | Harris et al. |
| 2018/0168642 | A1 | 6/2018 | Shelton, IV et al. |
| 2018/0168643 | A1 | 6/2018 | Shelton, IV et al. |
| 2018/0168644 | A1 | 6/2018 | Shelton, IV et al. |
| 2018/0168645 | A1 | 6/2018 | Shelton, IV et al. |
| 2018/0168646 | A1 | 6/2018 | Shelton, IV et al. |
| 2018/0168647 | A1 | 6/2018 | Shelton, IV et al. |
| 2018/0168648 | A1 | 6/2018 | Shelton, IV et al. |
| 2018/0168649 | A1 | 6/2018 | Shelton, IV et al. |
| 2018/0168650 | A1 | 6/2018 | Shelton, IV et al. |
| 2018/0168651 | A1 | 6/2018 | Shelton, IV et al. |
| 2018/0168715 | A1 | 6/2018 | Strobl |
| 2018/0199940 | A1 | 7/2018 | Zergiebel et al. |
| 2018/0206843 | A1 | 7/2018 | Yates et al. |
| 2018/0206906 | A1 | 7/2018 | Moua et al. |
| 2018/0214147 | A1 | 8/2018 | Merchant et al. |
| 2018/0221046 | A1 | 8/2018 | Demmy et al. |
| 2018/0221050 | A1 | 8/2018 | Kostrzewski et al. |
| 2018/0228490 | A1 | 8/2018 | Richard et al. |
| 2018/0242962 | A1 | 8/2018 | Walen et al. |
| 2018/0250001 | A1 | 9/2018 | Aronhalt et al. |
| 2018/0250020 | A1 | 9/2018 | Carusillo |
| 2018/0250086 | A1 | 9/2018 | Grubbs |
| 2018/0271520 | A1 | 9/2018 | Shelton, IV et al. |
| 2018/0273597 | A1 | 9/2018 | Stimson |
| 2018/0280020 | A1 | 10/2018 | Hess et al. |
| 2018/0286274 | A1 | 10/2018 | Kamiguchi et al. |
| 2018/0289369 | A1 | 10/2018 | Shelton, IV et al. |
| 2018/0296211 | A1 | 10/2018 | Timm et al. |
| 2018/0296215 | A1 | 10/2018 | Baxter, III et al. |
| 2018/0296216 | A1 | 10/2018 | Shelton, IV et al. |
| 2018/0296217 | A1 | 10/2018 | Moore et al. |
| 2018/0303481 | A1 | 10/2018 | Shelton, IV et al. |
| 2018/0303482 | A1 | 10/2018 | Shelton, IV et al. |
| 2018/0310931 | A1 | 11/2018 | Hall et al. |
| 2018/0311002 | A1 | 11/2018 | Giordano et al. |
| 2018/0317907 | A1 | 11/2018 | Kostrzewski |
| 2018/0317916 | A1 | 11/2018 | Wixey |
| 2018/0317917 | A1 | 11/2018 | Huang et al. |
| 2018/0317918 | A1 | 11/2018 | Shelton, IV |
| 2018/0317919 | A1 | 11/2018 | Shelton, IV et al. |
| 2018/0325528 | A1 | 11/2018 | Windolf et al. |
| 2018/0333155 | A1 | 11/2018 | Hall et al. |
| 2018/0333169 | A1 | 11/2018 | Leimbach et al. |
| 2018/0344319 | A1 | 12/2018 | Shelton, IV et al. |
| 2018/0353170 | A1 | 12/2018 | Overmyer et al. |
| 2018/0353176 | A1 | 12/2018 | Shelton, IV et al. |
| 2018/0353177 | A1 | 12/2018 | Shelton, IV et al. |
| 2018/0353178 | A1 | 12/2018 | Shelton, IV et al. |
| 2018/0353179 | A1 | 12/2018 | Shelton, IV et al. |
| 2018/0360443 | A1 | 12/2018 | Shelton, IV et al. |
| 2018/0360445 | A1 | 12/2018 | Shelton, IV et al. |
| 2018/0360446 | A1 | 12/2018 | Shelton, IV et al. |
| 2018/0360447 | A1 | 12/2018 | Shelton, IV et al. |
| 2018/0360448 | A1 | 12/2018 | Harris et al. |
| 2018/0360449 | A1 | 12/2018 | Shelton, IV et al. |
| 2018/0360450 | A1 | 12/2018 | Shelton, IV et al. |
| 2018/0360452 | A1 | 12/2018 | Shelton, IV et al. |
| 2018/0360454 | A1 | 12/2018 | Shelton, IV et al. |
| 2018/0360455 | A1 | 12/2018 | Shelton, IV et al. |
| 2018/0360456 | A1 | 12/2018 | Shelton, IV et al. |
| 2018/0360471 | A1 | 12/2018 | Parfett et al. |
| 2018/0360472 | A1 | 12/2018 | Harris et al. |
| 2018/0360473 | A1 | 12/2018 | Shelton, IV et al. |
| 2018/0360549 | A1 | 12/2018 | Hares et al. |
| 2018/0368822 | A1 | 12/2018 | Shelton, IV et al. |
| 2018/0368833 | A1 | 12/2018 | Shelton, IV et al. |
| 2018/0368837 | A1 | 12/2018 | Morgan et al. |
| 2018/0368838 | A1 | 12/2018 | Shelton, IV et al. |

(56) References Cited

U.S. PATENT DOCUMENTS

| | | | |
|---|---|---|---|
| 2018/0368839 | A1 | 12/2018 | Shelton, IV et al. |
| 2018/0368840 | A1 | 12/2018 | Shelton, IV et al. |
| 2018/0368841 | A1 | 12/2018 | Shelton, IV et al. |
| 2018/0368842 | A1 | 12/2018 | Shelton, IV et al. |
| 2018/0368843 | A1 | 12/2018 | Shelton, IV et al. |
| 2018/0368844 | A1 | 12/2018 | Bakos et al. |
| 2018/0368845 | A1 | 12/2018 | Bakos et al. |
| 2018/0368846 | A1 | 12/2018 | Shelton, IV et al. |
| 2018/0368847 | A1 | 12/2018 | Shelton, IV et al. |
| 2019/0000446 | A1 | 1/2019 | Shelton, IV et al. |
| 2019/0000448 | A1 | 1/2019 | Shelton, IV et al. |
| 2019/0000450 | A1 | 1/2019 | Shelton, IV et al. |
| 2019/0000454 | A1 | 1/2019 | Swayze et al. |
| 2019/0000456 | A1 | 1/2019 | Shelton, IV et al. |
| 2019/0000457 | A1 | 1/2019 | Shelton, IV et al. |
| 2019/0000458 | A1 | 1/2019 | Shelton, IV et al. |
| 2019/0000459 | A1 | 1/2019 | Shelton, IV et al. |
| 2019/0000460 | A1 | 1/2019 | Shelton, IV et al. |
| 2019/0000461 | A1 | 1/2019 | Shelton, IV et al. |
| 2019/0000462 | A1 | 1/2019 | Shelton, IV et al. |
| 2019/0000463 | A1 | 1/2019 | Shelton, IV et al. |
| 2019/0000464 | A1 | 1/2019 | Shelton, IV et al. |
| 2019/0000465 | A1 | 1/2019 | Shelton, IV et al. |
| 2019/0000466 | A1 | 1/2019 | Shelton, IV et al. |
| 2019/0000467 | A1 | 1/2019 | Shelton, IV et al. |
| 2019/0000468 | A1 | 1/2019 | Adams et al. |
| 2019/0000469 | A1 | 1/2019 | Shelton, IV et al. |
| 2019/0000470 | A1 | 1/2019 | Yates et al. |
| 2019/0000471 | A1 | 1/2019 | Shelton, IV et al. |
| 2019/0000472 | A1 | 1/2019 | Shelton, IV et al. |
| 2019/0000473 | A1 | 1/2019 | Shelton, IV et al. |
| 2019/0000474 | A1 | 1/2019 | Shelton, IV et al. |
| 2019/0000475 | A1 | 1/2019 | Shelton, IV et al. |
| 2019/0000476 | A1 | 1/2019 | Shelton, IV et al. |
| 2019/0000477 | A1 | 1/2019 | Shelton, IV et al. |
| 2019/0000478 | A1 | 1/2019 | Messerly et al. |
| 2019/0000479 | A1 | 1/2019 | Harris et al. |
| 2019/0000525 | A1 | 1/2019 | Messerly et al. |
| 2019/0000528 | A1 | 1/2019 | Yates et al. |
| 2019/0000530 | A1 | 1/2019 | Yates et al. |
| 2019/0000531 | A1 | 1/2019 | Messerly et al. |
| 2019/0000534 | A1 | 1/2019 | Messerly et al. |
| 2019/0000538 | A1 | 1/2019 | Widenhouse et al. |
| 2019/0000555 | A1 | 1/2019 | Schings et al. |
| 2019/0000565 | A1 | 1/2019 | Shelton, IV et al. |
| 2019/0003292 | A1 | 1/2019 | Balan et al. |
| 2019/0008509 | A1 | 1/2019 | Shelton, IV et al. |
| 2019/0008511 | A1 | 1/2019 | Kerr et al. |
| 2019/0015096 | A1 | 1/2019 | Shelton, IV et al. |
| 2019/0015102 | A1 | 1/2019 | Baber et al. |
| 2019/0015165 | A1 | 1/2019 | Giordano et al. |
| 2019/0029675 | A1 | 1/2019 | Yates et al. |
| 2019/0029676 | A1 | 1/2019 | Yates et al. |
| 2019/0029677 | A1 | 1/2019 | Yates et al. |
| 2019/0029678 | A1 | 1/2019 | Shelton, IV et al. |
| 2019/0029681 | A1 | 1/2019 | Swayze et al. |
| 2019/0029682 | A1 | 1/2019 | Huitema et al. |
| 2019/0029701 | A1 | 1/2019 | Shelton, IV et al. |
| 2019/0033955 | A1 | 1/2019 | Leimbach et al. |
| 2019/0038279 | A1 | 2/2019 | Shelton, IV et al. |
| 2019/0038281 | A1 | 2/2019 | Shelton, IV et al. |
| 2019/0038282 | A1 | 2/2019 | Shelton, IV et al. |
| 2019/0038283 | A1 | 2/2019 | Shelton, IV et al. |
| 2019/0038292 | A1 | 2/2019 | Zhang |
| 2019/0038371 | A1 | 2/2019 | Wixey et al. |
| 2019/0046181 | A1 | 2/2019 | McCuen |
| 2019/0046187 | A1 | 2/2019 | Yates et al. |
| 2019/0059886 | A1 | 2/2019 | Shelton, IV et al. |
| 2019/0090870 | A1 | 3/2019 | Shelton, IV et al. |
| 2019/0090871 | A1 | 3/2019 | Shelton, IV et al. |
| 2019/0091183 | A1 | 3/2019 | Tomat et al. |
| 2019/0099177 | A1 | 4/2019 | Yates et al. |
| 2019/0099178 | A1 | 4/2019 | Leimbach et al. |
| 2019/0099179 | A1 | 4/2019 | Leimbach et al. |
| 2019/0099180 | A1 | 4/2019 | Leimbach et al. |
| 2019/0099181 | A1 | 4/2019 | Shelton, IV et al. |
| 2019/0099182 | A1 | 4/2019 | Bakos et al. |
| 2019/0099183 | A1 | 4/2019 | Leimbach et al. |
| 2019/0099184 | A1 | 4/2019 | Setser et al. |
| 2019/0099224 | A1 | 4/2019 | Leimbach et al. |
| 2019/0099229 | A1 | 4/2019 | Spivey et al. |
| 2019/0102930 | A1 | 4/2019 | Leimbach et al. |
| 2019/0105035 | A1 | 4/2019 | Shelton, IV et al. |
| 2019/0105036 | A1 | 4/2019 | Morgan et al. |
| 2019/0105037 | A1 | 4/2019 | Morgan et al. |
| 2019/0105038 | A1 | 4/2019 | Schmid et al. |
| 2019/0105039 | A1 | 4/2019 | Morgan et al. |
| 2019/0105043 | A1 | 4/2019 | Jaworek et al. |
| 2019/0105044 | A1 | 4/2019 | Shelton, IV et al. |
| 2019/0105049 | A1 | 4/2019 | Moore et al. |
| 2019/0110791 | A1 | 4/2019 | Shelton, IV et al. |
| 2019/0110792 | A1 | 4/2019 | Shelton, IV et al. |
| 2019/0110793 | A1 | 4/2019 | Parihar et al. |
| 2019/0117216 | A1 | 4/2019 | Overmyer et al. |
| 2019/0117217 | A1 | 4/2019 | Overmyer et al. |
| 2019/0117222 | A1 | 4/2019 | Shelton, IV et al. |
| 2019/0117224 | A1 | 4/2019 | Setser et al. |
| 2019/0117225 | A1 | 4/2019 | Moore et al. |
| 2019/0125343 | A1 | 5/2019 | Wise et al. |
| 2019/0125344 | A1 | 5/2019 | DiNardo et al. |
| 2019/0125345 | A1 | 5/2019 | Baber et al. |
| 2019/0125365 | A1 | 5/2019 | Parfett et al. |
| 2019/0125380 | A1 | 5/2019 | Hunter et al. |
| 2019/0125475 | A1 | 5/2019 | Wise et al. |
| 2019/0133585 | A1 | 5/2019 | Smith et al. |
| 2019/0142421 | A1 | 5/2019 | Shelton, IV |
| 2019/0183490 | A1 | 6/2019 | Shelton, IV et al. |
| 2019/0183491 | A1 | 6/2019 | Shelton, IV et al. |
| 2019/0183492 | A1 | 6/2019 | Shelton, IV et al. |
| 2019/0183493 | A1 | 6/2019 | Shelton, IV et al. |
| 2019/0183494 | A1 | 6/2019 | Shelton, IV et al. |
| 2019/0183495 | A1 | 6/2019 | Shelton, IV et al. |
| 2019/0183496 | A1 | 6/2019 | Shelton, IV et al. |
| 2019/0183497 | A1 | 6/2019 | Shelton, IV et al. |
| 2019/0183498 | A1 | 6/2019 | Shelton, IV et al. |
| 2019/0183499 | A1 | 6/2019 | Shelton, IV et al. |
| 2019/0183500 | A1 | 6/2019 | Shelton, IV et al. |
| 2019/0183501 | A1 | 6/2019 | Shelton, IV et al. |
| 2019/0183502 | A1 | 6/2019 | Shelton, IV et al. |
| 2019/0183503 | A1 | 6/2019 | Shelton, IV et al. |
| 2019/0183504 | A1 | 6/2019 | Shelton, IV et al. |
| 2019/0183505 | A1 | 6/2019 | Vendely et al. |
| 2019/0183592 | A1 | 6/2019 | Shelton, IV et al. |
| 2019/0183594 | A1 | 6/2019 | Shelton, IV et al. |
| 2019/0183597 | A1 | 6/2019 | Shelton, IV et al. |
| 2019/0192137 | A1 | 6/2019 | Shelton, IV et al. |
| 2019/0192138 | A1 | 6/2019 | Shelton, IV et al. |
| 2019/0192141 | A1 | 6/2019 | Shelton, IV et al. |
| 2019/0192144 | A1 | 6/2019 | Parfett et al. |
| 2019/0192145 | A1 | 6/2019 | Shelton, IV et al. |
| 2019/0192146 | A1 | 6/2019 | Widenhouse et al. |
| 2019/0192147 | A1 | 6/2019 | Shelton, IV et al. |
| 2019/0192148 | A1 | 6/2019 | Shelton, IV et al. |
| 2019/0192149 | A1 | 6/2019 | Shelton, IV et al. |
| 2019/0192150 | A1 | 6/2019 | Widenhouse et al. |
| 2019/0192151 | A1 | 6/2019 | Shelton, IV et al. |
| 2019/0192152 | A1 | 6/2019 | Morgan et al. |
| 2019/0192153 | A1 | 6/2019 | Shelton, IV et al. |
| 2019/0192154 | A1 | 6/2019 | Shelton, IV et al. |
| 2019/0192155 | A1 | 6/2019 | Shelton, IV et al. |
| 2019/0192156 | A1 | 6/2019 | Simms et al. |
| 2019/0192157 | A1 | 6/2019 | Scott et al. |
| 2019/0192158 | A1 | 6/2019 | Scott et al. |
| 2019/0192159 | A1 | 6/2019 | Simms et al. |
| 2019/0192227 | A1 | 6/2019 | Shelton, IV et al. |
| 2019/0192235 | A1 | 6/2019 | Harris et al. |
| 2019/0192236 | A1 | 6/2019 | Shelton, IV et al. |
| 2019/0200895 | A1 | 7/2019 | Shelton, IV et al. |
| 2019/0200991 | A1 | 7/2019 | Moore et al. |
| 2019/0200992 | A1 | 7/2019 | Moore et al. |
| 2019/0200993 | A1 | 7/2019 | Moore et al. |
| 2019/0200994 | A1 | 7/2019 | Moore et al. |
| 2019/0209164 | A1 | 7/2019 | Timm et al. |
| 2019/0209165 | A1 | 7/2019 | Timm et al. |

(56) References Cited

U.S. PATENT DOCUMENTS

| | | | |
|---|---|---|---|
| 2019/0209171 | A1 | 7/2019 | Shelton, IV et al. |
| 2019/0209172 | A1 | 7/2019 | Shelton, IV et al. |
| 2019/0209247 | A1 | 7/2019 | Giordano et al. |
| 2019/0209248 | A1 | 7/2019 | Giordano et al. |
| 2019/0209249 | A1 | 7/2019 | Giordano et al. |
| 2019/0209250 | A1 | 7/2019 | Giordano et al. |
| 2019/0216558 | A1 | 7/2019 | Giordano et al. |
| 2019/0223865 | A1 | 7/2019 | Shelton, IV et al. |
| 2019/0223871 | A1 | 7/2019 | Moore et al. |
| 2019/0261991 | A1 | 8/2019 | Beckman et al. |
| 2019/0267403 | A1 | 8/2019 | Li et al. |
| 2019/0269400 | A1 | 9/2019 | Mandakolathur Vasudevan et al. |
| 2019/0269402 | A1 | 9/2019 | Murray et al. |
| 2019/0269403 | A1 | 9/2019 | Baxter, III et al. |
| 2019/0269407 | A1 | 9/2019 | Swensgard et al. |
| 2019/0290263 | A1 | 9/2019 | Morgan et al. |
| 2019/0290264 | A1 | 9/2019 | Morgan et al. |
| 2019/0290265 | A1 | 9/2019 | Shelton, IV et al. |
| 2019/0290274 | A1 | 9/2019 | Shelton, IV |
| 2019/0321040 | A1 | 10/2019 | Shelton, IV |
| 2019/0321041 | A1 | 10/2019 | Shelton, IV |
| 2019/0350582 | A1 | 11/2019 | Shelton, IV et al. |
| 2019/0365384 | A1 | 12/2019 | Baxter et al. |

FOREIGN PATENT DOCUMENTS

| | | | |
|---|---|---|---|
| CA | 1015829 | A | 8/1977 |
| CA | 1125615 | A | 6/1982 |
| CA | 2520413 | A1 | 3/2007 |
| CA | 2725181 | A1 | 11/2007 |
| CA | 2851239 | A1 | 11/2007 |
| CA | 2664874 | A1 | 11/2009 |
| CA | 2813230 | A1 | 4/2012 |
| CA | 2940510 | A1 | 8/2015 |
| CA | 2698728 | C | 8/2016 |
| CN | 1163558 | A | 10/1997 |
| CN | 2488482 | Y | 5/2002 |
| CN | 1634601 | A | 7/2005 |
| CN | 2716900 | Y | 8/2005 |
| CN | 2738962 | Y | 11/2005 |
| CN | 1777406 | A | 5/2006 |
| CN | 2796654 | Y | 7/2006 |
| CN | 2868212 | Y | 2/2007 |
| CN | 200942099 | Y | 9/2007 |
| CN | 200984209 | Y | 12/2007 |
| CN | 200991269 | Y | 12/2007 |
| CN | 201001747 | Y | 1/2008 |
| CN | 101143105 | A | 3/2008 |
| CN | 201029899 | Y | 3/2008 |
| CN | 101378791 | A | 3/2009 |
| CN | 101522120 | A | 9/2009 |
| CN | 101669833 | A | 3/2010 |
| CN | 101721236 | A | 6/2010 |
| CN | 101828940 | A | 9/2010 |
| CN | 101873834 | A | 10/2010 |
| CN | 201719298 | U | 1/2011 |
| CN | 102038532 | A | 5/2011 |
| CN | 201879759 | U | 6/2011 |
| CN | 201949071 | U | 8/2011 |
| CN | 102217961 | A | 10/2011 |
| CN | 102217963 | A | 10/2011 |
| CN | 101779977 | B | 12/2011 |
| CN | 101912284 | B | 7/2012 |
| CN | 102125450 | B | 7/2012 |
| CN | 202313537 | U | 7/2012 |
| CN | 202397539 | U | 8/2012 |
| CN | 202426586 | U | 9/2012 |
| CN | 202489990 | U | 10/2012 |
| CN | 102228387 | B | 11/2012 |
| CN | 102835977 | A | 12/2012 |
| CN | 202568350 | U | 12/2012 |
| CN | 103690212 | A | 4/2014 |
| CN | 203564285 | U | 4/2014 |
| CN | 203564287 | U | 4/2014 |
| CN | 203597997 | U | 5/2014 |
| CN | 103829981 | A | 6/2014 |
| CN | 103829983 | A | 6/2014 |
| CN | 103908313 | A | 7/2014 |
| CN | 203693685 | U | 7/2014 |
| CN | 203736251 | U | 7/2014 |
| CN | 103981635 | A | 8/2014 |
| CN | 203815517 | U | 9/2014 |
| CN | 102783741 | B | 10/2014 |
| CN | 102973300 | B | 10/2014 |
| CN | 104337556 | A | 2/2015 |
| CN | 204158440 | U | 2/2015 |
| CN | 204158441 | U | 2/2015 |
| CN | 102469995 | B | 3/2015 |
| CN | 204636451 | U | 9/2015 |
| CN | 103860225 | B | 3/2016 |
| CN | 103750872 | B | 5/2016 |
| DE | 273689 | C | 5/1914 |
| DE | 1775926 | A | 1/1972 |
| DE | 3036217 | A1 | 4/1982 |
| DE | 3210466 | A1 | 9/1983 |
| DE | 3709067 | A1 | 9/1988 |
| DE | 19534043 | A1 | 3/1997 |
| DE | 19851291 | A1 | 1/2000 |
| DE | 19924311 | A1 | 11/2000 |
| DE | 20016423 | U1 | 2/2001 |
| DE | 20112837 | U1 | 10/2001 |
| DE | 20121753 | U1 | 4/2003 |
| DE | 202004012389 | U1 | 9/2004 |
| DE | 10314072 | A1 | 10/2004 |
| DE | 102004014011 | A1 | 10/2005 |
| DE | 102004063606 | A1 | 7/2006 |
| DE | 202007003114 | U1 | 6/2007 |
| DE | 102010013150 | A1 | 9/2011 |
| EP | 0000756 | A1 | 2/1979 |
| EP | 0122046 | A1 | 10/1984 |
| EP | 0129442 | B1 | 11/1987 |
| EP | 0255631 | A1 | 2/1988 |
| EP | 0169044 | B1 | 6/1991 |
| EP | 0541950 | A1 | 5/1993 |
| EP | 0548998 | A1 | 6/1993 |
| EP | 0594148 | A1 | 4/1994 |
| EP | 0646357 | A1 | 4/1995 |
| EP | 0505036 | B1 | 5/1995 |
| EP | 0669104 | A1 | 8/1995 |
| EP | 0705571 | A1 | 4/1996 |
| EP | 0528478 | B1 | 5/1996 |
| EP | 0770355 | A1 | 5/1997 |
| EP | 0625335 | B1 | 11/1997 |
| EP | 0879742 | A1 | 11/1998 |
| EP | 0650701 | B1 | 3/1999 |
| EP | 0923907 | A1 | 6/1999 |
| EP | 0484677 | B2 | 7/2000 |
| EP | 1034747 | A1 | 9/2000 |
| EP | 1034748 | A1 | 9/2000 |
| EP | 0726632 | B1 | 10/2000 |
| EP | 1053719 | A1 | 11/2000 |
| EP | 1055399 | A1 | 11/2000 |
| EP | 1055400 | A1 | 11/2000 |
| EP | 1080694 | A1 | 3/2001 |
| EP | 1090592 | A1 | 4/2001 |
| EP | 1095627 | A1 | 5/2001 |
| EP | 0806914 | B1 | 9/2001 |
| EP | 1234587 | A1 | 8/2002 |
| EP | 1284120 | A1 | 2/2003 |
| EP | 0717967 | B1 | 5/2003 |
| EP | 0869742 | B1 | 5/2003 |
| EP | 1374788 | A1 | 1/2004 |
| EP | 1407719 | A2 | 4/2004 |
| EP | 0996378 | B1 | 6/2004 |
| EP | 1157666 | B1 | 9/2005 |
| EP | 0880338 | B1 | 10/2005 |
| EP | 1158917 | B1 | 11/2005 |
| EP | 1344498 | B1 | 11/2005 |
| EP | 1330989 | B1 | 12/2005 |
| EP | 1632191 | A2 | 3/2006 |
| EP | 1082944 | B1 | 5/2006 |
| EP | 1253866 | B1 | 7/2006 |
| EP | 1723914 | A1 | 11/2006 |
| EP | 1285633 | B1 | 12/2006 |

(56) References Cited

FOREIGN PATENT DOCUMENTS

| | | | |
|---|---|---|---|
| EP | 1011494 | B1 | 1/2007 |
| EP | 1767163 | A1 | 3/2007 |
| EP | 1837041 | A1 | 9/2007 |
| EP | 0922435 | B1 | 10/2007 |
| EP | 1599146 | B1 | 10/2007 |
| EP | 1330201 | B1 | 6/2008 |
| EP | 2039302 | A2 | 3/2009 |
| EP | 1719461 | B1 | 6/2009 |
| EP | 2116196 | A2 | 11/2009 |
| EP | 1769754 | B1 | 6/2010 |
| EP | 1627605 | B1 | 12/2010 |
| EP | 2316345 | A1 | 5/2011 |
| EP | 1962711 | B1 | 2/2012 |
| EP | 2486862 | A2 | 8/2012 |
| EP | 2486868 | A2 | 8/2012 |
| EP | 2517638 | A1 | 10/2012 |
| EP | 2606812 | A1 | 6/2013 |
| EP | 2649948 | A1 | 10/2013 |
| EP | 2649949 | A1 | 10/2013 |
| EP | 2668910 | A2 | 12/2013 |
| EP | 2687164 | A2 | 1/2014 |
| EP | 2713902 | A1 | 4/2014 |
| EP | 2743042 | A2 | 6/2014 |
| EP | 2764827 | A2 | 8/2014 |
| EP | 2777524 | A2 | 9/2014 |
| EP | 2842500 | A1 | 3/2015 |
| EP | 2853220 | A1 | 4/2015 |
| EP | 2298220 | B1 | 6/2016 |
| EP | 2510891 | B1 | 6/2016 |
| EP | 3031404 | A1 | 6/2016 |
| EP | 3047806 | A1 | 7/2016 |
| EP | 3078334 | A1 | 10/2016 |
| EP | 2364651 | B1 | 11/2016 |
| EP | 2747235 | B1 | 11/2016 |
| EP | 2789299 | B1 | 5/2017 |
| EP | 3225190 | A2 | 10/2017 |
| EP | 3363378 | A1 | 8/2018 |
| FR | 459743 | A | 11/1913 |
| FR | 999646 | A | 2/1952 |
| FR | 1112936 | A | 3/1956 |
| FR | 2598905 | A1 | 11/1987 |
| FR | 2689749 | B1 | 7/1994 |
| FR | 2765794 | A1 | 1/1999 |
| FR | 2815842 | A1 | 5/2002 |
| GB | 939929 | A | 10/1963 |
| GB | 1210522 | A | 10/1970 |
| GB | 1217159 | A | 12/1970 |
| GB | 1339394 | A | 12/1973 |
| GB | 2024012 | A | 1/1980 |
| GB | 2109241 | A | 6/1983 |
| GB | 2090534 | B | 6/1984 |
| GB | 2272159 | A | 5/1994 |
| GB | 2336214 | A | 10/1999 |
| GB | 2509523 | A | 7/2014 |
| GR | 930100110 | A | 11/1993 |
| JP | S4711908 | Y1 | 5/1972 |
| JP | S5033988 | U | 4/1975 |
| JP | S5367286 | A | 6/1978 |
| JP | S56112235 | A | 9/1981 |
| JP | S60113007 | A | 6/1985 |
| JP | S62170011 | U | 10/1987 |
| JP | S63270040 | A | 11/1988 |
| JP | H0129503 | B2 | 6/1989 |
| JP | H0378514 | U | 8/1991 |
| JP | H0385009 | U | 8/1991 |
| JP | H04215747 | A | 8/1992 |
| JP | H04131860 | U | 12/1992 |
| JP | H0584252 | A | 4/1993 |
| JP | H05123325 | A | 5/1993 |
| JP | H05226945 | A | 9/1993 |
| JP | H0630945 | A | 2/1994 |
| JP | H06237937 | A | 8/1994 |
| JP | H06327684 | A | 11/1994 |
| JP | H079622 | U | 2/1995 |
| JP | H07124166 | A | 5/1995 |
| JP | H07163573 | A | 6/1995 |
| JP | H07255735 | A | 10/1995 |
| JP | H07285089 | A | 10/1995 |
| JP | H0833642 | A | 2/1996 |
| JP | H08164141 | A | 6/1996 |
| JP | H08182684 | A | 7/1996 |
| JP | H08507708 | A | 8/1996 |
| JP | H08229050 | A | 9/1996 |
| JP | H08289895 | A | 11/1996 |
| JP | H09-323068 | A | 12/1997 |
| JP | H10118090 | A | 5/1998 |
| JP | H10-200699 | A | 7/1998 |
| JP | H10296660 | A | 11/1998 |
| JP | 2000014632 | A | 1/2000 |
| JP | 2000033071 | A | 2/2000 |
| JP | 2000112002 | A | 4/2000 |
| JP | 2000166932 | A | 6/2000 |
| JP | 2000171730 | A | 6/2000 |
| JP | 2000271141 | A | 10/2000 |
| JP | 2000287987 | A | 10/2000 |
| JP | 2000325303 | A | 11/2000 |
| JP | 2001087272 | A | 4/2001 |
| JP | 2001514541 | A | 9/2001 |
| JP | 2001276091 | A | 10/2001 |
| JP | 2002051974 | A | 2/2002 |
| JP | 2002054903 | A | 2/2002 |
| JP | 2002085415 | A | 3/2002 |
| JP | 2002143078 | A | 5/2002 |
| JP | 2002153481 | A | 5/2002 |
| JP | 2002528161 | A | 9/2002 |
| JP | 2002314298 | A | 10/2002 |
| JP | 2003135473 | A | 5/2003 |
| JP | 2003521301 | A | 7/2003 |
| JP | 3442423 | B2 | 9/2003 |
| JP | 2003300416 | A | 10/2003 |
| JP | 2004147701 | A | 5/2004 |
| JP | 2004162035 | A | 6/2004 |
| JP | 2004229976 | A | 8/2004 |
| JP | 2005013573 | A | 1/2005 |
| JP | 2005080702 | A | 3/2005 |
| JP | 2005131163 | A | 5/2005 |
| JP | 2005131164 | A | 5/2005 |
| JP | 2005131173 | A | 5/2005 |
| JP | 2005131211 | A | 5/2005 |
| JP | 2005131212 | A | 5/2005 |
| JP | 2005137423 | A | 6/2005 |
| JP | 2005187954 | A | 7/2005 |
| JP | 2005211455 | A | 8/2005 |
| JP | 2005328882 | A | 12/2005 |
| JP | 2005335432 | A | 12/2005 |
| JP | 2005342267 | A | 12/2005 |
| JP | 3791856 | B2 | 6/2006 |
| JP | 2006187649 | A | 7/2006 |
| JP | 2006218228 | A | 8/2006 |
| JP | 2006281405 | A | 10/2006 |
| JP | 2006346445 | A | 12/2006 |
| JP | 2008220032 | A | 9/2008 |
| JP | 2009507526 | A | 2/2009 |
| JP | 200990113 | A | 4/2009 |
| JP | 2009189838 | A | 8/2009 |
| JP | 2009189846 | A | 8/2009 |
| JP | 2009207260 | A | 9/2009 |
| JP | 2009226028 | A | 10/2009 |
| JP | 2009538684 | A | 11/2009 |
| JP | 2009539420 | A | 11/2009 |
| JP | 2010069307 | A | 4/2010 |
| JP | 2010069310 | A | 4/2010 |
| JP | 2010098844 | A | 4/2010 |
| JP | 2010214128 | A | 9/2010 |
| JP | 2011072574 | A | 4/2011 |
| JP | 4722849 | B2 | 7/2011 |
| JP | 2011524199 | A | 9/2011 |
| JP | 2012143283 | A | 8/2012 |
| JP | 2012145767 | A | 8/2012 |
| JP | 5154710 | B1 | 2/2013 |
| JP | 2014121599 | A | 7/2014 |
| JP | 2016512057 | A | 4/2016 |
| KR | 20100110134 | A | 10/2010 |
| KR | 20110003229 | A | 1/2011 |

(56) References Cited

FOREIGN PATENT DOCUMENTS

| | | | |
|---|---|---|---|
| RU | 1814161 | C | 5/1993 |
| RU | 2008830 | C1 | 3/1994 |
| RU | 2052979 | C1 | 1/1996 |
| RU | 2066128 | C1 | 9/1996 |
| RU | 2069981 | C1 | 12/1996 |
| RU | 2098025 | C1 | 12/1997 |
| RU | 2104671 | C1 | 2/1998 |
| RU | 2110965 | C1 | 5/1998 |
| RU | 2141279 | C1 | 11/1999 |
| RU | 2144791 | C1 | 1/2000 |
| RU | 2161450 | C1 | 1/2001 |
| RU | 2181566 | C2 | 4/2002 |
| RU | 2187249 | C2 | 8/2002 |
| RU | 32984 | U1 | 10/2003 |
| RU | 2225170 | C2 | 3/2004 |
| RU | 42750 | U1 | 12/2004 |
| RU | 61114 | U1 | 2/2007 |
| RU | 61122 | U1 | 2/2007 |
| RU | 2430692 | C2 | 10/2011 |
| SU | 189517 | A | 1/1967 |
| SU | 297156 | A | 5/1971 |
| SU | 328636 | A | 9/1972 |
| SU | 511939 | A1 | 4/1976 |
| SU | 674747 | A1 | 7/1979 |
| SU | 728848 | A1 | 4/1980 |
| SU | 1009439 | A | 4/1983 |
| SU | 1271497 | A1 | 11/1986 |
| SU | 1333319 | A2 | 8/1987 |
| SU | 1377052 | A1 | 2/1988 |
| SU | 1377053 | A1 | 2/1988 |
| SU | 1443874 | A1 | 12/1988 |
| SU | 1509051 | A1 | 9/1989 |
| SU | 1561964 | A1 | 5/1990 |
| SU | 1708312 | A1 | 1/1992 |
| SU | 1722476 | A1 | 3/1992 |
| SU | 1752361 | A1 | 8/1992 |
| SU | 1814161 | A1 | 5/1993 |
| WO | WO-9315648 | A1 | 8/1993 |
| WO | WO-9420030 | A1 | 9/1994 |
| WO | WO-9517855 | A1 | 7/1995 |
| WO | WO-9520360 | A1 | 8/1995 |
| WO | WO-9623448 | A1 | 8/1996 |
| WO | WO-9635464 | A1 | 11/1996 |
| WO | WO-9639086 | A1 | 12/1996 |
| WO | WO-9639088 | A1 | 12/1996 |
| WO | WO-9724073 | A1 | 7/1997 |
| WO | WO-9734533 | A1 | 9/1997 |
| WO | WO-9903407 | A1 | 1/1999 |
| WO | WO-9903409 | A1 | 1/1999 |
| WO | WO-9948430 | A1 | 9/1999 |
| WO | WO-0024322 | A1 | 5/2000 |
| WO | WO-0024330 | A1 | 5/2000 |
| WO | WO-0053112 | A2 | 9/2000 |
| WO | WO-0057796 | A1 | 10/2000 |
| WO | WO-0105702 | A1 | 1/2001 |
| WO | WO-0154594 | A1 | 8/2001 |
| WO | WO-0158371 | A1 | 8/2001 |
| WO | WO-0162164 | A2 | 8/2001 |
| WO | WO-0162169 | A2 | 8/2001 |
| WO | WO-0191646 | A1 | 12/2001 |
| WO | WO-0219932 | A1 | 3/2002 |
| WO | WO-0226143 | A1 | 4/2002 |
| WO | WO-0236028 | A1 | 5/2002 |
| WO | WO-02065933 | A2 | 8/2002 |
| WO | WO-03055402 | A1 | 7/2003 |
| WO | WO-03094747 | A1 | 11/2003 |
| WO | WO-03079909 | A3 | 3/2004 |
| WO | WO-2004019803 | A1 | 3/2004 |
| WO | WO-2004032783 | A1 | 4/2004 |
| WO | WO-2004047626 | A1 | 6/2004 |
| WO | WO-2004047653 | A2 | 6/2004 |
| WO | WO-2004056277 | A1 | 7/2004 |
| WO | WO-2004078050 | A2 | 9/2004 |
| WO | WO-2004078051 | A2 | 9/2004 |
| WO | WO-2004096015 | A2 | 11/2004 |
| WO | WO-2006044581 | A2 | 4/2006 |
| WO | WO-2006051252 | A1 | 5/2006 |
| WO | WO-2006059067 | A1 | 6/2006 |
| WO | WO-2006073581 | A2 | 7/2006 |
| WO | WO-2006085389 | A1 | 8/2006 |
| WO | WO-2007015971 | A2 | 2/2007 |
| WO | WO-2007074430 | A1 | 7/2007 |
| WO | WO-2007129121 | A1 | 11/2007 |
| WO | WO-2007137304 | A2 | 11/2007 |
| WO | WO-2007142625 | A2 | 12/2007 |
| WO | WO-2008021969 | A2 | 2/2008 |
| WO | WO-2008061566 | A1 | 5/2008 |
| WO | WO-2008089404 | A2 | 7/2008 |
| WO | WO-2009005969 | A2 | 1/2009 |
| WO | WO-2009067649 | A2 | 5/2009 |
| WO | WO-2009091497 | A2 | 7/2009 |
| WO | WO-2010126129 | A1 | 11/2010 |
| WO | WO-2010134913 | A1 | 11/2010 |
| WO | WO-2011008672 | A2 | 1/2011 |
| WO | WO-2011044343 | A2 | 4/2011 |
| WO | WO-2012006306 | A2 | 1/2012 |
| WO | WO-2012013577 | A1 | 2/2012 |
| WO | WO-2012044606 | A2 | 4/2012 |
| WO | WO-2012061725 | A1 | 5/2012 |
| WO | WO-2012072133 | A1 | 6/2012 |
| WO | WO-2012166503 | A1 | 12/2012 |
| WO | WO-2013087092 | A1 | 6/2013 |
| WO | WO-2013151888 | A1 | 10/2013 |
| WO | WO-2014004209 | A2 | 1/2014 |
| WO | WO-2014113438 | A1 | 7/2014 |
| WO | WO-2015032797 | A1 | 3/2015 |
| WO | WO-2015138760 | A1 | 9/2015 |
| WO | WO-2015187107 | A1 | 12/2015 |

OTHER PUBLICATIONS

Covidien Brochure, “Endo GIA™ Black Reload with Tri-Staple™ Technology,” (2012), 2 pages.

The Sodem Aseptic Battery Transfer Kit, Sodem Systems, 2000, 3 pages.

Schellhammer et al., “Poly-Lactic-Acid for Coating of Endovascular Stents: Preliminary Results in Canine Experimental Av-Fistulae,” Mat.-wiss. u. Werkstofftech., 32, pp. 193-199 (2001).

Data Sheet of LM4F230H5QR, 2007.

Serial Communication Protocol; Michael Lemmon Feb. 1, 2009; http://www3.nd.edu/~lemmon/courses/ee224/web-manual/web-manual/lab12/node2.html; Wayback Machine to Apr. 29, 2012.

Miyata et al., “Biomolecule-Sensitive Hydrogels,” Advanced Drug Delivery Reviews, 54 (2002) pp. 79-98.

Jeong et al., “Thermosensitive Sol-Gel Reversible Hydrogels,” Advanced Drug Delivery Reviews, 54 (2002) pp. 37-51.

Covidien Brochure, “Endo GIA™ Ultra Universal Stapler,” (2010), 2 pages.

Qiu et al., “Environment-Sensitive Hydrogels for Drug Delivery,” Advanced Drug Delivery Reviews, 53 (2001) pp. 321-339.

Hoffman, “Hydrogels for Biomedical Applications,” Advanced Drug Delivery Reviews, 43 (2002) pp. 3-12.

Hoffman, “Hydrogels for Biomedical Applications,” Advanced Drug Delivery Reviews, 54 (2002) pp. 3-12.

Peppas, “Physiologically Responsive Hydrogels,” Journal of Bioactive and Compatible Polymers, vol. 6 (Jul. 1991) pp. 241-246.

Peppas, Editor “Hydrogels in Medicine and Pharmacy,” vol. I, Fundamentals, CRC Press, 1986.

Young, “Microcellular foams via phase separation,” Journal of Vacuum Science & Technology A 4(3), (May/Jun. 1986).

Chen et al., “Elastomeric Biomaterials for Tissue Engineering,” Progress in Polymer Science 38 (2013), pp. 584-671.

Ebara, “Carbohydrate-Derived Hydrogels and Microgels,” Engineered Carbohydrate-Based Materials for Biomedical Applications: Polymers, Surfaes, Dendrimers, Nanoparticles, and Hydrogels, Edited by Ravin Narain, 2011, pp. 337-345.

Matsuda, “Thermodynamics of Formation of Porous Polymeric Membrane from Solutions,” Polymer Journal, vol. 23, No. 5, pp. 435-444 (1991).

(56) References Cited

OTHER PUBLICATIONS

Byrne et al., "Molecular Imprinting Within Hydrogels," Advanced Drug Delivery Reviews, 54 (2002) pp. 149-161.
Covidien Brochure, "Endo GIA™ Reloads with Tri-Staple™ Technology," (2010), 1 page.
Covidien Brochure, "Endo GIA™ Reloads with Tri-StapleTm Technology and Endo GIA™ Ultra Universal Staplers," (2010), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
http://ninpgan.net/publications/51-100/89.pdf; 2004, Ning Pan, on Uniqueness of Fibrous Materials, Design & Nature II. Eds: Colins, M. and Brebbia, C. WIT Press, Boston, 493-504.
D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20., pp. 1744-1748.
Patrick J. Sweeney: "RFID for Dummies", Mar. 11, 2010, pp. 365-365, XP055150775, ISBN: 978-1-11-805447-5, Retrieved from the Internet: URL: books.google.de/books?isbn=1118054474 [retrieved on Nov. 4, 2014]—book not attached.
Datasheet for Panasonic TK Relays Ultra Low Profile 2 A Polarized Relay, Copyright Matsushita Electric Works, Ltd. (Known of at least as early as Aug. 17, 2010), 5 pages.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
"Indian Standard: Automotive Vehicles—Brakes and Braking Systems (IS 11852-1:2001)", Mar. 1, 2001.
Disclosed Anonymously, "Motor-Driven Surgical Stapler Improvements," Research Disclosure Database No. 526041, Published: Feb. 2008.
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
ASTM procedure D2240-00, "Standard Test Method for Rubber Property-Durometer Hardness," (Published Aug. 2000).
ASTM procedure D2240-05, "Standard Test Method for Rubber Property-Durometer Hardness," (Published Apr. 2010).
Pitt et al., "Attachment of Hyaluronan to Metallic Surfaces," J. Biomed. Mater. Res. 68A: pp. 95-106, 2004.
Solorio et al., "Gelatin Microspheres Crosslinked with Genipin for Local Delivery of Growth Factors," J. Tissue Eng. Regen. Med. (2010), 4(7): pp. 514-523.
Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Staple™ Technology," (23 pages).
Covidien "iDrive™ Ultra Powered Stapling System, A Guide for Surgeons," (6 pages).
Covidien "iDrive™ Ultra Powered Stapling System, Cleaning and Sterilization Guide," (2 pages).
Covidien Brochure "iDrive™ Ultra Powered Stapling System," (6 pages).
Seils et al., Covidien Summary: Clinical Study "UCONN Biodynamics: Final Report on Results," (2 pages).
"Biomedical Coatings," Fort Wayne Metals, Research Products Corporation, obtained online at www.fwmetals.com on Jun. 21, 2010 (1 page).
Allegro MicroSystems, LLC, Automotive Full Bridge MOSFET Driver, A3941-DS, Rev. 5, 21 pages, http://www.allegromicro.com/~/media/Files/Datasheets/A3941-Datasheet.ashx?la=en.
Lyon et al. "The Relationship Between Current Load and Temperature for Quasi-Steady State and Transient Conditions," SPIE—International Society for Optical Engineering. Proceedings, vol. 4020, (pp. 62-70), Mar. 30, 2000.
Anonymous: "Sense & Control Application Note Current Sensing Using Linear Hall Sensors," Feb. 3, 2009, pp. 1-18. Retrieved from the Internet: URL: http://www.infineon.com/dgdl/Current_Sensing_Rev.1.1.pdf?fileId=db3a304332d040720132d939503e5f17 [retrieved on Oct. 18, 2016].
Mouser Electronics, "LM317M 3-Terminal Adjustable Regulator with Overcurrent/Overtemperature Self Protection", Mar. 31, 2014 (Mar. 31, 2014), XP0555246104, Retrieved from the Internet: URL: http://www.mouser.com/ds/2/405/lm317m-440423.pdf, pp. 1-8.
Mouser Electronics, "LM317 3-Terminal Adjustable Regulator with Overcurrent/Overtemperature Self Protection", Sep. 30, 2016 (Sep. 30, 2016), XP0555246104, Retrieved from the Internet: URL: http://www.mouser.com/ds/2/405/lm317m-440423.pdf, pp. 1-9.
Cuper et al., "The Use of Near-Infrared Light for Safe and Effective Visualization of Subsurface Blood Vessels to Facilitate Blood Withdrawal in Children," Medical Engineering & Physics, vol. 35, No. 4, pp. 433-440 (2013).
Anonymous, Analog Devices Wiki, Chapter 11: The Current Mirror, Aug. 20, 2017, 22 pages. https://wiki.analog.com/university/courses/electronics/text/chapter-11?rev=1503222341.
Yan et al, Comparison of the effects of Mg—6Zn and Ti—3Al-2.5V alloys on TGF-β/TNF-α/VEGF/b-FGF in the healing of the intestinal track in vivo, Biomed. Mater. 9 (2014), 11 pages.
Yan et al., "Comparison of the effects of Mg—6Zn and titanium on intestinal tract in vivo," J Mater Sci: Mater Med (2013), 11 pages.
Brar et al., "Investigation of the mechanical and degradation properties of Mg—Sr and Mg—Zn—Sr alloys for use as potential biodegradable implant materials," J. Mech. Behavior of Biomed. Mater. 7 (2012) pp. 87-95.
Pellicer et al. "On the biodegradability, mechanical behavior, and cytocompatibility of amorphous Mg72Zn23Ca5 and crystalline Mg70Zn23Ca5Pd2 alloys as temporary implant materials," J Biomed Mater Res Part A ,2013:101A:502-517.
Texas Instruments: "Current Recirculation and Decay Modes," Application Report SLVA321—Mar. 2009; Retrieved from the Internet: URL:http://www.ti.com/lit/an/slva321/slva321 [retrieved on Apr. 25, 2017], 7 pages.
Qiu Li Loh et al.: "Three-Dimensional Scaffolds for Tissue Engineering Applications: Role of Porosity and Pore Size", Tissue Engineering Part B—Reviews, vol. 19, No. 6, Dec. 1, 2013, pp. 485-502.
Gao et al., "Mechanical Signature Enhancement of Response Vibrations in the Time Lag Domain," Fifth International Congress on Sound and Vibration, Dec. 15-18, 1997, pp. 1-8.
Trendafilova et al., "Vibration-based Methods for Structural and Machinery Fault Diagnosis Based on Nonlinear Dynamics Tools," In: Fault Diagnosis in Robotic and Industrial Systems, IConcept Press Ltd, 2012, pp. 1-29.
Youtube.com; video by Fibran (retrieved from URL https://www.youtube.com/watch?v=vN2Qjt51gFQ); (Year: 2018).
"Foot and Ankle: Core Knowledge in Orthopaedics"; by DiGiovanni MD, Elsevier; (p. 27, left column, heading "Materials for Soft Orthoses", 7th bullet point); (Year: 2007).
Lee, Youbok, "Antenna Circuit Design for RFID Applications," 2003, pp. 1-50, DS00710C, Microchip Technology Inc., Available: http://ww1.microchip.com/downloads/en/AppNotes/00710c.pdf.
Kawamura, Atsuo, et al. "Wireless Transmission of Power and Information Through One High-Frequency Resonant AC Link Inverter for Robot Manipulator Applications," Journal, May/Jun. 1996, pp. 503-508, vol. 32, No. 3, IEEE Transactions on Industry Applications.
Honda HS1332AT and ATD Model Info, powerequipment.honda.com [online], published on or before Mar. 22, 2016, [retrieved on May 31, 2019], retrieved from the Internet [URL: https://powerequipment.honda.com/snowblowers/models/hss1332at-hss1332atd] {Year: 2016).

(56) References Cited

OTHER PUBLICATIONS

Slow Safety Sign, shutterstock.com [online], published on or before May 9, 2017, [retrieved on May 31, 2019], retrieved from the https://www.shutterstock.com/image-victor/slow-safety-sign-twodimensional-turtle-symbolizing- . . . see PDF in file for full URL] (Year: 2017).

Warning Sign Beveled Buttons, by Peter, flarestock.com [online], published on or before Jan. 1, 2017, [retrieved on Jun. 4, 2019], retrieved from the Internet [URL: https://www.flarestock.com/stock-images/warning-sign-beveled-buttons/70257] (Year: 2017).

Arrow Sign Icon Next Button, by Blan-k, shutterstock.com [online], published on or before Aug. 6, 2014, [retrieved on Jun. 4, 2019], retrieved from the Internet [URL:https://www.shutterstock.com/de/image-vector/arrow-sign-icon-next-button-navigation-207700303?irgwc=1&utm . . . see PDF in file for full URL] (Year: 2014).

Elite Icons, by smart/icons, iconfinder.com [online], published on Aug. 18, 2016, [retrieved on Jun. 4, 2019], retrieved from the Internet [URL: https://www.iconfinder.com/iconsets/elite] (Year: 2016).

"Tutorial overview of inductively coupled RFID Systems," UPM, May 2003, pp. 1-7, UPM Rafsec,<http://cdn.mobiusconsulting.com/papers/rfidsystems.pdf>.

Schroeter, John, "*Demystifying UHF Gen 2 RFID, HF RFID,*" Online Article, Jun. 2, 2008, pp. 1-3, <https://www.edn.com/design/industrial-control/4019123/Demystifying-UHF-Gen-2-RFID-HF-RFID>.

Adeeb, et al., "An Inductive Link-Based Wireless Power Transfer System for Biomedical Applications," *Research Article,* Nov. 14, 2011, pp. 1-12, vol. 2012, Article ID 879294, Hindawi Publishing Corporation.

"Pushing Pixels (GIF)", published on dribble.com, 2013.

"Sodium stearate C18H35NaO2", Chemspider Search and Share Chemistry, Royal Society of Chemistry, pp. 1-3, 2015, http://www.chemspider.com/Chemical-Structure.12639.html, accessed May 23, 2016.

NF Monographs: Sodium Stearate, U.S. Pharmacopeia, http://www.pharmacopeia.cn/v29240/usp29nf24s0_m77360.html, accessed May 23, 2016.

Fischer, Martin H, "Colloid-Chemical Studies on Soaps", The Chemical Engineer, pp. 184-193, Aug. 1919.

V.K. Ahluwalia and Madhuri Goyal, A Textbook of Organic Chemistry, Section 19.11.3, p. 356, 2000.

A.V. Kasture and S.G. Wadodkar, Pharmaceutical Chemistry—II: Second Year Diploma in Pharmacy, Nirali Prakashan, p. 339, 2007.

Forum discussion regarding "Speed Is Faster", published on Oct. 1, 2014 and retrieved on Nov. 8, 2019 from URL https://english.stackexchange.com/questions/199018/how-is-that-correct-speed-is-faster-or-prices-are-cheaper (Year: 2014).

* cited by examiner

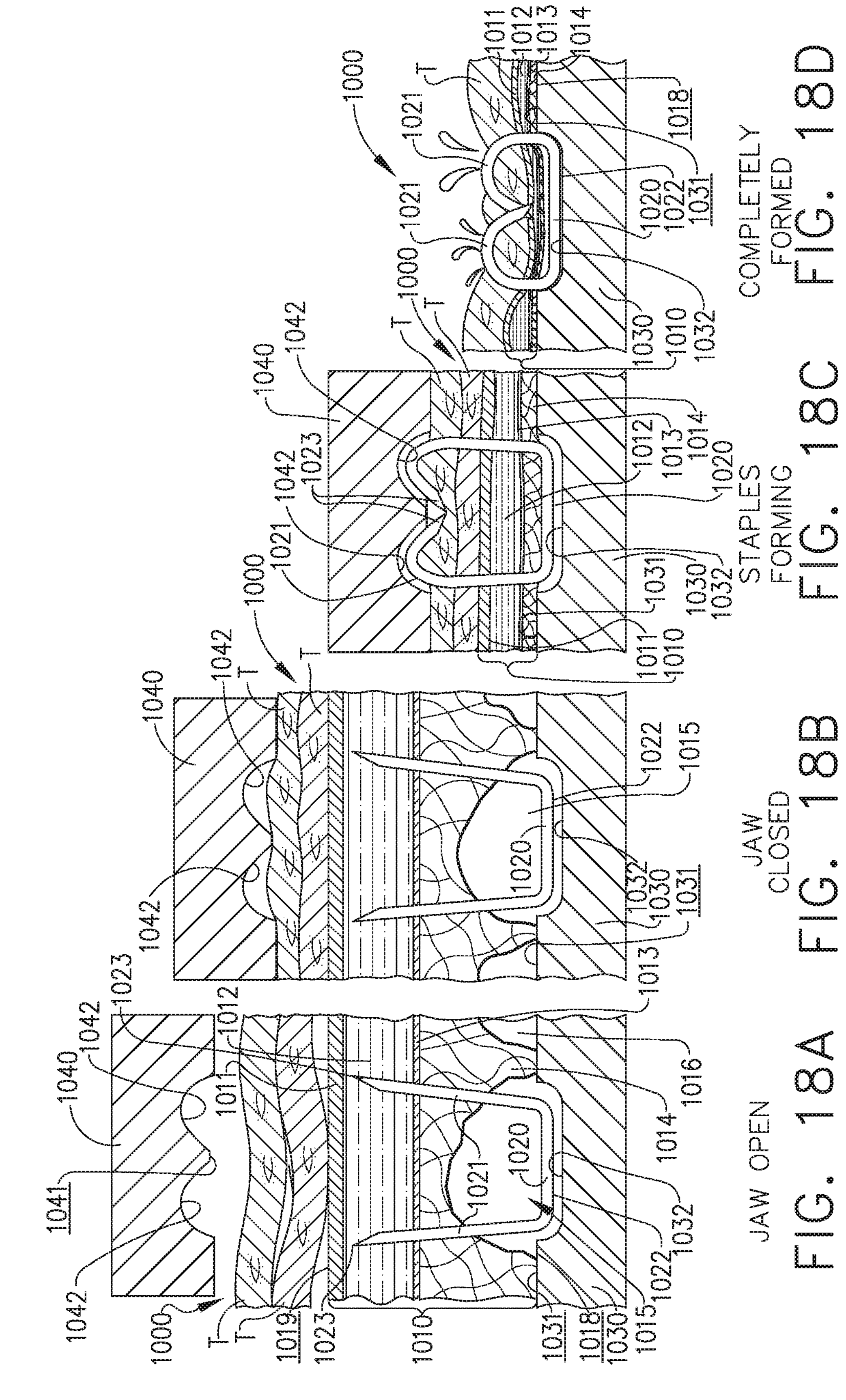
JAW OPEN FIG. 18A
JAW CLOSED FIG. 18B
STAPLES FORMING FIG. 18C
COMPLETELY FORMED FIG. 18D FIG. 34
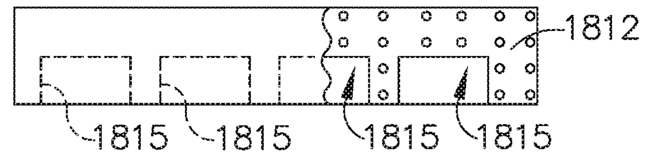
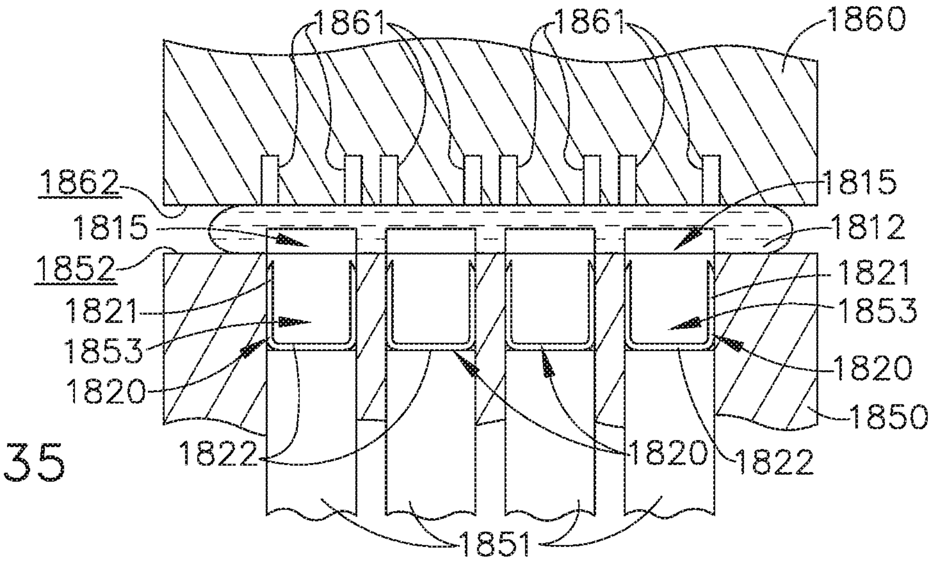
FIG. 35
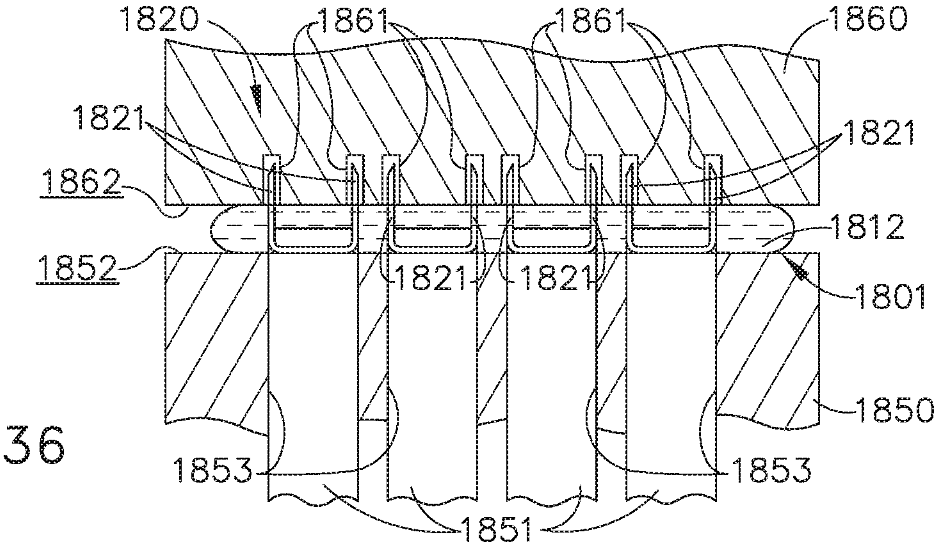
FIG. 36

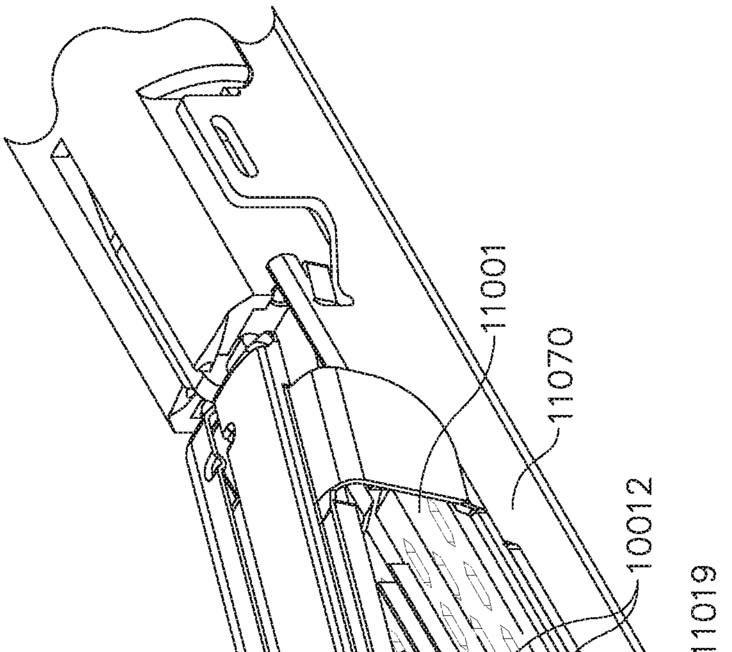
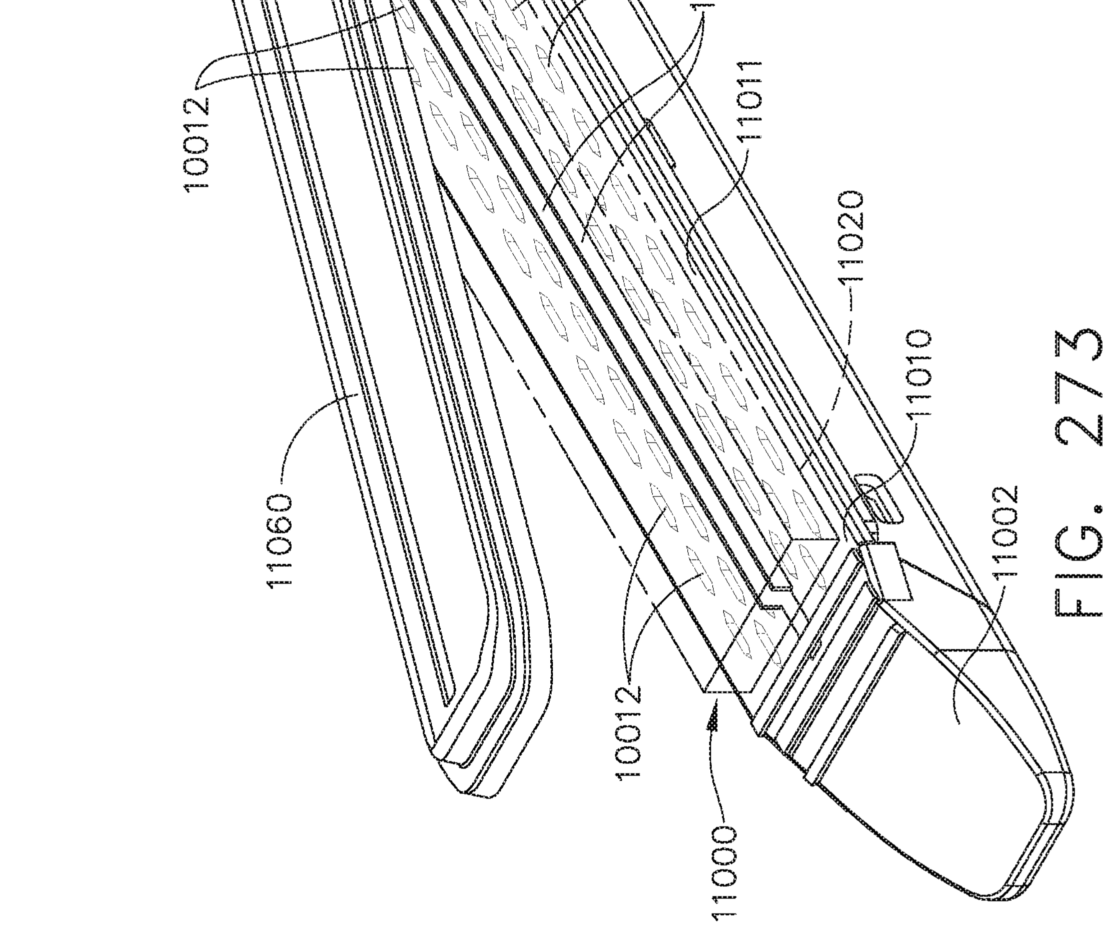
FIG. 273
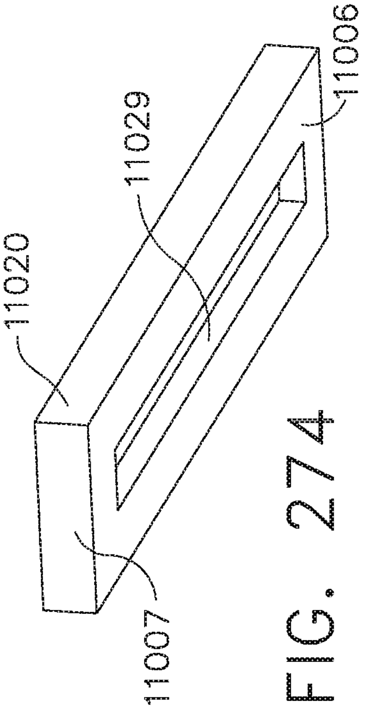
FIG. 274

13829

30060
52020
52024
52024a
52080
52099
30030
30012
52024b
T
30050

60120
60122a
60124
60122b
60132

60122a
60132
60224
60122b
60220

63020
63026
63032
20000'
12'
63022a
63024
63022b 60320
60122a
60324
60122b
60132

60122a
60424
60132
60122b
60420

60122a
60524
60122b
60520
60132

60620
60122a
60624
60122b
60132

60720
60122a
60724
60122b
60132

60820
60122a
60828
60122b
60824
60132

STAPLE CARTRIDGE COMPRISING AN ABSORBABLE ADJUNCT

CROSS-REFERENCE TO RELATED APPLICATIONS

This application is a continuation application claiming priority under 35 U.S.C. § 120 to U.S. patent application Ser. No. 14/540,731, entitled TISSUE THICKNESS COMPENSATOR COMPRISING CAPSULES DEFINING A LOW PRESSURE ENVIRONMENT, filed Nov. 13, 2014, now U.S. Pat. No. 9,974,538, which is a continuation application claiming priority under 35 U.S.C. § 120 to U.S. patent application Ser. No. 13/433,115, entitled TISSUE THICKNESS COMPENSATOR COMPRISING CAPSULES DEFINING A LOW PRESSURE ENVIRONMENT, filed Mar. 28, 2012, which issued on Dec. 8, 2015 as U.S. Pat. No. 9,204,880, the entire disclosures of which are hereby incorporated by reference herein.

BACKGROUND

The present invention relates to surgical instruments and, in various embodiments, to surgical cutting and stapling instruments and staple cartridges therefor that are designed to cut and staple tissue.

BRIEF DESCRIPTION OF THE DRAWINGS

The features and advantages of this invention, and the manner of attaining them, will become more apparent and the invention itself will be better understood by reference to the following description of embodiments of the invention taken in conjunction with the accompanying drawings, wherein:

FIGS. 18A-18D diagram the deformation of a surgical staple positioned within a collapsible staple cartridge body in accordance with at least one embodiment;

FIG. 34 is partial cut-away view of an inner layer of a compressible staple cartridge body;

FIG. 35 is a diagram illustrating the inner layer of FIG. 34 compressed between a transfer plate and a support plate;

FIG. 36 is a diagram illustrating staples being inserted into the compressed inner layer of FIG. 35;

FIG. 110 is a top view of a retention aperture of a retention matrix comprising a retention tab extending into the retention aperture in accordance with at least one embodiment;

FIG. 111 is a top view of a retention aperture of a retention matrix comprising a retention tab extending into the retention aperture in accordance with at least one alternative embodiment;

FIG. 112 is a perspective view of a fastening system comprising a plurality of staples, a retention matrix engaged with the staples, and an alignment matrix configured to align the staples;

FIG. 113 is a perspective view of the retention matrix of FIG. 112;

FIG. 114 is a perspective view of the alignment matrix of FIG. 112;

FIG. 115 is a partial top view of the retention matrix of FIG. 112 engaged with the staples of FIG. 112;

FIG. 116 is a partial bottom view of the retention matrix of FIG. 112 engaged with the staples of FIG. 112;

FIG. 117 is a partial elevational view of the fastening system of FIG. 112;

FIG. 118 is a partial perspective view of the fastening system of FIG. 112;

FIG. 119 is a partial cross-sectional view of the retention matrix of FIG. 112 engaged with the staples of FIG. 112;

FIG. 120 is a partial cross-sectional view of the fastening system of FIG. 112;

FIG. 121 is a perspective view of the fastening system of FIG. 112 further comprising protective caps assembled to the legs of the staples;

Figures 29, 30, 31, 32, 33:
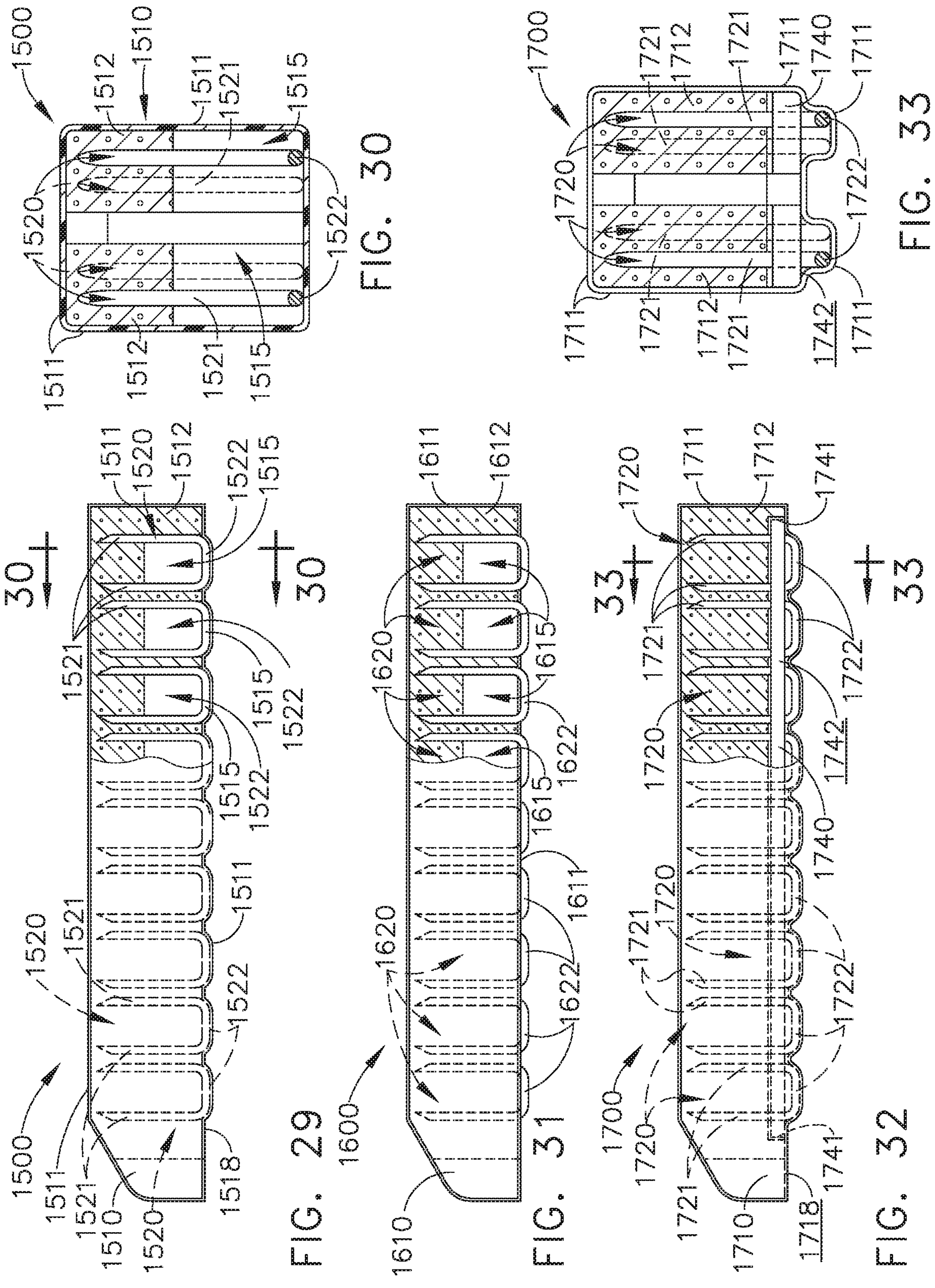
FIG. 29 is a partial break-away view of a staple cartridge in accordance with at least one embodiment comprising staples at least partially embedded in a collapsible staple cartridge body, the staples being at least partially positioned in a staple cavity void in the staple cartridge body.
FIG. 30 is a cross-sectional view of the staple cartridge of FIG. 29 taken along line 30-30 in FIG. 29.
FIG. 31 is a partial break-away view of a staple cartridge in accordance with at least one embodiment.
FIG. 32 is a partial break-away view of a staple cartridge in accordance with at least one embodiment comprising staples at least partially embedded within a collapsible staple cartridge body and an alignment matrix connecting the staples and aligning the staples with respect to each other.
FIG. 33 is a cross-sectional view of the staple cartridge of FIG. 32 taken along line 33-33 in FIG. 32.
Figure 121:
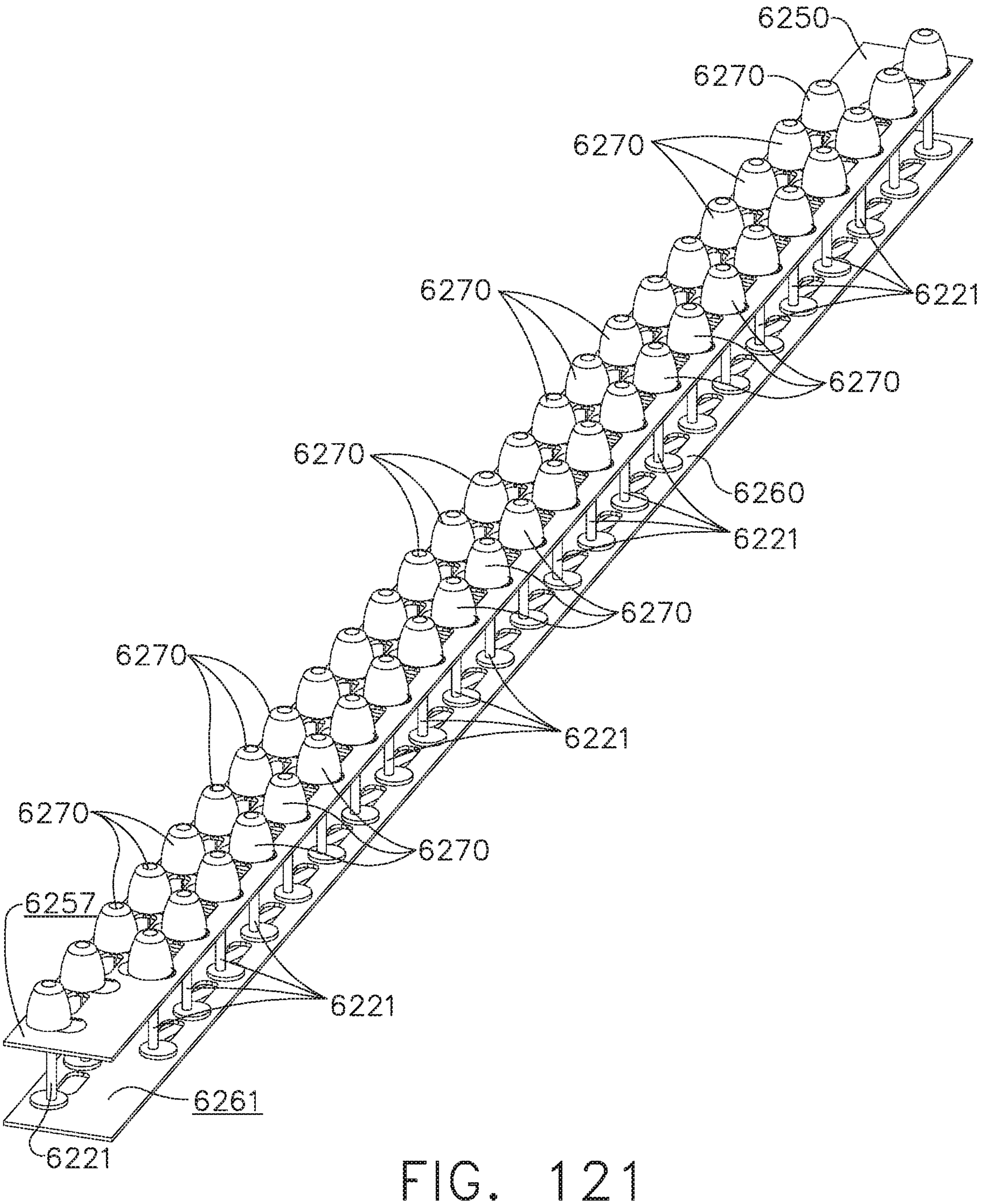
Figure 122:
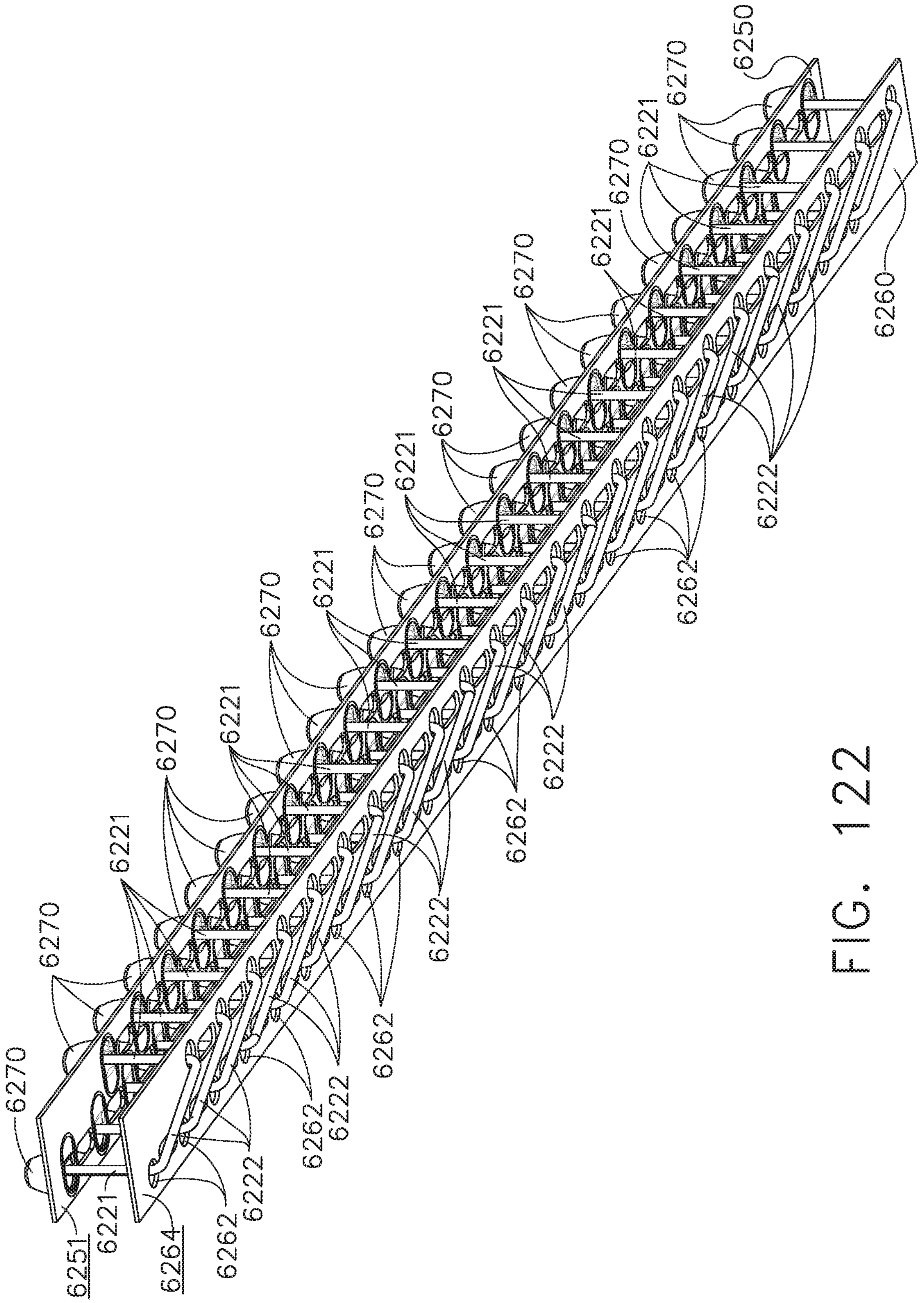
Figure 123:
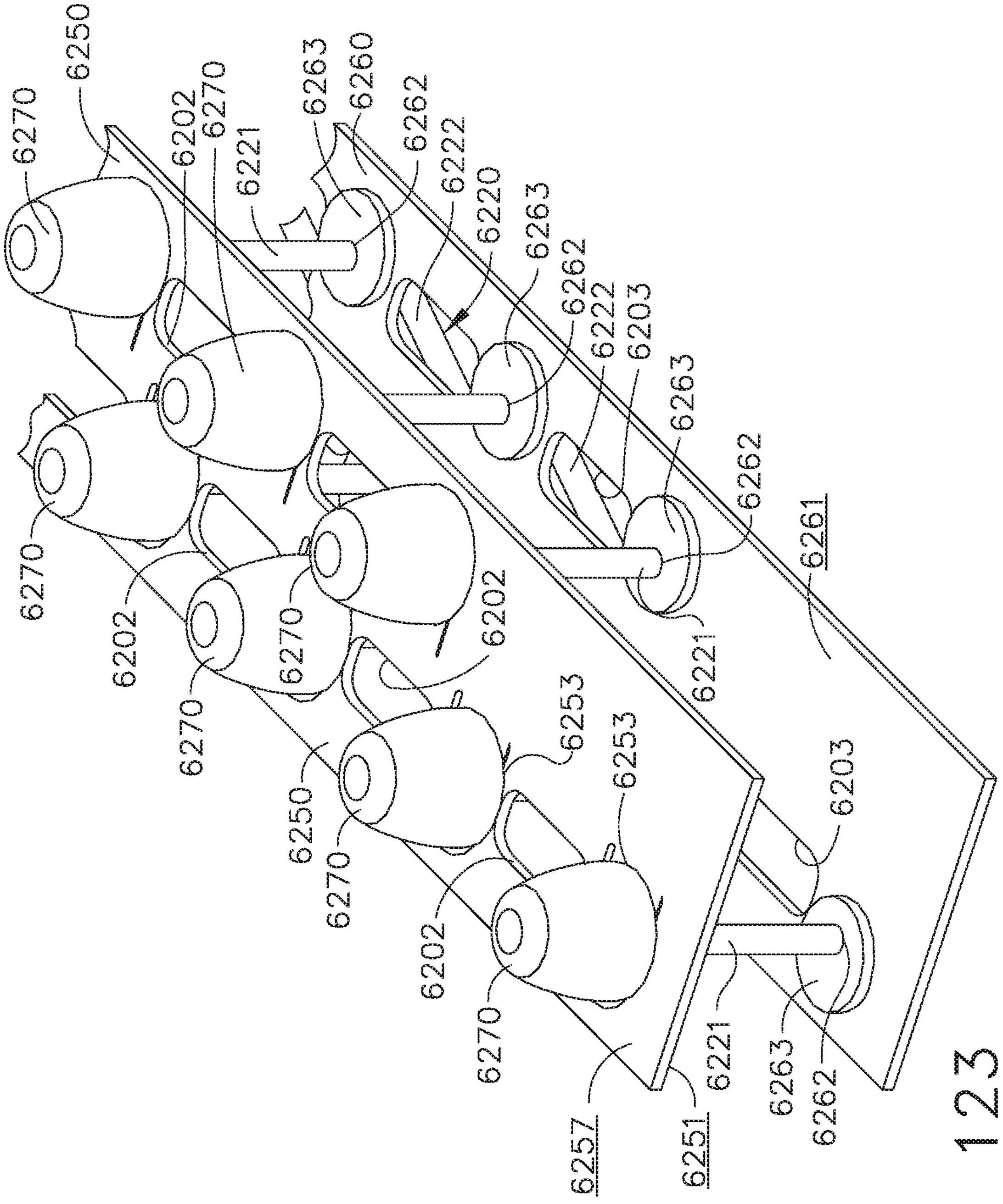
Figure 124:
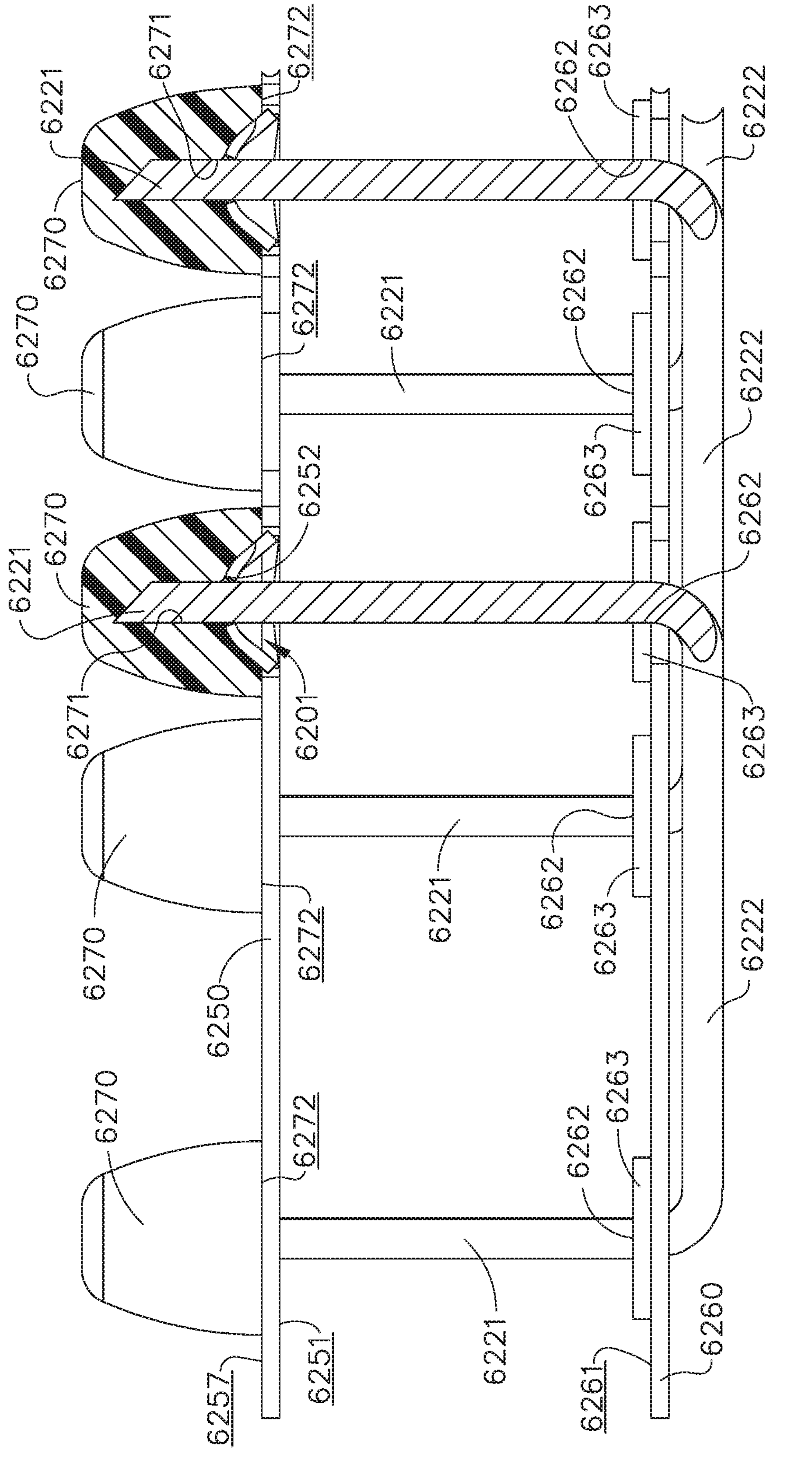
Figure 125:
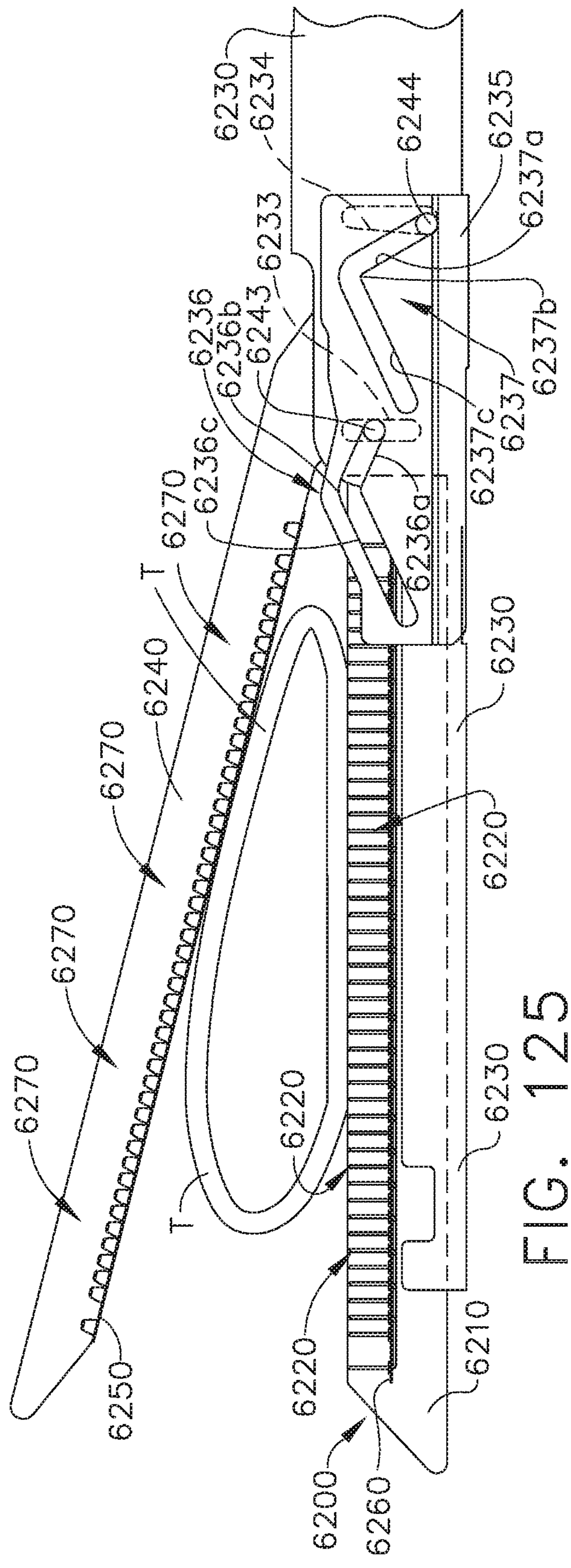
Figure 126:
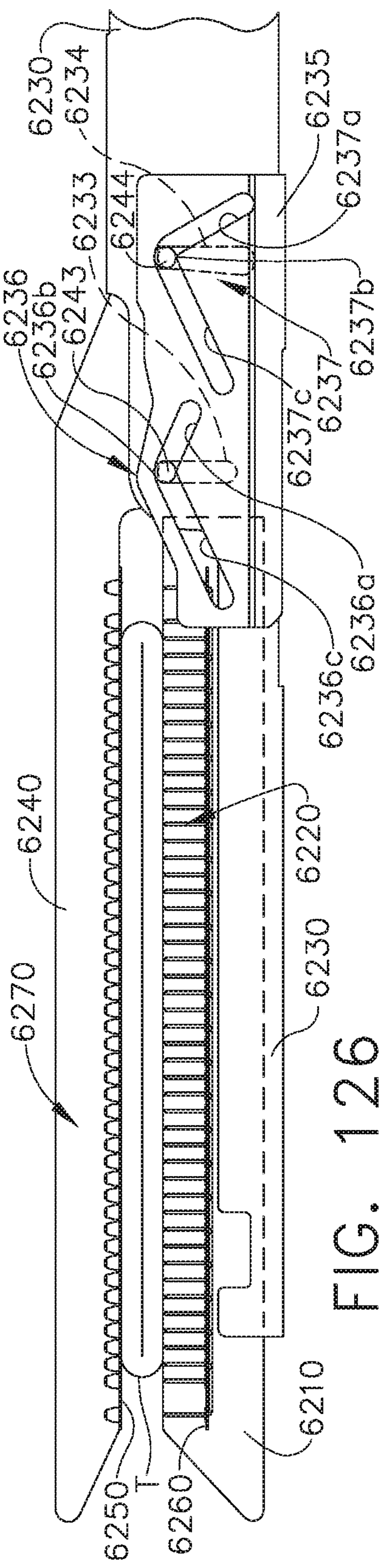
Figure 127:
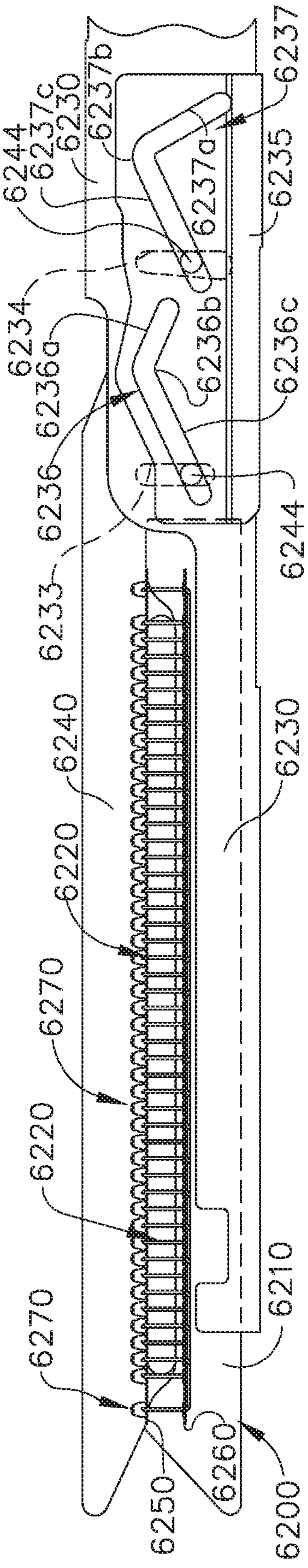
Figure 128:
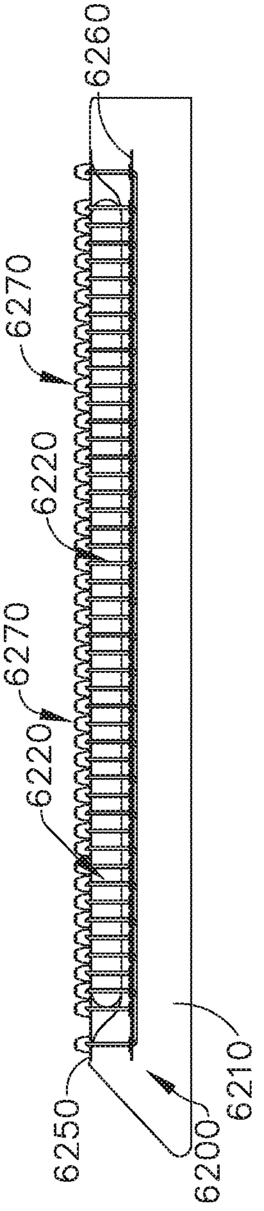
Figure 129:
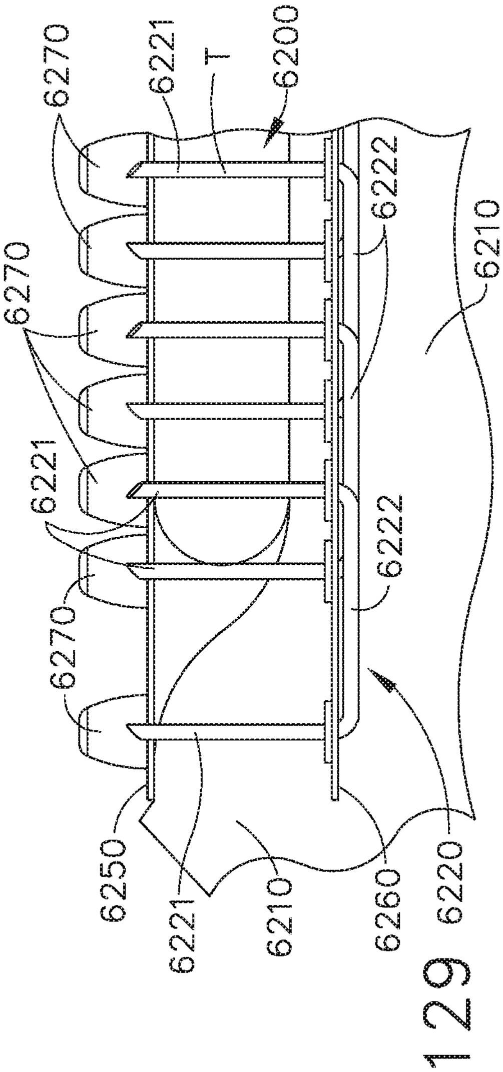
Figure 130:
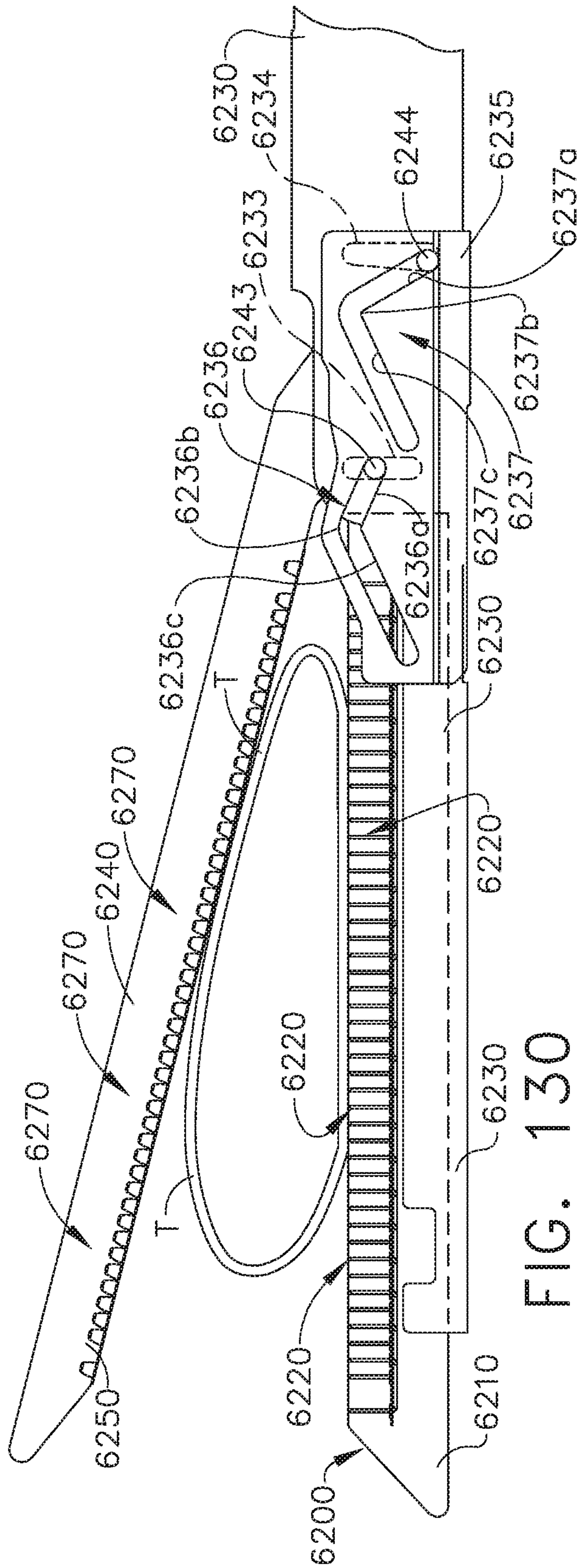
Figure 131:
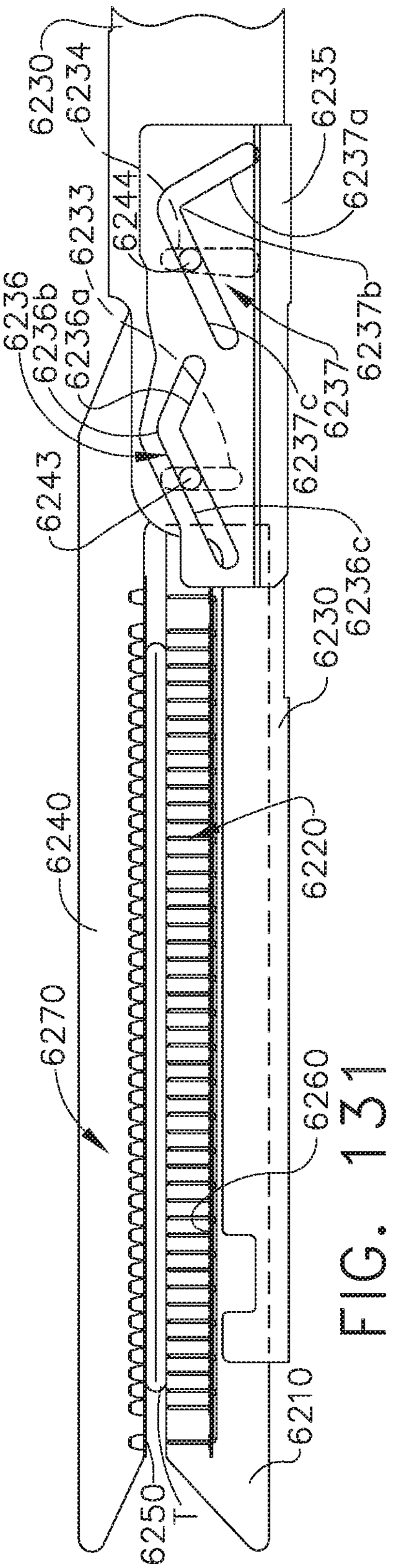
Figure 132:
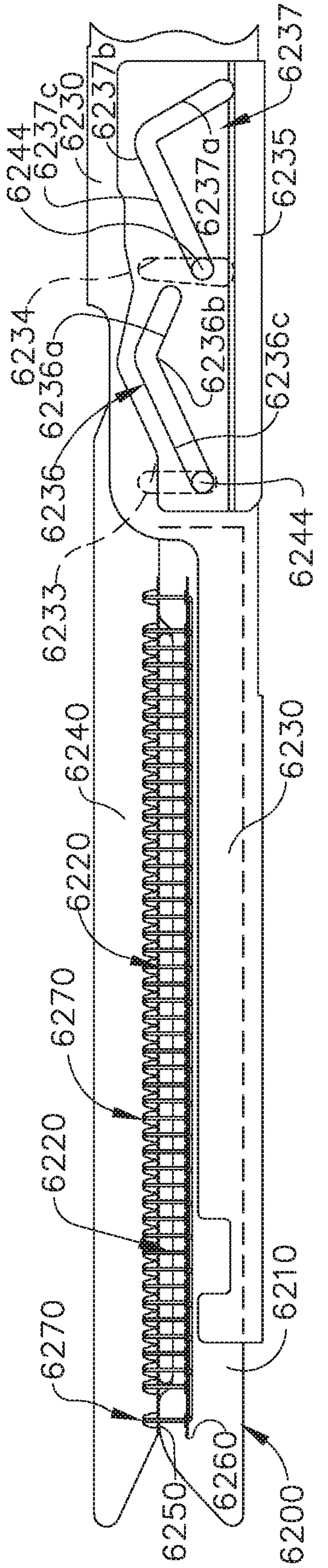
Figure 133:
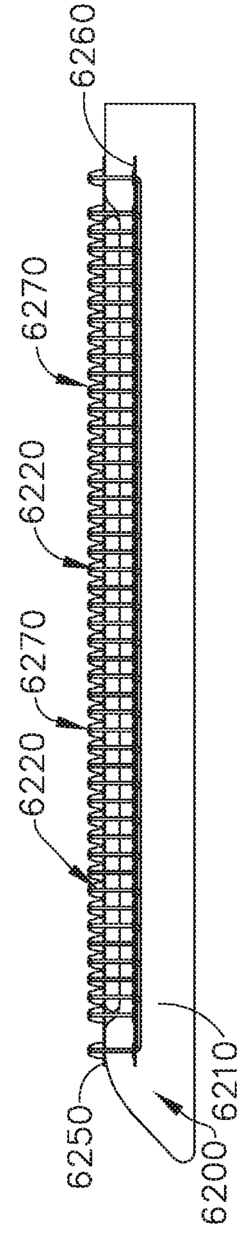
Figure 134:
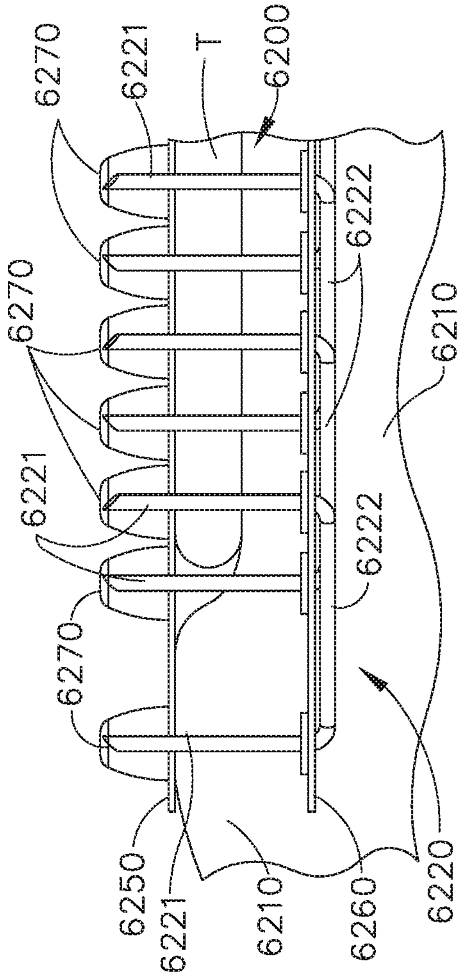
Figure 135:
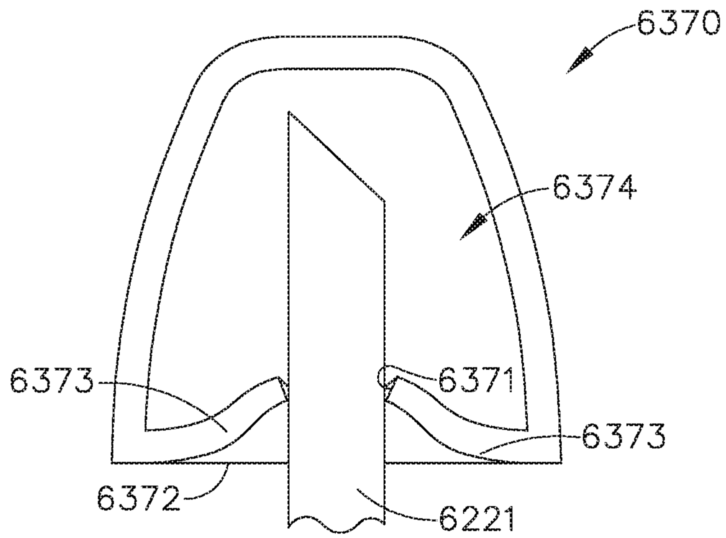
Figure 136:
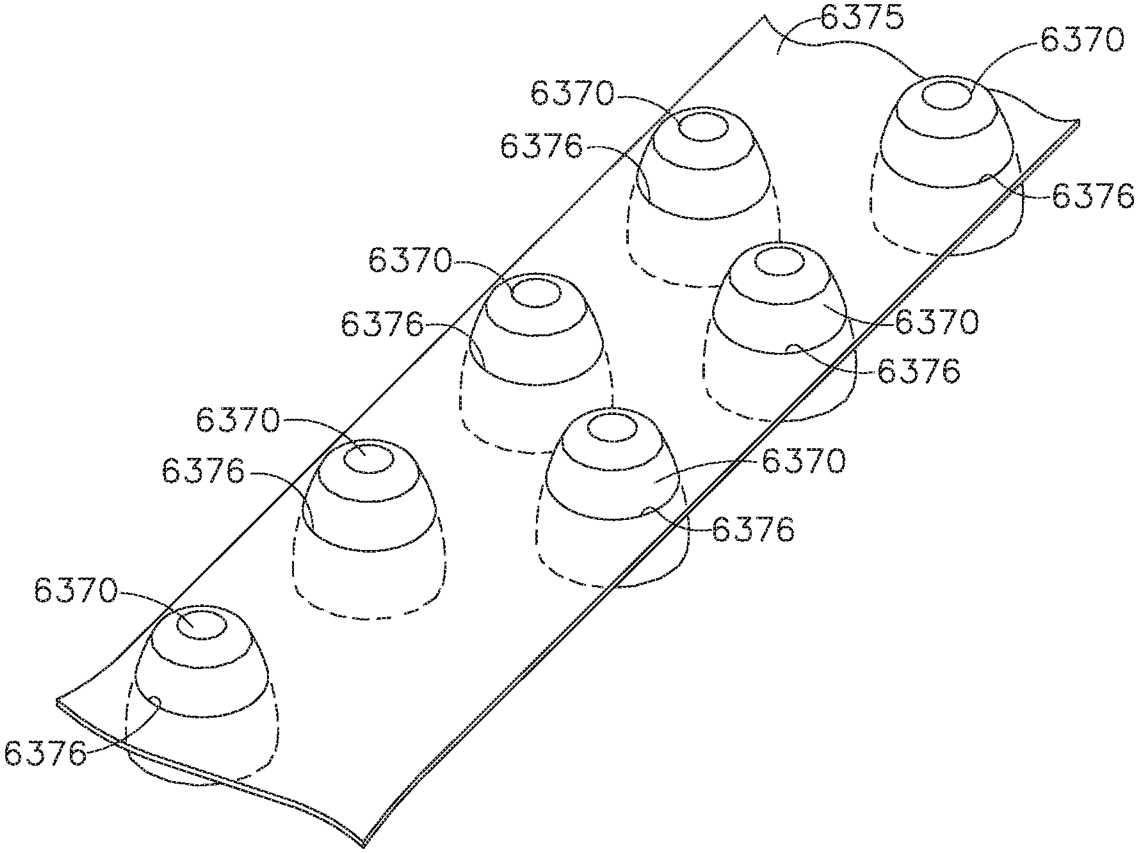
Figure 137:
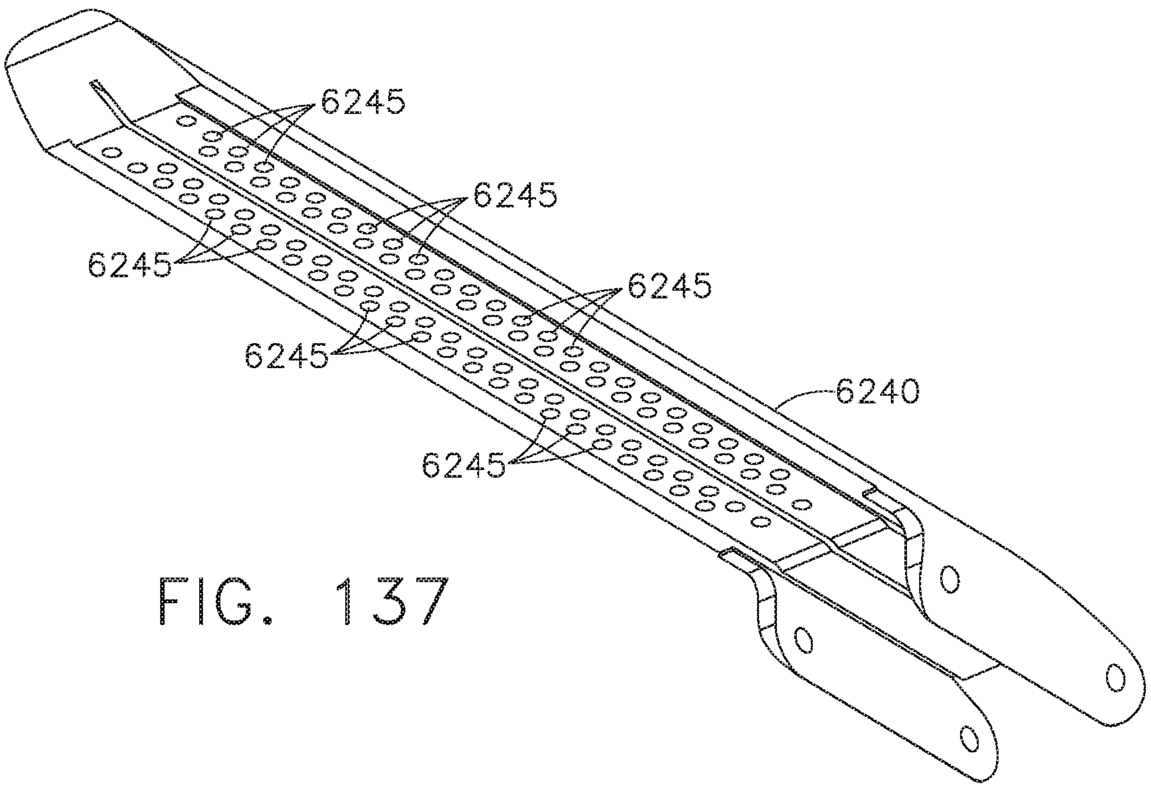
Figure 138:
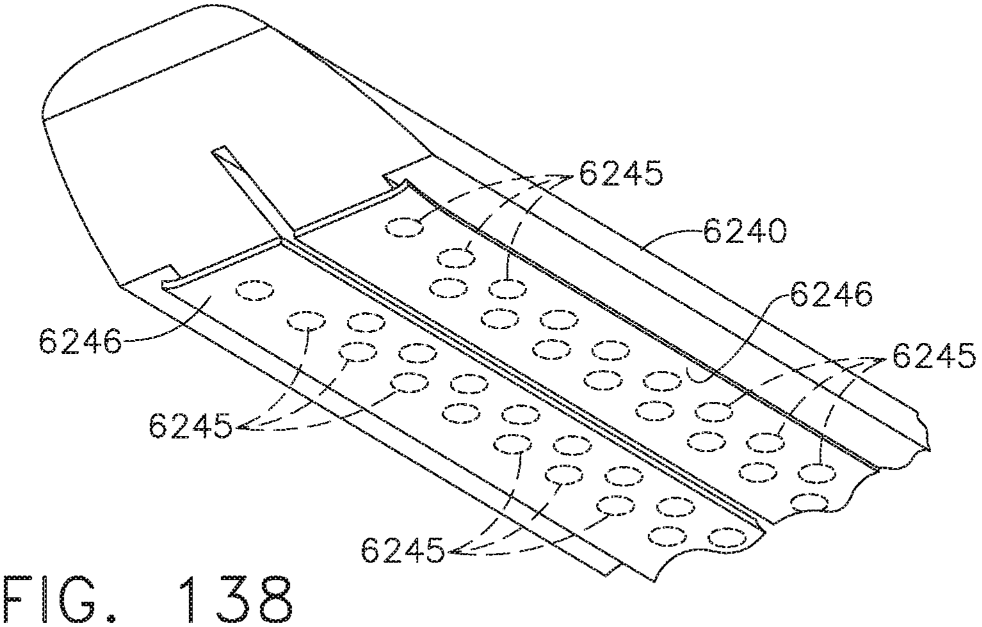
Figure 139:
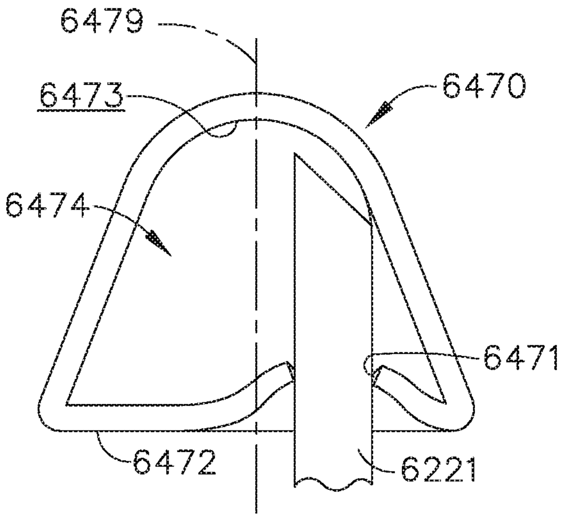
Figure 140:
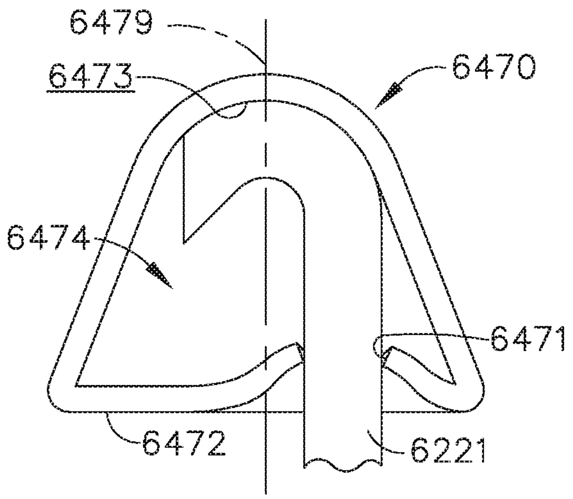
Figure 141:
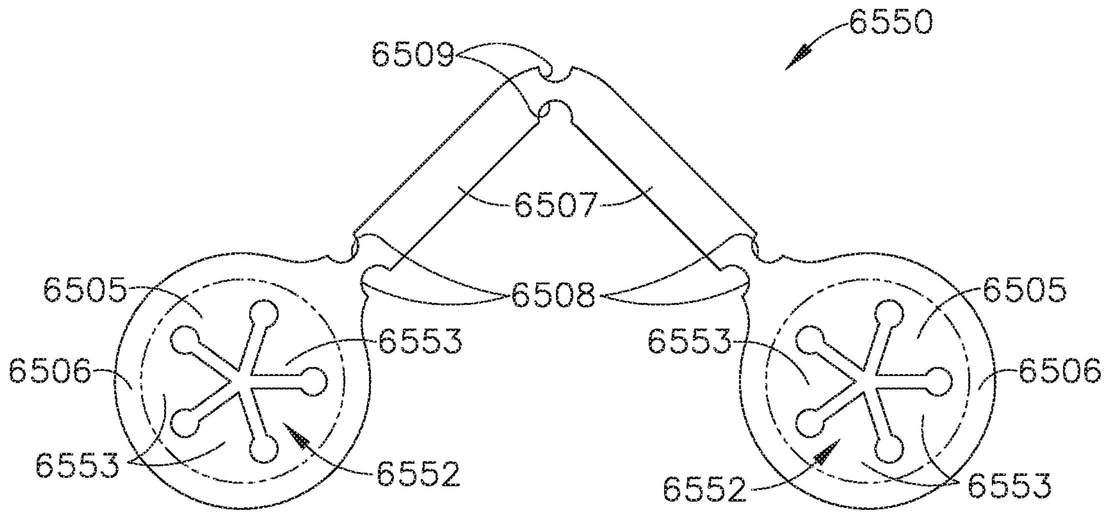
Figure 142:
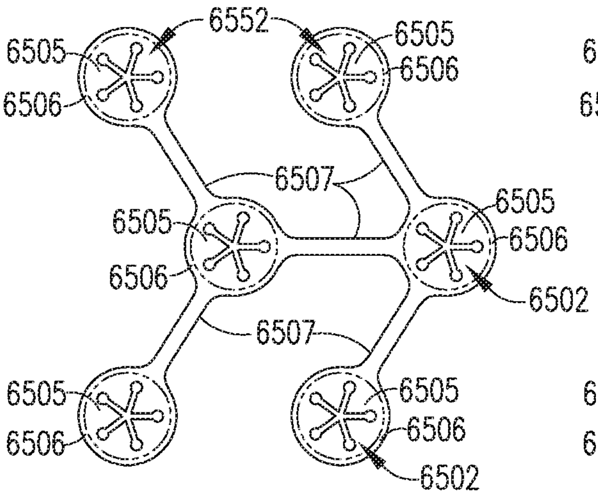
Figure 143:
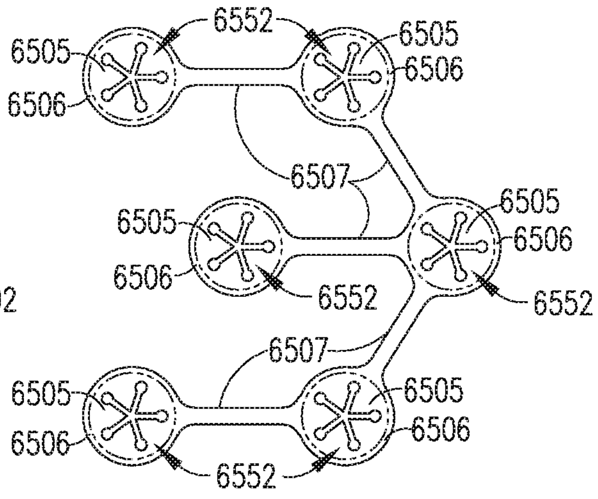
Figure 144:
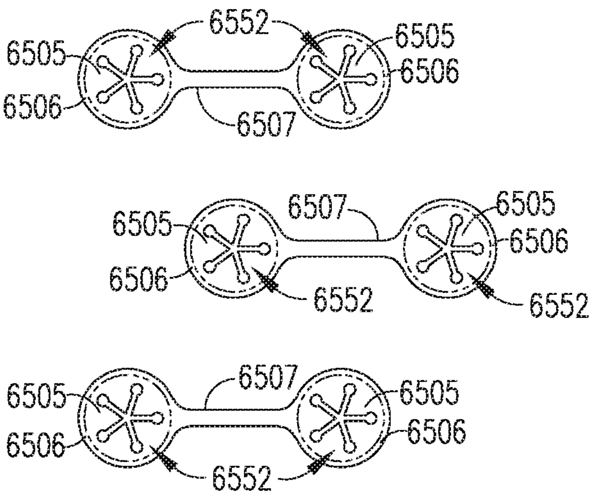
Figure 145:
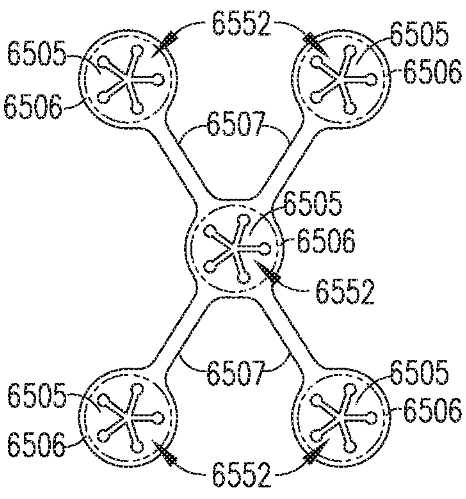
Figure 146:
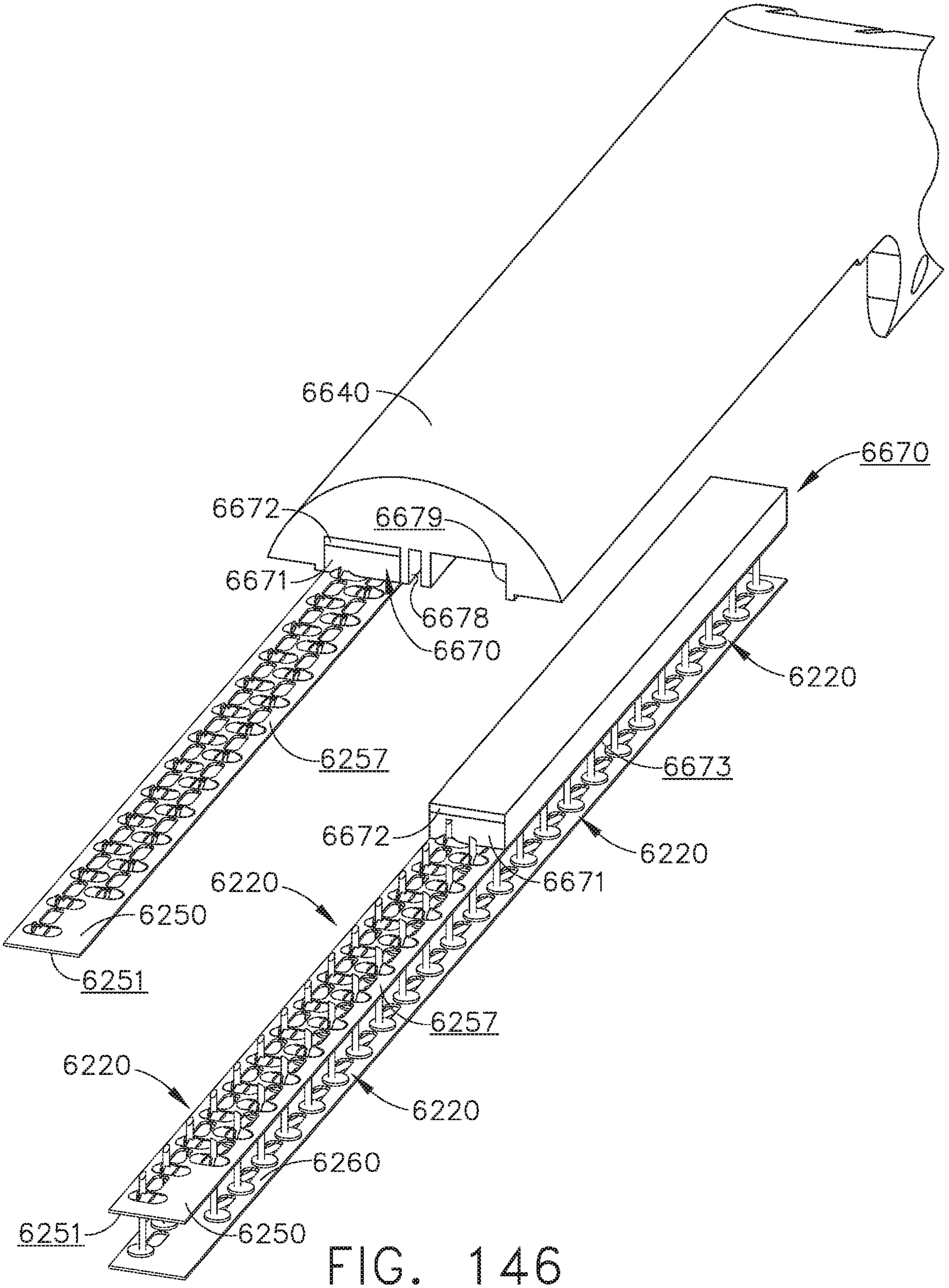
Figure 147:
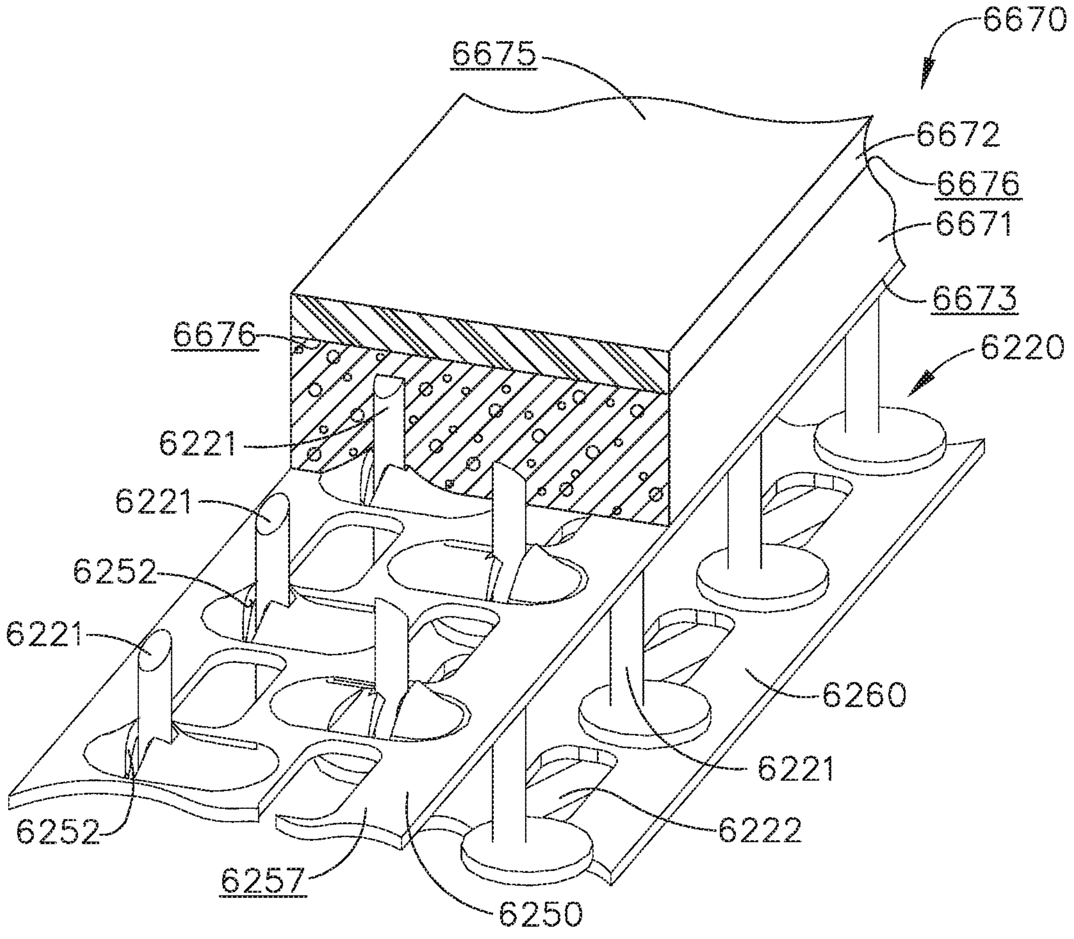
Figure 148:
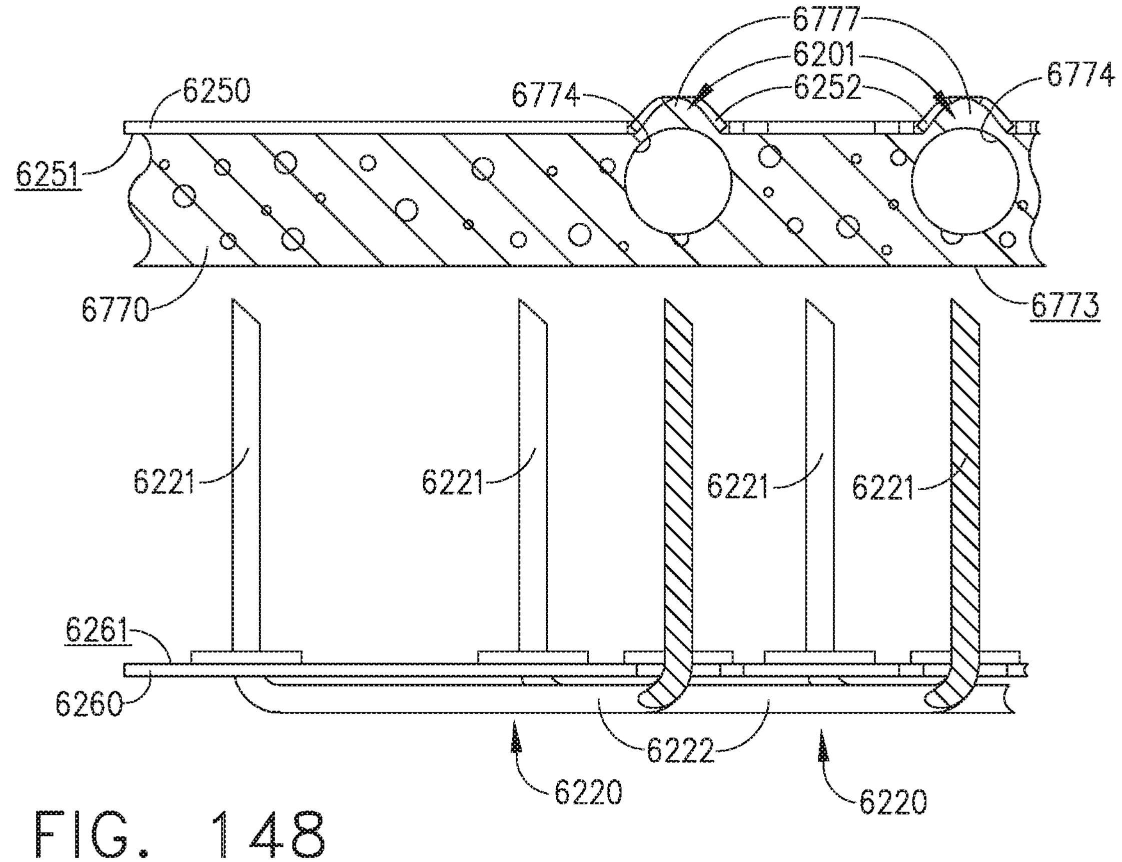
Figure 149:
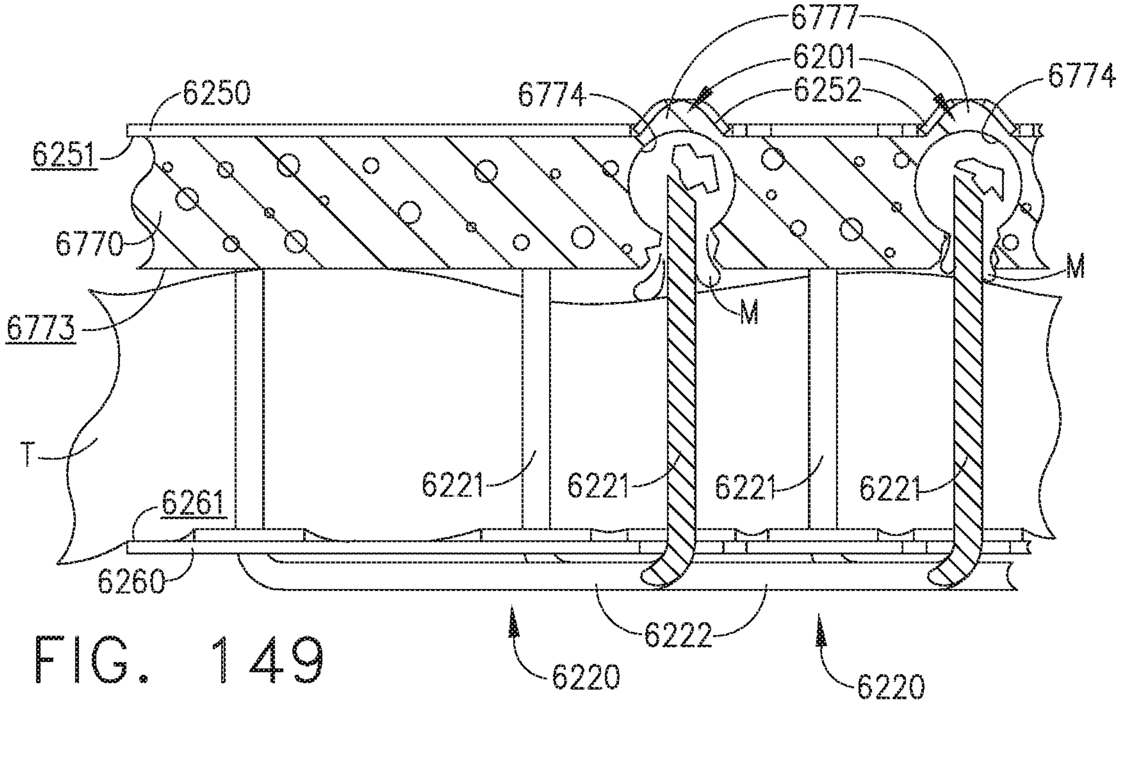
Figure 150:
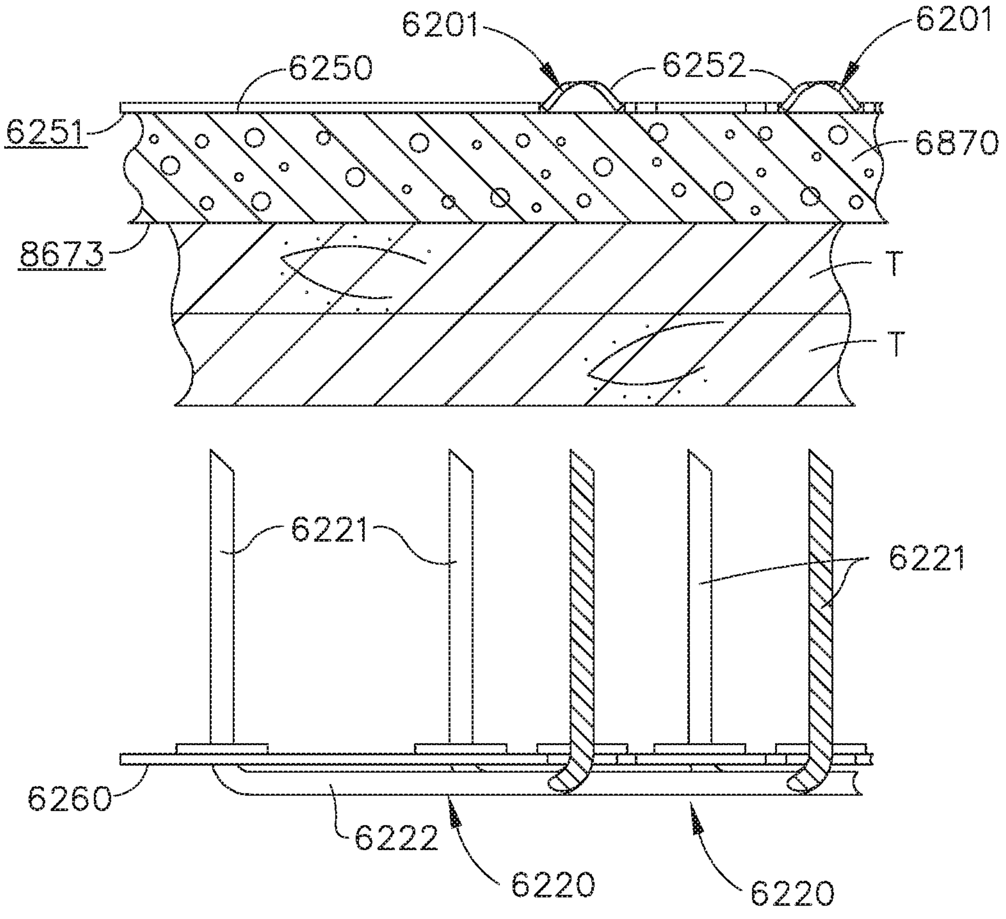
Figure 151:
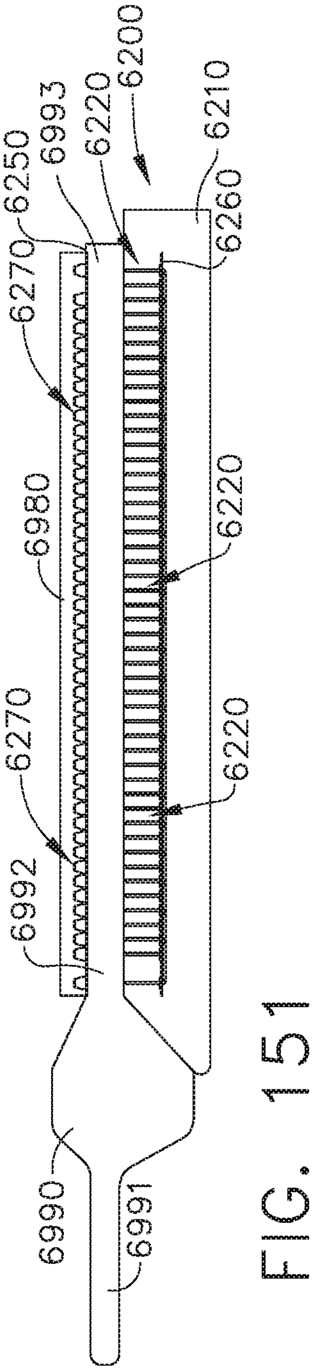
Figure 152:
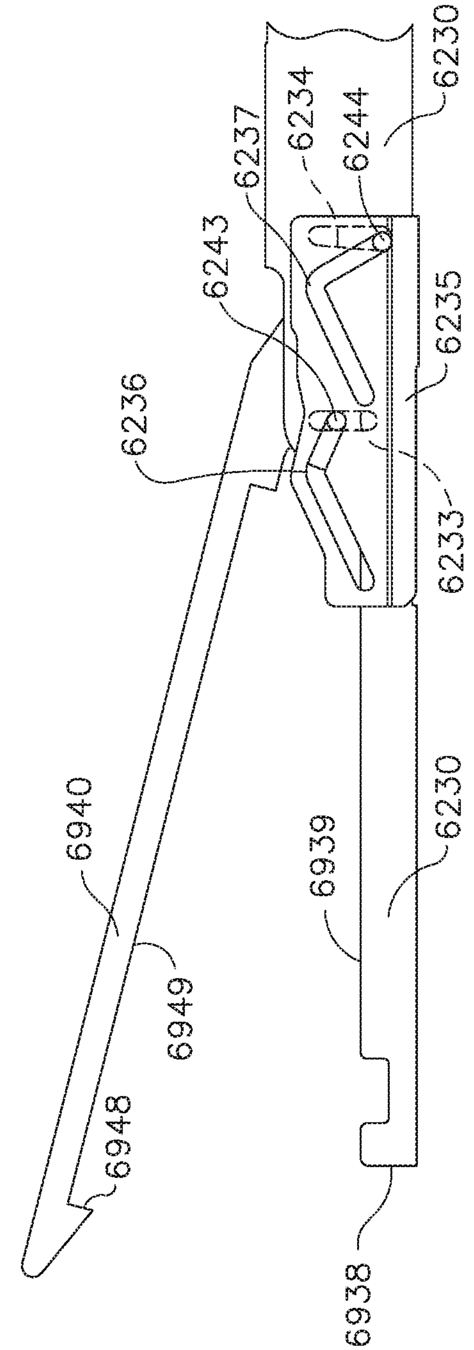
Figure 153:
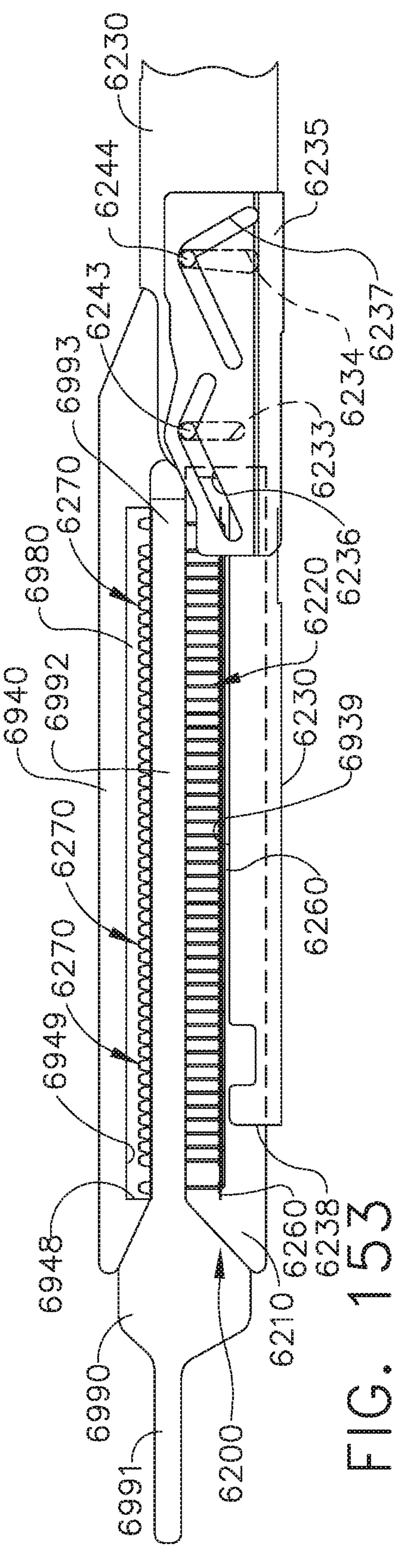
Figure 154:
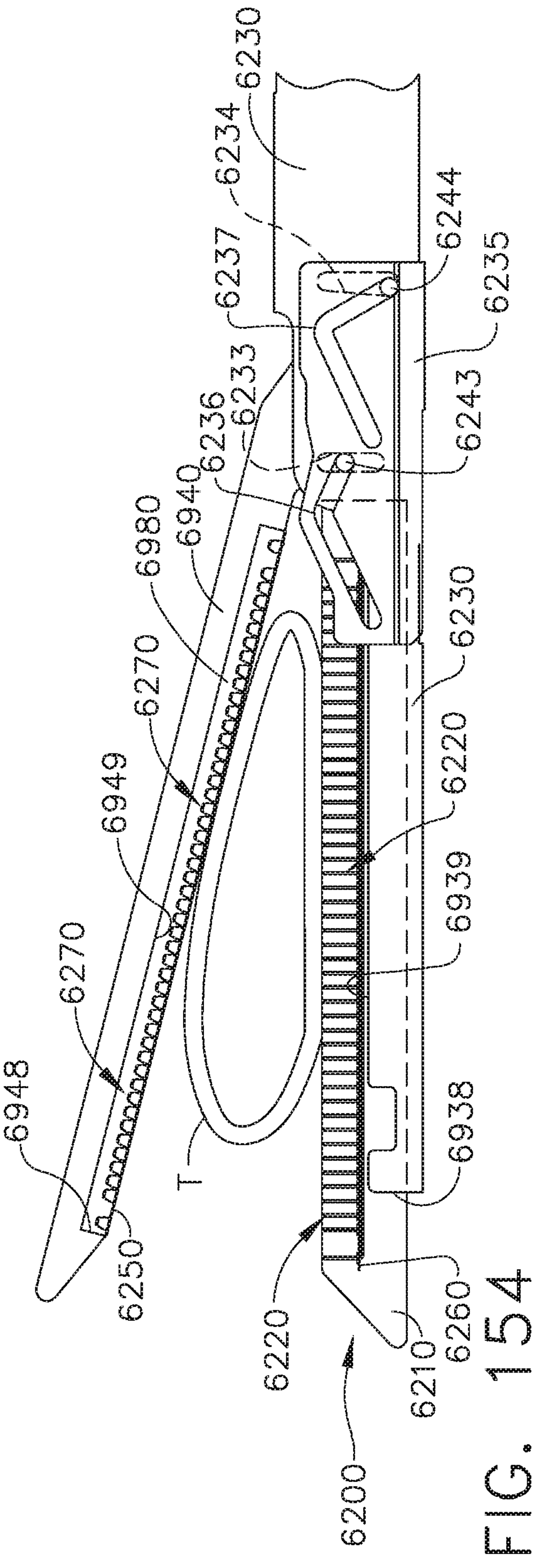
Figure 155:
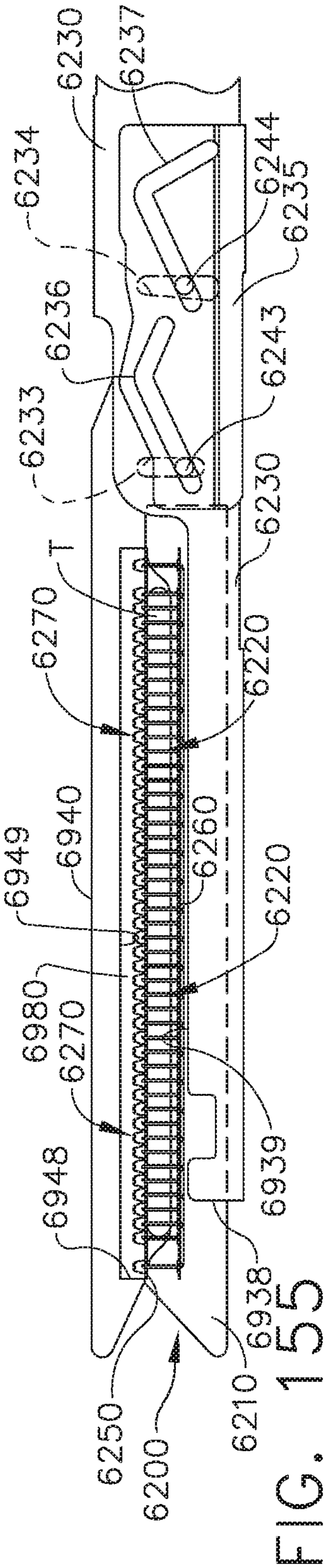
Figure 156:
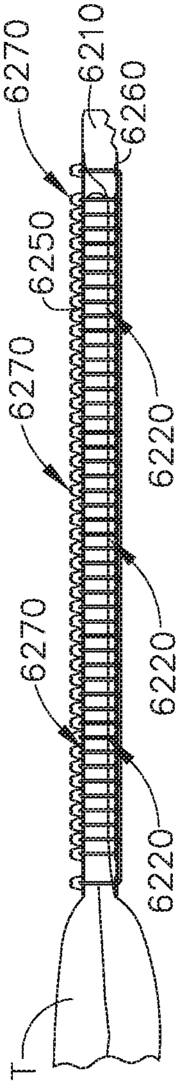
Figure 157:
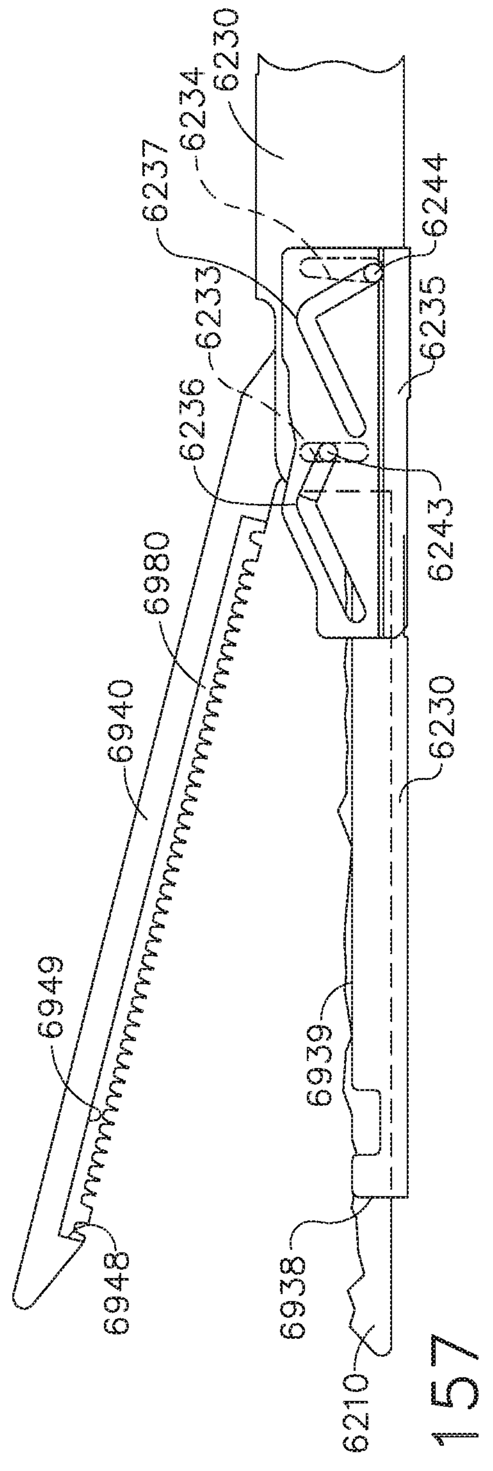
Figure 158:
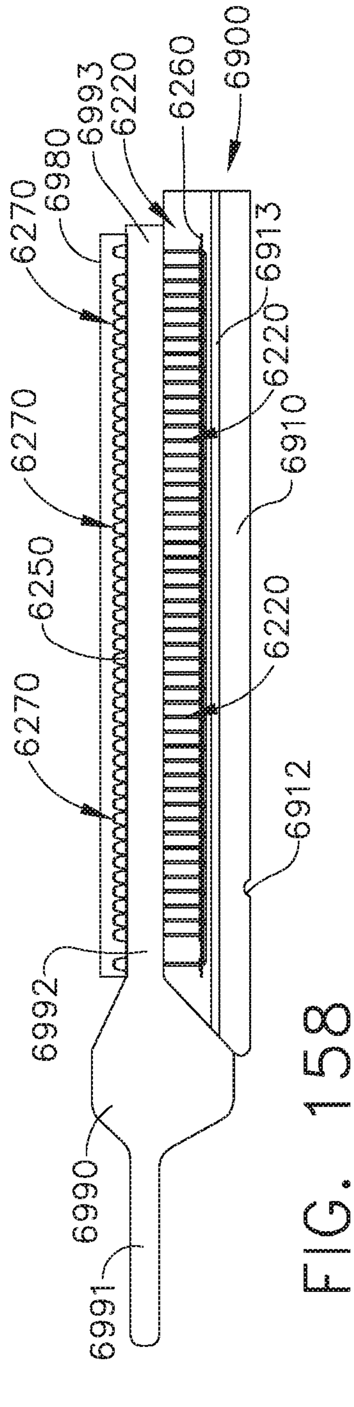
Figure 159:
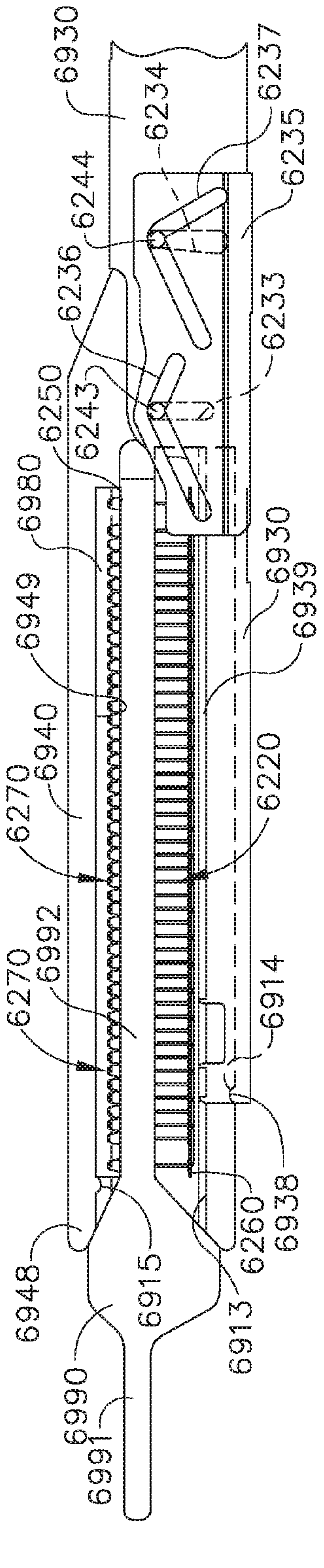
Figure 160:
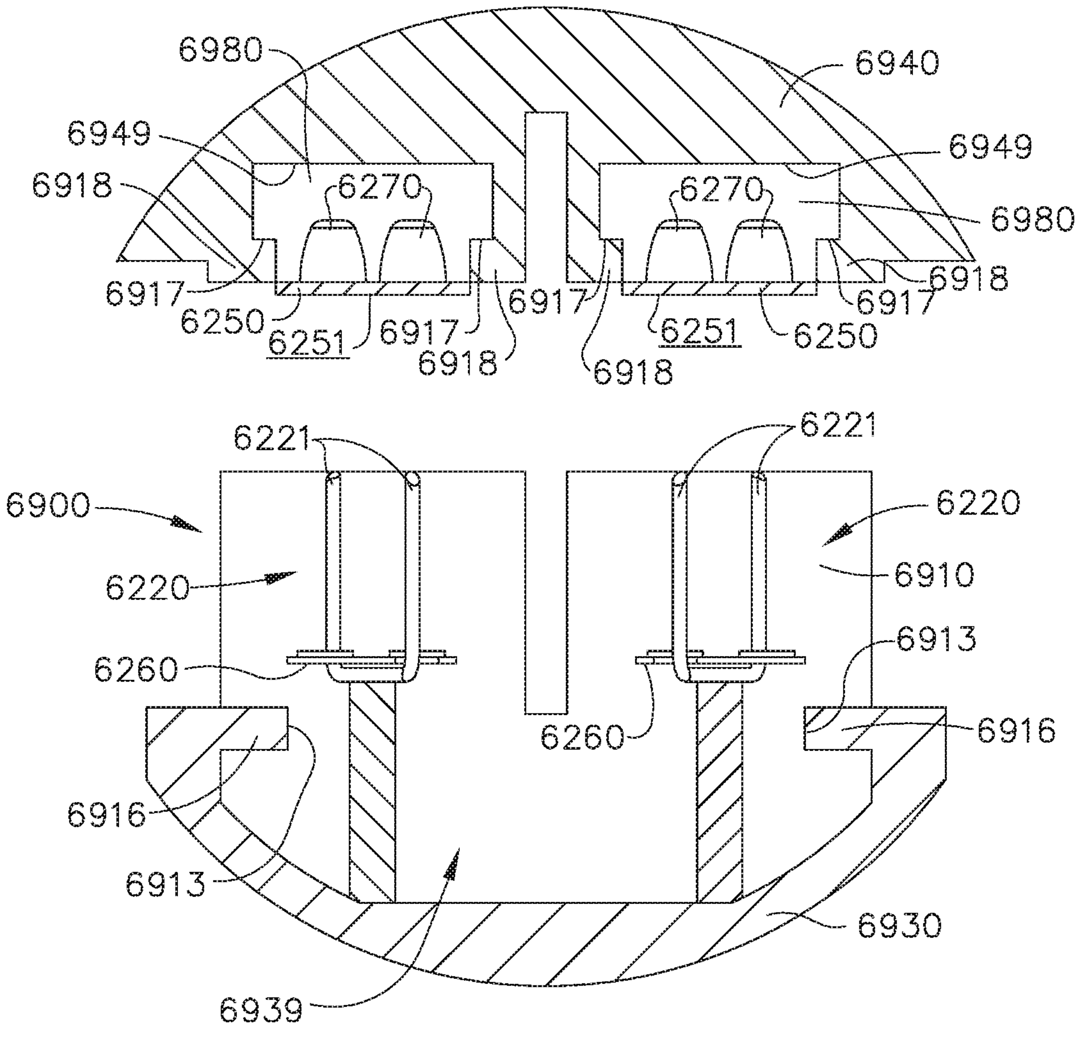
Figure 161:
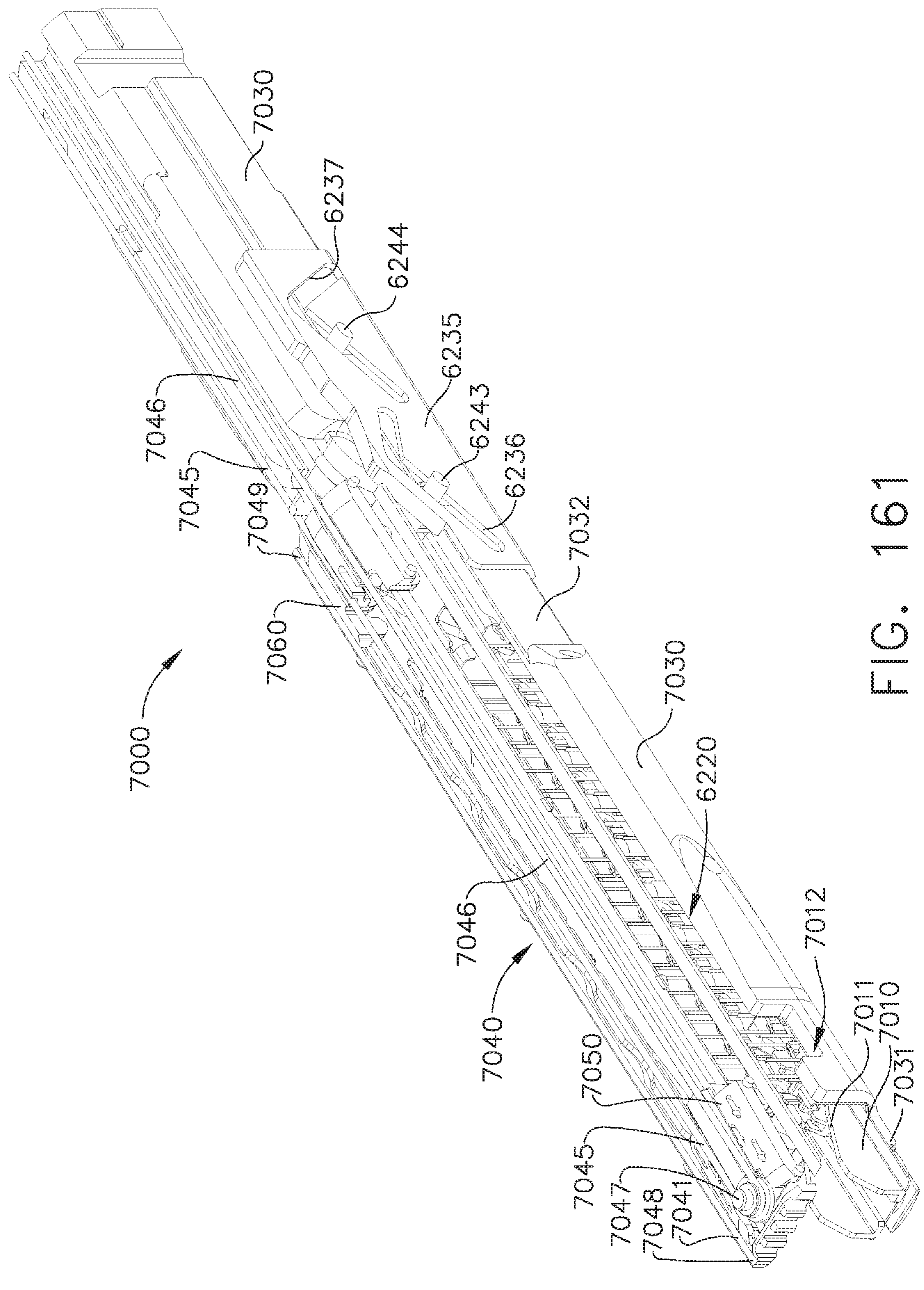
Figure 162:
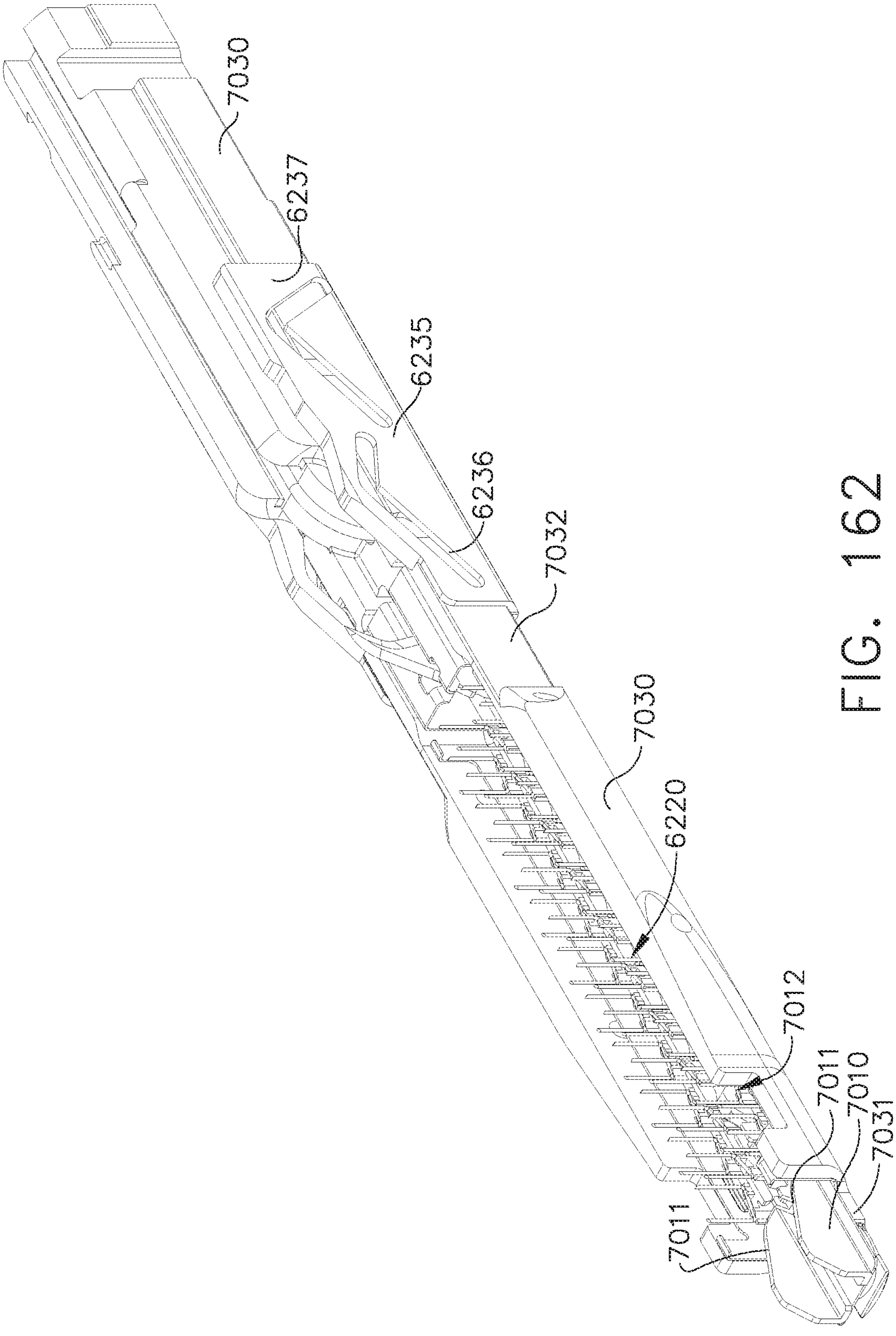
Figure 163:
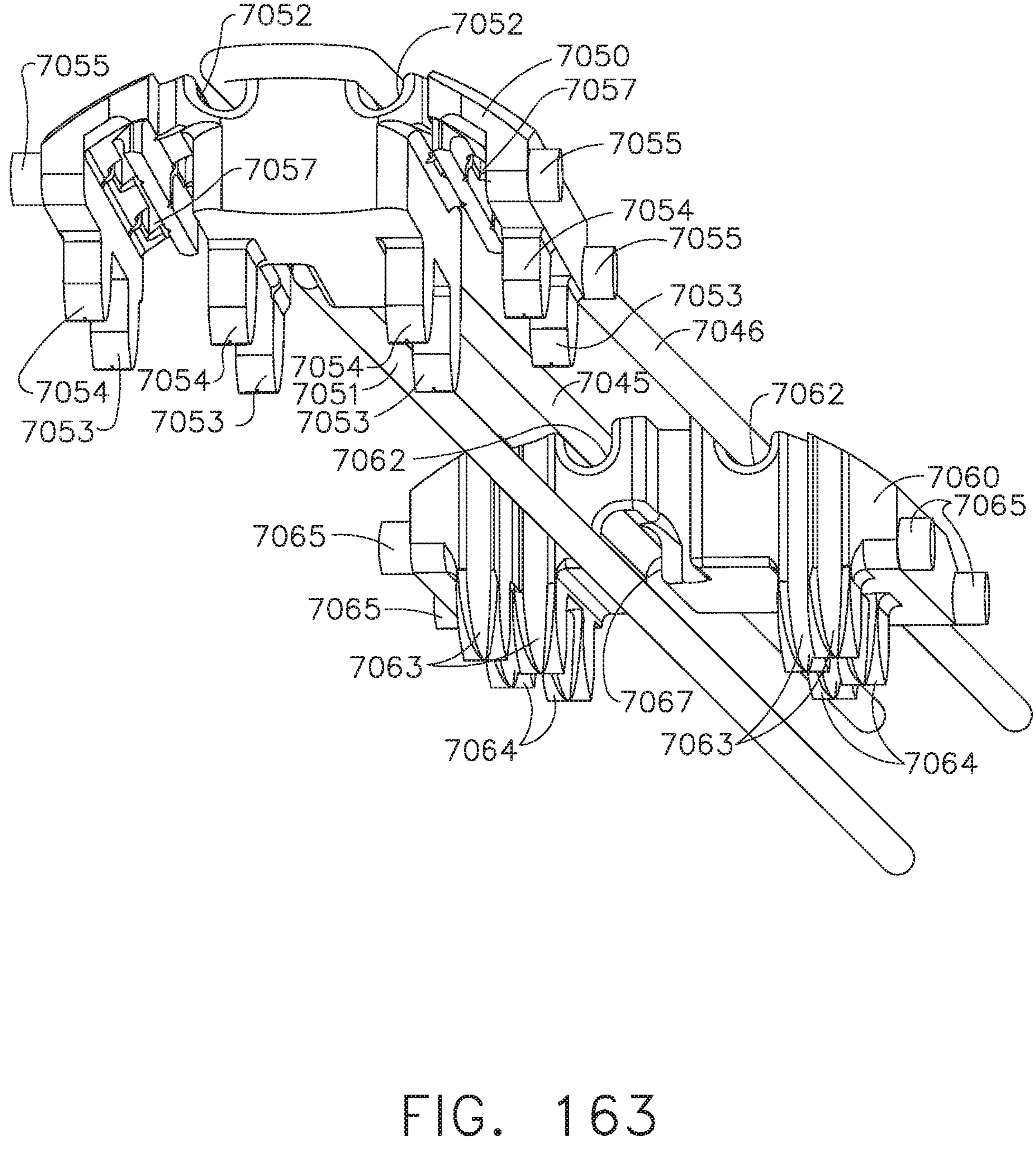
Figure 164:
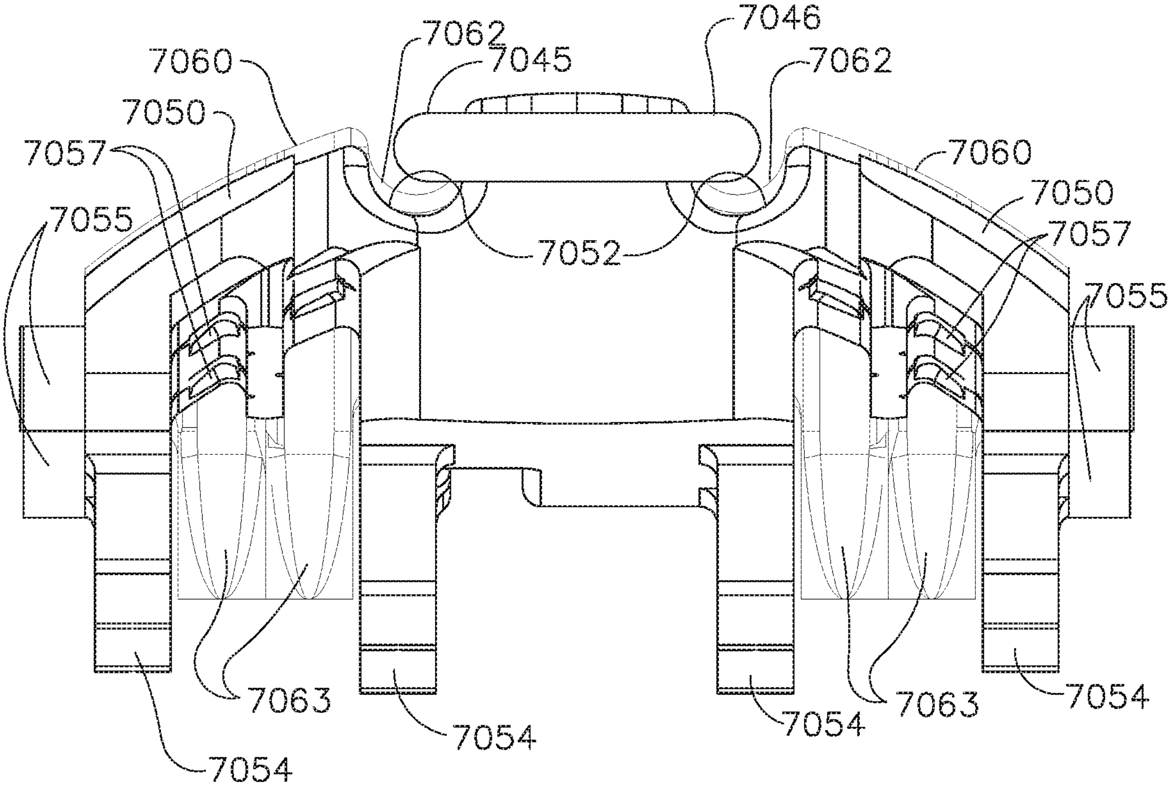
Figure 165:
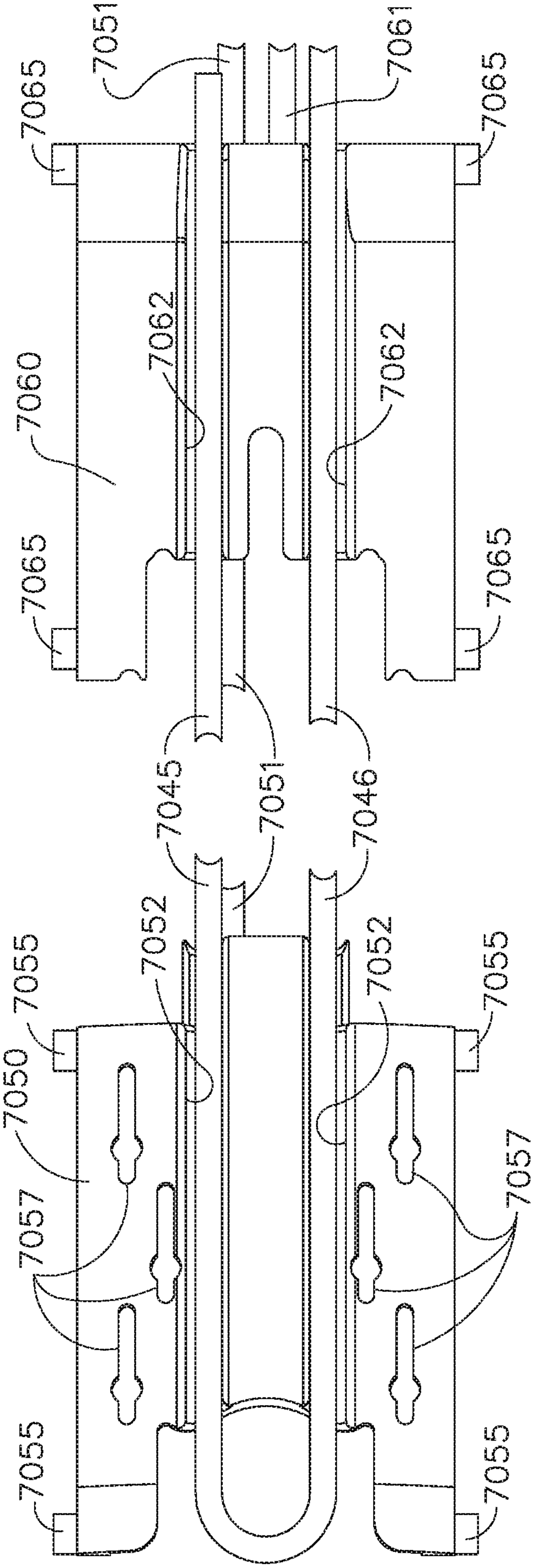
Figure 166:
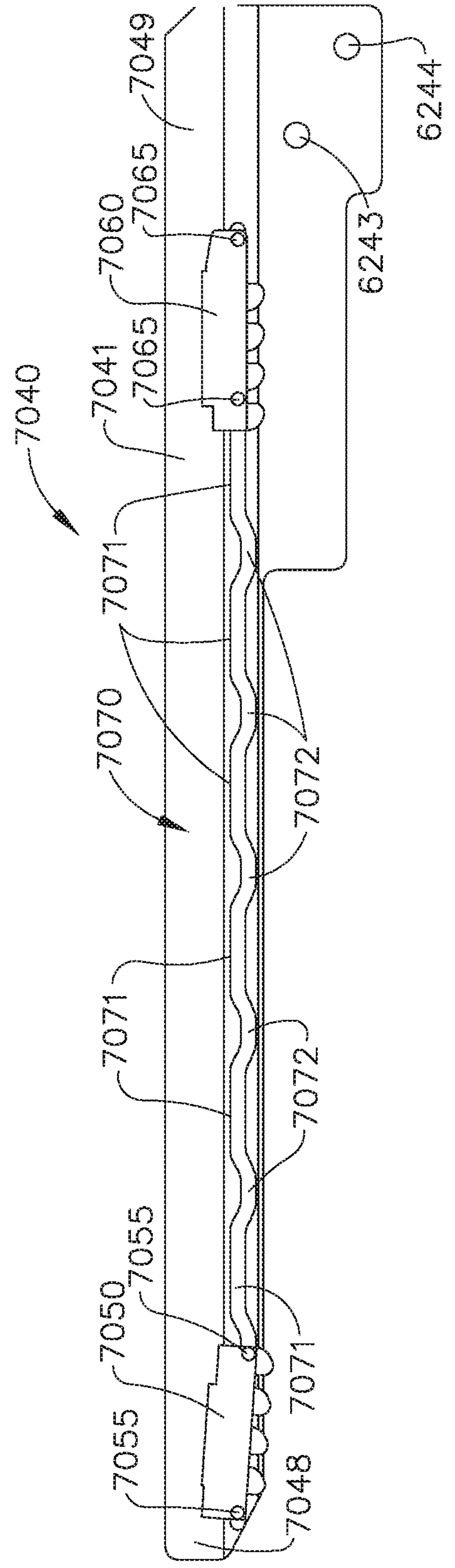
Figure 167:
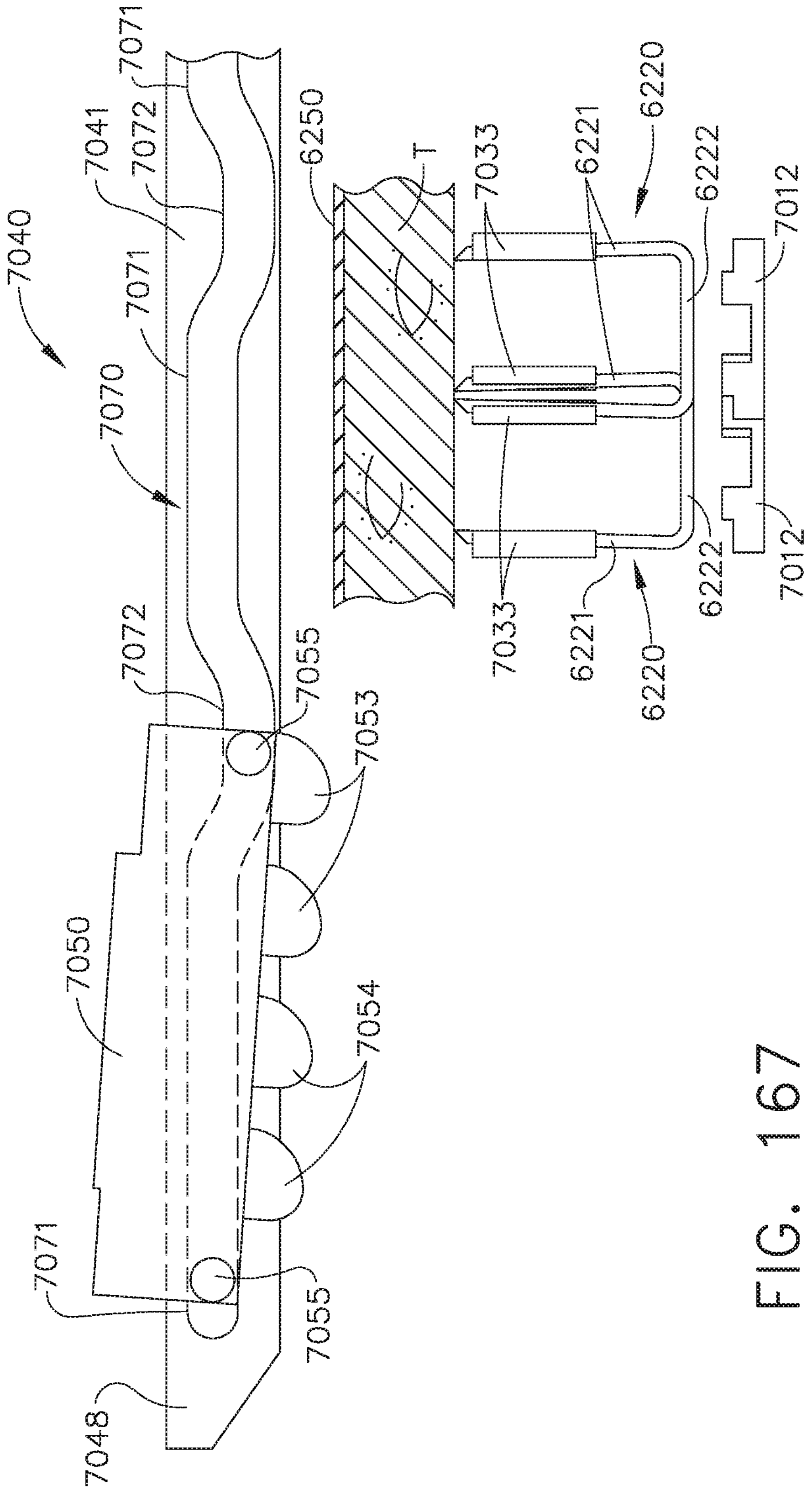
Figure 168:
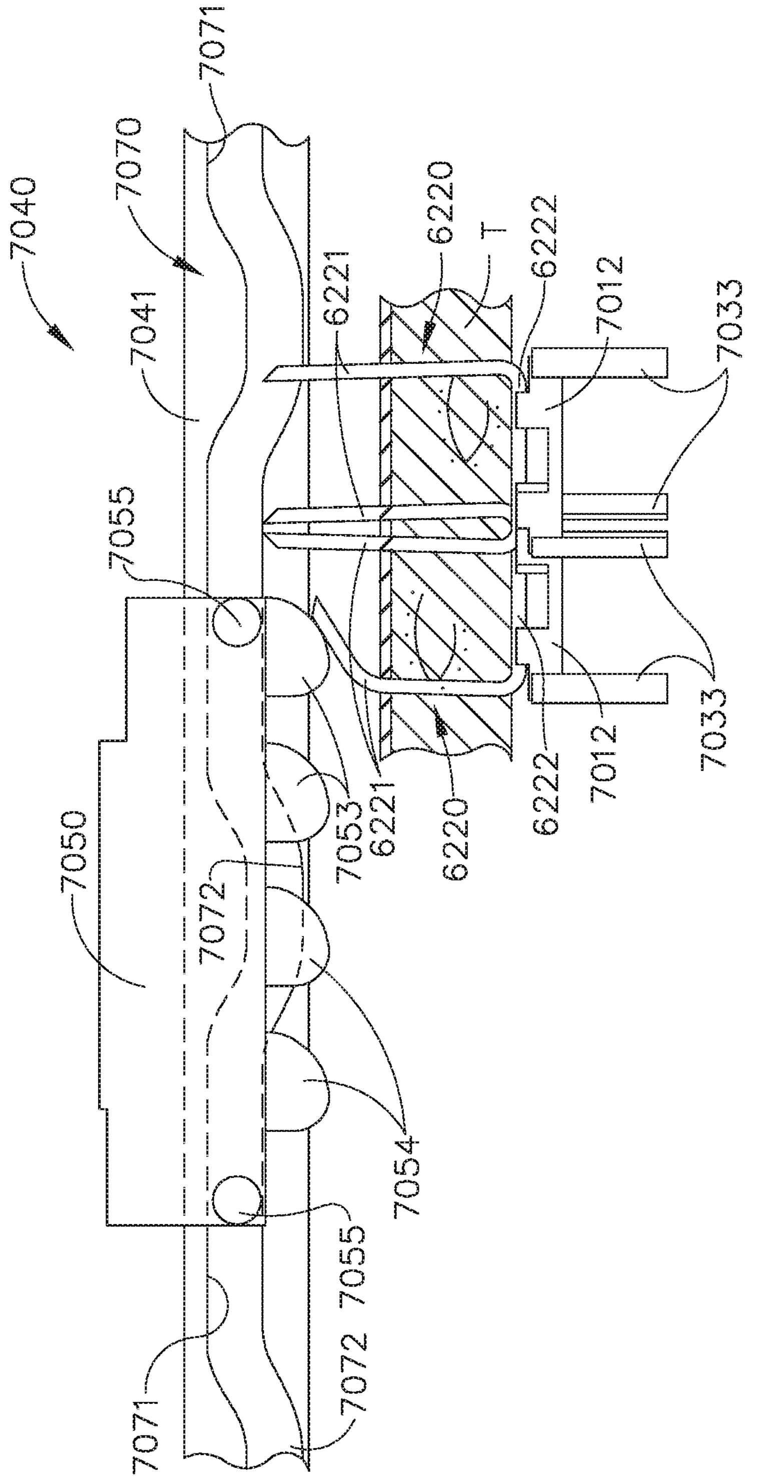
Figure 169:
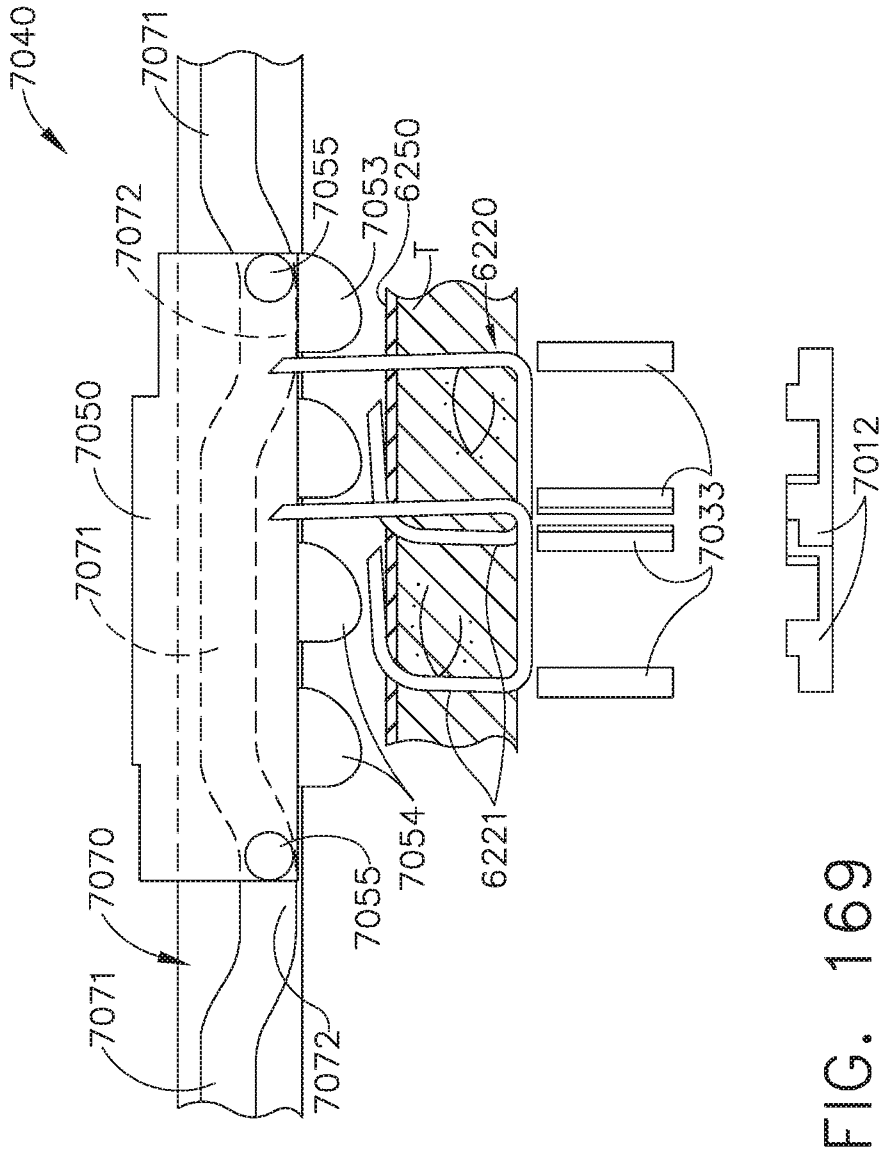
Figure 170:
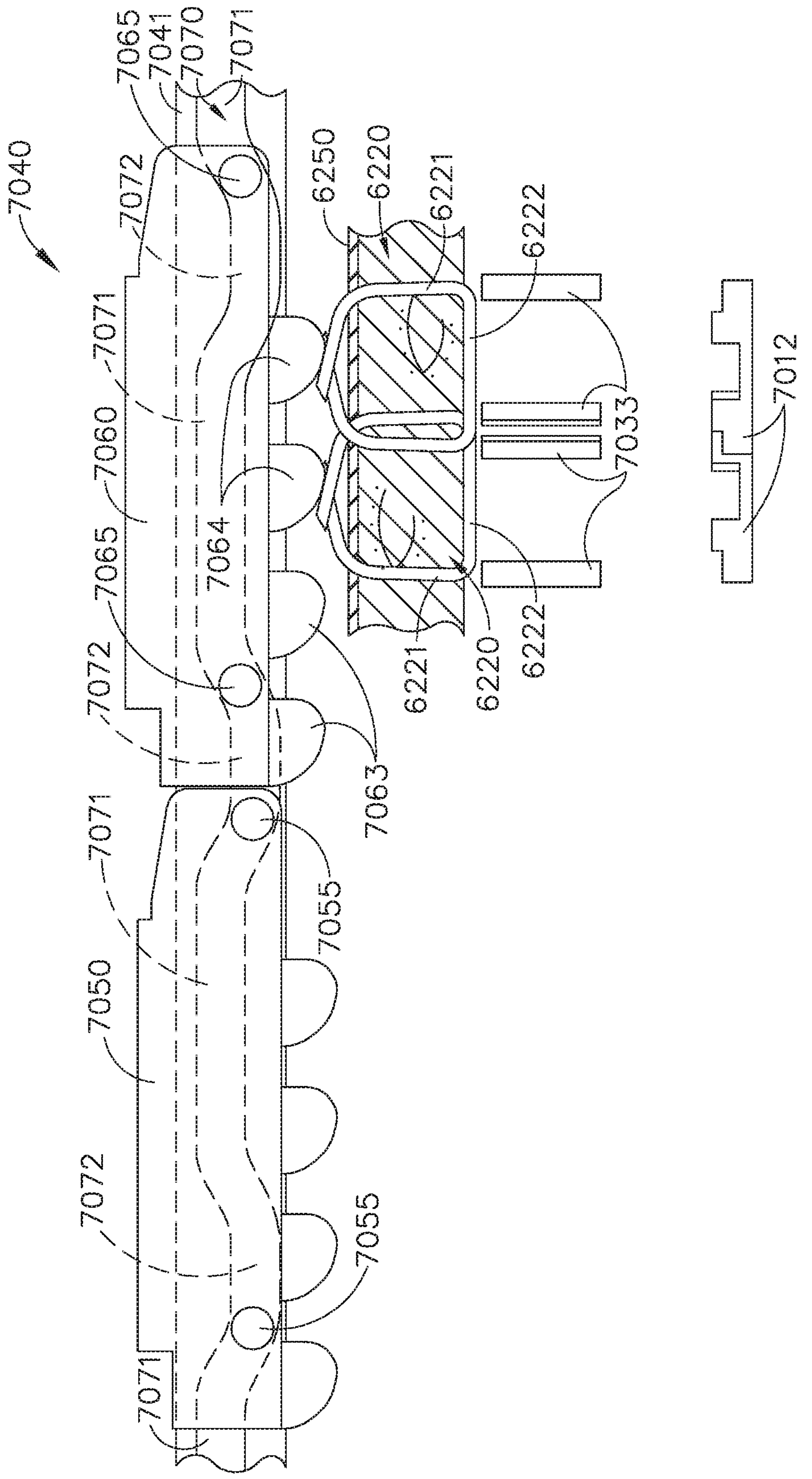
Figure 171:
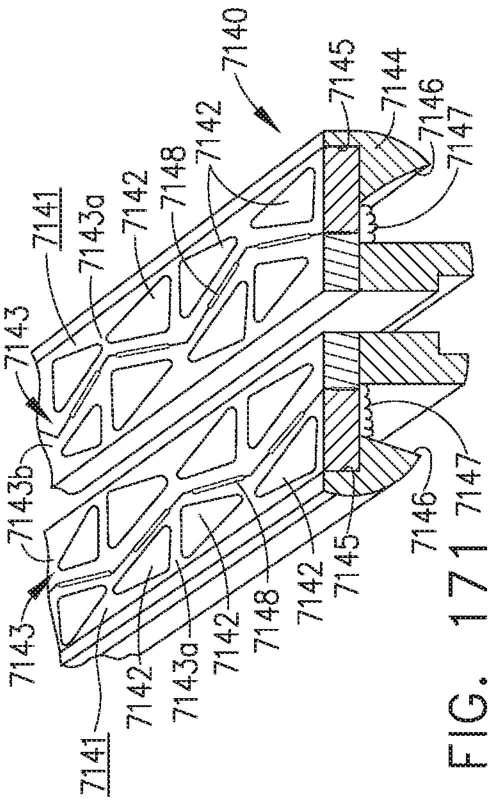
Figure 172:
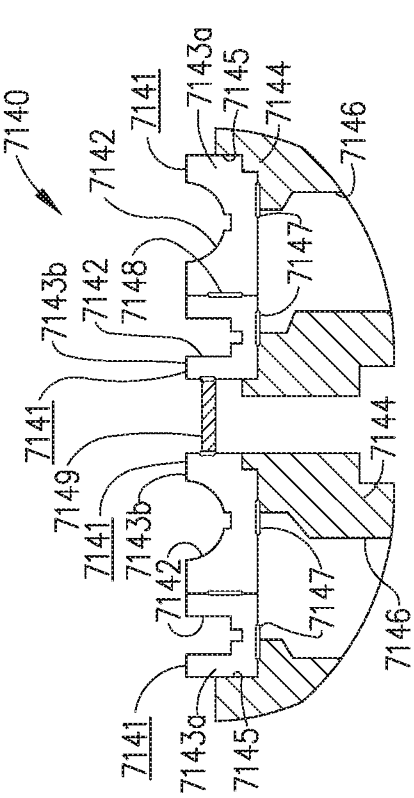
Figure 173:
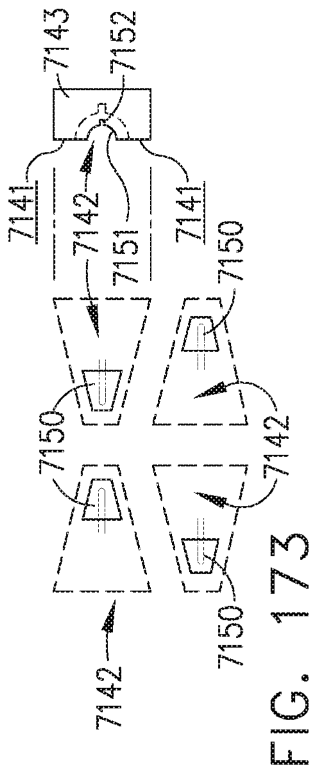
Figure 174:
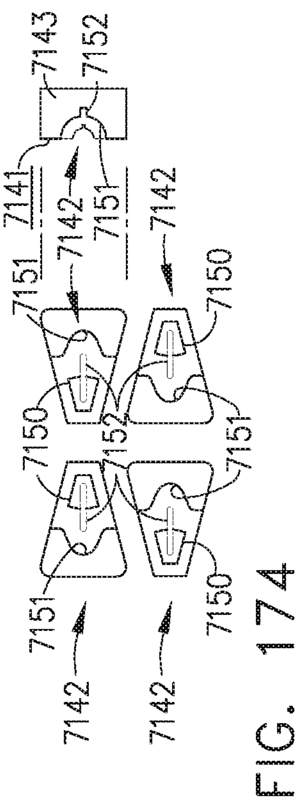
Figure 175:
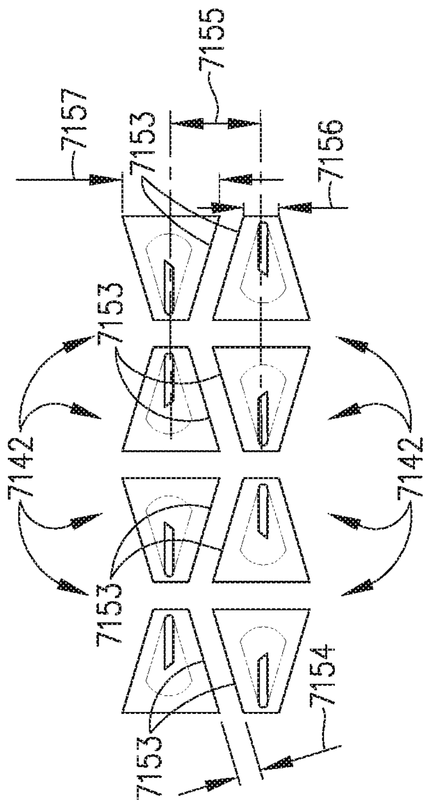
Figure 177:
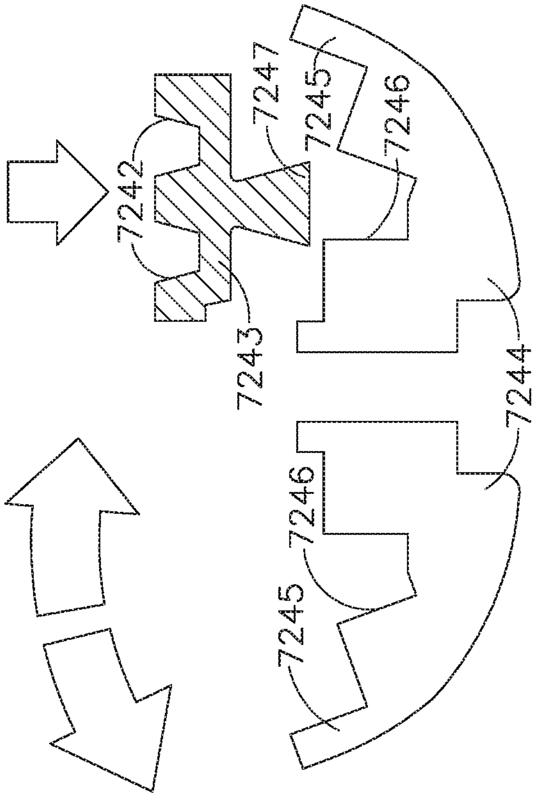
Figure 176:
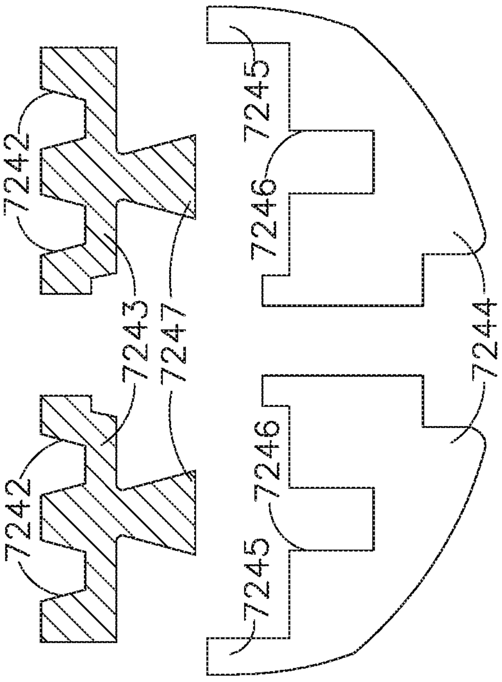
Figure 178:
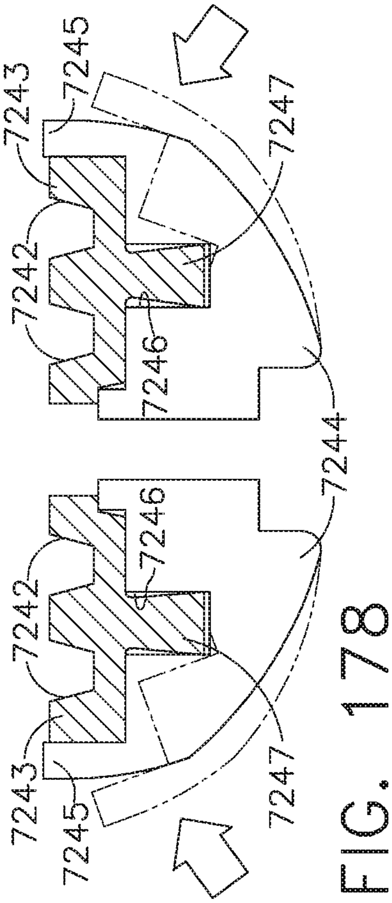
Figure 179:
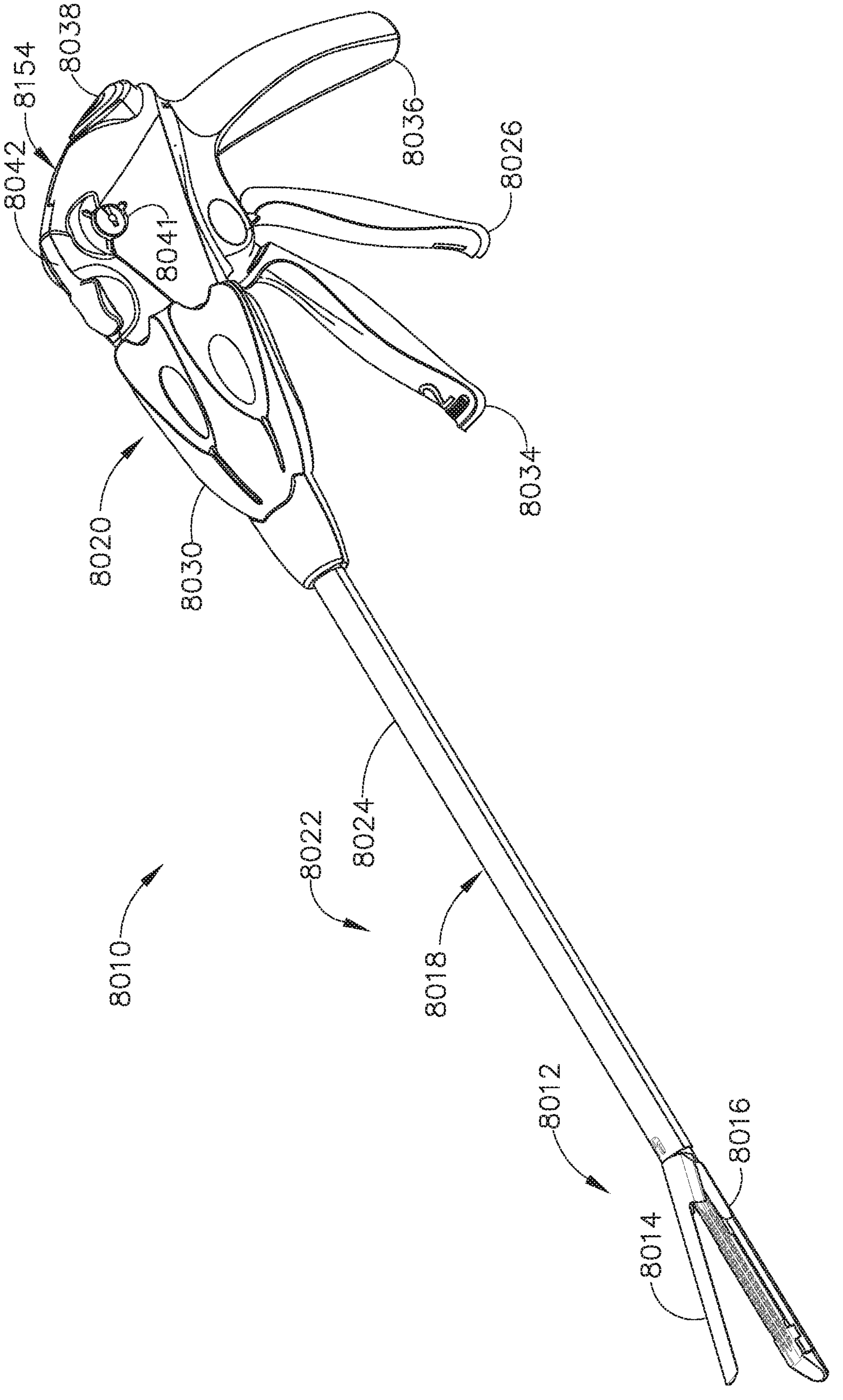
Figure 180:
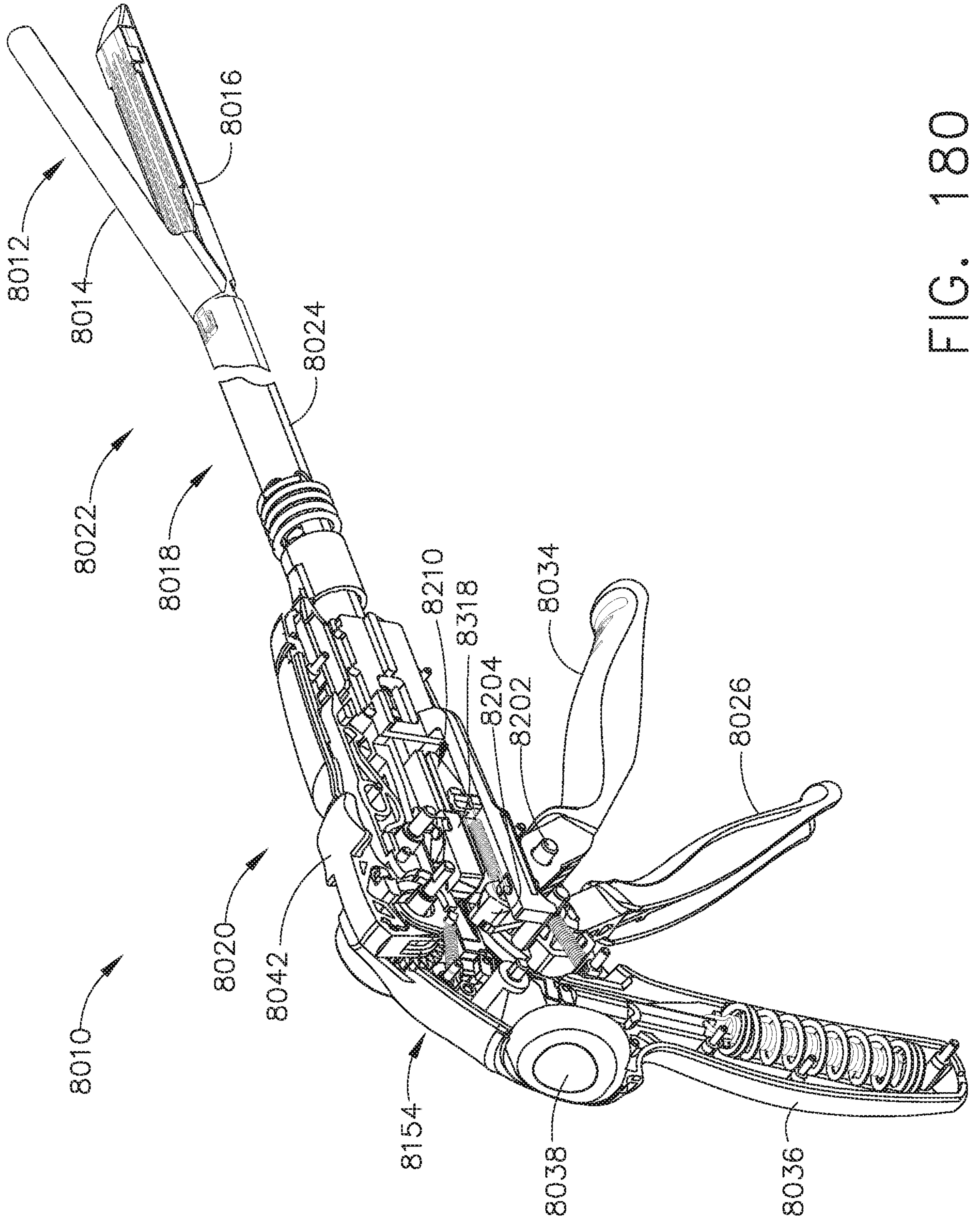
Figure 181:
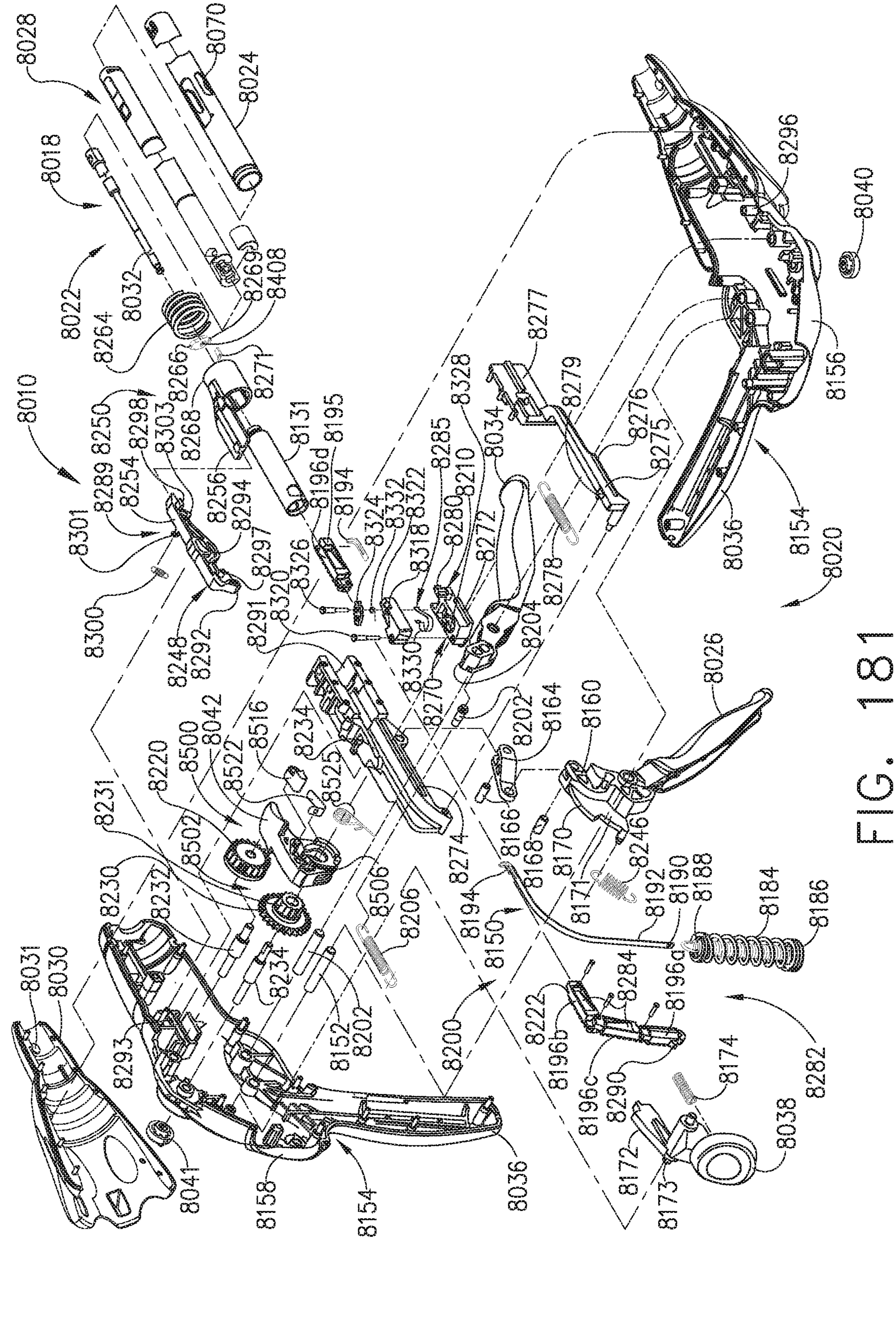
Figure 182:
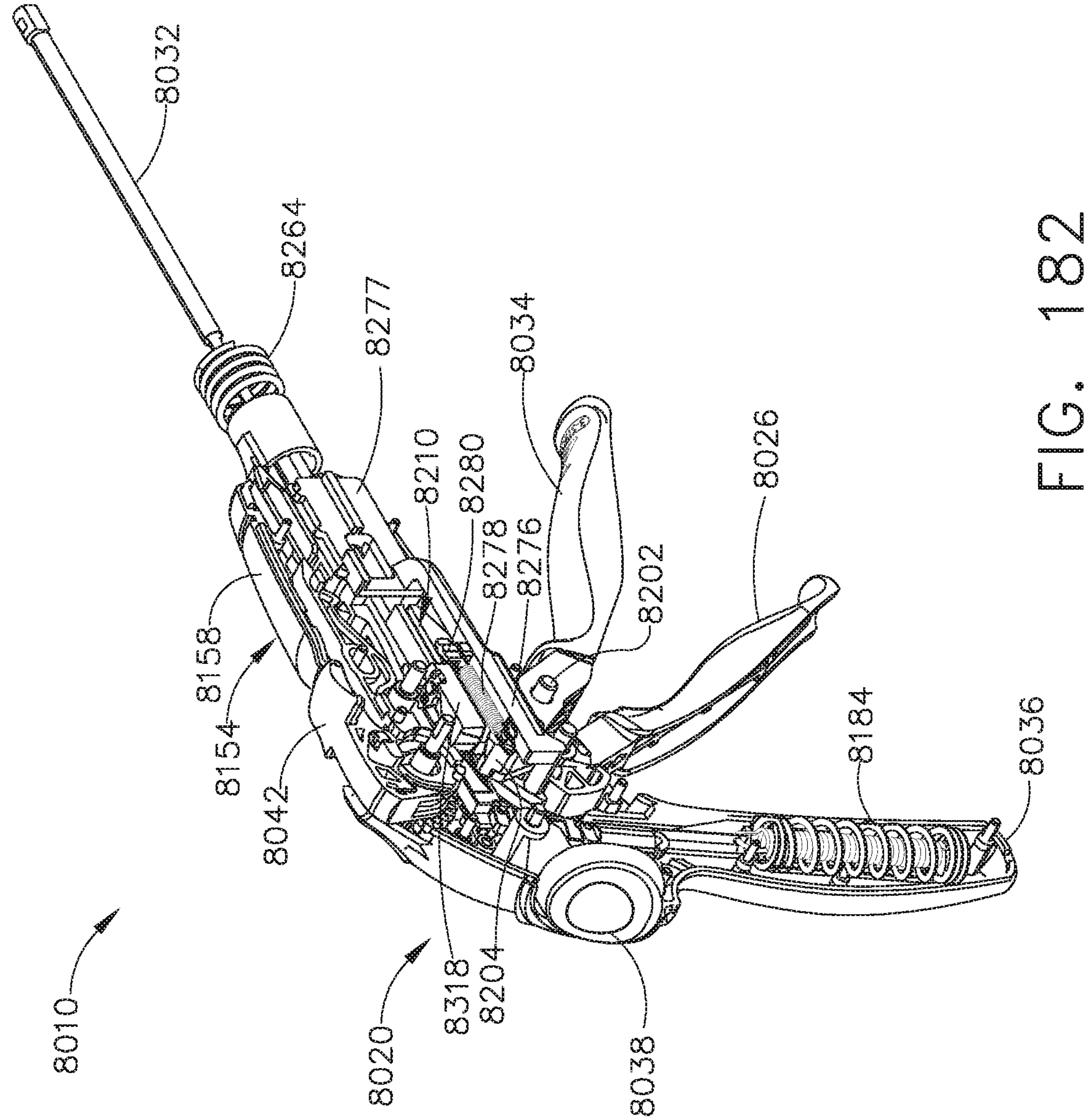
Figure 183:
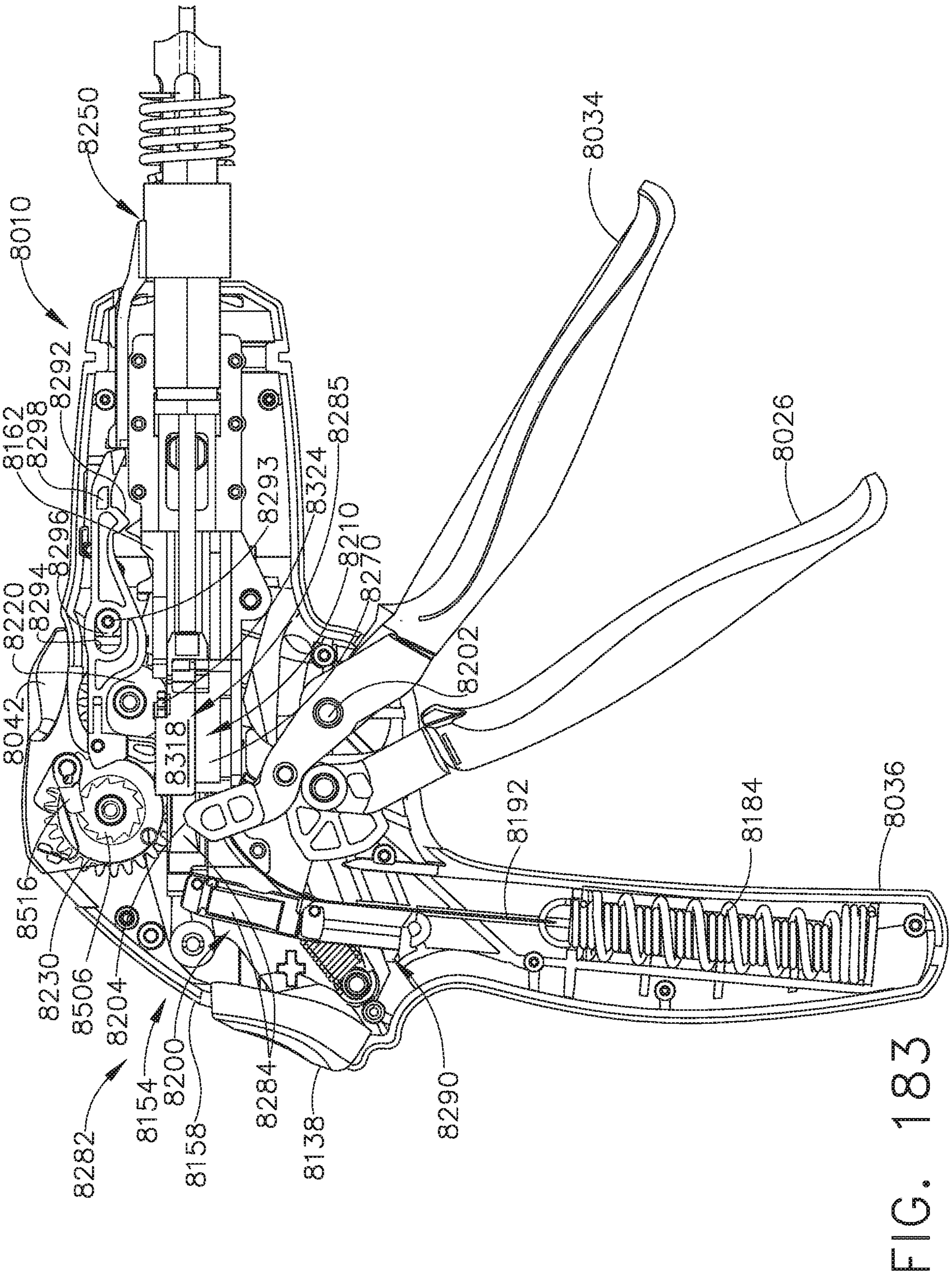
Figure 184:
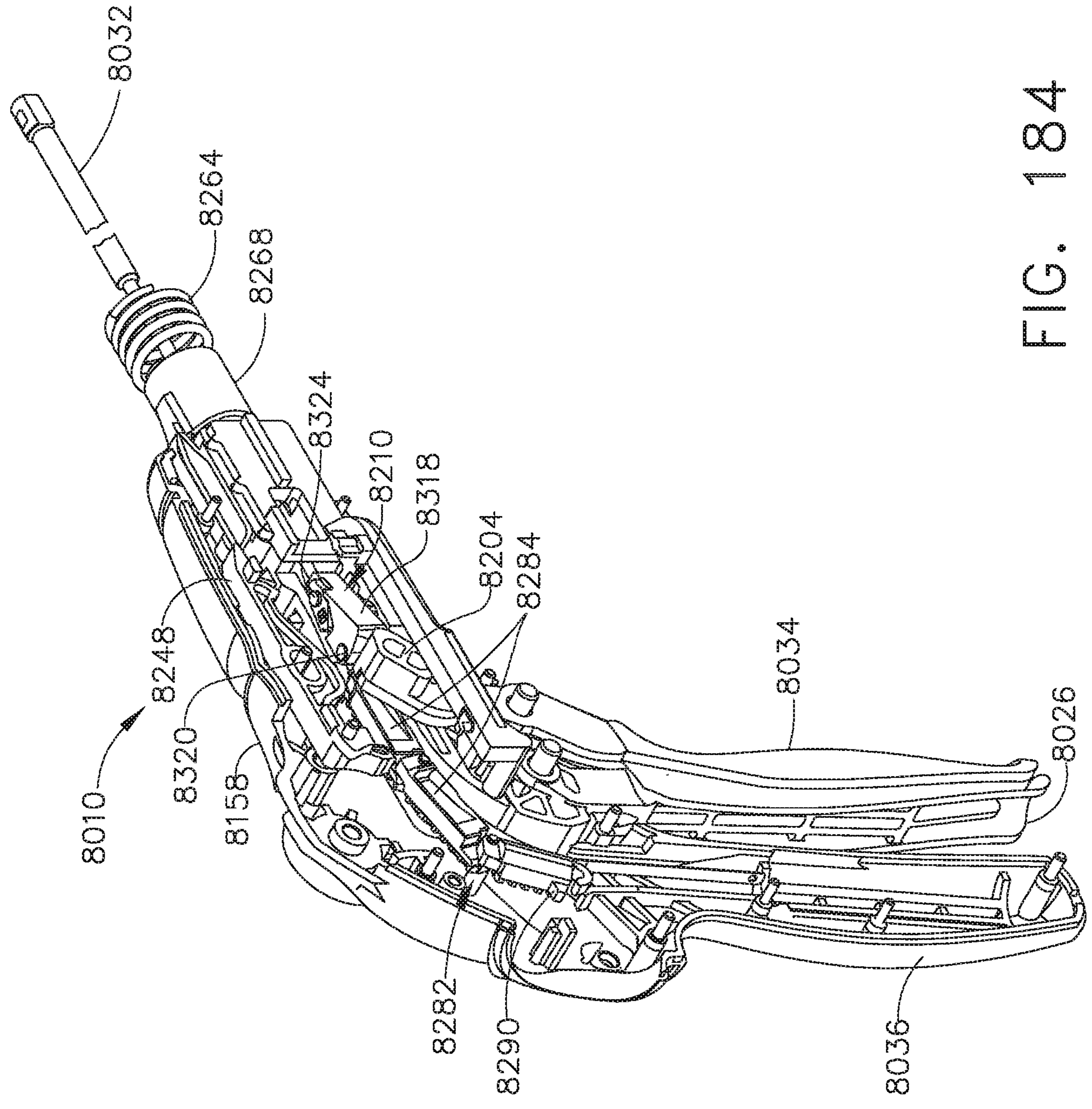
Figure 185:
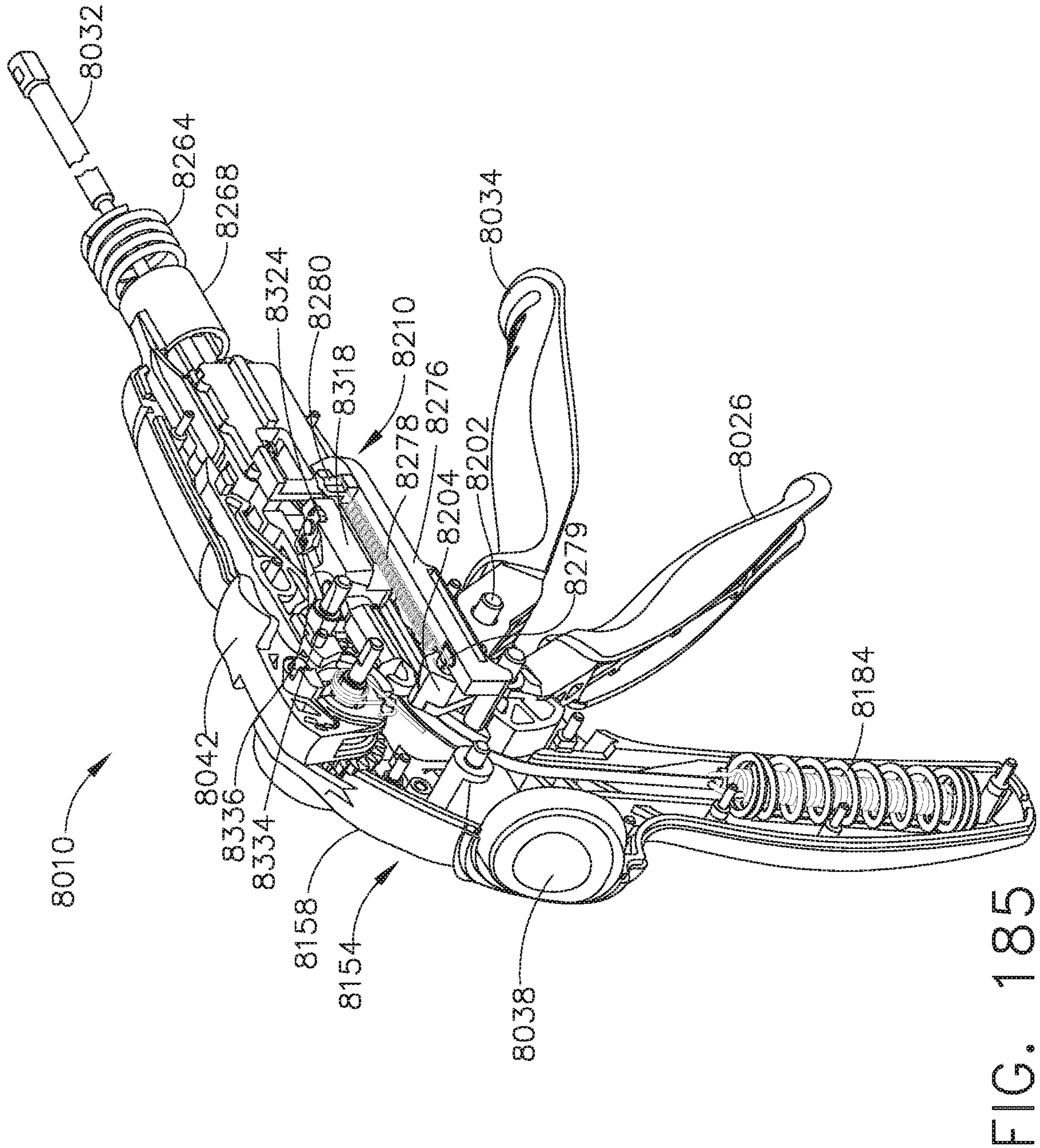
Figure 186:
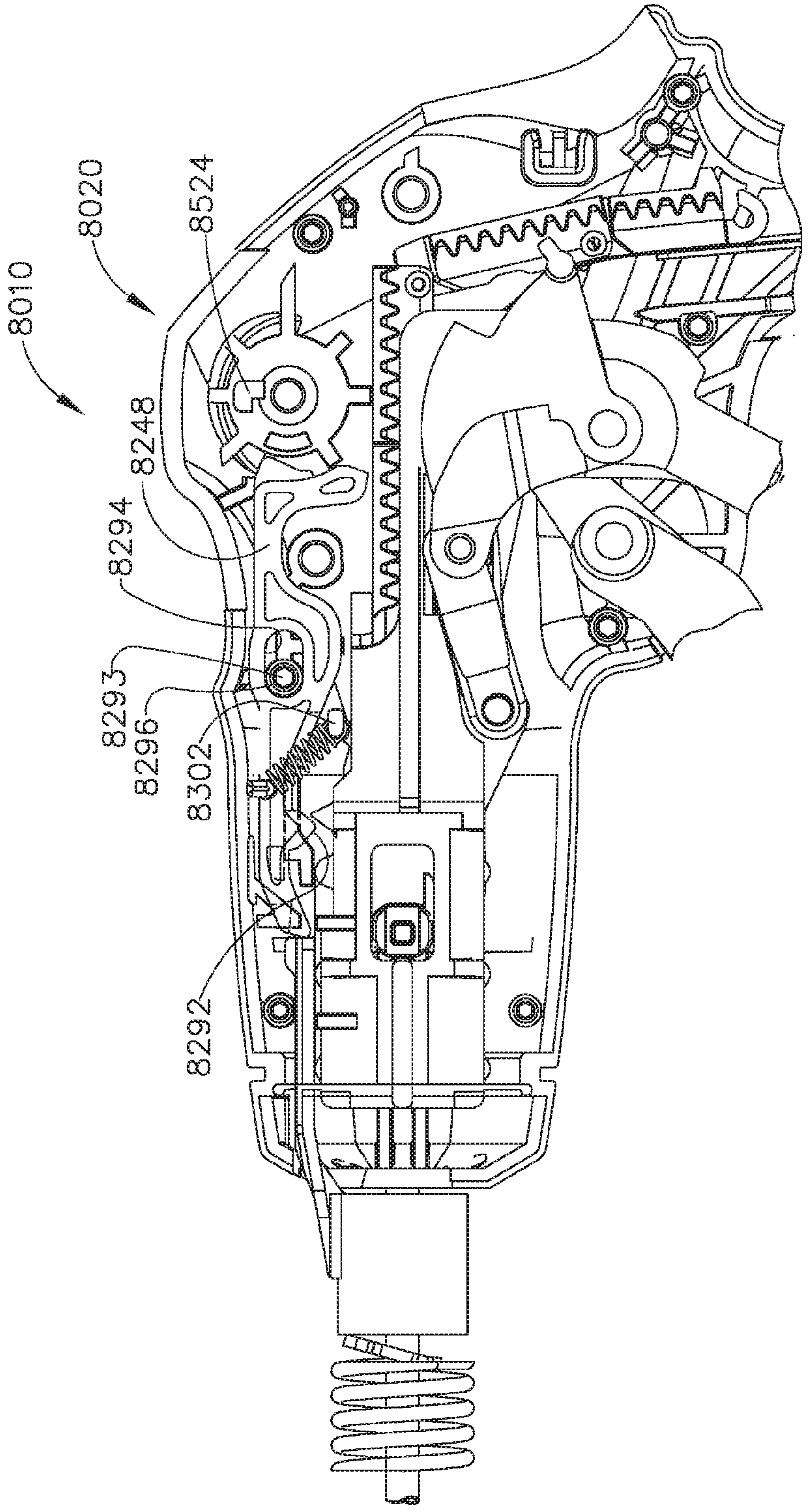
Figure 187:
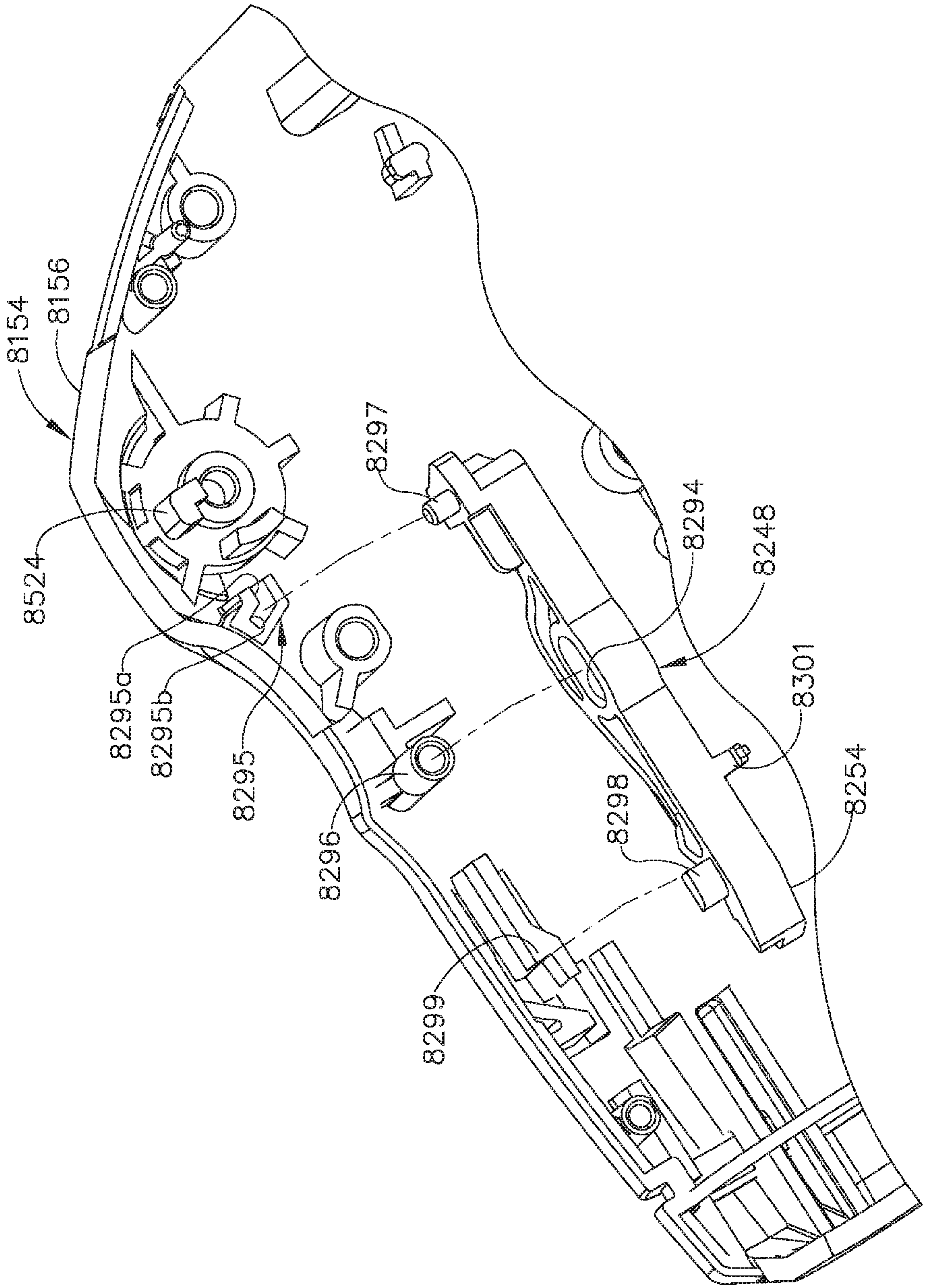
Figure 188:
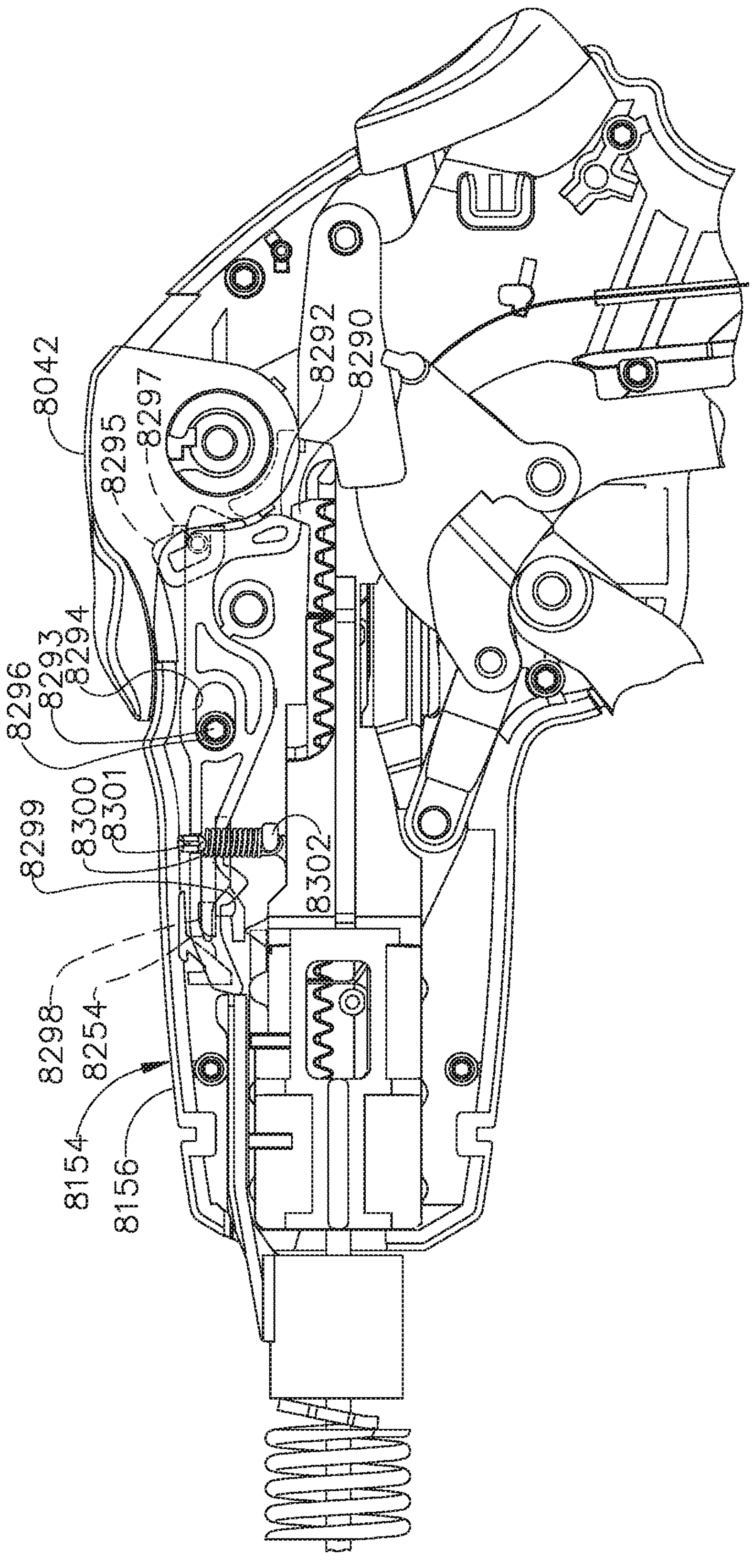
Figure 189:
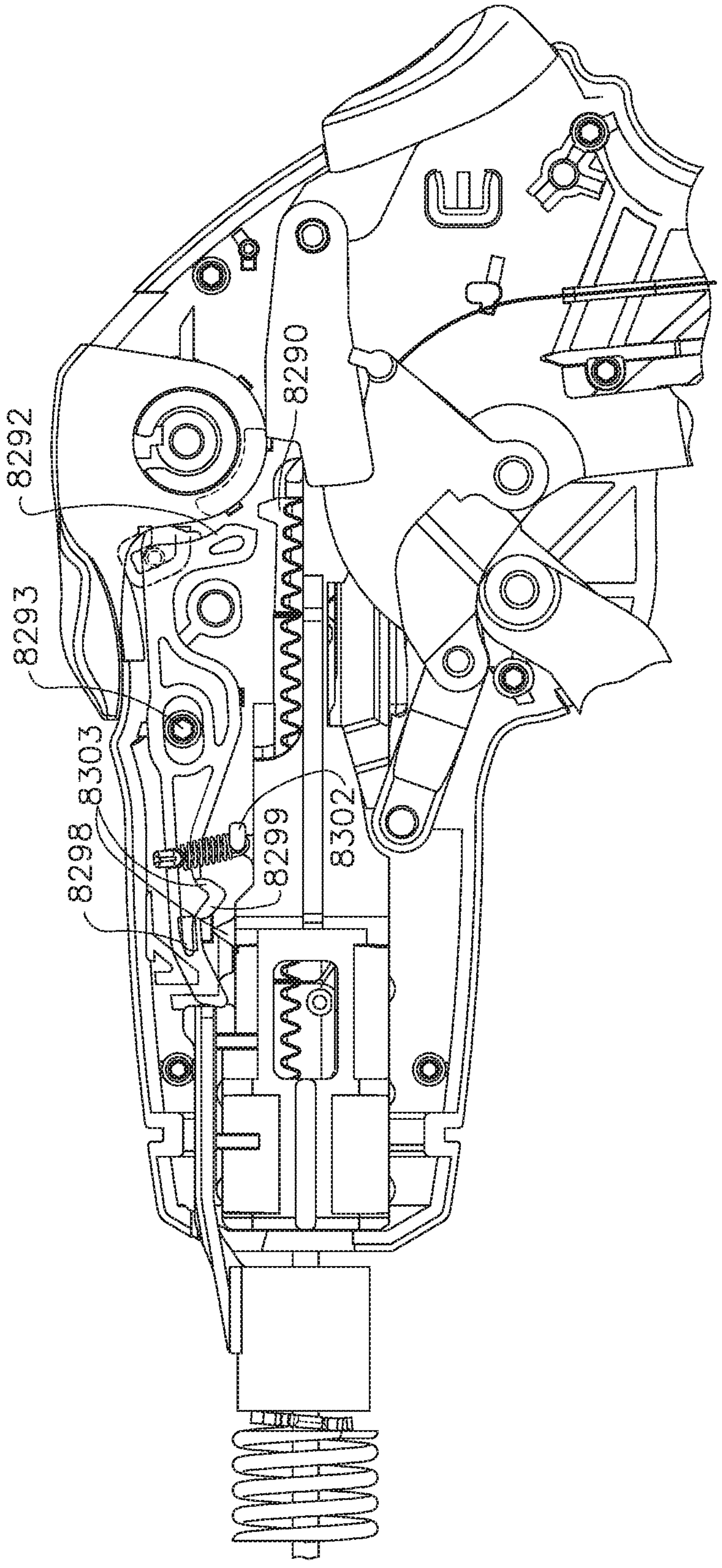
Figure 190:
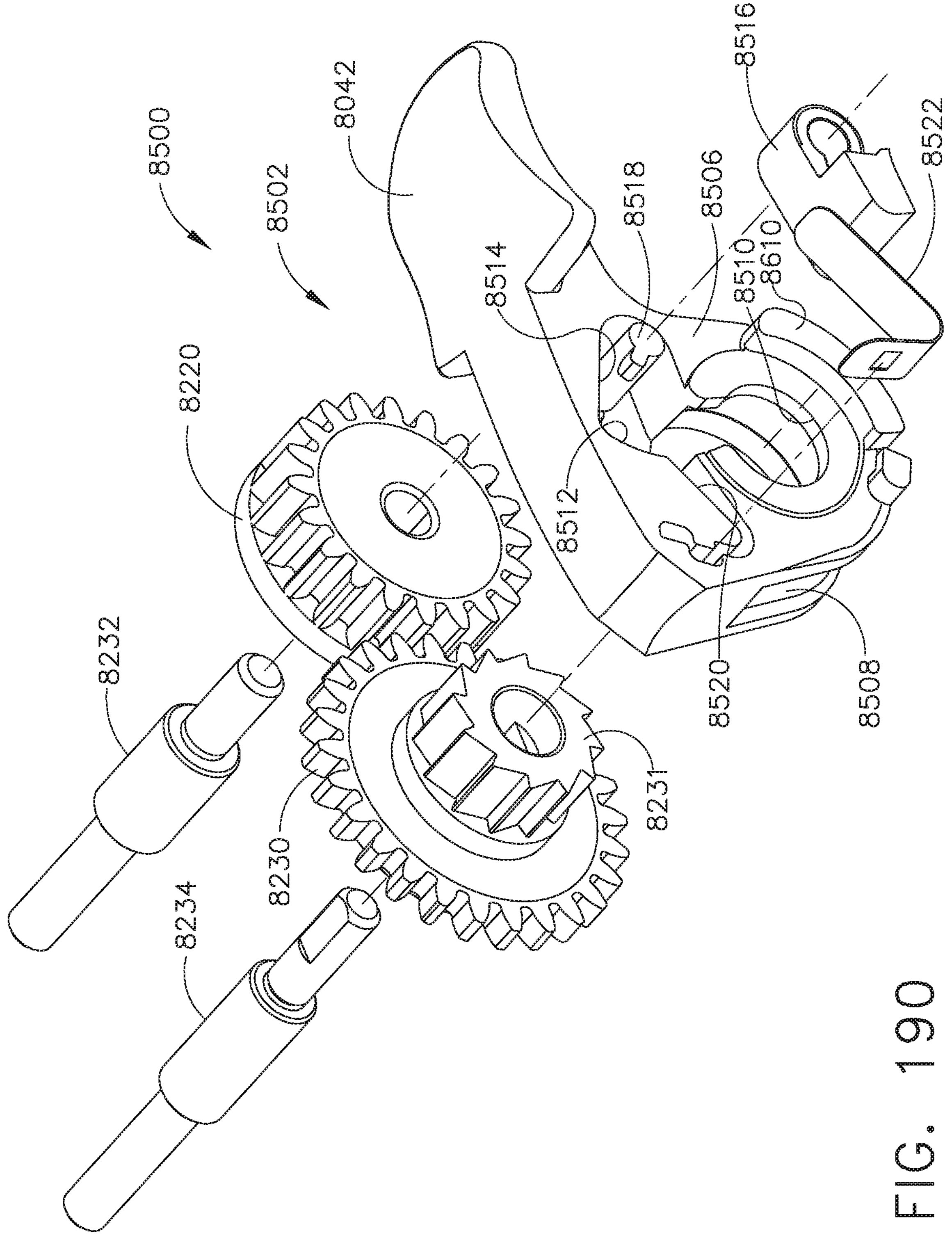
Figure 191:
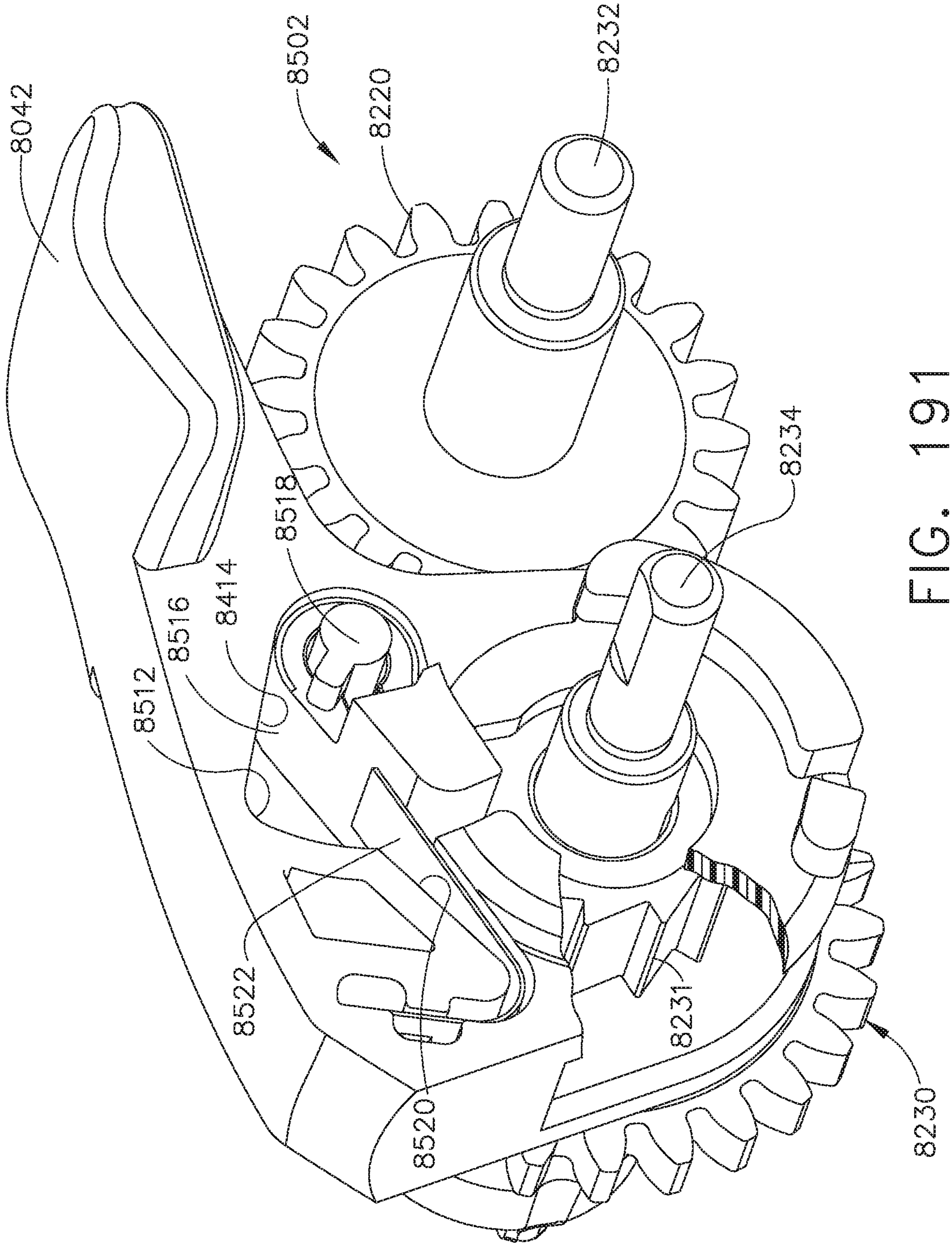
Figure 192:
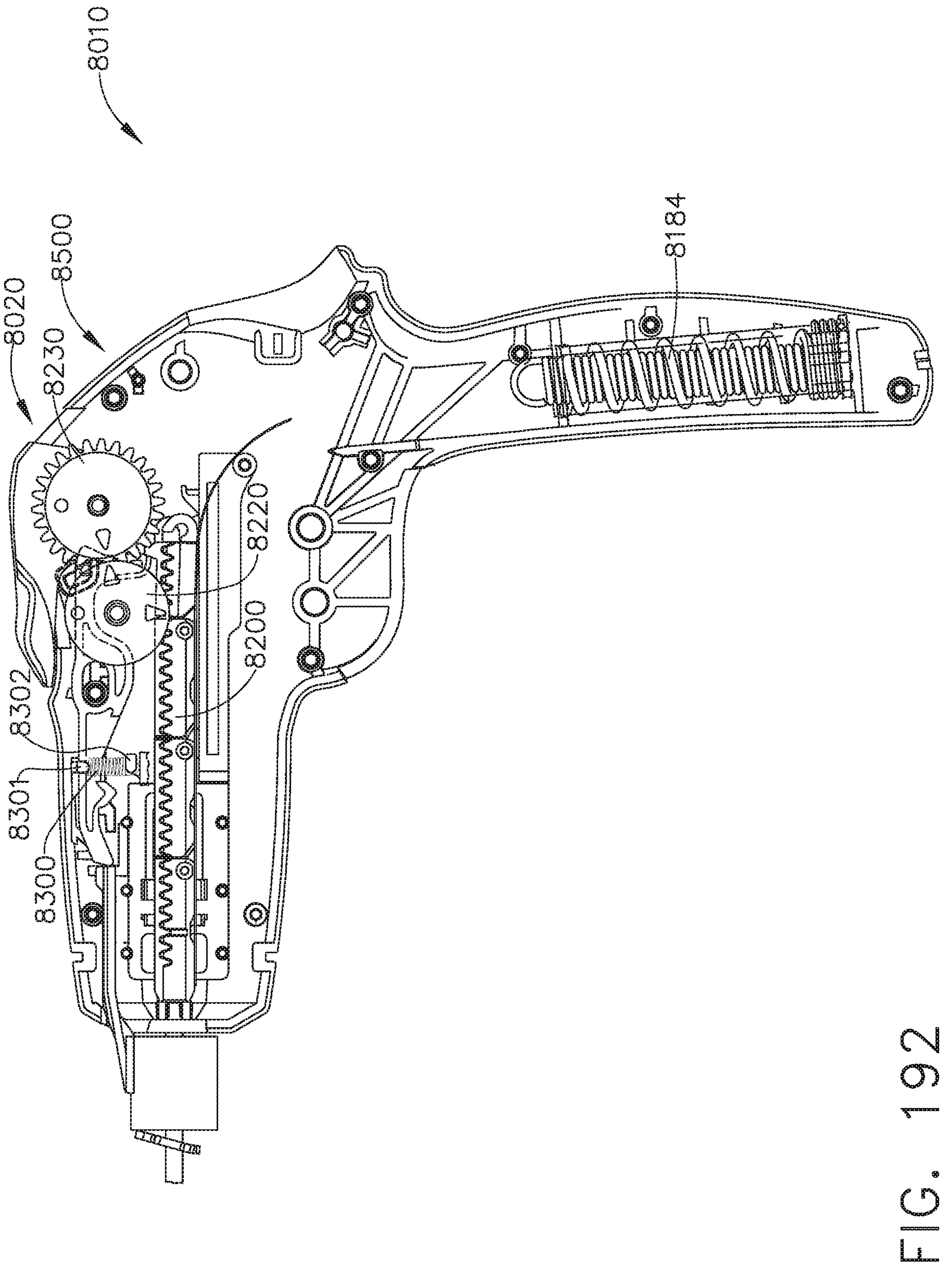
Figure 193:
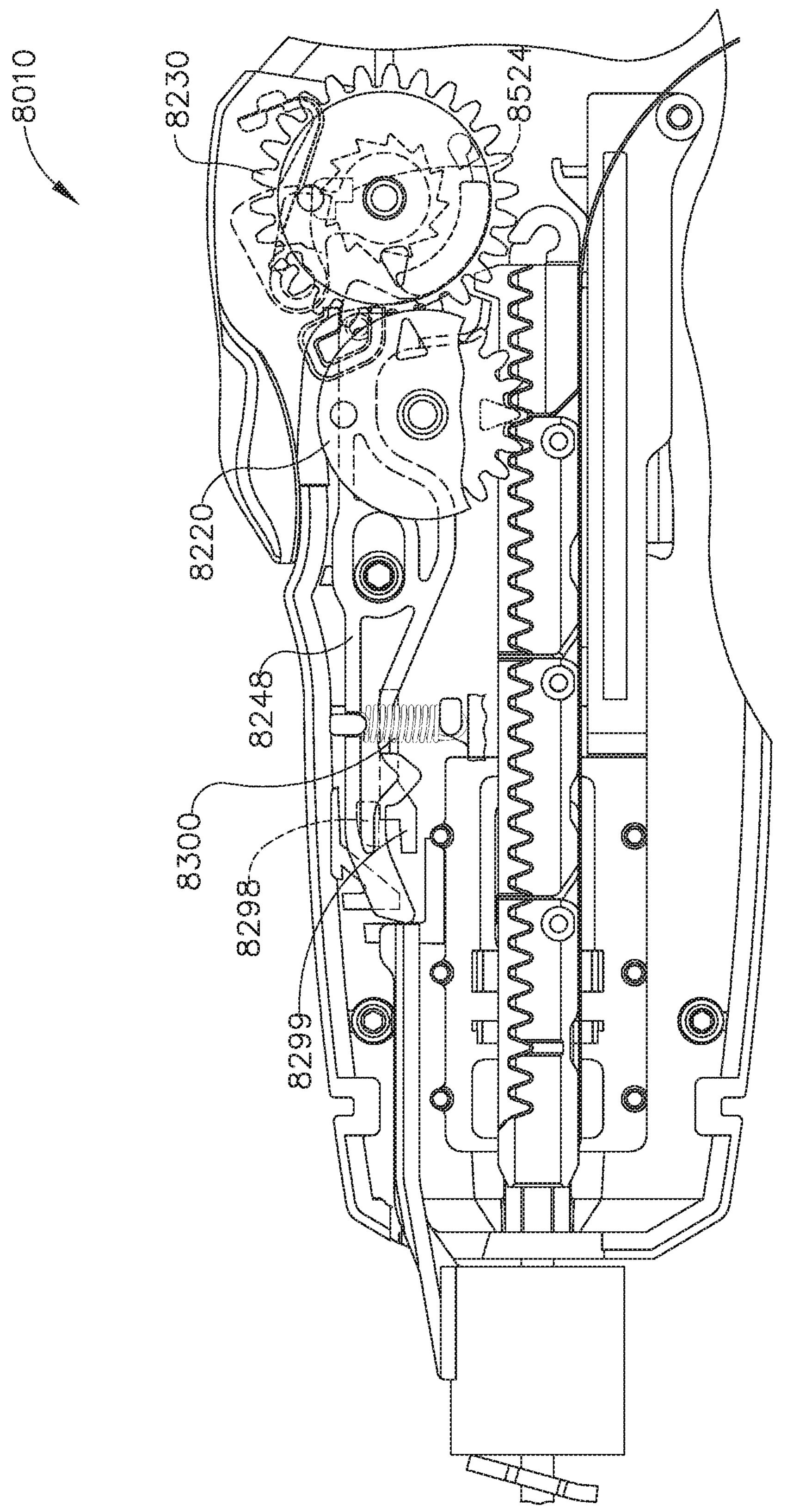
Figure 194:
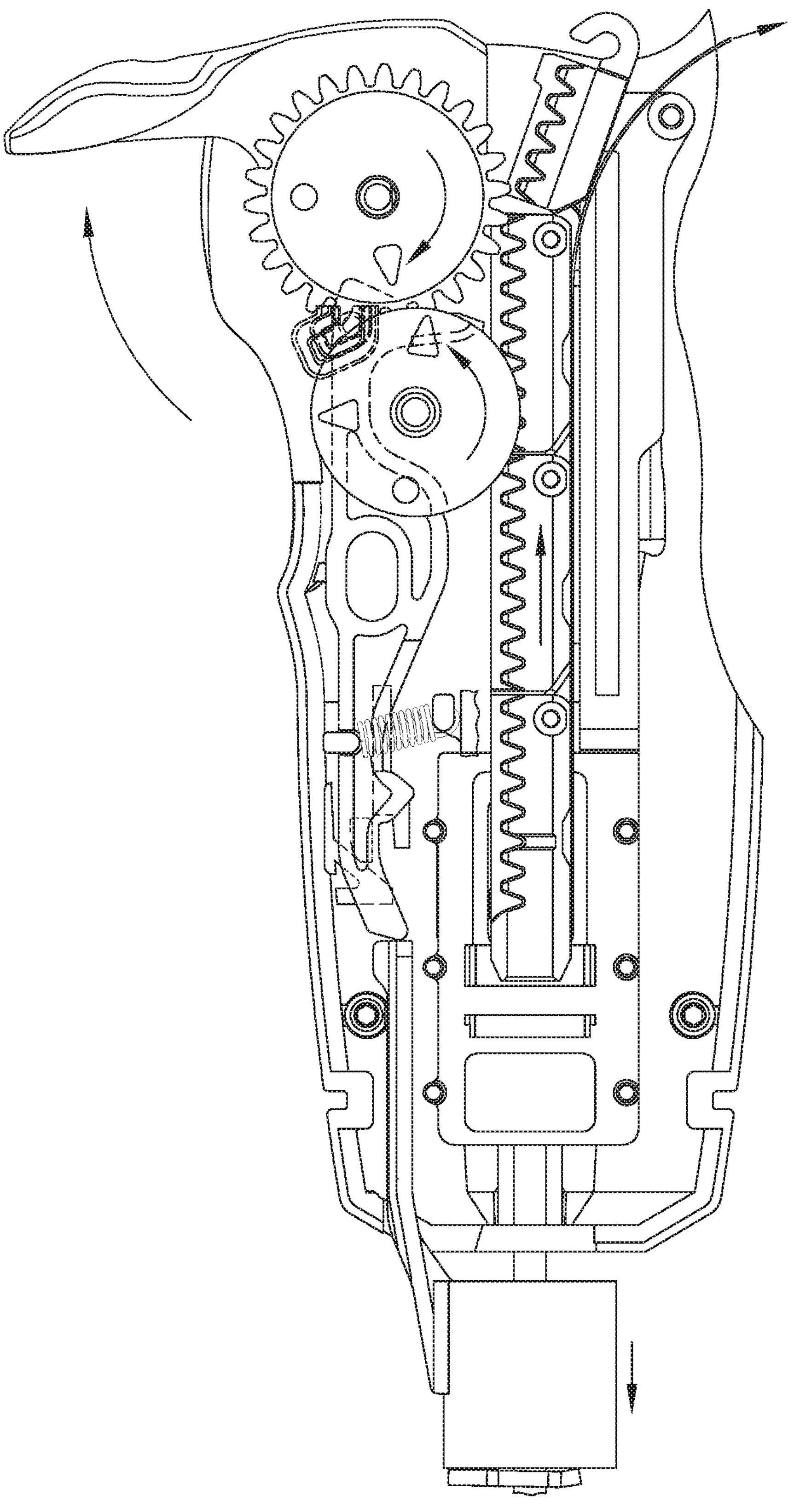
Figure 195:
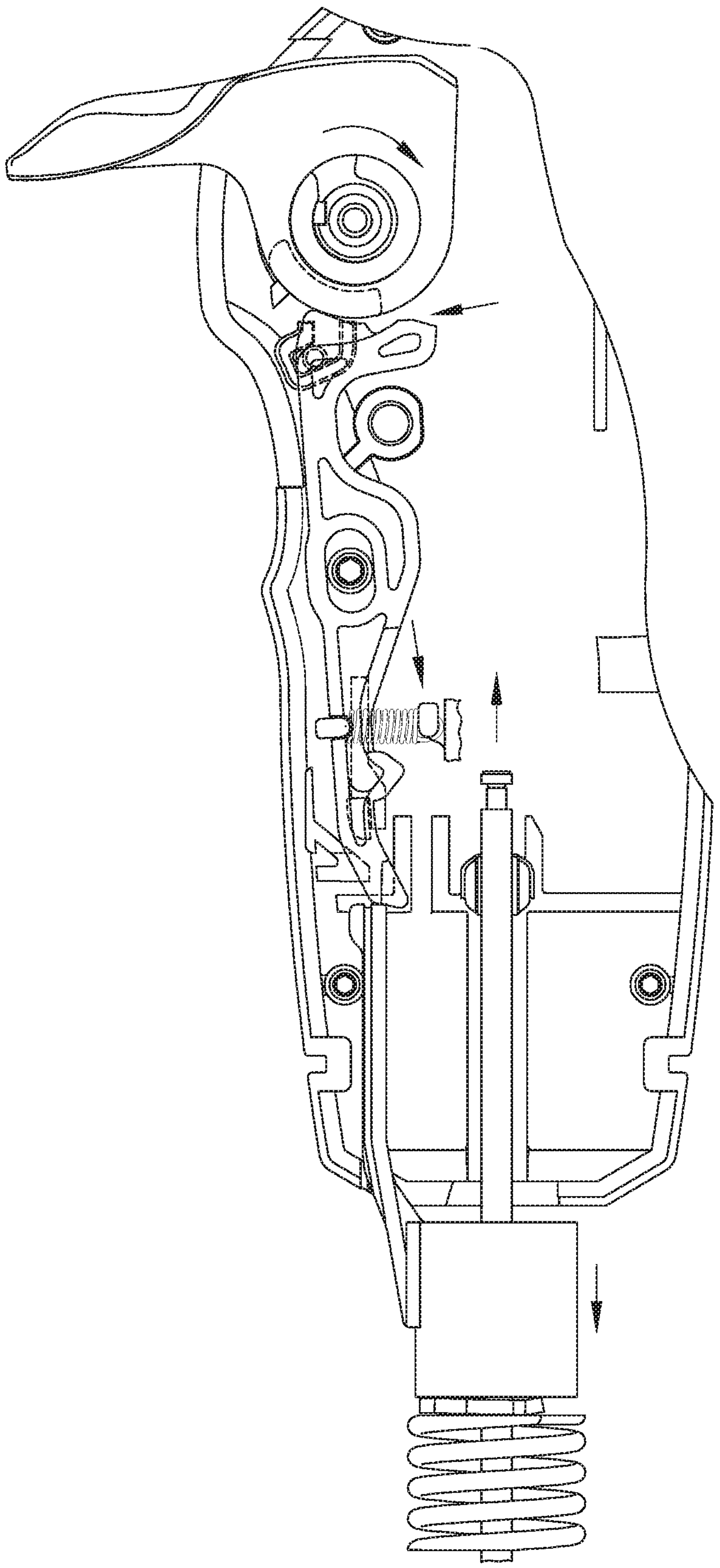
Figure 196:
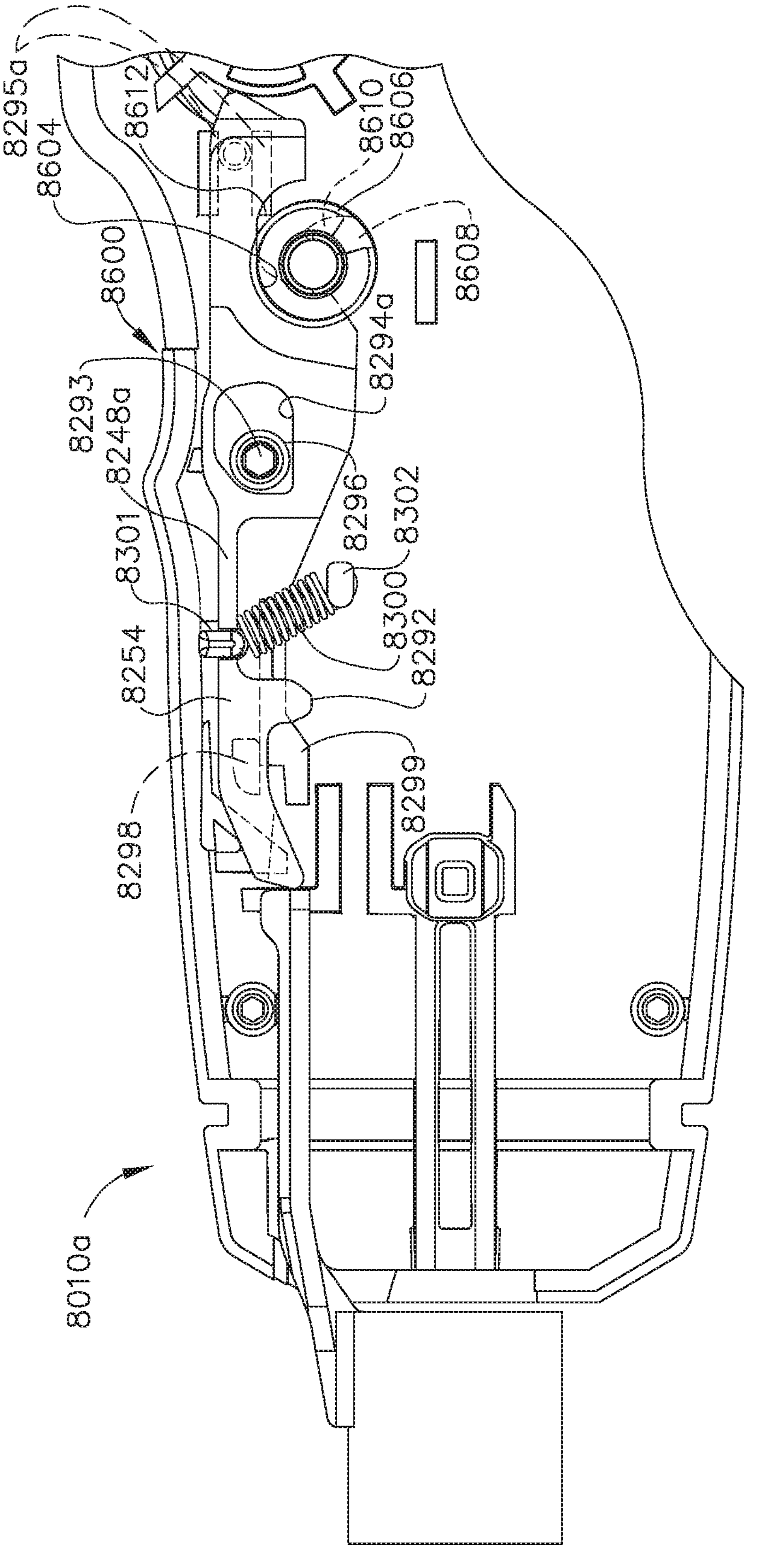
Figure 197:
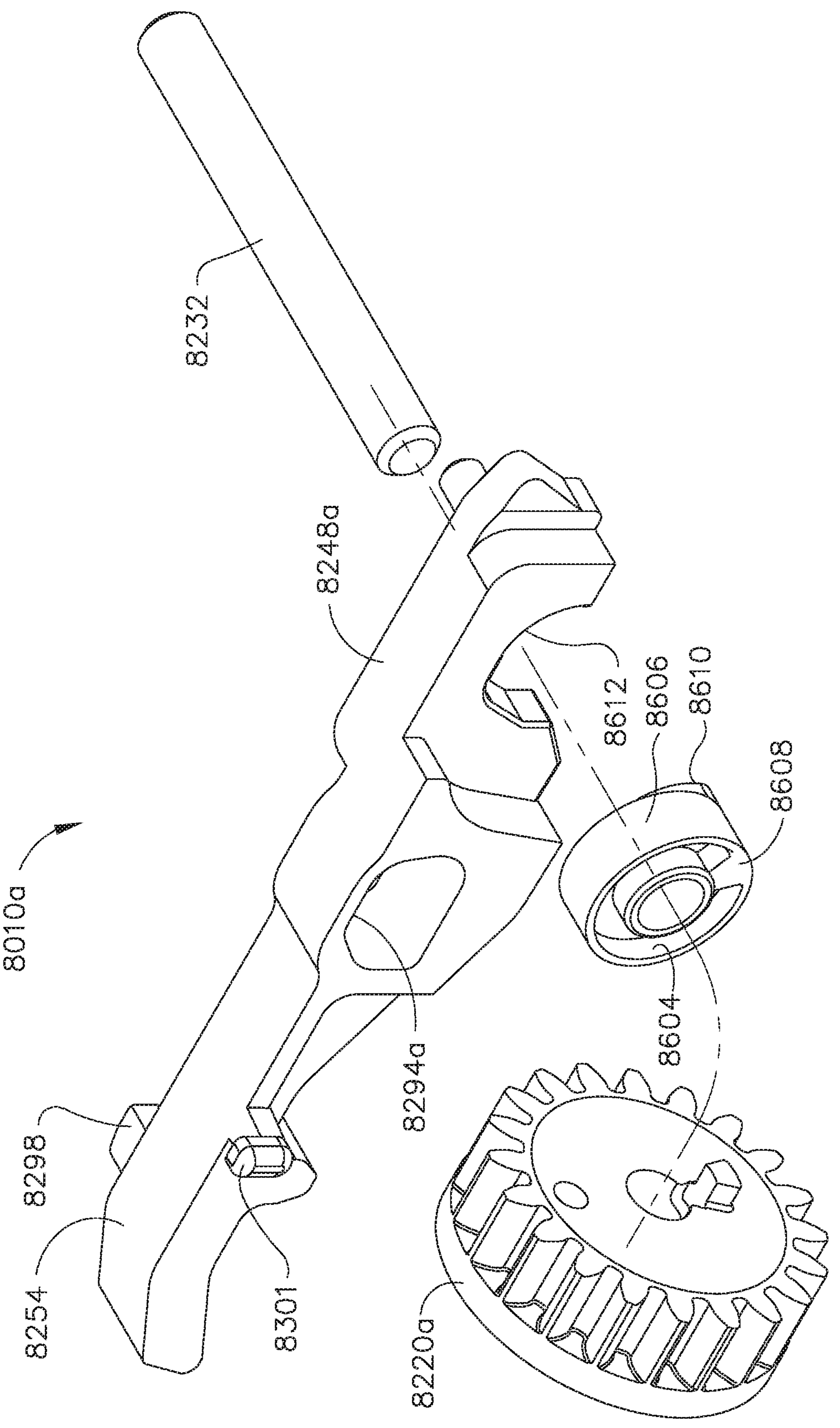
Figure 198:
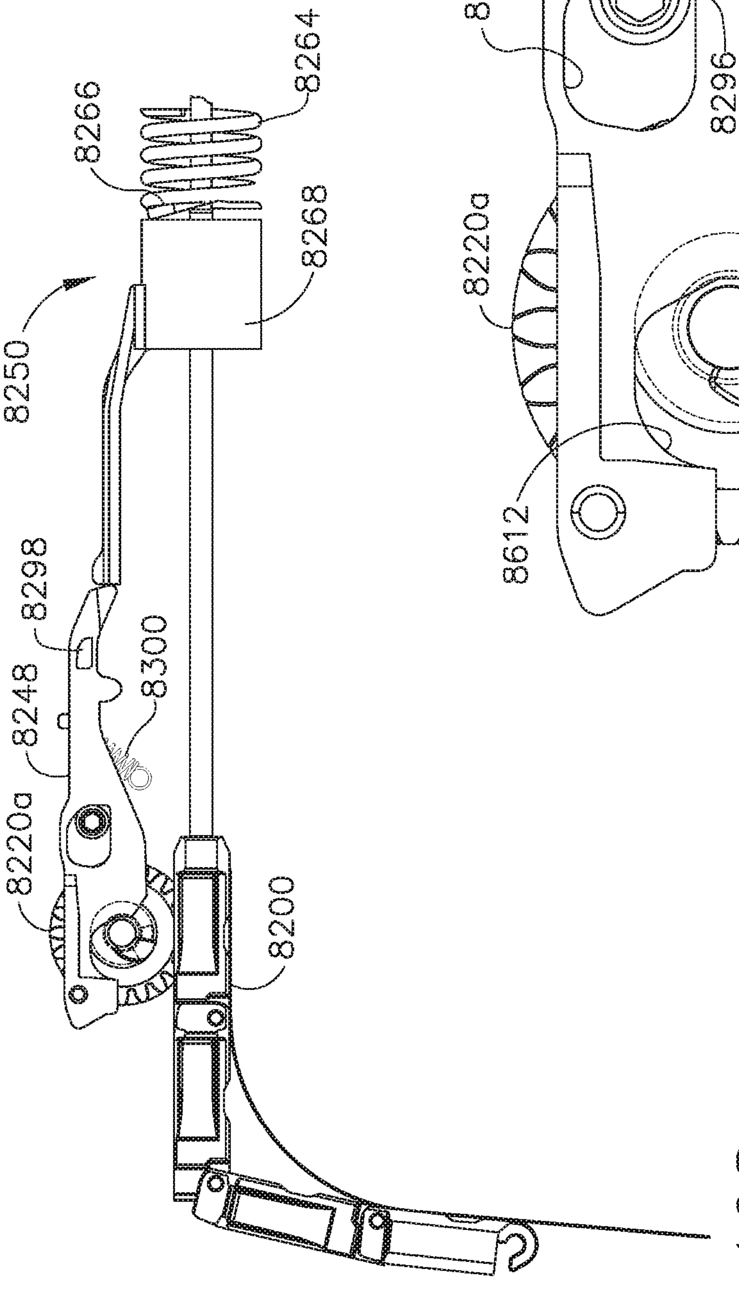
Figure 198A:
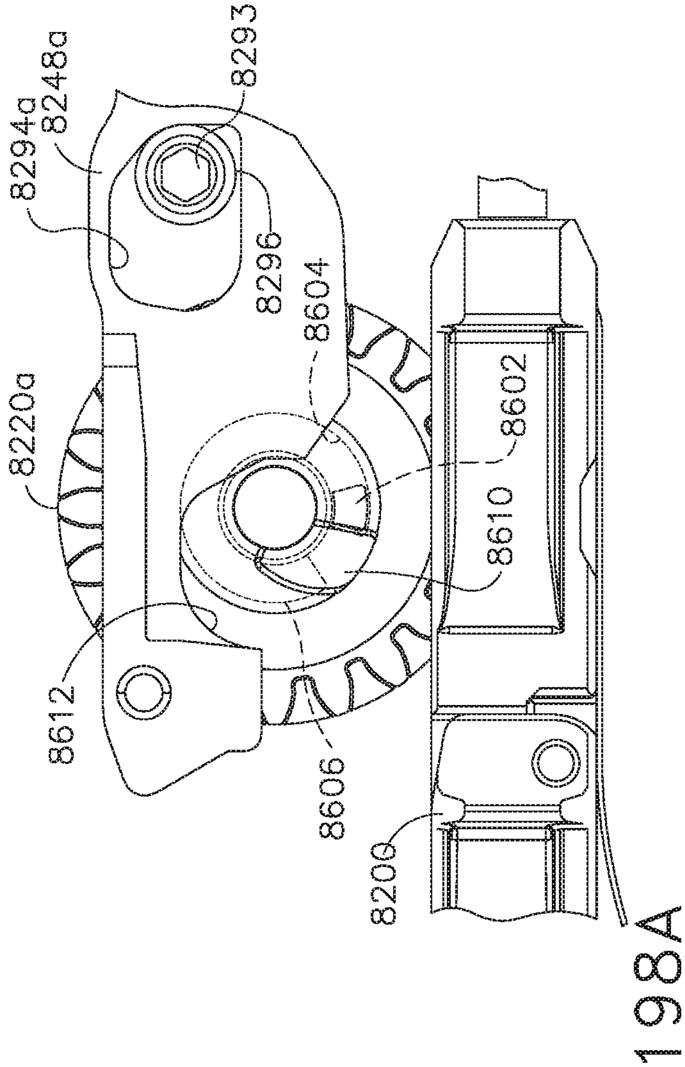
Figure 199:
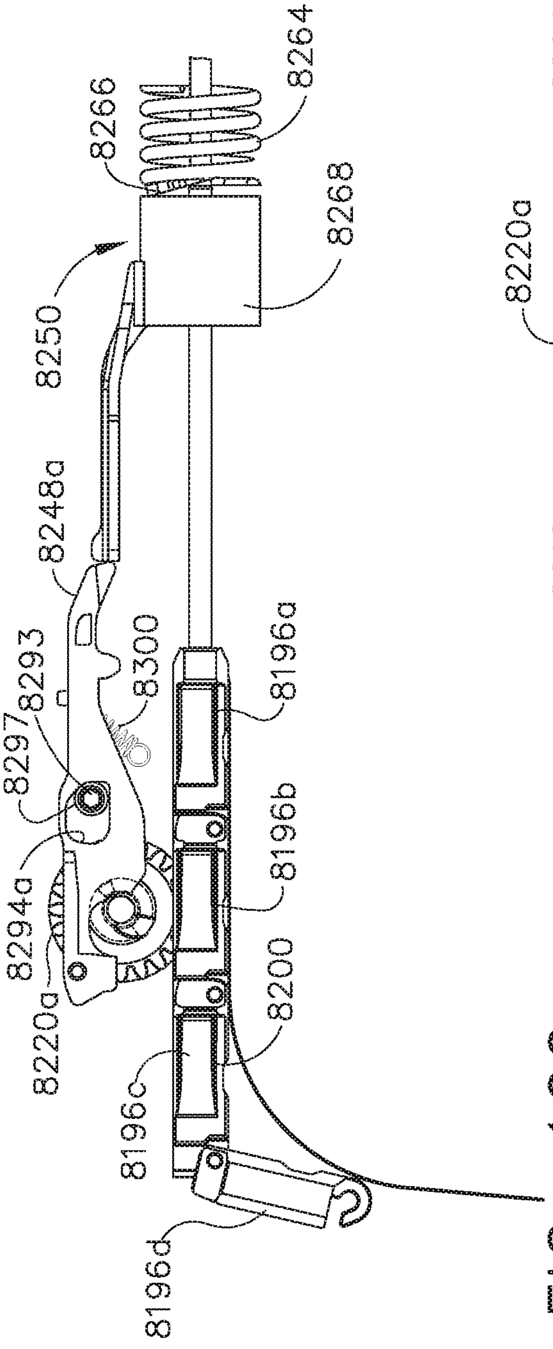
Figure 199A:
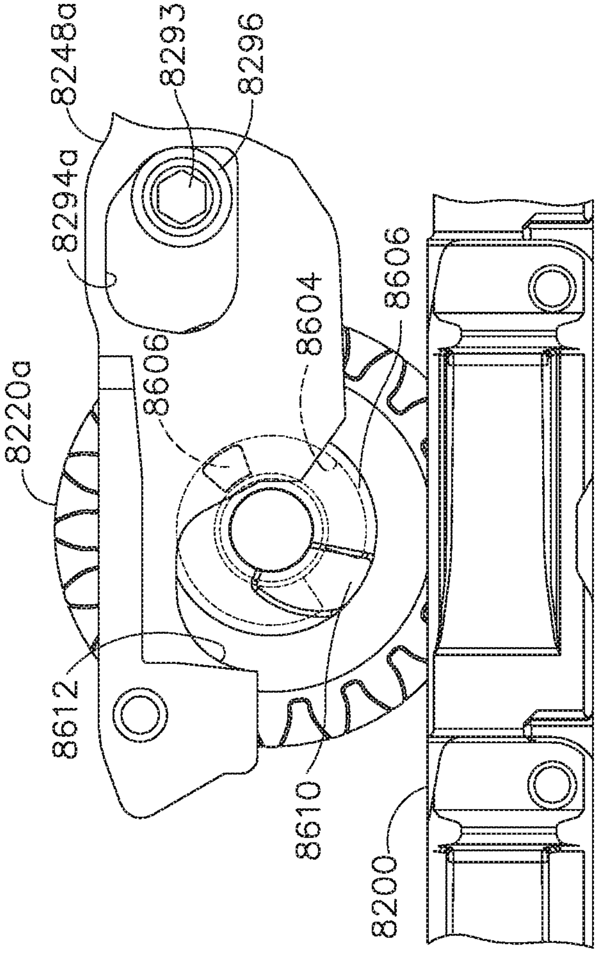
Figure 200:
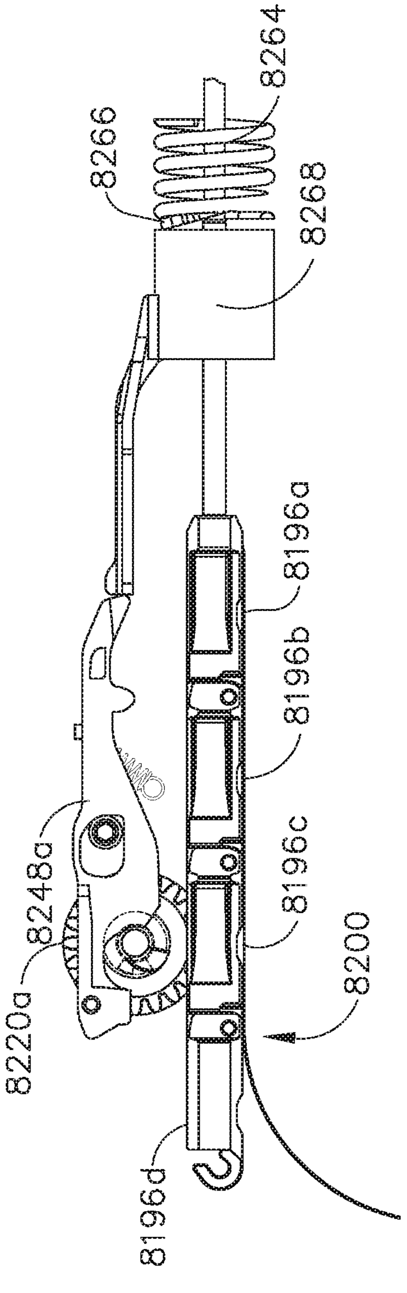
Figure 200A:
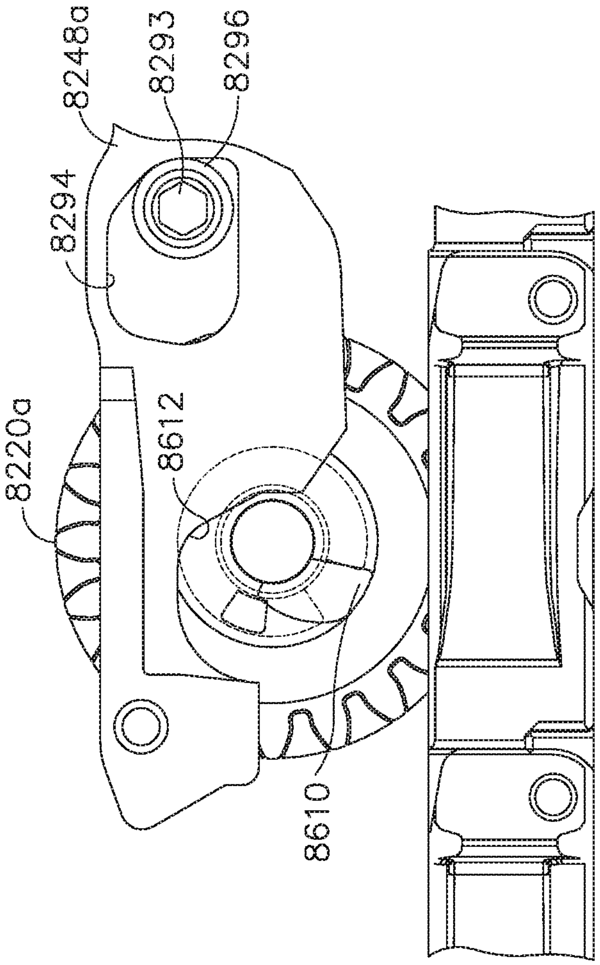
Figure 201:
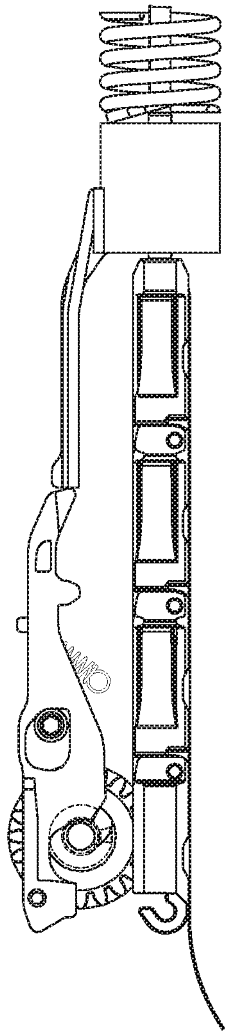
Figure 201A:
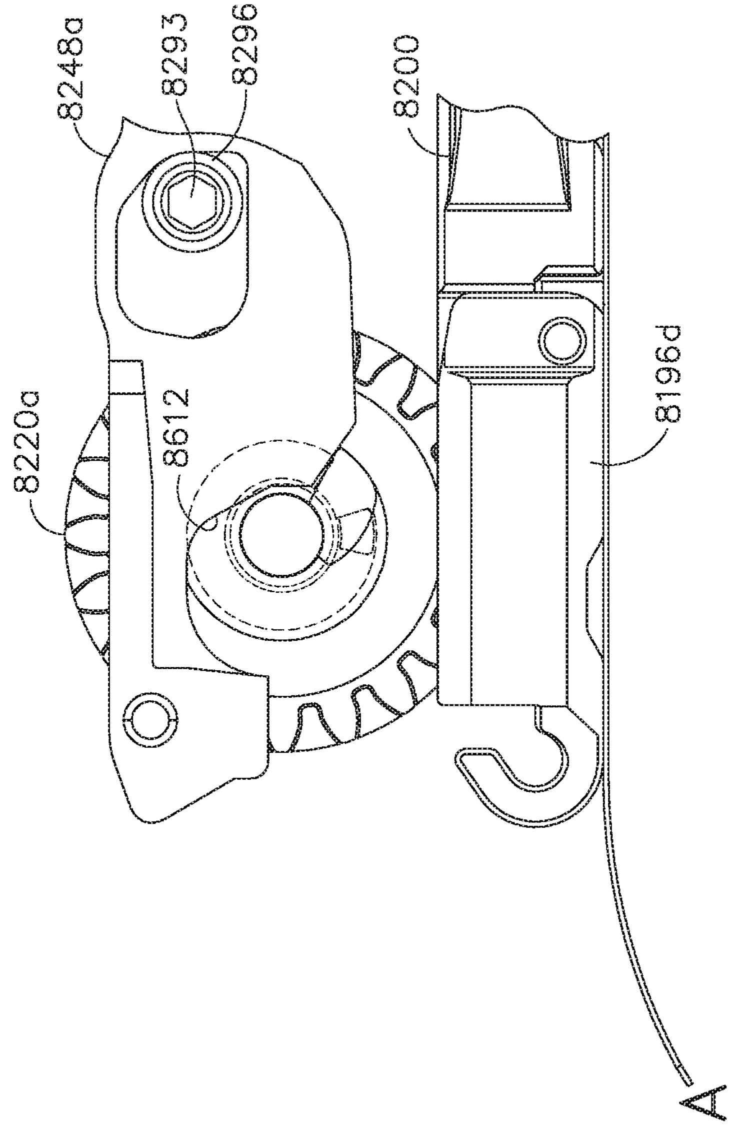
Figure 202:
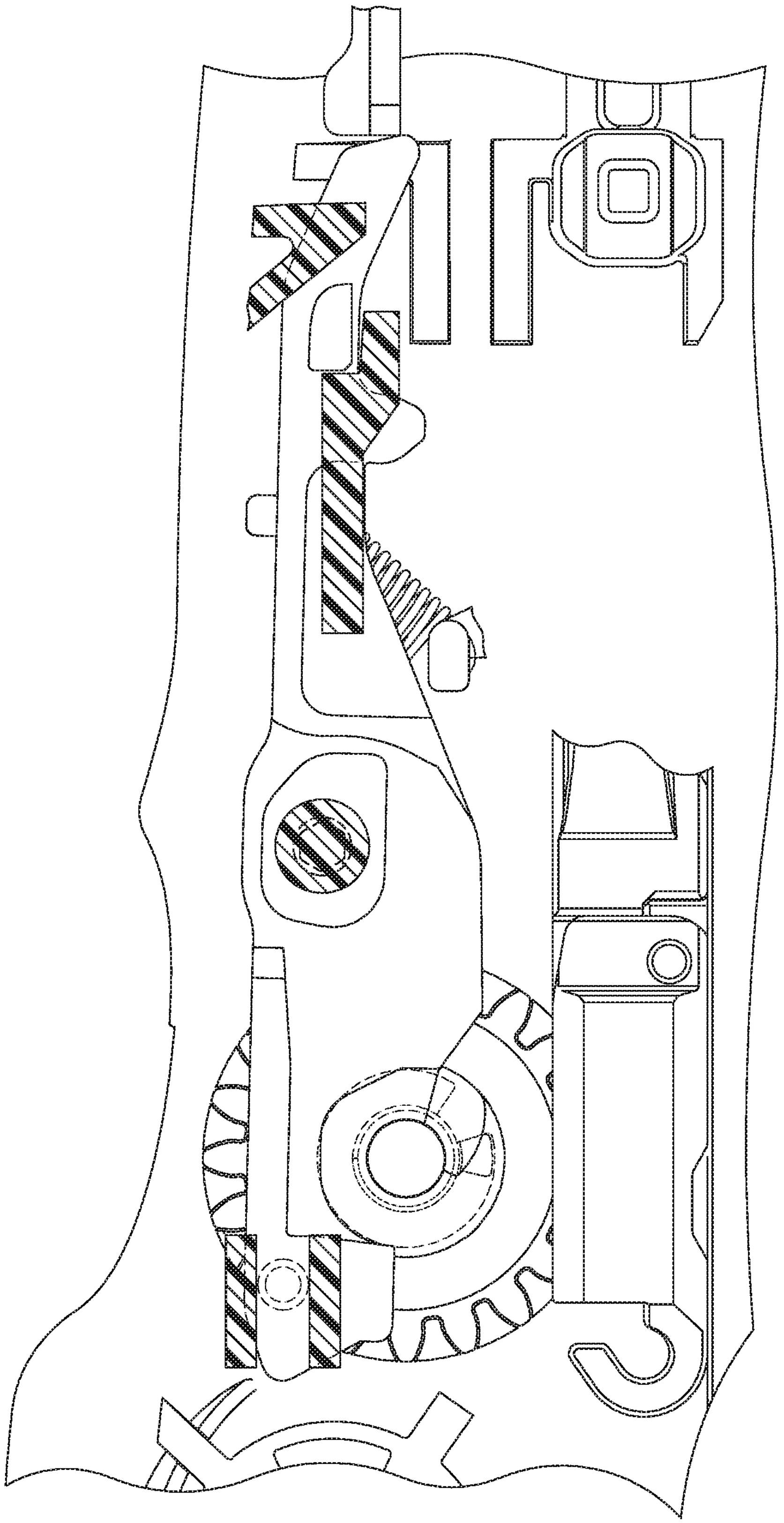
Figure 203:
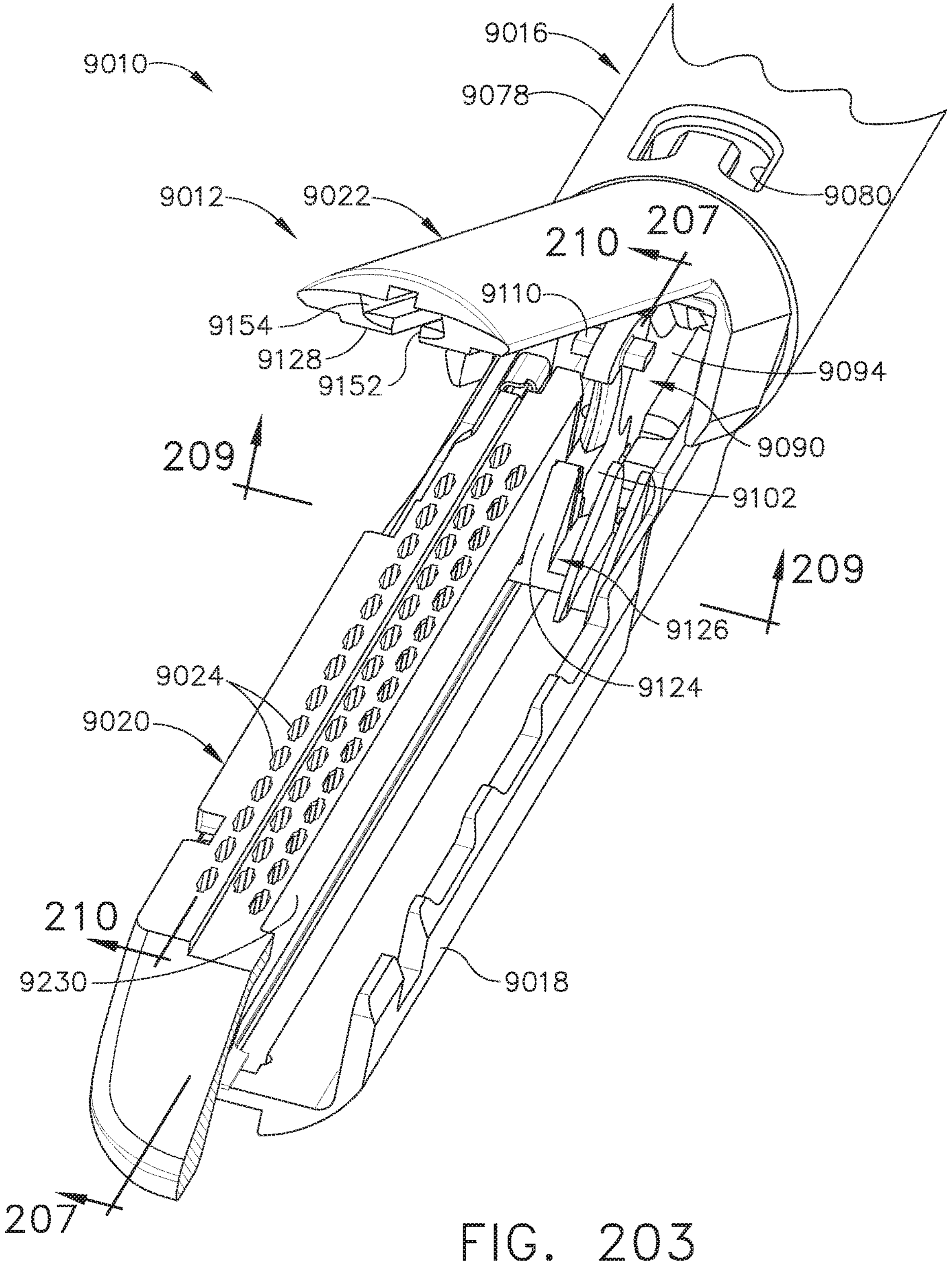
Figure 204:
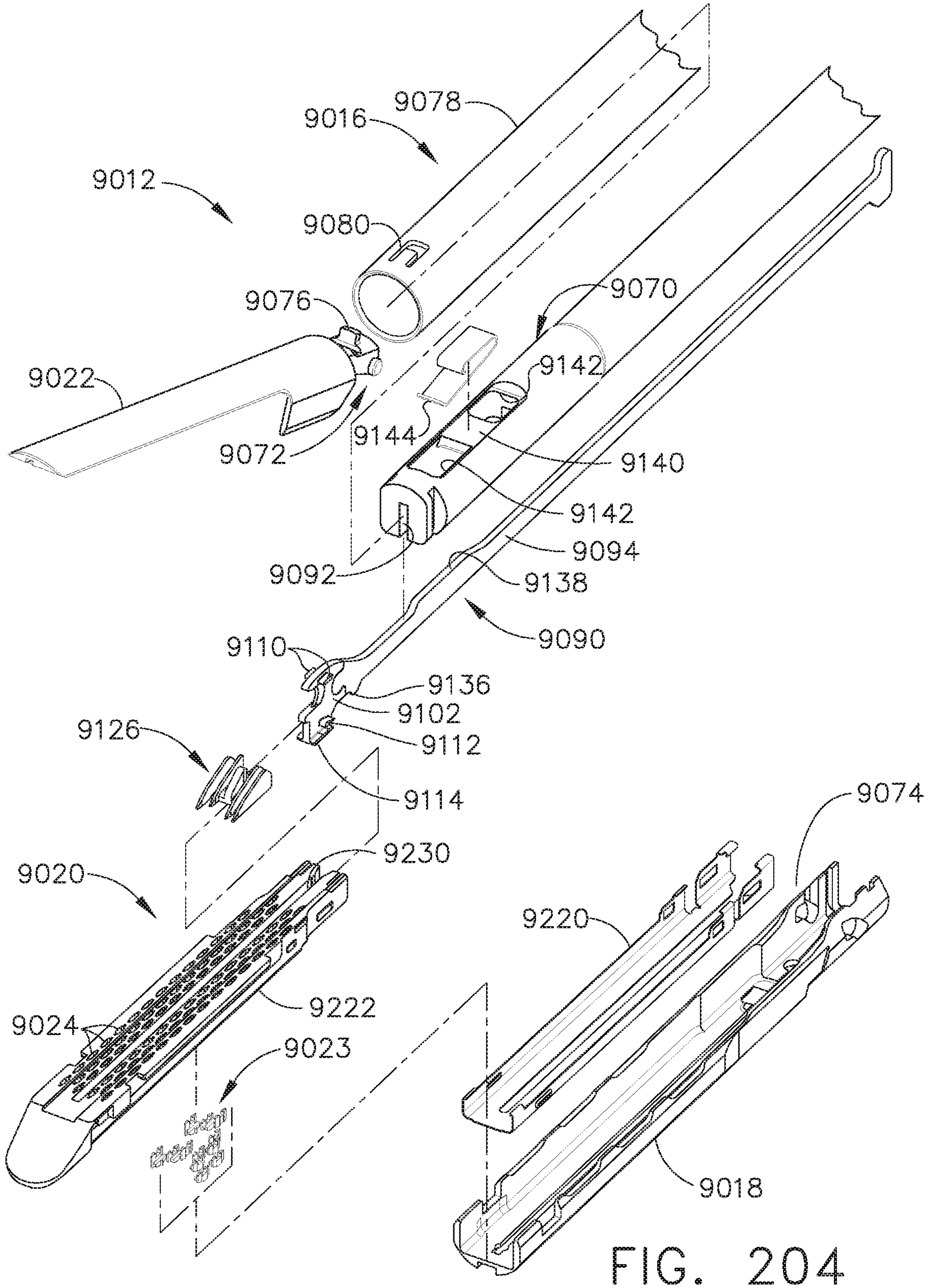
Figure 206:
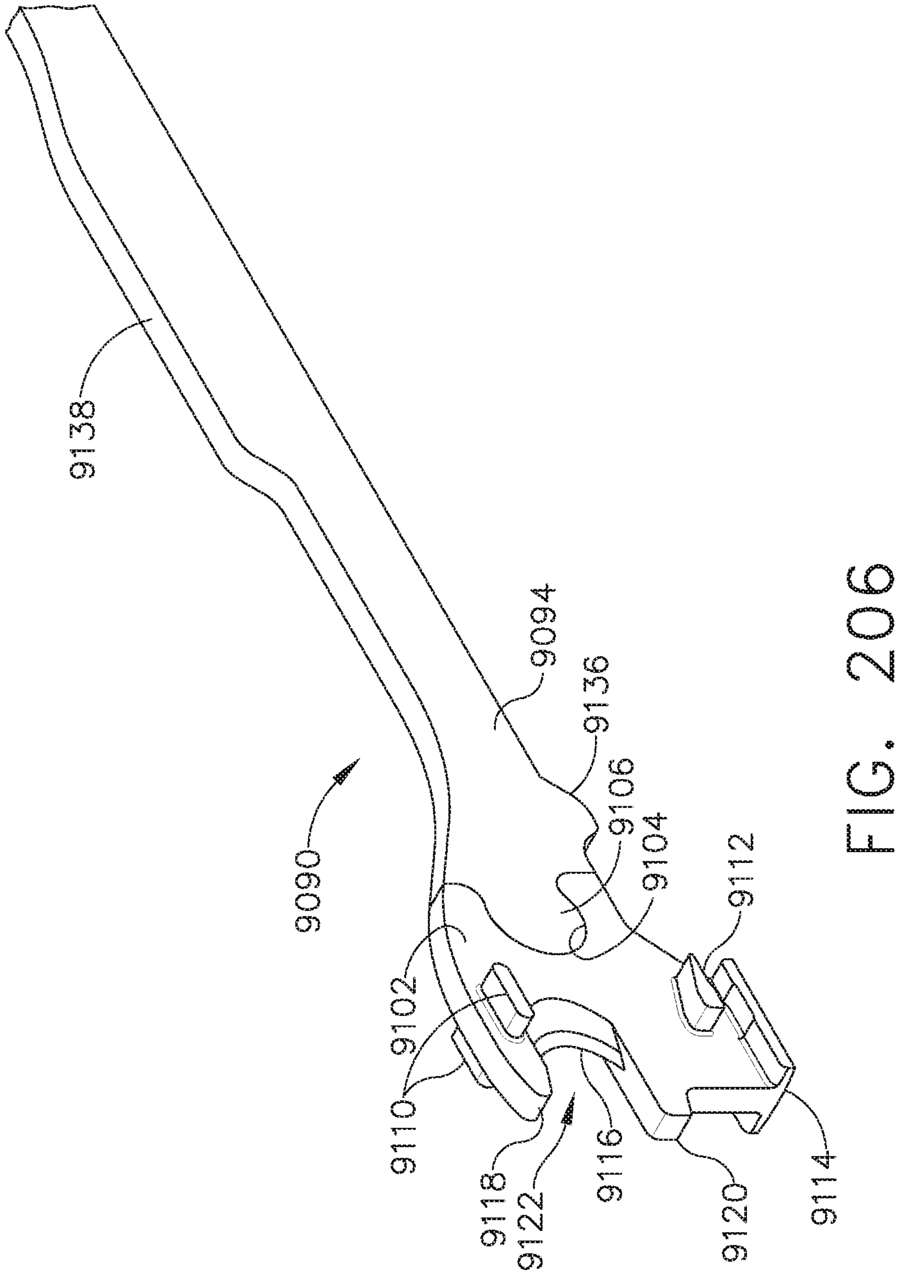
Figure 205:
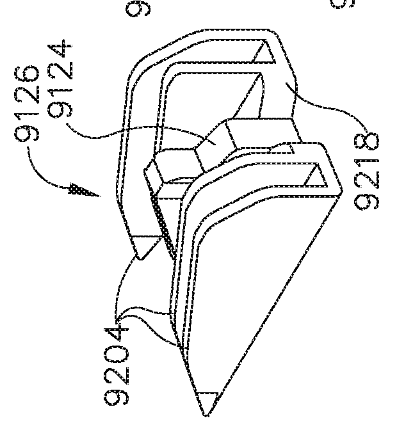
Figure 207:
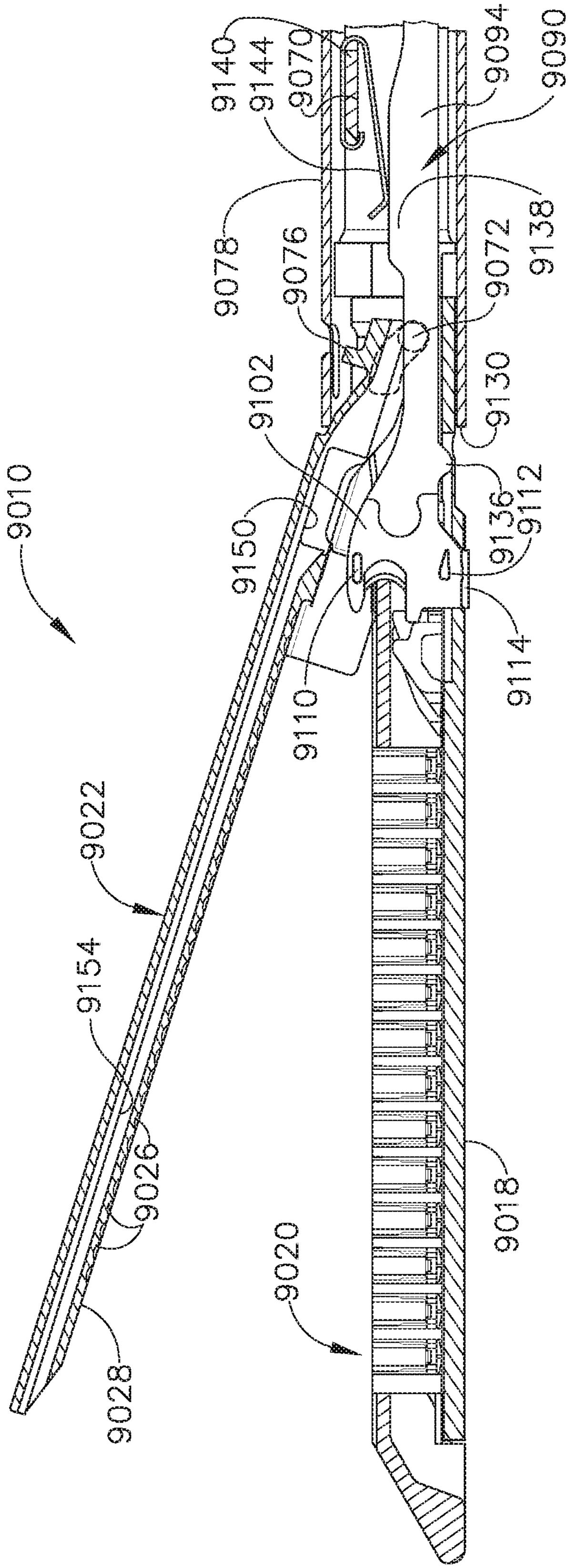
Figure 208:
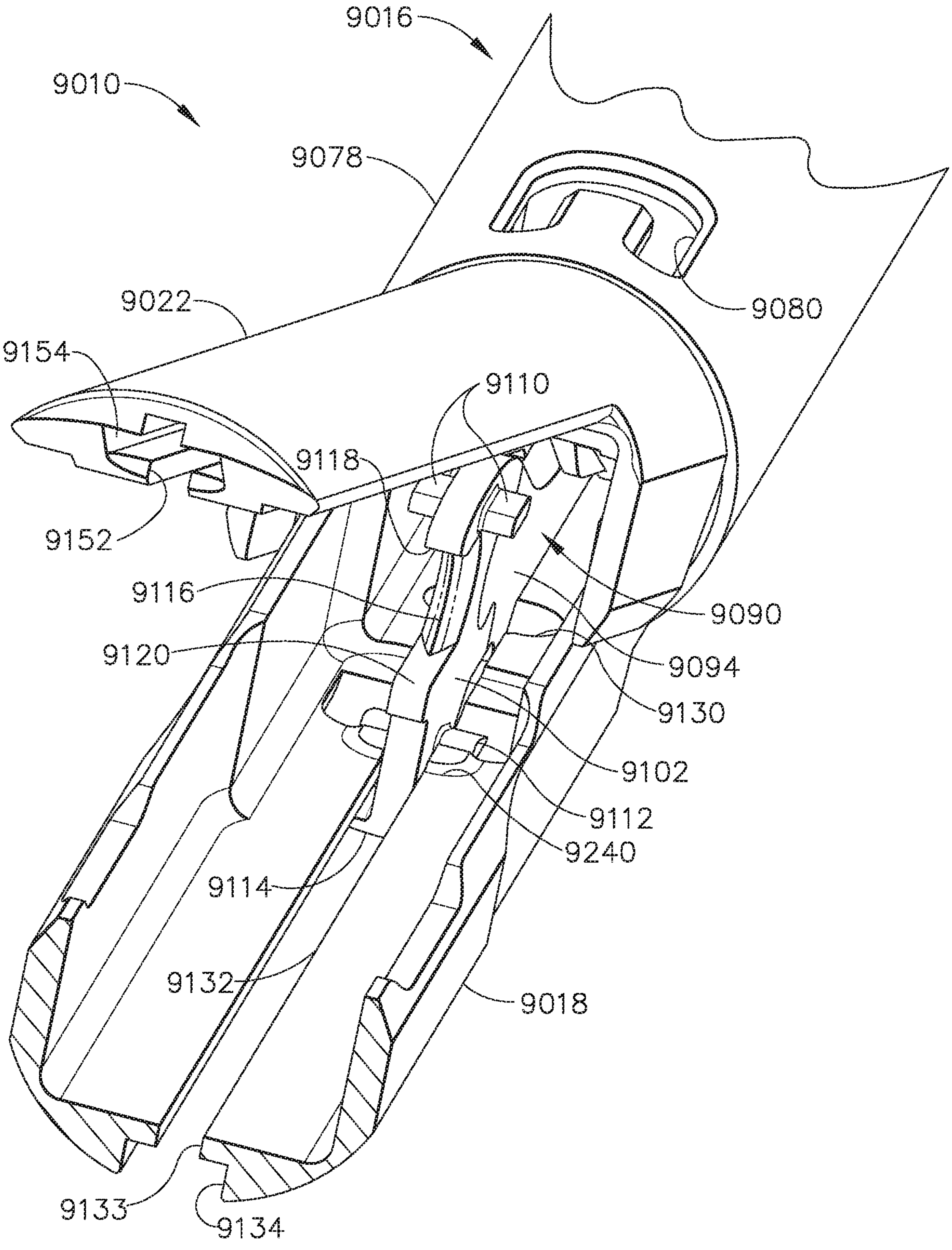
Figure 209:
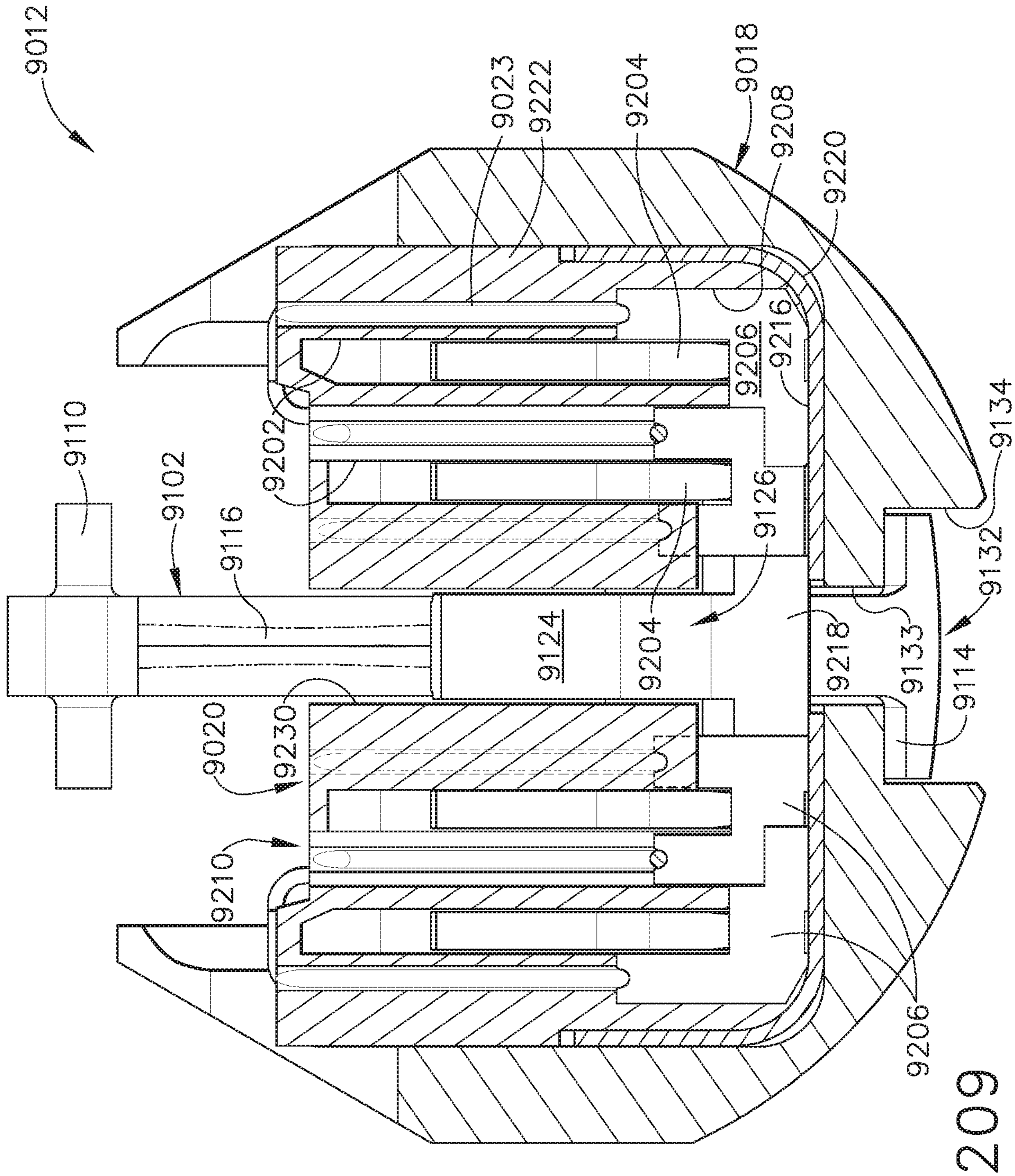
Figure 210:
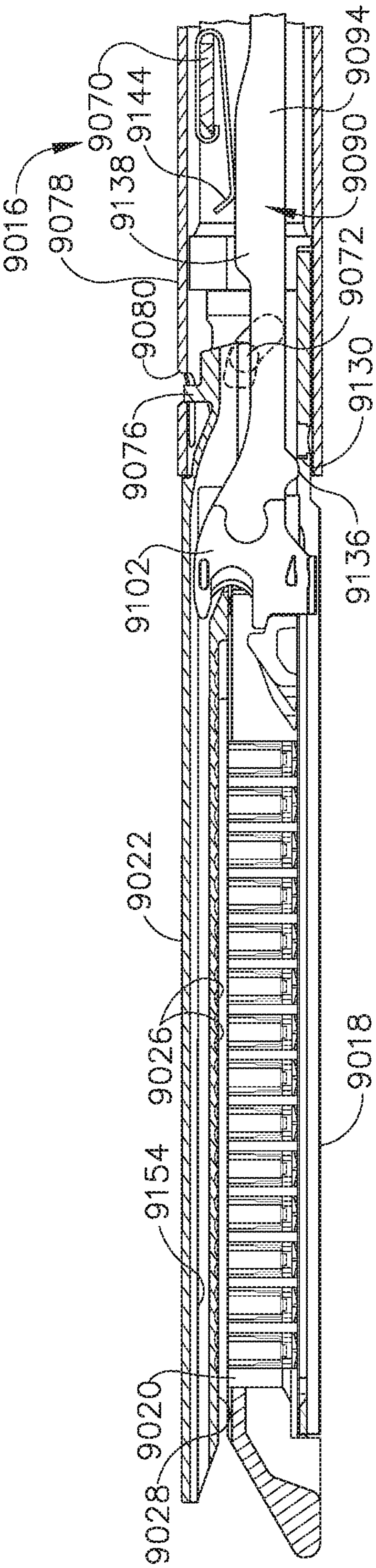
Figure 211:
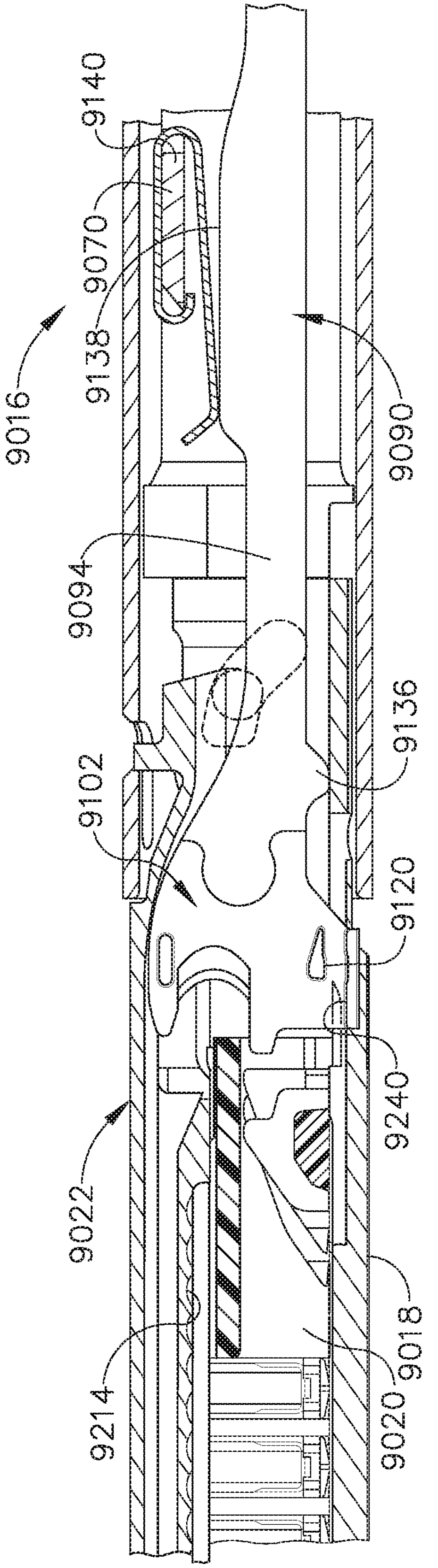
Figure 212:
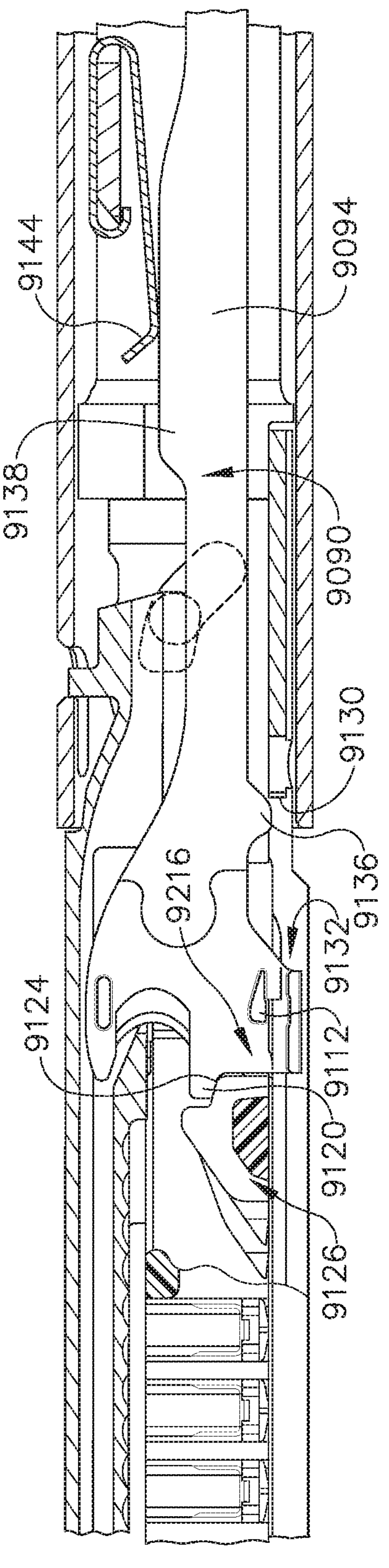
Figure 213:
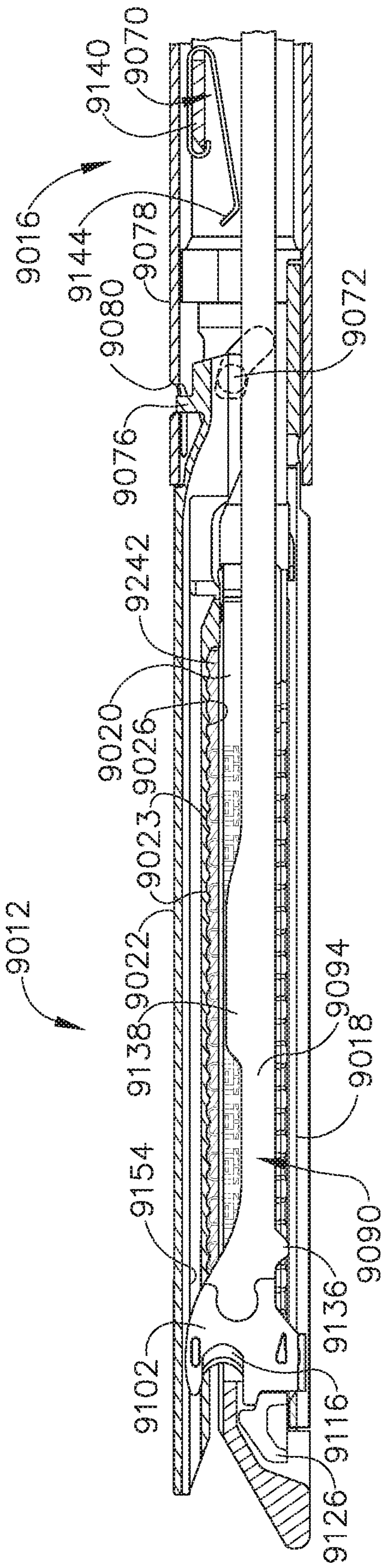
Figure 214:
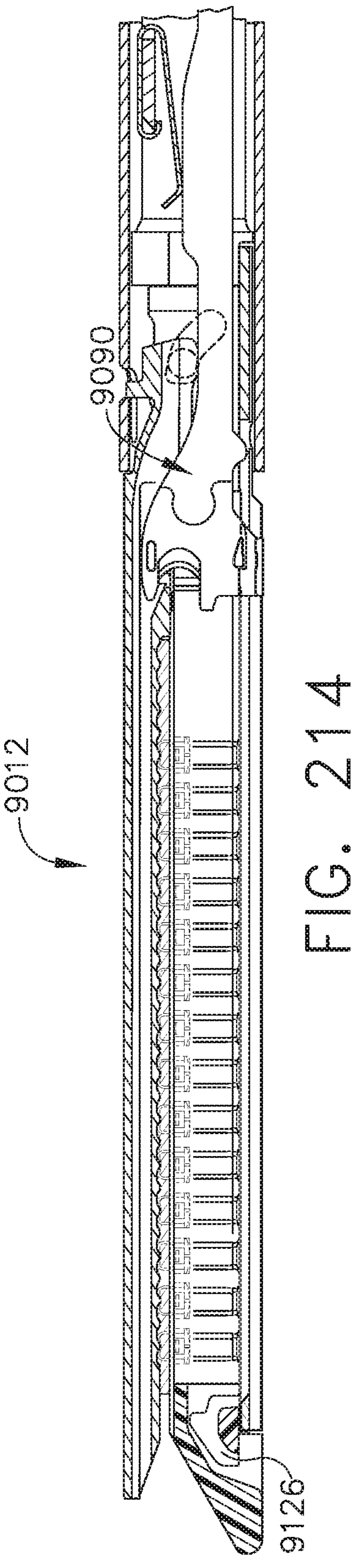
Figure 215:
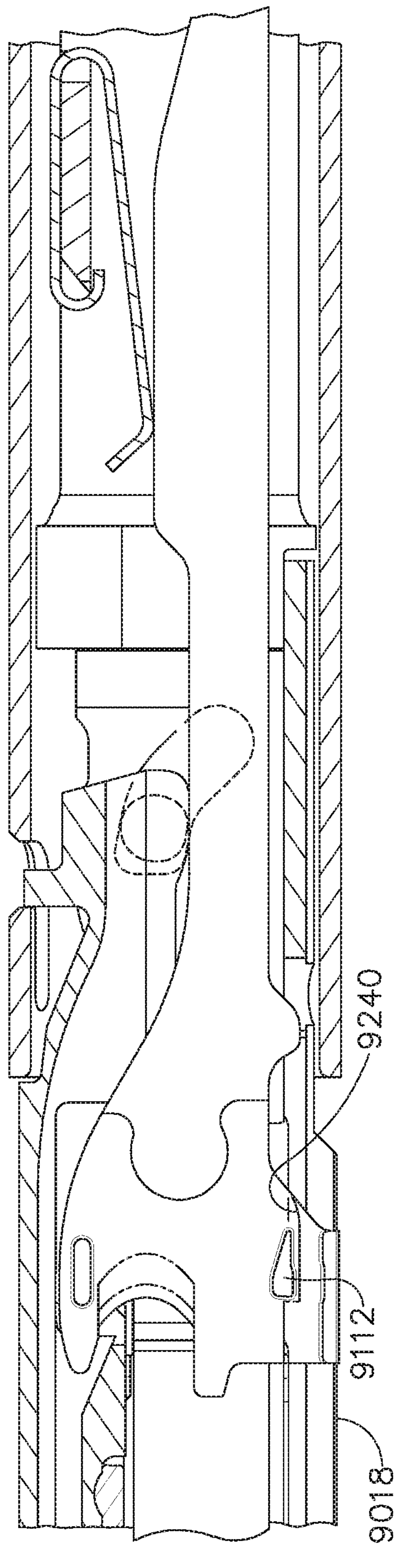
Figure 216:
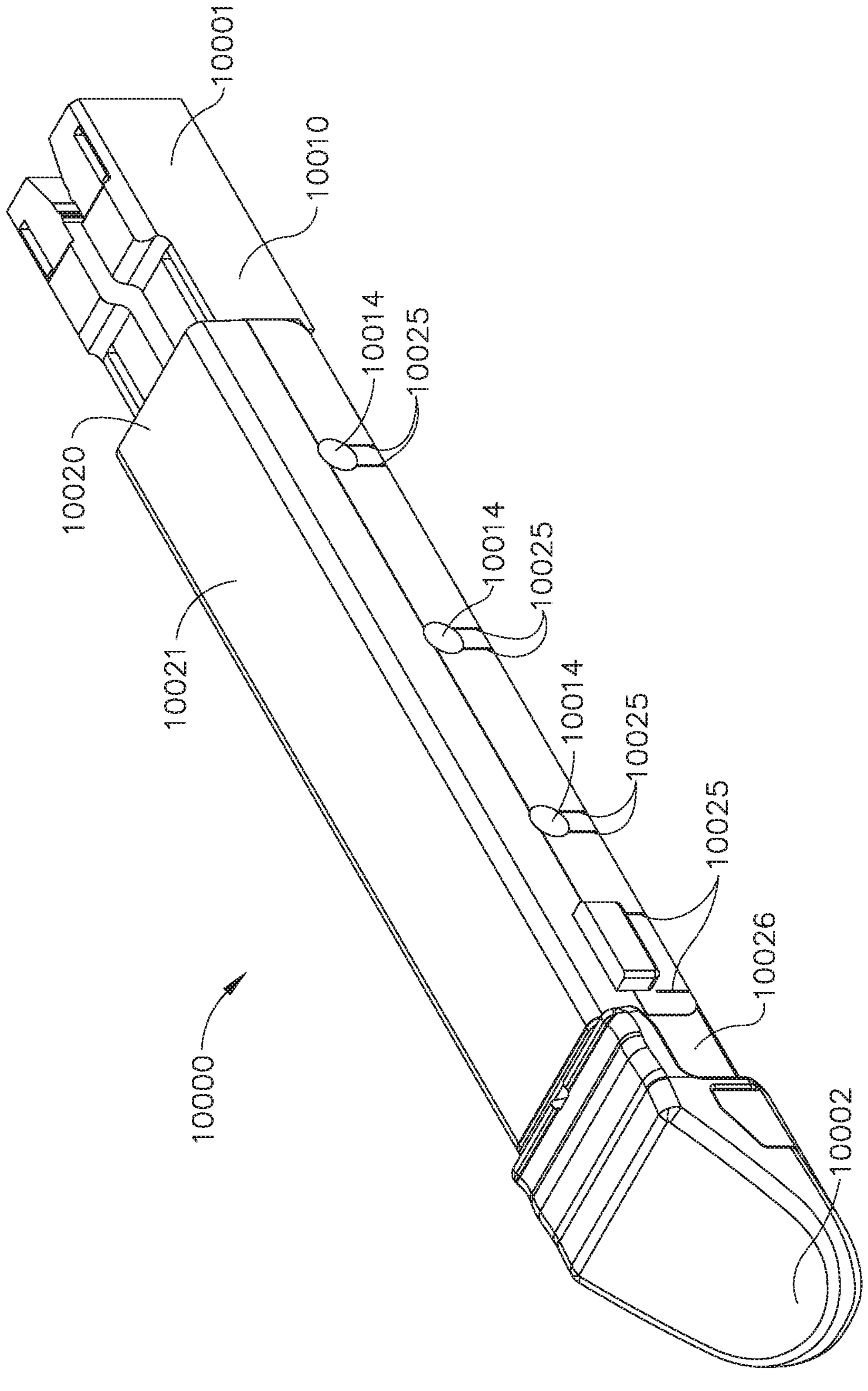
Figure 217:
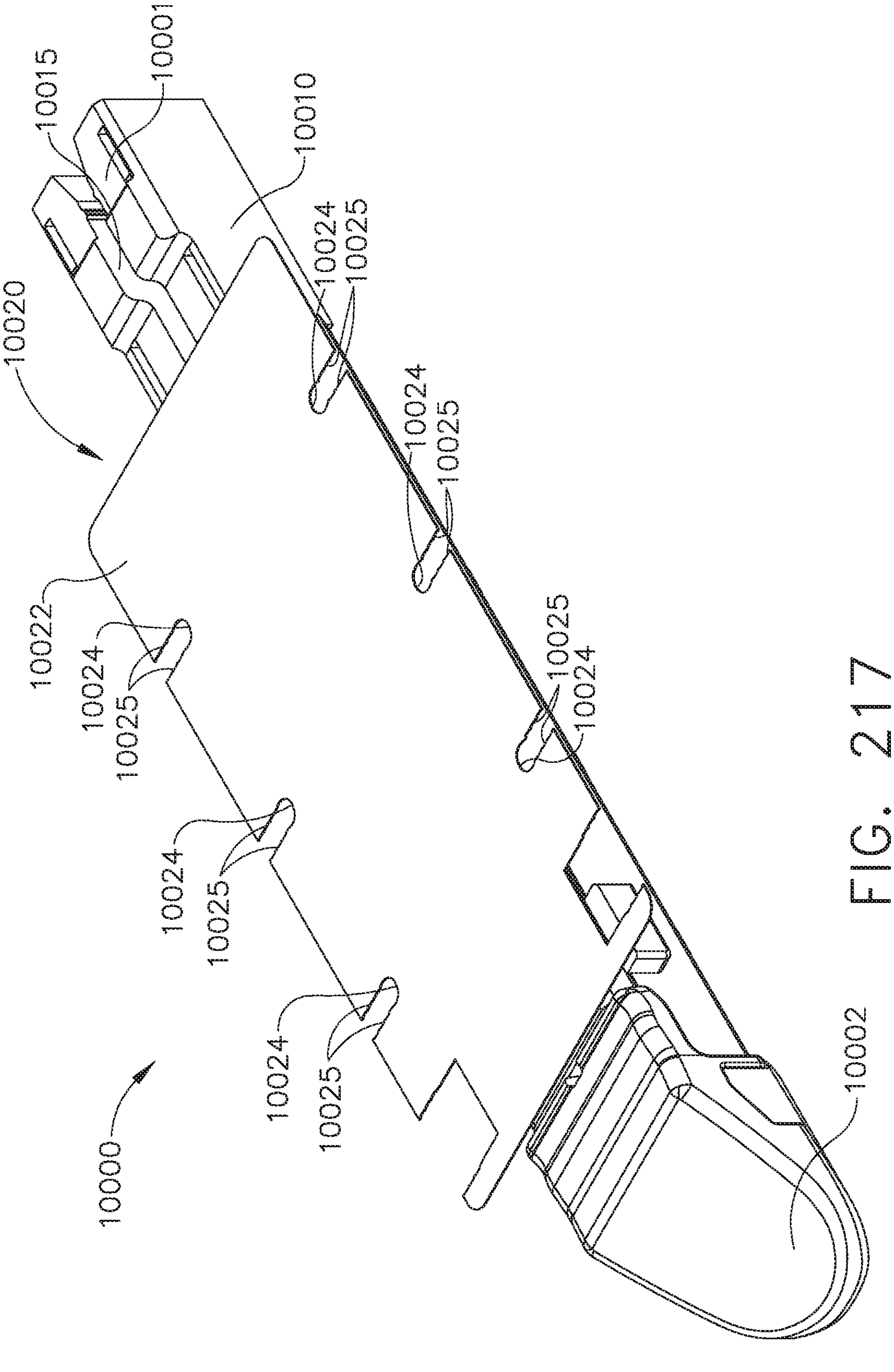
Figure 218:
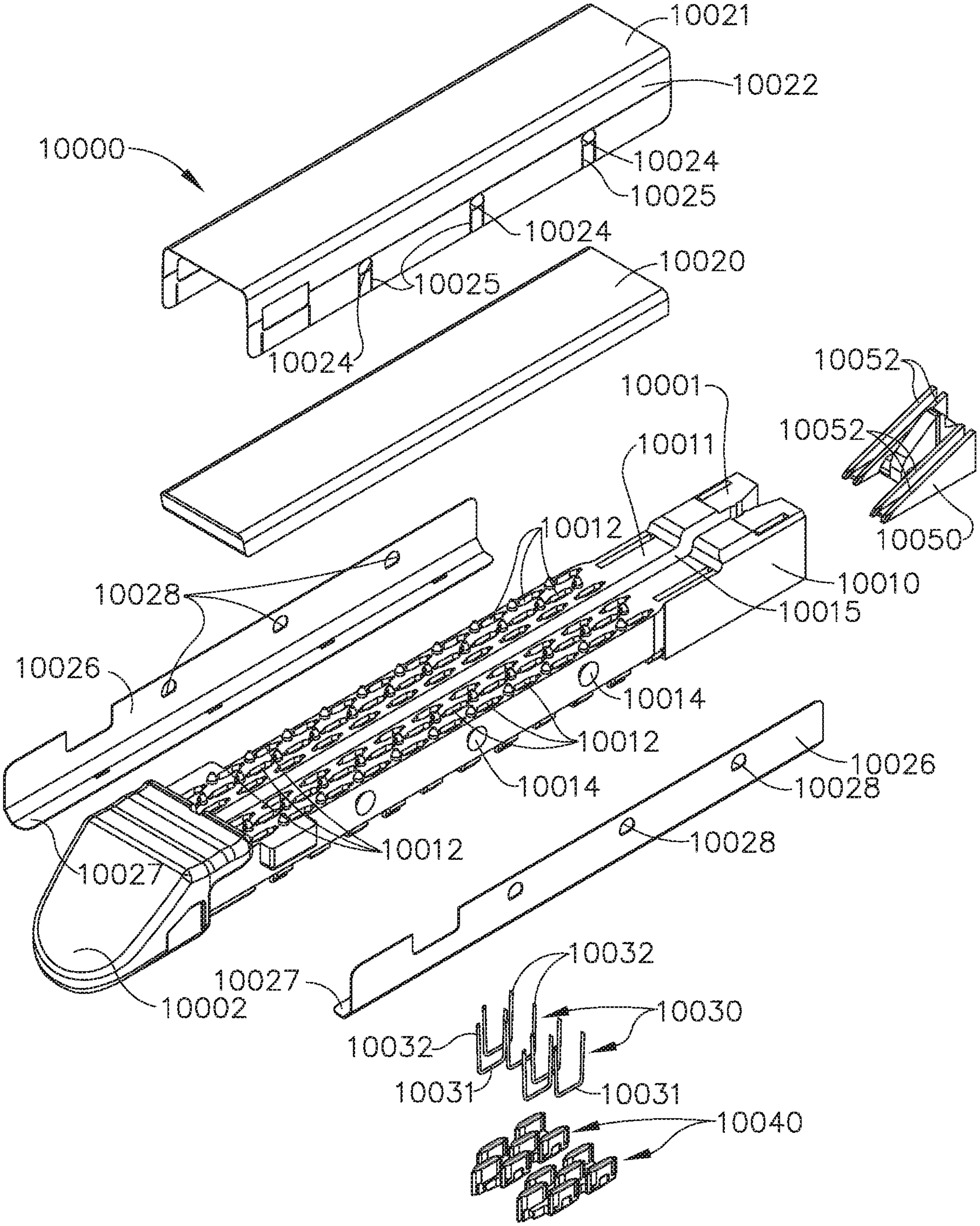
Figure 219:
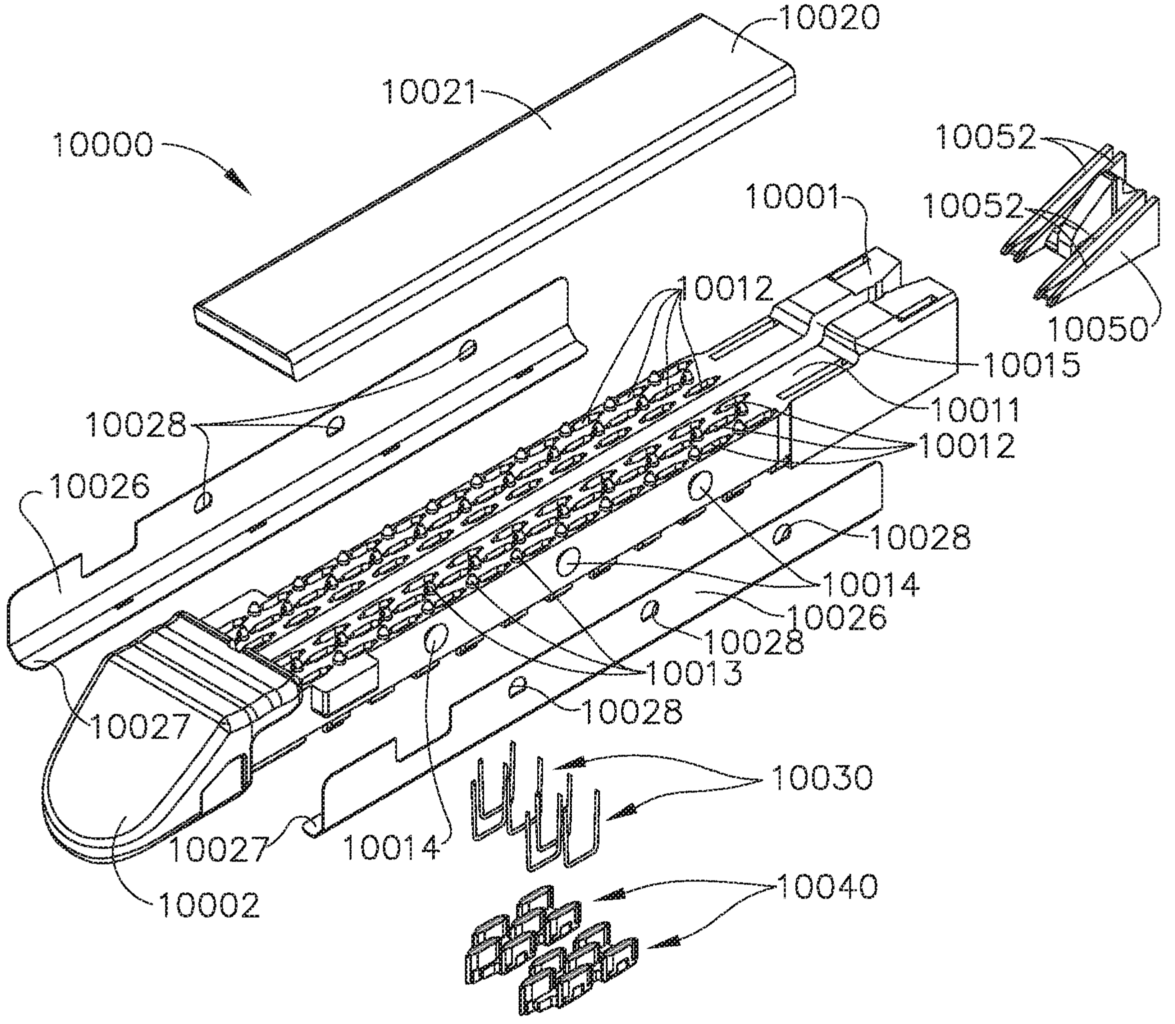
Figure 220:
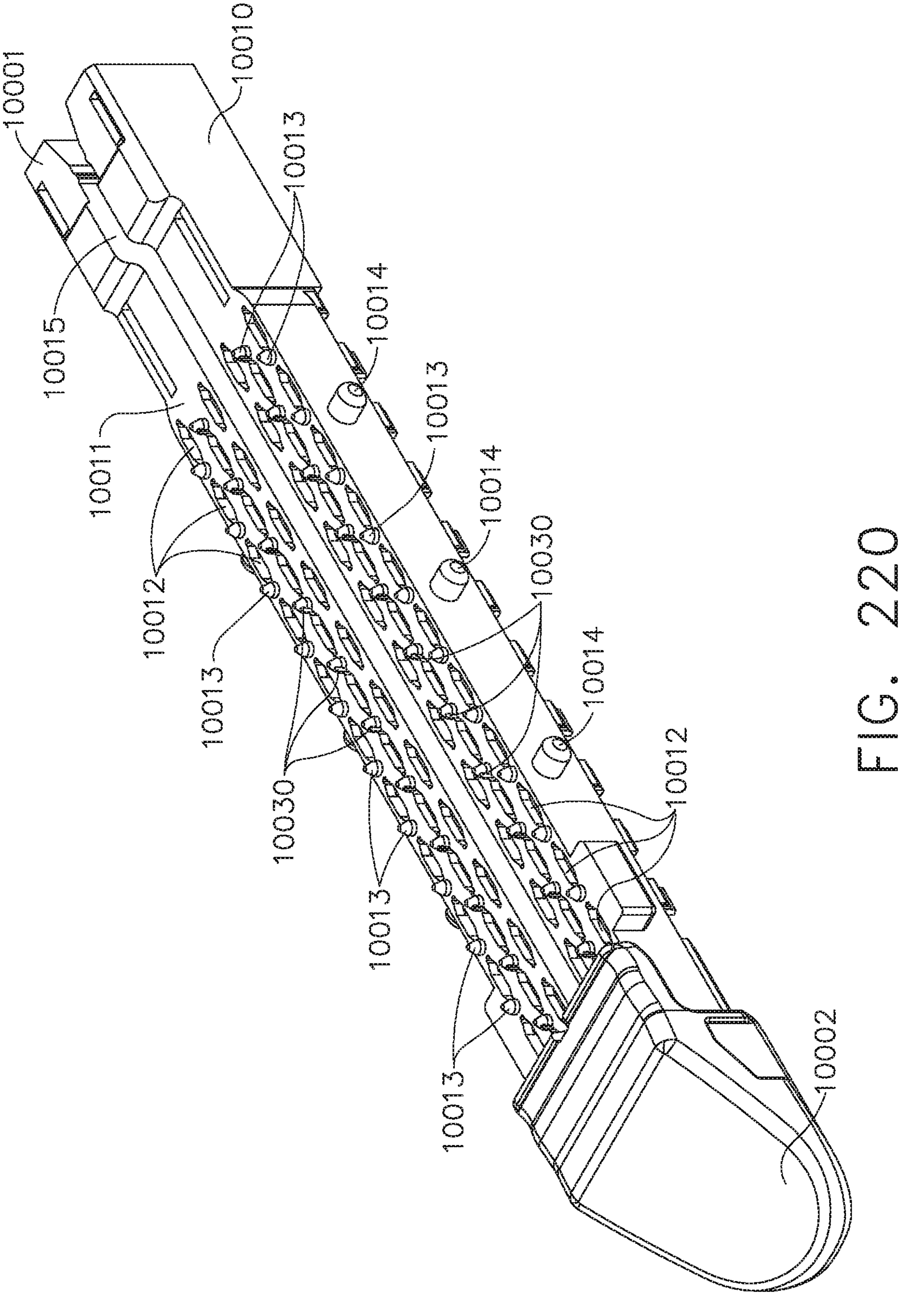
Figure 221:
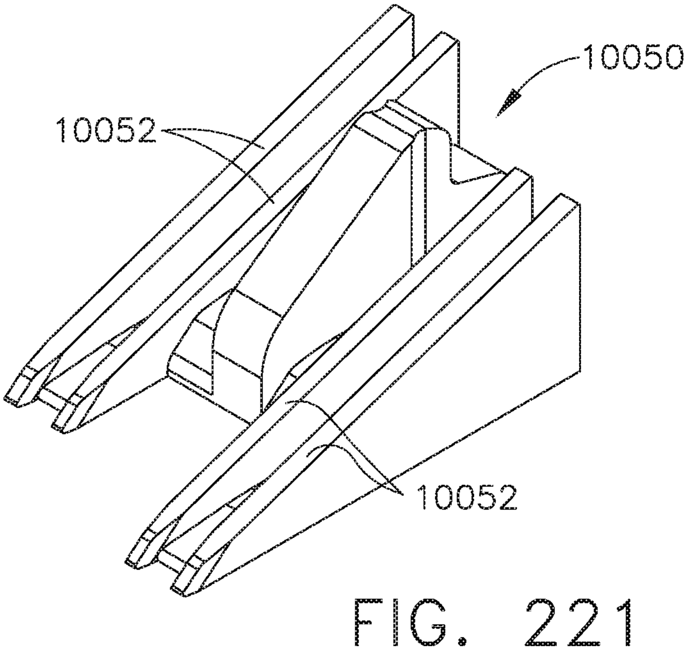
Figure 222:
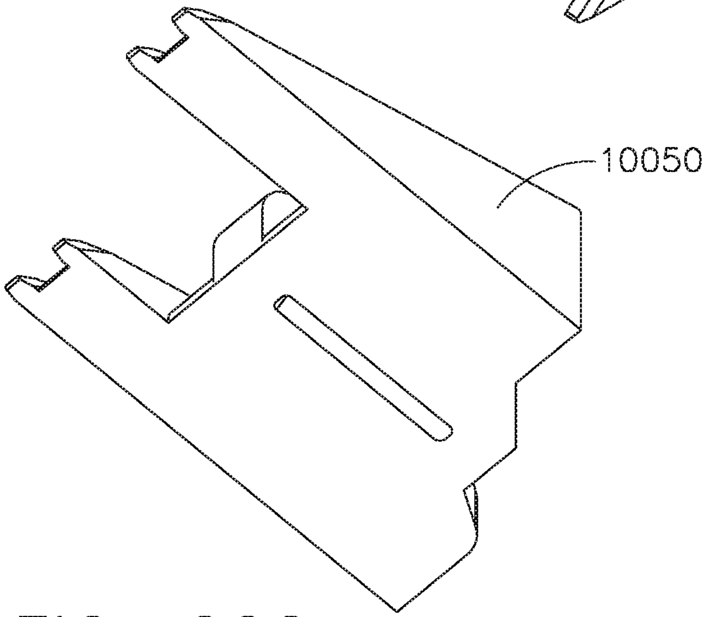
Figure 223:
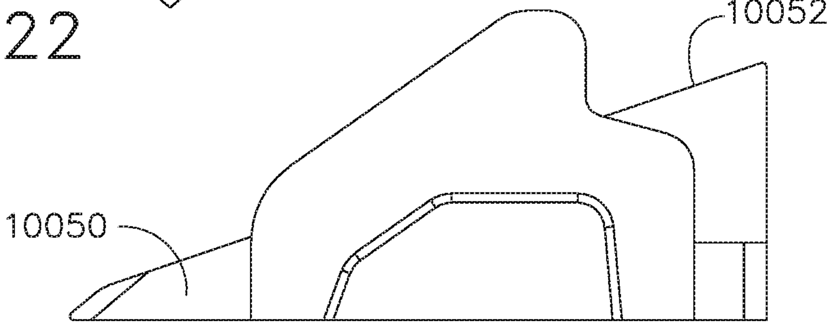
Figure 224:
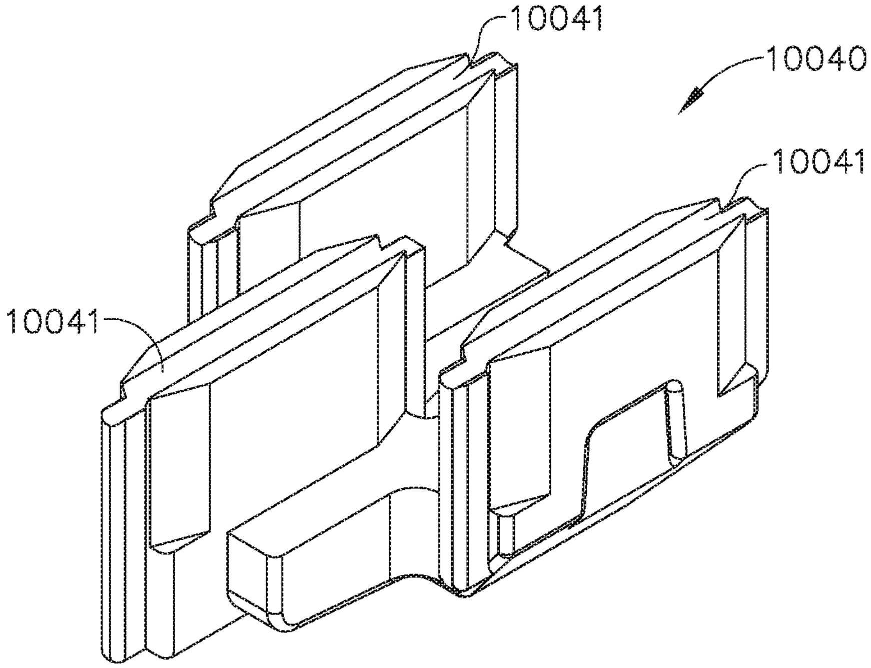
Figure 225:
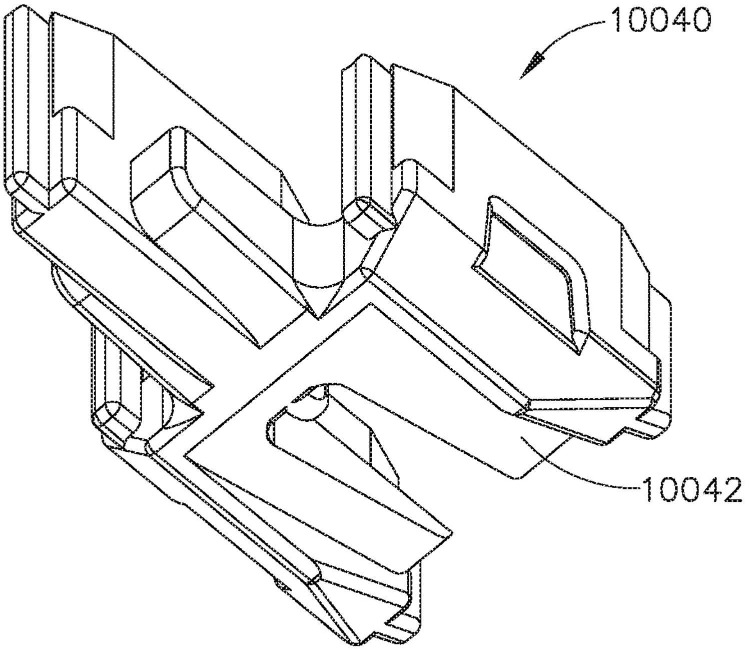
Figure 226:
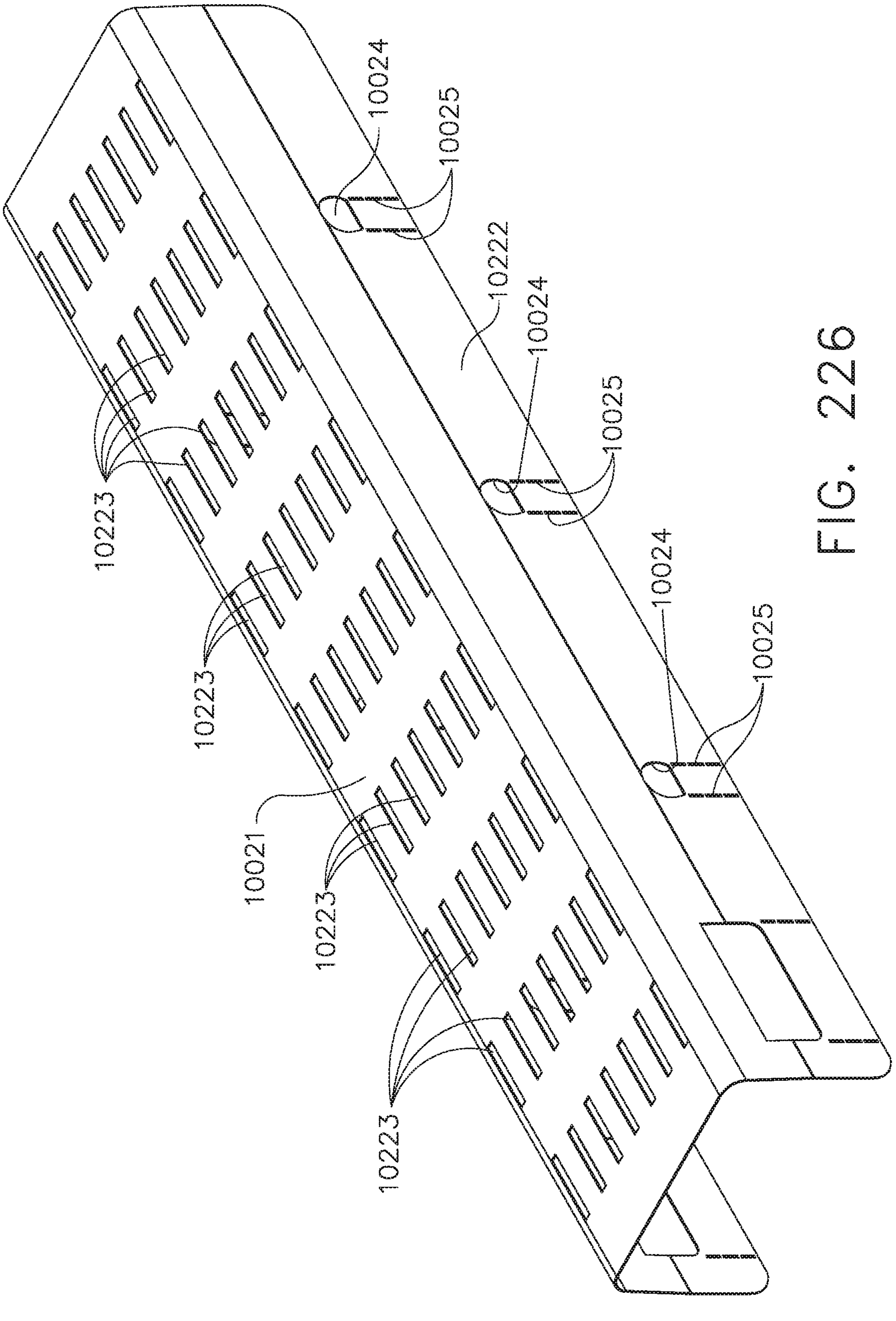
Figure 227:
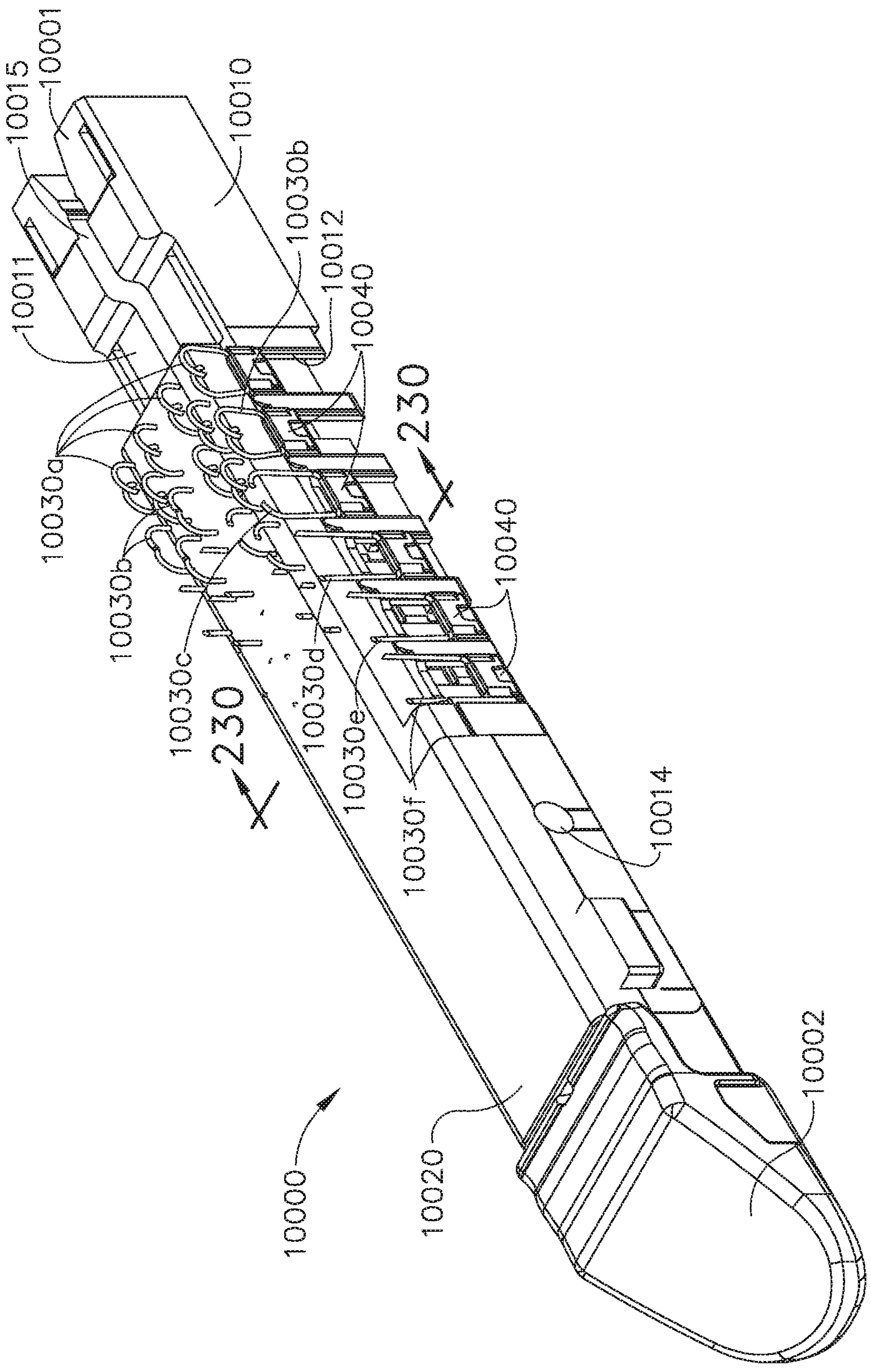
Figure 228:
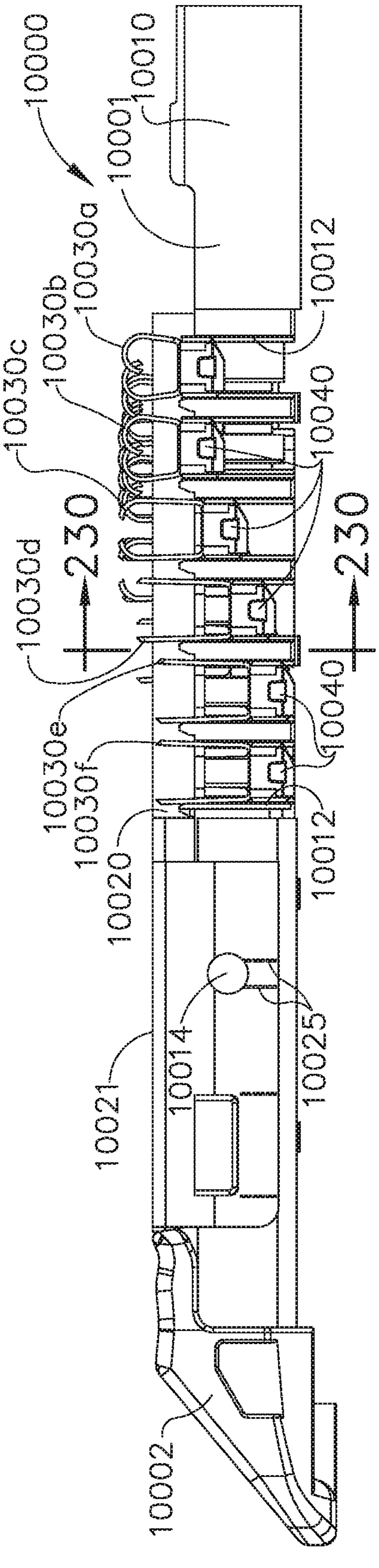
Figure 229:
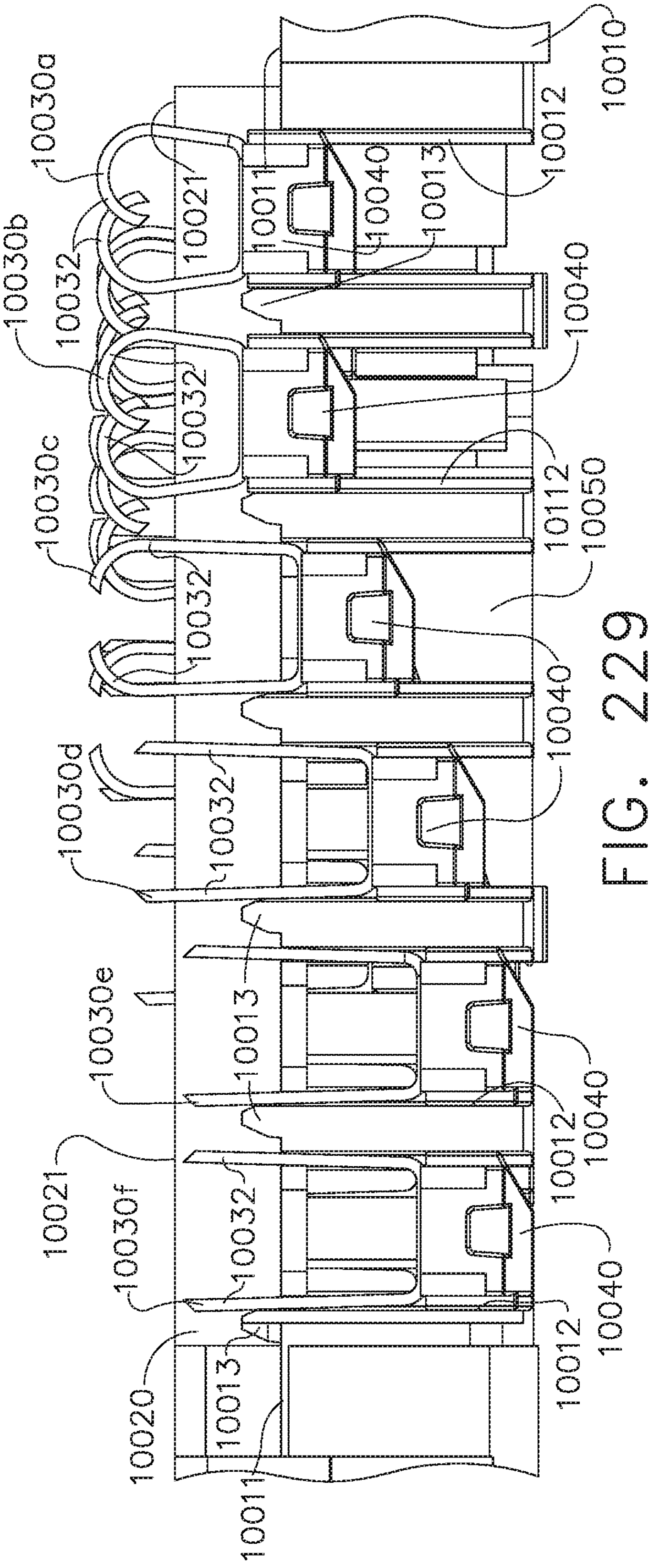
Figure 230:
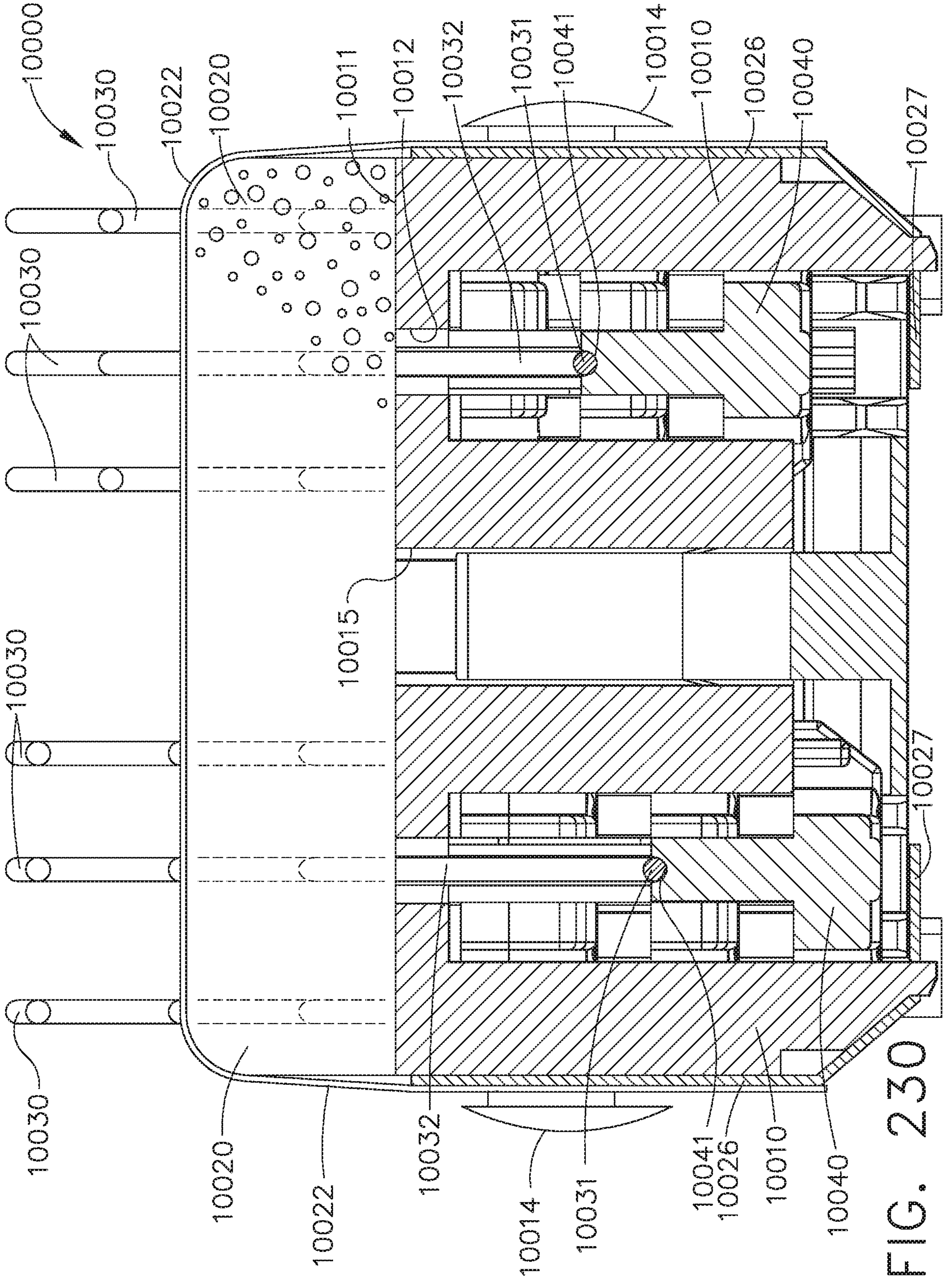
Figure 231:
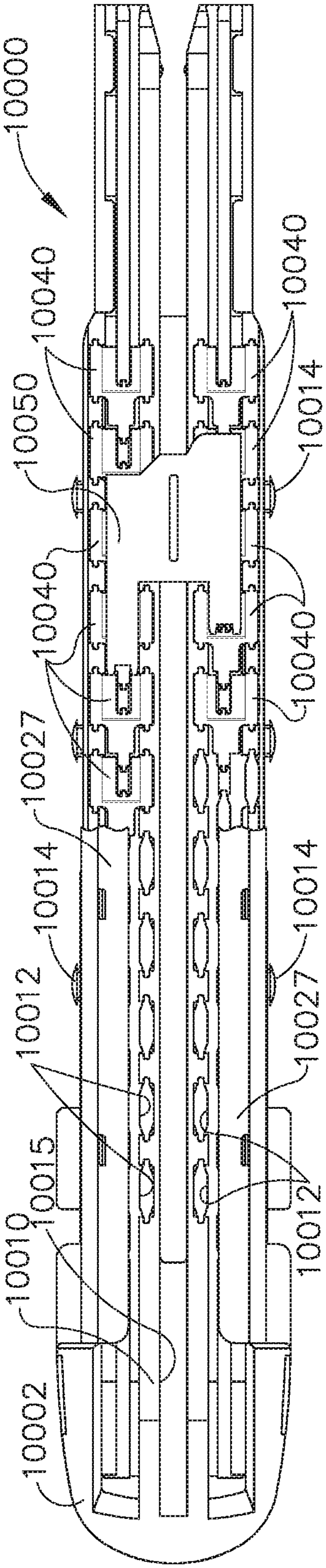
Figure 232:
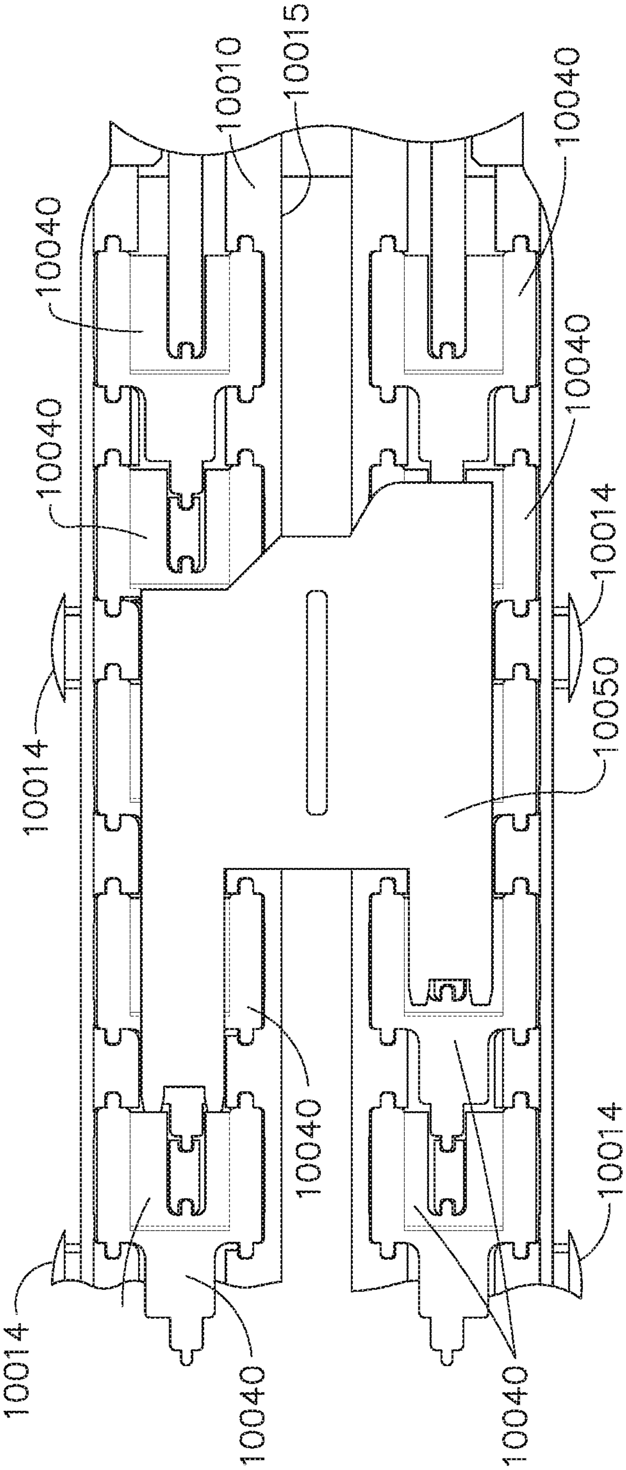
Figure 233:
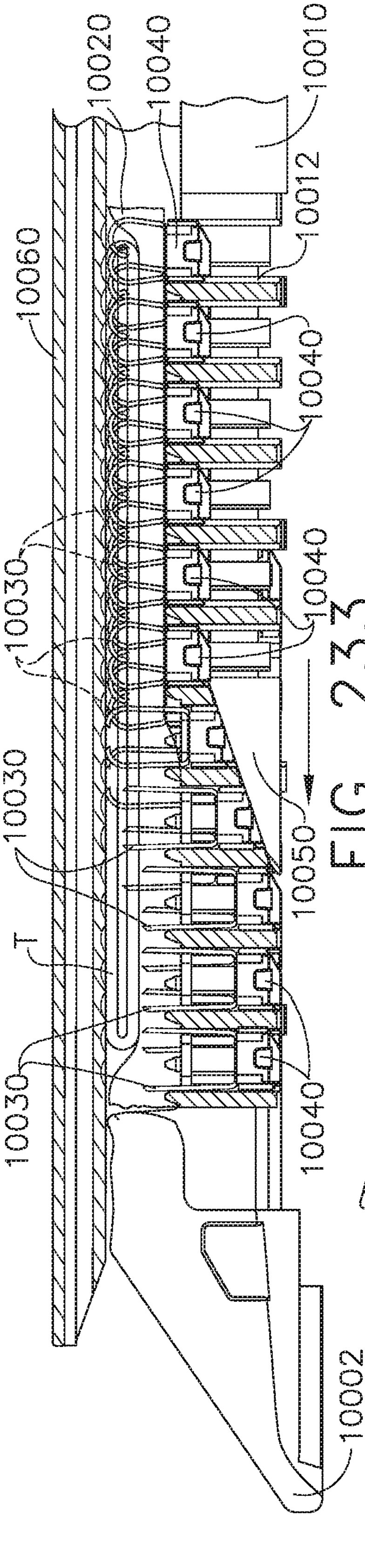
Figure 234:
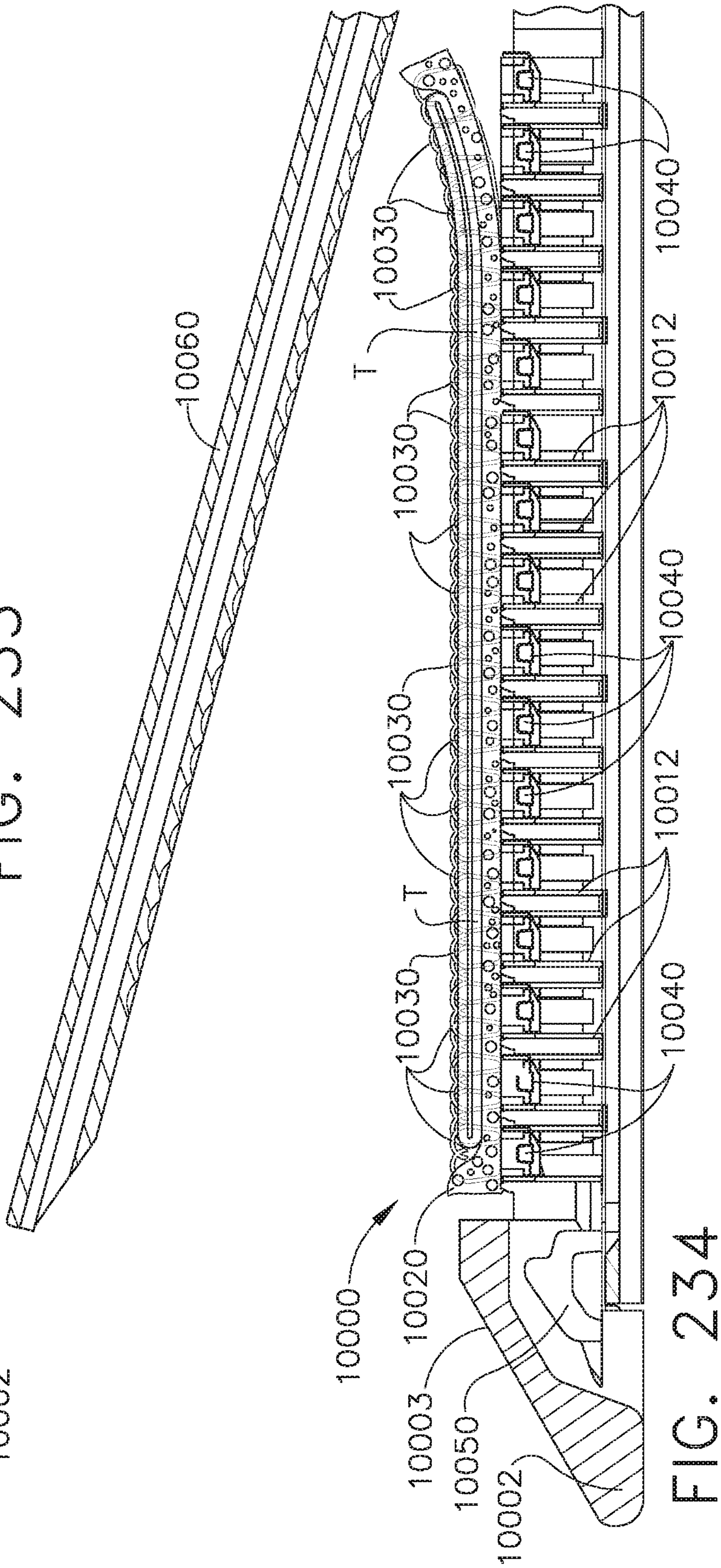
Figure 235:
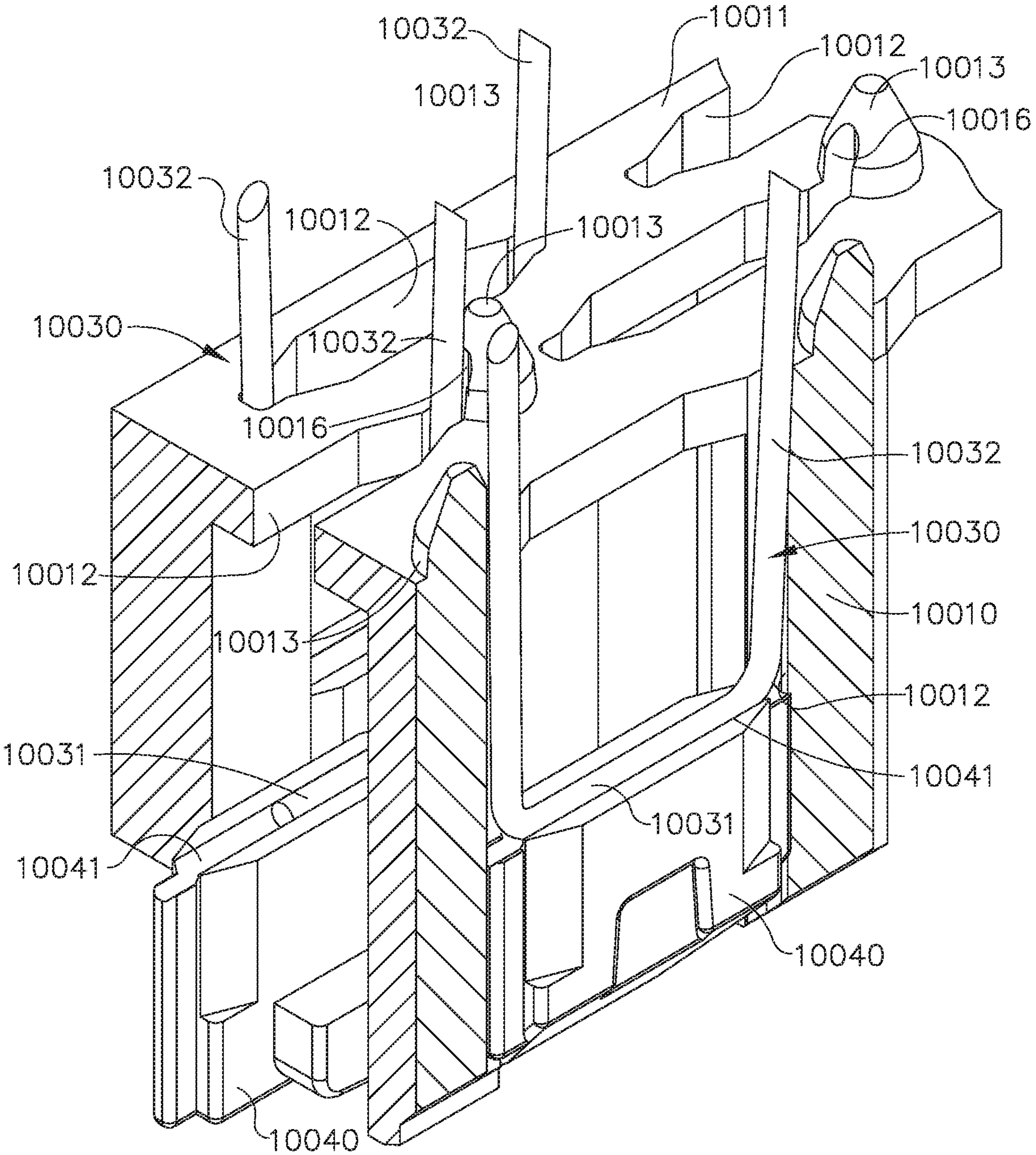
Figure 236:
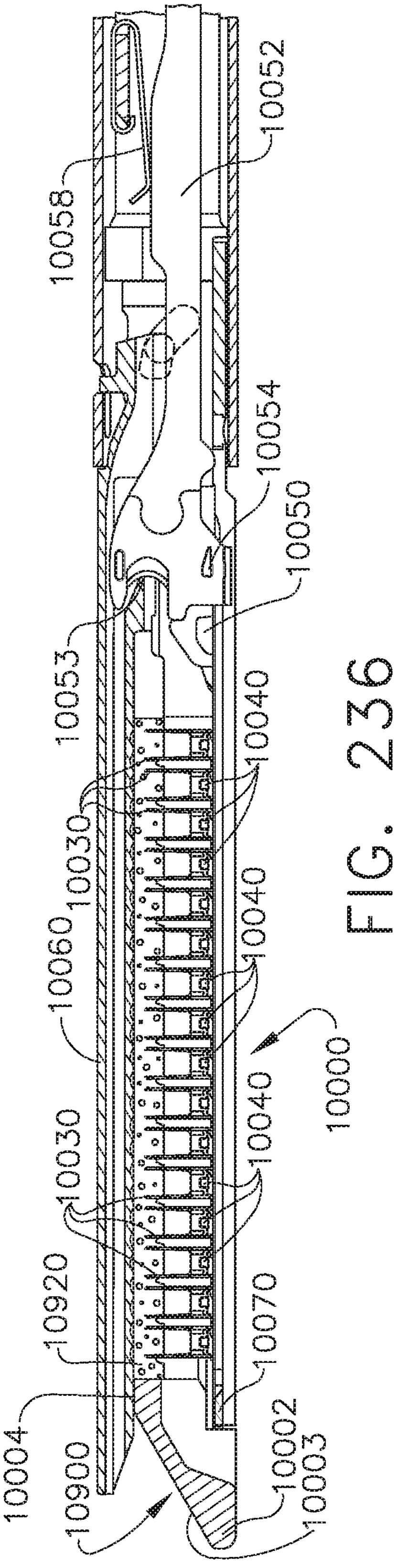
Figure 237:
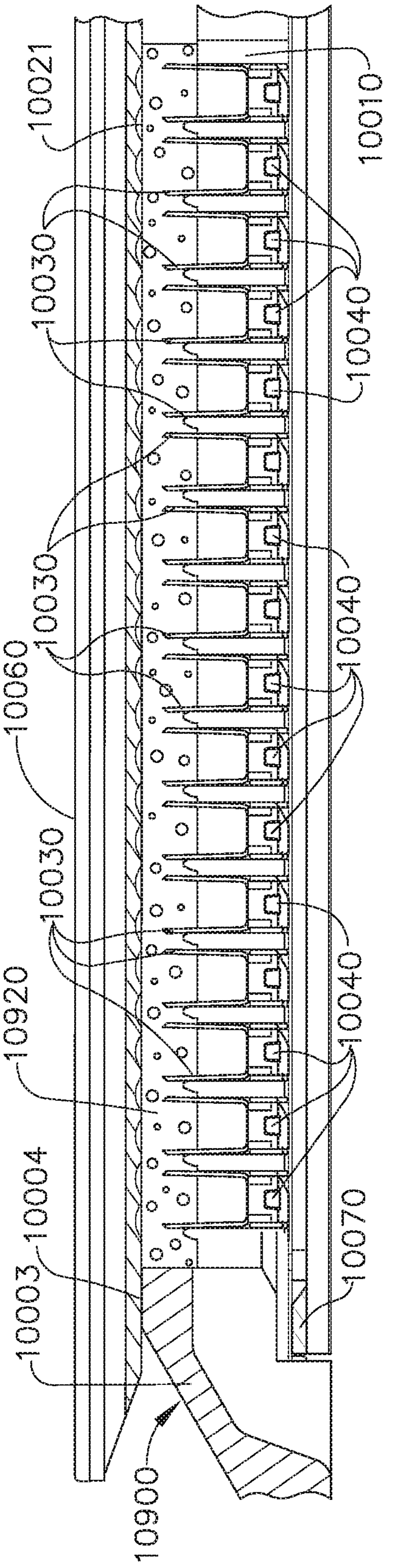
Figure 238:
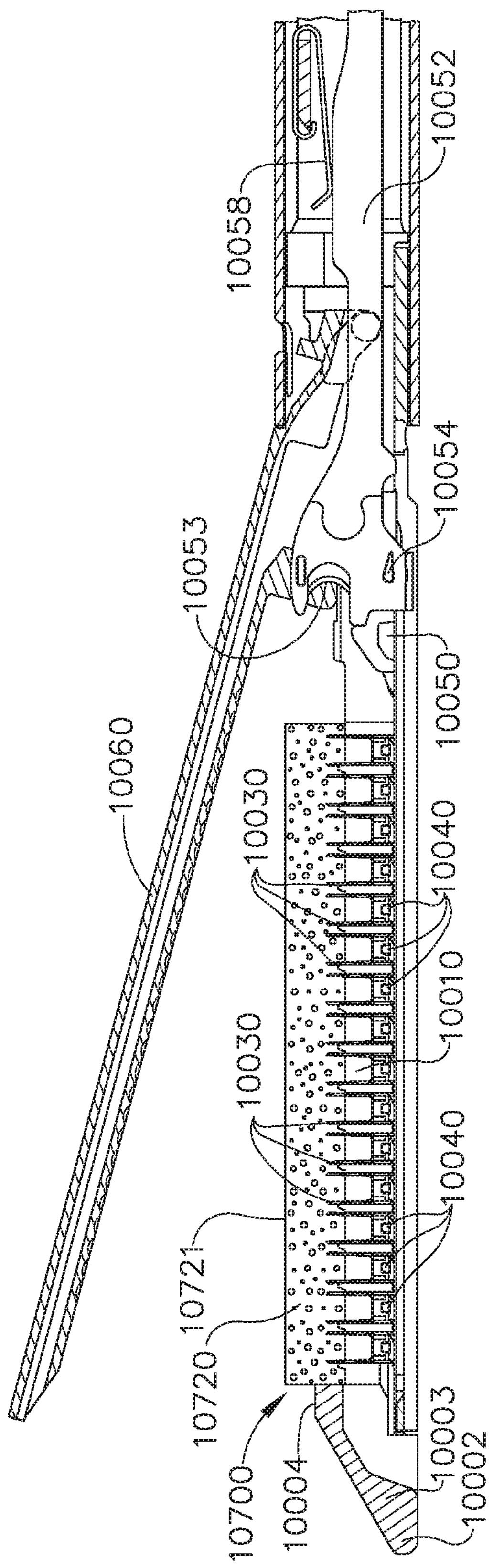
Figure 239:
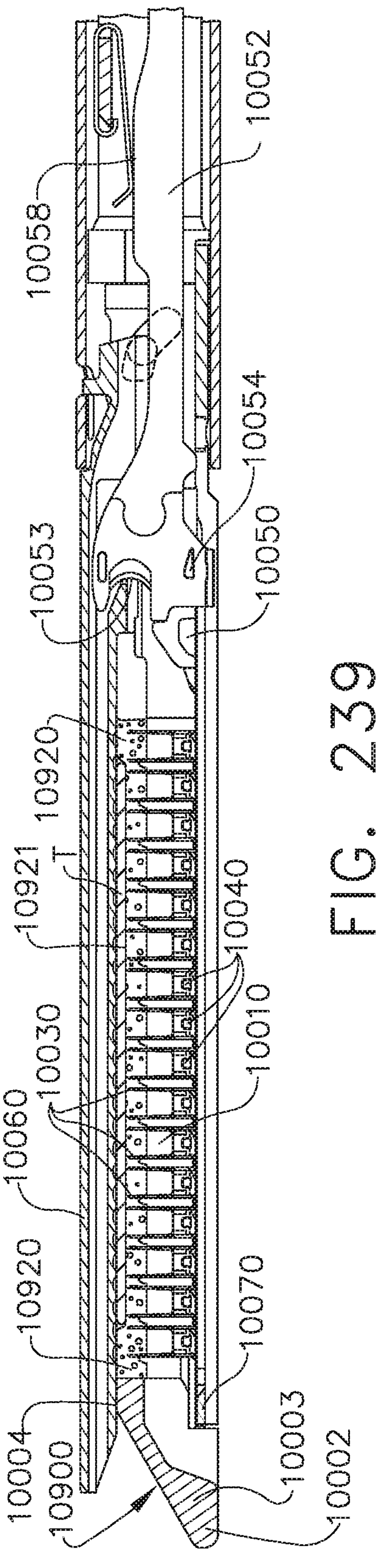
Figure 240:
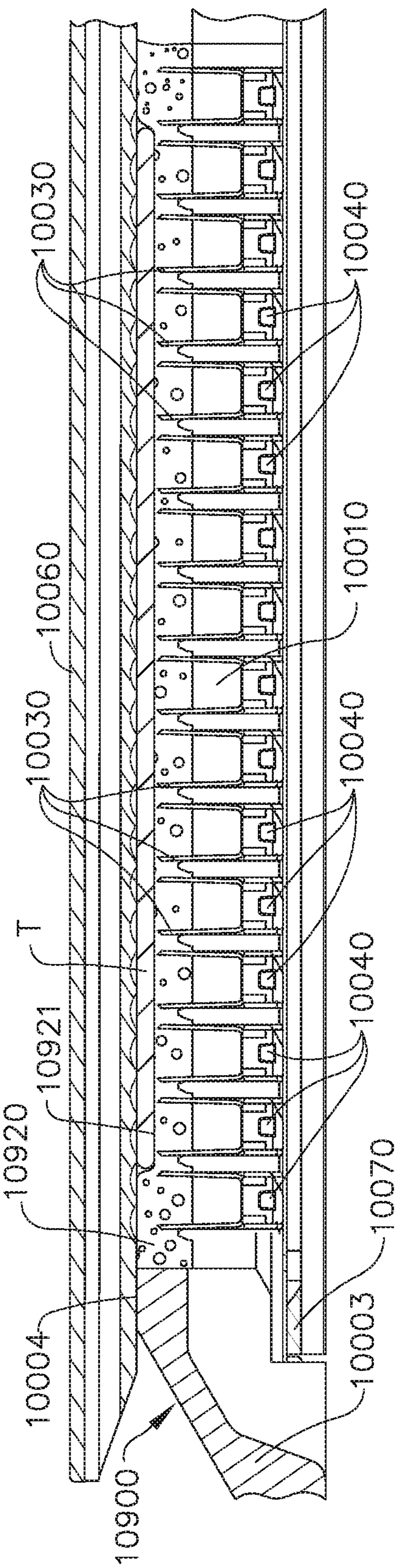
Figure 241:
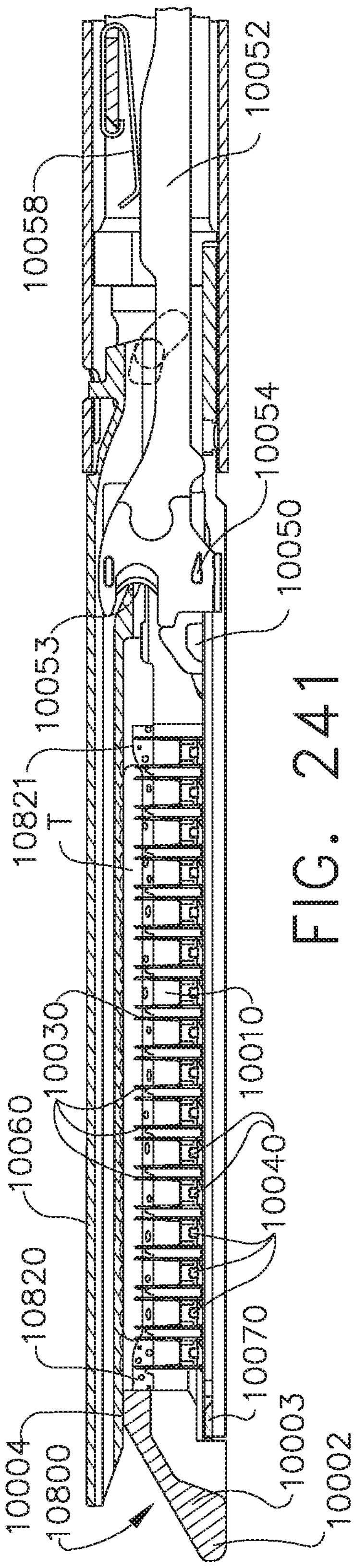
Figure 242:
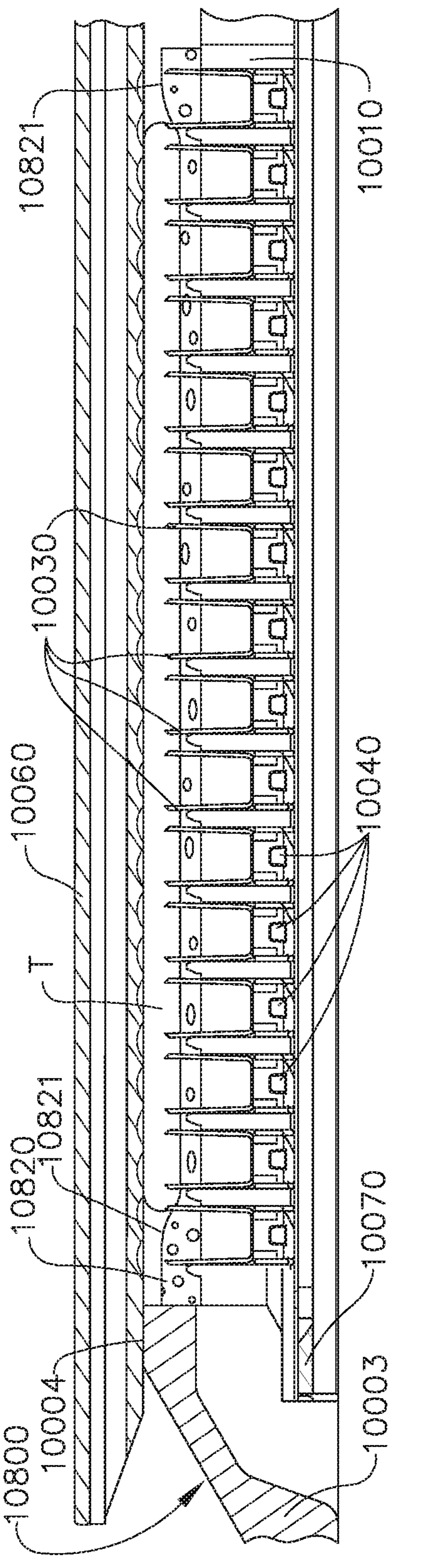
Figure 243:
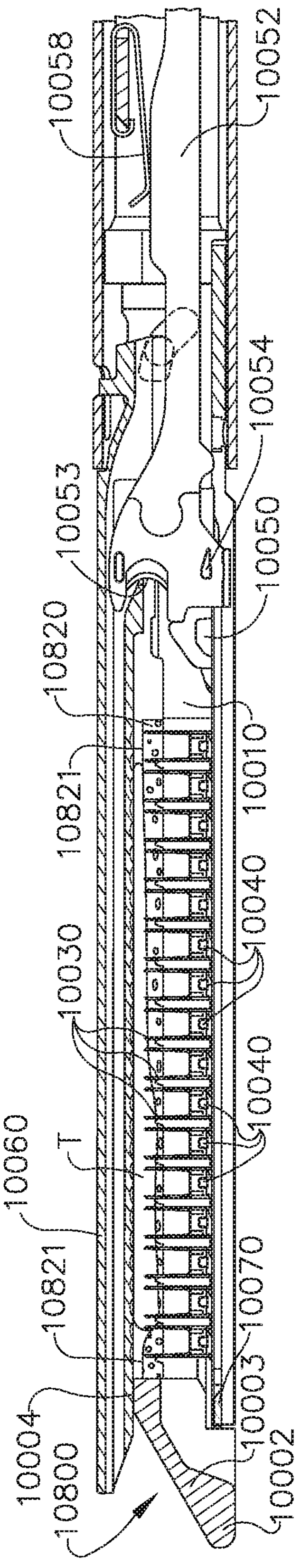
Figure 244:
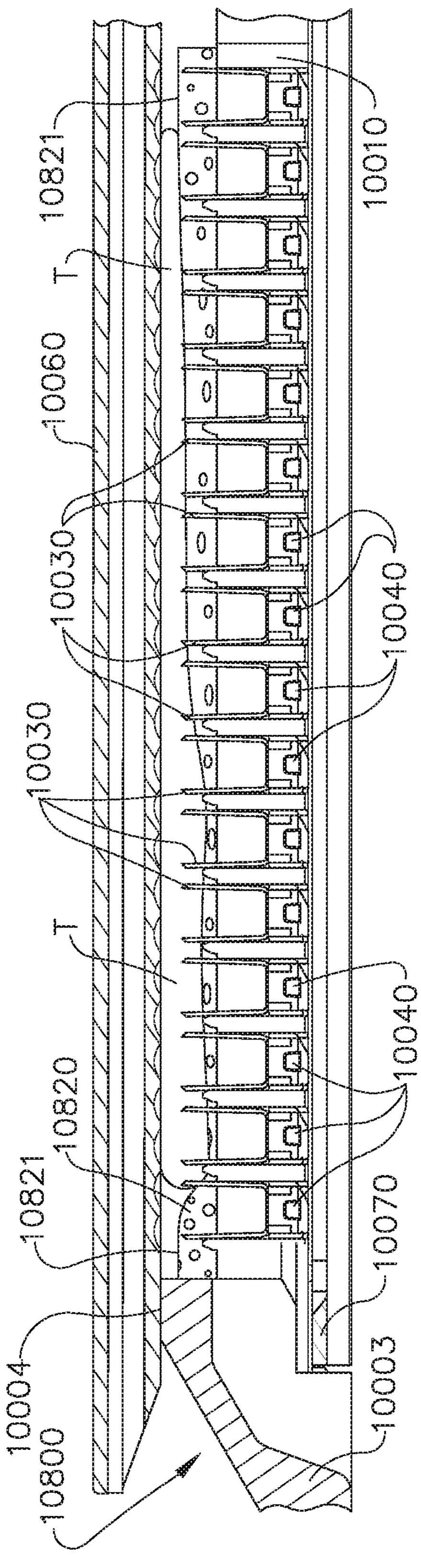
Figure 245:
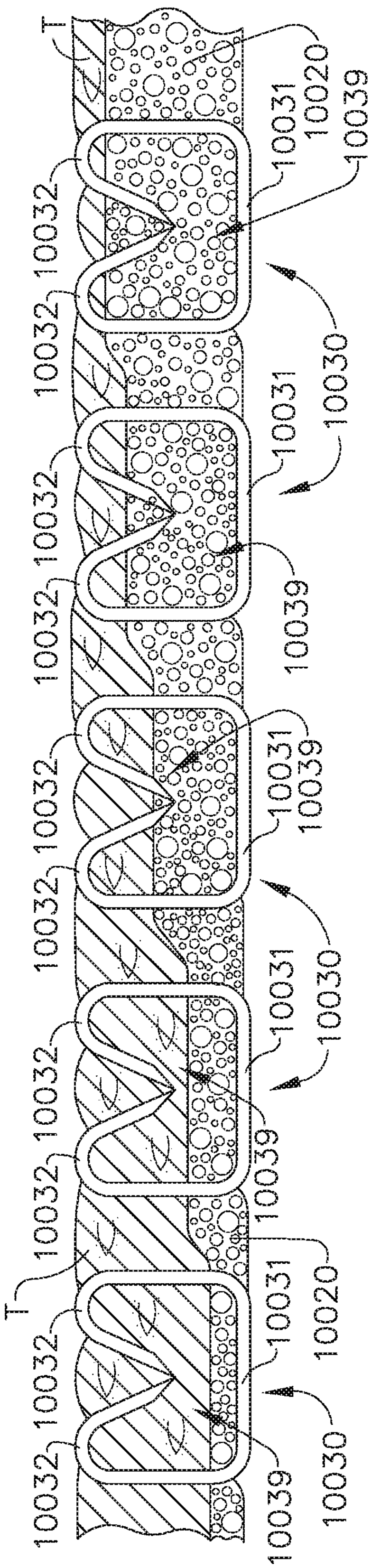
Figure 246:
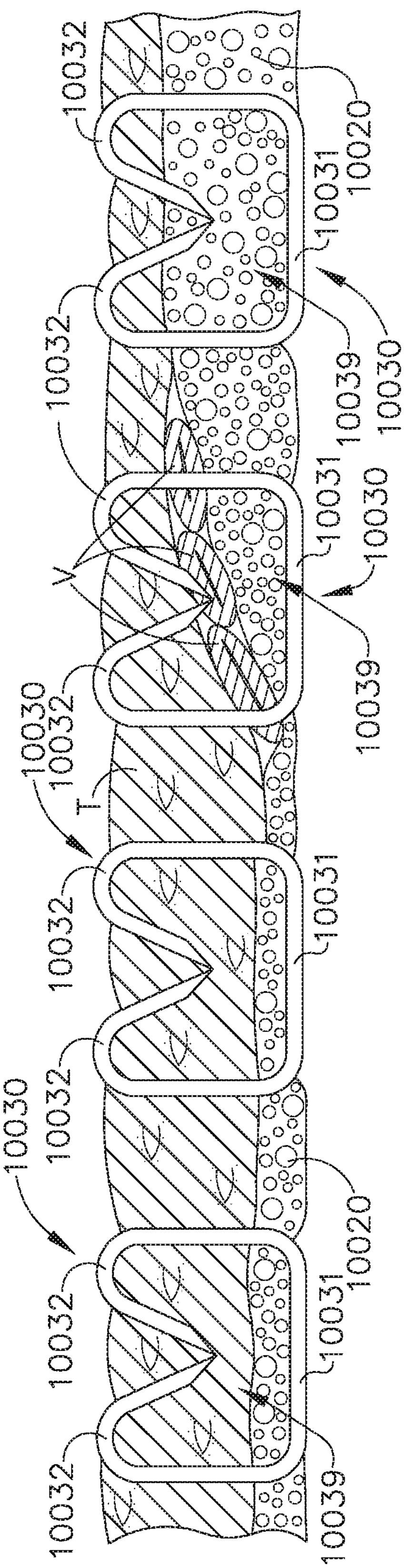
Figure 247:
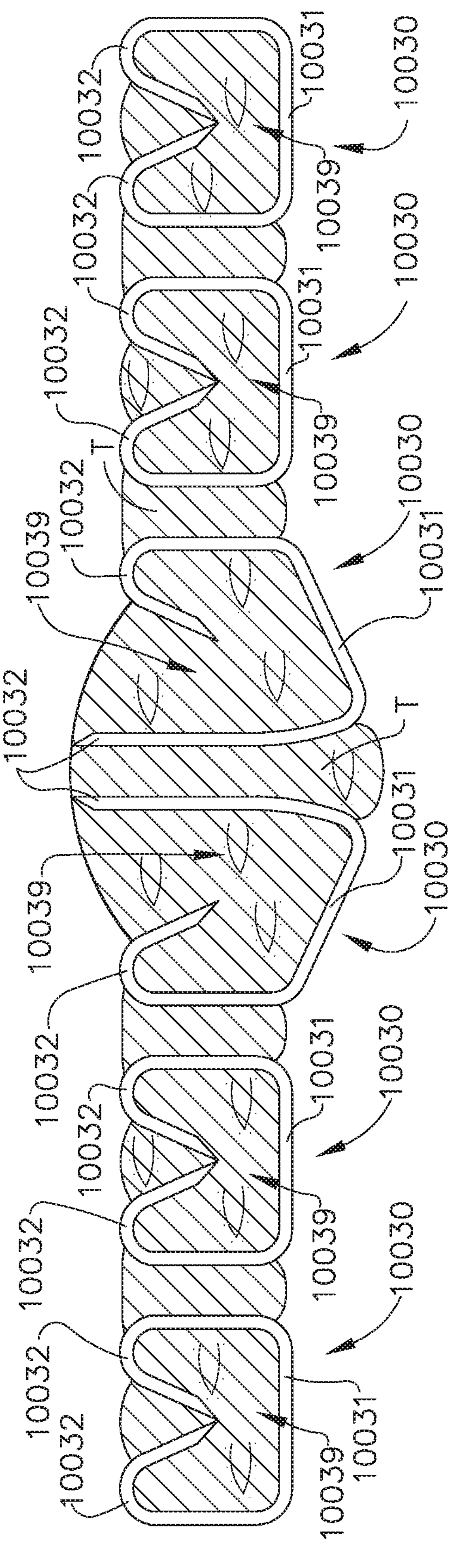
Figure 248:
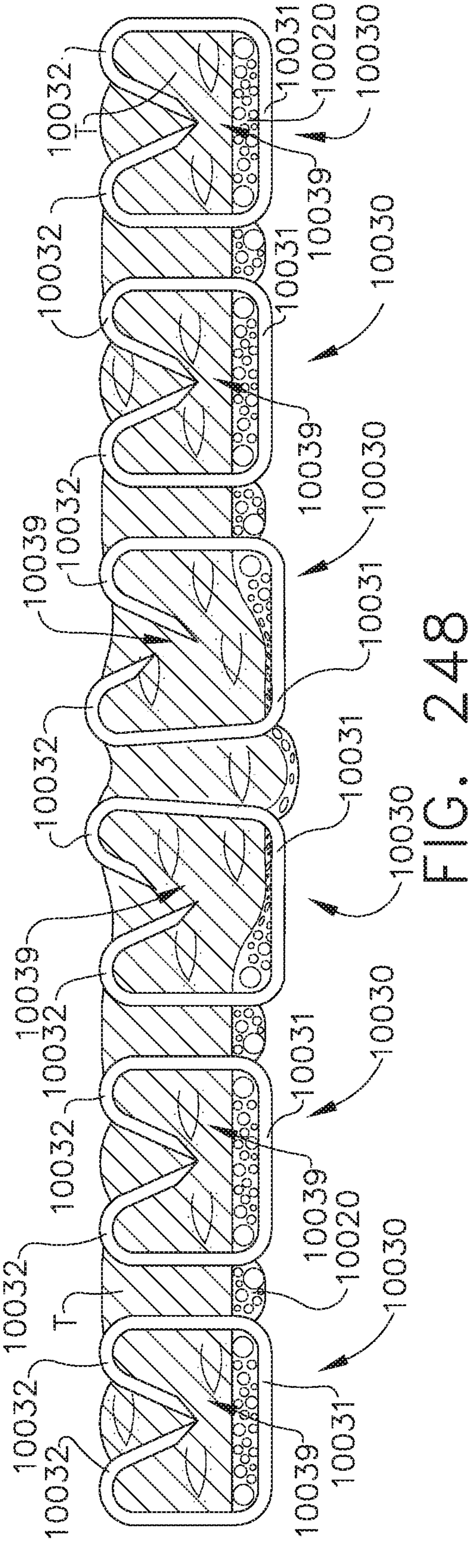
Figure 249:
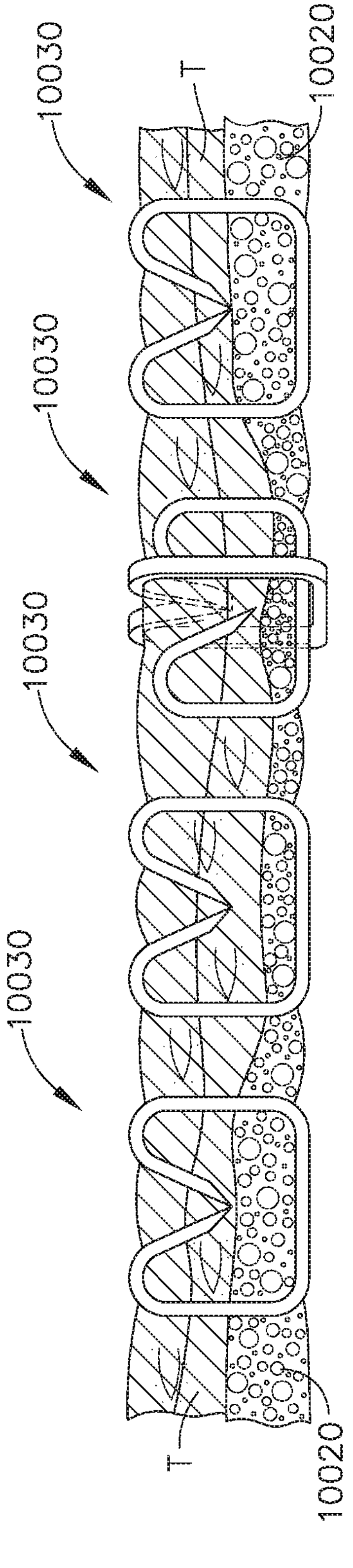
Figure 251:
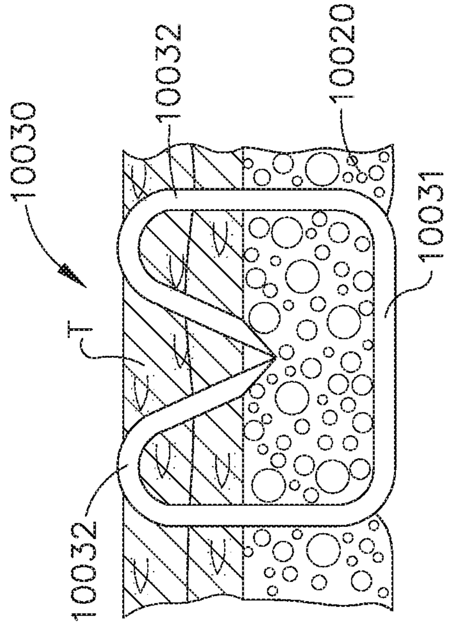
Figure 250:
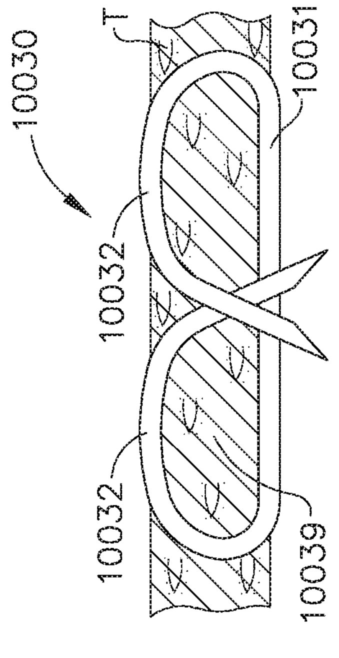
Figure 253:
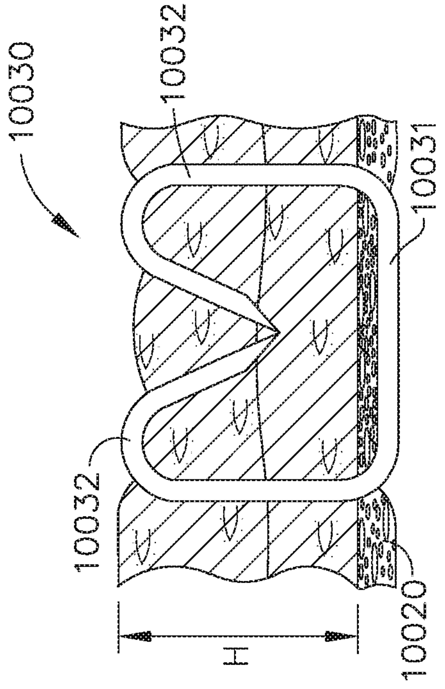
Figure 252:
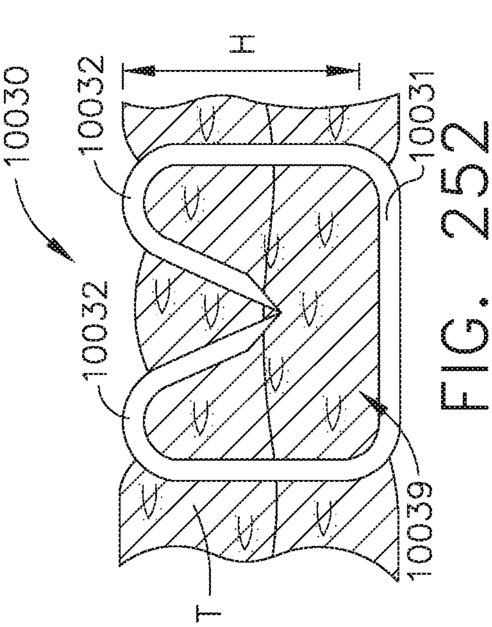
Figure 255:
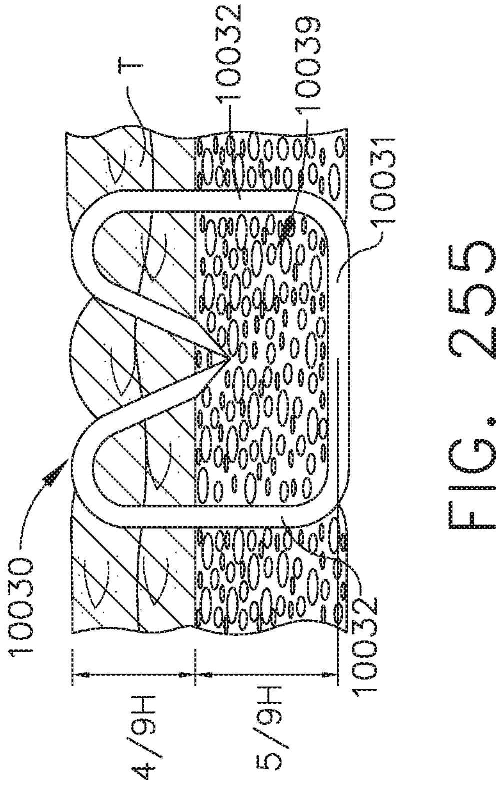
Figure 254:
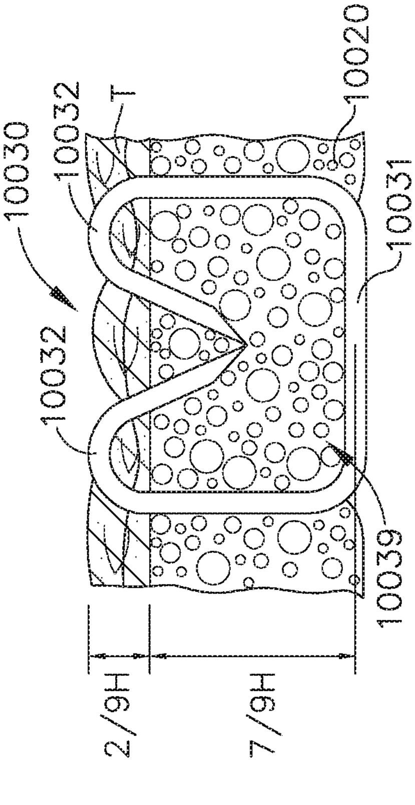
Figure 257:
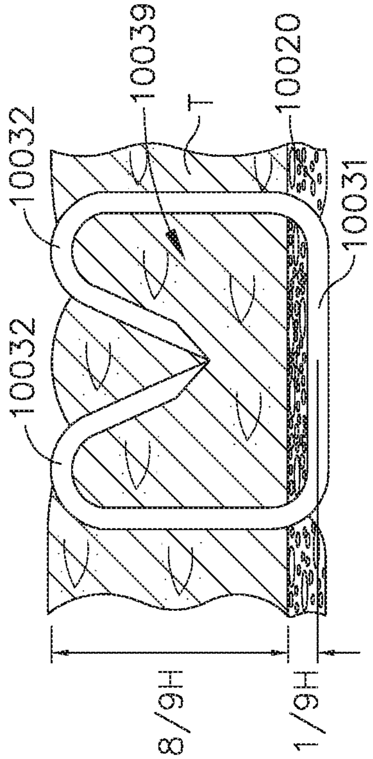
Figure 256:
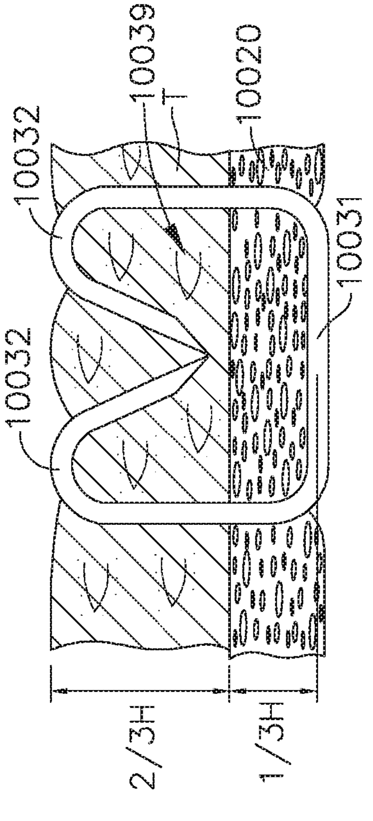
Figure 258:
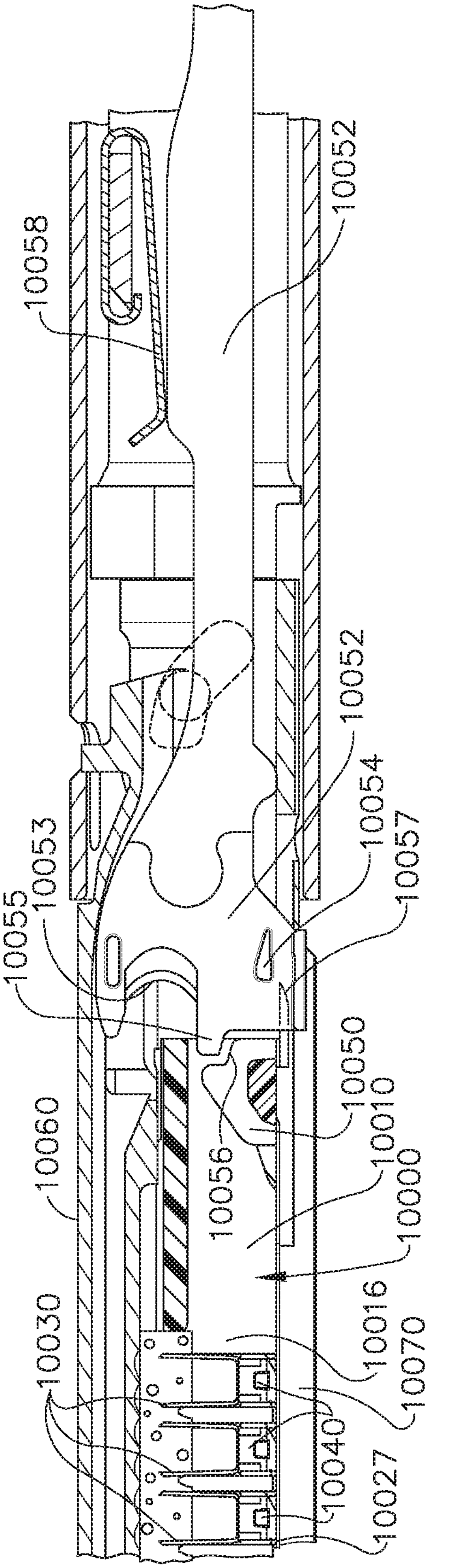
Figure 259:
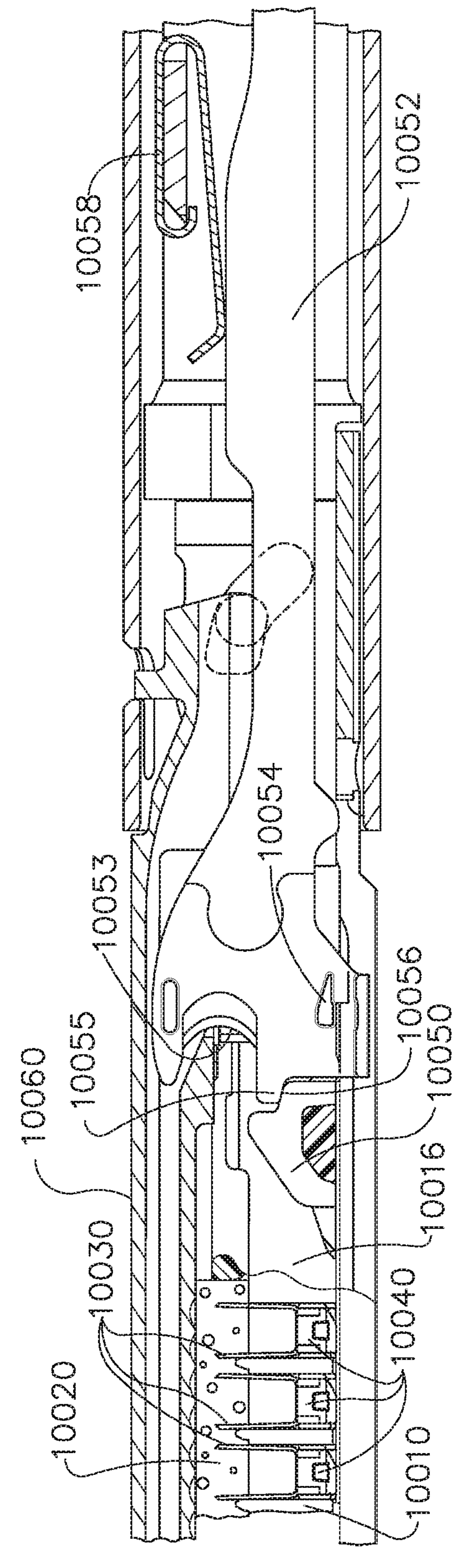
Figure 260:
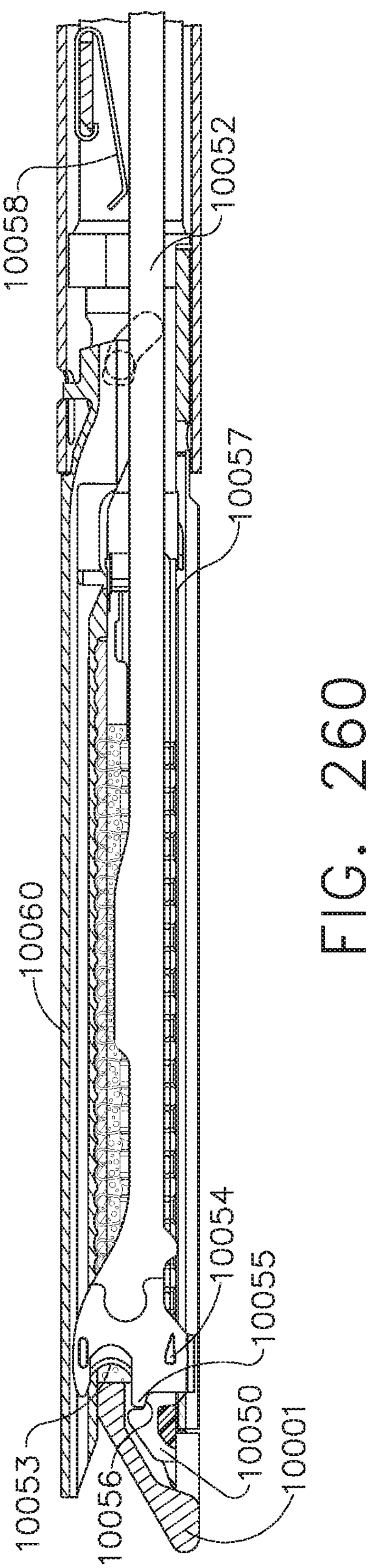
Figure 261:
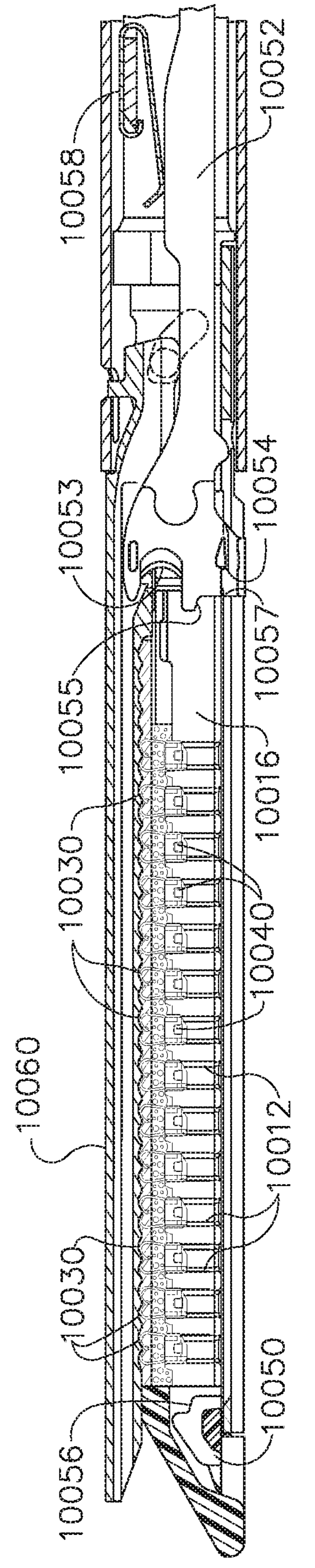
Figure 262:
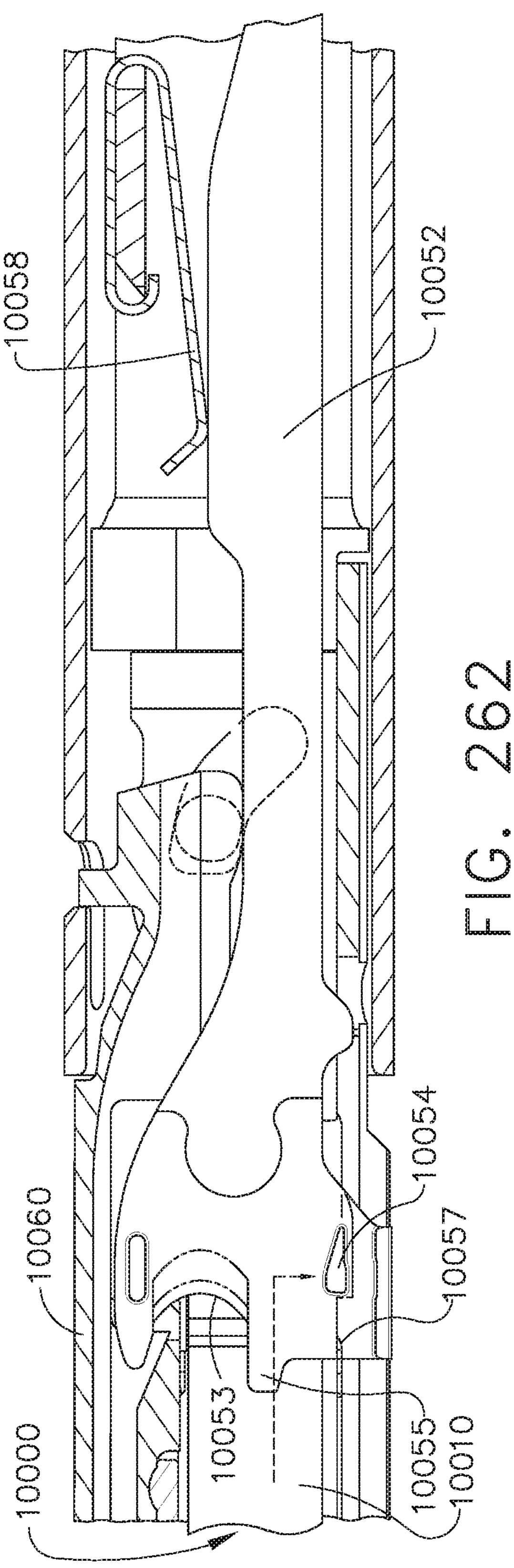
Figure 263:
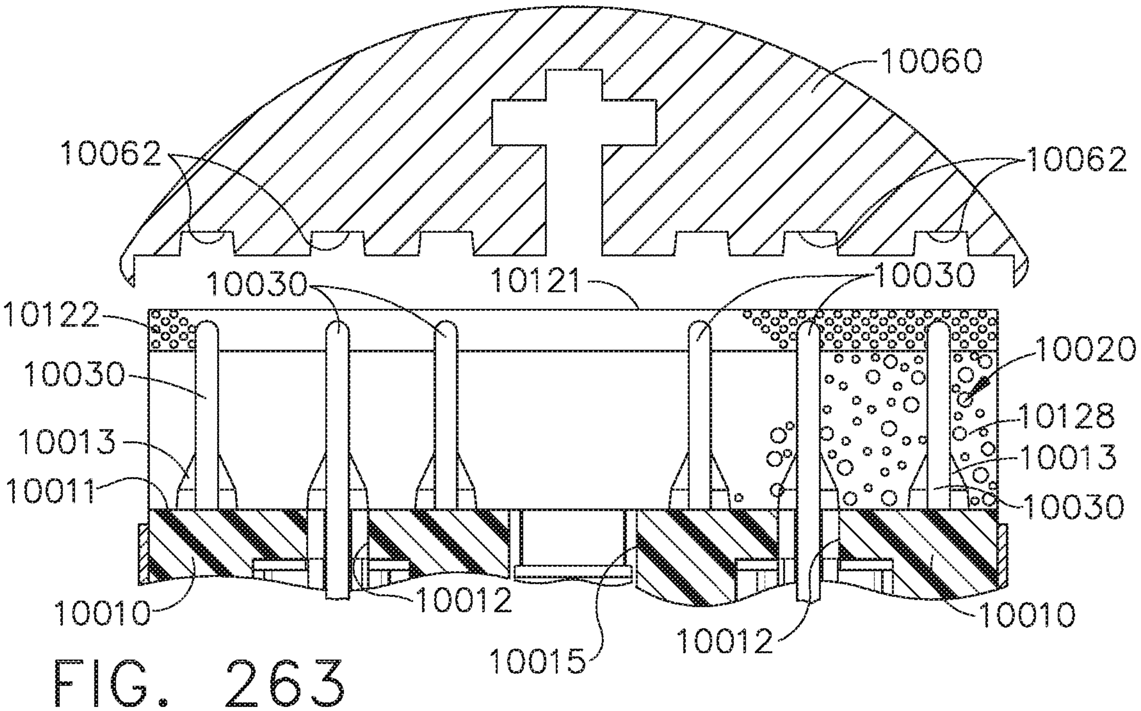
Figure 264:
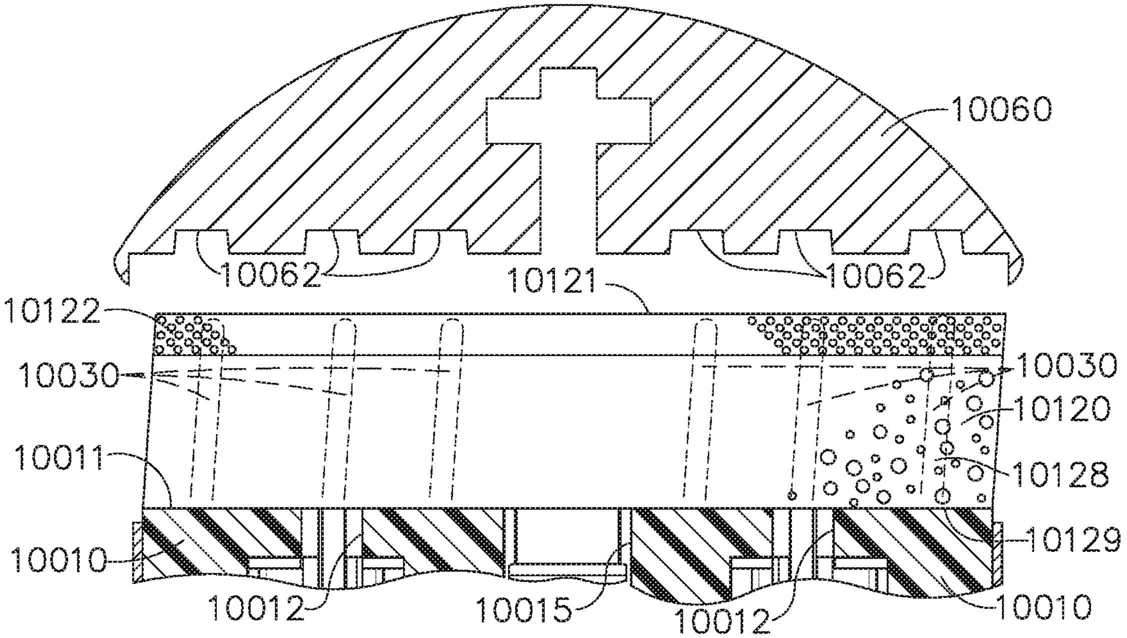
Figure 265:
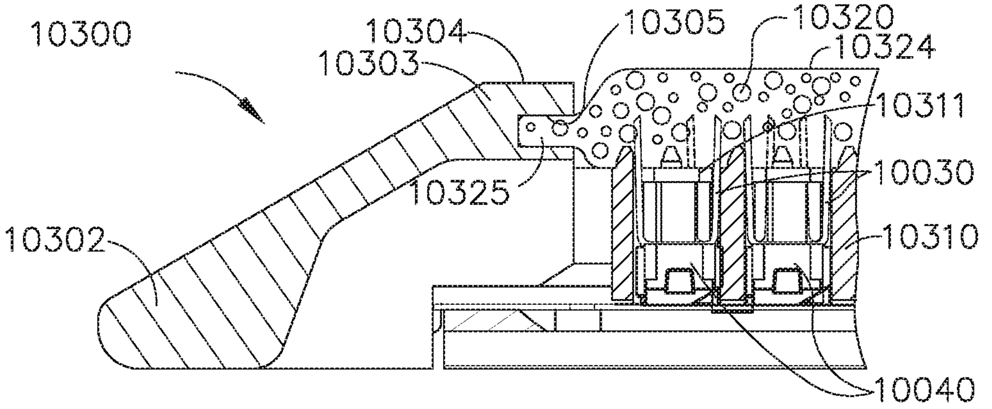
Figure 266:
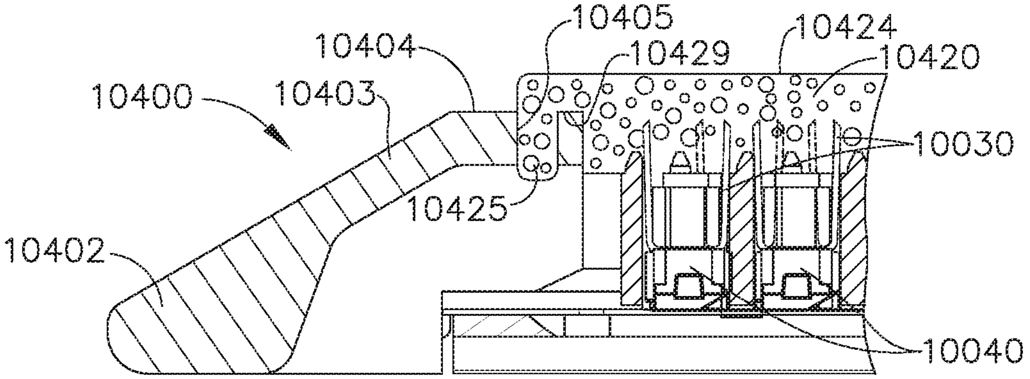
Figure 267:
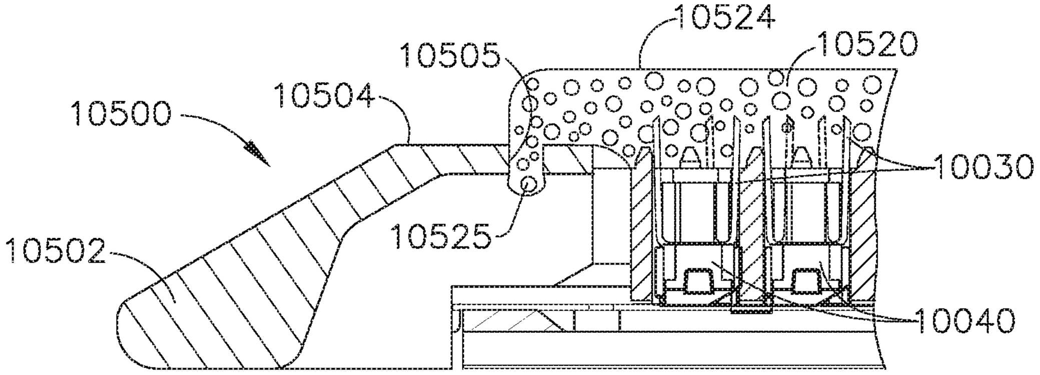
Figure 268:
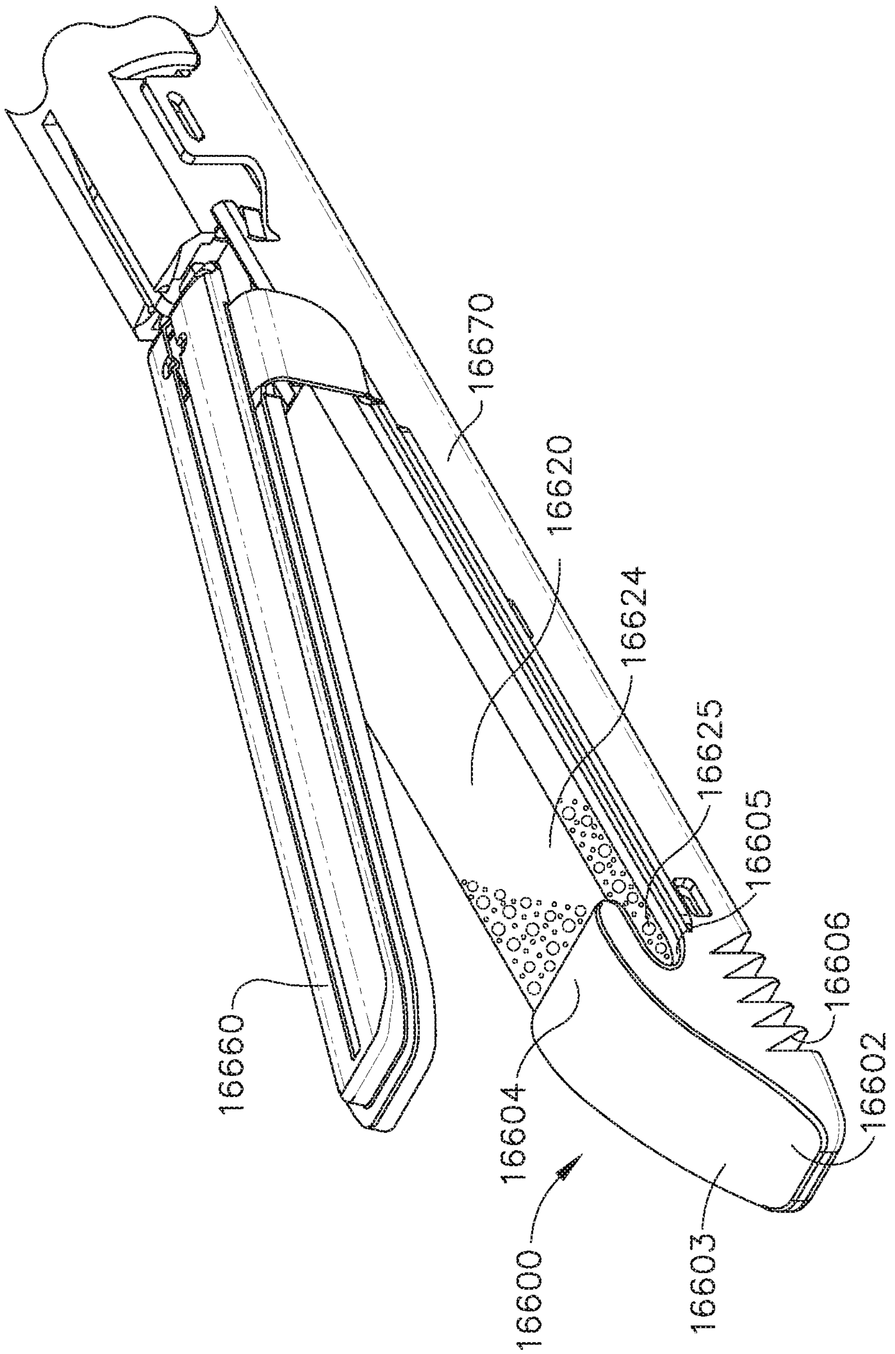
Figure 269:
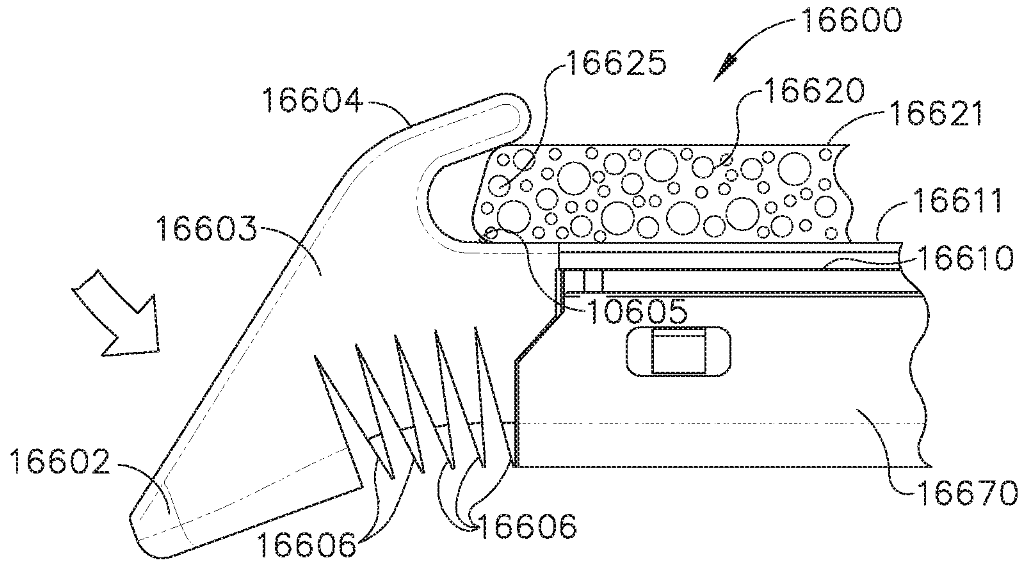
Figure 270:
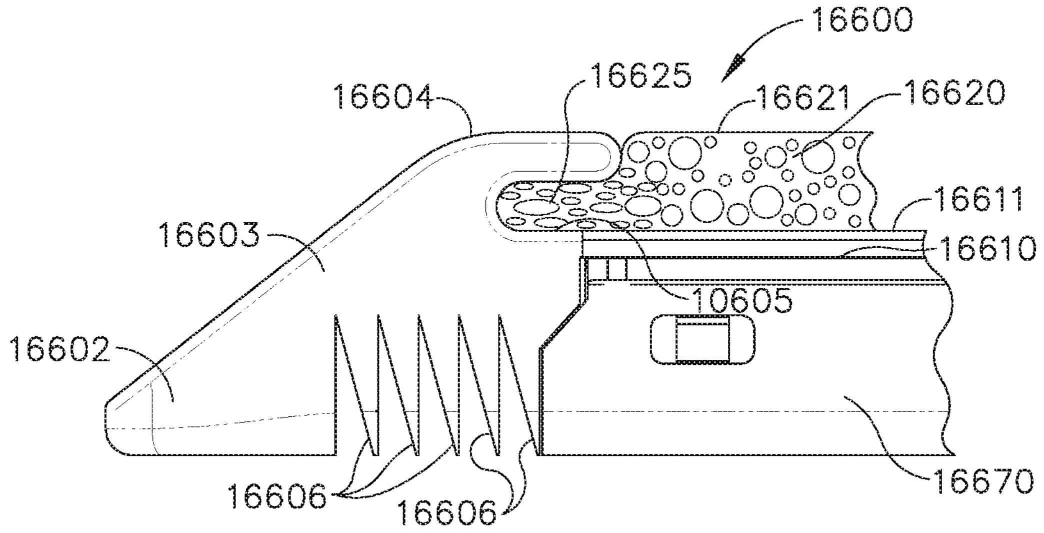
Figures 271, 272:
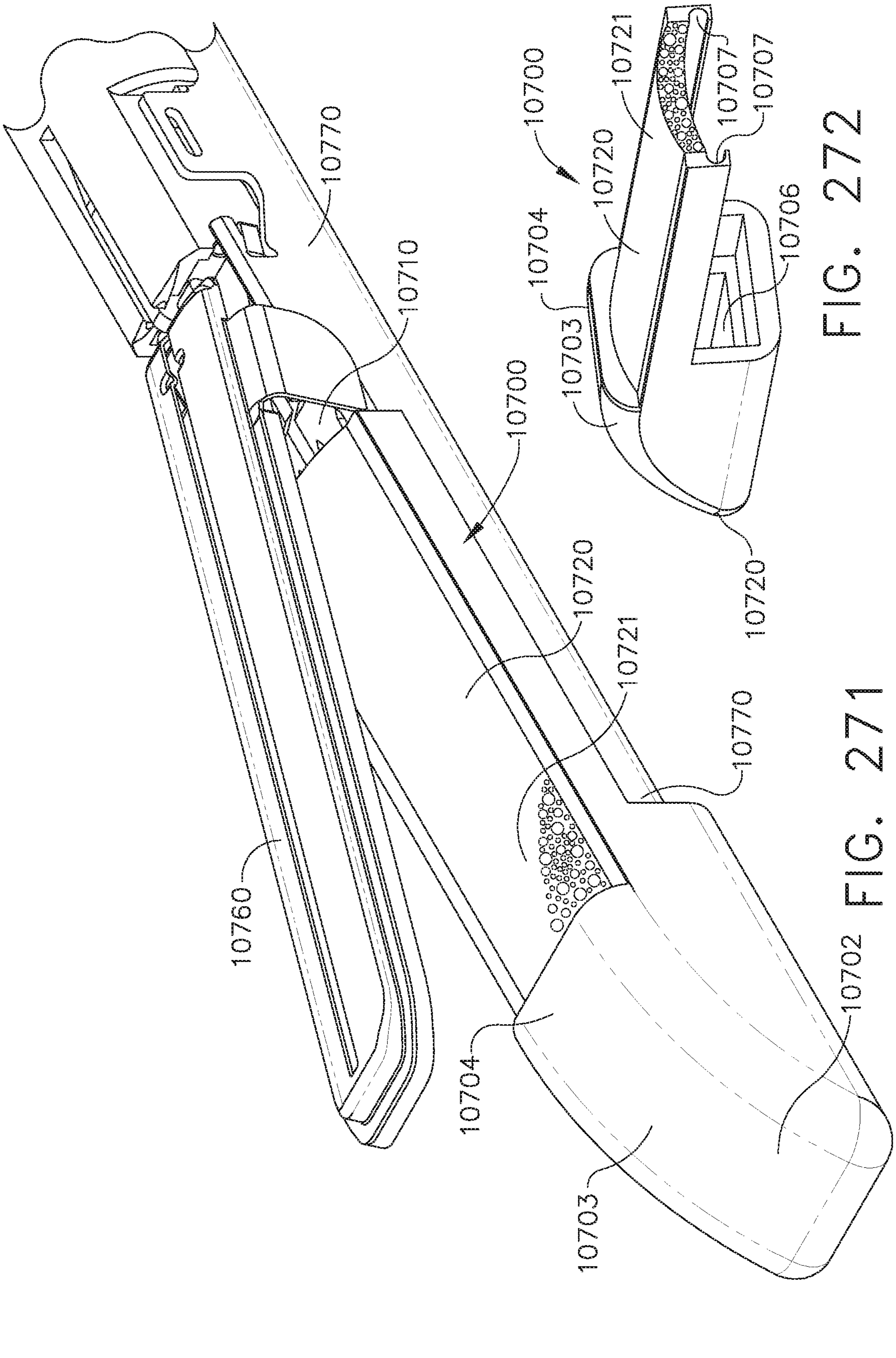
Figure 275:
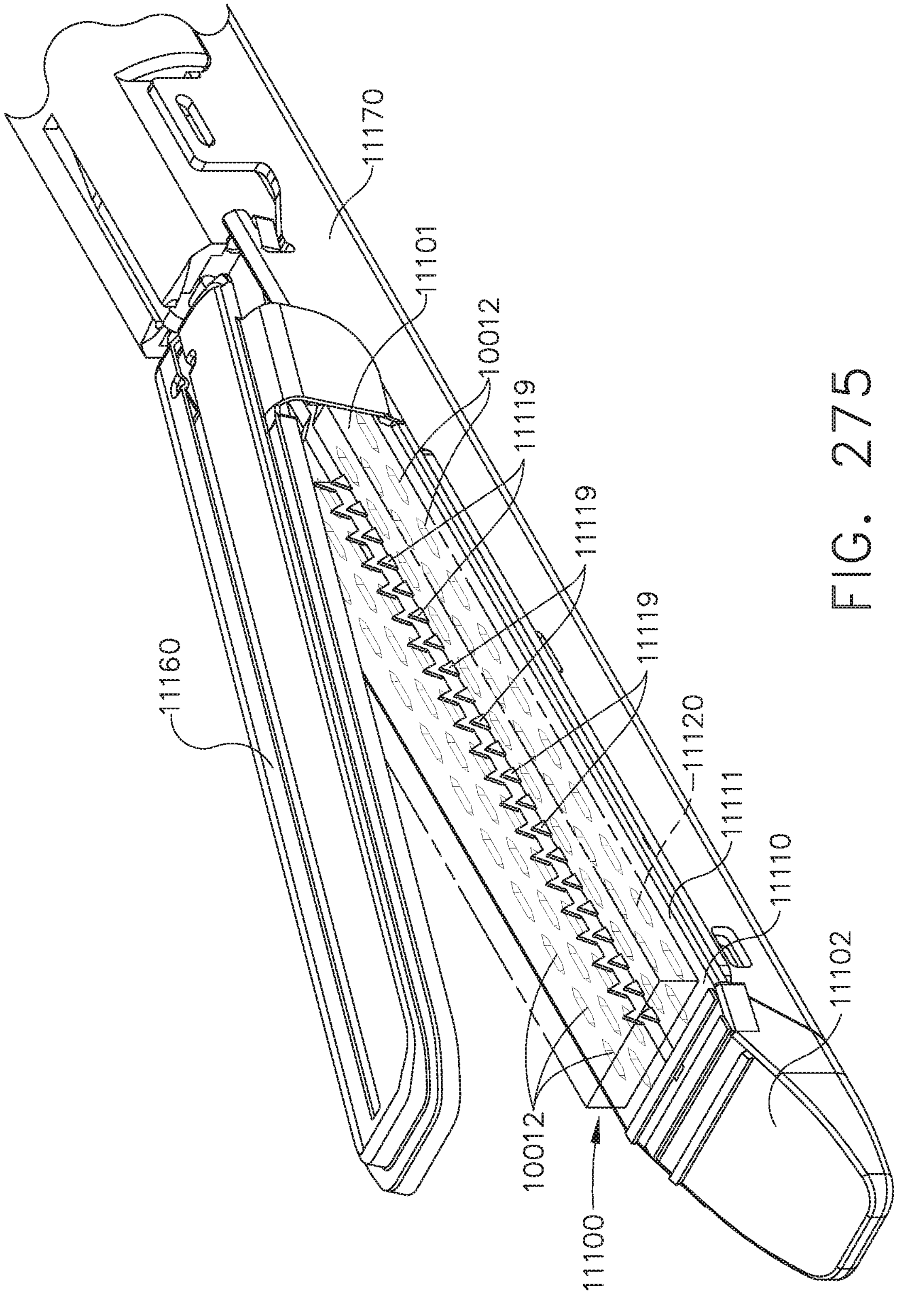
Figure 276:
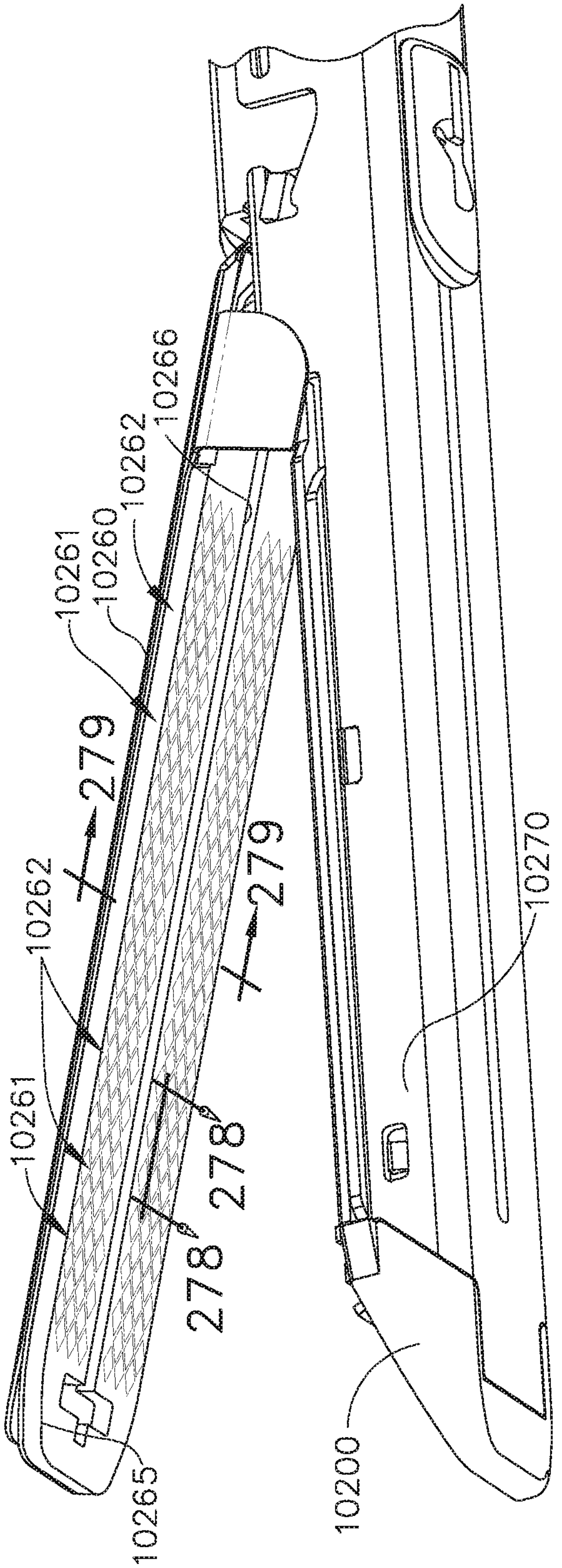
Figure 277:
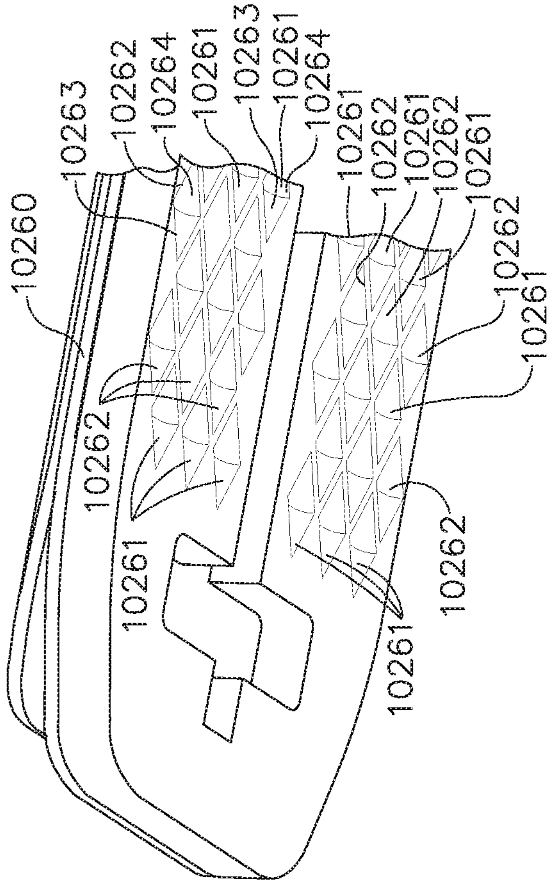
Figure 279:
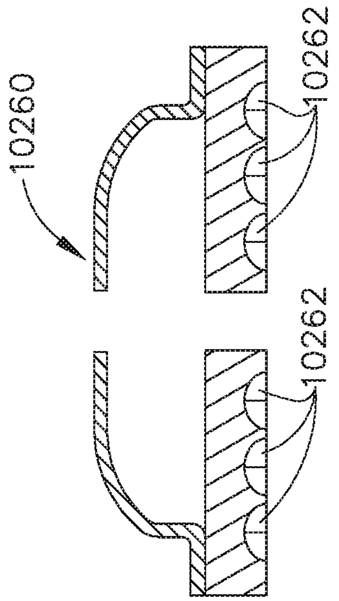
Figure 278:
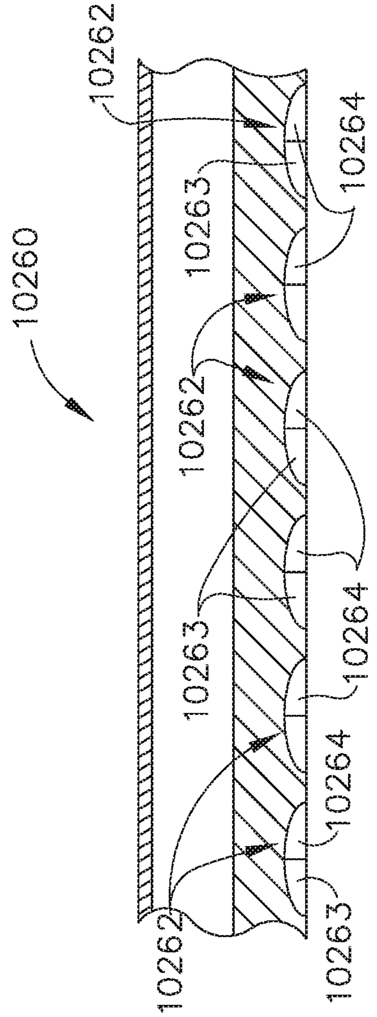
Figure 282:
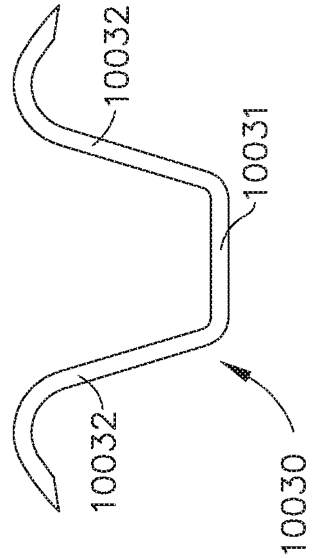
Figure 281:
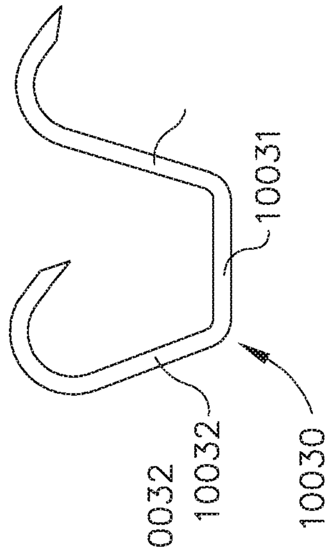
Figure 280:
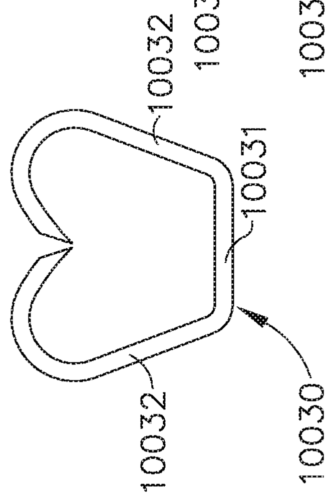
Figure 283:
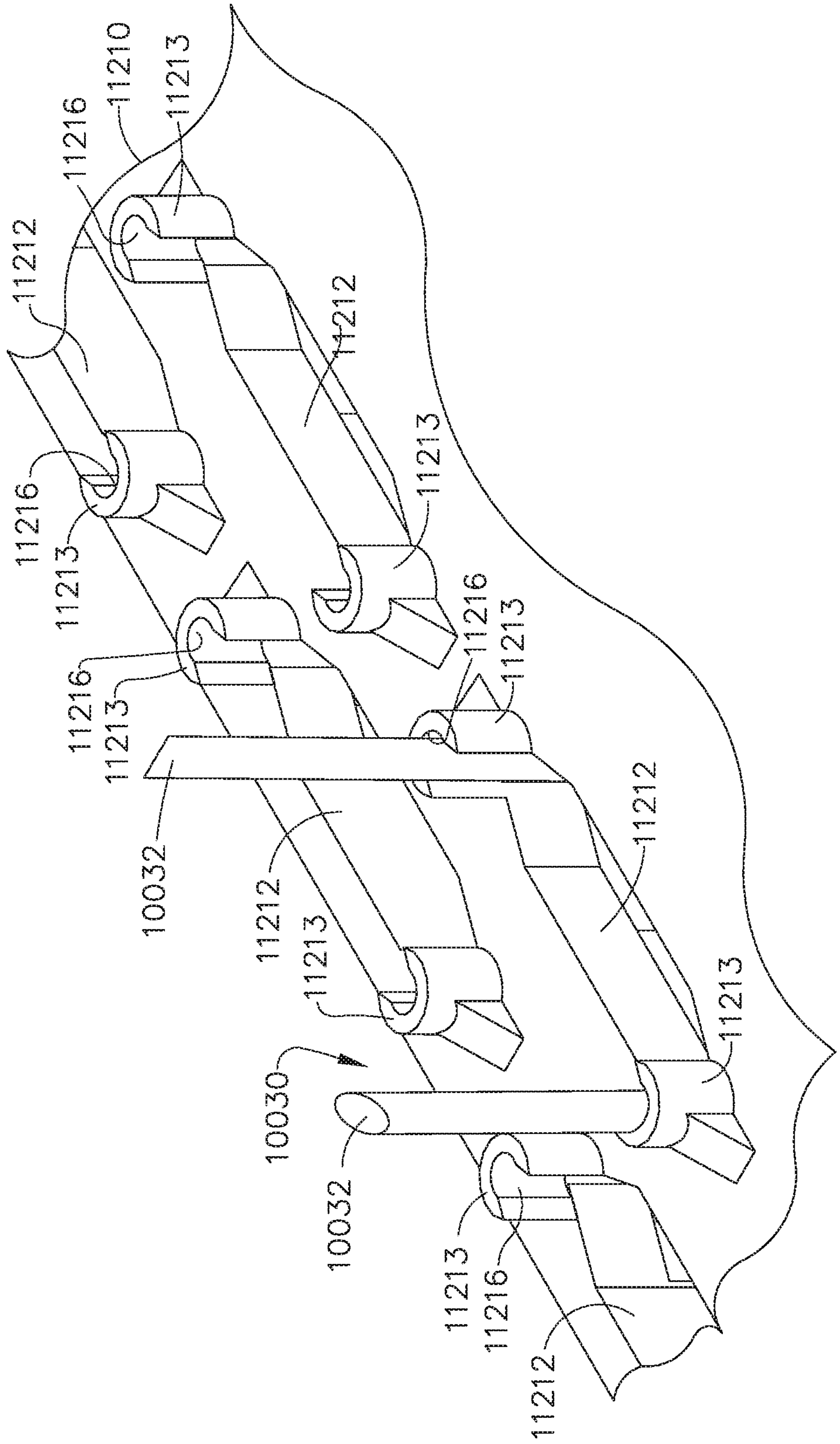
Figure 284:
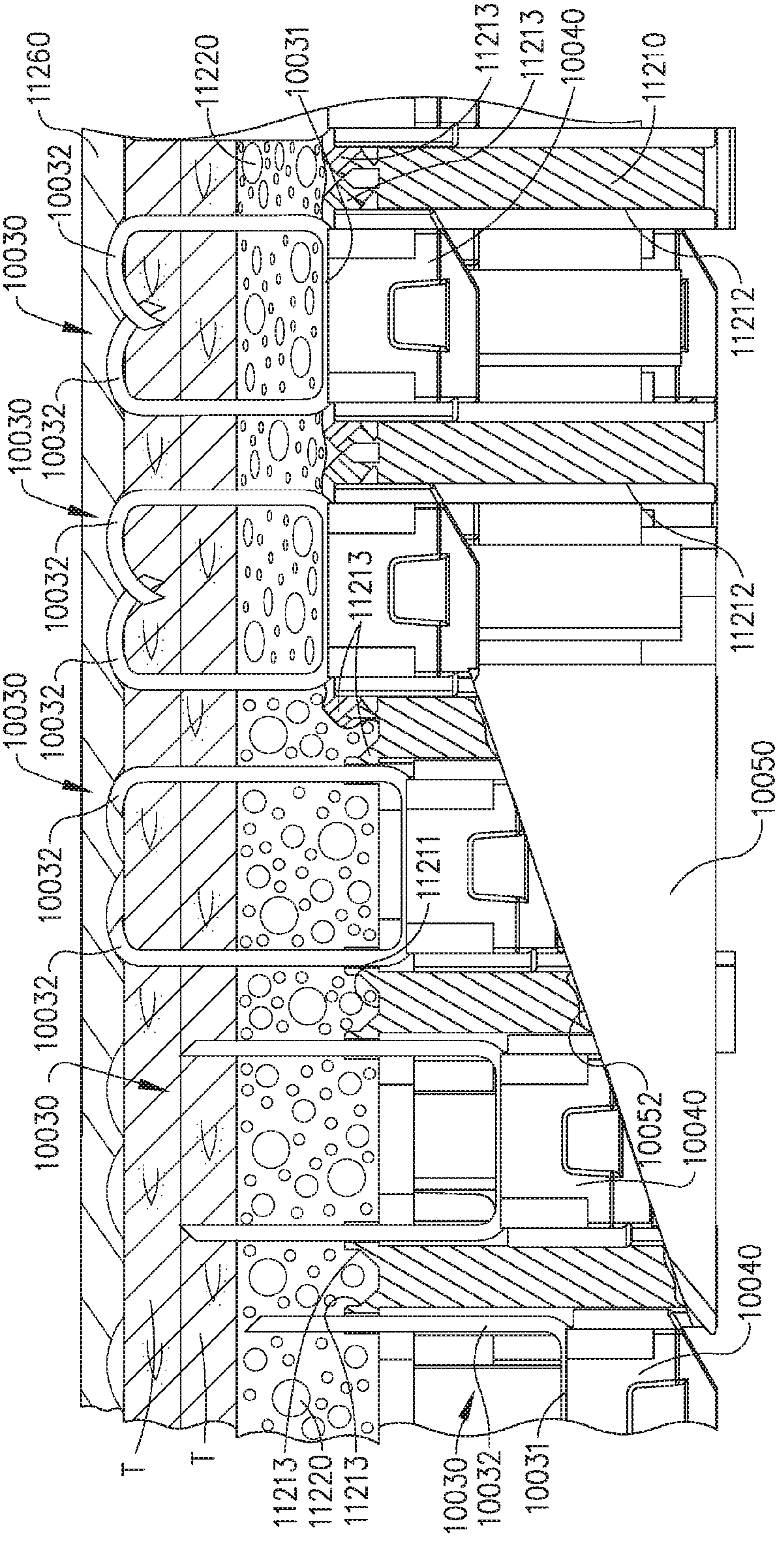
Figure 285:
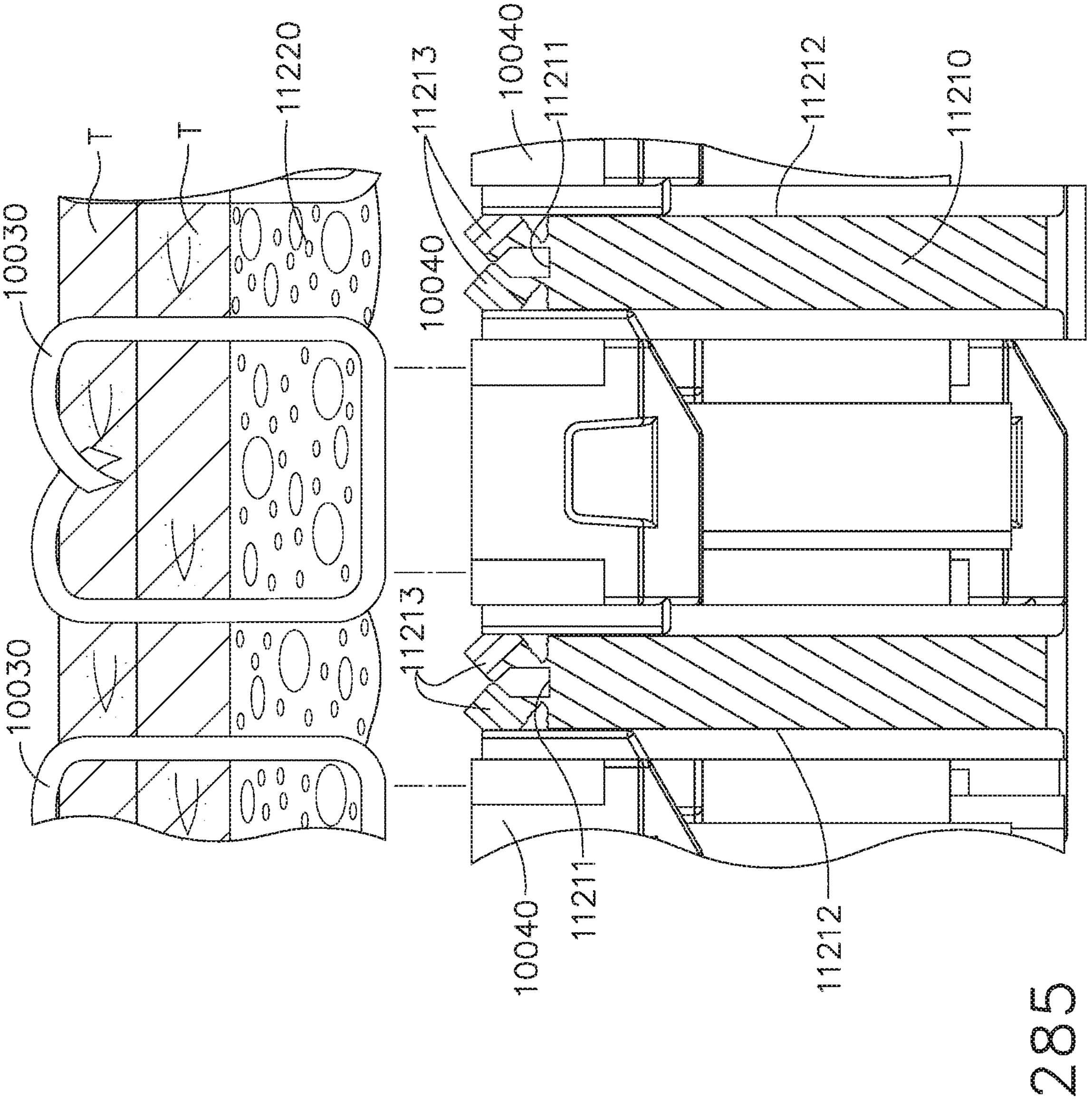
Figure 286:
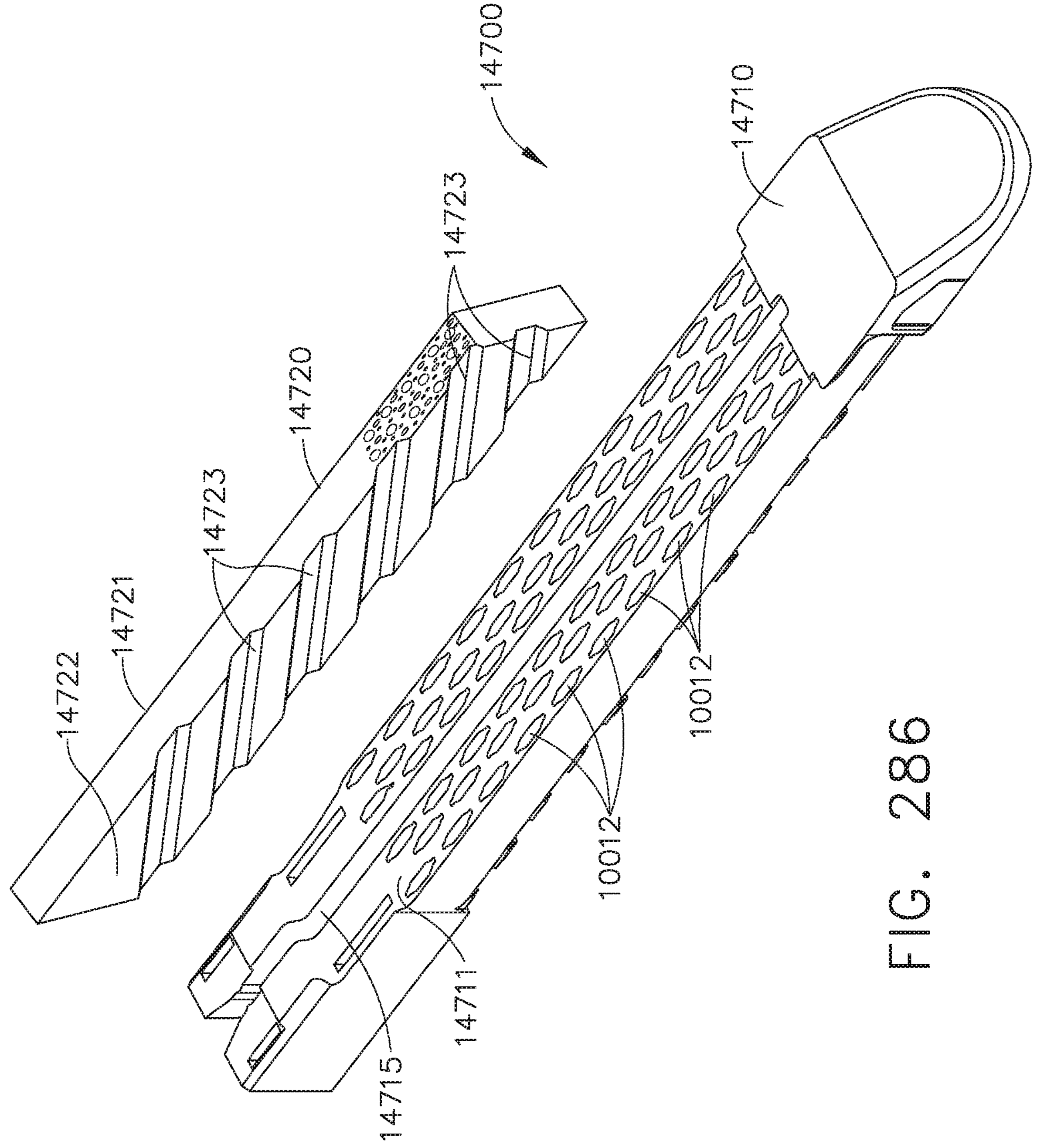
Figure 287:
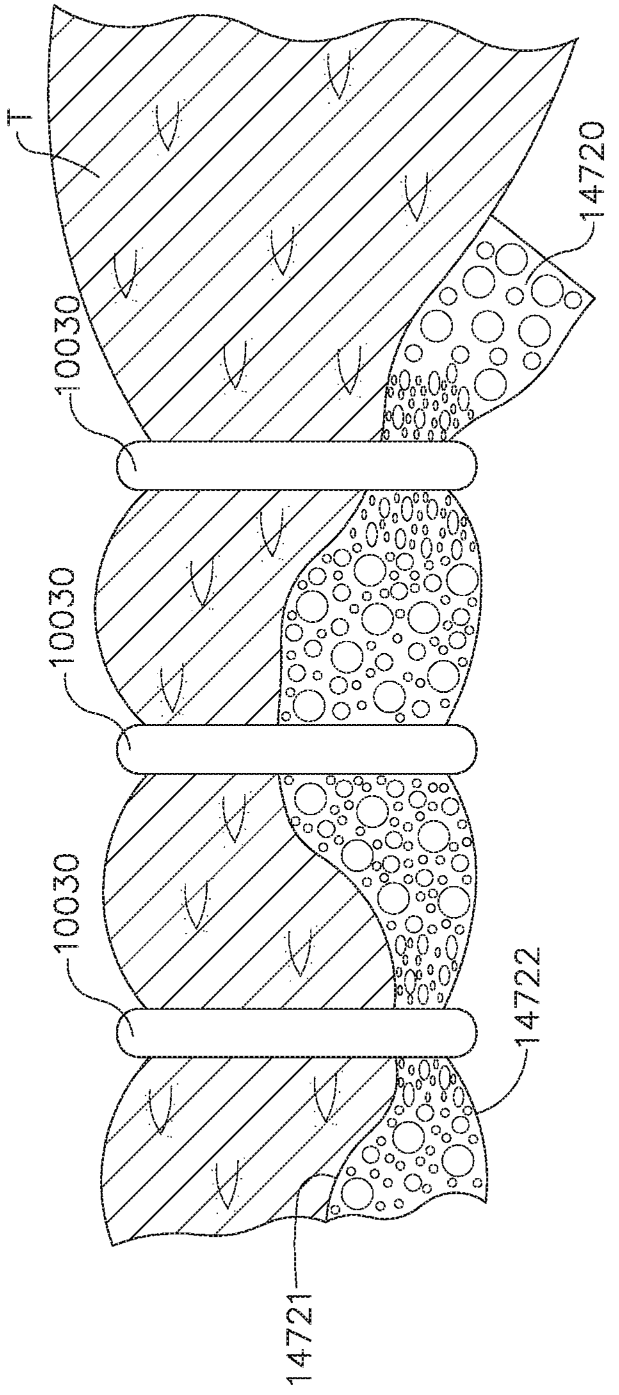
Figure 288:
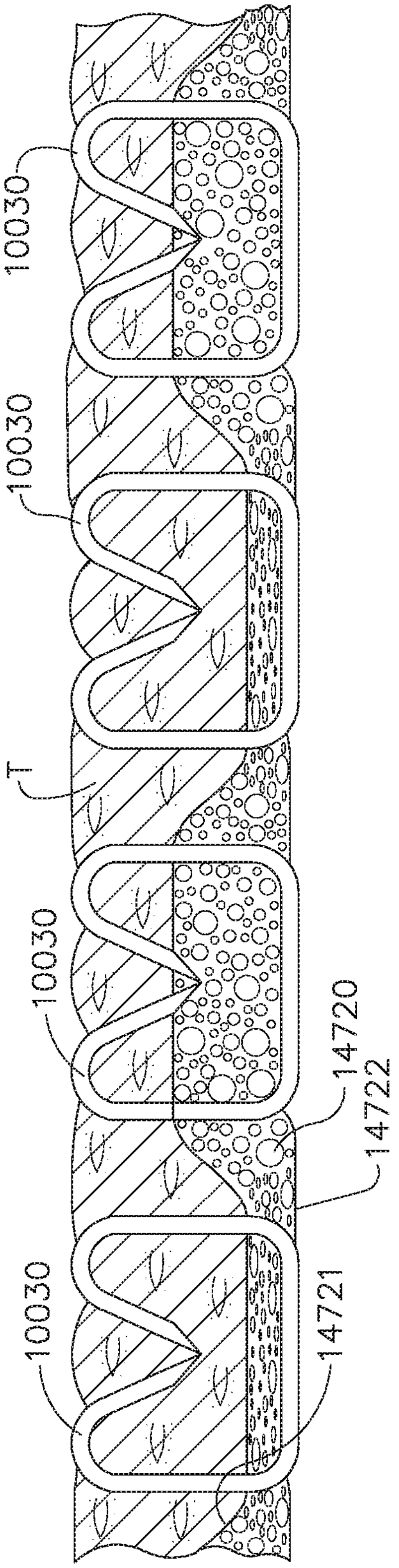
Figure 289:
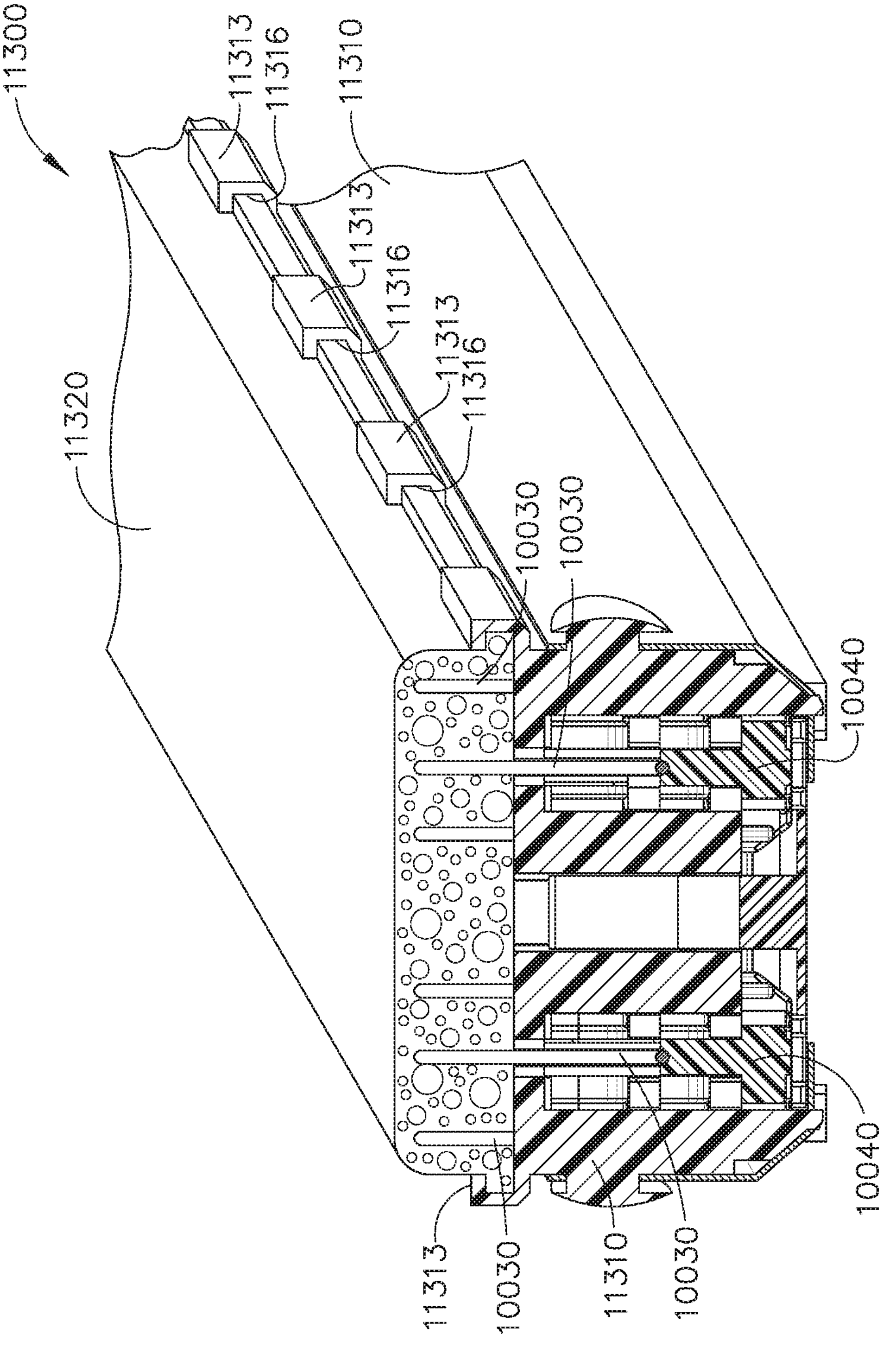
Figure 290:
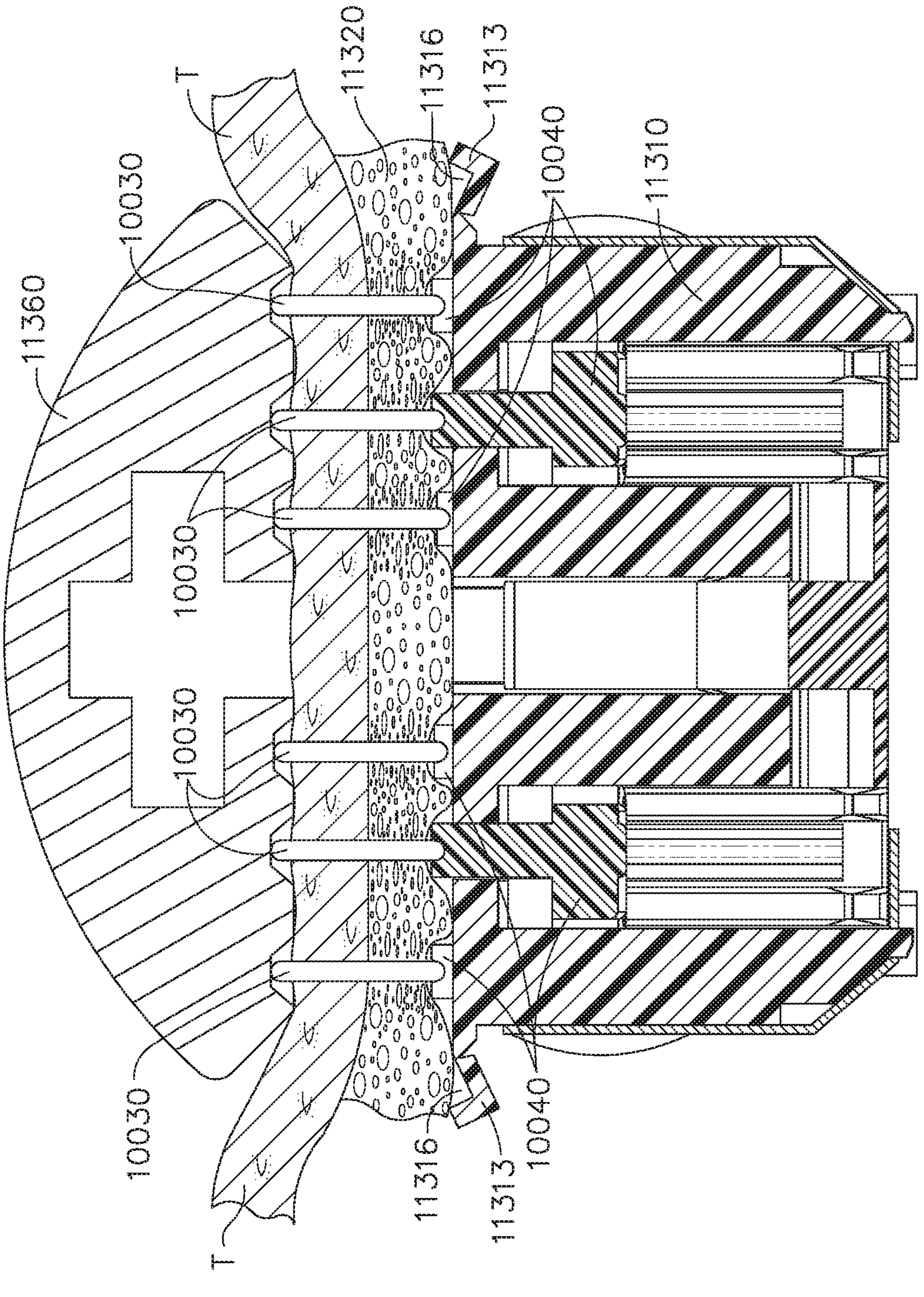
Figure 291:
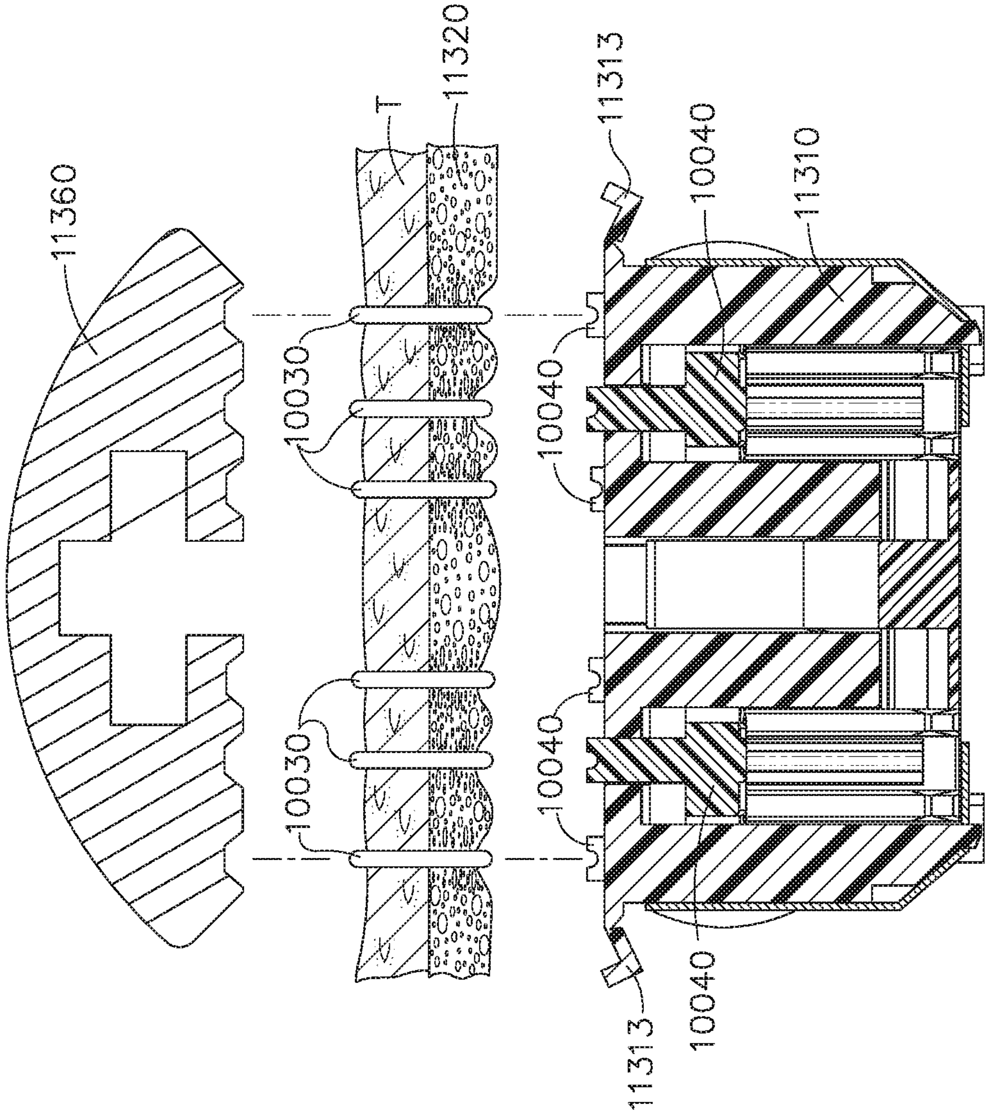
Figure 292:
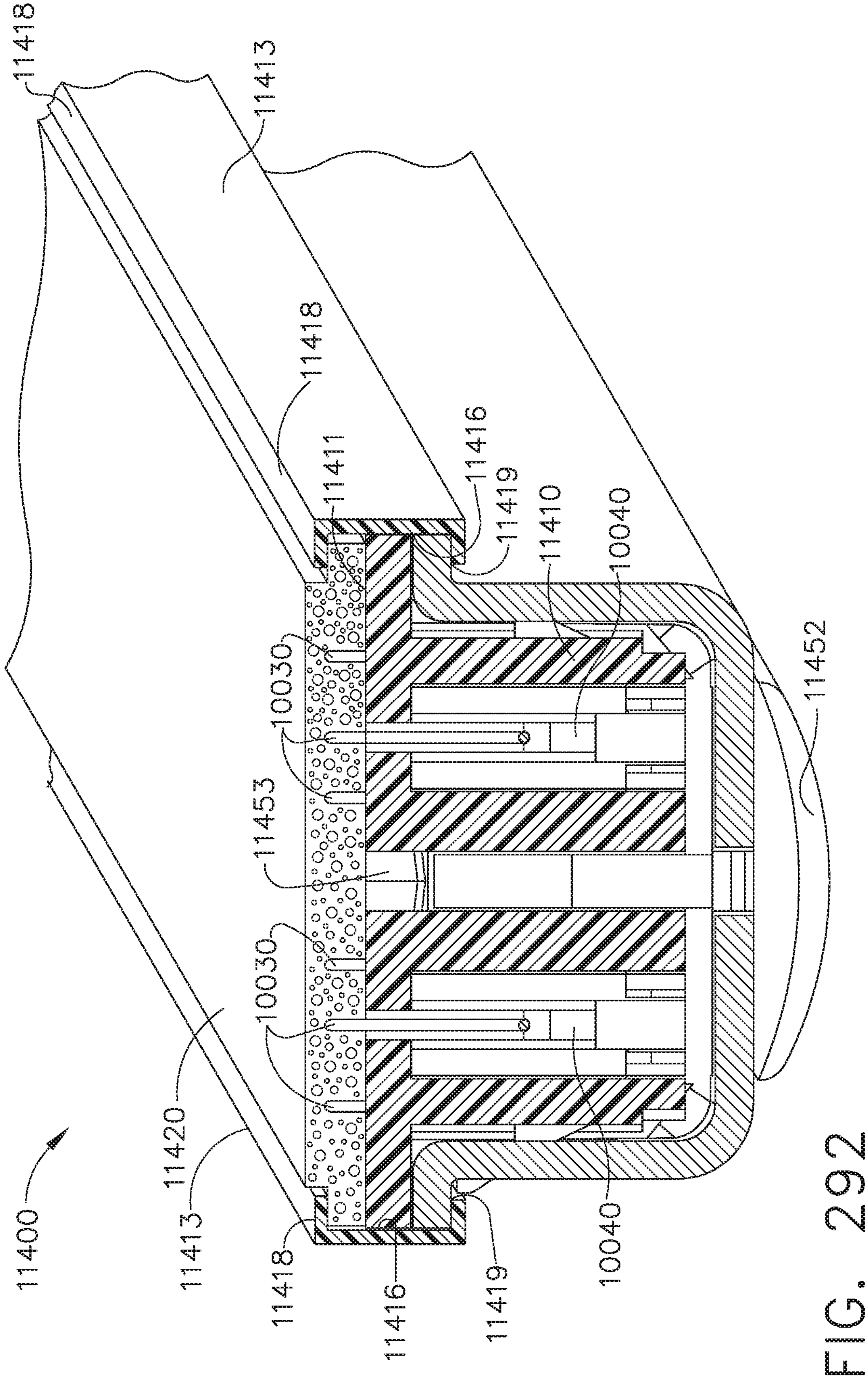
Figure 293:
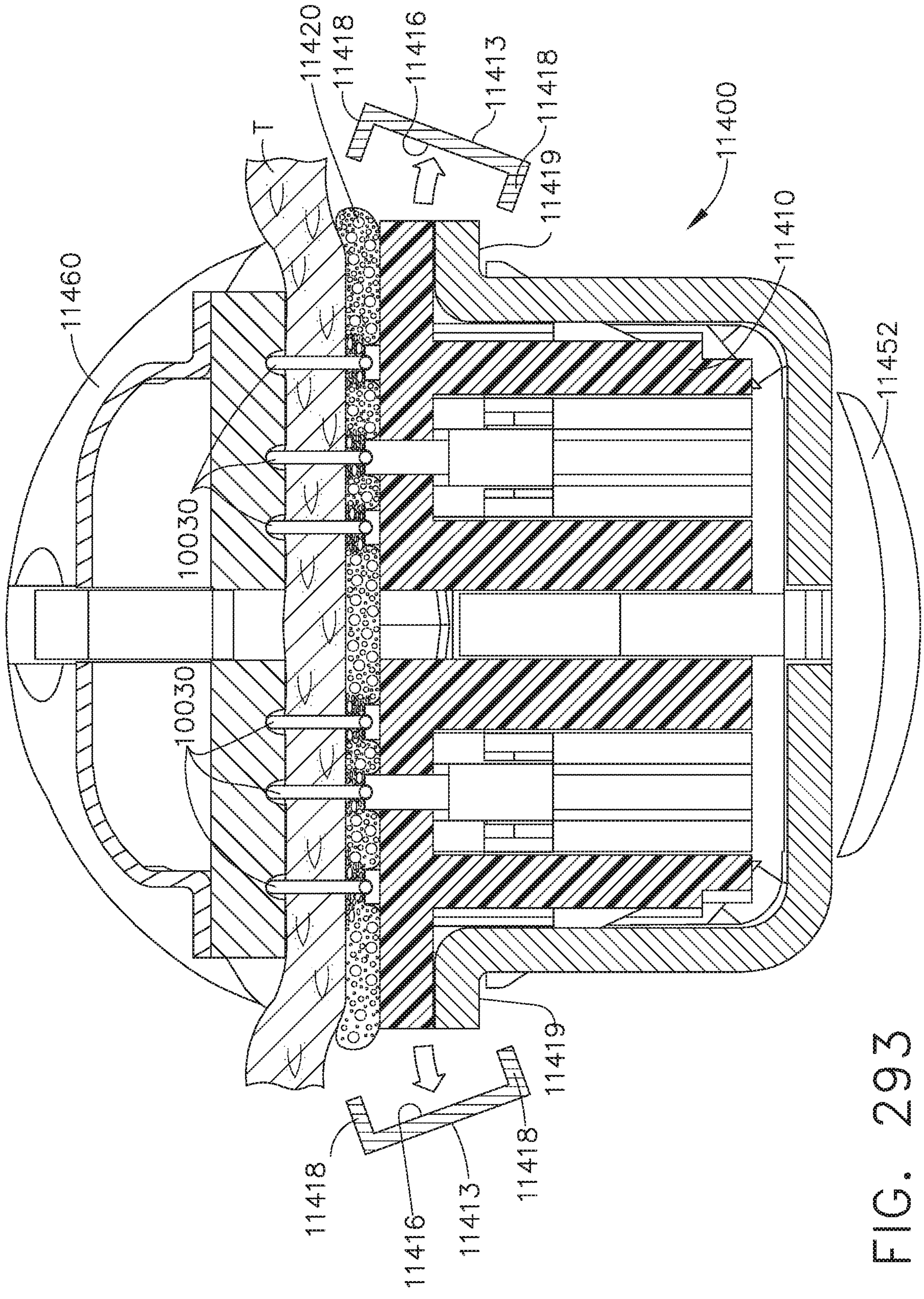
Figure 294:
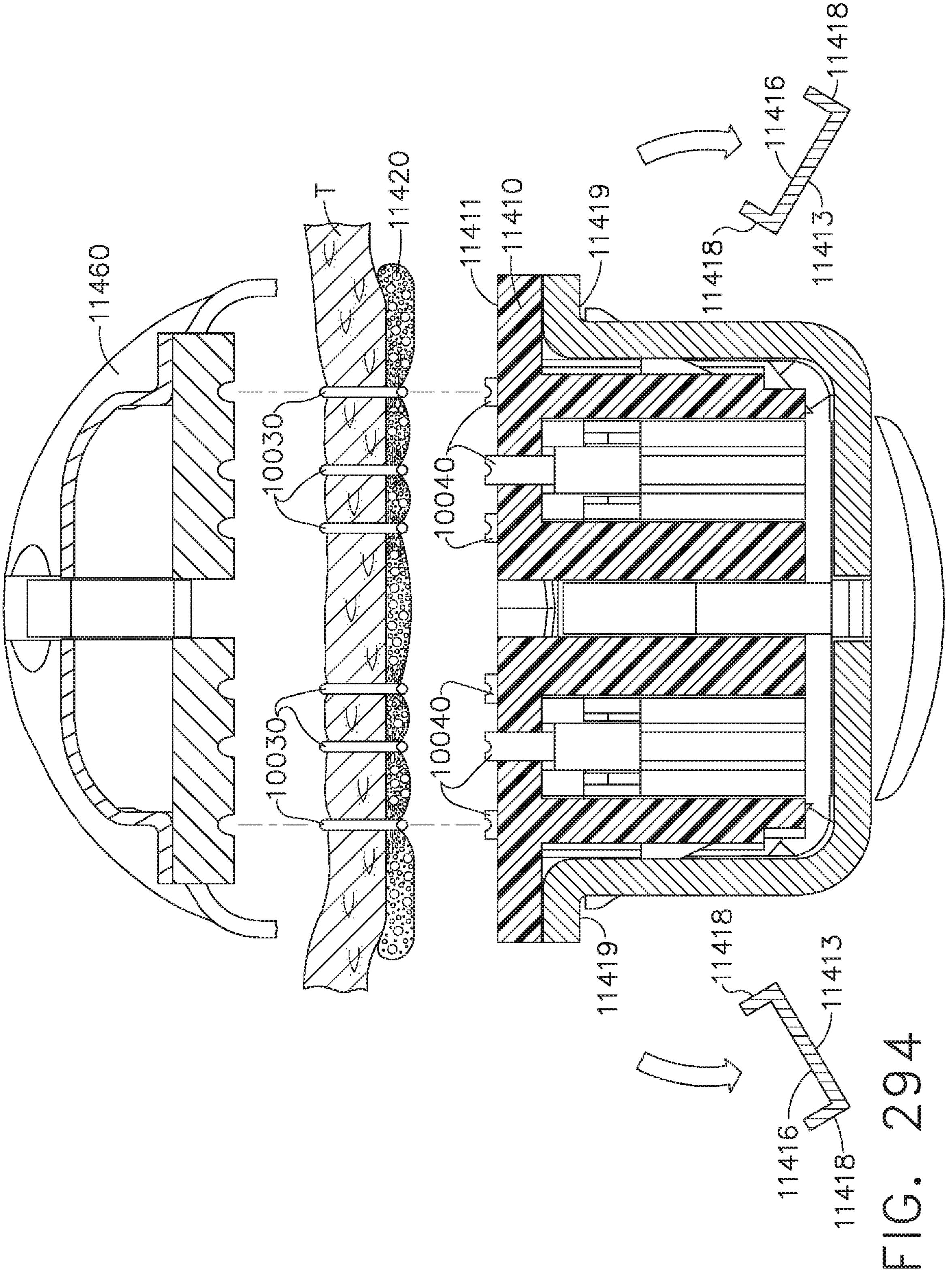
Figure 295:
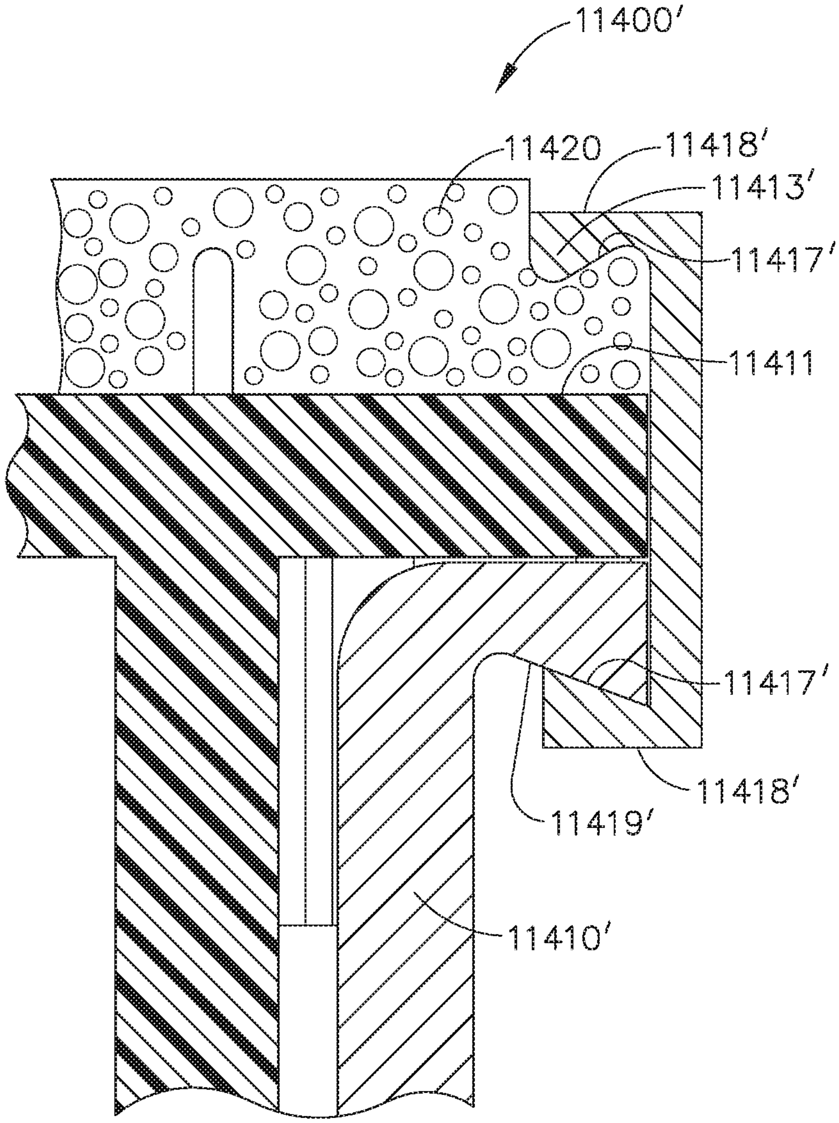
Figures 296, 296A:
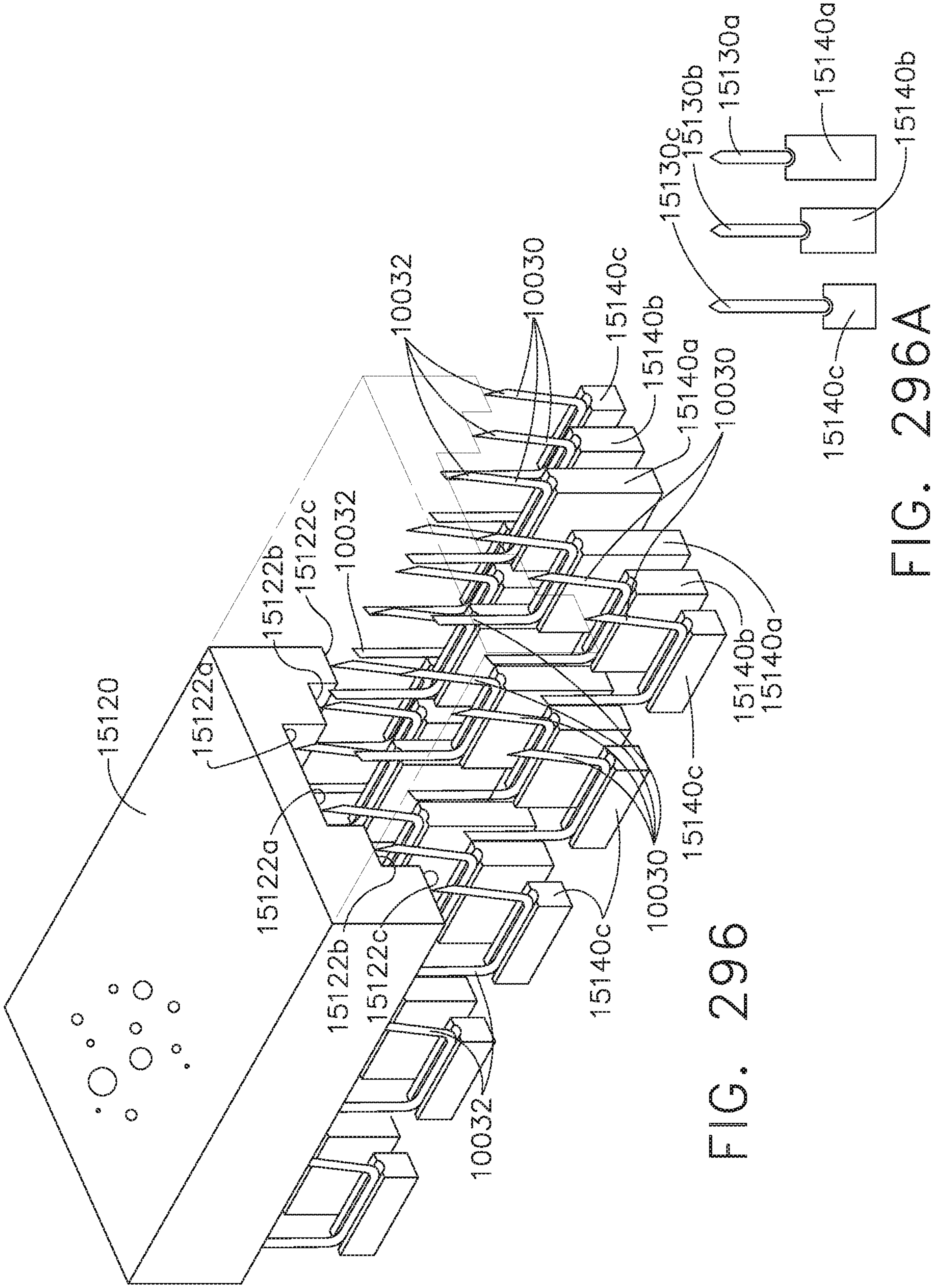
Figure 297:
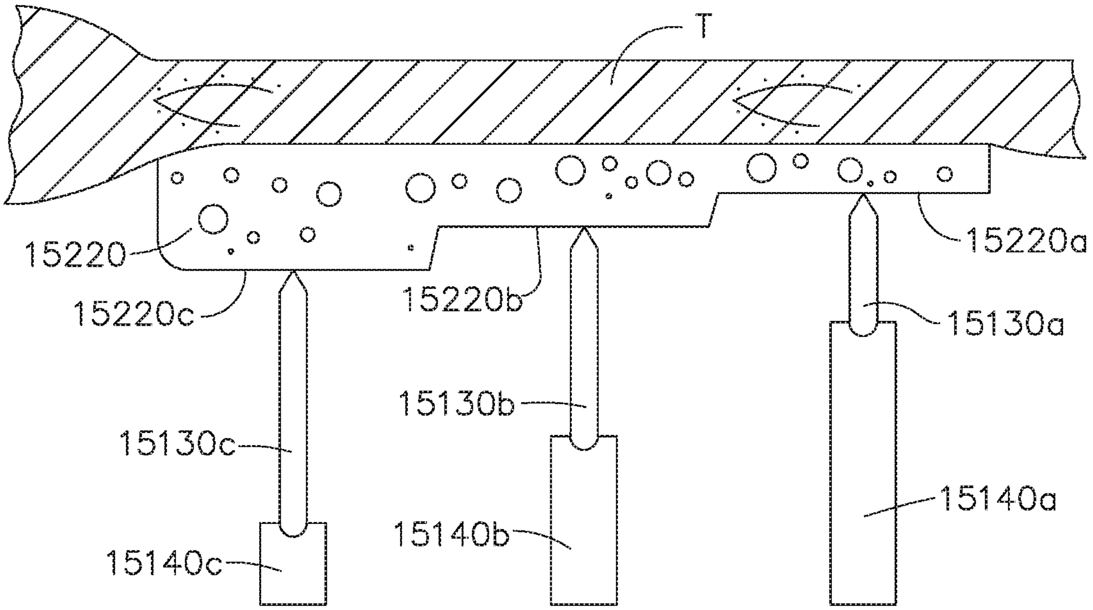
Figure 298:
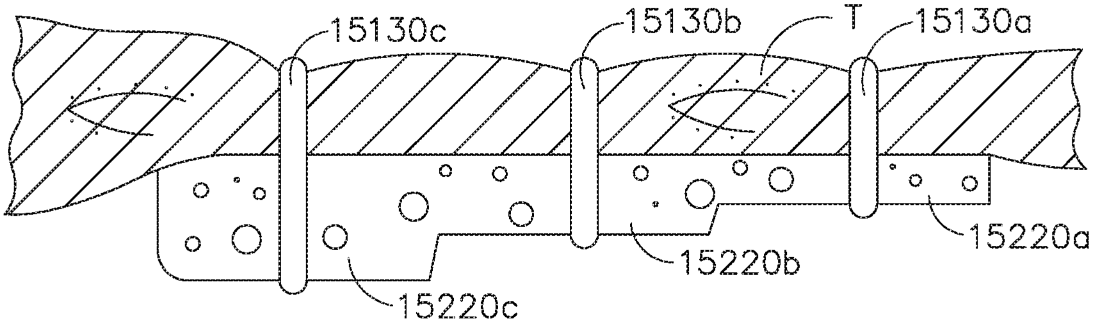
Figure 299:
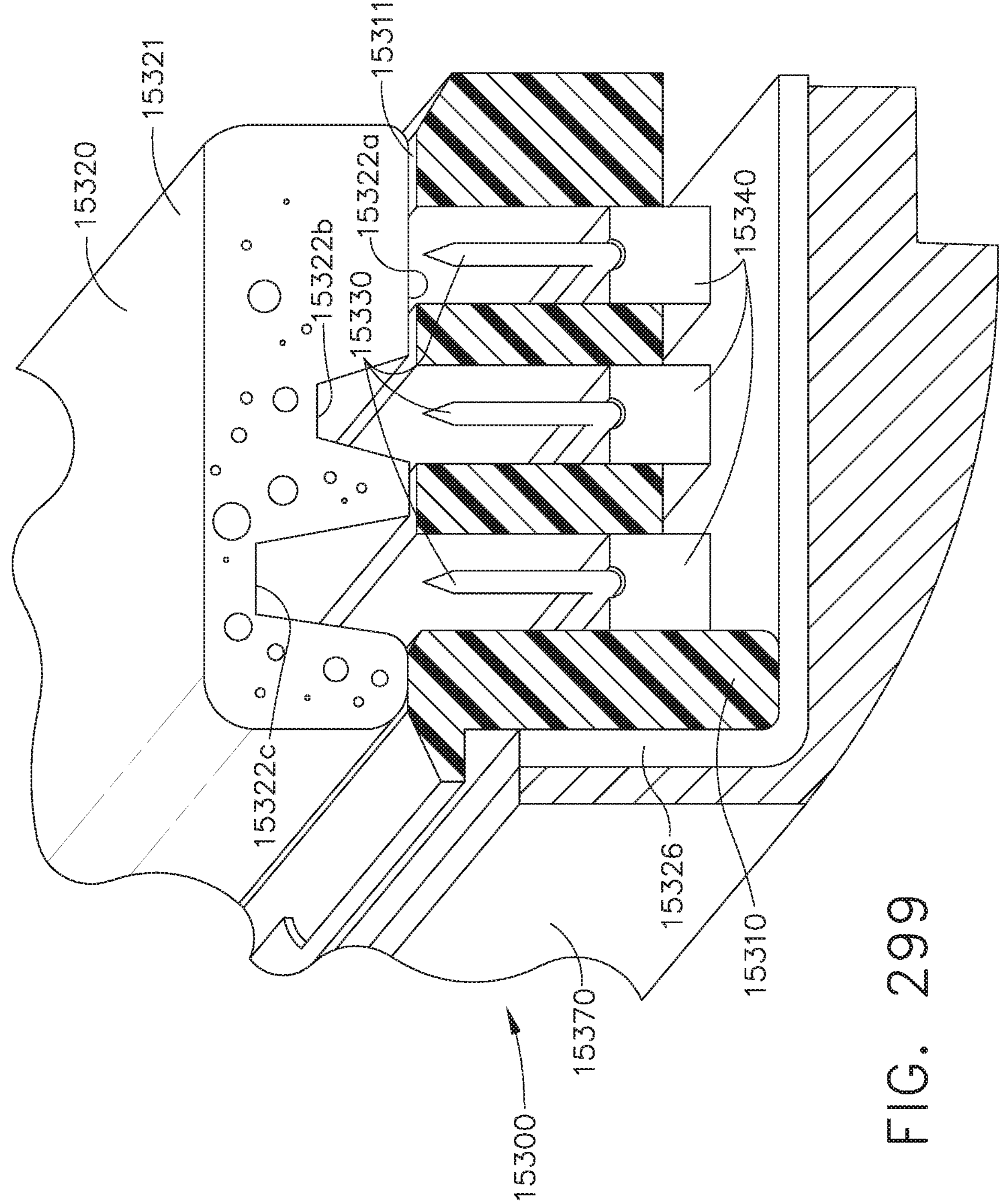
Figure 300:
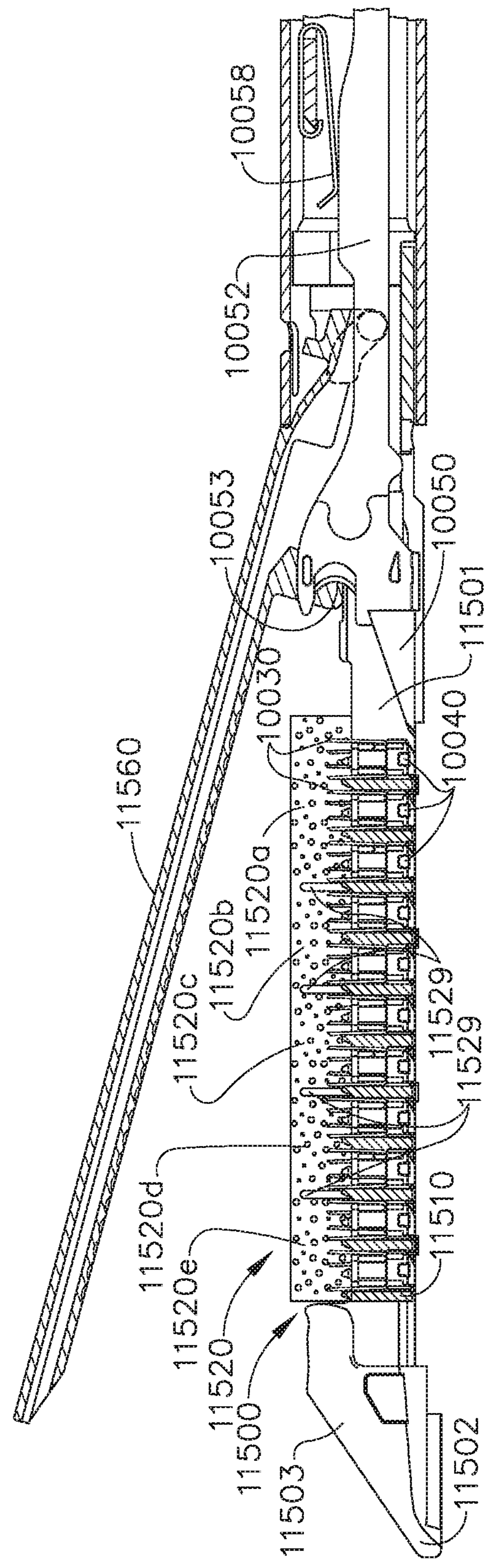
Figure 301:
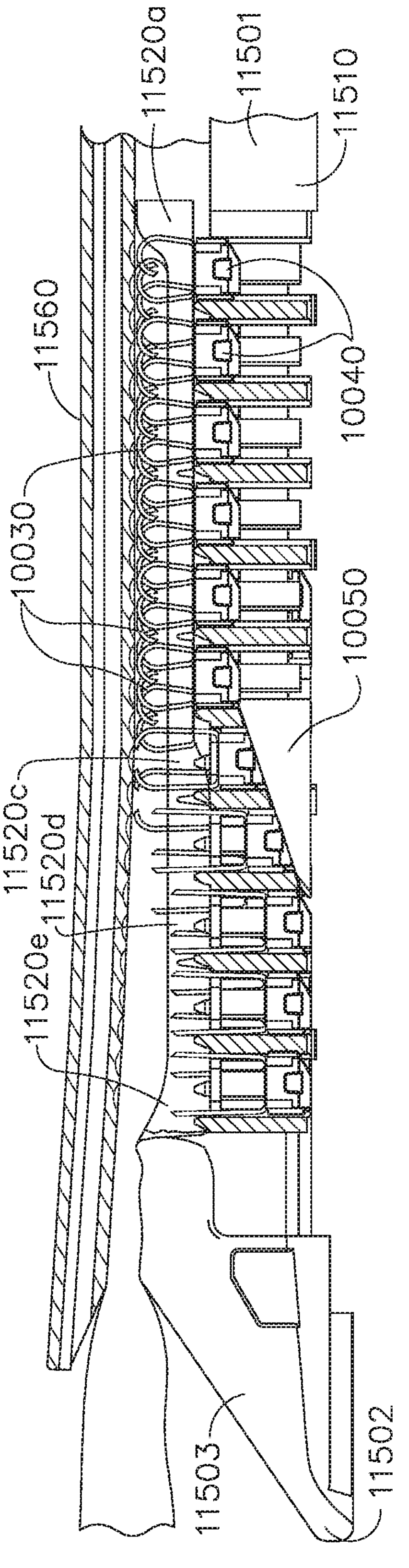
Figure 302:
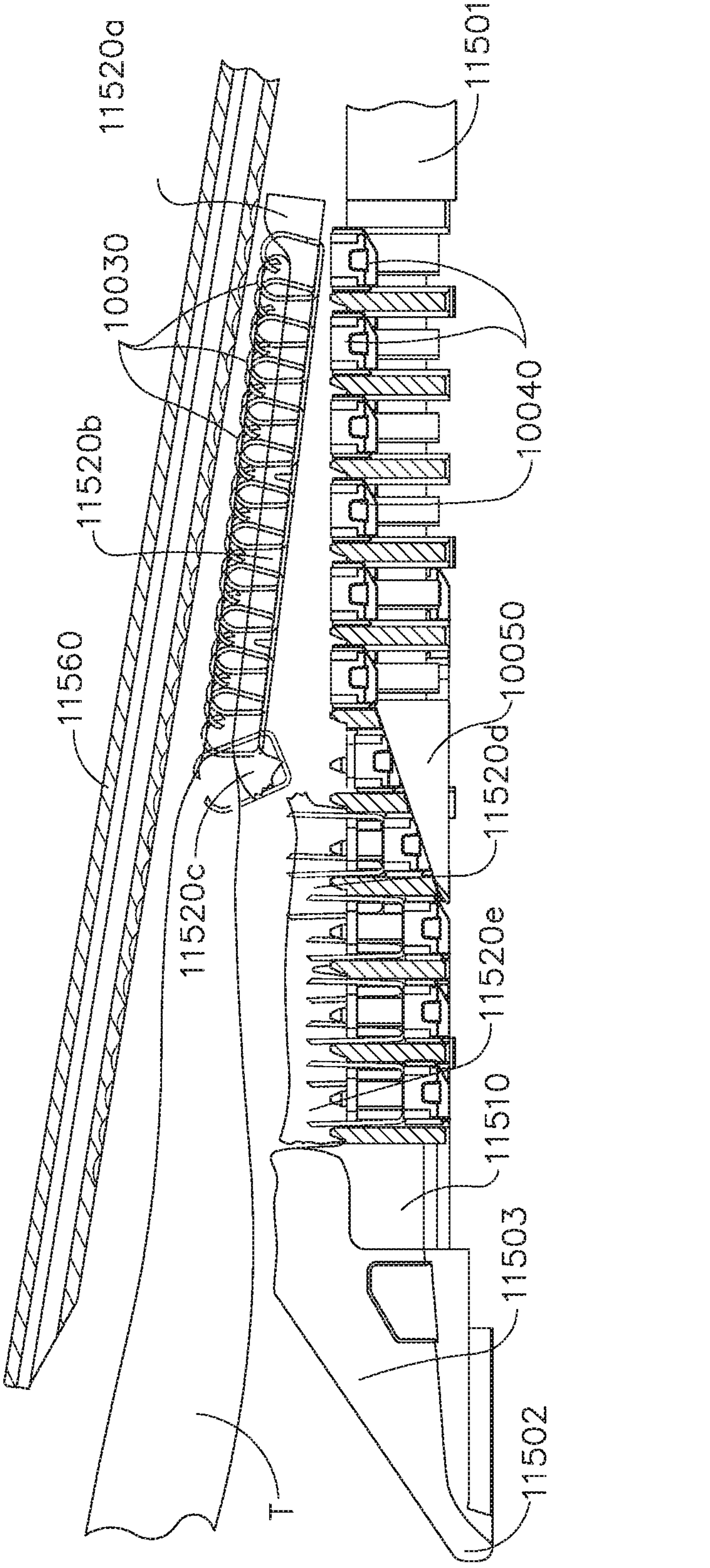
Figure 303:
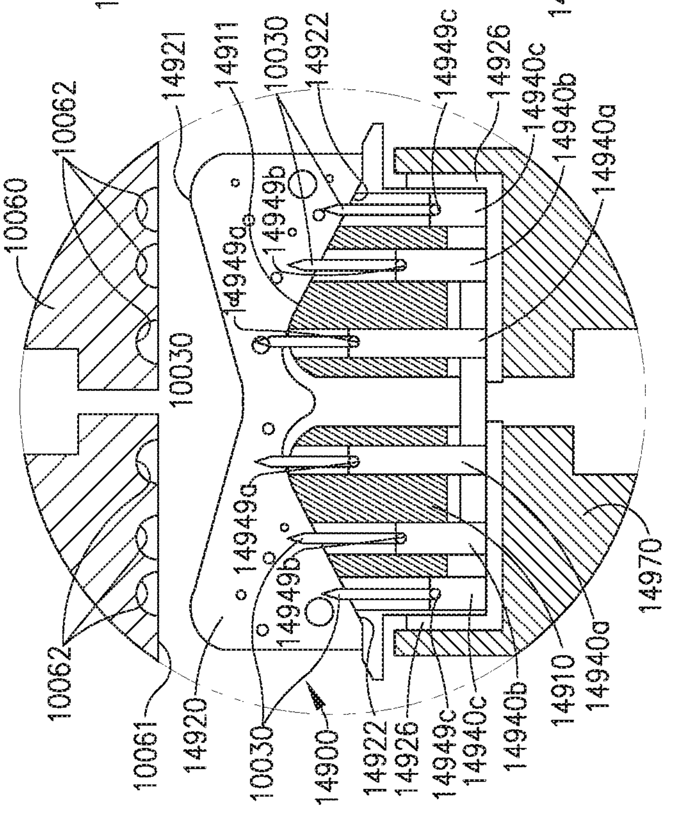
Figure 304:
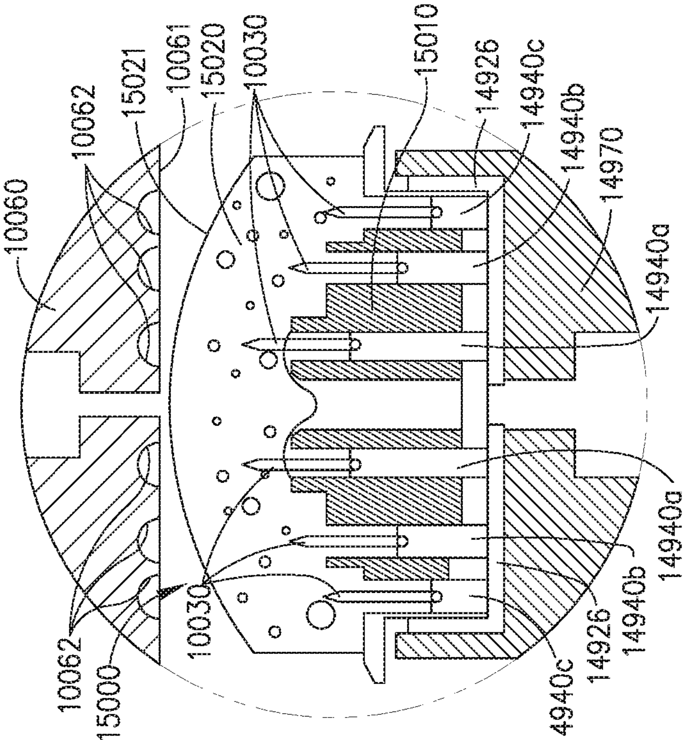
Figure 305:
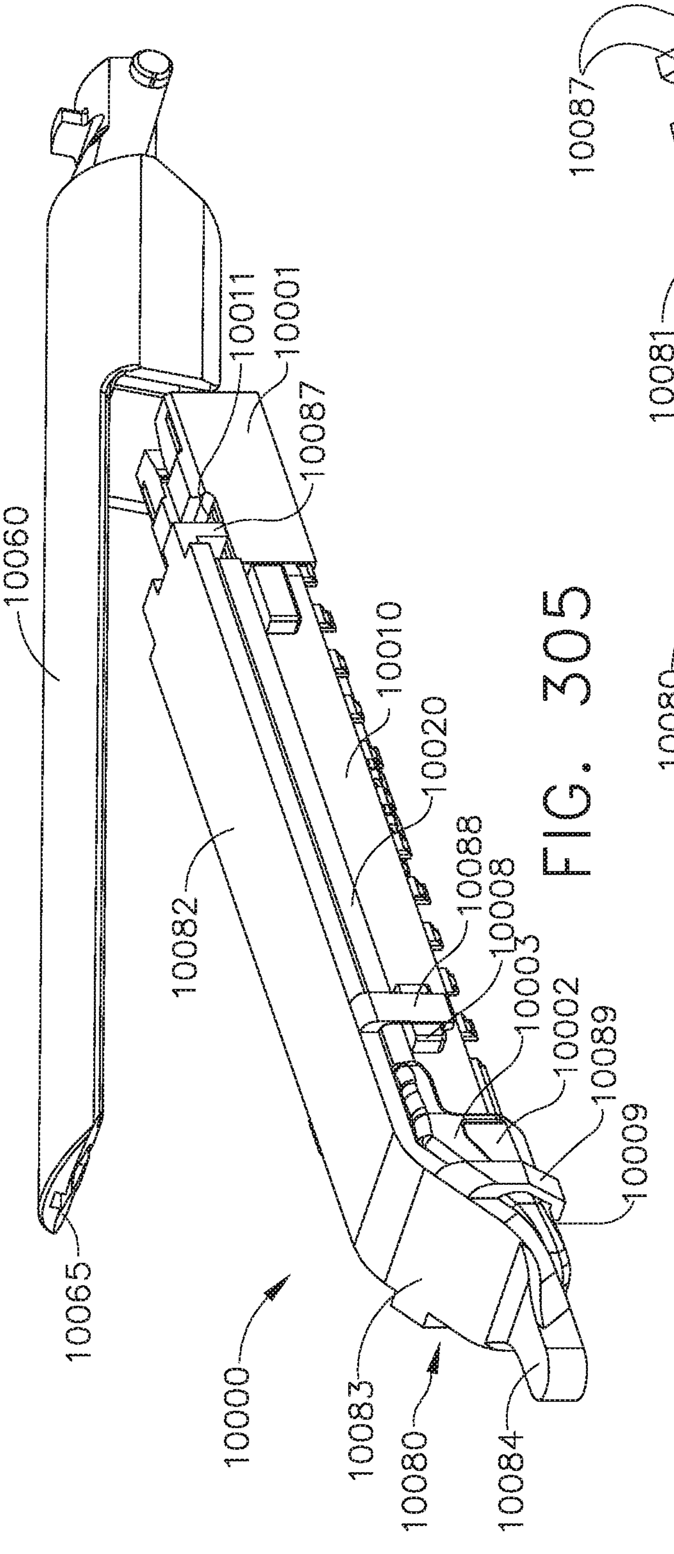
Figure 306:
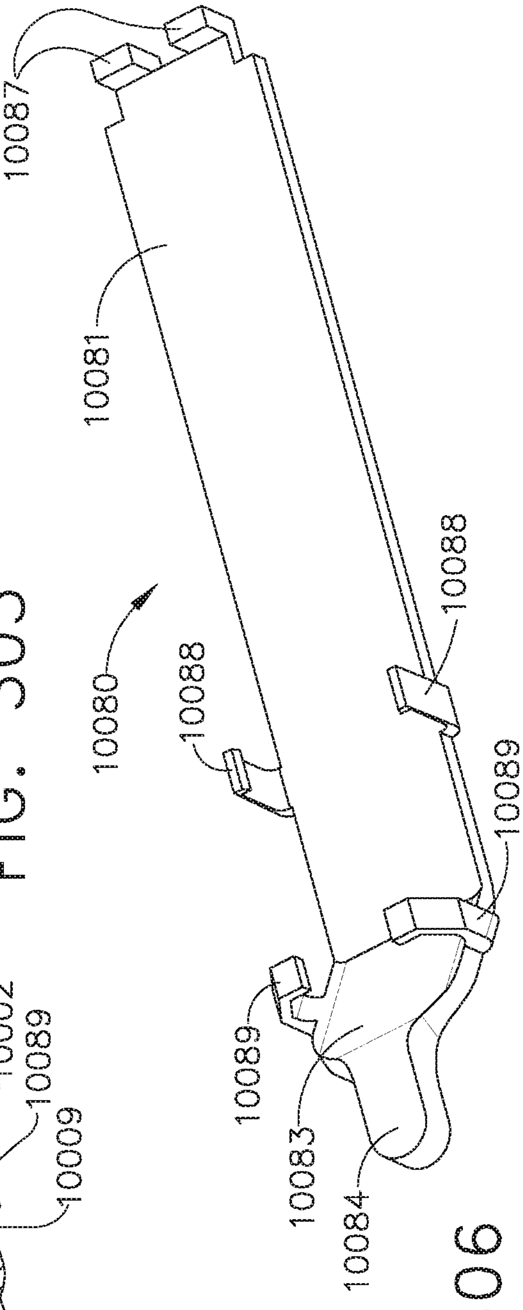
Figure 307:
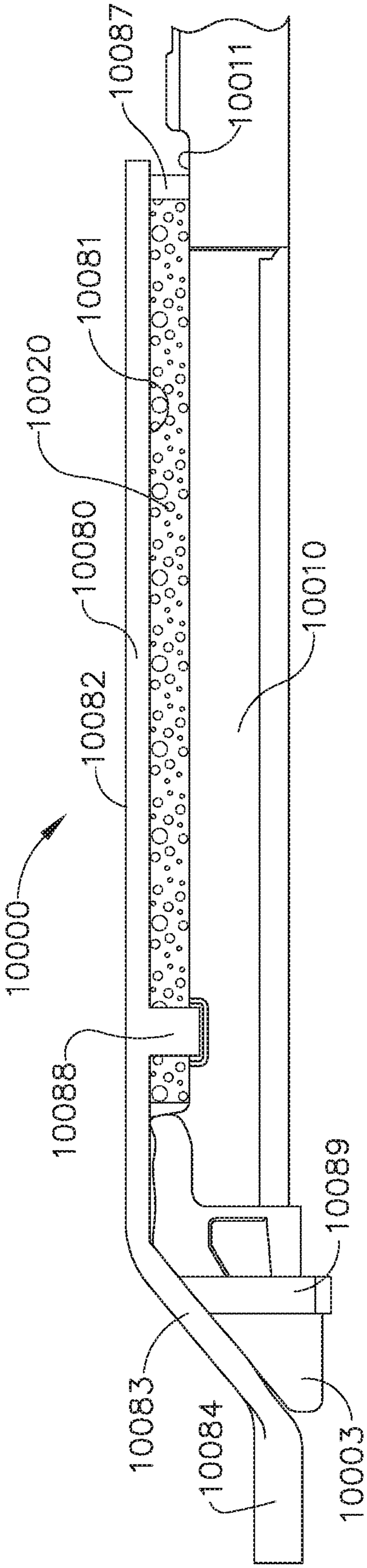
Figure 308:
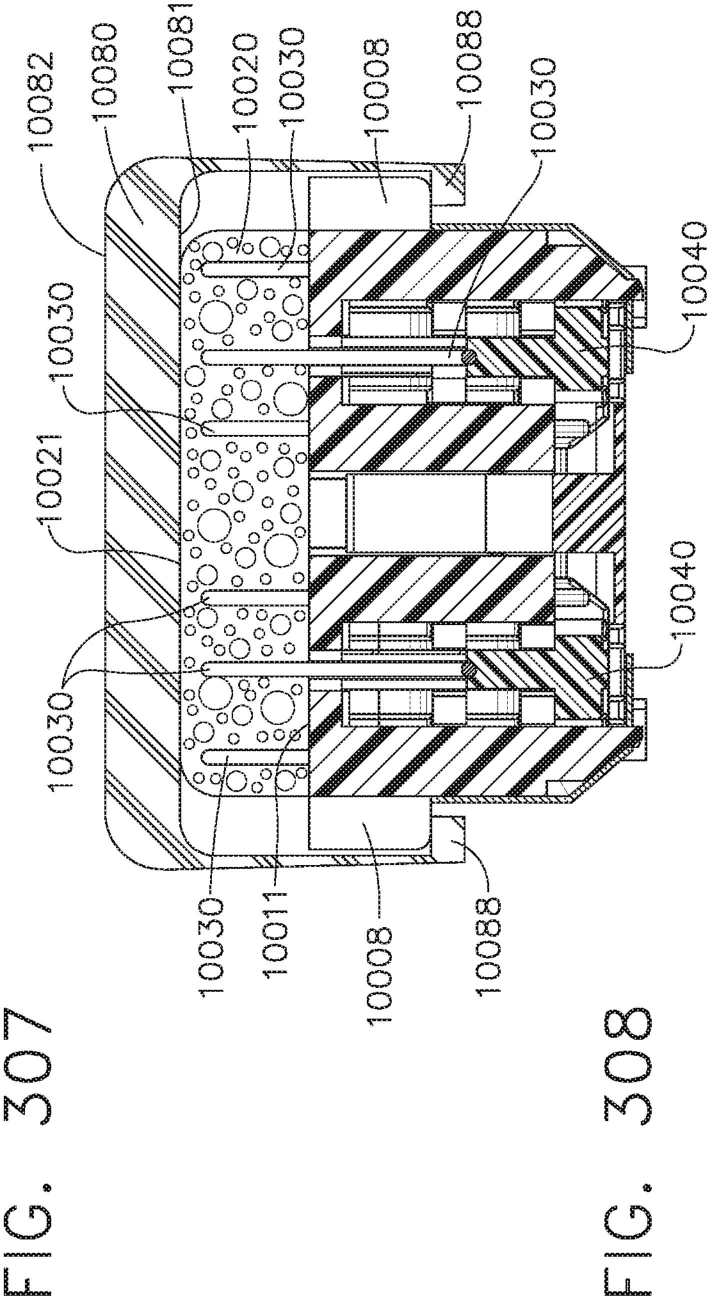
Figure 309:
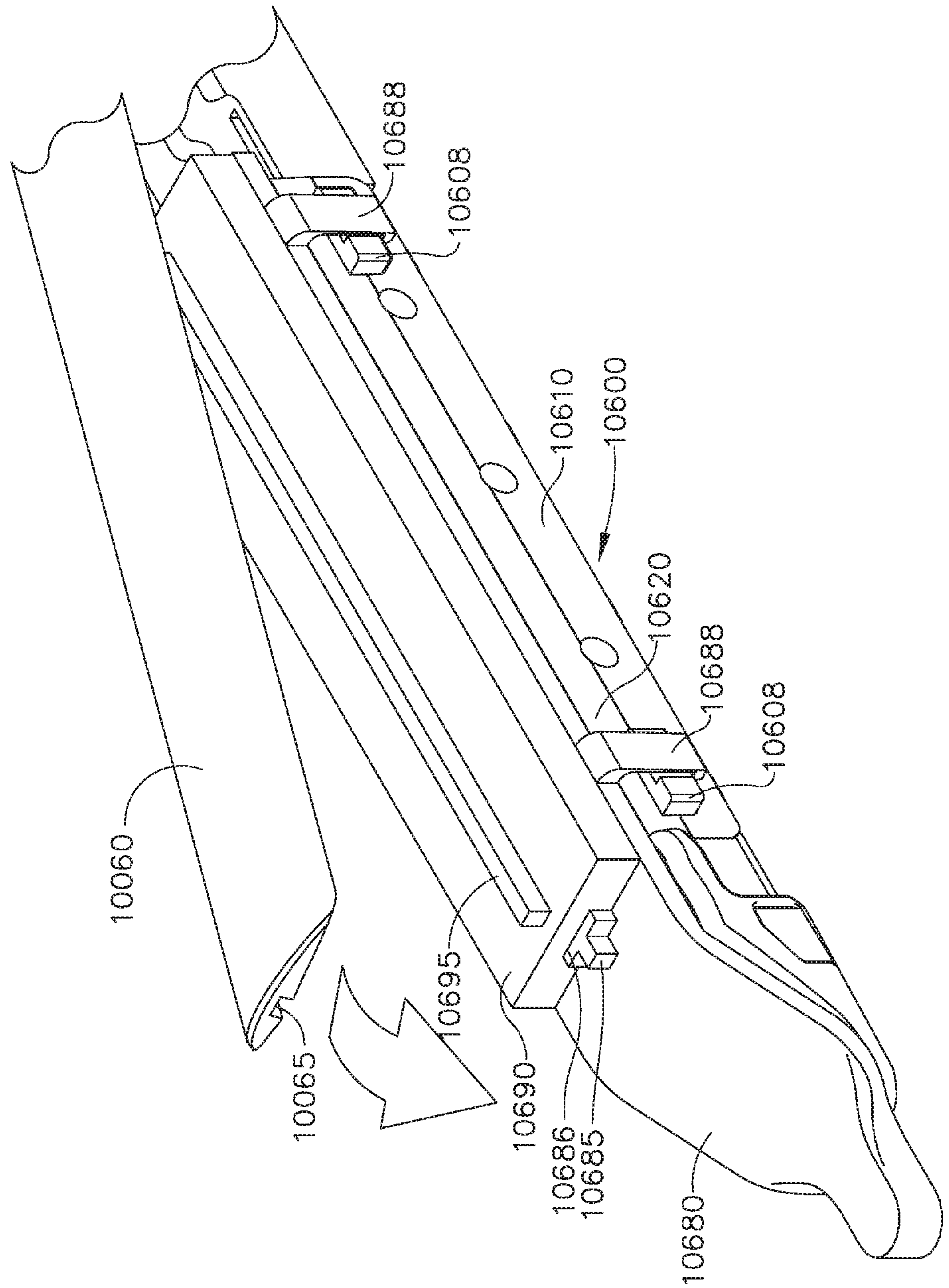
Figure 310:
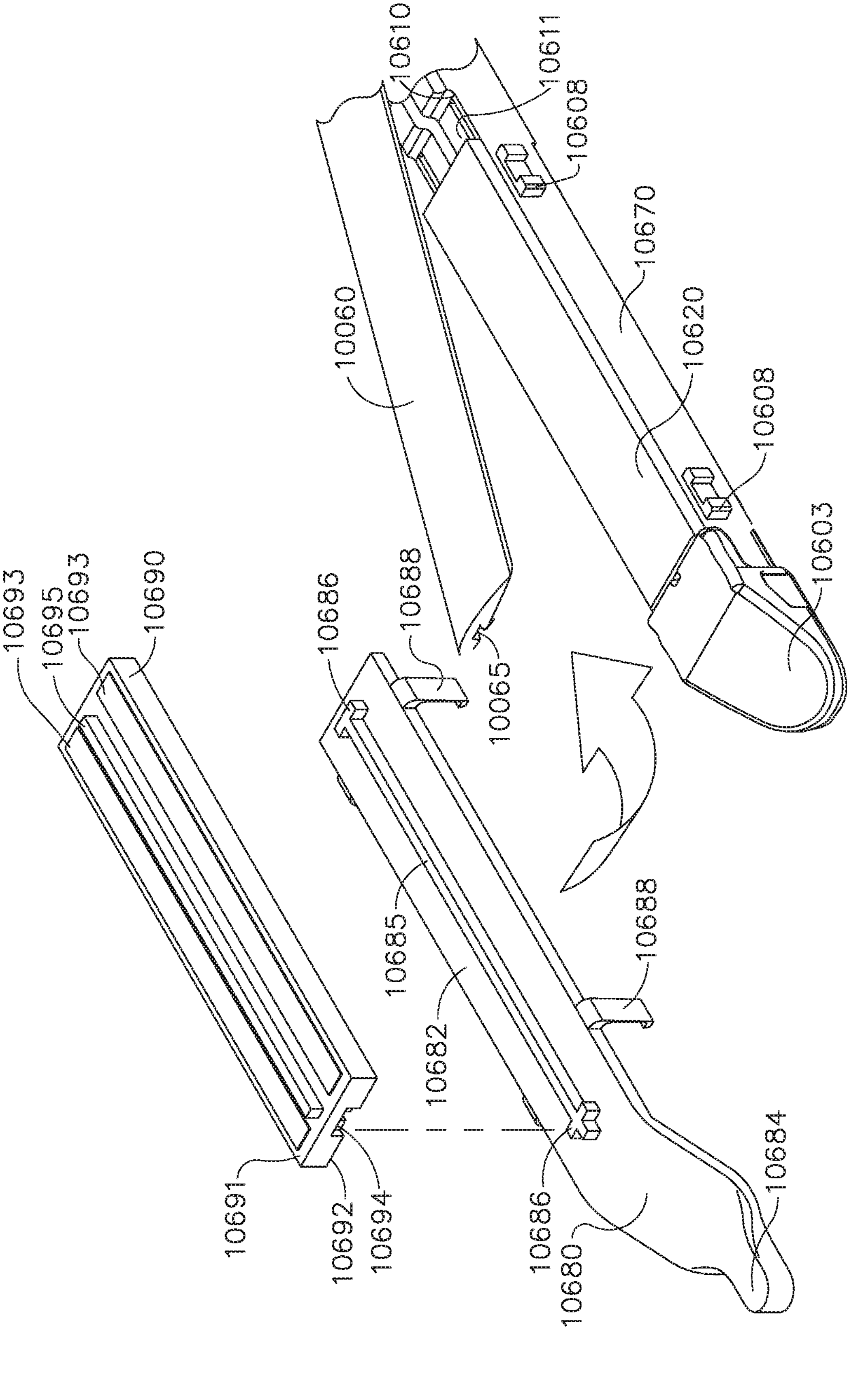
Figure 310A:
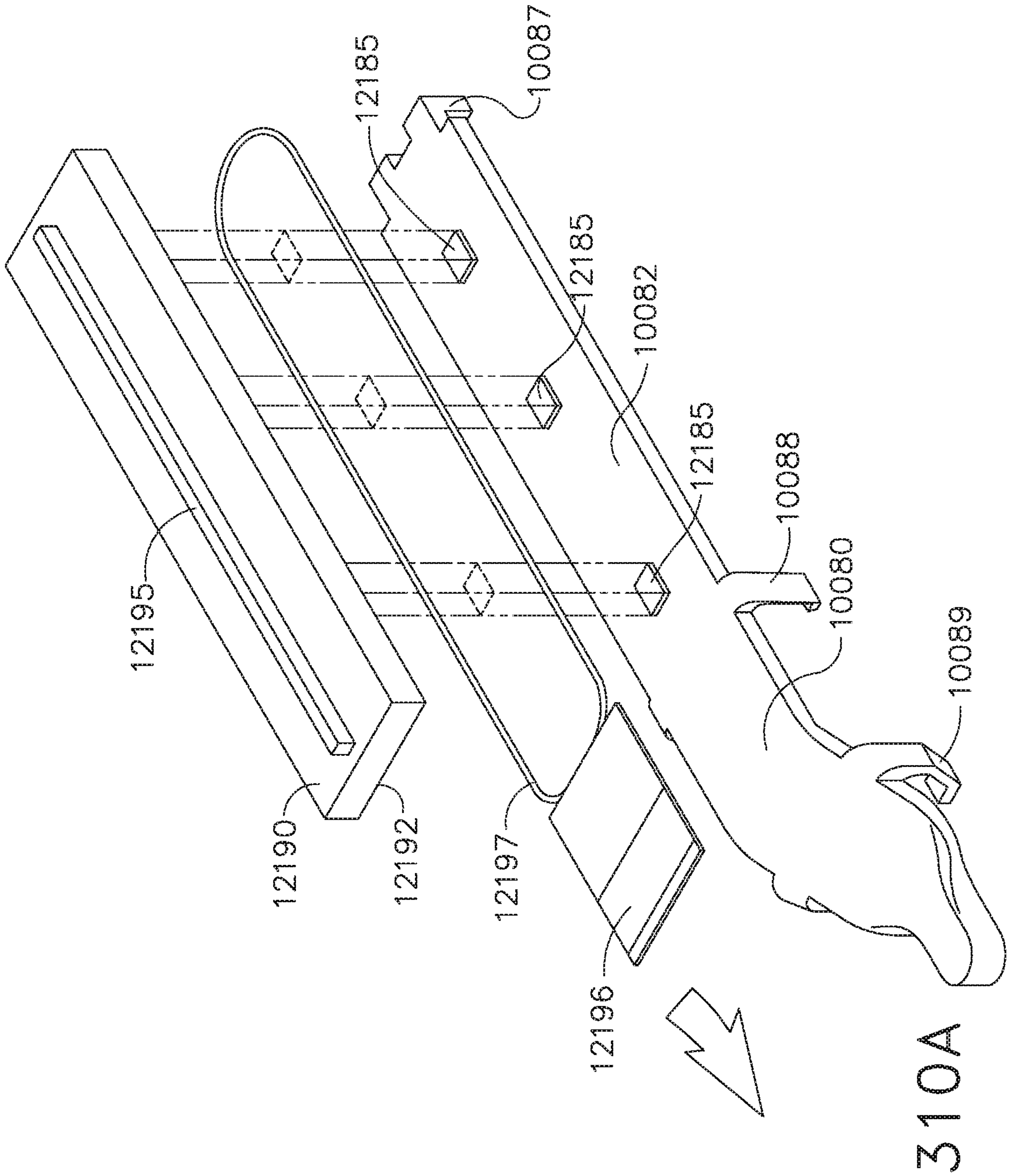
Figure 311:
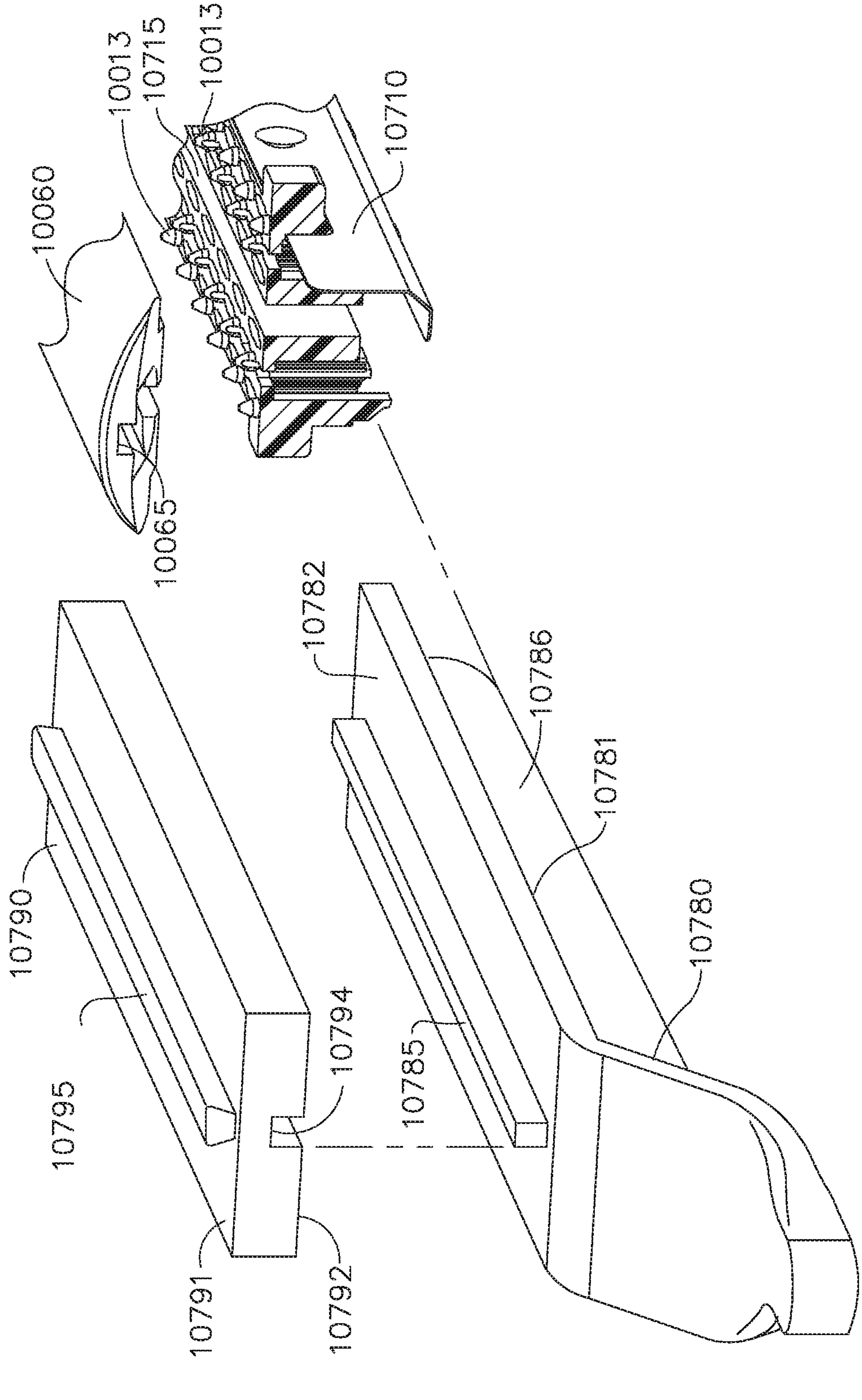
Figure 312:
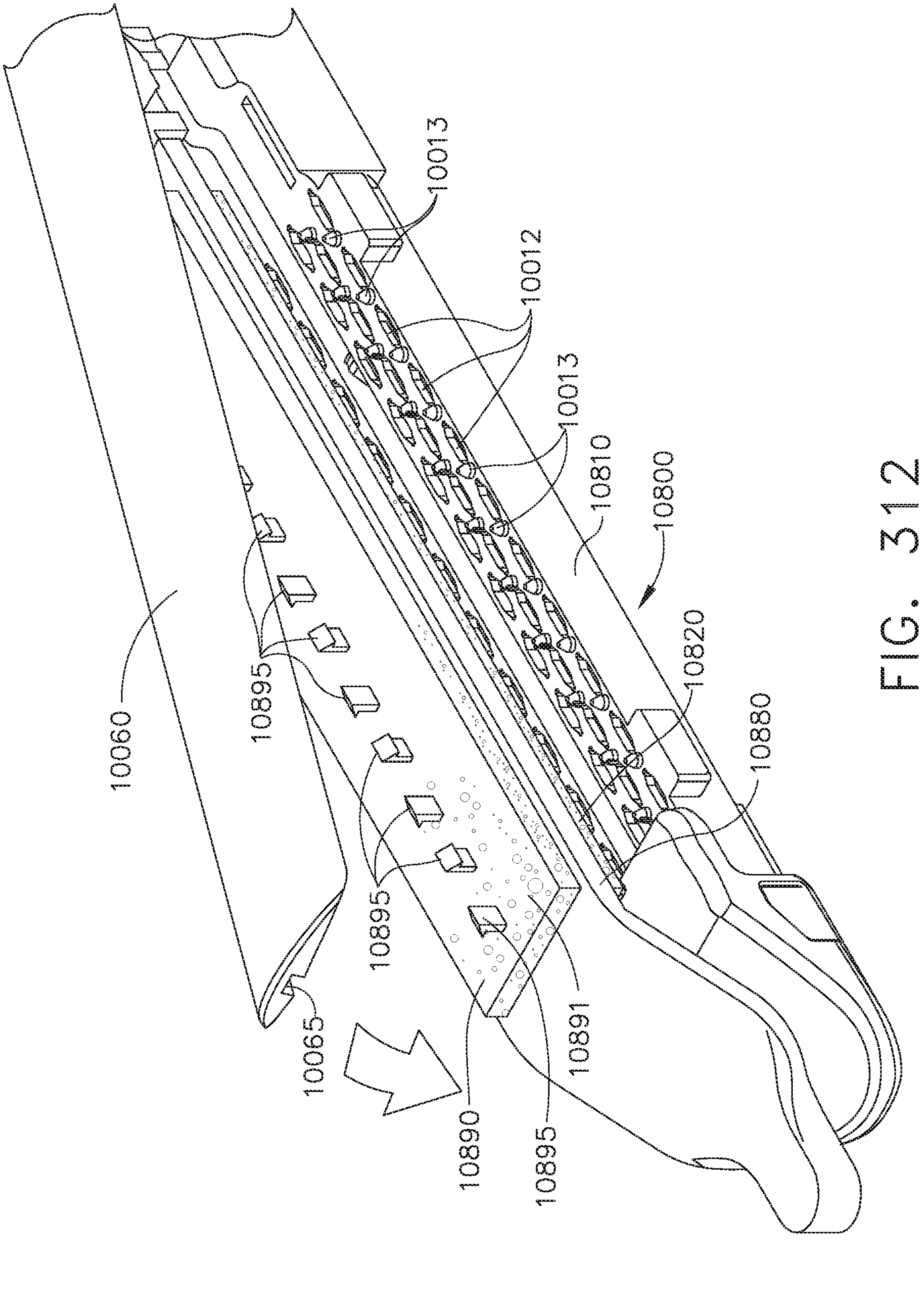
Figure 313:
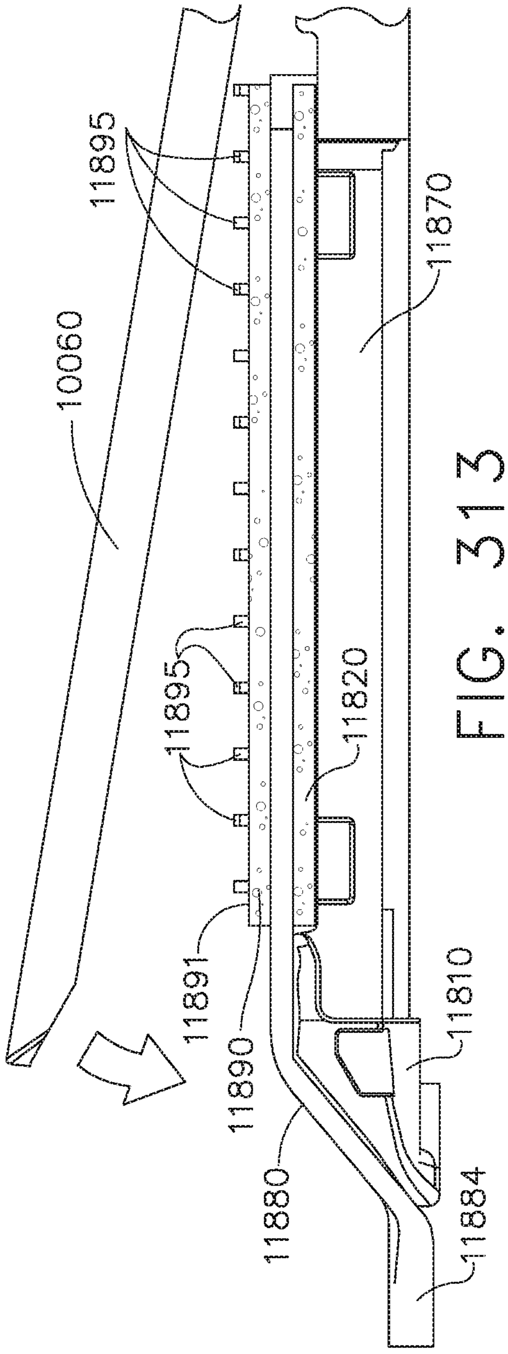
Figure 314:
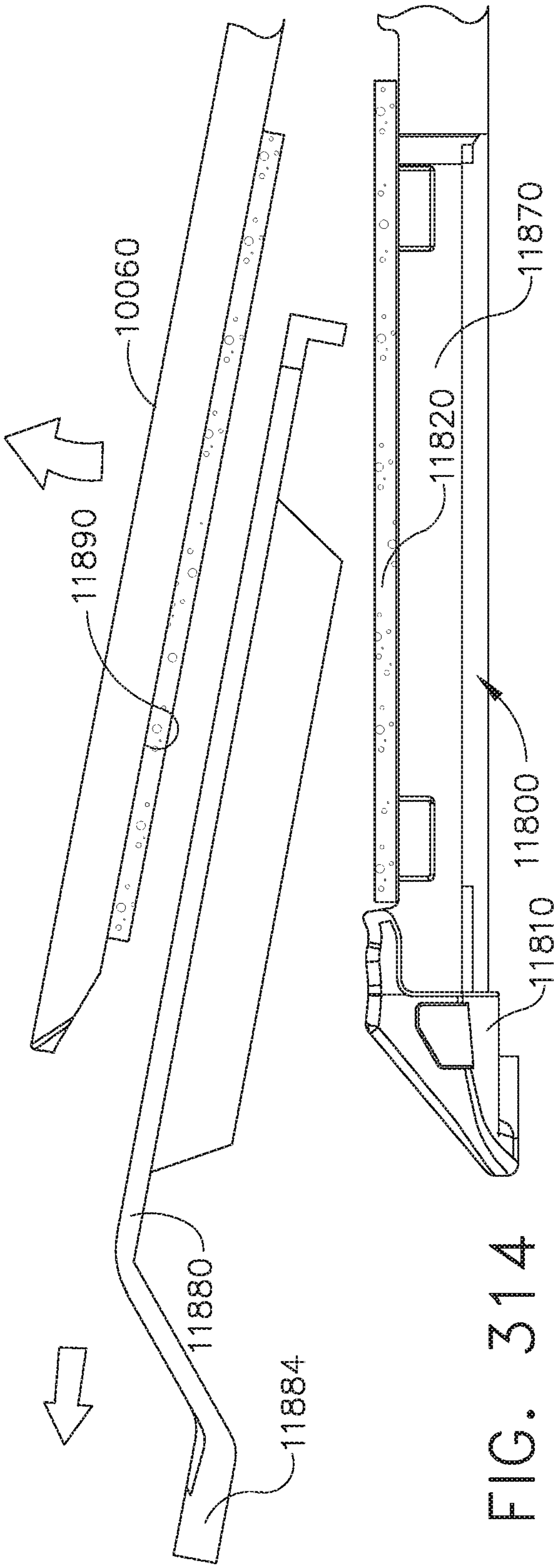
Figure 314B:
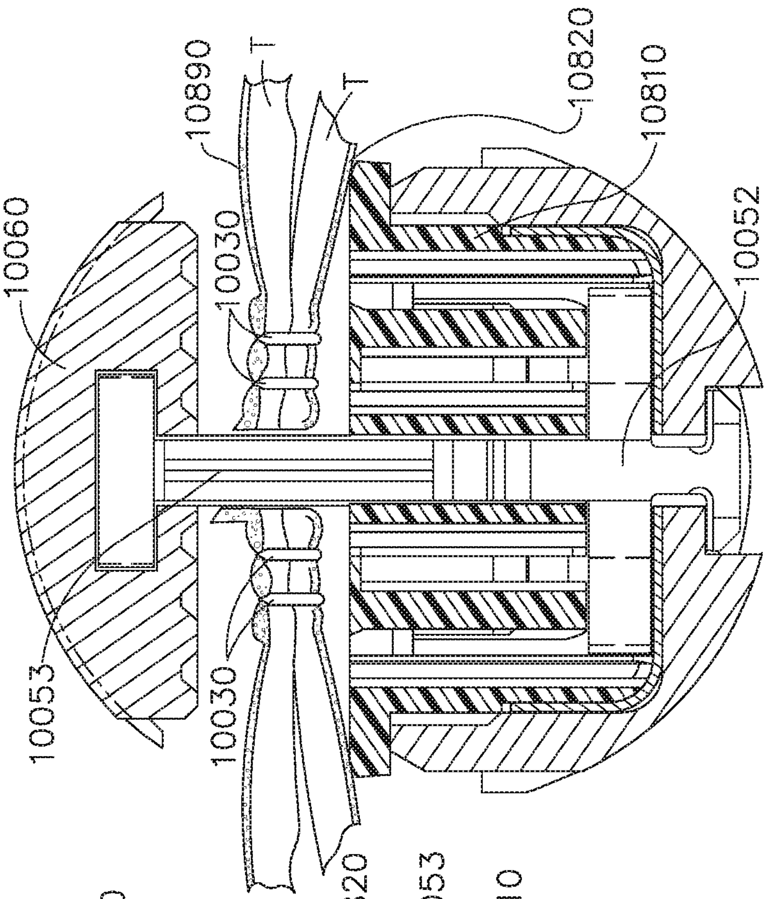
Figure 314A:
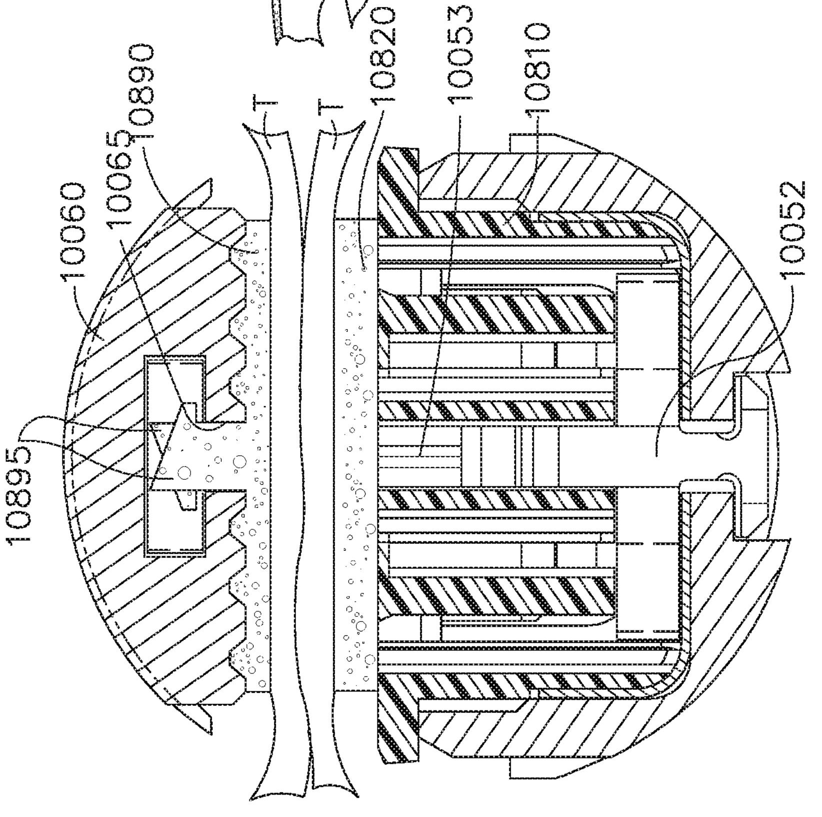
Figure 316:
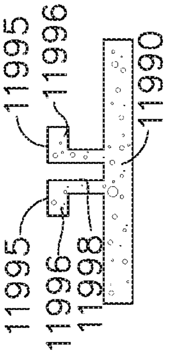
Figure 315:
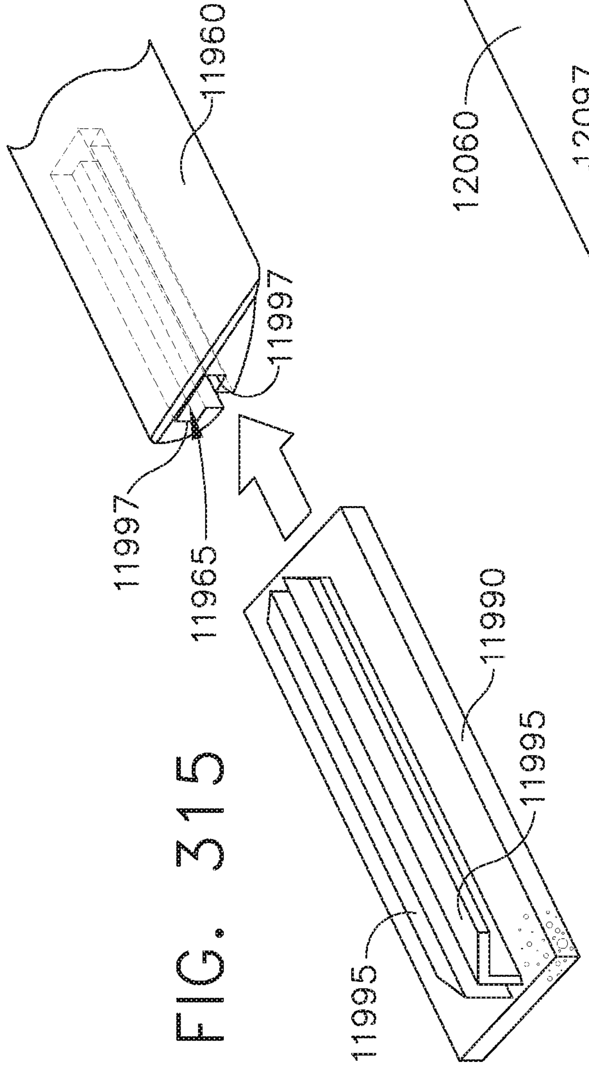
Figure 317:
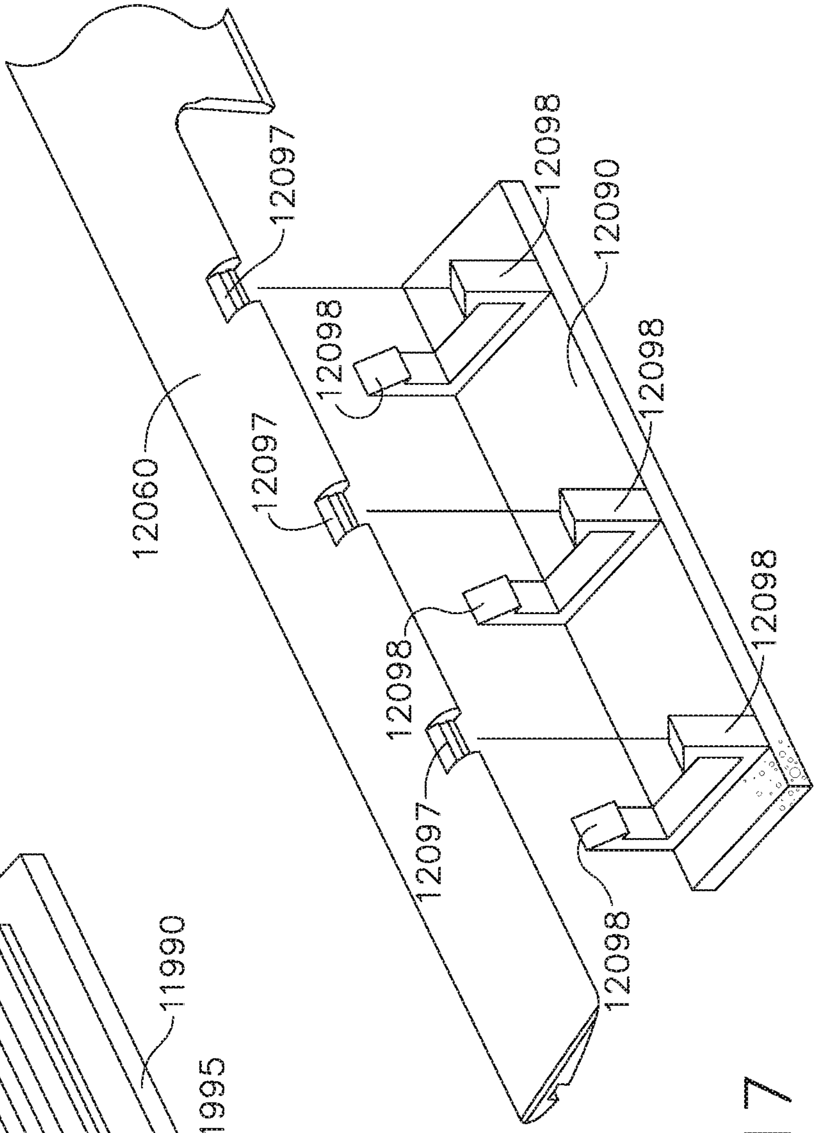
Figure 318:
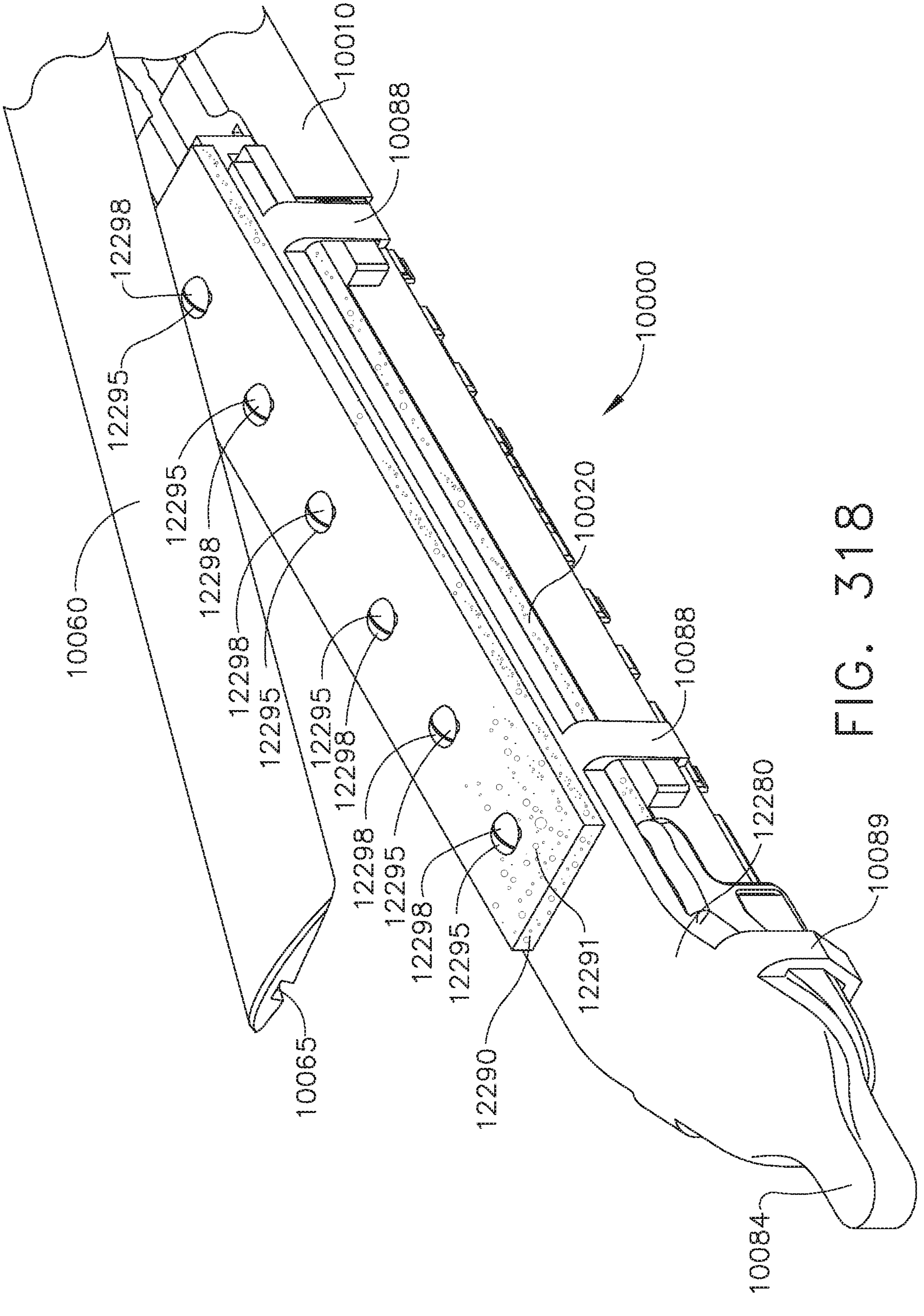
Figure 319:
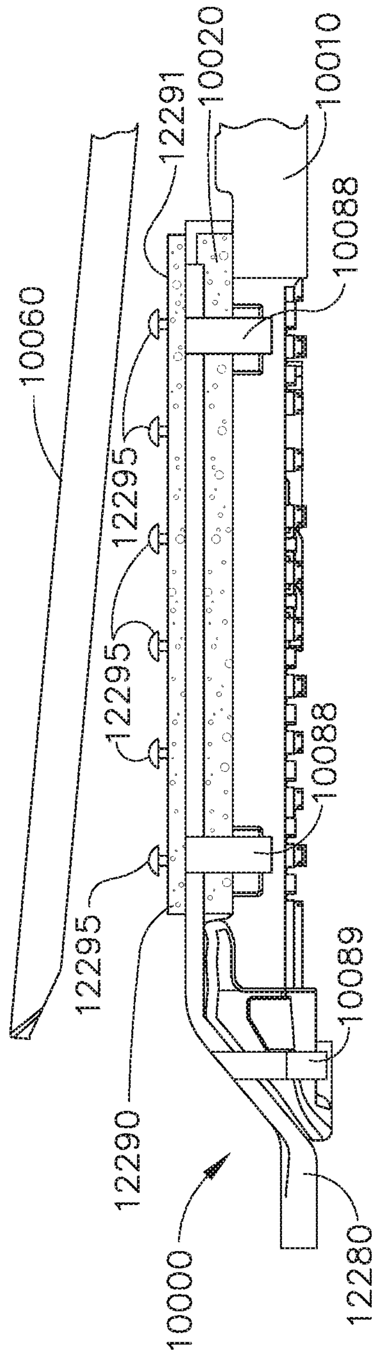
Figure 320:
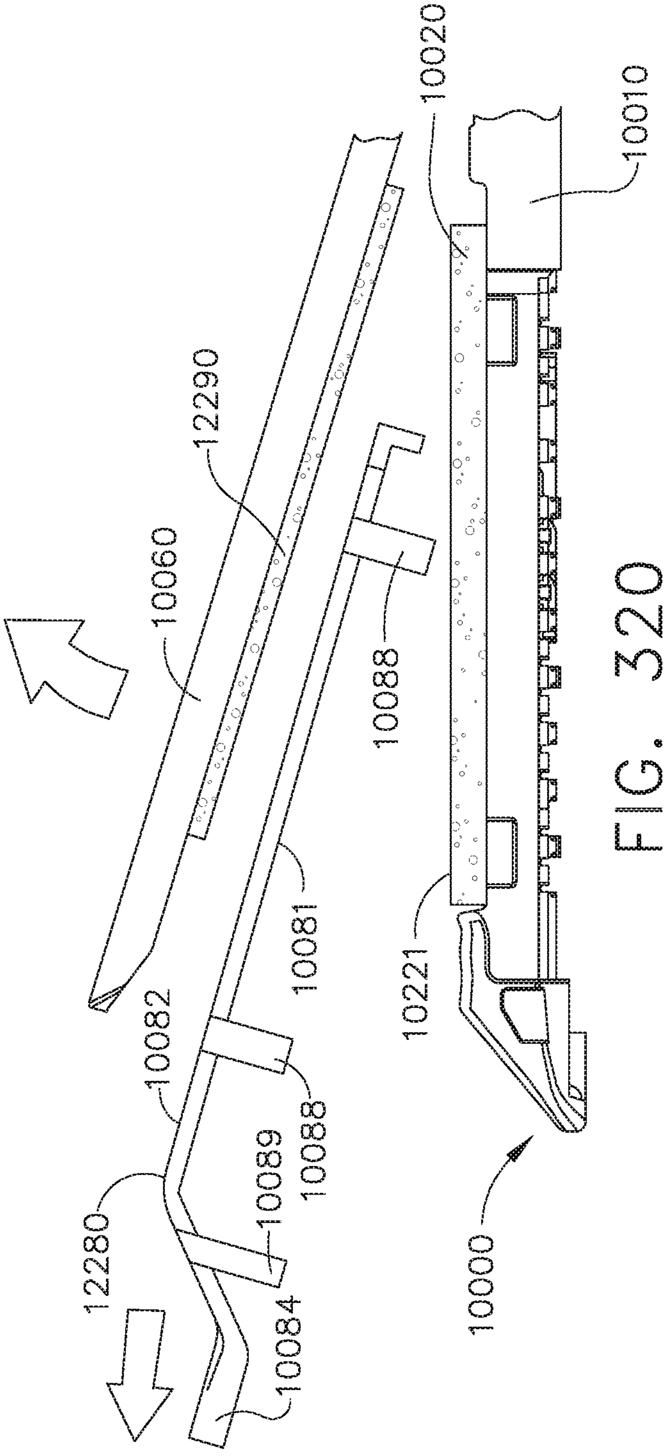
Figure 322:
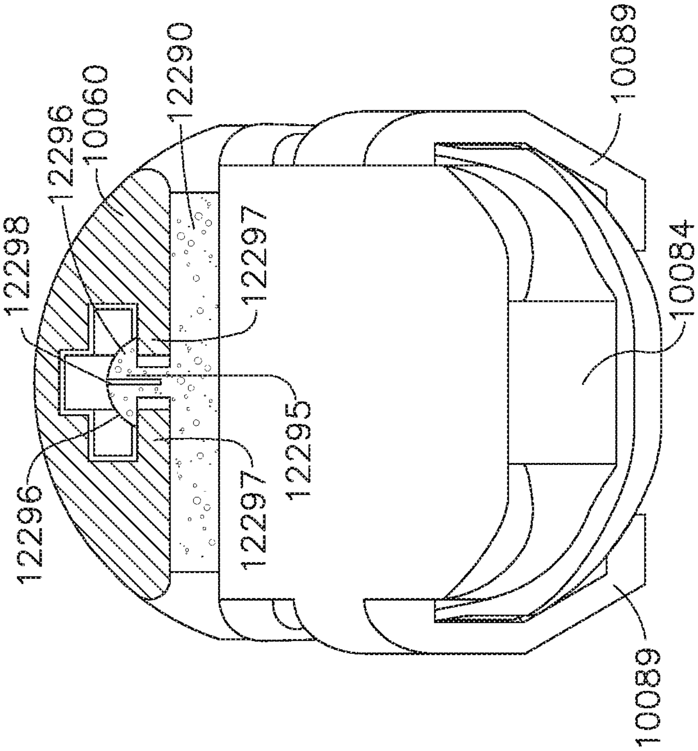
Figure 321:
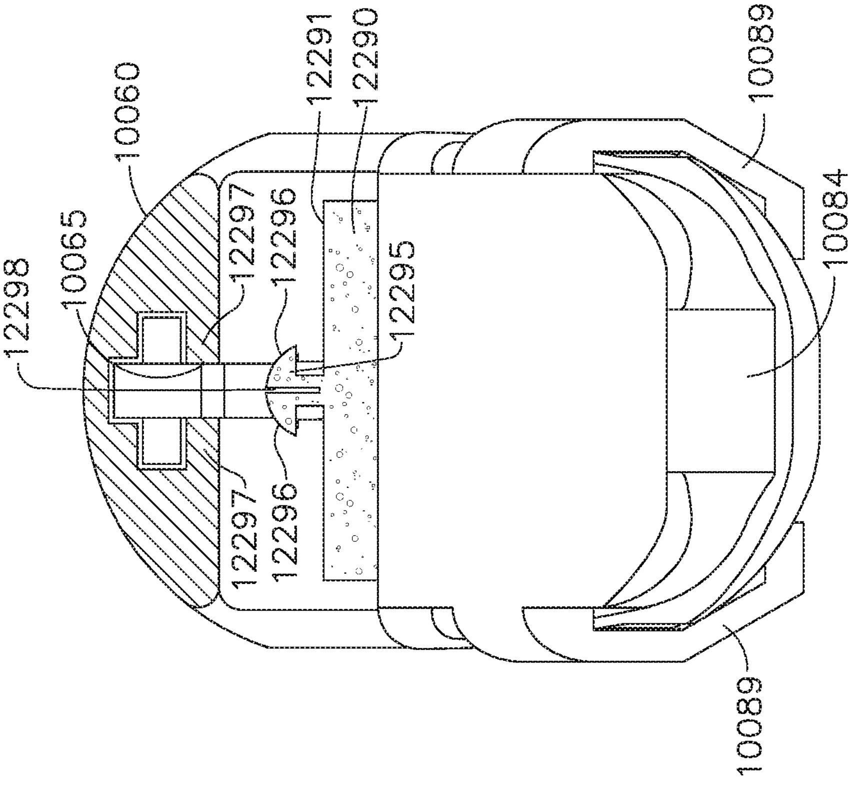
Figure 323:
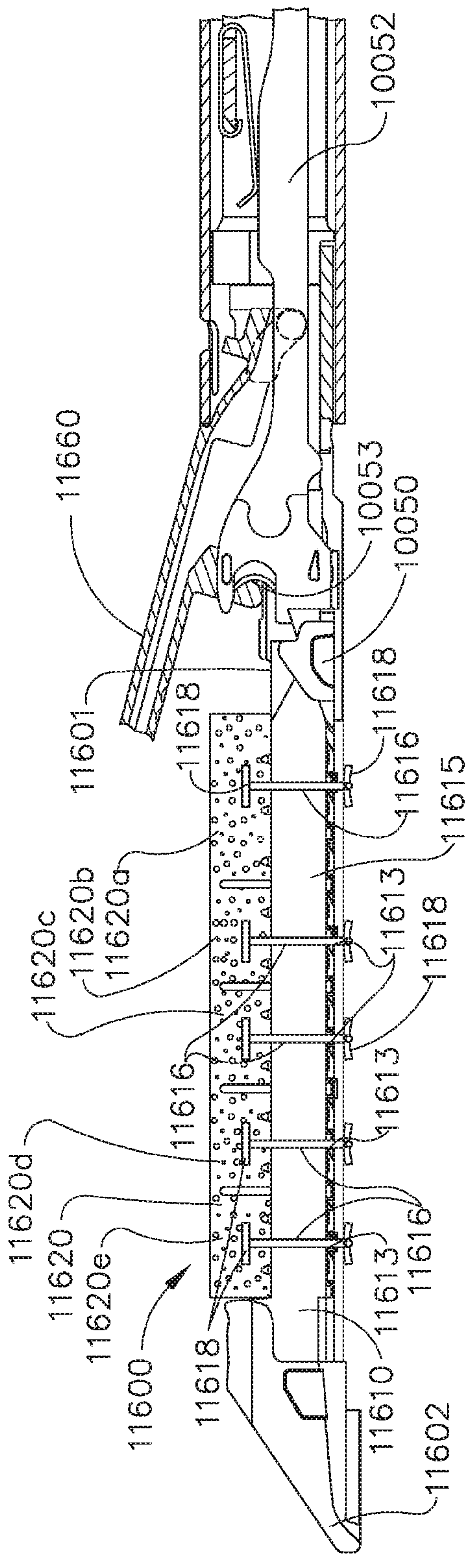
Figures 324, 325:
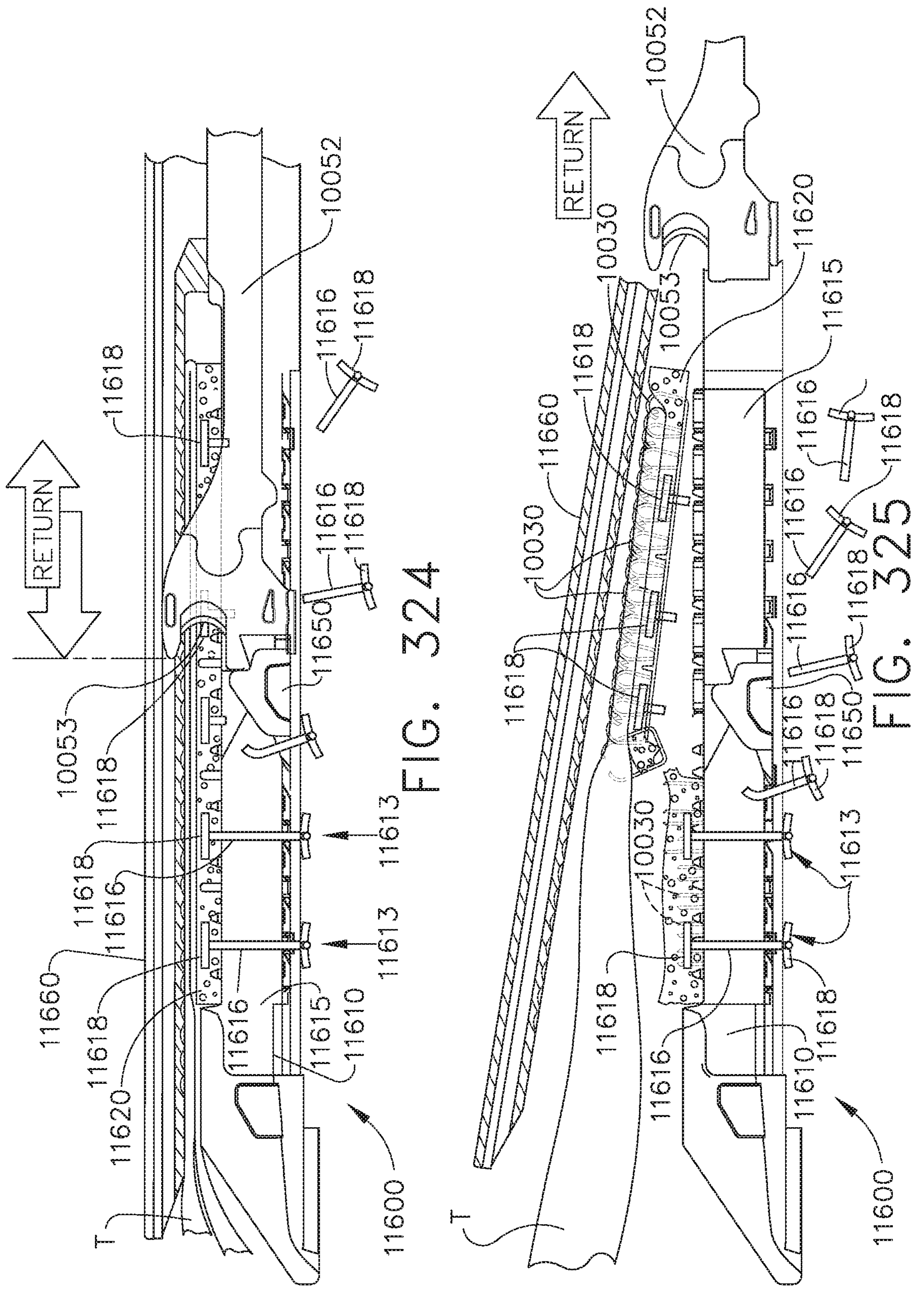
Figure 326:
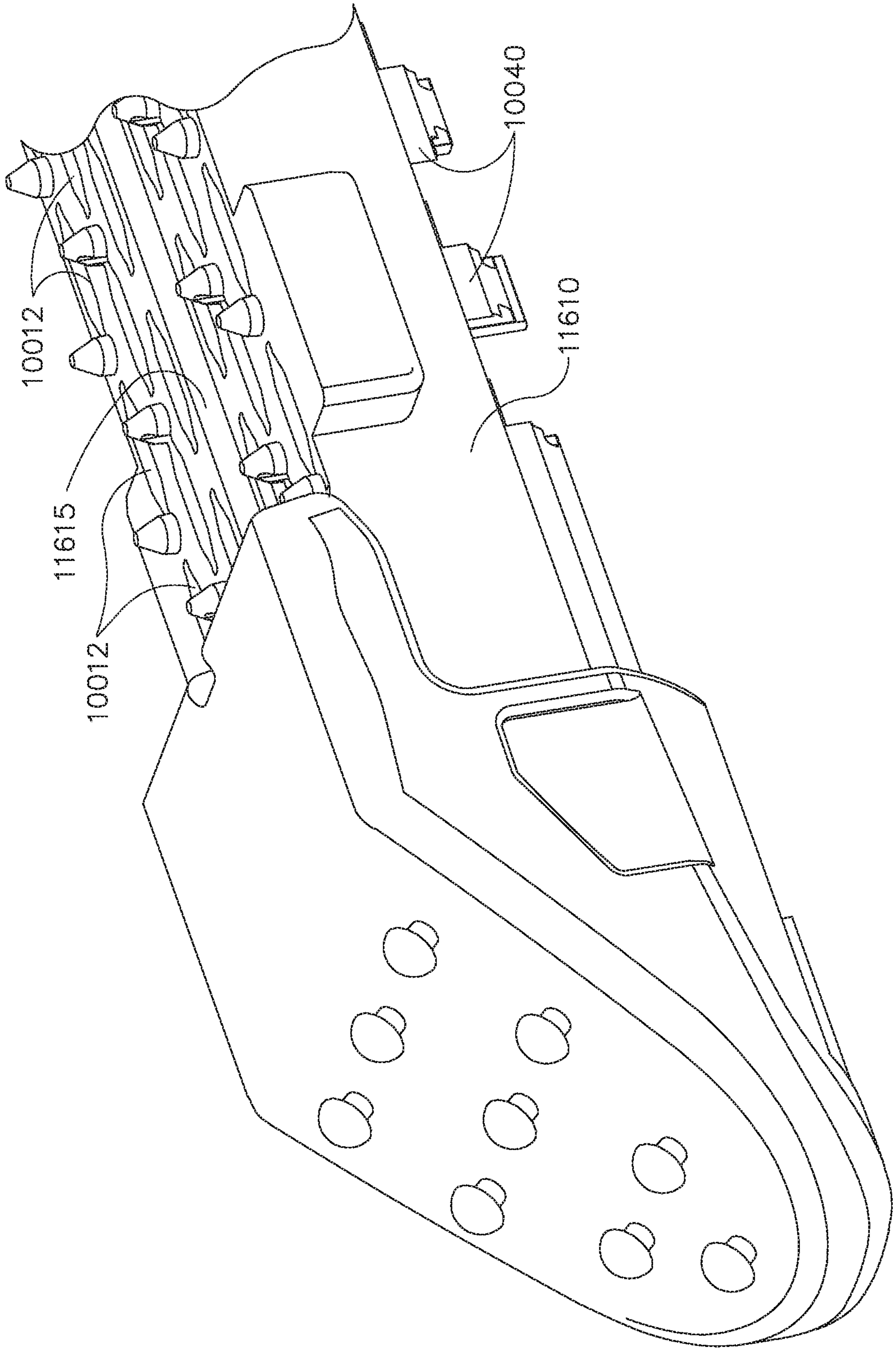
Figure 327:
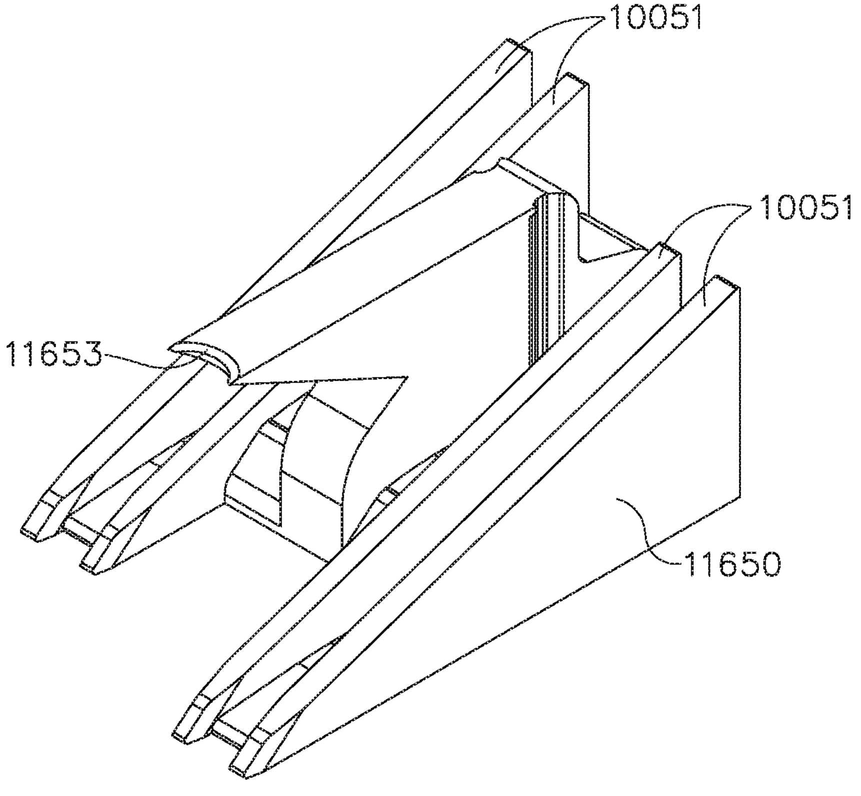
Figure 328:
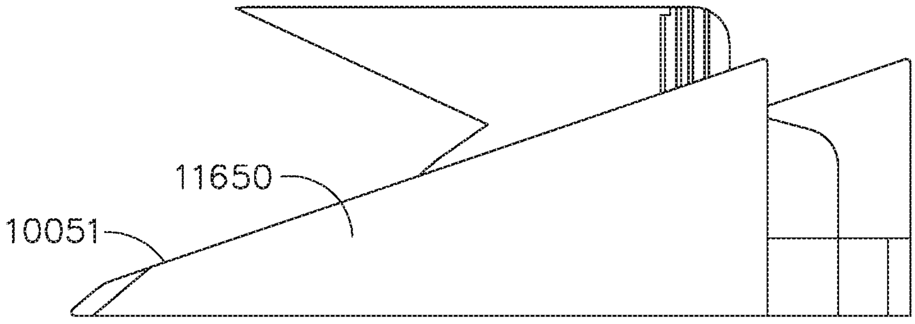
Figure 329:
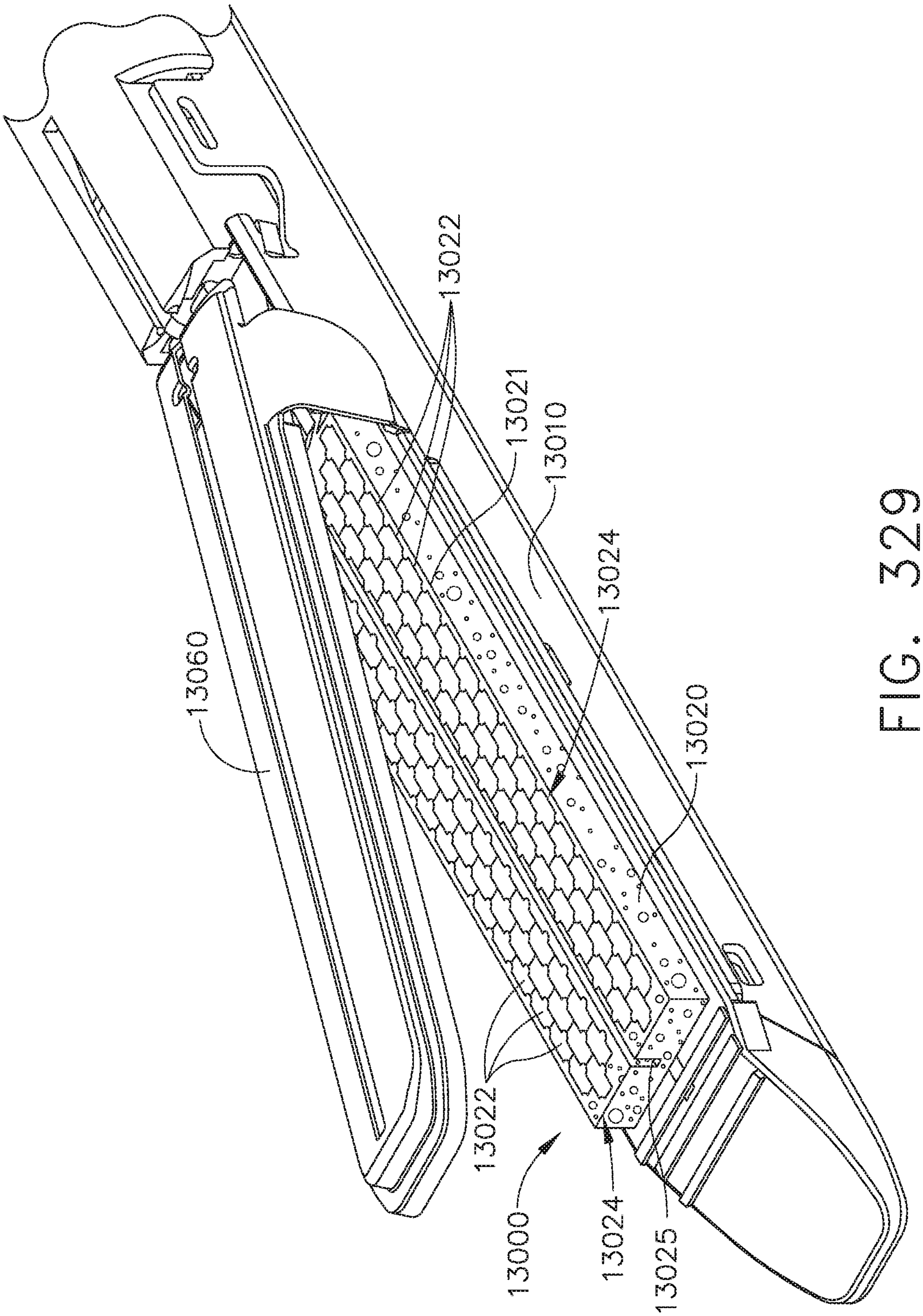
Figure 330:
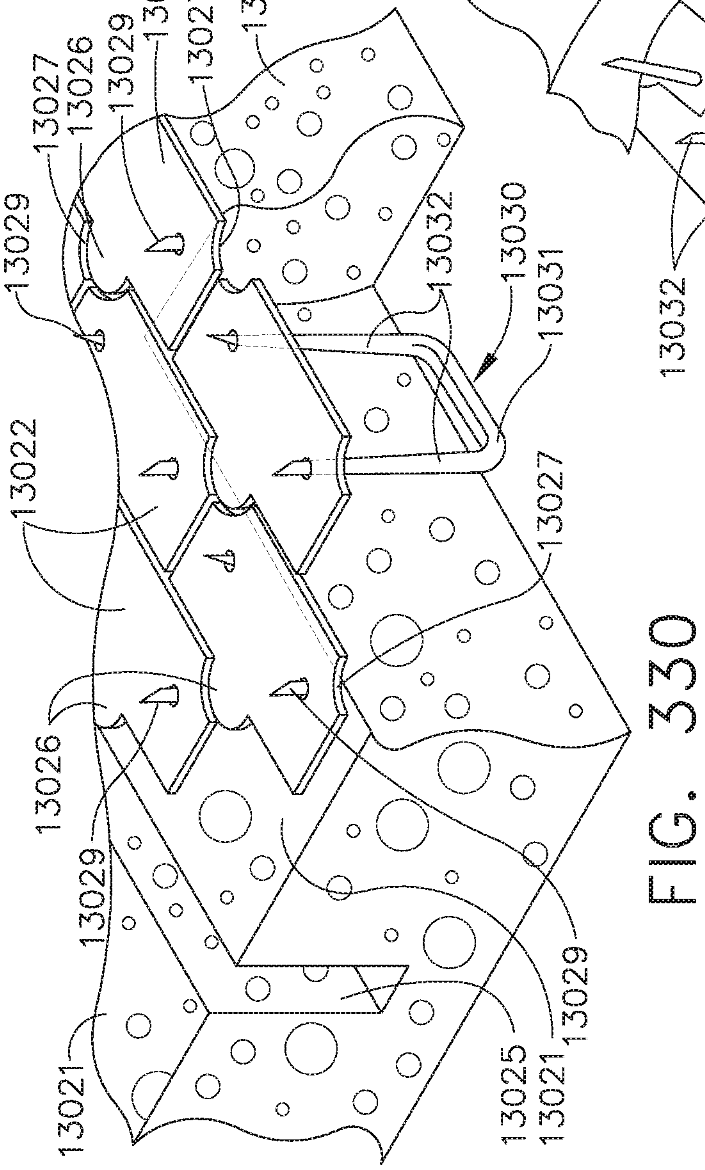
Figure 331:
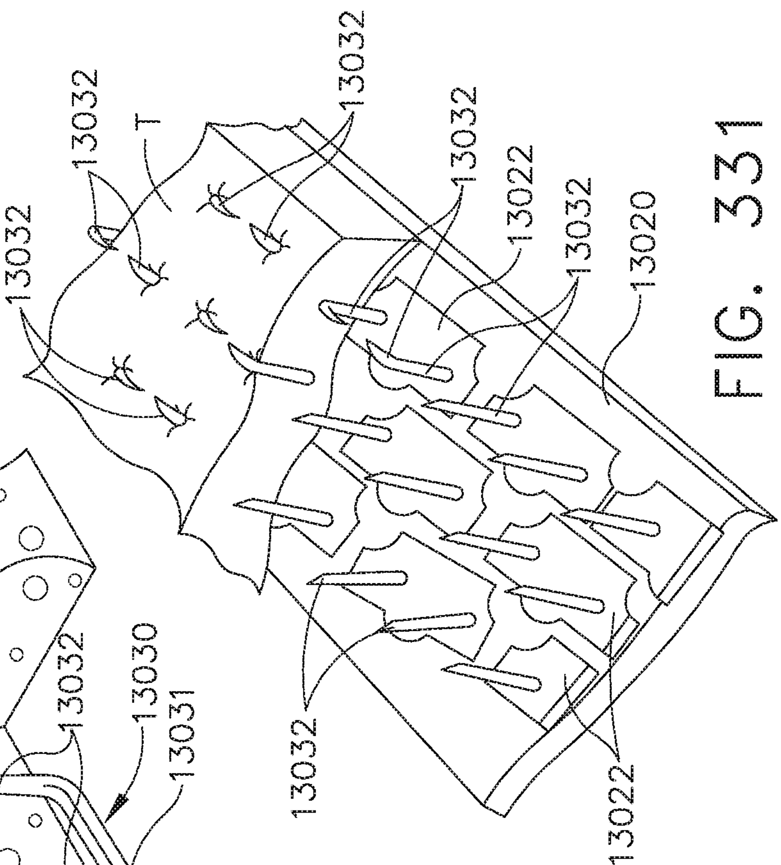
Figure 333:
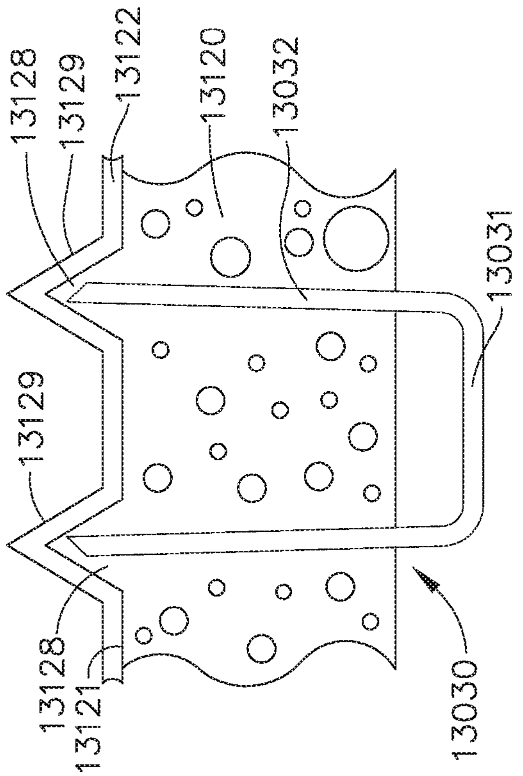
Figure 335:
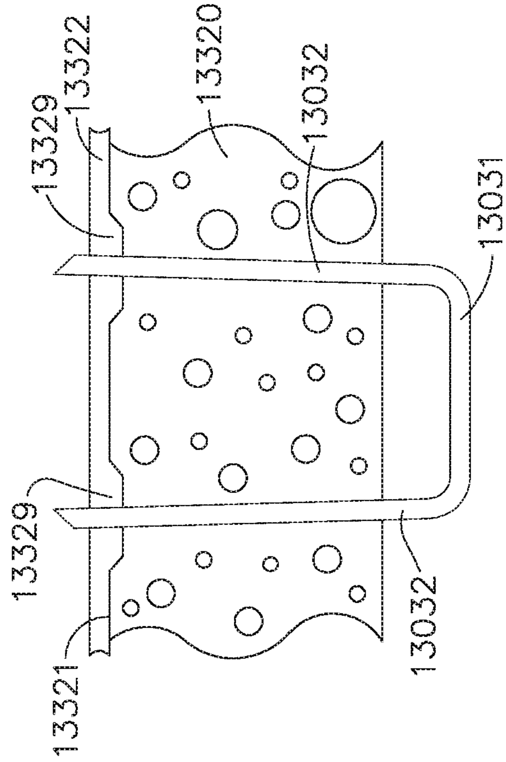
Figure 332:
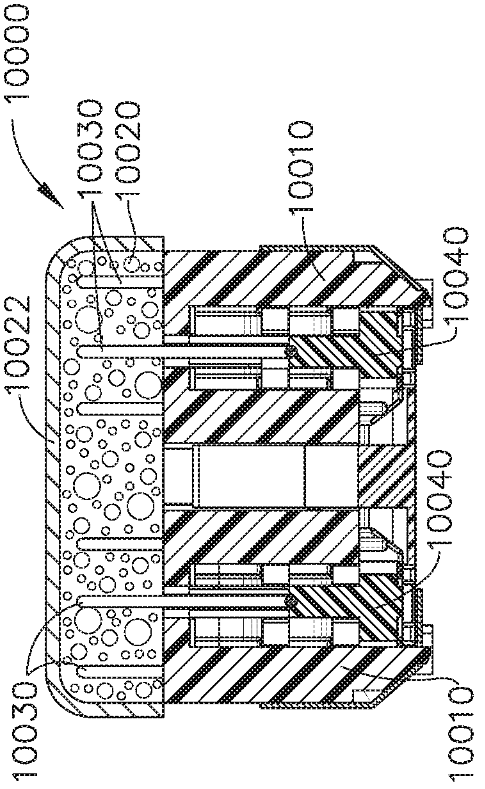
Figure 334:
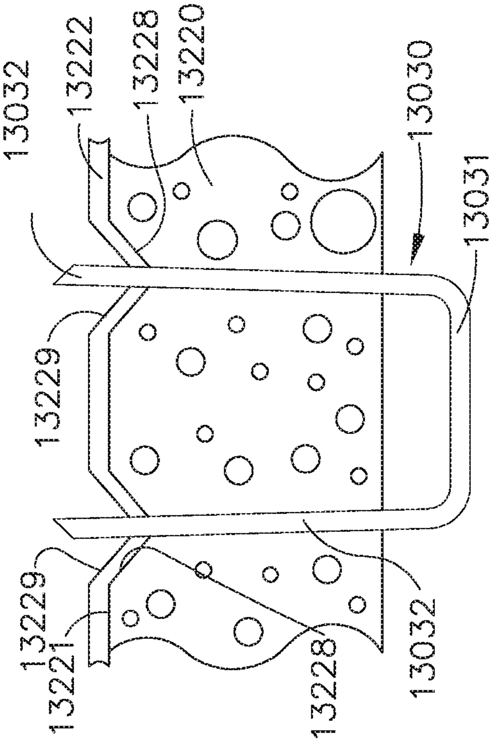
Figure 337:
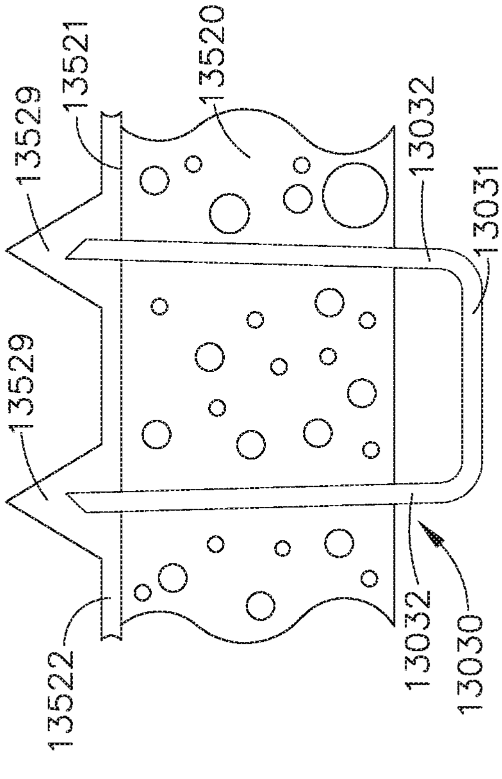
Figure 338:
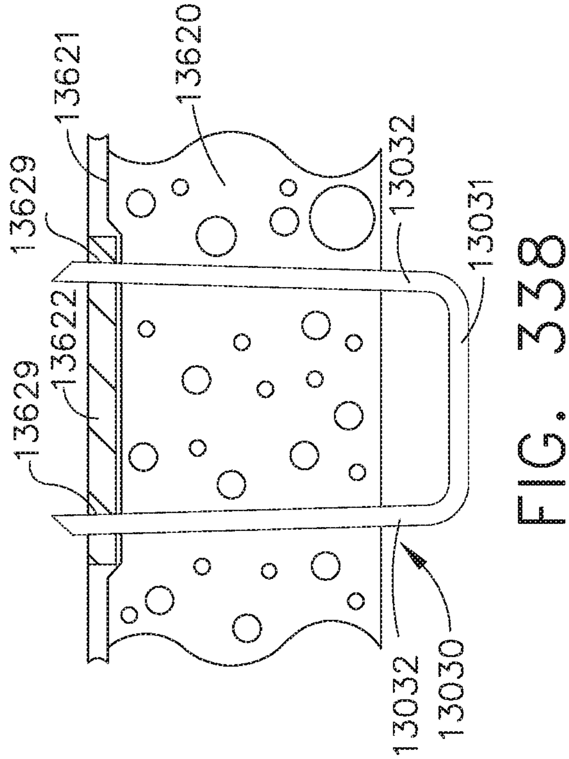
Figure 336:
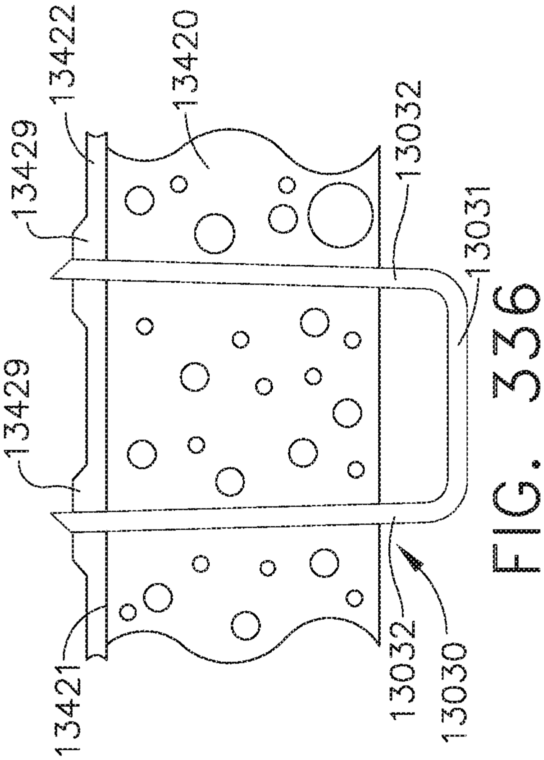
Figure 340:
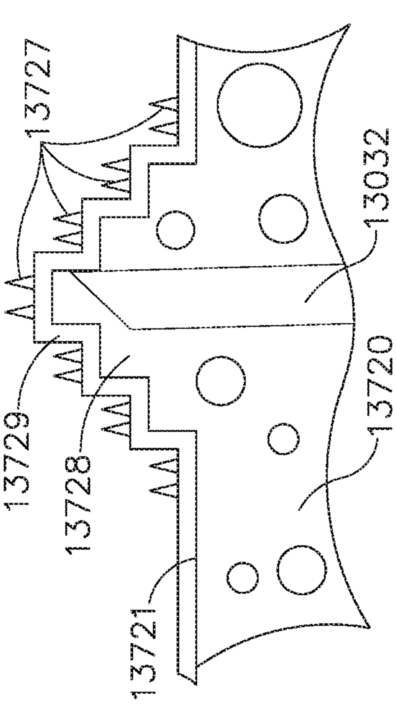
Figure 342:
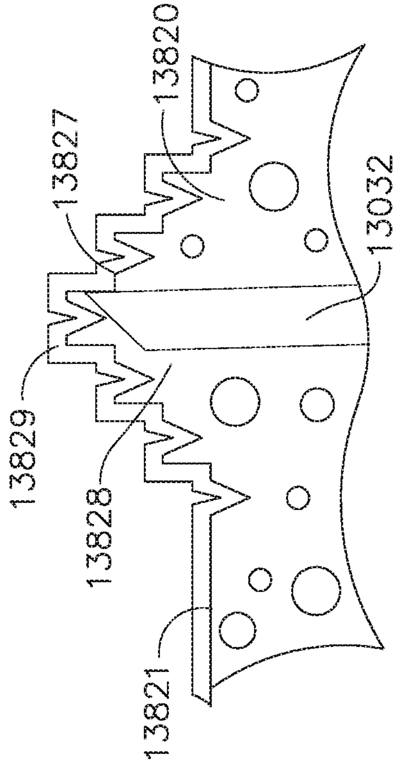
Figure 339:
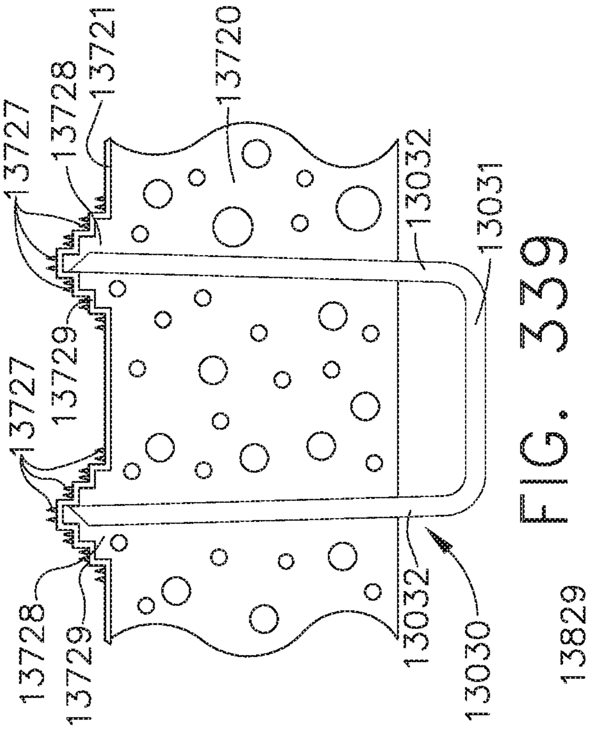
Figure 341:
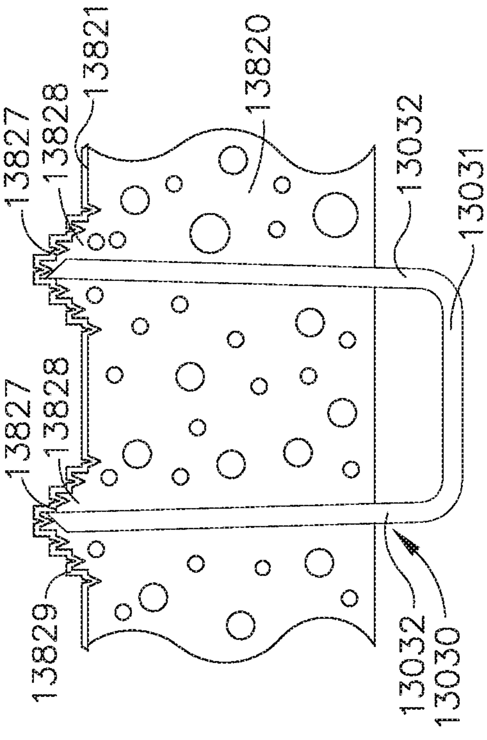
Figure 344:
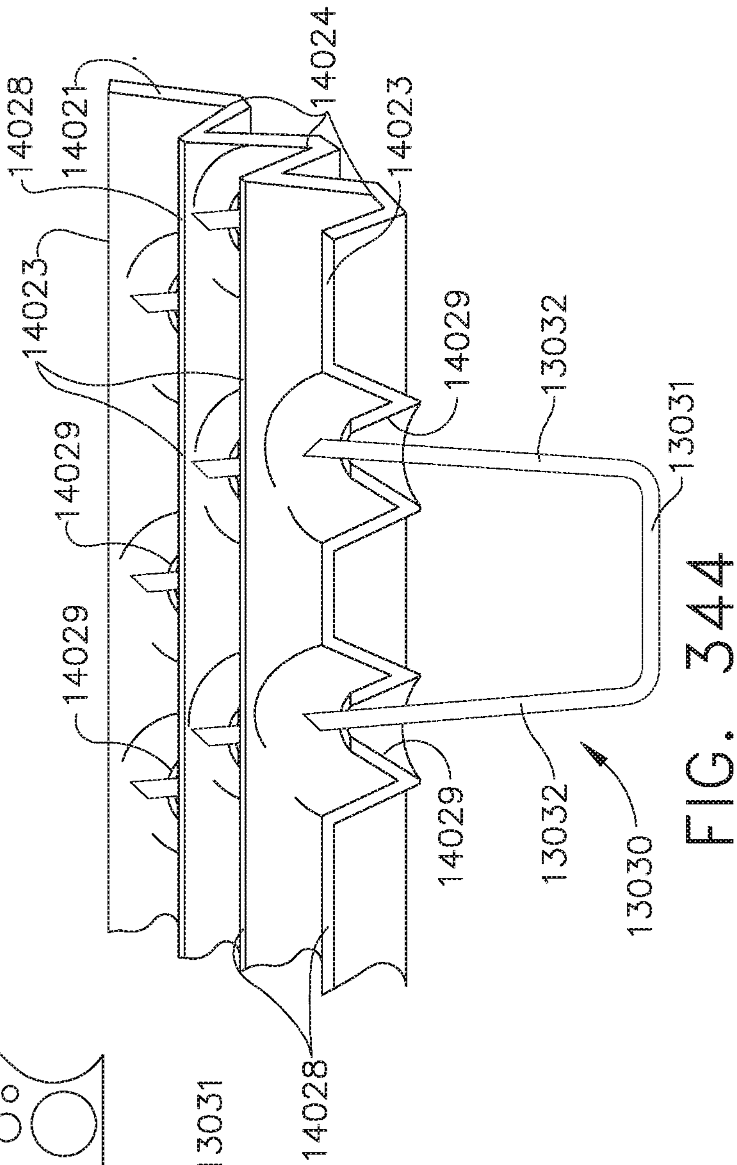
Figure 343:
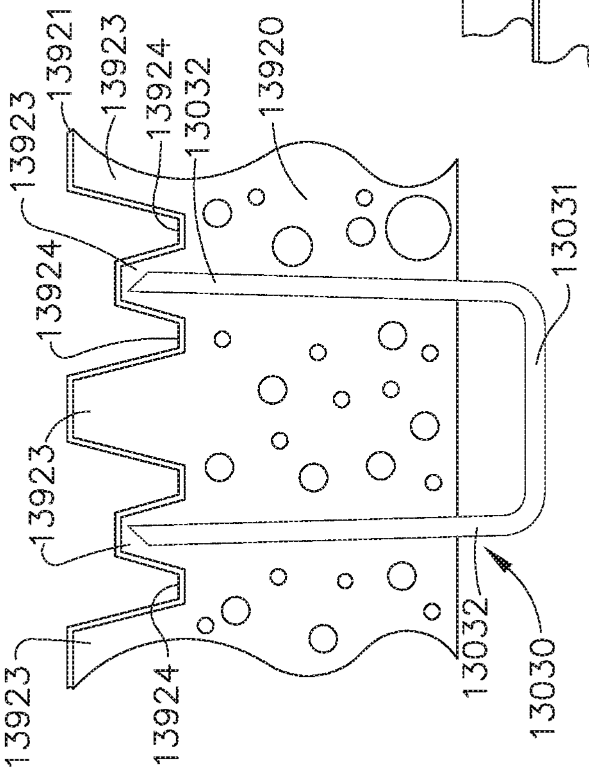
Figure 346:
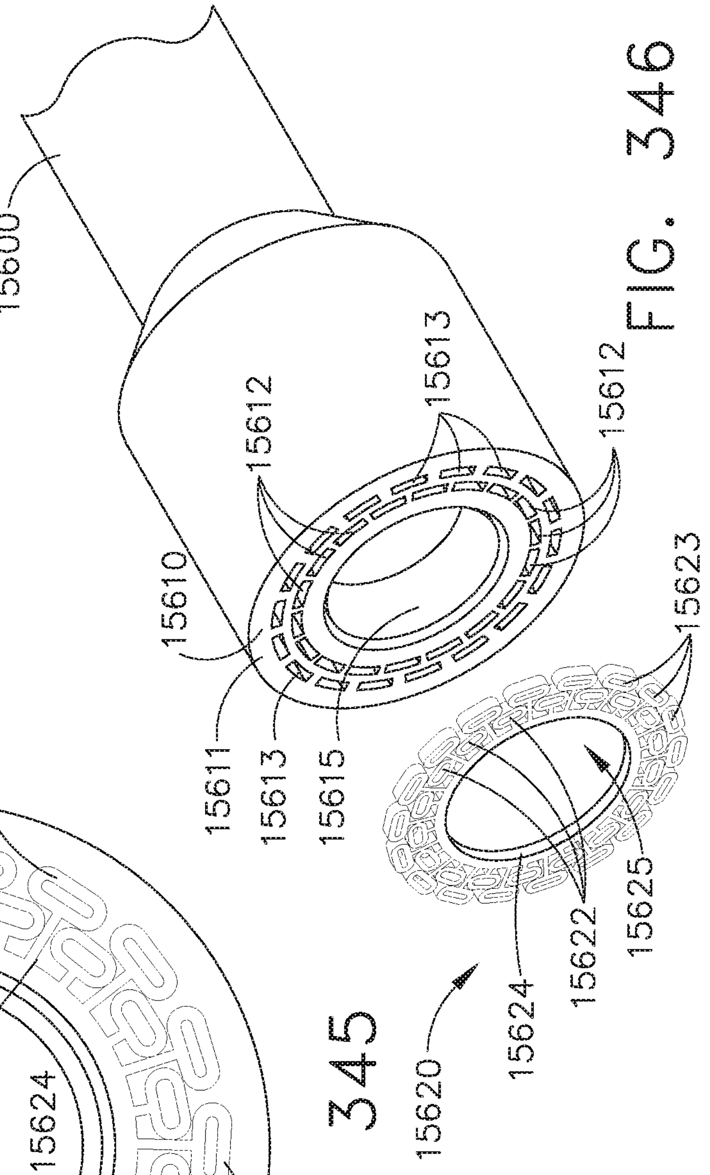
Figure 345:
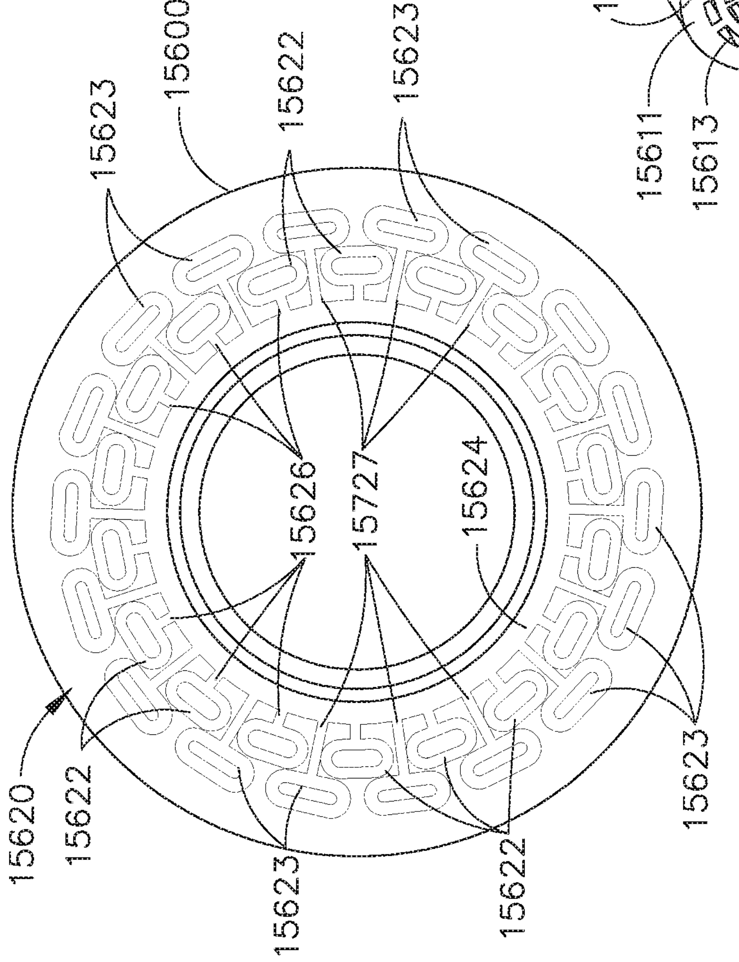
Figure 348:
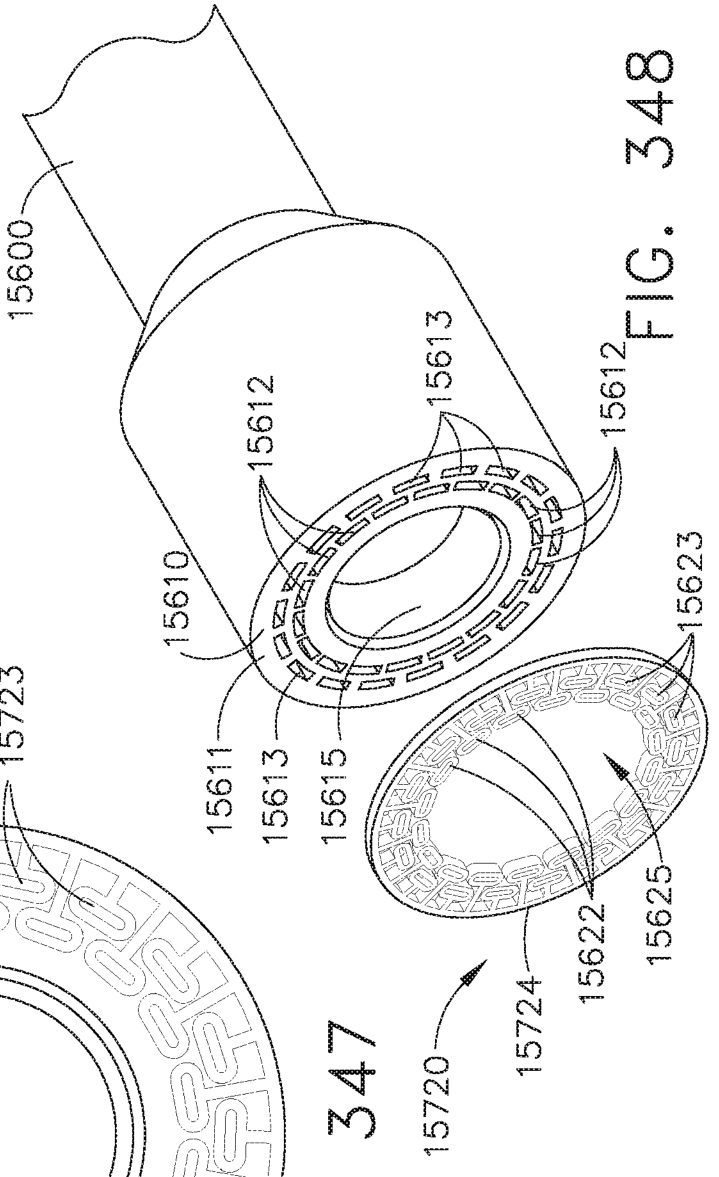
Figure 347:
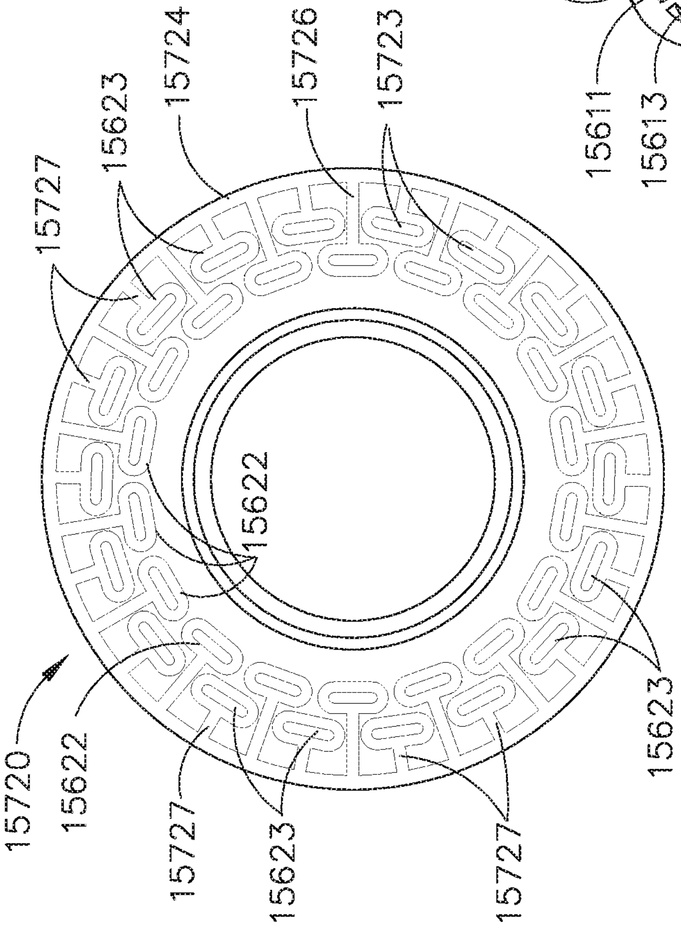
Figure 350:
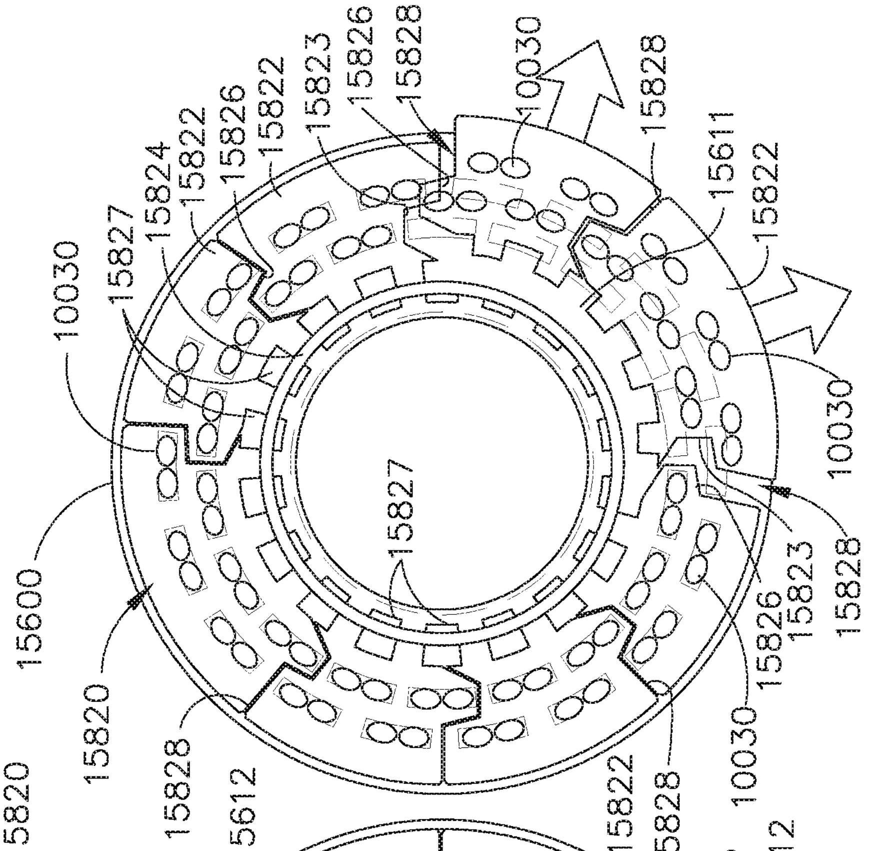
Figure 349:
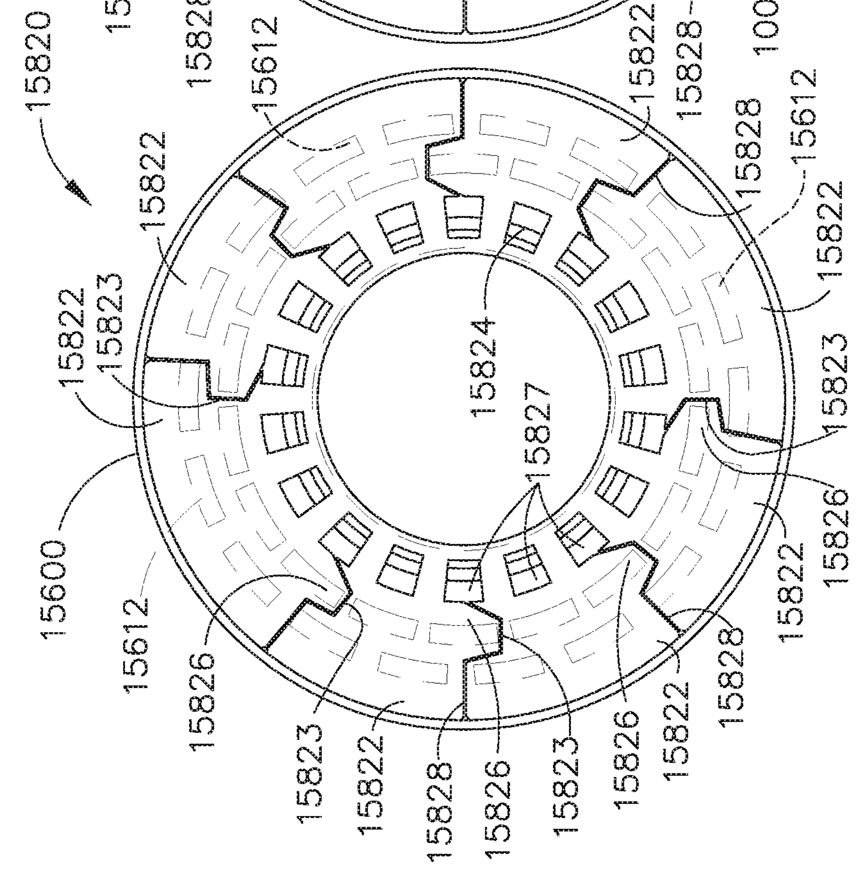
Figure 351:
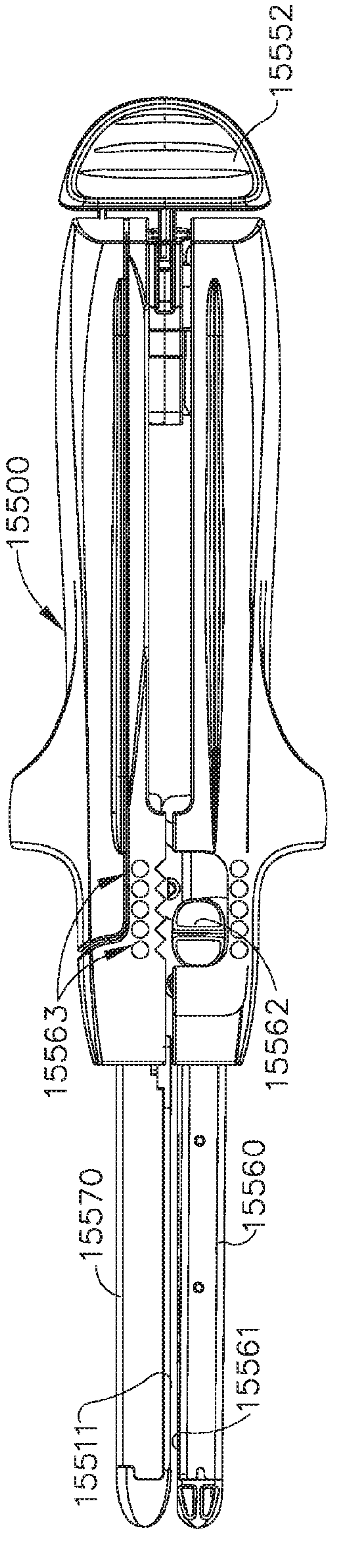
Figure 353:
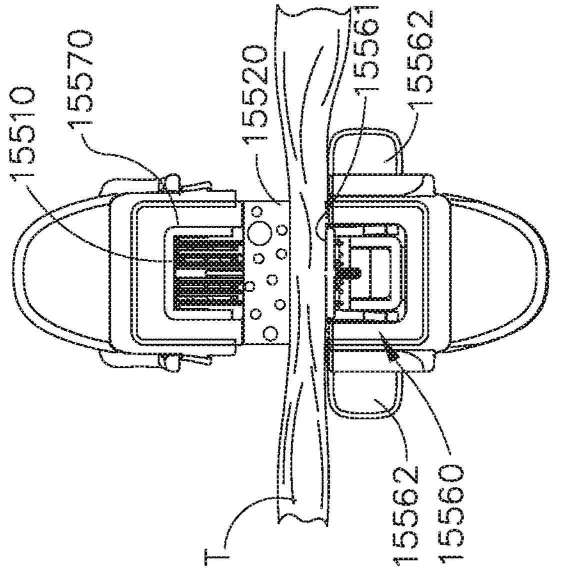
Figure 352:
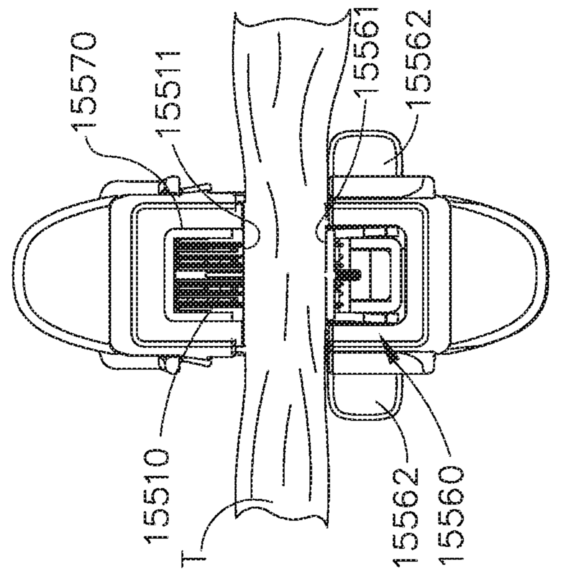
Figure 355:
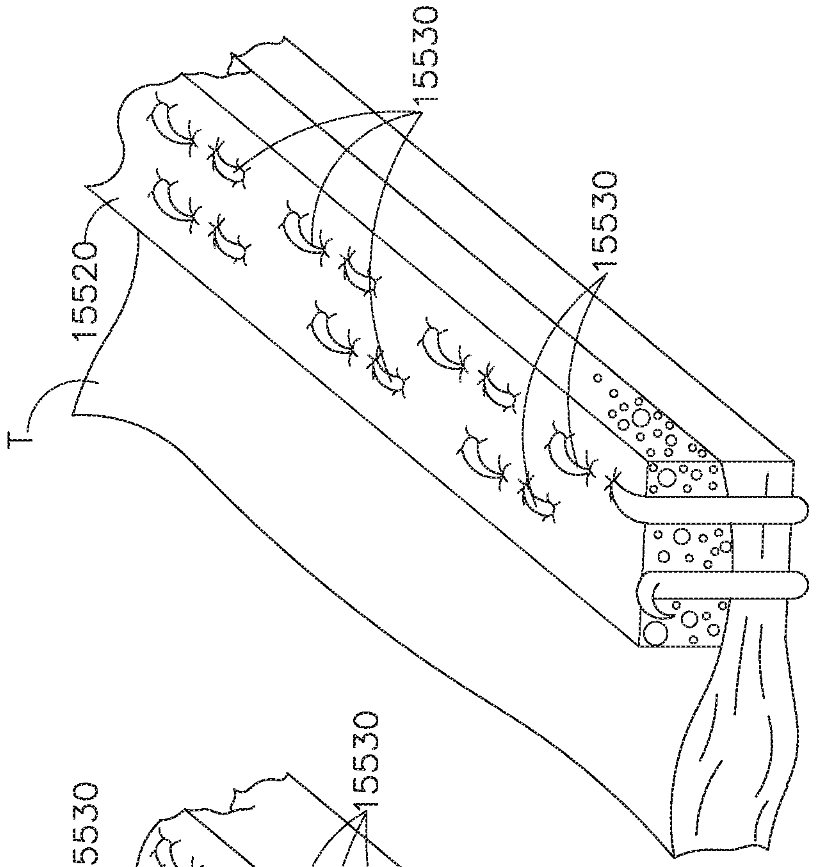
Figure 354:
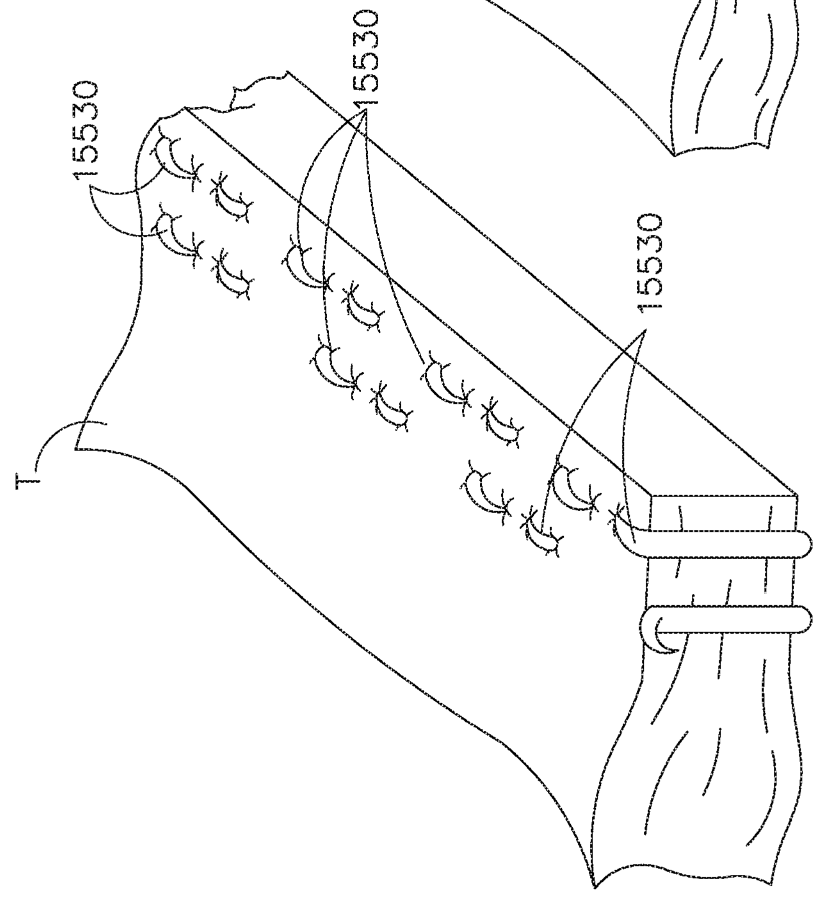
Figure 356:
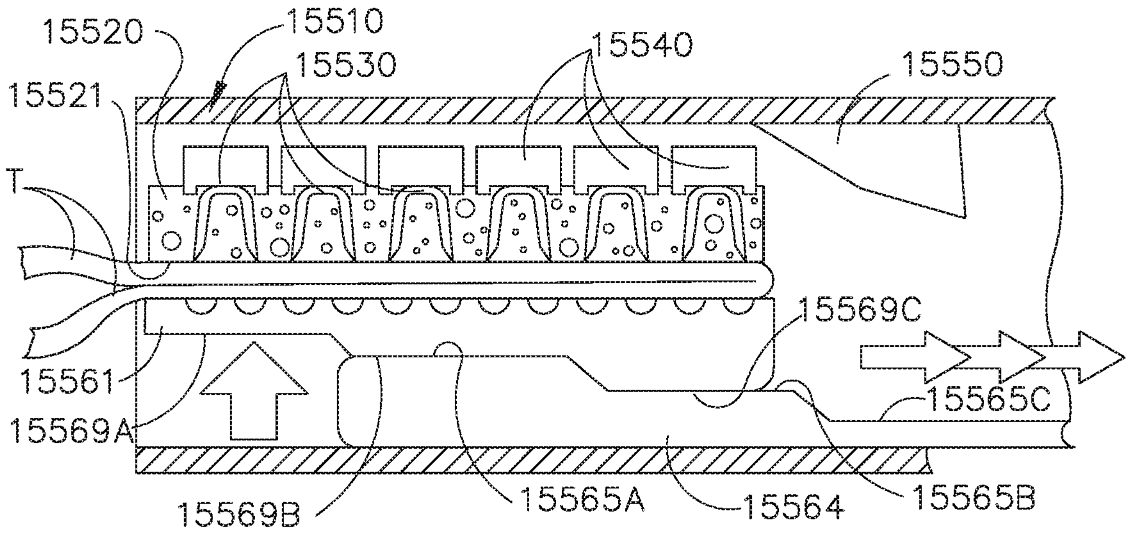
Figure 357:
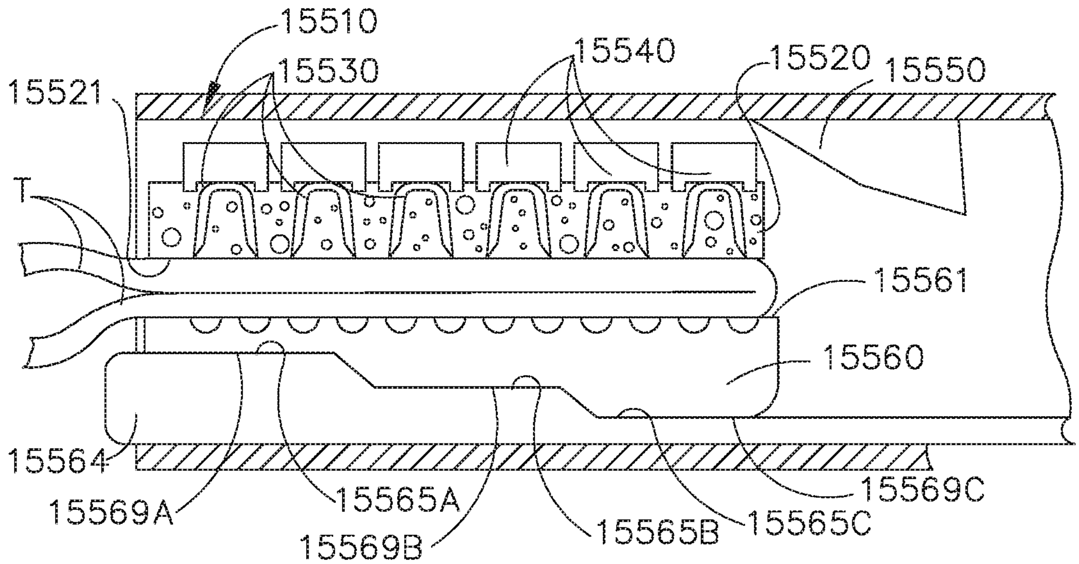
Figure 358:
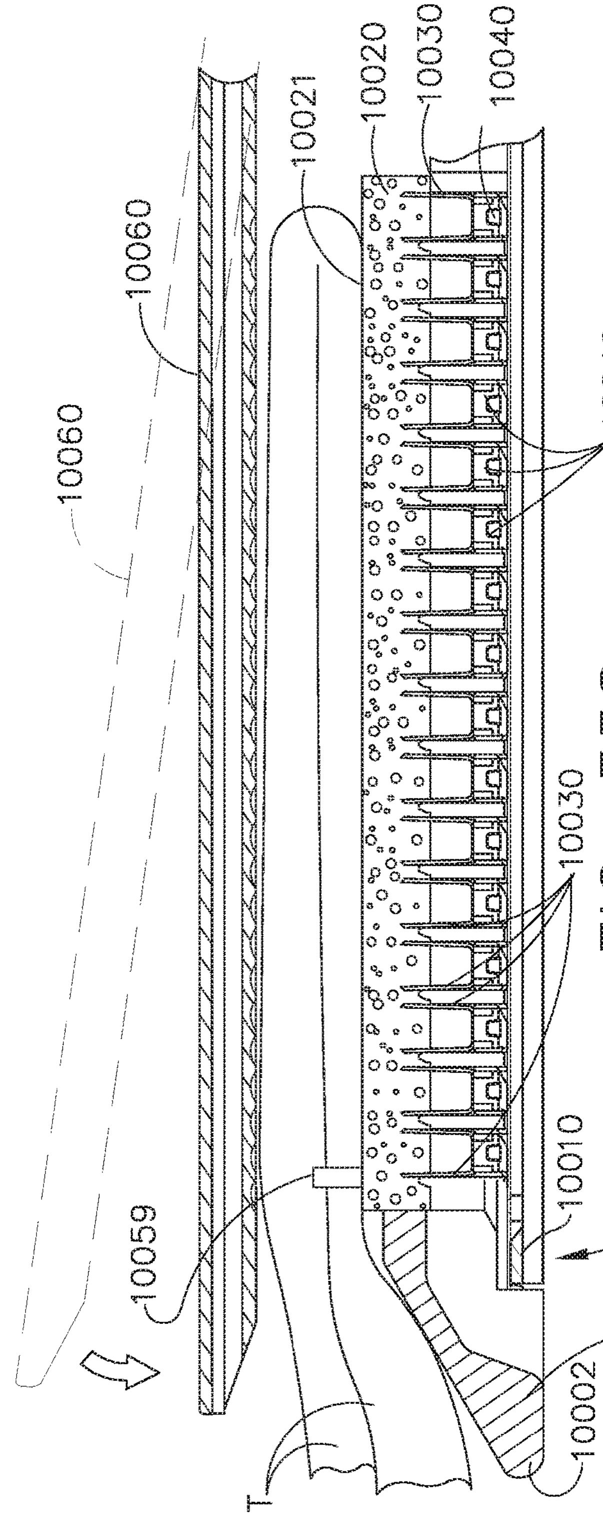
Figure 359:
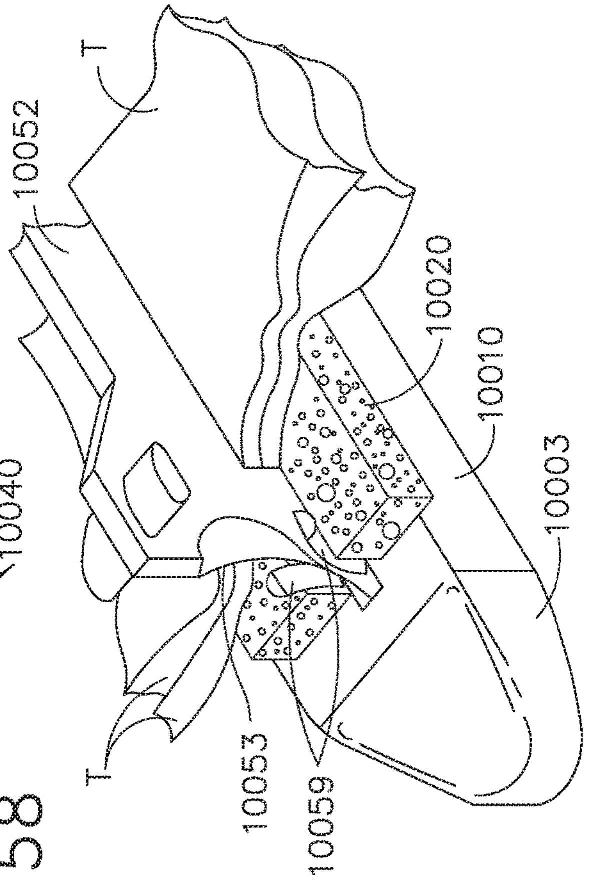
Figure 360:
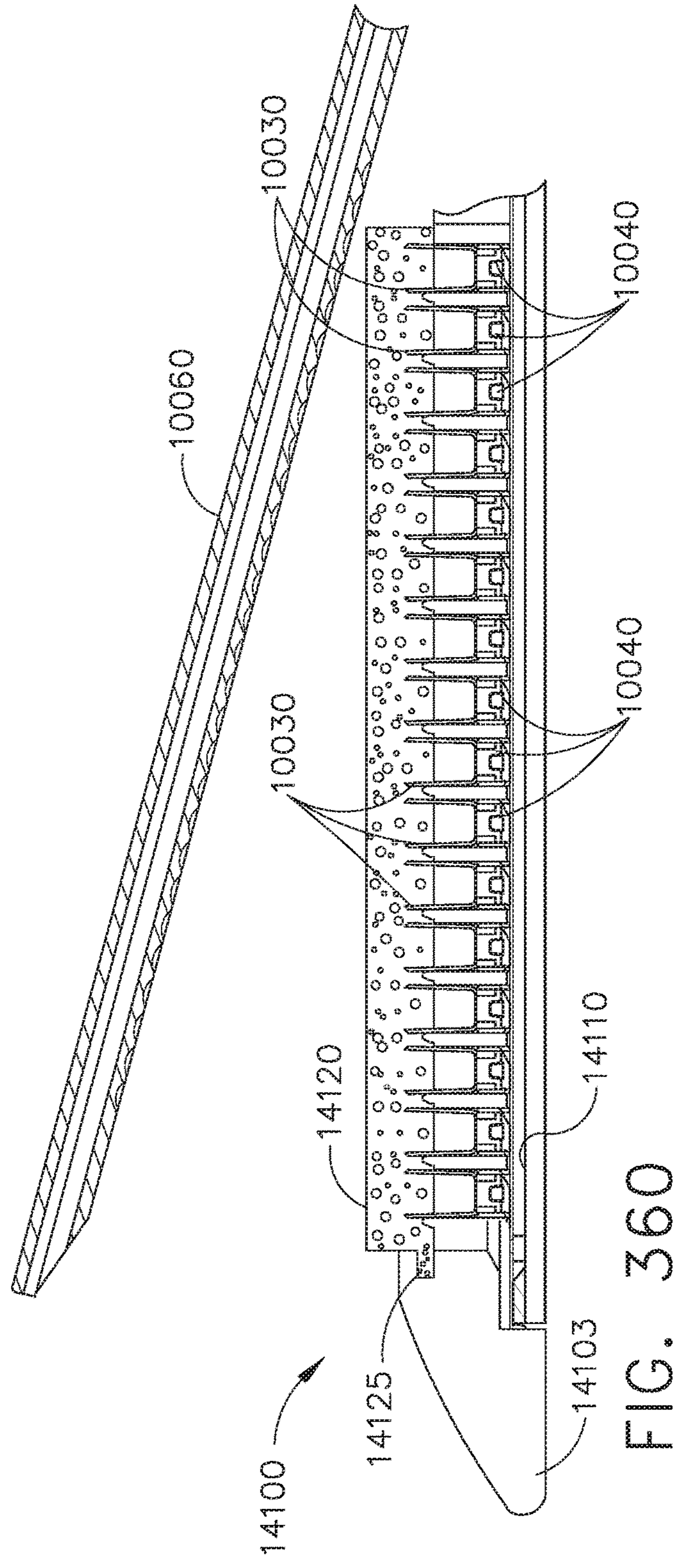
Figure 361:
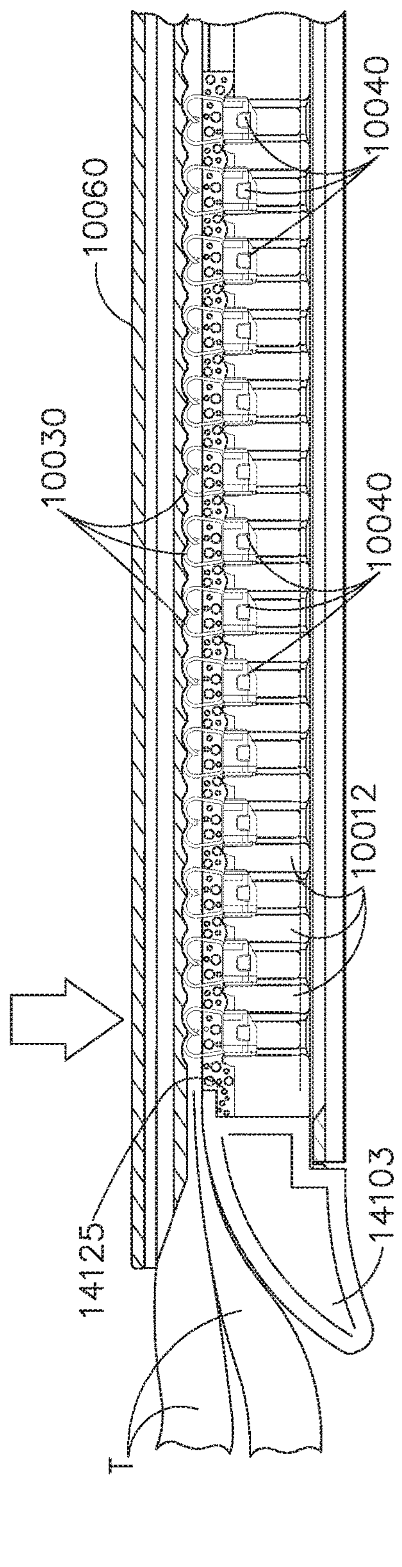
Figure 362:
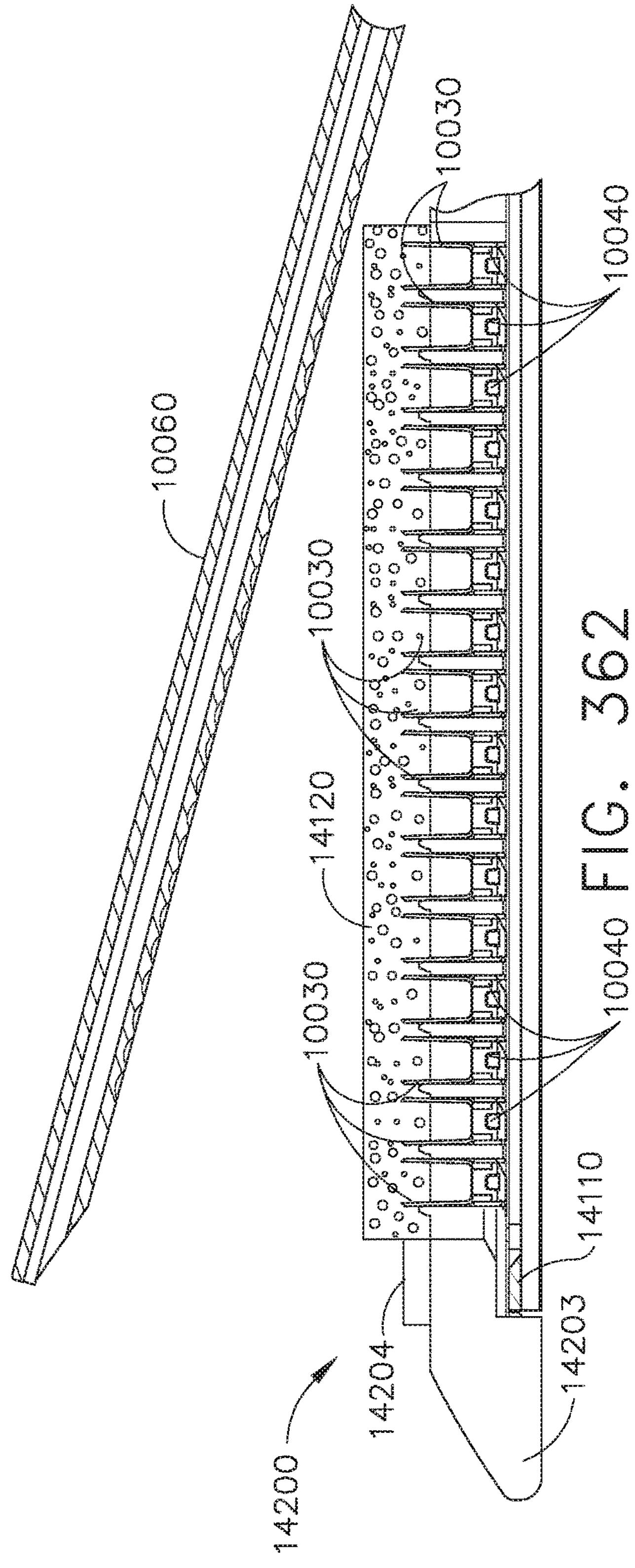
Figure 363:
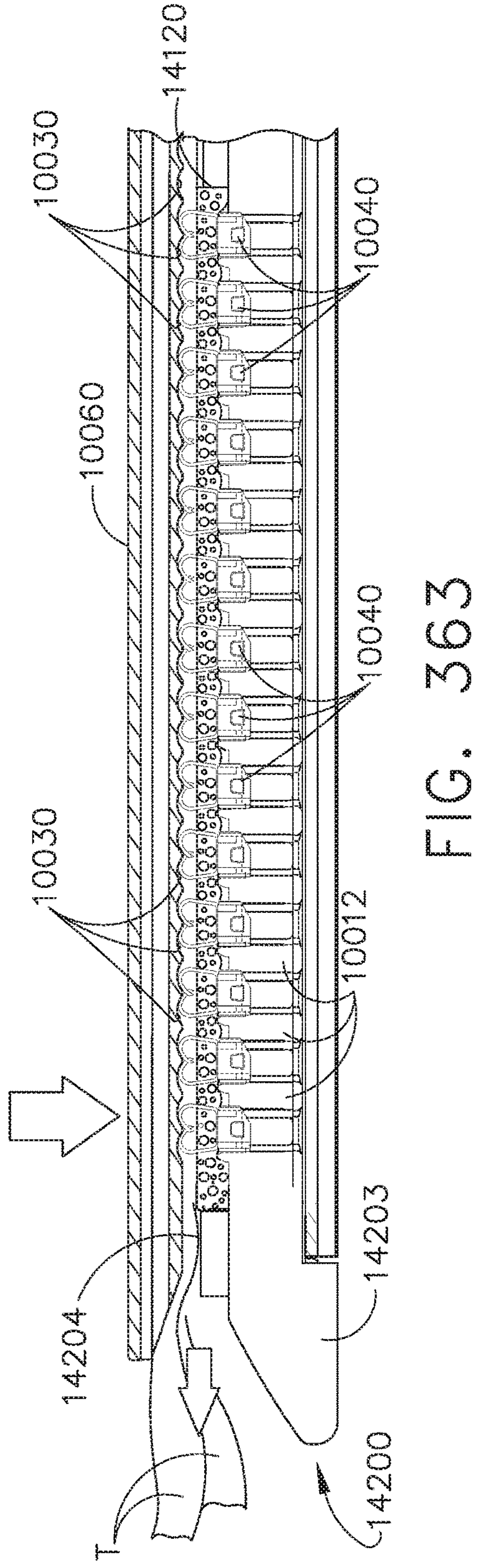
Figure 364:
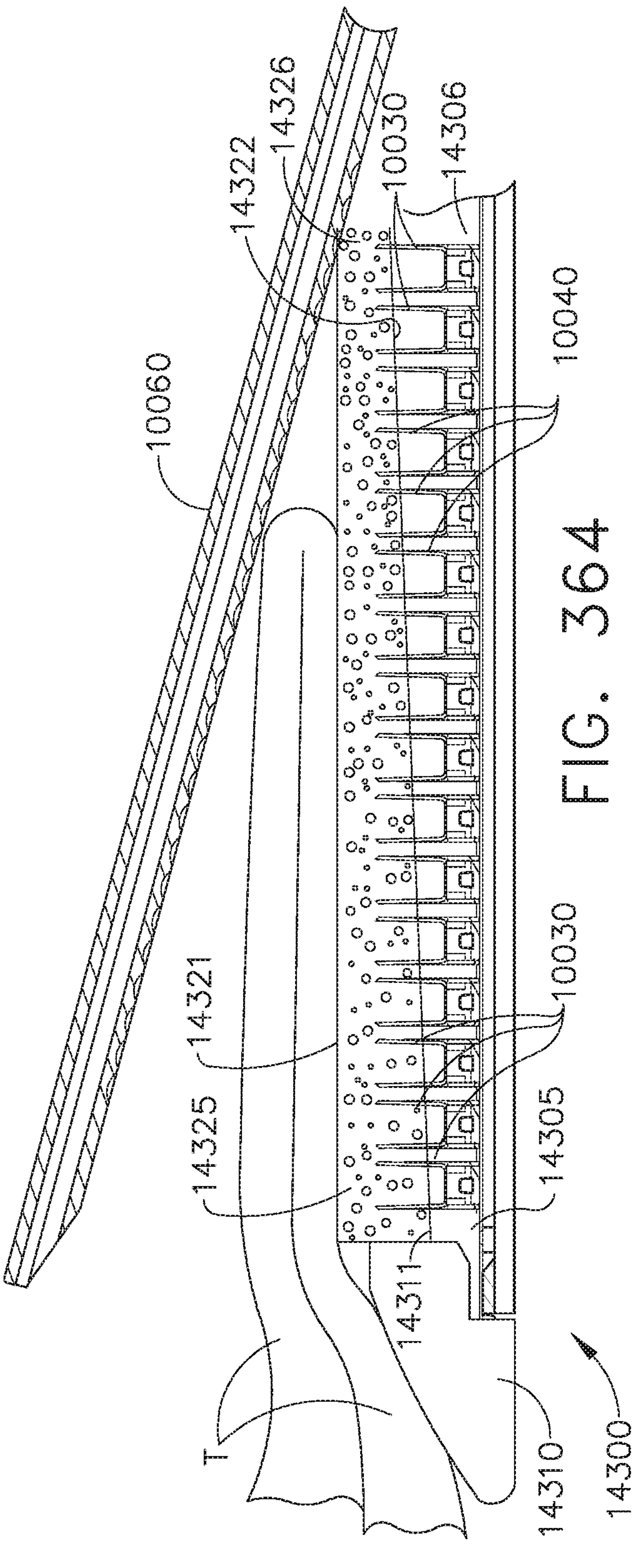
Figure 365:
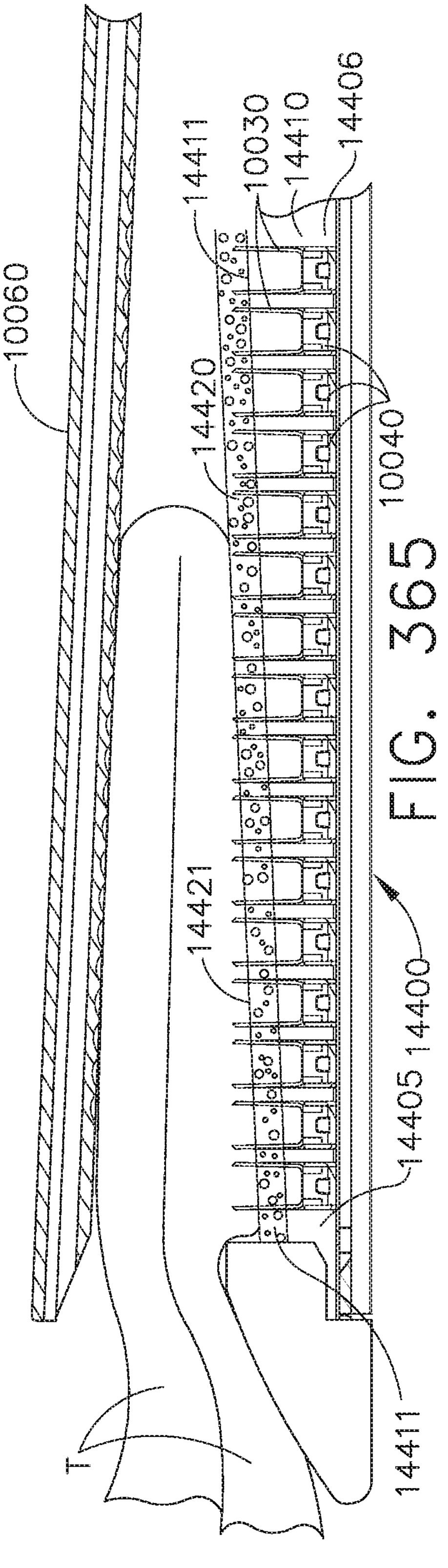
Figure 367:
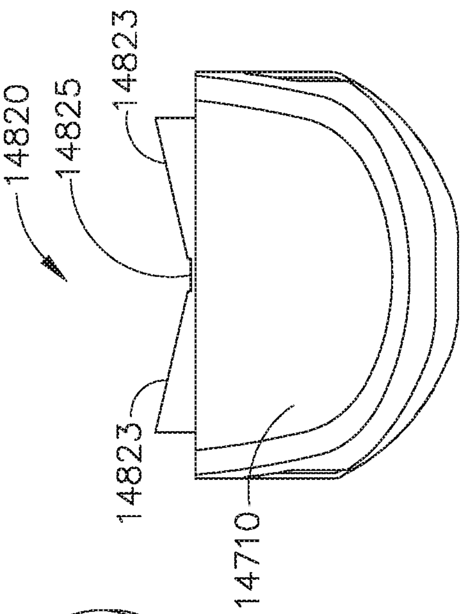
Figure 366:
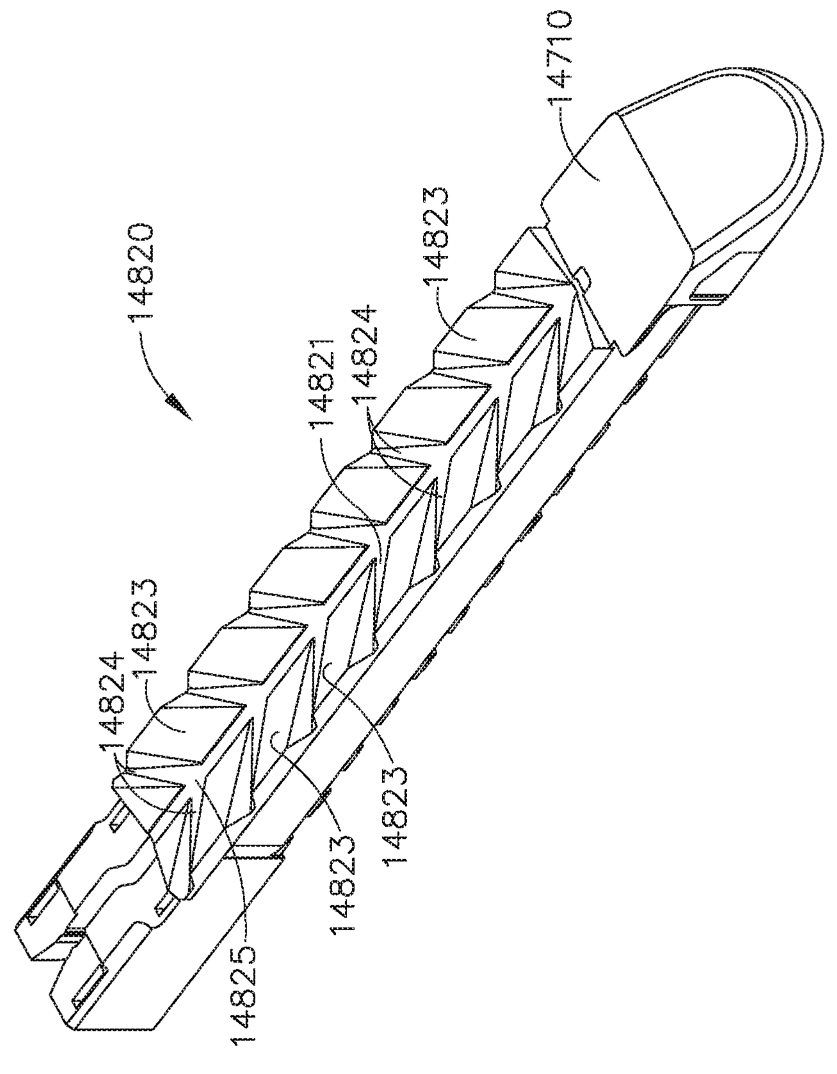
Figure 368:
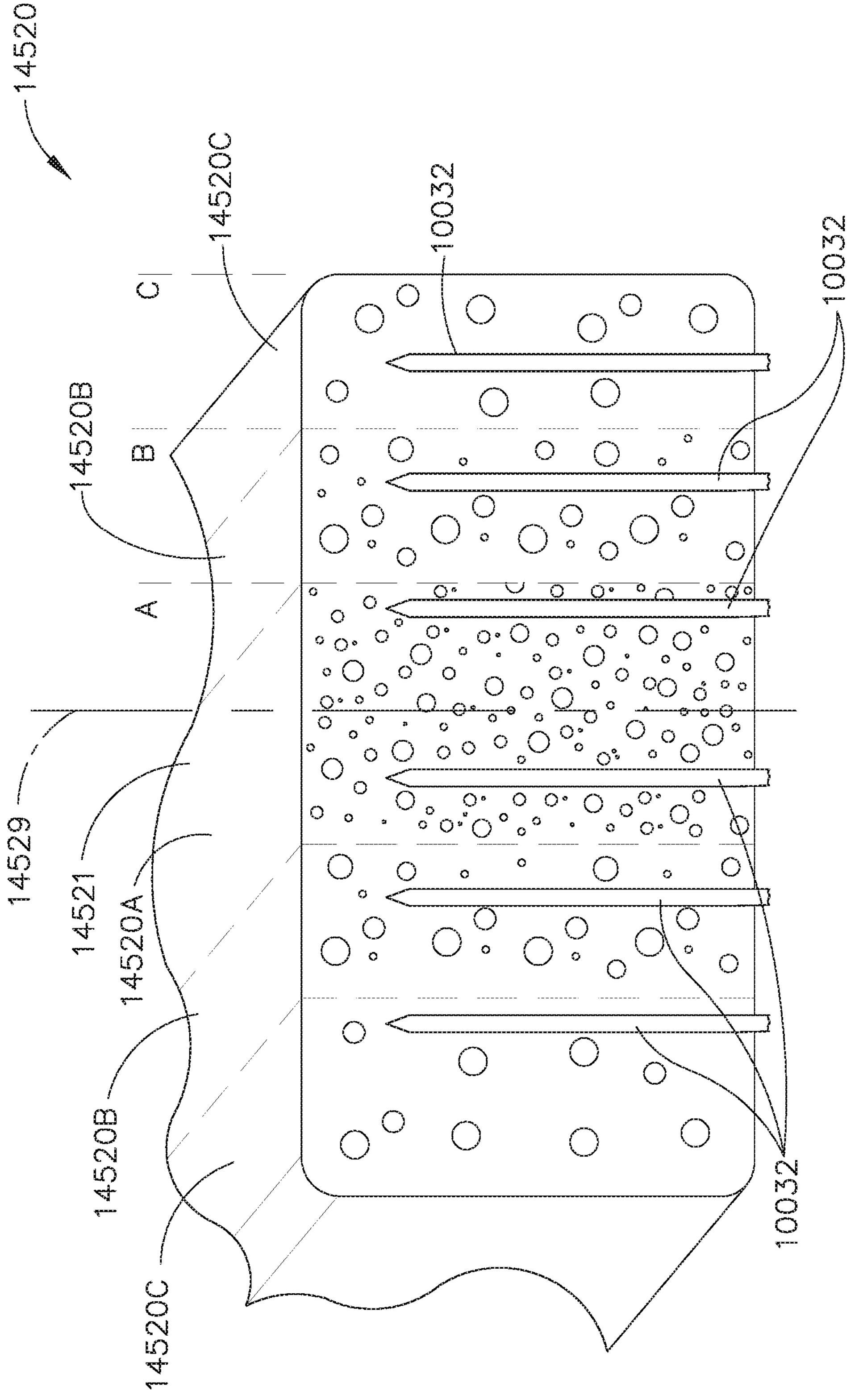
Figure 369:
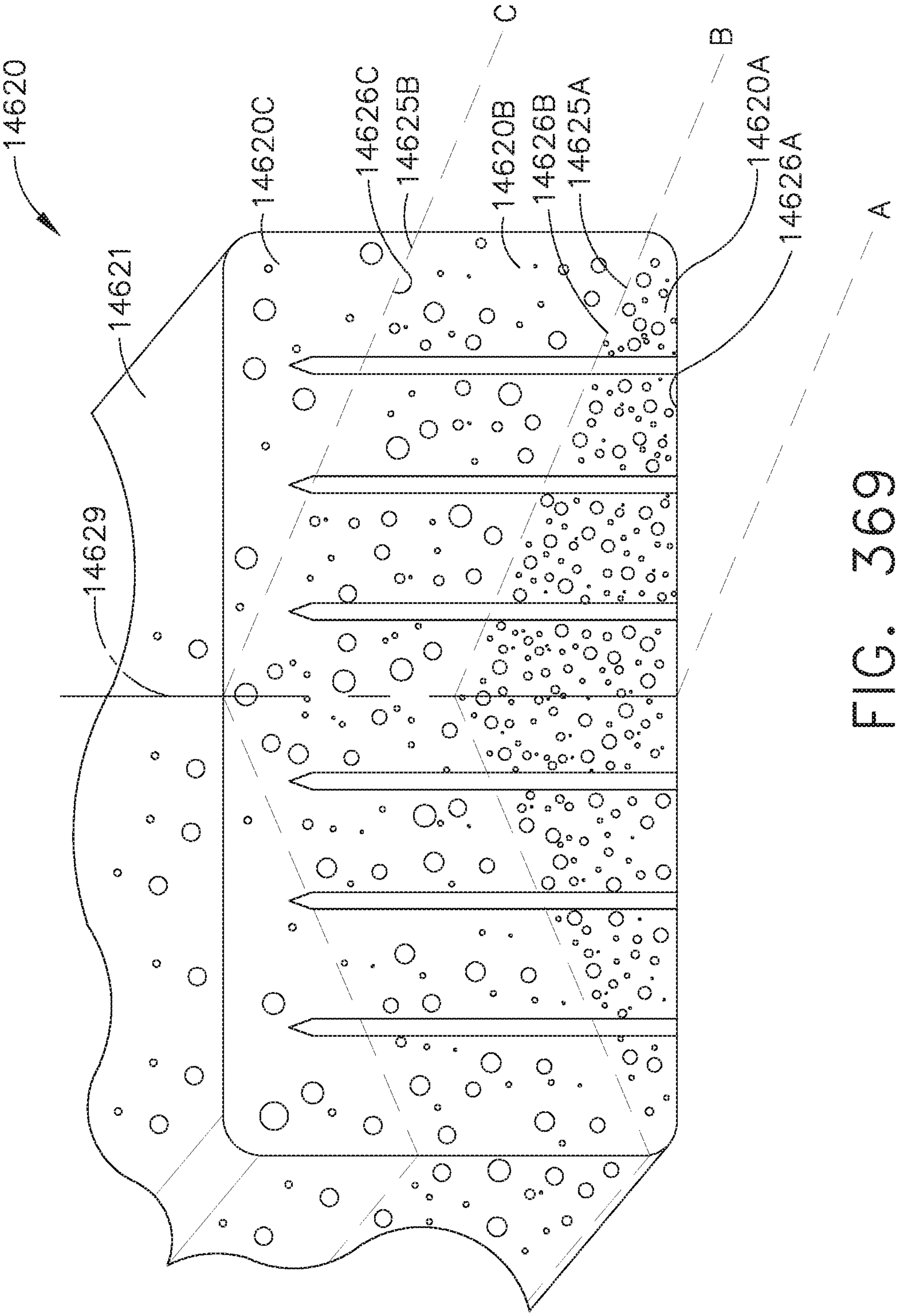
Figure 370:
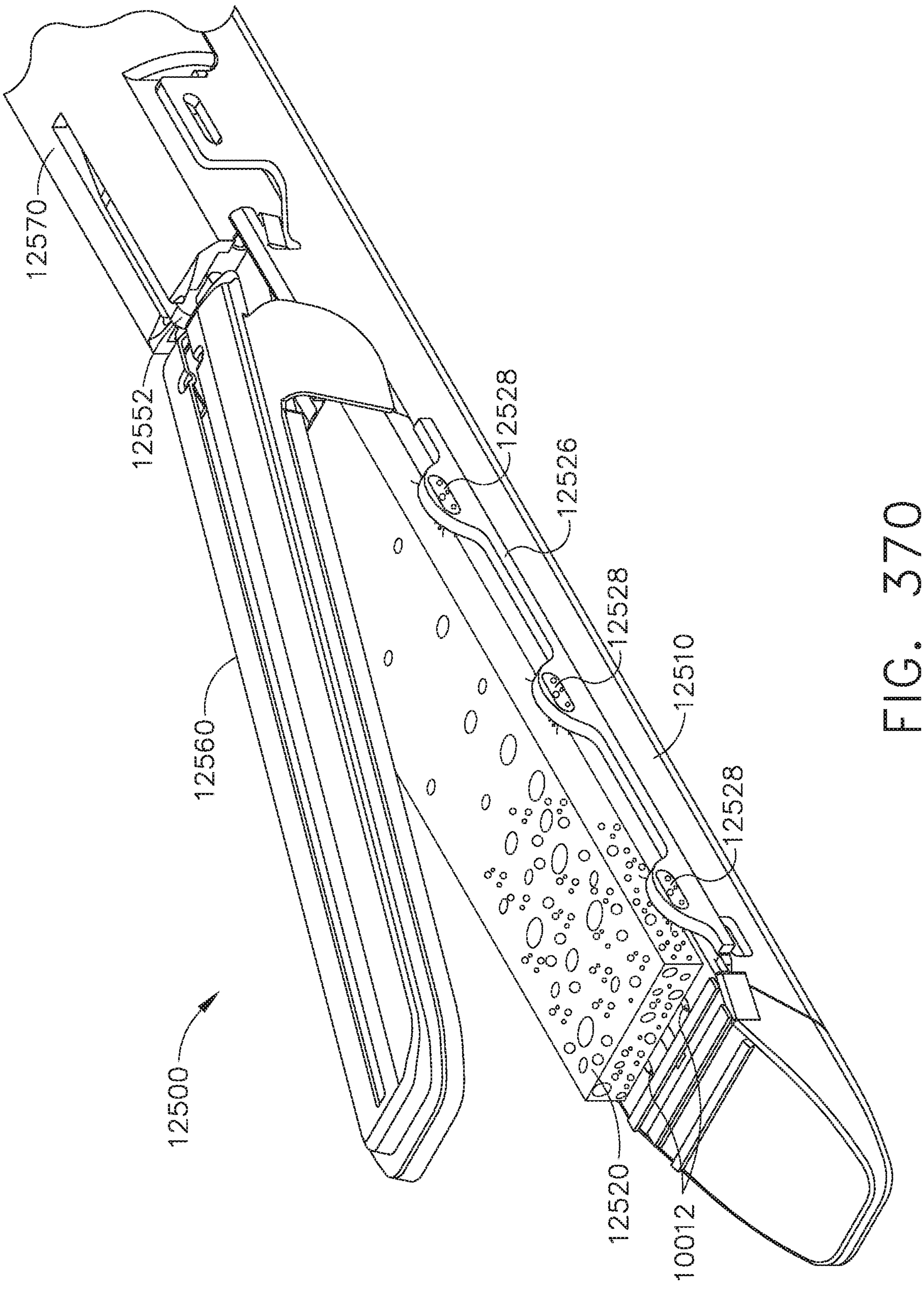
Figures 371, 372, 373:
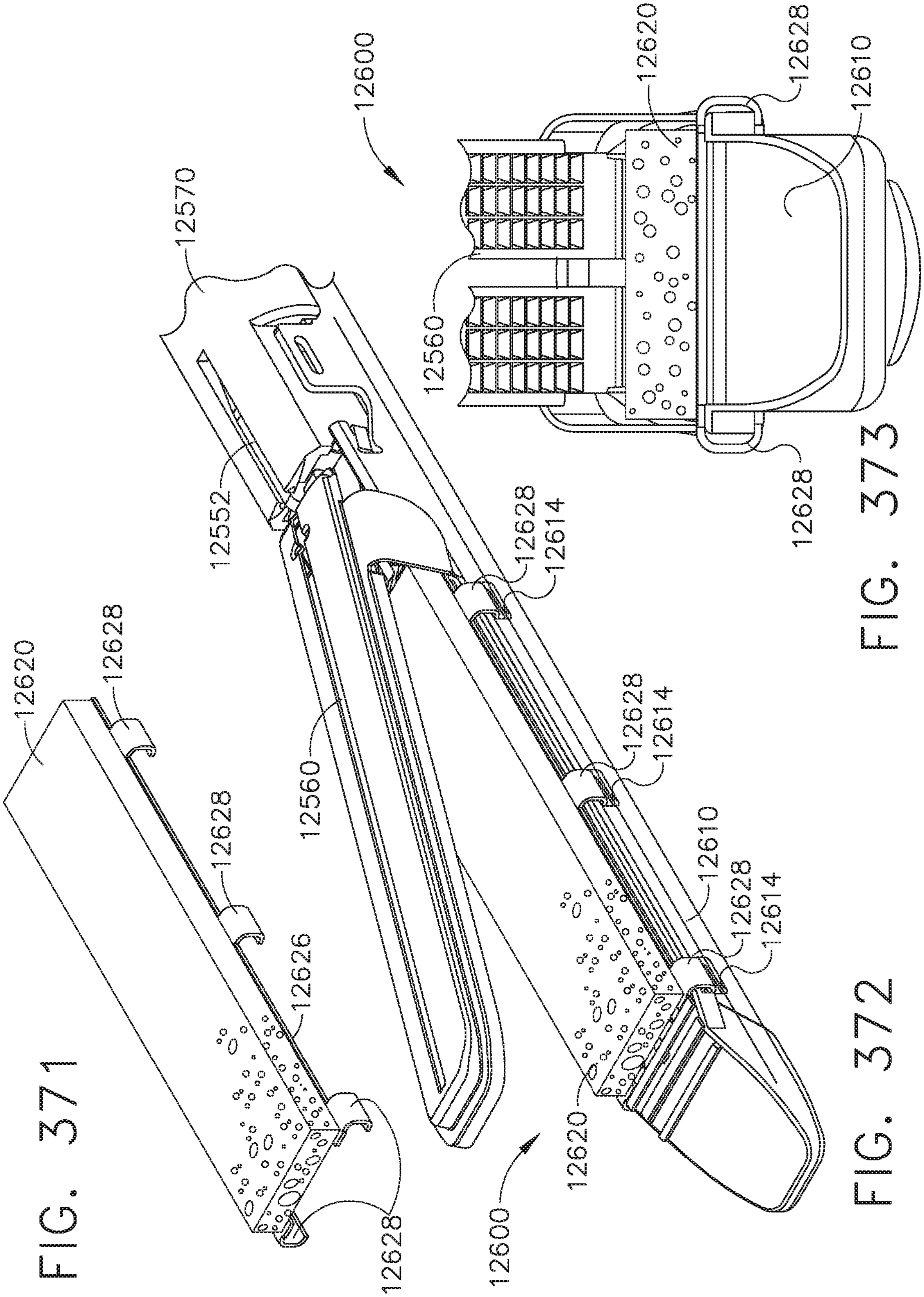
Figures 374, 375, 376:
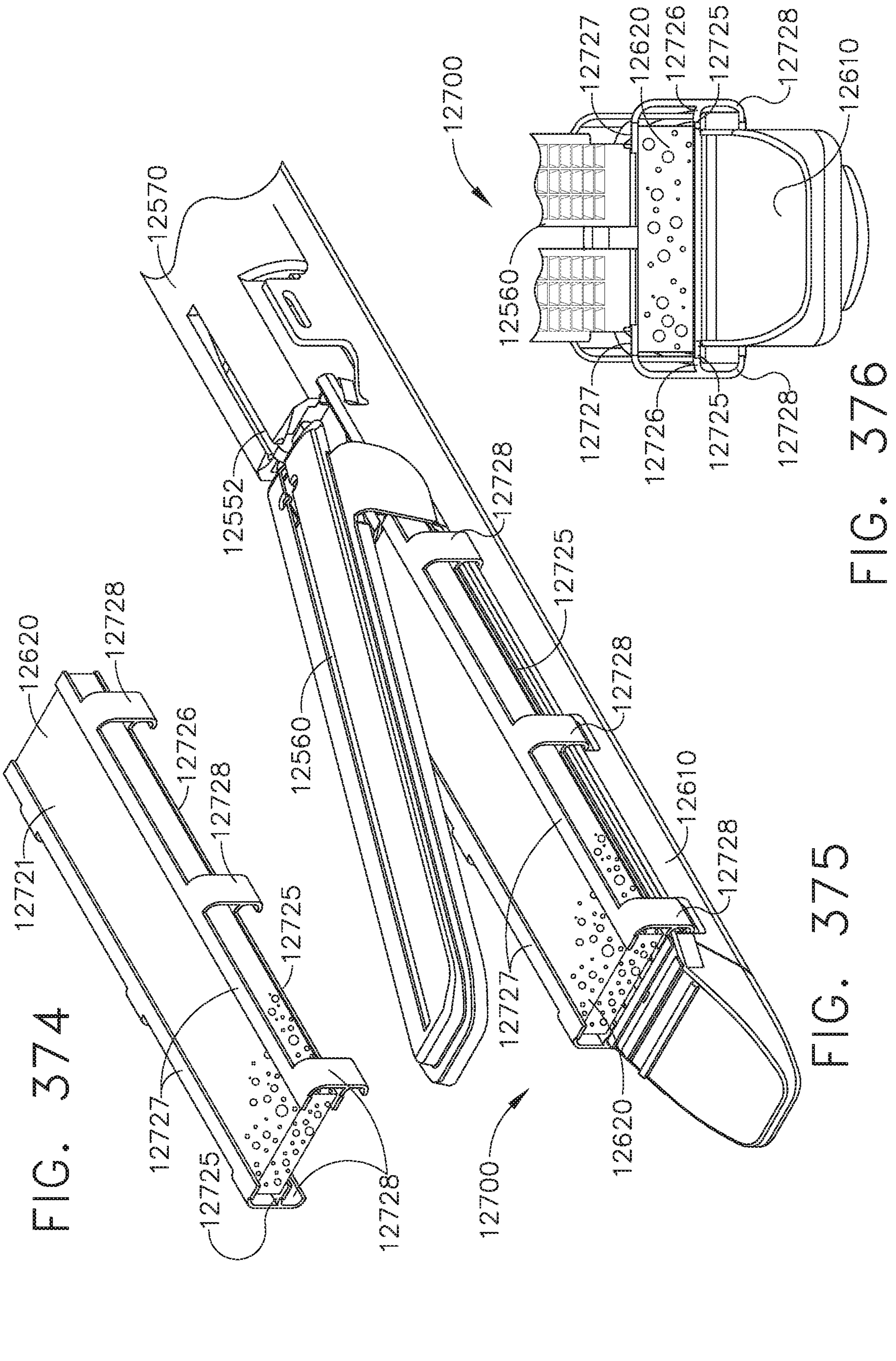
Figures 377, 378:
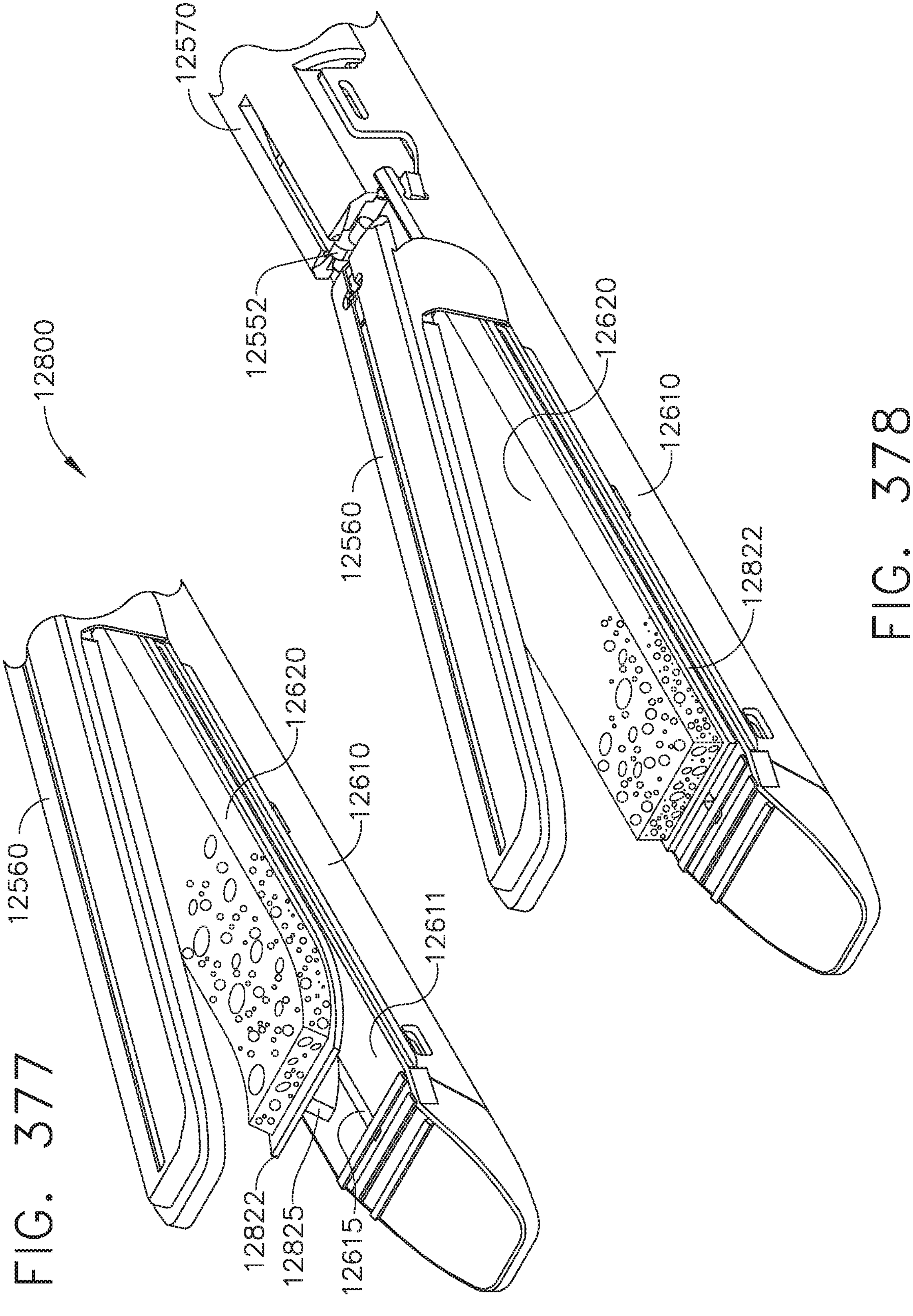
Figure 379:
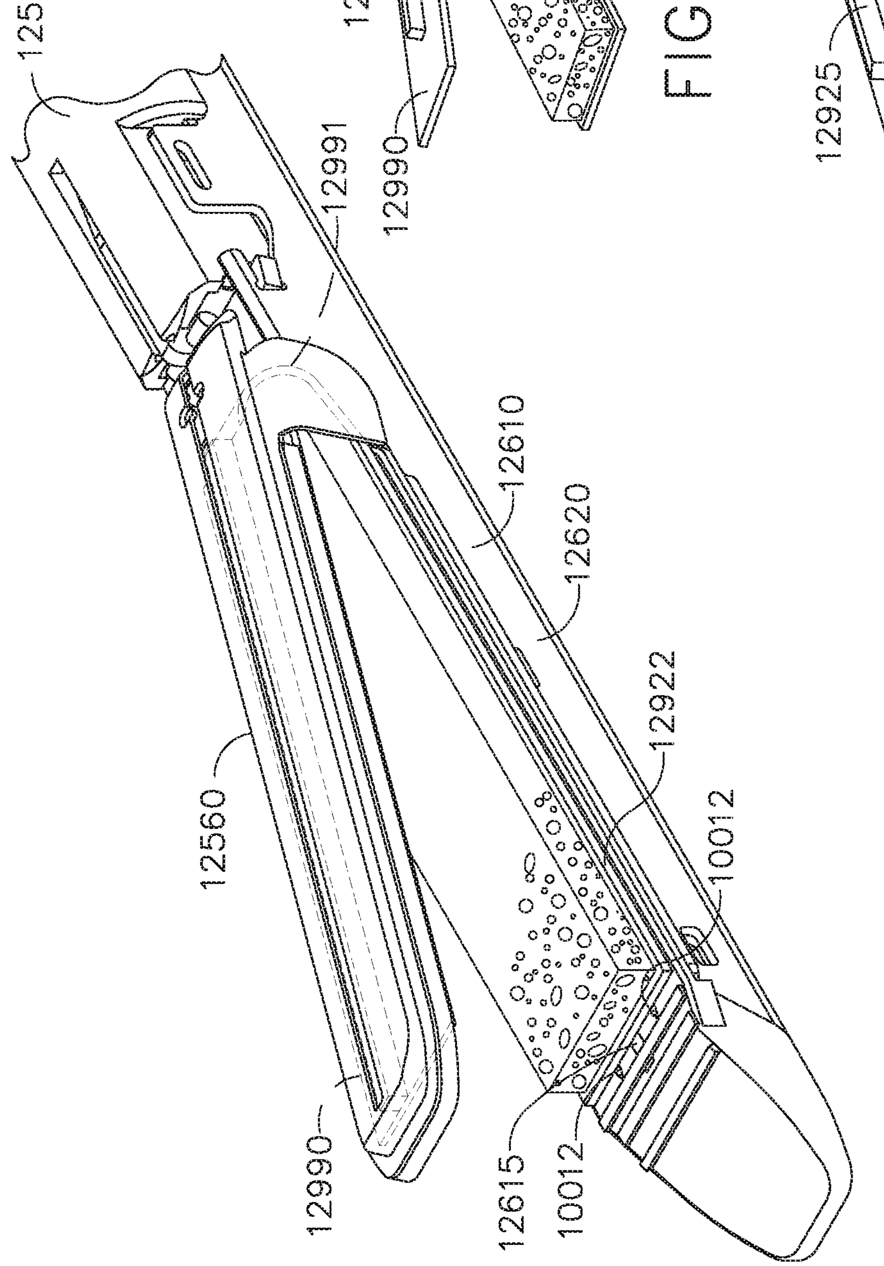
Figure 380:
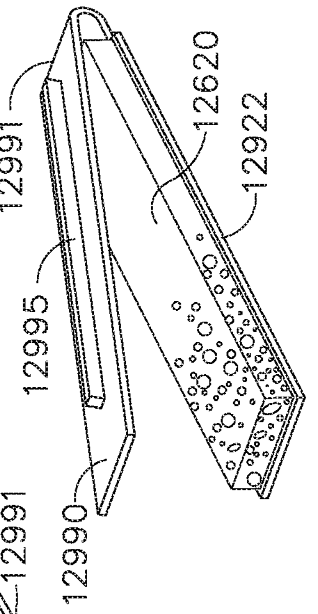
Figure 381:
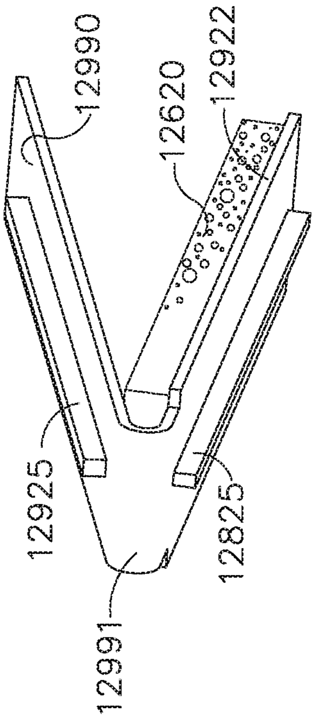
Figure 382:
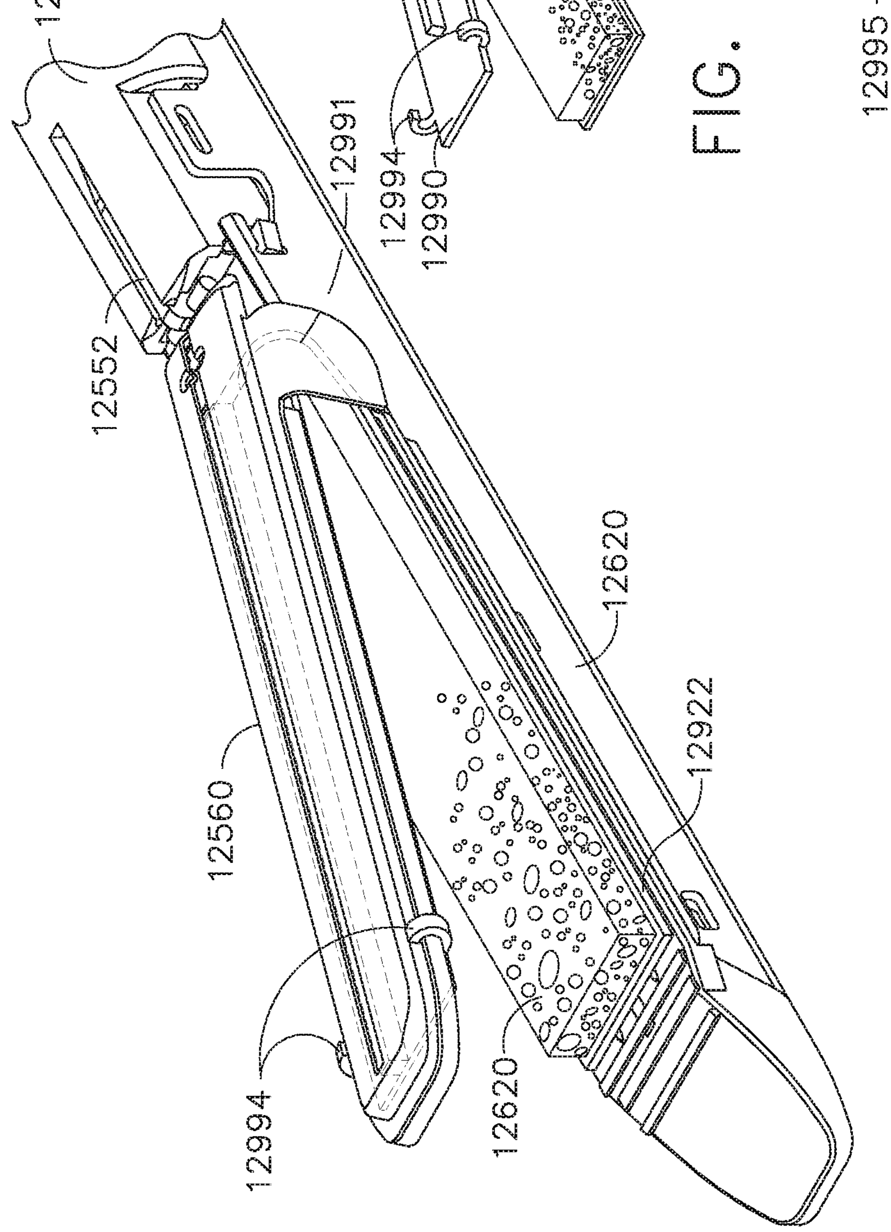
Figure 383:
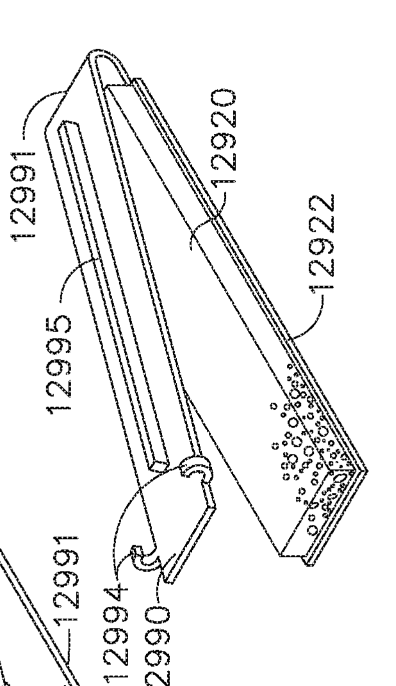
Figure 384:
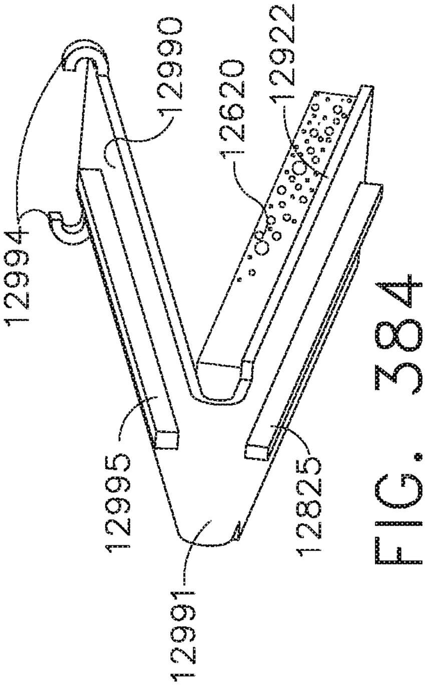
Figure 385:
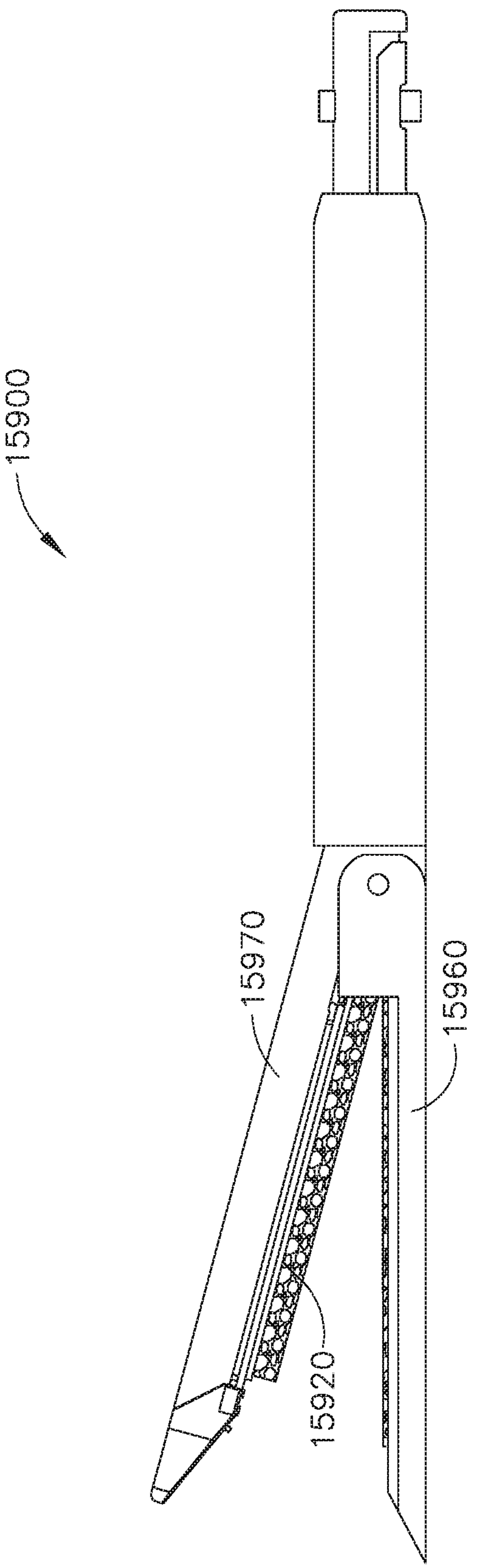
Figure 386:
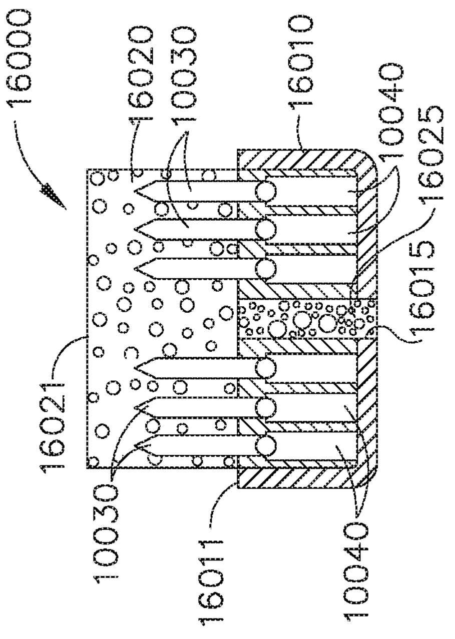
Figure 387:
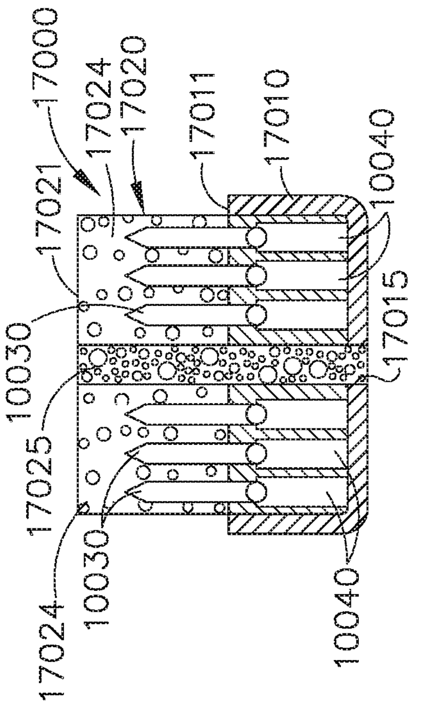
Figure 388:
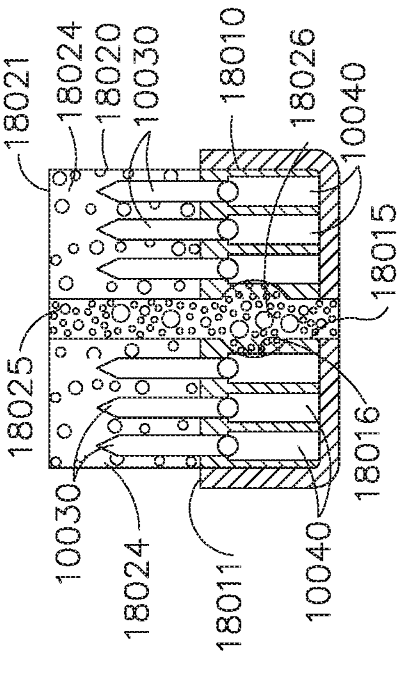
Figure 389:
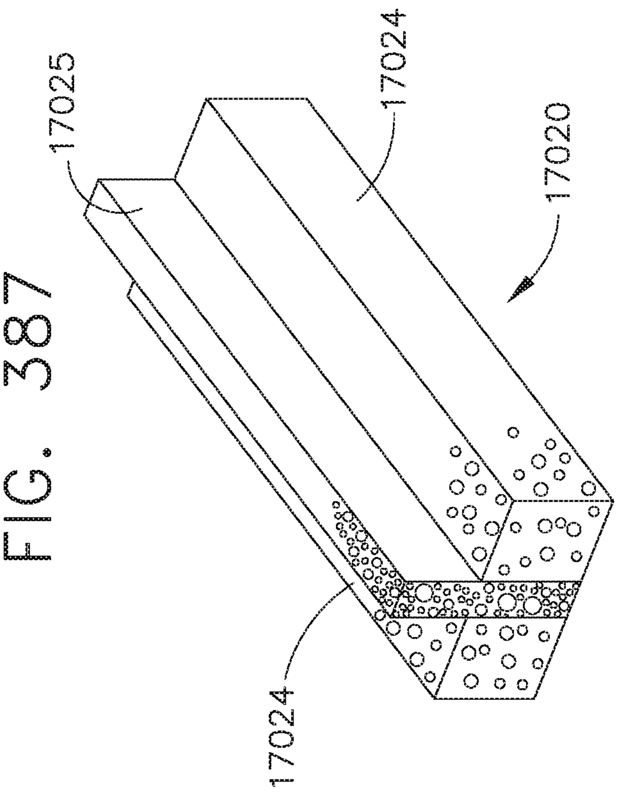
Figure 390:
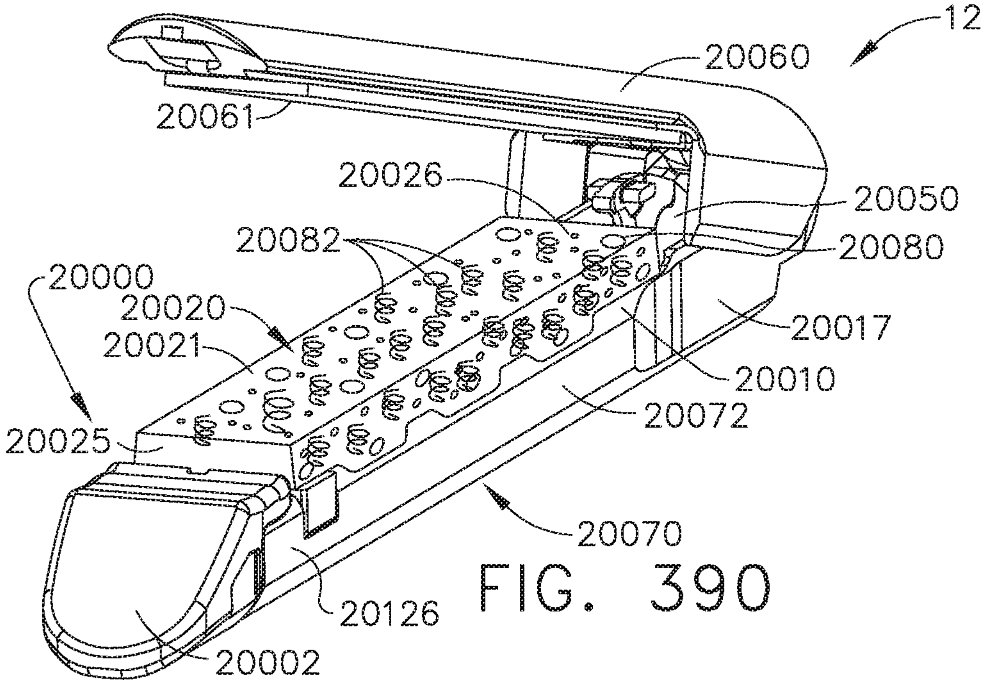
Figure 391:
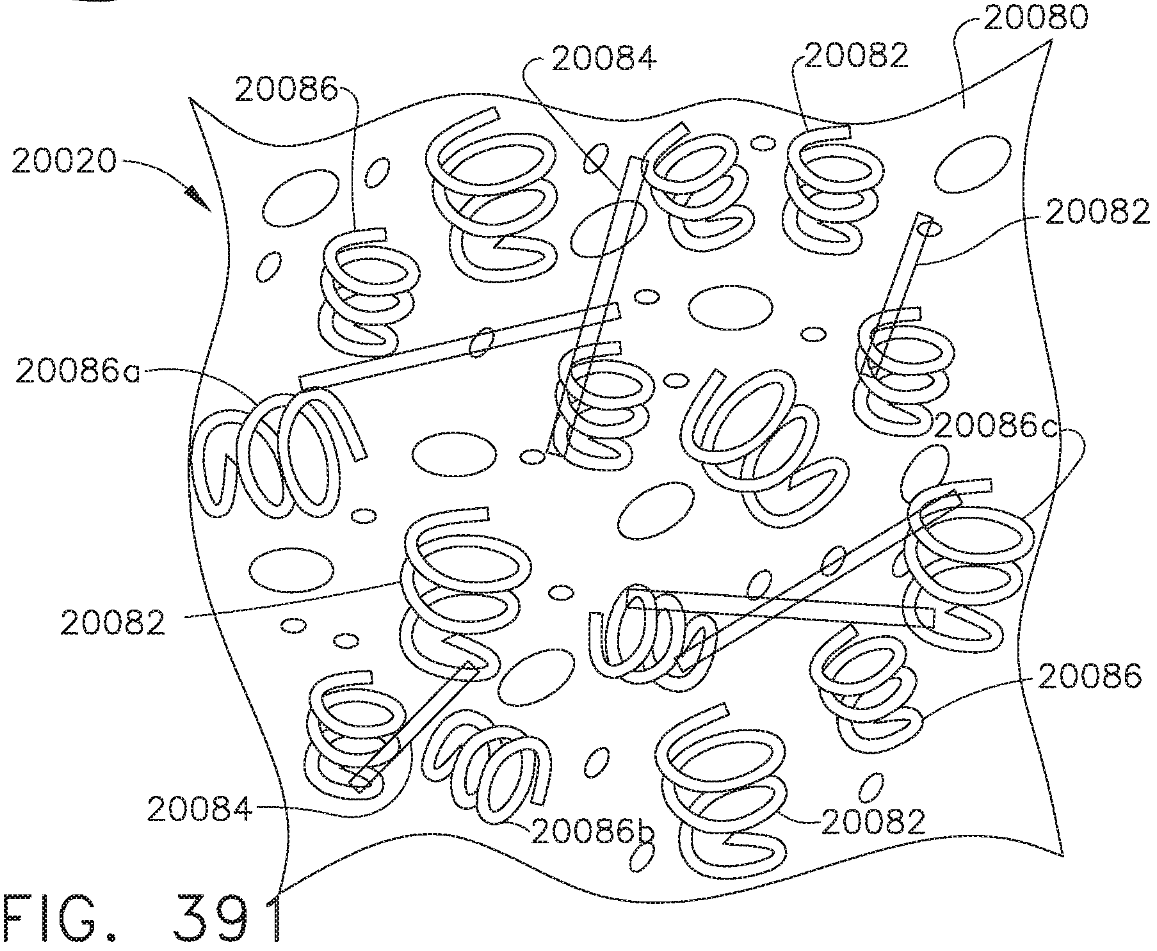
Figure 392:
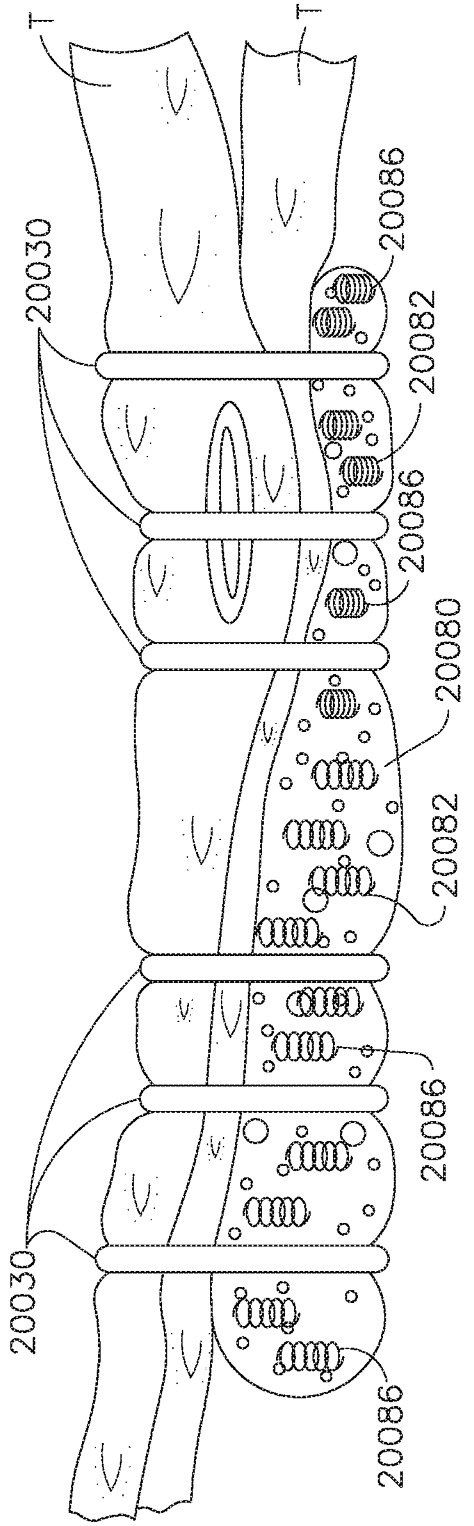
Figure 393:
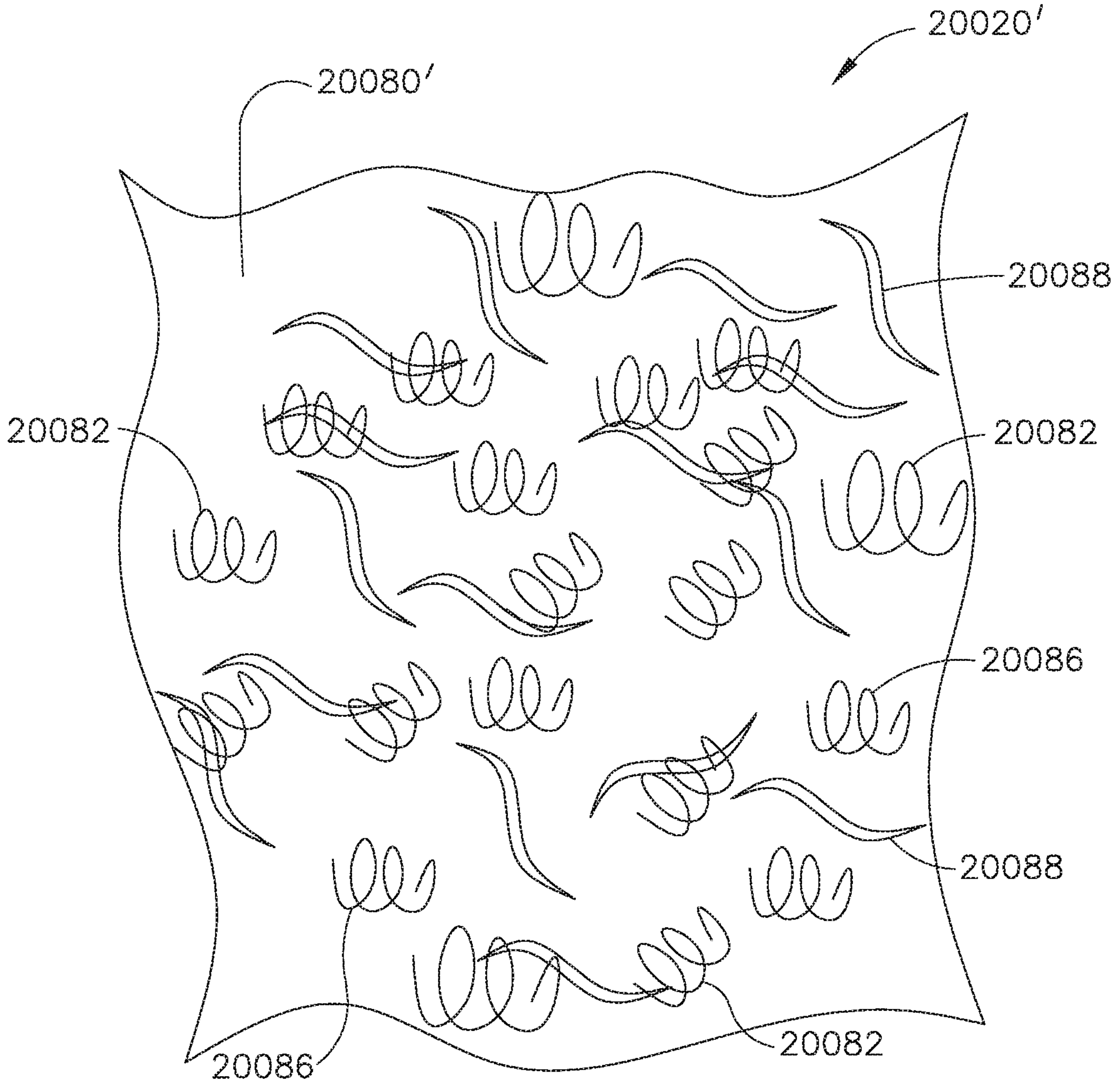
Figure 394:
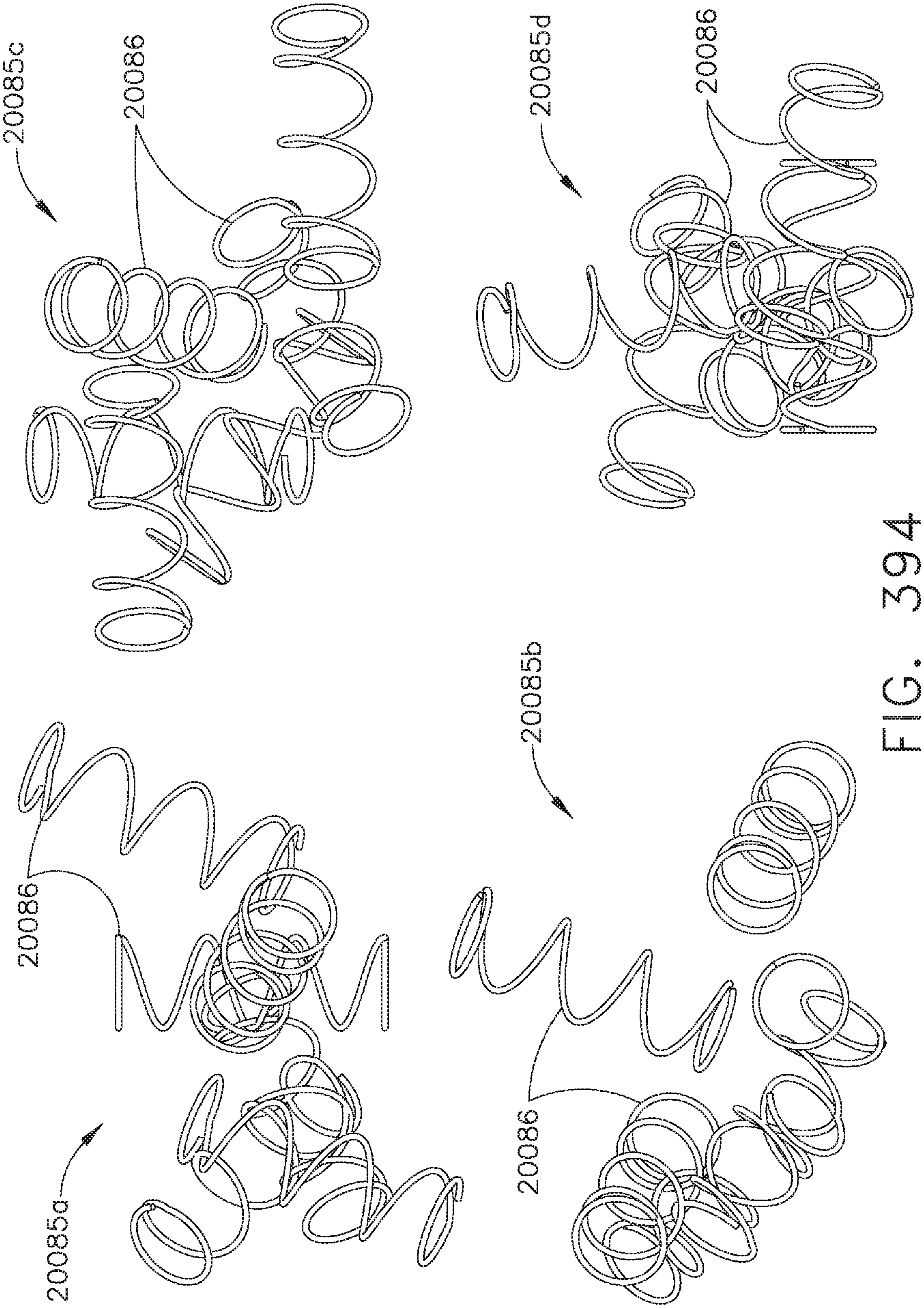
Figure 395:
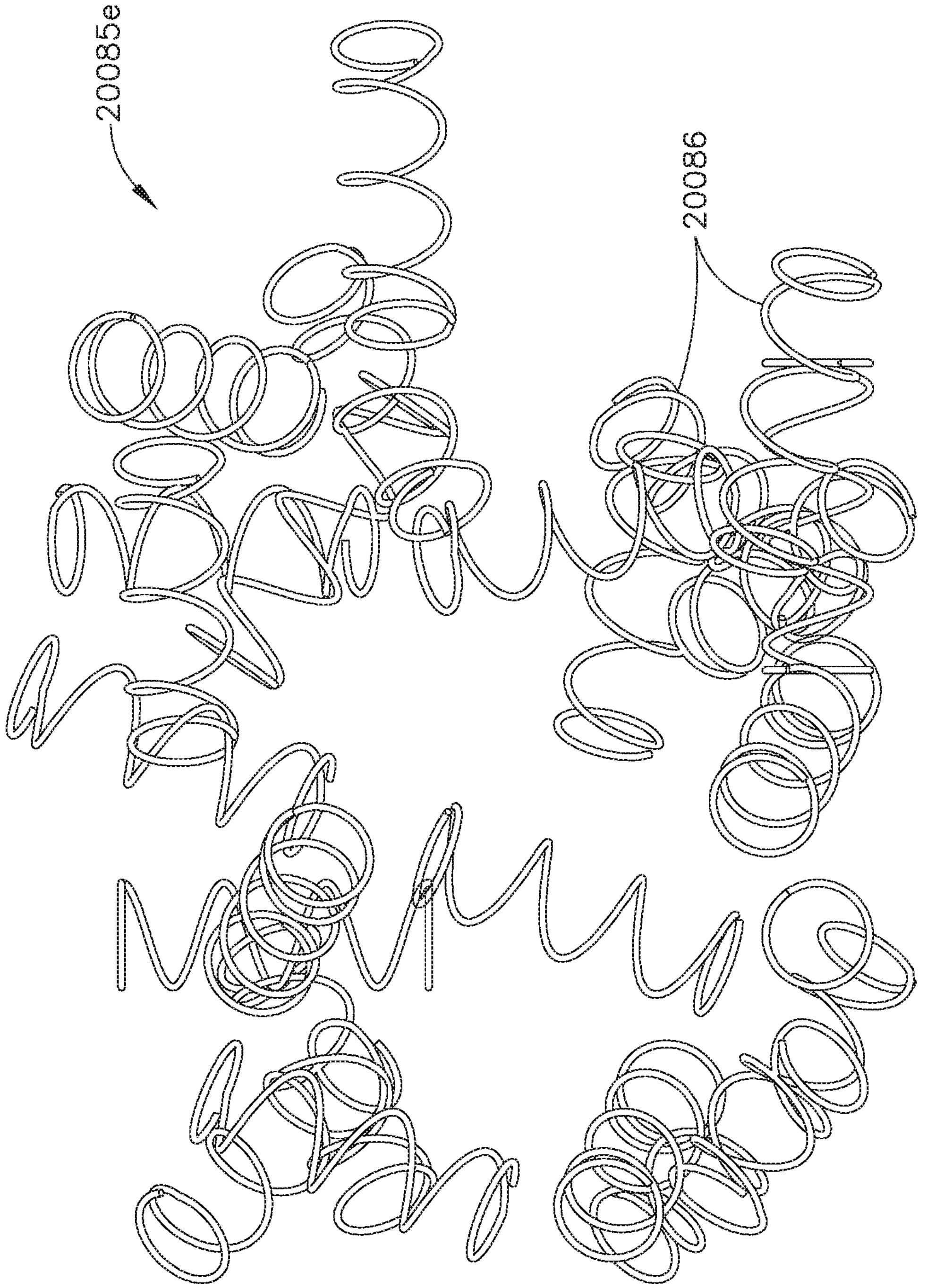
Figure 397:
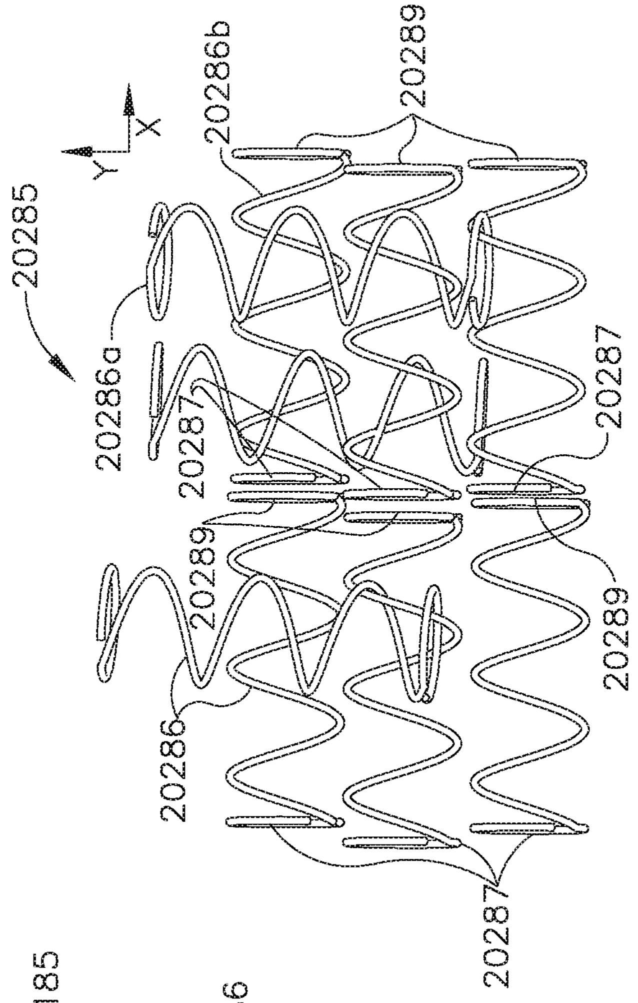
Figure 396:
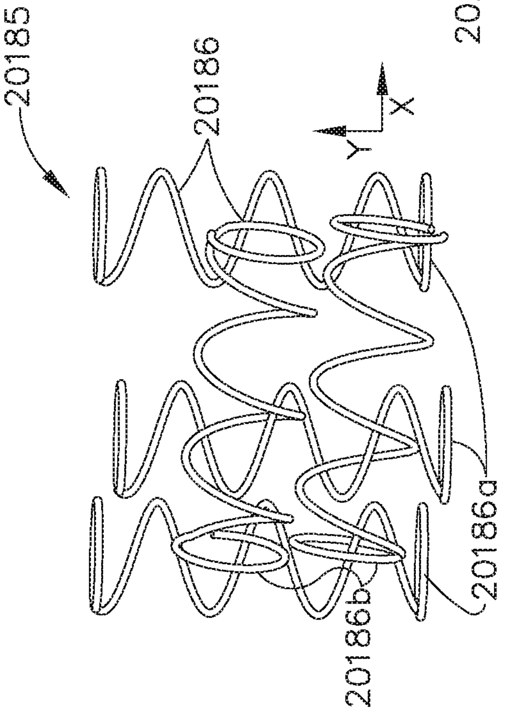
Figure 398:
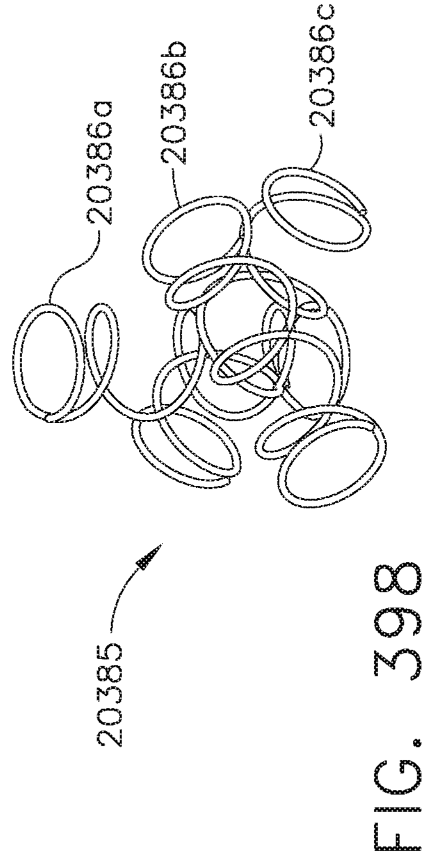
Figure 399A:
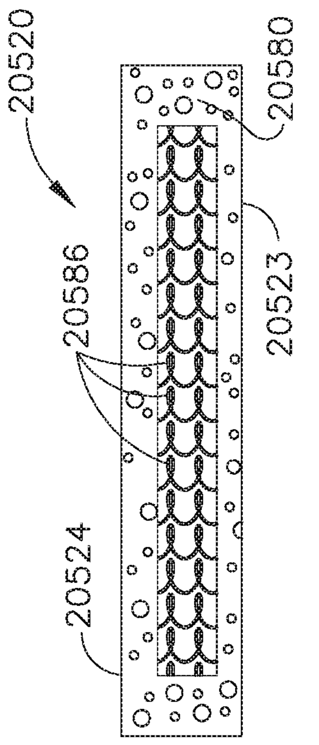
Figure 399:
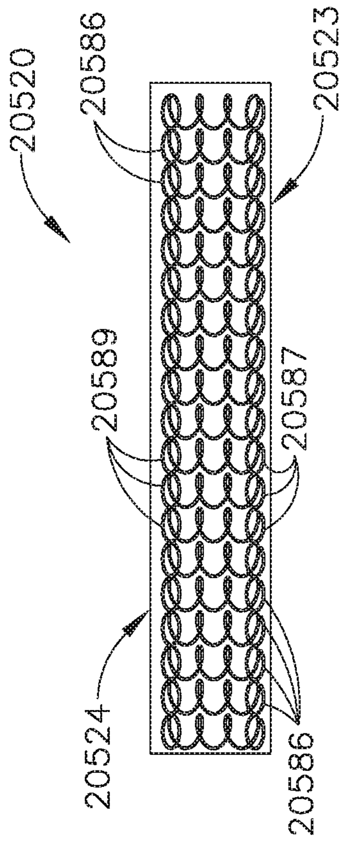
Figure 399B:
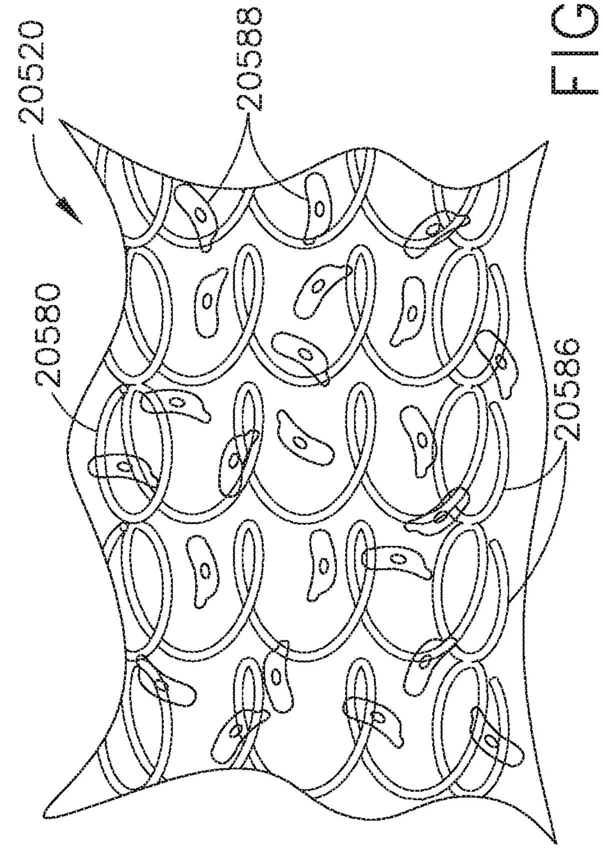
Figures 400, 401:
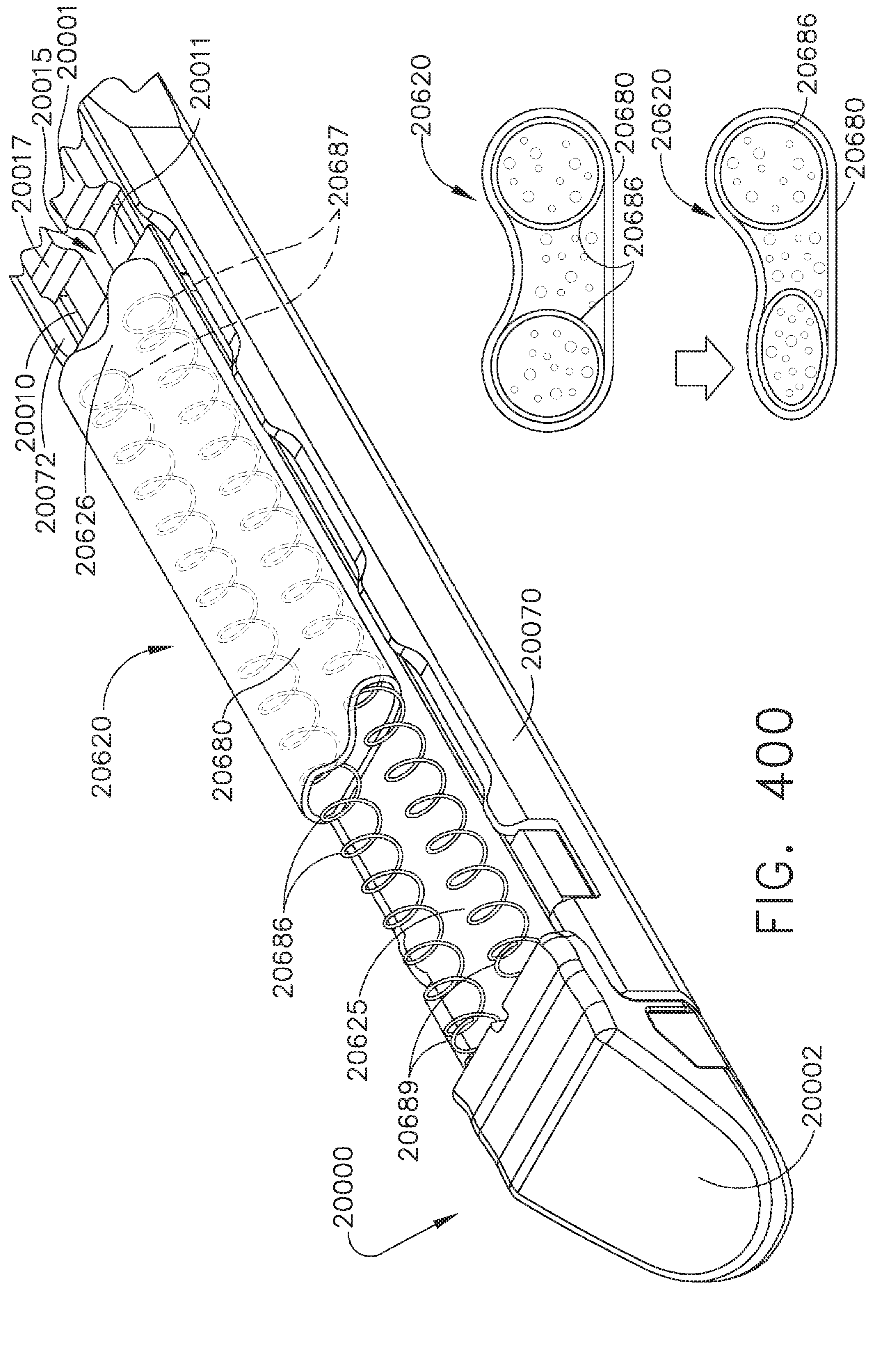
Figure 402:
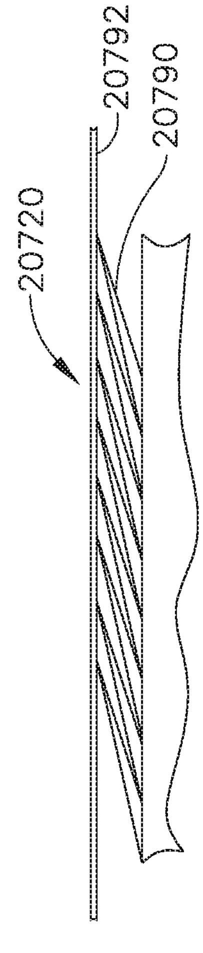
Figure 403:
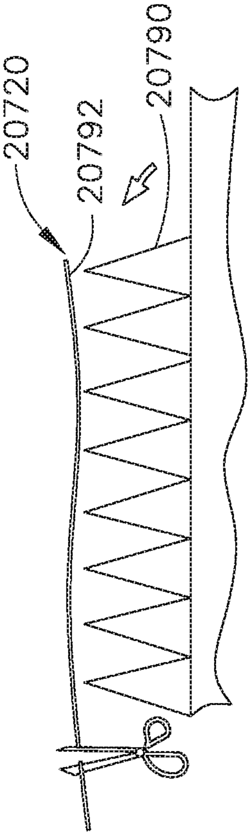
Figure 404:
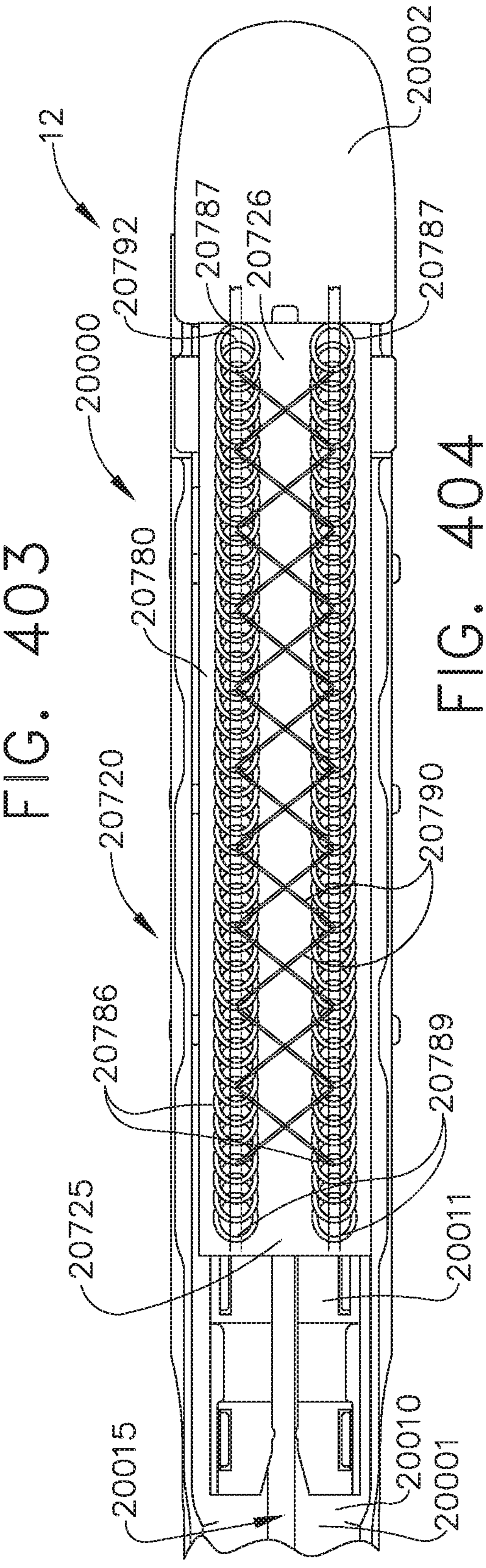
Figure 405:
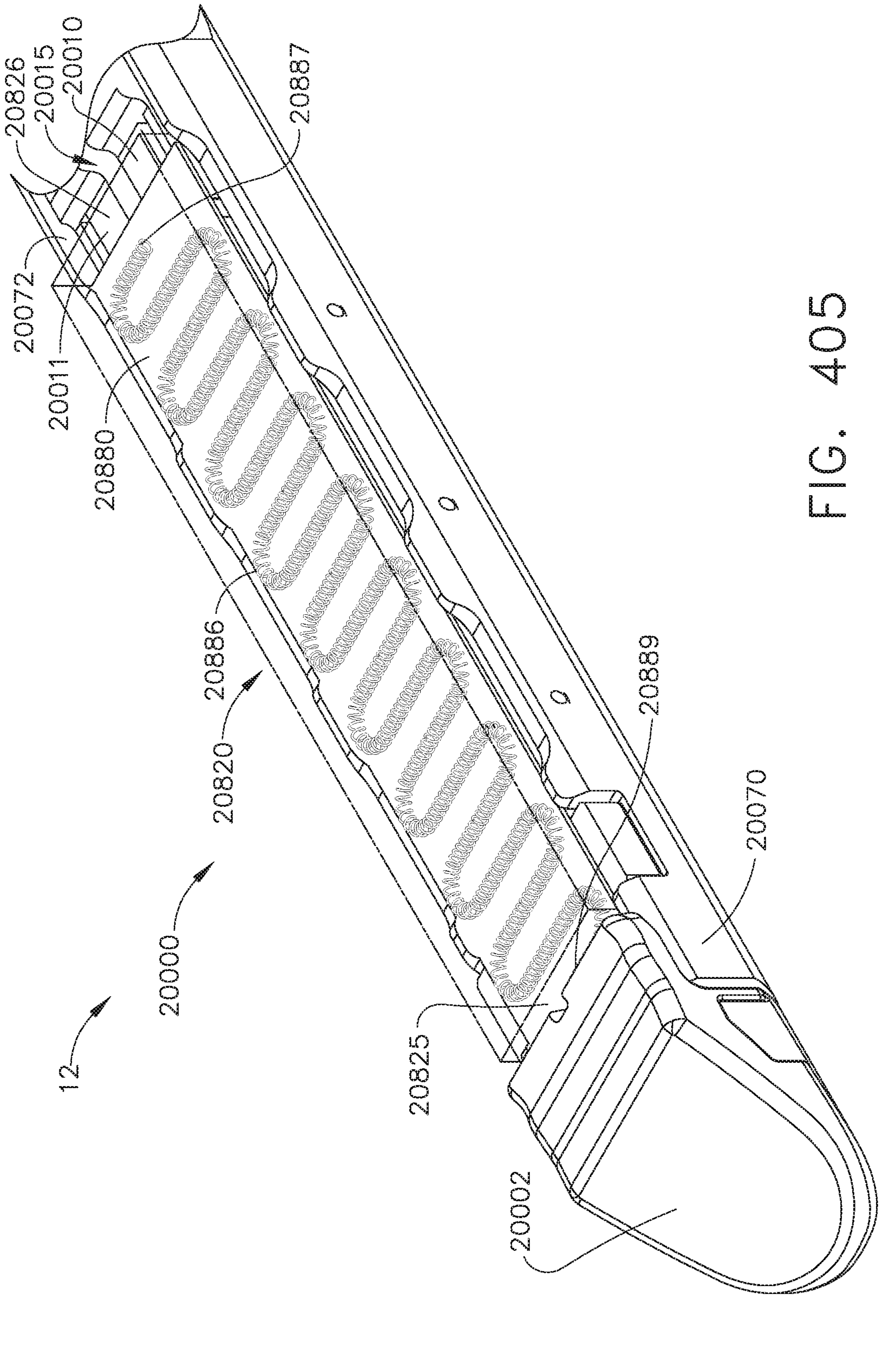
Figure 406:
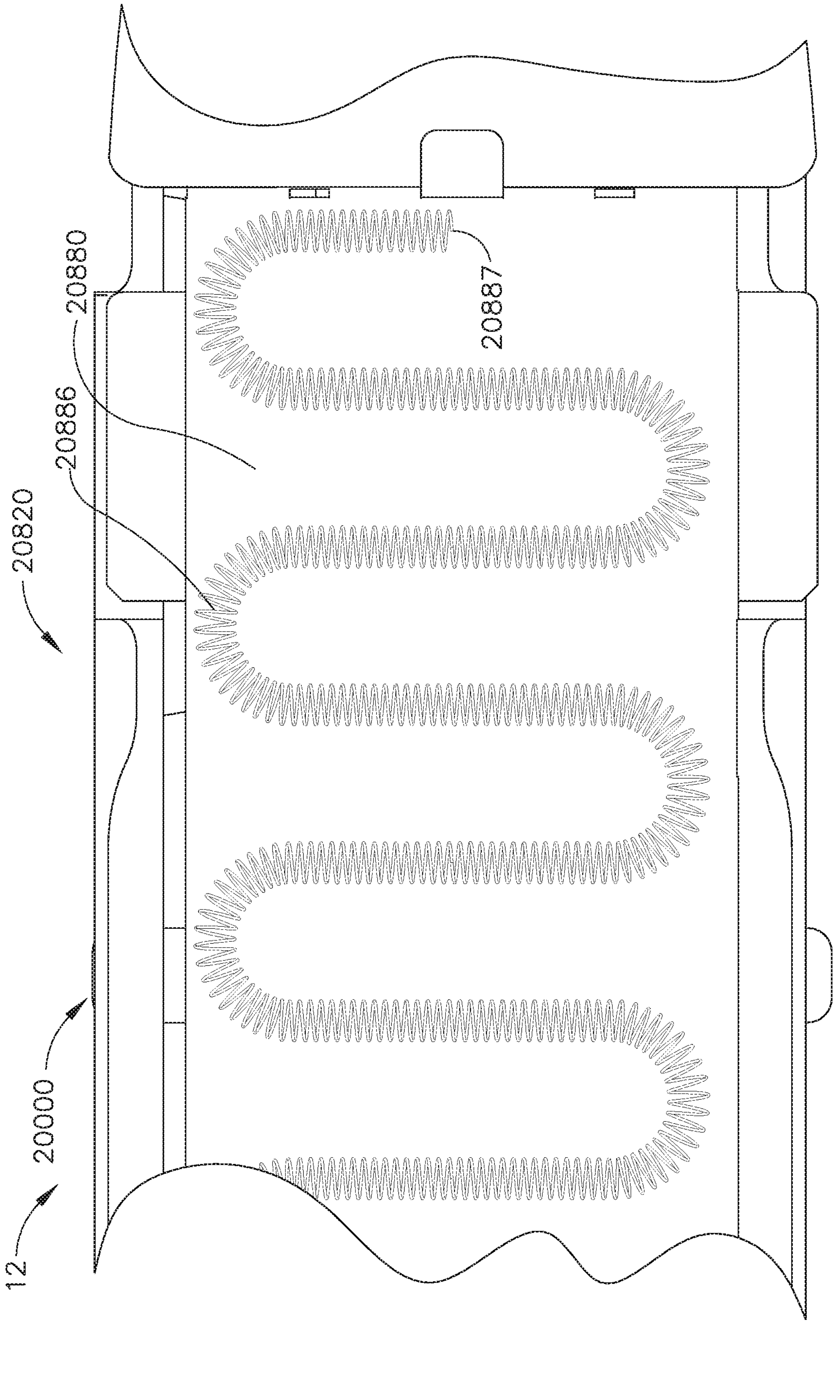
Figure 407:
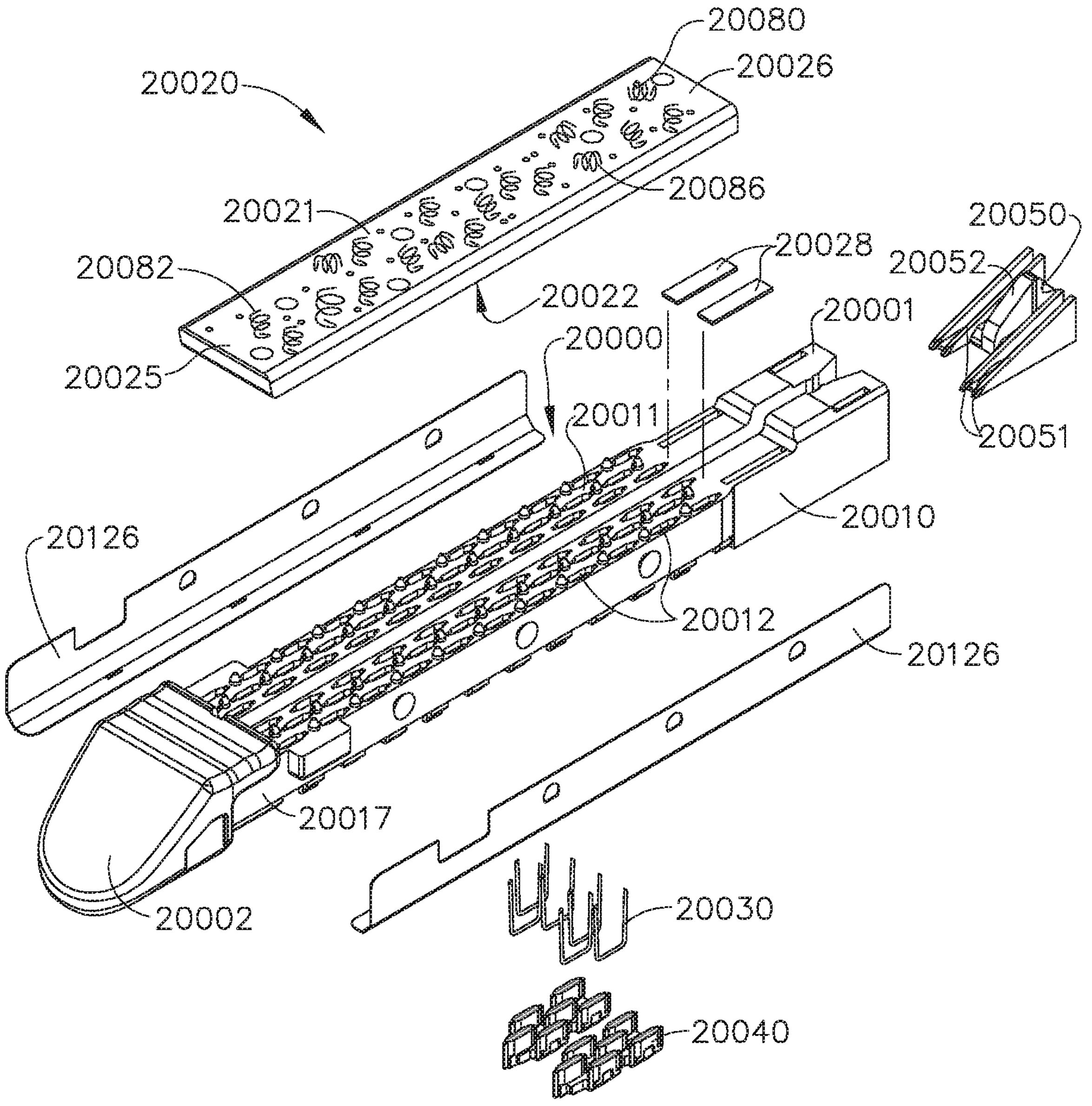
Figure 408:
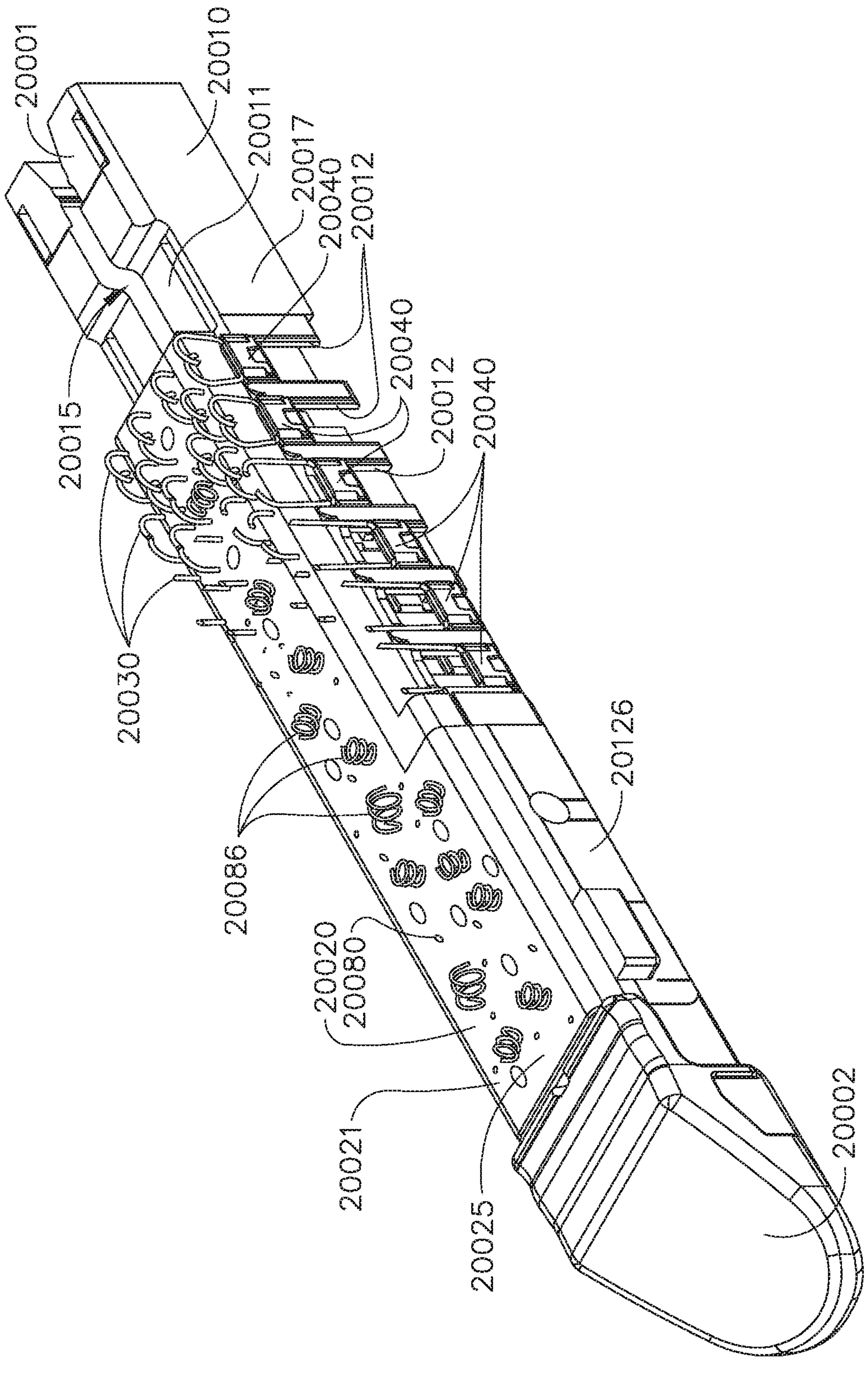
Figure 409:
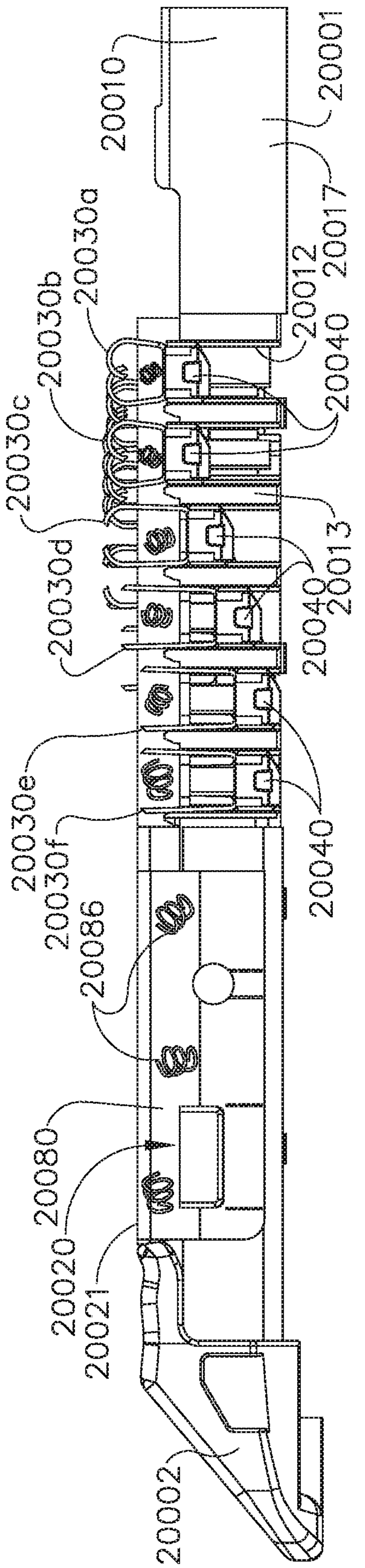
Figure 410:
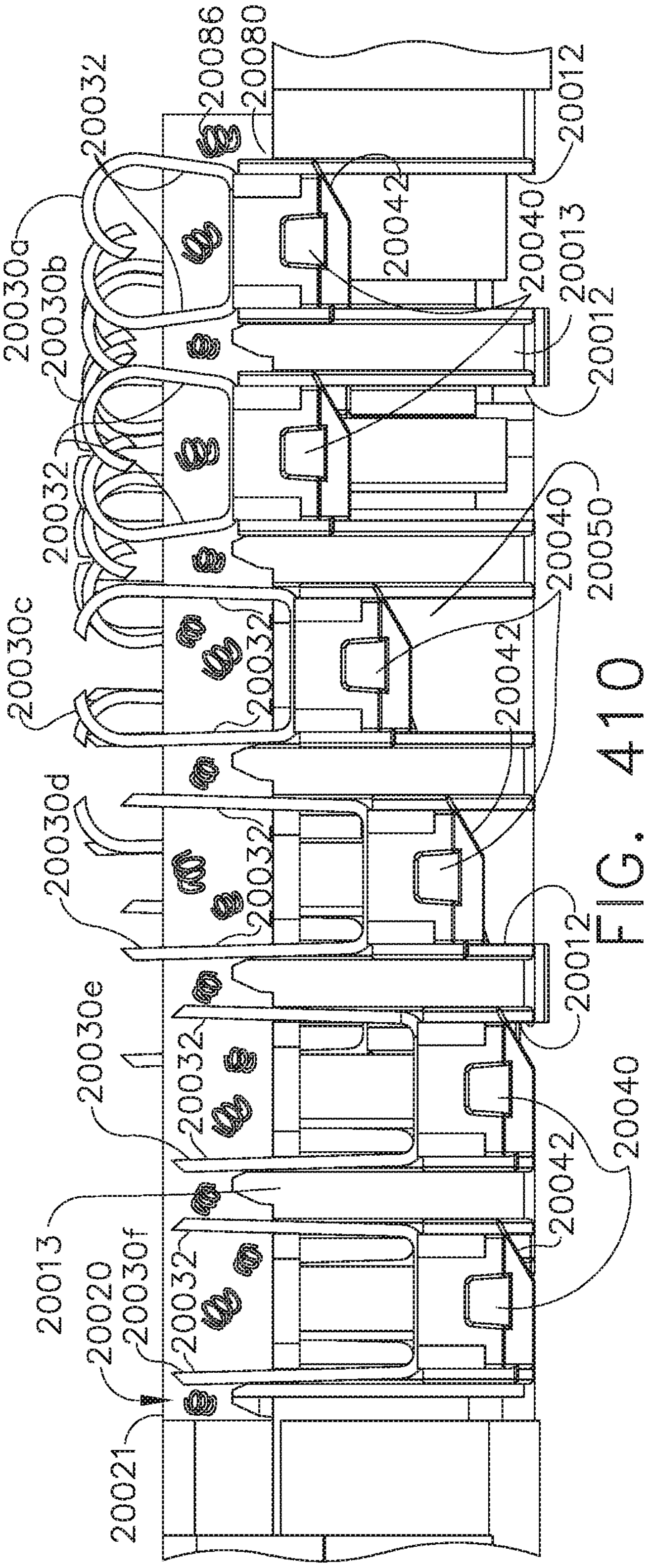
Figure 411:
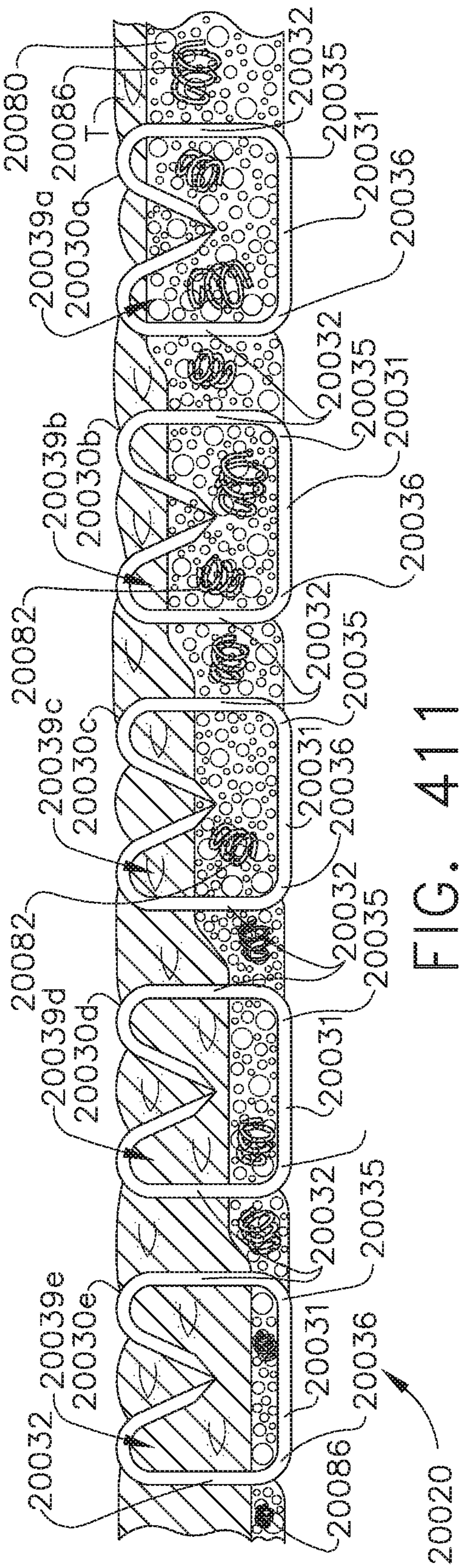
Figure 412:
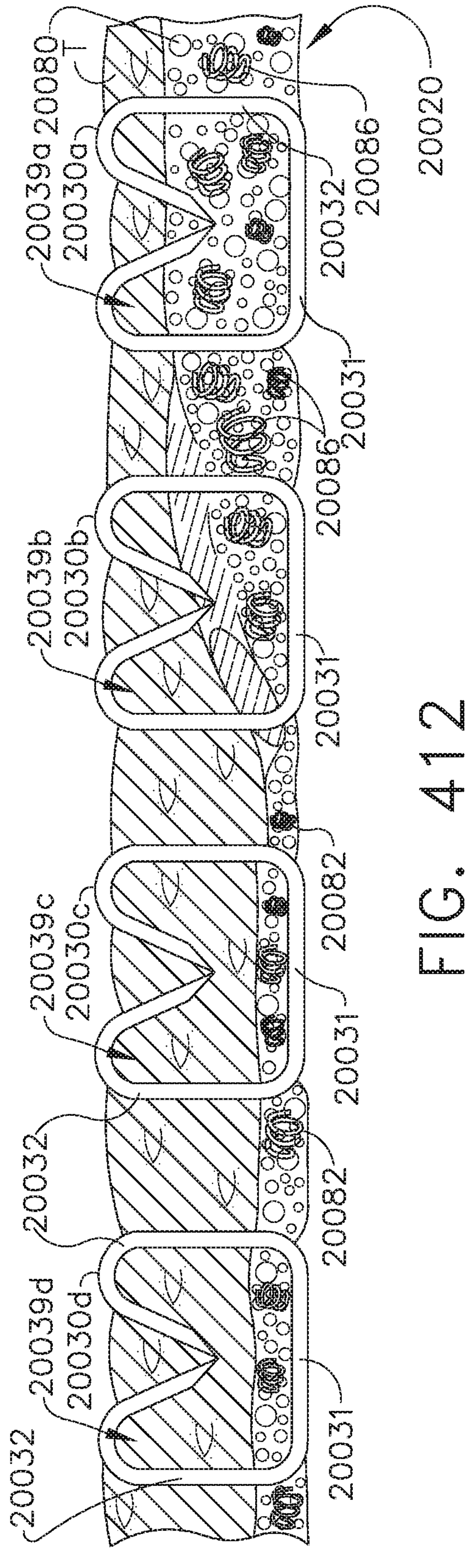
Figure 413:
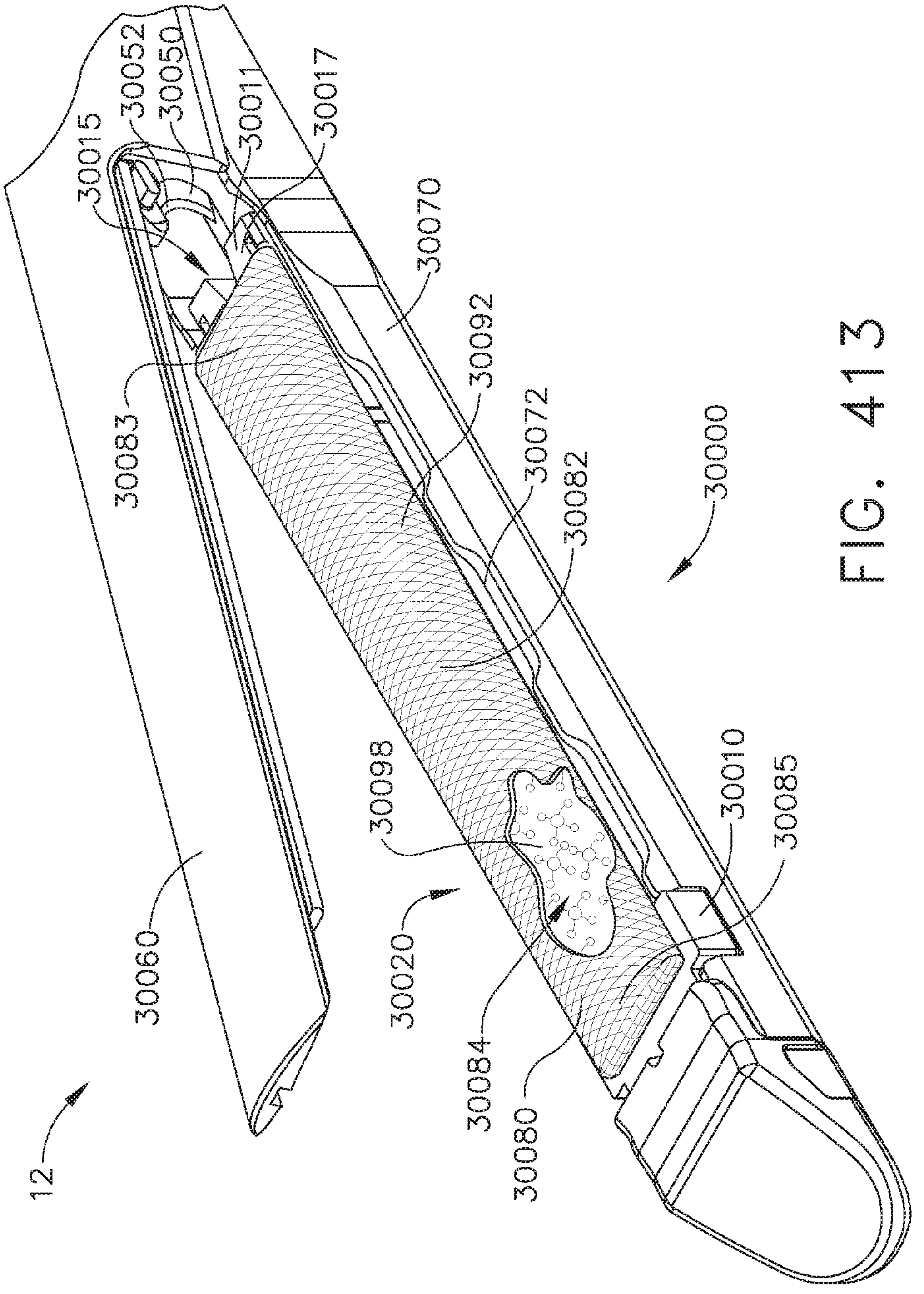
Figure 415:
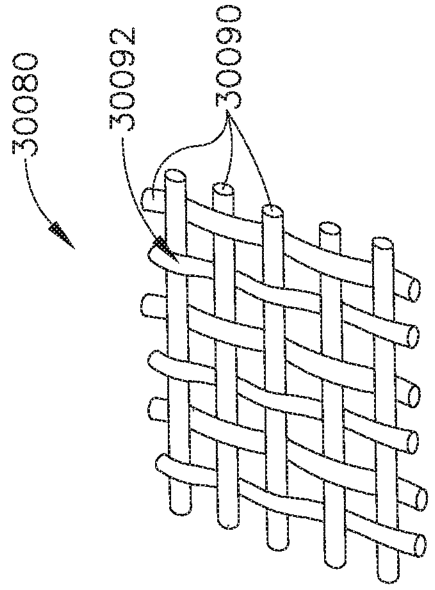
Figure 414:
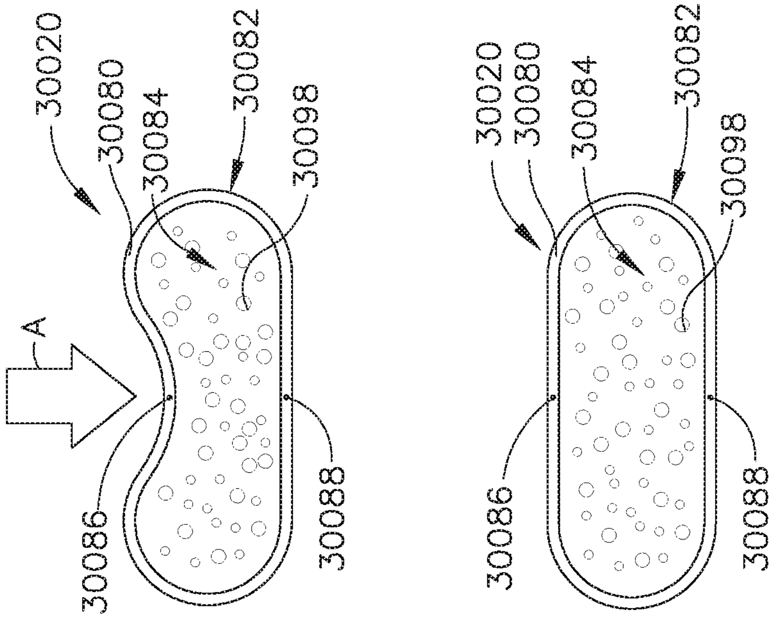
Figure 416:
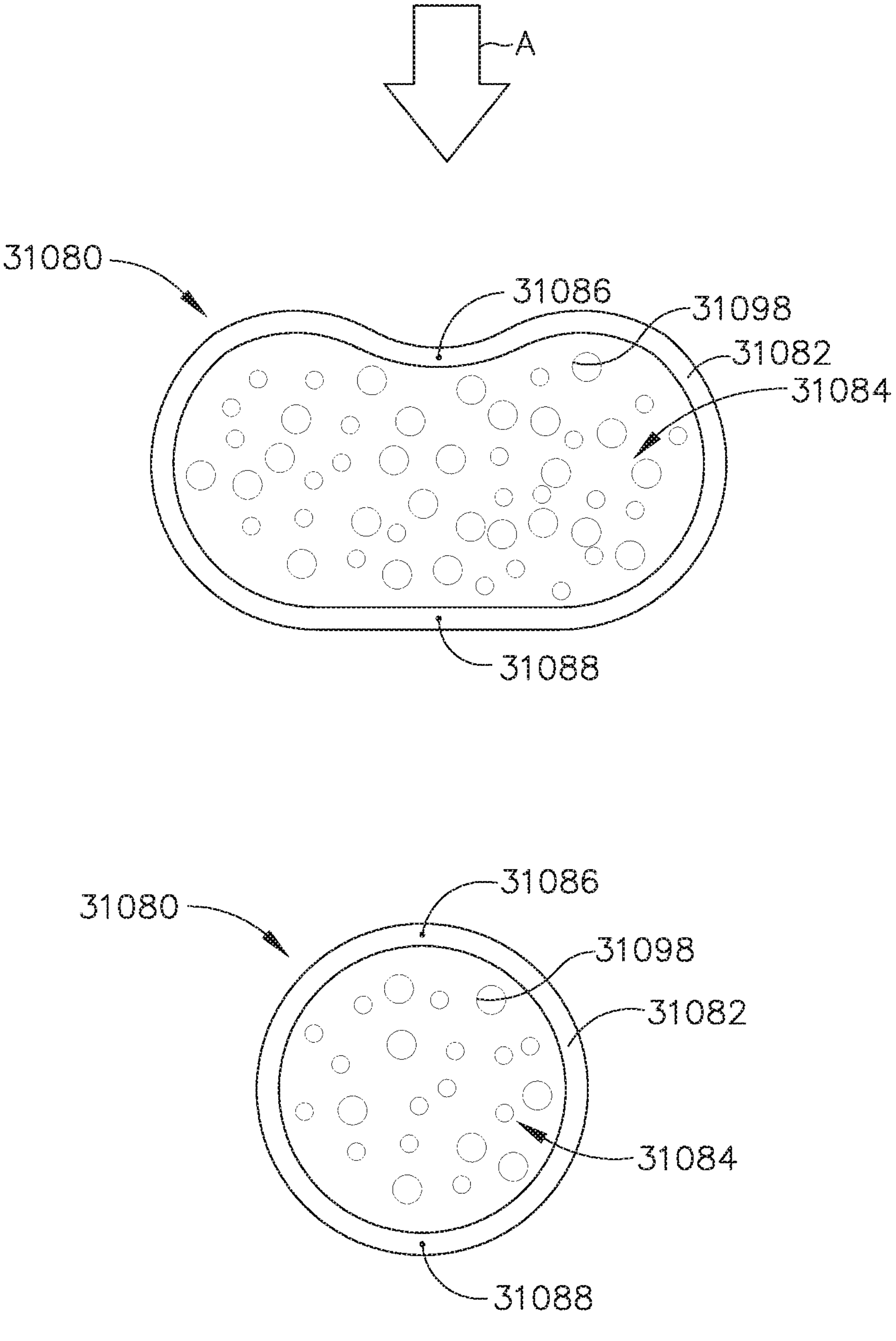
Figure 417:
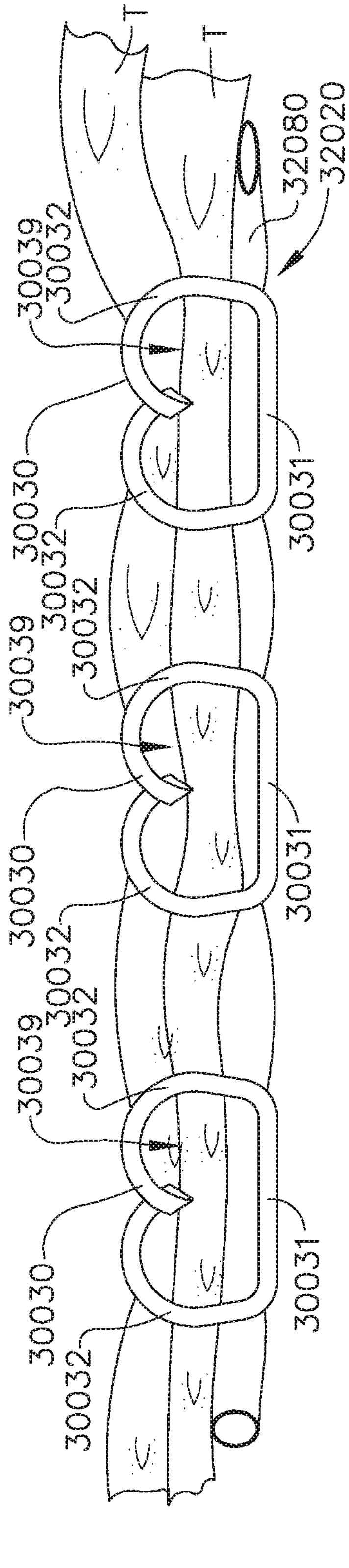
Figure 418:
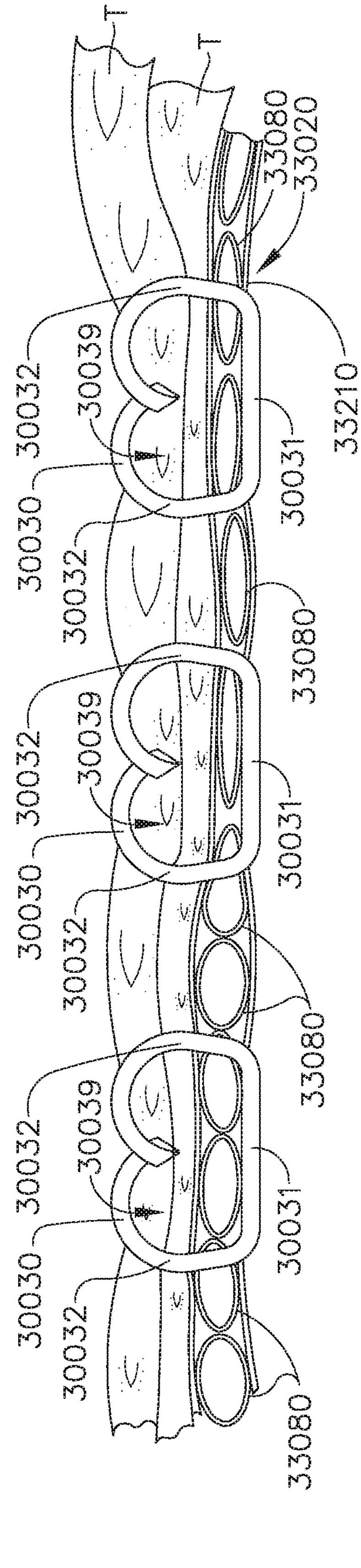
Figure 419:
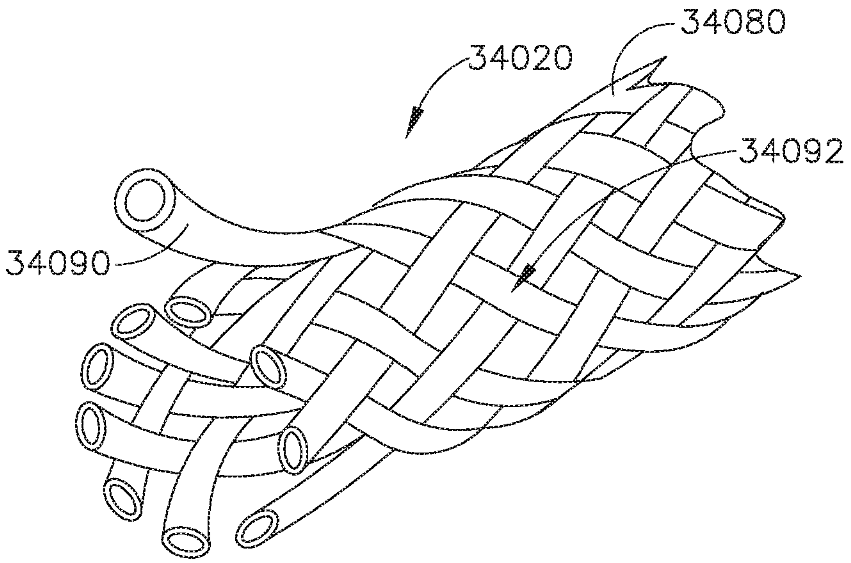
Figure 420:
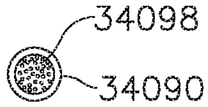

FIG. 122 is a bottom perspective view of the fastening system arrangement of FIG. 121;

FIG. 123 is a partial perspective view of the fastening system arrangement of FIG. 121;

FIG. 124 is a partial cross-sectional view of the fastening system arrangement of FIG. 121;

FIG. 125 is an elevational view of an end effector in accordance with at least one embodiment comprising a jaw in an open position, a retention matrix and a plurality of protective caps positioned in the jaw, and a staple cartridge positioned in a staple cartridge channel;

FIG. 126 is an elevational view of the end effector of FIG. 125 in a closed position;

FIG. 127 is an elevational view of the end effector of FIG. 125 in a fired position;

FIG. 128 is an elevational view of the retention matrix and protective caps of FIG. 125 assembled to the staple cartridge of FIG. 125;

FIG. 129 is a detail view of the arrangement of FIG. 128;

FIG. 130 is an elevational view of the end effector of FIG. 125 illustrating the jaw in an open position with thinner tissue positioned between the retention matrix and the staple cartridge;

FIG. 131 is an elevational view of the end effector of FIG. 125 illustrating the jaw in a closed position against the thinner tissue of FIG. 130;

FIG. 132 is an elevational view of the end effector of FIG. 125 illustrating the jaw in a fired position to capture the thinner tissue of FIG. 130 between the retention matrix and the staple cartridge;

FIG. 133 is an elevational view of the retention matrix and the protective caps of FIG. 125 assembled to the staple cartridge of FIG. 125 with the thin tissue of FIG. 130 positioned therebetween;

FIG. 134 is a detail view of the arrangement of FIG. 133;

FIG. 135 is a cross-sectional view of a protective cap positioned on the tip of a staple leg in accordance with at least one alternative embodiment;

FIG. 136 is a perspective view of a plurality of protective caps embedded within a sheet of material;

FIG. 137 is a perspective view of a jaw comprising a plurality of recesses configured to receive a plurality of protective caps therein;

FIG. 138 is a detail view of a portion of a jaw comprising a sheet covering the protective caps positioned within the jaw of FIG. 137;

FIG. 139 is a cross-sectional view of a protective cap positioned on a tip of a staple leg in accordance with at least one alternative embodiment wherein the protective cap comprises an interior forming surface;

FIG. 140 is another cross-sectional view of the protective cap of FIG. 139 illustrating the staple leg being deformed against the forming surface;

FIG. 141 is a top view of an alternative embodiment of a retention matrix comprising a plurality of connected matrix elements;

FIG. 142 is a top view of an alternative embodiment of a retention matrix comprising a plurality of connected matrix elements;

FIG. 143 is a top view of an alternative embodiment of a retention matrix comprising a plurality of connected matrix elements;

FIG. 144 is a top view of an alternative embodiment of an array of retention matrices comprising a plurality of connected matrix elements;

FIG. 145 is a top view of an alternative embodiment of a retention matrix comprising a plurality of connected matrix elements;

FIG. 146 is a partial exploded view of a jaw comprising a retention matrix including a compressible cover;

FIG. 147 is a detail view of the retention matrix of FIG. 146;

FIG. 148 is a partial cross-sectional view of a fastening system comprising a retention matrix including a compressible layer and a plurality of cells encapsulating one or more medicaments;

FIG. 149 is a diagram illustrating staple legs which have pierced the cells of FIG. 148 as they are being engaged with the retention matrix;

FIG. 150 is a partial cross-sectional view of a fastening system comprising a retention matrix including a compressible layer;

FIG. 151 is an elevational view of a fastener cartridge insertion assembly comprising a holder, a first fastener cartridge, and a second fastener cartridge;

FIG. 152 is an elevational view of an end effector of a surgical stapler comprising a first jaw and a second jaw, the second jaw being illustrated in an open configuration;

FIG. 153 is an elevational view of the end effector of FIG. 152 illustrating the second jaw in a closed configuration and the fastener cartridge insertion assembly of FIG. 151 being used to load the first jaw with the first cartridge and the second jaw with the second cartridge;

FIG. 154 is an elevational view of the loaded end effector of FIG. 153 illustrating the cartridge insertion assembly removed from the end effector, the second jaw in an open configuration once again, and tissue positioned intermediate the first jaw and the second jaw;

FIG. 155 is an elevational view of the loaded end effector of FIG. 154 in a fired configuration;

FIG. 156 is an elevational view of the first cartridge and the second cartridge in an implanted condition;

FIG. 157 is an elevational view of the end effector of FIG. 152 illustrating a portion of the first cartridge still engaged with the first jaw in accordance with at least one embodiment;

FIG. 158 is an elevational view of an alternative embodiment of a fastener cartridge insertion assembly comprising a holder, a first fastener cartridge, and a second fastener cartridge;

FIG. 159 is an elevational view of the fastener cartridge insertion assembly of FIG. 158 being used to load a first jaw of an end effector with the first cartridge and a second jaw with the second cartridge;

FIG. 160 is a cross-sectional view of the loaded end effector of FIG. 159;

FIG. 161 is a perspective view of a surgical stapler comprising a bottom jaw and a top jaw in accordance with at least one embodiment illustrated with portions of the surgical stapler removed;

FIG. 162 is a perspective view of the surgical stapler of FIG. 161 with the top jaw removed;

FIG. 163 is a perspective view of a slidable anvil system of the top jaw of the surgical stapler of FIG. 161 comprising a first slidable anvil and a second slidable anvil;

FIG. 164 is an end view of the slidable anvil system of FIG. 163;

FIG. 165 is a top view of the slidable anvil system of FIG. 163;

FIG. 166 is a diagram illustrating the slidable anvil system of FIG. 163 in an unfired condition;

FIG. 167 is a diagram illustrating the first slidable anvil of the slidable anvil system of FIG. 163 in an unfired position and staples positioned within the bottom jaw in an undeployed position;

FIG. 168 is a diagram illustrating the staples in the bottom jaw in a deployed configuration and the first slidable anvil of FIG. 167 being pulled proximally to deform a first group of staple legs of the staples;

FIG. 169 is a diagram illustrating the first group of staples of FIG. 168 deformed to a fully deformed state;

FIG. 170 is a diagram illustrating the second slidable anvil of the slidable anvil system of FIG. 163 being pushed distally to deform a second group of staple legs;

FIG. 171 is a partial perspective view of an anvil comprising a plurality of forming pockets in at least one embodiment;

FIG. 172 is a cross-sectional end view of the anvil of FIG. 171;

FIG. 173 is a diagram illustrating a first step in manufacturing the forming pockets of FIG. 171;

FIG. 174 is a diagram illustrating a second step in manufacturing the forming pockets of FIG. 171;

FIG. 175 is a top view of the forming pocket arrangement of the anvil of FIG. 171;

FIG. 176 is a diagram illustrating a first step of a manufacturing process for producing an anvil;

FIG. 177 is a diagram illustrating a second step in the manufacturing process of FIG. 176;

FIG. 178 is a diagram illustrating a third step in the manufacturing process of FIG. 176;

FIG. 179 is a left front perspective view of a surgical stapling and severing instrument with a handle portion including a link triggered automatic retraction and a ratcheting manual retraction mechanism;

FIG. 180 is a right aft perspective view of the surgical stapling and severing instrument of FIG. 179 with a portion of an elongate shaft cut away and a right half shell of a handle housing removed to expose an automatic end-of-firing travel retraction mechanism and a manual firing retraction mechanism;

FIG. 181 is a right aft perspective disassembled view of the handle portion and an elongate shaft of the surgical stapling and severing instrument of FIG. 179;

FIG. 182 is a right aft perspective view of the surgical stapling and severing instrument of FIG. 31 with a right half shell and outer portions of the implement portion removed to expose the closure and firing mechanisms in an initial state;

FIG. 183 is a right side view in elevation of the partially disassembled surgical stapling and severing instrument of FIG. 182;

FIG. 184 is a right aft perspective view of the partially disassembled surgical stapling and severing instrument of FIG. 182 with a closure mechanism closed and clamped and the side pawl firing mechanism completing a first stroke and with a manual retraction mechanism removed to expose a distal link of the linked rack that triggers automatic retraction of the firing mechanism;

FIG. 185 is a right aft perspective view of the partially disassembled surgical stapling and severing instrument of FIG. 183 with the side pawl firing mechanism disengaged and the distal link approaching automatic retraction;

FIG. 186 is left side view in elevation of the partially disassembled surgical stapling and severing instrument of FIG. 183 in an initial state of end effector open and anti-backup mechanism engaged;

FIG. 187 is a left side detail view of the right half shell and an anti-backup release lever of the handle portion of FIG. 186;

FIG. 188 is a left side detail view in elevation of the disassembled surgical stapling and severing instrument of FIG. 179 with the closure trigger clamped, the firing trigger performing a final stroke and the distal link positioned to trip automatic retraction;

FIG. 189 is a left side detail in elevation of the disassembled surgical stapling and severing instrument of FIG. 188 immediately after the distal link has actuated and locked forward the anti-backup release lever, allowing the linked rack to retract;

FIG. 190 is a right disassembled perspective view of the idler and aft gears and manual retraction lever and ratcheting pawl of a manual retraction mechanism of the surgical stapling and severing instrument of FIG. 179;

FIG. 191 is a right perspective view of the manual retraction mechanism of FIG. 190 with the manual retraction lever partially cut away to expose a smaller diameter ratchet gear on the aft gear engaging the ratcheting pawl;

FIG. 192 is a partially disassembled left side view in elevation of a surgical stapling and severing instrument of FIG. 179 with the anti-backup mechanism engaged to a fully fired linked rack that is disconnected from a combination tension/compression spring prior to actuation of the manual retraction lever of FIG. 190;

FIG. 193 is a partially disassembled left side view in elevation of the surgical stapling and severing instrument of FIG. 192 with hidden portions of the anti-backup release lever, aft gear, and manual firing release lever shown in phantom;

FIG. 194 is a partially disassembled left side view in elevation of the surgical stapling and severing instrument of FIG. 193 after actuation of the manual firing release lever has manually retracted the link rack;

FIG. 195 is a partially disassembled left side view in elevation of the surgical stapling and severing instrument of FIG. 194 with the linked rack omitted depicting the manual firing release lever disengaging the anti-backup mechanism;

FIG. 196 is a left side detail view of an alternative anti-backup release lever and handle housing for the surgical stapling and severing instrument of FIG. 179;

FIG. 197 is a left perspective disassembled view of the alternative anti-backup release lever, aft gear axle, and automatic retraction cam wheel of FIG. 196;

FIG. 198 is a right side view in elevation of the alternative anti-backup release mechanism of FIG. 196 with the linked rack in a retracted position and the anti-backup release lever proximally positioned with the anti-backup plate engaged to the firing rod;

FIG. 198A is a right detail side view in elevation of the aft gear, automatic retraction cam wheel and distal-most link of FIG. 198;

FIG. 199 is a right side view in elevation of the anti-backup release mechanism of FIG. 198 after a first firing stroke;

FIG. 199A is a right detail side view in elevation of the aft gear, automatic retraction cam wheel and a second link of FIG. 199;

FIG. 200 is a right side view in elevation of the anti-backup release mechanism of FIG. 199 after a second firing stroke;

FIG. 200A is a right detail side view in elevation of the aft gear, automatic retraction cam wheel and third link of FIG. 200;

FIG. 201 is a right detail side view in elevation of the anti-backup release mechanism of FIG. 200 after a third firing and final stroke;

FIG. 201A is a right detail side view in elevation of the aft gear, automatic retraction cam wheel and proximal-most fourth link of FIG. 201;

FIG. 202 is a right side view in elevation of the automatic release mechanism of FIG. 201 after a further firing stroke causes the automatic retraction cam wheel to distally slide and lock the anti-backup release lever, disengaging the anti-backup mechanism;

FIG. 203 is a left, front perspective view of an open staple applying assembly with a right half portion of a replaceable staple cartridge included in a staple channel;

FIG. 204 is an exploded perspective view of the staple applying assembly of FIG. 203 with a complete replaceable staple cartridge and an nonarticulating shaft configuration;

FIG. 205 is a perspective view of a two-piece knife and firing bar ("E-beam") of the staple applying assembly of FIG. 203;

FIG. 206 is a perspective view of a wedge sled of a staple cartridge of a staple applying assembly;

FIG. 207 is a left side view in elevation taken in longitudinal cross section along a centerline line 207-207 of the staple applying assembly of FIG. 203;

FIG. 208 is a perspective view of the open staple applying assembly of FIG. 203 without the replaceable staple cartridge, a portion of the staple channel proximate to a middle pin of two-piece knife and firing bar, and without a distal portion of a staple channel;

FIG. 209 is a front view in elevation taken in cross section along line 209-209 of the staple applying assembly of FIG. 203 depicting internal staple drivers of the staple cartridge and portions of the two-piece knife and firing bar;

FIG. 210 is a left side view in elevation taken generally along the longitudinal axis of line 207-207 of a closed staple applying assembly of FIG. 203 to include center contact points between the two-piece knife and wedge sled but also laterally offset to show staples and staple drivers within the staple cartridge;

FIG. 211 is a left side detail view in elevation of the staple applying assembly of FIG. 210 with the two-piece knife retracted slightly more as typical for staple cartridge replacement;

FIG. 212 is a left side detail view in elevation of the staple applying assembly of FIG. 211 with the two-piece knife beginning to fire, corresponding to the configuration depicted in FIG. 210;

FIG. 213 is a left side cross-sectional view in elevation of the closed staple applying assembly of FIG. 210 after the two-piece knife and firing bar has distally fired;

FIG. 214 is a left side cross-sectional view in elevation of the closed staple applying assembly of FIG. 213 after firing of the staple cartridge and retraction of the two-piece knife;

FIG. 215 is a left side cross-sectional detail view in elevation of the staple applying assembly of FIG. 214 with the two-piece knife allowed to drop into a lockout position;

FIG. 216 is a perspective view of a staple cartridge comprising a rigid support portion and a compressible tissue thickness compensator for use with a surgical stapling instrument in accordance with at least one embodiment of the invention;

FIG. 217 is a partially exploded view of the staple cartridge of FIG. 216;

FIG. 218 is a fully exploded view of the staple cartridge of FIG. 216;

FIG. 219 is another exploded view of the staple cartridge of FIG. 216 without a warp covering the tissue thickness compensator;

FIG. 220 is a perspective view of a cartridge body, or support portion, of the staple cartridge of FIG. 216;

FIG. 221 is a top perspective view of a sled movable within the staple cartridge of FIG. 216 to deploy staples from the staple cartridge;

FIG. 222 is a bottom perspective view of the sled of FIG. 221;

FIG. 223 is an elevational view of the sled of FIG. 221;

FIG. 224 is a top perspective view of a driver configured to support one or more staples and to be lifted upwardly by the sled of FIG. 221 to eject the staples from the staple cartridge;

FIG. 225 is a bottom perspective view of the driver of FIG. 224;

FIG. 226 is a wrap configured to at least partially surround a compressible tissue thickness compensator of a staple cartridge;

FIG. 227 is a partial cut away view of a staple cartridge comprising a rigid support portion and a compressible tissue thickness compensator illustrated with staples being moved from an unfired position to a fired position during a first sequence;

FIG. 228 is an elevational view of the staple cartridge of FIG. 227;

FIG. 229 is a detail elevational view of the staple cartridge of FIG. 227;

FIG. 230 is a cross-sectional end view of the staple cartridge of FIG. 227;

FIG. 231 is a bottom view of the staple cartridge of FIG. 227;

FIG. 232 is a detail bottom view of the staple cartridge of FIG. 227;

FIG. 233 is a longitudinal cross-sectional view of an anvil in a closed position and a staple cartridge comprising a rigid support portion and a compressible tissue thickness compensator illustrated with staples being moved from an unfired position to a fired position during a first sequence;

FIG. 234 is another cross-sectional view of the anvil and the staple cartridge of FIG. 233 illustrating the anvil in an open position after the firing sequence has been completed;

FIG. 235 is a partial detail view of the staple cartridge of FIG. 233 illustrating the staples in an unfired position;

FIG. 236 is a cross-sectional elevational view of a staple cartridge comprising a rigid support portion and a compressible tissue thickness compensator illustrating the staples in an unfired position;

FIG. 237 is a detail view of the staple cartridge of FIG. 236;

FIG. 238 is an elevational view of an anvil in an open position and a staple cartridge comprising a rigid support portion and a compressible tissue thickness compensator illustrating the staples in an unfired position;

FIG. 239 is an elevational view of an anvil in a closed position and a staple cartridge comprising a rigid support portion and a compressible tissue thickness compensator illustrating the staples in an unfired position and tissue captured between the anvil and the tissue thickness compensator;

FIG. 240 is a detail view of the anvil and staple cartridge of FIG. 239;

FIG. 241 is an elevational view of an anvil in a closed position and a staple cartridge comprising a rigid support portion and a compressible tissue thickness compensator illustrating the staples in an unfired position illustrating thicker tissue positioned between the anvil and the staple cartridge;

FIG. 242 is a detail view of the anvil and staple cartridge of FIG. 241;

FIG. 243 is an elevational view of the anvil and staple cartridge of FIG. 241 illustrating tissue having different thicknesses positioned between the anvil and the staple cartridge;

FIG. 244 is a detail view of the anvil and staple cartridge of FIG. 241 as illustrated in FIG. 243;

FIG. 245 is a diagram illustrating a tissue thickness compensator which is compensating for different tissue thickness captured within different staples;

FIG. 246 is a diagram illustrating a tissue thickness compensator applying a compressive pressure to one or more vessels that have been transected by a staple line;

FIG. 247 is a diagram illustrating a circumstance wherein one or more staples have been improperly formed;

FIG. 248 is a diagram illustrating a tissue thickness compensator which could compensate for improperly formed staples;

FIG. 249 is a diagram illustrating a tissue thickness compensator positioned in a region of tissue in which multiple staples lines have intersected;

FIG. 250 is a diagram illustrating tissue captured within a staple;

FIG. 251 is a diagram illustrating tissue and a tissue thickness compensator captured within a staple;

FIG. 252 is a diagram illustrating tissue captured within a staple;

FIG. 253 is a diagram illustrating thick tissue and a tissue thickness compensator captured within a staple;

FIG. 254 is a diagram illustrating thin tissue and a tissue thickness compensator captured within a staple;

FIG. 255 is a diagram illustrating tissue having an intermediate thickness and a tissue thickness compensator captured within a staple;

FIG. 256 is a diagram illustrating tissue having another intermediate thickness and a tissue thickness compensator captured within a staple;

FIG. 257 is a diagram illustrating thick tissue and a tissue thickness compensator captured within a staple;

FIG. 258 is a partial cross-sectional view of an end effector of a surgical stapling instrument illustrating a firing bar and staple-firing sled in a retracted, unfired position;

FIG. 259 is another partial cross-sectional view of the end effector of FIG. 258 illustrating the firing bar and the staple-firing sled in a partially advanced position;

FIG. 260 is a cross-sectional view of the end effector of FIG. 258 illustrating the firing bar in a fully advanced, or fired, position;

FIG. 261 is a cross-sectional view of the end effector of FIG. 258 illustrating the firing bar in a retracted position after being fired and the staple-firing sled left in its fully fired position;

FIG. 262 is a detail view of the firing bar in the retracted position of FIG. 261;

FIG. 263 is a partial cross-sectional view of an end effector of a surgical stapling instrument including a staple cartridge comprising a tissue thickness compensator and staples at least partially positioned therein;

FIG. 264 is another partial cross-sectional view of the end effector of FIG. 263 illustrating the staples at least partially moved and/or rotated relative to an anvil positioned opposite the staple cartridge;

FIG. 265 is a partial cross-sectional view of an end effector of a surgical stapling instrument in accordance with at least one embodiment;

FIG. 266 is a partial cross-sectional view of an end effector in accordance with at least one alternative embodiment;

FIG. 267 is a partial cross-sectional view of an end effector in accordance with another alternative embodiment;

FIG. 268 is a perspective view of an end effector of a surgical stapling instrument in accordance with at least one embodiment;

FIG. 269 is a partial cross-sectional view of the end effector of FIG. 268 illustrated in a flexed condition;

FIG. 270 is a partial cross-sectional view of the end effector of FIG. 269 in a released condition;

FIG. 271 is a perspective view of an end effector comprising a tissue thickness compensator sock;

FIG. 272 is a rear perspective of the tissue thickness compensator sock in FIG. 271;

FIG. 273 is a perspective view of an end effector comprising a plurality of rails extending from a support portion and a tissue thickness compensator having a longitudinal cavity defined therein;

FIG. 274 is a perspective view of the tissue thickness compensator of FIG. 273;

FIG. 275 is a perspective view of an end effector comprising a plurality of teeth extending from a support portion and a tissue thickness compensator engaged therewith;

FIG. 276 is a perspective view of an anvil comprising a pocket array in accordance with at least one embodiment;

FIG. 277 is a partial detail view of the anvil of FIG. 276;

FIG. 278 is a partial longitudinal cross-sectional view of the anvil of FIG. 276;

FIG. 279 is a transverse cross-sectional view of the anvil of FIG. 276;

FIG. 280 is an elevational view of a fired staple comprising a substantially B-shaped configuration;

FIG. 281 is an elevational view of a fired staple comprising one leg deformed inwardly and one leg deformed outwardly;

FIG. 282 is an elevational view of a fired staple comprising both legs formed outwardly;

FIG. 283 is a partial perspective view of a support portion of a staple cartridge comprising detachable and/or displaceable staple leg guides;

FIG. 284 is a partial cross-sectional view of the staple cartridge of FIG. 283 illustrating staples being deployed from the staple cartridge;

FIG. 285 is a detail view of the cross-sectional view of FIG. 284 after the staple cartridge has been fired;

FIG. 286 is an exploded view of a staple cartridge including a tissue thickness compensator comprising voids defined therein;

FIG. 287 is a diagram illustrating the tissue thickness compensator of FIG. 286 implanted against tissue;

FIG. 288 is another diagram illustrating the tissue thickness compensator of FIG. 286 implanted against tissue;

FIG. 289 is a cross-sectional perspective view of a staple cartridge comprising lateral retention members extending from a support portion thereof configured to hold a tissue thickness compensator in position;

FIG. 290 is a cross-sectional view of the staple cartridge of FIG. 289 being utilized to staple tissue;

FIG. 291 is another cross-sectional view of the staple cartridge of FIG. 289 illustrating the support portion being moved away from the implanted tissue thickness compensator;

FIG. 292 is a cross-sectional perspective view of a staple cartridge comprising lateral retention members configured to hold a tissue thickness compensator to a support portion;

FIG. 293 is a cross-sectional view of the staple cartridge of FIG. 292 being utilized to staple tissue;

FIG. 294 is another cross-sectional view of the staple cartridge of FIG. 292 illustrating the support portion being moved away from the implanted tissue thickness compensator;

FIG. 295 is a cross-sectional detail view of a retainer holding a tissue thickness compensator to a support portion of a staple cartridge in accordance with at least one embodiment;

FIG. 296 is partial cut-away view of a staple cartridge comprising staple drivers having different heights in accordance with at least one embodiment;

FIG. 296A is a diagram illustrating the staple drivers of FIG. 296 and staples having different unfired heights supported thereon;

FIG. 297 is a diagram illustrating a tissue thickness compensator comprising a varying thickness, staple drivers having different heights, and staples having different unformed heights;

FIG. 298 is a diagram illustrating the staples and the tissue thickness compensator of FIG. 297 implanted to tissue;

FIG. 299 is a partial cross-sectional view of a staple cartridge comprising a tissue thickness compensator comprising a varying thickness in accordance with at least one embodiment;

FIG. 300 is a cross-sectional view of an end effector of a surgical stapling instrument in an open configuration;

FIG. 301 is cross-sectional view of the end effector of FIG. 300 illustrated in a partially-fired configuration;

FIG. 302 is a cross-sectional view of the end effector of FIG. 300 illustrated in a re-opened configuration;

FIG. 303 is a cross-sectional view of an end effector of a surgical stapling instrument comprising staple drivers having different heights and a contoured deck surface in accordance with at least one embodiment;

FIG. 304 is a cross-sectional view of an end effector of a surgical stapling instrument comprising staple drivers having different heights and a stepped deck surface in accordance with at least one embodiment;

FIG. 305 is a perspective view of a staple cartridge being loaded into an effector of a surgical stapling instrument utilizing a staple cartridge applicator;

FIG. 306 is a bottom perspective view of the staple cartridge applicator of FIG. 305;

FIG. 307 is a side view of the staple cartridge applicator of FIG. 305 assembled to a staple cartridge;

FIG. 308 is a cross-sectional view of the assembly of FIG. 307;

FIG. 309 is a perspective view of a staple cartridge applicator assembly further including an upper tissue thickness compensator positioned on the top surface of the staple cartridge applicator in accordance with at least one embodiment;

FIG. 310 is an exploded view of the upper tissue thickness compensator and the staple cartridge applicator of FIG. 309;

FIG. 310A is an exploded view of a staple cartridge applicator assembly comprising a pull member configured to detach an upper tissue thickness compensator adhered to the staple cartridge applicator;

FIG. 311 is a partial exploded view of a staple cartridge applicator assembly in accordance with at least one alternative embodiment;

FIG. 312 is a perspective view of a staple cartridge applicator assembly comprising an upper tissue thickness compensator including a plurality of retention features extending therefrom and a staple cartridge comprising a lower tissue thickness compensator;

FIG. 313 is an elevational view of the staple cartridge applicator assembly of FIG. 312 positioned within a staple cartridge channel and an anvil being closed onto the staple cartridge applicator assembly;

FIG. 314 is an elevational view of the anvil of FIG. 313 in a re-opened position and the staple cartridge applicator of FIG. 312 being removed from the end effector;

FIG. 314A is a cross-sectional view of tissue positioned intermediate the upper tissue thickness compensator and the lower tissue thickness compensator of FIG. 312;

FIG. 314B is a cross-sectional view illustrating the upper tissue thickness compensator and the lower tissue thickness compensator stapled to the tissue and severed by a cutting member;

FIG. 315 is a diagram illustrating a tissue thickness compensator being inserted into an anvil in accordance with at least one embodiment;

FIG. 316 is a cross-sectional view of the tissue thickness compensator of FIG. 315;

FIG. 317 is an exploded view of a tissue thickness compensator and an anvil in accordance with at least one alternative embodiment;

FIG. 318 is a perspective view of staple cartridge applicator assembly comprising an upper tissue thickness compensator configured to be attached to an anvil in accordance with at least one embodiment;

FIG. 319 is an elevational view of the staple cartridge applicator assembly of FIG. 318 positioned within a staple cartridge channel and an anvil being moved toward the upper tissue thickness compensator;

FIG. 320 illustrates the staple cartridge applicator of FIG. 318 being removed from the end effector after the upper tissue thickness compensator has been engaged with the anvil;

FIG. 321 is a cross-sectional end view of the anvil being moved toward the upper tissue thickness compensator of FIG. 318;

FIG. 322 is a cross-sectional end view of the anvil engaged with the upper tissue thickness compensator;

FIG. 323 is a cross-sectional view of an end effector of a surgical stapling instrument comprising a staple cartridge including a segmentable tissue thickness compensator attached to a support portion of the staple cartridge by a plurality of fasteners;

FIG. 324 is a cross-sectional view of the end effector of FIG. 323 illustrating a firing member in a partially-fired position;

FIG. 325 is a cross-sectional view of the end effector of FIG. 323 illustrating the support portion being moved away from the partially-implanted tissue thickness compensator;

FIG. 326 is a partial perspective view of the support portion of FIG. 323;

FIG. 327 is a perspective view of a staple-deploying sled in accordance with at least one embodiment;

FIG. 328 is an elevational view of the sled of FIG. 327;

FIG. 329 is a perspective view of an end effector of a surgical stapling instrument comprising a staple cartridge including a tissue thickness compensator and a plurality of staple guides positioned on the tissue thickness compensator;

FIG. 330 is a partial cross-sectional view of the tissue thickness compensator and the staple guides of FIG. 329 in an unfired configuration;

FIG. 331 is a partial cross-sectional view of the tissue thickness compensator and the staple guides of FIG. 329 in a fired configuration;

FIG. 332 is a cross-sectional view of a staple cartridge comprising a tissue thickness compensator and a support portion in accordance with at least one embodiment;

FIG. 333 is a partial cross-sectional view of a tissue thickness compensator, a staple guide layer, and a staple in an unfired position;

FIG. 334 is a partial cross-sectional view of a tissue thickness compensator, a staple guide layer, and a staple in an unfired position in accordance with at least one alternative embodiment;

FIG. 335 is a partial cross-sectional view of a tissue thickness compensator, a staple guide layer, and a staple in an unfired position in accordance with at least one alternative embodiment;

FIG. 336 is a partial cross-sectional view of a tissue thickness compensator, a staple guide layer, and a staple in an unfired position in accordance with at least one alternative embodiment;

FIG. 337 is a partial cross-sectional view of a tissue thickness compensator, a staple guide layer, and a staple in an unfired position in accordance with at least one alternative embodiment;

FIG. 338 is a partial cross-sectional view of a tissue thickness compensator, a staple guide layer, and a staple in an unfired position in accordance with at least one alternative embodiment;

FIG. 339 is a partial cross-sectional view of a tissue thickness compensator, a staple guide layer, and a staple in an unfired position in accordance with at least one alternative embodiment;

FIG. 340 is a detail view of a region surrounding a tip of the staple of FIG. 339;

FIG. 341 is a partial cross-sectional view of a tissue thickness compensator, a staple guide layer, and a staple in an unfired position in accordance with at least one alternative embodiment;

FIG. 342 is a detail view of a region surrounding a tip of the staple of FIG. 341;

FIG. 343 is a partial cross-sectional view of a tissue thickness compensator, a staple guide layer, and a staple in an unfired position in accordance with at least one alternative embodiment;

FIG. 344 is a perspective view of a staple guide layer and a plurality of staples in an unfired position in accordance with at least one alternative embodiment;

FIG. 345 is an end view of a tissue thickness compensator configured to be used with a circular surgical stapler;

FIG. 346 is a perspective view of the tissue thickness compensator and the circular surgical stapler of FIG. 345;

FIG. 347 is an end view of a tissue thickness compensator configured to be used with a circular surgical stapler in accordance with at least one alternative embodiment;

FIG. 348 is a perspective view of the tissue thickness compensator and the circular surgical stapler of FIG. 347;

FIG. 349 is an end view of a tissue thickness compensator configured to be used with a circular surgical stapler;

FIG. 350 is an end view of the tissue thickness compensator of FIG. 349 in a partially expanded configuration;

FIG. 351 is an elevational view of a surgical stapling instrument comprising a staple cartridge in accordance with at least one embodiment;

FIG. 352 is an end view of the surgical stapling instrument of FIG. 351 positioned relative to tissue;

FIG. 353 is an end view of the surgical stapling instrument of FIG. 351 further comprising a tissue thickness compensator positioned between the staple cartridge and the tissue;

FIG. 354 is a partial perspective view of staples deployed into tissue from the surgical stapling instrument of FIG. 351 without a tissue thickness compensator;

FIG. 355 is a partial perspective view of staples deployed into tissue from the surgical stapling instrument of FIG. 351 with a tissue thickness compensator;

FIG. 356 is a partial cross-sectional view of the end effector of the surgical stapling instrument of FIG. 351 comprising an anvil plate in a first position;

FIG. 357 is a partial cross-sectional view of the end effector of the surgical stapling instrument of FIG. 351 illustrating the anvil plate of FIG. 356 in a second position;

FIG. 358 is a cross-sectional view of an end effector of a surgical stapling instrument comprising a staple cartridge including a gap setting element;

FIG. 359 is a perspective view illustrating a firing member cutting the gap setting element of FIG. 358 at the end of firing stroke of the firing member;

FIG. 360 is a cross-sectional view of an end effector of a surgical stapling instrument comprising a staple cartridge including a flexible nose;

FIG. 361 is a cross-sectional view of the end effector of FIG. 360 illustrating the nose in a flexed configuration;

FIG. 362 is a cross-sectional view of an end effector of a surgical stapling instrument comprising a staple cartridge including a slidable portion;

FIG. 363 is a cross-sectional view of the end effector of FIG. 362 illustrating the slidable portion slid distally;

FIG. 364 is a cross-sectional view of an end effector of a surgical stapling instrument comprising a support portion comprising an inclined deck surface and a tissue thickness compensator comprising a varying thickness;

FIG. 365 is a cross-sectional view of an end effector of a surgical stapling instrument comprising a support portion comprising an inclined deck surface and a tissue thickness compensator comprising a uniform thickness;

FIG. 366 is a perspective view of a staple cartridge comprising a tissue thickness compensator having a varying thickness;

FIG. 367 is an end view of the staple cartridge of FIG. 366;

FIG. 368 is a cross-sectional perspective view of a tissue thickness compensator comprising longitudinal layers;

FIG. 369 is a cross-sectional perspective view of a tissue thickness compensator comprising a plurality of layers in accordance with at least one alternative embodiment;

FIG. 370 is a perspective view of a disposable loading unit comprising retention members configured to releasably hold a tissue thickness compensator thereto;

FIG. 371 is a perspective view of a tissue thickness compensator including retention members configured to releasably hold the tissue thickness compensator to a disposable loading unit;

FIG. 372 is a perspective view of the tissue thickness compensator of FIG. 371 attached to a disposable loading unit;

FIG. 373 is an end view of the disposable loading unit of FIG. 372;

FIG. 374 is a perspective view of a tissue thickness compensator including retention members configured to releasably hold the tissue thickness compensator to a disposable loading unit;

FIG. 375 is a perspective view of the tissue thickness compensator of FIG. 374 attached to a disposable loading unit;

FIG. 376 is an end view of the disposable loading unit of FIG. 375;

FIG. 377 is a perspective view of a tissue thickness compensator including a retention member configured to releasably hold the tissue thickness compensator to a disposable loading unit;

FIG. 378 is a perspective view of the tissue thickness compensator of FIG. 377 attached to a disposable loading unit;

FIG. 379 is a perspective view of a tissue thickness compensator applicator positioned within an effector of a disposable loading unit;

FIG. 380 is a top perspective view of the tissue thickness compensator applicator of FIG. 379;

FIG. 381 is a bottom perspective view of the tissue thickness compensator applicator of FIG. 379;

FIG. 382 is a perspective view of a tissue thickness compensator applicator positioned within an effector of a disposable loading unit in accordance with at least one alternative embodiment;

FIG. 383 is a top perspective view of the tissue thickness compensator applicator of FIG. 382;

FIG. 384 is a bottom perspective view of the tissue thickness compensator applicator of FIG. 382;

FIG. 385 is an elevational view of a disposable loading unit including a pivotable jaw configured to support a staple cartridge;

FIG. 386 is a cross-sectional view of a staple cartridge comprising a tissue thickness compensator attached to a support portion of the staple cartridge in accordance with at least one embodiment;

FIG. 387 is a cross-sectional view of a staple cartridge comprising a tissue thickness compensator attached to a support portion of the staple cartridge in accordance with at least one embodiment;

FIG. 388 is a cross-sectional view of a staple cartridge comprising a tissue thickness compensator attached to a support portion of the staple cartridge in accordance with at least one embodiment;

FIG. 389 is a perspective view of the tissue thickness compensator of FIG. 387;

FIG. 390 is a perspective view of a tissue thickness compensator in an end effector of a surgical instrument according to at least one embodiment;

FIG. 391 is a detail view of nonwoven material of the tissue thickness compensator of FIG. 390;

FIG. 392 is an elevational view depicting the tissue thickness compensator of FIG. 390 implanted against tissue and released from the end effector;

FIG. 393 is a detail view of nonwoven material of a tissue thickness compensator according to at least one embodiment;

FIG. 394 is a schematic depicting clusters of randomly oriented crimped fibers according to at least one embodiment;

FIG. 395 is a schematic depicting a cluster of randomly oriented crimped fibers according to at least one embodiment;

FIG. 396 is a schematic depicting an arrangement of crimped fibers according to at least one embodiment;

FIG. 397 is a schematic depicting an arrangement of crimped fibers according to at least one embodiment;

FIG. 398 is a schematic depicting an arrangement of crimped fibers according to at least one embodiment;

FIG. 399 is a plan cross-sectional view of coiled fibers in a tissue thickness compensator according to at least one embodiment;

FIG. 399A is a plan cross-sectional view of the coiled fibers of FIG. 399;

FIG. 399B is a cross-sectional detail view of the tissue thickness compensator of FIG. 399;

FIG. 400 is a perspective view of a tissue thickness compensator in an end effector of a surgical instrument according to at least one embodiment;

FIG. 401 is a diagram depicting deformation of the tissue thickness compensator of FIG. 400;

FIG. 402 is a schematic of woven suture for a tissue thickness compensator depicting the woven suture in a loaded configuration according to at least one embodiment;

FIG. 403 is a schematic of the woven suture of FIG. 402 depicting the woven suture in a released configuration;

FIG. 404 is a plan view of a tissue thickness compensator having the woven suture of FIG. 402 in an end effector of a surgical instrument;

FIG. 405 is a perspective view of a tissue thickness compensator in an end effector of a surgical instrument according to at least one embodiment;

FIG. 406 is a partial plan view of the tissue thickness compensator of FIG. 405;

FIG. 407 is an exploded view of the fastener cartridge assembly of the end effector and tissue thickness compensator of FIG. 390;

FIG. 408 is a partial cross-sectional view of the fastener cartridge assembly of FIG. 407 depicting unfired, partially fired, and fired fasteners;

FIG. 409 is an elevational view of the fastener cartridge assembly of FIG. 407 depicting a driver firing fasteners from staple cavities of the fastener cartridge assembly into the tissue thickness compensator;

FIG. 410 is a detail view of the fastener cartridge assembly of FIG. 409;

FIG. 411 is an elevational view of the tissue thickness compensator of FIG. 390 and tissue captured within fired fasteners;

FIG. 412 is an elevational view of the tissue thickness compensator of FIG. 390 and tissue captured within fired fasteners;

FIG. 413 is a perspective view of a tissue thickness compensator in an end effector of a surgical instrument according to at least one embodiment;

FIG. 414 is a diagram depicting deformation of a deformable tube of the tissue thickness compensator of FIG. 413;

FIG. 415 is a detail view of the deformable tube of the tissue thickness compensator of FIG. 413;

FIG. 416 is a diagram depicting deformation of a deformable tube of a tissue thickness compensator according to at least one embodiment;

FIG. 417 is an elevational view of a tissue thickness compensator comprising a tubular element implanted against tissue according to at least one embodiment;

FIG. 418 is an elevational view of a tissue thickness compensator comprising tubular elements implanted against tissue according to at least one embodiment;

FIG. 419 is a partial perspective view of a deformable tube comprising a tubular lattice according to at least one embodiment;

FIG. 420 is an elevational view of a tubular strand of the deformable tube of FIG. 419.

Figure 421:
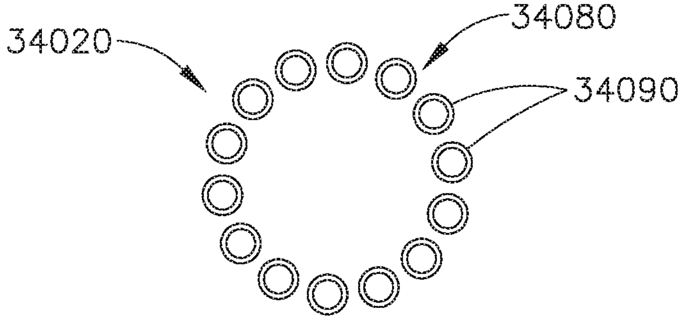
Figure 422:
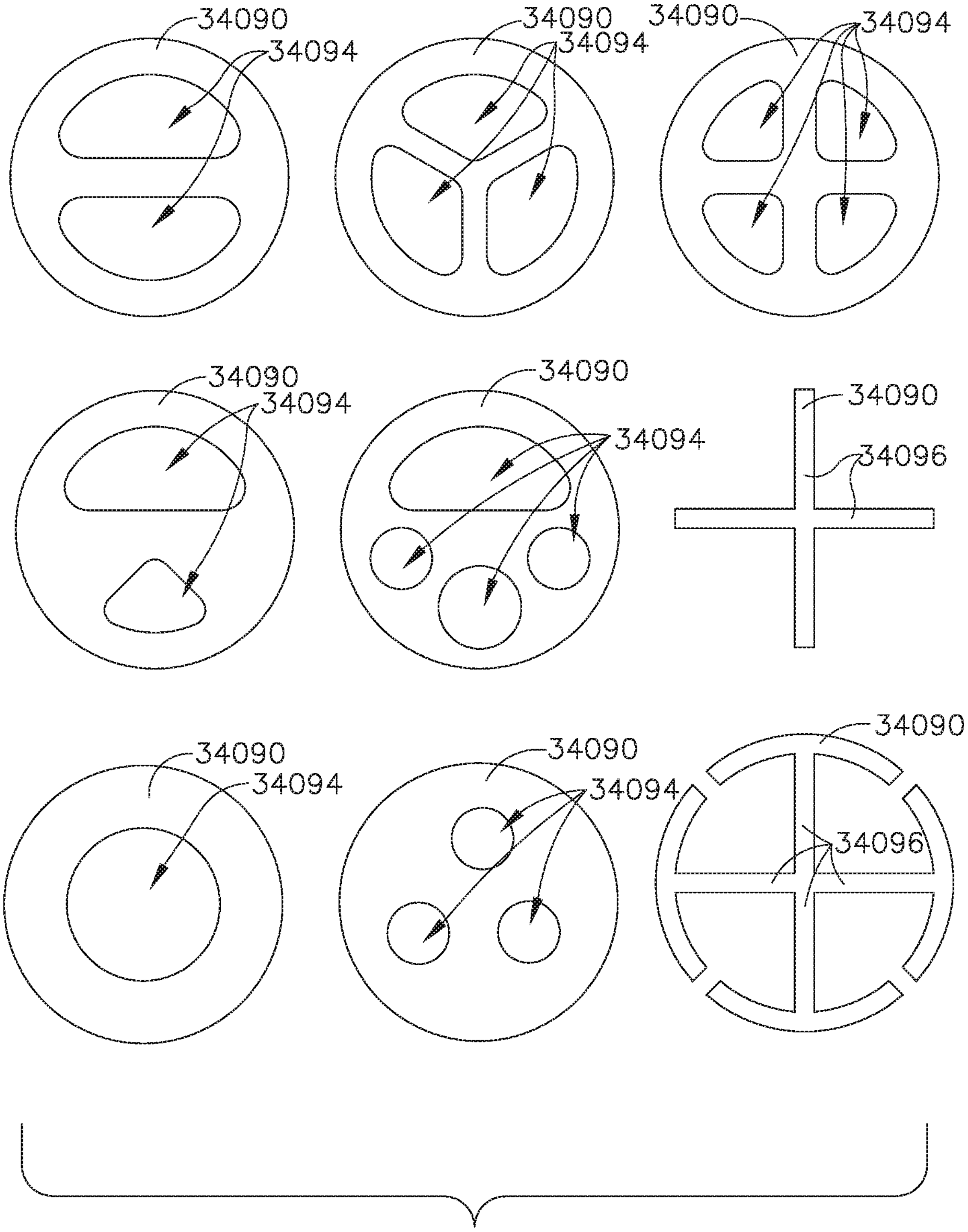
Figure 423:
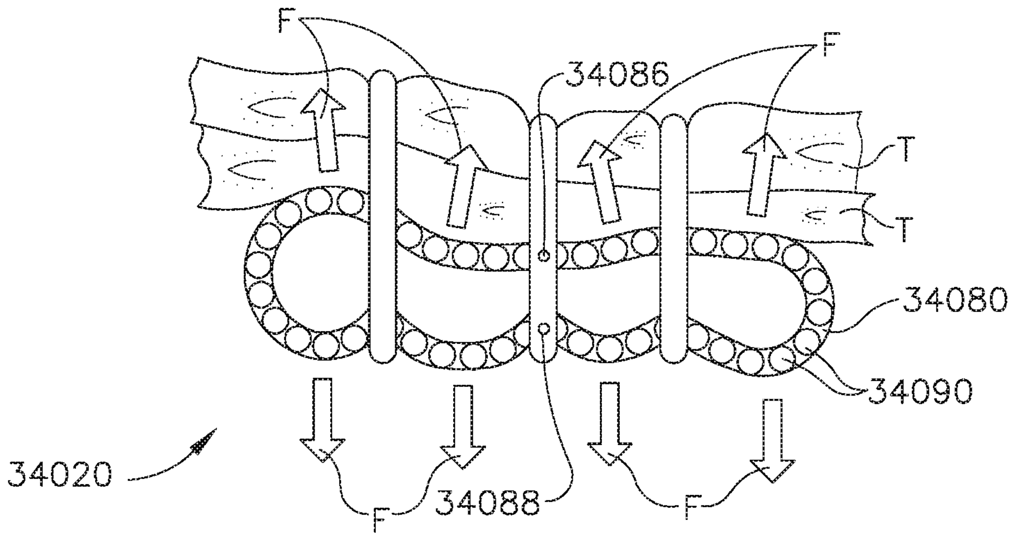
Figure 424:
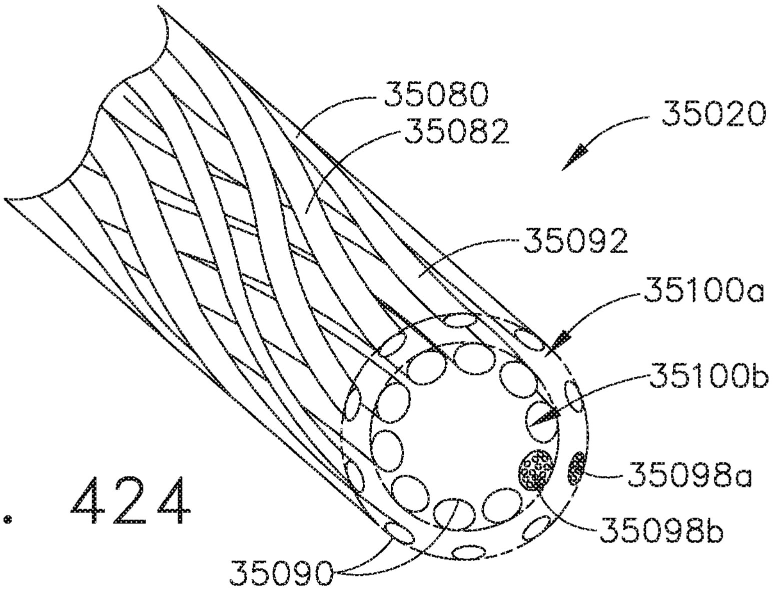
Figure 425:
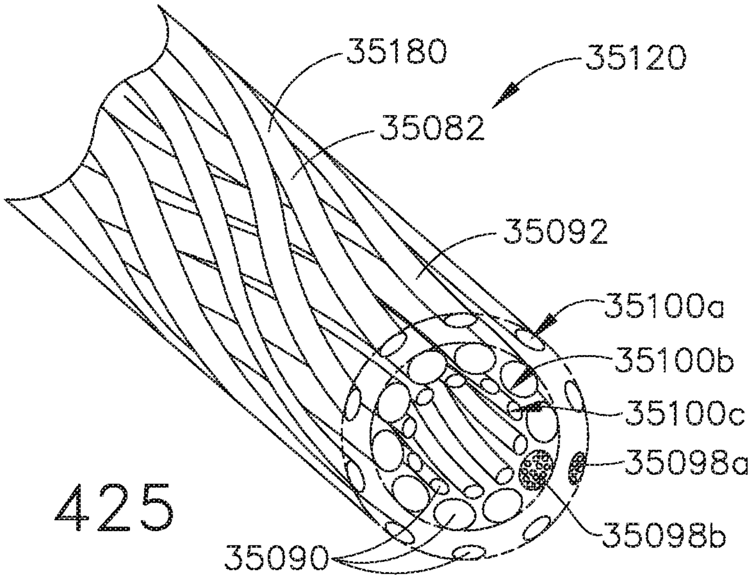
Figure 426:
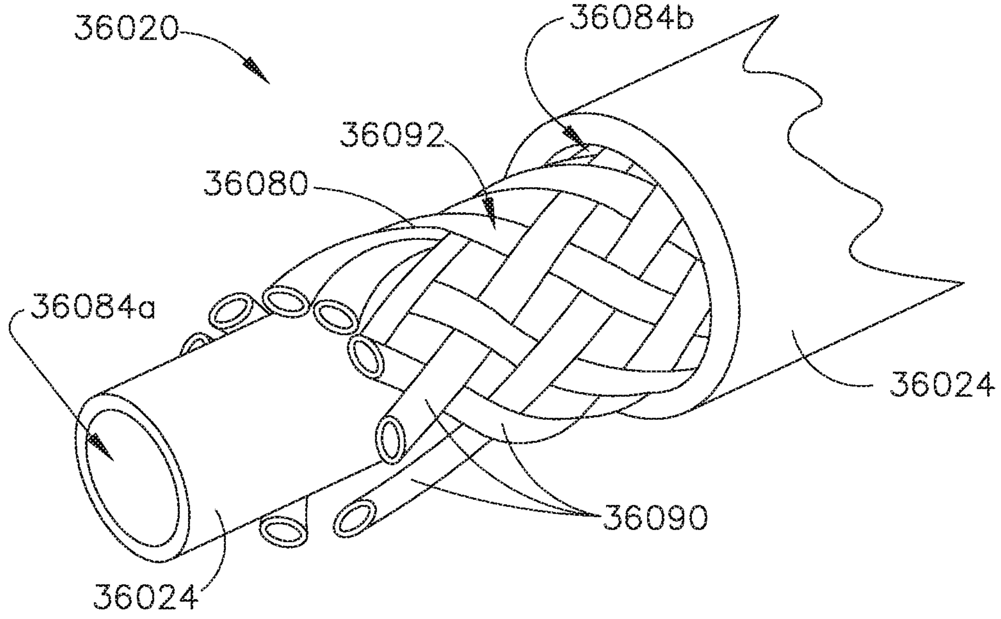
Figure 427:
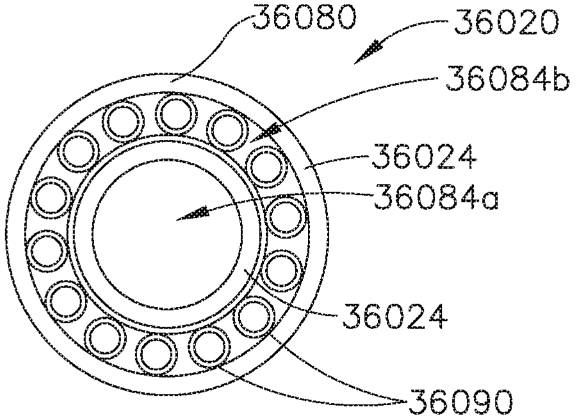
Figure 428:
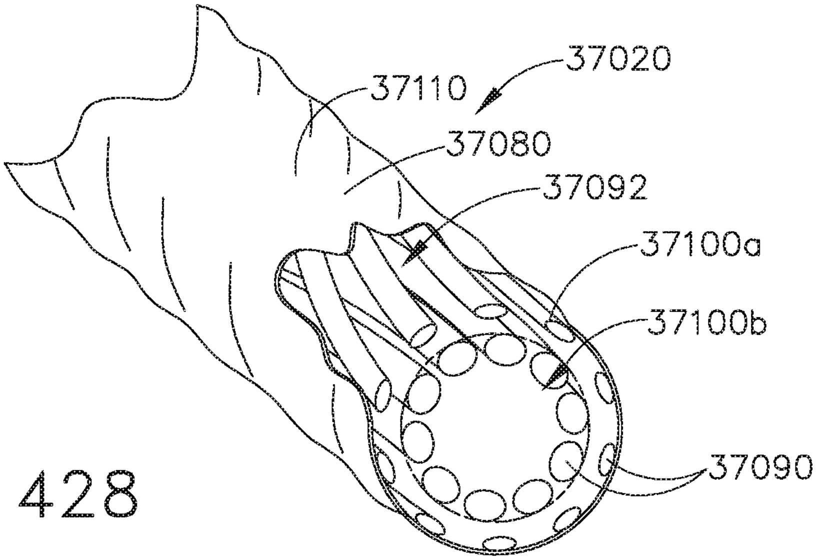
Figure 429:
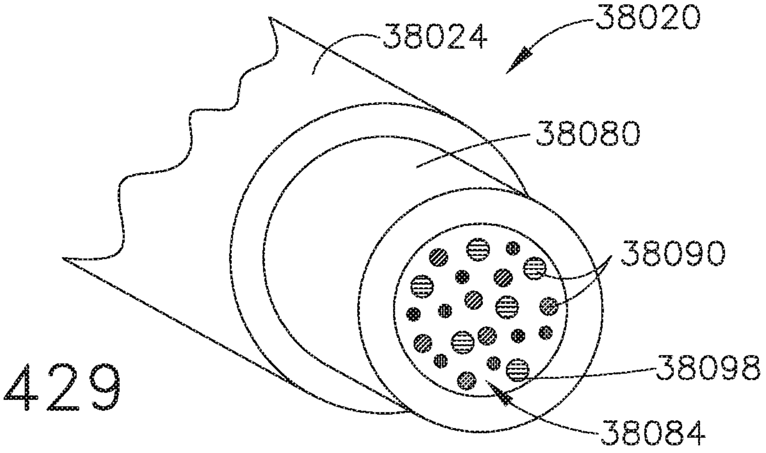
Figure 430:
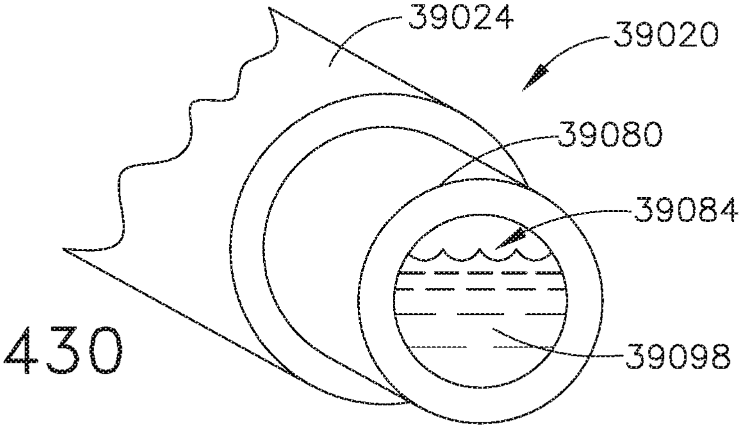
Figure 431:
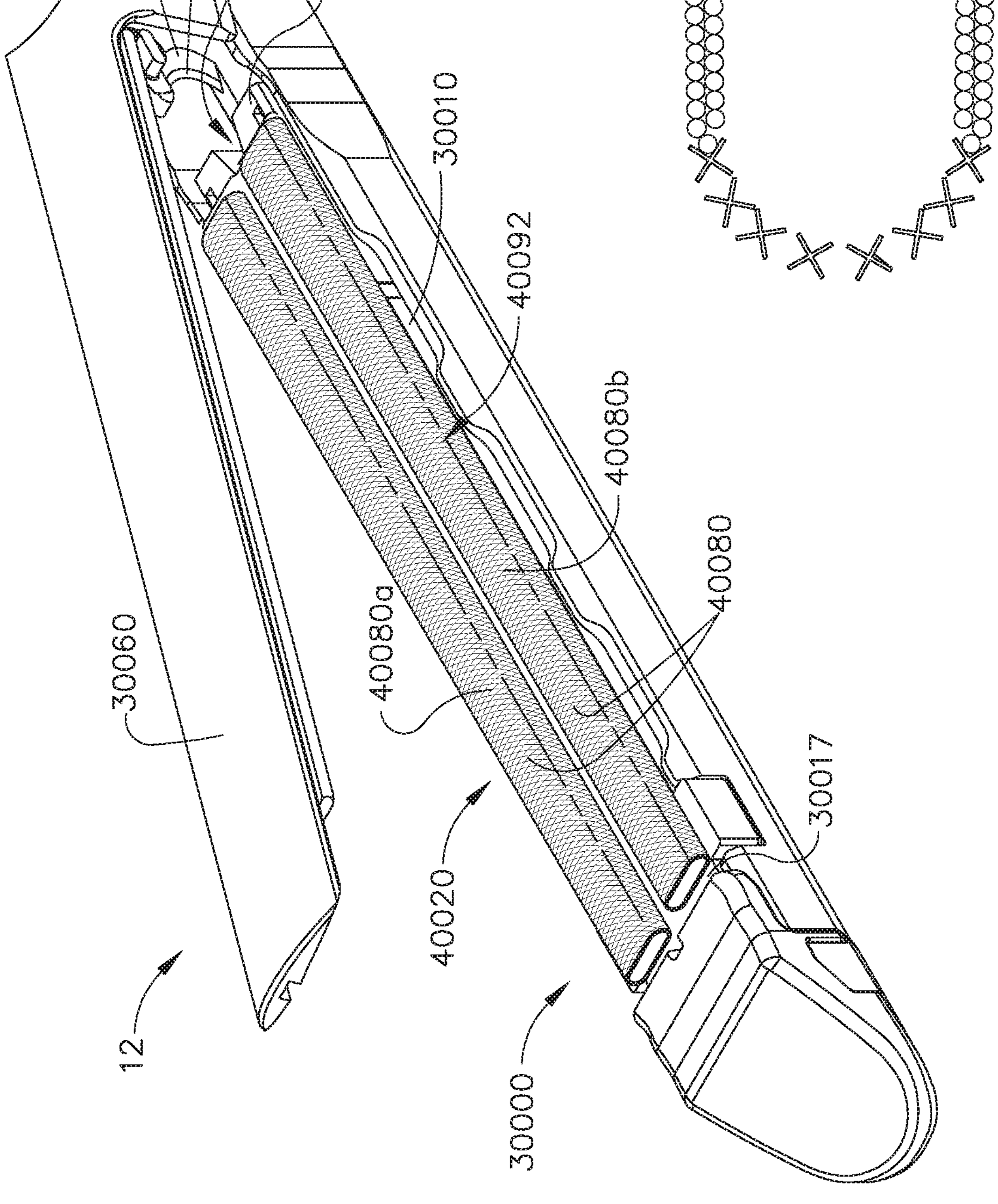
Figure 432:
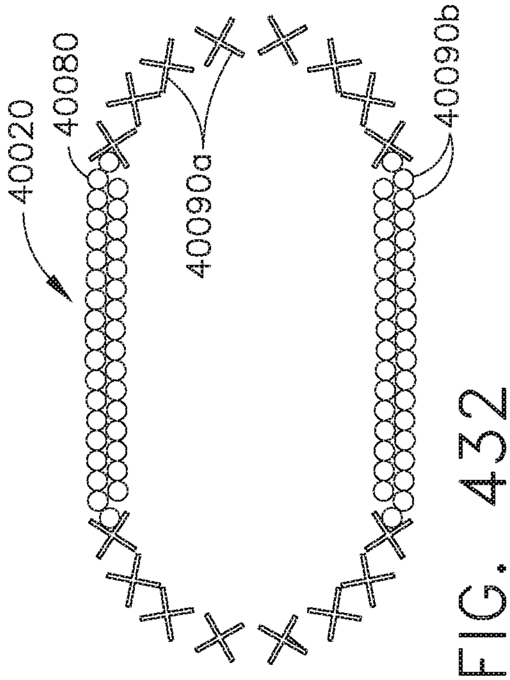
Figure 433:
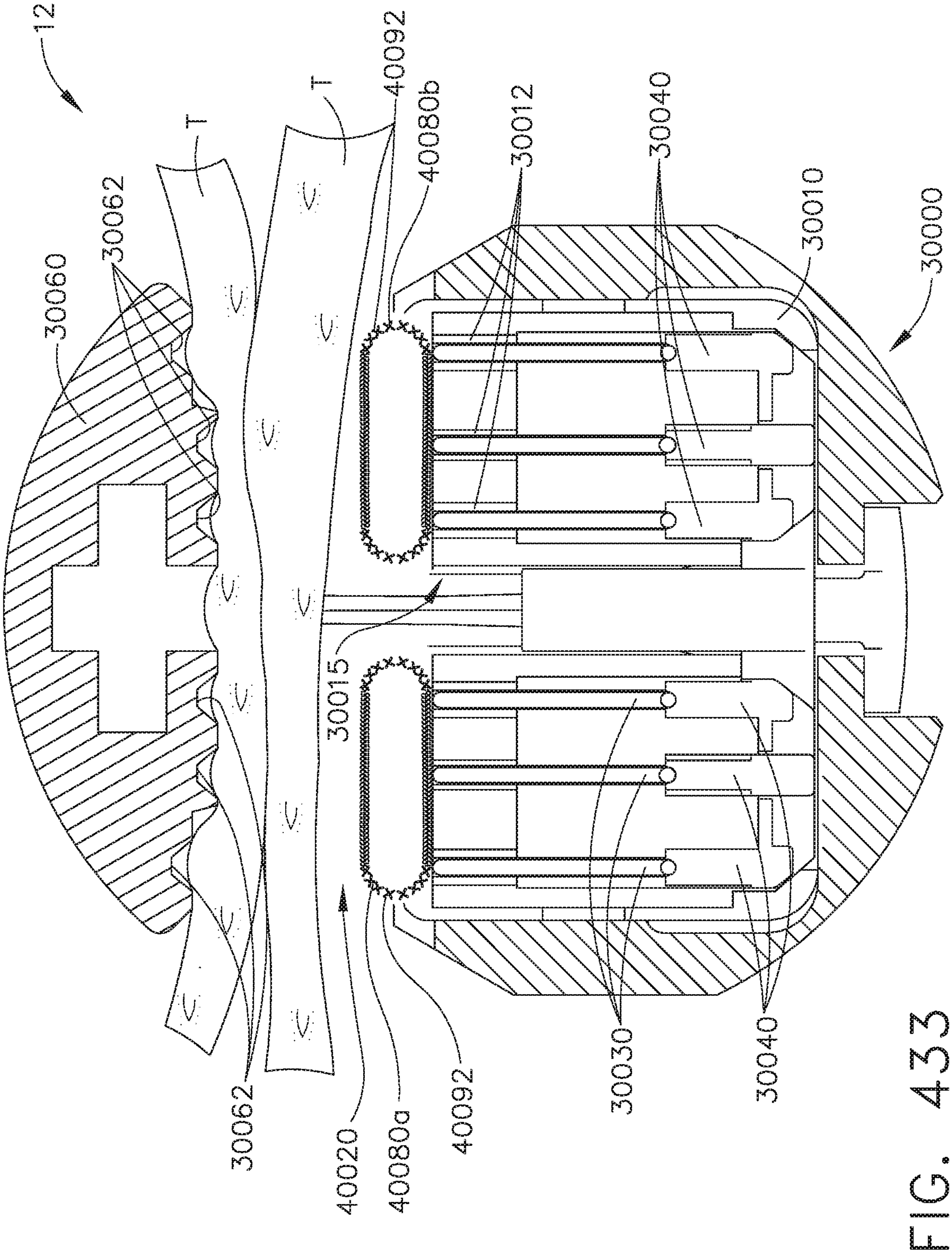
Figure 434:
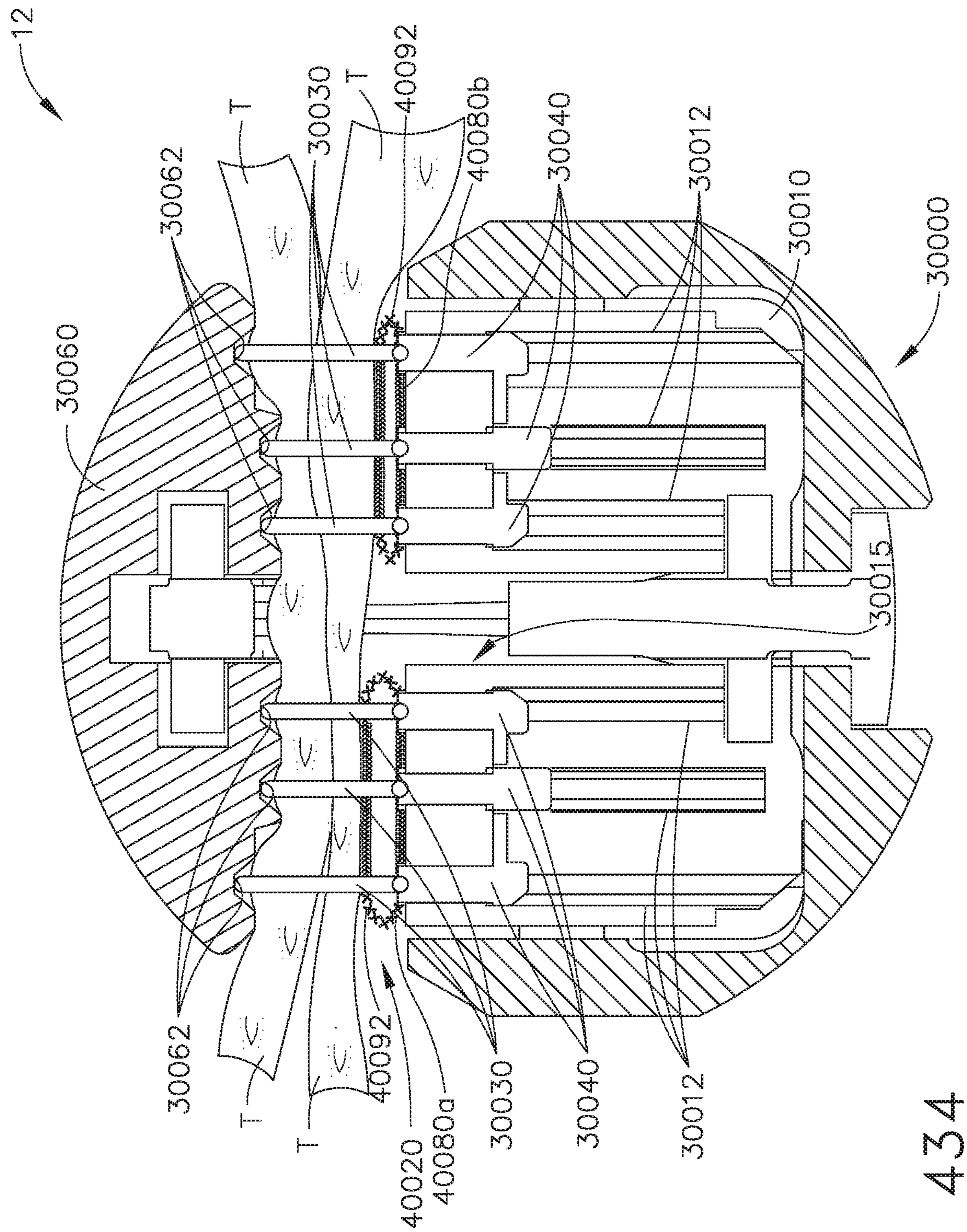
Figure 435:
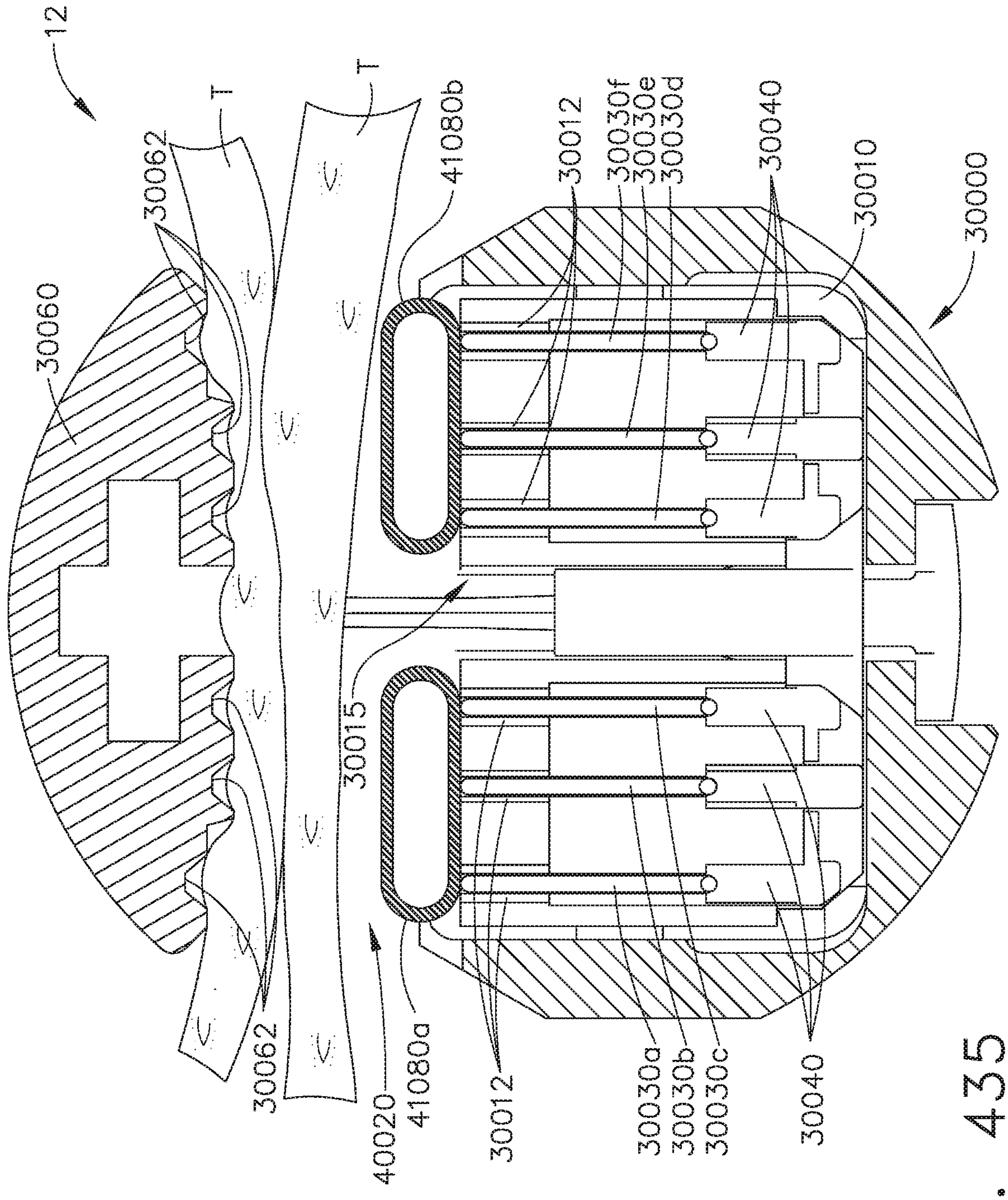
Figure 436:
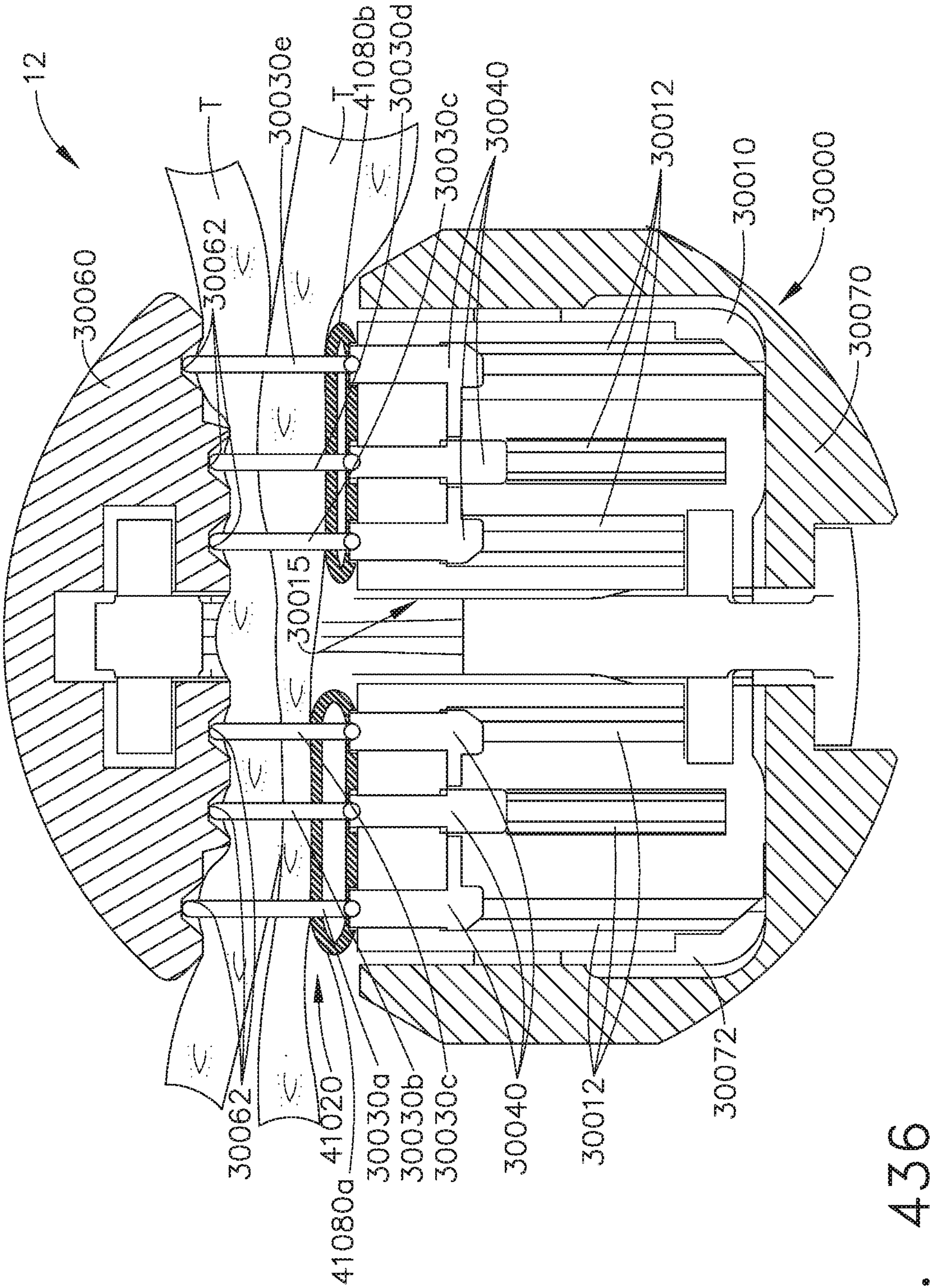
Figure 437:
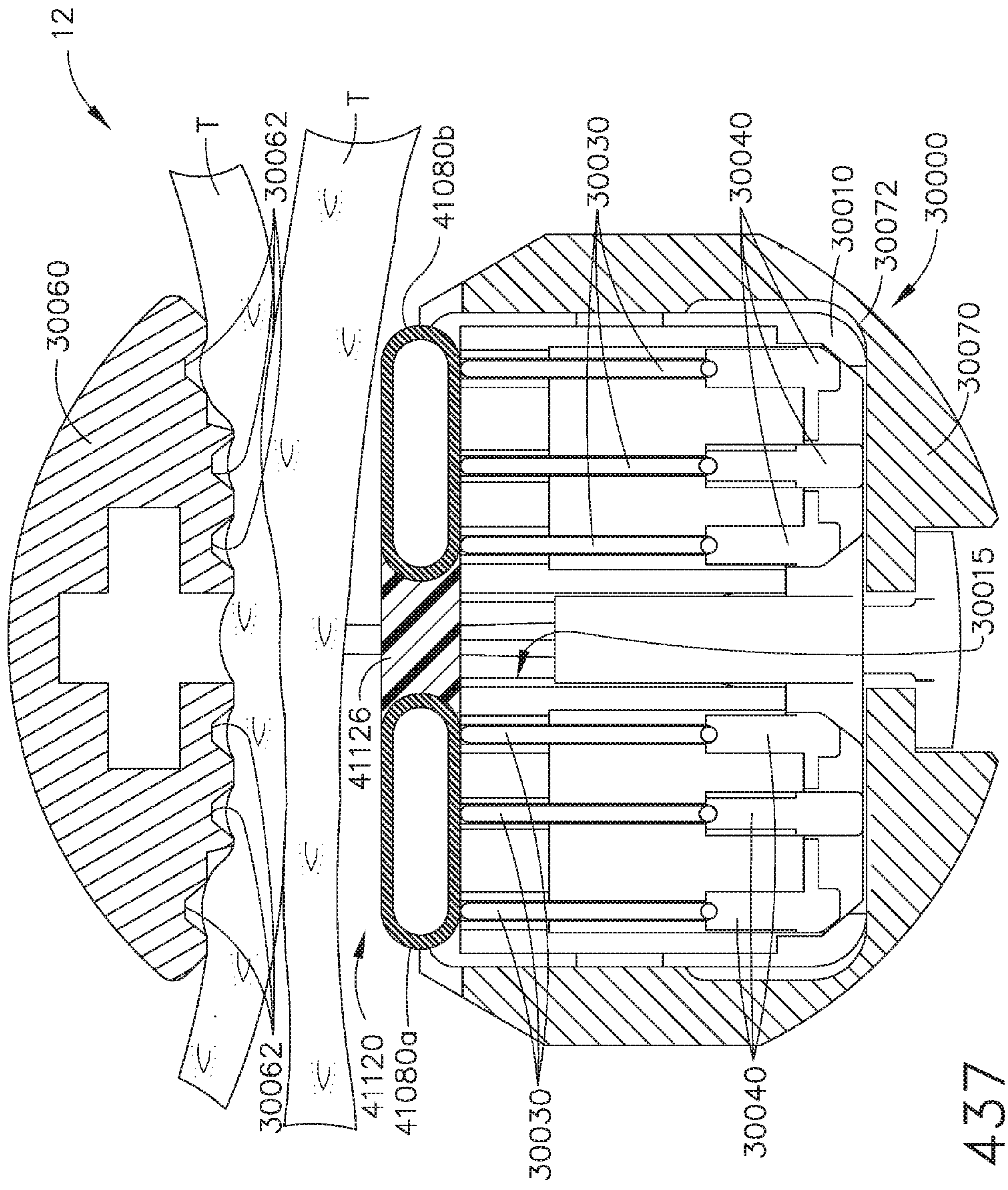
Figure 438:
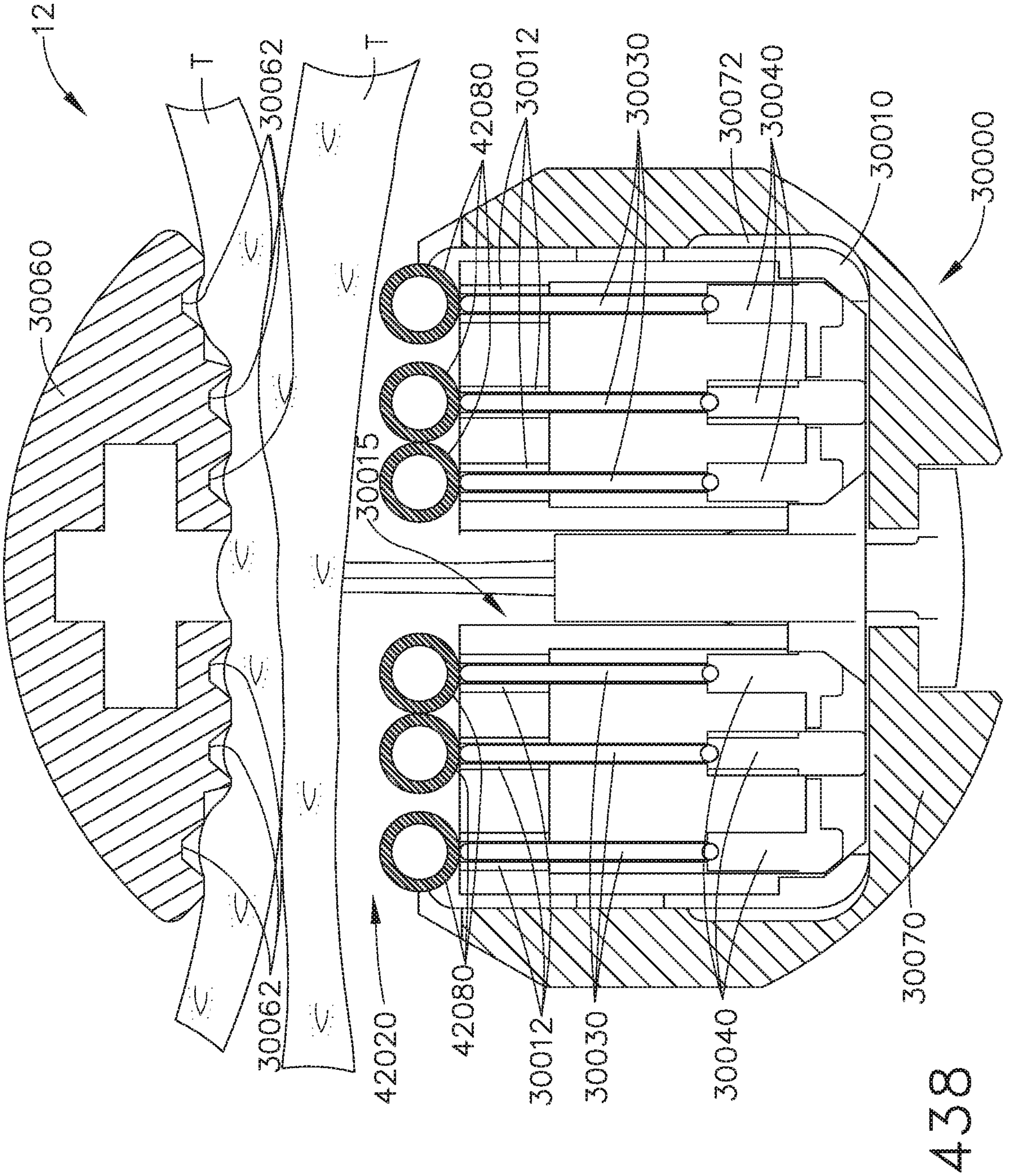
Figure 439:
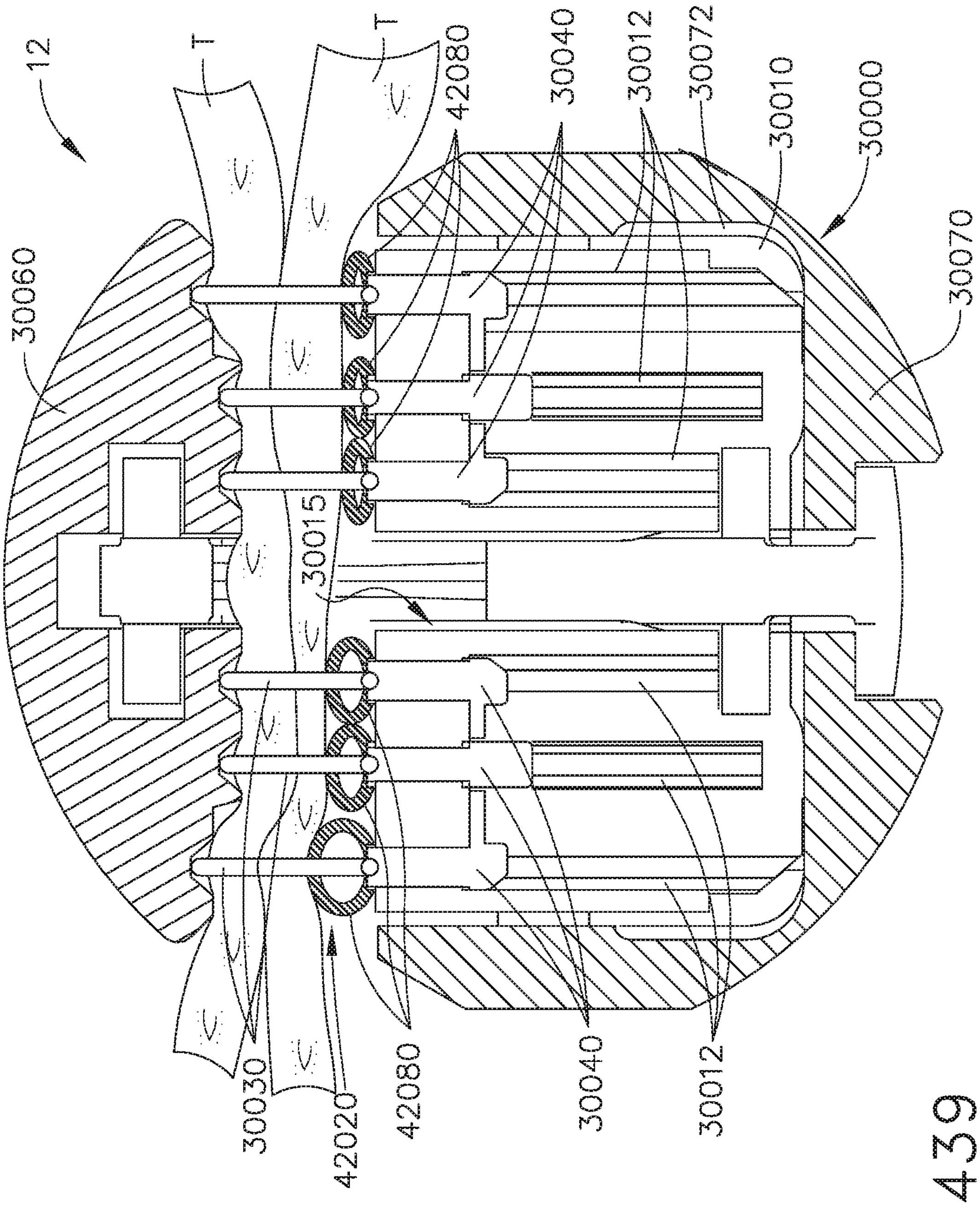
Figure 440:
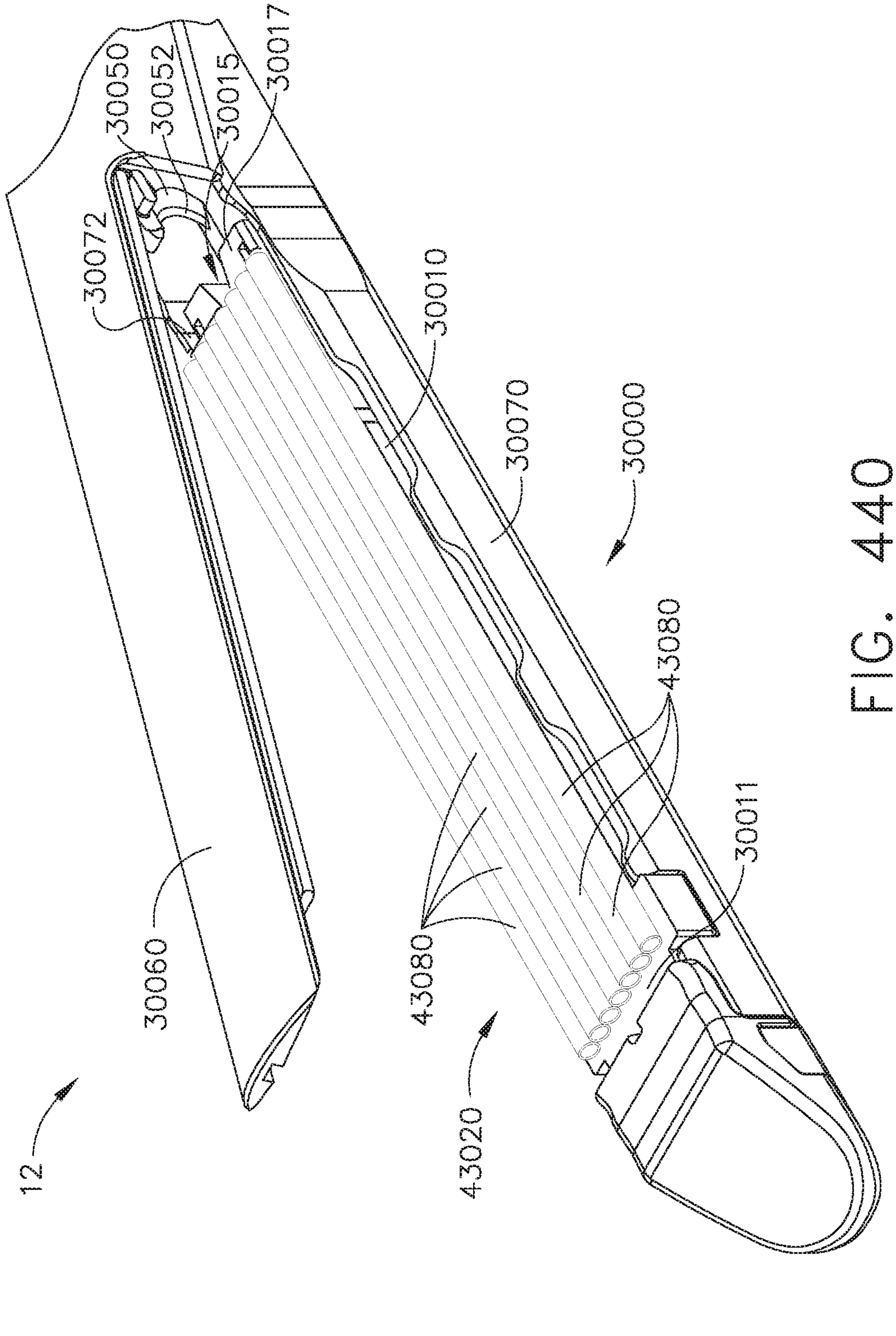
Figure 441:
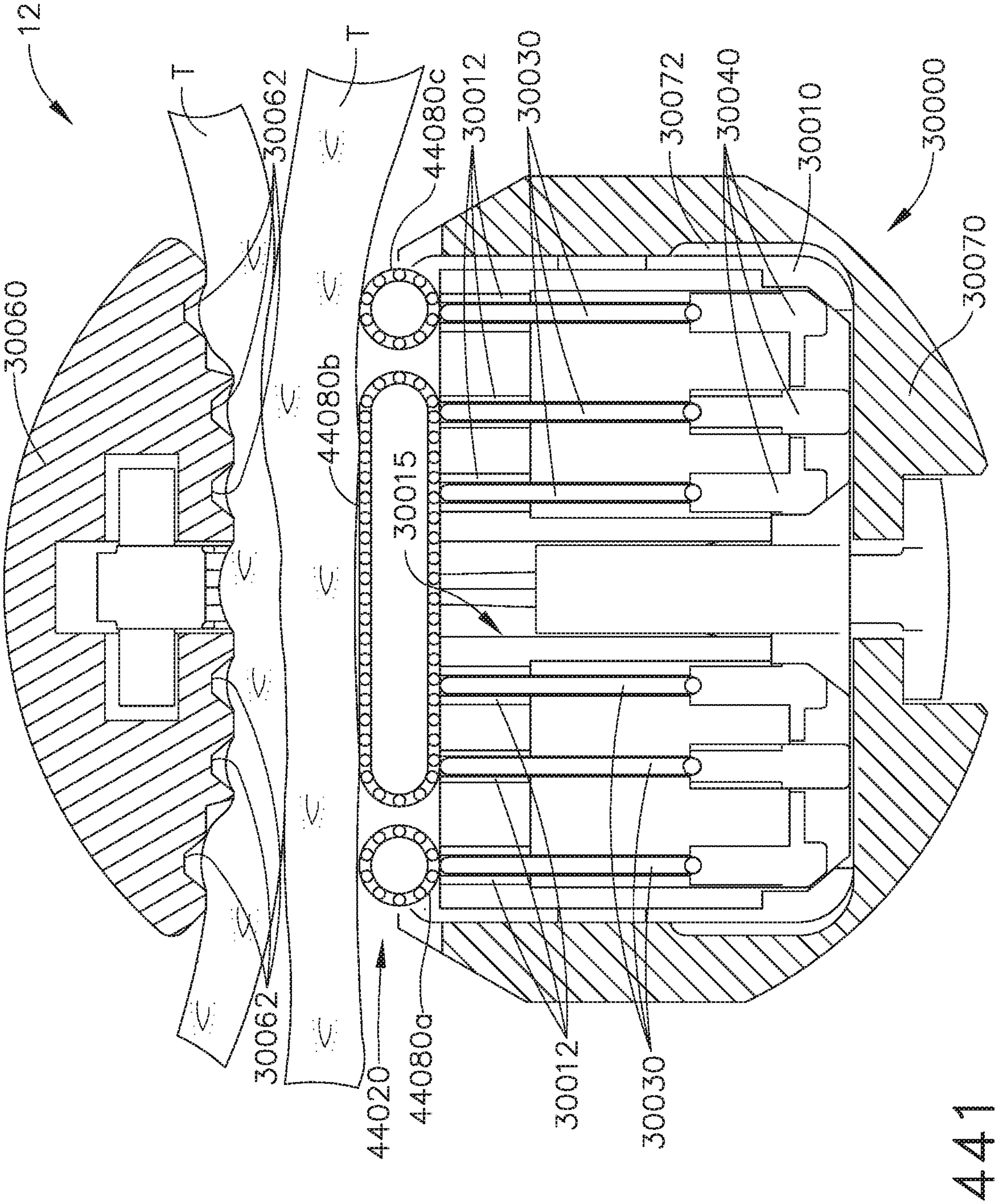
Figure 442:
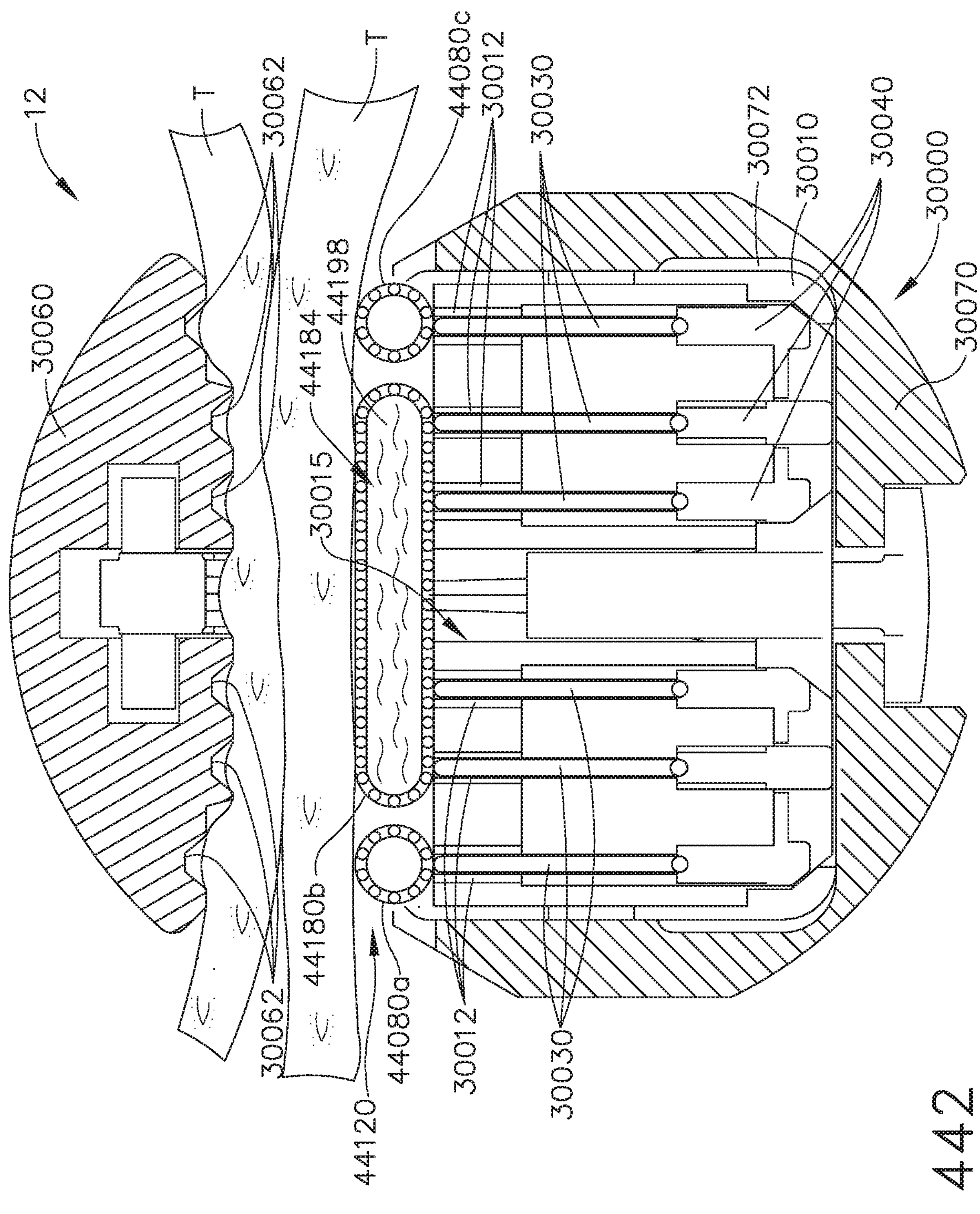
Figure 443:
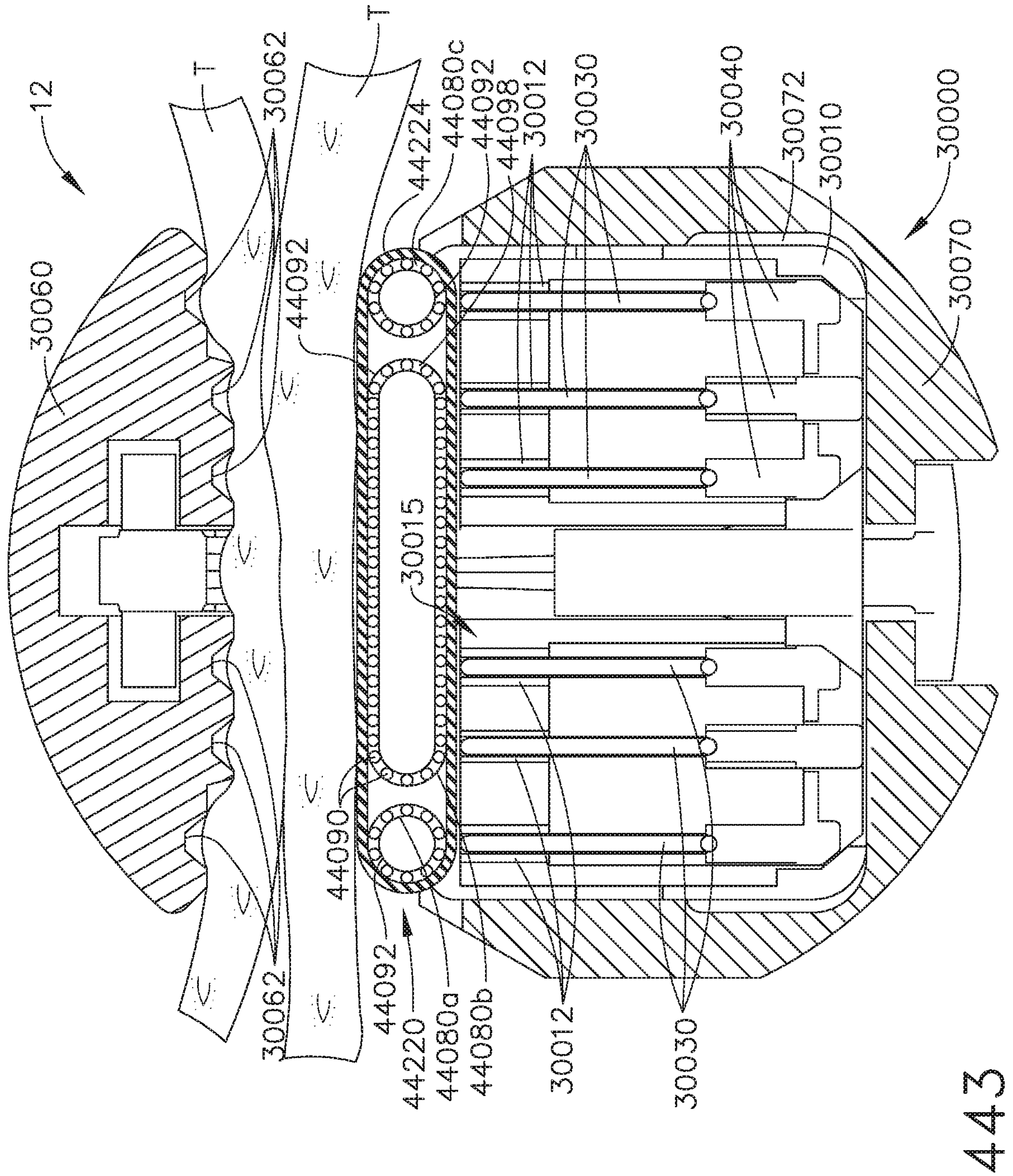
Figure 444:
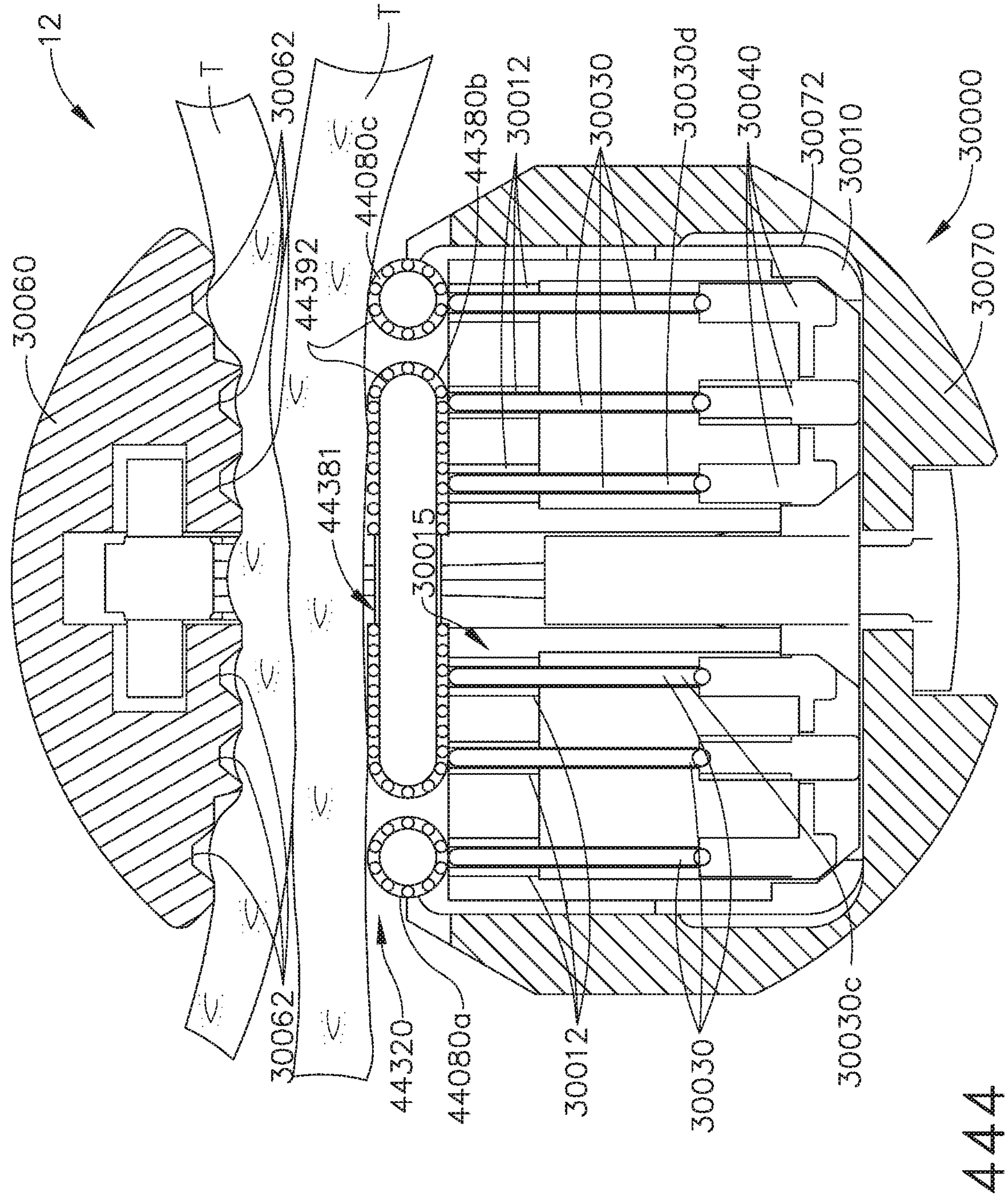
Figure 445:
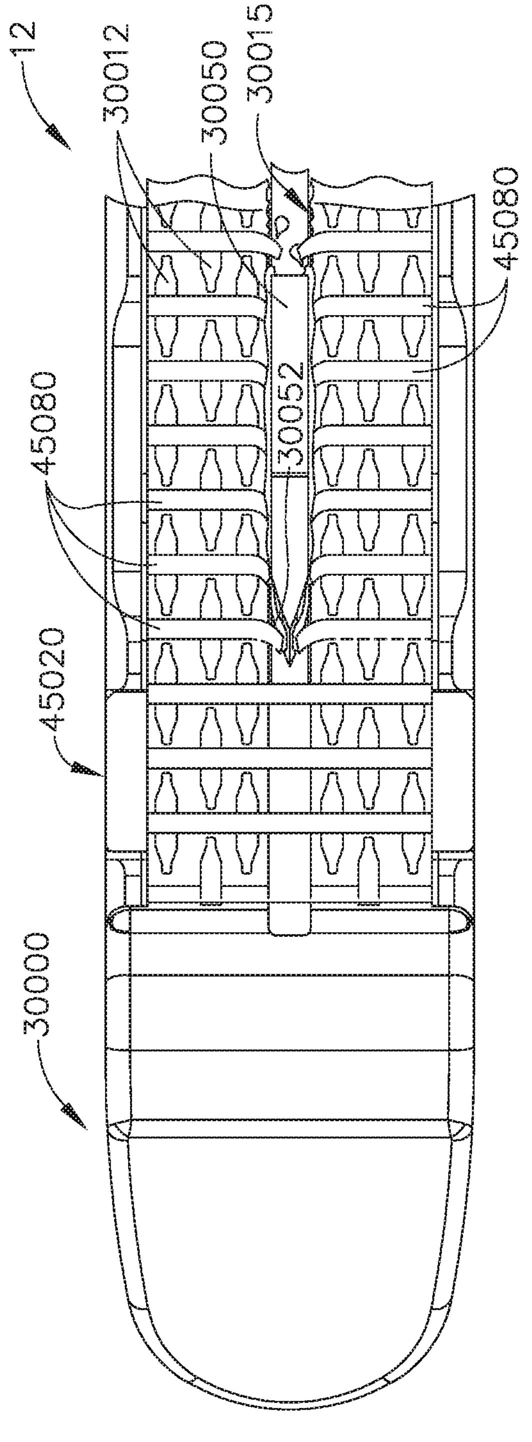
Figure 446:
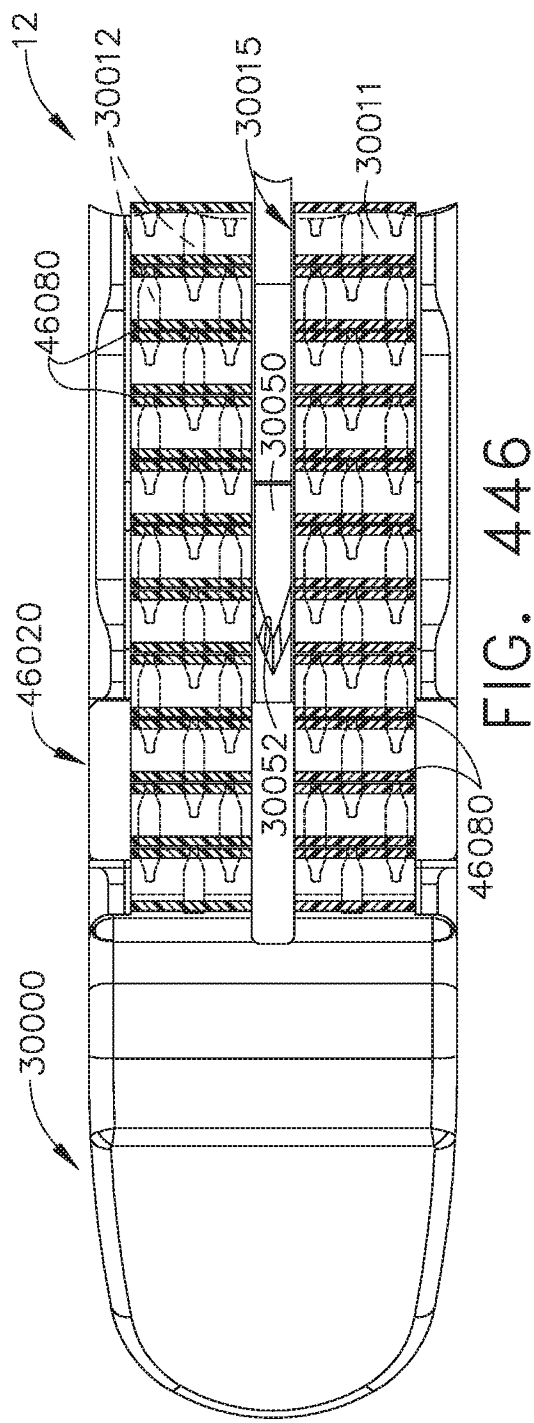
Figure 447:
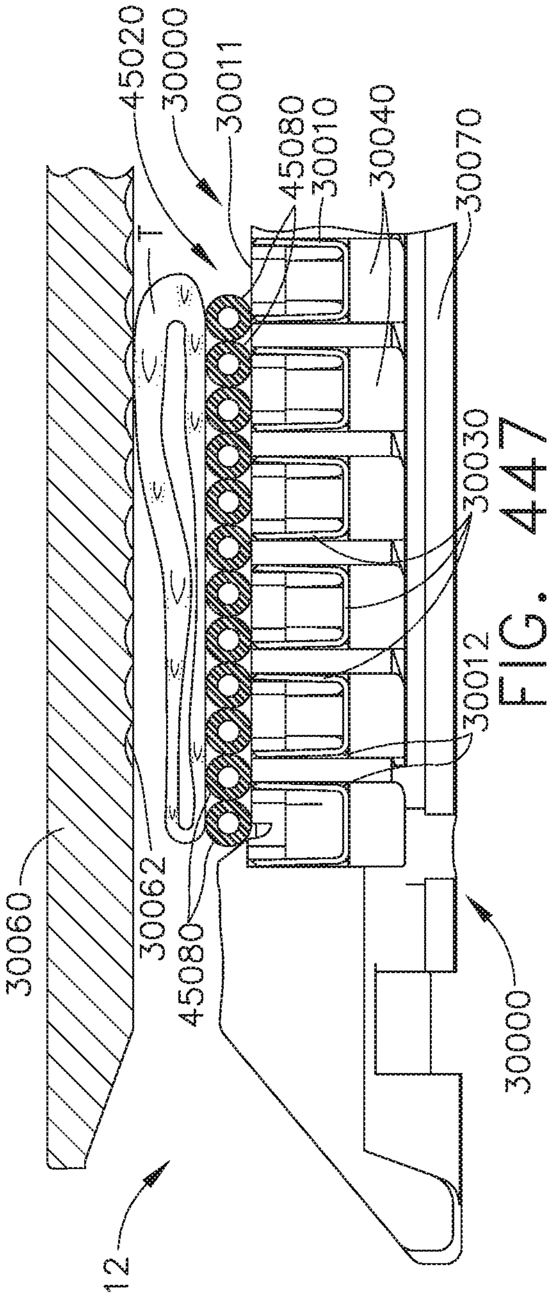
Figure 448:
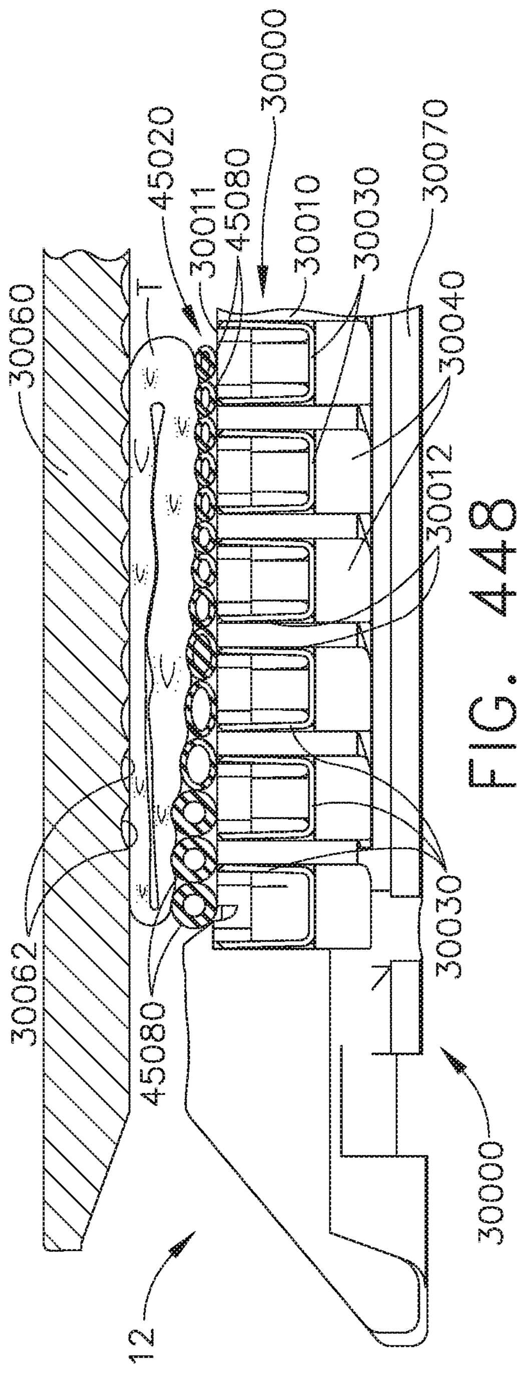
Figure 449:
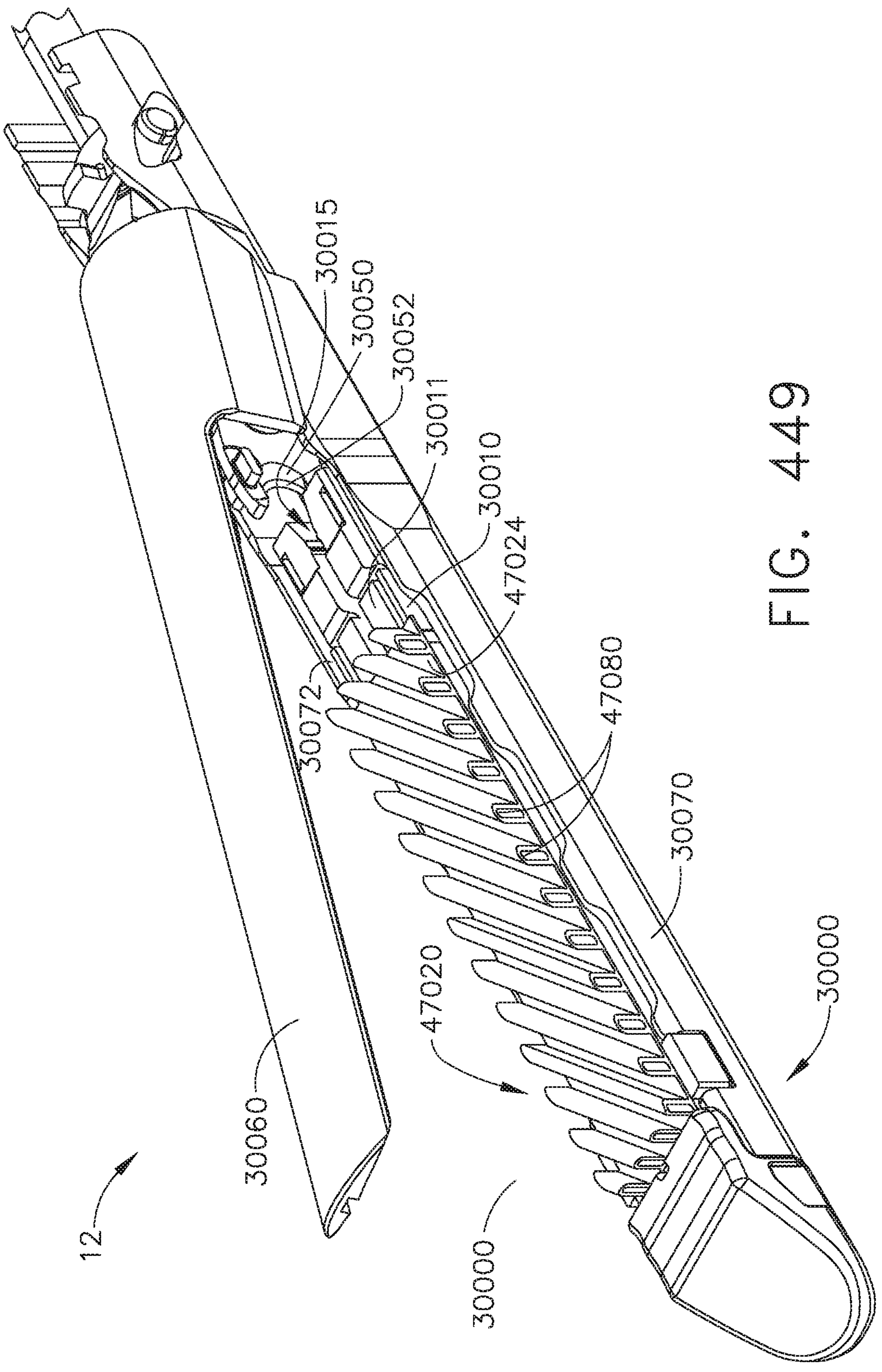
Figure 450:
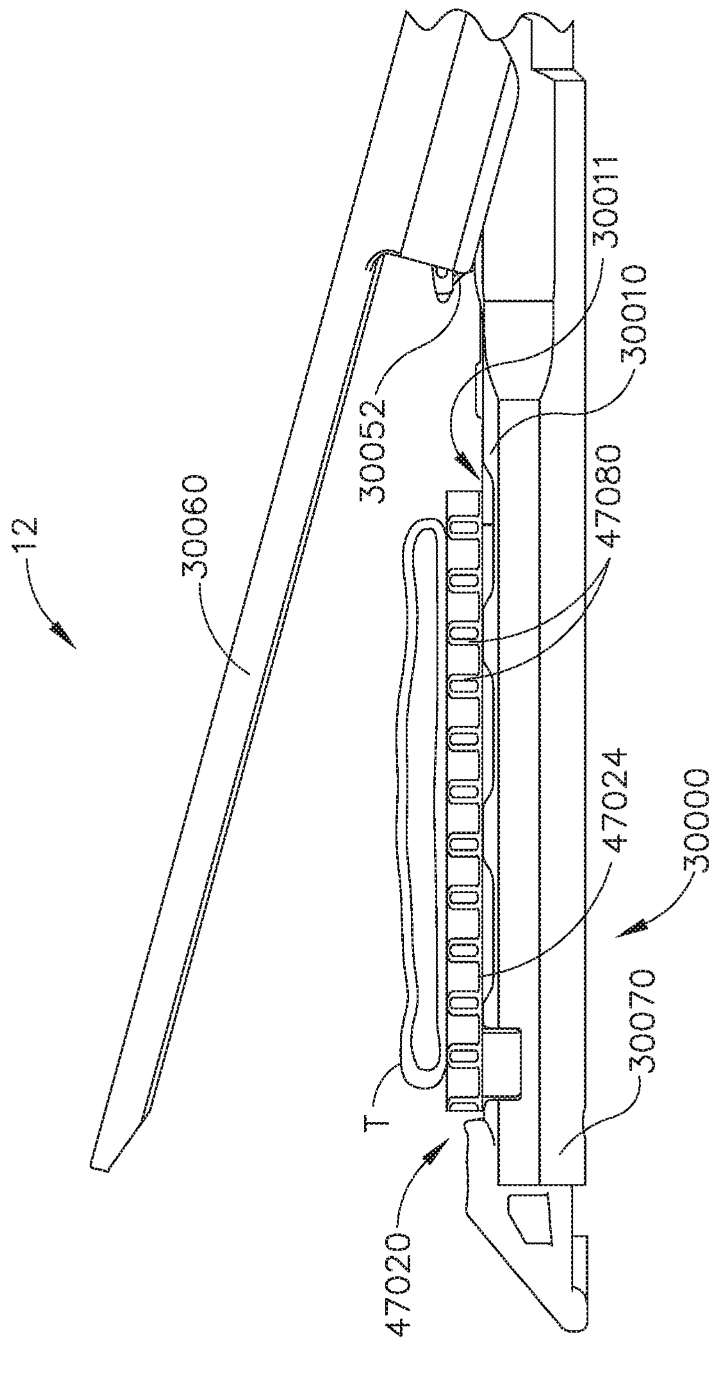
Figure 451:
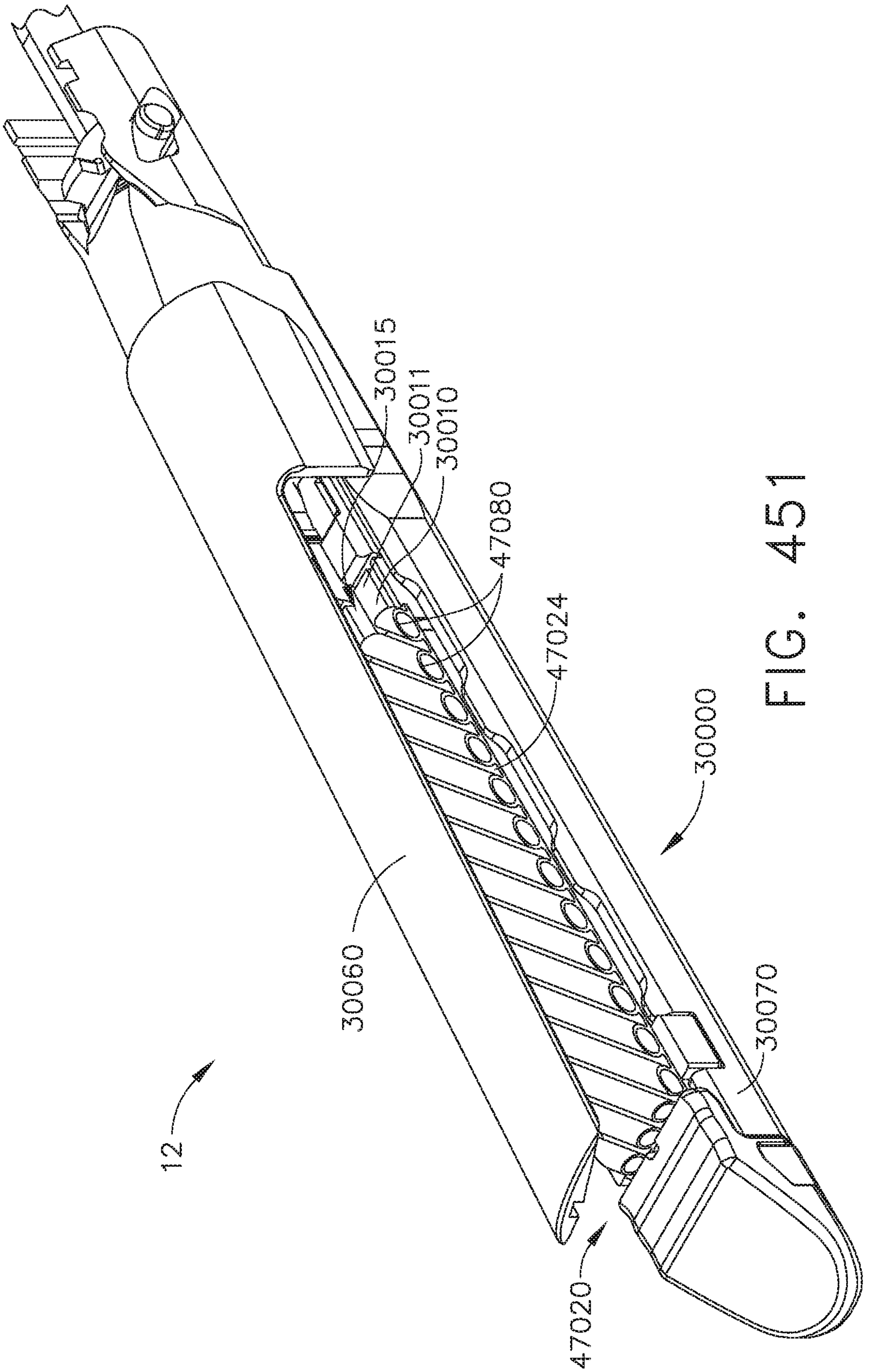
Figure 452:
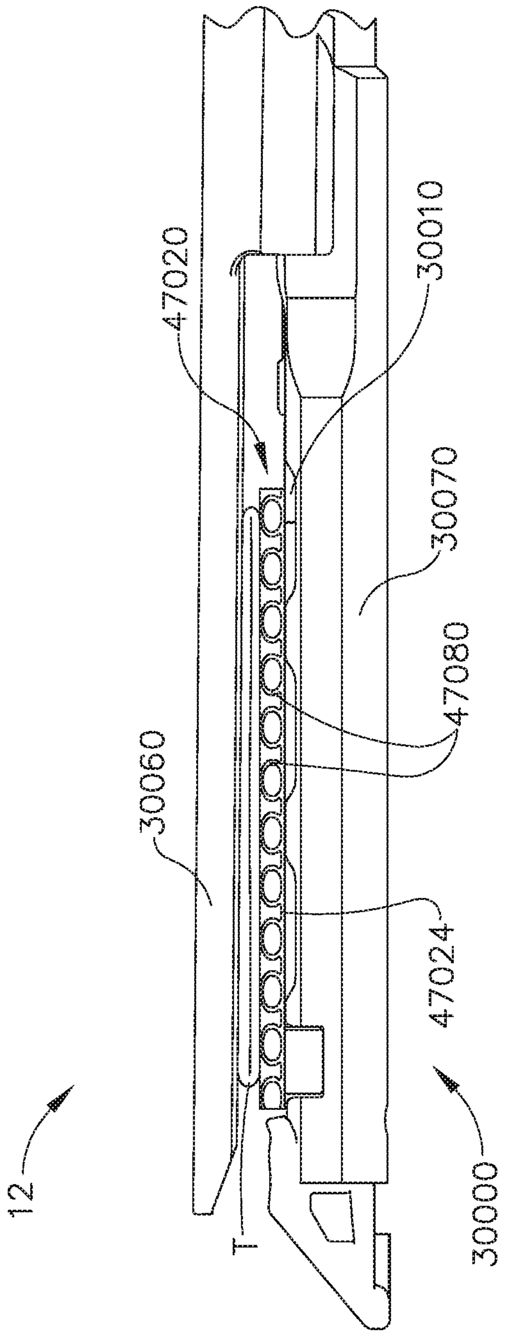
Figure 453:
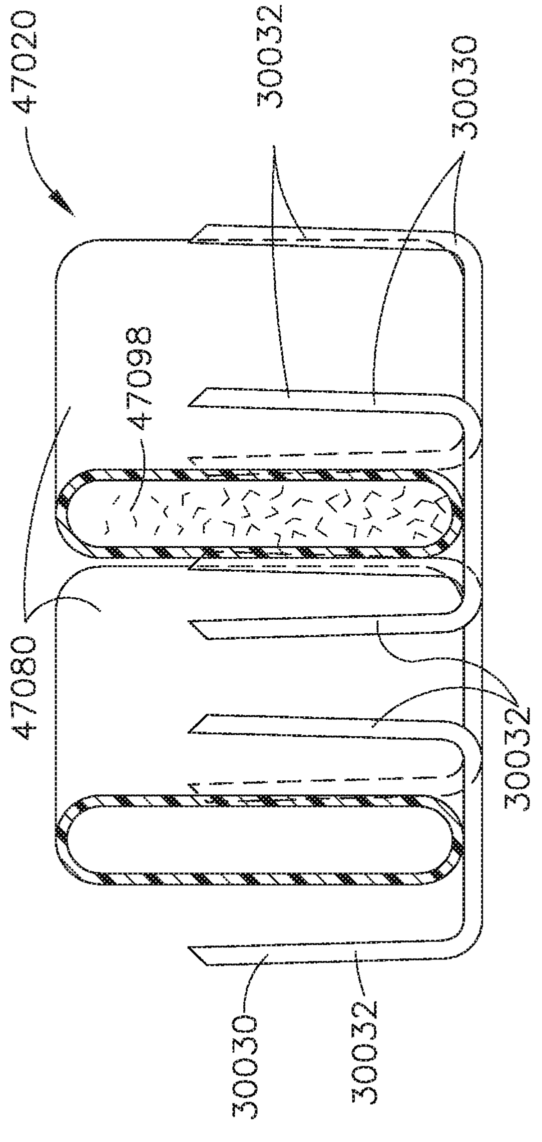
Figure 454:
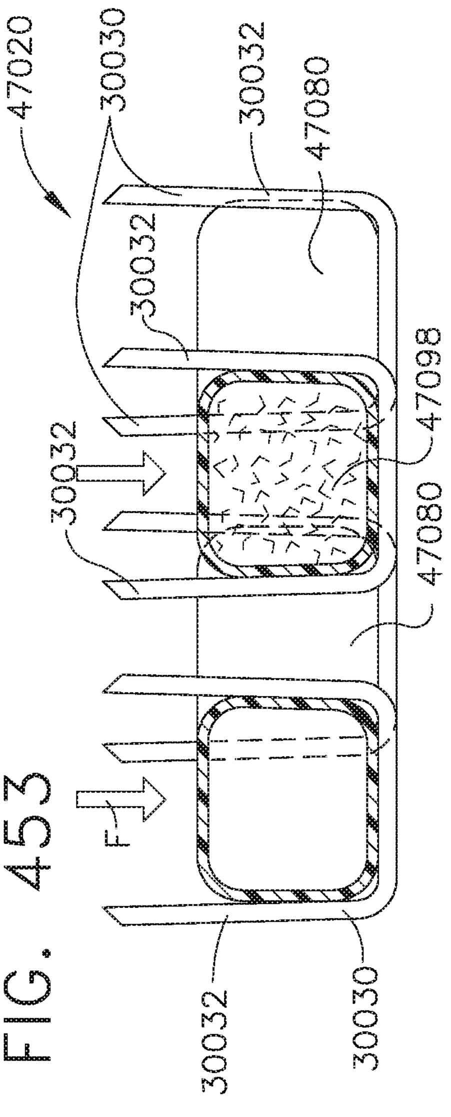
Figure 455:
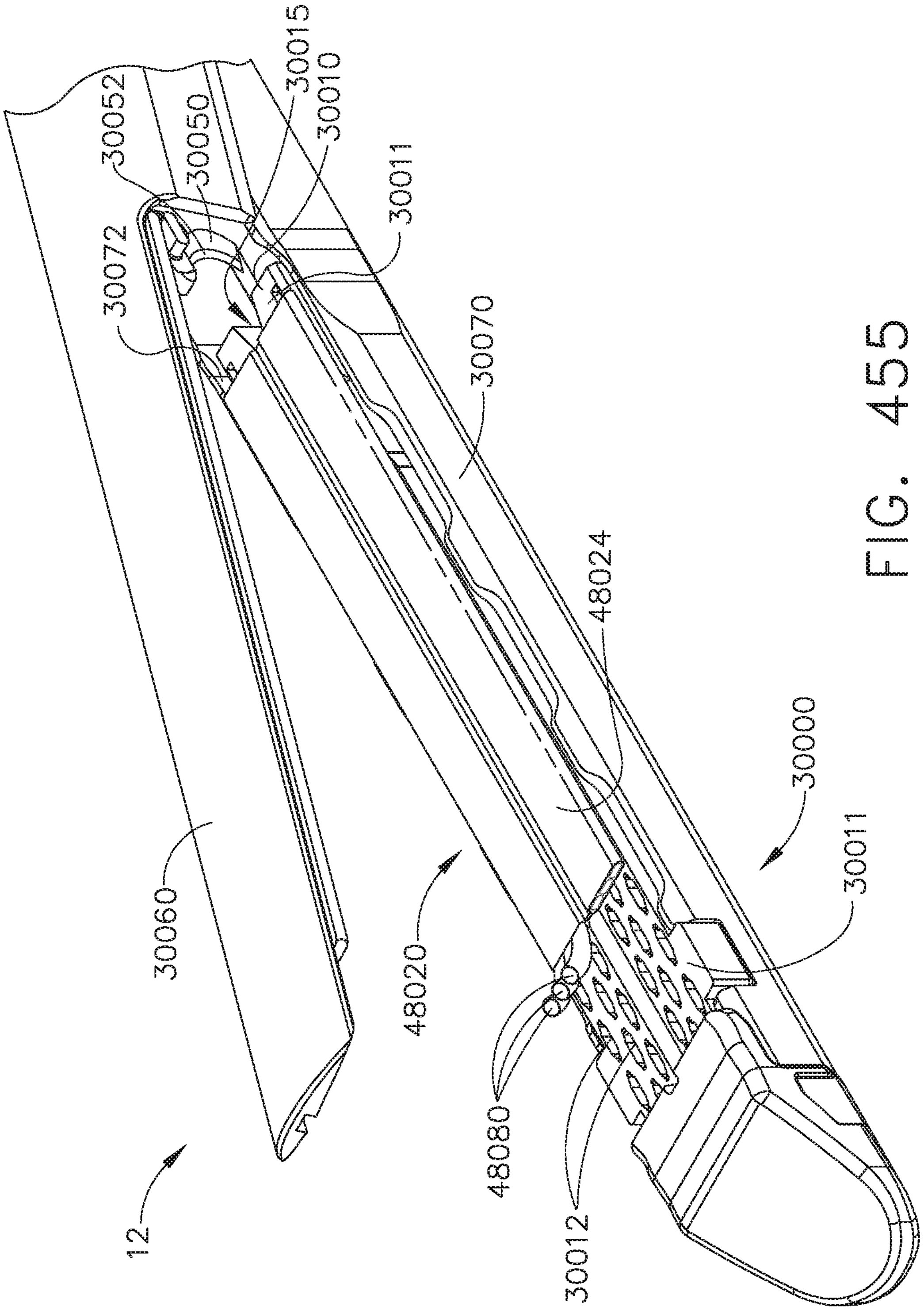
Figure 456:
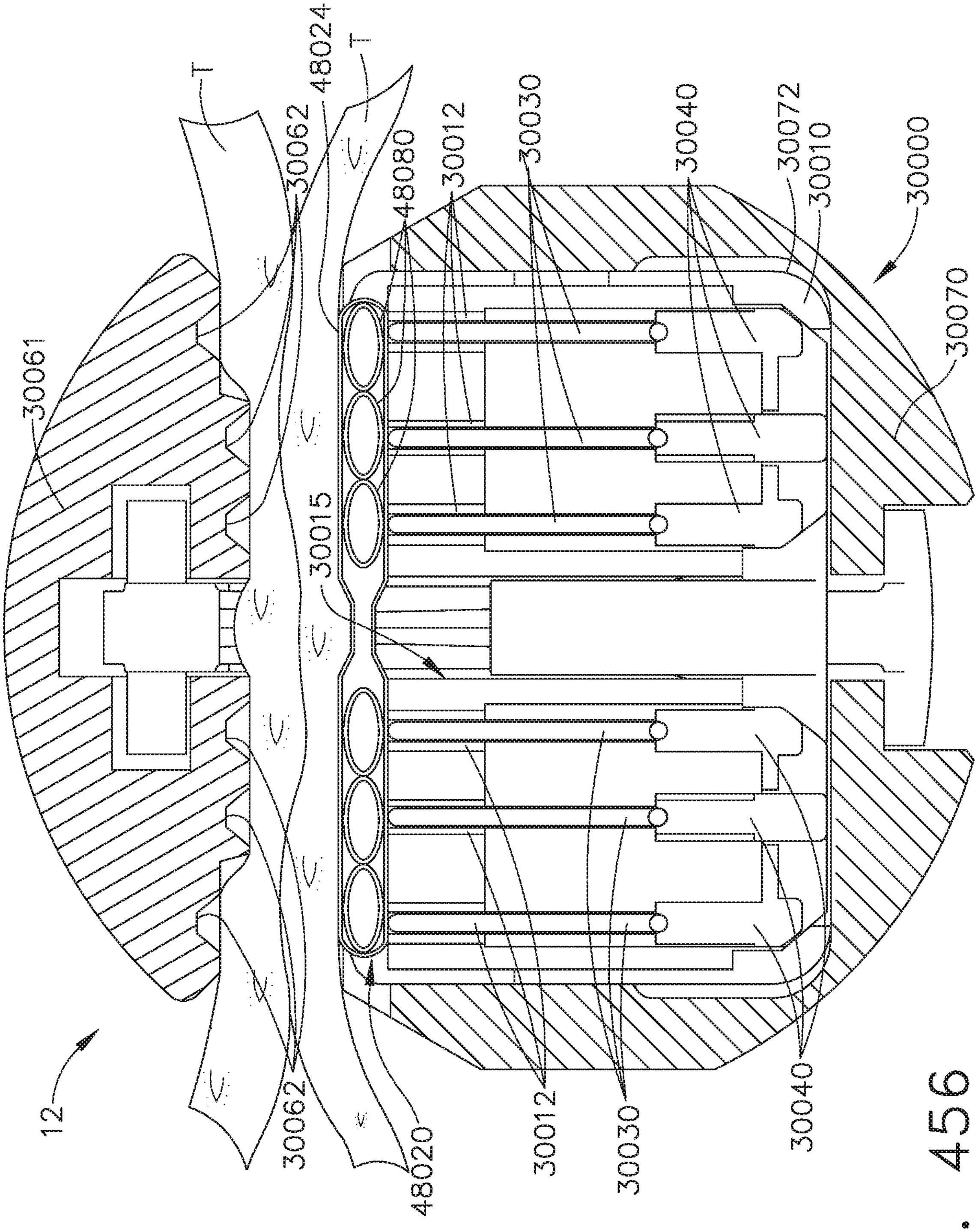
Figure 457:
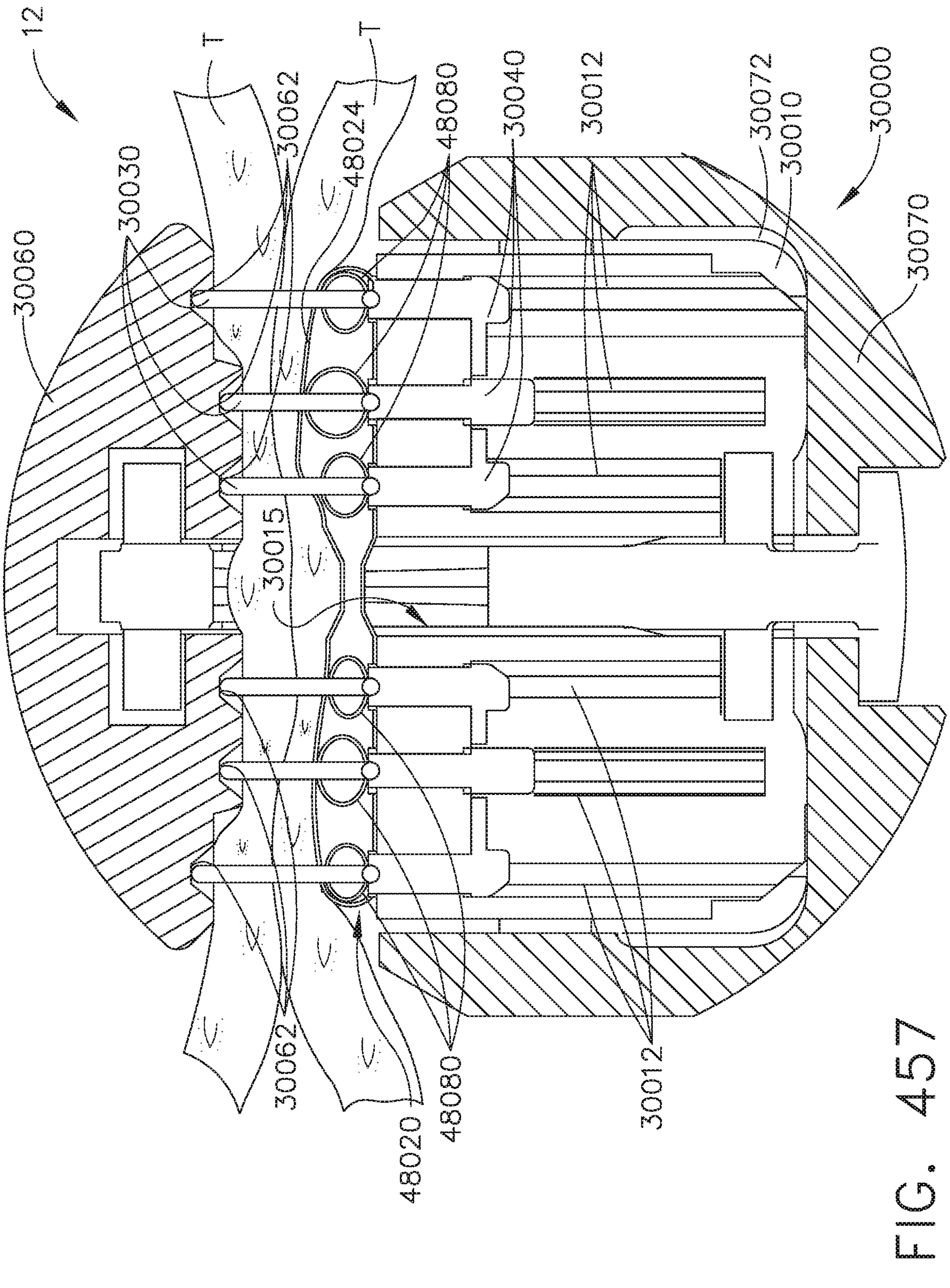
Figure 458:
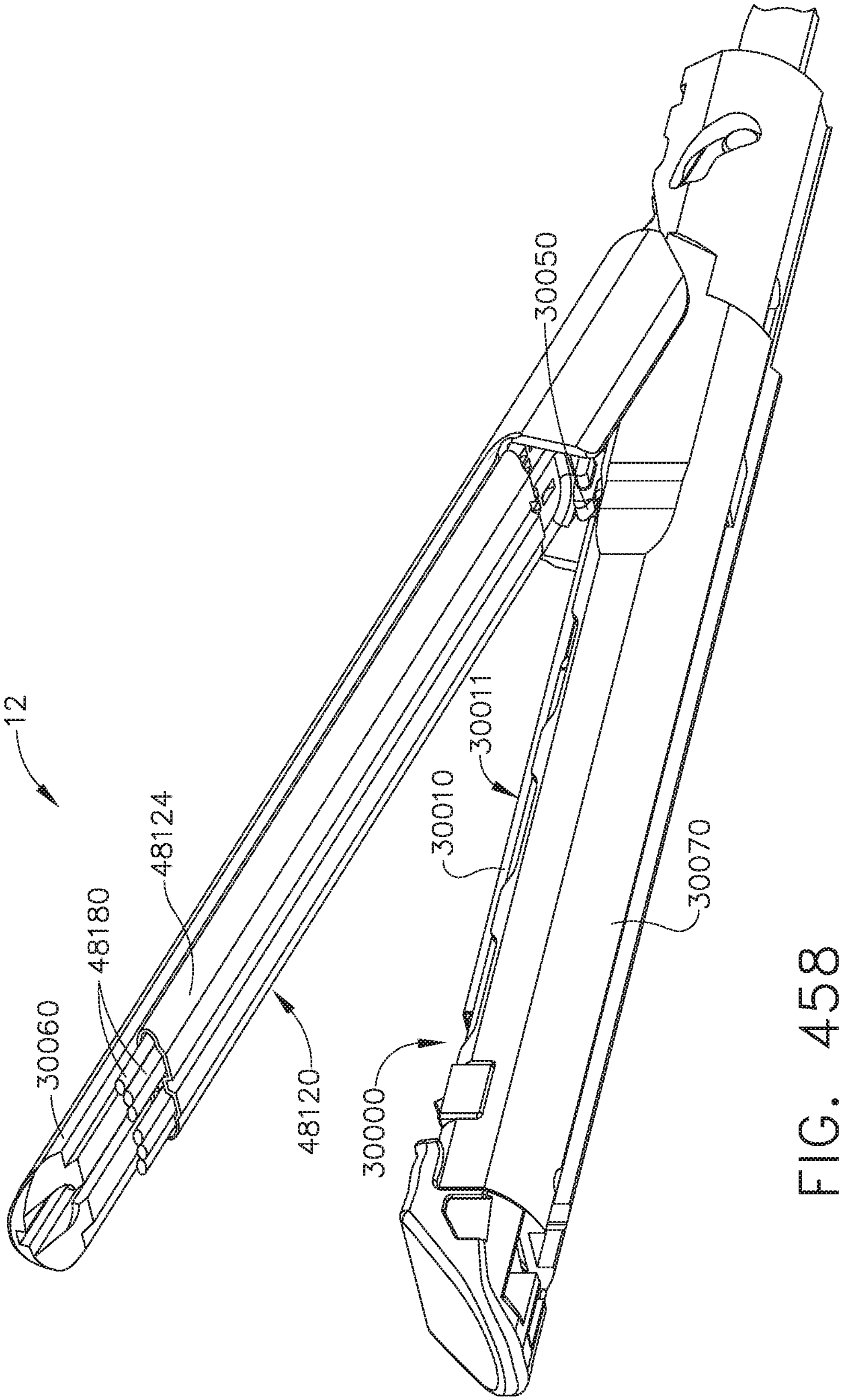
Figure 459:
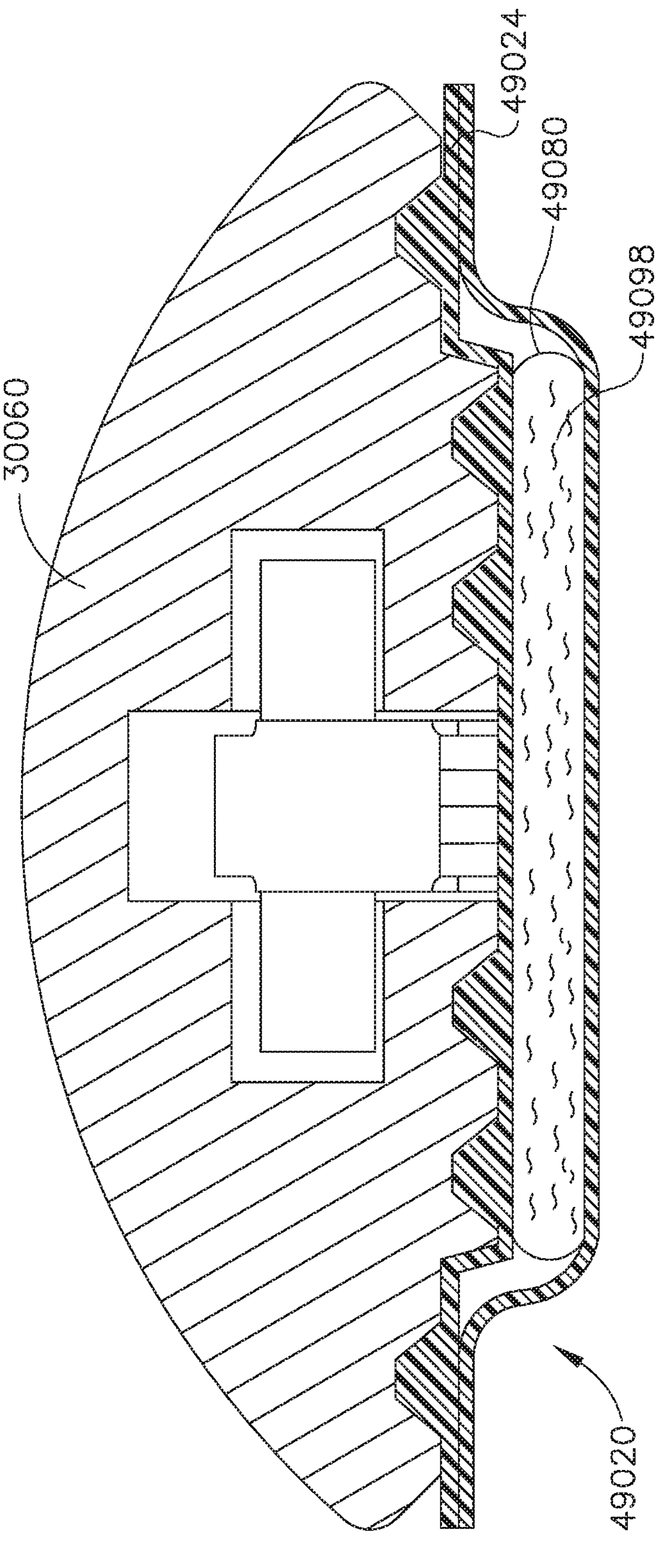
Figure 460:
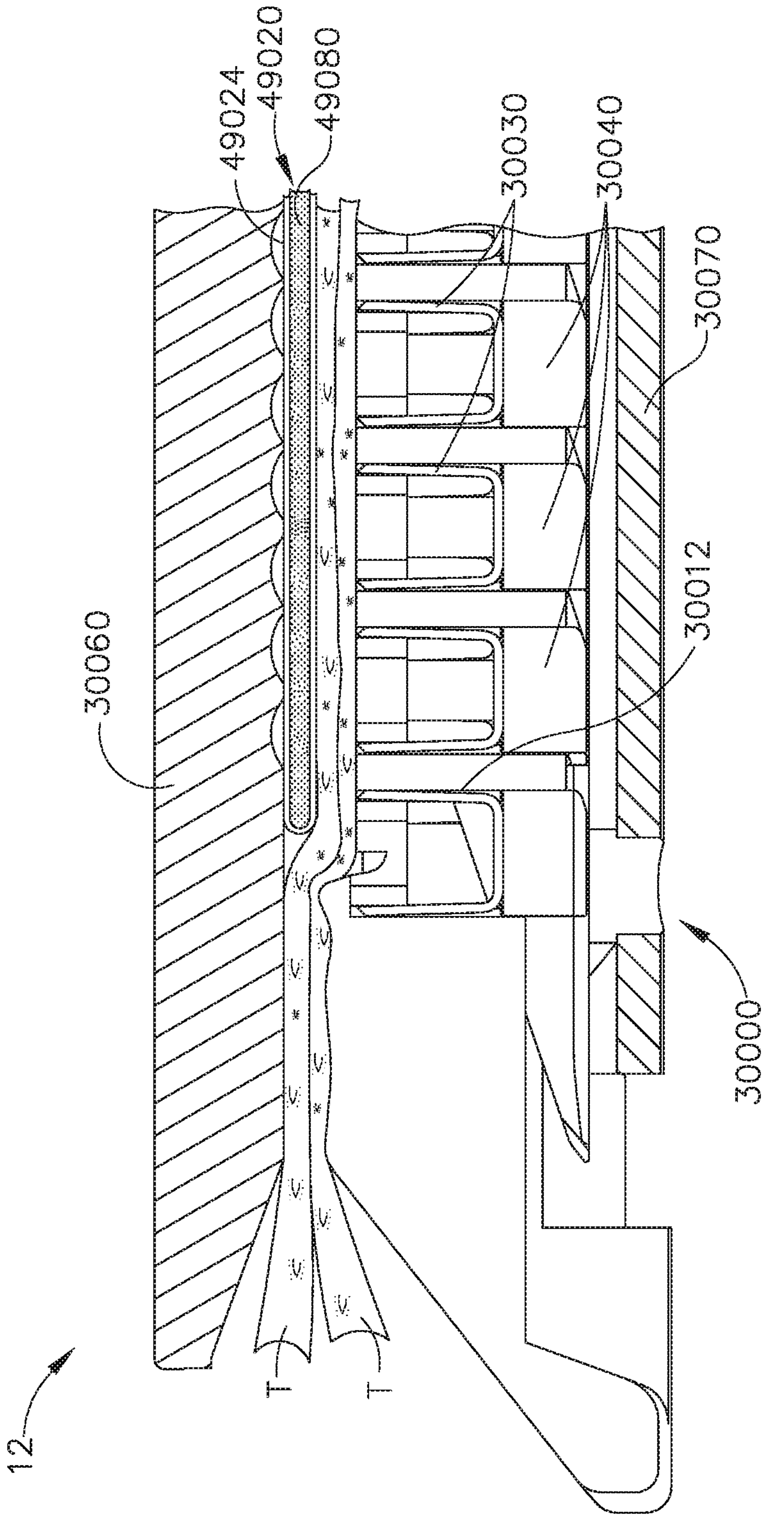
Figure 461:
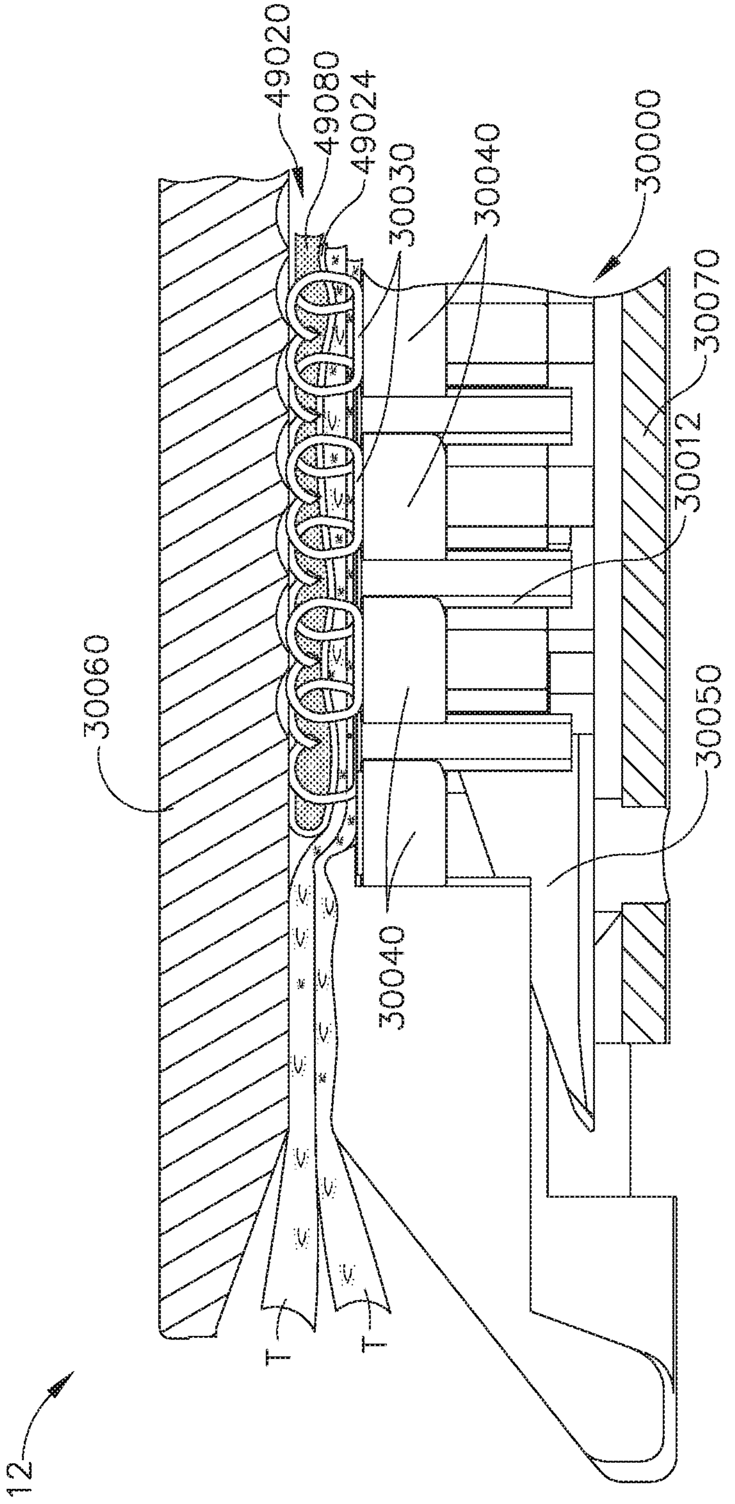
Figure 462:
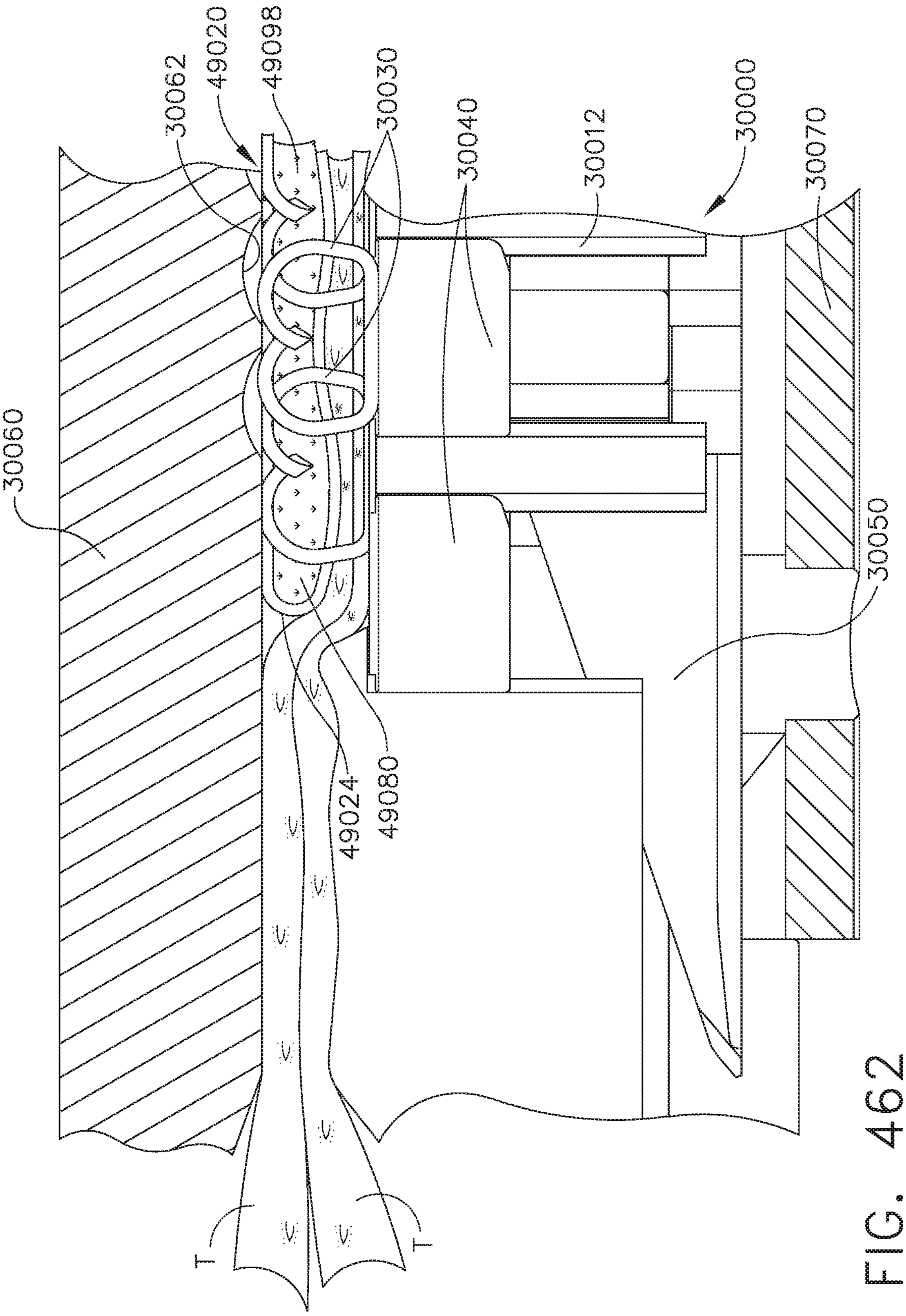
Figure 463:
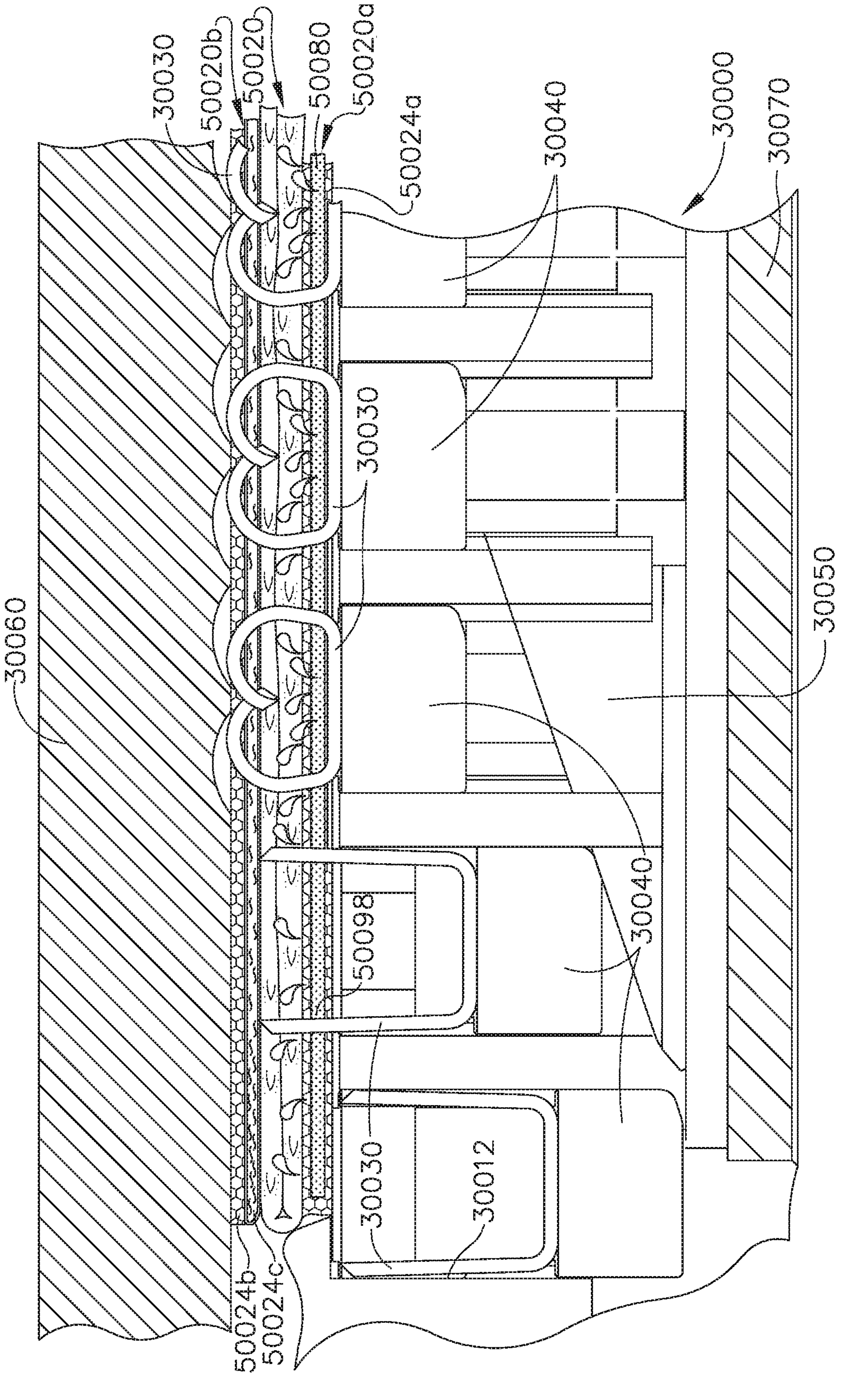
Figure 464:
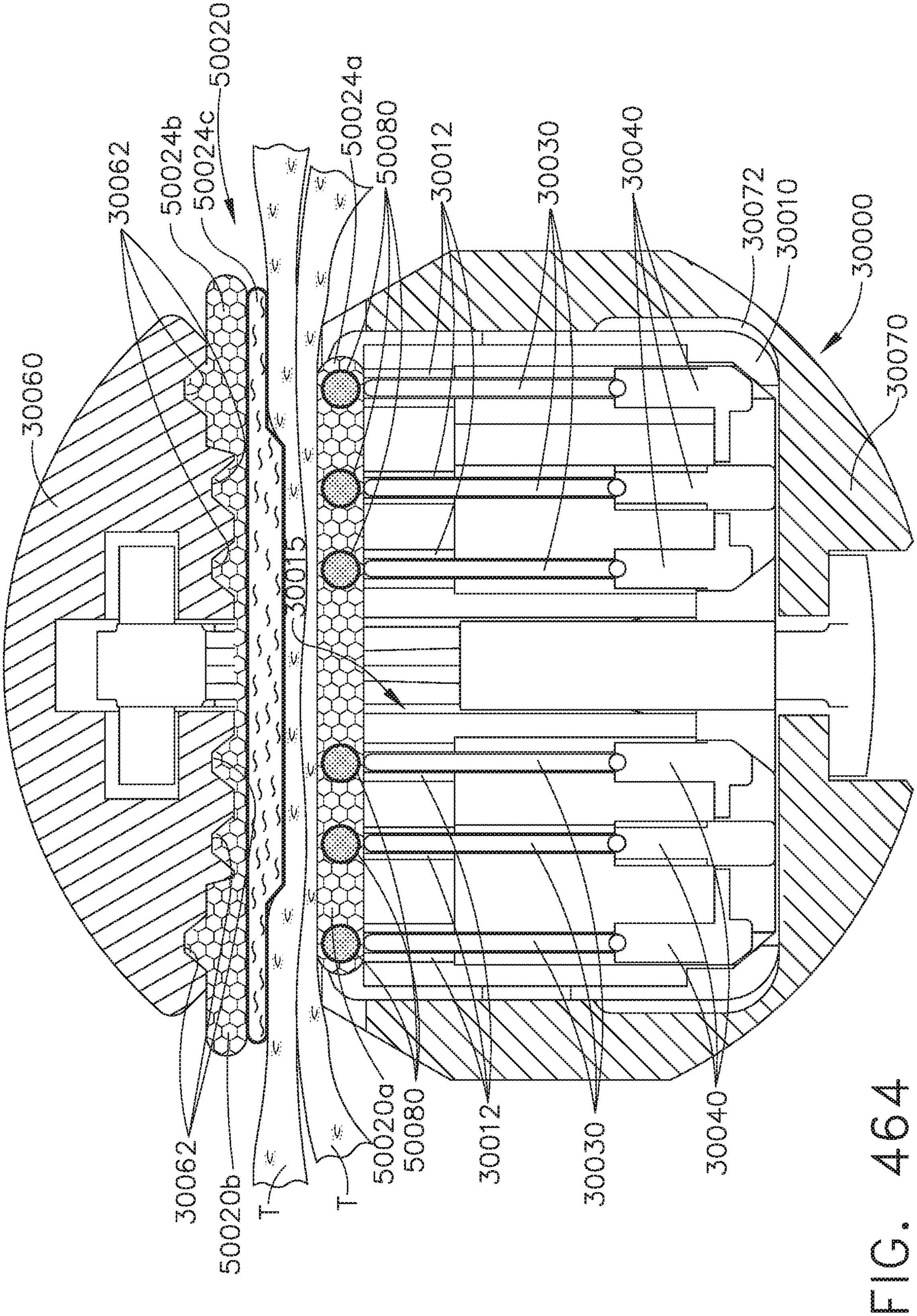
Figure 465:
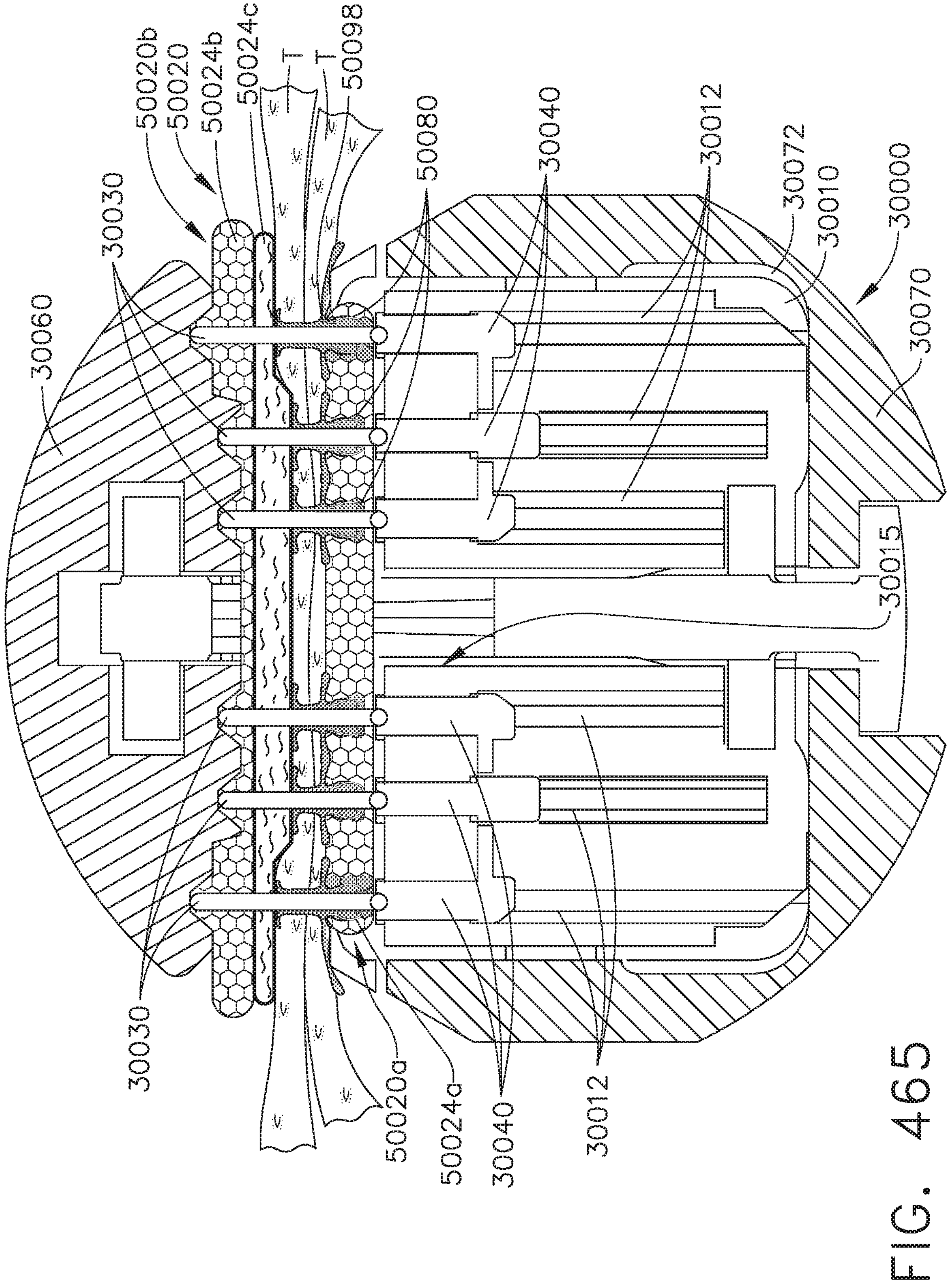
Figure 466:
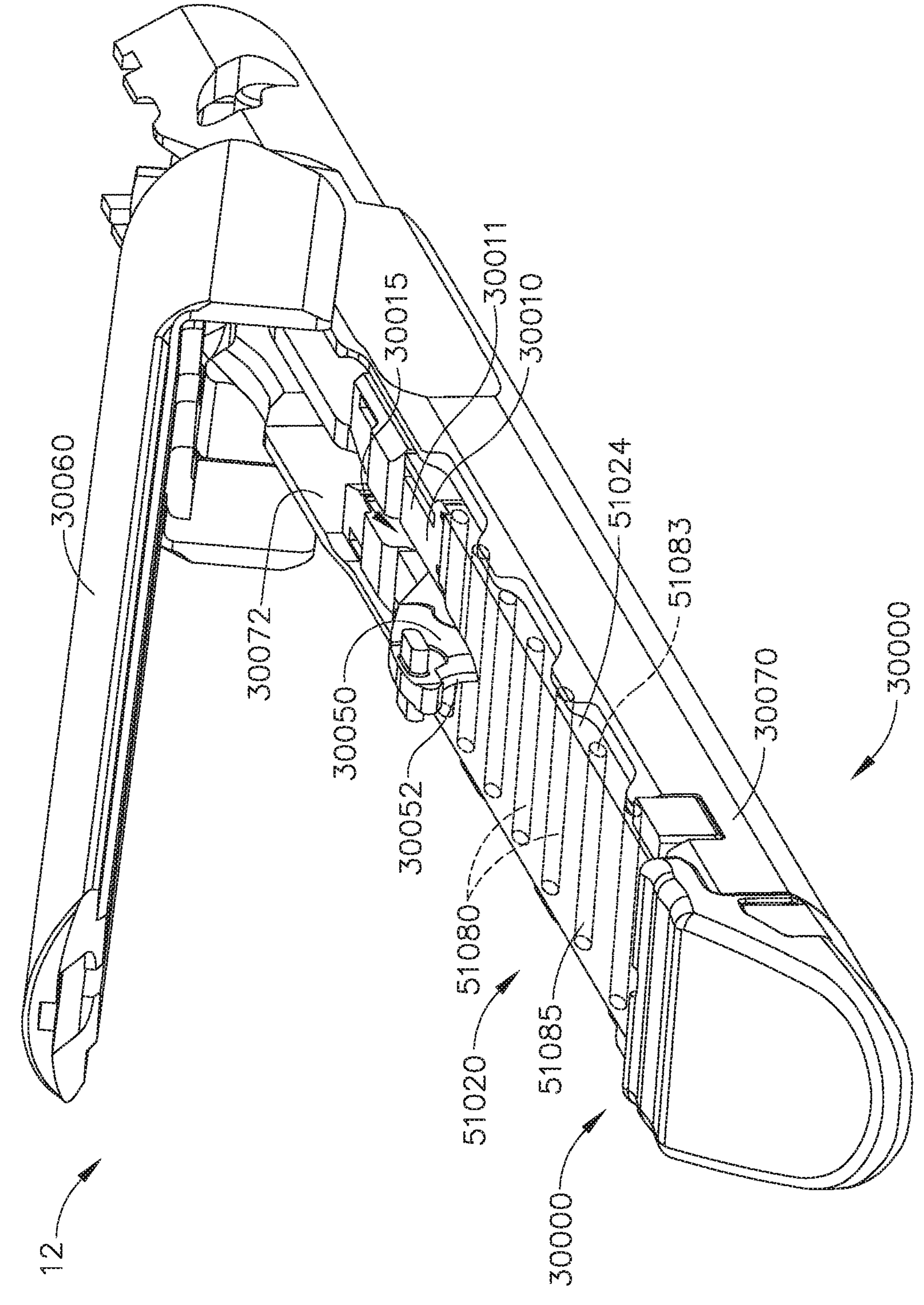
Figure 467:
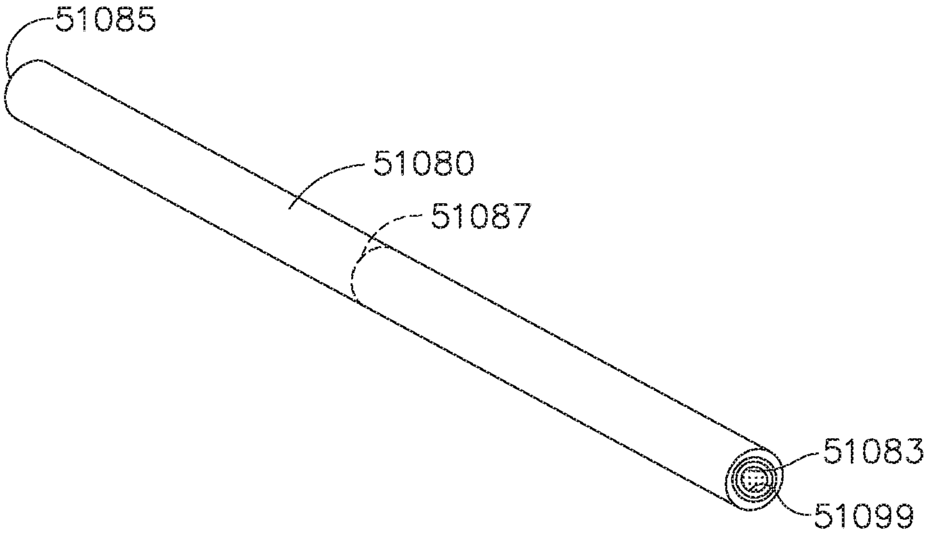
Figure 468:
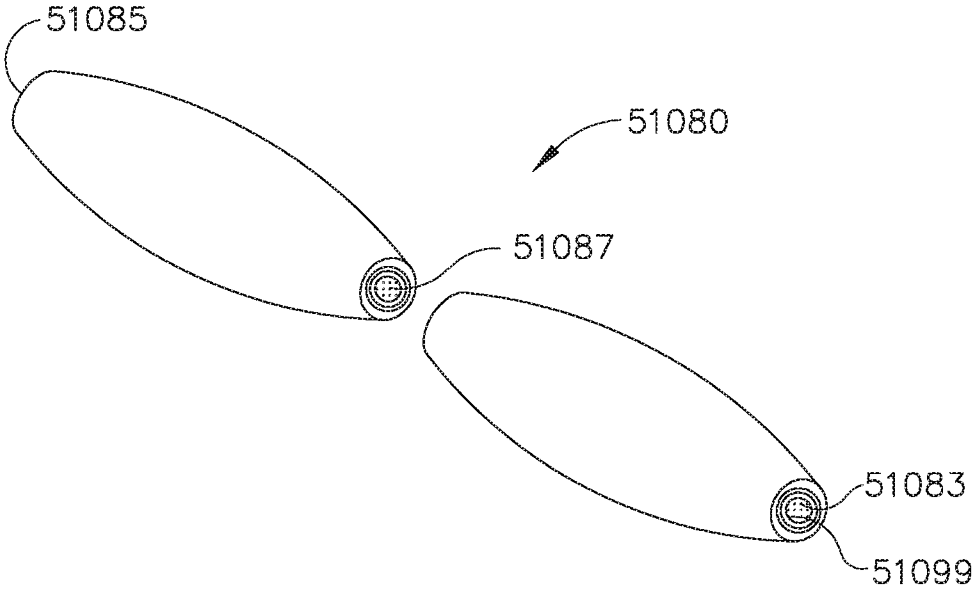
Figure 469:
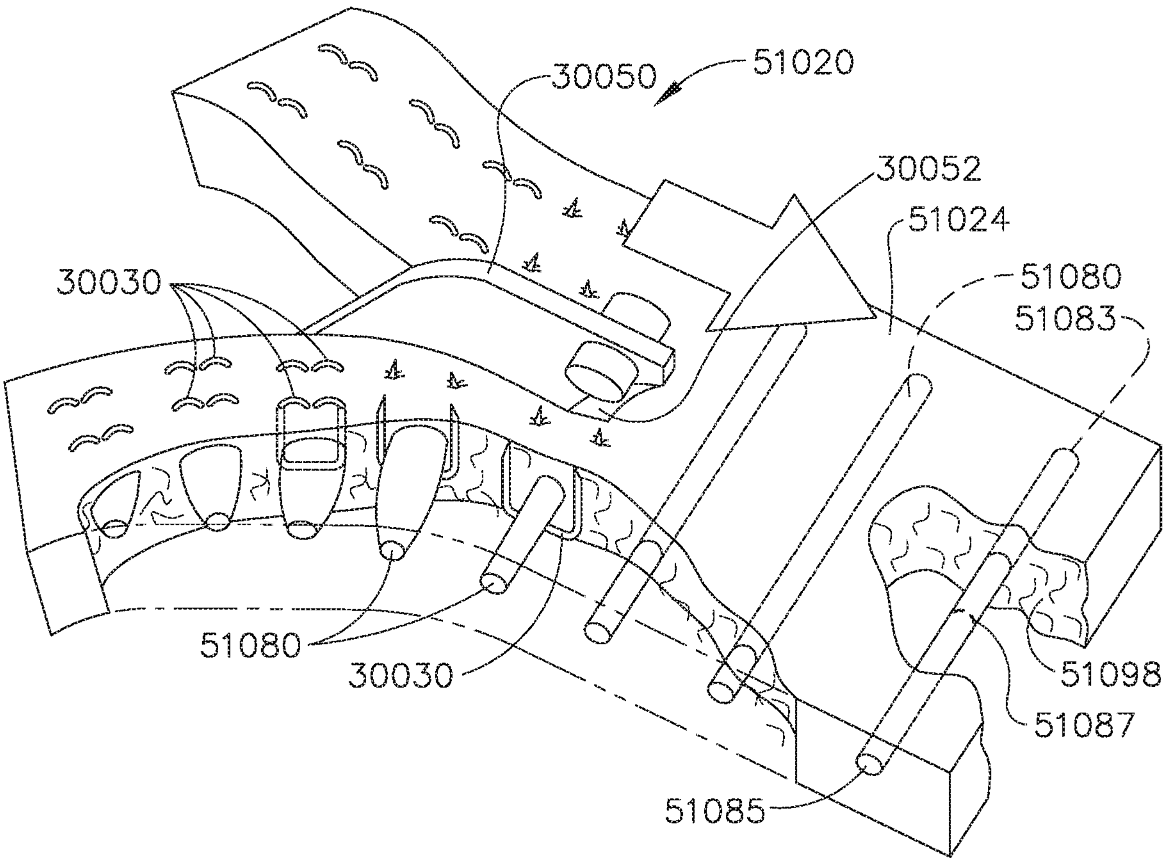
Figure 470:
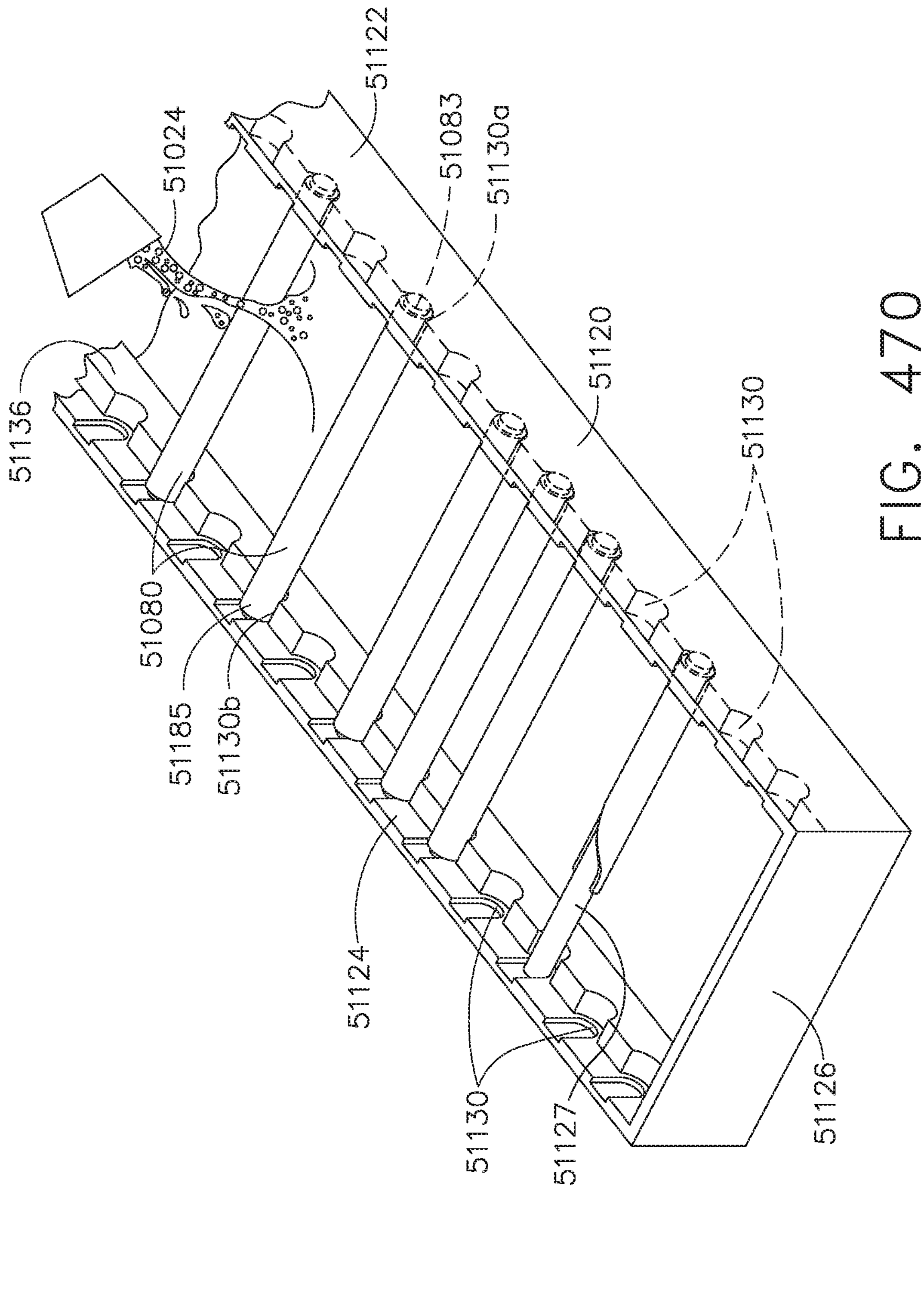
Figure 471:
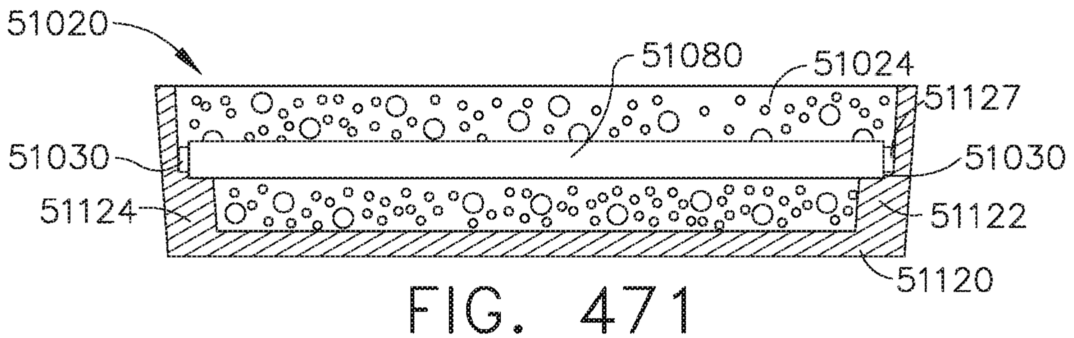
Figure 472:
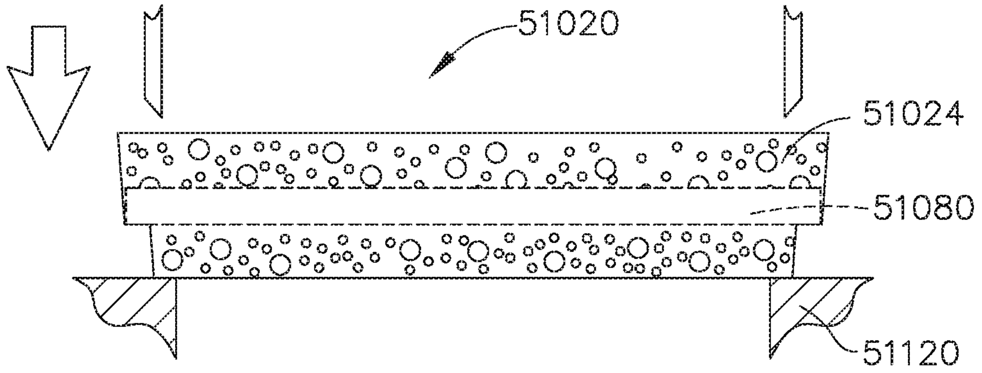
Figure 473:
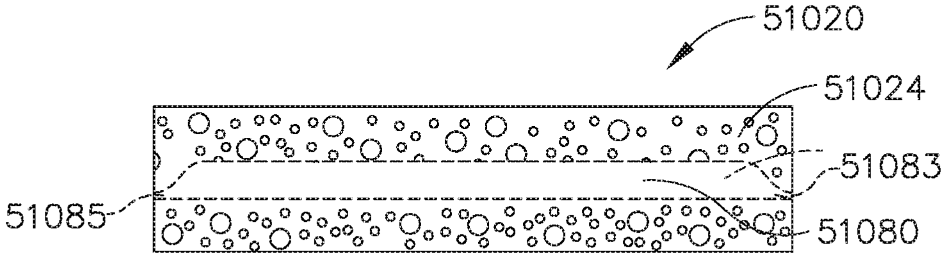
Figure 474:
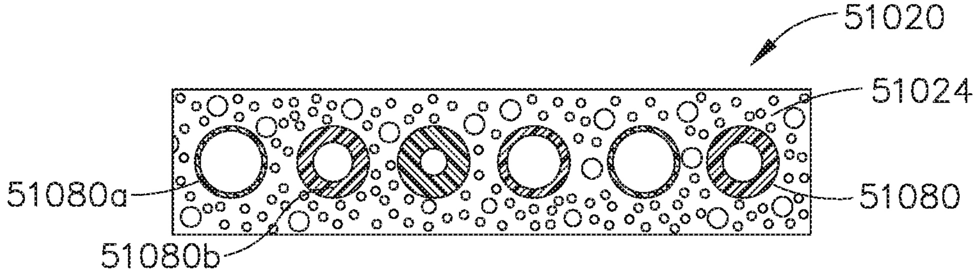
Figure 475:
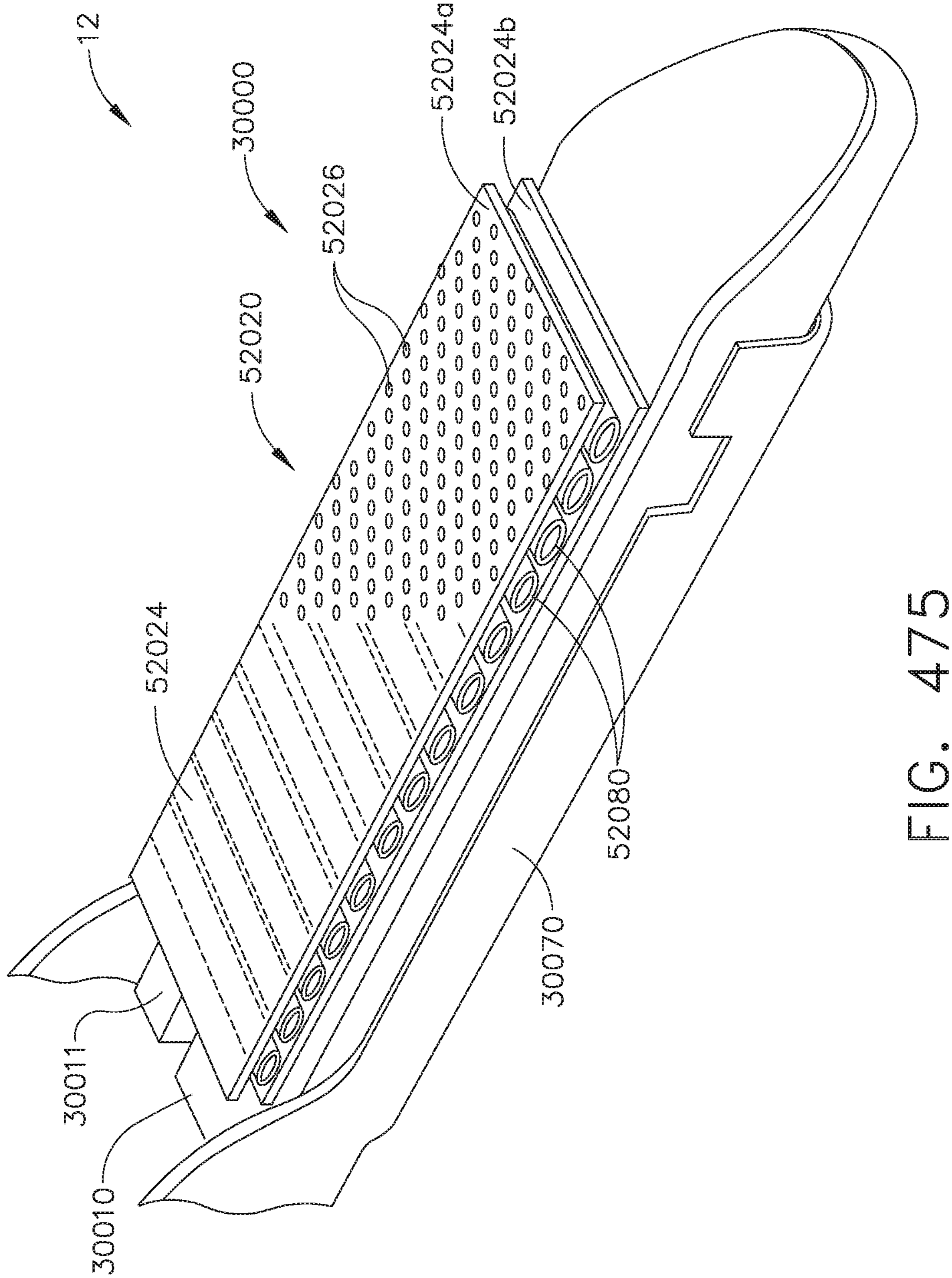
Figure 476:
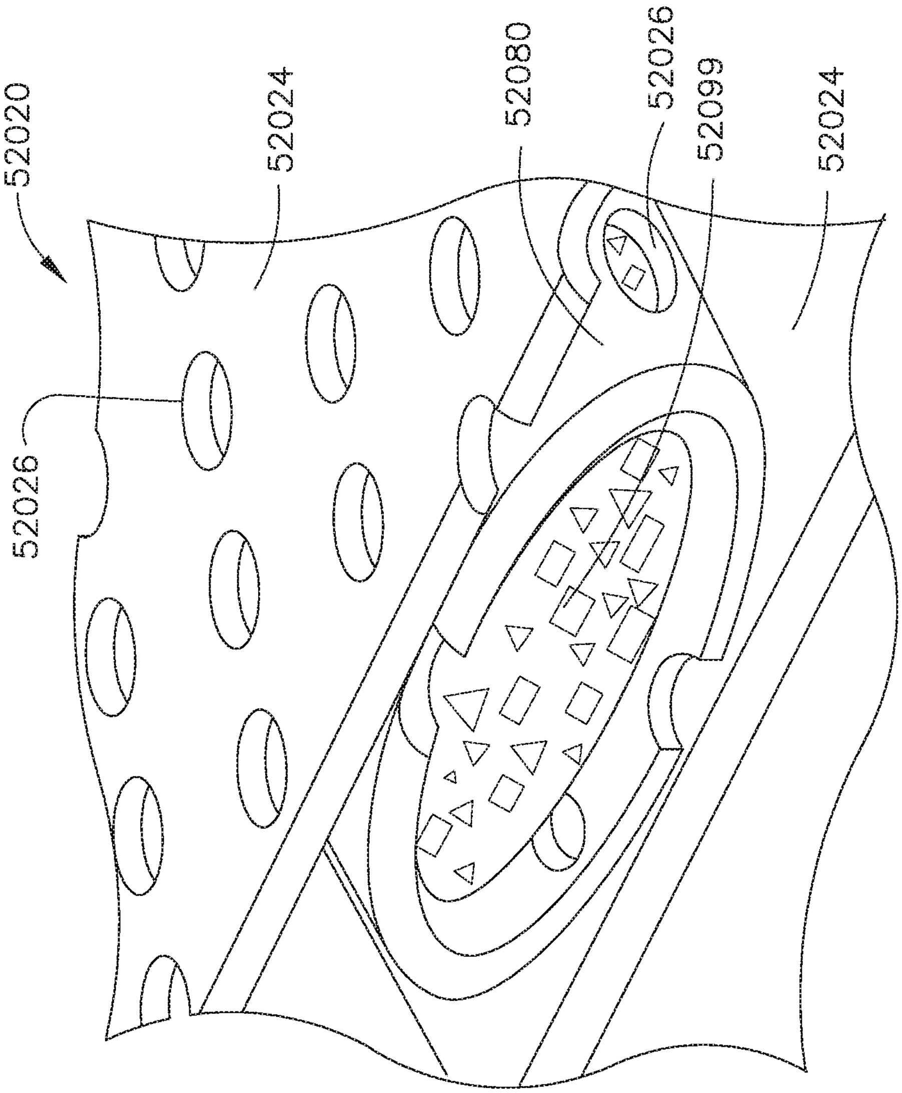
Figure 478:
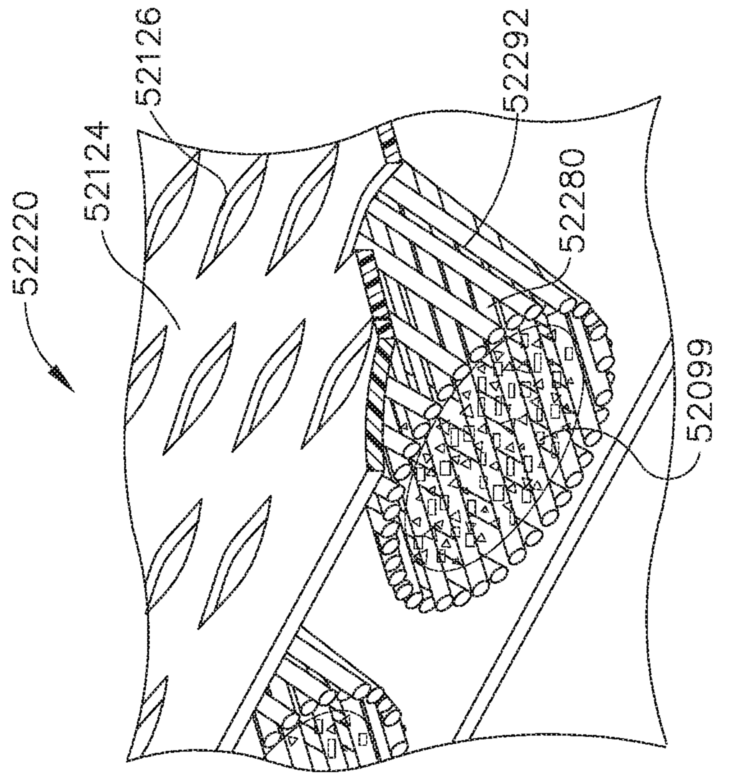
Figure 477:
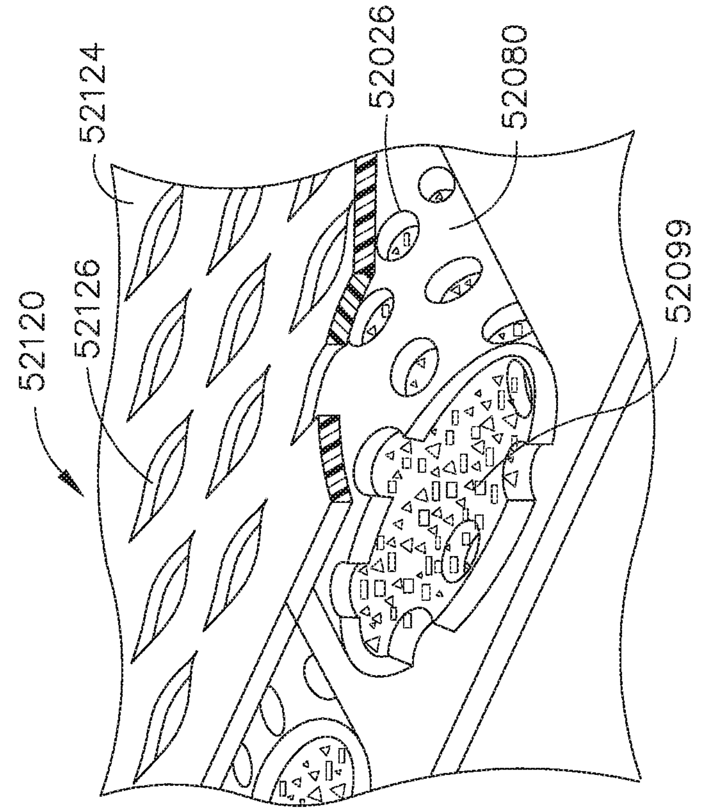
Figures 479A, 479B, 479C, 479D, 479E:
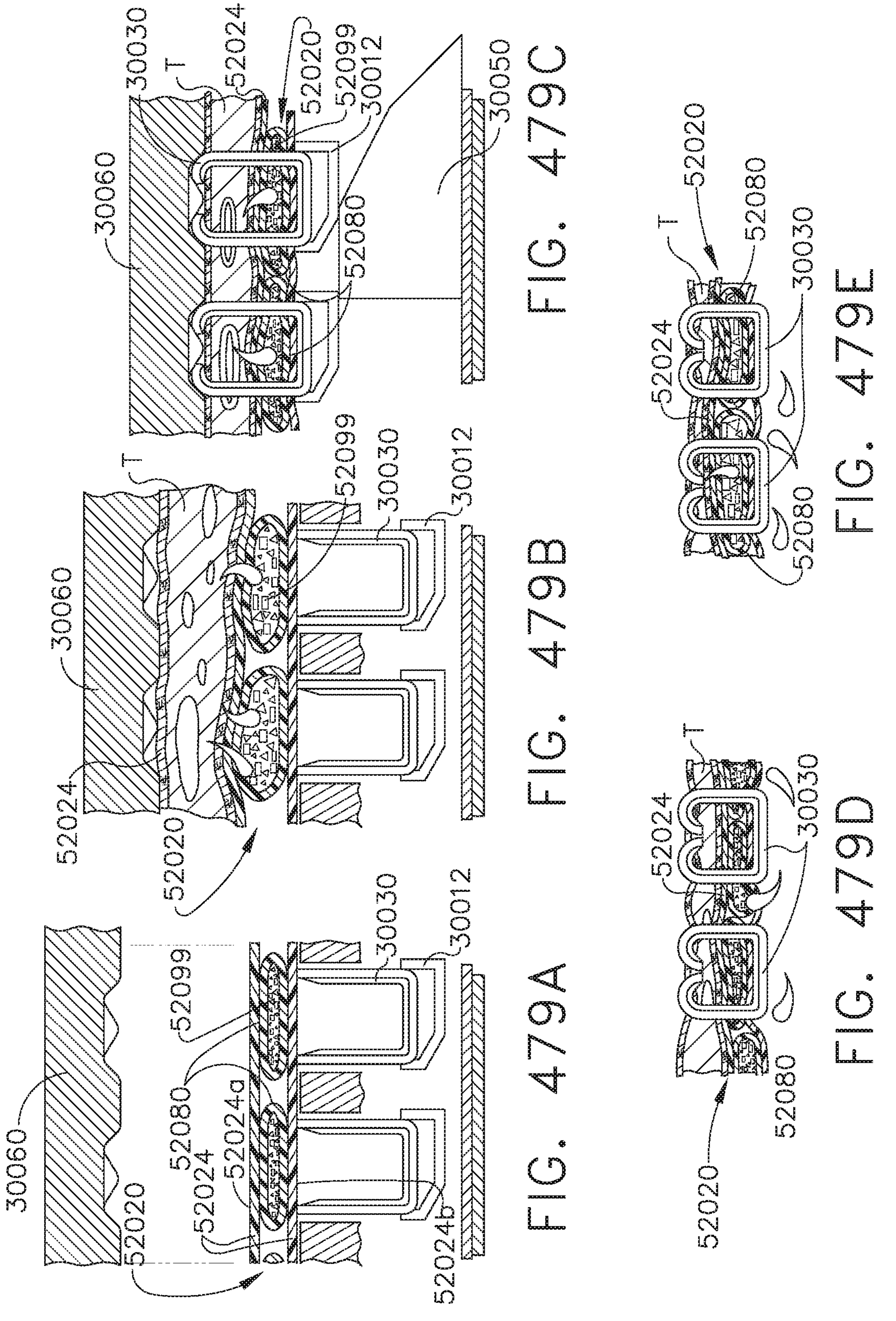
Figure 480:
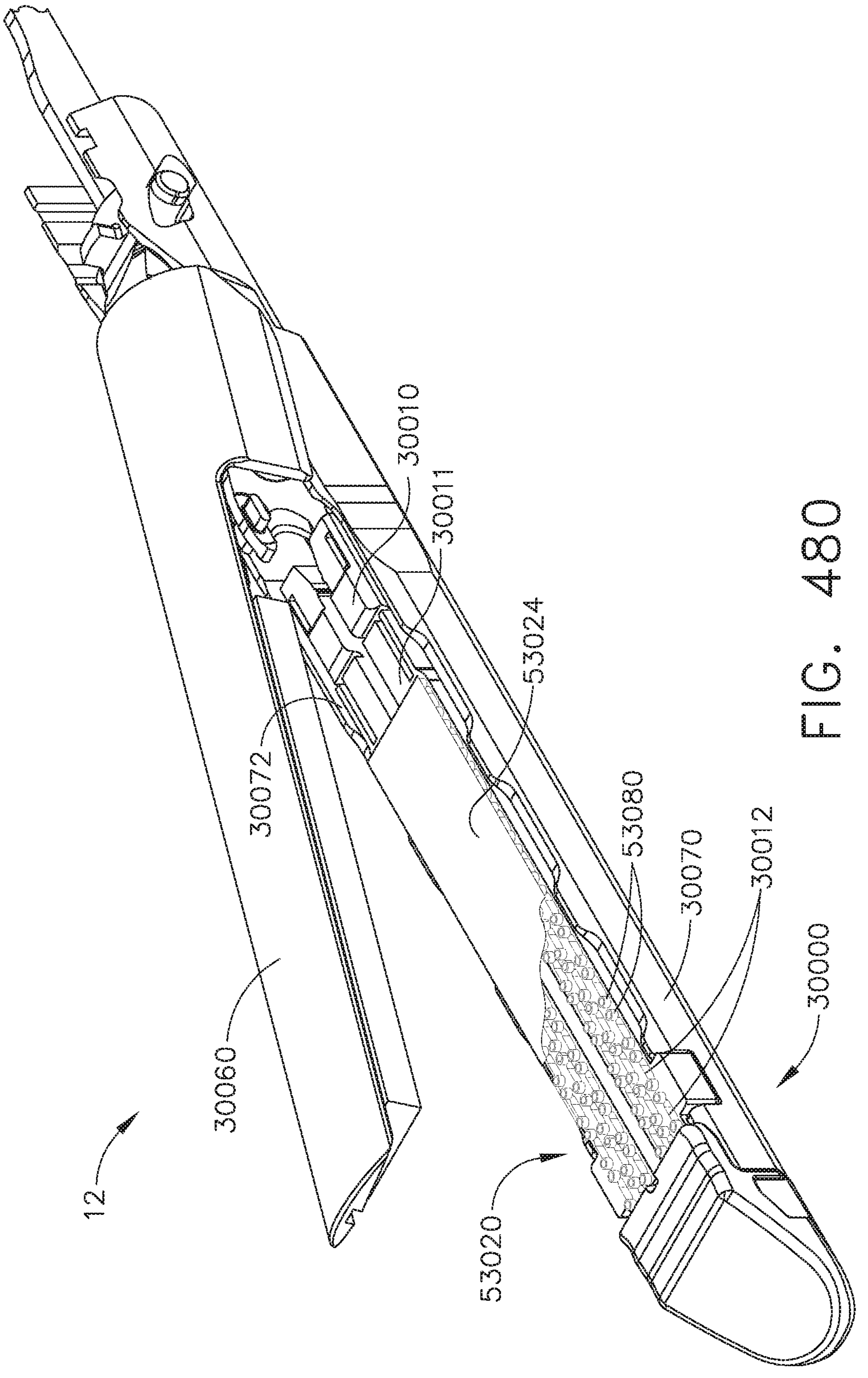
Figure 481:
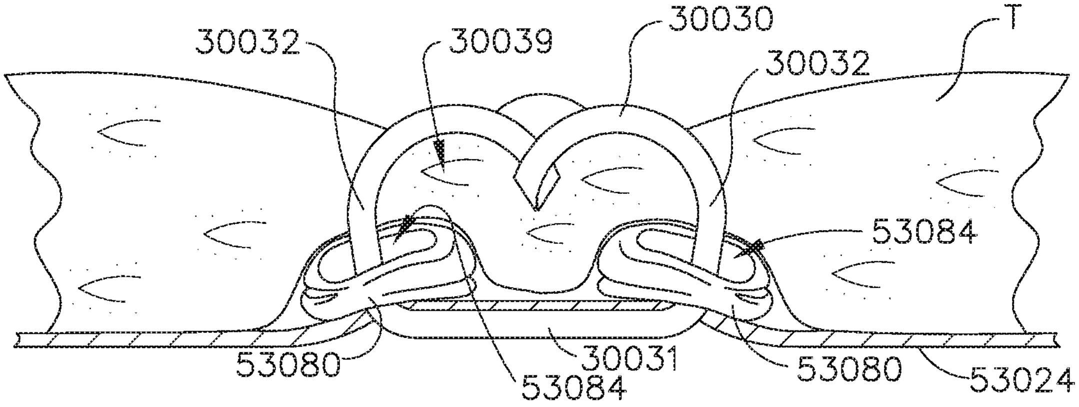
Figure 482:
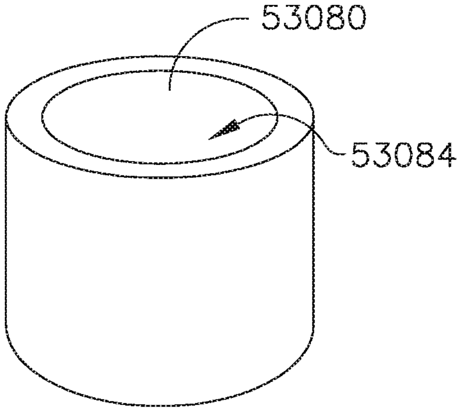
Figure 483:
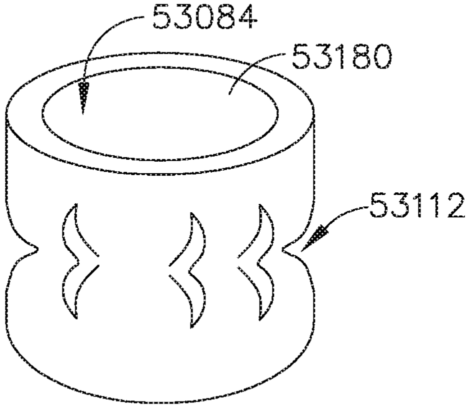
Figure 484:
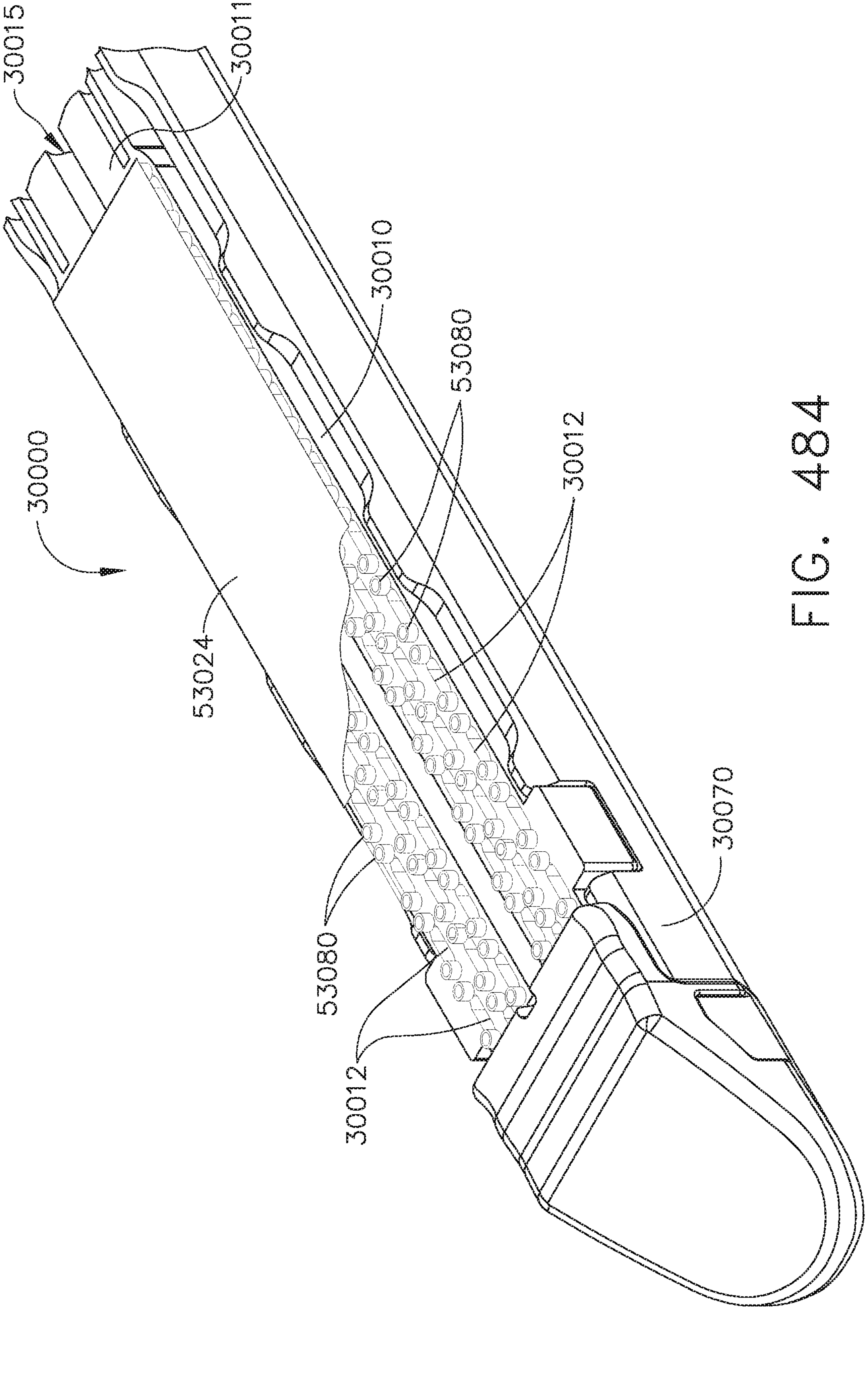
Figure 485:
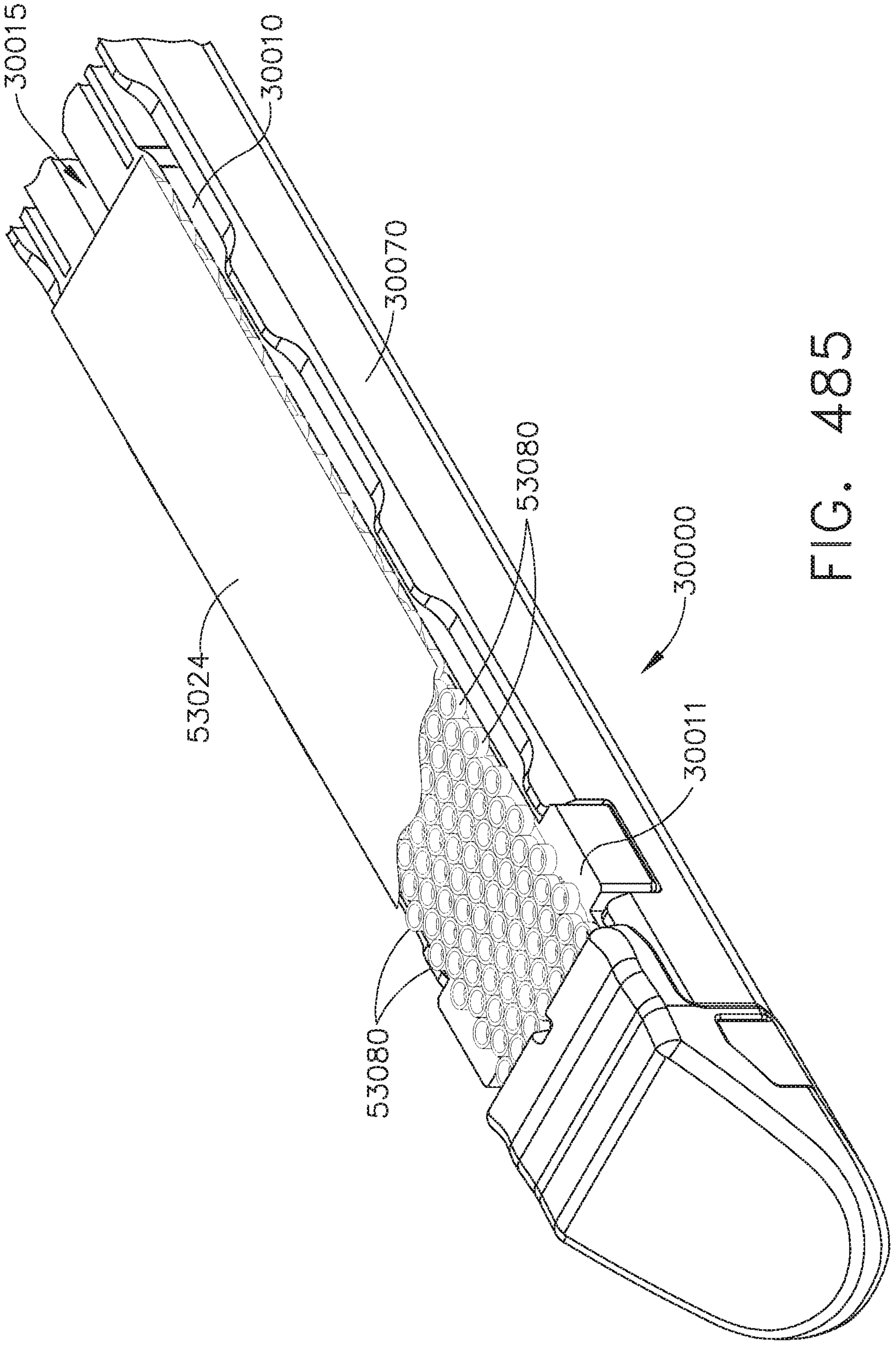
Figure 486:
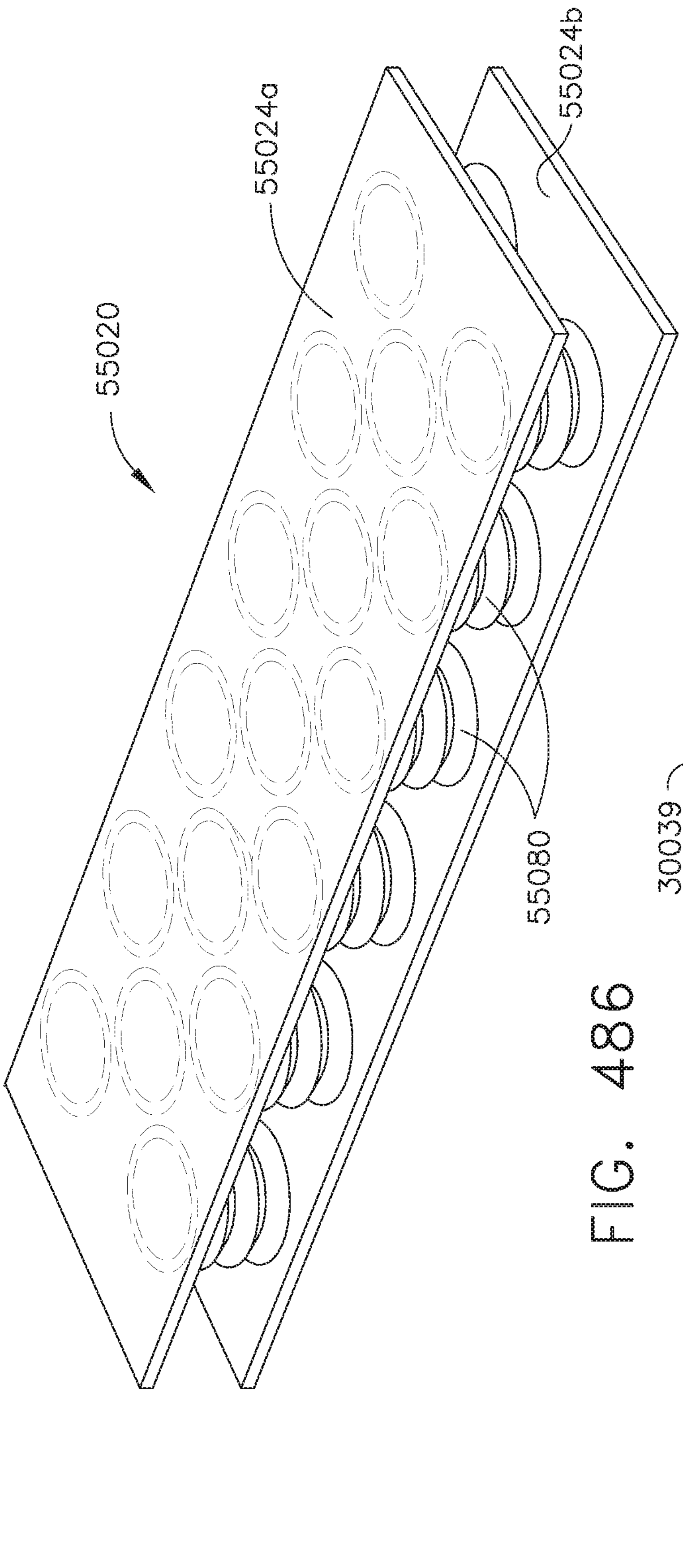
Figure 487:
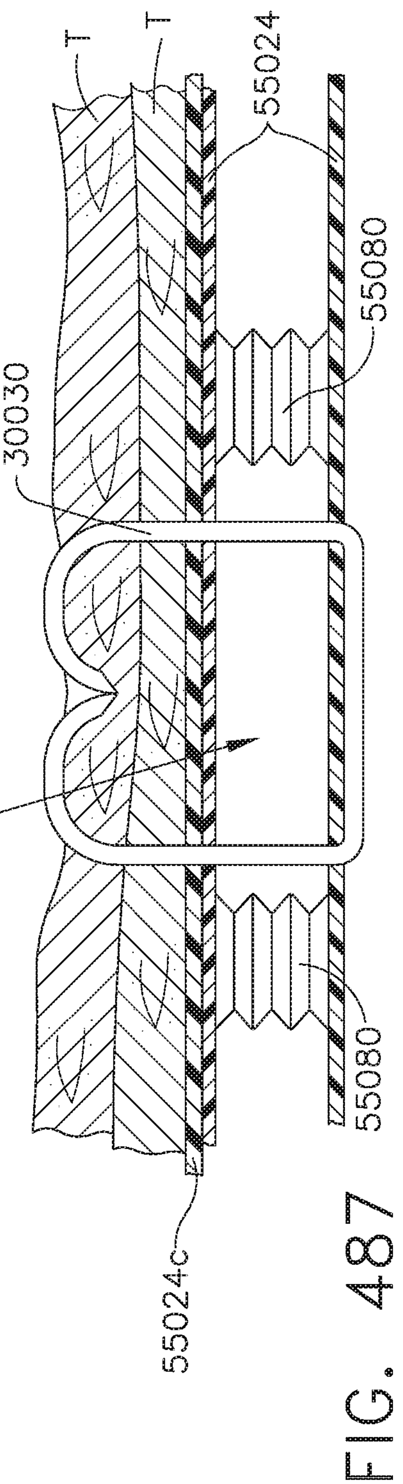
Figure 488:
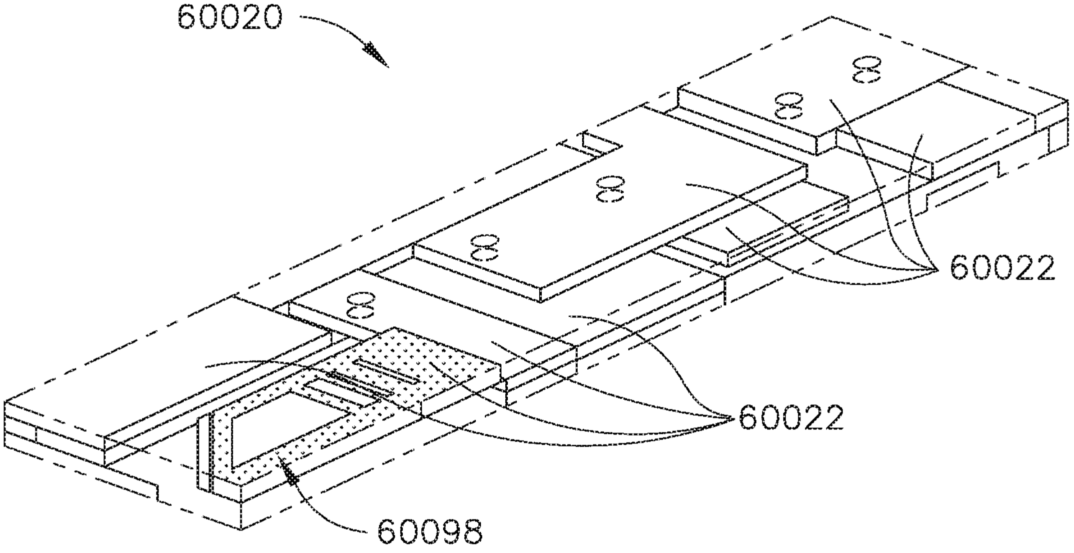
Figures 489, 490, 491, 492, 493, 494, 495, 496, 497:
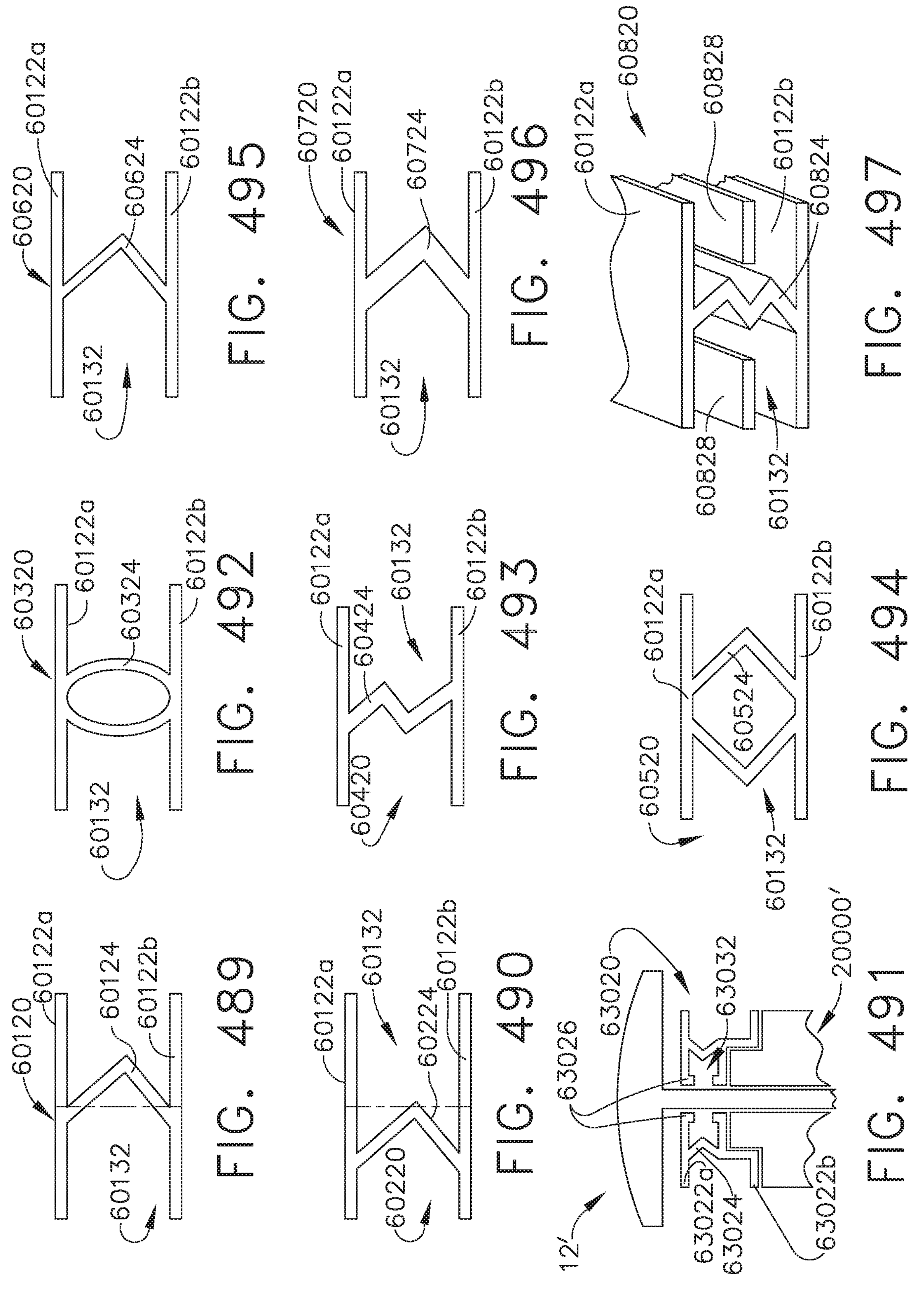
Figure 498:
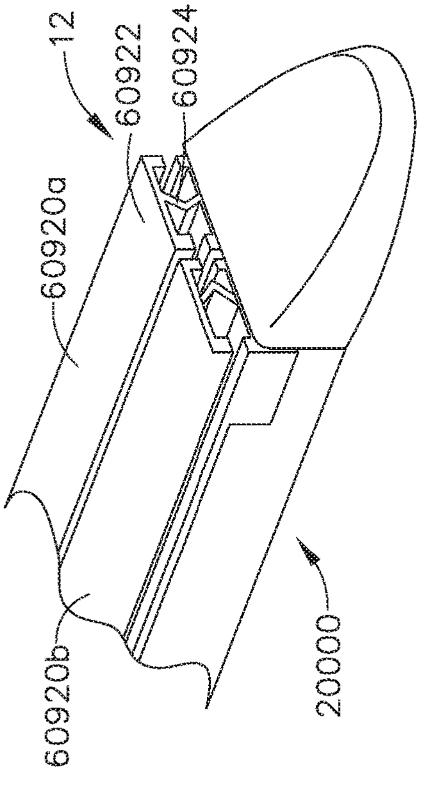
Figure 499:
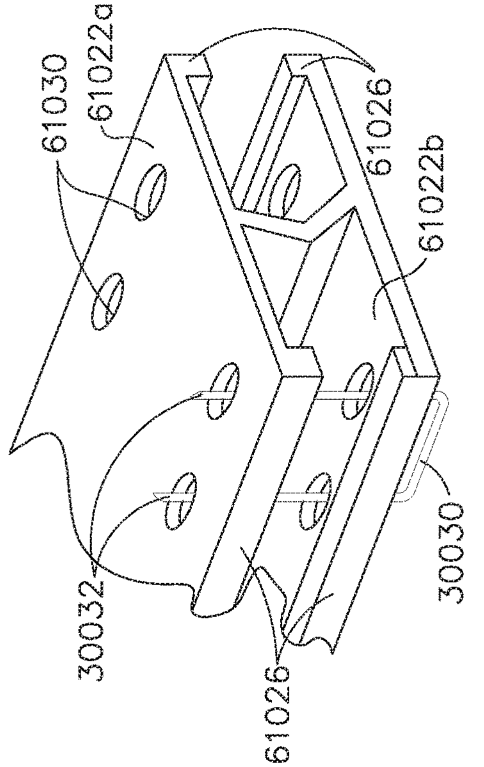
Figure 500:
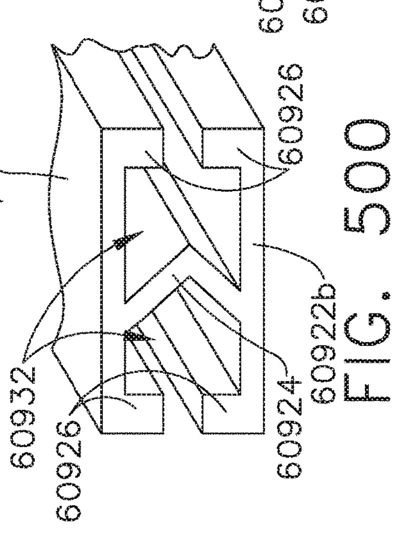
Figure 501:
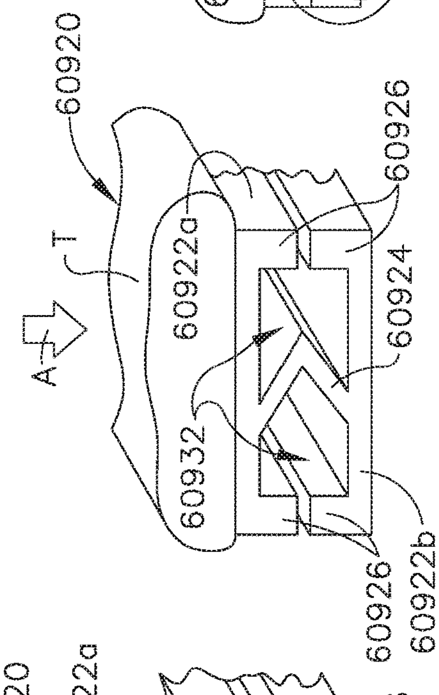
Figure 502:
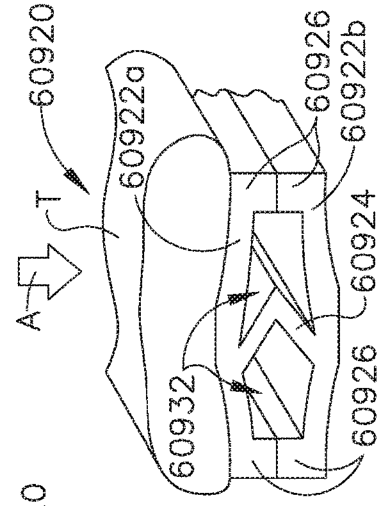
Figure 503:
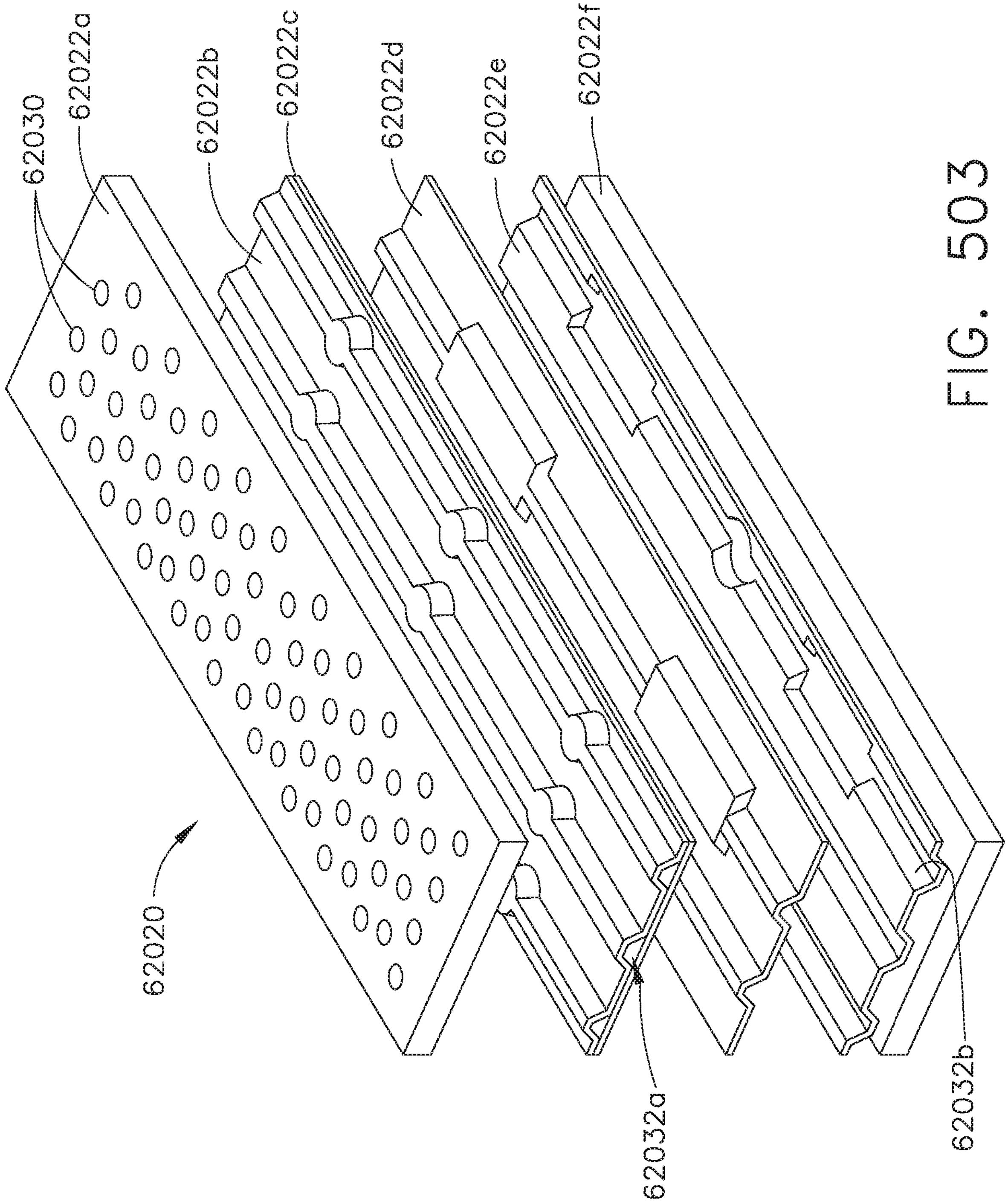
Figure 504:
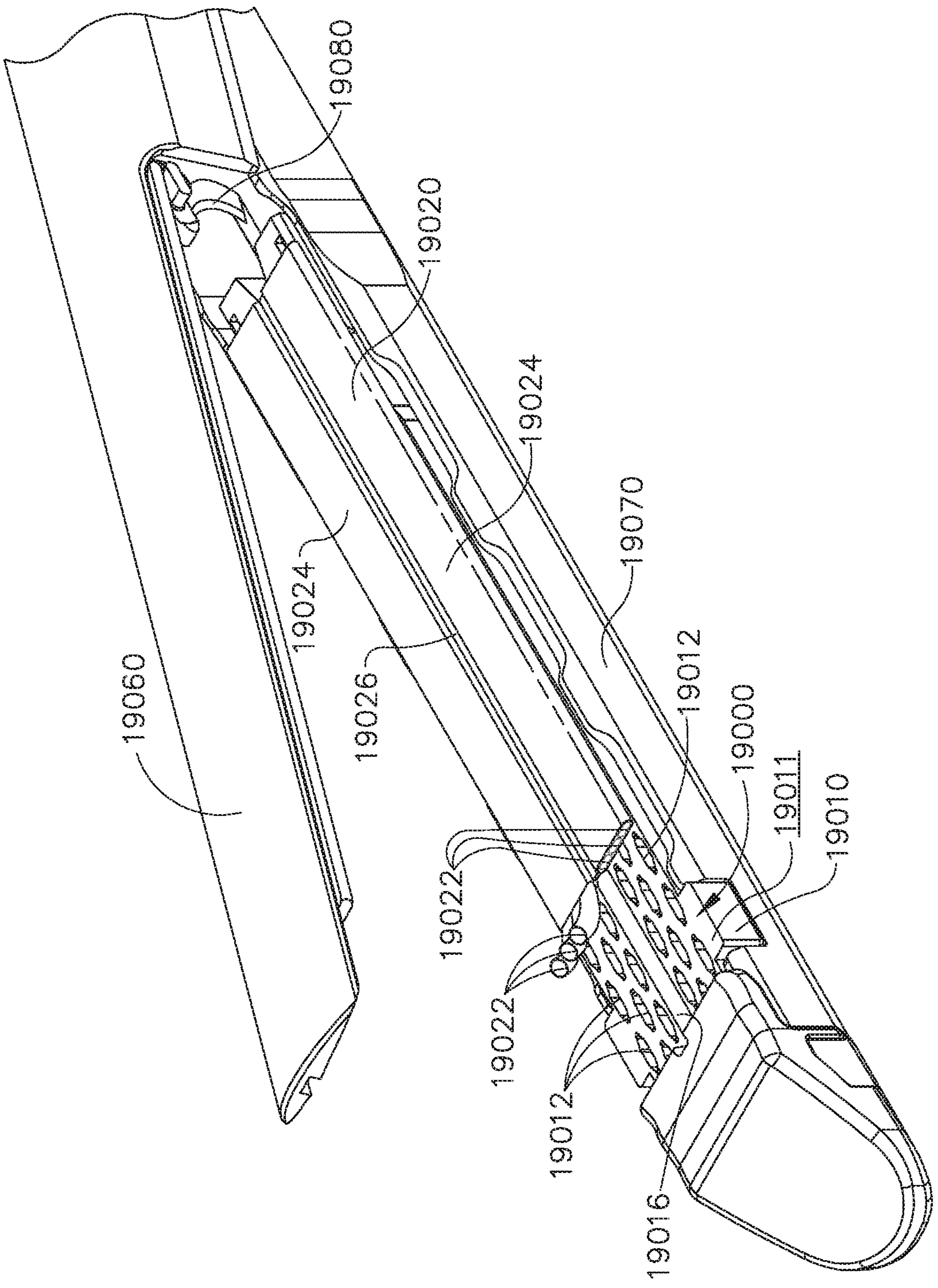
Figure 505:
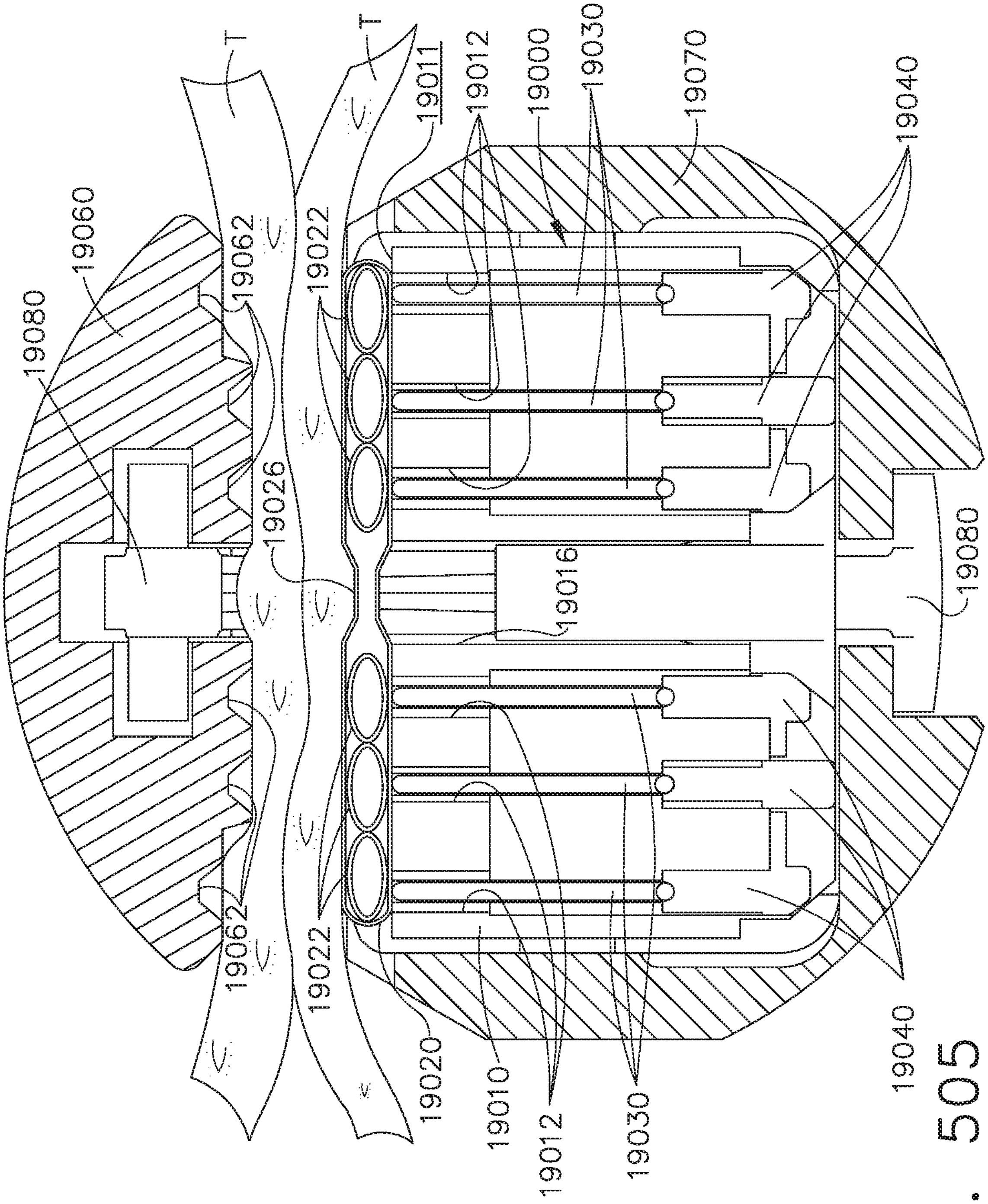
Figure 506:
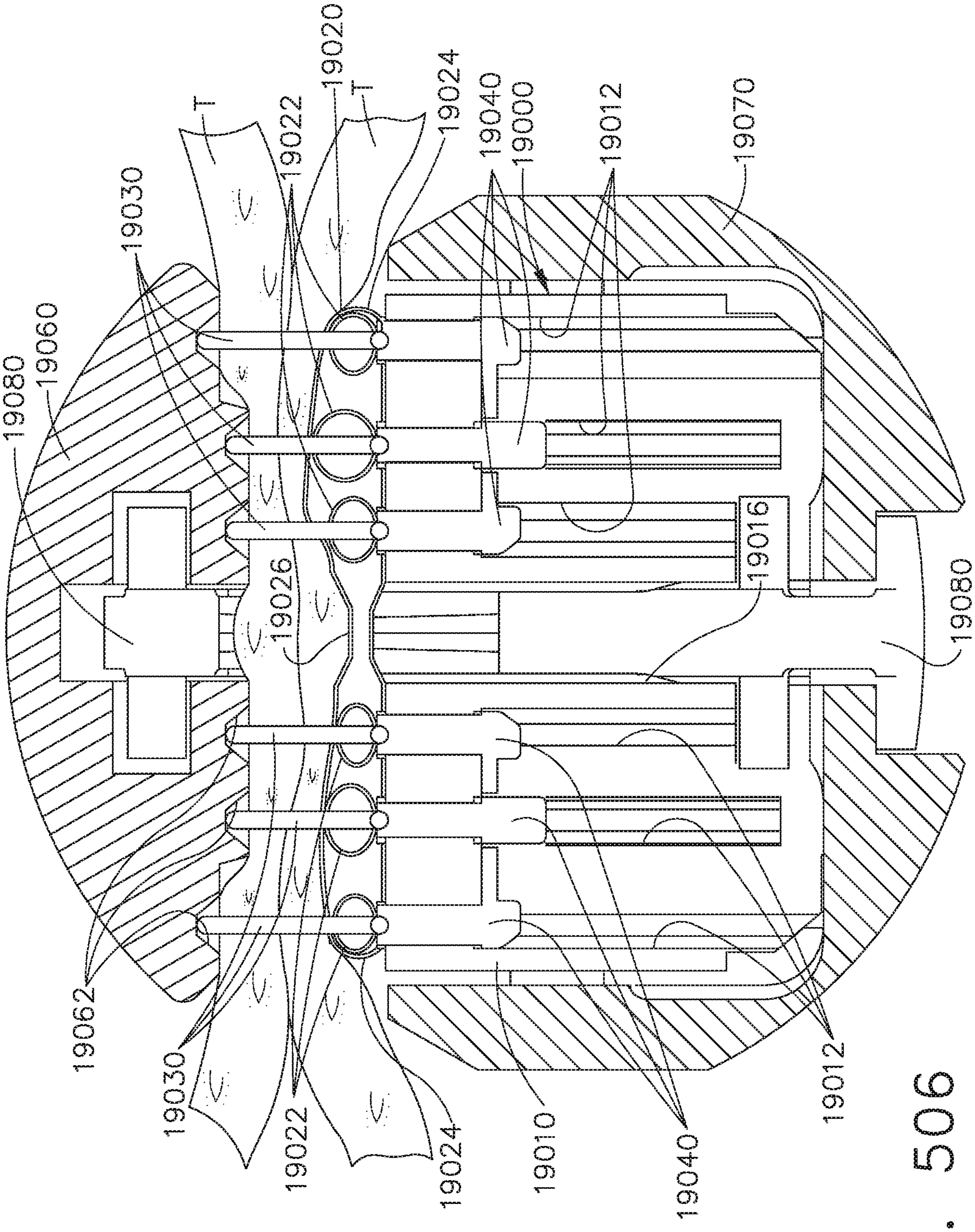
Figure 507:
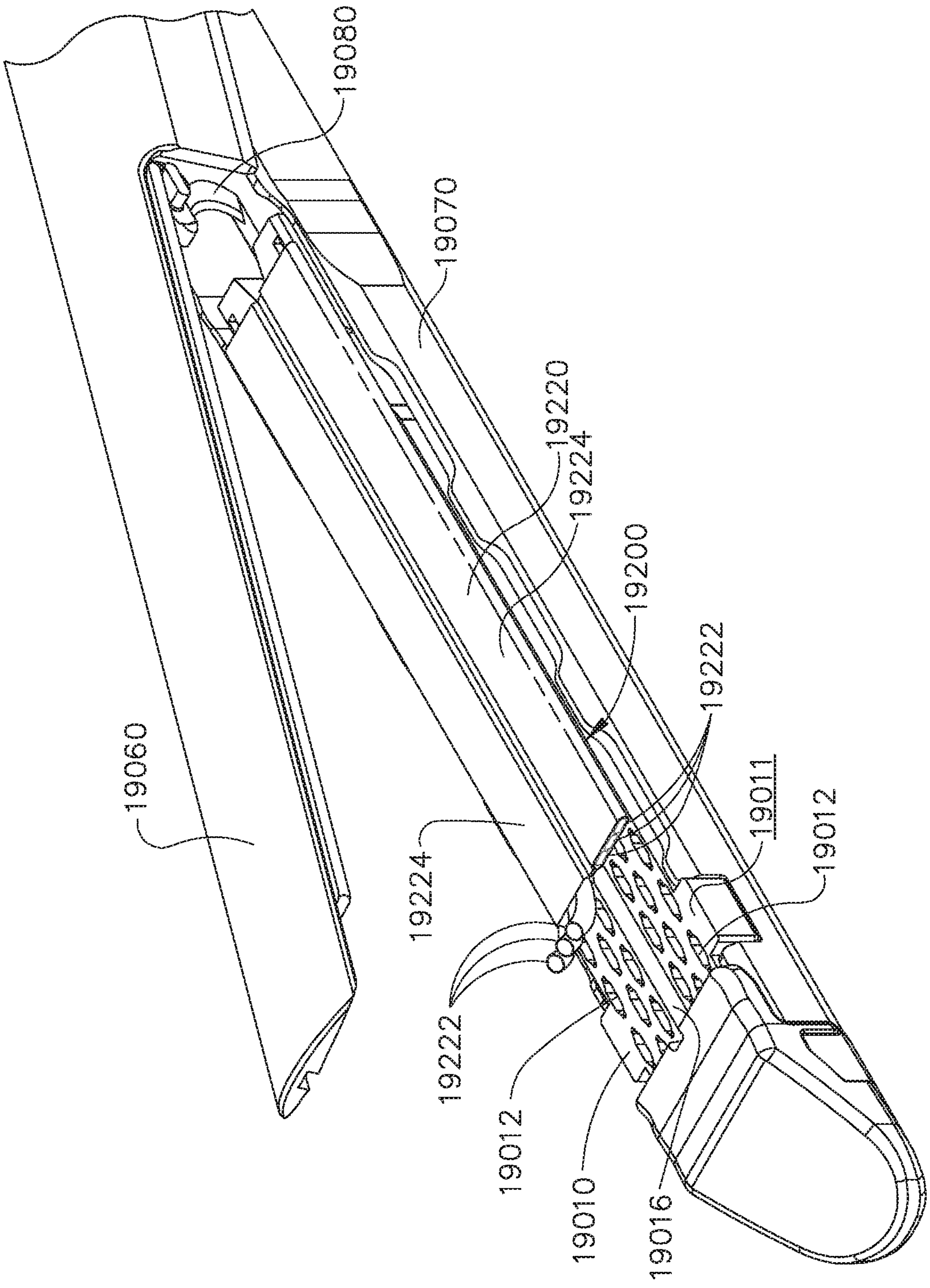
Figure 508:
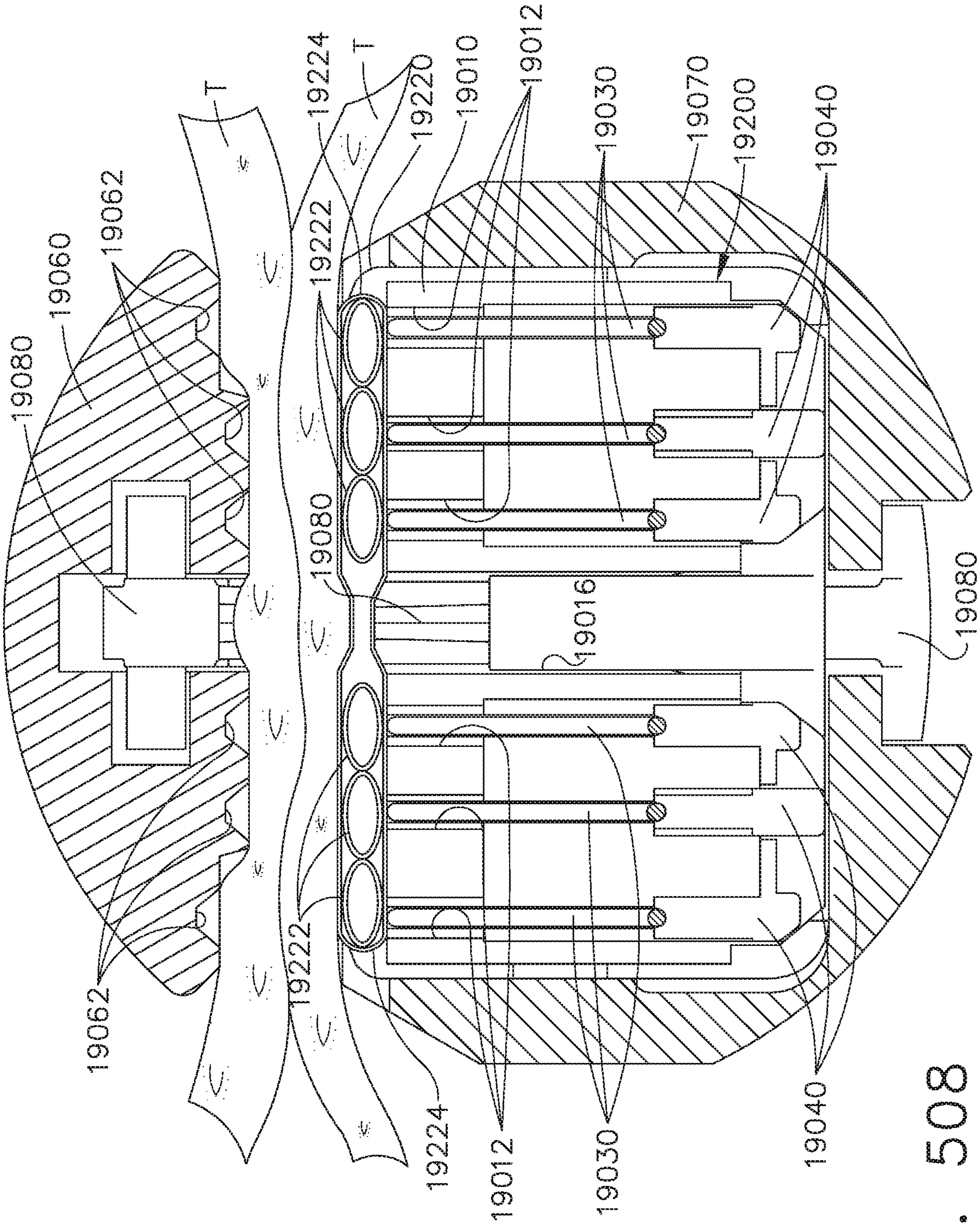
Figure 509:
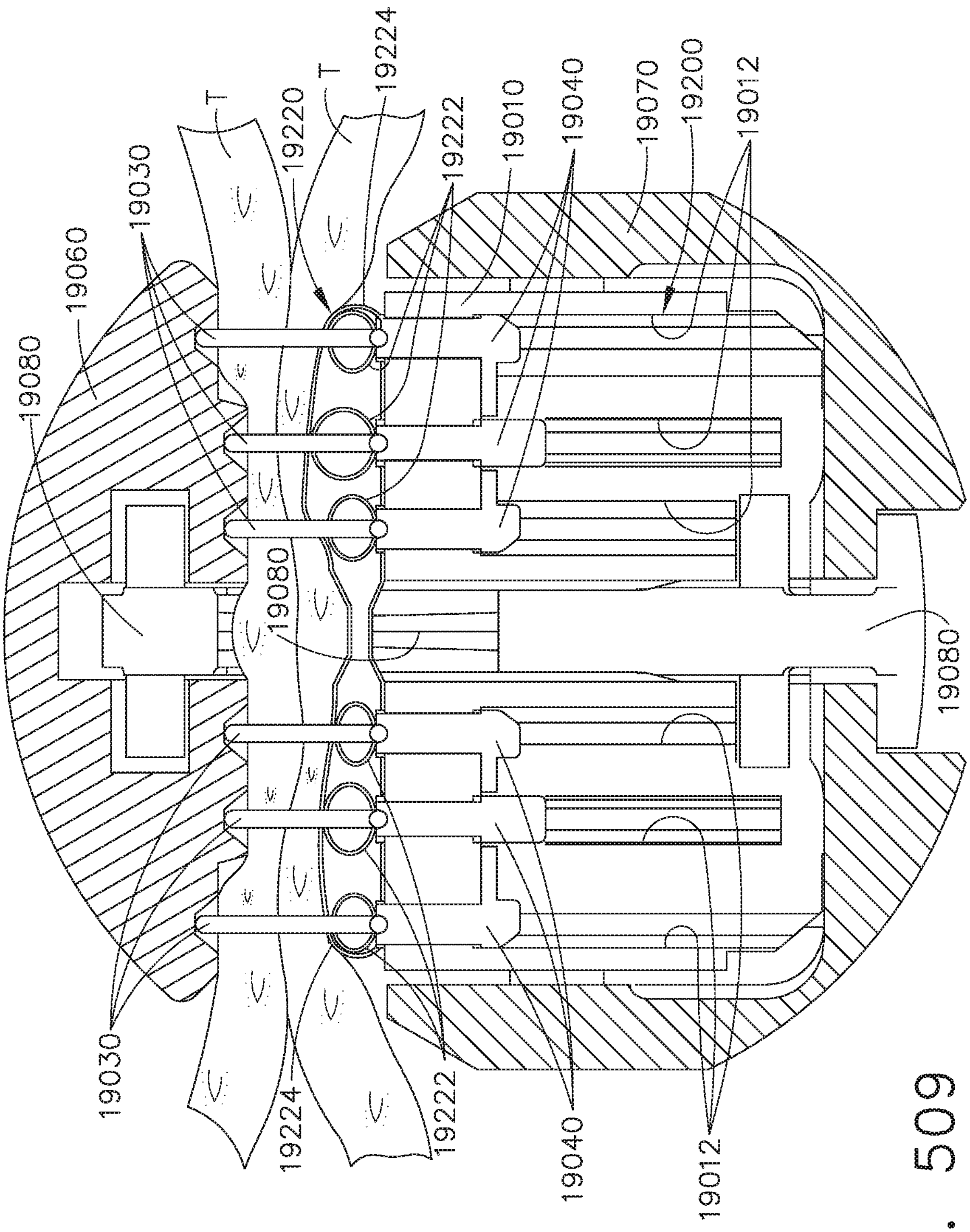
Figure 510:
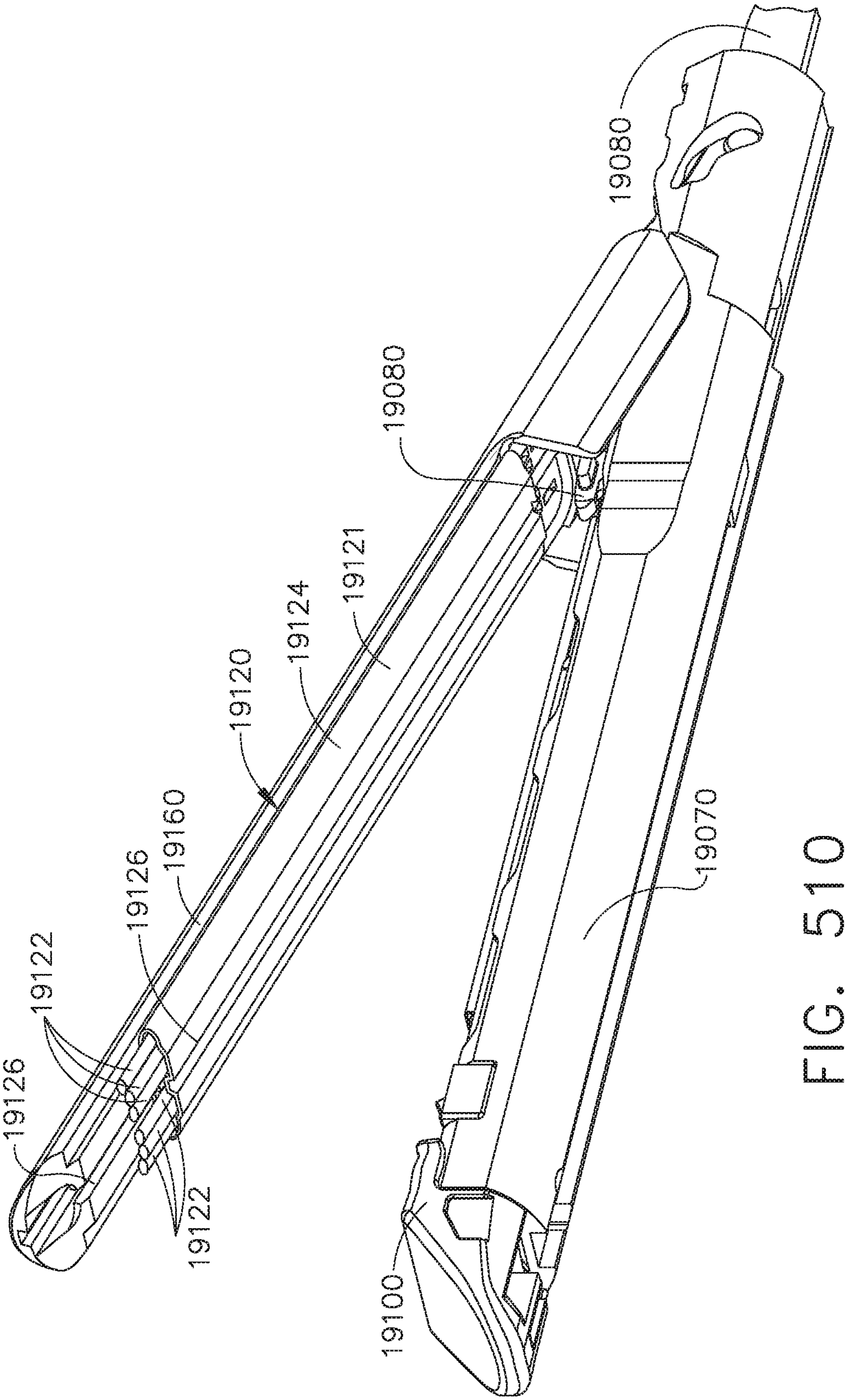
Figure 511:
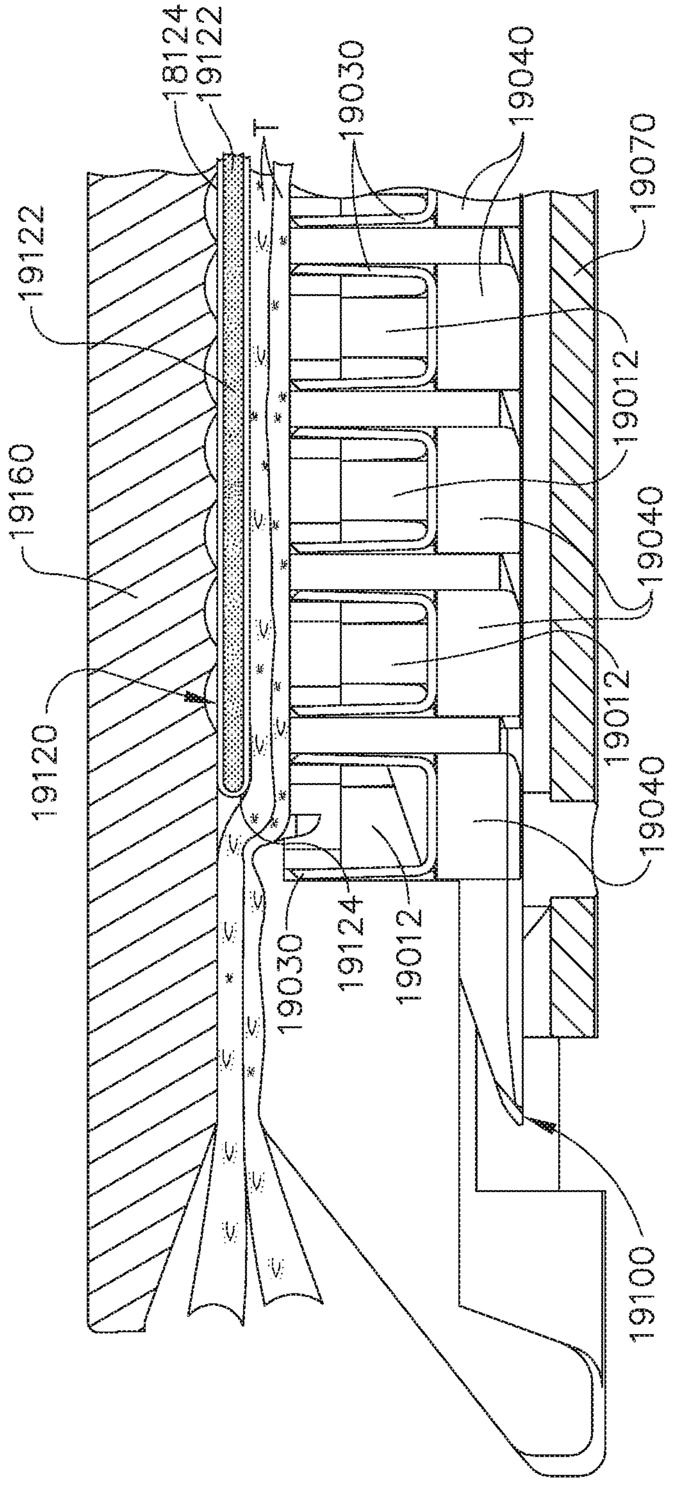
Figure 512:
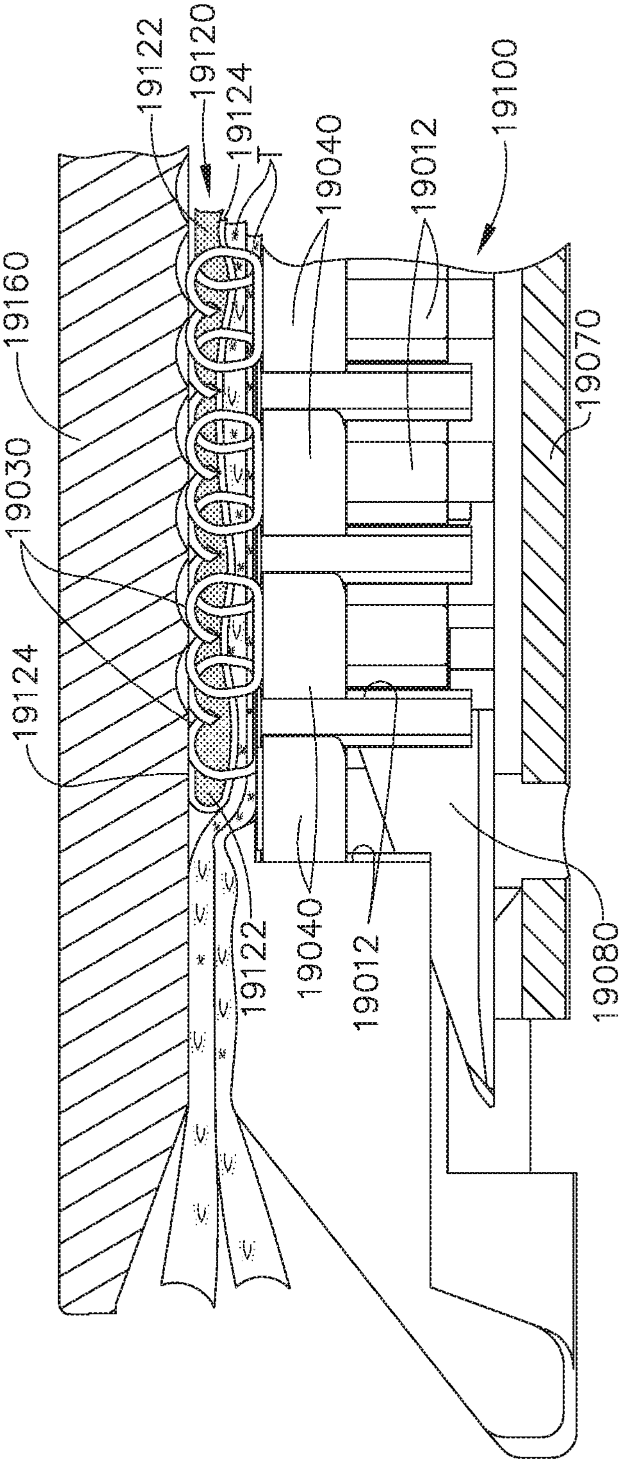
Figure 513:
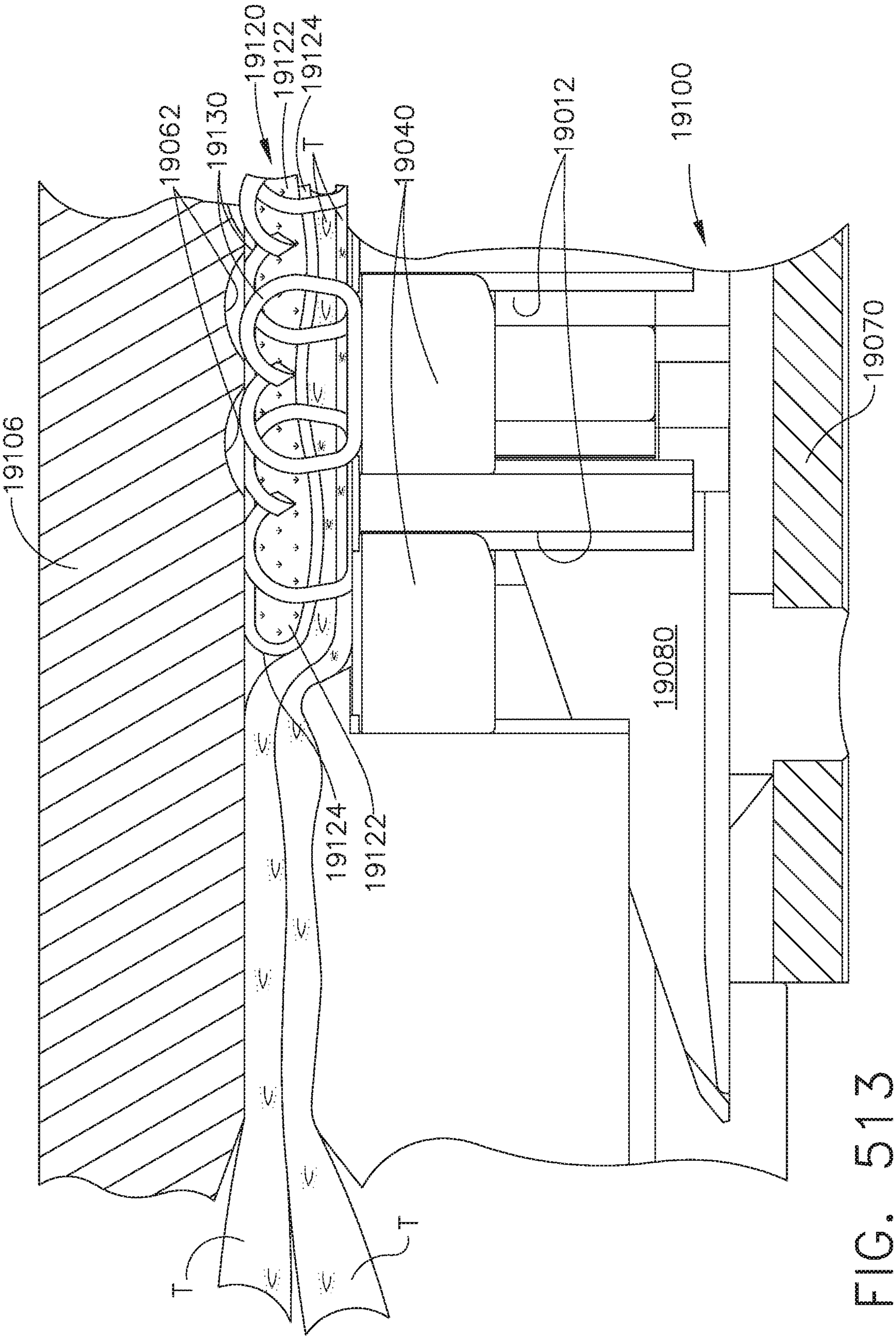
Figure 514:
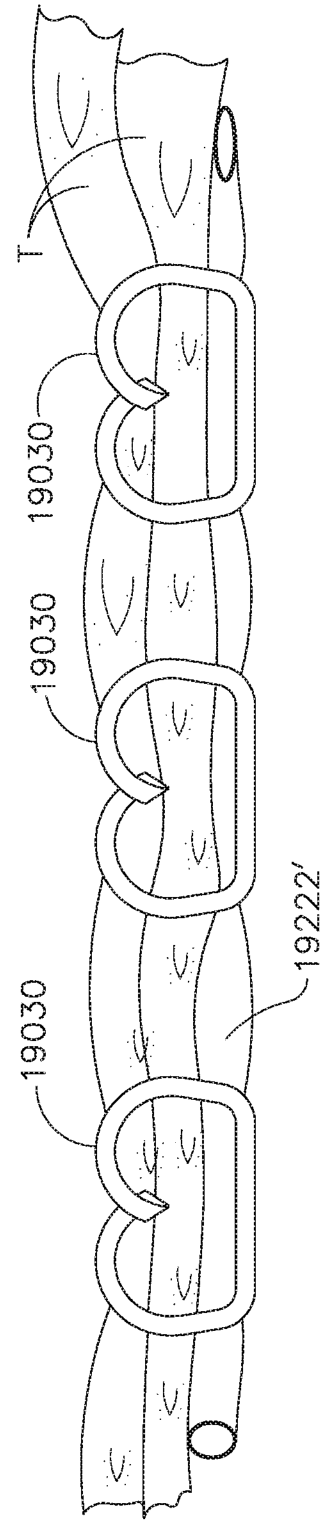
Figure 515:
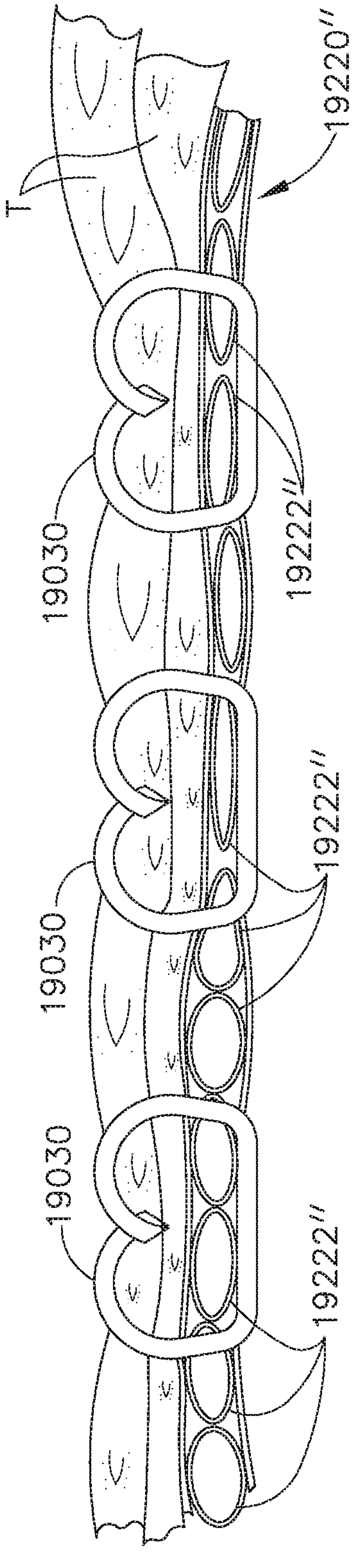
Figure 516:
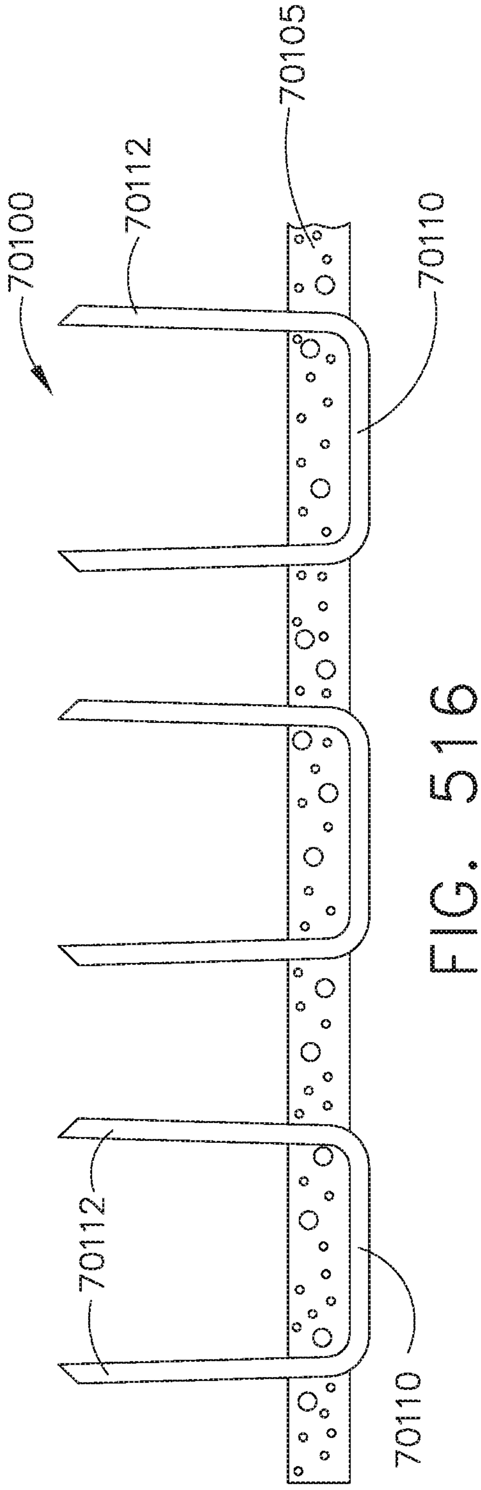
Figure 517:
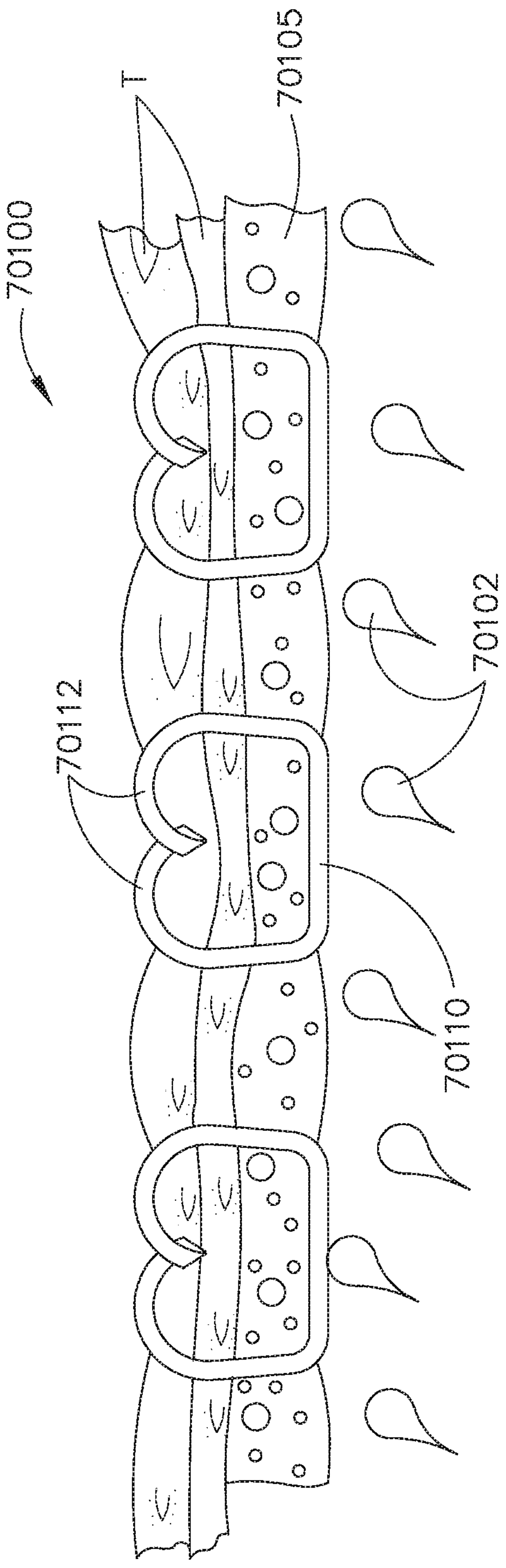
Figure 518A:
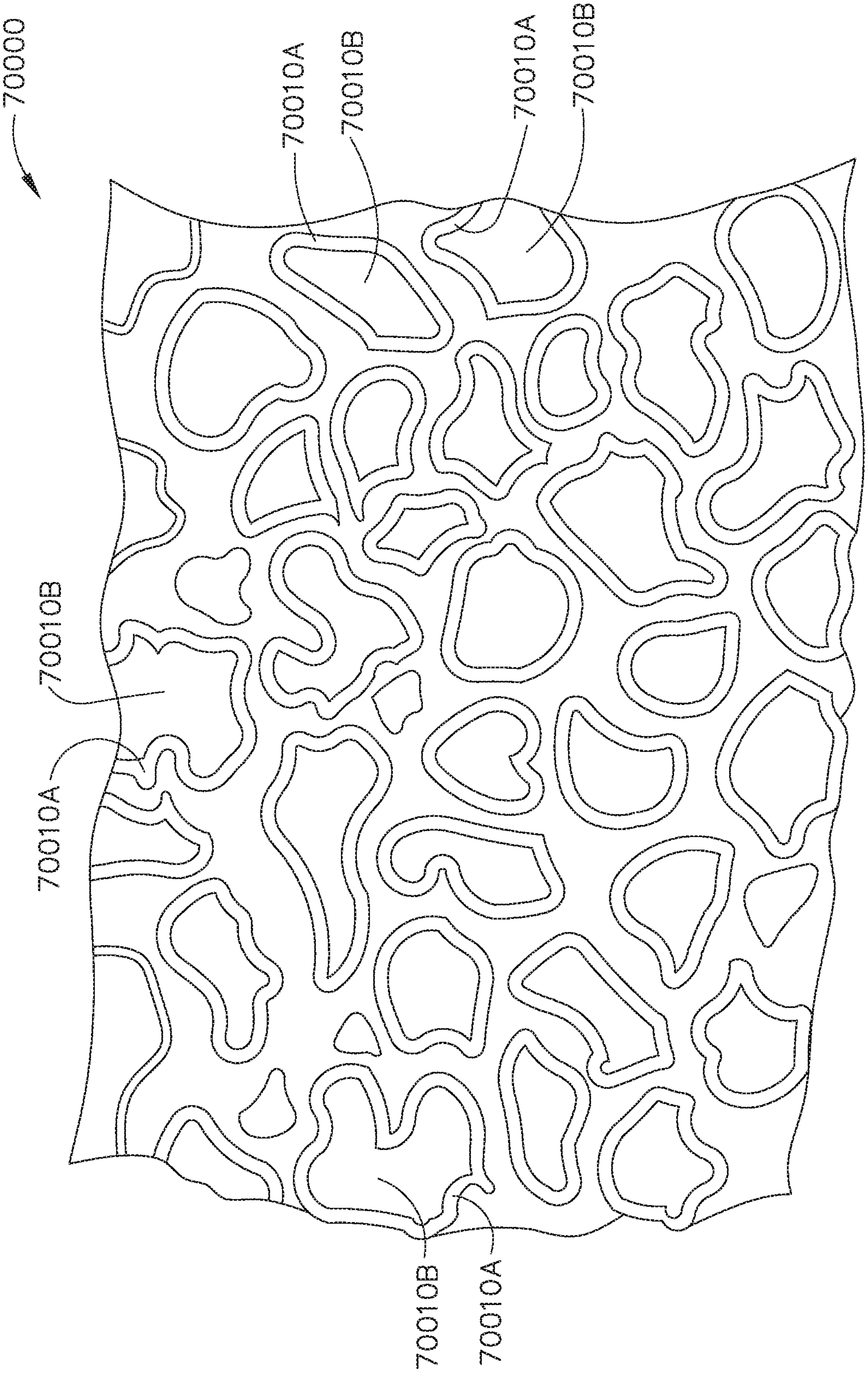
Figure 518B:
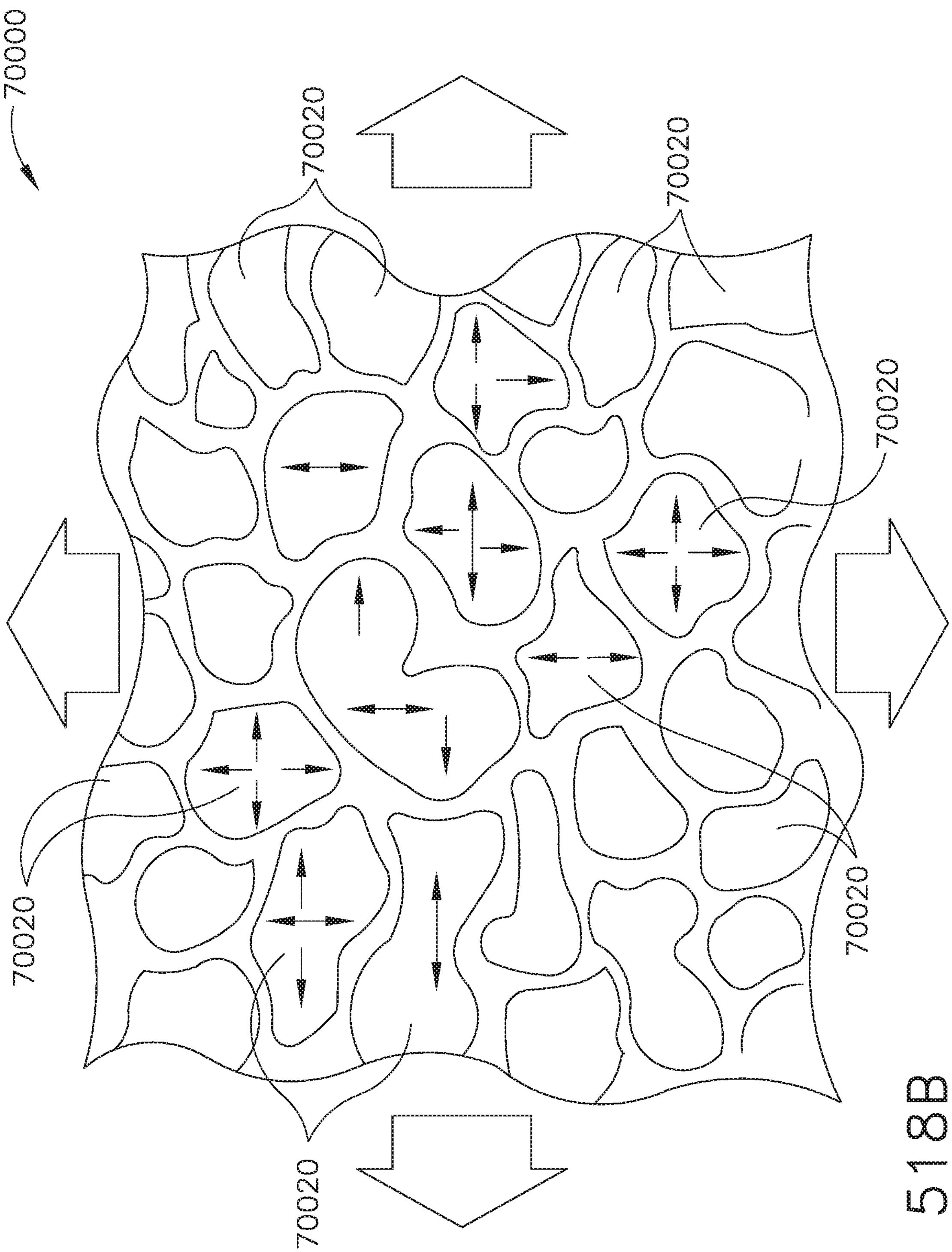
Figure 519:
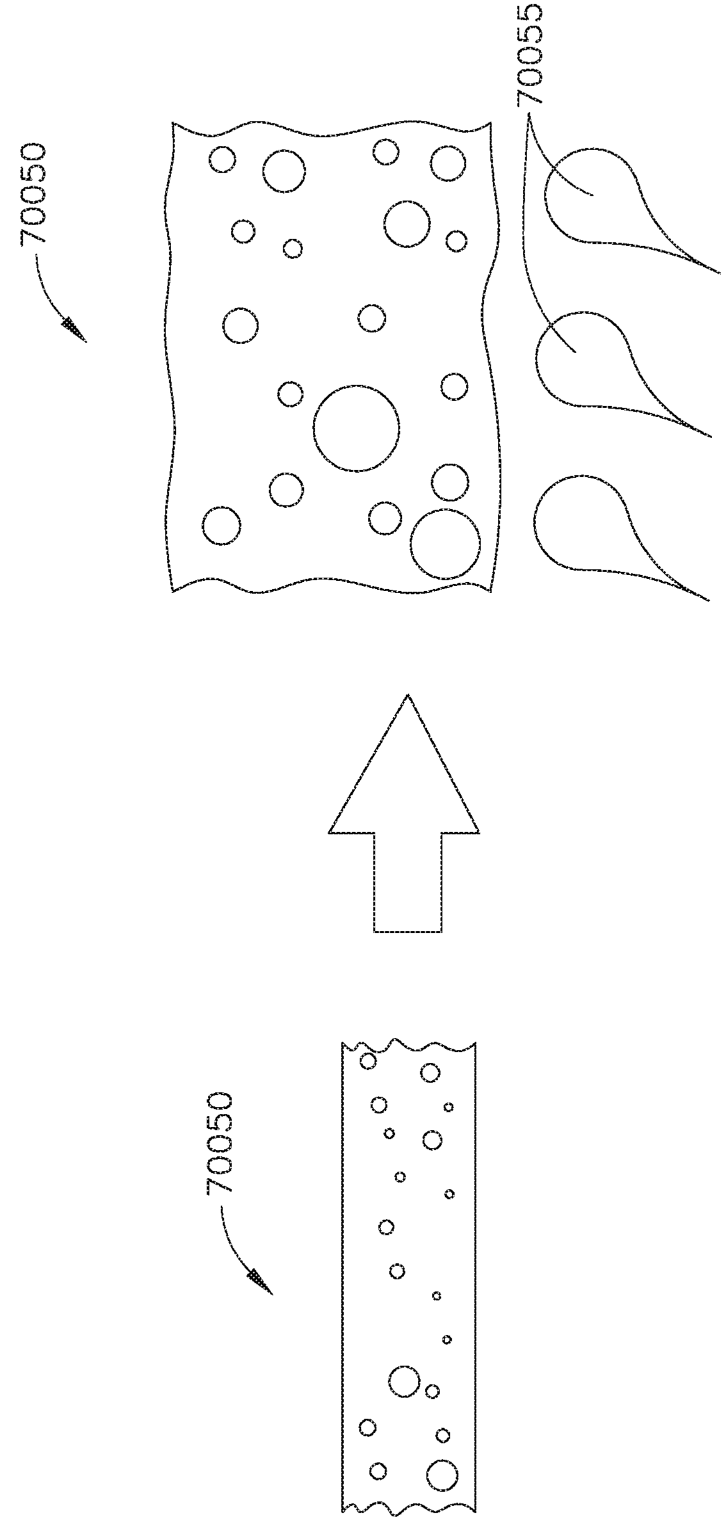
Figure 520:
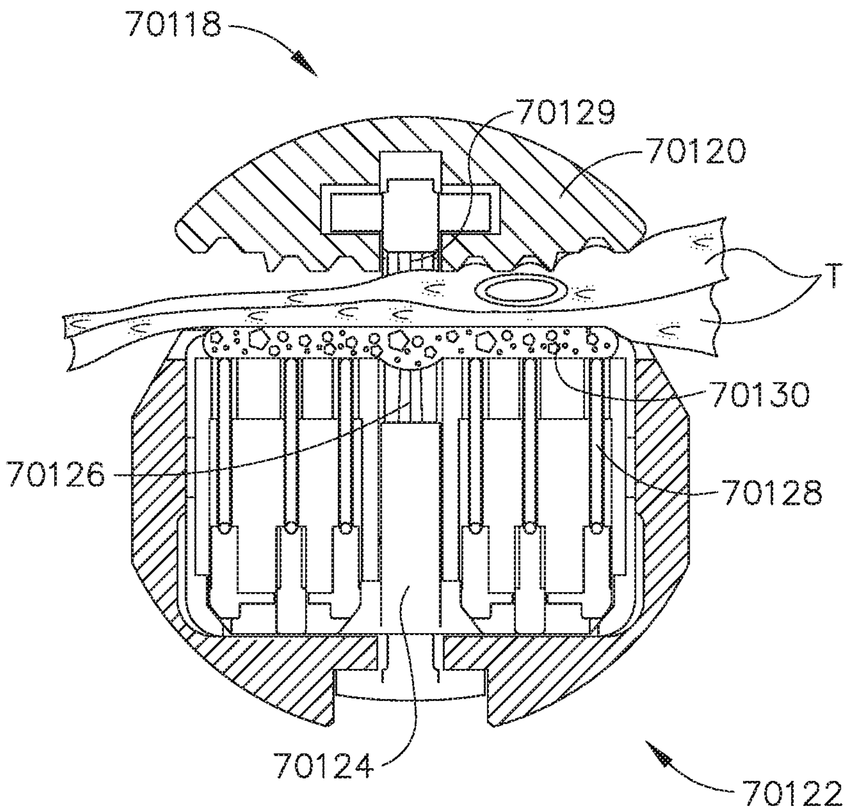
Figure 521:
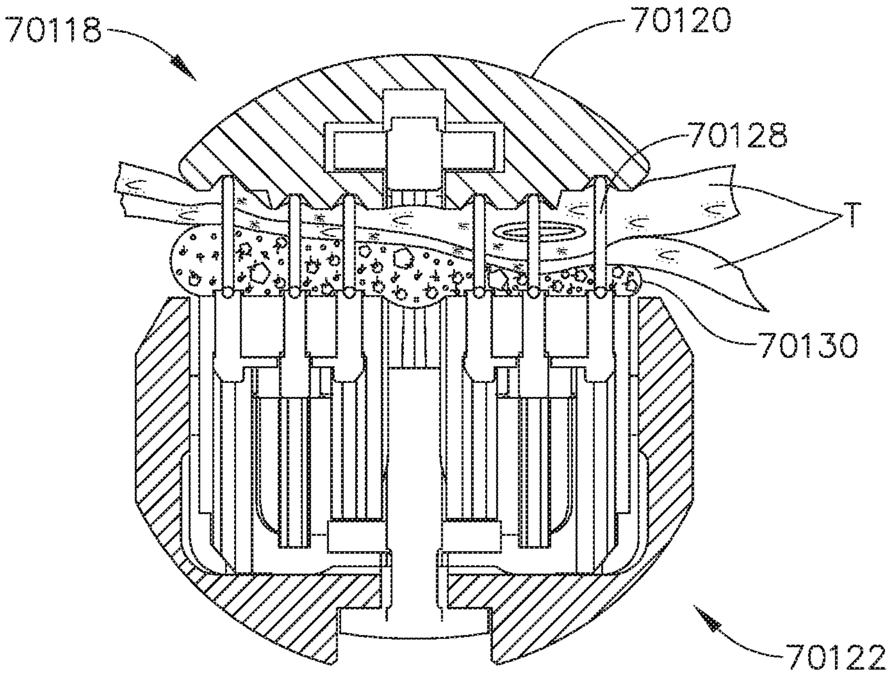
Figure 522:
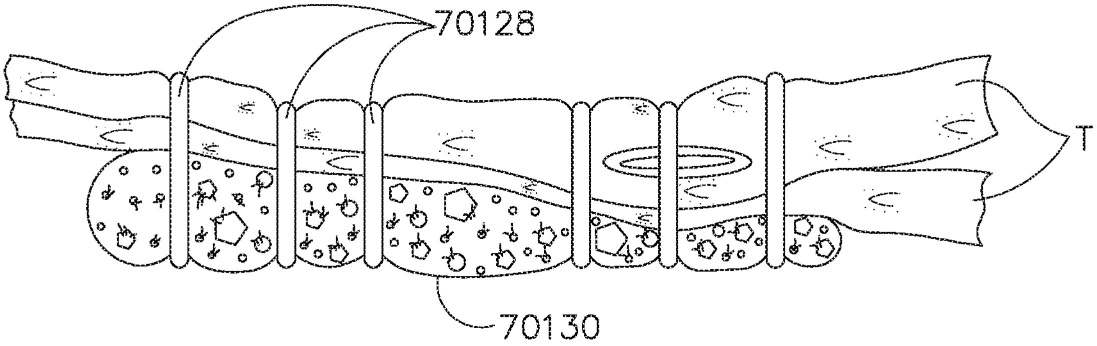
Figure 523:
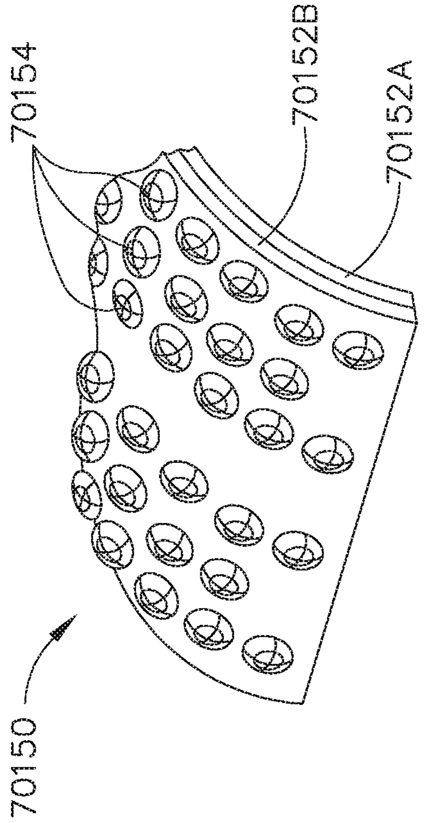
Figure 524:
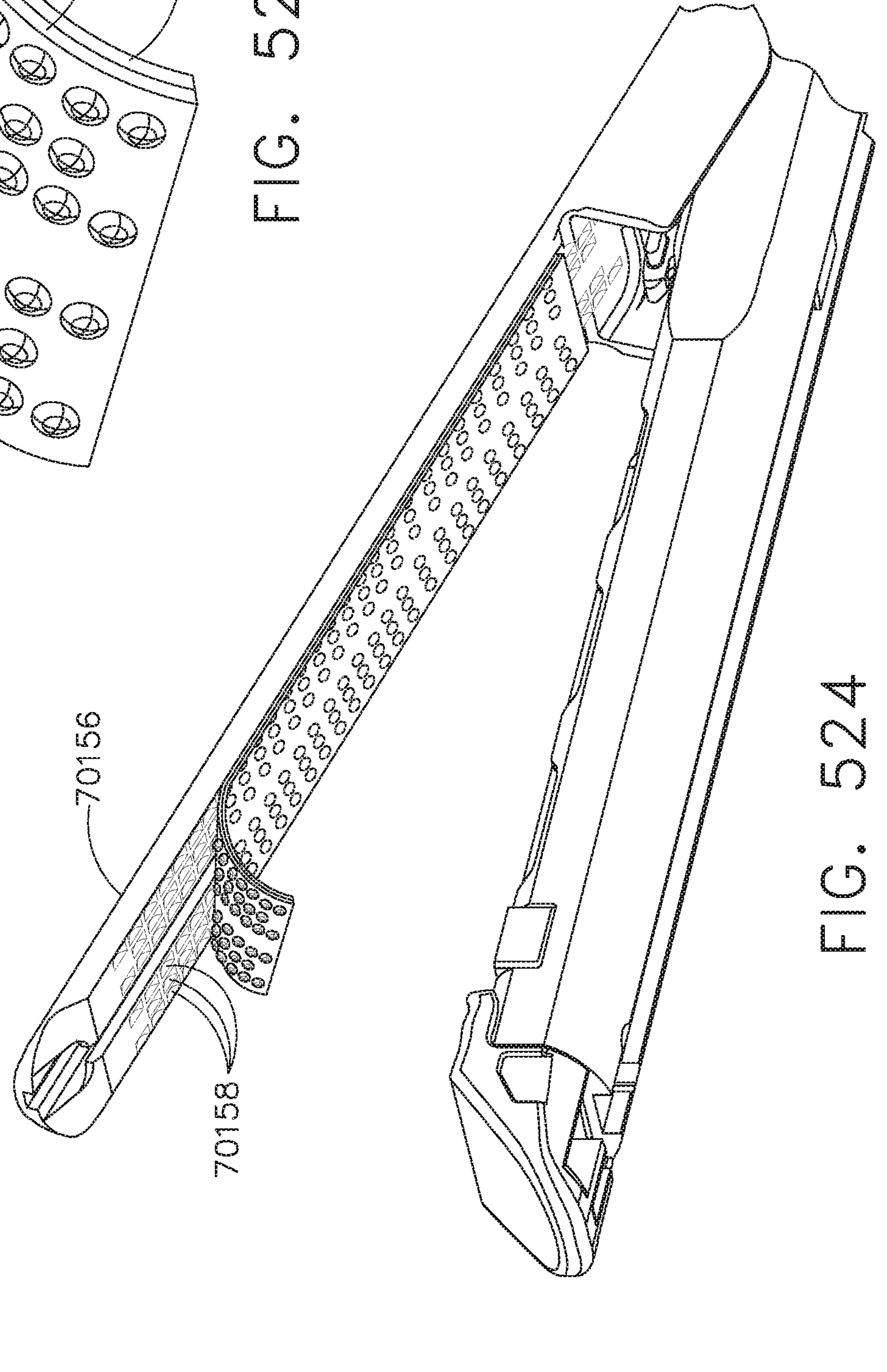
Figure 525:
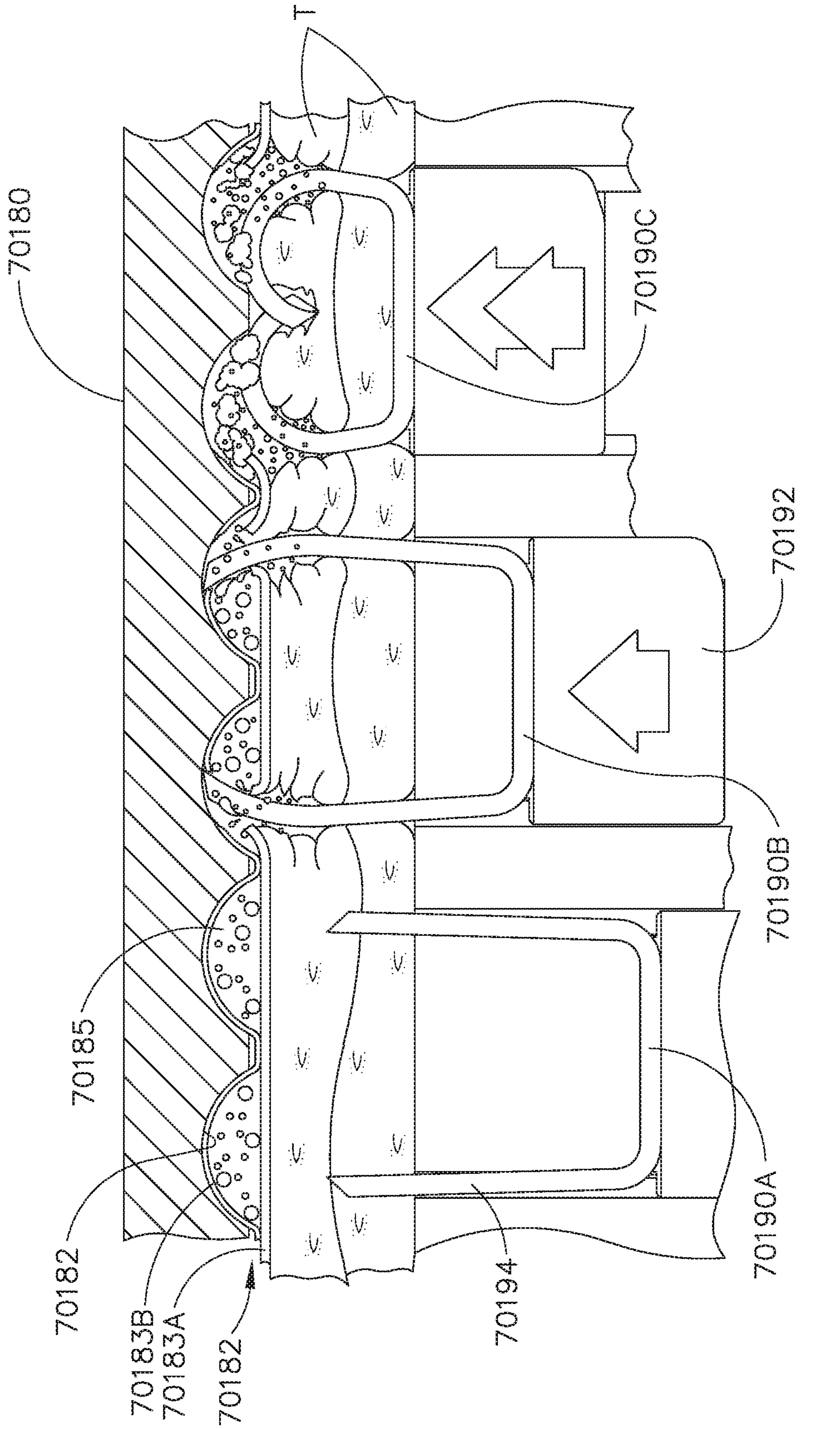
Figure 526:
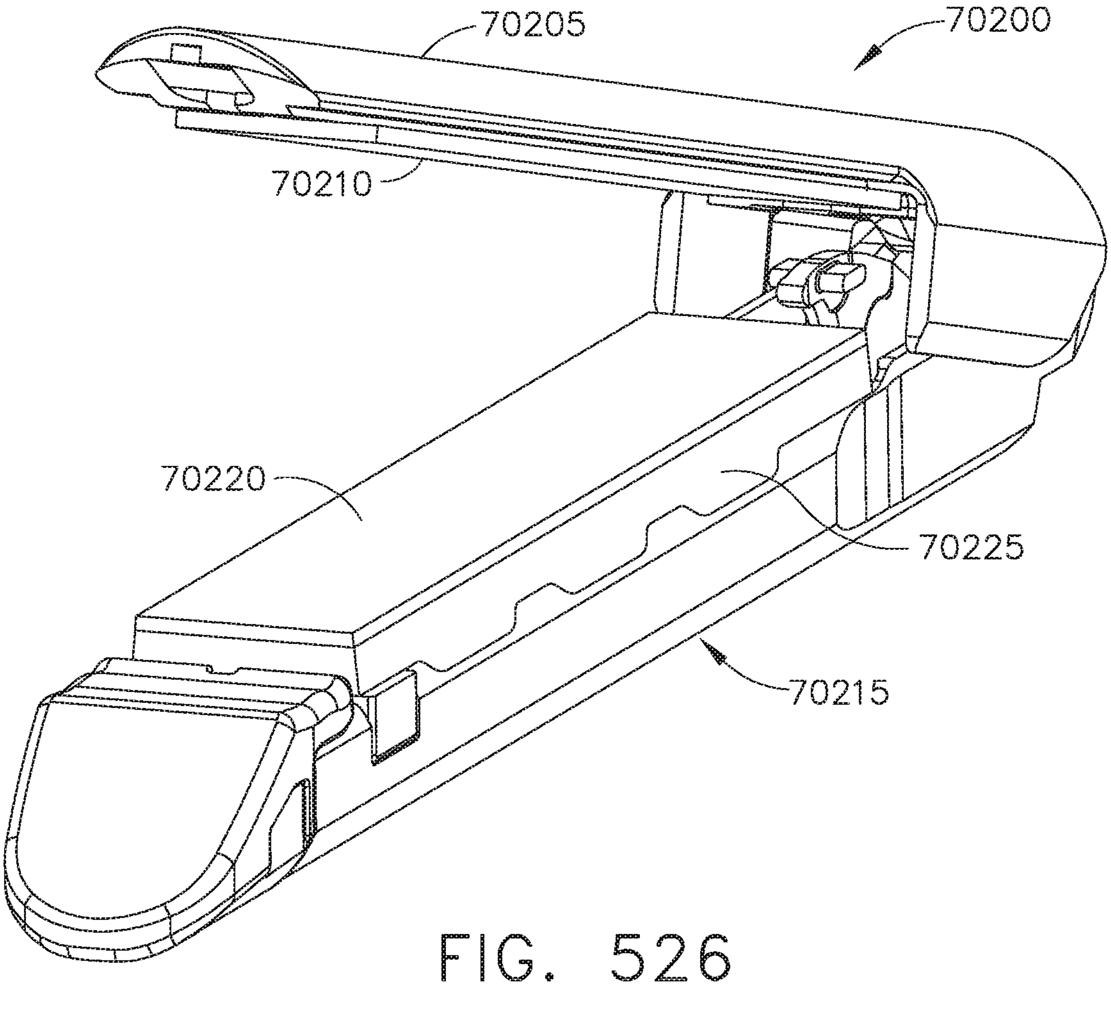
Figure 527A:
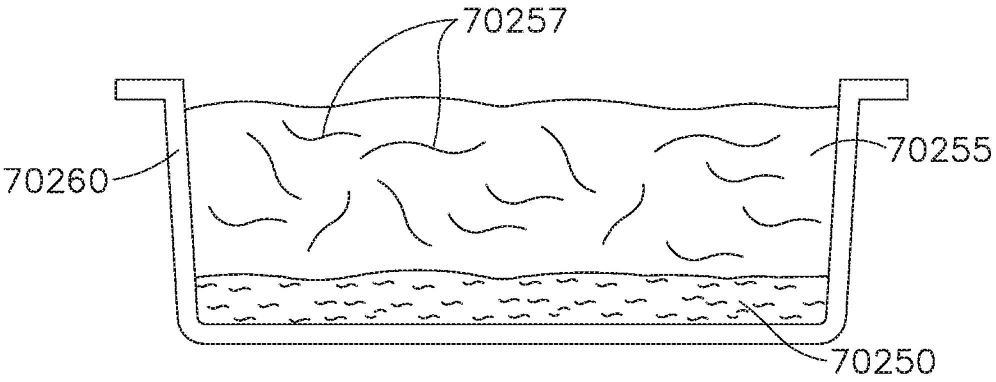
Figure 527B:
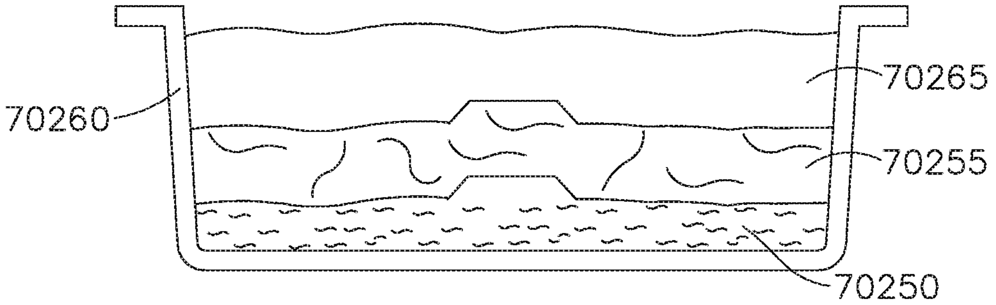
Figure 528:
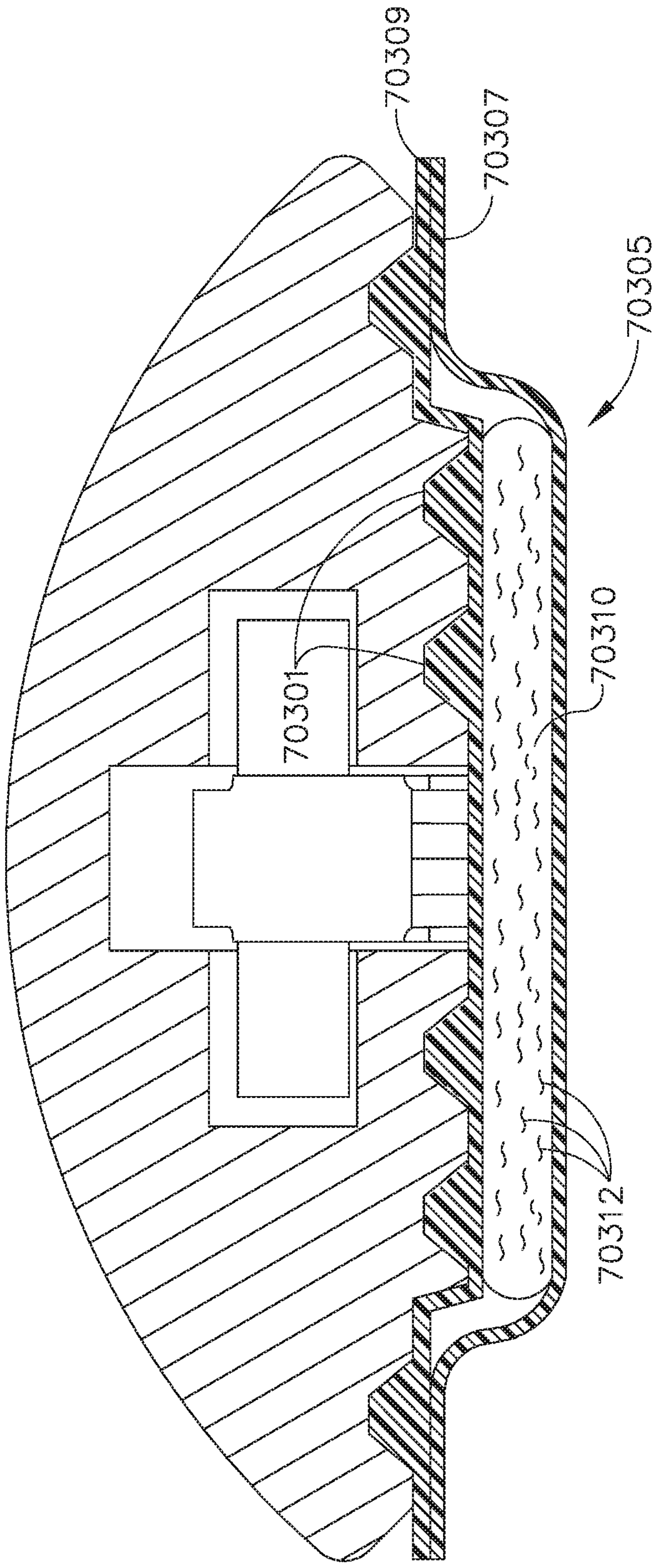
Figure 529:
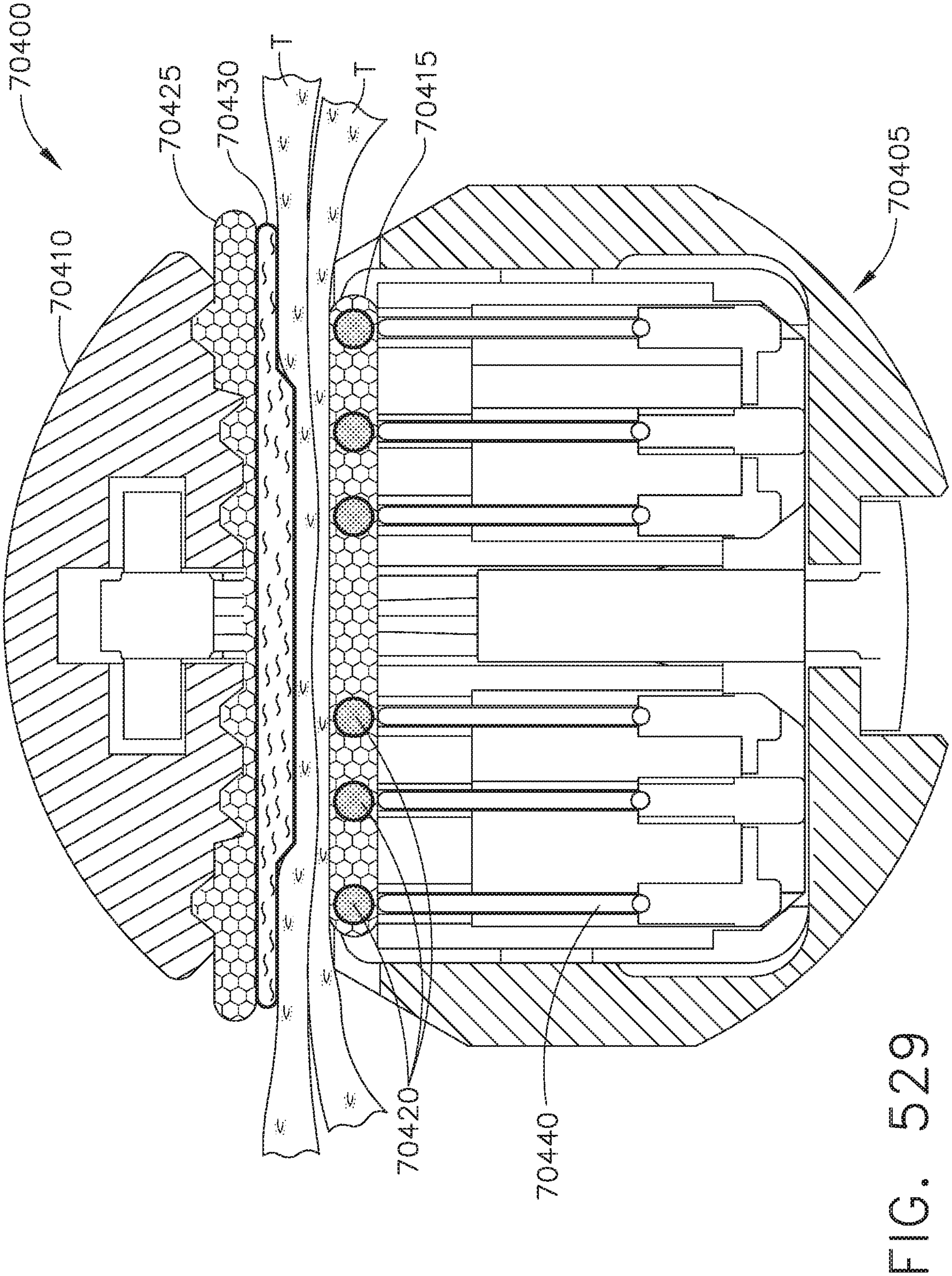
Figure 530:
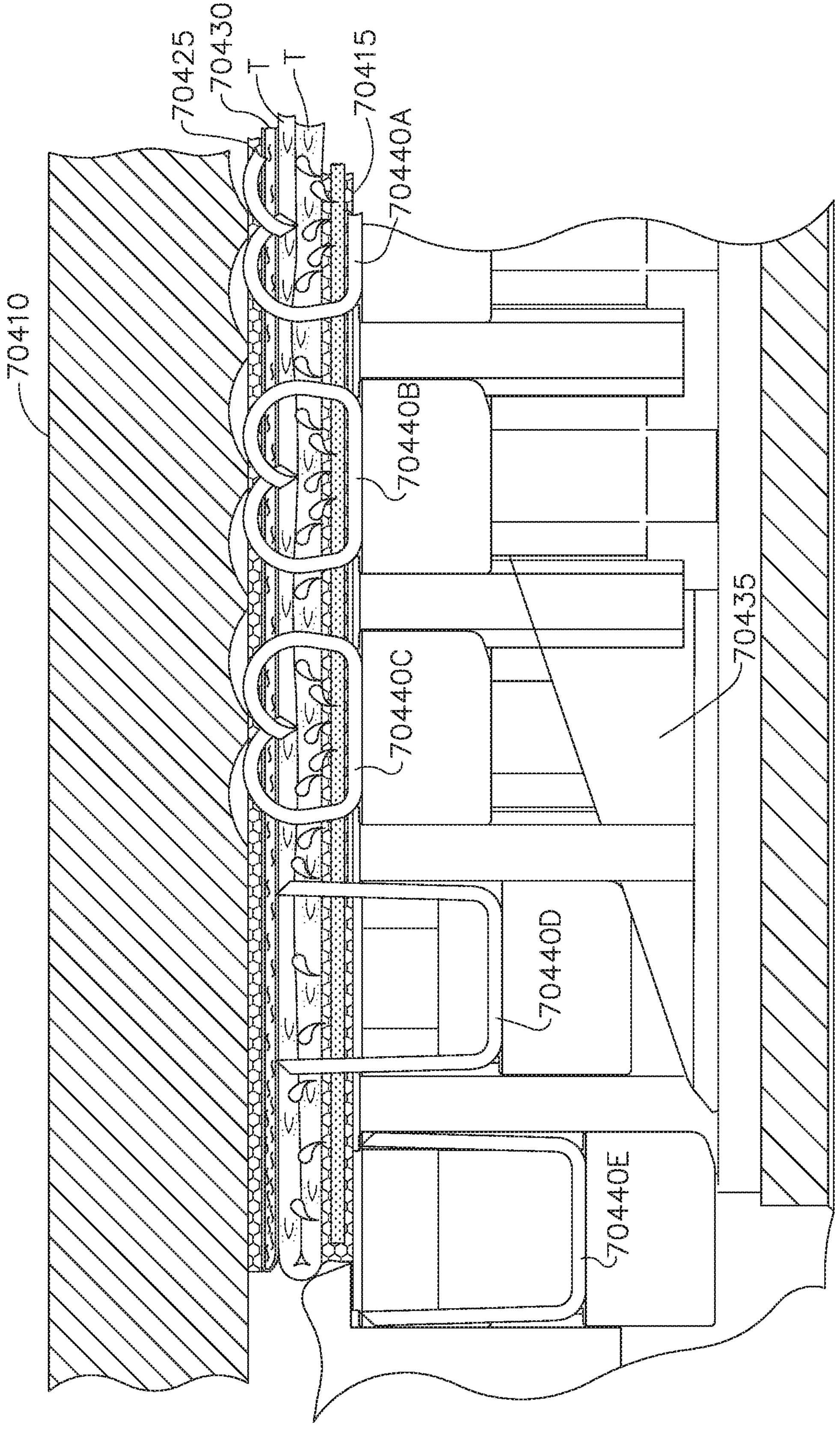
Figure 531:
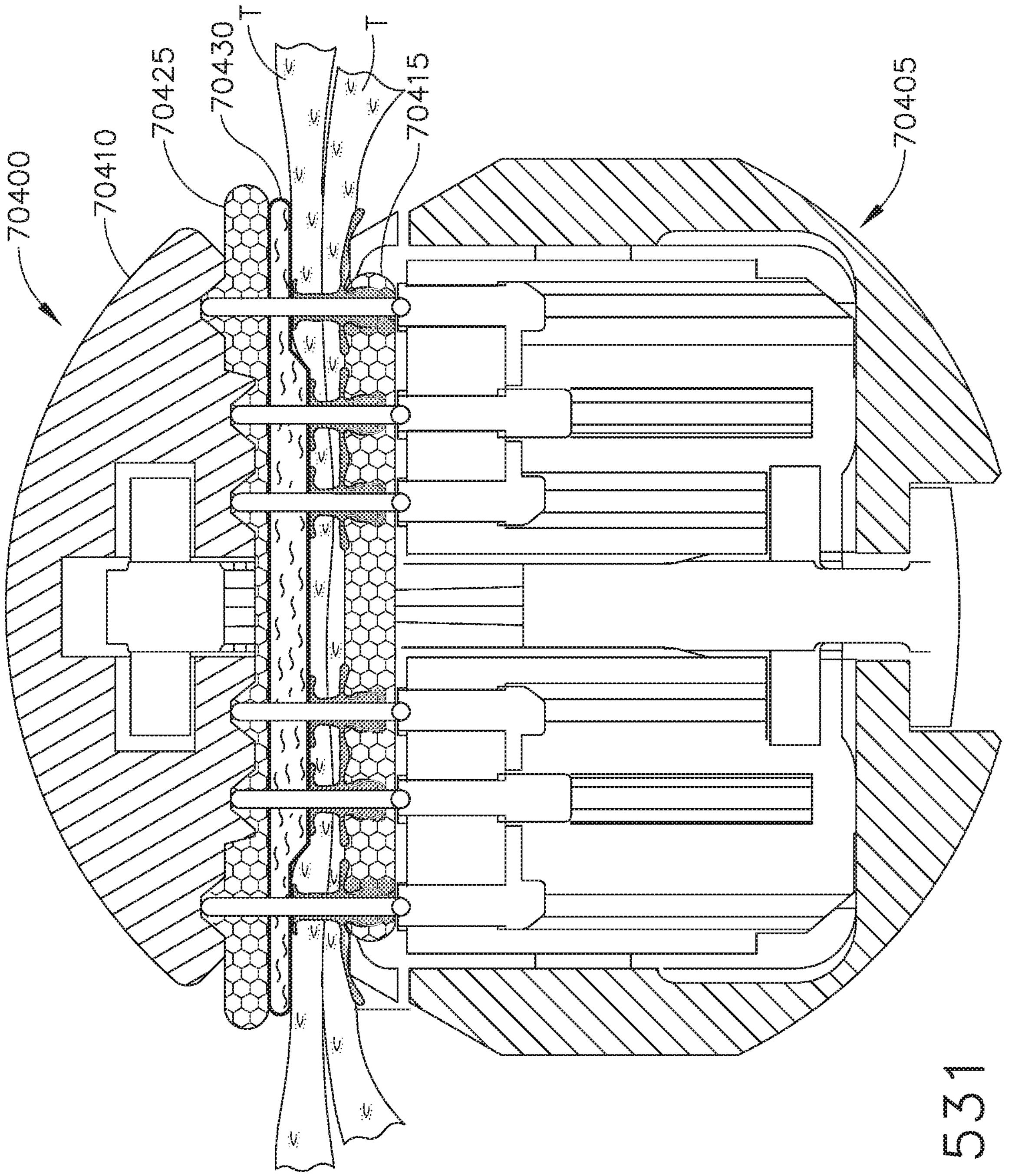
Figure 532A:
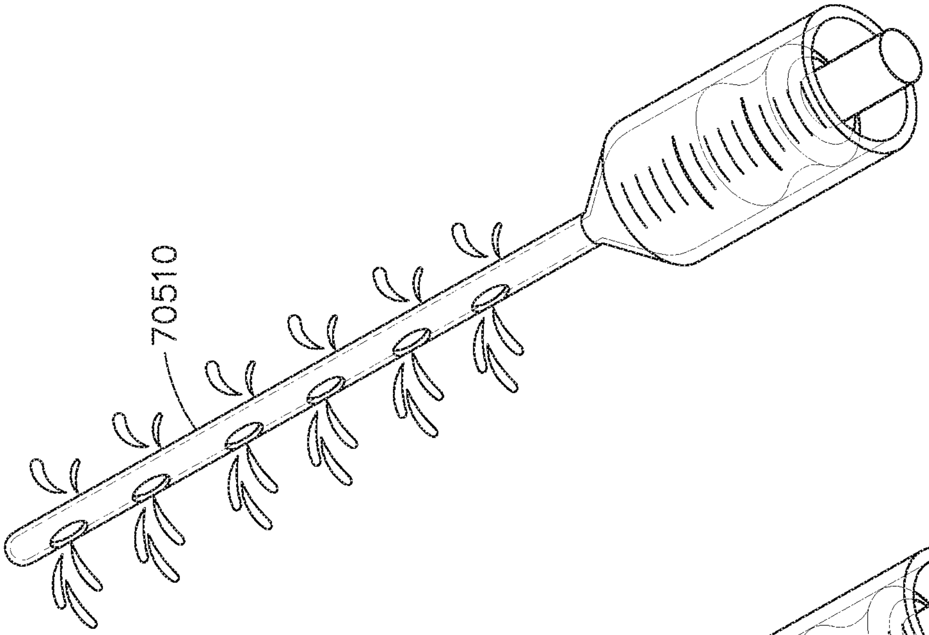
Figure 532B:
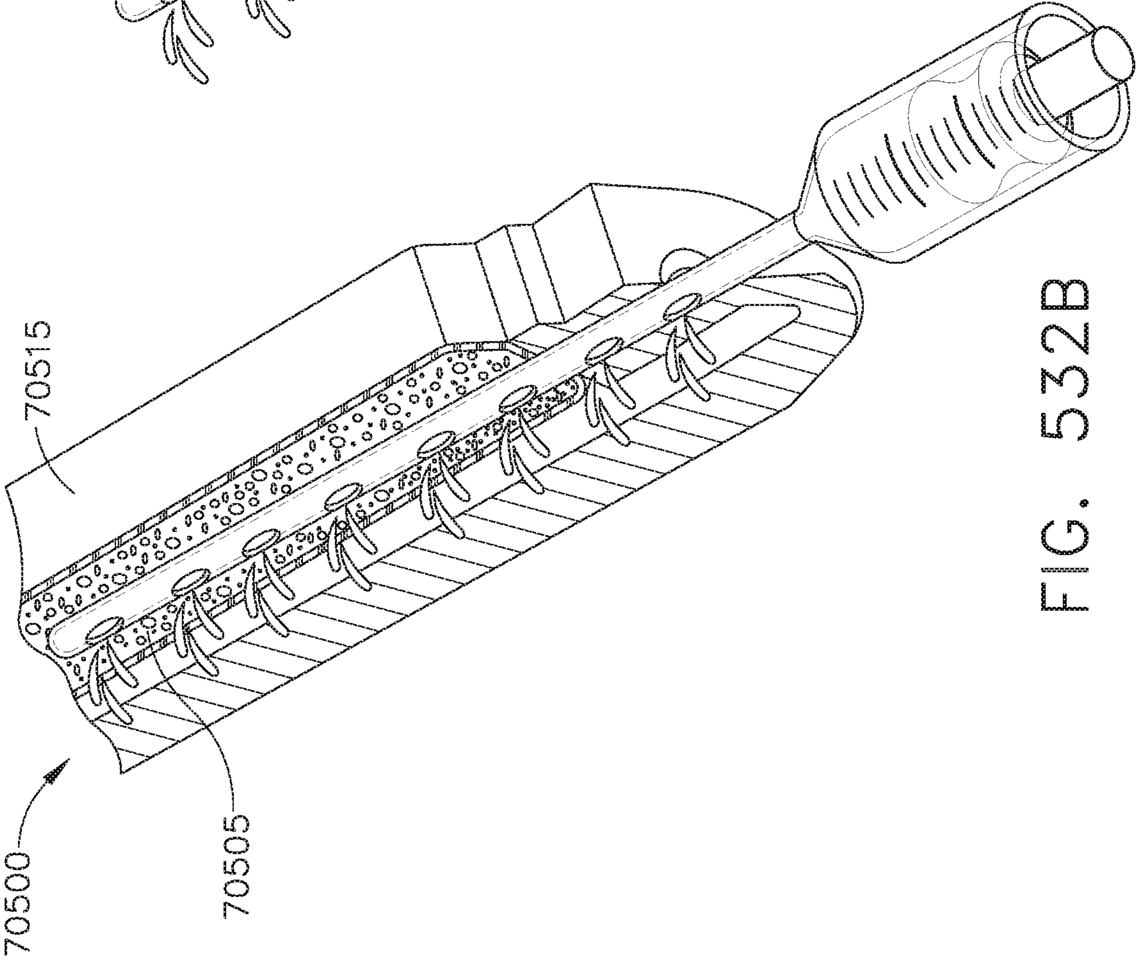
Figure 533:
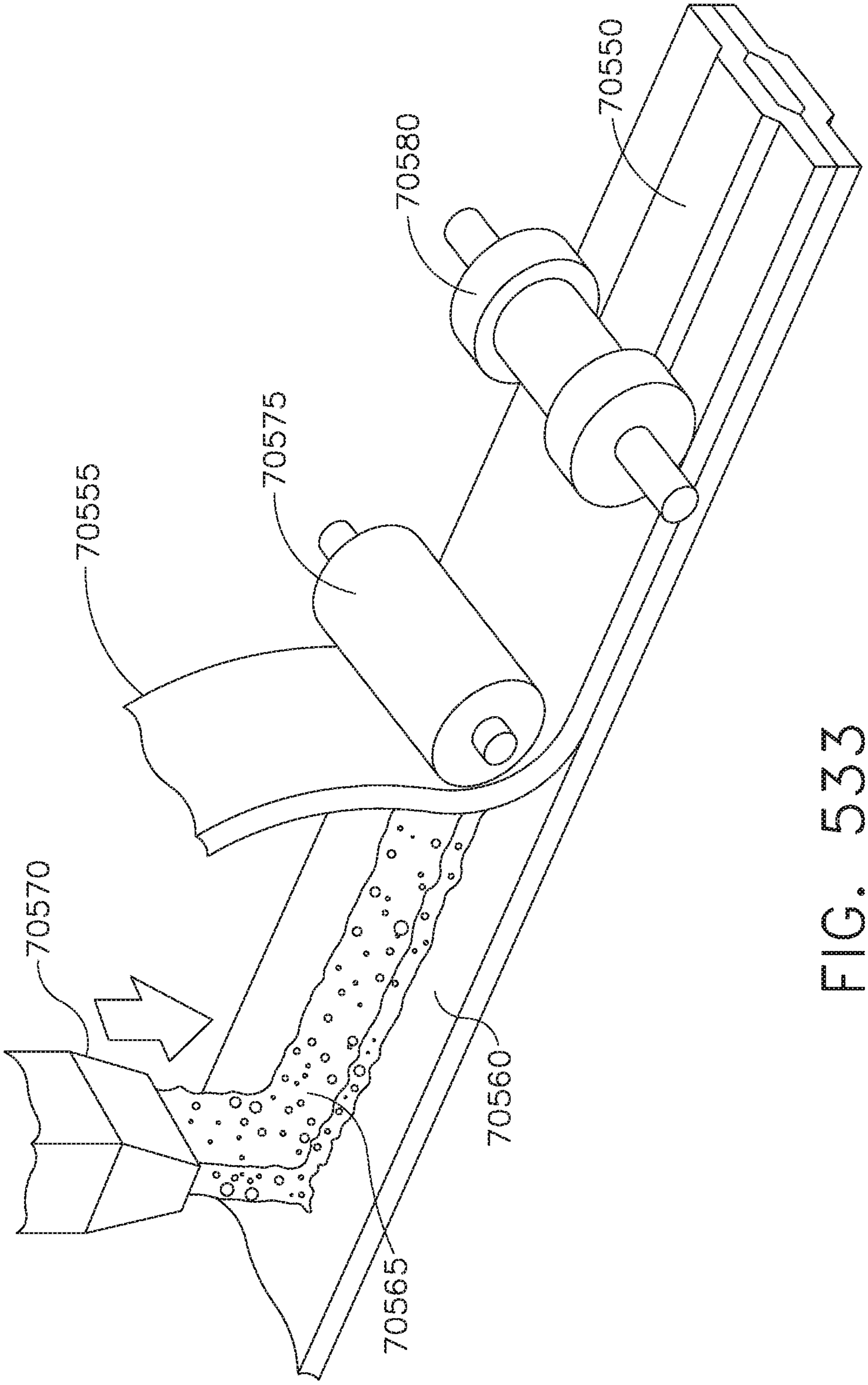
Figure 534:
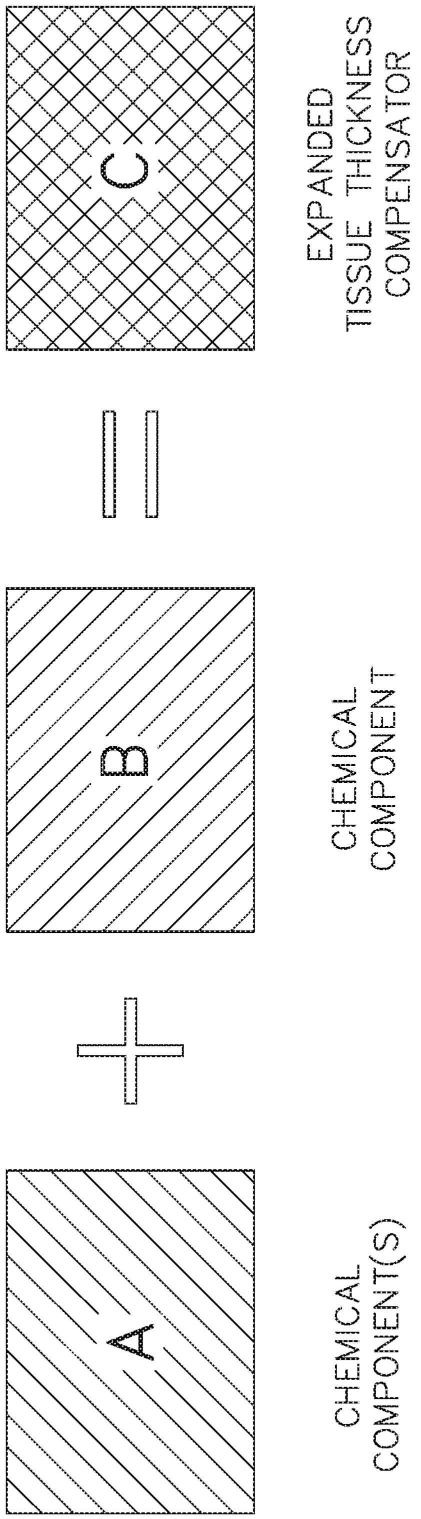
Figure 535:
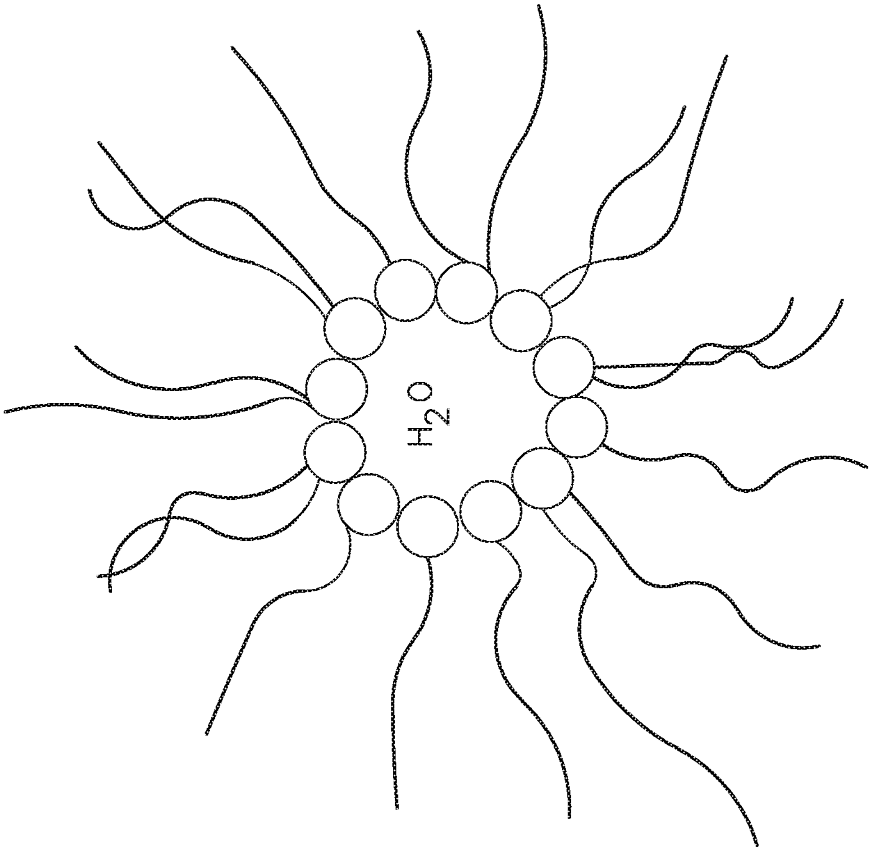

FIG. 421 is an elevational view of the deformable tube of FIG. 419;

FIG. 422 is an elevational view of multiple tubular strands for the deformable tube of FIG. 419 according to various embodiments;

FIG. 423 is an elevational view of the tubular lattice of FIG. 419 implanted against tissue;

FIG. 424 is a partial perspective view of a deformable tube according to at least one embodiment;

FIG. 425 is a partial perspective view of a deformable tube according to at least one embodiment;

FIG. 426 is a partial perspective view of a deformable tube according to at least one embodiment;

FIG. 427 is an elevational view of the deformable tube of FIG. 426;

FIG. 428 is a partial perspective view of a deformable tube according to at least one embodiment;

FIG. 429 is a partial perspective view of a deformable tube according to at least one embodiment;

FIG. 430 is a partial perspective view of a deformable tube according to at least one embodiment;

FIG. 431 is a perspective view of a tissue thickness compensator positioned in an end effector of a surgical instrument according to at least one embodiment;

FIG. 432 is an elevational view of a tubular element of the tissue thickness compensator of FIG. 431;

FIG. 433 is an elevational cross-sectional view of the tissue thickness compensator and the end effector of FIG. 431 depicting the end effector in an unclamped configuration;

FIG. 434 is an elevational cross-sectional view of the tissue thickness compensator and the end effector of FIG. 431 depicting the end effector in a clamped and fired configuration;

FIG. 435 is an elevational cross-sectional view of a tissue thickness compensator positioned in an end effector of a surgical instrument according to at least one embodiment;

FIG. 436 is an elevational cross-sectional view of the tissue thickness compensator and the end effector of FIG. 435 depicting the end effector in a clamped and fired configuration;

FIG. 437 is an elevational cross-sectional view of a tissue thickness compensator in the end effector of a surgical instrument according to at least one embodiment;

FIG. 438 is a cross-sectional elevational view of a tissue thickness compensator positioned in an end effector of a surgical instrument according to at least one embodiment;

FIG. 439 is a cross-sectional elevational view of the tissue thickness compensator and the end effector of FIG. 438 depicting the end effector in a clamped and fired configuration;

FIG. 440 is a perspective view of a tissue thickness compensator positioned in an end effector of a surgical instrument according to at least one embodiment;

FIG. 441 is an elevational cross-sectional view of a tissue thickness compensator positioned in an end effector of a surgical instrument according to at least one embodiment;

FIG. 442 is an elevational cross-sectional view of a tissue thickness compensator positioned in an end effector of a surgical instrument according to at least one embodiment;

FIG. 443 is an elevational cross-sectional view of a tissue thickness compensator positioned in an end effector of a surgical instrument according to at least one embodiment;

FIG. 444 is an elevational cross-sectional view of a tissue thickness compensator positioned in an end effector of a surgical instrument according to at least one embodiment;

FIG. 445 is a partial plan view of a tissue thickness compensator positioned in an end effector of a surgical instrument according to at least one embodiment;

FIG. 446 is a partial plan view of a tissue thickness compensator positioned in an end effector of a surgical instrument according to at least one embodiment;

FIG. 447 is a partial elevational cross-sectional view of the tissue thickness compensator and the end effector of FIG. 445 depicting the end effector in an unclamped configuration;

FIG. 448 is a partial elevational cross-sectional view of the tissue thickness compensator and the end effector of FIG. 445 depicting the end effector in a clamped configuration;

FIG. 449 is a perspective view of a tissue thickness compensator in an end effector of a surgical instrument according to at least one embodiment;

FIG. 450 is an elevational view of the tissue thickness compensator and the end effector of FIG. 449;

FIG. 451 is a perspective view of the tissue thickness compensator and the end effector of FIG. 449 depicting the anvil of the end effector moving towards a clamped configuration;

FIG. 452 is an elevational view of the tissue thickness compensator and the end effector of FIG. 449 depicting the end effector in a clamped configuration;

FIG. 453 is an elevational cross-sectional view of tubular elements of the tissue thickness compensator of FIG. 449 in an undeformed configuration;

FIG. 454 is an elevational cross-sectional view of tubular elements of the tissue thickness compensator of FIG. 449 in a deformed configuration;

FIG. 455 is a perspective view of a tissue thickness compensator in an end effector of a surgical instrument according to at least one embodiment;

FIG. 456 is an elevational cross-sectional view of the tissue thickness compensator and the end effector of FIG. 455 depicting the end effector in a clamped configuration;

FIG. 457 is an elevational cross-sectional view of the tissue thickness compensator and the end effector of FIG. 455 depicting the end effector in a fired and partially unclamped configuration;

FIG. 458 is a perspective view of a tissue thickness compensator positioned in an end effector of a surgical instrument according to at least one embodiment;

FIG. 459 is an elevational cross-sectional view of a tissue thickness compensator secured to an anvil of an end effector of a surgical instrument according to at least one embodiment;

FIG. 460 is an elevational cross-sectional view of the tissue thickness compensator and the end effector of FIG. 459 depicting the end effector in a clamped configuration;

FIG. 461 is an elevational cross-sectional view of the tissue thickness compensator and the end effector of FIG. 459 depicting the end effector in a fired and partially unclamped configuration;

FIG. 462 is a detail view of the tissue thickness compensator and the end effector of FIG. 461;

FIG. 463 is an elevational cross-sectional view of a tissue thickness compensator clamped in an end effector of a surgical instrument depicting deployment of staples by a staple-firing sled according to at least one embodiment;

FIG. 464 is an elevational cross-sectional view of the tissue thickness compensator and the end effector of FIG. 463 depicting the end effector in a clamped configuration;

FIG. 465 is an elevational cross-sectional view of the tissue thickness compensator and the end effector of FIG. 463 depicting the end effector in a fired configuration;

FIG. 466 is a perspective view of a tissue thickness compensator in an end effector of a surgical instrument according to at least one embodiment;

FIG. 467 is a perspective view of a tubular element of the tissue thickness compensator of FIG. 466;

FIG. 468 is a perspective view of the tubular element of FIG. 467 severed between a first and second end;

FIG. 469 is a perspective view of the tissue thickness compensator of FIG. 466 depicting a cutting element severing the tissue thickness compensator and staples engaging the tissue thickness compensator;

FIG. 470 is perspective view of a frame configured to make the tissue thickness compensator of FIG. 466 according to at least one embodiment;

FIG. 471 is an elevational cross-sectional view of the frame of FIG. 470 depicting the tissue thickness compensator of FIG. 466 curing in the frame;

FIG. 472 is an elevational cross-sectional view of the tissue thickness compensator removed from the frame of FIG. 471 and prepared for trimming by at least one cutting instrument;

FIG. 473 is an elevational cross-sectional view of the tissue thickness compensator of FIG. 472 after at least one cutting instrument has trimmed the tissue thickness compensator;

FIG. 474 is an elevational cross-sectional view of the tissue thickness compensator formed in the frame of FIG. 471 depicting severable tubes having various cross-sectional geometries;

FIG. 475 is a perspective view of a tissue thickness compensator in an end effector of a surgical instrument according to at least one embodiment;

FIG. 476 is a detail view of the tissue thickness compensator of FIG. 475 according to at least one embodiment;

FIG. 477 is a partial perspective view of a tissue thickness compensator according to at least one embodiment;

FIG. 478 is a partial perspective view of a tissue thickness compensator according to at least one embodiment;

FIG. 479A is an elevational cross-sectional view of the tissue thickness compensator and the end effector of FIG. 475 depicting the end effector in an unclamped configuration;

FIG. 479B is an elevational cross-sectional view of the tissue thickness compensator and the end effector of FIG. 475 depicting the end effector in a clamped configuration;

FIG. 479C is an elevational cross-sectional view of the tissue thickness compensator and the end effector of FIG. 475 depicting the end effector in a clamped and fired configuration;

FIG. 479D is an elevational cross-sectional view of the tissue thickness compensator of FIG. 475 captured in fired staples;

FIG. 479E is an elevational cross-sectional view of the tissue thickness compensator of FIG. 475 captured in fired staples depicting further expansion of the tissue thickness compensator;

FIG. 480 is a perspective cross-sectional view of a tissue thickness compensator in an end effector of a surgical instrument according to at least one embodiment;

FIG. 481 is a partial elevational view of the tissue thickness compensator of FIG. 480 captured in a fired staple;

FIG. 482 is an elevational view of a deformable tube of the tissue thickness compensator of FIG. 480;

FIG. 483 is an elevational view of a deformable tube according to at least one embodiment;

FIG. 484 is a perspective cross-sectional view of the tissue thickness compensator of FIG. 480;

FIG. 485 is a perspective cross-sectional view of a tissue thickness compensator in an end effector of a surgical instrument according to at least one embodiment;

FIG. 486 is a perspective view of a tissue thickness compensator according to at least one embodiment;

FIG. 487 is a partial elevational cross-sectional view of the tissue thickness compensator of FIG. 486 depicting a fastener engaged with tissue and with the tissue thickness compensator;

FIG. 488 is a perspective cross-sectional view of a tissue thickness compensator according to at least one embodiment;

FIG. 489 is an elevational view of a tissue thickness compensator according to at least one embodiment;

FIG. 490 is an elevational view of a tissue thickness compensator according to at least one embodiment;

FIG. 491 is an elevational view of a tissue thickness compensator positioned in a circular end effector of a surgical instrument according to at least one embodiment;

FIG. 492 is an elevational view of a tissue thickness compensator according to at least one embodiment;

FIG. 493 is an elevational view of a tissue thickness compensator according to at least one embodiment;

FIG. 494 is an elevational view of a tissue thickness compensator according to at least one embodiment;

FIG. 495 is an elevational view of a tissue thickness compensator according to at least one embodiment;

FIG. 496 is an elevational view of a tissue thickness compensator according to at least one embodiment;

FIG. 497 is a partial perspective view of a tissue thickness compensator according to at least one embodiment;

FIG. 498 is a partial perspective view of a tissue thickness compensator positioned in an end effector of a surgical instrument according to at least one embodiment;

FIG. 499 is a partial perspective view of a tissue thickness compensator with a fastener positioned in the apertures thereof according to at least one embodiment;

FIG. 500 is a partial perspective view of the tissue thickness compensator of FIG. 498 depicting the tissue thickness compensator in an undeformed configuration;

FIG. 501 is a partial perspective view of the tissue thickness compensator of FIG. 498 depicting the tissue thickness compensator in a partially deformed configuration;

FIG. 502 is a partial perspective view of the tissue thickness compensator of FIG. 498 depicting the tissue thickness compensator in a deformed configuration;

FIG. 503 is a perspective view of a tissue thickness compensator according to at least one embodiment;

FIG. 504 is a perspective view of an end effector of a stapling instrument comprising an anvil and a staple cartridge in accordance with at least one embodiment;

FIG. 505 is a cross-sectional view of the end effector of FIG. 504 illustrating staples positioned within the staple cartridge in an unfired state and a tissue thickness compensator comprising a sealed vessel in an unpunctured state, wherein the vessel is depicted with portions thereof removed for the purposes of illustration;

FIG. 506 is a cross-sectional view of the end effector of FIG. 504 illustrating the staples of FIG. 505 in an at least partially fired state and the vessel in an at least partially punctured state;

FIG. 507 is a perspective view of an end effector of a stapling instrument comprising an anvil and a staple cartridge in accordance with at least one embodiment;

FIG. 508 is a cross-sectional view of the end effector of FIG. 507 illustrating staples positioned within the staple cartridge in an unfired state and sealed vessels positioned within a tissue thickness compensator of the staple cartridge in an unpunctured state, wherein the vessels are depicted with portions thereof removed for the purposes of illustration;

FIG. 509 is a cross-sectional view of the end effector of FIG. 507 illustrating the staples of FIG. 508 in an at least partially fired state and the vessels in the staple cartridge in an at least partially punctured state;

FIG. 510 is a perspective view of an end effector of a stapling instrument comprising an anvil and a sealed vessel attached to the anvil in accordance with at least one alternative embodiment wherein the vessel is depicted with portions thereof removed for the purposes of illustration;

FIG. 511 is a cross-sectional view of the end effector of FIG. 510 illustrating staples at least partially fired from a staple cartridge and the vessels attached to the anvil in an at least partially punctured state;

FIG. 512 is a cross-sectional view of the vessel attached to the anvil of FIG. 510 illustrated in an expanded state;

FIG. 513 is a detail view of the vessel attached to the anvil of FIG. 512 illustrated in an expanded state;

FIG. 514 illustrates a vessel extending in a direction transverse to a line of staples;

FIG. 515 illustrates a plurality of vessels extending in directions which are transverse to a line of staples;

FIG. 516 is a cross-sectional view of a staple cartridge in accordance with various embodiments;

FIG. 517 is a partial cross-section view of FIG. 516 in an implanted condition;

FIG. 518A is a partial perspective view of a tissue thickness compensator prior to expansion;

FIG. 518B is a partial perspective view of a tissue thickness compensator of FIG. 518 during expansion;

FIG. 519 is a partial perspective view of a tissue thickness compensator comprising a fluid swellable composition according to various embodiments;

FIG. 520 is a cross-sectional view of tissue positioned adjacent a tissue thickness compensator according to various embodiments;

FIG. 521 is a partial cross-sectional view of FIG. 520 after the staple cartridge has been fired;

FIG. 522 is a diagram illustrating the tissue thickness compensator of FIG. 520 implanted adjacent the tissue;

FIG. 523 is a partial perspective view of a tissue thickness compensator according to various embodiments;

FIG. 524 is a perspective view of a jaw configured to receive the tissue thickness compensator of FIG. 523;

FIG. 525 is a partial cross-sectional view of a staple cartridge illustrating staples being deployed from the staple cartridge;

FIG. 526 is a perspective view of an upper tissue thickness compensator and a lower tissue thickness compensator positioned within an effector of a disposable loading unit;

FIG. 527A is a cross-sectional view of the lower tissue thickness compensator of FIG. 526 being manufactured in a mold in accordance with various embodiments;

FIG. 527B is a cross-sectional view of a trilayer tissue thickness compensator being manufactured in a mold in accordance with various embodiments;

FIG. 528 is a cross-sectional view of an anvil comprising a tissue thickness compensator comprising reinforcement material in accordance with various embodiments;

FIG. 529 is cross-sectional view of a tissue positioned intermediate the upper tissue thickness compensator and lower tissue thickness compensator in accordance with various embodiments;

FIG. 530 is a cross-sectional view of FIG. 529 illustrating staples being deployed from the staple cartridge;

FIG. 531 is a cross-sectional view of FIG. 529 after the staple cartridge has been fired;

FIG. 532A illustrates a needle configured to deliver a fluid to a tissue thickness compensator attached to a staple cartridge according to various embodiments;

FIG. 532B is a cross-sectional view of a staple cartridge comprising a tissue thickness compensator configured to receive the needle of FIG. 532A;

FIG. 533 illustrates a method of manufacturing a tissue thickness compensator according to various embodiments;

FIG. 534 is a diagram and a method of forming an expanding thickness compensator according to various embodiments;

FIG. 535 illustrates a micelle comprising a hydrogel precursor; and

Figure 536:
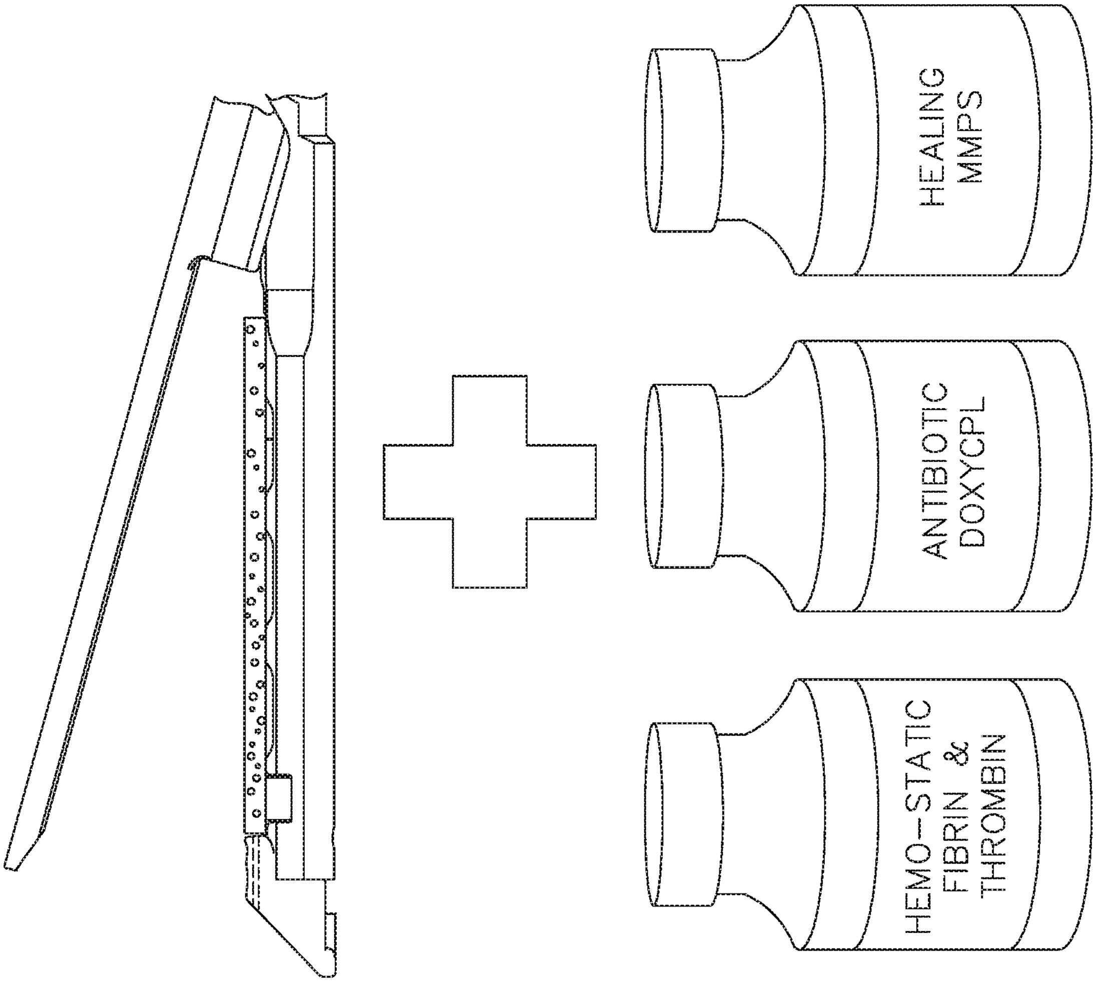

FIG. 536 is a diagram of a surgical instrument comprising a tissue thickness compensator and fluids that may be delivered to the tissue thickness compensator according to various embodiments.

Figure 537:
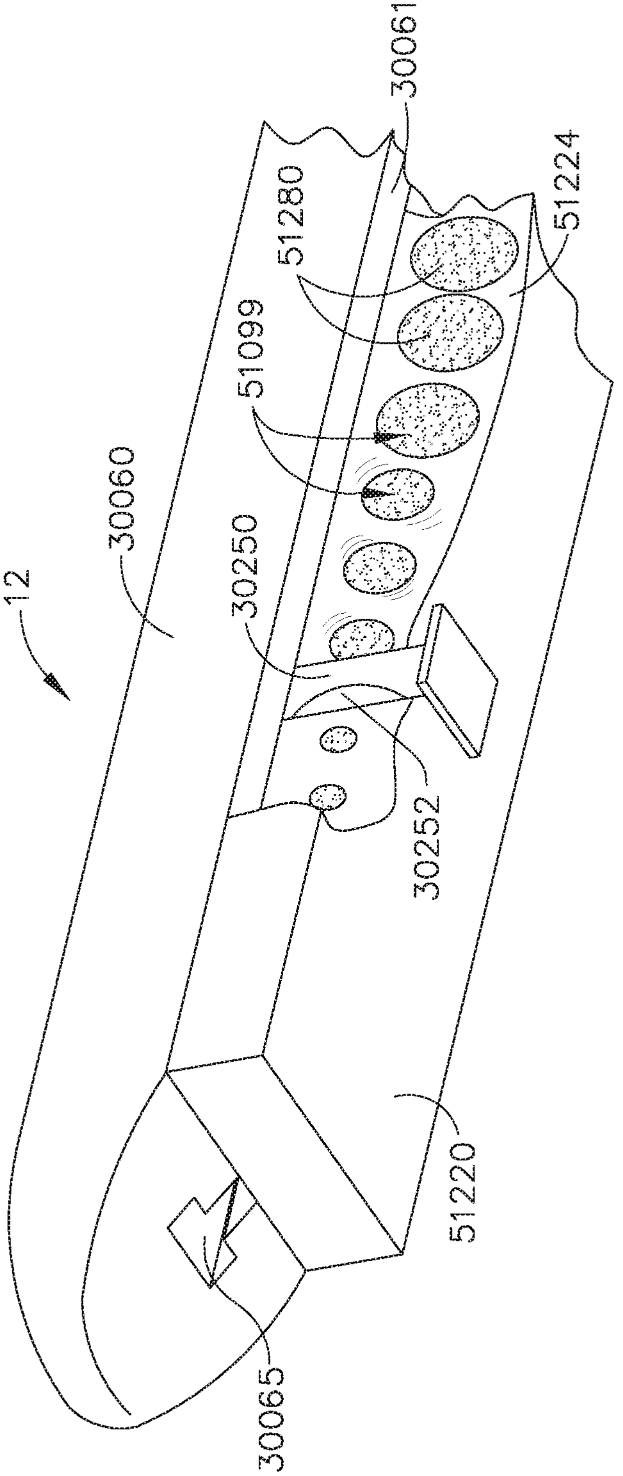

FIG. 537 is a partial perspective view of a tissue thickness compensator secured to an anvil of an end effector of a surgical instrument according to at least one embodiment.

Figure 538:
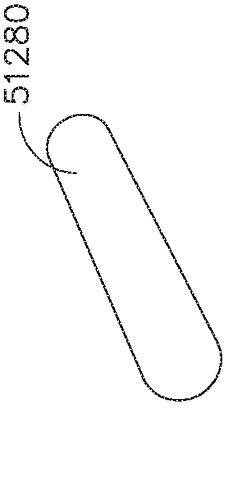

FIG. 538 is a perspective view of a tubular element of the tissue thickness compensator of FIG. 537.

Figure 539:
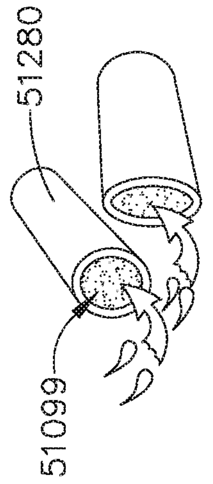

FIG. 539 is a perspective view of the tubular element of FIG. 538 depicting the tubular element severed into two halves and fluid contacting the hydrophilic substance within each half.

Figure 540:
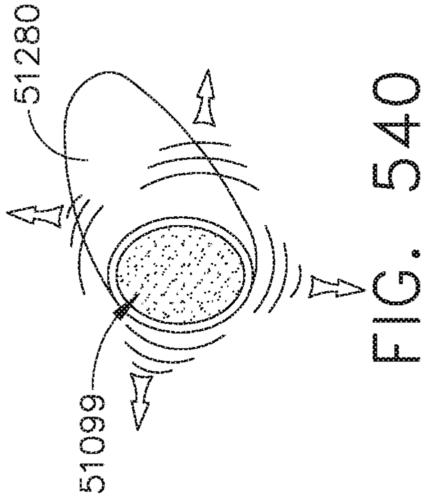

FIG. 540 is a perspective view of a half of the severed tubular element of FIG. 539 depicting expansion of the severed tubular element.

Corresponding reference characters indicate corresponding parts throughout the several views. The exemplifications set out herein illustrate certain embodiments of the invention, in one form, and such exemplifications are not to be construed as limiting the scope of the invention in any manner.

DETAILED DESCRIPTION

The Applicant of the present application also owns the U.S. Patent Applications identified below which are each herein incorporated by reference in their respective entirety:

U.S. patent application Ser. No. 12/894,311, entitled SURGICAL INSTRUMENTS WITH RECONFIGURABLE SHAFT SEGMENTS, now U.S. Pat. No. 8,763,877;

U.S. patent application Ser. No. 12/894,340, entitled SURGICAL STAPLE CARTRIDGES SUPPORTING NON-LINEARLY ARRANGED STAPLES AND SURGICAL STAPLING INSTRUMENTS WITH COMMON STAPLE-FORMING POCKETS, now U.S. Pat. No. 8,899,463;

U.S. patent application Ser. No. 12/894,327, entitled JAW CLOSURE ARRANGEMENTS FOR SURGICAL INSTRUMENTS, now U.S. Pat. No. 8,978,956;

U.S. patent application Ser. No. 12/894,351, entitled SURGICAL CUTTING AND FASTENING INSTRUMENTS WITH SEPARATE AND DISTINCT FASTENER DEPLOYMENT AND TISSUE CUTTING SYSTEMS, now U.S. Pat. No. 9,113,864;

U.S. patent application Ser. No. 12/894,338, entitled IMPLANTABLE FASTENER CARTRIDGE HAVING A NON-UNIFORM ARRANGEMENT, now U.S. Pat. No. 8,864,007;

U.S. patent application Ser. No. 12/894,369, entitled IMPLANTABLE FASTENER CARTRIDGE COMPRIS- ING A SUPPORT RETAINER, now U.S. Patent Application Publication No. 2012/0080344;

U.S. patent application Ser. No. 12/894,312, entitled IMPLANTABLE FASTENER CARTRIDGE COMPRISING MULTIPLE LAYERS, now U.S. Pat. No. 8,925,782;

U.S. patent application Ser. No. 12/894,377, entitled SELECTIVELY ORIENTABLE IMPLANTABLE FASTENER CARTRIDGE, now U.S. Pat. No. 8,393,514;

U.S. patent application Ser. No. 12/894,339, entitled SURGICAL STAPLING INSTRUMENT WITH COMPACT ARTICULATION CONTROL ARRANGEMENT, now U.S. Pat. No. 8,840,003;

U.S. patent application Ser. No. 12/894,360, entitled SURGICAL STAPLING INSTRUMENT WITH A VARIABLE STAPLE FORMING SYSTEM, now U.S. Pat. No. 9,113,862;

U.S. patent application Ser. No. 12/894,322, entitled SURGICAL STAPLING INSTRUMENT WITH INTERCHANGEABLE STAPLE CARTRIDGE ARRANGEMENTS, now U.S. Pat. No. 8,740,034;

U.S. patent application Ser. No. 12/894,350, entitled SURGICAL STAPLE CARTRIDGES WITH DETACHABLE SUPPORT STRUCTURES AND SURGICAL STAPLING INSTRUMENTS WITH SYSTEMS FOR PREVENTING ACTUATION MOTIONS WHEN A CARTRIDGE IS NOT PRESENT, now U.S. Patent Application Publication No. 2012/0080478;

U.S. patent application Ser. No. 12/894,383, entitled IMPLANTABLE FASTENER CARTRIDGE COMPRISING BIOABSORBABLE LAYERS, now U.S. Pat. No. 8,752,699;

U.S. patent application Ser. No. 12/894,389, entitled COMPRESSIBLE FASTENER CARTRIDGE, now U.S. Pat. No. 8,740,037;

U.S. patent application Ser. No. 12/894,345, entitled FASTENERS SUPPORTED BY A FASTENER CARTRIDGE SUPPORT, now U.S. Pat. No. 8,783,542;

U.S. patent application Ser. No. 12/894,306, entitled COLLAPSIBLE FASTENER CARTRIDGE, now U.S. Pat. No. 9,044,227;

U.S. patent application Ser. No. 12/894,318, entitled FASTENER SYSTEM COMPRISING A PLURALITY OF CONNECTED RETENTION MATRIX ELEMENTS, now U.S. Pat. No. 8,814,024;

U.S. patent application Ser. No. 12/894,330, entitled FASTENER SYSTEM COMPRISING A RETENTION MATRIX AND AN ALIGNMENT MATRIX, now U.S. Pat. No. 8,757,465;

U.S. patent application Ser. No. 12/894,361, entitled FASTENER SYSTEM COMPRISING A RETENTION MATRIX, now U.S. Pat. No. 8,529,600;

U.S. patent application Ser. No. 12/894,367, entitled FASTENING INSTRUMENT FOR DEPLOYING A FASTENER SYSTEM COMPRISING A RETENTION MATRIX, now U.S. Pat. No. 9,033,203;

U.S. patent application Ser. No. 12/894,388, entitled FASTENER SYSTEM COMPRISING A RETENTION MATRIX AND A COVER, now U.S. Pat. No. 8,474,677;

U.S. patent application Ser. No. 12/894,376, entitled FASTENER SYSTEM COMPRISING A PLURALITY OF FASTENER CARTRIDGES, now U.S. Pat. No. 9,044,228;

U.S. patent application Ser. No. 13/097,865, entitled SURGICAL STAPLER ANVIL COMPRISING A PLURALITY OF FORMING POCKETS, now U.S. Pat. No. 9,295,464;

U.S. patent application Ser. No. 13/097,936, entitled TISSUE THICKNESS COMPENSATOR FOR A SURGICAL STAPLER, now U.S. Pat. No. 8,657,176;

U.S. patent application Ser. No. 13/097,954, entitled STAPLE CARTRIDGE COMPRISING A VARIABLE THICKNESS COMPRESSIBLE PORTION, now U.S. Patent Application Publication No. 2012/0080340;

U.S. patent application Ser. No. 13/097,856, entitled STAPLE CARTRIDGE COMPRISING STAPLES POSITIONED WITHIN A COMPRESSIBLE PORTION THEREOF, now U.S. Patent Application Publication No. 2012/0080336;

U.S. patent application Ser. No. 13/097,928, entitled TISSUE THICKNESS COMPENSATOR COMPRISING DETACHABLE PORTIONS, now U.S. Pat. No. 8,746,535;

U.S. patent application Ser. No. 13/097,891, entitled TISSUE THICKNESS COMPENSATOR FOR A SURGICAL STAPLER COMPRISING AN ADJUSTABLE ANVIL, now U.S. Pat. No. 8,864,009;

U.S. patent application Ser. No. 13/097,948, entitled STAPLE CARTRIDGE COMPRISING AN ADJUSTABLE DISTAL PORTION, now U.S. Pat. No. 8,978,954;

U.S. patent application Ser. No. 13/097,907, entitled COMPRESSIBLE STAPLE CARTRIDGE ASSEMBLY, now U.S. Pat. No. 9,301,755;

U.S. patent application Ser. No. 13/097,861, entitled TISSUE THICKNESS COMPENSATOR COMPRISING PORTIONS HAVING DIFFERENT PROPERTIES, now U.S. Pat. No. 9,113,865;

U.S. patent application Ser. No. 13/097,869, entitled STAPLE CARTRIDGE LOADING ASSEMBLY, now U.S. Pat. No. 8,857,694;

U.S. patent application Ser. No. 13/097,917, entitled COMPRESSIBLE STAPLE CARTRIDGE COMPRISING ALIGNMENT MEMBERS, now U.S. Pat. No. 8,777,004;

U.S. patent application Ser. No. 13/097,873, entitled STAPLE CARTRIDGE COMPRISING A RELEASABLE PORTION, now U.S. Pat. No. 8,740,038;

U.S. patent application Ser. No. 13/097,938, entitled STAPLE CARTRIDGE COMPRISING COMPRESSIBLE DISTORTION RESISTANT COMPONENTS, now U.S. Pat. No. 9,016,542;

U.S. patent application Ser. No. 13/097,924, entitled STAPLE CARTRIDGE COMPRISING A TISSUE THICKNESS COMPENSATOR, now U.S. Pat. No. 9,168,038;

U.S. patent application Ser. No. 13/242,029, entitled SURGICAL STAPLER WITH FLOATING ANVIL, now U.S. Pat. No. 8,893,949;

U.S. patent application Ser. No. 13/242,066, entitled CURVED END EFFECTOR FOR A STAPLING INSTRUMENT, now U.S. Patent Application Publication No. 2012/0080498;

U.S. patent application Ser. No. 13/242,086, entitled STAPLE CARTRIDGE INCLUDING COLLAPSIBLE DECK, now U.S. Pat. No. 9,055,941;

U.S. patent application Ser. No. 13/241,912, entitled STAPLE CARTRIDGE INCLUDING COLLAPSIBLE DECK ARRANGEMENT, now U.S. Pat. No. 9,050,084;

U.S. patent application Ser. No. 13/241,922, entitled SURGICAL STAPLER WITH STATIONARY STAPLE DRIVERS, now U.S. Pat. No. 9,216,019;

U.S. patent application Ser. No. 13/241,637, entitled SURGICAL INSTRUMENT WITH TRIGGER ASSEMBLY FOR GENERATING MULTIPLE ACTUATION MOTIONS, now U.S. Pat. No. 8,789,741; and U.S. patent application Ser. No. 13/241,629, entitled SURGICAL INSTRUMENT WITH SELECTIVELY ARTICULATABLE END EFFECTOR, now U.S. Patent Application Publication No. 2012/0074200.

The Applicant of the present application also owns the U.S. Patent Applications identified below which were filed on Mar. 28, 2012 and which are each herein incorporated by reference in their respective entirety:

U.S. patent application Ser. No. 13/433,096, entitled TISSUE THICKNESS COMPENSATOR COMPRISING A PLURALITY OF CAPSULES, now U.S. Pat. No. 9,301,752;

U.S. patent application Ser. No. 13/433,103, entitled TISSUE THICKNESS COMPENSATOR COMPRISING A PLURALITY OF LAYERS, now U.S. Pat. No. 9,433,419;

U.S. patent application Ser. No. 13/433,098 entitled EXPANDABLE TISSUE THICKNESS COMPENSATOR, now U.S. Pat. No. 9,301,753;

U.S. patent application Ser. No. 13/433,102, entitled TISSUE THICKNESS COMPENSATOR COMPRISING A RESERVOIR, now U.S. Pat. No. 9,232,941;

U.S. patent application Ser. No. 13/433,114, entitled RETAINER ASSEMBLY INCLUDING A TISSUE THICKNESS COMPENSATOR, now U.S. Pat. No. 9,386,988;

U.S. patent application Ser. No. 13/433,136, entitled TISSUE THICKNESS COMPENSATOR COMPRISING AT LEAST ONE MEDICAMENT, now U.S. Patent Application Publication No. 2012/0241492;

U.S. patent application Ser. No. 13/433,141, entitled TISSUE THICKNESS COMPENSATOR COMPRISING CONTROLLED RELEASE AND EXPANSION, now U.S. Patent Application Publication No. 2012/0241493;

U.S. patent application Ser. No. 13/433,144, entitled TISSUE THICKNESS COMPENSATOR COMPRISING FIBERS TO PRODUCE A RESILIENT LOAD, now U.S. Pat. No. 9,277,919;

U.S. patent application Ser. No. 13/433,148, entitled TISSUE THICKNESS COMPENSATOR COMPRISING STRUCTURE TO PRODUCE A RESILIENT LOAD, now U.S. Pat. No. 9,220,500;

U.S. patent application Ser. No. 13/433,155, entitled TISSUE THICKNESS COMPENSATOR COMPRISING RESILIENT MEMBERS, now U.S. Pat. No. 9,480,476;

U.S. patent application Ser. No. 13/433,163, entitled METHODS FOR FORMING TISSUE THICKNESS COMPENSATOR ARRANGEMENTS FOR SURGICAL STAPLERS, now U.S. Patent Application Publication No. 2012/0248169;

U.S. patent application Ser. No. 13/433,167, entitled TISSUE THICKNESS COMPENSATORS, now U.S. Pat. No. 9,220,501;

U.S. patent application Ser. No. 13/433,175, entitled LAYERED TISSUE THICKNESS COMPENSATOR, now U.S. Pat. No. 9,332,974;

U.S. patent application Ser. No. 13/433,179, entitled TISSUE THICKNESS COMPENSATORS FOR CIRCULAR SURGICAL STAPLERS, now U.S. Pat. No. 9,364,233;

U.S. patent application Ser. No. 13/433,118, entitled TISSUE THICKNESS COMPENSATOR COMPRISED OF A PLURALITY OF MATERIALS, now U.S. Pat. No. 9,414,838;

U.S. patent application Ser. No. 13/433,135, entitled MOVABLE MEMBER FOR USE WITH A TISSUE THICKNESS COMPENSATOR, now U.S. Pat. No. 9,517,063;

U.S. patent application Ser. No. 13/433,129, entitled TISSUE THICKNESS COMPENSATOR COMPRISING A PLURALITY OF MEDICAMENTS, now U.S. Pat. No. 9,211,120;

U.S. patent application Ser. No. 13/433,140, entitled TISSUE THICKNESS COMPENSATOR AND METHOD FOR MAKING THE SAME, now U.S. Pat. No. 9,241,714;

U.S. patent application Ser. No. 13/433,147, entitled TISSUE THICKNESS COMPENSATOR COMPRISING CHANNELS, now U.S. Pat. No. 9,351,730;

U.S. patent application Ser. No. 13/433,126, entitled TISSUE THICKNESS COMPENSATOR COMPRISING TISSUE INGROWTH FEATURES, now U.S. Pat. No. 9,320,523; and U.S. patent application Ser. No. 13/433,132, entitled DEVICES AND METHODS FOR ATTACHING TISSUE THICKNESS COMPENSATING MATERIALS TO SURGICAL STAPLING INSTRUMENTS, now U.S. Patent Application Publication No. 2013/0256373.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment", or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the person of ordinary skill in the art will readily appreciate that the various methods and devices disclosed herein can be used in numerous surgical procedures and applications including, for example, in connection with open surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongated shaft of a surgical instrument can be advanced.

Figure 1:
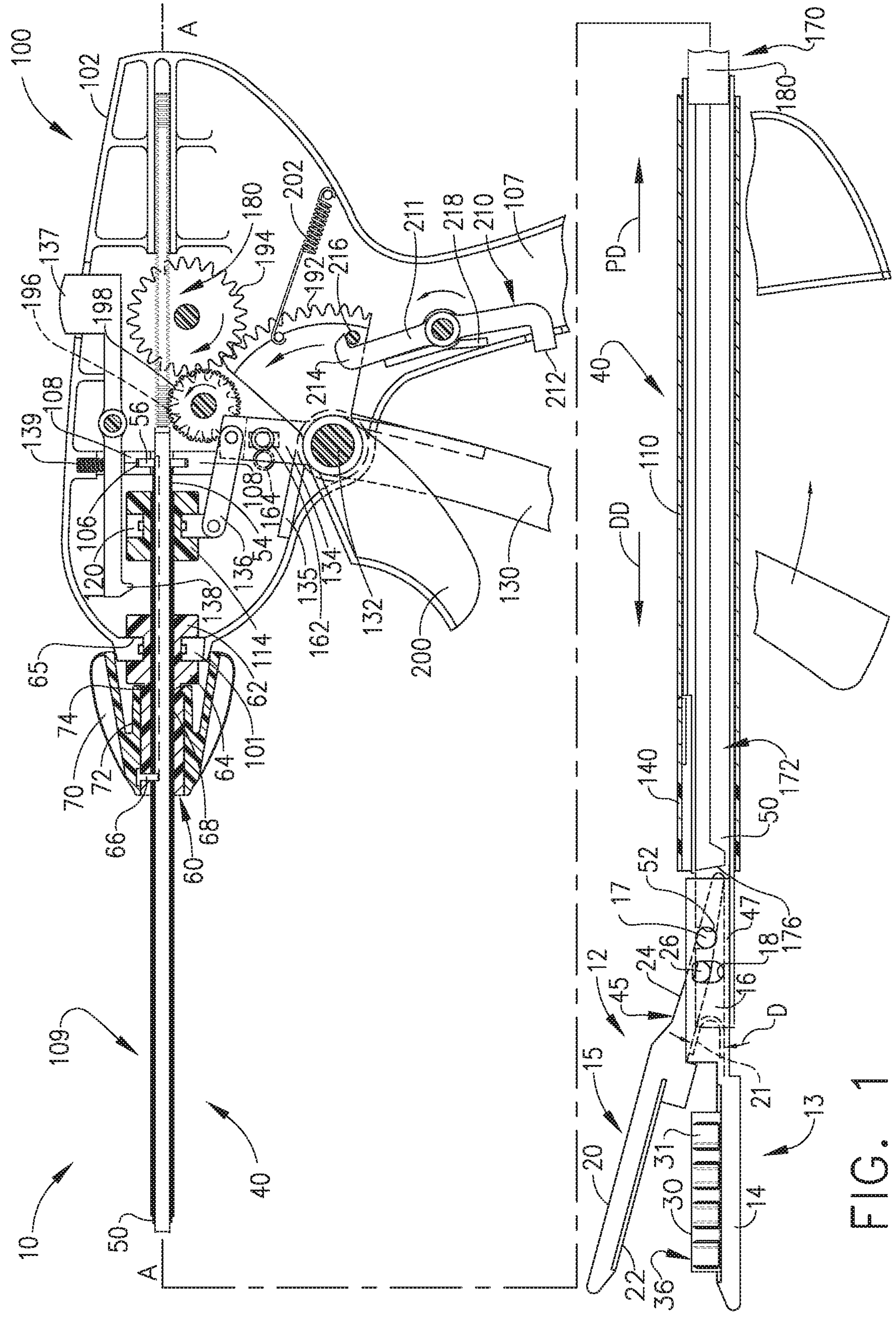
FIG. 1 is a cross-sectional view of a surgical instrument embodiment.

Turning to the Drawings wherein like numerals denote like components throughout the several views, FIG. 1 depicts a surgical instrument 10 that is capable of practicing several unique benefits. The surgical stapling instrument 10 is designed to manipulate and/or actuate various forms and sizes of end effectors 12 that are operably attached thereto. In the embodiment depicted in FIGS. 1-1E, for example, the end effector 12 includes an elongated channel 14 that forms a lower jaw 13 of the end effector 12. The elongated channel 14 is configured to support an "implantable" staple cartridge 30 and also movably support an anvil 20 that functions as an upper jaw 15 of the end effector 12.

In various embodiments, the elongated channel 14 may be fabricated from, for example, 300 & 400 Series, 17-4 & 17-7 stainless steel, titanium, etc. and be formed with spaced side walls 16. The anvil 20 may be fabricated from, for example, 300 & 400 Series, 17-4 & 17-7 stainless steel, titanium, etc. and have a staple forming undersurface, generally labeled as 22 that has a plurality of staple forming pockets 23 formed therein. See FIGS. 1B-1E. In addition, the anvil 20 has a bifurcated ramp assembly 24 that protrudes proximally therefrom. An anvil pin 26 protrudes from each lateral side of the ramp assembly 24 to be received within a corresponding slot or opening 18 in the side walls 16 of the elongated channel 14 to facilitate its movable or pivotable attachment thereto.

Figure 1A:
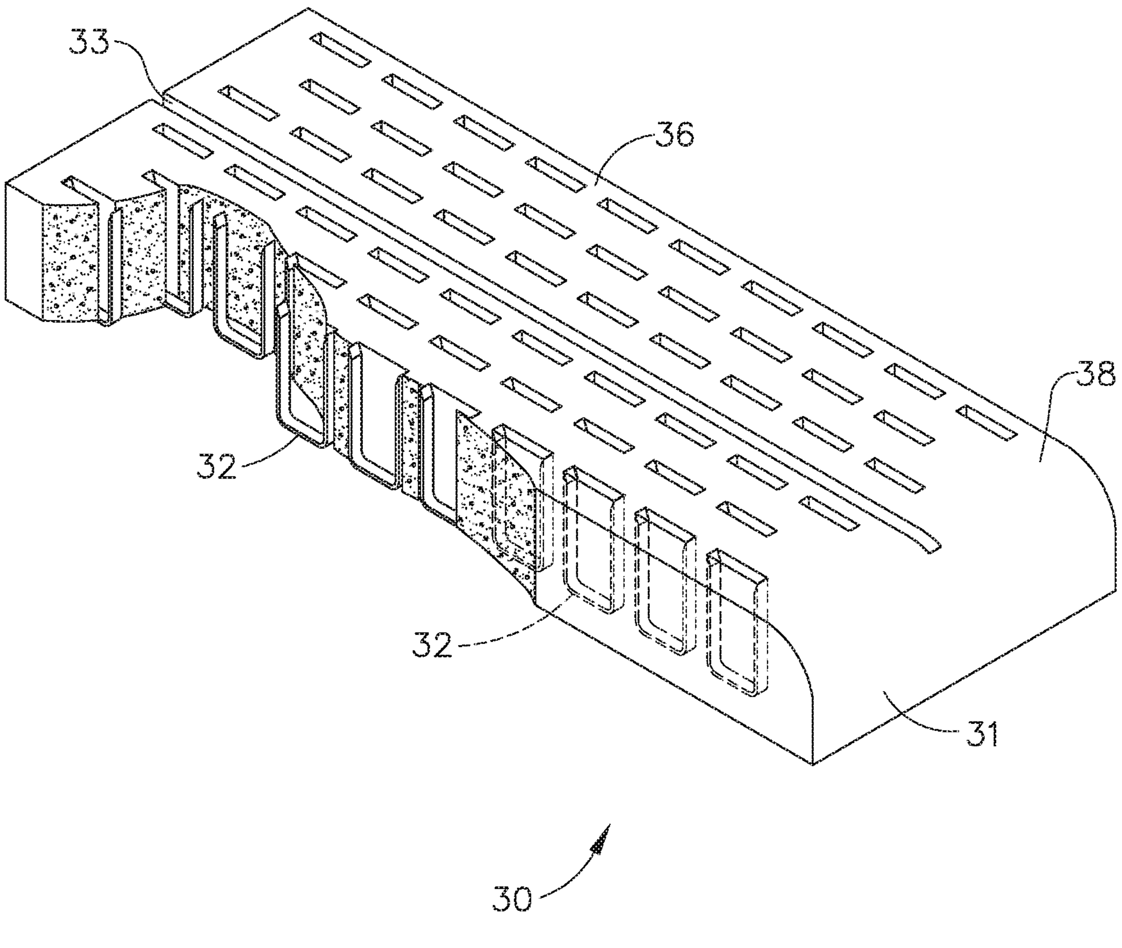
FIG. 1A is a perspective view of one embodiment of an implantable staple cartridge.

Various forms of implantable staple cartridges may be employed with the various embodiments of the surgical instruments disclosed herein. Specific staple cartridge configurations and constructions will be discussed in further detail below. However, in the embodiment depicted in FIG. 1A, an implantable staple cartridge 30 is shown. In at least one embodiment, the staple cartridge 30 has a body portion 31 that consists of a compressible hemostat material such as, for example, oxidized regenerated cellulose ("ORC") or a bio-absorbable foam in which lines of unformed metal staples 32 are supported. In at least some embodiments, in order to prevent the staple from being affected and the hemostat material from being activated during the introduction and positioning process, the entire cartridge may be coated or wrapped in a biodegradable film 38 such as a polydioxanon film sold under the trademark PDS® or with a Polyglycerol sebacate (PGS) film or other biodegradable films formed from PGA (Polyglycolic acid, marketed under the trade mark Vicryl), PCL (Polycaprolactone), PLA or PLLA (Polylactic acid), PHA (polyhydroxyalkanoate), PGCL (poliglecaprone 25, sold under the trademark Monocryl) or a composite of PGA, PCL, PLA, PDS that would be impermeable until ruptured. The body 31 of staple cartridge 30 is sized to be removably supported within the elongated channel 14 as shown such that each staple 32 therein is aligned with corresponding staple forming pockets 23 in the anvil when the anvil 20 is driven into forming contact with the staple cartridge 30.

In use, once the end effector 12 has been positioned adjacent the target tissue, the end effector 12 is manipulated to capture or clamp the target tissue between an upper face 36 of the staple cartridge 30 and the staple forming surface 22 of the anvil 20. The staples 32 are formed by moving the anvil 20 in a path that is substantially parallel to the elongated channel 14 to bring the staple forming surface 22 and, more particularly, the staple forming pockets 23 therein into substantially simultaneous contact with the upper face 36 of the staple cartridge 30. As the anvil 20 continues to move into the staple cartridge 30, the legs 34 of the staples 32 contact a corresponding staple forming pocket 23 in anvil 20 which serves to bend the staple legs 34 over to form the staples 32 into a "B shape". Further movement of the anvil 20 toward the elongated channel 14 will further compress and form the staples 32 to a desired final formed height "FF".

Figures 1B, 1C, 1D, 1E:
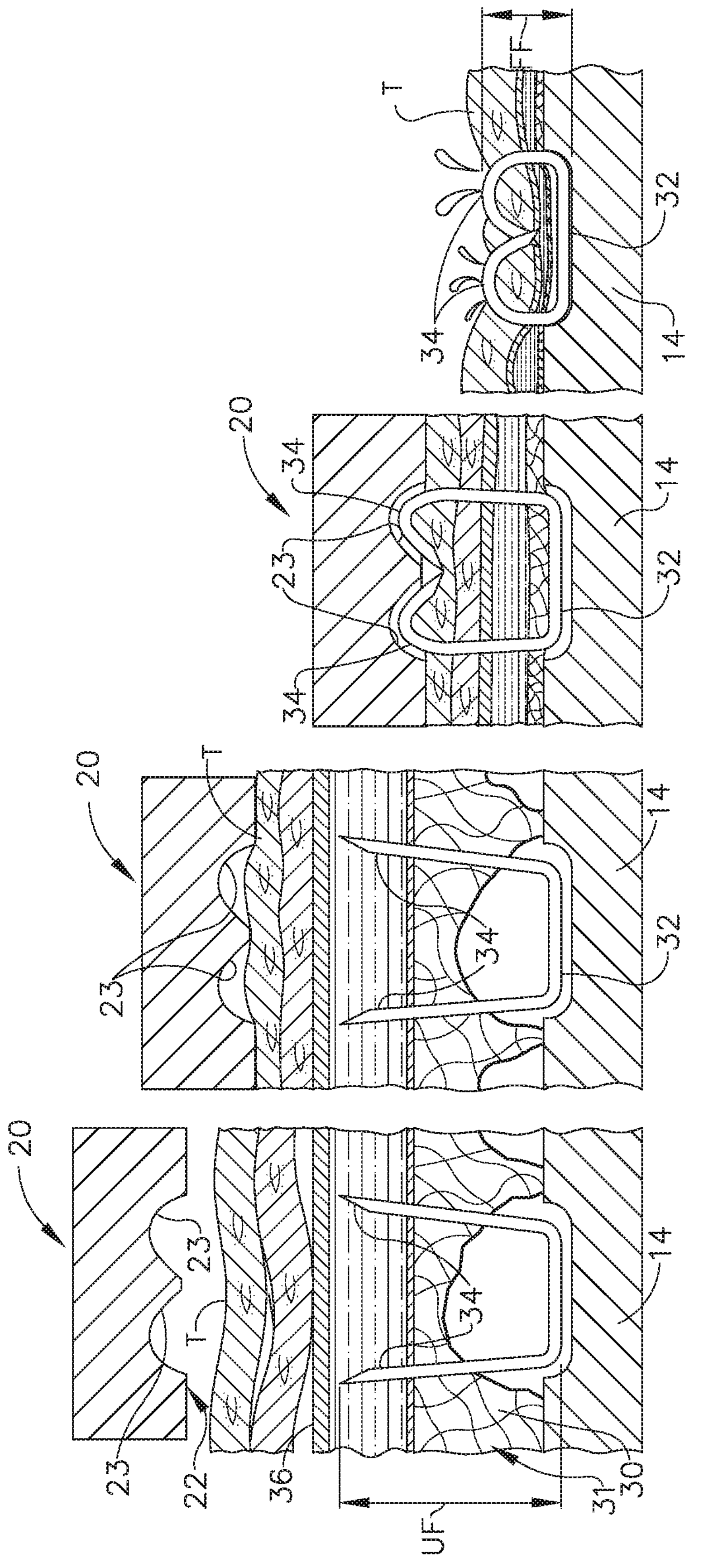
FIGS. 1B-1E illustrate portions of an end effector clamping and stapling tissue with an implantable staple cartridge.

The above-described staple forming process is generally depicted in FIGS. 1B-1E. For example, FIG. 1B illustrates the end effector 12 with target tissue "T" between the anvil 20 and the upper face 36 of the implantable staple cartridge 30. FIG. 1C illustrates the initial clamping position of the anvil 20 wherein the anvil has 20 been closed onto the target tissue "T" to clamp the target tissue "T" between the anvil 20 and the upper face 36 of the staple cartridge 30. FIG. 1D illustrates the initial staple formation wherein the anvil 20 has started to compress the staple cartridge 30 such that the legs 34 of the staples 32 are starting to be formed by the staple forming pockets 23 in the anvil 20. FIG. 1E illustrates the staple 32 in its final formed condition through the target tissue "T" with the anvil 20 removed for clarity purposes. Once the staples 32 have been formed and fastened to the target tissue "T", the surgeon will move the anvil 20 to the open position to enable the cartridge body 31 and the staples 32 to remain affixed to the target tissue while the end effector 12 is being withdrawn from the patient. The end effector 12 forms all of the staples simultaneously as the two jaws 13, 15 are clamped together. The remaining "crushed" body materials 31 act as both a hemostat (the ORC) and a staple line reinforcement (PGA, PDS or any of the other film compositions mentioned above 38). Also, since the staples 32 never have to leave the cartridge body 31 during forming, the likelihood of the staples 32 being malformed during forming is minimized. As used herein the term "implantable" means that, in addition to the staples, the cartridge body materials that support the staples will also remain in the patient and may eventually be absorbed by the patient's body. Such implantable staple cartridges are distinguishable from prior cartridge arrangements that remain positioned within the end effector in their entirety after they have been fired.

In various implementations, the end effector 12 is configured to be coupled to an elongated shaft assembly 40 that protrudes from a handle assembly 100. The end effector 12 (when closed) and the elongated shaft assembly 40 may have similar cross-sectional shapes and be sized to operably pass through a trocar tube or working channel in another form of access instrument. As used herein, the term "operably pass" means that the end effector and at least a portion of the elongated shaft assembly may be inserted through or passed through the channel or tube opening and can be manipulated therein as needed to complete the surgical stapling procedure. In some embodiments, when in a closed position, the jaws 13 and 15 of the end effector 12 may provide the end effector with a roughly circular cross-sectional shape that facilitates its passage through a circular passage/opening. However, the end effectors of various embodiments of the present invention, as well as the elongated shaft assembly embodiments, could conceivably be provided with other cross-sectional shapes that could otherwise pass through access passages and openings that have non-circular cross-sectional shapes. Thus, an overall size of a cross-section of a closed end effector will be related to the size of the passage or opening through which it is intended to pass. Thus, one end effector for example, may be referred to as a "5 mm" end effector which means it can operably pass through an opening that is at least approximately 5 mm in diameter.

In various embodiments, the elongated shaft assembly 40 may have an outer diameter that is substantially the same as the outer diameter of the end effector 12 when in a closed position. For example, a 5 mm end effector may be coupled to an elongated shaft assembly 40 that has 5 mm cross-sectional diameter. However, as the present Detailed Description proceeds, it will become apparent that various embodiments of the present may be effectively used in connection with different sizes of end effectors. For example, a 10 mm end effector may be attached to an elongated shaft that has a 5 mm cross-sectional diameter. Conversely, for those applications wherein a 10 mm or larger access opening or passage is provided, the elongated shaft assembly 40 may have a 10 mm (or larger) cross-sectional diameter, but may also be able to actuate a 5 mm or 10 mm end effector. Accordingly, the outer shaft 40 may have an outer diameter that is the same as or is different from the outer diameter of a closed end effector 12 attached thereto.

As depicted, the elongated shaft assembly 40 extends distally from the handle assembly 100 in a generally straight line to define a longitudinal axis A-A. In various embodiments, for example, the elongated shaft assembly 40 may be approximately 9-16 inches (229-406 mm) long. However, the elongated shaft assembly 40 may be provided in other lengths and, in other embodiments, may have joints therein or be otherwise configured to facilitate articulation of the end effector 12 relative to other portions of the shaft or handle assembly as will be discussed in further detail below. In various embodiments, the elongated shaft assembly 40 includes a spine member 50 that extends from the handle assembly 100 to the end effector 12. The proximal end of the elongated channel 14 of the end effector 12 has a pair of retention trunnions 17 protruding therefrom that are sized to be received within corresponding trunnion openings or cradles 52 that are provided in a distal end of the spine member 50 to enable the end effector 12 to be removably coupled the elongated shaft assembly 40. The spine member 50 may be fabricated from, for example, 6061 or 7075 aluminum, stainless steel, titanium, etc.

In various embodiments, the handle assembly 100 comprises a pistol grip-type housing that may be fabricated in two or more pieces for assembly purposes. For example, the handle assembly 100 as shown comprises a right hand case member 102 and a left hand case member (not illustrated) that are molded or otherwise fabricated from a polymer or plastic material and are designed to mate together. Such case members may be attached together by snap features, pegs and sockets molded or otherwise formed therein and/or by adhesive, screws, etc. The spine member 50 has a proximal end 54 that has a flange 56 formed thereon. The flange 56 is configured to be rotatably supported within a groove 106 formed by mating ribs 108 that protrude inwardly from each of the case members 102, 104. Such arrangement facilitates the attachment of the spine member 50 to the handle assembly 100 while enabling the spine member 50 to be rotated relative to the handle assembly 100 about the longitudinal axis A-A in a 360° path.

As can be further seen in FIG. 1, the spine member 50 passes through and is supported by a mounting bushing 60 that is rotatably affixed to the handle assembly 100. The mounting bushing 60 has a proximal flange 62 and a distal flange 64 that define a rotational groove 65 that is configured to rotatably receive a nose portion 101 of the handle assembly 100 therebetween. Such arrangement enables the mounting bushing 60 to rotate about longitudinal axis A-A relative to the handle assembly 100. The spine member 50 is non-rotatably pinned to the mounting bushing 60 by a spine pin 66. In addition, a rotation knob 70 is attached to the mounting bushing 60. In one embodiment, for example, the rotation knob 70 has a hollow mounting flange portion 72 that is sized to receive a portion of the mounting bushing 60 therein. In various embodiments, the rotation knob 70 may be fabricated from, for example, glass or carbon filled Nylon, polycarbonate, Ultem®, etc. and is affixed to the mounting bushing 60 by the spine pin 66 as well. In addition, an inwardly protruding retention flange 74 is formed on the mounting flange portion 72 and is configured to extend into a radial groove 68 formed in the mounting bushing 60. Thus, the surgeon may rotate the spine member 50 (and the end effector 12 attached thereto) about longitudinal axis A-A in a 360° path by grasping the rotation knob 70 and rotating it relative to the handle assembly 100.

In various embodiments, the anvil 20 is retained in an open position by an anvil spring 21 and/or another biasing arrangement. The anvil 20 is selectively movable from the open position to various closed or clamping and firing positions by a firing system, generally designated as 109. The firing system 109 includes a "firing member" 110 which, in various embodiments, comprises a hollow firing tube 110. The hollow firing tube 110 is axially movable on the spine member 50 and thus forms the outer portion of the elongated shaft assembly 40. The firing tube 110 may be fabricated from a polymer or other suitable material and have a proximal end that is attached to a firing yoke 114 of the firing system 109. In various embodiments for example, the firing yoke 114 may be over-molded to the proximal end of the firing tube 110. However, other fastener arrangements may be employed.

As can be seen in FIG. 1, the firing yoke 114 may be rotatably supported within a support collar 120 that is configured to move axially within the handle assembly 100. In various embodiments, the support collar 120 has a pair of laterally extending fins that are sized to be slidably received within fin slots formed in the right and left hand case members. Thus, the support collar 120 may slide axially within the handle housing 100 while enabling the firing yoke 114 and firing tube 110 to rotate relative thereto about the longitudinal axis A-A. In various embodiments, a longitudinal slot is provided through the firing tube 110 to enable the spine pin 66 to extend therethrough into the spine member 50 while facilitating the axial travel of the firing tube 110 on the spine member 50.

The firing system 109 further comprises a firing trigger 130 which serves to control the axial travel of the firing tube 110 on the spine member 50. See FIG. 1. Such axial movement in the distal direction of the firing tube 110 into firing interaction with the anvil 20 is referred to herein as "firing motion". As can be seen in FIG. 1, the firing trigger 130 is movably or pivotally coupled to the handle assembly 100 by a pivot pin 132. A torsion spring 135 is employed to bias the firing trigger 130 away from the pistol grip portion 107 of the handle assembly 100 to an un-actuated "open" or starting position. As can be seen in FIG. 1, the firing trigger 130 has an upper portion 134 that is movably attached to (pinned) firing links 136 that are movably attached to (pinned) the support collar 120. Thus, movement of the firing trigger 130 from the starting position (FIG. 1) toward an ending position adjacent the pistol grip portion 107 of the handle assembly 100 will cause the firing yoke 114 and the firing tube 110 to move in the distal direction "DD". Movement of the firing trigger 130 away from the pistol grip portion 107 of the handle assembly 100 (under the bias of the torsion spring 135) will cause the firing yoke 114 and firing tube 110 to move in the proximal direction "PD" on the spine member 50.

Various embodiments of the present invention may be employed with different sizes and configurations of implantable staple cartridges. For example, the surgical instrument 10, when used in connection with a first firing adapter 140, may be used with a 5 mm end effector 12 that is approximately 20 mm long (or in other lengths) which supports an implantable staple cartridge 30. Such end effector size may be particularly well-suited, for example, to complete relatively fine dissection and vascular transactions. However, as will be discussed in further detail below, the surgical instrument 10 may also be employed, for example, in connection with other sizes of end effectors and staple cartridges by replacing the first firing adapter 140 with a second firing adapter. In still other embodiments, the elongated shaft assembly 40 may configured to be attached to only one form or size of end effector.

One method of removably coupling the end effector 12 to the spine member 50 will now be explained. The coupling process is commenced by inserting the retention trunnions 17 on the elongated channel 14 into the trunnion cradles 52 in the spine member 50. Thereafter, the surgeon advances the firing trigger 130 toward the pistol grip 107 of the housing assembly 100 to distally advance the firing tube 110 and the first firing adapter 140 over a proximal end portion 47 of the elongated channel 14 to thereby retain the trunnions 17 in their respective cradles 52. Such position of the first firing adapter 140 over the trunnions 17 is referred to herein as the "coupled position". Various embodiments of the present invention may also have an end effector locking assembly for locking the firing trigger 130 in position after an end effector 12 has been attached to the spine member 50.

More specifically, one embodiment of the end effector locking assembly 160 includes a retention pin 162 that is movably supported in the upper portion 134 of the firing trigger 130. As discussed above, the firing tube 110 must initially be advanced distally to the coupled position wherein the first firing adapter 140 retains the retention trunnions 17 of the end effector 12 in the trunnion cradles 52 in the spine member 50. The surgeon advances the firing adapter 140 distally to the coupled position by pulling the firing trigger 130 from the starting position toward the pistol grip 107. As the firing trigger 130 is initially actuated, the retention pin 162 is moved distally until the firing tube 110 has advanced the first firing adapter 140 to the coupled position at which point the retention pin 162 is biased into a locking cavity 164 formed in the case member. In various embodiments, when the retention pin 162 enters into the locking cavity 164, the pin 162 may make an audible "click" or other sound, as well as provide a tactile indication to the surgeon that the end effector 12 has been "locked" onto the spine member 50. In addition, the surgeon cannot inadvertently continue to actuate the firing trigger 130 to start to form staples 32 in the end effector 12 without intentionally biasing the retention pin 162 out of the locking cavity 164. Similarly, if the surgeon releases the firing trigger 130 when in the coupled position, it is retained in that position by the retention pin 162 to prevent the firing trigger 130 from returning to the starting position and thereby releasing the end effector 12 from the spine member 50.

Various embodiments of the present invention may further include a firing system lock button 137 that is pivotally attached to the handle assembly 100. In one form, the firing system lock button 137 has a latch 138 formed on a distal end thereof that is oriented to engage the firing yoke 114 when the firing release button is in a first latching position. As can be seen in FIG. 1, a latch spring 139 serves to bias the firing system lock button 137 to the first latching position. In various circumstances, the latch 138 serves to engage the firing yoke 114 at a point where the position of the firing yoke 114 on the spine member 50 corresponds to a point wherein the first firing adapter 140 is about to distally advance up the clamping ramp 28 on the anvil 20. It will be understood that, as the first firing adapter 140 advances axially up the clamping ramp 28, the anvil 20 will move in a path such that its staple forming surface portion 22 is substantially parallel to the upper face 36 of the staple cartridge 30.

After the end effector 12 has been coupled to the spine member 50, the staple forming process is commenced by first depressing the firing system lock button 137 to enable the firing yoke 114 to be further moved distally on the spine member 50 and ultimately compress the anvil 20 into the staple cartridge 30. After depressing the firing system lock button 137, the surgeon continues to actuate the firing trigger 130 towards the pistol grip 107 thereby driving the first staple collar 140 up the corresponding staple forming ramp 29 to force the anvil 20 into forming contact with the staples 32 in the staple cartridge 30. The firing system lock button 137 prevents the inadvertent forming of the staples 32 until the surgeon is ready to start that process. In this embodiment, the surgeon must depress the firing system lock button 137 before the firing trigger 130 may be further actuated to begin the staple forming process.

The surgical instrument 10 may be solely used as a tissue stapling device if so desired. However, various embodiments of the present invention may also include a tissue cutting system, generally designated as 170. In at least one form, the tissue cutting system 170 comprises a knife member 172 that may be selectively advanced from an un-actuated position adjacent the proximal end of the end effector 12 to an actuated position by actuating a knife advancement trigger 200. The knife member 172 is movably supported within the spine member 50 and is attached or otherwise protrudes from a knife rod 180. The knife member 172 may be fabricated from, for example, 420 or 440 stainless steel with a hardness of greater than 38HRC (Rockwell Hardness C-scale) and have a tissue cutting edge 176 formed on the distal end 174 thereof and be configured to slidably extend through a slot in the anvil 20 and a centrally disposed slot 33 in the staple cartridge 30 to cut through tissue that is clamped in the end effector 12. In various embodiments, the knife rod 180 extends through the spine member 50 and has a proximal end portion which drivingly interfaces with a knife transmission that is operably attached to the knife advance trigger 200. In various embodiments, the knife advance trigger 200 is attached to pivot pin 132 such that it may be pivoted or otherwise actuated without actuating the firing trigger 130. In various embodiments, a first knife gear 192 is also attached to the pivot pin 132 such that actuation of the knife advance trigger 200 also pivots the first knife gear 192. A firing return spring 202 is attached between the first knife gear 192 and the handle housing 100 to bias the knife advancement trigger 200 to a starting or un-actuated position.

Various embodiments of the knife transmission also include a second knife gear 194 that is rotatably supported on a second gear spindle and in meshing engagement with the first knife gear 192. The second knife gear 194 is in meshing engagement with a third knife gear 196 that is supported on a third gear spindle. Also supported on the third gear spindle 195 is a fourth knife gear 198. The fourth knife gear 198 is adapted to drivingly engage a series of annular gear teeth or rings on a proximal end of the knife rod 180. Thus, such arrangement enables the fourth knife gear 198 to axially drive the knife rod 180 in the distal direction "DD" or proximal direction "PD" while enabling the firing rod 180 to rotate about longitudinal axis A-A with respect to the fourth knife gear 198. Accordingly, the surgeon may axially advance the firing rod 180 and ultimately the knife member 172 distally by pulling the knife advancement trigger 200 towards the pistol grip 107 of the handle assembly 100.

Various embodiments of the present invention further include a knife lockout system 210 that prevents the advancement of the knife member 172 unless the firing trigger 130 has been pulled to the fully fired position. Such feature will therefore prevent the activation of the knife advancement system 170 unless the staples have first been fired or formed into the tissue. As can be seen in FIG. 1, various implementations of the knife lockout system 210 comprise a knife lockout bar 211 that is pivotally supported within the pistol grip portion 107 of the handle assembly 100. The knife lockout bar 211 has an activation end 212 that is adapted to be engaged by the firing trigger 130 when the firing trigger 130 is in the fully fired position. In addition, the knife lockout bar 211 has a retaining hook 214 on its other end that is adapted to hookingly engage a latch rod 216 on the first cut gear 192. A knife lock spring 218 is employed to bias the knife lockout bar 211 to a "locked" position wherein the retaining hook 214 is retained in engagement with the latch rod 216 to thereby prevent actuation of the knife advancement trigger 200 unless the firing trigger 130 is in the fully fired position.

After the staples have been "fired" (formed) into the target tissue, the surgeon may depress the firing trigger release button 167 to enable the firing trigger 130 to return to the starting position under the bias of the torsion spring 135 which enables the anvil 20 to be biased to an open position under the bias of spring 21. When in the open position, the surgeon may withdraw the end effector 12 leaving the implantable staple cartridge 30 and staples 32 behind. In applications wherein the end effector was inserted through a passage, working channel, etc. the surgeon will return the anvil 20 to the closed position by activating the firing trigger 130 to enable the end effector 12 to be withdrawn out through the passage or working channel. If, however, the surgeon desires to cut the target tissue after firing the staples, the surgeon activates the knife advancement trigger 200 in the above-described manner to drive the knife bar 172 through the target tissue to the end of the end effector. Thereafter, the surgeon may release the knife advancement trigger 200 to enable the firing return spring 202 to cause the firing transmission to return the knife bar 172 to the starting (un-actuated) position. Once the knife bar 172 has been returned to the starting position, the surgeon may open the end effector jaws 13, 15 to release the implantable cartridge 30 within the patient and then withdraw the end effector 12 from the patient. Thus, such surgical instruments facilitate the use of small implantable staple cartridges that may be inserted through relatively smaller working channels and passages, while providing the surgeon with the option to fire the staples without cutting tissue or if desired to also cut tissue after the staples have been fired.

Various unique and novel embodiments of the present invention employ a compressible staple cartridge that supports staples in a substantially stationary position for forming contact by the anvil. In various embodiments, the anvil is driven into the unformed staples wherein, in at least one such embodiment, the degree of staple formation attained is dependent upon how far the anvil is driven into the staples. Such an arrangement provides the surgeon with the ability to adjust the amount of forming or firing pressure applied to the staples and thereby alter the final formed height of the staples. In other various embodiments of the present invention, surgical stapling arrangements can employ staple driving elements which can lift the staples toward the anvil. Such embodiments are described in greater detail further below.

In various embodiments, with regard to the embodiments described in detail above, the amount of firing motion that is applied to the movable anvil is dependent upon the degree of actuation of the firing trigger. For example, if the surgeon desires to attain only partially formed staples, then the firing trigger is only partially depressed inward towards the pistol grip 107. To attain more staple formation, the surgeon simply compresses the firing trigger further which results in the anvil being further driven into forming contact with the staples. As used herein, the term "forming contact" means that the staple forming surface or staple forming pockets have contacted the ends of the staple legs and have started to form or bend the legs over into a formed position. The degree of staple formation refers to how far the staple legs have been folded over and ultimately relates to the forming height of the staple as referenced above. Those of ordinary skill in the art will further understand that, because the anvil 20 moves in a substantially parallel relationship with respect to the staple cartridge as the firing motions are applied thereto, the staples are formed substantially simultaneously with substantially the same formed heights.

Figure 2:
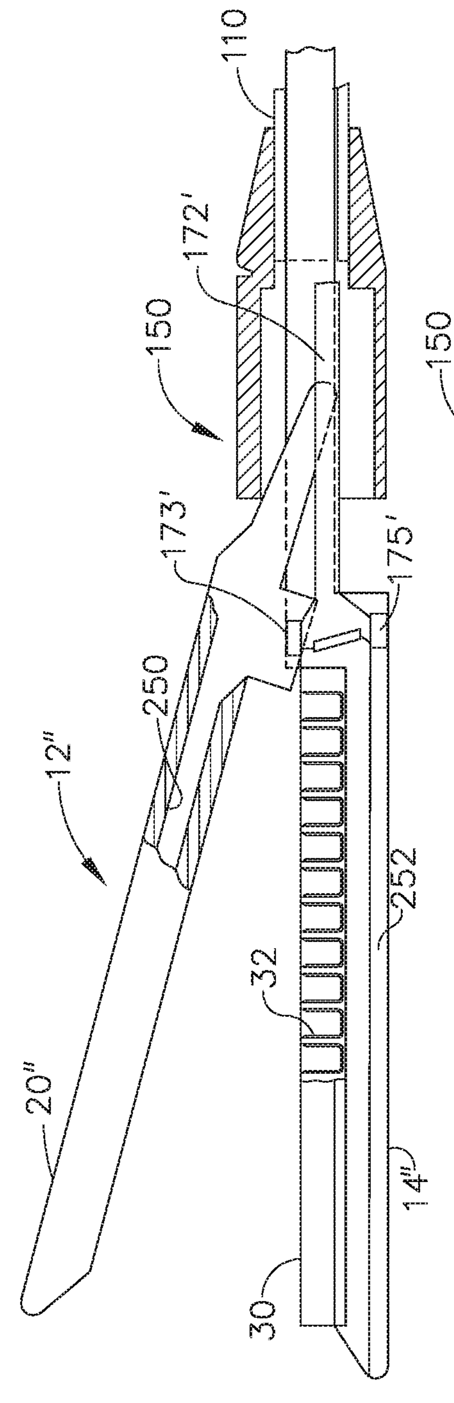
FIG. 2 is a partial cross-sectional side view of another end effector coupled to a portion of a surgical instrument with the end effector supporting a surgical staple cartridge and with the anvil thereof in an open position.
Figure 3:
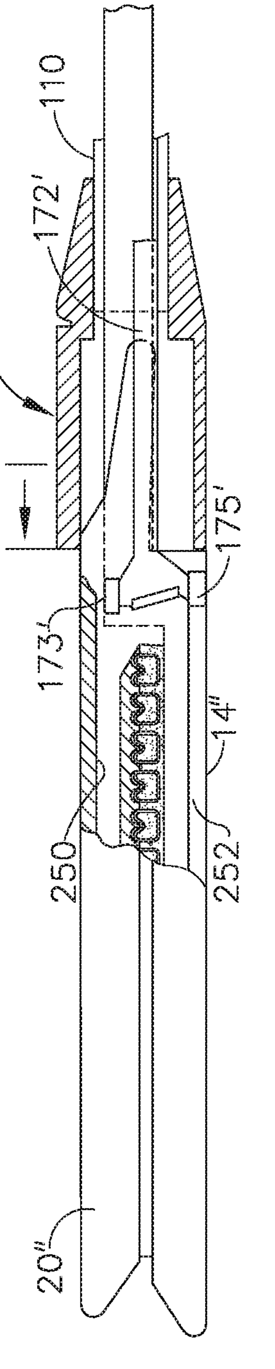
FIG. 3 is another partial cross-sectional side view of the end effector of FIG. 2 in a closed position.

FIGS. 2 and 3 illustrate an alternative end effector 12" that is similar to the end effector 12' described above, except with the following differences that are configured to accommodate a knife bar 172'. The knife bar 172' is coupled to or protrudes from a knife rod 180 and is otherwise operated in the above described manner with respect to the knife bar 172. However, in this embodiment, the knife bar 172' is long enough to traverse the entire length of the end effector 12" and therefore, a separate distal knife member is not employed in the end effector 12". The knife bar 172' has an upper transverse member 173' and a lower transverse member 175' formed thereon. The upper transverse member 173' is oriented to slidably transverse a corresponding elongated slot 250 in anvil 20" and the lower transverse member 175' is oriented to traverse an elongated slot 252 in the elongated channel 14" of the end effector 12". A disengagement slot (not shown) is also provide din the anvil 20" such that when the knife bar 172' has been driven to an ending position with thin end effector 12", the upper transverse member 173' drops through the corresponding slot to enable the anvil 20" to move to the open position to disengage the stapled and cut tissue. The anvil 20" may be otherwise identical to anvil 20 described above and the elongated channel 14" may be otherwise identical to elongated channel 14 described above.

Figure 4:
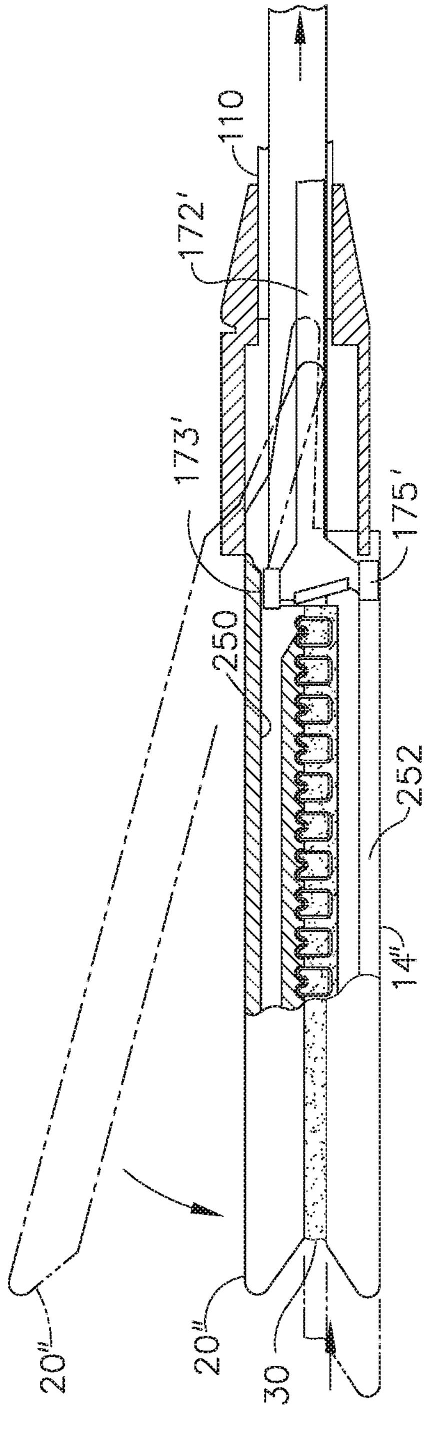
FIG. 4 is another partial cross-sectional side view of the end effector of FIGS. 2 and 3 as the knife bar is starting to advance through the end effector.
Figure 5:
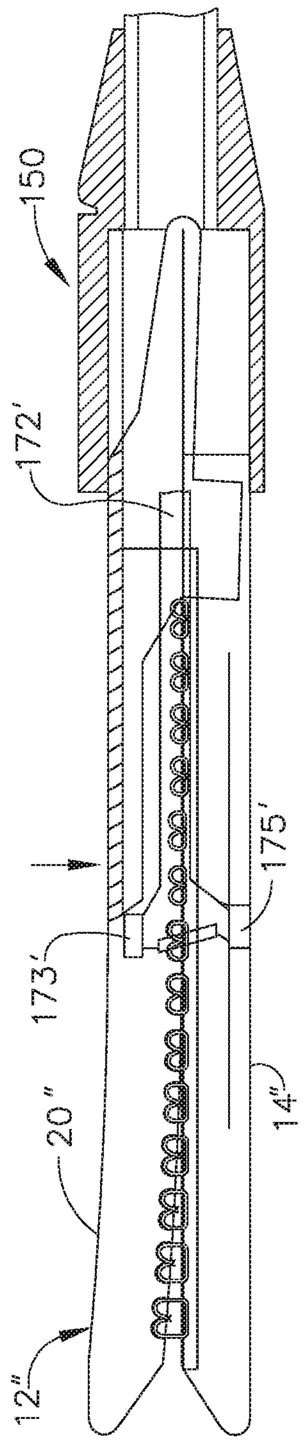
FIG. 5 is another partial cross-sectional side view of the end effector of FIGS. 2-4 with the knife bar partially advanced therethrough.

In these embodiments, the anvil 20" is biased to a fully open position (FIG. 2) by a spring or other opening arrangement (not shown). The anvil 20" is moved between the open and fully clamped positions by the axial travel of the firing adapter 150 in the manner described above. Once the firing adapter 150 has been advanced to the fully clamped position (FIG. 3), the surgeon may then advance the knife bar 172" distally in the manner described above. If the surgeon desires to use the end effector as a grasping device to manipulate tissue, the firing adapter may be moved proximally to allow the anvil 20" to move away from the elongated channel 14" as represented in FIG. 4 in broken lines. In this embodiment, as the knife bar 172" moves distally, the upper transverse member 173' and the lower transverse member 175' draw the anvil 20" and elongated channel 14" together to achieve the desired staple formation as the knife bar 172" is advanced distally through the end effector 12". See FIG. 5. Thus, in this embodiment, staple formation occurs simultaneously with tissue cutting, but the staples themselves may be sequentially formed as the knife bar 172" is driven distally.

The unique and novel features of the various surgical staple cartridges and the surgical instruments of the present invention enable the staples in those cartridges to be arranged in one or more linear or non-linear lines. A plurality of such staple lines may be provided on each side of an elongated slot that is centrally disposed within the staple cartridge for receiving the tissue cutting member therethrough. In one arrangement, for example, the staples in one line may be substantially parallel with the staples in adjacent line(s) of staples, but offset therefrom. In still other embodiments, one or more lines of staples may be non-linear in nature. That is, the base of at least one staple in a line of staples may extend along an axis that is substantially transverse to the bases of other staples in the same staple line. For example, as will be discussed in further detail below, in alternative embodiments, the lines of staples on each side of the elongated slot may have a zigzag appearance. Such non-linear staple arrangements may attain better tissue fastening results with less staples than various linear staple arrangements employed in prior staple cartridges.

Figure 6:
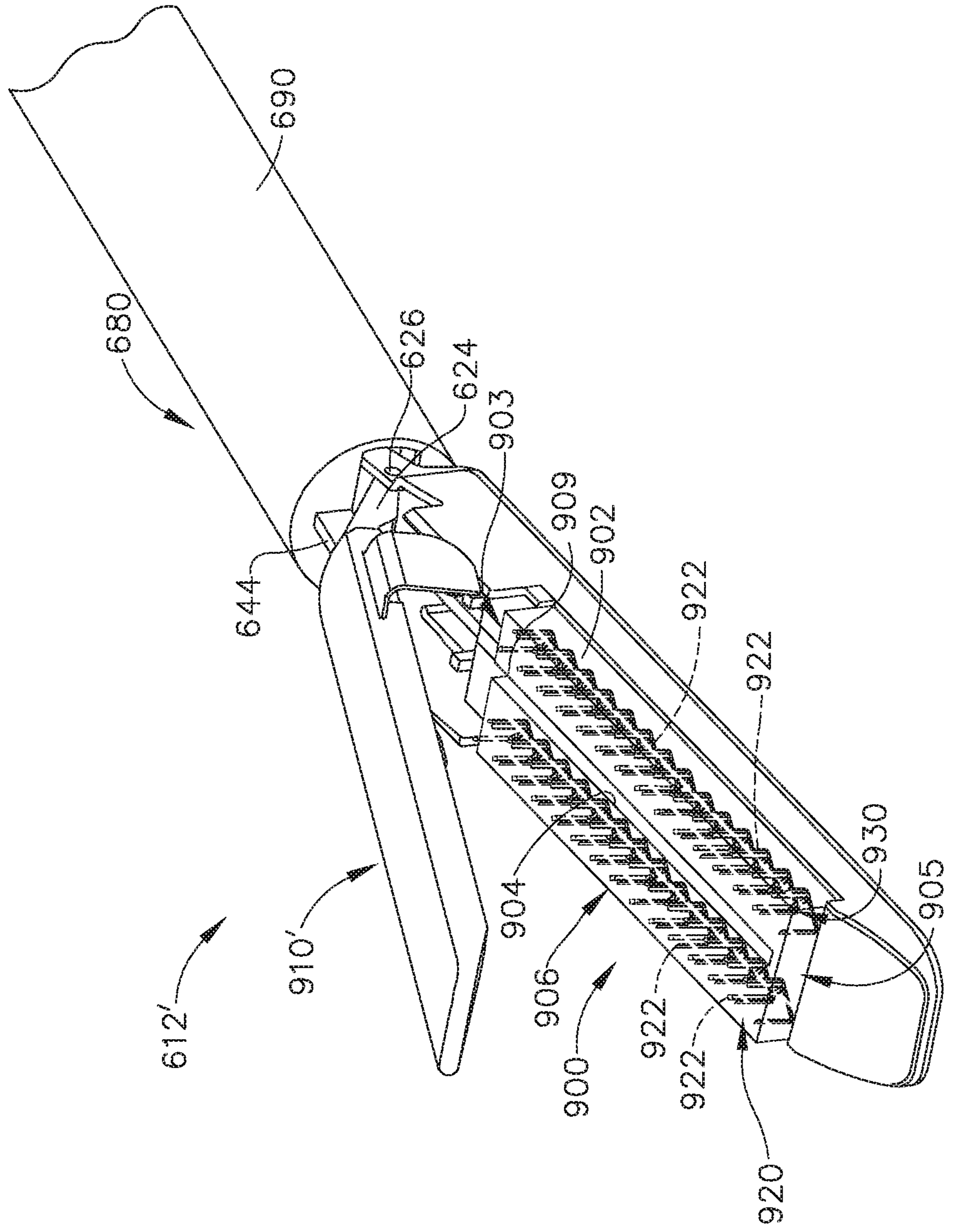
FIG. 6 is a perspective view of an alternative staple cartridge embodiment installed in a surgical cutting and stapling device.
Figure 7:
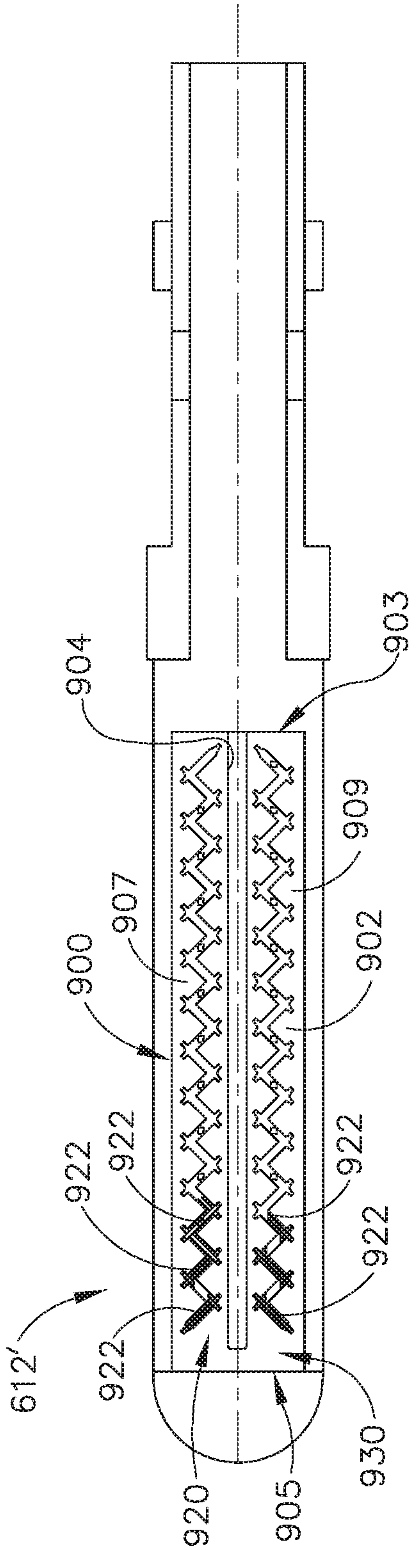
FIG. 7 is a top view of the surgical staple cartridge and elongated channel of the device depicted in FIG. 6.

FIG. 6 illustrates use of a surgical staple cartridge embodiment 900 in an end effector embodiment 612'. As can be seen in FIGS. 6 and 7, an embodiment of the surgical staple cartridge 900 has a cartridge body 902 that has a centrally disposed elongated slot 904 extending through a proximal end 903 to an area adjacent a distal end 905. The elongated slot 904 is configured to permit a knife body to axially move therethrough during a tissue cutting operation in the manner described above. In at least one embodiment, the cartridge body 902 consists of a compressible hemostat material such as, for example, oxidized regenerated cellulose ("ORC") or a bio-absorbable foam fabricated from, for example, PGA (Polyglycolic acid, sold under the trademark Vicryl), PCL (polycaprolactone), PLA or PLLA (Polyactic acid), PDS (Polydioxanone), PHA (polyhydroxyalkanoate), PGCL (poliglecaprone 25, sold under the trademark Monocryl) or a composite of PGA, PCL, PLA and PDS in which lines 920, 930 of unformed staples 922 are supported. However, the cartridge body 902 may be fabricated from other materials that serve to support the unformed staples 922 in a desired orientation such that they may be compressed as the anvil 910' is brought into contact therewith. As with various other embodiments described above, the staple cartridge 900 is implantable and is left attached to the stapled tissue after the stapling procedure has been completed. In at least some embodiments, in order to prevent the staples 922 from being affected and the hemostat material from being activated during the introduction and positioning process, the entire cartridge 900 may be coated or wrapped in a biodegradable film 906 such as a polydioxanon film sold under the trademark PDS® or with a Polyglycerol sebacate (PGS) film or other biodegradable films fabricated from, for example, PGA (Polyglycolic acid, marketed under the trade mark Vicryl), PCL (Polycaprolactone), PLA or PLLA (Polylactic acid), PHA (polyhydroxyalkanoate), PGCL (poliglecaprone 25, sold under the trademark Monocryl) or a composite of PGA, PCL, PLA, PDS that would be impermeable until ruptured. The cartridge body 902 of staple cartridge 900 is sized to be removably supported within the elongated channel of the end effector 612'.

Figure 10:
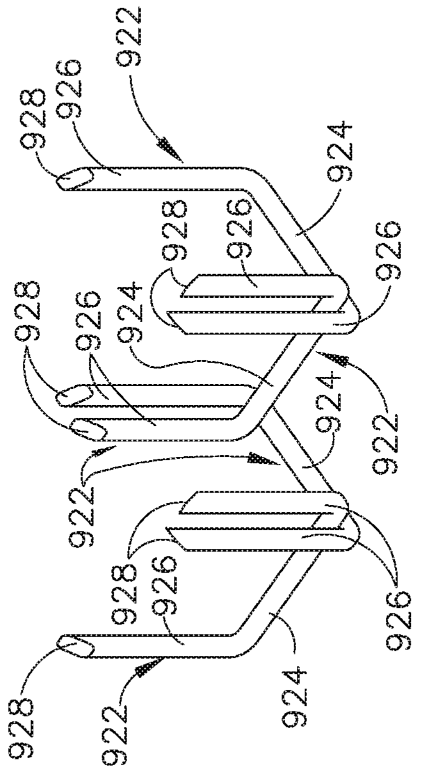
FIG. 10 is a partial perspective view of a plurality of staples forming a portion of a staple line.
Figure 11:
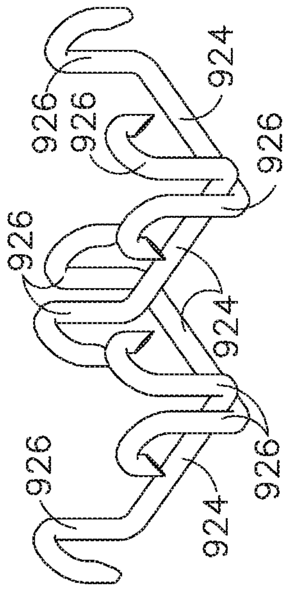
FIG. 11 is another partial perspective view of the staple line of FIG. 10 with the staples thereof after being formed by being contacted by the anvil of the surgical cutting and stapling device.

In the embodiment depicted in FIGS. 6, 10, and 11, the surgical staple cartridge 900 operably supports a first line 920 of staples 922 on one lateral side 907 of the elongated slot 904 and a second line 930 of staples 922 on the other lateral side 909 of the elongated slot 904. In various embodiments, the staples 922 may be fabricated from a metal material such as, for example, Titanium, Titanium alloys (e.g., 6AI-4V Titanium, 3al-2.5V Titanium), Stainless Steel, etc. and have a staple base 924 and two upstanding staple legs 926 protruding therefrom. Each staple leg 926 may have a tissue-piercing tip 928 formed thereon. In the first line 920 of staples 922, the staple base 924 of at least one staple 922 overlaps the staple base of another staple 922. In a preferred embodiment, the staple base 924 of each staple 922 overlaps the staple bases 924 of two adjacent staples 922, except for the base 924 of the last staple 922 on each end of the first staple line 920. See FIG. 10. Thus, the first staple line 920 has a substantially non-linear shape. More particularly, when viewed from above, the first staple line 920 has a substantially zigzag appearance.

Figure 9:
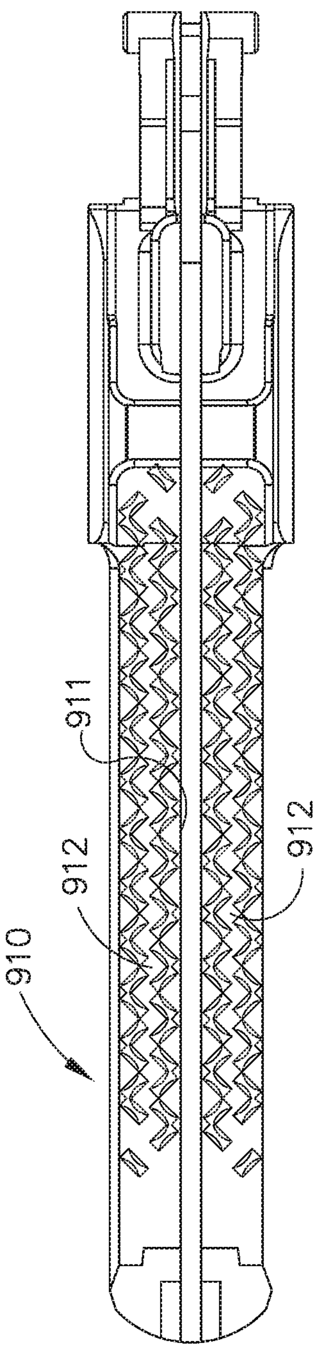
FIG. 9 is a bottom view of an anvil.

As can be seen in FIG. 9, the anvil 90 has two sequential longitudinal staple forming pockets 912 that each has a substantial zigzag shape that corresponds to the shape of the first line 920 of staples 922 such that, when the anvil 910 is brought into forming contact with the staples 922, the legs 926 thereof are formed as shown in FIG. 11. Thus, the distal leg of one staple shares the same pocket as the proximal leg of the next staple longitudinally. Such arrangement allows for a denser pocket pattern, even to a point where the staples themselves interact (e.g., are folded over one another). In prior staple pocket arrangements, in general, there has to be between 0.005 and 0.015 inches of metal/space from one set of pockets to the next. This embodiment of the present invention, however, has a spacing arrangement from 0 to 0.02 inches of interference/overlap (essentially a −0.020") because one staple mates with the next staple, for example. Such arrangements allow for 15-30% more staples in the same space. Furthermore, when the staples interlock, there is less need for multiple lateral rows of staples. Prior arrangements commonly employ three rows on each side of the tissue cut line to prevent the existing of an open path through which blood may pass. Lines of interlocking staples are less likely to leave paths through which blood may pass. Another distinct advantage provided by the various interlocking staple arrangements of the present invention relates to improved "burst strength" which relates to the amount of force required to tear a staple line open.

Another staple forming pocket arrangement may comprise a common staple forming pocket. As used herein, the term "common staple forming pocket" means that one forming pocket can form all of the staples in a single line of staples as opposed to prior anvil designs wherein a discrete forming pocket is provided for each leg of each staple to be formed.

Figure 12:
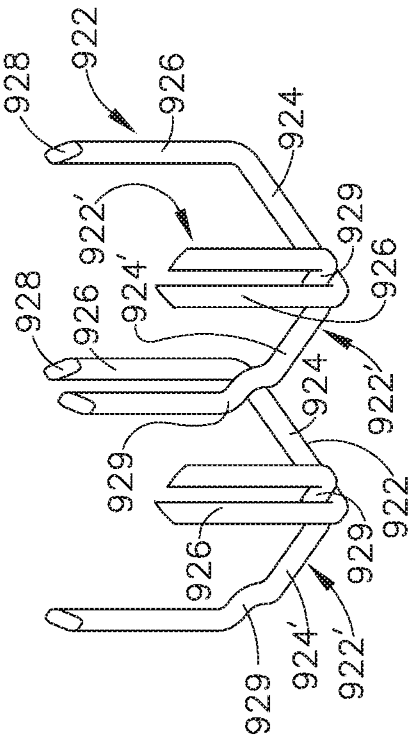
FIG. 12 is a partial perspective view of alternative staples forming a portion of another staple line.

FIG. 12 illustrates yet another staple embodiment 922' wherein the base 924' has an offset portion 929 to facilitate a tighter overlap of the bases 924'. As indicated above, the staple cartridge 900 has a second line 930 of staples 922 supported on a second lateral side 909 of the elongated slot 904. The second line 930 of staples 922 is substantially identical to the first line 920 of staples 922. Thus, the anvil 910 has a second common staple forming pocket 912 that corresponds to the second line of staples 930 for forming contact therewith. In alternative embodiments, however, the second line 930 of staples 922 may differ from the first line 920 of staples in shape and, perhaps, number of staples.

Figure 8:
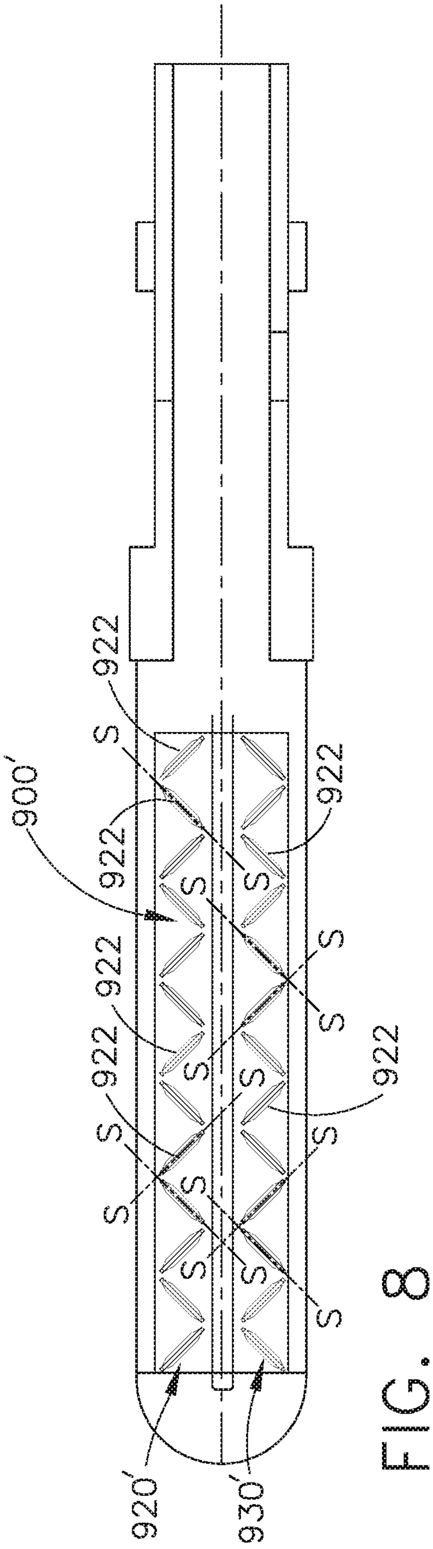
FIG. 8 is a top view of another surgical staple cartridge embodiment installed in an elongated channel of an end effector.
Figure 13:
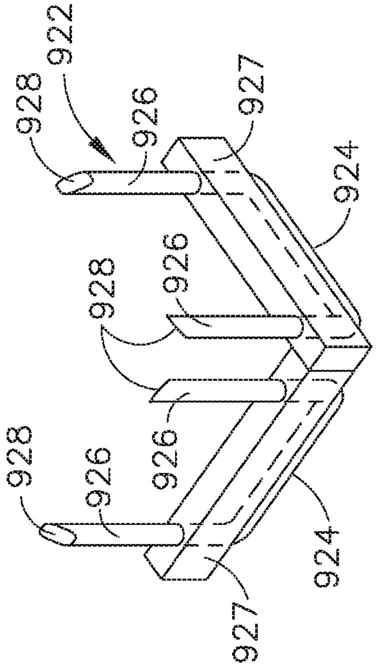
FIG. 13 is a partial perspective view of alternative staples forming a portion of another staple line.

FIG. 8 illustrates a surgical staple cartridge 900' that is substantially identical to the staple cartridge 900 described above, with the exception of the lines 920', 930' of staples 922 supported therein. For example, in this embodiment, the line 920' of staples 922 are arranged relative to each other such that a base axis S-S of at least one staple base 924 is substantially transverse to the base axis S-S of the staple base 924 of at least one other adjacent staple 922. Such predetermined pattern of staples, when viewed from above, comprises a substantially zigzag arrangement. In the embodiment depicted in FIG. 13, the respective bases 924 of staples 922 may additionally have a base support member 927 overmolded thereon as shown. In various embodiments, the base support member 927 may be fabricated from, for example, non-absorbable plastic such as Polyether ether ketone “PEEK” or absorbable plastic such as, for example, Polyglycolic acid “PGA”, Polylactic acid “PLA” or “PLLA”, Polydioxanone “PDS”, PCL (polycaprolactone), PHA (polyhydroxyalkanoate), Polyglycerol sebacate (PGS), PGCL (poliglecaprone 25, sold under the trademark Monocryl) or various composite mixes of PGS, PDS, PLA, PGA, and PCL. The base support members 927 facilitate interlocking between the staples without making the staples themselves overlap. Thus, such arrangements could form staples with “B” shapes or inverted “W” shapes without the legs of the staples themselves overlapping. However, the crowns are connected by the base support members so they act like overlapping staples. Such arrangements allow the combined pockets to have two discrete paths for each leg.

Figure 14:
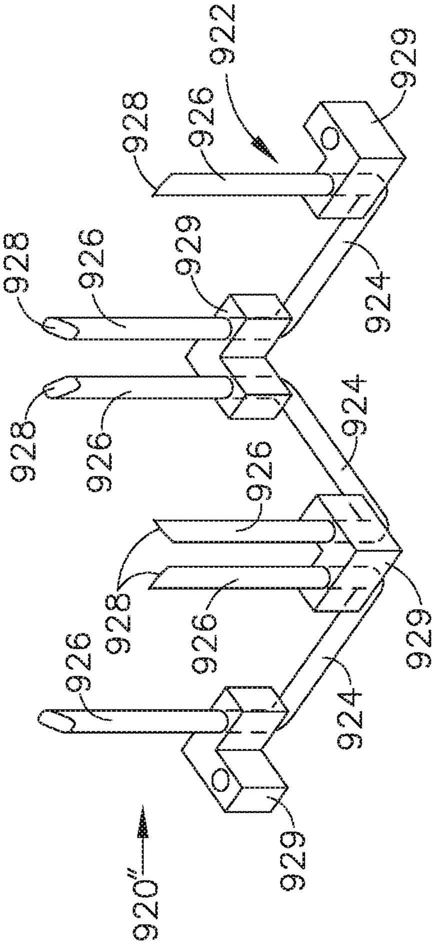
FIG. 14 is a partial perspective view of alternative staples forming a portion of another staple line embodiment.

The embodiment depicted in FIG. 14 employs a staple line 920" wherein the legs 926 of adjacent staples 922 are coupled together by a coupler portion 929 molded or otherwise attached thereto. Each coupler portion 929 may be fabricated from, for example, Polyether ether ketone “PEEK” or absorbable plastic such as, for example, Polyglycolic acid “PGA”, Polylactic acid “PLA” or “PLLA”, Polydioxanone “PDS”, PCL (polycaprolactone), PHA (polyhydroxyalkanoate), PGCL (poliglecaprone 25, sold under the trademark Monocryl) or various composite mixes if PGS, PDS, PLA, PGA, and PCL. Such staple line 920" has substantial zigzag appearance when viewed from above. While the various surgical staple cartridge embodiments 900, 900' have been explained with reference to use with the end effector 612', it will be understood that the staple cartridges 900, 900' may be effectively employed with the various other end effectors and surgical instruments described hereinabove, with appropriate staple forming pocket arrangements being provided in the anvils of those instruments in order to achieved the desired amount of staple formation upon movement of the anvils into forming contact with the staples.

Figure 15:
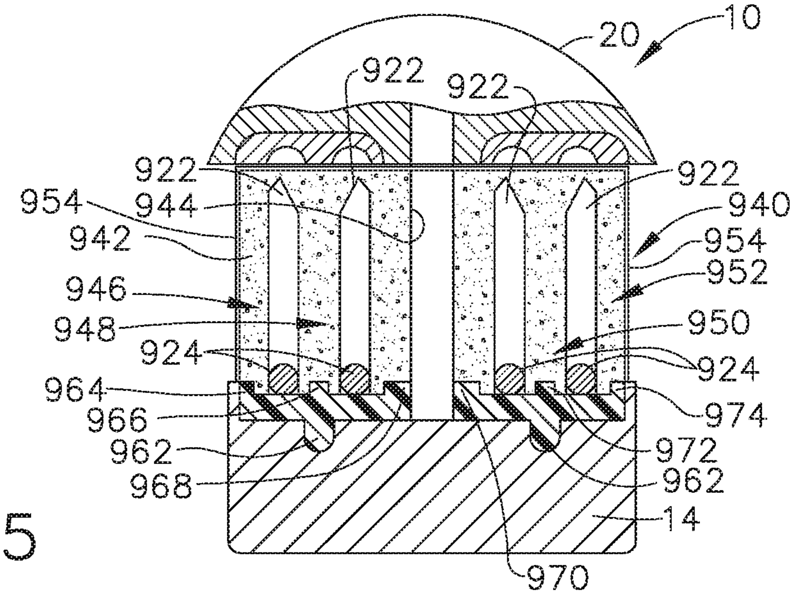
FIG. 15 is a cross-sectional view of an end effector supporting a staple cartridge.
Figure 16:
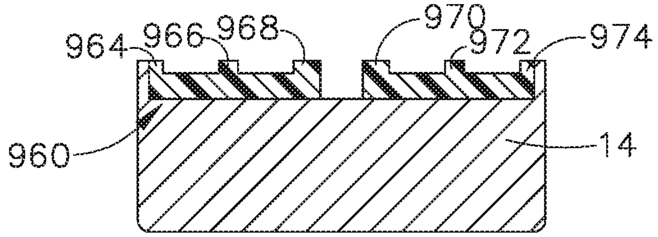
FIG. 16 is a cross-sectional view of the elongated channel portion of the end effector of FIG. 15 after the implantable staple cartridge body portion and staples have been removed therefrom.

FIGS. 15 and 16 illustrate another surgical staple cartridge 940 embodiment supported in an elongated channel 14 of a surgical instrument 10. In at least one embodiment, the surgical staple cartridge 940 includes a cartridge body 942 that has a centrally disposed elongated slot 944 extending at least partially therethrough. The elongated slot 944 is configured to permit a knife body of the surgical instrument 10 to axially move therethrough during a tissue cutting operation in the manner described above. In various embodiments, the cartridge body 942 consists of a compressible hemostat material such as, for example, oxidized regenerated cellulose (“ORC”) or a bio-absorbable foam of the types described above or below in which lines 946, 948, 950, 952 of unformed staples 922 are supported. In at least some embodiments, in order to prevent the staples 922 from being affected and the hemostat material from being activated during the introduction and positioning process, the entire cartridge 940 may be coated or wrapped in a biodegradable film 954 such as a polydioxanon film sold under the trademark PDS® or with a Polyglycerol sebacate (PGS) film or other biodegradable films fabricated from, for example, PGA (Polyglycolic acid, marketed under the trade mark Vicryl), PCL (Polycaprolactone), PLA or PLLA (Polylactic acid), PHA (polyhydroxyalkanoate), PGCL (poliglecaprone 25, sold under the trademark Monocryl) or a composite of PGA, PCL, PLA, PDS that would be impermeable until ruptured.

In the embodiment depicted in FIG. 15, the cartridge 940 further includes a cartridge support member 960 that is coupled to the cartridge body 942. In various embodiments, the cartridge support member 960 may be fabricated from a rigid material such as, for example, Titanium, Stainless Steel, Aluminum, any alloy of the foregoing, etc. and may be partially embedded within the cartridge body 942. In various embodiments, the cartridge support member 960 may be held in place by, for example, film 954. In still other embodiments wherein a limited bond is desired, sporadic use of cyanoacylate could be used to “glue” the two components together. In yet other embodiments, the cartridge body 942 may be heated and “welded” or “fused” to the cartridge support member 960. In various embodiments, the cartridge support member 960 forms at least a portion of the bottom surface of the cartridge body 942 for mating with the elongated channel 14. In at least one embodiment, the cartridge support member 960 has one or more snap features 962 protruding therefrom for releasably coupling the cartridge support member 960 to the elongated channel 14. Other forms of snap features/fastener arrangements may be employed for releasably coupling the cartridge support member 960 to the elongated channel 14.

Figure 17:
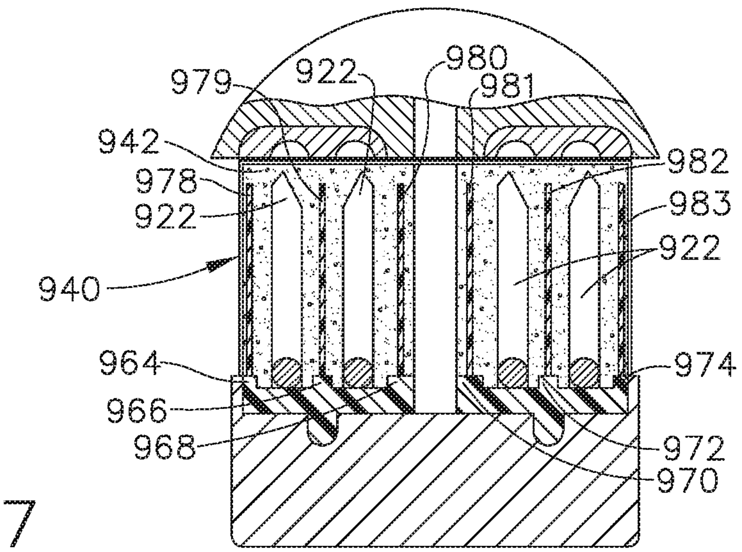
FIG. 17 is a cross-sectional view of an end effector supporting another staple cartridge.

In various embodiments, the cartridge support member 960 has a series of support ridges 964, 966, 968, 970, 972, 974, 976 formed thereon to provide some lateral support to the bases 924 of the staples 922 in the staple lines 946, 948, 950, 952 as shown in FIG. 15. Thus, in at least some embodiments, the support ridges are substantially coextensive with the staple lines. FIG. 17 illustrates an alternative staple cartridge embodiment 940' that is substantially identical to cartridge 940, except for the inclusion of upstanding fin portions 978, 979, 980, 981, 982, 983 that protrude from the support ridges 964, 966, 968, 970, 972, 976, respectively to provide additional lateral support to the staples 922. In various embodiments, the fin portions may be integrally formed with the cartridge support member 960 and have a height that is about ½ or less of the height of the cartridge. Thus, in various embodiments, for example, any standing features supporting the foam cannot extend above the maximum compression height of the foam. Thus, if the cartridge is designed, for example, to compress to ⅓ of its original height when fired, the fins would between 66% of the uncompressed height, all the way down to 10% of uncompressed height.

In use, once the staples 922 have been formed through contact with the anvil 20 in the manner described above, the anvil 20 is opened and the end effector 12 is pulled away from the stapled tissue. As the end effector 12 is pulled away from the stapled tissue, the cartridge body 942 remains fastened to the stapled tissue and is then separated from the cartridge support member 960 which remains coupled to the elongated channel 14. In various embodiments, the cartridge support member 960 is provided with a color that differs from the color of the material comprising the cartridge body 942 as well as the color of the elongated channel 14. Such arrangement provides the surgeon with an easily recognizable indication that no staple cartridge is present within the end effector. Thus, the surgeon will not inadvertently attempt to reinsert/use the end effector without first installing a new staple cartridge therein. To do so, the surgeon simply disconnects the snap features of the cartridge support member 960 from the elongated channel 14 to enable the cartridge support member 960 of a new staple cartridge 940 to be placed therein. While the staple cartridges 940, 940' have been explained with reference to surgical instrument 10, it will be understood that those cartridges may be effectively employed with many of the other surgical instrument embodiments disclosed herein without departing from the spirit and scope of the present invention.

In various embodiments, a staple cartridge can comprise a cartridge body and a plurality of staples stored within the cartridge body. In use, the staple cartridge can be introduced into a surgical site and positioned on a side of the tissue being treated. In addition, a staple-forming anvil can be positioned on the opposite side of the tissue. In various embodiments, the anvil can be carried by a first jaw and the staple cartridge can be carried by a second jaw, wherein the first jaw and/or the second jaw can be moved toward the other. Once the staple cartridge and the anvil have been positioned relative to the tissue, the staples can be ejected from the staple cartridge body such that the staples can pierce the tissue and contact the staple-forming anvil. Once the staples have been deployed from the staple cartridge body, the staple cartridge body can then be removed from the surgical site. In various embodiments disclosed herein, a staple cartridge, or at least a portion of a staple cartridge, can be implanted with the staples. In at least one such embodiment, as described in greater detail further below, a staple cartridge can comprise a cartridge body which can be compressed, crushed, and/or collapsed by the anvil when the anvil is moved from an open position into a closed position. When the cartridge body is compressed, crushed, and/or collapsed, the staples positioned within the cartridge body can be deformed by the anvil. Alternatively, the jaw supporting the staple cartridge can be moved toward the anvil into a closed position. In either event, in various embodiments, the staples can be deformed while they are at least partially positioned within the cartridge body. In certain embodiments, the staples may not be ejected from the staple cartridge while, in some embodiments, the staples can be ejected from the staple cartridge along with a portion of the cartridge body.

Referring now to FIGS. 18A-18D, a compressible staple cartridge, such as staple cartridge 1000, for example, can comprise a compressible, implantable cartridge body 1010 and, in addition, a plurality of staples 1020 positioned in the compressible cartridge body 1010, although only one staple 1020 is depicted in FIGS. 18A-18D. FIG. 18A illustrates the staple cartridge 1000 supported by a staple cartridge support, or staple cartridge channel, 1030, wherein the staple cartridge 1000 is illustrated in an uncompressed condition. In such an uncompressed condition, the anvil 1040 may or may not be in contact with the tissue T. In use, the anvil 1040 can be moved from an open position into contact with the tissue T as illustrated in FIG. 18B and position the tissue T against the cartridge body 1010. Even though the anvil 1040 can position the tissue T against a tissue-contacting surface 1019 of staple cartridge body 1010, referring again to FIG. 18B, the staple cartridge body 1010 may be subjected to little, if any, compressive force or pressure at such point and the staples 1020 may remain in an unformed, or unfired, condition. As illustrated in FIGS. 18A and 18B, the staple cartridge body 1010 can comprise one or more layers and the staple legs 1021 of staples 1020 can extend upwardly through these layers. In various embodiments, the cartridge body 1010 can comprise a first layer 1011, a second layer 1012, a third layer 1013, wherein the second layer 1012 can be positioned intermediate the first layer 1011 and the third layer 1013, and a fourth layer 1014, wherein the third layer 1013 can be positioned intermediate the second layer 1012 and the fourth layer 1014. In at least one embodiment, the bases 1022 of the staples 1020 can be positioned within cavities 1015 in the fourth layer 1014 and the staple legs 1021 can extend upwardly from the bases 1022 and through the fourth layer 1014, the third layer 1013, and the second layer 1012, for example. In various embodiments, each deformable leg 1021 can comprise a tip, such as sharp tip 1023, for example, which can be positioned in the second layer 1012, for example, when the staple cartridge 1000 is in an uncompressed condition. In at least one such embodiment, the tips 1023 may not extend into and/or through the first layer 1011, wherein, in at least one embodiment, the tips 1023 may not protrude through the tissue-contacting surface 1019 when the staple cartridge 1000 is in an uncompressed condition. In certain other embodiments, the sharp tips 1023 may be positioned in the third layer 1013, and/or any other suitable layer, when the staple cartridge is in an uncompressed condition. In various alternative embodiments, a cartridge body of a staple cartridge may have any suitable number of layers such as less than four layers or more than four layers, for example.

In various embodiments, as described in greater detail below, the first layer 1011 can be comprised of a buttress material and/or plastic material, such as polydioxanone (PDS) and/or polyglycolic acid (PGA), for example, and the second layer 1012 can be comprised of a bioabsorbable foam material and/or a compressible haemostatic material, such as oxidized regenerated cellulose (ORC), for example. In various embodiments, one or more of the first layer 1011, the second layer 1012, the third layer 1013, and the fourth layer 1014 may hold the staples 1020 within the staple cartridge body 1010 and, in addition, maintain the staples 1020 in alignment with one another. In various embodiments, the third layer 1013 can be comprised of a buttress material, or a fairly incompressible or inelastic material, which can be configured to hold the staple legs 1021 of the staples 1020 in position relative to one another. Furthermore, the second layer 1012 and the fourth layer 1014, which are positioned on opposite sides of the third layer 1013, can stabilize, or reduce the movement of, the staples 1020 even though the second layer 1012 and the fourth layer 1014 can be comprised of a compressible foam or elastic material. In certain embodiments, the staple tips 1023 of the staple legs 1021 can be at least partially embedded in the first layer 1011. In at least one such embodiment, the first layer 1011 and the third layer 1013 can be configured to co-operatively and firmly hold the staple legs 1021 in position. In at least one embodiment, the first layer 1011 and the third layer 1013 can each be comprised of a sheet of bioabsorbable plastic, such as polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example, and the second layer 1012 and the fourth layer 1014 can each be comprised of at least one haemostatic material or agent.

Although the first layer 1011 can be compressible, the second layer 1012 can be substantially more compressible than the first layer 1011. For example, the second layer 1012 can be about twice as compressible, about three times as compressible, about four times as compressible, about five times as compressible, and/or about ten times as compressible, for example, as the first layer 1011. Stated another way, the second layer 1012 may compress about two times, about three times, about four times, about five times, and/or about ten times as much as first layer 1011, for a given force. In certain embodiments, the second layer 1012 can be between about twice as compressible and about ten times as compressible, for example, as the first layer 1011. In at least one embodiment, the second layer 1012 can comprise a plurality of air voids defined therein, wherein the amount and/or size of the air voids in the second layer 1012 can be controlled in order to provide a desired compressibility of the second layer 1012. Similar to the above, although the third layer 1013 can be compressible, the fourth layer 1014 can be substantially more compressible than the third layer 1013. For example, the fourth layer 1014 can be about twice as compressible, about three times as compressible, about four times as compressible, about five times as compressible, and/or about ten times as compressible, for example, as the third layer 1013. Stated another way, the fourth layer 1014 may compress about two times, about three times, about four times, about five times, and/or about ten times as much as third layer 1013, for a given force. In certain embodiments, the fourth layer 1014 can be between about twice as compressible and about ten times as compressible, for example, as the third layer 1013. In at least one embodiment, the fourth layer 1014 can comprise a plurality of air voids defined therein, wherein the amount and/or size of the air voids in the fourth layer 1014 can be controlled in order to provide a desired compressibility of the fourth layer 1014. In various circumstances, the compressibility of a cartridge body, or cartridge body layer, can be expressed in terms of a compression rate, i.e., a distance in which a layer is compressed for a given amount of force. For example, a layer having a high compression rate will compress a larger distance for a given amount of compressive force applied to the layer as compared to a layer having a lower compression rate. This being said, the second layer 1012 can have a higher compression rate than the first layer 1011 and, similarly, the fourth layer 1014 can have a higher compression rate than the third layer 1013. In various embodiments, the second layer 1012 and the fourth layer 1014 can be comprised of the same material and can comprise the same compression rate. In various embodiments, the second layer 1012 and the fourth layer 1014 can be comprised of materials having different compression rates. Similarly, the first layer 1011 and the third layer 1013 can be comprised of the same material and can comprise the same compression rate. In certain embodiments, the first layer 1011 and the third layer 1013 can be comprised of materials having different compression rates.

As the anvil 1040 is moved toward its closed position, the anvil 1040 can contact tissue T and apply a compressive force to the tissue T and the staple cartridge 1000, as illustrated in FIG. 18C. In such circumstances, the anvil 1040 can push the top surface, or tissue-contacting surface 1019, of the cartridge body 1010 downwardly toward the staple cartridge support 1030. In various embodiments, the staple cartridge support 1030 can comprise a cartridge support surface 1031 which can be configured to support the staple cartridge 1000 as the staple cartridge 1000 is compressed between the cartridge support surface 1031 and the tissue-contacting surface 1041 of anvil 1040. Owing to the pressure applied by the anvil 1040, the cartridge body 1010 can be compressed and the anvil 1040 can come into contact with the staples 1020. More particularly, in various embodiments, the compression of the cartridge body 1010 and the downward movement of the tissue-contacting surface 1019 can cause the tips 1023 of the staple legs 1021 to pierce the first layer 1011 of cartridge body 1010, pierce the tissue T, and enter into forming pockets 1042 in the anvil 1040. As the cartridge body 1010 is further compressed by the anvil 1040, the tips 1023 can contact the walls defining the forming pockets 1042 and, as a result, the legs 1021 can be deformed or curled inwardly, for example, as illustrated in FIG. 18C. As the staple legs 1021 are being deformed, as also illustrated in FIG. 18C, the bases 1022 of the staples 1020 can be in contact with or supported by the staple cartridge support 1030. In various embodiments, as described in greater detail below, the staple cartridge support 1030 can comprise a plurality of support features, such as staple support grooves, slots, or troughs 1032, for example, which can be configured to support the staples 1020, or at least the bases 1022 of the staples 1020, as the staples 1020 are being deformed. As also illustrated in FIG. 18C, the cavities 1015 in the fourth layer 1014 can collapse as a result of the compressive force applied to the staple cartridge body 1010. In addition to the cavities 1015, the staple cartridge body 1010 can further comprise one or more voids, such as voids 1016, for example, which may or may not comprise a portion of a staple positioned therein, that can be configured to allow the cartridge body 1010 to collapse. In various embodiments, the cavities 1015 and/or the voids 1016 can be configured to collapse such that the walls defining the cavities and/or walls deflect downwardly and contact the cartridge support surface 1031 and/or contact a layer of the cartridge body 1010 positioned underneath the cavities and/or voids.

Upon comparing FIG. 18B and FIG. 18C, it is evident that the second layer 1012 and the fourth layer 1014 have been substantially compressed by the compressive pressure applied by the anvil 1040. It may also be noted that the first layer 1011 and the third layer 1013 have been compressed as well. As the anvil 1040 is moved into its closed position, the anvil 1040 may continue to further compress the cartridge body 1010 by pushing the tissue-contacting surface 1019 downwardly toward the staple cartridge support 1030. As the cartridge body 1010 is further compressed, the anvil 1040 can deform the staples 1020 into their completely-formed shape as illustrated in FIG. 18D. Referring to FIG. 18D, the legs 1021 of each staple 1020 can be deformed downwardly toward the base 1022 of each staple 1020 in order to capture at least a portion of the tissue T, the first layer 1011, the second layer 1012, the third layer 1013, and the fourth layer 1014 between the deformable legs 1021 and the base 1022. Upon comparing FIGS. 18C and 18D, it is further evident that the second layer 1012 and the fourth layer 1014 have been further substantially compressed by the compressive pressure applied by the anvil 1040. It may also be noted upon comparing FIGS. 18C and 18D that the first layer 1011 and the third layer 1013 have been further compressed as well. After the staples 1020 have been completely, or at least sufficiently, formed, the anvil 1040 can be lifted away from the tissue T and the staple cartridge support 1030 can be moved away, and/or detached from, the staple cartridge 1000. As depicted in FIG. 18D, and as a result of the above, the cartridge body 1010 can be implanted with the staples 1020. In various circumstances, the implanted cartridge body 1010 can support the tissue along the staple line. In some circumstances, a haemostatic agent, and/or any other suitable therapeutic medicament, contained within the implanted cartridge body 1010 can treat the tissue over time. A haemostatic agent, as mentioned above, can reduce the bleeding of the stapled and/or incised tissue while a bonding agent or tissue adhesive can provide strength to the tissue over time. The implanted cartridge body 1010 can be comprised of materials such as ORC (oxidized regenerated cellulose), extracellular proteins such as collagen, polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. In certain circumstances, the cartridge body 1010 can comprise an antibiotic and/or anti-microbial material, such as colloidal silver and/or triclosan, for example, which can reduce the possibility of infection in the surgical site.

In various embodiments, the layers of the cartridge body 1010 can be connected to one another. In at least one embodiment, the second layer 1012 can be adhered to the first layer 1011, the third layer 1013 can be adhered to the second layer 1012, and the fourth layer 1014 can be adhered to the third layer 1013 utilizing at least one adhesive, such as fibrin and/or protein hydrogel, for example. In certain embodiments, although not illustrated, the layers of the cartridge body 1010 can be connected together by interlocking mechanical features. In at least one such embodiment, the first layer 1011 and the second layer 1012 can each comprise corresponding interlocking features, such as a tongue and groove arrangement and/or a dovetail joint arrangement, for example. Similarly, the second layer 1012 and the third layer 1013 can each comprise corresponding interlocking features while the third layer 1013 and the fourth layer 1014 can each comprise corresponding interlocking features. In certain embodiments, although not illustrated, the staple cartridge 1000 can comprise one or more rivets, for example, which can extend through one or more layers of the cartridge body 1010. In at least one such embodiment, each rivet can comprise a first end, or head, positioned adjacent to the first layer 1011 and a second head positioned adjacent to the fourth layer 1014 which can be either assembled to or formed by a second end of the rivet. Owing to the compressible nature of the cartridge body 1010, in at least one embodiment, the rivets can compress the cartridge body 1010 such that the heads of the rivets can be recessed relative to the tissue-contacting surface 1019 and/or the bottom surface 1018 of the cartridge body 1010, for example. In at least one such embodiment, the rivets can be comprised of a bioabsorbable material, such as polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. In certain embodiments, the layers of the cartridge body 1010 may not be connected to one another other than by the staples 1020 contained therein. In at least one such embodiment, the frictional engagement between the staple legs 1021 and the cartridge body 1010, for example, can hold the layers of the cartridge body 1010 together and, once the staples have been formed, the layers can be captured within the staples 1020. In certain embodiments, at least a portion of the staple legs 1021 can comprise a roughened surface or rough coating which can increase the friction forces between the staples 1020 and the cartridge body 1010.

As described above, a surgical instrument can comprise a first jaw including the staple cartridge support 1030 and a second jaw including the anvil 1040. In various embodiments, as described in greater detail further below, the staple cartridge 1000 can comprise one or more retention features which can be configured to engage the staple cartridge support 1030 and, as a result, releasably retain the staple cartridge 1000 to the staple cartridge support 1030. In certain embodiments, the staple cartridge 1000 can be adhered to the staple cartridge support 1030 by at least one adhesive, such as fibrin and/or protein hydrogel, for example. In use, in at least one circumstance, especially in laparoscopic and/or endoscopic surgery, the second jaw can be moved into a closed position opposite the first jaw, for example, such that the first and second jaws can be inserted through a trocar into a surgical site. In at least one such embodiment, the trocar can define an approximately 5 mm aperture, or cannula, through which the first and second jaws can be inserted. In certain embodiments, the second jaw can be moved into a partially-closed position intermediate the open position and the closed position which can allow the first and second jaws to be inserted through the trocar without deforming the staples 1020 contained in the staple cartridge body 1010. In at least one such embodiment, the anvil 1040 may not apply a compressive force to the staple cartridge body 1010 when the second jaw is in its partially-closed intermediate position while, in certain other embodiments, the anvil 1040 can compress the staple cartridge body 1010 when the second jaw is in its partially-closed intermediate position. Even though the anvil 1040 can compress the staple cartridge body 1010 when it is in such an intermediate position, the anvil 1040 may not sufficiently compress the staple cartridge body 1010 such that the anvil 1040 comes into contact with the staples 1020 and/or such that the staples 1020 are deformed by the anvil 1040. Once the first and second jaws have been inserted through the trocar into the surgical site, the second jaw can be opened once again and the anvil 1040 and the staple cartridge 1000 can be positioned relative to the targeted tissue as described above.

Figure 19A:
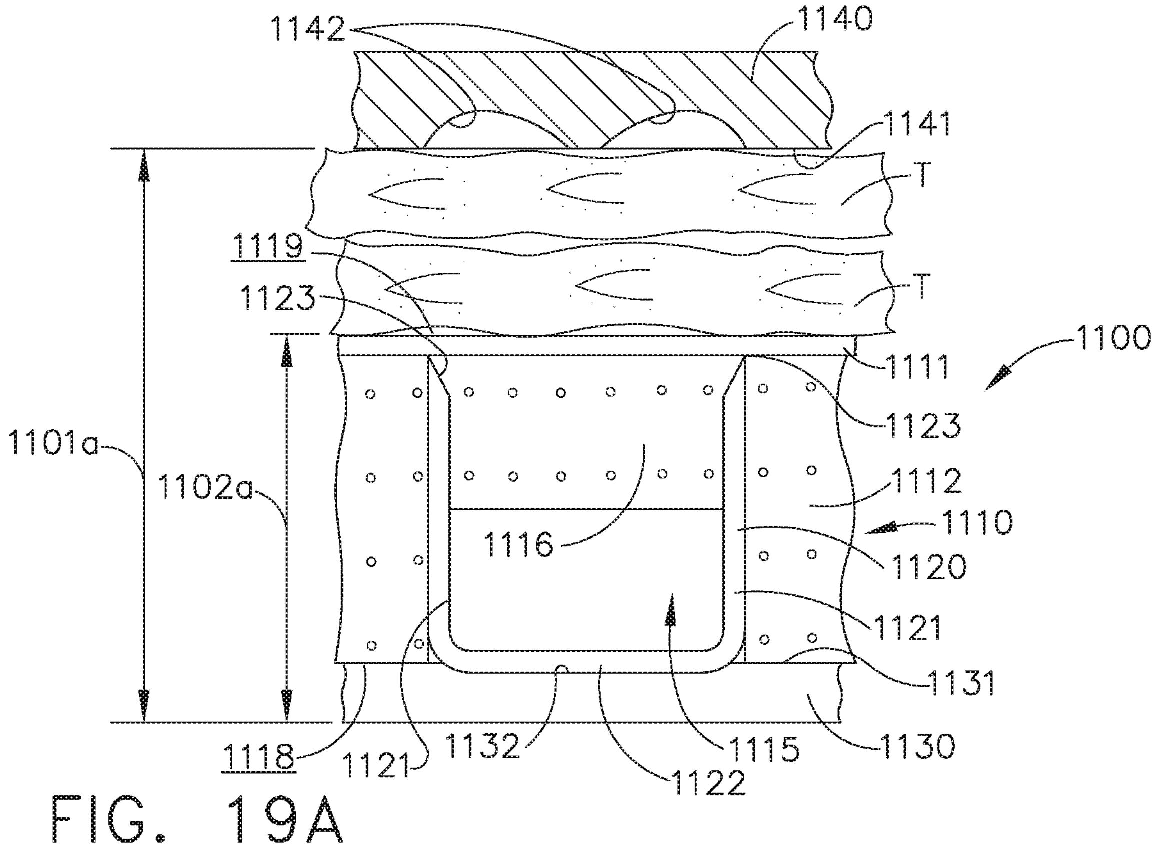
FIG. 19A is a diagram illustrating a staple positioned in a crushable staple cartridge body.
Figure 19B:
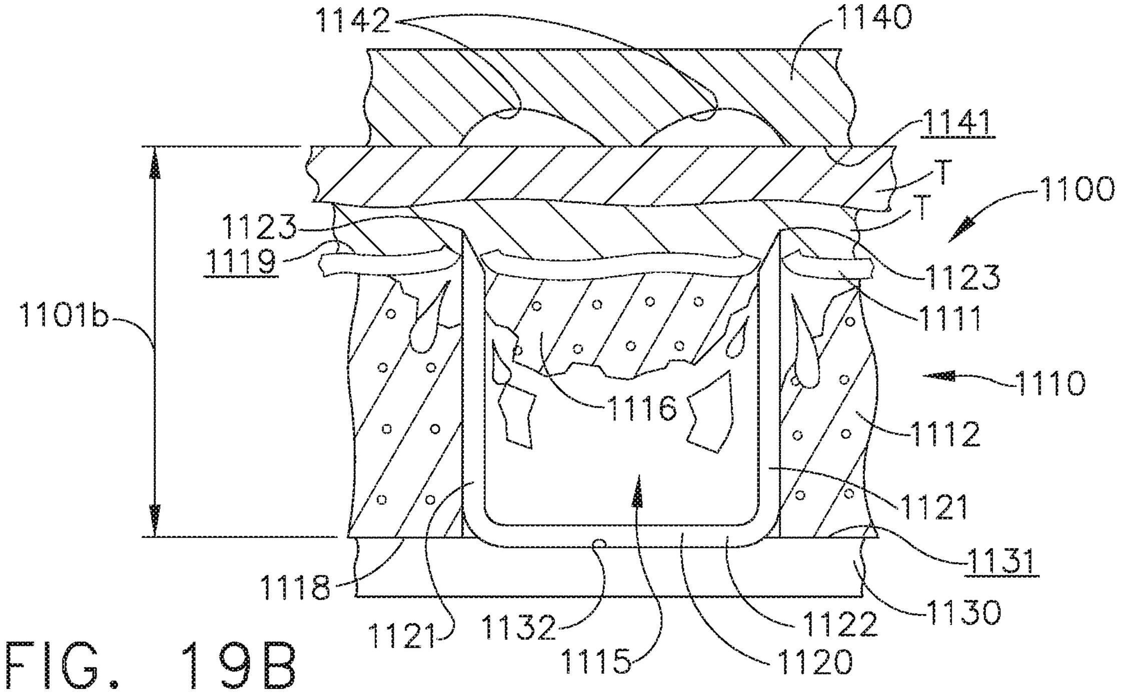
FIG. 19B is a diagram illustrating the crushable staple cartridge body of FIG. 19A being crushed by an anvil.
Figure 19C:
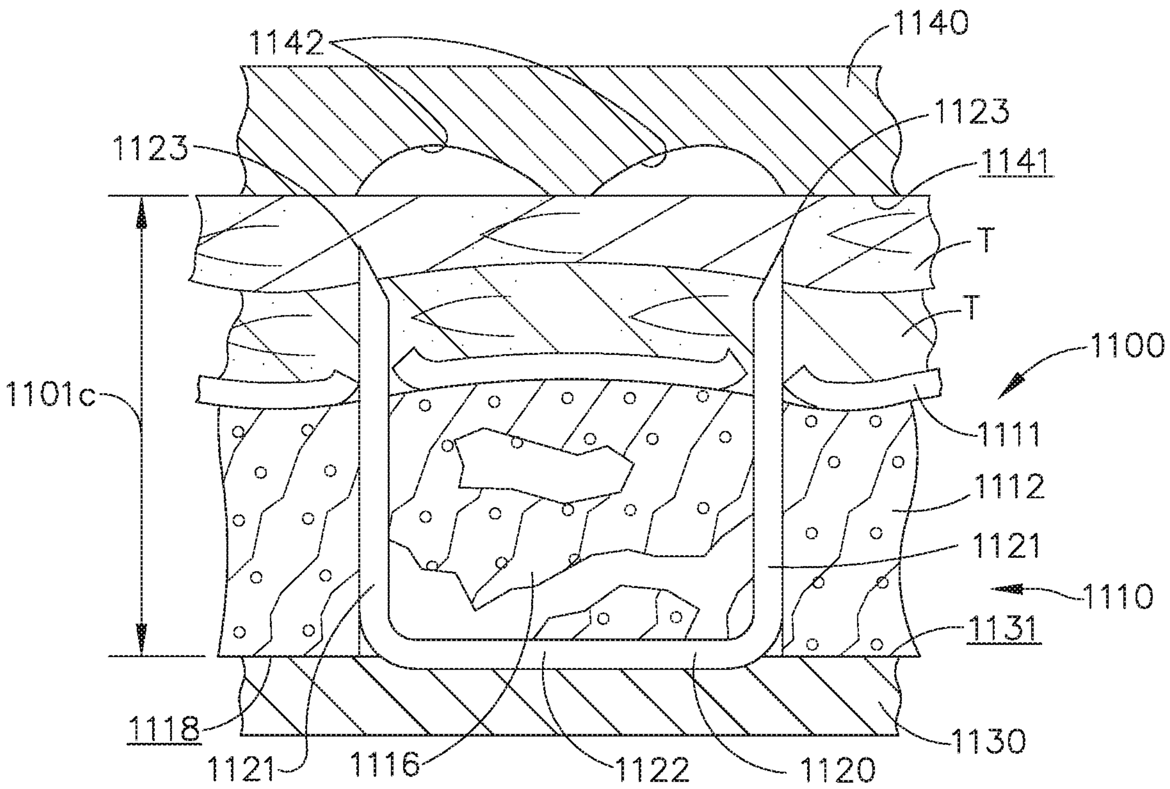
FIG. 19C is a diagram illustrating the crushable staple cartridge body of FIG. 19A being further crushed by the anvil.

In various embodiments, referring now to FIGS. 19A-19D, an end effector of a surgical stapler can comprise an implantable staple cartridge 1100 positioned intermediate an anvil 1140 and a staple cartridge support 1130. Similar to the above, the anvil 1140 can comprise a tissue-contacting surface 1141, the staple cartridge 1100 can comprise a tissue-contacting surface 1119, and the staple cartridge support 1130 can comprise a support surface 1131 which can be configured to support the staple cartridge 1100. Referring to FIG. 19A, the anvil 1140 can be utilized to position the tissue T against the tissue contacting surface 1119 of staple cartridge 1100 without deforming the staple cartridge 1100 and, when the anvil 1140 is in such a position, the tissue-contacting surface 1141 can be positioned a distance 1101*a* away from the staple cartridge support surface 1131 and the tissue-contacting surface 1119 can be positioned a distance 1102*a* away from the staple cartridge support surface 1131. Thereafter, as the anvil 1140 is moved toward the staple cartridge support 1130, referring now to FIG. 19B, the anvil 1140 can push the top surface, or tissue-contacting surface 1119, of staple cartridge 1100 downwardly and compress the first layer 1111 and the second layer 1112 of cartridge body 1110. As the layers 1111 and 1112 are compressed, referring again to FIG. 19B, the second layer 1112 can be crushed and the legs 1121 of staples 1120 can pierce the first layer 1111 and enter into the tissue T. In at least one such embodiment, the staples 1120 can be at least partially positioned within staple cavities, or voids, 1115 in the second layer 1112 and, when the second layer 1112 is compressed, the staple cavities 1115 can collapse and, as a result, allow the second layer 1112 to collapse around the staples 1120. In various embodiments, the second layer 1112 can comprise cover portions 1116 which can extend over the staple cavities 1115 and enclose, or at least partially enclose, the staple cavities 1115. FIG. 19B illustrates the cover portions 1116 being crushed downwardly into the staple cavities 1115. In certain embodiments, the second layer 1112 can comprise one or more weakened portions which can facilitate the collapse of the second layer 1112. In various embodiments, such weakened portions can comprise score marks, perforations, and/or thin cross-sections, for example, which can facilitate a controlled collapse of the cartridge body 1110. In at least one embodiment, the first layer 1111 can comprise one or more weakened portions which can facilitate the penetration of the staple legs 1121 through the first layer 1111. In various embodiments, such weakened portions can comprise score marks, perforations, and/or thin cross-sections, for example, which can be aligned, or at least substantially aligned, with the staple legs 1121.

Figure 19D:
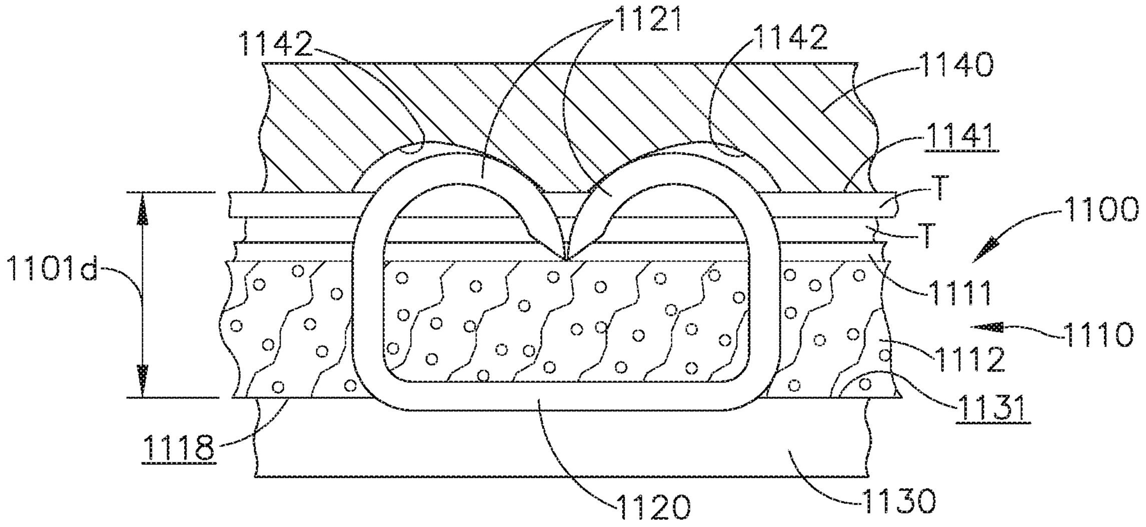
FIG. 19D is a diagram illustrating the staple of FIG. 19A in a fully formed configuration and the crushable staple cartridge of FIG. 19A in a fully crushed condition.

When the anvil 1140 is in a partially closed, unfired position, referring again to FIG. 19A, the anvil 1140 can be positioned a distance 1101*a* away from the cartridge support surface 1131 such that a gap is defined therebetween. This gap can be filled by the staple cartridge 1100, having a staple cartridge height 1102*a*, and the tissue T. As the anvil 1140 is moved downwardly to compress the staple cartridge 1100, referring again to FIG. 19B, the distance between the tissue contacting surface 1141 and the cartridge support surface 1131 can be defined by a distance 1101*b* which is shorter than the distance 1101*a*. In various circumstances, the gap between the tissue-contacting surface 1141 of anvil 1140 and the cartridge support surface 1131, defined by distance 1101*b*, may be larger than the original, undeformed staple cartridge height 1102*a*. As the anvil 1140 is moved closer to the cartridge support surface 1131, referring now to FIG. 19C, the second layer 1112 can continue to collapse and the distance between the staple legs 1121 and the forming pockets 1142 can decrease. Similarly, the distance between the tissue-contacting surface 1141 and the cartridge support surface 1131 can decrease to a distance 1101*c* which, in various embodiments, may be greater than, equal to, or less than the original, undeformed cartridge height 1102*a*. Referring now to FIG. 19D, the anvil 1140 can be moved into a final, fired position in which the staples 1120 have been fully formed, or at least formed to a desired height. In such a position, the tissue-contacting surface 1141 of anvil 1140 can be a distance 1101*d* away from the cartridge support surface 1131, wherein the distance 1101*d* can be shorter than the original, undeformed cartridge height 1102*a*. As also illustrated in FIG. 19D, the staple cavities 1115 may be fully, or at least substantially, collapsed and the staples 1120 may be completely, or at least substantially, surrounded by the collapsed second layer 1112. In various circumstances, the anvil 1140 can be thereafter moved away from the staple cartridge 1100. Once the anvil 1140 has been disengaged from the staple cartridge 1100, the cartridge body 1110 can at least partially re-expand in various locations, i.e., locations intermediate adjacent staples 1120, for example. In at least one embodiment, the crushed cartridge body 1110 may not resiliently re-expand. In various embodiments, the formed staples 1120 and, in addition, the cartridge body 1110 positioned intermediate adjacent staples 1120 may apply pressure, or compressive forces, to the tissue T which may provide various therapeutic benefits.

As discussed above, referring again to the embodiment illustrated in FIG. 19A, each staple 1120 can comprise staple legs 1121 extending therefrom. Although staples 1120 are depicted as comprising two staple legs 1121, various staples can be utilized which can comprise one staple leg or, alternatively, more than two staple legs, such as three staple legs or four staple legs, for example. As illustrated in FIG. 19A, each staple leg 1121 can be embedded in the second layer 1112 of the cartridge body 1110 such that the staples 1120 are secured within the second layer 1112. In various embodiments, the staples 1120 can be inserted into the staple cavities 1115 in cartridge body 1110 such that the tips 1123 of the staple legs 1121 enter into the cavities 1115 before the bases 1122. After the tips 1123 have been inserted into the cavities 1115, in various embodiments, the tips 1123 can be pressed into the cover portions 1116 and incise the second layer 1112. In various embodiments, the staples 1120 can be seated to a sufficient depth within the second layer 1112 such that the staples 1120 do not move, or at least substantially move, relative to the second layer 1112. In certain embodiments, the staples 1120 can be seated to a sufficient depth within the second layer 1112 such that the bases 1122 are positioned or embedded within the staple cavities 1115. In various other embodiments, the bases 1122 may not be positioned or embedded within the second layer 1112. In certain embodiments, referring again to FIG. 19A, the bases 1122 may extend below the bottom surface 1118 of the cartridge body 1110. In certain embodiments, the bases 1122 can rest on, or can be directly positioned against, the cartridge support surface 1130. In various embodiments, the cartridge support surface 1130 can comprise support features extending therefrom and/or defined therein wherein, in at least one such embodiment, the bases 1122 of the staples 1120 may be positioned within and supported by one or more support grooves, slots, or troughs, 1132, for example, in the staple cartridge support 1130, as described in greater detail further below.

Figure 20:
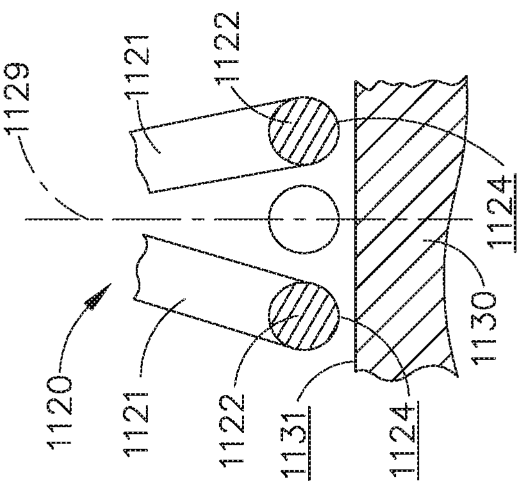
FIG. 20 is a diagram depicting a staple positioned against a staple cartridge support surface and illustrating potential relative movement therebetween.
Figure 21:
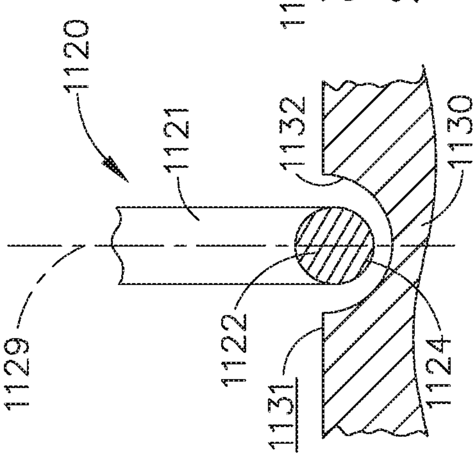
FIG. 21 is a cross-sectional view of a staple cartridge support surface comprising a slot, or trough, configured to stabilize the base of the staple of FIG. 20.

Further to the above, referring now to FIG. 20, the bases 1122 of the staples 1120 can be positioned directly against the support surface 1131 of staple cartridge support 1130. In various embodiments, including embodiments where the staple bases 1122 comprise circular or arcuate bottom surfaces 1124, for example, the staple bases 1122 may move or slide along the staple cartridge support surface 1131. Such sliding can occur when the anvil 1140 is pressed against the tips 1123 of the staple legs 1121 during the staple forming process. In certain embodiments, as described above and referring now to FIG. 21, the staple cartridge support 1130 can comprise one or more support slots 1132 therein which can be configured to eliminate, or at least reduce, the relative movement between the staple bases 1122 and the cartridge support surface 1131. In at least one such embodiment, each support slot 1132 can be defined by a surface contour which matches, or at least substantially matches, the contour of the bottom surface of the staple positioned therein. For example, the bottom surface 1124 of the base 1122 depicted in FIG. 21 can comprise a circular, or at least substantially circular, surface and the support slot 1132 can also comprise a circular, or at least substantially circular, surface. In at least one such embodiment, the surface defining the slot 1132 can be defined by a radius of curvature which is greater than or equal to a radius of curvature which defines bottom surface 1124. Although the slots 1132 may assist in preventing or reducing relative sliding movement between the staples 1120 and the staple cartridge support 1130, the slots 1132 may also be configured to prevent or reduce relative rotational movement between the staples 1120 and the staple cartridge support 1130. More particularly, in at least one embodiment, the slots 1132 can be configured to closely receive the bases 1122 in order to prevent or reduce the rotation of the staples 1120 about axes 1129, for example, such that the staples 1120 do not rotate or twist when they are being deformed.

Figure 22:
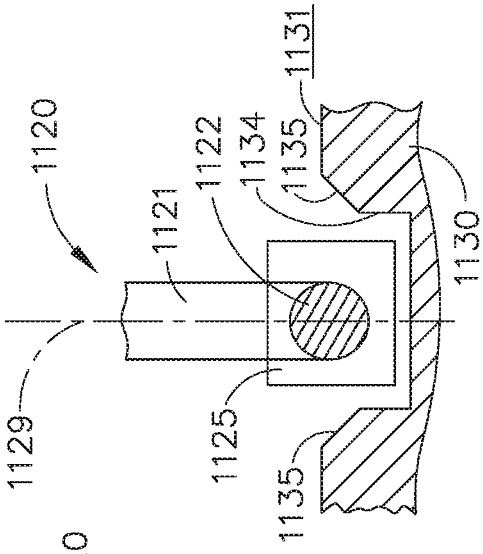
FIG. 22 is a cross-sectional view of a staple comprising an overmolded crown and a slot, or trough, configured to receive a portion of the crown in accordance with at least one alternative embodiment.

In various embodiments, further to the above, each staple 1120 can be formed from a round, or an at least substantially round, wire. In certain embodiments, the legs and the base of each staple can be formed from a wire having a non-circular cross-section, such as a rectangular cross-section, for example. In at least one such embodiment, the staple cartridge support 1130 can comprise corresponding non-circular slots, such as rectangular slots, for example, configured to receive the bases of such staples. In various embodiments, referring now to FIG. 22, each staple 1120 can comprise a crown, such as a crown 1125, for example, overmolded onto a base 1122 wherein each crown 1125 can be positioned within a support slot in the staple cartridge support 1130. In at least one such embodiment, each crown 1125 can comprise a square and/or rectangular cross-section, for example, which can be configured to be received within square and/or rectangular slots 1134, for example, in the staple cartridge support 1130. In various embodiments, the crowns 1125 can be comprised of a bioabsorbable plastic, such as polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example, and can be formed around the bases 1122 of the staples 1120 by an injection molding process, for example. Various crowns and methods for forming various crowns are disclosed in U.S. patent application Ser. No. 11/541,123, entitled SURGICAL STAPLES HAVING COMPRESSIBLE OR CRUSHABLE MEMBERS FOR SECURING TISSUE THEREIN AND STAPLING INSTRUMENTS FOR DEPLOYING THE SAME, filed on Sep. 29, 2006, now U.S. Pat. No. 7,794,475, the entire disclosure of which is incorporated be reference herein. Referring again to FIG. 22, the slots 1134 can further comprise lead-ins, or bevels, 1135 which can be configured to facilitate the insertion of the crowns 1125 into the slots 1134. In various embodiments, the bases and/or crowns of the staples 1120 may be positioned within the slots 1134 when the staple cartridge 1100 is assembled to the staple cartridge support 1130. In certain embodiments, the crowns 1125 of the staples 1120 may be aligned with the slots 1134 when the staple cartridge 1100 is assembled to the staple cartridge support 1130. In at least one such embodiment, the crowns 1125 may not enter into the slots 1134 until a compressive force is applied to the staple legs 1121 and the bases and/or crowns of the staples 1120 are pushed downwardly into the slots 1134.

Figure 23:
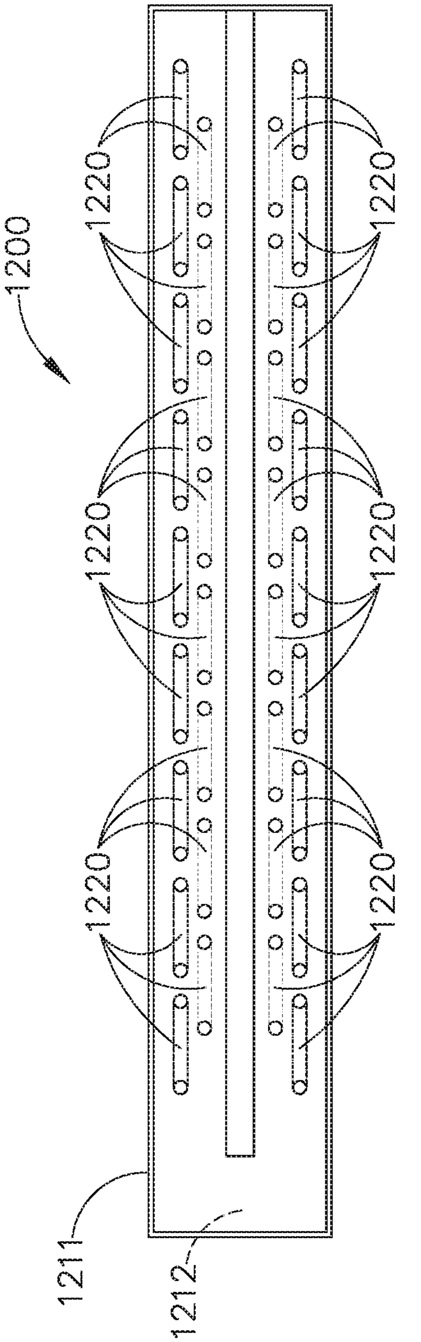
FIG. 23 is a top view of a staple cartridge in accordance with at least one embodiment comprising staples embedded in a collapsible staple cartridge body.
Figure 24:
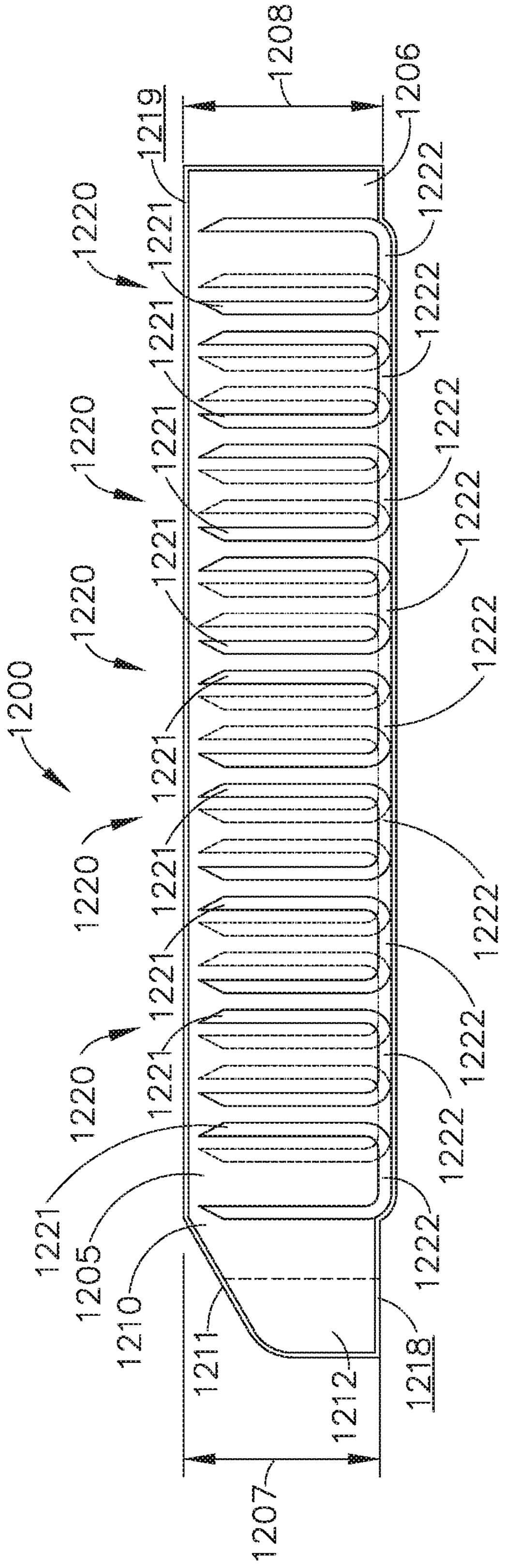
FIG. 24 is an elevational view of the staple cartridge of FIG. 23.

In various embodiments, referring now to FIGS. 23 and 24, a staple cartridge, such as staple cartridge 1200, for example, can comprise a compressible, implantable cartridge body 1210 comprising an outer layer 1211 and an inner layer 1212. Similar to the above, the staple cartridge 1200 can comprise a plurality of staples 1220 positioned within the cartridge body 1210. In various embodiments, each staple 1220 can comprise a base 1222 and one or more staple legs 1221 extending therefrom. In at least one such embodiment, the staple legs 1221 can be inserted into the inner layer 1212 and seated to a depth in which the bases 1222 of the staples 1220 abut and/or are positioned adjacent to the bottom surface 1218 of the inner layer 1212, for example. In the embodiment depicted in FIGS. 23 and 24, the inner layer 1212 does not comprise staple cavities configured to receive a portion of the staples 1220 while, in other embodiments, the inner layer 1212 can comprise such staple cavities. In various embodiments, further to the above, the inner layer 1212 can be comprised of a compressible material, such as bioabsorbable foam and/or oxidized regenerated cellulose (ORC), for example, which can be configured to allow the cartridge body 1210 to collapse when a compressive load is applied thereto. In various embodiments, the inner layer 1212 can be comprised of a lyophilized foam comprising polylactic acid (PLA) and/or polyglycolic acid (PGA), for example. The ORC may be commercially available under the trade name Surgicel and can comprise a loose woven fabric (like a surgical sponge), loose fibers (like a cotton ball), and/or a foam. In at least one embodiment, the inner layer 1212 can be comprised of a material including medicaments, such as freeze-dried thrombin and/or fibrin, for example, contained therein and/or coated thereon which can be water-activated and/or activated by fluids within the patient's body, for example. In at least one such embodiment, the freeze-dried thrombin and/or fibrin can be held on a Vicryl (PGA) matrix, for example. In certain circumstances, however, the activatable medicaments can be unintentionally activated when the staple cartridge 1200 is inserted into a surgical site within the patient, for example. In various embodiments, referring again to FIGS. 23 and 24, the outer layer 1211 can be comprised of a water impermeable, or at least substantially water impermeable, material such that liquids do not come into contact with, or at least substantially contact, the inner layer 1212 until after the cartridge body 1210 has been compressed and the staple legs have penetrated the outer layer 1211 and/or after the outer layer 1211 has been incised in some fashion. In various embodiments, the outer layer 1211 can be comprised of a buttress material and/or plastic material, such as polydioxanone (PDS) and/or polyglycolic acid (PGA), for example. In certain embodiments, the outer layer 1211 can comprise a wrap which surrounds the inner layer 1212 and the staples 1220. More particularly, in at least one embodiment, the staples 1220 can be inserted into the inner layer 1212 and the outer layer 1211 can be wrapped around the sub-assembly comprising the inner layer 1212 and the staples 1220 and then sealed.

Figure 25:
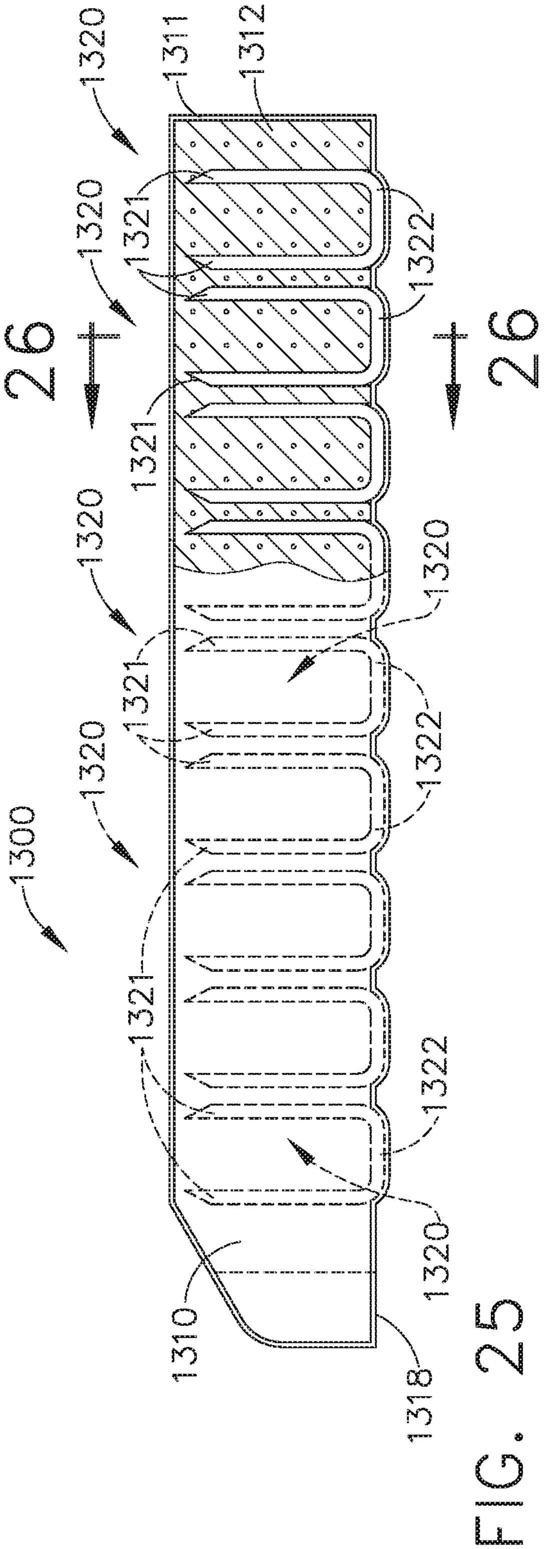
FIG. 25 is an elevational view of a staple cartridge in accordance with at least one embodiment comprising a protective layer surrounding staples positioned within a collapsible staple cartridge body.
Figure 26:
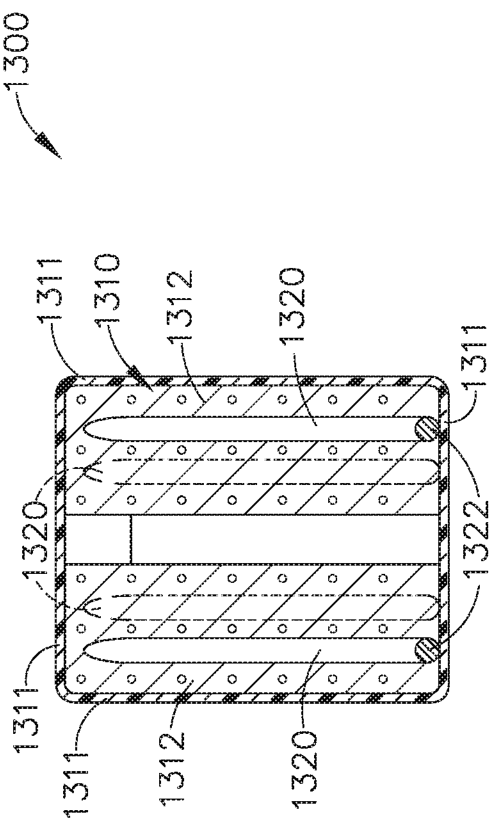
FIG. 26 is a cross-sectional view of the staple cartridge of FIG. 25 taken along line 26-26 in FIG. 25.

In various embodiments, referring now to FIGS. 25 and 26, a staple cartridge, such as staple cartridge 1300, for example, can comprise a compressible, implantable cartridge body 1310 including an outer layer 1311 and an inner layer 1312. Similar to the above, the staple cartridge 1300 can further comprise staples 1320 positioned within the cartridge body 1310 wherein each staple 1320 can comprise a base 1322 and one or more legs 1321 extending therefrom.

Figure 27:
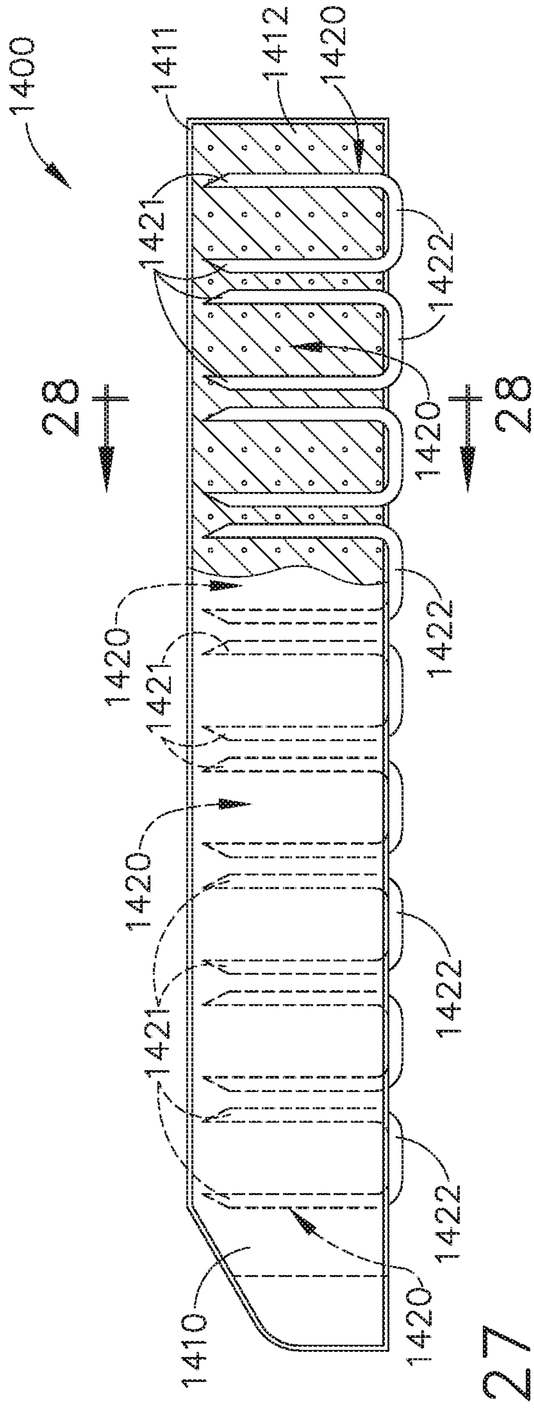
FIG. 27 is an elevational view of a staple cartridge in accordance with at least one embodiment comprising staples at least partially extending outside of a collapsible staple cartridge body and a protective layer surrounding the staple cartridge body.
Figure 28:
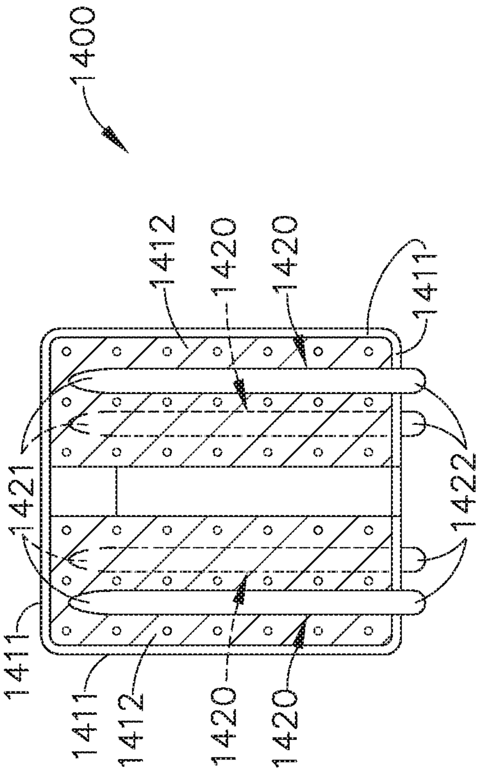
FIG. 28 is a cross-sectional view of the staple cartridge of FIG. 27 taken along line 28-28 in FIG. 27.

Similar to staple cartridge 1200, the bases 1322 of staples 1320 can extend below the bottom surface 1318 of the inner layer 1312 and the outer layer 1311 can surround the bases 1322. In at least one such embodiment, the outer layer 1311 can be sufficiently flexible so as to envelop each staple base 1322 such that the outer layer 1311 conforms to the contour of the bases 1322. In at least one alternative embodiment, referring again to FIG. 24, the outer layer 1211 can be sufficiently rigid such that it extends around the bases 1222 without conforming to each base 1222. In any event, in various embodiments, the outer layer 1311 can be positioned intermediate the bases 1322 of staples 1320 and a staple cartridge support surface, such as support surfaces 1031 or 1131, for example, supporting the staple cartridge 1300. In at least one such embodiment, the outer layer 1311 can be positioned intermediate the bases 1322 and support slots, such as slots 1032 or 1132, for example, defined in the staple cartridge support surface. In at least one such embodiment, further to the above, the outer layer 1311 can be configured to limit the movement of the bases 1322 and/or increase the coefficient of friction between the bases 1322 and the staple cartridge support surface and/or support slots in order to reduce relative movement therebetween. In various alternative embodiments, referring now to FIGS. 27 and 28, the outer layer of a staple cartridge, such as staple cartridge 1400, for example, may not entirely surround the staples positioned therein. In at least one such embodiment, an outer layer 1411 of a compressible, implantable cartridge body 1410 may be assembled to the inner layer 1412 before the staple legs 1421 of staples 1420 are inserted into the cartridge body 1410. As a result of the above, the bases 1422 of staples 1420 may extend outside of the outer layer 1411 and, in at least one such embodiment, the bases 1422 may be positioned directly into the support slots 1032 or 1132 within the staple cartridge support surfaces 1031 or 1131, for example. In various embodiments, the staple legs 1421 may incise the outer layer 1411 when they are inserted therethrough. In various circumstances, the holes created by the staple legs 1421 may closely surround the staple legs 1421 such that very little, if any, fluid can leak between the staple legs 1421 and the outer layer 1411 which can reduce the possibility of, or prevent, the medicament contained within the staple cartridge body 1410 from being activated and/or leaking out of the cartridge body 1410 prematurely.

As discussed above, referring again to FIGS. 23 and 24, the legs 1221 of the staples 1220 can be embedded within the cartridge body 1210 and the bases 1222 of staples 1220 may extend outwardly from the bottom surface 1218 of the inner layer 1212. In various embodiments, further to the above, the inner layer 1212 may not comprise staple cavities configured to receive the staples 1220. In various other embodiments, referring now to FIGS. 29 and 30, a staple cartridge, such as staple cartridge 1500, for example, may comprise a compressible, implantable cartridge body 1510 comprising staple cavities 1515 which can be configured to receive at least a portion of the staples 1520 therein. In at least one such embodiment, a top portion of the staple legs 1521 of the staples 1520 may be embedded in the inner layer 1512 while a bottom portion of the staple legs 1521, and the bases 1522, may be positioned within the staple cavities 1515. In certain embodiments, the bases 1522 may be entirely positioned in the staple cavities 1515 while, in some embodiments, the bases 1522 may at least partially extend below the bottom surface 1518 of the inner layer 1512. Similar to the above, the outer layer 1511 may enclose the inner layer 1512 and the staples 1520 positioned therein. In certain other embodiments, referring now to FIG. 31, a staple cartridge 1600 may comprise staples 1620 positioned within staple cavities 1615 in a compressible, implantable cartridge body 1610 wherein at least a portion of the staples 1620 are not enclosed by the outer layer 1611. In at least one such embodiment, each staple 1620 can comprise staple legs 1621 which are at least partially embedded in the inner layer 1612 and, in addition, bases 1622 which extend outwardly around the outer layer 1611.

In various embodiments, referring now to FIGS. 32 and 33, a staple cartridge, such as staple cartridge 1700, for example, can comprise a compressible, implantable cartridge body 1710 and a plurality of staples 1720 at least partially positioned within the cartridge body 1710. The cartridge body 1710 can comprise an outer layer 1711, an inner layer 1712, and, in addition, an alignment matrix 1740 which can be configured to align and/or retain the staples 1720 in position within the cartridge body 1710. In at least one embodiment, the inner layer 1712 can comprise a recess 1741 which can be configured to receive the alignment matrix 1740 therein. In various embodiments, the alignment matrix 1140 can be press-fit within the recess 1741 and/or otherwise suitably secured to the inner layer 1712 utilizing at least one adhesive, such as fibrin and/or protein hydrogel, for example. In at least one embodiment, the recess 1741 can be configured such that the bottom surface 1742 of alignment matrix 1740 is aligned, or at least substantially aligned, with the bottom surface 1718 of the inner layer 1712. In certain embodiments, the bottom surface 1742 of the alignment matrix can be recessed with respect to and/or extend from the bottom surface 1718 of the second layer 1712. In various embodiments, each staple 1720 can comprise a base 1722 and one or more legs 1721 extending from the base 1722, wherein at least a portion of the staple legs 1721 can extend through the alignment matrix 1740. The alignment matrix 1740 can further comprise a plurality of apertures and/or slots, for example, extending therethrough which can be configured to receive the staple legs 1721 therein. In at least one such embodiment, each aperture can be configured to closely receive a staple leg 1721 such that there is little, if any, relative movement between the staple leg 1721 and the sidewalls of the aperture. In certain embodiments, the alignment matrix apertures may not extend entirely through the alignment matrix 1740 and the staple legs 1721 may be required to incise the alignment matrix 1740 as the staple legs 1721 are pushed therethrough.

In various embodiments, the alignment matrix 1740 can be comprised of a molded plastic body which, in at least one embodiment, can be stiffer or less compressible than the inner layer 1712 and/or the outer layer 1711. In at least one such embodiment, the alignment matrix 1740 can be comprised of a plastic material and/or any other suitable material, such as polydioxanone (PDS) and/or polyglycolic acid (PGA), for example. In certain embodiments, the alignment matrix 1740 can be assembled to the inner layer 1712 and the staple legs 1721 can thereafter be inserted through the alignment matrix 1740 and embedded into the inner layer 1712. In various embodiments, the bottom surface 1742 of the alignment matrix 1740 can comprise one or more grooves, slots, or troughs, for example, which can be configured to at least partially receive the bases 1722 of the staples 1720. Similar to the above, the outer layer 1711 can then be placed around the subassembly comprising the inner layer 1712, the alignment matrix 1740, and the staples 1720. Alternatively, the outer layer 1711 can be placed around a subassembly comprising the inner layer 1712 and the alignment matrix 1740 wherein the staples 1720 can be thereafter inserted through the outer layer 1711, the alignment matrix 1740, and the inner layer 1712. In any event, as a result of the above, the inner layer 1712, the alignment matrix 1740, and/or the outer layer 1711 can be configured to retain the staples 1720 in position until and/or after they are deformed by an anvil as described above. In at least one such embodiment, the alignment matrix 1740 can serve to hold the staples 1720 in place before the staple cartridge 1700 is implanted within a patient and, in addition, secure the tissue along the staple line after the staple cartridge 1700 has been implanted. In at least one embodiment, the staples 1720 may be secured within the alignment matrix 1740 without being embedded in the inner layer 1712 and/or the outer layer 1711, for example.

In various embodiments, referring now to FIGS. 34-40, a staple cartridge, such as staple cartridge 1800, for example, can be assembled by compressing an inner layer 1812, inserting staples, such as staples 1820, for example, into the inner layer 1812, and wrapping the inner layer 1812 with an outer layer 1811. Referring primarily to FIG. 34, a compressible inner layer 1812 is illustrated as comprising a plurality of staple cavities 1815 defined therein, although other embodiments are envisioned in which the inner layer 1812 does not comprise staple cavities, as described above. Referring now to FIG. 35, the compressible inner layer 1812 can be positioned intermediate a transfer plate 1850 and a support plate 1860 and compressed between the compression surfaces 1852 and 1862 thereof, respectively. As illustrated in FIG. 35, the top and bottom surfaces of the inner layer 1812 can be compressed toward one another and, in response thereto, the inner layer 1812 can bulge outwardly in the lateral directions. In certain embodiments, the inner layer 1812 can be compressed to a height which is approximately one-third of its original height, for example, and can have a height or thickness between approximately 0.06" and approximately 0.08" in its compressed state, for example. As also illustrated in FIG. 35, the transfer plate 1850 can further comprise a plurality of staples, such as staples 1820, for example, positioned within a plurality of staple wells 1853. In addition, the transfer plate 1850 can further comprise a plurality of drivers 1851 which can be configured to push the staples 1820 upwardly and out of the staple wells 1853. Referring now to FIG. 36, the drivers 1851 can be utilized to push the staple legs 1821 of the staples 1820 into and through the compressed inner layer 1812. In various embodiments, the drivers 1851 can be configured such that the top surfaces thereof are positioned flush, or at least nearly flush, with the compression surface 1852 of the transfer plate 1850 when the staples 1820 have been fully deployed from the staple wells 1853 of transfer plate 1850. In certain embodiments, as also illustrated in FIG. 36, the support plate 1860 can comprise a plurality of receiving apertures 1861 which can be configured to receive the staple legs 1821, or at least the tips of the staple legs 1821, after they are pushed through the inner layer 1812. The receiving apertures 1861, or the like, may be necessitated in embodiments where the inner layer 1812 has been compressed to a height which is shorter than the height of the staples 1820 and, thus, when the staples 1820 have been fully ejected from the staple wells 1853, the staple legs 1821 may protrude from the top surface of the compressed inner layer 1812. In certain other embodiments, the inner layer 1812 may be compressed to a height which is taller than the height of the staples 1820 and, as a result, the receiving apertures 1861 in support plate 1860 may be unnecessary.

Figure 37:
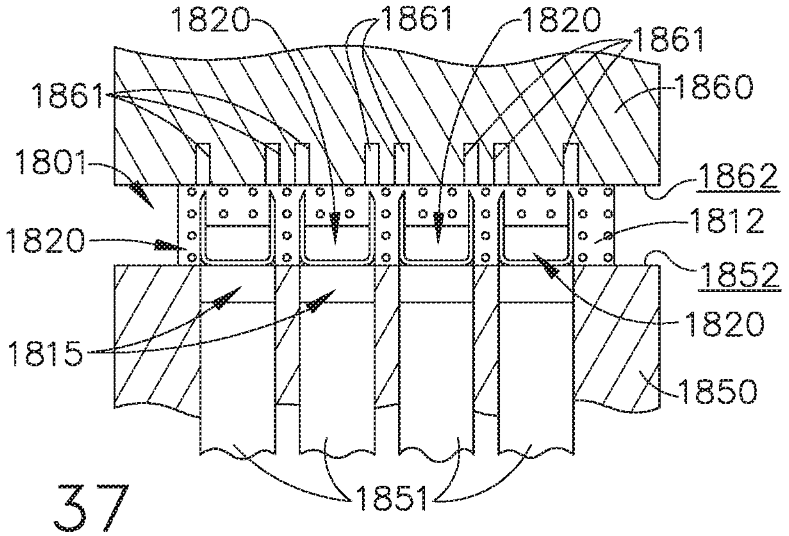
FIG. 37 is a diagram of the support plate of FIG. 35 being removed away from the inner layer.
Figure 38:
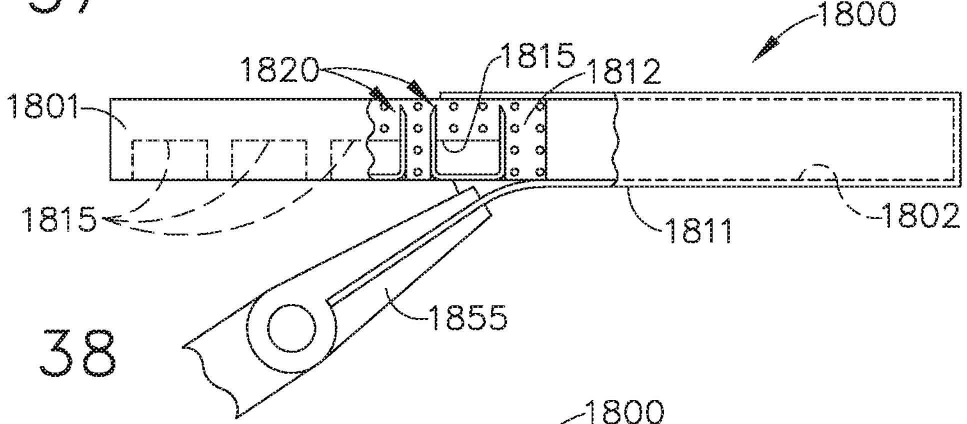
FIG. 38 is a diagram of a subassembly comprising the inner layer of FIG. 34 and the staples of FIG. 36 being inserted into an outer layer.
Figure 39:
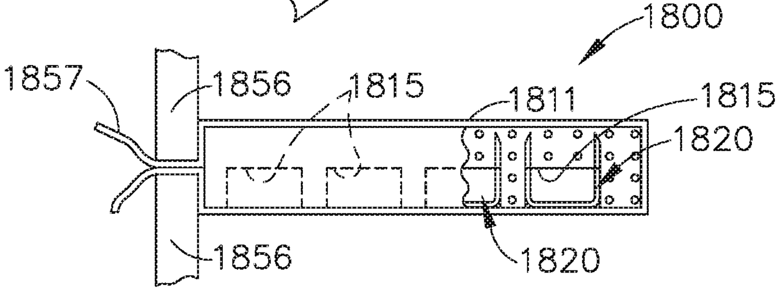
FIG. 39 is a diagram illustrating the outer layer of FIG. 38 being sealed to form a sealed staple cartridge.
Figure 40:
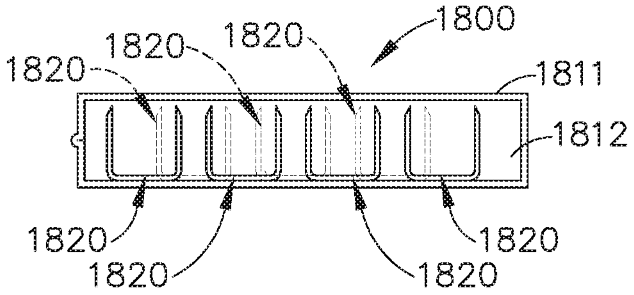
FIG. 40 is a cross-sectional view of the sealed staple cartridge of FIG. 39.

After the staples 1820 have been inserted into the inner layer 1812, referring now to FIG. 37, the support plate 1860 can be moved away from the transfer plate 1850 in order to allow the inner layer 1812 to decompress. In such circumstances, the inner layer 1812 can resiliently re-expand to its original, or at least near-original, uncompressed height. As the inner layer 1812 re-expands, the height of the inner layer 1812 can increase such that it exceeds the height of the staples 1820 and such that the staple legs 1821 of the staples 1820 no longer protrude from the top surface of the inner layer 1812. In various circumstances, the receiving apertures 1861 can be configured to hold the staple legs 1821 in position at least until the support plate 1860 has been sufficiently moved away such that the legs 1821 are no longer positioned within the receiving apertures 1861. In such circumstances, the receiving apertures 1861 can assist in maintaining the relative alignment of the staples 1820 within the inner layer 1812 as it re-expands. In various circumstances, the inner layer 1812 and the staples 1820 positioned therein can comprise a subassembly 1801 which, referring now to FIG. 38, can be inserted into an outer layer 1811, for example. In at least one such embodiment, the outer layer 1811 can comprise a cavity 1802 defined therein which can be configured to receive the subassembly 1801 therein. In various circumstances, a tool, such as pliers 1855, for example, can be utilized to pull the outer layer 1811 onto the subassembly 1801. Once the subassembly 1801 has been sufficiently positioned within the outer layer 1811, referring now to FIG. 39, the outer layer 1811 can be sealed. In various embodiments, the outer layer 1811 can be sealed utilizing the application of heat energy to a portion thereof. More particularly, in at least one embodiment, the outer layer 1811 can be comprised of a plastic material wherein the open end of the outer layer 1811 can be heat-staked by one or more heated elements, or irons, 1856 in order to bond and/or seal the perimeter of the open end of the outer layer 1811 together. In at least one such embodiment, referring now to FIG. 40, an excess portion 1857 of the outer layer 1811 can be removed and the staple cartridge 1800 can then be used as described herein.

Figure 41:
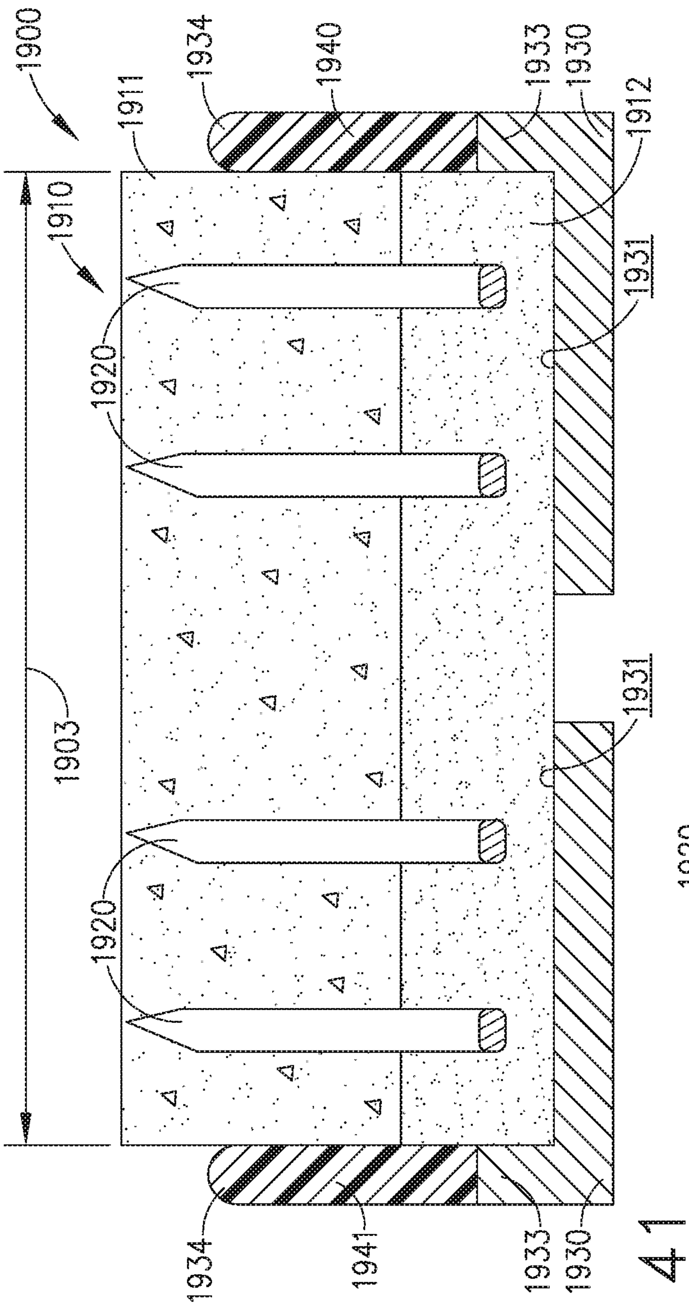
FIG. 41 is a cross-sectional view of a staple cartridge and staple cartridge channel in accordance with at least one embodiment.
Figure 42:
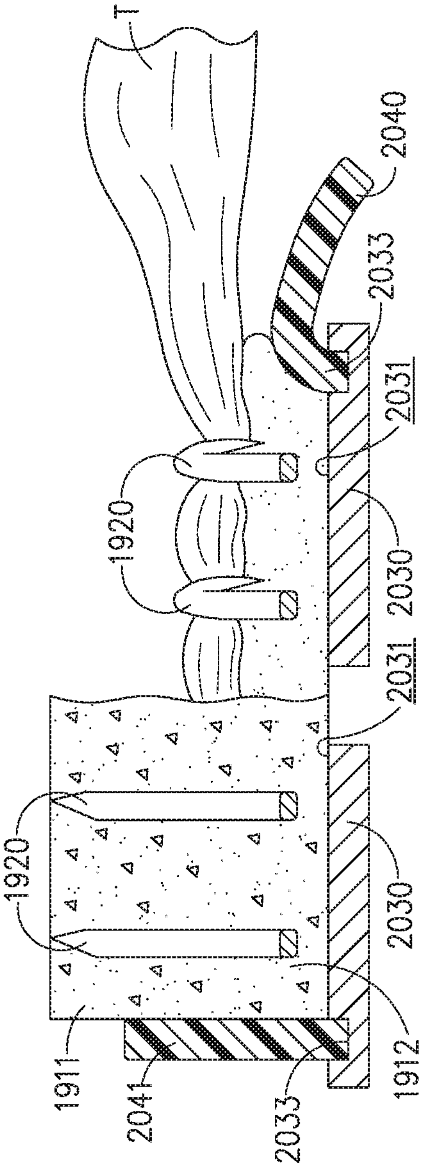
FIG. 42 is a diagram illustrating a portion of the staple cartridge of FIG. 41 in a deformed state.

As described above, a staple cartridge can be positioned within and/or secured to a staple cartridge attachment portion. In various embodiments, referring now to FIGS. 41 and 42, a staple cartridge attachment portion can comprise a staple cartridge channel, such as staple cartridge channel 1930, for example, which can be configured to receive at least a portion of a staple cartridge, such as staple cartridge 1900, for example, therein. In at least one embodiment, the staple cartridge channel 1930 can comprise a bottom support surface 1931, a first lateral support wall 1940, and a second lateral support wall 1941. In use, the staple cartridge 1900 can be positioned within the staple cartridge channel 1930 such that the staple cartridge 1900 is positioned against and/or adjacent to the bottom support surface 1931 and positioned intermediate the first lateral support wall 1940 and the second lateral support wall 1941. In certain embodiments, the first lateral support wall 1940 and the second lateral support wall 1941 can define a lateral gap therebetween. In at least one such embodiment, the staple cartridge 1900 can comprise a lateral width 1903 which is the same as and/or wider than the lateral gap defined between the support walls 1940 and 1941 such that a compressible, implantable cartridge body 1910 of the staple cartridge 1900 can fit securely between the walls 1940 and 1941. In certain other embodiments, the lateral width 1903 of the staple cartridge 1900 can be shorter than the gap defined between the first and second side walls 1940 and 1941. In various embodiments, at least a portion of the walls 1940 and 1941 and the bottom support surface 1931 can be defined by a stamped metal channel while, in at least one embodiment, at least a portion of the lateral support wall 1940 and/or lateral support wall 1941 can be comprised of a flexible material, such as an elastomeric material, for example. Referring primarily to FIG. 41, the first side wall 1940 and the second side wall 1941 of the staple cartridge channel 1930 can each be comprised of a rigid portion 1933 extending upwardly from the bottom support surface 1931 and a flexible portion 1934 extending upwardly from the rigid portions 1933.

In various embodiments, further to the above, the cartridge body 1910 of staple cartridge 1900 can be comprised of one or more compressible layers, such as first layer 1911 and second layer 1912, for example. When the cartridge body 1910 is compressed against the bottom support surface 1931 by an anvil, as described above, the side portions of the cartridge body 1910 can expand laterally. In embodiments where the staple cartridge 1930 is comprised of rigid side walls, the lateral expansion of the cartridge body 1910 can be prevented, or at least limited, by the rigid side walls and, as a result, a significant amount of internal pressure, or stress, can be developed within the cartridge body 1910. In embodiments where at least a portion of the staple cartridge 1930 is comprised of flexible side walls, the flexible side walls can be configured to flex laterally and permit the side portions of the cartridge body 1910 to expand laterally, thereby reducing the internal pressure, or stress, generated within the cartridge body 1910. In embodiments where the cartridge channel does not comprise lateral side walls, or comprises lateral sidewalls which are relatively shorter than the staple cartridge, the side portions of the staple cartridge may expand laterally uninhibited, or at least substantially uninhibited. In any event, referring now to FIG. 42, a staple cartridge channel 2030 can comprise lateral sidewalls 2040 and 2041 which can be entirely comprised of a flexible material, such as an elastomeric material, for example. The staple cartridge channel 2030 can further comprise lateral slots 2033 extending along the sides of the bottom support surface 2031 of the staple cartridge channel 2030 which can be configured to receive and secure at least a portion of the lateral sidewalls 2040 and 2041 therein. In certain embodiments, the lateral side walls 2040 and 2041 can be secured in the slots 2033 via a snap-fit and/or press-fit arrangement while, in at least some embodiments, the lateral side walls 2040 and 2041 can be secured in the slots 2033 by one or more adhesives. In at least one embodiment, the sidewalls 2040 and 2041 may be detachable from the bottom support surface 2031 during use. In any event, a compressible, implantable cartridge body 2010 can be detached and/or disengaged from the lateral side walls 2040 and 2041 when the cartridge body 2010 is implanted with the staples 2020.

Figure 43:
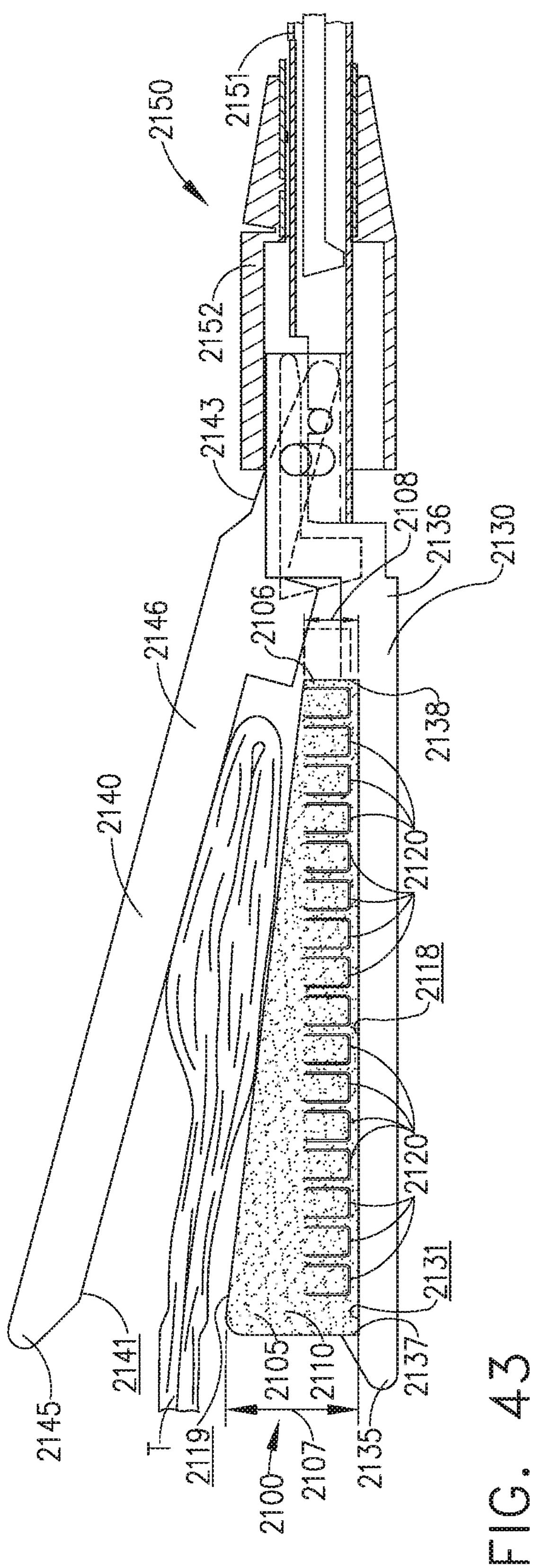
FIG. 43 is an elevational view of an end effector of a surgical stapler comprising an anvil in an open position and a staple cartridge positioned within a staple cartridge channel.

In various embodiments, referring now to FIG. 43, a surgical instrument can comprise a shaft 2150 and an end effector extending from the distal end of the shaft 2150. The end effector can comprise, similar to the above, a staple cartridge channel 2130, an anvil 2140 movable between an open position and a closed position, and a staple cartridge 2100 positioned intermediate the staple cartridge channel 2130 and the anvil 2140. Also similar to the above, the staple cartridge 2100 can comprise a compressible, implantable cartridge body 2110 and a plurality of staples 2120 positioned in the cartridge body 2110. In various embodiments, the staple cartridge channel 2130 can comprise, one, a bottom support surface 2131 against which the staple cartridge 2100 can be positioned, two, a distal end 2135 and, three, a proximal end 2136. In at least one embodiment, as illustrated in FIG. 43, the staple cartridge 2100 can comprise a first end 2105 which can be positionable in the distal end 2135 of the staple cartridge channel 2130 and a second end 2106 which can be positionable in the proximal end 2136 of the staple cartridge channel 2130. In various embodiments, the distal end 2135 of the staple cartridge channel 2130 can comprise at least one distal retention feature, such as a retention wall 2137, for example, and, similarly, the proximal end 2136 can comprise at least one proximal retention feature, such as a retention wall 2138, for example. In at least one such embodiment, the distal retention wall 2137 and the proximal retention wall 2138 can define a gap therebetween which can be equal to or less than the length of the staple cartridge 2100 such that the staple cartridge 2100 can fit securely within the staple cartridge channel 2130 when the staple cartridge 2100 is inserted therein.

In various embodiments, referring again to FIGS. 23 and 24, a staple cartridge, such as staple cartridge 1200, for example, can comprise a flat, or at least substantially flat, tissue-contacting surface 1219. In at least one such embodiment, the staple cartridge body 1210 of staple cartridge 1200 can comprise a first end 1205 which can be defined by a first height, or thickness, 1207 and a second end 1206 which can be defined by a second height, or thickness, 1208, wherein the first height 1207 can be equal to, or at least substantially equal to, the second height 1208. In certain embodiments, the cartridge body 1210 can comprise a constant, or at least substantially constant, height, or thickness, between the first end 1205 and the second end 1206. In at least one such embodiment, the tissue-contacting surface 1219 can be parallel, or at least substantially parallel, to the bottom surface 1218 of the cartridge body 1210. In various embodiments, referring once again to FIG. 43, the first end 2105 of the cartridge body 2110 of staple cartridge 2100 can be defined by a first height 2107 which is different than a second height 2108 of the second end 2106. In the illustrated embodiment, the first height 2107 is larger than the second height 2108, although the second height 2108 could be larger than the first height 2107 in alternative embodiments. In various embodiments, the height of the cartridge body 2110 can decrease linearly and/or geometrically between the first end 2105 and the second end 2106. In at least one such embodiment, the tissue-contacting surface 2119, which extends between the first end 2105 and the second end 2106, can be oriented along an angle defined therebetween. In at least one such embodiment, the tissue-contacting surface 2119 may not be parallel to the bottom surface 2118 of the cartridge body 2110 and/or parallel to the support surface 2131 of the staple cartridge channel 2130.

In various embodiments, referring again to FIGS. 43 and 44, the anvil 2140 can comprise a tissue-contacting surface 2141 which can be parallel, or at least substantially parallel, to the support surface 2131 of the staple cartridge channel 2130 when the anvil 2140 is in a closed position, as illustrated in FIG. 44. When the anvil 2140 is in a closed position, the anvil 2140 can be configured to compress the first end 2105 of the staple cartridge 2100 more than the second end 2106 owing to the taller height of the first end 2105 and the shorter height of the second end 2106. In some circumstances, including circumstances where the tissue T positioned intermediate the tissue contacting surfaces 2119 and 2141 has a constant, or at least substantially constant, thickness, the pressure generated within the tissue T and the cartridge 2100 can be greater at the distal end of the end effector than the proximal end of the end effector. More particularly, when the tissue T between the anvil 2140 and the staple cartridge 2100 has a substantially constant thickness, the tissue T positioned intermediate the distal end 2145 of the anvil 2140 and the first end 2105 of the staple cartridge 2100 can be more compressed than the tissue T positioned intermediate the proximal end 2146 of the anvil 2140 and the second end 2106 of the staple cartridge 2100. In various embodiments, a pressure gradient can be generated within the tissue T between the proximal end and the distal end of the end effector. More particularly, in at least one embodiment, when the tissue T between the anvil 2140 and the staple cartridge 2100 has a substantially constant thickness and the height of the staple cartridge 2100 decreases linearly from the distal end to the proximal end of the end effector, the pressure within the tissue T can decrease linearly from the distal end of the end effector to the proximal end of the end effector. Similarly, in at least one embodiment, when the tissue T between the anvil 2140 and the staple cartridge 2100 has a substantially constant thickness and the height of the staple cartridge 2100 decreases geometrically from the distal end to the proximal end of the end effector, the pressure within the tissue T can decrease geometrically from the distal end of the end effector to the proximal end of the end effector.

Figure 44:
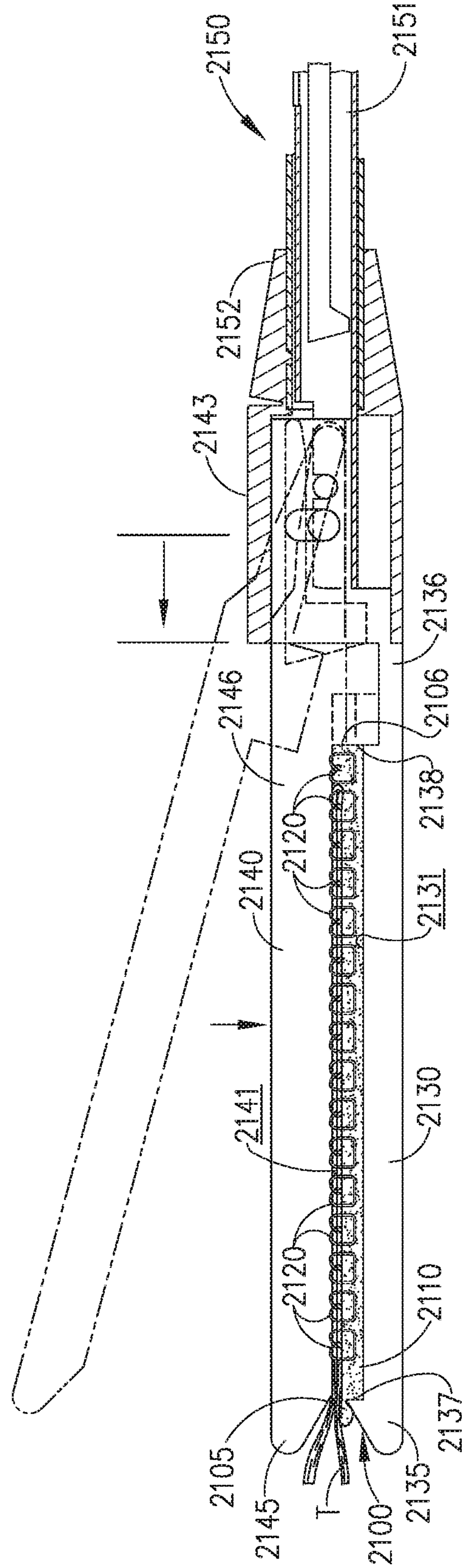
FIG. 44 is an elevational view of the end effector of FIG. 43 illustrating the anvil in a closed position and the staple cartridge compressed between the anvil and the staple cartridge channel.

In various embodiments, referring again to FIG. 43, the tissue T positioned intermediate the staple cartridge 2100 and the anvil 2140 may not have a constant thickness throughout. In at least one such circumstance, the tissue T positioned between the proximal end 2146 of the anvil 2140 and the second end 2106 of the staple cartridge 2100 may be thicker than the tissue T positioned between the distal end 2145 of the anvil 2140 and the first end 2105 of the staple cartridge 2100. In such circumstances, as a result, the thicker tissue T may be generally positioned above the shorter proximal end 2106 of the staple cartridge 2100 and the thinner tissue T may be generally positioned above the taller distal end 2105. In use, the firing collar 2152 of the shaft 2150 can be advanced distally along the shaft spine 2151 such that the firing collar 2152 engages the cam portion 2143 of the anvil 2140 and rotates the anvil 2140 toward the staple cartridge 2100 as illustrated in FIG. 44. Once the anvil 2140 has been rotated into a fully-closed position, the tissue T may be compressed between the tissue-contacting surfaces 2119 and 2141 and, even though the height of the staple cartridge 2100 may not be constant between the proximal and distal ends of the end effector, the pressure or compressive forces applied to the tissue T may be constant, or at least substantially constant, thereacross. More particularly, as the thinner tissue T may be associated with the taller height of the staple cartridge 2100 and the thicker tissue T may be associated with the shorter height of the staple cartridge 2100, the cumulative, or summed, height of the tissue T and the staple cartridge 2100 may be constant, or at least substantially constant, between the proximal and distal ends of the end effector and, as a result, the compression of this cumulative height by the anvil 2140 may be constant, or at least substantially constant, thereacross.

Figure 45:
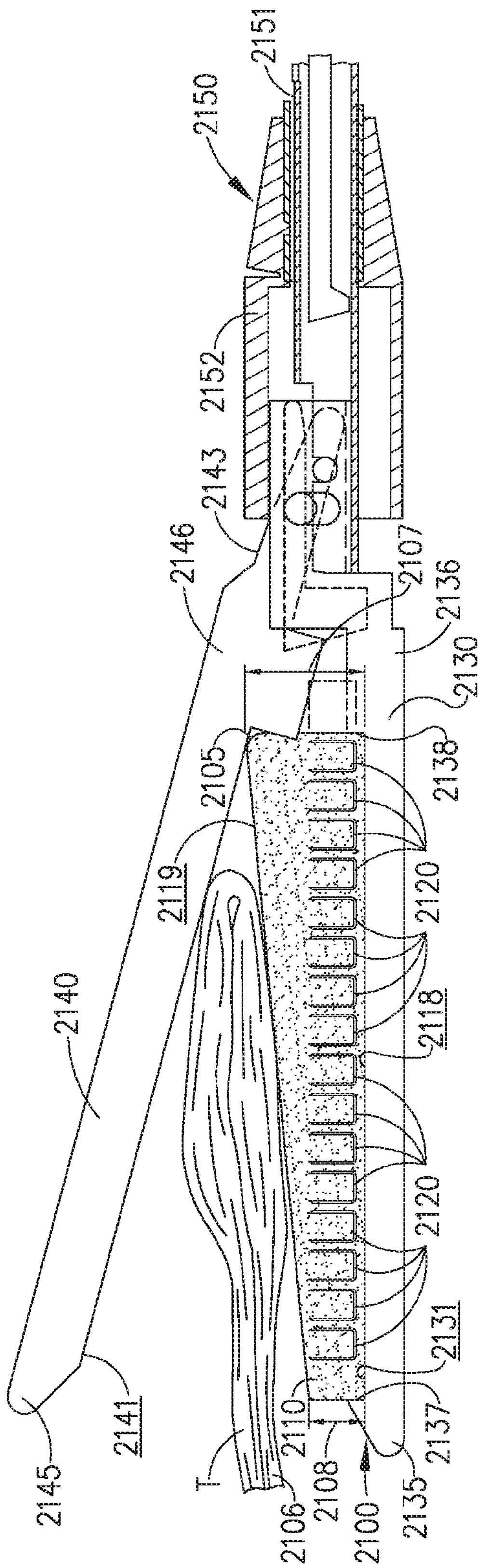
FIG. 45 is an elevational view of the end effector of FIG. 43 illustrating the staple cartridge of FIG. 43 positioned within the staple cartridge channel in an alternative manner.

In various embodiments, referring again to FIGS. 43 and 44, the staple cartridge 2100 can comprise an asymmetrical configuration. In at least one such embodiment, for example, the height of the staple cartridge 2100 at the first end 2105 thereof may be higher than the height of the staple cartridge 2100 at the second end 2106 thereof. In certain embodiments, the staple cartridge 2100 and/or the staple cartridge channel 2130 can comprise one or more alignment and/or retention features which can be configured to assure that the staple cartridge 2100 can only be positioned within the staple cartridge channel 2130 in one orientation, i.e., an orientation in which the first end 2105 is positioned in the distal end 2135 of the staple cartridge channel 2130 and the second end 2106 is positioned in the proximal end 2136. In various alternative embodiments, the staple cartridge 2100 and/or the staple cartridge channel 2130 can comprise one or more alignment and/or retention features which can be configured to permit the staple cartridge 2100 to be positioned within the staple cartridge channel 2130 in more than one orientation. Referring now to FIG. 45, for example, the staple cartridge 2100 can be positioned within the staple cartridge channel 2130 such that the first end 2105 of the staple cartridge 2100 can be positioned in the proximal end 2136 of the staple cartridge channel 2130 and the second end 2106 can be positioned in the distal end 2135. In various embodiments, as a result, the shorter height of the staple cartridge 2100 can be positioned proximate the distal retention wall 2137 and the taller height of the staple cartridge 2100 can be positioned proximate to the proximal retention wall 2138. In at least one such embodiment, the staple cartridge 2100 can be suitably arranged to apply a constant, or at least substantially constant, clamping pressure to tissue T having a thicker portion within the distal end of the end effector and a thinner portion within the proximal end of the end effector. In various embodiments, the staple cartridge 2100, for example, can be selectively oriented within the staple cartridge channel 2130. In at least one such embodiment, the alignment and/or retention features of the staple cartridge 2100 can be symmetrical and a surgeon can selectively orient the staple cartridge 2100 within the staple cartridge channel 2130 in the orientations depicted in FIG. 43 and FIG. 45, for example.

Further to the above, the implantable cartridge body 2110 can comprise a longitudinal axis 2109 which, when the staple cartridge 2100 is positioned in the staple cartridge channel 2130, can extend between the proximal and distal ends of the end effector. In various embodiments, the thickness of the cartridge body 2110 can generally decrease and/or generally increase between the first end 2105 and the second end 2106 along the longitudinal axis 2109. In at least one such embodiment, the distance, or height, between the bottom surface 2118 and the tissue-contacting surface 2119 can generally decrease and/or generally increase between the first end 2105 and the second end 2106. In certain embodiments, the thickness of the cartridge body 2110 can both increase and decrease along the longitudinal axis 2109. In at least one such embodiment, the thickness of the cartridge body 2110 can comprise one or more portions which increase in thickness and one or more portions which can decrease in thickness. In various embodiments, the staple cartridge 2100 can comprise a plurality of staples 2120 positioned therein. In use, as described above, the staples 2120 can be deformed when the anvil 2140 is moved into a closed position. In certain embodiments, each staple 2120 can have the same, or at least substantially the same, height. In at least one such embodiment, the height of a staple can be measured from the bottom of the base of the staple to the top, or tip, of the tallest leg of the staple, for example.

In various embodiments, the staples within a staple cartridge can have different staple heights. In at least one such embodiment, a staple cartridge can comprise a first group of staples having a first staple height which are positioned in a first portion of a compressible cartridge body and a second group of staples having a second staple height which are positioned in a second portion of the compressible cartridge body. In at least one embodiment, the first staple height can be taller than the second staple height and the first group of staples can be positioned in the first end 2105 of the staple cartridge 2100 while the second group of staples can be positioned in the second end 2106. Alternatively, the taller first group of staples can be positioned in the second end 2106 of the staple cartridge 2100 while the shorter second group of staples can be positioned in the first end 2105. In certain embodiments, a plurality of staple groups, each group having a different staple height, can be utilized. In at least one such embodiment, a third group having an intermediate staple height can be positioned in the cartridge body 2110 intermediate the first group of staples and the second group of staples. In various embodiments, each staple within a staple row in the staple cartridge can comprise a different staple height. In at least one embodiment, the tallest staple within a staple row can be positioned on a first end of a staple row and the shortest staple can be positioned on an opposite end of the staple row. In at least one such embodiment, the staples positioned intermediate the tallest staple and the shortest staple can be arranged such that the staple heights descend between the tallest staple and the shortest staple, for example.

Figure 47:
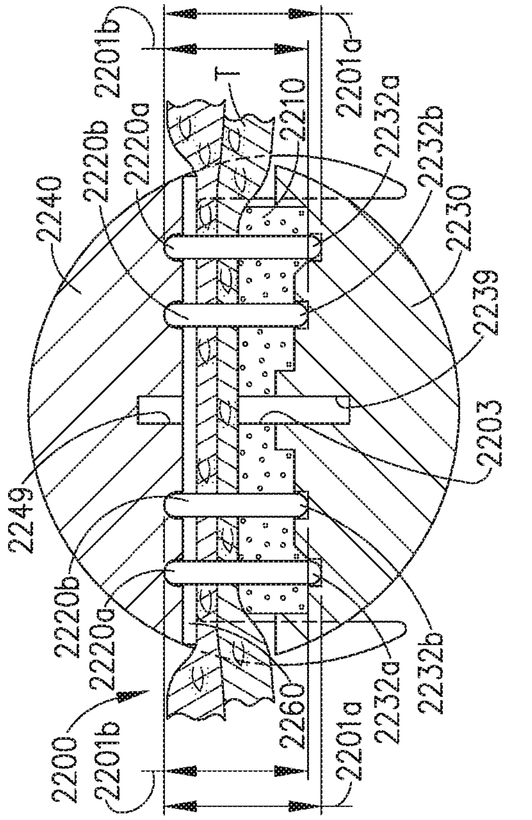
FIG. 47 is a cross-sectional view of the end effector of FIG. 46 illustrating the anvil in a closed position.
Figure 46:
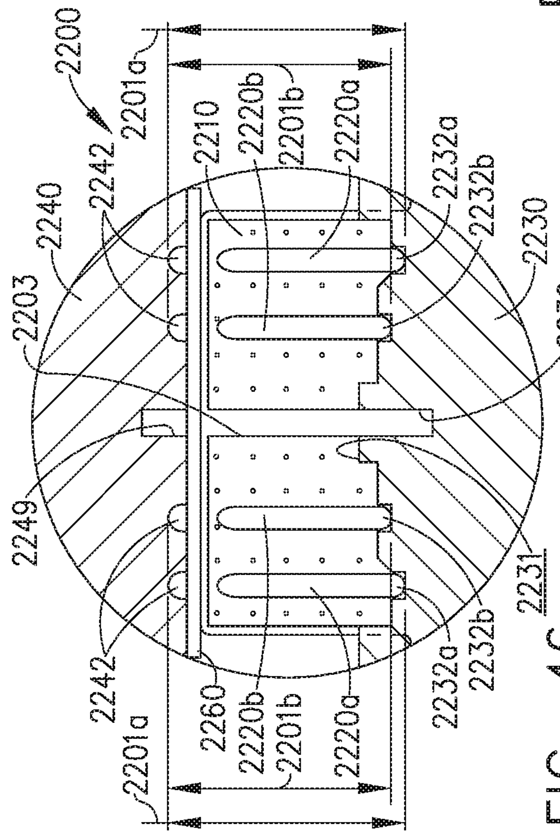
FIG. 46 is a cross-sectional view of an end effector of a surgical stapler comprising a compressible staple cartridge positioned within a staple cartridge channel and a piece of buttress material attached to an anvil.

In various embodiments, referring now to FIG. 46, an end effector of a surgical stapler can comprise an anvil 2240, a staple cartridge channel 2230, and a staple cartridge 2200 supported by the staple cartridge channel 2230. The staple cartridge 2200 can comprise a compressible, implantable cartridge body 2210 and a plurality of staples, such as staples 2220*a* and staples 2220*b*, for example, positioned therein. In various embodiments, the staple cartridge channel 2230 can comprise a cartridge support surface 2231 and a plurality of staple support slots, such as support slots 2232*a* and 2232*b*, for example, defined therein. In at least one such embodiment, the staple cartridge 2200 can comprise two outer rows of staples 2220*a* and two inner rows of staples 2220*b*, wherein the support slots 2232*a* can be configured to support the staples 2220*a* and the support slots 2232*b* can be configured to support the staples 2220*b*. Referring to FIGS. 46 and 47, the anvil 2240 can comprise a plurality of staple forming pockets 2242 defined therein which can be configured to receive and deform the staples 2220*a* and 2220*b* when the anvil 2240 is moved toward the staple cartridge 2200. In at least one such embodiment, the bottom surfaces of the support slots 2232*a* can be a first distance 2201*a* away from the top surfaces of the staple forming pockets 2242 while the bottom surfaces of the support slots 2232*b* can be a second distance 2201*b* away from the top surfaces of the staple forming pockets 2242. In at least one such embodiment, the support slots 2232*b* are positioned closer to the anvil 2240 owing to the raised step in the support surface 2231 in which they are defined. Owing to the different distances 2201*a* and 2201*b*, in various embodiments, the outer rows of staples 2220*a* and the inner rows of staples 2220*b* can be deformed to different formed heights. In various circumstances, staples deformed to different formed heights can apply different clamping pressures or forces to the tissue T being stapled. In addition to the above, the staples can begin with different unformed staple heights. In at least one such embodiment, referring again to FIG. 46, the outer staples 2220*a* can have an initial, unformed height which is greater than the initial, unformed height of the inner staples 2220*b*. As illustrated in FIGS. 46 and 47, the inner staples 2220*b*, which have a shorter unformed height than the outer staples 2220*a*, can also have a shorter formed height than the outer staples 2220*b*. In various alternative embodiments, the inner staples 2220*b* may have a taller unformed height than the outer staples 2220*a* yet have a shorter deformed staple height than the outer staples 2220*a*.

In various embodiments, further to the above, the anvil 2240 can be moved into a closed position, as illustrated in FIG. 47, in order to compress the cartridge body 2210 and deform the staples 2220*a* and 2220*b*. In certain embodiments, a surgical stapler comprising the end effector depicted in FIGS. 46 and 47, for example, can further comprise a cutting member which can be configured to transect the tissue T positioned intermediate the anvil 2240 and the staple cartridge 2200. In at least one such embodiment, the anvil 2240, the staple cartridge channel 2230 and/or the staple cartridge 2200 can define a slot configured to slidably receive a cutting member therein. More particularly, the anvil 2240 can comprise a slot portion 2249, the staple cartridge channel 2230 can comprise a slot portion 2239, and the staple cartridge 2200 can comprise a slot portion 2203 which can be aligned, or at least substantially aligned, with one another when the anvil 2240 is in a closed, or at least substantially closed, position. In various embodiments, the cutting member can be moved from the proximal end of the end effector toward the distal end of the end effector after the anvil 2240 has been closed and the staples 2220*a*, 2220*b* have been deformed. In at least one embodiment, the cutting member can be moved independently of the staple deformation process. In certain embodiments, the cutting member can be advanced at the same time that the staples are being deformed. In any event, in at least one embodiment, the cutting member can be configured to incise the tissue along a path positioned intermediate the inner rows of staples 2220*b*.

In various embodiments, as illustrated in FIG. 47, the inner staples 2220*b* can be formed to a shorter height than the outer staples 2220*a* wherein the inner staples 2220*b* can apply a larger clamping pressure or force to the tissue adjacent to the cut line created by the cutting member. In at least one such embodiment, the larger clamping pressure or force created by the inner staples 2220*b* can provide various therapeutic benefits such as reducing bleeding from the incised tissue T while the smaller clamping pressure created by the outer staples 2220*a* can provide flexibility within the stapled tissue. In various embodiments, referring again to FIGS. 46 and 47, the anvil 2240 can further comprise at least one piece of buttress material, such as buttress material 2260, for example, attached thereto. In at least one such embodiment, the legs of the staples 2220*a*, 2220*b* can be configured to incise the buttress material 2260 and/or pass through apertures in the buttress material 2260 when the staple cartridge 2200 is compressed by the anvil 2240 and thereafter contact the staple forming pockets 2242 in the anvil 2240. As the legs of the staples 2220*a*, 2220*b* are being deformed, the legs can contact and/or incise the buttress material 2260 once again. In various embodiments, the buttress material 2260 can improve the hemostasis of and/or provide strength to the tissue being stapled.

Figure 49:
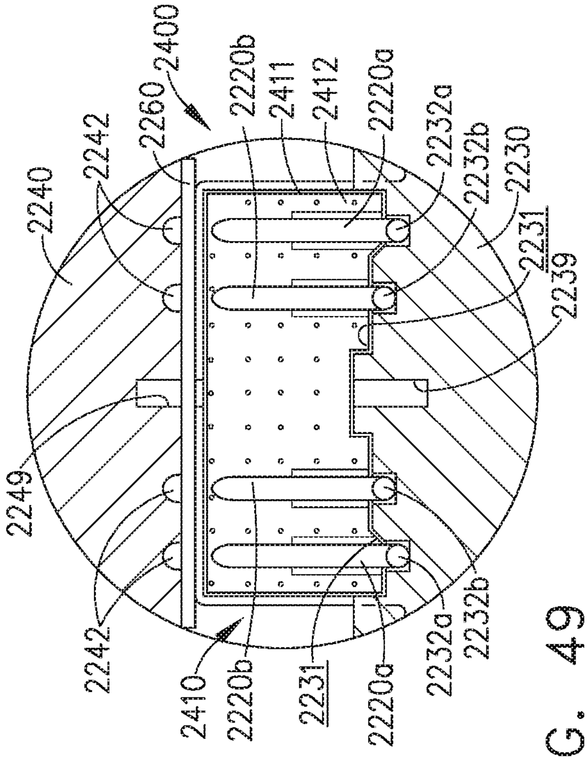
FIG. 49 is a cross-sectional view of another alternative embodiment of an end effector of a surgical stapler.
Figure 48:
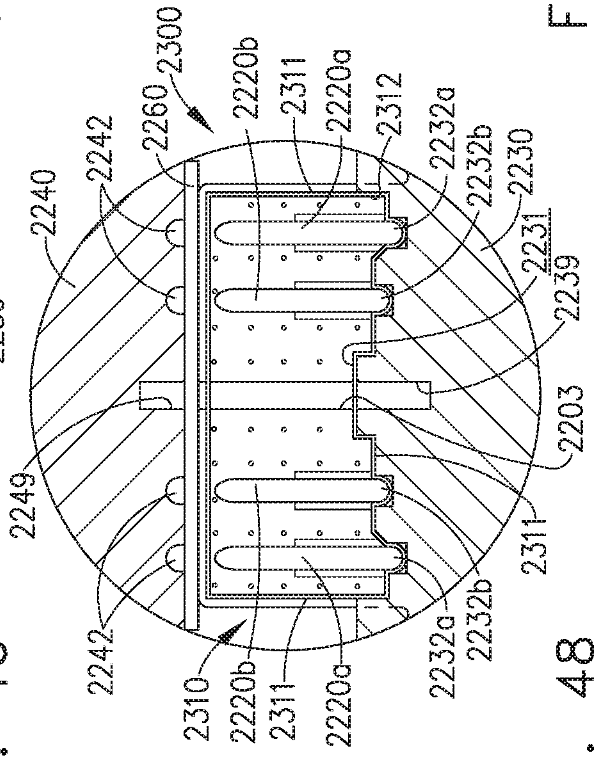
FIG. 48 is a cross-sectional view of an alternative embodiment of an end effector of a surgical stapler comprising a staple cartridge comprising a water impermeable layer.

In various embodiments, referring again to FIGS. 46 and 47, the bottom surface of the cartridge body 2210 can comprise a stepped contour which matches, or at least substantially matches, the stepped contour of the cartridge support surface 2231. In certain embodiments, the bottom surface of the cartridge body 2210 can deform to match, or at least substantially match, the contour of the cartridge support surface 2231. In various embodiments, referring now to FIG. 48, an end effector, similar to the end effector depicted in FIG. 46, for example, can comprise a staple cartridge 2300 positioned therein. The staple cartridge 2300 can comprise a compressible, implantable body 2310 comprising an inner layer 2312 and an outer layer 2311 wherein, further to the above, the outer layer 2311 can be comprised of a water impermeable material in at least one embodiment. In various embodiments, the outer layer 2311 can extend around the staples 2220*a*, 2220*b* and can be positioned intermediate the staples 2220*a*, 2220*b* and the support slots 2232*a*, 2232*b*, respectively. In various embodiments, referring now to FIG. 49, an end effector, similar to the end effector depicted in FIG. 46, for example, can comprise a staple cartridge 2400 positioned therein. Similar to the staple cartridge 2300, the compressible, implantable cartridge body 2410 of staple cartridge 2400 can comprise an inner layer 2412 and an outer layer 2411; however; in at least one embodiment, the cartridge body 2410 may not comprise a cutting member slot therein. In at least one such embodiment, the cutting member may be required to incise the inner layer 2412 and/or the outer layer 2411, for example, as it is advanced through the staple cartridge.

Figure 50:
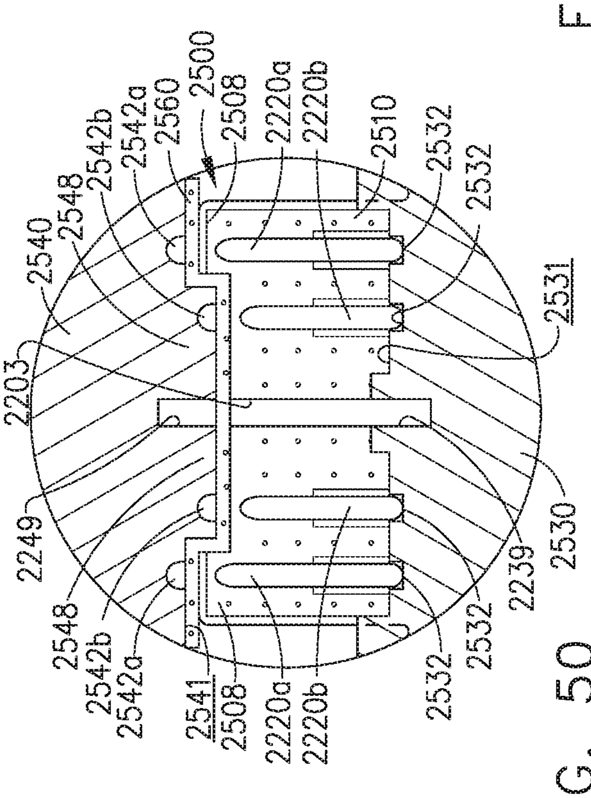
FIG. 50 is a cross-sectional view of an alternative embodiment of an end effector of a surgical stapler comprising a stepped anvil and a staple cartridge comprising a stepped cartridge body.

In various embodiments, referring now to FIG. 50, an end effector of a surgical stapler can comprise an anvil 2540, a staple cartridge channel 2530, and a staple cartridge 2500 positioned in the staple cartridge channel 2530. Similar to the above, the staple cartridge 2500 can comprise a compressible, implantable cartridge body 2510, outer rows of staples 2220*a*, and inner rows of staples 2220*b*. The staple cartridge channel 2530 can comprise a flat, or an at least substantially flat, cartridge support surface 2531 and staple support slots 2532 defined therein. The anvil 2540 can comprise a stepped surface 2541 and a plurality of staple forming pockets, such as forming pockets 2542*a* and 2542*b*, for example, defined therein. Similar to the above, the forming pockets 2542*a* and the support slots 2532 can define a distance therebetween which is greater than the distance between the forming pockets 2452*b* and the support slots 2532. In various embodiments, the anvil 2540 can further comprise a piece of buttress material 2560 attached to the stepped surface 2541 of the anvil 2540. In at least one such embodiment, the buttress material 2560 can conform, or at least substantially conform, to the stepped surface 2541. In various embodiments, the buttress material 2560 can be removably attached to the surface 2541 by at least one adhesive, such as fibrin and/or protein hydrogel, for example. In certain embodiments, the cartridge body 2510 can also comprise a stepped profile which, in at least one embodiment, parallels, or at least substantially parallels, the stepped surface 2541 of the anvil 2540. More particularly, in at least one embodiment, the anvil 2540 can comprise steps 2548 extending toward the staple cartridge 2500 wherein the steps 2548 can comprise a step height which equals, or at least substantially equals, the step height of the steps 2508 extending from the cartridge body 2510. In at least one such embodiment, as a result of the above, the amount of the compressible cartridge body 2510 that can be captured in the first staples 2220*a* can be different than the amount of the compressible cartridge body 2510 that can be captured in the second staples 2220*b*, for example.

Figure 51:
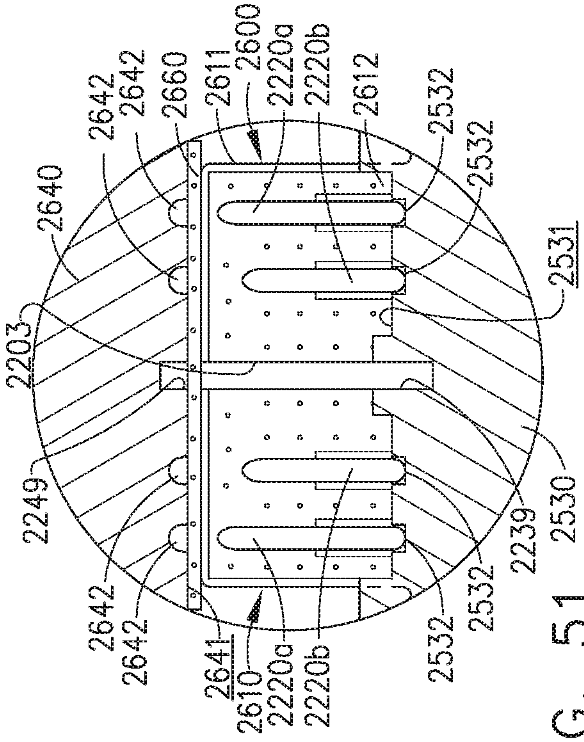
FIG. 51 is a cross-sectional view of another alternative embodiment of an end effector of a surgical stapler.

In various embodiments, referring now to FIG. 51, an end effector can comprise an anvil 2640, a staple cartridge channel 2530, and a staple cartridge 2600 positioned therebetween. The staple cartridge 2600 can comprise a compressible, implantable cartridge body 2610 including an inner layer 2612, an outer layer 2611, and a plurality of staples, such as staples 2220*a* and 2200*b*, for example, positioned therein. In various embodiments, the anvil 2640 can comprise a plurality of staple forming pockets 2642 in surface 2641 and the staple cartridge channel 2530 can comprise a plurality of staple forming slots 2532 defined in the support surface 2531. As illustrated in FIG. 51, the anvil surface 2641 can be parallel, or at least substantially parallel, to the cartridge support surface 2531 wherein each forming pocket 2642 can be positioned an equal, or at least substantially equal, distance away from an opposing and corresponding staple support slot 2532. In various embodiments, the staple cartridge 2600 can comprise staples having the same, or at least substantially the same, initial, unformed staple height and, in addition, the same, or at least substantially the same, formed staple height. In certain other embodiments, the outer rows of staples can comprise staples 2220*a* and the inner rows of staples can comprise staples 2220*b* wherein, as discussed above, the staples 2220*a* and 2220*b* can have different unformed staple heights. When the anvil 2640 is moved toward the staple cartridge 2600 into a closed position, the staples 2220*a* and 2220*b* can be formed such that they have the same, or at least substantially the same, formed staple height. In at least one such embodiment, as a result of the above, the formed outer staples 2220*a* and the inner staples 2220*b* may have the same, or at least substantially the same, amount of compressible cartridge body 2610 contained therein; however, as the outer staples 2220*a* have a taller unformed staple height than the inner staples 2220*b* and may have the same formed staple height nonetheless, a greater clamping pressure can be generated in the outer staples 2220*a* than the inner staples 2220*b*, for example.

Figure 52:
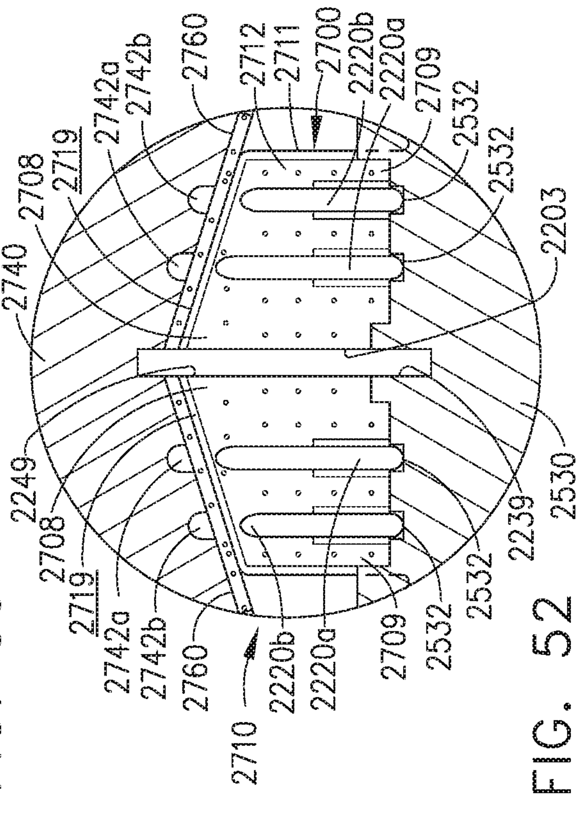
FIG. 52 is a cross-sectional view of an alternative embodiment of an end effector of a surgical stapler comprising inclined tissue-contacting surfaces.

In various embodiments, referring now to FIG. 52, an end effector of a surgical stapler can comprise an anvil 2740, a staple cartridge channel 2530, and a staple cartridge 2700 positioned within the staple cartridge channel 2530. Similar to the above, the staple cartridge 2700 can comprise a compressible, implantable cartridge body 2710 comprising an inner layer 2712, an outer layer 2711, and a plurality of staples, such as staples 2220*a* and 2220*b*, for example, positioned therein. In at least one embodiment, the thickness of the cartridge body 2710 can vary across its width. In at least one such embodiment, the cartridge body 2710 can comprise a center portion 2708 and side portions 2709, wherein the center portion 2708 can comprise a thickness which is greater than the thickness of the side portions 2709. In various embodiments, the thickest portion of the cartridge body 2710 can be located at the center portion 2708 while the thinnest portion of the cartridge body 2710 can be located at the side portions 2709. In at least one such embodiment, the thickness of the cartridge body 2710 can decrease gradually between the center portion 2708 and the side portions 2709. In certain embodiments, the thickness of the cartridge body 2710 can decrease linearly and/or geometrically between the center portion 2708 and the side portions 2709. In at least one such embodiment, the tissue-contacting surface 2719 of cartridge body 2710 can comprise two inclined, or angled, surfaces which slope downwardly from the center portion 2708 toward the side portions 2709. In various embodiments, the anvil 2740 can comprise two inclined, or angled, surfaces which parallel, or at least substantially parallel, the inclined tissue-contacting surfaces 2719. In at least one embodiment, the anvil 2740 can further comprise at least one piece of buttress material 2760 attached to the inclined surfaces of the anvil 2740.

In various embodiments, further to the above, the inner rows of staples in the staple cartridge 2700 can comprise the taller staples 2220*a* and the outer rows of staples can comprise the shorter staples 2220*b*. In at least one embodiment, the taller staples 2220*a* can be positioned within and/or adjacent to the thicker center portion 2708 while the staples 2220*b* can be positioned within and/or adjacent to the side portions 2709. In at least one such embodiment, as a result of the above, the taller staples 2220*a* can capture more material of the implantable cartridge body 2710 than the shorter staples 2220*b*. Such circumstances could result in the staples 2220*a* applying a greater clamping pressure to the tissue T than the staples 2220*b*. In certain embodiments, even though the taller staples 2220*a* may capture more material of the cartridge body 2710 therein than the shorter staples 2220*b*, the taller staples 2220*a* may have a taller formed staple height than the shorter staples 2220*b* owing to the inclined arrangement of the staple forming pockets 2742*a* and 2742*b*. Such considerations can be utilized to achieve a desired clamping pressure within the tissue captured by the staples 2220*a* and 2220*b* wherein, as a result, the clamping pressure in the staples 2220*a* can be greater than, less than, or equal to the clamping pressure applied to the tissue by the staples 2220*b*, for example. In various alternative embodiments to the end effector illustrated in FIG. 52, the shorter staples 2220*b* can be positioned within and/or adjacent to the thicker center portion 2708 of the cartridge body 2710 and the taller staples 2220*a* can be positioned within and/or adjacent to the thinner side portions 2709. Furthermore, although the staple cartridge 2700 is depicted as comprising inner and outer rows of staples, the staple cartridge 2700 may comprise additional rows of staples, such as staple rows positioned intermediate the inner and outer rows of staples, for example. In at least one such embodiment, the intermediate staple rows can comprise staples having an unformed staple height which is intermediate the unformed staple heights of the staples 2220*a* and 2220*b* and a formed staple height which is intermediate the formed staple heights of the staples 2220*a* and 2220*b*, for example.

Figure 53:
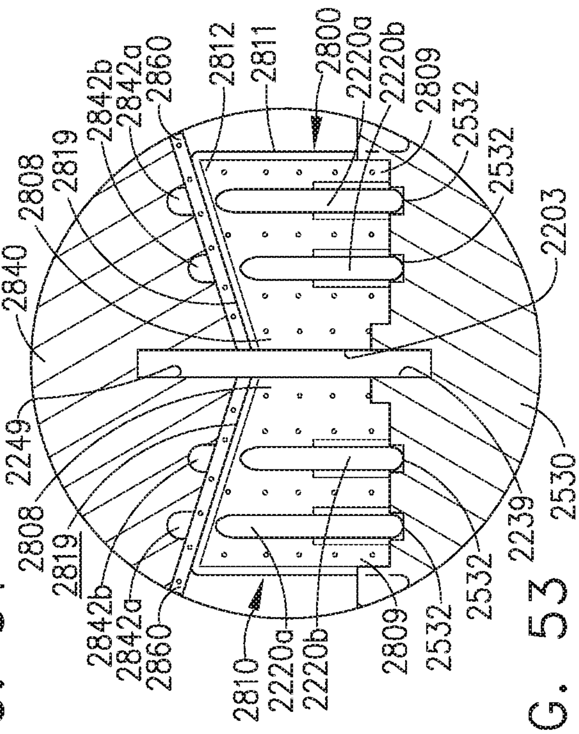
FIG. 53 is a cross-sectional view of another alternative embodiment of an end effector of a surgical stapler comprising inclined tissue-contacting surfaces.

In various embodiments, referring now to FIG. 53, an end effector of a surgical stapler can comprise an anvil 2840, a staple cartridge channel 2530, and a staple cartridge 2800 positioned within the staple cartridge channel 2530. Similar to the above, the staple cartridge 2800 can comprise a compressible, implantable cartridge body 2810 comprising an inner layer 2812, an outer layer 2811, and a plurality of staples, such as staples 2220*a* and 2220*b*, for example, positioned therein. In at least one embodiment, the thickness of the cartridge body 2810 can vary across its width. In at least one such embodiment, the cartridge body 2810 can comprise a center portion 2808 and side portions 2809, wherein the center portion 2808 can comprise a thickness which is less than the thickness of the side portions 2809. In various embodiments, the thinnest portion of the cartridge body 2810 can be located at the center portion 2808 while the thickest portion of the cartridge body 2810 can be located at the side portions 2809. In at least one such embodiment, the thickness of the cartridge body 2810 can increase gradually between the center portion 2808 and the side portions 2809. In certain embodiments, the thickness of the cartridge body 2810 can increase linearly and/or geometrically between the center portion 2808 and the side portions 2809. In at least one such embodiment, the tissue-contacting surface 2819 of cartridge body 2810 can comprise two inclined, or angled, surfaces which slope upwardly from the center portion 2808 toward the side portions 2809. In various embodiments, the anvil 2840 can comprise two inclined, or angled, surfaces which parallel, or at least substantially parallel, the inclined tissue-contacting surfaces 2819. In at least one embodiment, the anvil 2840 can further comprise at least one piece of buttress material 2860 attached to the inclined surfaces of the anvil 2840. In various embodiments, further to the above, the outer rows of staples in the staple cartridge 2800 can comprise the taller staples 2220*a* and the inner rows of staples can comprise the shorter staples 2220*b*. In at least one embodiment, the taller staples 2220*a* can be positioned within and/or adjacent to the thicker side portions 2809 while the staples 2220*b* can be positioned within and/or adjacent to the center portion 2808. In at least one such embodiment, as a result of the above, the taller staples 2220*a* can capture more material of the implantable cartridge body 2810 than the shorter staples 2220*b*.

Figure 54:
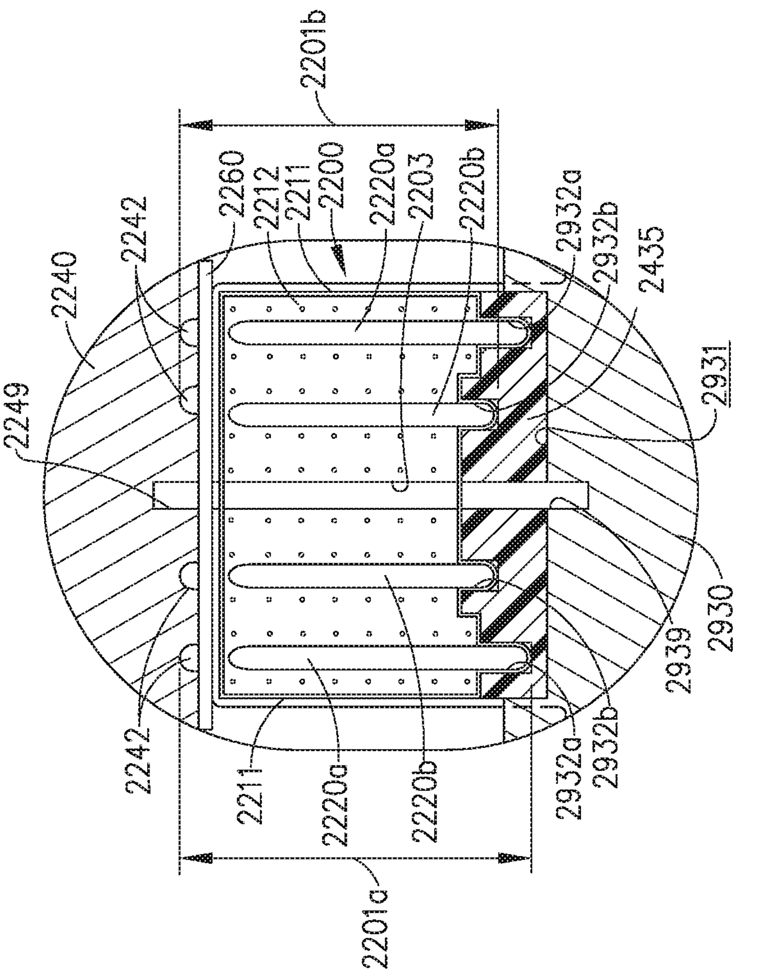
FIG. 54 is a cross-sectional view of an alternative embodiment of an end effector of a surgical stapler comprising a support insert configured to support a staple cartridge.

As described above with regard to the embodiment of FIG. 46, for example, the staple cartridge channel 2230 can comprise a stepped support surface 2231 which can be configured to support the staples 2220*a* and 2220*b* at different heights with respect the anvil 2240. In various embodiments, the staple cartridge channel 2230 can be comprised of metal and the steps in the support surface 2231 may be formed in the support surface 2231 by a grinding operation, for example. In various embodiments, referring now to FIG. 54, an end effector of a surgical instrument can comprise a staple cartridge channel 2930 comprising a support insert 2935 positioned therein. More particularly, in at least one embodiment, the staple cartridge channel 2930 can be formed such that it has a flat, or at least substantially flat, support surface 2931, for example, which can be configured to support the insert 2935 which comprises the stepped surfaces for supporting the staples 2220*a* and 2220*b* of the staple cartridge 2200 at different heights. In at least one such embodiment, the insert 2935 can comprise a flat, or at least substantially flat, bottom surface which can be positioned against the support surface 2931. The insert 2935 can further comprise support slots, grooves, or troughs 2932*a* and 2932*b* which can be configured to support the staples 2220*a* and 2220*b*, respectively, at different heights. Similar to the above, the insert 2935 can comprise a knife slot 2939 defined therein which can be configured to permit a cutting member to pass therethrough. In various embodiments, the staple cartridge channel 2930 can be comprised of the same material as or a different material than the support insert 2935. In at least one embodiment, the staple cartridge channel 2930 and the support insert 2935 can both be comprised of metal, for example, while, in other embodiments, the staple cartridge channel 2930 can be comprised of metal, for example, and the support insert 2935 can be comprised of plastic, for example. In various embodiments, the support insert 2935 can be fastened and/or welded into the staple cartridge channel 2930. In certain embodiments, the support insert 2935 can be snap-fit and/or press-fit into the staple cartridge channel 2930. In at least one embodiment the support insert 2935 can be secured in the staple cartridge channel 2930 using an adhesive.

Figure 55:
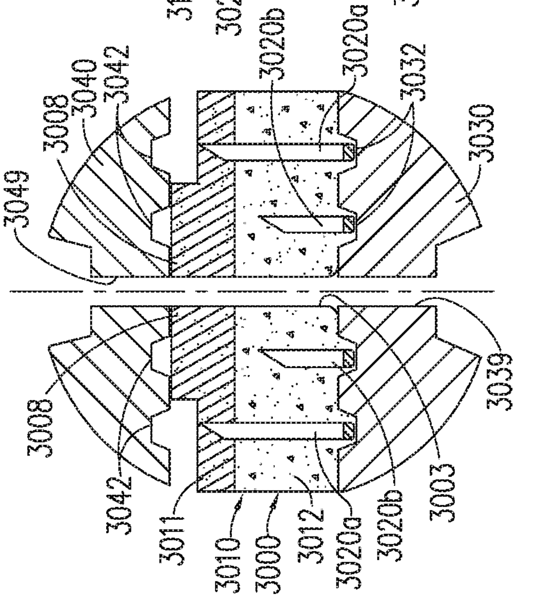
FIG. 55 is a cross-sectional view of an alternative embodiment of an end effector of a surgical stapler comprising a staple cartridge comprising a plurality of compressible layers.

In various embodiments, referring now to FIG. 55, an end effector of a surgical stapler can comprise an anvil 3040, a staple cartridge channel 3030, and a compressible, implantable staple cartridge 3000 positioned in the staple cartridge channel 3030. Similar to the above, the anvil 3040 can comprise a plurality of staple-forming pockets 3042 defined therein and a knife slot 3049 which can be configured to slidably receive a cutting member therein. Also similar to the above, the staple cartridge channel 3030 can comprise a plurality of staple support slots 3032 defined therein and a knife slot 3039 which can also be configured to slidably receive a cutting member therein. In various embodiments, the staple cartridge 3000 can comprise a first layer 3011, a second layer 3012, and a plurality of staples, such as staples 3020*a* and 3020*b*, for example, positioned therein. In at least one embodiment, the staples 3020*a* can comprise an unformed staple height which is taller than the unformed staple height of the staples 3020*b*. In various embodiments, the first layer 3011 can be comprised of a first compressible material and the second layer 3012 can be comprised of a second compressible material. In certain embodiments, the first compressible material can be compressed at a rate which is higher than the second compressible material while, in certain other embodiments, the first compressible material can be compressed at a rate which is lower than the second compressible material. In at least one embodiment, the first compressible material can be comprised of a resilient material which can comprise a first spring rate and the second compressible material can be comprised of a resilient material which can comprise a second spring rate which is different than the first spring rate. In various embodiments, the first compressible material can comprise a spring rate which is greater than the spring rate of the second compressible material. In certain other embodiments, the first compressible material can comprise a spring rate which is less than the spring rate of the second compressible material. In various embodiments, the first compressible layer can comprise a first stiffness and the second compressible layer can comprise a second stiffness, wherein the first stiffness is different than the second stiffness. In various embodiments, the first compressible layer can comprise a stiffness which is greater than the stiffness of the second compressible layer. In certain other embodiments, the first compressible layer can comprise a stiffness which is less than the stiffness of the second compressible layer.

In various embodiments, referring again to FIG. 55, the second layer 3012 of the staple cartridge 3000 can comprise a constant, or at least substantially constant, thickness across the width thereof. In at least one embodiment, the first layer 3011 can comprise a thickness which varies across the width thereof. In at least one such embodiment, the first layer 3011 can comprise one or more steps 3008 which can increase the thickness of the cartridge body 3010 in certain portions of the cartridge body 3010, such as the center portion, for example. Referring again to FIG. 55, the shorter staples **3020*b* can be positioned in or aligned with the steps 3008, i.e., the thicker portions of the cartridge body 3010, and the taller staples 3020*a* can be positioned in or aligned with the thinner portions of the cartridge body 3010. In various embodiments, as a result of the thicker and thinner portions of the cartridge body 3010, the stiffness of the cartridge body 3010 can be greater along the inner rows of staples 3020*b* than the outer rows of staples 3020*a*. In various embodiments, the first layer 3011 can be connected to the second layer 3012. In at least one such embodiment, the first layer 3011 and the second layer 3012 can comprise interlocking features which can retain the layers 3011 and 3012 together. In certain embodiments, the first layer 3011 can comprise a first laminate and the second layer 3012 can comprise a second laminate, wherein the first laminate can be adhered to the second laminate by one or more adhesives. In various embodiments, the staple cartridge 3000 can comprise a knife slot 3003** which can be configured to slidably receive a cutting member therein.

Figure 57:
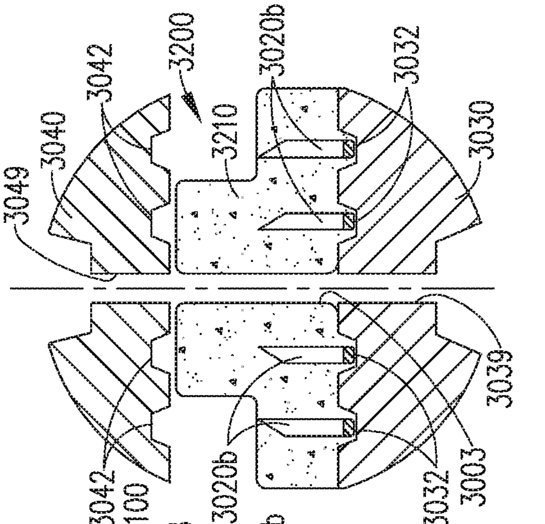
FIG. 57 is a cross-sectional view of another alternative embodiment of an end effector of a surgical stapler comprising a staple cartridge comprising a stepped compressible cartridge body.
Figure 56:
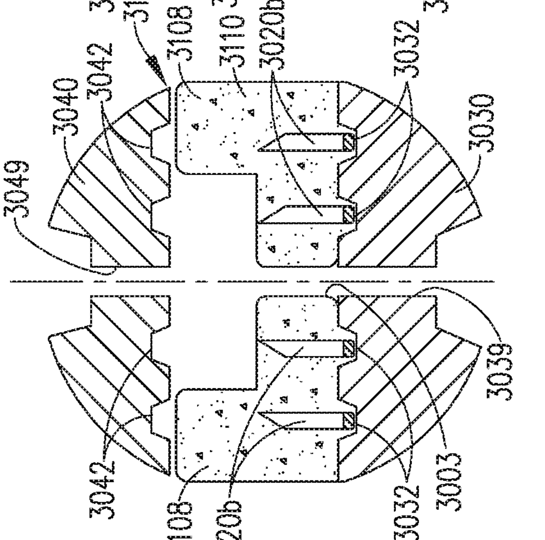
FIG. 56 is a cross-sectional view of an alternative embodiment of an end effector of a surgical stapler comprising a staple cartridge comprising a stepped compressible cartridge body.
Figure 59:
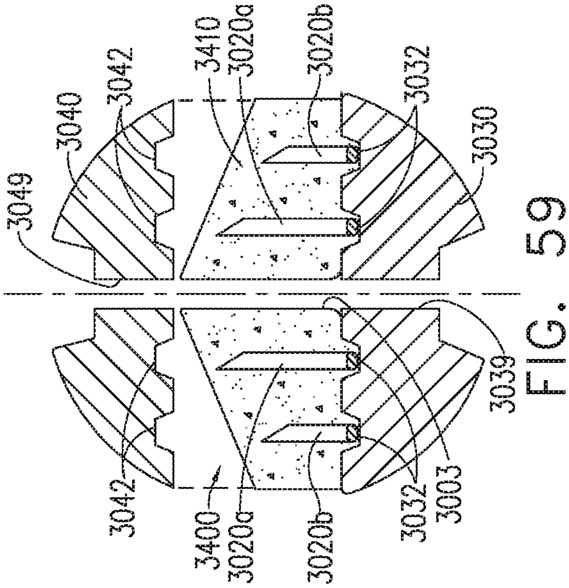
FIG. 59 is a cross-sectional view of an alternative embodiment of an end effector of a surgical stapler comprising a staple cartridge having an inclined tissue-contacting surface.
Figure 58:
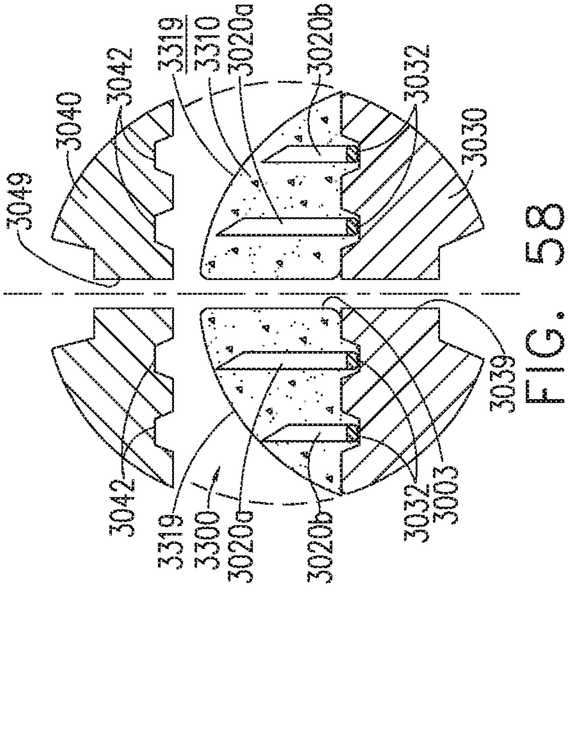
FIG. 58 is a cross-sectional view of an alternative embodiment of an end effector of a surgical stapler comprising a staple cartridge comprising a curved tissue-contacting surface.

In various embodiments, referring now to FIG. 56, a staple cartridge 3100 can comprise a compressible, implantable cartridge body 3110 comprising a single layer of compressible material and, in addition, a plurality of staples, such as staples **3020*b*, for example, positioned therein. In at least one embodiment, the thickness of the cartridge body 3110 can vary across the width thereof. In at least one such embodiment, the cartridge body 3110 can comprise steps 3108 extending along the side portions thereof. In various embodiments, referring now to FIG. 57, a staple cartridge 3200 can comprise a compressible, implantable cartridge body 3210 comprising a single layer of compressible material and, in addition, a plurality of staples, such as staples 3020*b*, for example, positioned therein. In at least one embodiment, the thickness of the cartridge body 3210 can vary across the width thereof. In at least one such embodiment, the cartridge body 3210 can comprise steps 3208 extending along the center portion thereof. In various embodiments, referring now to FIG. 58, a staple cartridge 3300 can comprise a compressible, implantable cartridge body 3310 wherein, similar to the above, the thickness of the cartridge body 3310 can vary across the width thereof. In at least one embodiment, the thickness of the cartridge body 3310 can increase geometrically between the side portions and the center portion of the cartridge body 3310. In at least one such embodiment, the thickness of the cartridge body 3310 can be defined by an arcuate or curved profile and can comprise an arcuate or curved tissue-contacting surface 3319. In certain embodiments, the thickness of the cartridge body 3310, and the contour of the tissue-contacting surface 3319, can be defined by one radius of curvature or, alternatively, by several radiuses of curvature, for example. In various embodiments, referring now to FIG. 59, a staple cartridge 3400 can comprise a compressible, implantable cartridge body 3410 wherein the thickness of the cartridge body 3410 can increase linearly, or at least substantially linearly, between the side portions and the center portion of the cartridge body 3410**.

Figure 60:
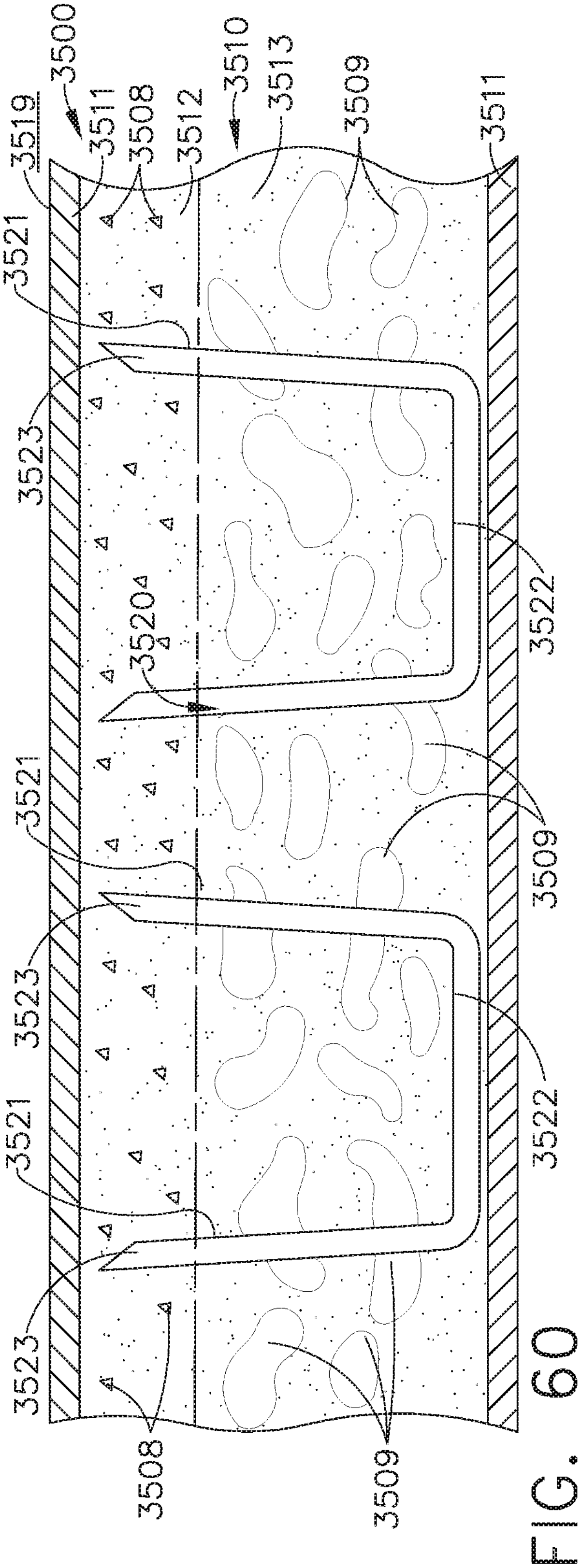
FIG. 60 is a cross-sectional view of a compressible staple cartridge comprising staples and at least one medicament stored therein.
Figure 61:
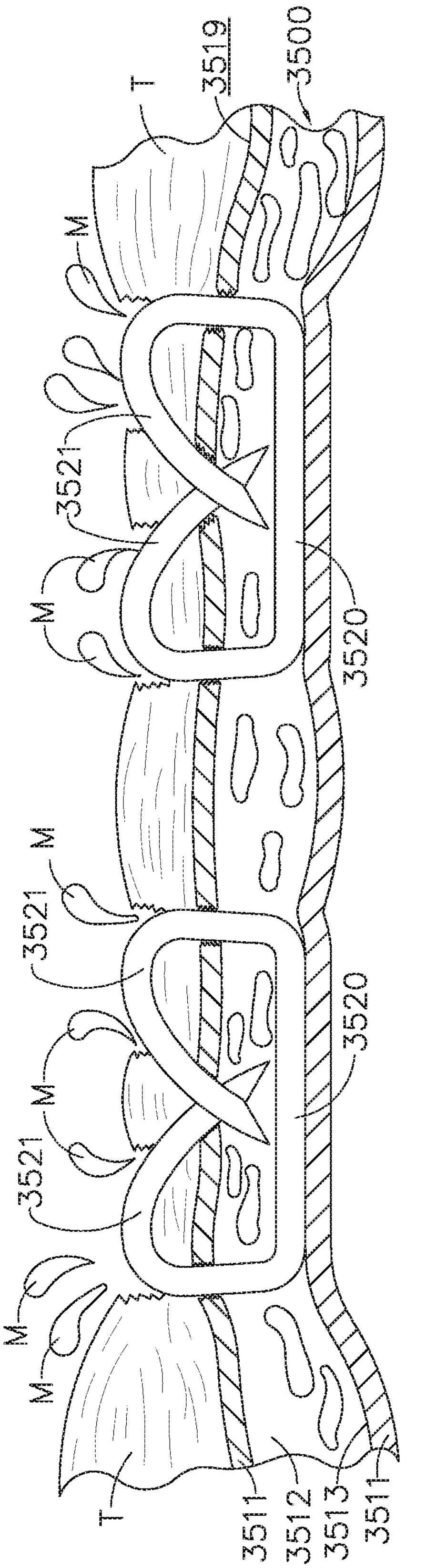
FIG. 61 is a diagram illustrating the compressible staple cartridge of FIG. 60 after it has been compressed and the staples contained therein have been deformed.

In various embodiments, referring now to FIG. 60, a staple cartridge 3500 can comprise a compressible, implantable cartridge body 3510 and a plurality of staples 3520 positioned therein. The implantable cartridge body 3510 can comprise a first inner layer 3512, a second inner layer 3513, and an outer layer 3511. In at least one embodiment, the first inner layer 3512 can comprise a first thickness and the second inner layer 3513 can comprise a second thickness wherein the second inner layer 3513 can be thicker than the first inner layer 3512. In at least one alternative embodiment, the first inner layer 3512 can be thicker than the second inner layer 3513. In another alternative embodiment, the first inner layer 3512 can have the same, or at least substantially the same, thickness as the second inner layer 3513. In certain embodiments, each staple 3520 can comprise a base 3522 and one or more deformable legs 3521 extending from the base 3522. In various embodiments, each leg 3521 can comprise a tip 3523 which is embedded in the first inner layer 3511 and, in addition, each base 3522 of the staples 3520 can be embedded in the second inner layer 3512. In at least one embodiment, the first inner layer 3512 and/or the second inner layer 3513 can comprise at least one medicament stored therein and, in various embodiments, the outer layer 3511 can encapsulate and seal the first inner layer 3512 and the second inner layer 3513 such that the medicament does not flow out of the staple cartridge body 3510 until after the outer layer 3511 has been punctured by the staples 3520. More particularly, further to the above, an anvil can be pushed downwardly against tissue positioned against the tissue-contacting surface 3519 of staple cartridge 3500 such that the cartridge body 3510 is compressed and the surface 3519 is moved downwardly toward, and at least partially below, the staple tips 3523 such that the tips 3523 rupture or puncture the outer layer 3511. After the outer layer 3511 has been breached by the staple legs 3521, the at least one medicament M can flow out of the cartridge body 3510 around the staple legs 3521. In various circumstances, additional compression of the cartridge body 3510 can squeeze additional medicament M out of the cartridge body 3510 as illustrated in FIG. 61.

In various embodiments, referring again to FIG. 60, the outer layer 3511 can comprise a water impermeable, or at least substantially impermeable, wrap which can configured to, one, keep the medicament from prematurely flowing out of the staple cartridge 3500 and, two, prevent fluids within a surgical site, for example, from prematurely entering into the staple cartridge 3500. In certain embodiments, the first inner layer 3512 can comprise a first medicament stored, or absorbed, therein and the second inner layer 3513 can comprise a second medicament stored, or absorbed, therein, wherein the second medicament can be different than the first medicament. In at least one embodiment, an initial compression of the cartridge body 3510, which causes the rupture of the outer layer 3511, can generally express the first medicament out of the first inner layer 3512 and a subsequent compression of the cartridge body 3510 can generally express the second medicament out of the second inner layer 3513. In such embodiments, however, portions of the first medicament and the second medicament may be expressed simultaneously although a majority of the medicament that is initially expressed can be comprised of the first medicament and a majority of the medicament subsequently expressed thereafter can be comprised of the second medicament. In certain embodiments, further to the above, the first inner layer 3512 can be comprised of a more compressible material than the second inner layer 3513 such that the initial compression forces or pressure, which can be lower than the subsequent compression forces or pressure, can cause a larger initial deflection within the first inner layer 3512 than the second inner layer 3513. This larger initial deflection within the first inner layer 3512 can cause a larger portion of the first medicament to be expressed from the first inner layer 3512 than the second medicament from the second inner layer 3513. In at least one embodiment, the first inner layer 3512 can be more porous and/or more flexible than the second inner layer 3513. In at least one such embodiment, the first inner layer 3512 can comprise a plurality of pores, or voids, 3508 defined therein and the second inner layer 3513 can comprise a plurality of pores, or voids, 3509 defined therein wherein, in various embodiments, the pores 3508 can be configured to store the first medicament in the first inner layer 3512 and the pores 3509 can be configured to store the second medicament in the second inner layer 3513. In certain embodiments, the size and density of the pores 3508 within the first inner layer 3512 and the pores 3509 within the second inner layer 3513 can be selected so as to provide a desired result described herein.

In various embodiments, referring again to FIGS. 60 and 61, the outer layer 3511, the first inner layer 3512, and/or the second inner layer 3513 can be comprised of a bioabsorbable material. In at least one embodiment, the first inner layer 3512 can be comprised of a first bioabsorbable material, the second inner layer 3513 can be comprised of a second bioabsorbable material, and the outer layer 3511 can be comprised of a third bioabsorbable material, wherein the first bioabsorbable material, the second bioabsorbable material, and/or the third bioabsorbable material can be comprised of different materials. In certain embodiments, the first bioabsorbable material can be bioabsorbed at a first rate, the second bioabsorbable material can be bioabsorbed at a second rate, and the third bioabsorbable material can be bioabsorbed at a third rate, wherein the first rate, the second rate, and/or the third rate can be different. In at least one such embodiment, when a material is bioabsorbed at a particular rate, such a rate can be defined as the amount of material mass that is absorbed by a patient's body over a unit of time. As it is known, the bodies of different patients may absorb different materials at different rates and, thus, such rates may be expressed as average rates in order to account for such variability. In any event, a faster rate may be a rate in which more mass is bioabsorbed for a unit of time than a slower rate. In various embodiments, referring again to FIGS. 60 and 61, the first inner layer 3512 and/or the second inner layer 3513 can be comprised of a material which bioabsorbs faster than the material comprising the outer layer 3511. In at least one such embodiment, the first inner layer 3512 and/or the second inner layer 3513 can be comprised of a bioabsorbable foam, tissue sealant, and/or haemostatic material, such as oxidized regenerated cellulose (ORC), for example, and the outer layer 3511 can be comprised of a buttress material and/or plastic material, such as polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. In such embodiments, the first inner layer 3512 and/or the second inner layer 3513 can immediately treat the tissue and can reduce bleeding from the tissue, for example, wherein the outer layer 3514 can provide longer-term structural support and can be bioabsorbed at a slower rate.

Owing to the slower rate of bioabsorbability of the outer layer 3511, further to the above, the outer layer 3511 can buttress or structurally reinforce the tissue within the staple line as it heals. In certain embodiments, one of the first inner layer 3512 and the second inner layer 3513 can be comprised of a material which can be bioabsorbed faster than the other such that, in at least one embodiment, one of the layers can provide an initial release of a therapeutic material and the other layer can provide a sustained release of the same therapeutic material and/or a different therapeutic material. In at least one such embodiment, the rate in which a therapeutic material can be released from a layer 3512, 3513 can be a function of the bioabsorbability of the substrate layer in which the medicament is absorbed or dispersed. For example, in at least one embodiment, the substrate comprising the first inner layer 3512 can be bioabsorbed faster than the substrate comprising the second inner layer 3513 and, as a result, a medicament can be release from the first inner layer 3512 faster than the second inner layer 3513, for example. In various embodiments, as described herein, one or more of the layers 3511, 3512, and 3513 of the cartridge body 3510 can be adhered to one another by at least one adhesive, such as fibrin and/or protein hydrogel, for example. In certain embodiments, the adhesive can be water soluble and can be configured to release the connection between the layers as the staple cartridge 3500 is being implanted and/or some time thereafter. In at least one such embodiment, the adhesive can be configured to bioabsorb faster than the outer layer 3511, the first inner layer 3512, and/or the second inner layer 3513.

Figure 62:
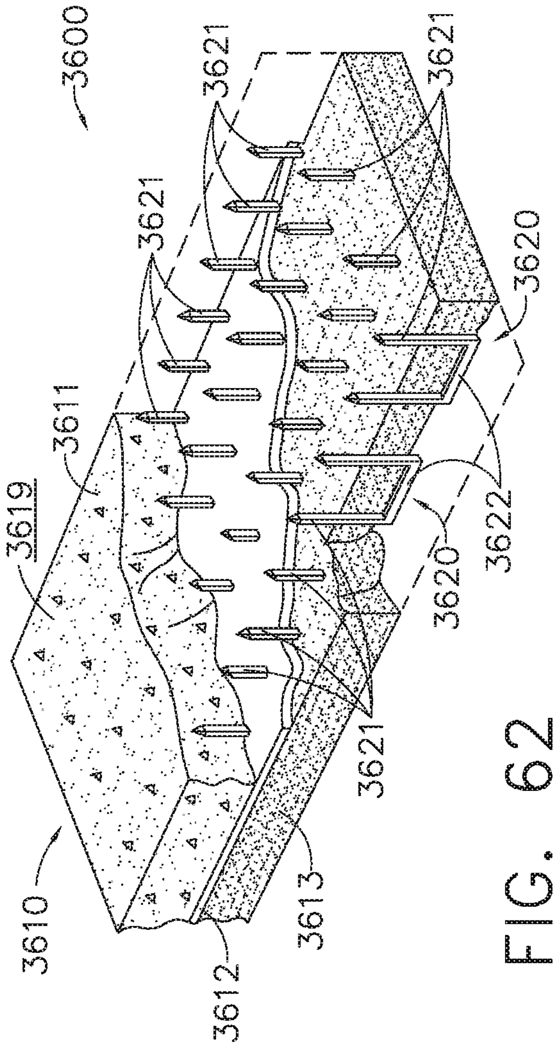
FIG. 62 is a partial cut-away view of a staple cartridge in accordance with at least one embodiment.
Figure 63:
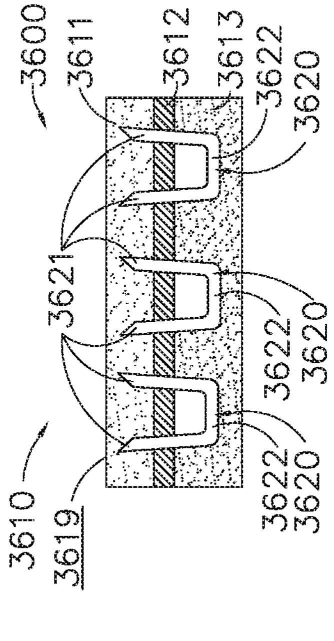
FIG. 63 is a cross-sectional view of the staple cartridge of FIG. 62.

In various embodiments, referring now to FIGS. 62 and 63, a staple cartridge, such as staple cartridge 3600, for example, can comprise a cartridge body 3610 including a compressible first layer 3611, a second layer 3612 attached to the first layer 3611, and a removable compressible layer 3613 attached to the second layer 3612. In at least one such embodiment, the first layer 3611 can be comprised of a compressible foam material, the second layer 3612 can comprise a laminate material adhered to the first layer 3611 utilizing one or more adhesives, and the third layer 3613 can comprise a compressible foam material removably adhered to the second layer 3612 utilizing one or more adhesives, for example. In various embodiments, the staple cartridge 3600 can further comprise a plurality of staples, such as staples 3620, for example, positioned in the cartridge body 3610. In at least one such embodiment, each staple 3620 can comprise a base 3622 positioned in the third layer 3613 and one or more deformable legs 3621 extending upwardly from the base 3622 through the second layer 3612 and into the first layer 3611, for example. In use, further to the above, the top surface 3619 of the staple cartridge body 3610 can be pushed downwardly by an anvil until the staple legs 3621 penetrate through the top surface 3619 and the targeted tissue and contact the anvil. After the staple legs 3621 have been sufficiently deformed, the anvil can be moved away from the staple cartridge 3600 such that the compressible layers thereof can at least partially re-expand. In various circumstances, the insertion of the staples through the tissue can cause the tissue to bleed. In at least one embodiment, the third layer 3613 can be comprised of an absorbent material, such as protein hydrogel, for example, which can draw blood away from the stapled tissue. In addition to or in lieu of the above, the third layer 3613 can be comprised of a haemostatic material and/or tissue sealant, such as freeze-dried thrombin and/or fibrin, for example, which can be configured to reduce the bleeding from the tissue. In certain embodiments, the third layer 3613 may provide a structural support to the first layer 3611 and the second layer 3612 wherein the third layer 3613 may be comprised of a bioabsorbable material and/or a non-bioabsorbable material. In any event, in various embodiments, the third layer 3613 can be detached from the second layer 3612 after the staple cartridge 3610 has been implanted. In embodiments where the third layer 3613 comprises an implantable-quality material, the surgeon can elect whether to remove the third layer 3613 of the cartridge body 3610. In at least one embodiment, the third layer 3613 can be configured to be removed from the second layer 3612 in one piece.

Figure 64:
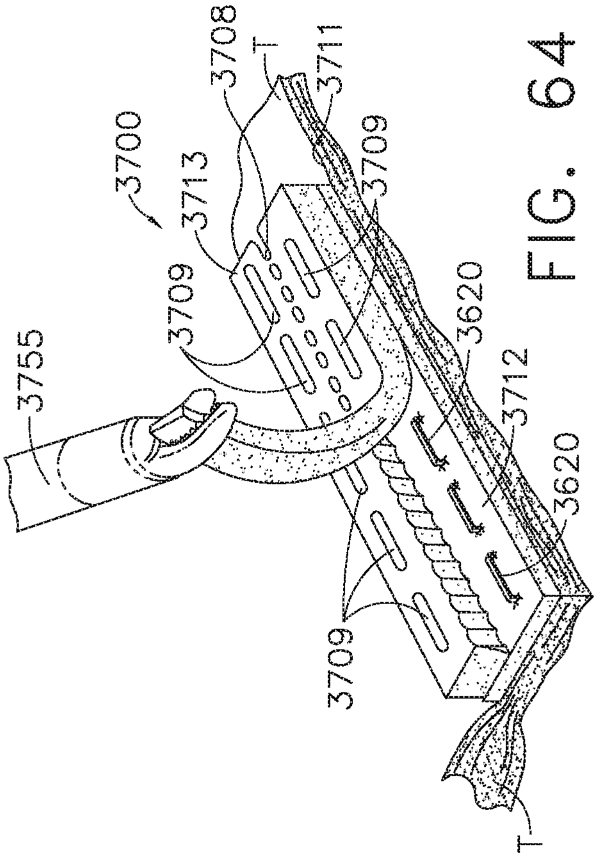
FIG. 64 is a perspective view of an implanted staple cartridge in accordance with at least one alternative embodiment.
Figure 65:
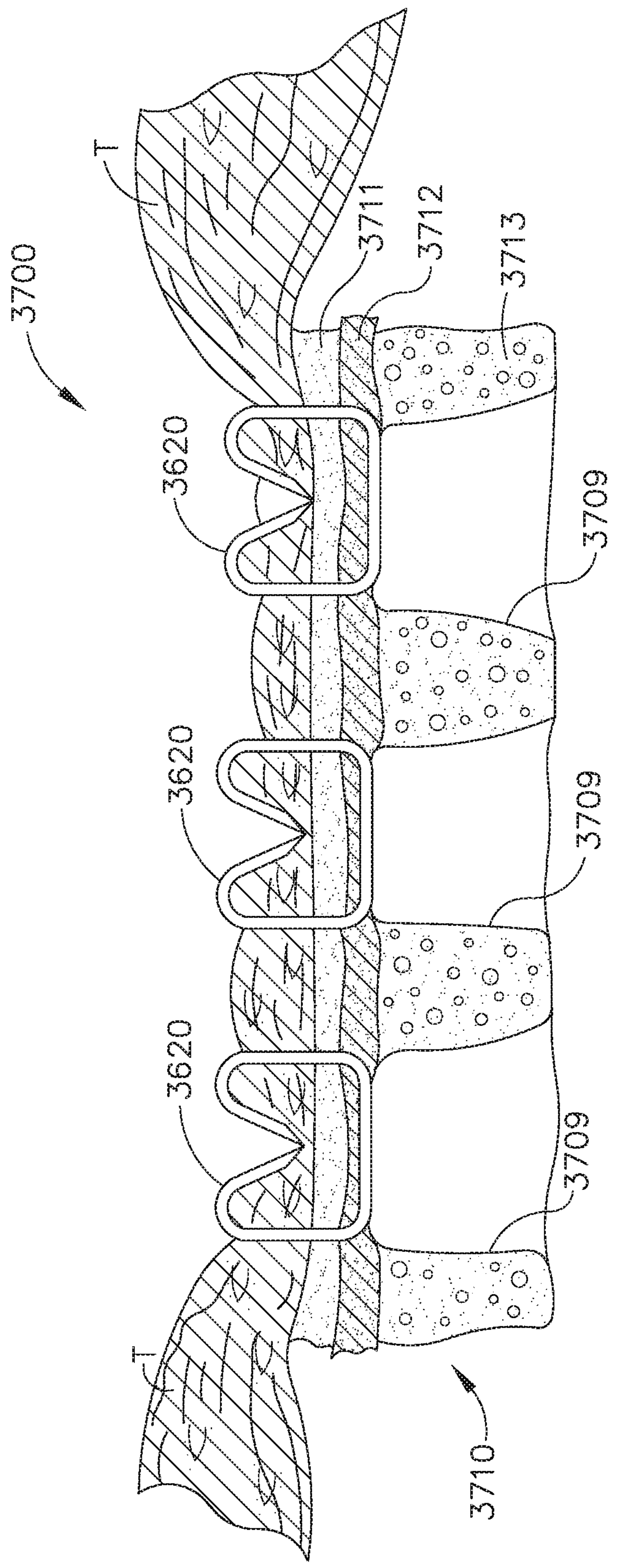
FIG. 65 is a cross-sectional view of the implanted staple cartridge of FIG. 64.

In various embodiments, the first layer 3611 can be comprised of a first foam material and the third layer 3613 can be comprised of a second foam material which can be different than the first foam material. In at least one embodiment, the first foam material can have a first density and the second foam material can have a second density wherein the first density can be different than the second density. In at least one such embodiment, the second density can be higher than the first density wherein, as a result, the third layer 3613 may be less compressible, or have a lower compression rate, than the first layer 3611. In at least one alternative embodiment, the first density can be higher than the second density wherein, as a result, the first layer 3611 may be less compressible, or have a lower compression rate, than the third layer 3613. In various embodiments, referring now to FIGS. 64 and 65, a staple cartridge 3700, similar to the staple cartridge 3600, can comprise a cartridge body 3710 comprising a first compressible foam layer 3711, a second layer 3712 attached to the first layer 3711, and a detachable third compressible foam layer 3713 removably attached to the second layer 3712. In at least one such embodiment, the third layer 3713 can comprise a plurality of staple receiving slots, or cut-outs, 3709 which can each be configured to receive at least a portion of a staple 3620, such as a staple base 3622, for example, therein. In certain embodiments, the staples 3620 can be configured to slide within the staple receiving slots 3709 or, stated another way, the third layer 3713 can be configured to slide relative to the staples 3620 when the staple cartridge 3700 is positioned against the targeted tissue and compressed by an anvil, for example. In at least one embodiment, the receiving slots 3709 can be configured such that there is clearance between the staples 3620 and the side walls of the receiving slots 3709. In at least one such embodiment, as a result of the above, the staples 3620 may not capture a portion of the third layer 3713 therein when the staples 3620 are deformed, as illustrated in FIGS. 64 and 65. In certain other embodiments, the ends of the staple receiving slots 3709 adjacent to the second layer 3712 can be closed by a portion of the third layer 3713 and, as a result, at least a portion of the third layer 3713 can be captured within the staples 3620 when they are deformed. In any event, the third layer 3713 can comprise one or more perforations and/or score marks 3708, for example, which can be configured to permit the third layer 3713 to be removed from the second layer 3712 in two or more pieces as illustrated in FIG. 64. In FIG. 64, one of the pieces of the third layer 3713 is illustrated as being removed by a tool 3755. In various embodiments, the perforations 3708 can be arranged along a line positioned intermediate a first row of staples and a second row of staples.

In various embodiments, referring again to FIGS. 64 and 65, the bases 3622 of the staples 3620 can be positioned within the receiving slots 3709 wherein, in at least one embodiment, the side walls of the receiving slots 3709 can be configured to contact and releasable retain the staple legs 3621 in position. In certain embodiments, although not illustrated, the third layer 3713 can comprise an elongated slot surrounding all of the staples within a staple line. In at least one such embodiment, a staple cartridge comprising four staple rows, for example, can comprise an elongate slot aligned with each staple row in the bottom layer of the staple cartridge. Further to the above, at least a portion of the staple cartridge 3600 and/or the staple cartridge 3700 can be implanted within a patient and at least a portion of the staple cartridge can be removable from the patient. In at least one embodiment, referring again to FIGS. 64 and 65, the first layer 3711 and the second layer 3712 can be captured within the staples 3620 and can be implanted with the staples 3620, whereas the third layer 3713 can be optionally removed or detached from the staple cartridge 3700. In various circumstances, the removal of a portion of the implanted staple cartridge can reduce the amount of material that the patient's body has to reabsorb which can provide various therapeutic benefits. In the event that a portion of a staple cartridge is detached and removed, such as by a laparoscopic tool 3755, for example, the detached staple cartridge portion can be removed from the surgical site through a trocar, such as a trocar having a 5 mm aperture, for example. In certain embodiments, a cartridge body can comprise more than one layer that can be removed. For example, the cartridge body 3710 can comprise a fourth layer wherein the third layer of 3713 of the cartridge body 3710 can be comprised of a haemostatic material and the fourth layer can be comprised of a support layer. In at least one such embodiment, a surgeon can remove the support layer and then elect whether to remove the haemostatic layer, for example.

Figure 66:
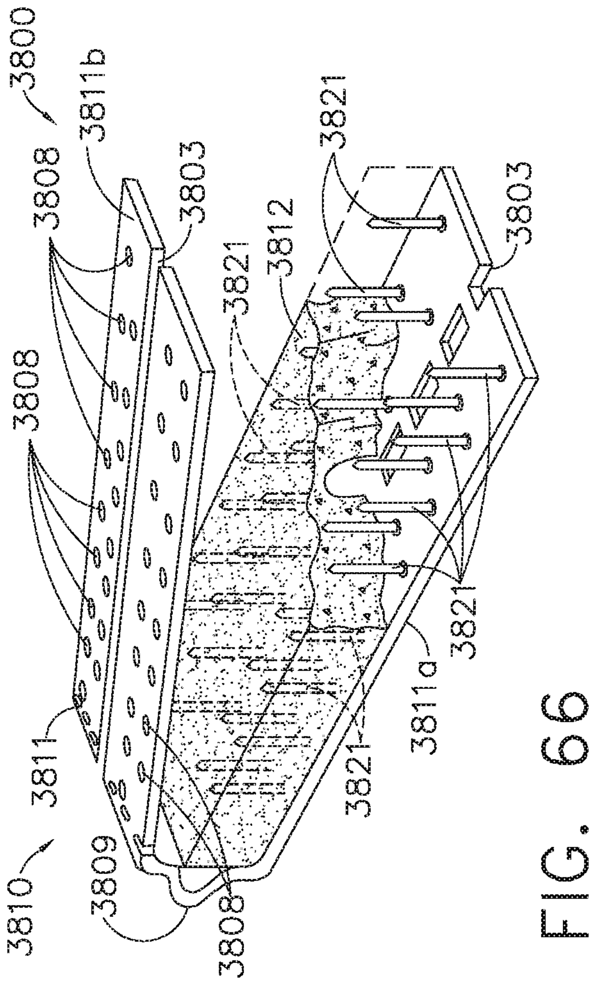
FIG. 66 is a perspective view of an alternative embodiment of a staple cartridge comprising deformable members extending from an outer layer of the staple cartridge.

In various embodiments, referring now to FIG. 66, a staple cartridge, such as staple cartridge 3800, for example, can comprise a cartridge body 3810 including an outer layer 3811 and an inner layer 3812. The inner layer 3812 can be comprised of a compressible foam material and the outer layer 3811 can be at least partially wrapped around the inner layer 3812. In at least one embodiment, the outer layer 3811 can comprise a first portion 3811*a* configured to be positioned on a first side of the inner layer 3812 and a second portion 3811*b* configured to be positioned on a second side of the inner layer 3812 wherein the first portion 3811*a* and the second portion 3811*b* can be connected by a flexible hinge, such as hinge 3809, for example. In at least one such embodiment, at least one adhesive, such as fibrin and/or protein hydrogel, for example, can be applied to the first side and/or the second side of the inner layer 3812 in order to secure the portions of the outer layer 3811 thereto. In various embodiments, the outer layer 3811 can comprise one or more fastening members extending therefrom. In at least one such embodiment, the outer layer 3811 can comprise a plurality of deformable legs 3821 extending from one side of the outer layer 3811 which can be seated in the compressible inner layer 3812. In at least one such embodiment, the legs 3821 may not protrude from the second side of the inner layer 3812 while, in at least one alternative embodiment, the legs 3821 may at least partially protrude from the inner layer 3812. When the compressible cartridge body 3810 is compressed, in use, the legs 3821 can be configured to pierce the inner layer 3812 and the second portion 3811*b* of the outer layer 3811. In certain embodiments, the second portion 3811*b* of the outer layer 3811 can comprise apertures, such as apertures 3808, for example defined therein which can be configured to receive the staple legs 3821. In certain embodiments, at least portions of the staple cartridge 3800 can comprise a knife slot 3803 which can be configured to slidably receive a cutting member therein. In at least one such embodiment, the knife slot 3803 may not extend entirely through the thickness of the cartridge body 3810 and, as a result, the cutting member may incise the cartridge body 3810 as it is moved relative thereto.

Figure 67:
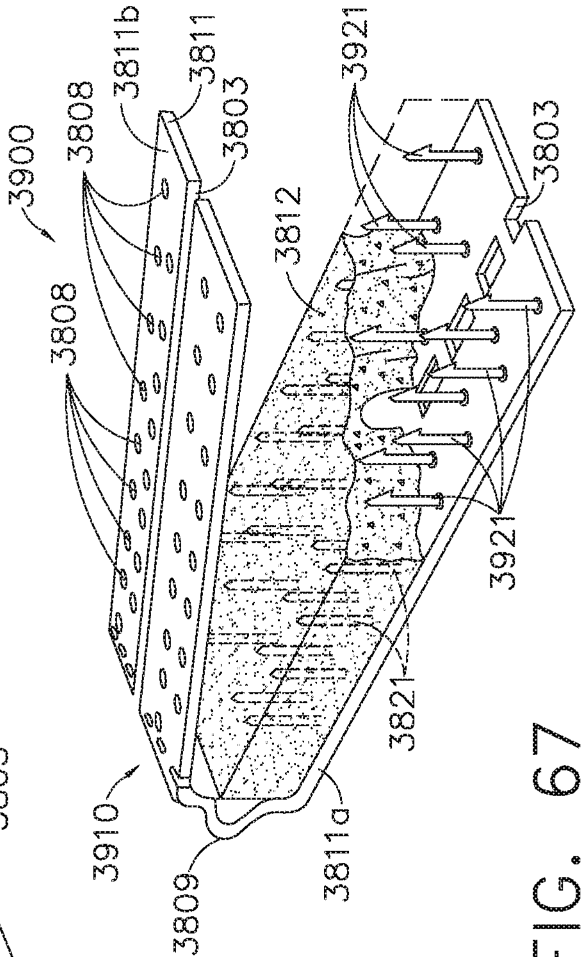
FIG. 67 is a perspective view of an alternative embodiment of a staple cartridge comprising an outer layer of the staple cartridge being assembled to an inner layer.
Figure 68:
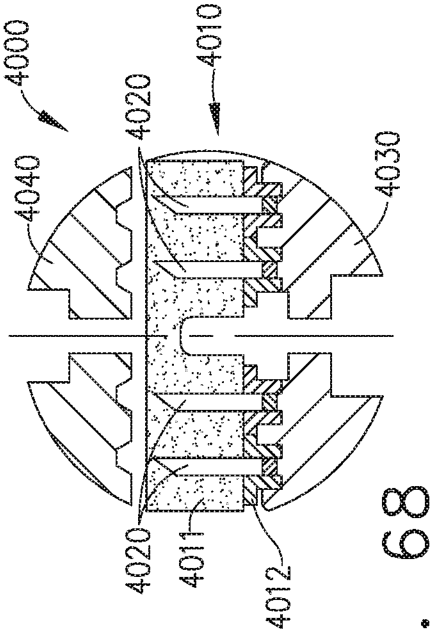
FIG. 68 is a cross-sectional view of an alternative embodiment of a staple cartridge comprising a plurality of staples, a compressible layer, and a pledget layer.
Figure 69:
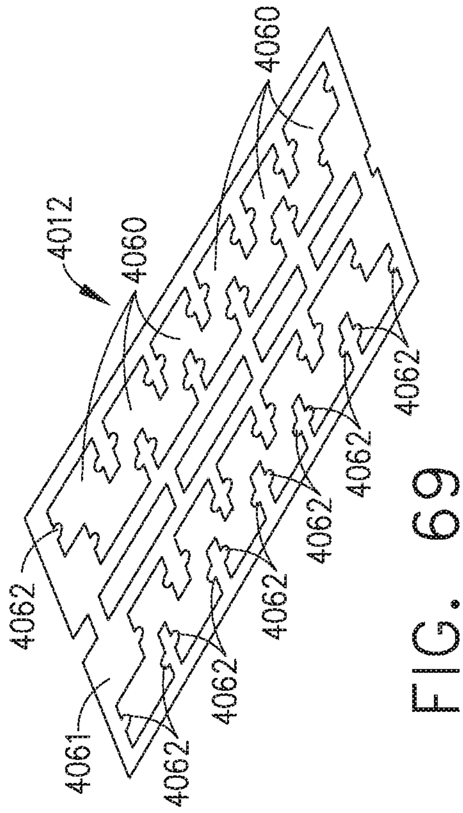
FIG. 69 is a perspective view of the pledget layer of FIG. 68.

In various embodiments, referring now to FIG. 67, a staple cartridge 3900 can comprise, similar to staple cartridge 3800, a cartridge body 3910 including an inner layer 3812 and an outer layer 3811, wherein the outer layer 3811 can comprise a first portion 3811*a* positioned adjacent to the first side of the inner layer 3812 and a second portion 3811*b* positioned adjacent to the second side of the inner layer 3812. In at least one embodiment, similar to the above, the outer layer 3811 can comprise one or more fastening members extending therefrom. In at least one such embodiment, the outer layer 3811 can comprise a plurality of deformable legs 3921 extending from one side of the outer layer 3811 which can be seated in the compressible inner layer 3812. In certain embodiments, each deformable leg 3921 can comprise at least one hook or barb 3923 protruding therefrom which can be configured to engage the second portion 3811*b* of the outer layer 3811 and, as a result, retain the outer layer 3811 to the inner layer 3812. In at least one such embodiment, the barbs 3923 can be configured to protrude from the second side of the inner layer 3812 and extend through the apertures 3808 in the second portion 3811*b* of the outer layer 3811 such that the barbs 3923 can engage the outside surface of the outer layer 3811 and lock the outer layer 3811 to the inner layer 3812. In order to construct the staple cartridge 3900, the inner layer 3812 may be at least partially compressed in order to cause the barbs to protrude therefrom and enter into the apertures 3808. In at least one such embodiment, the staple cartridge 3900 can be at least partially pre-compressed when it is inserted into a staple cartridge, for example. In certain embodiments, further to the above, at least a portion of the legs 3921 can be embedded within the first portion 3811*a* of the outer layer 3811 wherein, in at least one embodiment, the outer layer 3811 can be comprised of a plastic material, such as polydioxanone (PDS) and/or polyglycolic acid (PGA), for example, and the plastic material can be overmolded around at least a portion of the legs 3921.

Figure 70:
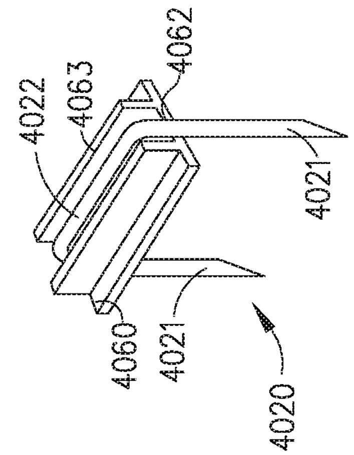
FIG. 70 is a perspective view of a pledget singulated from the pledget layer of FIG. 68 and a staple aligned with a groove in the pledget.
Figure 71:
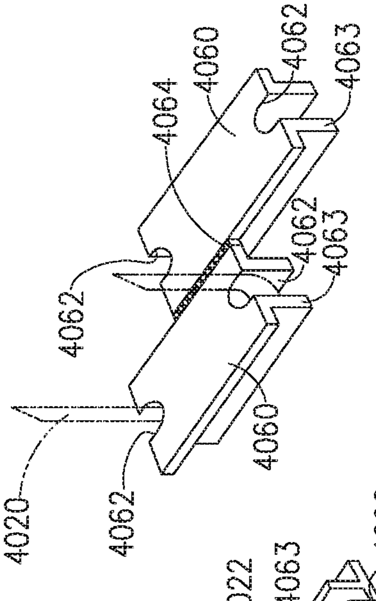
FIG. 71 is a perspective view of two connected pledgets from the pledget layer of FIG. 68.
Figure 72:
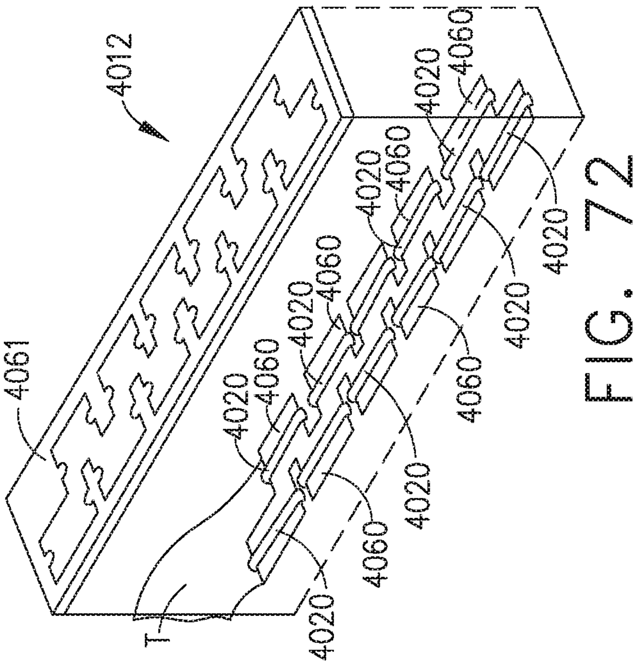
FIG. 72 is a perspective view of a pledget support frame of the pledget layer of FIG. 68 being removed from the singulated pledgets.

In various embodiments, referring now to FIGS. 68-72, a staple cartridge, such as staple cartridge 4000, for example, can comprise a cartridge body 4010 including a compressible first layer 4011 and a second layer 4012 and, in addition, a plurality of staples 4020 positioned within the cartridge body 4010. In certain embodiments, referring to FIG. 70, each staple 4020 can comprise a base 4022 and at least one deformable leg 4023 extending from the base 4022. In at least one embodiment, referring to FIG. 68, the staple cartridge 4000 can be positioned between a staple cartridge channel 4030 and an anvil 4040 of an end effector of a surgical stapler wherein the second layer 4012 of the cartridge body 4010 and/or the bases 4022 of the staples 4020 can be positioned against the staple cartridge channel 4030. In various embodiments, referring now to FIG. 69, the second layer 4012 can comprise a layer of pledgets 4060 interconnected to one another by a pledget support frame 4061. In at least one such embodiment, the pledgets 4060 and the pledget support frame 4061 can be comprised of a molded plastic material, such as polyglycolic acid (PGA), for example. Each pledget 4060 can comprise one or more apertures or slots 4062 which can be configured to receive a staple leg 4021 extending therethrough as illustrated in FIGS. 70 and 71. Each pledget 4060 can further comprise a receiving slot 4063 defined therein which can be configured to receive a base 4022 of a staple 4020. In various embodiments, referring again to FIG. 69, the pledgets 4060 and/or pledget support fame 4061 can comprise a plurality of score marks, perforations, or the like which can be configured to allow the pledgets 4060 to become detached from the pledget support frame 4061 at a desired location. Similarly, referring to FIG. 71, one or more pledgets 4060 can be connected to one another along a line comprising perforations and/or score marks 4064, for example. In use, the compressible foam layer 4011 can be positioned against the targeted tissue T and the cartridge body 4010 can be compressed by the anvil 4040 such that the anvil 4040 can deform the staples 4020. When the staples 4020 are deformed, the staple legs 4021 of each staple 4020 can capture the tissue T, a portion of the first layer 4011, and a pledget 4060 within the deformed staple. When the staple cartridge channel 4030 is moved away from the implanted staple cartridge 4060, for example, the pledget support frame 4061 can be detached from the pledgets 4060 and/or the pledgets 4060 can be detached from one another. In certain circumstances, the pledgets 4060 can be detached from the frame 4061 and/or each other when the staples 4020 are being deformed by the anvil 4040 as described above.

Figure 73:
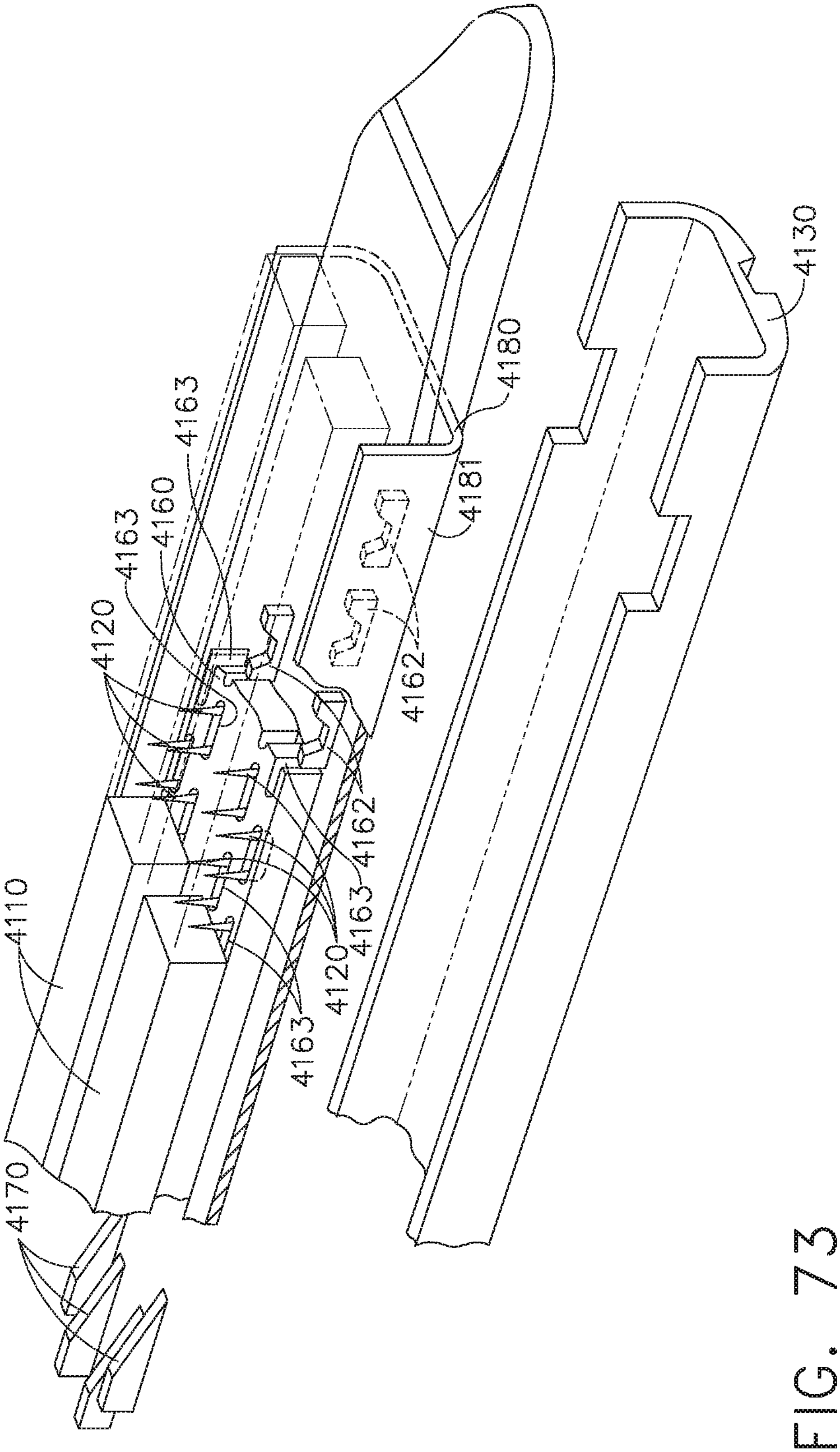
FIG. 73 is an exploded perspective view of an alternative embodiment of a compressible staple cartridge comprising staples therein and a system for driving the staples against an anvil.
Figure 73A:
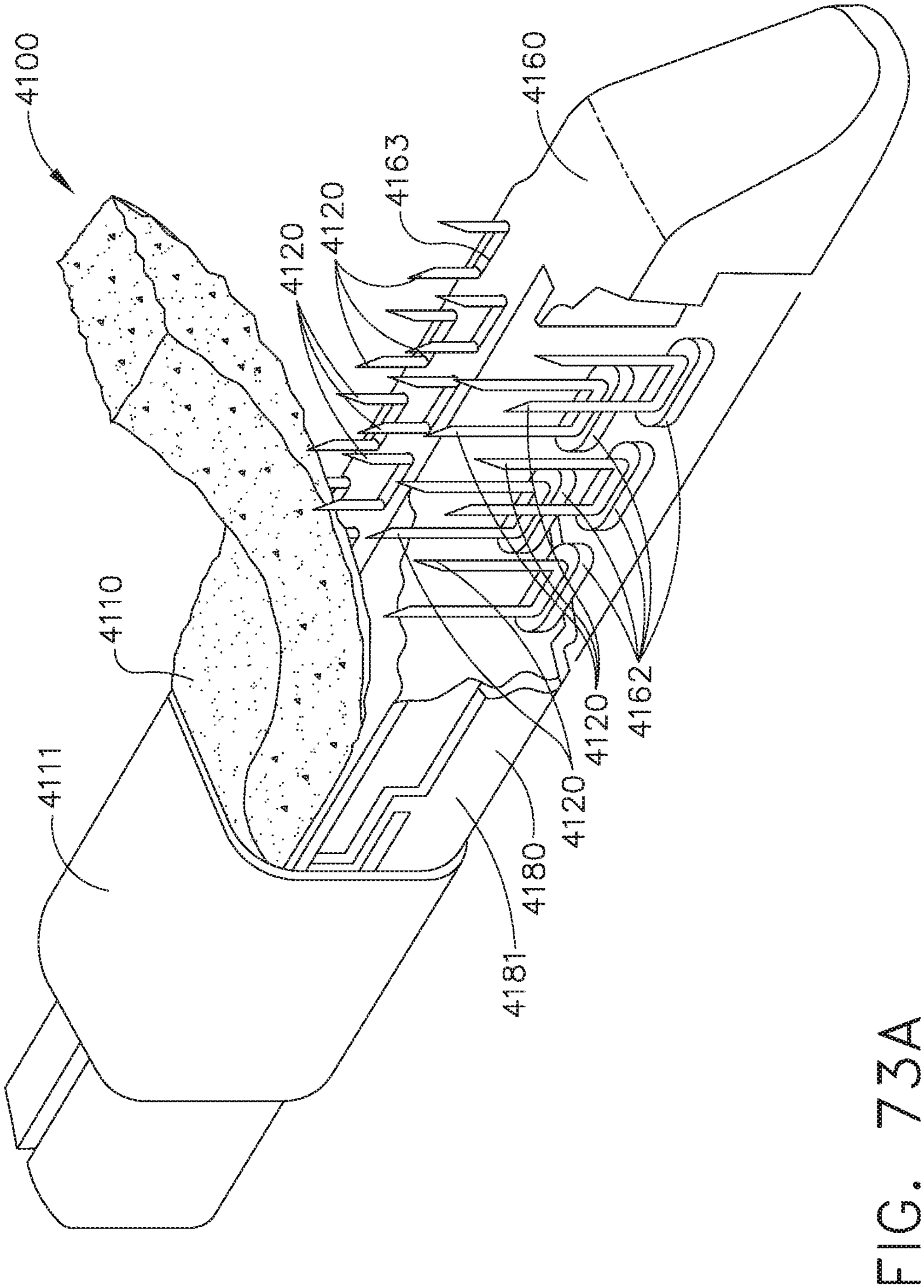
FIG. 73A is a partial cut-away view of an alternative embodiment of the staple cartridge of FIG. 73.
Figure 74:
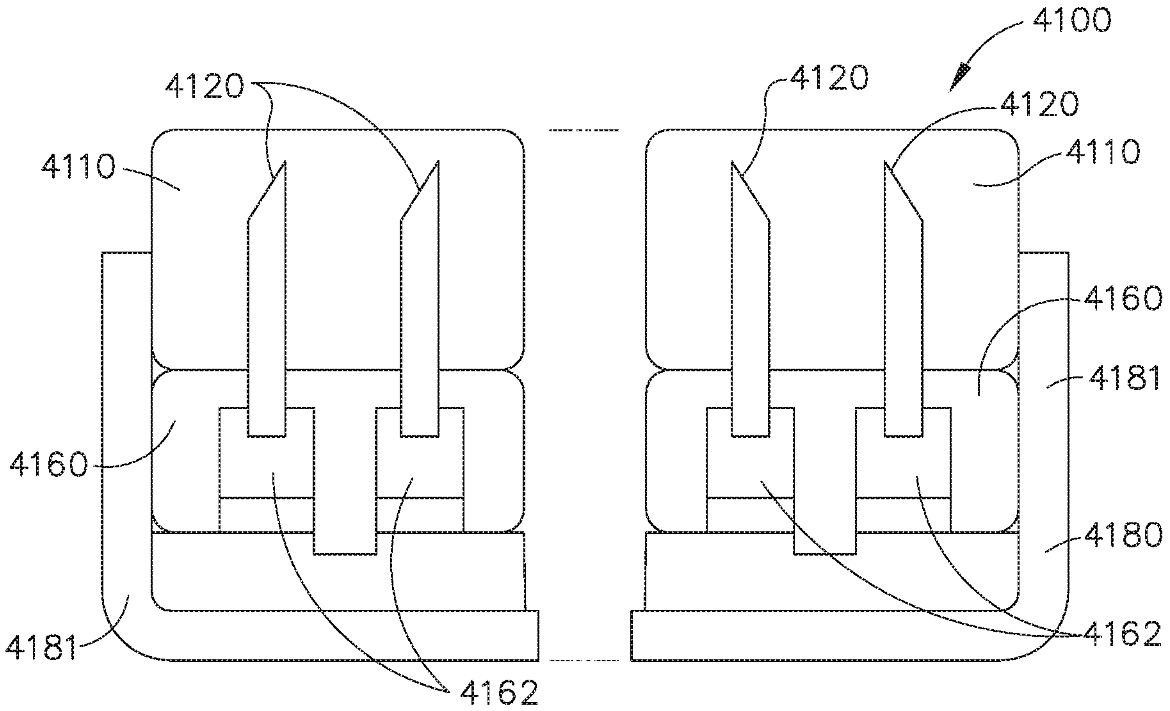
FIG. 74 is a cross-sectional view of the staple cartridge of FIG. 73.
Figure 75:
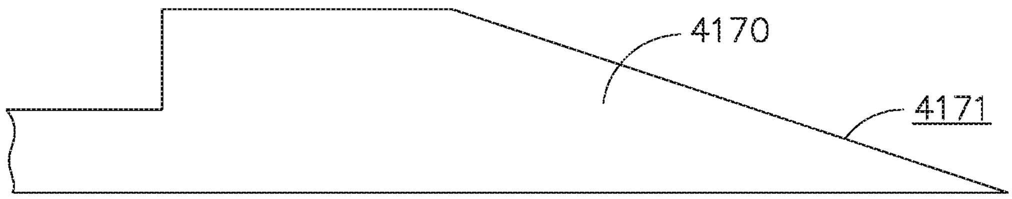
FIG. 75 is an elevational view of a sled configured to traverse the staple cartridge of FIG. 73 and move the staples to toward the anvil.

In various embodiments described herein, the staples of a staple cartridge can be fully formed by an anvil when the anvil is moved into a closed position. In various other embodiments, referring now to FIGS. 73-76, the staples of a staple cartridge, such as staple cartridge 4100, for example, can be deformed by an anvil when the anvil is moved into a closed position and, in addition, by a staple driver system which moves the staples toward the closed anvil. The staple cartridge 4100 can comprise a compressible cartridge body 4110 which can be comprised of a foam material, for example, and a plurality of staples 4120 at least partially positioned within the compressible cartridge body 4110. In various embodiments, the staple driver system can comprise a driver holder 4160, a plurality of staple drivers 4162 positioned within the driver holder 4160, and a staple cartridge pan 4180 which can be configured to retain the staple drivers 4162 in the driver holder 4160. In at least one such embodiment, the staple drivers 4162 can be positioned within one or more slots 4163 in the driver holder 4160 wherein the sidewalls of the slots 4163 can assist in guiding the staple drivers 4162 upwardly toward the anvil. In various embodiments, the staples 4120 can be supported within the slots 4163 by the staple drivers 4162 wherein, in at least one embodiment, the staples 4120 can be entirely positioned in the slots 4163 when the staples 4120 and the staple drivers 4162 are in their unfired positions. In certain other embodiments, at least a portion of the staples 4120 can extend upwardly through the open ends 4161 of slots 4163 when the staples 4120 and staple drivers 4162 are in their unfired positions. In at least one such embodiment, referring primarily now to FIG. 74, the bases of the staples 4120 can be positioned within the driver holder 4160 and the tips of the staples 4120 can be embedded within the compressible cartridge body 4110. In certain embodiments, approximately one-third of the height of the staples 4120 can be positioned within the driver holder 4160 and approximately two-thirds of the height of the staples 4120 can be positioned within the cartridge body 4110. In at least one embodiment, referring to FIG. 73A, the staple cartridge 4100 can further comprise a water impermeable wrap or membrane 4111 surrounding the cartridge body 4110 and the driver holder 4160, for example.

Figure 76:
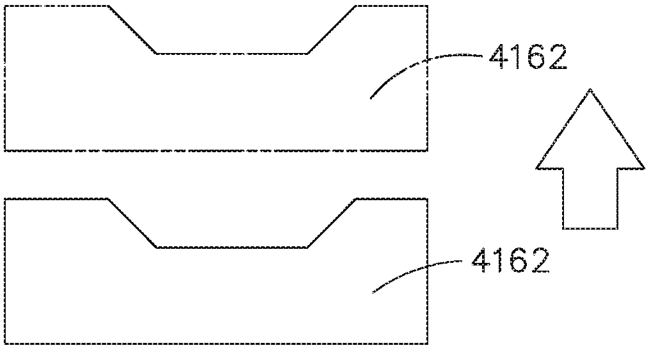
FIG. 76 is a diagram of a staple driver which can be lifted toward the anvil by the sled of FIG. 75.
Figure 77:
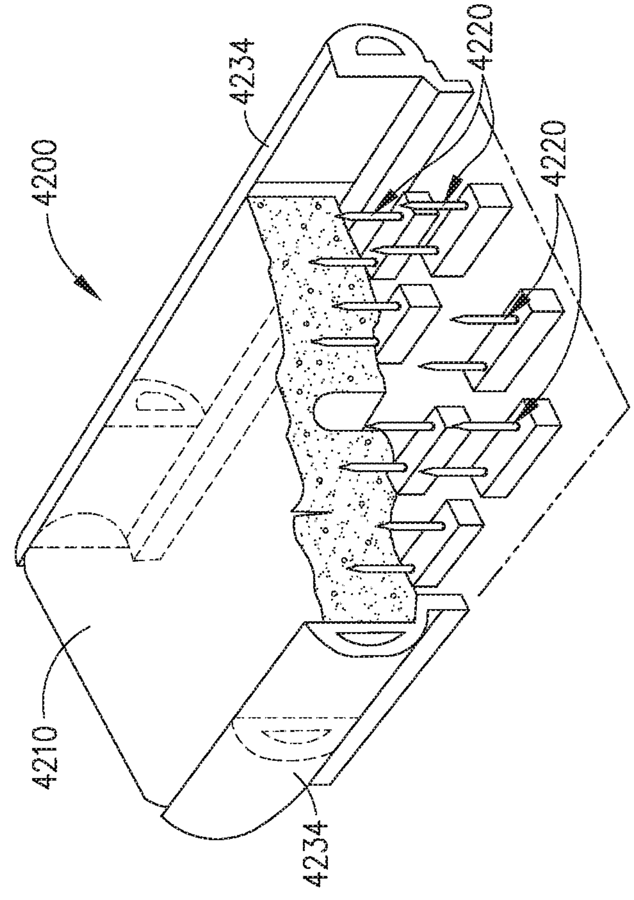
FIG. 77 is a break-away view of a staple cartridge in accordance with at least one alternative embodiment comprising staples positioned within staple drivers.
Figure 78:
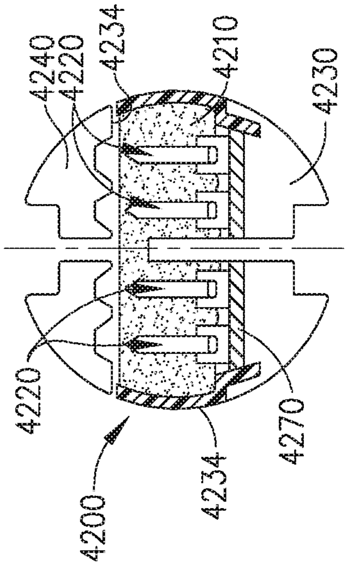
FIG. 78 is a cross-sectional view of the staple cartridge of FIG. 77 positioned within a staple cartridge channel.

In use, the staple cartridge 4100 can be positioned within a staple cartridge channel, for example, and the anvil can be moved toward the staple cartridge 4100 into a closed position. In various embodiments, the anvil can contact and compress the compressible cartridge body 4110 when the anvil is moved into its closed position. In certain embodiments, the anvil may not contact the staples 4120 when the anvil is in its closed position. In certain other embodiments, the anvil may contact the legs of the staples 4120 and at least partially deform the staples 4120 when the anvil is moved into its closed position. In either event, the staple cartridge 4100 can further comprise one or more sleds 4170 which can be advanced longitudinally within the staple cartridge 4100 such that the sleds 4170 can sequentially engage the staple drivers 4162 and move the staple drivers 4162 and the staples 4120 toward the anvil. In various embodiments, the sleds 4170 can slide between the staple cartridge pan 4180 and the staple drivers 4162. In embodiments where the closure of the anvil has started the forming process of the staples 4120, the upward movement of the staples 4120 toward the anvil can complete the forming process and deform the staples 4120 to their fully formed, or at least desired, height. In embodiments where the closure of the anvil has not deformed the staples 4120, the upward movement of the staples 4120 toward the anvil can initiate and complete the forming process and deform the staples 4120 to their fully formed, or at least desired, height. In various embodiments, the sleds 4170 can be advanced from a proximal end of the staple cartridge 4100 to a distal end of the staple cartridge 4100 such that the staples 4120 positioned in the proximal end of the staple cartridge 4100 are fully formed before the staples 4120 positioned in the distal end of the staple cartridge 4100 are fully formed. In at least one embodiment, referring to FIG. 75, the sleds 4170 can each comprise at least one angled or inclined surface 4711 which can be configured to slide underneath the staple drivers 4162 and lift the staple drivers 4162 as illustrated in FIG. 76.

In various embodiments, further to the above, the staples 4120 can be formed in order to capture at least a portion of the tissue T and at least a portion of the compressible cartridge body 4110 of the staple cartridge 4100 therein. After the staples 4120 have been formed, the anvil and the staple cartridge channel 4130 of the surgical stapler can be moved away from the implanted staple cartridge 4100. In various circumstances, the cartridge pan 4180 can be fixedly engaged with the staple cartridge channel 4130 wherein, as a result, the cartridge pan 4180 can become detached from the compressible cartridge body 4110 as the staple cartridge channel 4130 is pulled away from the implanted cartridge body 4110. In various embodiments, referring again to FIG. 73, the cartridge pan 4180 can comprise opposing side walls 4181 between which the cartridge body 4110 can be removably positioned. In at least one such embodiment, the compressible cartridge body 4110 can be compressed between the side walls 4181 such that the cartridge body 4110 can be removably retained therebetween during use and releasably disengaged from the cartridge pan 4180 as the cartridge pan 4180 is pulled away. In at least one such embodiment, the driver holder 4160 can be connected to the cartridge pan 4180 such that the driver holder 4160, the drivers 4162, and/or the sleds 4170 can remain in the cartridge pan 4180 when the cartridge pan 4180 is removed from the surgical site. In certain other embodiments, the drivers 4162 can be ejected from the driver holder 4160 and left within the surgical site. In at least one such embodiment, the drivers 4162 can be comprised of a bioabsorbable material, such as polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. In various embodiments, the drivers 4162 can be attached to the staples 4120 such that the drivers 4162 are deployed with the staples 4120. In at least one such embodiment, each driver 4162 can comprise a trough configured to receive the bases of the staples 4120, for example, wherein, in at least one embodiment, the troughs can be configured to receive the staple bases in a press-fit and/or snap-fit manner.

In certain embodiments, further to the above, the driver holder 4160 and/or the sleds 4170 can be ejected from the cartridge pan 4180. In at least one such embodiment, the sleds 4170 can slide between the cartridge pan 4180 and the driver holder 4160 such that, as the sleds 4170 are advanced in order to drive the staple drivers 4162 and staples 4120 upwardly, the sleds 4170 can move the driver holder 4160 upwardly out of the cartridge pan 4180 as well. In at least one such embodiment, the driver holder 4160 and/or the sleds 4170 can be comprised of a bioabsorbable material, such as polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. In various embodiments, the sleds 4170 can be integrally formed and/or attached to a drive bar, or cutting member, which pushes the sleds 4170 through the staple cartridge 4100. In such embodiments, the sleds 4170 may not be ejected from the cartridge pan 4180 and may remain with the surgical stapler while, in other embodiments in which the sleds 4170 are not attached to the drive bar, the sleds 4170 may be left in the surgical site. In any event, further to the above, the compressibility of the cartridge body 4110 can allow thicker staple cartridges to be used within an end effector of a surgical stapler as the cartridge body 4110 can compress, or shrink, when the anvil of the stapler is closed. In certain embodiments, as a result of the staples being at least partially deformed upon the closure of the anvil, taller staples, such as staples having an approximately 0.18" staple height, for example, could be used, wherein approximately 0.12" of the staple height can be positioned within the compressible layer 4110 and wherein the compressible layer 4110 can have an uncompressed height of approximately 0.14", for example.

Figure 79:
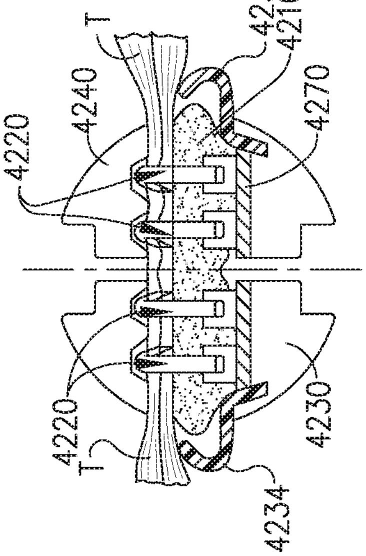
FIG. 79 is a cross-sectional view of the staple cartridge of FIG. 77 illustrating an anvil moved into a closed position and staples contained within the staple cartridge deformed by the anvil.
Figure 80:
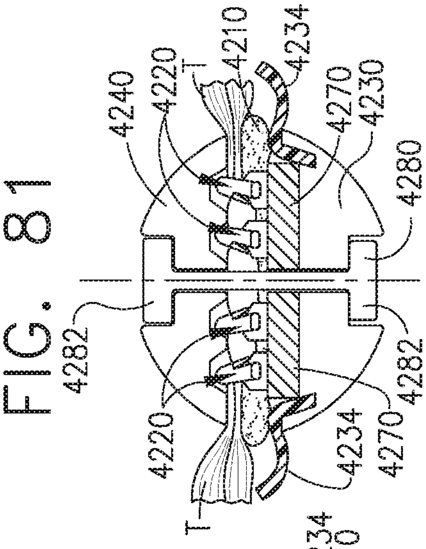
FIG. 80 is a cross-sectional view of the staple cartridge of FIG. 77 illustrating the staples moved upwardly toward the anvil.
Figure 82:
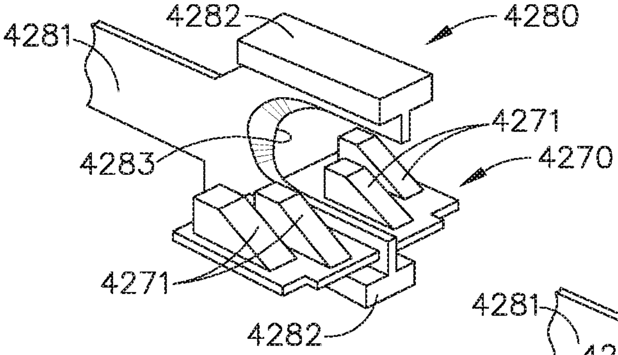
FIG. 82 is a perspective view of a sled and cutting member assembly.
Figure 83:
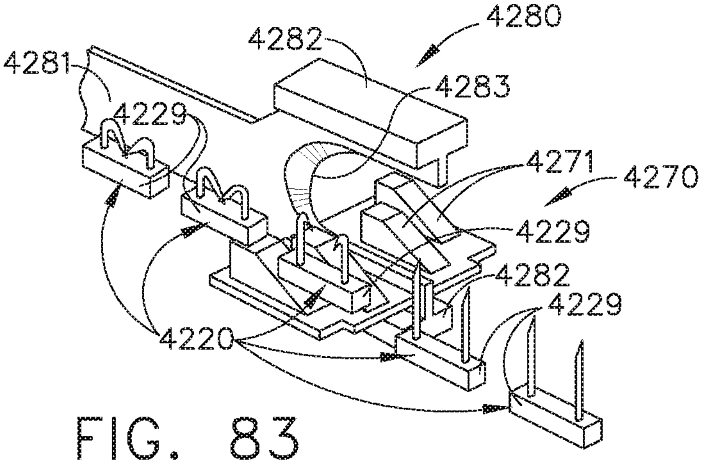
FIG. 83 is a diagram of the sled and cutting member assembly of FIG. 82 being used to lift the staples of the staple cartridge of FIG. 77.

In various embodiments, referring now to FIGS. 77-80, a staple cartridge, such as staple cartridge 4200, for example, can comprise a compressible cartridge body 4210, a plurality of staples 4220 positioned therein, and a plurality of flexible lateral support members 4234. In various embodiments, referring now to FIG. 78, the staple cartridge 4200 can be positioned intermediate an anvil 4240 and a staple cartridge channel 4230 wherein, in at least one embodiment, the lateral support members 4234 can be attached to the staple cartridge channel 4230. When the anvil 4240 is moved downwardly to compress the cartridge body 4210 and at least partially deform the staples 4220, as illustrated in FIG. 79, the side portions of the cartridge body 4210 can bulge laterally and push the lateral support members 4234 outwardly. In at least one such embodiment, the lateral support members 4234 can be attached to the cartridge body 4210 and, when the cartridge body 4210 bulges laterally as described above, the lateral support members 4234 can detach from the cartridge body 4210 as illustrated in FIG. 79. In at least one embodiment, the lateral support members 4234 can be adhered to the cartridge body 4210 utilizing at least one adhesive, such as fibrin and/or protein hydrogel, for example. Similar to the above, the closing of the anvil 4240 may only partially deform the staples 4220, wherein the formation of the staples 4220 can be completed by the advancement of one or more sleds 4270 through the staple cartridge 4200 as illustrated in FIG. 80. In various embodiments, referring now to FIGS. 82 and 83, the sleds 4270 can be advanced from a proximal end of the staple cartridge 4200 to a distal end of the staple cartridge 4200 by a cutting member 4280. In at least one such embodiment, the cutting member 4280 can comprise a cutting element, or knife, 4283, which can be advanced through the tissue T and/or the compressible cartridge body 4210. In certain embodiments, the cutting member 4280 can comprise camming members 4282 which can travel along the outside surfaces of the jaws 4230 and 4240 and move or hold the jaws in position. In various embodiments, as a result of the above, the staples 4220 can be formed into their final shapes at the same time, or at least substantially the same time, as the tissue T is incised. In at least one such embodiment, the sleds 4270 can be positioned distally with respect to the knife 4283 such that the tissue T is only incised when the proceeding portion of the tissue has been fully stapled, for example.

In various embodiments, referring again to FIGS. 82 and 83, the sleds 4270 can comprise separate slidable members which are advanced together by the cutting member 4280. In at least one such embodiment, the sleds 4270 can be contained within the staple cartridge 4200 and the cutting member 4280 can be advanced into the staple cartridge 4200 by a firing bar 4281 such that the cutting member 4280 engages the sleds 4270 and advances the sleds 4270 distally. In certain embodiments, the sleds 4270 can be connected to one another. In either event, each sled 4270 can comprise an angled surface, or cam, 4271 which can be configured to lift the staples 4220 aligned within a staple row. In certain embodiments, the angled surfaces 4271 can be integrally formed with the cutting member 4280. In at least one embodiment, referring again to FIGS. 82 and 83, each staple 4200 can comprise a base, at least one deformable member extending from the base, and a crown 4229 overmolded onto and/or positioned around at least a portion of the base and/or the deformable members of the staple 4200. In various embodiments, such crowns 4229 can be configured to be driven directly by a sled 4270, for example. More particularly, in at least one embodiment, the crowns 4229 of staples 4220 can be configured such that the angled surfaces 4271 of the sleds 4270 can slide underneath and directly contact the crowns 4229 without a staple driver positioned therebetween. In such embodiments, each crown 4229 can comprise at least one co-operating angled or inclined surface which can be engaged by an angled surface 4271 of the sleds 4270 such that the co-operating angled surfaces can drive the staples 4220 upwardly when the sleds 4270 are slid underneath the staples 4220.

Figure 81:
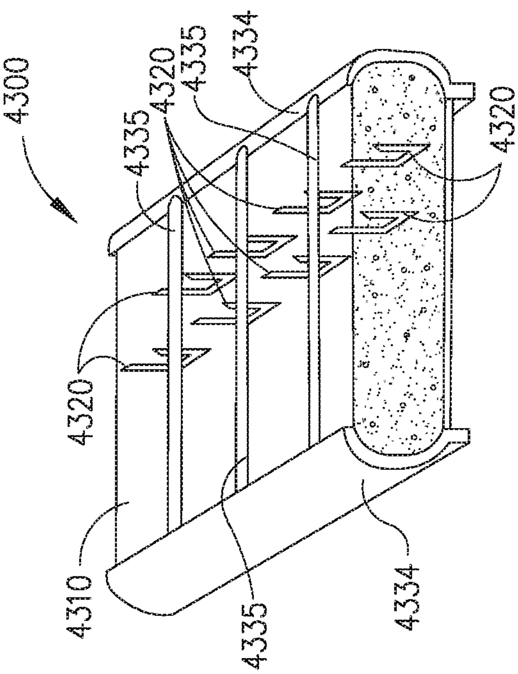
FIG. 81 is a perspective view of an alternative embodiment of a staple cartridge comprising straps connecting the flexible sides of the staple cartridge.

In various embodiments, referring now to FIG. 81, a staple cartridge, such as staple cartridge 4300, for example, can comprise a compressible body 4310 and a plurality of staples 4320 positioned within the compressible body 4310. Similar to the above, the staple cartridge 4300 can comprise flexible lateral supports 4334 which can be attached to a staple cartridge channel and/or adhered to the compressible body 4310. In addition to the above, the flexible lateral supports 4334 can be connected together by one or more struts, or connection members, 4335 which can be configured to hold the lateral supports 4334 together. In use, the connection members 4335 can be configured to prevent, or at least inhibit, the lateral supports 4334 from becoming prematurely detached from the cartridge body 4310. In certain embodiments, the connection members 4335 can be configured to hold the lateral supports 4334 together after the staple cartridge 4300 has been compressed by an anvil. In such embodiments, the lateral supports 4334 can resist the lateral bulging, or displacement, of the lateral portions of the cartridge body 4310. In certain embodiments, a cutting member, such as cutting member 4280, for example, can be configured to transect the connection members 4335 as the cutting member 4280 is moved distally within the cartridge body 4310. In at least one such embodiment, the cutting member 4280 can be configured to push one or more sleds, such as sleds 4270, for example, distally in order to form the staples 4320 against an anvil. The sleds 4270 can lead the cutting edge 4283 such that the cutting member 4280 does not transect a connection member 4335 until the staples 4320 adjacent to that connection member 4335 have been fully formed, or at least formed to a desired height. In various circumstances, the connection members 4335, in co-operation with the lateral supports 4334, can prevent, or at least reduce, the lateral movement of the compressible cartridge body 4310 and, concurrently, prevent, or at least reduce, the lateral movement of the staples 4320 positioned within the cartridge body 4310. In such circumstances, the connection members 4335 can hold the staples 4320 in position until after they are deformed and the connection members 4335 can be thereafter cut to release the lateral portions of the cartridge body 4310. As mentioned above, the lateral supports 4334 can be connected to the staple cartridge channel and, as a result, can be removed from the surgical site with the staple cartridge channel after the staple cartridge 4300 has been implanted. In certain embodiments, the lateral supports 4334 can be comprised of an implantable material and can be left within a surgical site. In at least one embodiment, the connection members 4335 can be positioned intermediate the cartridge body 4310 and the tissue T and, after the connection members 4335 have been detached from the lateral supports 4334, the connections members 4335 can remain implanted in the patient. In at least one such embodiment, the connection members 4335 can be comprised of an implantable material and, in certain embodiments, the connection members 4335 can be comprised of the same material as the lateral supports 4334, for example. In various embodiments, the connection members 4335 and/or lateral supports 4334 can be comprised of a flexible bioabsorbable material such as polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. In various embodiments, a connection member can comprise a sheet of material connecting the lateral supports 4334. In certain embodiments, a staple cartridge can comprise connection members extending across the top surface of the cartridge body 4310 and, in addition, connection members extending around the bottom surface of the cartridge body 4310.

Figure 84:
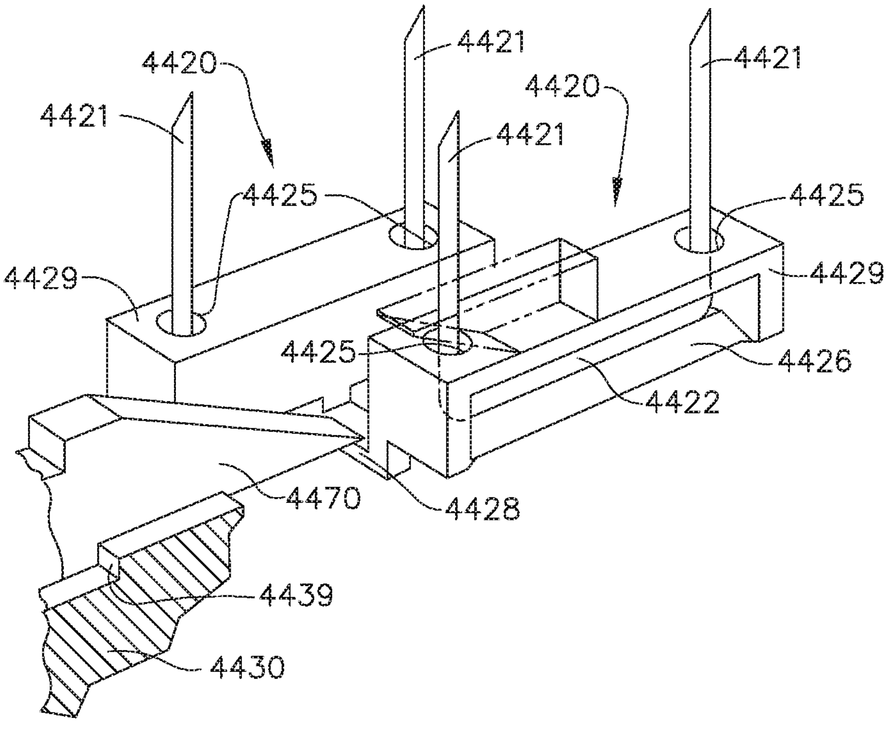
FIG. 84 is a diagram illustrating a sled configured to engage and lift staples toward an anvil and a lock-out system configured to selectively permit the sled to move distally.
Figure 85A:
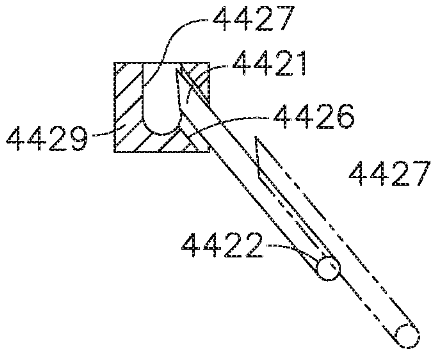
FIGS. 85A-85C illustrate the progression of a staple being inserted into a staple crown.
Figure 85B:
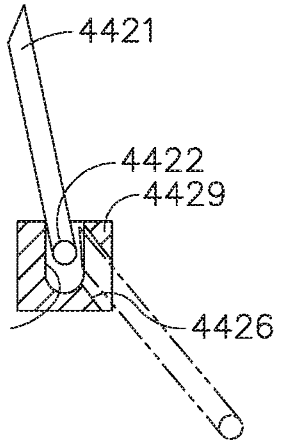
Figure 85C:
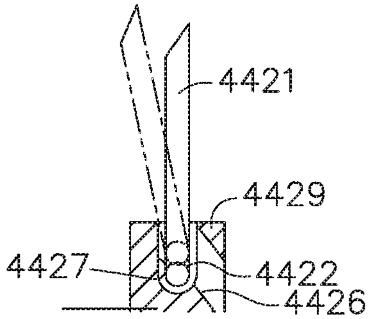

In various embodiments, referring now to FIG. 84, a staple cartridge can comprise staples, such as staples 4420, for example, which can comprise a wire portion inserted into a crown portion. In at least one embodiment, the wire portion can be comprised of metal, such as titanium and/or stainless steel, for example, and/or plastic, such as polydioxanone (PDS) and/or polyglycolic acid (PGA), for example. In at least one embodiment, the crown portion can be comprised of metal, such as titanium and/or stainless steel, for example, and/or plastic, such as polydioxanone (PDS) and/or polyglycolic acid (PGA), for example. In certain embodiments, the wire portion of each staple 4420 can comprise a base 4422 and deformable legs 4421 extending from the base 4422 wherein the crown portion of each staple 4420 can comprise a crown 4429 which can be configured to receive at least a portion of a base 4422 therein. In order to assemble the portions of each staple 4420, referring now to FIGS. 85A-85C, the legs 4421 of the wire portion can be inserted into an opening 4426 in a crown 4429 wherein the opening 4426 can be configured to guide the legs 4421 into a base chamber 4427. The wire portion can be further inserted into the crown 4429 such that the legs 4421 exit the base chamber 4427 and the base 4422 of the wire portion enters into the base chamber 4427. In at least one such embodiment, the base chamber 4427 can be configured such that the wire portion is rotated within the crown 4429 as the base 4422 enters into the base chamber 4427 such that the staple legs 4421 are pointed in an upward, or at least substantially upward, direction. In various embodiments, referring again to FIG. 84, the crown 4429 can comprise exit holes 4425 which can be configured to receive the staple legs 4421 therein.

In various embodiments, further to the above, a surgical stapler can comprise a sled 4470 configured to transverse the staple cartridge 4400 and staple cartridge channel 4430 and move the staples 4420 contained within the cartridge body 4410 toward an anvil. In various circumstances, the sled 4470 can be moved from a proximal end of the staple cartridge channel 4430 to a distal end of the cartridge channel 4430 in order to implant the cartridge body 4410 and the staples 4420. In certain circumstances, the sled 4470 can be retracted or returned to the proximal end of the cartridge channel 4430 and another staple cartridge 4400 can be inserted into the cartridge channel 4430. Once the new staple cartridge 4400 has been positioned within the cartridge channel 4430, the sled 4470 can be advanced distally once again. In various embodiments, the surgical stapler may comprise one or more lock-out features which can prevent the sled 4470 from being advanced distally once again without a new staple cartridge 4400 being positioned within the cartridge channel 4430. In at least one such embodiment, referring again to FIG. 84, the staple cartridge channel 4430 can comprise a lock-out shoulder 4439 which can be configured to prevent, or at least limit, the distal movement of the sled 4470. More particularly, the sled 4470 can be configured to abut the shoulder 4439 unless the sled 4470 is at least partially lifted upwardly over the shoulder 4439 by a lift feature 4428, for example, extending between the proximal-most staples 4420 within a staple cartridge 4400. Stated another way, absent the presence of the proximal-most staples 4420 in a new staple cartridge 4400, the sled 4470 cannot be advanced. Thus, when an expended staple cartridge 4400 is present within the cartridge channel 4430, or no staple cartridge 4400 is present in the cartridge channel 4430 at all, the sled 4470 cannot be advanced within the cartridge channel 4430.

Figure 86:
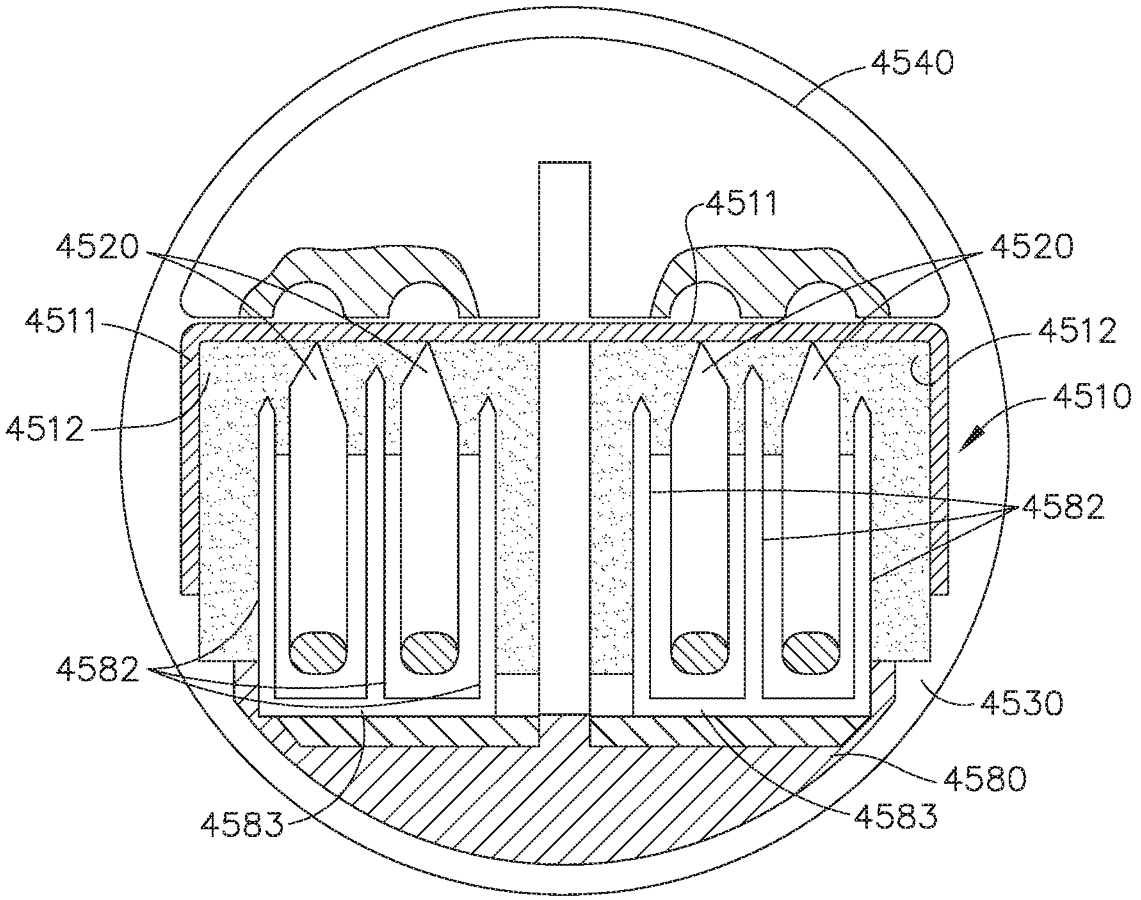
FIG. 86 is a cross-sectional view of a staple cartridge comprising a support pan or retainer.

Further to the above, referring now to FIG. 86, a staple cartridge, such as staple cartridge 4500, for example, can be positioned within a staple cartridge channel 4530 and can comprise a compressible cartridge body 4510, a plurality of staples 4520 positioned within the cartridge body 4510, and a cartridge pan, or retainer, 4580. In various embodiments, the compressible cartridge body 4510 can comprise an outer layer 4511 and an inner layer 4512 wherein, in at least one embodiment, the outer layer 4511 can sealingly enclose the inner layer 4512. In at least one such embodiment, the outer layer 4511 can extend between the inner layer 4512 and the cartridge pan 4580. In certain other embodiments, the outer layer 4511 may only partially surround the inner layer 4512 and, in at least one such embodiment, the outer layer 4511 and the cartridge pan 4580 can co-operate to encompass, or at least substantially encompass, the inner layer 4512. In various embodiments, further to the above, the staples 4520 can be supported by the cartridge pan 4580 wherein the cartridge pan 4580 can comprise one or more staple support channels configured to support the staples 4520. In certain embodiments, the cartridge pan 4580 can be attached to the cartridge body 4510 wherein, in at least one such embodiment, the cartridge body 4510 can be compressed laterally between opposing side walls of the cartridge pan 4580. In various embodiments, the side walls of the cartridge pan 4580 can support the cartridge body 4510 laterally and, in at least one such embodiment, the cartridge pan 4580 can comprise one or more walls, or fins, 4582 extending upwardly from the bottom support 4583 into the cartridge body 4510. In at least one such embodiment, the cartridge body 4510 can comprise one or more slots, or channels, therein which can be configured to receive and/or interlock with the walls 4582. In various embodiments, the walls 4582 can extend partially, or almost entirely, through the cartridge body 4510. In at least one such embodiment, the walls 4582 can extend longitudinally through the staple cartridge 4500 between a first row of staples 4520 and a second row of staples 4520.

In various embodiments, the cartridge body 4510 and/or the cartridge pan 4580 can comprise co-operating retention features which can provide a snap-fit between the cartridge pan 4580 and the cartridge body 4510. In certain embodiments, the staple cartridge 4500 can be positioned within the cartridge channel 4530 such that the cartridge pan 4580 is positioned against and/or attached to the cartridge channel 4530. In at least one embodiment, the cartridge pan 4580 can be detachably coupled to the cartridge channel 4530 such that, after the staple cartridge 4500 has been compressed by the anvil 4540 and the staples 4520 have been deformed, the cartridge pan 4580 can detach from the cartridge channel 4530 and can be implanted with the cartridge body 4510. In at least one such embodiment, the cartridge pan 4580 can be comprised of a bioabsorbable material such as polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. In certain embodiments, a surgical stapler can further comprise a firing mechanism and/or driver which can be slid intermediate the staple cartridge channel 4530 and a bottom drive surface on the cartridge pan 4580 which can be configured to lift or eject the cartridge pan 4580 from the cartridge channel 4530. In certain embodiments, the cartridge body 4510 can be detachably coupled to the cartridge pan 4580 such that, after the staple cartridge 4500 has been compressed by the anvil 4540 and the staples 4520 have been deformed, the cartridge body 4510 can detach from the cartridge pan 4580. In at least one such embodiment, the cartridge pan 4580 can remain fixedly engaged with the cartridge channel 4530 such that the cartridge pan 4580 is removed from the surgical site with the cartridge channel 4530. In certain embodiments, a surgical stapler can further comprise a firing mechanism and/or driver which can be slid intermediate the staple cartridge pan 4580 and a bottom drive surface on the cartridge body 4510 which can be configured to lift or eject the cartridge body 4510 from the cartridge pan 4580. In at least one such embodiment, the staple cartridge 4500 can further comprise staple drivers positioned intermediate the cartridge pan 4580 and the staples 4520 such that, as the firing mechanism is slid distally, the staple drivers and the staples 4520 can be driven upwardly toward the anvil. In at least one such embodiment, the staple drivers can be at least partially embedded within the compressible cartridge body 4510.

In various embodiments, similar to the above, the staple cartridge 4500 can comprise a lock-out feature which can be configured to prevent, or at least limit, the distal movement of a cutting member unless a unfired staple cartridge 4500 has been positioned within the staple cartridge channel 4530. In certain embodiments, the staple cartridge pan 4580 can comprise a surface which lifts the cutting member upwardly and over a locking surface within the staple cartridge channel 4530, for example. In the event that a staple cartridge 4500 comprising a cartridge pan 4580 is not present in the cartridge channel 4530, the cutting member cannot be advanced. In at least one embodiment, the proximal-most staples, and/or any other suitable staples, within a staple cartridge 4500 can comprise a lifting surface which can sufficiently lift the cutting member over the locking surface. In addition to or in lieu of the above, various portions of the staple cartridge 4500 can be comprised of materials having different colors. In such embodiments, a surgeon may be able to visually identify when an unfired and/or fired staple cartridge is present in the staple cartridge channel 4530. In at least one such embodiment, the outer layer 4511 of the cartridge body 4510 may have a first color, the cartridge pan 4580 may have a second color, and the staple cartridge channel 4530 may have a third color. In the event that the surgeon sees the first color, the surgeon may know that an unfired cartridge 4500 is present in the staple cartridge channel 4530; in the event that the surgeon sees the second color, the surgeon may know that a fired cartridge 4500 is present in the staple cartridge channel 4530 and that the remaining cartridge pan 4580 needs to be removed; and in the event that the surgeon sees the third color, the surgeon may know that no portion of a staple cartridge 4500 remains within the cartridge channel 4530.

Figure 88:
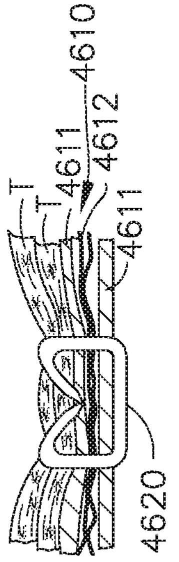
FIG. 88 is a diagram illustrating the staple cartridge of FIG. 87 in an implanted condition.
Figure 87:
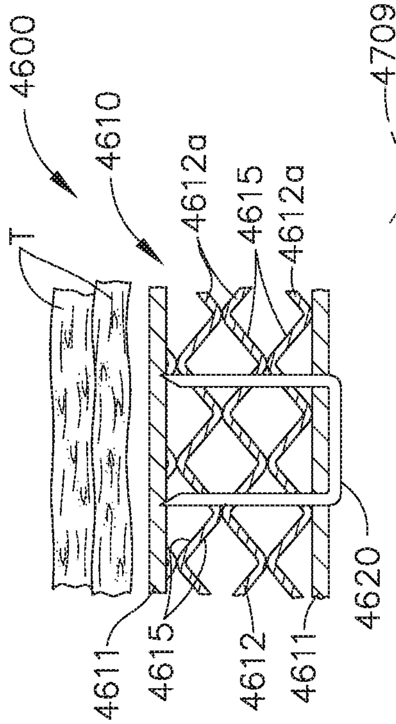
FIG. 87 is a partial cross-sectional view of a compressible staple cartridge in accordance with at least one alternative embodiment.

In various embodiments, referring now to FIG. 87, a staple cartridge, such as staple cartridge 4600, for example, can comprise a compressible, implantable cartridge body 4610 and a plurality of staples 4620 positioned therein. The cartridge body 4610 can comprise an outer layer 4611 and an inner layer 4612. In certain embodiments, the inner layer 4612 can comprise a plurality of pockets, such as pockets, or cavities, 4615, for example, defined therein which can facilitate the collapse of the cartridge body 4610. In at least one such embodiment, the inner layer 4612 can comprise a corrugated, or honeycomb-configured, lattice which can be configured to withstand a compressive force, or pressure, as long as the compressive force, or pressure, does not exceed a certain threshold value. When the threshold value has not been exceeded, the inner layer 4612 can deform at a linear, or at least substantially linear, rate with respect to the compressive force, or pressure, being applied. After the compressive force, or pressure, has exceeded the threshold value, the inner layer 4612 can suddenly succumb to large deflections and collapse, or buckle, as a result of the compressive load. In various embodiments, the lattice of the inner layer 4612 can be comprised of a plurality of sub-layers 4612*a* which can be connected together. In at least one embodiment, each sub-layer 4612*a* can comprise a plurality of alternating furrows and ridges, or waves, which can be aligned with the alternating furrows and ridges of an adjacent sub-layer 4612*a*. In at least one such embodiment, the furrows of a first sub-layer 4612*a* can be positioned adjacent to the ridges of a second sub-layer 4612*a* and, similarly, the ridges of the first sub-layer 4612*a* can be positioned adjacent to the furrows of the second sub-layer 4612*a*. In various embodiments, the adjacent sub-layers 4612*a* can be adhered to one another and/or the outer layer 4611 by at least one adhesive, such as fibrin and/or protein hydrogel, for example. FIG. 88 illustrates the staple cartridge 4600 after the cartridge body 4610 has been collapsed and the staples 4620 have been deformed in order to capture and hold tissue T against the cartridge body 4610.

Figure 89:
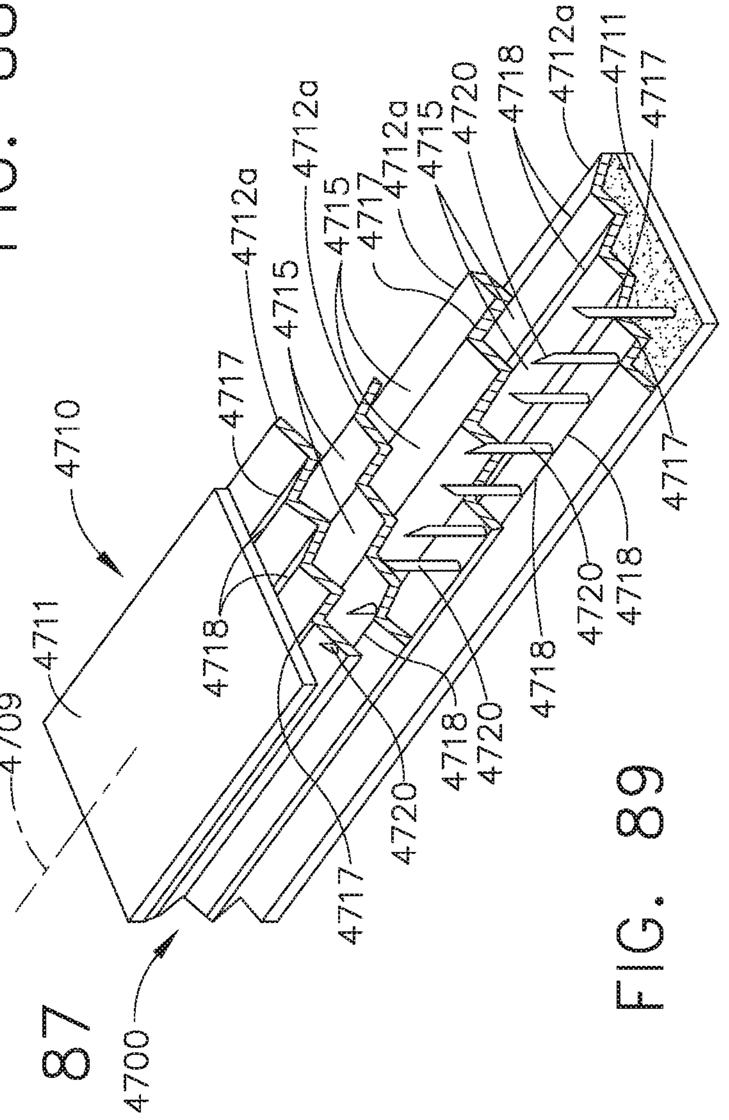
FIG. 89 is a partial cut-away view of a compressible staple cartridge in accordance with at least one alternative embodiment.
Figure 91:
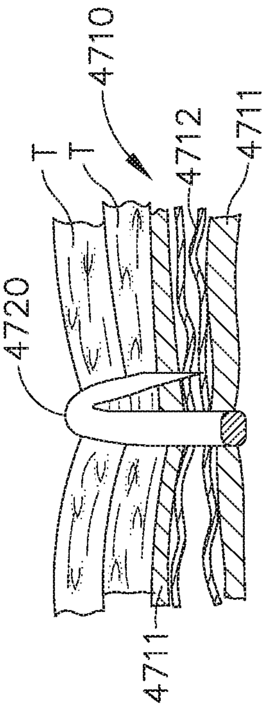
FIG. 91 is a diagram illustrating the staple cartridge of FIG. 89 in an implanted condition.
Figure 90:
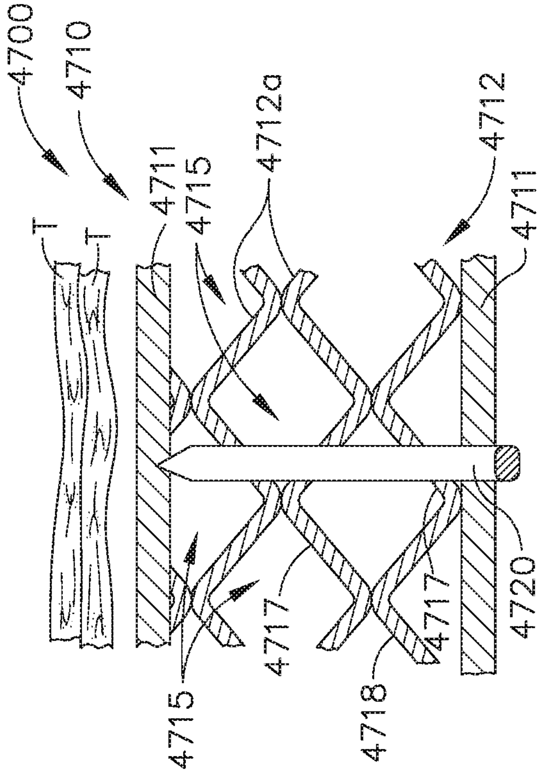
FIG. 90 is a partial cross-sectional view of the staple cartridge of FIG. 89.

In various embodiments, referring now to FIGS. 89-91, a staple cartridge, such as staple cartridge 4700, for example, can comprise a compressible, implantable cartridge body 4710 and a plurality of staples 4720 positioned within the cartridge body 4710. Similar to the above, the cartridge body 4710 can comprise an outer layer 4711 and an inner layer 4712, wherein the inner layer 4712 can comprise a plurality of sub-layers 4712*a*. Also similar to the above, each sub-layer 4712*a* can comprise alternating furrows 4717 and ridges 4718 which can be aligned with one another to define pockets, or cavities, 4715 therebetween. In at least one such embodiment, the furrows 4717 and/or the ridges 4718 can extend along axes which are parallel to one another and/or parallel to a longitudinal axis 4709. In various embodiments, the staples 4720 can be aligned in a plurality of staple rows which can extend along axes which are parallel to one another and/or parallel to the longitudinal axis 4709. In various alternative embodiments, referring again to FIGS. 87 and 88, the staples 4620 contained in the cartridge body 4600 can extend along axes which are traverse or perpendicular with respect to the axes defined by the furrows and ridges of the sub-layers 4612*a*. Referring again to FIGS. 89-91, the staples 4720 can extend through the furrows 4717 and the ridges 4718 wherein friction forces between the staples 4720 and the sub-layers 4712*a* can hold the staples 4720 within the cartridge body 4710. In certain embodiments, the plurality of sub-layers 4712*a* can be comprised of a buttress material and/or plastic material, such as polydioxanone (PDS) and/or polyglycolic acid (PGA), for example, which can be configured to hold the staples 4720 in an upright orientation, for example, and/or hold the staples 4720 in alignment with respect to each other as illustrated in FIGS. 89 and 90. FIG. 91 illustrates the staple cartridge 4700 after the cartridge body 4710 has been collapsed and the staples 4720 have been deformed in order to capture and hold tissue T against the cartridge body 4710.

Figure 92:
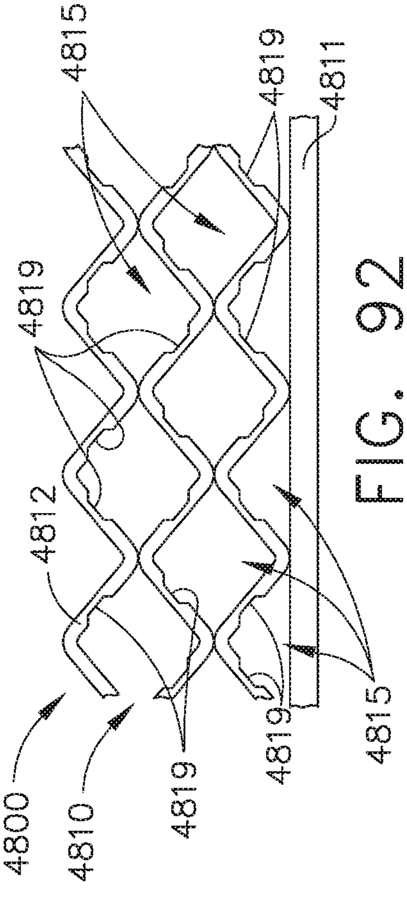
FIG. 92 is a partial cross-sectional view of a crushable staple cartridge in accordance with at least one alternative embodiment.

In various embodiments, referring again to FIGS. 89-91, the cartridge body 4710 can resiliently or elastically collapse when it is compressed. In at least one such embodiment, the waves formed within each sub-layer 4712*a* by the furrows 4717 and the ridges 4718 can be flattened, or at least substantially flattened, when the cartridge body 4710 is compressed which can collapse, or at least substantially collapse, the cavities 4715 defined therebetween. In various circumstances, the cartridge body 4710, or at least portions of the cartridge body 4710, can resiliently or elastically re-expand after the compressive force, or pressure, has been removed from the cartridge body 4710. In at least one such embodiment, the connections between the furrows 4717 and the ridges 4718 of adjacent sub-layers 4712*a* can remain intact, or at least substantially intact, when the cartridge body 4710 is compressed such that, after the compression force has been removed from the cartridge body 4710, the sub-layers 4712*a* can bias themselves away from each other and, as a result, at least partially re-expand the cartridge body 4710. In certain embodiments, the cartridge body 4710 can be plastically deformed, or crushed, when it is compressed and, as a result, the cartridge body 4710 may not re-expand after the compressive force, or pressure, has been removed from the cartridge body 4710. In certain embodiments, referring now to FIG. 92, a staple cartridge, such as staple cartridge 4800, for example, can comprise a crushable cartridge body 4810 comprising an outer layer 4811 and an inner layer 4812, wherein the inner layer 4812 can comprise a corrugated, honeycomb-configured, lattice having a plurality of pockets, or cavities, 4815 defined therein. In various embodiments, the walls defining the lattice of inner layer 4812 can comprise one or more weakened, or thin, cross-sections 4819 which can be configured to allow the walls defining the lattice to break when the cartridge body 4810 is compressed. In such circumstances, the cartridge body 4810 can be crushed when the staple cartridge 4800 is implanted.

Figure 94:
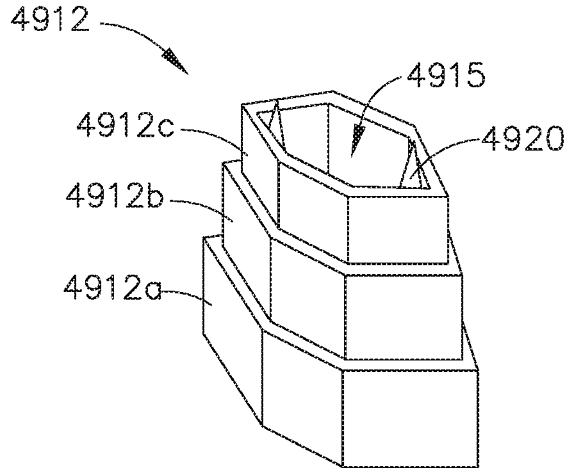
FIG. 94 is a perspective view of a collapsible element of FIG. 93 in an uncollapsed state.
Figure 95:
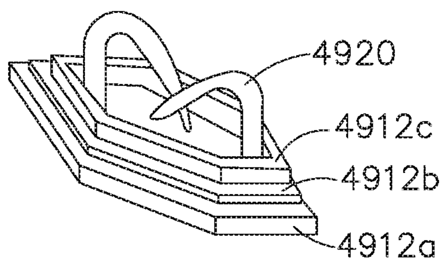
FIG. 95 is a perspective view of the collapsible element of FIG. 94 in a collapsed state.
Figure 93:
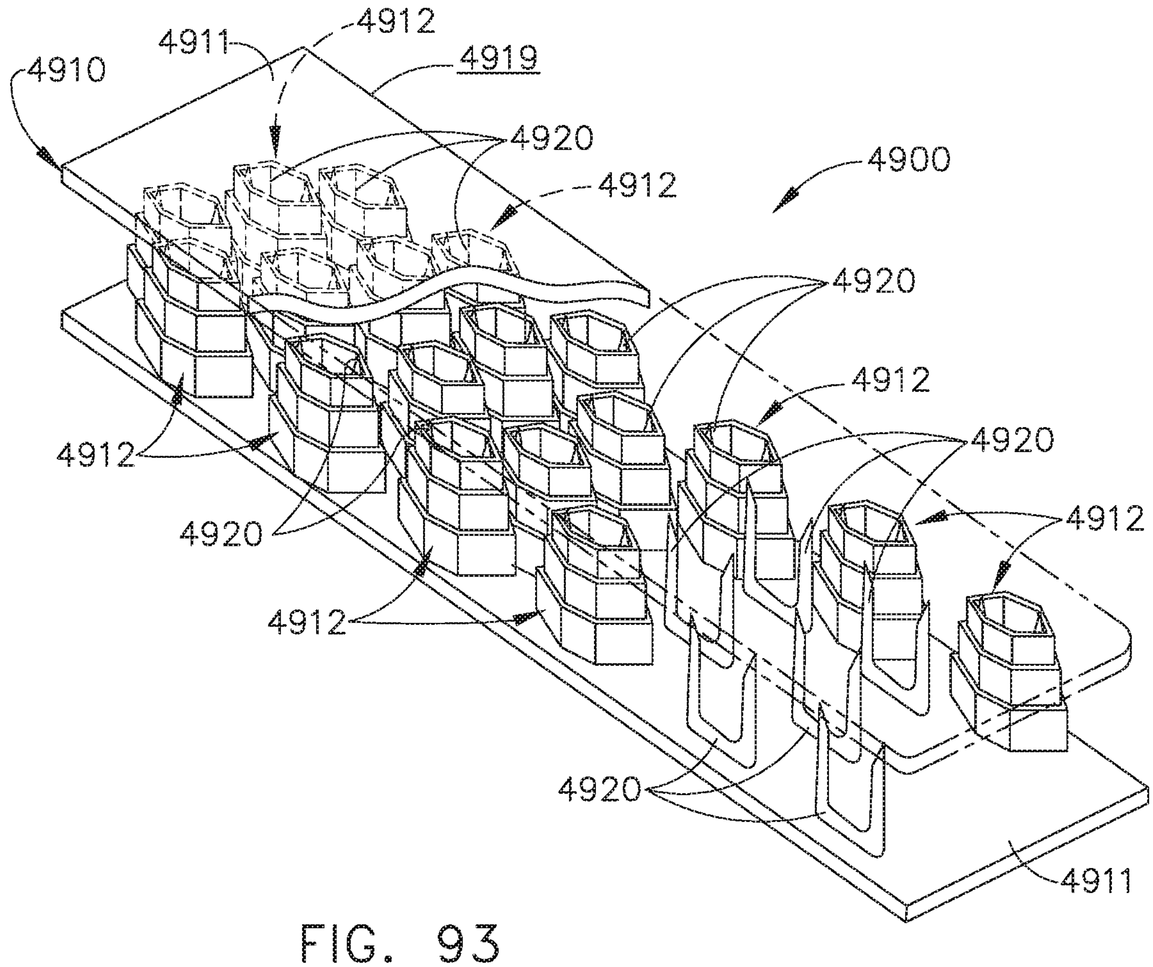
FIG. 93 is a partial cut-away view of a collapsible staple cartridge in accordance with at least one embodiment comprising a plurality of collapsible elements.

In various embodiments, referring now to FIGS. 93-95, a staple cartridge, such as staple cartridge 4900, for example, can comprise a cartridge body 4910 comprising an outer layer 4911 and a plurality of collapsible elements 4912 positioned intermediate top and bottom portions of the outer layer 4911, for example. Referring primarily to FIGS. 93 and 94, the staple cartridge 4900 can further comprise a plurality of staples 4920, wherein each staple 4920 can be positioned in a collapsible element 4912. More particularly, each collapsible element 4912 can comprise a first portion 4912*a*, a second portion 4012*b*, and a third portion 4012*c* which can co-operate to define a cavity 4915 therein which is configured to receive a staple 4920. In use, further to the above, the staple cartridge 4900 can be positioned within a staple cartridge channel and a compressive force can be applied to the tissue contacting surface 4919 in order to compress the cartridge body 4910. As the tissue contacting surface 4919 is moved downwardly, the collapsible elements 4912 can collapse. In such circumstances, the second portion 4912*b* of each collapsible element 4912 can collapse into a corresponding first portion 4912*a* and, similarly, the third portion 4912*c* of each collapsible element 4912 can collapse into a corresponding second portion 4912*b*. As the cartridge body 4910 is compressed and the collapsible elements 4912 are collapsed, the staples 4920 positioned within the collapsible elements 4912 can be deformed, as illustrated in FIG. 95. In various embodiments, the second portion 4912*b* of each collapsible element 4912 can be frictionally engaged and/or press-fit within a corresponding first portion 4912*a* such that, once the compressive force applied to the collapsible element 4912 exceeds the retention force retaining the first portion 4912*a* and the second portion 4912*b* in their extended position (FIG. 94), the first portion 4912*a* and the second portion 4912*b* can begin to slide relative to one another. Similarly, the third portion 4912*c* of each collapsible element 4912 can be frictionally engaged and/or press-fit within a corresponding second portion 4912*b* such that, once the compressive force applied to the collapsible element 4912 exceeds the retention force retaining the second portion 4912*b* and the third portion 4912*c* in their extended position (FIG. 94), the second portion 4912*b* and the third portion 4912*c* can begin to slide relative to one another.

In many embodiments described herein, a staple cartridge can comprise a plurality of staples therein. In various embodiments, such staples can be comprised of a metal wire deformed into a substantially U-shaped configuration having two staple legs. Other embodiments are envisioned in which staples can comprise different configurations such as two or more wires that have been joined together having three or more staple legs. In various embodiments, the wire, or wires, used to form the staples can comprise a round, or at least substantially round, cross-section. In at least one embodiment, the staple wires can comprise any other suitable cross-section, such as square and/or rectangular cross-sections, for example. In certain embodiments, the staples can be comprised of plastic wires. In at least one embodiment, the staples can be comprised of plastic-coated metal wires. In various embodiments, a cartridge can comprise any suitable type of fastener in addition to or in lieu of staples. In at least one such embodiment, such a fastener can comprise pivotable arms which are folded when engaged by an anvil. In certain embodiments, two-part fasteners could be utilized. In at least one such embodiment, a staple cartridge can comprise a plurality of first fastener portions and an anvil can comprise a plurality of second fastener portions which are connected to the first fastener portions when the anvil is compressed against the staple cartridge. In certain embodiments, as described above, a sled or driver can be advanced within a staple cartridge in order to complete the forming process of the staples. In certain embodiments, a sled or driver can be advanced within an anvil in order to move one or more forming members downwardly into engagement with the opposing staple cartridge and the staples, or fasteners, positioned therein.

In various embodiments described herein, a staple cartridge can comprise four rows of staples stored therein. In at least one embodiment, the four staple rows can be arranged in two inner staple rows and two outer staple rows. In at least one such embodiment, an inner staple row and an outer staple row can be positioned on a first side of a cutting member, or knife, slot within the staple cartridge and, similarly, an inner staple row and an outer staple row can be positioned on a second side of the cutting member, or knife, slot. In certain embodiments, a staple cartridge may not comprise a cutting member slot; however, such a staple cartridge may comprise a designated portion configured to be incised by a cutting member in lieu of a staple cartridge slot. In various embodiments, the inner staple rows can be arranged within the staple cartridge such that they are equally, or at least substantially equally, spaced from the cutting member slot. Similarly, the outer staple rows can be arranged within the staple cartridge such that they are equally, or at least substantially equally, spaced from the cutting member slot. In various embodiments, a staple cartridge can comprise more than or less than four rows of staples stored within a staple cartridge. In at least one embodiment, a staple cartridge can comprise six rows of staples. In at least one such embodiment, the staple cartridge can comprise three rows of staples on a first side of a cutting member slot and three rows of staples on a second side of the cutting member slot. In certain embodiments, a staple cartridge may comprise an odd number of staple rows. For example, a staple cartridge may comprise two rows of staples on a first side of a cutting member slot and three rows of staples on a second side of the cutting member slot. In various embodiments, the staple rows can comprise staples having the same, or at least substantially the same, unformed staple height. In certain other embodiments, one or more of the staple rows can comprise staples having a different unformed staple height than the other staples. In at least one such embodiment, the staples on a first side of a cutting member slot may have a first unformed height and the staples on a second side of a cutting member slot may have a second unformed height which is different than the first height, for example.

In various embodiments, referring now to FIGS. 96A-96D, an end effector of a surgical stapler can comprise a cartridge attachment portion, such as staple cartridge channel 5030, for example, a fastener cartridge removably positioned in the staple cartridge channel 5030, such as staple cartridge 5000, for example, and a jaw 5040 positioned opposite the staple cartridge 5000 and the staple cartridge channel 5030. The staple cartridge 5000 can comprise a compressible body 5010 and a plurality of staples 5020, and/or any other suitable fasteners, at least partially positioned in the compressible body 5010. In at least one such embodiment, each staple 5020 can comprise a base 5022 and, in addition, legs 5021 extending upwardly from the base 5022, wherein at least a portion of the legs 5021 can be embedded in the cartridge body 5010. In various embodiments, the compressible body 5010 can comprise a top, or tissue-contacting, surface 5019 and a bottom surface 5018, wherein the bottom surface 5018 can be positioned against and supported by a support surface 5031 of the staple cartridge channel 5030. Similar to the above, the support surface 5031 can comprise a plurality of support slots 5032 (FIG. 96D), for example, defined therein which can be configured to receive and support the bases 5022 of the staples 5020. In various embodiments, the end effector of the surgical stapler can further comprise a retention matrix, such as retention matrix 5050, for example, which can be configured to engage the staples 5020 and capture tissue therebetween. In at least one such embodiment, the retention matrix 5050 can be removably mounted to the jaw 5040. In use, once the staple cartridge 5000 has been positioned within the staple cartridge channel 5030, the jaw 5040, and the retention matrix 5050 attached thereto, can be moved toward the staple cartridge 5000 and the staple cartridge channel 5030. In at least one embodiment, the jaw 5040 can be moved downwardly along an axis 5099 such that the jaw 5040 and the staple cartridge channel 5030 remain parallel, or at least substantially parallel, to one another as the jaw 5040 is closed. More particularly, in at least one such embodiment, the jaw 5040 can be closed in a manner such that a tissue-contacting surface 5051 of the retention matrix 5050 is parallel, or at least substantially parallel, to the tissue-contacting surface 5019 of the staple cartridge 5000 as the jaw 5040 is moved toward the staple cartridge 5000.

Figure 96B:
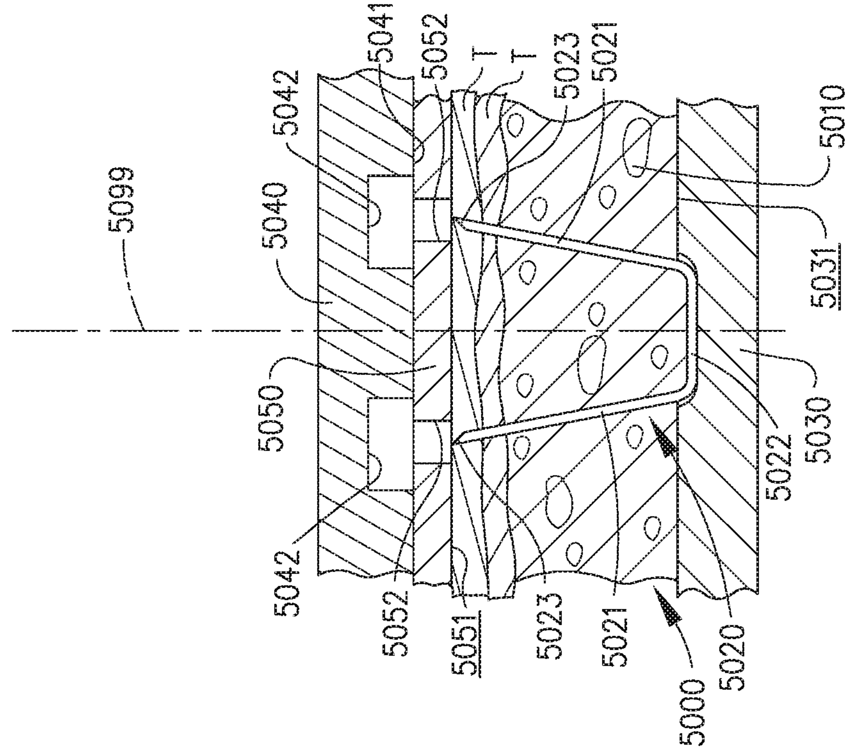
FIG. 96B is a partial cross-sectional view of the end effector of FIG. 96A illustrating the jaw being moved toward the staple cartridge channel, the staple cartridge being compressed by the anvil and the retention matrix, and a staple at least partially extending through tissue positioned intermediate the retention matrix and the staple cartridge.
Figure 96A:
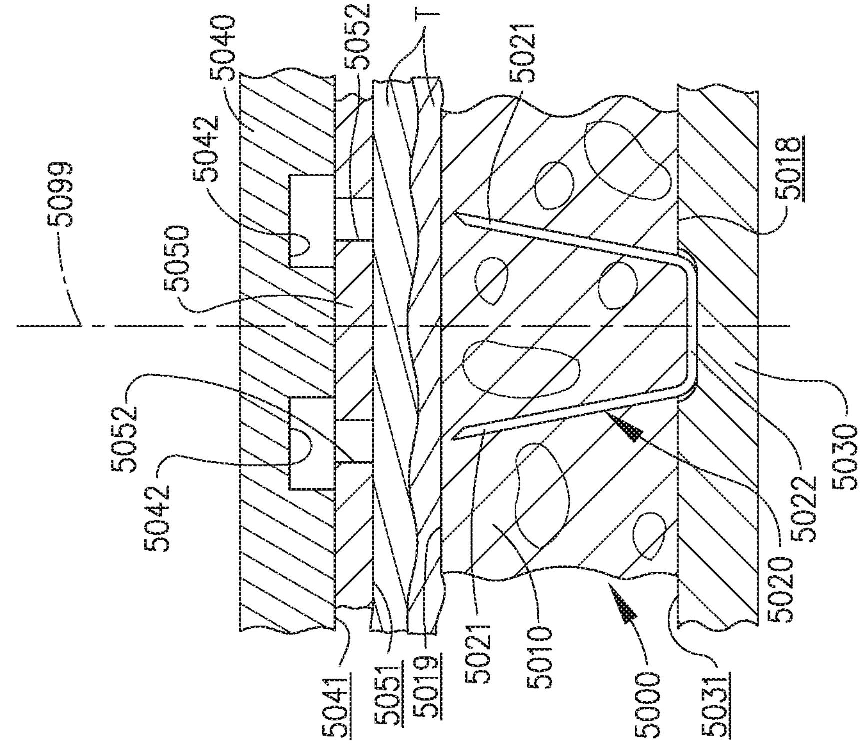
FIG. 96A is a partial cross-sectional view of an end effector of a surgical stapling instrument comprising a jaw, a staple cartridge channel positioned opposite the jaw, and a staple cartridge positioned within the staple cartridge channel, wherein the jaw comprises a retention matrix attached thereto.

In various embodiments, referring now to FIG. 96A, the retention matrix 5050 can be detachably secured to the jaw 5040 such that there is little, if any, relative movement between the retention matrix 5050 and the jaw 5040 when the retention matrix 5050 is attached to the jaw 5040. In at least one embodiment, the jaw 5040 can comprise one or more retention features which can be configured to hold the retention matrix 5050 in position. In at least one such embodiment, the retention matrix 5050 can be snap-fit and/or press-fit into the jaw 5040. In certain embodiments, the retention matrix 5050 can be adhered to the jaw 5040 utilizing at least one adhesive. In any event, the jaw 5040 can be moved into a position in which the retention matrix 5050 is in contact with the tissue T and the tissue T is positioned against the tissue-contacting surface 5019 of the staple cartridge 5000. When the tissue T is positioned against the staple cartridge 5000 by the jaw 5040, the compressible body 5010 of the staple cartridge 5000 may or may not be compressed by the jaw 5040. In either circumstance, in various embodiments, the legs 5021 of the staples 5200 may not protrude through the tissue-contacting surface 5019 of the staple cartridge 5000 as illustrated in FIG. 96A. Furthermore, as also illustrated in FIG. 96A, the jaw 5040 can hold the tissue T against the compressible body 5010 without engaging the retention matrix 5050 with the staples 5020. Such embodiments can permit a surgeon to open and close the jaw 5040 multiple times in order to obtain a desired positioning of the end effector within a surgical site, for example, without damaging the tissue T. Other embodiments are envisioned, however, where the staple tips 5023 can protrude from the tissue-contacting surface 5019 prior to the cartridge body 5010 being compressed by the anvil 5040. Once the end effector has been suitably positioned, referring now to FIG. 96B, the jaw 5040 can be moved downwardly toward the staple cartridge channel 5030 such that the compressible body 5010 is compressed by the anvil 5040 and such that the tissue-contacting surface 5019 is pushed downwardly relative to the staples 5020. As the tissue-contacting surface 5019 is pushed downwardly, the tips 5023 of the staple legs 5021 can pierce the tissue-contacting surface 5019 and pierce at least a portion of the tissue T. In such circumstances, the retention matrix 5050 may be positioned above the staples 5020 such that the retention apertures 5052 of retention matrix 5050 are aligned, or at least substantially aligned, with the tips 5023 of the staple legs 5021.

Figure 96D:
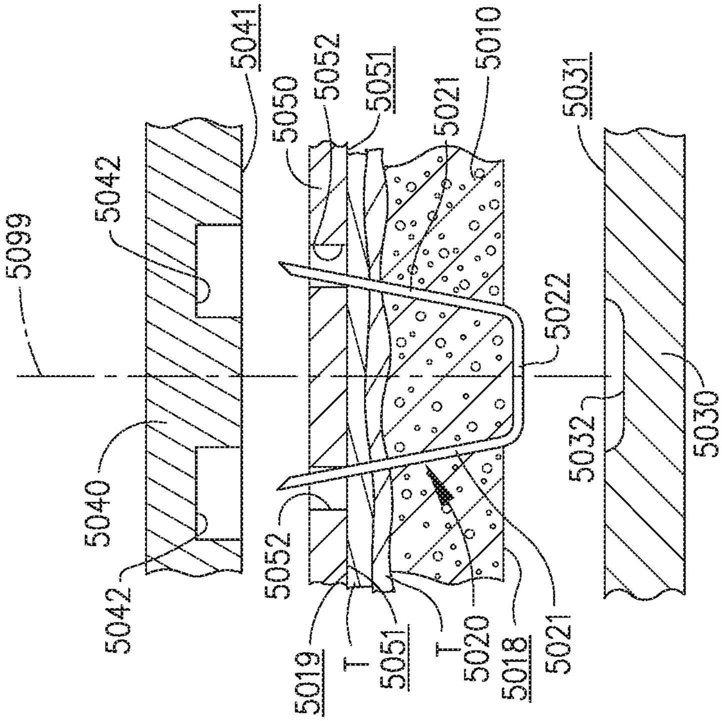
FIG. 96D is a partial cross-sectional view of the end effector of FIG. 96A illustrating the jaw and the staple cartridge channel being moved away from the implanted staple cartridge and retention matrix.
Figure 96C:
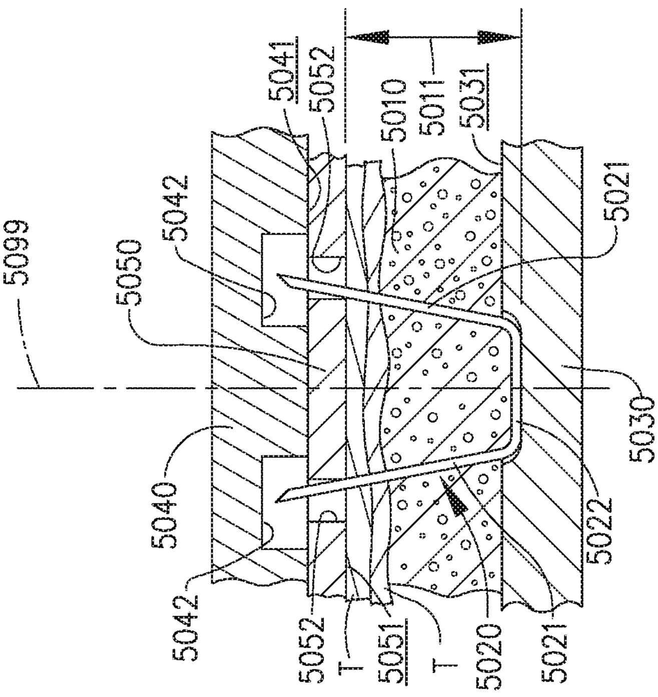
FIG. 96C is a partial cross-sectional view of the end effector of FIG. 96A illustrating the jaw in a final position and the retention matrix engaged with the staple of FIG. 96B.

As the retention matrix 5050 is pushed downwardly along the axis 5099, referring now to FIG. 96C, the staple legs 5021 of staples 5020 can enter into the retention apertures 5052. In various embodiments, the staple legs 5021 can engage the side walls of the retention apertures 5052. In certain embodiments, as described in greater detail below, the retention matrix 5050 can comprise one or more retention members extending into and/or around the retention apertures 5052 which can engage the staple legs 5021. In either event, the staple legs 5021 can be retained in the retention apertures 5052. In various circumstances, the tips 5023 of the staple legs 5021 can enter into the retention apertures 5052 and can frictionally engage the retention members and/or the side walls of the apertures 5052. As the retention matrix 5050 is pushed toward the bases 5022 of the staples 5020, the staple legs 5021 can slide relative to the side walls and/or the retention members. As a result of the above, sliding friction forces can be created between the staple legs 5021 and the retention matrix 5050 wherein such sliding friction forces can resist the insertion of the retention matrix 5050 onto the staples 5020. In various embodiments, the sliding friction forces between the retention matrix 5050 and the staples 5020 can be constant, or at least substantially constant, as the retention matrix 5050 is slid downwardly along the staple legs 5021 of the staples 5020. In certain embodiments, the sliding friction forces may increase and/or decrease as the retention matrix 5050 is slid downwardly along the staple legs 5021 owing to variations in geometry of the staple legs 5021, the retention apertures 5052, and/or the retention members extending into and/or around the retention apertures 5052, for example. In various embodiments, the insertion of the retention matrix 5050 onto the staples 5020 can also be resisted by the compressible body 5010 of the staple cartridge 5000. More particularly, the compressible body 5010 can be comprised of an elastic material, for example, which can apply a resistive force to the retention matrix 5050 which increases as the distance in which the compressible body 5010 is compressed increases. In at least one such embodiment, the increase in the resistive force generated by the cartridge body 5010 can be linearly proportional, or at least substantially linearly proportional, with respect to the distance in which the cartridge body 5010 is compressed. In certain embodiments, the increase in the resistive force generated by the cartridge body 5010 can be geometrically proportional with respect to the distance in which the cartridge body 5010 is compressed.

In various embodiments, further to the above, a sufficient firing force can be applied to the jaw 5040 and the retention matrix 5050 in order to overcome the resistive and friction forces described above. In use, the retention matrix 5050 can be seated to any suitable depth with respect to the staples 5020. In at least one embodiment, the retention matrix 5050 can be seated to a depth with respect to the bases 5022 of the staples 5020 in order to secure two or more layers of tissue together and generate compressive forces, or pressure, within the tissue. In various circumstances, the system comprising the retention matrix 5050 and the staples 5020 can allow a surgeon to select the amount of compressive forces, or pressure, that is applied the tissue by selecting the depth in which the retention matrix 5050 is seated. For example, the retention matrix 5050 can be pushed downwardly toward the staple bases 5022 of the staples 5020 until the retention matrix 5050 is seated a certain depth 5011 away from the bottom of the support slots 5032, wherein a shorter depth 5011 can result in higher compressive forces, or pressure, being applied to the tissue T than a taller depth 5011 which can result in lower compressive forces, or pressure, being applied to the tissue T. In various embodiments, the compressive forces, or pressures, applied to the tissue T can be linearly proportional, or at least substantially linearly proportional, to the depth 5011 in which the retention matrix 5050 is seated. In various circumstances, the compressive forces, or pressure, applied to the tissue T can depend on the thickness of the tissue T positioned between the retention matrix 5050 and the staple cartridge 5020. More particularly, for a given distance 5011, the presence of thicker tissue T can result in higher compression forces, or pressure, than the presence of thinner tissue T.

In various circumstances, further to the above, a surgeon can adjust the depth in which the retention matrix 5050 is seated in order to account for thicker and/or thinner tissue positioned within the end effector and to apply a certain or predetermined pressure to the tissue T regardless of the tissue thickness. For example, the surgeon can seat the retention matrix 5050 to a shorter depth 5011 when fastening thinner tissue T or a taller depth 5011 when fastening thicker tissue T in order to arrive at the same, or at least substantially the same, compression pressure within the tissue. In certain embodiments, further to the above, a surgeon can selectively determine the amount of compressive pressure to apply to the tissue T positioned between the retention matrix 5050 and the staple cartridge 5010. In various circumstances, a surgeon can engage the retention matrix 5050 with the staples 5020 and position the retention matrix 5050 a first distance away from the bases 5022 of the staples 5020 in order to apply a first compressive pressure to the tissue. The surgeon can alternatively position the retention matrix 5050 a second distance away from the bases 5022, which is shorter than the first distance, in order to apply a second compressive pressure to the tissue which is greater than the first pressure. The surgeon can alternatively position the retention matrix 5050 a third distance away from the bases 5022, which is shorter than the second distance, in order to apply a third compressive pressure to the tissue which is greater than the second pressure. In various embodiments, the fastening system comprising the retention matrix 5050 and the staples 5020 can be configured to permit a surgeon to apply a wide range of compressive pressures to the targeted tissue.

In various embodiments, referring now to FIG. 96D, the staple legs 5021 can be inserted through the retention matrix 5050 such that the staple leg tips 5023 extend above the top surface of the retention matrix 5050. In at least one embodiment, referring again to FIG. 96C, the jaw 5040 can further comprise clearance apertures 5042 defined therein which can be configured to receive the staple leg tips 5023 as they pass through the retention apertures 5052 in the retention matrix 5050. In at least one such embodiment, the clearance apertures 5042 can be aligned with the retention apertures 5052 such that the legs 5021 do not contact the jaw 5040. In various embodiments, the clearance apertures 5042 can have a sufficient depth such that the staple legs 5021 do not contact the jaw 5040 regardless of the distance in which the retention matrix 5050 is seated. After the retention matrix 5050 has been engaged with the staples 5020 and seated to a desired position, referring now to FIG. 96D, the staple cartridge channel 5030 and the jaw 5040 can be moved away from the tissue T. More particularly, the staple cartridge channel 5030 can be detached from the implanted staple cartridge 5000 and the anvil 5040 can be detached from the implanted retention matrix 5050. As the jaw 5040 is moved away from the retention matrix 5050 and the staple supports 5032 are moved away from the staple bases 5022, the distance 5011 between the retention matrix 5050 and the bottom of the bases 5022 can be maintained eventhough the jaw 5040 and the staple cartridge channel 5030 are no longer providing support thereto. In various embodiments, the static friction forces between the staple legs 5021 and the retention matrix 5050 can be sufficient to maintain the retention matrix 5050 in position despite a biasing force being applied to the retention matrix 5050 by the compressed cartridge body 5010 and/or the compressed tissue T. In at least one such embodiment, the cartridge body 5010 can be comprised of a resilient material which, when compressed, can apply an elastic biasing force to the retention matrix 5050 and the staples 5020 in a manner which tends to push the retention matrix 5050 and the staples 5020 apart, although such movement is opposed by the frictional engagement between the staple legs 5021 and the retention matrix 5050.

Figure 97:
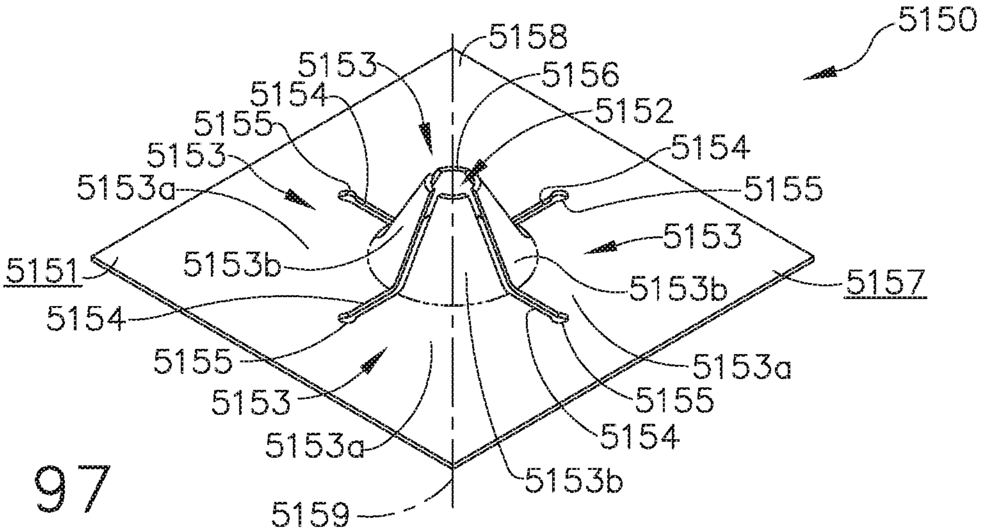
FIG. 97 is a perspective view of a retention aperture of a retention matrix in accordance with at least one alternative embodiment comprising a plurality of retention members configured to engage a fastener leg extending therethrough.

In various embodiments, as described above, a retention matrix can comprise a plurality of retention apertures, wherein each retention aperture can be configured to receive a leg of a fastener therein. In at least one embodiment, referring now to FIG. 97, a portion of a retention matrix 5150 is illustrated therein which can comprise a retention aperture 5152 defined by a perimeter 5156. In various embodiments, the perimeter 5156 of the aperture 5152 can comprise a circular, or at least substantially circular, profile and/or any other suitable profile. In certain embodiments, the retention matrix 5150 can comprise one or more retention members, such as retention members 5153, for example, which extend into the aperture 5152 and can be configured to engage a fastener leg when the fastener leg is inserted therethrough. In at least one such embodiment, each retention member 5153 can comprise a cantilever which extends inwardly toward a center axis 5159, i.e., toward the center of the aperture 5152. In various embodiments, each cantilever can comprise a first end which is attached to the retention matrix body 5158 and a second end which forms the perimeter 5156 of the retention aperture 5152. In certain embodiments, the perimeter 5156 of a retention aperture 5152 can be defined by a first diameter, or width, and a fastener leg can be defined by a second diameter, or width, wherein the second diameter can be larger than the first diameter. In at least one such embodiment, the fastener leg can be configured to contact and deflect one or more of the retention members 5153 in order to increase the diameter of the retention aperture 5152 as the fastener leg is being inserted therethrough. In certain embodiments, further to the above, the fastener leg can define a perimeter which is larger than the perimeter 5156 of the retention aperture 5152 such that the fastener leg can expand the perimeter 5156 when the fastener leg is inserted therein.

In various embodiments, referring again to FIG. 97, the aperture 5152 can be defined by the deformable members 5153, wherein each deformable member 5153 can be configured to deflect relative to, or independently of, the other deformable members 5153. In at least one such embodiment, adjacent deformable members 5153 can be separated by slots 5154 which can be configured to permit each deformable member 5153 to flex relative to the others. In certain embodiments, each slot 5154 can comprise a first end 5155 in the retention matrix body 5158, a second end opening into the retention aperture 5152, and a constant, or at least substantially constant, width extending between the first end 5155 and the second end. In various other embodiments, the width of each slot 5154 may not be constant and each slot 5154 may increase and/or decrease in width between the first and second ends thereof. In certain embodiments, the first ends 5155 of the slots 5154 can comprise an enlarged portion, such as a circular portion, which can provide, one, strain relief to the bases of the deformable members 5153 attached to the retention matrix body 5158 and, two, means for increasing the flexibility of the deformable members 5153. In various embodiments, the geometry of the deformable members 5153, and/or slots 5154, can be selected so as to provide the deformable members 5153 with a desired flexibility. In certain embodiments, for example, the slots 5154 can be lengthened in order to create longer deformable members 5153 which can be more flexible than deformable members 5153 having a shorter length. In at least one embodiment, the width of each deformable member 5153 can be selected so as to provide a desired flexibility thereof. More particularly, deformable members having a thinner width can be more flexible than deformable members having a thicker width. In certain embodiments, referring again to FIG. 97, the first ends of the cantilevers of deformable members 5153 attached to the retention matrix body 5158 can be wider than the second ends of the cantilevers. In at least one such embodiment, the cantilevers can be tapered in a linear, or at least substantially linear, manner between the first and second ends thereof.

In various embodiments, referring again to FIG. 97, the retention matrix body 5158 can comprise a flat, or at least substantially flat, sheet of material having a tissue-contacting surface 5151 and a top surface 5157. In at least one such embodiment, the tissue-contacting surface 5151 and the top surface 5157 can be parallel, or at least substantially parallel, to one another. In various embodiments, each deformable member 5153 can comprise a first portion **5153*a* and a second portion 5153*b*, wherein the first portion 5153*a* can extend in a first direction and the second portion 5153*b* can extend in a different, or second, direction. In at least one such embodiment, the retention matrix body 5158 can define a plane and the first portions 5153*a* of the deformable members 5153 can lie within such a plane. In various embodiments, the second portions 5153*b* of the deformable members 5153 can extend at an angle relative to the first portions 5153*a*. In at least one such embodiment, the second portions 5153*b* can extend in directions which are pointed away from the top surface 5157 of the retention matrix body 5158 and, in certain embodiments, the second portions 5153*b* can converge toward the central axis 5159 of the retention aperture 5152. In any event, in various embodiments, the second portions 5153*b* can be configured to deflect away from the central axis 5159 when the fastener leg is inserted therethrough. In embodiments where a staple leg 5021 of a staple 5020 is inserted into a retention aperture 5152, the deformable members 5153 can deform in a direction which is generally away from the bases 5122 of the staples 5120. In certain embodiments, as a result, the deformable members 5153 can deflect in a general direction which is the same as, or at least substantially the same as, the direction in which the staple legs 5021** are being inserted.

In various embodiments, referring again to FIG. 97, the second portions **5153*b* of the deformable members 5153 can each comprise a sharp tip, for example, which can be configured to slide against a staple leg 5021 as the staple leg 5021 is inserted therein. The sharp tips of the second portions 5153*b* can also be configured to bite into the staple leg 5021 in the event that the staple leg 5021 were to be pulled in the opposite direction, i.e., in a direction which would remove the staple leg 5021 from the retention aperture 5052. In certain circumstances, the second portions 5153*b* can be inclined at an angle relative to the side of the staple leg 5021 which is greater than 90 degrees and, as a result, the second portions 5153*b* may dig, or burrow, into the side of the staple leg 5021 when the staple leg 5021 experiences a force which tends to withdraw the staple leg 5021 from the retention aperture 5052. In certain embodiments, the staple legs 5021 can comprise indentations and/or concavities, such as microindentations, for example, in the surfaces thereof which can be configured to receive the tips of the deformable members 5053, for example, therein. In at least one such embodiment, the tips of the deformable members 5053 can catch in and burrow into the indentations in the staple legs 5021 when a withdrawing force is applied to the staple legs 5021. In various embodiments, as a result of the burrowing of the second portions 5153*b* into the staple legs 5021, forces acting to remove the staple legs 5021 from the retention apertures 5022 may only seat the second portions 5153*b* deeper into the staple legs 5021 and increase the force required to remove the staple legs 5021. Furthermore, owing to the upward inclination of the second portions 5153*b*, in at least one embodiment, the second portions 5153*b* can be more permissive to the insertion of a staple leg 5021 within a retention aperture 5152 and more resistive to withdrawal of the staple leg 5021. In at least one embodiment, as a result, the force required to insert a staple leg 5021 into a retention aperture 5022 may be less than the force required to remove the staple leg 5021 from the retention aperture 5022. In various embodiments, the force needed to remove the staple leg 5021 from the retention aperture 5022 can be approximately 50 percent greater than the force needed to insert the staple leg 5021 into the retention aperture 5022, for example. In various other embodiments, the force needed to remove the staple leg 5021 may between approximately 10 percent and approximately 100 percent greater than the force needed to insert the staple leg 5021, for example. In certain embodiments, the force needed to remove the staple leg 5021 may be approximately 100 percent, approximately 150 percent, approximately 200 percent, and/or greater than approximately 200 percent larger than the force needed to insert the staple leg 5021**, for example.

Figure 98:
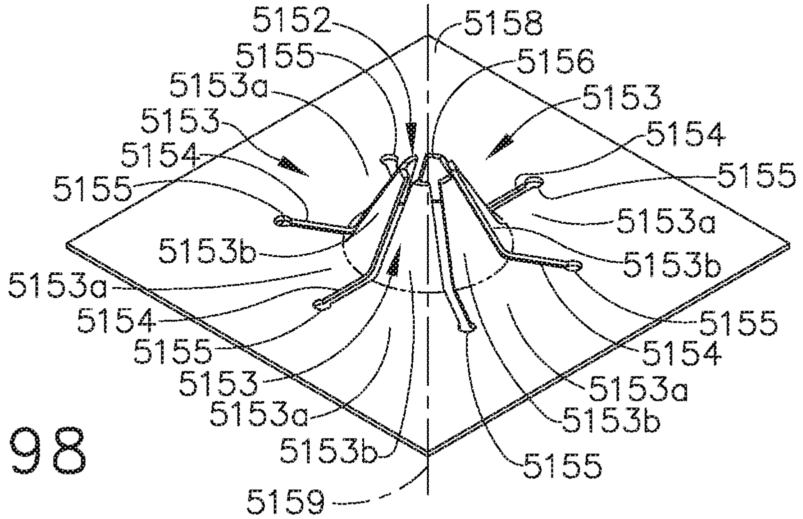
FIG. 98 is a perspective view of a retention aperture of a retention matrix in accordance with at least one alternative embodiment comprising six retention members.
Figure 99:
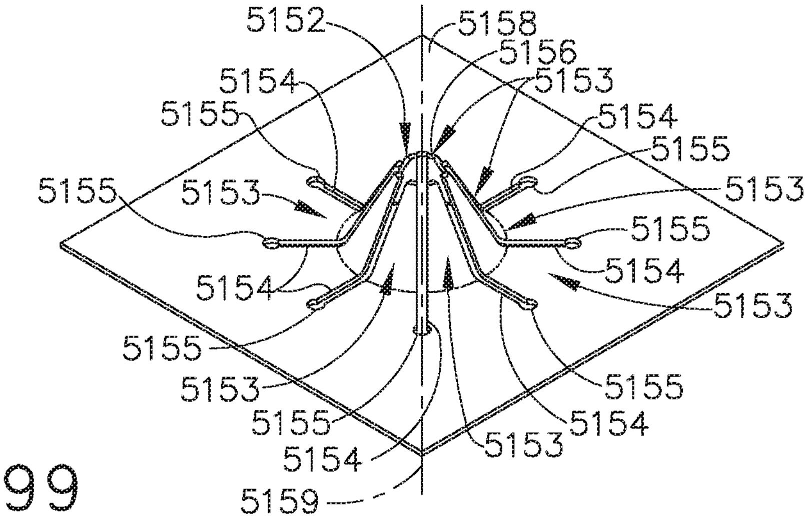
FIG. 99 is a perspective view of a retention aperture of a retention matrix in accordance with at least one alternative embodiment comprising eight retention members.
Figure 100:
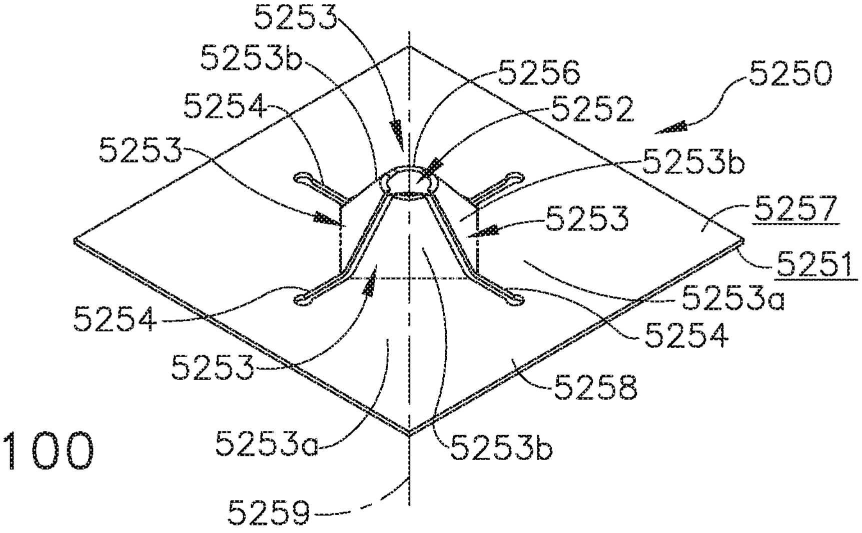
FIG. 100 is a perspective view of a retention aperture of a retention matrix in accordance with at least one alternative embodiment comprising a plurality of retention members configured to engage a fastener leg extending therethrough.

In certain embodiments, referring again to FIG. 97, the second portions 5153*b* can be arranged circumferentially around the aperture 5152 and can define a pocket therebetween. More particularly, the second portions 5153*b* can define a pocket 5160 which can be configured to receive the tip of the fastener leg when it is inserted into the retention aperture 5152. In various embodiments, the second portions 5153*b* of the deformable members 5153 can comprise an annular, or an at least substantially annular, contour which can co-operatively define an annular, or at least substantially annular, profile of the pocket 1560, for example. In at least one such embodiment, the second portions 5153*b* can define a conical or frustoconical pocket. In various embodiments, the pocket can be defined by a suitable number of deformable members, such as four deformable members 5153 (FIG. 97), six deformable members 5153 (FIG. 98), or eight deformable members 5153 (FIG. 99), for example. In certain embodiments, referring now to FIG. 100, the deformable members of a retention matrix, such as retention matrix 5250, for example, can form a pyramidal shape, or an at least substantially pyramidal shape, for example. In various embodiments, a retention matrix 5250 can comprise a plurality of retention apertures, such as retention aperture 5252, for example, which can be defined by a perimeter 5256. In various embodiments, the perimeter 5256 can comprise a polygonal, or at least substantially polygonal, profile and/or any other suitable profile. In certain embodiments, the retention matrix 5250 can comprise one or more retention members, such as retention members 5253, for example, which extend into the aperture 5252 and can be configured to engage a fastener leg when the fastener leg is inserted therethrough. In at least one such embodiment, each retention member 5253 can comprise a cantilever which extends inwardly toward a center axis 5259, i.e., toward the center of the aperture 5252. In various embodiments, each cantilever can comprise a first end which is attached to the retention matrix body 5258 and a second end which forms the perimeter 5256 of the retention aperture 5252. In certain embodiments, the perimeter 5256 of a retention aperture 5252 can be defined by a first diameter, or width, and a fastener leg can be defined by a second diameter, or width, wherein the second diameter can be larger than the first diameter. In at least one such embodiment, the fastener leg can be configured to contact and deflect one or more of the retention members 5253 in order to increase the diameter of the retention aperture 5252 as the fastener leg is being inserted therethrough. In certain embodiments, further to the above, the fastener leg can define a perimeter which is larger than the perimeter 5256 of the retention aperture 5252 such that the fastener leg can expand the perimeter 5256 when the fastener leg is inserted therein.

Figure 101:
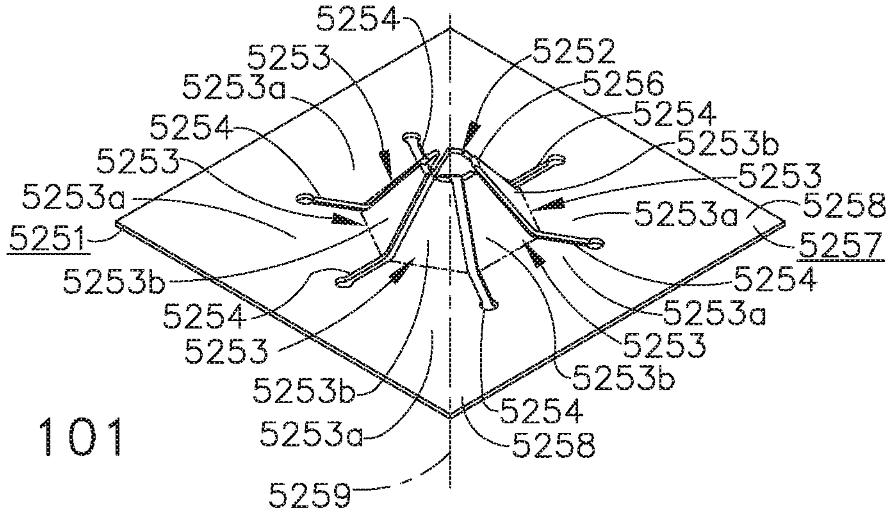
FIG. 101 is a perspective view of a retention aperture of a retention matrix in accordance with at least one alternative embodiment comprising six retention members.
Figure 102:
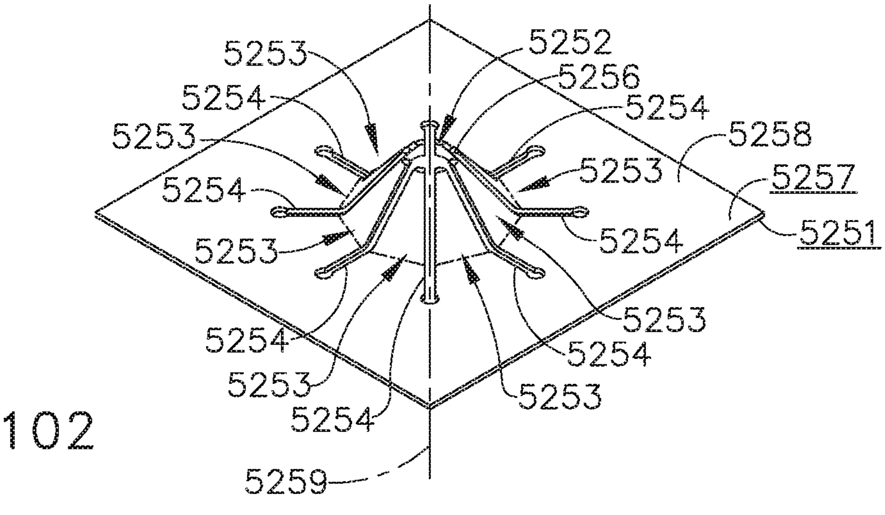
FIG. 102 is a perspective view of a retention aperture of a retention matrix in accordance with at least one alternative embodiment comprising eight retention members.

In various embodiments, referring again to FIG. 100, the aperture 5252 can be defined by the deformable members 5253, wherein each deformable member 5253 can be configured to deflect relative to, or independently of, the other deformable members 5253. In at least one such embodiment, adjacent deformable members 5253 can be separated by slots 5254 which can be configured to permit each deformable member 5253 to flex relative to the others. In various embodiments, the retention matrix body 5258 can comprise a flat, or at least substantially flat, sheet of material having a tissue-contacting surface 5251 and a top surface 5257. In at least one such embodiment, the tissue-contacting surface 5251 and the top surface 5257 can be parallel, or at least substantially parallel, to one another. In various embodiments, each deformable member 5253 can comprise a first portion 5253*a* and a second portion 5253*b*, wherein the first portion 5253*a* can extend in a first direction and the second portion 5253*b* can extend in a different, or second, direction. In at least one such embodiment, the retention matrix body 5258 can define a plane and the first portions 5253*a* of the deformable members 5253 can lie within such a plane. In various embodiments, the second portions 5253*b* of the deformable members 5253 can extend at an angle relative to the first portions 5253*a*. In at least one such embodiment, the second portions 5253*b* can extend in directions which are pointed away from the top surface 5257 of the retention matrix body 5258 and, in certain embodiments, the second portions 5253*b* can converge toward the central axis 5259 of the retention aperture 5252. In any event, in various embodiments, the second portions 5253*b* can be configured to deflect away from the central axis 5259 when the fastener leg is inserted therethrough. In certain embodiments, referring again to FIG. 100, the second portions 5253*b* can be arranged circumferentially around the aperture 5252 and can define a pocket therebetween. More particularly, the second portions 5253*b* can define a pocket which can be configured to receive the tip of the fastener leg when it is inserted into the retention aperture 5252. In various embodiments, the second portions 5253*b* of the deformable members 5253 can define a polygonal, or an at least substantially polygonal, pocket, for example. In various embodiments, the pocket can be defined by a suitable number of deformable members, such as four deformable members 5253 (FIG. 100) which can define a square, six deformable members 5253 (FIG. 101) which can define a hexagon, or eight deformable members 5253 (FIG. 102) which can define an octagon, for example.

Figure 103:
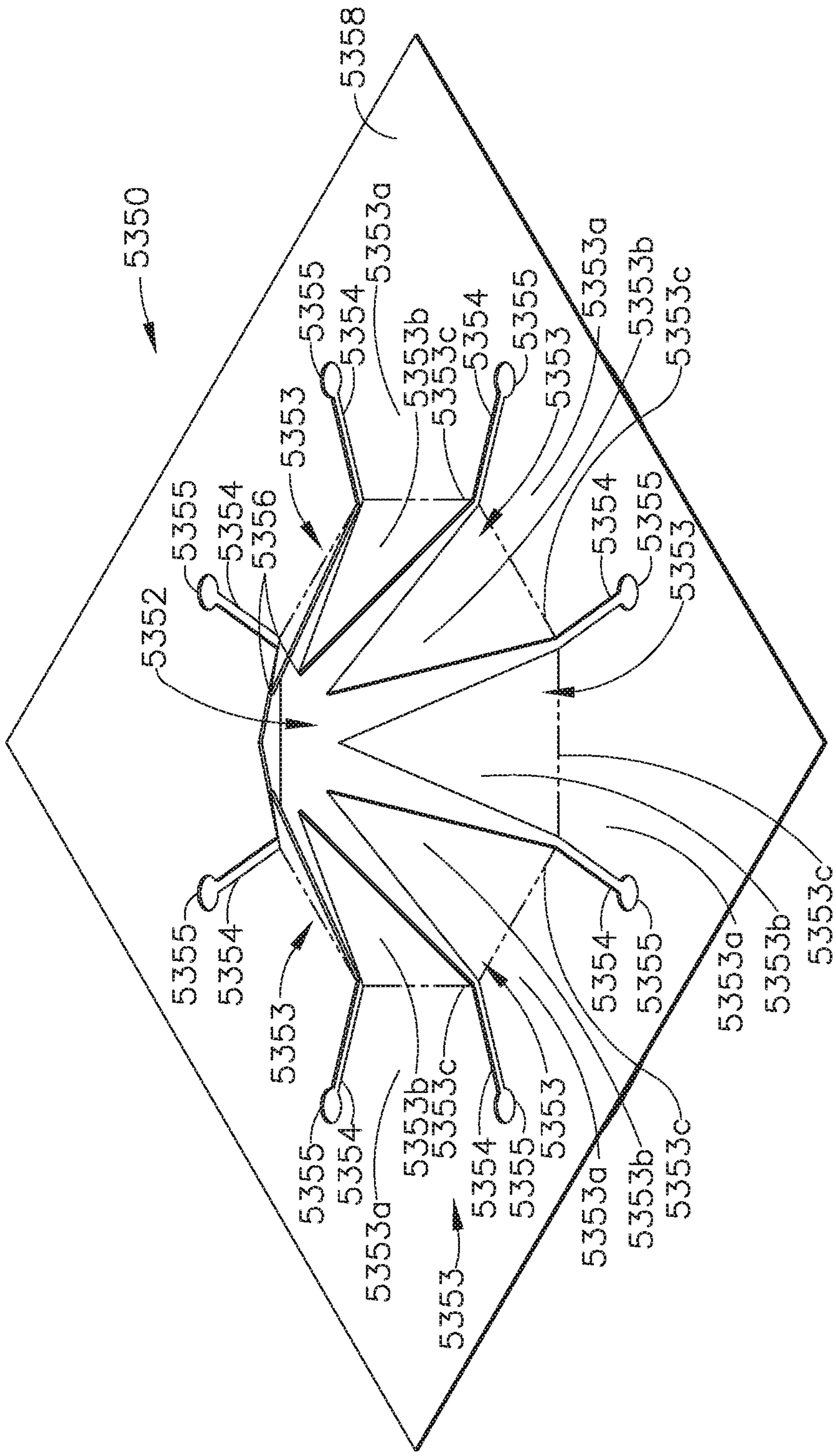
FIG. 103 is a perspective view of a retention aperture of a retention matrix in accordance with at least one alternative embodiment comprising a plurality of retention members that have been stamped from a sheet of metal.
Figure 104:
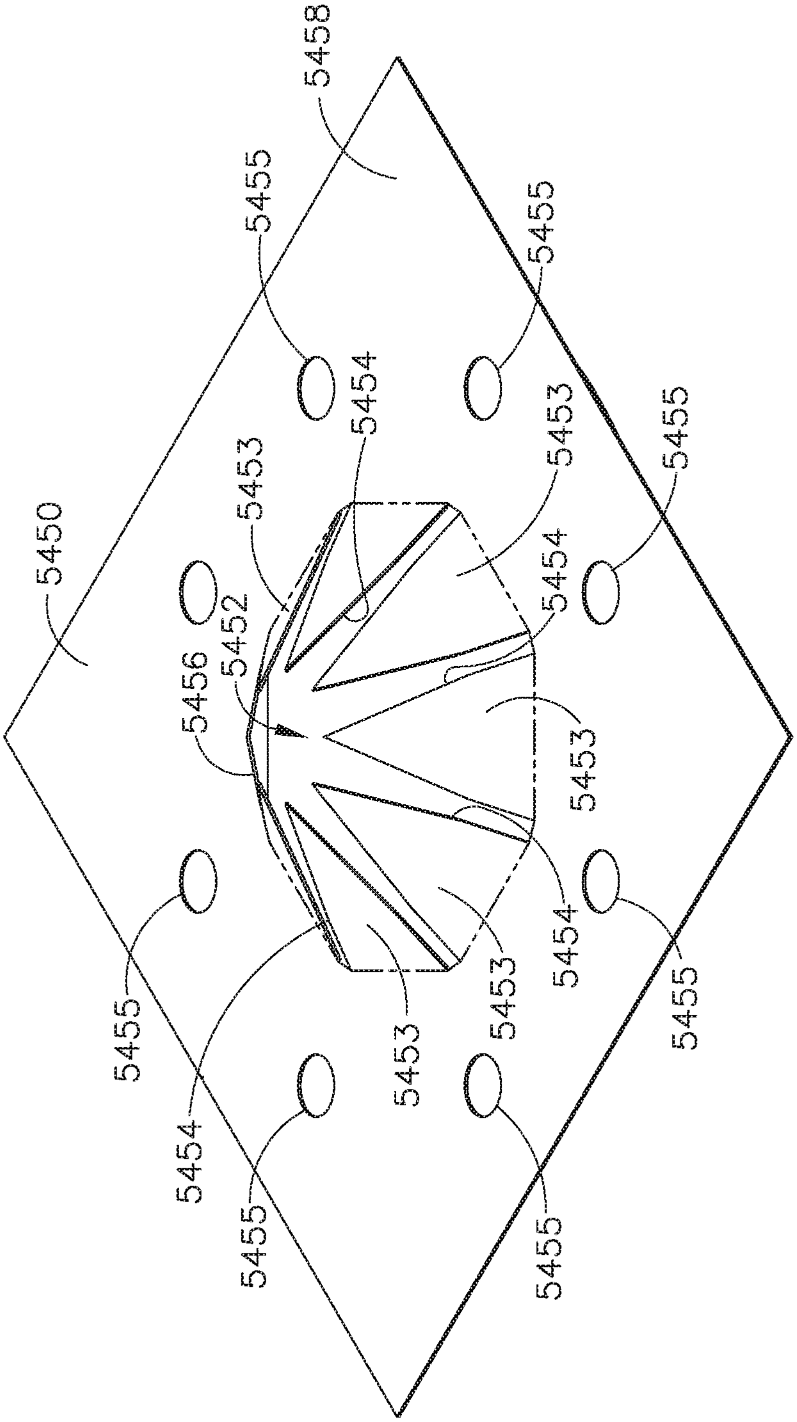
FIG. 104 is a perspective view of a retention aperture of a retention matrix in accordance with at least one alternative embodiment comprising a plurality of apertures extending around the perimeter of the retention aperture.

In various embodiments, referring now to FIG. 103, a retention matrix, such as retention matrix 5350, for example, can be formed from a flat, or an at least substantially flat, sheet of material such as titanium and/or stainless steel, for example. In at least one such embodiment, a plurality of apertures 5352 can be formed in the body 5358 of the retention matrix 5350 by one or more stamping processes. The sheet of material can be positioned in a stamping die which, when actuated, can punch out certain portions of the material in order to form slots 5354, apertures 5355 of slots 5354, and/or the perimeter 5356 of the retention aperture 5352, for example. The stamping die can also be configured to bend the deformable members 5353 in a suitable configuration. In at least one such embodiment, the stamping die can deform the second portions 5353*b* upwardly relative to the first portions 5353*a* along a crease line 5353*c*. In various embodiments, referring now to FIG. 104, a retention matrix, such as retention matrix 5450, for example, can comprise a plurality of retention apertures 5452. Similar to the above, the perimeter 5456 of each retention aperture 5452 can be defined by a plurality of deformable members 5453 separated by slots, or slits, 5454. In at least one such embodiment, the entirety of each deformable member 5453 can be bent upwardly wherein the free ends of the cantilevers comprising the deformable members 5453 can define the perimeter 5456. In various embodiments, the retention matrix 5450 can comprise a plurality of apertures 5455 surrounding, or at least substantially surrounding, the retention aperture 5452. In at least one such embodiment, the apertures 5455 can be arranged in a circular array surrounding or enclosing a perimeter defined by the fixed ends of the cantilevers of the deformable members 5453. In certain embodiments, each aperture 5455 can comprise a circular, or at least substantially circular, perimeter and/or any other suitable perimeter. In use, the apertures 5455 can provide, one, strain relief to the bases of the deformable members 5453 attached to the retention matrix body 5458 and, two, means for increasing the flexibility of the deformable members 5453. In various embodiments, larger apertures 5455 can provide more flexibility to the deformable members 5453 as compared to smaller apertures 5455. Furthermore, apertures 5455 which are closer to the deformable members 5453 can provide more flexibility as compared to apertures 5455 which are further away.

Figure 105:
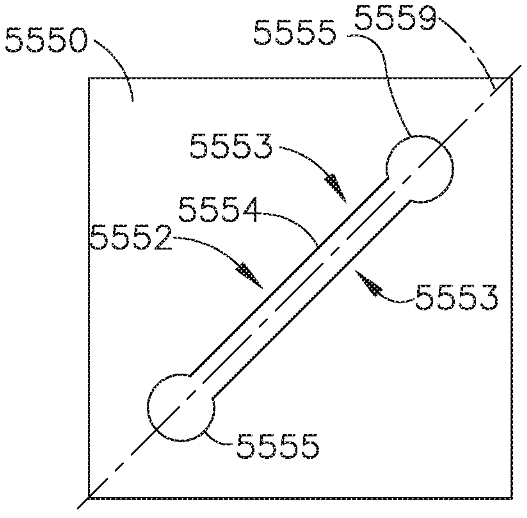
FIG. 105 is a top view of a retention aperture of a retention matrix in accordance with at least one alternative embodiment.
Figure 106:
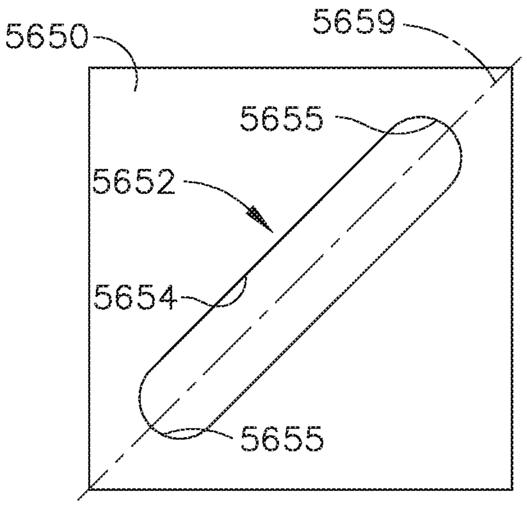
FIG. 106 is a top view of a retention aperture of a retention matrix in accordance with at least one alternative embodiment.

In various embodiments, referring now to FIG. 105, a retention matrix, such as retention matrix 5550, for example, can comprise a plurality of retention apertures 5552. Each retention aperture 5552 can comprise an elongate slot 5554 having enlarged circular, or at least substantially circular, ends 5555. In at least one such embodiment, the ends 5555 can be defined by a diameter which is wider than the slot 5554. In certain embodiments, the elongate slot 5554 and the ends 5555 can positioned along, and/or centered along, a longitudinal axis 5559. In various embodiments, the slot 5554 and the ends 5555 can define two opposing tabs 5553 which can be configured to engage a leg of a fastener and deflect as the fastener leg is inserted therethrough. In at least one embodiment, ends 5555 having a larger perimeter, or diameter, can define longer tabs 5553 which can be more flexible than tabs 5553 defined by ends 5555 having a smaller perimeter, or diameter. In various embodiments, the ends 5555 can have the same perimeter and diameter and, in at least one such embodiment, each tab 5553 can be symmetrical about an axis which is perpendicular, or at least substantially perpendicular, to the longitudinal axis 5559. Alternatively, the ends 5555 can have different perimeters and/or diameters wherein, in at least one embodiment, each tab 5553 may not be symmetrical about its axis. In at least one such alternative embodiment, the tabs 5553 may twist about their axes as the fastener leg is inserted through the retention aperture 5552. In various embodiments, referring now to FIG. 106, a retention matrix, such as retention matrix 5650, for example, can comprise a plurality of retention apertures 5652. Each retention aperture 5652 can comprise an elongate slot 5654 comprising circular, or at least substantially circular, ends 5655. In at least one such embodiment, the elongate slot 5654 and the ends 5655 can be positioned along, and/or centered along, a longitudinal axis 5659. In various embodiments, each end 5655 can be defined by a diameter which is the same as, or at least substantially the same as, the width of the slot 5654.

Figure 107:
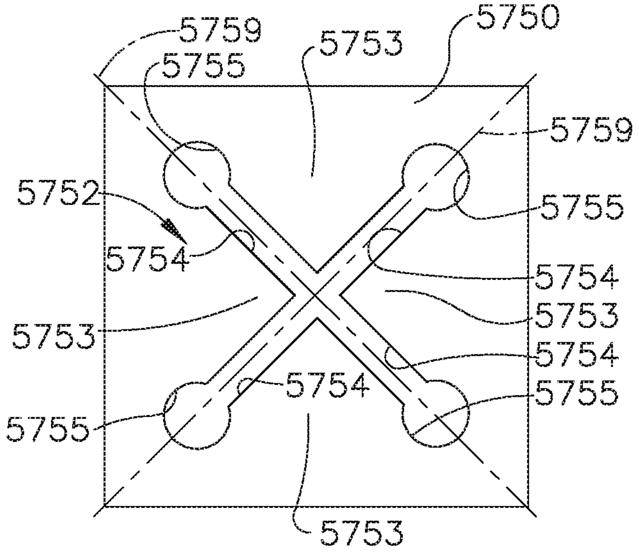
FIG. 107 is a top view of a retention aperture of a retention matrix in accordance with at least one alternative embodiment.
Figure 108:
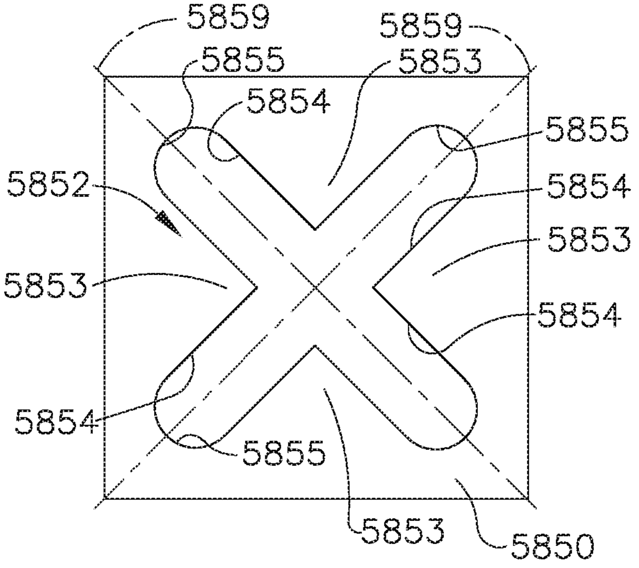
FIG. 108 is a top view of a retention aperture of a retention matrix in accordance with at least one alternative embodiment.

In various embodiments, referring now to FIG. 107, a retention matrix, such as retention matrix 5750, for example, can comprise a plurality of retention apertures 5752. Each retention aperture 5752 can comprise a plurality of slots, such as slots 5754, for example, having enlarged ends 5755. In at least one such embodiment, the slots 5754 and the ends 5755 can be positioned along and/or centered along longitudinal axes 5759. In various embodiments, the axes 5759 can extend in directions which are perpendicular or transverse to one another. In certain embodiments, the slots 5754 and the ends 5755 can define four tabs 5753, for example, which can be configured to engage a fastener leg and deflect when the fastener leg is inserted through the retention aperture 5752. In at least one embodiment, each tab 5753 can comprise a triangular, or at least substantially triangular, configuration, such as an equilateral triangle, for example. In various other embodiments, referring now to FIG. 108, a retention matrix, such as retention matrix 5850, for example, can comprise a plurality of retention apertures 5852. Each retention aperture 5852 can comprise a plurality of slots, such as slots 5854, for example, having ends 5855, wherein the slots 5854 and the ends 5855 can be positioned along and/or centered along longitudinal axes 5859. In various embodiments, the axes 5859 can extend in directions which are perpendicular or transverse to one another. In certain embodiments, the slots 5854 and the ends 5855 can define tabs 5853 which can be configured to engage a fastener leg and deflect when the fastener leg is inserted through the retention aperture 5852. In at least one embodiment, each tab 5853 can comprise an arcuate profile. More particularly, each tab 5853 can comprise a curved end, as opposed to a pointed end depicted in FIG. 105, which can be configured to contact the fastener leg.

Figure 109:
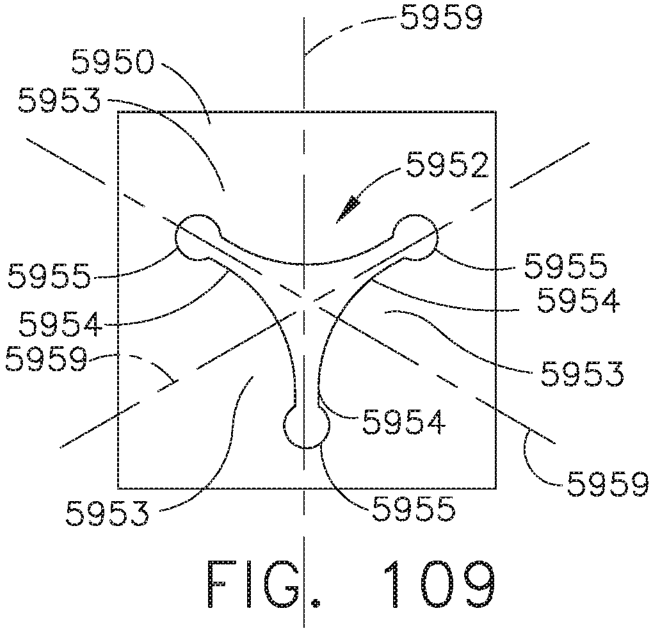
FIG. 109 is a top view of a retention aperture of a retention matrix in accordance with at least one alternative embodiment.
Figure 110:
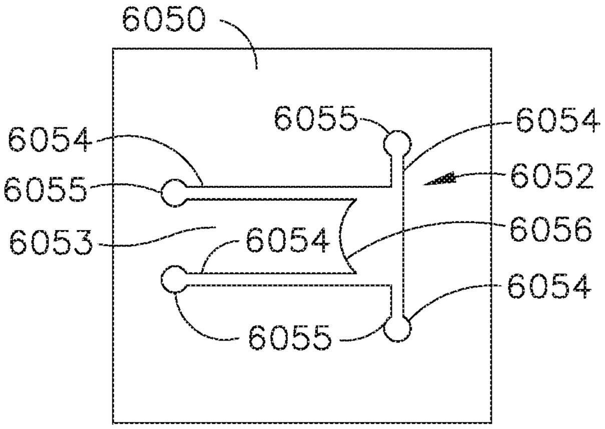

In various embodiments, referring now to FIG. 109, a retention matrix, such as retention matrix 5950, for example, can comprise a plurality of retention apertures 5952. Each retention aperture 5952 can comprise a plurality of slots, such as slots 5954, for example, wherein each slot 5954 can extend along, and/or can be centered along, an axis 5959. In various embodiments, the axes 5959 can be transverse to each other and, in at least one such embodiment, the axes 5959 can be arranged such that all of the axes 5959 extend through a center of the retention aperture 5952 and are spaced equidistantly, or at least substantially equidistantly, from each other. In at least one embodiment, each slot 5954 can comprise an open end facing the center of the retention aperture 5952 and a second, or closed, end 5955 at the opposite end of the slot 5954. Similar to the above, the slots 5954 and the ends 5955 can define three tabs 5953, for example, which can be configured to engage a fastener leg and deflect when the fastener leg is inserted into the retention aperture 5952. In various embodiments, each tab 5953 can comprise an arcuate configuration extending between adjacent ends 5955 of the slots 5954. In various embodiments, referring now to FIG. 110, a retention matrix, such as retention matrix 6050, for example, can comprise a plurality of retention apertures 6052. Each retention aperture 6052 can comprise a tab 6053 which can be configured to engage a fastener leg and to deflect when the fastener leg is inserted into the retention aperture 6052. In at least one such embodiment, the tab 6053 can comprise a base fixed to the retention matrix body 6058 and a free end comprising an arcuate or curved profile 6056 which can be configured to contact the fastener leg. In certain embodiments, the fastener leg can be a staple leg comprised of a round wire wherein the curved profile 6056 can be configured to match, or at least substantially match, a curved outer surface of the round wire.

Figure 111:
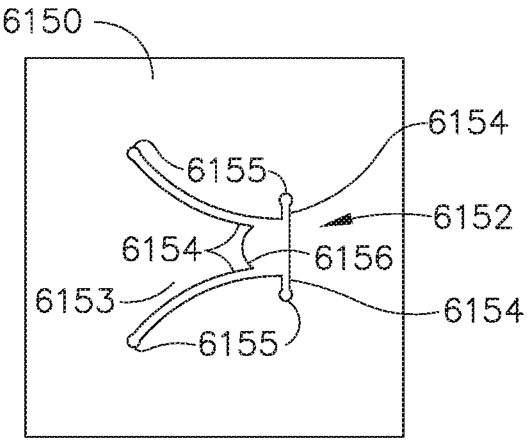

In various embodiments, referring again to FIG. 110, the retention matrix body 6058 can comprise a plurality of slots 6054 and apertures 6055 which can be configured to define the tab 6053 and various portions of the retention aperture 6052. In at least one embodiment, the tab 6053 can comprise a rectangular configuration comprising parallel, or at least substantially parallel, sides. In certain embodiments, referring now to FIG. 111, a retention matrix, such as retention matrix 6150, for example, can comprise a plurality of retention apertures 6152. Each retention aperture 6152 can comprise a tab 6153 which can be configured to engage a fastener leg and to deflect when the fastener leg is inserted into the retention aperture 6152. In at least one such embodiment, the tab 6153 can comprise a base fixed to the retention matrix body 6158 and a free end comprising an arcuate or curved profile 6156 which can be configured to contact the fastener leg. In various embodiments, the retention matrix body 6158 can comprise a plurality of slots 6154 and apertures 6155 which can be configured to define the tab 6153 and various portions of the retention aperture 6152. In at least one embodiment, the tab 6153 can comprise a tapered configuration comprising arcuate sides. In at least one such embodiment, the tab 6153 can taper geometrically with the base being wider than the free end, for example.

Figure 119:
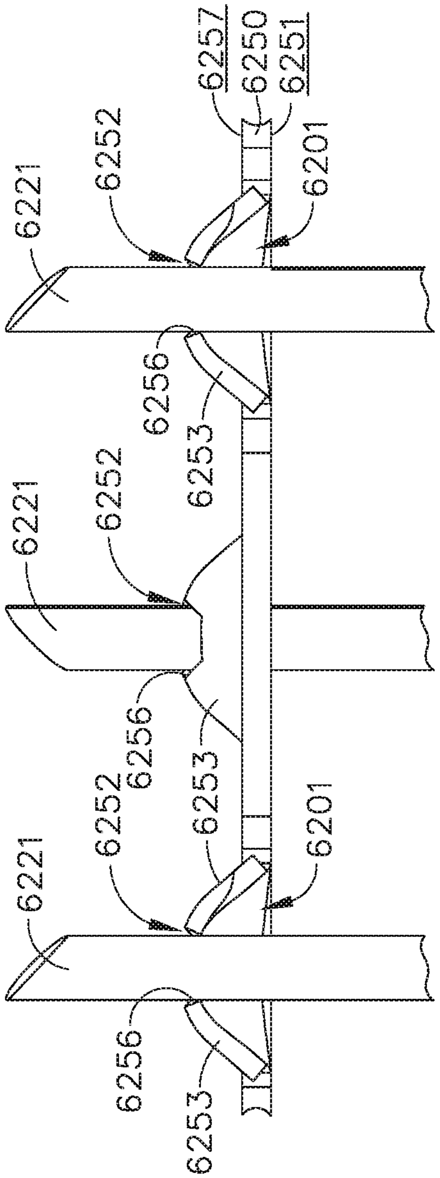
Figure 120:
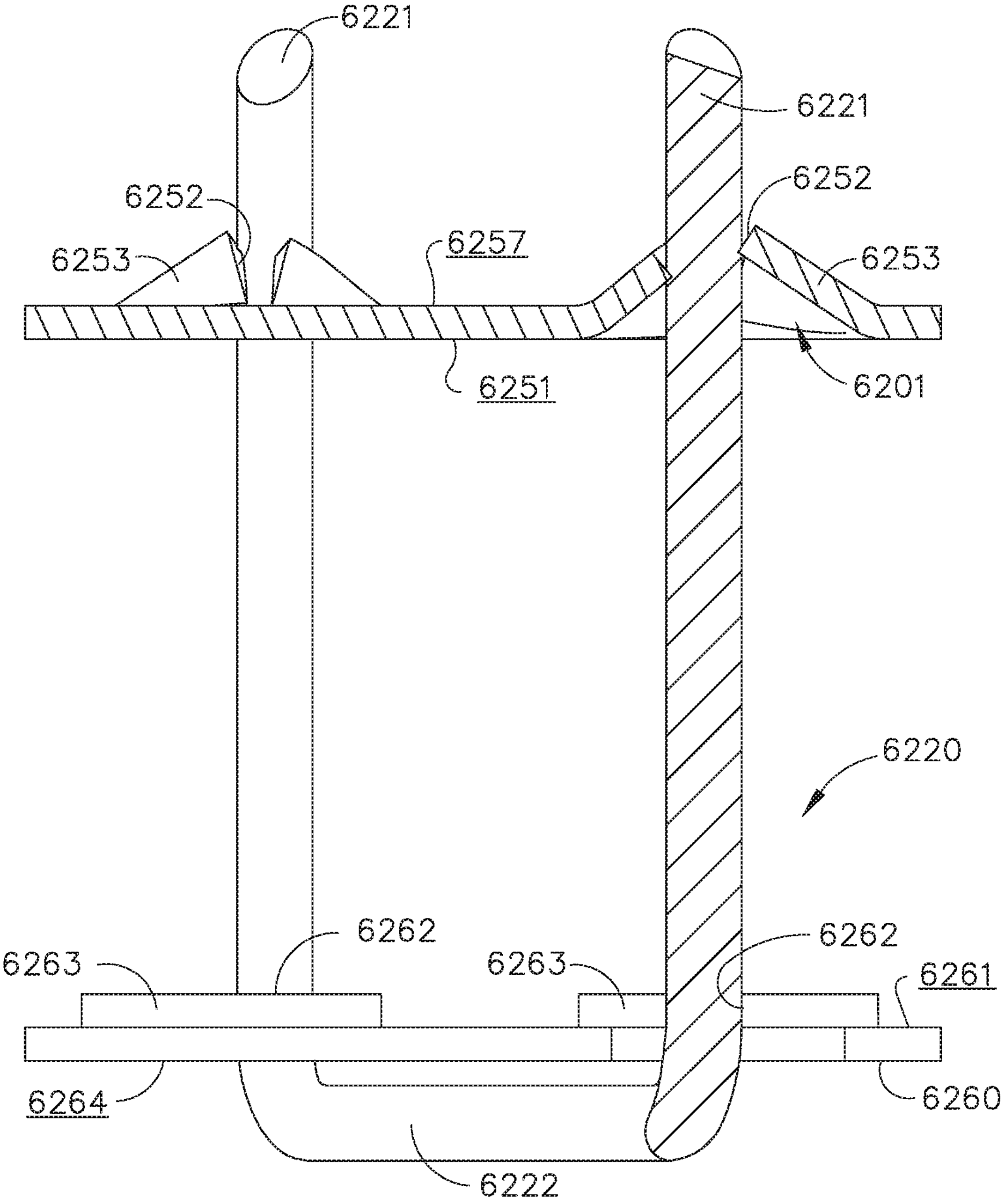

In various embodiments, as described above, a fastening system can comprise a plurality of staples comprising staple legs which are inserted through a plurality of retention apertures in a retention matrix. In certain embodiments, as described in greater detail below, the staples can be held in a first jaw and the retention matrix can be held in a second jaw, wherein at least one of the first jaw and the second jaw can be moved toward the other. In various circumstances, the staples positioned within the first jaw can be secured therein such that the staple legs are aligned with the retention apertures when the retention matrix is engaged with the staple legs. In certain embodiments, referring to FIGS. 112 and 113, a fastener system can comprise a staple cartridge 6200, for example, positioned in a first jaw of a surgical stapler and a retention matrix 6250, for example, positioned in a second jaw of the surgical stapler. Referring now to FIGS. 119 and 120, further to the above, the retention matrix 6250 can comprise a plurality of retention apertures 6252, wherein each retention aperture 6252 can comprise a perimeter 6256 defined by one or more deflectable members 6253. In at least one such embodiment, further to the above, the deflectable members 6253 defining each aperture 6252 can define a pocket 6201. In various embodiments, each pocket 6201 can comprise a curved and/or concave surface, for example, which can be configured to guide a tip of a staple leg into the aperture 6252 in the event that the staple leg is misaligned with the retention aperture 6252 and initially contacts the deflectable members 6253 and/or the tissue-contacting surface 6251, for example.

Figure 115:
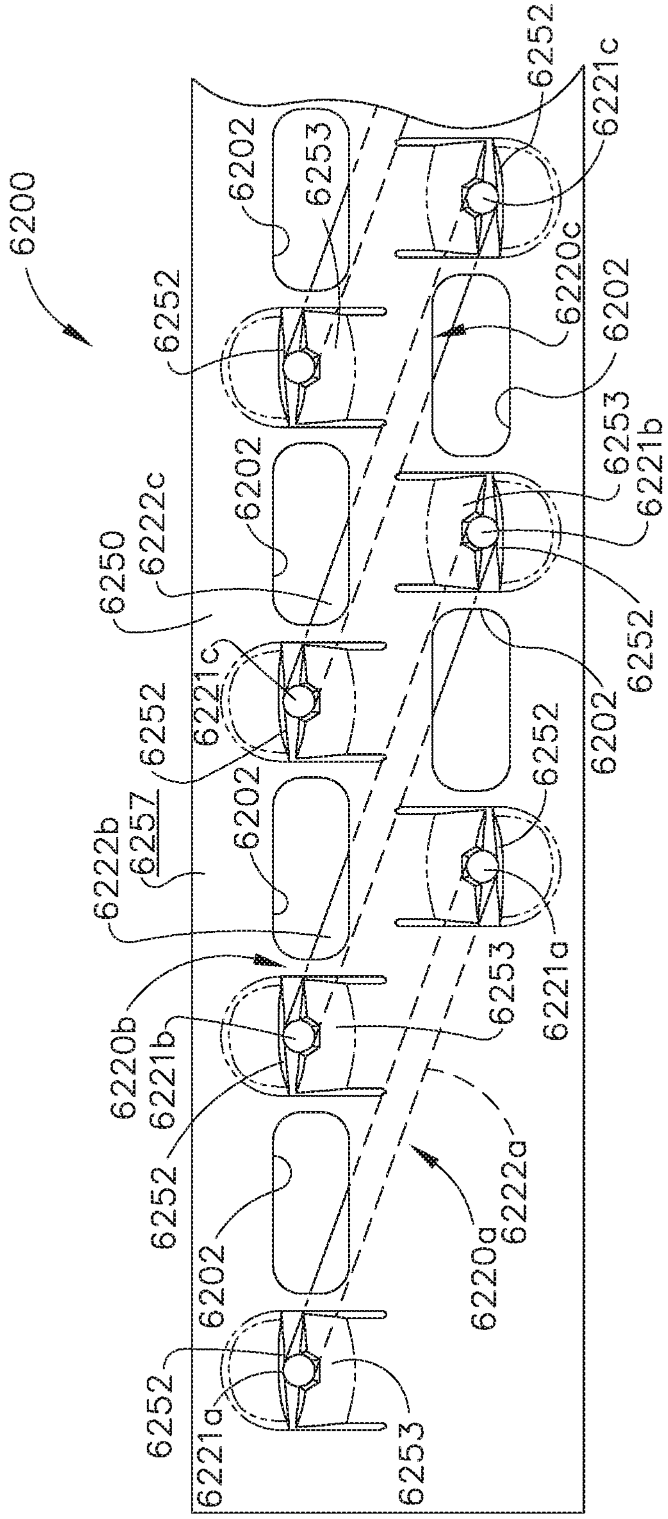
Figure 116:
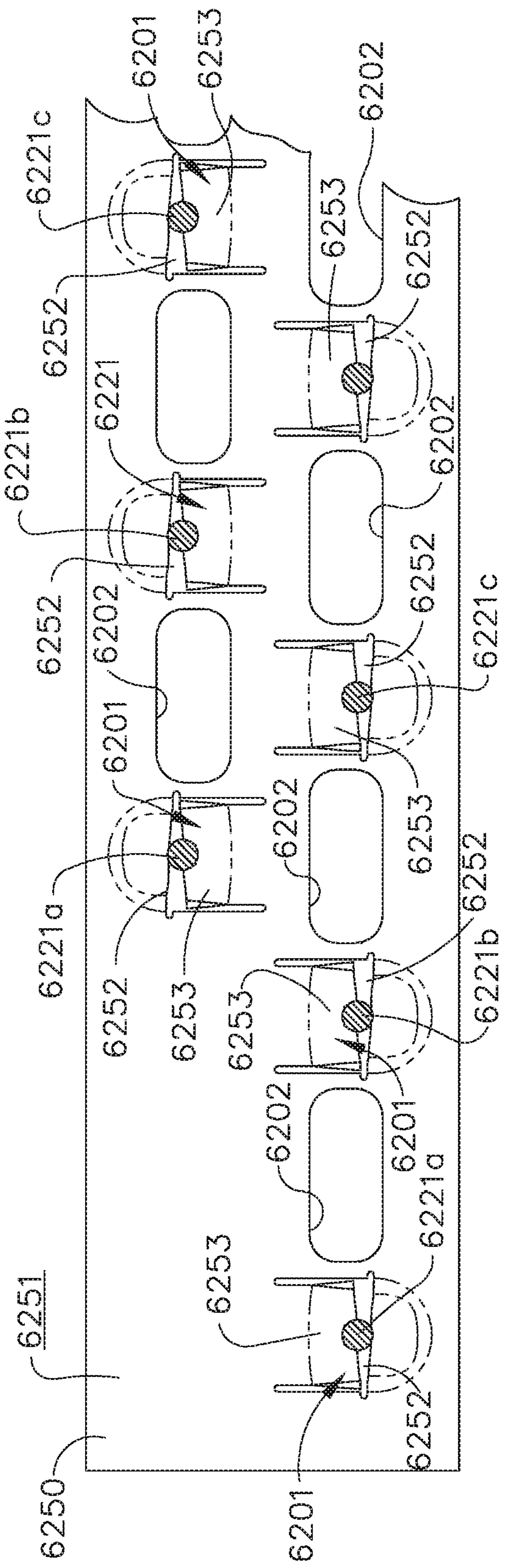

In various embodiments, further to the above, the fastening system can further comprise a plurality of staples 6220 comprising staple legs 6221 which can be inserted through the retention apertures 6252 in the retention matrix 6250. In at least one such embodiment, each staple 6220 can comprise a substantially U-shaped configuration, for example, comprising a base 6222 from which the staple legs 6221 can extend upwardly. In various embodiments, referring now to FIGS. 115 and 116, the retention apertures 6252 in the retention matrix 6250 can be arranged in two parallel, or at least substantially parallel, longitudinal rows, for example, which can extend along, or parallel to, a longitudinal axis of the retention matrix. In certain embodiments, the retention apertures 6252 in a first row can be offset, or staggered, with respect to the retention apertures 6252 in a second row. In at least one such embodiment, each staple 6220 can comprise a first staple leg 6221 positioned in a retention aperture 6252 in the first row of and a second staple leg 6221 positioned in a retention aperture 6252 in the second row wherein, as a result, the bases 6222 can extend in a direction which is transverse to the longitudinal axis of the retention matrix 6250. In at least one such embodiment, the staples 6220 can be parallel, or at least substantially parallel, to one another. More particularly, a base 6222*a* of a staple 6220*a* be parallel to, or at least substantially parallel to, a base 6222*b* of a staple 6220*b* which can be parallel to, or at least substantially parallel to, a base 6222*c* of a staple 6220*c*, for example. In at least one embodiment, the staple legs 6221*a* of staple 6220*a* can define a plane which is parallel to, or at least substantially parallel to, a plane defined by the staple legs 6221*b* of staple 6220*b* which can be parallel to, or at least substantially parallel to, a plane defined by the staple legs 6221 of staple 6220*c*, for example.

Figure 112:
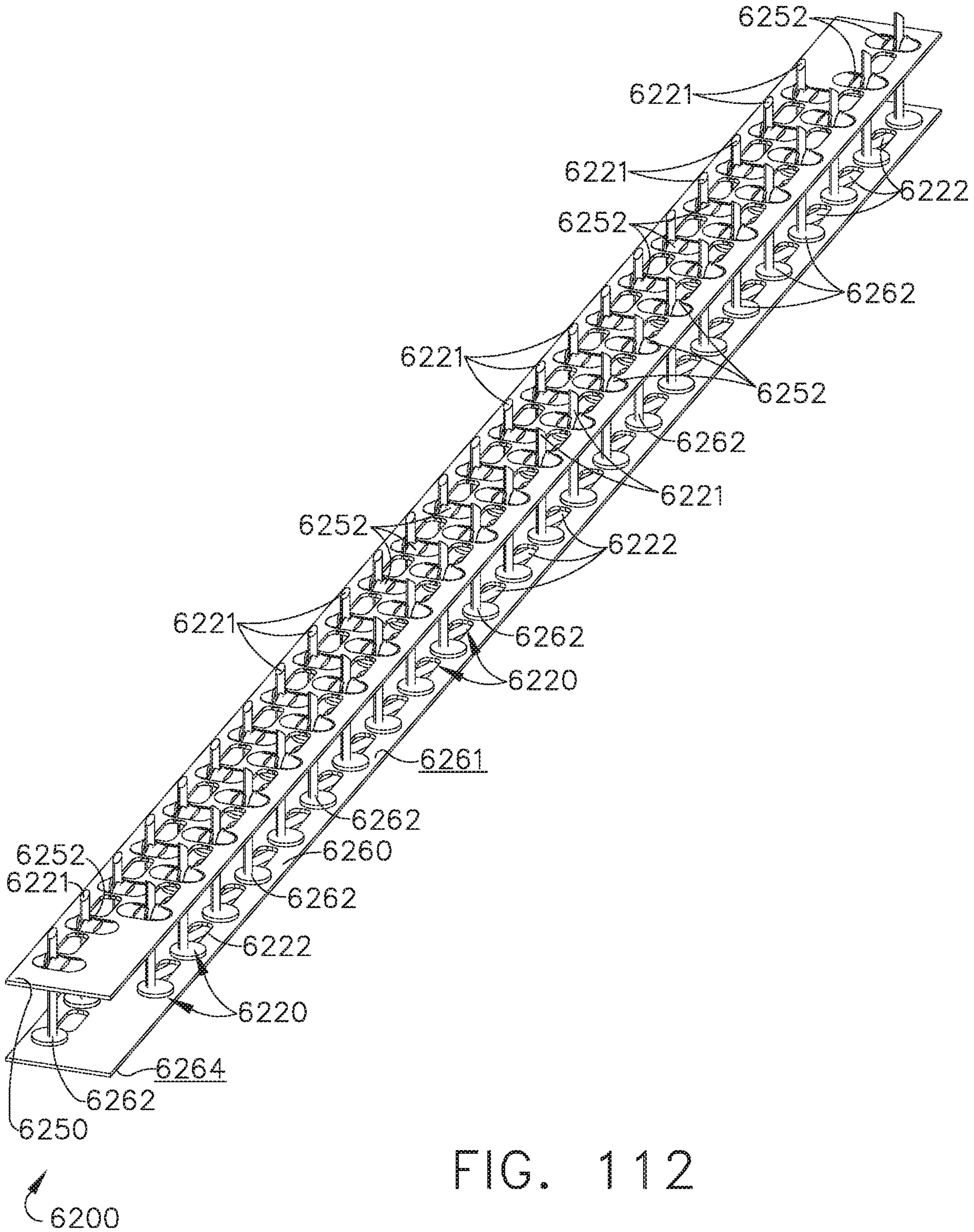
Figure 113:
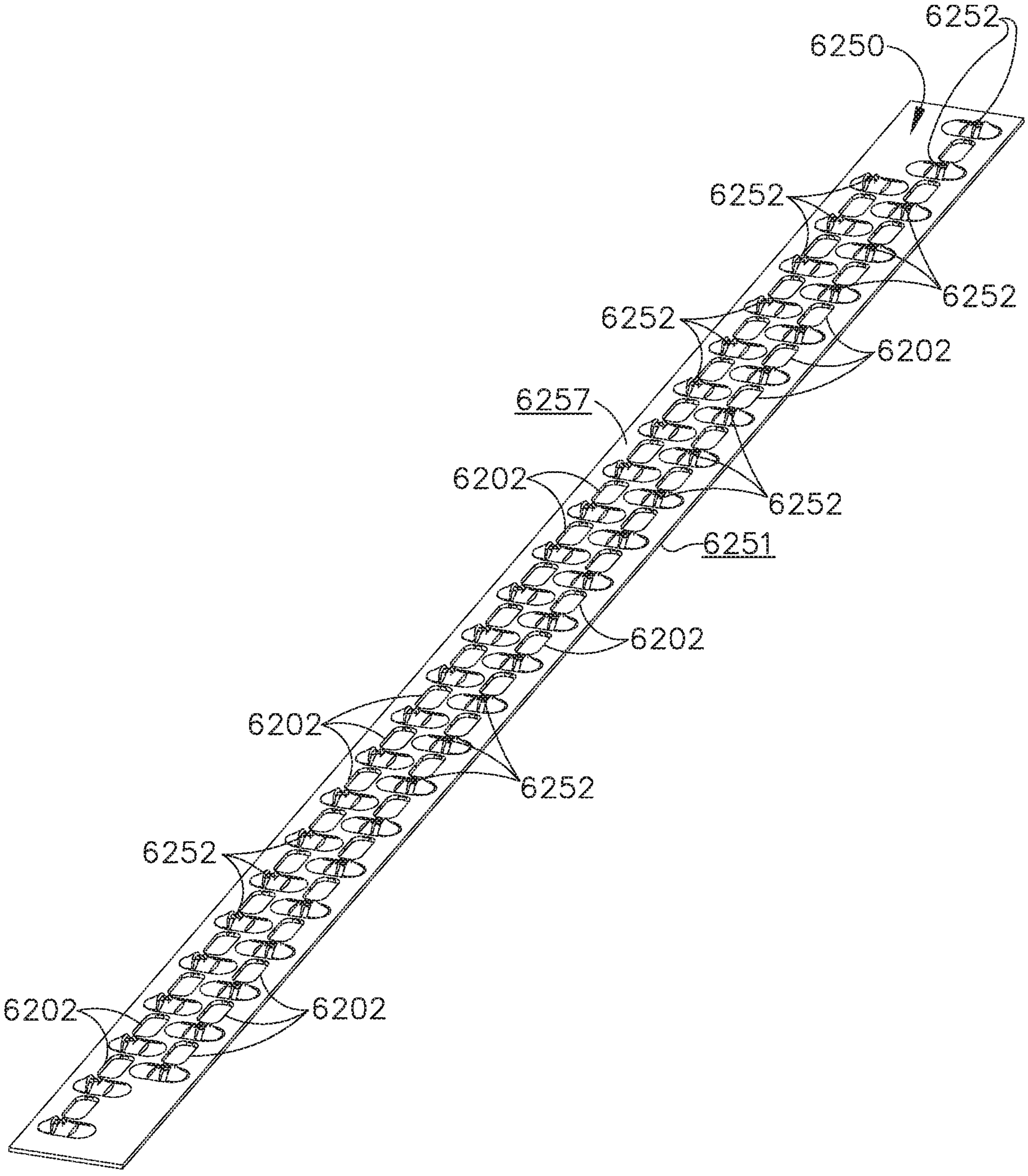
Figure 114:
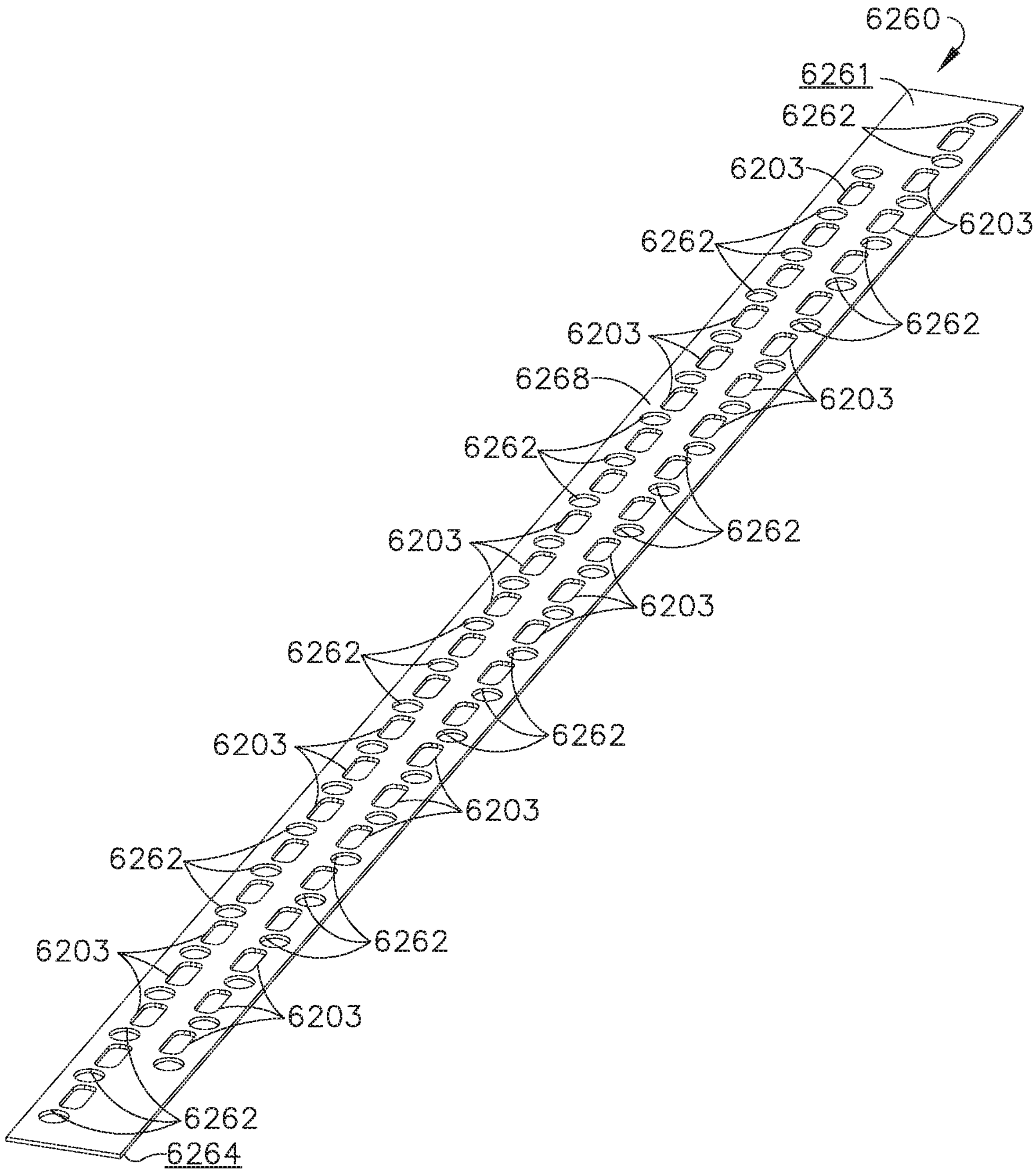
Figure 117:
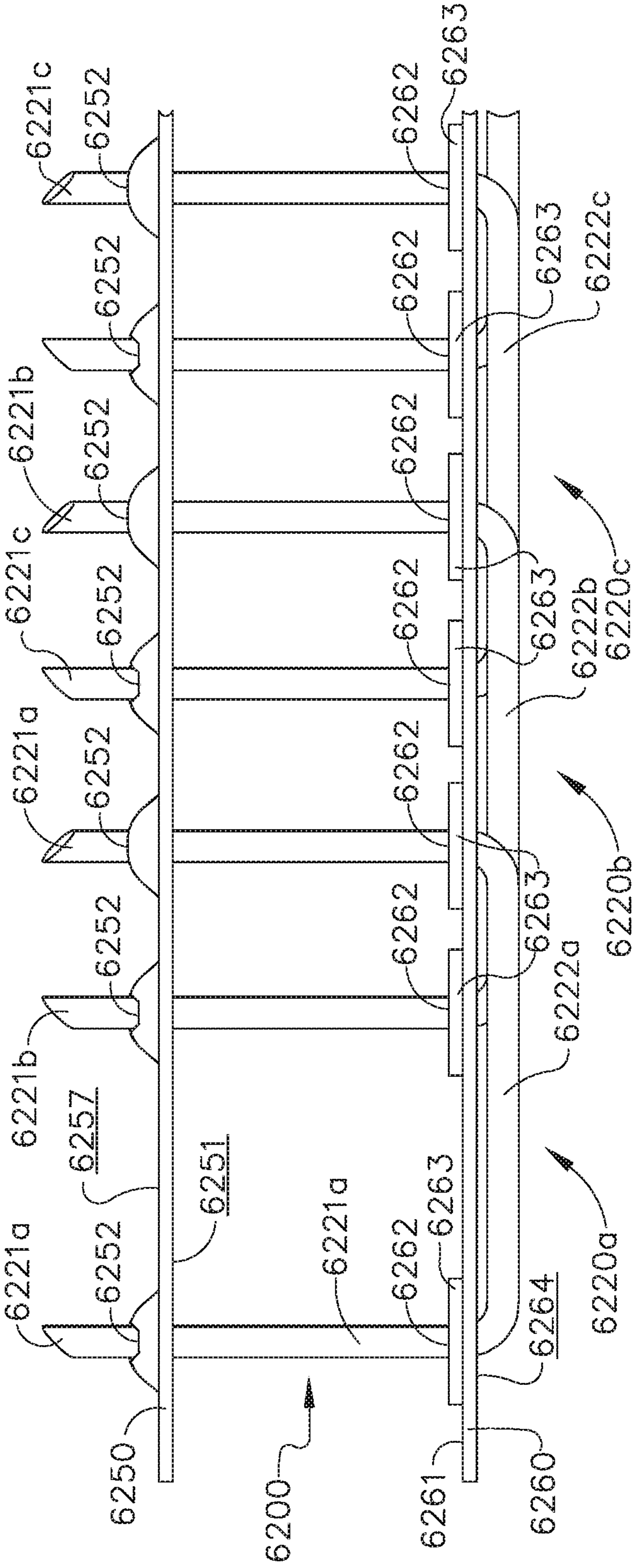
Figure 118:
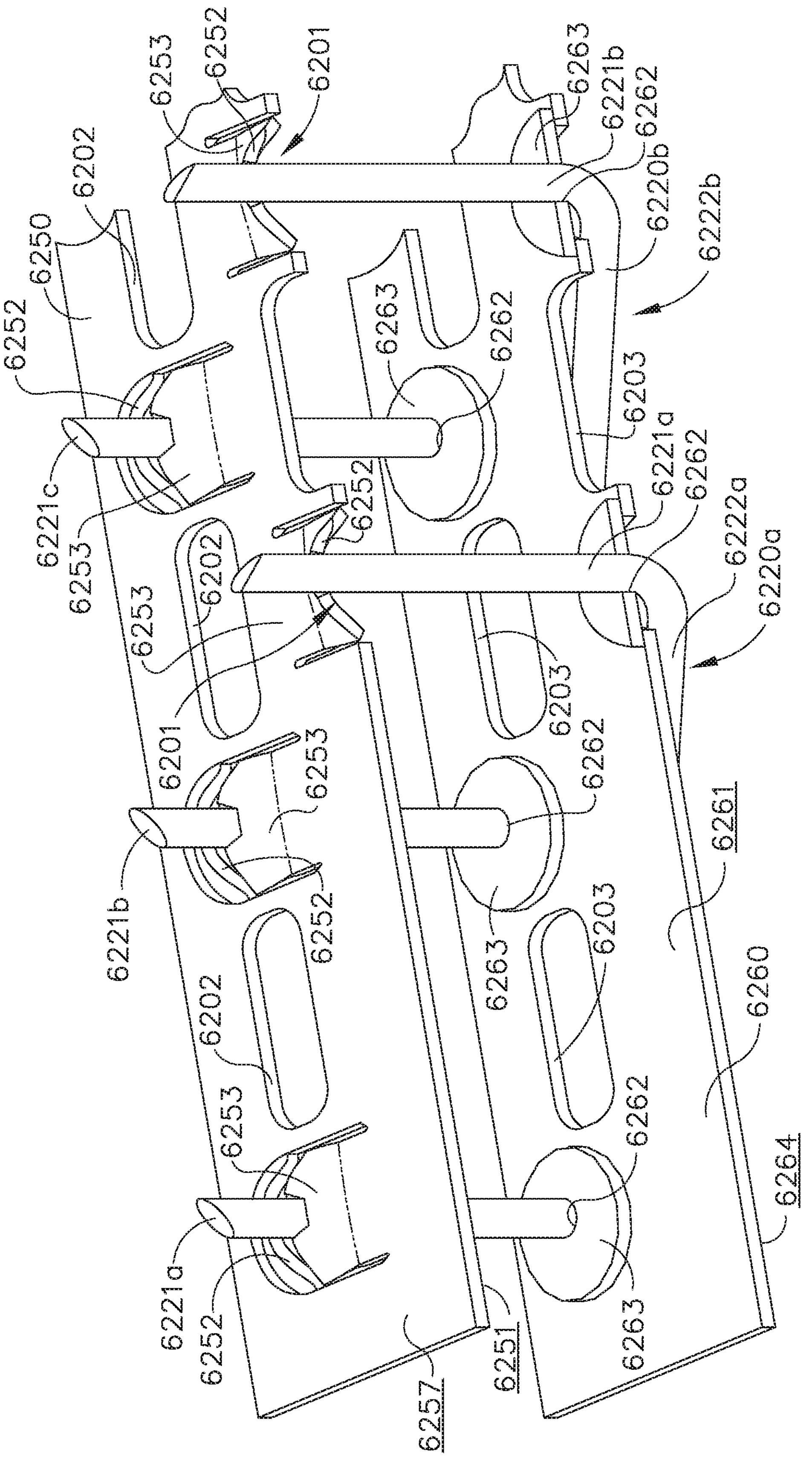

In various embodiments, referring now to FIGS. 112 and 114, the staple cartridge 6200 can comprise a plurality of staples 6220 and, in addition, an alignment matrix 6260 comprising a plurality of alignment guides, such as slots, grooves, and/or apertures, for example, which can be configured to align the staples 6220. In various circumstances, the alignment matrix 6260 can be configured such that the staple legs 6221 of the staples 6220 are aligned with the retention apertures 6252 in the retention matrix 6250 before the retention matrix 6250 is engaged with the staple legs 6221. In various embodiments, referring now to FIGS. 117 and 118, the alignment matrix 6260 can comprise a plurality of alignment apertures 6262 which can be configured to closely receive the staple legs 6221 of the staples 6220. In at least one such embodiment, each staple 6220 can comprise a base 6222 and two staple legs 6221 extending from the base 6222 wherein the bases 6222 of the staples 6220 can extend around a bottom surface 6264 of the retention matrix 6260 and the staple legs 6221 can extend upwardly through the alignment apertures 6262. In certain embodiments, each alignment aperture 6262 can be circular, or at least substantially circular, and can be defined by a diameter which is equal to or slightly larger than the diameter of the staple leg 6221 extending therethrough. In various embodiments, the alignment matrix 6260 can further comprise a plurality of raised members 6263 which can extend upwardly from the top surface 6261 of the alignment matrix 6260 and surround, or at least partially surround, the alignment apertures 6262. In certain embodiments, the raised members 6263 can provide for longer alignment apertures 6262 wherein, in various circumstances, longer apertures 6262 can provide more control over the alignment of the staple legs 6221 than shorter apertures 6262.

In use, in various embodiments, a first jaw supporting the staple cartridge 6200 can be positioned on one side of the tissue that is to be stapled and a second jaw supporting the retention matrix 6250 can be positioned on the other side of the tissue. Once the jaws have been suitably positioned relative to the tissue, in certain embodiments, the second jaw and the retention matrix 6250 can be moved toward the staple cartridge 6200. As the staple legs 6221 are being inserted through the retention apertures 6252 of the retention matrix 6250, in various embodiments, a tissue-contacting, or bottom, surface 6251 of the retention matrix 6250 can contact the tissue and press the tissue against the tissue-contacting, or top, surface 6261 of the alignment matrix 6260. In various other embodiments, as described in greater detail further below, the staple cartridge 6200 can further comprise a compressible cartridge body positioned above the top surface 6261 of the alignment matrix 6260, for example, which can contact the tissue. In certain embodiments, referring again to FIGS. 114 and 118, the alignment matrix 6260 can further comprise one or more apertures 6203 defined therein which, when the alignment matrix 6260 is positioned against tissue, can be configured to receive a portion of the tissue therein. In embodiments where a compressible cartridge body is positioned above and/or against the alignment matrix 6260, a portion of the compressible cartridge body can enter into the apertures 6203 when the cartridge body is compressed. Similarly, the retention matrix 6250 can comprise a plurality of apertures 6202 which can be configured to receive at least a portion of the tissue therein when the retention matrix 6250 is positioned against the tissue.

As the staple legs 6221 of the staples 6220 are inserted through the retention apertures 6252 of the retention matrix 6250, further to the above, the tips of the staple legs 6221 may protrude upwardly from the top surface 6257 of the retention matrix 6250. In various circumstances, as described above, the tips of the staple legs 6221 may remain unbent after they have been inserted through the retention apertures 6252. In certain embodiments, referring now to FIGS. 121-124, a fastening system comprising the staple cartridge 6200 and the retention matrix 6250 may further comprise a plurality of protective caps or covers, such as caps 6270, for example, which can be assembled to the staple legs 6221 protruding above the retention matrix 6250. In various embodiments, each cap 6270 can entirely, or at least partially, cover the sharp end of a staple leg 6221 such that the sharp end does not contact tissue positioned adjacent thereto. In at least one embodiment, referring now to FIG. 124, each cap 6270 can comprise an aperture 6271 defined therein which can be configured to closely receive a tip of a staple leg 6221 therein. In various embodiments, the caps 6270 can be comprised of an elastomeric material, such as silicone, polyisoprene, sanoprene, and/or natural rubber, for example. In at least one embodiment, the aperture 6271 can comprise a perimeter or diameter which is smaller than the perimeter or diameter of the staple leg 6221 inserted therein. In at least one such embodiment, the aperture 6271 in the protective cap 6270 can expand in order to receive the staple leg 6221 therein. In various alternative embodiments, the caps 6270 may not comprise apertures and the tips of the staple legs 6221 can be configured to incise the caps 6270 as the legs 6221 are inserted therein. In any event, in various embodiments, each cap 6270 can be seated onto a staple leg 6221 until the base 6272 of the cap 6270 abuts, or is positioned adjacent to, the top surface 6257 of the retention matrix 6250. In various circumstances, the caps 6270 can be configured such that they are seated snugly onto the tips of the staple legs 6221 such that they are not easily removed therefrom. In certain embodiments, each cap 6270 can comprise a conical, or at least substantially conical, outer surface, for example. In various embodiments, the caps 6270 can comprise any suitable shape, such as shapes comprising a parabolic, or at least substantially parabolic, outer surface, for example.

In various embodiments, the fastener system described above, for example, could be deployed using the surgical stapler depicted in FIGS. 125-127, for example. In various embodiments, the end effector can comprise a first jaw, or staple cartridge channel, 6230 which can be configured to support the staple cartridge 6200 therein and a second jaw 6240 which can be configured to support the retention matrix 6250 and the plurality of protective caps 6270. Referring primarily to FIG. 125, which illustrates the second jaw 6240 in an open configuration, the jaws 6230 and 6240 can be positioned relative to tissue T such that the tissue T is positioned intermediate the retention matrix 6250 and the staple cartridge 6200. In various embodiments, as discussed above, the staple cartridge 6200 can further comprise a compressible cartridge body, such as cartridge body 6210, for example, in which the staples 6220 and the alignment matrix 6260 can be positioned. In at least one such embodiment, the tissue T can be positioned against a top surface of the cartridge body 6210. In certain embodiments, the second jaw 6240 can comprise a plurality of recesses, or apertures, 6245 configured to receive the plurality of protective caps 6270 and, in addition, one or more retention features, or retainers, which can be configured to hold the retention matrix 6250 in position over the caps 6270. In at least one such embodiment, the retention matrix 6250 can be configured to retain the caps 6270 in the apertures 6245. In various embodiments, referring now to FIG. 137, each aperture 6245 can be configured to receive a portion of, or the entirety of, a cap 6270 therein. In certain embodiments, the apertures 6245 can be sufficiently sized and configured such that the caps 6270 can be secured therein by at least one of a press-fit and/or snap fit arrangement, for example. In some embodiments, at least one adhesive could be utilized to secure the caps 6270 in the apertures 6245. In at least one such embodiment, such an adhesive could be selected such that caps 6270 can detach from the second jaw 6240 after the caps 6270 have been engaged with the staple legs 6221 and the second jaw 6240 is moved away from the implanted fastener assembly. In certain embodiments, referring now to FIG. 138, the second jaw 6240 can further comprise at least one cover sheet 6246 which can be assembled to the second jaw 6240 and can extend over and retain the caps 6270 in the apertures 6245. In at least one such embodiment, at least a portion of the cover sheet 6246 can be secured to the jaw 6240 utilizing at least one adhesive, for example. In use, in at least one embodiment, the cover sheet 6246 can be at least partially detached from the jaw 6240 before the end effector is inserted into a surgical site. In certain embodiments, the cover sheet 6246 can be comprised of an implantable material, such as PDS and/or PGA, for example, which can be incised by the staple legs 6221 as the staple legs 6221 emerge from the retention matrix 6250. In at least one such embodiment, the cover sheet 6246 can be secured in the fastening system intermediate the covers 6270 and the retention matrix 6250.

Further to the above, referring now to FIG. 126, the jaw 6240 can be moved from an open position to a closed position in which the tissue T is positioned against the retention matrix 6250 and the cartridge body 6210. In such a position, the retention matrix 6250 may not yet be engaged with the staples 6220. In various embodiments, the jaw 6240 can be moved between its open position and its closed position by an actuator 6235. In at least one such embodiment, the jaw 6240 can comprise a distal pin 6243 and a proximal pin 6244 extending therefrom, wherein the distal pin 6243 can slide vertically, or at least substantially vertically, within a distal slot 6233 defined in the cartridge channel 6230, and wherein the proximal pin 6244 can slide vertically, or at least substantially vertically, within a proximal slot 6234 which is also defined in the staple cartridge channel 6230. In use, the actuator 6235 can be retracted proximally in order to drive the pins 6243 and 6244 into the upper ends of their respective slots 6233 and 6234 as illustrated in FIG. 126. In at least one such embodiment, the actuator 6235 can comprise a distal drive slot 6236 and a proximal drive slot 6237, wherein the sidewalls of the drive slots 6236 and 6237 can be configured to contact the distal pin 6243 and the proximal pin 6244, respectively, and drive the pins 6243 and 6244 upwardly as the actuator 6235 is moved proximally. More particularly, as the actuator 6235 is moved proximally, the distal pin 6243 can slide up an inclined first portion 6236*a* of the distal drive slot 6236 into an intermediate, or second, portion 6236*b* and, similarly, the proximal pin 6244 can slide up an inclined first portion 6237*a* of the distal drive slot 6237 into an intermediate, or second, portion 6237*b*. As the pins 6243 and 6244 are both moved upwardly, the jaw 6240 can be rotated downwardly toward the tissue T into a closed position.

Further to the above, referring now to FIG. 127, the actuator 6235 can be pulled further proximally in order to push the second jaw 6240 downwardly toward the first jaw 6230, compress the cartridge body 6210, and engage the retention matrix 6250 and the plurality of protective caps 6270 with the staple legs of the staples 6220. In at least one such embodiment, the additional proximal movement of the actuator 6235 can cause the sidewalls of the drive slots 6236 and 6237 to contact the pins 6243 and 6244, respectively, and drive the pins 6243 and 6244 downwardly toward the bottom ends of the slots 6233 and 6234, respectively. In such circumstances, the actuator 6235 can be pulled proximally such that, one, the distal pin 6243 exits the second portion 6236*b* of the drive slot 6236 and enters into an inclined third portion 6236*c* and, similarly, the proximal pin 6244 exits the second portion 6237*b* of the drive slot 6237 and enters into an inclined third portion 6237*c*. As the pins 6243 and 6244 are both moved downwardly, the second jaw 6240 can move downwardly toward the first jaw 6230 into a fired position. In at least one such embodiment, the second jaw 6240 can be moved downwardly such that the retention matrix 6250 remains parallel, or at least substantially parallel, to the top surface of the cartridge body 6210 and/or parallel, or at least substantially parallel, to the alignment matrix 6260. In any event, once the retention matrix 6250 and the protective caps 6270 have been engaged with the staple legs 6221 of the staples 6220, as illustrated in FIG. 129, the second jaw 6240 can be returned to an open, or an at least substantially open, position. In at least one such embodiment, the actuator 6235 can be pushed distally in order to drive the pins 6243 and 6244 to the top ends of the slots 6233 and 6234, respectively, and then driven downwardly toward the bottom ends of the slots 6233 and 6234 once the pins have passed through the intermediate portions 6236*b* and 6237*b* of the respective drive slots 6236 and 6237. Once the second jaw 6240 has been opened, the first jaw 6230 can be detached from the implanted staple cartridge 6200 and the first and second jaws 6230, 6240 can be removed away from the implanted fastener assembly, as illustrated in FIG. 128.

Referring to FIG. 127 once again, the reader will note that the pins 6243 and 6244 are not illustrated as being seated in the very bottoms of their respective slots 6233 and 6234 eventhough the retention matrix 6250 and the caps 6270 have been engaged with the staple legs 6221. Such circumstances can arise when thick tissue T is positioned between the retention matrix 6250 and the cartridge body 6210. In circumstances where thinner tissue T is positioned between the retention matrix 6250 and the cartridge body 6210, referring now to FIG. 130, the pins 6243 and 6244 can be drive further downwardly into their respective slots 6233 and 6234 as illustrated in FIG. 132. In general, in at least one such embodiment, the actuator 6235 can be pulled proximally in order to drive the pins 6243 and 6244 upwardly and downwardly through the progressions described above and illustrated in FIGS. 130-132 and, owing to the thinner tissue T, the retention matrix 6250 and the protective caps 6270 can be driven further onto the staple legs 6221 of the staples 6220, as illustrated in FIGS. 133 and 134. In various embodiments, as a result of the adjustability afforded by the retention matrix 6250, the same, or at least substantially the same, compressive pressure can be obtained in the fastened tissue regardless of whether the tissue captured within the end effector is thick or thin. In certain embodiments, the adjustability afforded by the retention matrix 6250 can allow a surgeon can select whether to apply a larger compressive pressure or a smaller compressive pressure to the tissue by selecting the depth to which the retention matrix 6250 is seated. In at least one such embodiment, the range in which the retention matrix 6250 can be seated onto the staple legs 6221 can be determined by the lengths, or ranges, of the slots 6233 and 6234, for example.

In various embodiments, as described above, the protective caps 6270 can be comprised of a soft or flexible material, for example, which can be configured to grip the ends of the staple legs 6221. In certain embodiments, the protective caps 6270 can be comprised of a bioabsorbable plastic, polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example, and/or a biocompatible metal, such as titanium and/or stainless steel, for example. As illustrated in FIG. 124, in at least one embodiment, each cap 6270 can be unconnected to the other caps 6270. In certain other embodiments, one or more caps 6270 can be mounted to the retention matrix 6250. In at least one such embodiment, the caps 6270 can be connected to the retention matrix 6250 by at least one adhesive, for example, wherein the apertures 6271 in the caps 6270 can be aligned, or at least substantially aligned, with the retention apertures 6252 in the retention matrix 6270. In various embodiments, referring now to FIG. 135, a protective cap, such as a cap 6370, for example, can define an inner cavity, or dome, 6374 which can be configured to receive a tip of a staple leg 6221, for example, therein. In at least one such embodiment, the cap 6370 can comprise a bottom 6372 and an aperture 6371 extending through the bottom 6372. In various embodiments, the aperture 6371 can be defined by one or more deflectable members 6373 which can be configured to deflect when the staple leg 6221 is inserted therethrough. In certain embodiments, two or more caps 6370, for example, can be connected together to form an array of caps 6370. In at least one such embodiment, referring now to FIG. 136, a plurality of caps 6370 can be connected together by a sheet of material 6375. In certain embodiments, the sheet 6375 can be sufficiently rigid in order to maintain a desired arrangement and/or alignment of the caps 6370. In at least one embodiment, the caps 6370 can be comprised of a biocompatible metal, such as titanium and/or stainless steel, for example, and the sheet 6375 can be comprised of a bioabsorbable plastic, polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. In various embodiments, a sheet 6375 can be comprised of a bioabsorbable material including an anti-microbial agent, such as colloidal silver and/or triclosan, for example, stored and/or dispersed therein which can be released as the sheet 6375 is bioabsorbed, for example.

In various embodiments, further to the above, the sheet 6375 can be injection molded around the caps 6370 utilizing an injection molding process, for example, such that the caps 6370 are embedded in the sheet 6375. In certain other embodiments, the sheet 6375 can be molded utilizing an injection molding process, for example, wherein apertures 6376 can be formed in the sheet 6375 during the injection molding process and/or after the injection molding process utilizing a stamping process, for example. In either event, the caps 6370 can be inserted into and secured in the apertures 6376 utilizing a press-fit and/or snap-fit interconnection and/or at least one adhesive. In certain embodiments, each cap 6370 can comprise an annular groove surrounding, or at least partially surrounding, the perimeter of the cap 6370 which can be configured to receive the perimeter of an aperture 6376 therein. In certain embodiments, the sheet 6375 can be comprised of a flexible and/or pliable material which can permit relative movement between the caps 6370. In at least one such embodiment, the flexible sheet 6375 can be comprised of a rubber, plastic, and/or silicone material, for example, and the caps 6370 can be comprised of a rigid material, such as metal, for example. In at least one such embodiment, similar to the above, the flexible material can be molded around the caps 6370. In certain embodiments, the caps 6370 can be pressed into a pre-molded sheet 6375, for example. In various embodiments, the durometer of the flexible material can be selected to provide a desired stiffness of the sheet 6375. In certain embodiments, the sheet 6375 can be configured such that it comprises a flexible band. In any event, the sheet 6375 can facilitate the assembly of the caps 6370 into an end effector as a plurality of the caps 6370 can be positioned and/or aligned simultaneously within the end effector. Furthermore, the sheet 6375 connecting the caps 6370, once implanted, can strengthen or bolster the tissue along the staple line, for example. In addition to or in lieu of a sheet connecting the caps 6370, the caps 6370 can be connected together by a plurality of links. In at least one such embodiment, such links can be flexible and can permit relative movement between the caps 6370.

In various embodiments, referring now to FIGS. 139 and 140, a protective cap, such as cap 6470, for example, can comprise a forming surface which can be configured to deform a tip of a staple leg. In at least one such embodiment, the cap 6470 can comprise a base 6472 which can include an aperture 6471 extending therethrough. In various embodiments, the aperture 6471 can be configured to closely receive a staple leg, such as a staple leg 6221, for example, therein. In at least one embodiment, the aperture 6471 can be defined by a diameter or perimeter which can be equal to or larger than the diameter or perimeter of the staple leg 6221. In various embodiments, the cap 6470 can further comprise a cavity, or dome, 6474 which can be configured to receive the tip of the staple leg 6221 as it is inserted into the cap 6470. Referring primarily to FIG. 140, the cap 6470 can further comprise an anvil, or forming surface, 6473 which can be configured to deflect and deform the staple leg 6221. In various circumstances, the forming surface 6473 can be curved and/or concave, for example, and can be configured to curl the staple leg 6221 as it is inserted into the cap 6470. In certain embodiments, the staple leg 6221 can be sufficiently deformed such that it cannot be withdrawn through the aperture 6471 and, as a result, the cap 6470 can become locked to the staple leg 6221. In at least one such embodiment, the base 6472 of the cap 6470 can define a lip extending around the aperture 6471 which can prevent the deformed staple leg 6221 from being removed from the cavity 6474. In various circumstances, as a result of the above, one or more caps 6470 can prevent, or inhibit, a retention matrix, such as retention matrix 6250, for example, from backing up or being disengaged from the staples 6220. In various embodiments, although not illustrated, the cap 6470 can be symmetrically, or at least substantially symmetrically, formed, and the aperture 6471 can be located along a central axis 6479 extending through the cap 6470. In various alternative embodiments, referring again to FIG. 139, the aperture 6471 can be offset with respect to the central axis 6479. In at least one such embodiment, the offset aperture 6471 can allow the staple leg 6221 to contact a side of the forming surface 6473 and curl over to the other side of the forming surface 6473 instead of contacting the center of the forming surface 6473, as may occur in embodiments comprising a centered aperture 6471 mentioned above.

In various embodiments, as discussed above, a retention matrix, such as retention matrix 6250, for example, can be comprised of a sheet of material and a plurality of retention apertures 6252 extending therethrough. In at least some embodiments, the sheet of material comprising the retention matrix 6250 can be rigid or substantially inflexible. In certain other embodiments, a retention matrix can be comprised of an array of retention matrix elements and a plurality of flexible connectors, or links, connecting the retention matrix elements. In various embodiments, referring now to FIG. 141, a retention matrix, or a portion of retention matrix, 6550 can comprise a plurality of element bodies 6505 which can be connected together by one or more connecting links 6507. In at least one embodiment, each element body 6505 can comprise a plurality of deformable members 6553 which define a retention aperture 6552 therein. In certain embodiments, the element bodies 6505 and the connecting links 6507 of a retention matrix 6550 can be integrally formed and can comprise a unitary piece of material. In various embodiments, the retention matrix 6550 can be stamped or cast, for example, from a metal material, such as titanium and/or stainless steel, for example. In at least one embodiment, the retention matrix 6550 can be comprised of plastic, such as polyetheretherketone (PEEK), polypropylene which is marketed under the trade name Prolene, polyester, polyethylene terephthalate which is marketed under the trade names Ethibond and Mersilene, polyvinylidene fluoride, polyvinylidene fluoride-co-hexafluoropropylene, poly hexafluoropropylene-VDF which is marketed under the trade name Pronova, and/or long-chain aliphatic polymers Nylon 6 and Nylon 6,6 which are marketed under the trade names Ethilon & Nurolon, for example, and can be formed by an injection molding process, for example. In certain embodiments, the element bodies 6505 may not be integrally formed with the connecting links 6507. In various embodiments, a plurality of singular element bodies 6505 can be produced which are subsequently connected together and embedded in a retention matrix. In at least one such embodiment, the element bodies 6505 can be stamped from a metal material, such as titanium and/or stainless steel, for example, and placed in a plastic injection mold wherein a plastic material can be injected into the mold to form, one, a rim 6506 of material surrounding, or at least partially surrounding, the element bodies 6505 and, two, connecting links 6507 extending from the rims 6506. In certain other embodiments, one or more connector lattices can be formed comprising apertures defined within a plurality of rims 6506 wherein each such aperture can be configured to receive an element body 6505 therein. In at least one embodiment, each element body 6505 can comprise a circular, or at least substantially circular, outer perimeter and, similarly, each rim 6506 can define a circular, or at least substantially circular, aperture therein, wherein the diameter of the aperture can be equal to or smaller than the diameter of the element body 6505. In at least one such embodiment, the element bodies 6505 can be press-fit or embedded into the apertures in the rims 6505. In certain embodiments, the element bodies 6505 can be secured in the apertures utilizing at least one adhesive.

In various embodiments, further to the above, a retention matrix can comprise a plurality of element bodies 6505 and a plurality of connecting links 6507 which can connect the element bodies 6505 in any suitable array, such as those illustrated in FIGS. 142-145, for example. Regardless of the pattern of the array, in various embodiments, the connecting links 6507 can be configured to allow the element bodies 6505 and the retention apertures 6552 to move relative to one another. In at least one such embodiment, the lattice of element bodies 6505 and connecting links 6507 comprising the retention matrix 6550, once engaged with tissue, can be configured to stretch, twist, contract, and/or otherwise flex in order to permit at least some movement within the tissue yet, at the same time, resist larger movements thereof. In various embodiments, each connecting link 6507 can comprise a flexible member configured to stretch, twist, and/or contract in order to permit the retention matrix 6550 to flex intermediate the matrix retention elements 6505, for example. Referring again to FIG. 141, each link 6507 extending from a rim 6506 can be defined by a width which is narrower than the width of the element body 6505 and/or the rim 6506. In certain embodiments, referring to FIGS. 142-145, one or more links 6507 can comprise straight portions which extend along a line between adjacent element bodies 6506, for example. In at least one such embodiment, each link 6507 can comprise a first end attached to a first rim 6506 and a second end attached to a second rim 6506. In certain embodiments, referring once again to FIG. 141, two or more links 6507 can be connected to one another. In at least one such embodiment, two or more links 6507 can be connected at an intermediate hinge 6509, for example. In various embodiments, the hinge 6509 can comprise a reduction in cross-sectional thickness in one or more directions as compared to the cross-sectional thickness of the links 6507 which can permit the connected links 6507 to move relative to each other, for example. In certain embodiments, the retention matrix 6550 can further comprise hinges 6508 which can connect the links 6507 to the rims 6506 and permit relative movement between the links 6507 and the rims 6506. Similar to hinges 6509, hinges 6508 can comprise a reduction in cross-sectional thickness in one or more directions as compared to the cross-sectional thickness of the links 6507, for example.

In various embodiments, further to the above, the connected links 6507 can extend in different directions. In at least one such embodiment, a first link 6507 can extend in a first direction and a second link 6507 can extend in a second direction, wherein the first direction can be different than the second direction. In certain embodiments, the first link 6507 can extend along a first line and the second link 6507 can extend along a second line, wherein the first line and the second line can intersect each other at an angle, such as approximately 30 degrees, approximately 45 degrees, approximately 60 degrees, and/or approximately 90 degrees, for example. In various embodiments, the hinges 6508 and/or hinges 6509 can comprise living hinges which can permit the links 6507 to move relative to each other a number of times without breaking. In certain embodiments, the hinges 6508 and/or hinges 6509 can comprise frangible, or easily-breakable, portions which can break when flexed too far and/or flexed too many times. In at least one such embodiment, such frangible portions can permit one or more portions of the retention matrix 6550 to break away from another portion of the retention matrix 6550. In various embodiments, the hinges 6508 and/or hinges 6509, for example, can comprise sections of the retention matrix 6550 which are easier to incise than the other portions of the retention matrix 6550. More particularly, an implanted retention matrix, and the tissue fastened by the implanted retention matrix, may oftentimes by incised by a cutting member for various reasons and, in order to facilitate such cross-cutting, the hinges 6508 and/or hinges 6509 can provide avenues, or thin sections, through which a cutting member can more easily pass through the retention matrix 6550, for example. In various embodiments, further to the above, the connecting links 6507 can comprise one or more coined features or material upsets, for example, defined therein which can facilitate the bending, breakage, and/or incision of the connecting links 6507.

In various embodiments, a retention matrix can comprise a plurality of retention matrix elements, such as matrix element bodies 6505, for example, which can be embedded in a flexible sheet, or band, of material. In at least one embodiment, a flexible sheet of material can be formed from a bioabsorbable, elastomeric material, such as silicone, for example, wherein the flexible sheet can be produced with a plurality of apertures defined therein. In at least one such embodiment, a solid flexible sheet can be molded and a plurality of apertures can be punched out of the flexible sheet. In various alternative embodiments, the flexible sheet can be molded and the apertures defined therein can be formed during the molding process. In either event, the retention matrix elements 6505, for example, can be inserted into and retained within the flexible sheet. In certain other embodiments, similar to the above, the flexible sheet can be formed around the matrix elements 6505. In at least one embodiment, the flexible sheet can be comprised of a woven mesh, for example, and/or any other suitable material. Such a woven mesh, further to the above, may be easy to cross-cut.

In various embodiments, referring now to FIGS. 146 and 147, a fastener system comprising a retention matrix, such as retention matrix 6250, for example, can further comprise a cover, such as cover 6670, for example, which can cover the tips of the staple legs 6221 when they extend above the top surface 6257 of the retention matrix 6250. In various embodiments, the cover 6670 can be attached to the retention matrix 6250. In certain embodiments, the cover 6670 and/or the retention matrix 6250 can comprise retention features which can be configured to retain the cover 6670 to the retention matrix 6250. In at least one embodiment, at least one adhesive can be utilized to adhere the cover 6670 to the retention matrix 6250. In at least one embodiment, the cover 6670 can be comprised of a single layer, although the cover 6670 is illustrated as comprising two layers as described in greater detail further below. In various embodiments, referring primarily to FIG. 147, the tips of the staple legs 6221 can extend through a bottom surface 6673 of the cover 6670; however, the cover 6670 can comprise a sufficient thickness such that the staple tips do not extend through the top surface 6675 of the cover 6670. In at least one such embodiment, as a result, the tips of the staple legs 6221 may not protrude from the cover 6670. In various embodiments, the cover 6670 can comprise a plurality of layers. In at least one such embodiment, the cover 6670 can comprise a first layer 6671 and a second layer 6672. In at least one embodiment, the first layer 6671 and the second layer 6672 can be attached to one another wherein, in at least one embodiment, the second layer 6672 can comprise a bottom surface 6676 which is adhered to the first layer 6671. In various embodiments, the first layer 6671 and the second layer 6672 can comprise different thicknesses while, in certain embodiments, they can comprise the same thickness. In at least one embodiment, the first layer 6671 and the second layer 6672 can comprise substantially the same width and/or length. In alternative embodiments, the layers 6671 and 6672 can comprise different widths and/or lengths.

In various embodiments, further to the above, the first layer 6671 can be comprised of a compressible foam, mesh material, and/or hydrogel, for example, which can be incised by the staple legs 6211. In at least one embodiment, the second layer 6672 can be comprise of a tougher material, or skin, such as PGA and/or PDS, for example, and/or any suitable buttress material. In at least one such embodiment, the staple legs 6221 can be configured to penetrate the first layer 6671; however, in various embodiments, the staple legs 6221 may be unable to penetrate the second layer 6672. In certain embodiments, the second layer 6672 can be comprised of a material having a sufficient resiliency and/or toughness which can permit the second layer 6672 to be contacted and displaced by the staple leg 6221 but not be incised, or only marginally incised, by the staple tip of the staple leg 6221. Although not illustrated, a cover can comprise more than two layers wherein one or more of such layers may be penetration-resistant. In use, in at least one such embodiment, the retention matrix 6250 can be positioned against the tissue to be fastened and pushed downwardly such that the staple legs 6221 of the staples 6220 are pushed through the tissue T and the retention apertures 6252 in the retention matrix 6250 and enter into the first layer 6271 of the cover 6270. In various embodiments, the tips of the staple legs 6221 may not enter, or at least substantially enter, into the second layer 6272 of the cover 6270. After the retention matrix 6250 has been suitably positioned, the jaw 6240 can be opened and the cover 6670 and the retention matrix 6250 can detach from the jaw 6240 as illustrated in FIG. 146. As illustrated in FIG. 146, a jaw 6640 can be configured to hold more than one retention matrix 6250 and cover 6670. In at least one such embodiment, the jaw 6640 can comprise two channels 6679 which each can be configured to receive a cover 6670 therein and a retention matrix 6250 positioned thereover such that the tissue-contacting surface 6251 of each retention matrix 6250 depends downwardly from the bottom of the jaw 6240. In at least one such embodiment, a retention matrix 6250 and a cover 6270 can be housed in the jaw 6640 on each side of a knife slot 6678. In use, both retention matrices 6250 and covers 6670 can be deployed simultaneously and/or to the same depth with respect to opposing staple cartridges, such as cartridges 6200, for example, positioned thereacross. Thereafter, in various embodiments, the fastened tissue can be incised along a cutting line by a cutting member that traverses the knife slot 6678 wherein the jaw 6640 can then be re-opened. In certain embodiments, the covers 6670 may not be attached to the retention matrix 6250. In at least one such embodiment, the covers 6670 can be positioned in the channels 6679 and can be retained in the channels 6679 by the retention matrices 6250 which can be secured to the jaw 6640. In various embodiments, the each retention matrix 6250 can be wider and/or longer than their respective covers 6670 such that the retention matrices 6250 can retain the entirety of their covers 6670 in position. In certain embodiments, each retention matrix 6250 can comprise the same width and/or length as their respective cover 6670, for example.

In various embodiments, as described above, a fastener system can comprise a layer of material which can be attached to a retention matrix, such as retention matrix 6250, for example. In at least one embodiment, referring now to FIG. 150, a layer of material 6870 can be attached to the bottom surface 6251 of the retention matrix 6250. In certain embodiments, the layer 6870 and/or the retention matrix 6250 can comprise retention features which can be configured to retain the layer 6870 to the retention matrix 6250. In at least one embodiment, at least one adhesive can be utilized to adhere the layer 6870 to the retention matrix 6250. In any event, the layer 6870 can comprise a bottom, or tissue-contacting, surface 6873 which can be configured to contact the tissue T when the retention matrix 6250 is moved downwardly toward the staples 6220 to engage the retention apertures 6252 with the staple legs 6221. In at least one such embodiment, the layer 6870 can be comprised of a compressible material, such as a bioabsorbable foam, for example, which can be compressed between the bottom surface 6251 of the retention matrix 6250 and the tissue T. In various embodiments, the layer 6870 can further comprise at least one medicament stored and/or absorbed therein which can be expressed from the layer 6870 as the layer 6870 is compressed. In at least one embodiment, the medicament can comprise at least one tissue sealant, haemostatic agent, and/or anti-microbial material, such as ionized silver and/or triclosan, for example. In various embodiments, the compression of the layer 6870 can squeeze the medicament from the layer 6870 such that the entirety of, or at least a significant portion of, the surface of the tissue T is covered with the medicament. Furthermore, as the layer 6870 is compressed and the staple legs 6221 penetrate the tissue T and the layer 6870, the medicament can flow down the staple legs 6221 and treat the tissue that has just been incised by the staple legs 6221, for example. In various embodiments, the body of the retention matrix 6250 can comprise a first layer which is comprised of a biocompatible material, such as titanium and/or stainless steel, for example, and the bottom layer 6870 can comprise a second layer comprised of a bioabsorbable material, such as oxidized regenerated cellulose (ORC), biologically active agents like fibrin and/or thrombin (either in their liquid state or freeze dried), glycerin, absorbable porcine gelatin in either flue or foam configurations, and/or anti-microbials, such as ionized silver and/or triclosan, for example. Additional bioabsorbable materials can comprise Surgicel Nu-Knit, Surgicel Fibrillar, collagen/ORC which is a hybrid with a built in collagen matrix and is marketed under the trade name Promogran, polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. Although only one layer 6870 is illustrated in FIG. 150, any suitable number of layers could be used. In at least one embodiment, a first layer comprising a first medicament could be attached to the retention matrix 6250 and a second layer comprising a second, or different, medicament could be attached to the first layer. In at least one such embodiment, a plurality of layers could be used wherein each layer can comprise a different medicament and/or a different combination of medicaments contained therein.

In various embodiments, referring now to FIG. 148, a fastener system can comprise a layer of material 6770 attached to the bottom surface 6251 of the retention matrix 6250. In certain embodiments, the layer 6770 and/or the retention matrix 6250 can comprise retention features which can be configured to retain the layer 6770 to the retention matrix 6250. In at least one embodiment, at least one adhesive can be utilized to adhere the layer 6770 to the retention matrix 6250. In any event, the layer 6770 can comprise a bottom, or tissue-contacting, surface 6773 which can be configured to contact the tissue T when the retention matrix 6250 is moved downwardly toward the staples 6220 to engage the retention apertures 6252 with the staple legs 6221. In at least one such embodiment, the layer 6770 can be comprised of a compressible material, such as a bioabsorbable foam, for example, which can be compressed between the surface 6251 of the retention matrix 6250 and the tissue T. In various embodiments, the layer 6770 can further comprise one or more encapsulations, or cells, 6774 which can be configured to store at least one medicament therein. In certain embodiments, referring to FIG. 149, the encapsulations 6774 can be aligned, or at least substantially aligned, with the retention apertures 6252 such that, when the staple legs 6221 are pushed through the tissue T and the layer 6770, the staple legs 6221 can puncture and/or otherwise rupture the encapsulations 6774. After the encapsulations 6774 have been ruptured, the at least one medicament M stored in the encapsulations 6774 can flow out onto the tissue T. In at least one such embodiment, the medicament M can comprise a fluid which can flow or wick down the staple legs 6221 and treat the tissue T that was just incised by the staple legs. As a result of the above, the medicament stored within the encapsulations 6774 can provide a localized treatment to the tissue. In certain embodiments, the encapsulations 6774 in the sheet 6770 can comprise different medicaments stored therein. For example, a first group of encapsulations 6774 can comprise a first medicament, or a first combination of medicaments, stored therein and a second group of encapsulations can comprise a different medicament, or a different combination of medicaments, stored therein. In various embodiments, the layer 6770 can be comprised of a flexible silicone sheet and the encapsulations 6774 can represent voids in the silicone sheet. In at least one such embodiment, the silicone sheet can comprise two layers that can be attached to one another wherein the encapsulations 6774 can be defined between the two layers. In various embodiments, the layer 6770 can comprise one or more thin sections or weakened portions, such as partial perforations, for example, which can facilitate the incision of the layer 6770 and the rupture of the encapsulations 6774 by the legs 6221. In certain embodiments, at least a portion of the encapsulations 6774 can be positioned within domes 6777, wherein the domes 6777 can extend upwardly from the sheet 6770. In at least one such embodiment, the domes 6777 and/or at least a portion of the encapsulations 6774 can be positioned within the pockets 6201 formed within the retention matrix 6250. In certain embodiments, the encapsulations 6774 may comprise discrete cells which are unconnected to each other. In certain other embodiments, one or more of the encapsulations 6774 can be in fluid communication with each other via one or more passageways, conduits, and/or channels, for example, extending through the layer 6770. The disclosure of U.S. Pat. No. 7,780,685, entitled ADHESIVE AND MECHANICAL FASTENER, which issued on Aug. 24, 2010, is hereby incorporated by reference in its entirety.

In various embodiments, further to the above, a staple cartridge comprising a cartridge body, staples, and/or an alignment matrix therein can be loaded into a first jaw of an end effector and, similarly, a retention matrix and/or one or more covers can be loaded into a second jaw of the end effector. In certain embodiments, referring now to FIG. 151, an instrument, such as cartridge loader 6990, for example, can be used to insert two or more fastener cartridges into an end effector at the same. In at least one embodiment, the cartridge loader 6990 can comprise a handle 6991 and a cartridge carrier 6992, wherein the cartridge carrier 6992 can comprise a first retention portion configured to retain the cartridge body 6210 of the staple cartridge 6200 thereto and, in addition, a second retention portion configured to retain a cartridge body 6980 which supports, one, a plurality of protective caps 6270 therein and, two, a retention matrix 6250 along the bottom surface thereof, for example. In various embodiments, the first and second retention portions can each comprise one or more retention members configured to releasably engage the cartridge bodies 6210 and 6980. In use, referring now to FIGS. 152 and 153, an end effector can comprise a first, or bottom, jaw 6230 and a second, or top, jaw 6940, wherein the staple cartridge 6200 can be loaded into the first jaw 6230 and the cartridge body 6980 can be loaded into the second jaw 6940. In various circumstances, the top jaw 6940 can be rotated from an open position (FIG. 152) to a closed position (FIG. 153) by an actuator 6235, wherein the operation of the actuator 6235 is described above and is not repeated herein for the sake of brevity. Once the top jaw 6940 is in its closed position, referring now to FIG. 153, the distal end 6993 of the cartridge carrier 6992 can be inserted into the end effector such that the staple cartridge 6200 is slid through the distal end 6938 of the first jaw 6930 and into a first attachment portion, or channel, 6939 in the first jaw 6230. Similarly, the distal end 6993 of the cartridge carrier 6992 can be inserted into the end effector such that the cartridge body 6980 is slid through the distal end 6948 of the second jaw 6940 and into a second attachment portion, or channel, 6949 in the second jaw 6940. A surgeon, or other clinician, holding the handle 6991 of the cartridge loader 6990 can push the staple cartridge 6200 and the cartridge body 6980 through the channels 6939 and 6949, respectively, until the staple cartridge 6200 and the cartridge body 6980 are fully seated therein.

As the staple cartridge 6200 and the cartridge body 6980 are being seated, the staple cartridge 6200 and the cartridge body 6980 can each engage one or more retention portions in their respective jaws 6230 and 6940, as described in greater detail further below. In any event, once the staple cartridge 6200 and the cartridge body 6980 have been seated, referring now to FIG. 154, the cartridge loader 6990 can be detached from the staple cartridge 6200 and the cartridge body 6980 and removed from the end effector. In at least one such embodiment, the retention force holding the staple cartridge 6200 in the first jaw 6230 can be greater than the retention force holding the staple cartridge 6200 to the cartridge carrier 6992 such that, as the cartridge carrier 6992 is pulled distally out of the end effector, the staple cartridge 6200 can remain behind in the first jaw 6230. Similarly, the retention force holding the cartridge body 6980 in the second jaw 6940 can be greater than the retention force holding the cartridge body 6940 to the cartridge carrier 6992 such that, as the cartridge carrier 6992 is pulled distally out of the end effector, the cartridge body 6940 can remain behind in the second jaw 6940. Once the cartridge loader 6990 has been removed from the end effector, the loaded first jaw 6230 and the loaded second jaw 6940 can be positioned relative to the tissue T that is to be stapled. Referring now to FIG. 155, the second jaw 6940 can be moved from an open position (FIG. 154) to a fired position (FIG. 155) in order to engage the retention matrix 6250 and the plurality of protective caps 6270 carried by the cartridge body 6980 with the staples 6220 positioned within the staple cartridge 6200.

Referring now to FIGS. 156 and 157, the second jaw 6940 can be re-opened and the plurality of protective caps 6270 and the retention matrix 6250 can detach from the cartridge body 6980 such that the caps 6270 and the retention matrix 6250 can remain engaged with the tissue T and the staple cartridge 6200. In at least one embodiment, the cartridge body 6980 can comprise a plurality of pockets in which the plurality of caps 6270 can be removably positioned and one or more retention slots configured to removably retain the retention matrix 6250 thereto. In various embodiments, the retention members of the second jaw 6940 engaged with the cartridge body 6980 can retain the cartridge body 6980 in the second jaw 6940 after the second jaw 6940 has been opened. In certain embodiments, the cartridge body 6980 can be configured to tear as the second jaw 6940 is opened such that a portion of the cartridge body 6980 is implanted with the caps 6270 and the retention matrix 6250 and a portion of the cartridge body 6980 remains in the second jaw 6940. Similarly, referring again to FIGS. 156 and 157, the retention members of the first jaw 6230 engaged with the cartridge body 6210 can retain the cartridge body 6210 in the first jaw 6230 after the second jaw 6940 has been opened. In certain embodiments, the cartridge body 6210 can be configured to tear as the first jaw 6230 is pulled away from the implanted cartridge 6200 such that a portion of the cartridge body 6210 is implanted with the staples 6220 and alignment matrix 6260 and a portion of the cartridge body 6210 remains in the first jaw 6230. In various embodiments, referring now to FIGS. 158-160, a staple cartridge, such as staple cartridge 6900, for example, can comprise one or more longitudinal retention slots 6913 extending along the length of the cartridge body 6910 which, when the staple cartridge 6900 is inserted into a jaw 6930, for example, can be configured to receive one or more longitudinal retention rails 6916 extending from the jaw 6930 therein. In use, in at least one embodiment, an end of the retention slots 6913 can be aligned with the distal ends of the retention rails 6916 before the staple cartridge 6900 is slid through the distal end 6938 of the retention channel 6939, for example.

In various embodiments, referring again to FIG. 160, the jaw 6940 can comprise two retention channels 6949, wherein each retention channel 6949 can be configured to receive a cartridge body 6980 comprising a plurality of caps 6270 and a retention matrix 6250 therein. In certain embodiments, each cartridge body 6980 can comprise one or more longitudinal retention shoulders 6917 which can be configured to be slid along one or more longitudinal retention rails 6918 of the second jaw 6940 as the cartridge bodies 6980 are inserted into their respective retention channels 6949 in jaw 6940. In various embodiments, the retention rails 6918 and the retention shoulders 6917 can co-operate to retain the cartridge body 6980 in the second jaw 6940 as the cartridge bodies 6980 are detached from the caps 6270 and the retention matrix 6250 stored therein. In various embodiments, referring now to FIG. 159, the second jaw 6940 can further comprise one or more distal bumps, or retention members, 6915 extending therefrom which can be configured to removably lock the cartridge bodies 6980 in their respective retention channels. In at least one such embodiment, the second jaw 6940 can comprise a distal bump 6915 configured and positioned relative to each retention channel 6949 such that each cartridge body 6980 can flex around the bumps 6915 as the cartridge bodies 6980 are being inserted into the channels 6949 wherein, just as the cartridge bodies 6915 are being fully seated in the channels 6949, the distal ends of the cartridge bodies 6980 can clear and snap over the bumps 6915. In order to remove the cartridge bodies 6980 after they have been expended, as described above, the cartridge bodies 6980 can be pulled back over the bumps 6915 and removed from the retention channels 6949. Similar to the above, the first jaw 6930 can comprise one or more distal retention bumps 6914 extending therefrom which can be configured to be received in one or more retention grooves, or slots, 6912 (FIG. 158) in the cartridge body 6910 when the staple cartridge 6900 has been fully seated.

In various embodiments, further to the above, a first fastener cartridge comprising a plurality of first fasteners positioned therein can be positioned in a first jaw of a surgical fastening device and a second fastener cartridge comprising a plurality of second fasteners positioned therein can be positioned in a second jaw of the surgical fastening device. In use, the first jaw and/or the second jaw can be moved toward the other in order to engage the first fasteners with the second fasteners and secure tissue therebetween. In certain embodiments, the first fastener cartridge and the second fastener cartridge can be engaged with each other as the first fasteners are engaged with the second fasteners. In at least one embodiment, the body of the first fastener cartridge can be comprised of a first compressible material and the body of the second fastener cartridge can be comprised of a second compressible material, wherein the first body and/or the second body can be compressed against the tissue being fastened. After the tissue has been fastened, the first jaw can be moved away from the implanted first fastener cartridge and the second jaw can be moved away from the implanted second fastener cartridge. Thereafter, the first jaw can be reloaded with another first fastener cartridge, or the like, and the second jaw can be reloaded with another second fastener cartridge, or the like, and the surgical fastening instrument can be reused. While staples can be used in some embodiments, other embodiments are envisioned comprising other types of fasteners, such as two-part fasteners which are locked together when they are engaged with one another, for example. In at least one such embodiment, the first fastener cartridge can comprise a first storage portion for storing the first fastener portions and the second fastener cartridge can comprise a second storage portion for storing the second fastener portions. In various embodiments, the fastening systems described herein can utilize fasteners comprising any suitable type of material and/or form. In certain embodiments, the fasteners can comprise penetrating members. Such penetrating members could be comprised of a polymer, a composite, and/or a multi-layered substrate, for example. An example of a multi-layered substrate could be a wire or a sheet substrate with an elastomeric or polymeric coating. It could be a thin sheet formed such that penetrating members are oriented perpendicular, or at least substantially perpendicular, to the connecting member. The penetrating members could comprise a rectangular profile, semi-circular profile, and/or any beam profile. In various embodiments, the fasteners described herein can be manufactured utilizing any suitable process, such as a wire extruding process, for example. Another possibility is the use of microfabrication to create hollow penetrating members. These penetrating members could be fabricated from a process which is different than a wire extruded process and could use a combination of materials.

As described above, the tips of staple legs protruding through a retention matrix can be covered by one or more caps and/or covers. In certain embodiments, the tips of the staple legs can be deformed after they have been inserted through the retention matrix. In at least one embodiment, a jaw holding the retention matrix can further comprise anvil pockets positioned above and/or aligned with the retention apertures which can be configured to deform the staple legs as they protrude above the retention matrix. In various embodiments, the staple legs of each staple can be curled inwardly toward each other and/or toward the center of the staple, for example. In certain other embodiments, one or more of the staple legs of a staple can be curled outwardly away from the other staple legs and/or away from the center of the staple. In various embodiments, regardless of the direction in which the staple legs are curled, the tips of the staple legs can contact the body of the retention matrix and may not re-enter the tissue that has been fastened by the staples. In at least one embodiment, the deformation of the staple legs after they have passed through the retention matrix can lock the retention matrix in position.

In various embodiments, referring now to FIGS. 161 and 162, a surgical stapling instrument, such as surgical stapler 7000, for example, can comprise a first jaw 7030 and a second jaw 7040, wherein the second jaw 7040 can be moved toward and away from the first jaw 7030 by the movement of actuator 6235. The operation of actuator 6235 is described above and is not repeated herein for the sake of brevity. In various embodiments, the first jaw 7030 can comprise a distal end 7031 and a proximal end 7032, wherein the first jaw 7030 can define a channel extending between the distal end 7031 and the proximal end 7032 which is configured to receive a staple cartridge. For the purposes of illustration, the cartridge body of such a staple cartridge is not depicted in FIG. 161, although such a staple cartridge can comprise a cartridge body, staples 6220 positioned within the cartridge body, and staple drivers 7012 positioned underneath the staples 6220. In certain embodiments, although not illustrated in FIG. 161 for the sake of clarity, the second jaw 7040 can be configured to hold a retention matrix, such as retention matrix 6250, for example, over the staples 6220 and/or move the retention matrix into engagement with the legs of the staples 6220 as described above. In at least one embodiment, the surgical stapler 7000 can further comprise a sled 7010 positioned in the first jaw 7030 which can be slid from the distal end 7031 of the first jaw 7030 toward the proximal end 7032, for example, and lift the staple drivers 7012, and the staple 6220 supported thereon, toward the retention matrix and the second jaw 7040. In various other embodiments, the sled 7010 can be moved from the proximal end 7032 toward the distal end 7031 in order to deploy the staples 6020, for example. In at least one embodiment, the sled 7010 can comprise one or more inclined ramps, or cams, 7011 which can be configured to slide underneath the staple drivers 7012 and lift the staple drivers 7012 upwardly. In various embodiments, the surgical stapler 7000 can further comprise a pull, or push, rod operably coupled to the sled 7010 which can be moved proximally and/or distally by an actuator located on a handle and/or shaft of the surgical stapler 7000, for example.

In various embodiments, referring again to FIG. 161, the second jaw 7040 of the surgical stapler 7000 can comprise a frame 7041, a distal end 7048, and a proximal end 7049 positioned opposite the distal end 7048. In certain embodiments, the second jaw 7040 can further comprise a guide system comprising one or more guide rails, such as guide rails 7045 and 7046, for example, extending along the longitudinal axis of the frame 7041 which, as described in greater detail further below, can be configured to guide one or more anvils, or cams, which can engage and deform the staple legs of the staples 6220 after the staple legs 6221 of the staples 6220 have passed through the retention matrix. In at least one such embodiment, the guide rails 7045 and 7046 can comprise a guide wire or cable which extends along a top portion or surface of the frame 7041, around a distal post 7047, and back along the top portion or surface of the frame 7041, for example. In various embodiments, as mentioned above and referring primarily now to FIGS. 163 and 165, the second jaw 7040 can further comprise one or more anvils, or cams, such as first anvil 7050 and second anvil 7060, for example, which can be moved longitudinally along the second jaw 7040 in order to deform the legs of the staples 6220 after they have passed through the retention matrix. In at least one embodiment, the surgical stapler 7000 can further comprise a first anvil driver, or actuator, 7051 connected to and/or operably coupled to the first anvil 7050 which can be configured to pull the first anvil 7050 proximally and/or push the first anvil 7050 distally. Similarly, in at least one embodiment, the surgical stapler 7000 can further comprise a second anvil driver, or actuator, connected to and/or operably coupled to the second anvil 7060 which can be configured to push the second anvil 7060 distally and/or pull the second anvil 7060 proximally. In various embodiments, the first anvil 7050 can comprise guide slots 7052 and the second anvil 7060 can comprise guide slots 7062 which can each be configured to slidably receive guide rail 7045 or guide rail 7046 therein. In at least one such embodiment, the guide rails 7045 and 7046 can be closely received within the guide slots 7052 and 7062 such that relative lateral, or side-to-side, movement therebetween can be prevented, or at least limited.

In certain embodiments, further to the above, the first anvil 7050 can be pulled proximally and the second anvil 7060 can be pulled distally. In at least one embodiment, referring to FIG. 161, the guide rails 7045 and 7046 and the distal post 7047 can comprise a pulley system configured to pull the second anvil 7060 distally and/or pull the second anvil 7060 proximally. In at least one such embodiment, the guide rail 7045 and the guide rail 7046 can comprise a continuous wire or cable extending around the distal post 7047, wherein a portion of the continuous wire can be pulled in order to cycle the wire around the distal post 7047. In various embodiments, the guide rail 7046, for example, can be mounted to the second anvil 7060 such that, when the continuous cable is cycled in a first direction, the second anvil 7060 can be pulled distally toward the distal end 7048 of the jaw 7040 and, when the continuous cable is cycled in a second, or opposite, direction, the second anvil 7060 can be pulled proximally toward the proximal end 7049. In at least one embodiment, referring now to FIG. 163, the guide rail 7046 can be secured within a guide slot 7062 such that a pulling force can be transmitted therebetween. In at least one such embodiment, the guide rail 7045 can be configured to slide within the other guide slot 7062. In various embodiments, the first anvil 7050 may operate independently of the second anvil 7060 and the pulley system and the guide slots 7052 defined in the first anvil 7050 may be configured to slidably receive the guide rails 7045 and 7046 such that relative movement is permitted therebetween. In various embodiments, the continuous cable comprising guide rails 7045 and 7046 can be sufficiently flexible in order to accommodate the opening and closing of the top jaw 7040. The continuous cable can also be sufficiently flexible in order to accommodate the vertical movement of the second anvil 7060 toward and away from the bottom jaw 7030, which is described in greater detail further below.

In various embodiments, referring again to FIGS. 163 and 165, the first anvil 7050 can comprise cam followers 7055 extending therefrom which can be configured to ride in one or more cam slots, or guide slots, such as cam slot 7070 (FIG. 166), for example, defined in the frame 7041 of the second jaw 7040. More particularly, in at least one embodiment, the frame 7041 can comprise a first cam slot 7070 extending longitudinally along a first side of the frame 7041 and a second cam 7070 extending longitudinally along a second, or opposite, side of the frame 7041, wherein the cam followers 7055 extending from a first side of the first anvil 7050 can ride in the first cam slot 7070 and the cam followers 7055 extending from a second side of the first anvil 7050 can ride in the second cam slot 7070. In at least one such embodiment, the contours of each cam slot 7070 can be identical, or at least substantially identical, and can be aligned, or at least substantially aligned, with one another. Similarly, in various embodiments, the second anvil 7060 can comprise cam followers 7065 extending therefrom which can be configured to ride in the cam slots 7070 (FIG. 166) defined in the frame 7041 of the second jaw 7040. More particularly, in at least one embodiment, the cam followers 7065 extending from a first side of the second anvil 7060 can ride in the first cam slot 7070 and the cam followers 7065 extending from a second side of the second anvil 7060 can ride in the second cam slot 7070. In use, the cam followers 7055 of the first anvil 7050 and the cam followers 7065 of the second anvil 7060 can slide within the cam slots 7070 such that first anvil 7050 and the second anvil 7060 follow the contours of the cam slots 7070 as the first anvil 7050 and the second anvil 7060 are pulled proximally and/or pushed distally. In various embodiments, each cam slot 7070 can comprise a plurality of dwell, or upper, portions 7071 and a plurality of driver, or lower, portions 7072 which can be configured to move the anvils 7050 and 7060 vertically, i.e., toward and away from the bottom jaw 7030, at the same time that the anvils 7050 and 7060 are being moved longitudinally, i.e., between the distal end 7048 and the proximal end 7049 of the frame 7041, as described in greater detail further below.

When the surgical stapler 7000 is in an unfired condition, referring to FIG. 166, the first anvil 7050 can be positioned at the distal end 7048 of the frame 7041 and the second anvil 7060 can be positioned at the proximal end 7049 of the frame 7041; furthermore, referring now to FIG. 167, the staples 6220 positioned in the first jaw 7030 may not yet be inserted into the tissue T and/or the retention matrix positioned thereabove when the surgical stapler 7000 is in an unfired condition. In use, referring now to FIG. 168, the staples 6220 can be driven upwardly within the staple cavities 7033 of a staple cartridge by the staple drivers 7012 and, in addition, the first anvil 7050 can be moved proximally from the distal end 7048 of the frame 7041 toward the distal end 7049 in order to engage the staple legs 6221 of the staples 6220. In at least one embodiment, the staples 6220 can be driven upwardly before the first anvil 7050 is engaged with the staple legs 6221 thereof. In various embodiments, all of the staples 6220 may be deployed upwardly by the sled 7010 before the first anvil 7050 is advanced into contact with the staple legs 6221 or, alternatively, the sled 7010 may be moved proximally at the same time that the first anvil 7050 is moved proximally, although the sled 7010 may sufficiently lead the first anvil 7050 in order to deploy the staples 6220 ahead of the first anvil 7050. In various embodiments, as illustrated in FIG. 168, the cam slots 7070 can be configured and arranged such that the forming surfaces, such as forming, or camming, surfaces 7053 and 7054, for example, of the first cam 7050 can contact at least some of the staple legs 6221 when the first cam 7050 is passing through a dwell, or upper, position. In various circumstances, the cam followers 7055 of the first anvil 7050 can each be positioned in a dwell portion 7071 of the cam slots

7070 such that the forming surfaces 7053 and 7054 are in a raised position and such that the staple legs 6221 are only partially deformed when the anvil 7050 passes thereby in the dwell position. As the first cam 7050 is moved further along the cam slots 7070, as illustrated in FIG. 169, the cam followers 7055 of the first anvil 7050 can be driven into driven, or lower, portions 7072 of the cam slots 7070 such that the forming surfaces 7053 and 7054 are moved vertically downwardly toward the staple legs 6021 in order to drive the staple legs 6021 into their finally formed configurations. Thereafter, as the first anvil 7050 is progressed further along the cam slots 7070, the first anvil 7050 can be driven vertically upwardly into another set of dwell portions 7071 of the cam slots 7070. As illustrated in FIGS. 168 and 169, the reader will note that the first anvil 7050 may only engage some of the staple legs and not others. In at least one such embodiment, the first anvil 7050 can be configured to only deform a group of staple legs comprising the distal staple legs 6221 of the staples 6220, for example. In at least one such embodiment, the first anvil 7050 can be configured to deform the distal staple legs 6221 toward the center of the staples 6220. In various embodiments, each proximal staple leg 6221 can be contacted twice by the first anvil 7050, i.e., by a first forming surface 7053 and by a second forming surface 7054 aligned with the first forming surface 7053. In at least one such embodiment, the first forming surfaces 7053 can deform the distal staple legs 6221 into a partially-deformed configuration when the first anvil 7050 is in a dwell, or upper, position and the second forming surfaces 7054 can deform the distal staple legs 6221 into a fully-formed configuration when the first anvil 7050 is moved into a driven, or lower, position. In various embodiments, referring now to FIGS. 163 and 164, the first anvil 7050 can comprise a plurality of first forming surfaces 7053 and a plurality of second forming surfaces 7054 in order to deform the distal staple legs 6221 of staples 6220 when the staple legs 6221 are arranged in more than one row or line. In various embodiments, as described in greater detail further below, the proximal staple legs 6221 of the staples 6020 can be deformed by the second anvil 7060, for example.

In various embodiments, further to the above, the first anvil 7050 can be moved from the distal end 7048 of the frame 7041 to the proximal end 7049 in order to deform all of the distal staple legs 6221 of the staples 6220. As the reader will note, the first anvil 7050 can be moved up and down relative to the undeformed proximal staple legs 6221 and, in order to accommodate such relative movement, in various embodiments, the first anvil 7050 can comprise one or more clearance slots 7057 (FIG. 165) which can be configured to receive the unbent proximal staple legs 6221 as the first anvil 7050 bends the distal staple legs 6221. Similarly, referring again to FIG. 163, the second anvil 7060 can comprise a clearance slot 7067 which can be configured to accommodate the vertical movement of the first cam actuator 7051 which moves up and down as the first anvil 7050 is moved between its dwell and driven positions as described above. After all of the distal staple legs 6221 have been bent, in at least one embodiment, the second anvil 7060 can be moved from the proximal end 7049 of the frame 7041 to the distal end 7048 by the anvil actuator 7061. Similar to the above, referring now to FIG. 170, the cam followers 7065 of the second anvil 7060 can slide within the cam slots 7070 such that the second anvil 7060 is moved between dwell, or upper, positions and driven, or lower, positions in order to deform the proximal staple legs 6221 inwardly toward the centers of the staples 6220, for example. Similar to the above, the second anvil 7060 can comprise a plurality of first forming, or camming, surfaces 7063 and a plurality of second forming, or camming, surfaces 7064 which can each be configured to at least partially deform and/or completely deform one or more of the proximal staple legs 6021. Referring again to FIG. 164, the second anvil 7060 can comprise a plurality of first forming surface 7063 and a plurality of second forming surfaces 7064 which can be configured to deform the proximal staple legs 6221 of staples 6220 arranged in a plurality of rows, or lines, for example. As also illustrated in FIG. 164, the first forming surfaces 7063 and the second forming surfaces 7064 of the second anvil 7060 may not be aligned with the first forming surfaces 7053 and the second forming surfaces 7054 of the first anvil 7050 wherein, as a result, the proximal legs 6221 of the staples 6220 may be positioned in different rows, or lines, than the distal legs 6221 of the staples 6220. As the reader will also note, the second anvil 7060 can push the first anvil 7050 as the second anvil 7060 is moved distally. In at least one such embodiment, the second anvil 7060 can push the first anvil 7050 back into the distal end 7048 of the frame 7041 such that the first anvil 7050 can be returned to its initial, or unfired, position. After all of the proximal staple legs 6221 of the staples 6220 have been deformed, the second anvil 7060 can be retracted proximally and returned to its initial, or unfired, position. In this way, the surgical stapler 7000 can be reset such that a new staple cartridge can be positioned in the first jaw 7030 and a new retention matrix can be positioned in the second jaw 7040 in order to use the surgical stapler 7000 once again.

In various embodiments, as described above, a surgical stapler can comprise two or more anvils which can travel longitudinally in order to engage the legs of a plurality of staples in a transverse direction. In certain embodiments, a surgical stapler can comprise an anvil which is moved proximally, for example, in order to deform a first group of staple legs and distally, for example, in order to deform a second group of staple legs. In at least one such embodiment, such an anvil can comprise forming surfaces facing proximally and forming surfaces facing distally, for example.

In various embodiments, referring now to FIG. 171, an anvil, such as anvil 7140, for example, can comprise a bottom, or tissue-contacting, surface 7141 and a plurality of forming pockets 7142 defined therein. In at least one embodiment, the anvil 7140 can comprise more than one plate, such as pocket plates 7143, for example, which can be welded into a frame 7144. In at least one such embodiment, each pocket plate 7143 can be positioned in a plate channel 7145 in the frame 7144 and welded to the frame 7144 through a weld slot 7146 extending through the frame 7144 in order to form a longitudinal weld 7147. In various circumstances, the longitudinal weld 7147 can comprise a continuous weld extending along the entire length of the weld slot 7146 or a series of spaced-apart spot welds extending along the length thereof, for example. In various embodiments, each pocket plate 7143 can comprise two or more plate portions that have been welded together. In at least one such embodiment, each pocket plate 7143 can comprise a first plate portion 7143*a* and a second plate portion 7143*b* which can be welded together along a seam 7148. In various embodiments, the first plate portion 7143*a* and the second plate portion 7143*b* of each plate 7143 can be welded together before the plates 7143 are welded into the plate channels 7145 in the frame 7144. In at least one such embodiment, the first plate portion 7143*a* and the second plate portion 7143*b* can comprise co-operating profiles, such as the toothed profiles illustrated in FIG. 171, for example, which can be fitted together to form a tight seam 7148. In at least one embodiment, each plate 7143 can comprise a height of approximately 0.02", for example, which can be taller than the depth of the plate channels 7145 such that the tissue-contacting surfaces 7141 thereof extend from the frame 7044 of the anvil 7040. In certain embodiments, referring now to FIG. 172, the plates 7143 can be connected together by at least one weld 7149 at the distal ends of the plates 7143, for example.

As illustrated in FIGS. 171 and 172, each pocket plate 7143 can comprise a plurality of forming pockets 7142 defined therein. In various embodiments, the forming pockets 7142 can be formed in the plates 7143 by any suitable manufacturing process, such as a grinding process and/or electrode-burning process, for example. In at least one such embodiment, referring now to FIGS. 173 and 174, each forming pocket 7142 can be manufactured by first forming a deep well 7150, then forming an arcuate or curved surface 7151 surrounding the deep well 7150, and then forming a staple leg guide groove 7152 in the curved surface 7151, for example. In various other embodiments, these steps can be performed in any suitable order. In various embodiments, referring now to FIG. 175, the staple forming pockets 7142 can be formed such that the inner edges 7153 of the forming pockets are separated by a consistent, or at least substantially consistent, gap 7154. In at least one such embodiment, the gap 7154 can be approximately 0.008", for example. Furthermore, in at least one such embodiment, the forming pockets 7142 can be positioned along two or more rows, or lines, the centerlines of which can be separated by a consistent, or at least substantially consistent, spacing 7155. In at least one such embodiment, the spacing 7155 between the centerlines can be approximately 0.035", for example. In various embodiments, referring again to FIG. 175, each forming pocket 7142 can taper between a narrow width 7156 and a wide width 7157. In at least one such embodiment, the narrow width 7156 can be approximately 0.045" and the wide width 7157 can be approximately 0.075", for example. In various embodiments, the plates 7143 can be comprised of the same material as the frame 7144. In at least one such embodiment, the plates 7143 and the frame 7144 can both be comprised of stainless steel, such as a 300 series or a 400 series stainless steel, for example, and/or titanium, for example. In various other embodiments, the plates 7143 and the frame 7144 can be comprised of different materials. In at least one such embodiment, the plates 7143 can be comprised of a ceramic material, for example, and the frame 7144 can be comprised of a stainless steel and/or titanium, for example. In various circumstances, depending on the materials used, at least one brazing process could be used to secure the plates 7143 in the frame 7144 in addition to or in lieu of the welding processes described above, for example.

In various embodiments, referring now to FIGS. 176-178, an anvil 7240 can comprise a frame 7244 and a plurality of pocket plates 7243 which can be inserted into the frame 7244. Similar to the above, each pocket plate 7243 can comprise a plurality of forming pockets 7242 defined therein. In at least one embodiment, the anvil frame 7244 can comprise retention slots 7246 defined therein which can each be configured to receive a retention rail 7247 extending from a pocket plate 7243. In order to assemble the pocket plates 7243 to the anvil frame 7244, the side walls 7245 of the anvil frame 7244 can be flexed or splayed outwardly, as illustrated in FIG. 177, in order to widen the retention slots 7246 such that each retention slot 7246 can receive a retention rail 7247 of a pocket plate 7243 therein. Once the retention rails 7247 have been positioned in the retention slots 7246, the side walls 7245 can be released, as illustrated in FIG. 178, thereby allowing the frame 7244 to resiliently contract and/or return to its unflexed state. In such circumstances, the retention slots 7246 can contract and thereby capture the retention rails 7247 therein. In certain embodiments, the retention rails 7247 and/or the retention slots 7246 can comprise one or more co-operating tapered surfaces which, after the flexed retention slots 7246 have been released, can form a taper-lock engagement which can retain the retention rails 7247 in the retention slots 7246. Similar to the above, the pocket plates 7243 can be comprised of the same material as or a different material than the frame 7244. In at least one such embodiment, the plates 7243 can be comprised of a ceramic material, for example, and the frame 7244 can be comprised of a stainless steel and/or titanium, for example. In various circumstances, depending on the materials used, at least one brazing process and/or at least one welding process, for example, could be used to secure the plates 7243 in the frame 7244.

In FIGS. 179 and 180, a surgical stapling and severing instrument 8010 can comprise an anvil 8014 which may be repeatably opened and closed about its pivotal attachment to an elongate staple channel 8016. A staple applying assembly 8012 can comprise the anvil 8014 and the channel 8016, wherein the assembly 8012 can be proximally attached to the elongate shaft 8018 forming an implement portion 8022. When the staple applying assembly 8012 is closed, or at least substantially closed, the implement portion 8022 can present a sufficiently small cross-section suitable for inserting the staple applying assembly 8012 through a trocar. In various embodiments, the assembly 8012 can be manipulated by a handle 8020 connected to the shaft 8018. The handle 8020 can comprise user controls such as a rotation knob 8030 that rotates the elongate shaft 8018 and staple applying assembly 8012 about a longitudinal axis of the shaft 8018. A closure trigger 8026, which can pivot in front of a pistol grip 8036 about a closure trigger pin 8152 (FIG. 181) engaged laterally across the handle housing 8154, can be depressed to close the staple applying assembly 8012. In various embodiments, a closure release button 8038 can be outwardly presented on the handle 8020 when the closure trigger 8026 is clamped such that the release button 8038 can be depressed to unclamp the closure trigger 8026 and open the staple applying assembly 8012, as described in greater detail below. A firing trigger 8034, which can pivot in front of the closure trigger 8026, can cause the staple applying assembly 8012 to simultaneously sever and staple tissue clamped therein. In various circumstances, as described in greater detail below, multiple firing strokes can be employed using the firing trigger 8034 to reduce the amount of force required to be applied by the surgeon's hand per stroke. In certain embodiments, the handle 8020 can comprise rotatable right and/or left indicator wheels 8040, 8041 (FIG. 181) which can indicate the firing progress. For instance, full firing travel may require three full firing strokes of firing trigger 8034 and thus the indicator wheels 8040, 8041 can rotate up to one-third of a revolution each per stroke of firing trigger 8034. As described in greater detail below, a manual firing release lever 8042 can allow the firing system to be retracted before full firing travel has been completed, if desired, and, in addition, the firing release lever 8042 can allow a surgeon, or other clinician, to retract the firing system in the event that the firing system binds and/or fails.

With reference to FIGS. 179 and 181, the elongate shaft 8018 can comprise an outer structure including a longitudinally reciprocating closure tube 8024 that pivots the anvil 8014 toward its close position in response to the proximal depression of the closure trigger 8026 of handle 8020. The elongate channel 8018 can be connected to the handle 8020 by a frame 8028 (FIG. 181) that is internal to the closure tube 8024. The frame 8028 can be rotatably engaged to the handle 8020 so that the rotation of the rotation knob 8030 (FIG. 179) can rotate the implement portion 8022. With particular reference to FIG. 181, the rotation knob 8030 can be comprised of two half-shells which can include one or more inward projections 8031 that can extend through one or more elongate side openings 8070 in the closure tube 8024 and engage the frame 8028. As a result of the above, the rotation knob 8030 and the frame 8028 can be rotated together, or synchronously, such that the rotated position of knob 8030 determines the rotated position of the implement portion 8022. In various embodiments, the longitudinal length of the longer opening 8070 is sufficiently long to allow the longitudinal closure motion, and opening motion, of the closure tube 8024. With regard to generating the closure motion of closure tube 8024, referring primarily to FIGS. 181 and 183, an upper portion 8160 of the closure trigger 8026 can push forward a closure yoke 8162 via a closure link 8164. The closure link 8164 is pivotally attached at its distal end by a closure yoke pin 8166 to the closure yoke 8162 and is pivotally attached at its proximal end by a closure link pin 8168. In various embodiments, the closure trigger 8026 can be urged to an open position by a closure trigger tension spring 8246 that is connected proximally to the upper portion 8160 of the closure trigger 8026 and a handle housing 8154 formed by right and left half shells 8156, 8158. The tension force applied by the tension spring 8246 can be overcome by a closing force applied to the closure trigger 8026 in order to advance the yoke 8162, closure link 8164, and the closure tube 8024 distally.

As the closure trigger 8026 is actuated, or depressed, as described above, the closure release button 8038 can be positioned such that the surgeon, or other clinician, can push the closure release button 8038, if desired, and allow the closure trigger 8026, and the rest of the surgical instrument, to return to an unactuated state. In various embodiments, the closure release button 8038 can be connected to a pivoting locking arm 8172 by a central lateral pivot 8173 such that motion can be transferred between the release button 8038 and the locking arm 8172. Referring again to FIG. 181, a compression spring 8174 can bias the closure release button 8038 proximally, i.e., clockwise about the central lateral pivot 8173 as viewed from the right and the upper portion 8160 of the closure trigger 8026 can include a proximal crest 8170 with an aft notch 8171. As the closure trigger 8026 is depressed, the pivoting locking arm 8172 can ride upon the proximal crest 8170 and when the closure trigger 8026 reaches its fully depressed position, it should be appreciated that the aft notch 8171 is presented below the pivoting locking arm 8172 which drops into and locks against the aft notch 8171 under the urging of the compression spring 8174. At such point, manual depression of the closure release button 8038 rotates the pivoting locking arm 8172 upward and out of aft notch 8171 thereby unlocking the closure trigger 8026 and allowing the closure trigger 8026 to be returned to its unclamped position.

Once the closure trigger 8026 is proximally clamped, as discussed above, the firing trigger 8034 can be drawn toward the pistol grip 8036 in order to advance a firing rod 8032 distally from the handle 8020. In various embodiments, the firing trigger 8034 can pivot about a firing trigger pin 8202 that laterally traverses and is engaged with the right and left half shells 8156, 8158 of the handle 8020. The firing trigger 8034, when actuated, can advance a linked transmission firing mechanism 8150. The linked transmission firing mechanism 8150 can be urged into a retracted, unfired, position by a spring 8184 that is, one, attached to the pistol grip 8036 of the handle 8020 and, two, attached to one of the links, for example, of the linked transmission firing mechanism 8150 as described in greater detail below. The spring 8184 can comprise a nonmoving end 8186 connected to the housing 8154 and a moving end 8188 connected to a proximal end 8190 of a steel band 8192. A distally-disposed end 8194 of the steel band 8192 can be attached to an attachment feature 8195 on a front link 8196*a* of a plurality of links 8196*a*-8196*d* that form a linked rack 8200. Linked rack 8200 can be flexible such that it can readily retract into the pistol grip 8036 and minimize the length of the handle 8020 and yet form a straight rigid rack assembly that may transfer a significant firing force to and/or through the firing rod 8032. As described in greater detail below, the firing trigger 8034 can be engaged with a first link 8196*a* during a first actuation of the firing trigger 8034, engaged with a second link 8196*b* during a second actuation of the firing trigger 8034, engaged with a third link 8196*c* during a third actuation of the firing trigger 8034, and engaged with a fourth link 8196*d* during a fourth actuation of the firing trigger 8034, wherein each actuation of the firing trigger 8034 can advance the linked rack 8200 distally an incremental amount. In various embodiments, further to the above, the multiple strokes of firing trigger 1034 can rotate the right and left indicator gauge wheels 1040, 1041 to indicate the distance in which the linked rack 8200 has been advanced.

Referring now to FIGS. 181 and 183, an anti-backup mechanism 8250 can prevent the combination tension/compression spring 8184 from retracting the linked rack 8200 between firing strokes. In various embodiments, a coupling slide tube 8131 abuts the first link 8196*a* and connects to the firing rod 8032 to communicate the firing motion. The firing rod 8032 extends proximally out of a proximal end of the frame 8028 and through a through hole 8408 of an anti-backup plate 8266. The through hole 8408 is sized to slidingly receive the firing rod 8032 when perpendicularly aligned but to bind when tipped. A lower tab attachment 8271 extends proximally from a lower lip of the proximal end of the frame 8028, extending through an aperture 8269 on a lower edge of the anti-backup plate 8266. This lower tab attachment 8271 draws the lower portion of the anti-backup plate 8266 proximate to the frame 8028 so that the anti-backup plate 8266 is perpendicular when the firing rod 8032 is distally advanced and allowed to tip top aft into a binding state when the firing rod 8032 attempts to retract. An anti-backup compression spring 8264 is distally constrained by the proximal end of the frame 8028 and proximally abuts a top portion of the anti-backup plate 8266, biasing the anti-backup plate 8266 to a locking state. Opposing the spring bias, an anti-backup cam tube 8268 slidingly encompasses the coupling slide tube 8131 and abuts the anti-backup plate 8266. A proximally projecting anti-backup yoke 8256 attached to the anti-backup cam tube 8268 extends overtop of the closure yoke 8162.

Referring to FIG. 181, a link triggered automatic retraction mechanism 8289 is incorporated into the surgical stapling and severing instrument 8010 to cause knife retraction at the end of full firing travel. To that end, the distal link 8196*d* includes a tang 8290 that projects upwardly when the distal link 8196*d* is advanced into rack channel 8291 (FIG. 181) formed in the closure yoke 8162. This tang 8290 is aligned to activate a bottom proximal cam 8292 on an anti-backup release lever 8248 (FIG. 186). With particular reference to FIGS. 186 and 187, structures formed in the right and left half shells 8156, 8158 constrain movement of the anti-backup release lever 8248. A pin receptacle 8296 and circular pin 8293 formed respectively between right and left half shells 8156, 8158 is received through a longitudinally elongate aperture 8294 formed in the anti-backup release lever 8248 distal to the bottom proximal cam 8292, thus allowing longitudinal translation as well as rotation about the circular pin 8293. In the right half shell 8156, a proximally open channel 8295 includes a proximal horizontal portion 8295*a* that communicates with an upwardly and distally angled portion 8295*b* that receives a rightward aft pin 8297 (FIG. 187) near the proximal end of the anti-backup release lever 8248, thus imparting an upward rotation as the anti-backup release lever 8248 reaches the distal most portion of its translation. A blocking structure formed in the right half shell 8156 proximal to the anti-backup release lever 8248 prevents proximal movement thereof once assembled to maintain rightward aft pin 8297 in the proximally open channel 8295.

Further to the above, as depicted in FIGS. 187 and 188, a distal end 8254 of the anti-backup release lever 8248 thus is urged distally and downwardly, causing a rightward front pin 8298 to drop into distally open step structure 8299 formed in the right half shell 8156, which is urged into this engagement by a compression spring 8300 (FIG. 188) hooked to a leftward hook 8301 on the anti-backup release lever 8248 between the rightward front pin 8298 and the longitudinally elongate aperture 8294. The other end of the compression spring 8300 is attached to a hook 8302 (FIGS. 186, 188, 189) formed in the right half shell 8156 in a more proximal and lower position just above the closure yoke 8266. The compression spring 8300 thus pulls the distal end 8254 of the anti-backup release lever 8248 down and aft, which results in the rightward front pin 8298 locking into the distally open step structure 8299 when distally advanced. Thus, once tripped, referring to FIG. 189, the anti-backup release lever 8248 remains forward holding the anti-backup plate 8266 perpendicularly and thus allowing the linked rack 8200 to be retracted. When the closure yoke 8266 is subsequently retracted when unclamping the end effector 8012, an upwardly projecting reset tang 8303 on the closure yoke 8266 contacts a bottom distal cam 8305 of the anti-backup release lever 8248, lifting the rightward front pin 8298 out of the distally open step structure 8299 so that the anti-backup compression spring 8264 can proximally push the anti-backup cam tube 8268 and the anti-backup release lever 8248 to their retracted positions (FIG. 186).

In various embodiments, referring to FIGS. 179 and 189, the firing trigger 8034 can be operably engaged to the linked rack 8200 in any suitable manner. With particular reference to FIGS. 180 and 185, the firing trigger 8034 pivots about a firing trigger pin 8202 that is connected to the housing 8154. An upper portion 8204 of the firing trigger 8034 moves distally about the firing trigger pin 8202 as the firing trigger 8034 is depressed towards pistol grip 8036, stretching a proximally placed firing trigger tension spring 8206 (FIG. 181) proximally connected between the upper portion 8204 of the firing trigger 8034 and the housing 8154. The upper portion 8204 of the firing trigger 8034 engages the linked rack 8200 during each firing trigger depression via a spring biased side pawl mechanism 8210. When the firing trigger is released, the side pawl mechanism is disengaged from the linked rack 8200 and the firing trigger can be returned to an undepressed, or unfired, position. In use, a ramped right-side track formed by a proximally and rightwardly facing beveled surface 8284 in each of the links 8196*a*-8196*d* is engaged by a side pawl assembly 8285. In particular, a pawl slide 8270 (FIGS. 181 and 183) has right and left lower guides 8272 that slide respectively in a left track 8274 (FIG. 181) formed in the closure yoke 8266 below the rack channel 8291 and a right track 8275 in a closure yoke rail 8276 that parallels rack channel 8291 and is attached to a rack channel cover 8277 that closes a rightwardly open portion of the rack channel 8291 in the closure yoke 8266 that is distal to the travel of the pawl slide 8270. In FIGS. 181, 182, and 185, a compression spring 8278 is attached between a hook 8279 on a top proximal position on the closure yoke rail 8276 and a hook 8280 on a distal right-side of the pawl slide 8270, which keeps the pawl slide 8270 drawn proximally into contact with the upper portion 8204 of the firing trigger 8034.

With particular reference to FIG. 181, a pawl block 8318 sits on the pawl slide 8270 pivoting about a vertical aft pin 8320 that passes through a left proximal corner of pawl block 8318 and pawl slide 8270. A kick-out block recess 8322 is formed on a distal portion of a top surface of the block 8318 to receive a kick-out block 8324 pivotally pinned therein by a vertical pin 8326 whose bottom tip extends into a pawl spring recess 8328 on a top surface of the pawl slide 8270. A pawl spring 8330 in the pawl spring recess 8328 extends to the right of the vertical front pin 8326 urging the pawl block 8318 to rotate counterclockwise when viewed from above into engagement with the ramped right-side track 8282. A small coil spring 8332 in the kick-out block recess 8322 urges the kick-out block 8324 to rotate clockwise when viewed from above, its proximal end urged into contact with a contoured lip 8334 formed in the closure yoke 8266 above the rack channel 8291. As shown in FIG. 184, the stronger mechanical advantage of the pawl spring 8330 over the small coil spring 8332 means that the pawl block 8318 tends toward engagement with the kick-out block 8324 rotated clockwise. In FIG. 185, as the firing trigger 8034 is fully depressed and begins to be release, the kick-out block 8324 encounters a ridge 8336 in the contoured lip 8334 as the pawl slide 8270 retracts, forcing the kick-out block 8324 to rotate clockwise when viewed from above and thereby kicking out the pawl block 8318 from engagement with the linked rack 8200. The shape of the kick-out block recess 8322 stops the clockwise rotation of the kick-out block 8324 to a perpendicular orientation to the contoured lip 8334 maintaining this disengagement during the full retraction and thereby eliminating a ratcheting noise.

In FIGS. 181, 183, 190, and 195, the surgical stapling and severing instrument 8010 can include a manual retraction mechanism 8500 that provides for a manual release of the firing mechanism, manual retraction, and in one version (FIGS. 196-202) further performs automatic retraction at the end of full firing travel. Referring now to FIGS. 181, 190, and 191, in particular, a front idler gear 8220 is engaged with a toothed upper, left surface 8222 of the linked rack 8200 wherein the front idler gear 8220 also engages an aft idler gear 8230 having a smaller right-side ratchet gear 8231. Both the front idler gear 8220 and aft idler gear 8230 are rotatably connected to the handle housing 8154 respectively on front idler axle 8232 and aft idler axle 8234. Each end of the aft axle 8232 extend through the respective right and left housing half shells 8156, 8158 and are attached to the left and right indicator gauge wheels 8040, 8041 and, since the aft axle 8234 is free spinning in the handle housing 8154 and has a keyed engagement to the aft gear 8230, the indicator gauge wheels 8040, 8041 rotate with the aft gear 8230. The gear relationship between the linked rack 8200, idler gear 8220 and aft gear 8230 may be advantageously selected so that the toothed upper surface 8222 has tooth dimensions that are suitably strong and that the aft gear 8230 makes no more than one revolution during the full firing travel of the linked transmission firing mechanism 8150. In addition to gear mechanism 8502 visually indicating the firing travel, or progress, the gear mechanism 8502 can also be used to manual retract the knife. In various embodiments, the smaller right-side ratchet gear 8231 of the aft idler gear 8230 extends into a hub 8506 of the manual retraction lever 8042, specifically aligned with a vertical longitudinally-aligned slot 8508 (FIG. 190) bisecting the hub 8506. A lateral through hole 8510 of the hub 8506 communicates with an upper recess 8512. A front portion 8514 is shaped to receive a proximally directed locking pawl 8516 that pivots about a rightward lateral pin 8518 formed in a distal end of the upper recess 8512. An aft portion 8520 is shaped to receive an L-shaped spring tab 8522 that urges the locking pawl 8516 downward into engagement with the right-side smaller ratchet gear 8231. A hold-up structure 8524 (FIGS. 186 and 193) projects from the right half shell 8156 into the upper recess 8512 holding up the locking pawl 8516 from engaging the smaller right-side ratchet gear 8231 when the manual retraction lever 8042 is down (FIG. 193). A coil spring 8525 (FIG. 181) urges the manual retraction lever 8042 down.

In use, as depicted in FIGS. 192 and 193, the combination tension/compression spring 8184 may become disconnected with the linked rack distally positioned. In FIGS. 194 and 195, as the manual retraction lever 8042 is raised, the locking pawl 8516 rotates clockwise and no longer is held up by the hold-up structure 8524 and engages the smaller right-side ratcheting gear 8231, rotating the aft idler gear 8230 clockwise when viewed from the left. Thus, the forward idler gear 8220 responds counterclockwise retracting the linked rack 8200. In addition, a rightward curved ridge 8510 projects out from the hub 8506, sized to contact and distally move the anti-backup release lever 8248 to release the anti-backup mechanism 8250 as the manual retraction lever 8042 is rotated.

In FIGS. 196-202, an automatic retraction mechanism 8600 for a surgical stapling and severing instrument 8010*a* can incorporate automatic retraction at the end of full firing travel into a front idler gear 8220*a* having a tooth 8602 that moves within a circular groove 8604 in a cam wheel 8606 until encountering a blockage 8608 after nearly a full rotation corresponding to three firing strokes. In such circumstances, rightward ridge 8610 is rotated upward into contact a bottom cam recess 8612 to distally move an anti-backup release lever 8248*a*. With particular reference to FIG. 197, the anti-backup release lever 8248*a* includes the distal end 8254 that operates as previously described. The circular pin 8293 and pin receptacle 8296 formed between right and left half shells 8156, 8158 is received through a generally rectangular aperture 8294*a* formed in the anti-backup release lever 8248*a* aft of the bottom cam 8192, thus allowing longitudinal translation as well as downward locking motion of the distal end 8254 of the anti-backup release lever 8248*a*. In the right half shell 8156, a horizontal proximally open channel 8295*a* receives the rightward aft pin 8297 near the proximal end of the anti-backup release lever 8248*a*.

In operation, before firing in FIGS. 198, 198A, the linked rack 8200 and the anti-backup cam tube 8268 are in a retracted position, locking the anti-backup mechanism 8250 as the anti-backup compression spring 8264 proximally tips the anti-backup plate 8266. The automatic retraction mechanism 8600 is at an initial state with the anti-backup release lever 8248*a* retracted with link 8196*a* in contact with the forward idler gear 8220*a*. The tooth 8602 is at a six o'clock position with full travel of the circular groove 8604 progressing counterclockwise thereof with the rightward ridge 8610 just proximal to the tooth 8602. In FIGS. 199, 199A, one firing stroke has occurred moving up one distal link 8196*b* into contact with the forward idler gear 8220*a*. The tooth 8602 has progressed one third of a turn through the circular groove 8604 of the immobile cam wheel 8606. In FIGS. 200, 200A, a second firing stroke has occurred moving up one more link 8196*c* into contact with the forward idler gear 8220*a*. The tooth 8602 has progressed two thirds of a turn through the circular groove 8604 of the immobile cam wheel 8606. In FIGS. 201, 201A, a third firing stroke has occurred moving up one distal link 8196*d* into contact with the forward idler gear 8220*a*. The tooth 8602 has progressed fully around the circular groove 8604 into contact with the blockage 8608 initiating counterclockwise rotation (when viewed from the right) of the cam wheel 8606 bringing the rightward ridge 8608 into contact with the anti-backup release lever 8248*a*. In FIG. 202, the anti-backup release lever 8248*a* has moved distally in response thereto, locking the rightward front pin 8298 into the distally open step structure 8299 and releasing the anti-backup mechanism 8250. Similar surgical stapling instruments are disclosed in U.S. Pat. No. 7,083,075, which issued on Aug. 1, 2006, the entire disclosure of which is incorporated by reference herein.

Referring to FIG. 203, the staple applying assembly 9012 of a surgical stapling instrument 9010 accomplishes the functions of clamping onto tissue, driving staples and severing tissue by two distinct motions transferred longitudinally down the shaft 9016 relative to a shaft frame 9070. This shaft frame 9070 is proximally attached to a handle of a surgical stapling instrument and is coupled thereto for rotation about a longitudinal axis. An illustrative multistroke handle for the surgical stapling and severing instrument is described in greater detail in commonly-owned U.S. Patent Application entitled SURGICAL STAPLING INSTRUMENT INCORPORATING A MULTISTROKE FIRING POSITION INDICATOR AND RETRACTION MECHANISM, Ser. No. 10/674,026, now U.S. Pat. No. 7,364,061, the disclosure of which is hereby incorporated by reference in its entirety. Other applications consistent with the present invention may incorporate a single firing stroke, such as described in commonly owned U.S. Patent Application SURGICAL STAPLING INSTRUMENT HAVING SEPARATE DISTINCT CLOSING AND FIRING SYSTEMS, Ser. No. 10/441,632, now U.S. Pat. No. 7,000,818, the disclosure of which is hereby incorporated by reference in its entirety.

With particular reference to FIG. 204, the distal end of the shaft frame 9070 is attached to the staple channel 9018. The anvil 9022 has a proximal pivoting end 9072 that is pivotally received within a proximal end 9074 of the staple channel 9018, just distal to its engagement to the shaft frame 9070. When the anvil 9022 is pivoted downwardly, the anvil 9022 moves a tissue contacting surface 9028 and forming pockets 9026 toward an opposing staple cartridge, described in greater detail further below. The pivoting end 9072 of the anvil 9022 includes a closure feature 9076 proximate but distal to its pivotal attachment with the staple channel 9018. Thus, a closure tube 9078, whose distal end includes a horseshoe aperture 9080 that engages this closure feature 9076, selectively imparts an opening motion to the anvil 9022 during proximal longitudinal motion and a closing motion to the anvil 9022 during distal longitudinal motion of the closure tube 9078 sliding over the shaft frame 9070 in response to a closure trigger, similar to the above. The shaft frame 9070 encompasses and guides a firing motion from the handle through a longitudinally reciprocating, two-piece knife and firing bar 9090. In particular, the shaft frame 9070 includes a longitudinal firing bar slot 9092 that receives a proximal portion of the two-piece knife and firing bar 9090, specifically a laminate tapered firing bar 9094. It should be appreciated that the laminated tapered firing bar 9094 may be substituted with a solid firing bar and/or any other suitable materials.

An E-beam 9102 is the distal portion of the two-piece knife and firing bar 9090, which facilitates separate closure and firing as well as spacing of the anvil 9022 from the elongate staple channel 9018 during firing. With particular reference to FIGS. 204 and 205, in addition to any attachment treatment such as brazing or an adhesive, the knife and firing bar 9090 are formed of a female vertical attachment aperture 9104 proximally formed in the E-beam 9102 that receives a corresponding male attachment member 9106 distally presented by the laminated tapered firing bar 9094, allowing each portion to be formed of a selected material and process suitable for their disparate functions (e.g., strength, flexibility, friction). The E-beam 9102 may be advantageously formed of a material having suitable material properties for forming a pair of top pins 9110, a pair of middle pins 9112 and a bottom pin or foot 9114, as well as being able to acquire a sharp cutting edge 9116. In addition, integrally formed and proximally projecting top guide 9118 and middle guide 9120 bracketing each vertical end of the cutting edge 9116 further define a tissue staging area 9122 assisting in guiding tissue to the sharp cutting edge 9116 prior to being severed. The middle guide 9120 also serves to engage and fire the staple applying apparatus 9012 by abutting a stepped central member 9124 of a wedge sled 9126 (FIG. 206) that effects staple formation by the staple applying assembly 9012, as described in greater detail below. Forming these features (e.g., top pins 9110, middle pins 9112, and bottom foot 9114) integrally with the E-beam 9102 facilitates manufacturing at tighter tolerances relative to one another as compared to being assembled from a plurality of parts, ensuring desired operation during firing and/or effective interaction with various lockout features of the staple applying assembly 9012.

In FIGS. 207 and 208, the staple applying assembly 9012 is shown open, with the E-beam 9102 fully retracted. During assembly, the lower foot 9114 of the E-beam 9102 is dropped through a widened hole 9130 in the staple channel 9018 and the E-beam 9102 is then advanced such that the E-beam 9102 slides distally along a lower track 9132 formed in the staple channel 9018. In particular, the lower track 9132 includes a narrow slot 9133 that opens up as a widened slot 9134 on an undersurface of the staple channel 9018 to form an inverted T-shape in lateral cross section, as depicted particularly in FIGS. 208 and 209, which communicates with the widened hole 9130. Once assembled, the components proximally coupled to the laminate tapered firing bar 9094 do not allow the lower foot 9114 to proximally travel again to the widened hole 9130 to permit disengagement. Referring to FIG. 210, the laminate tapered firing bar 9094 facilitates insertion of the staple applying assembly 9012 through a trocar. In particular, a more distal, downward projection 9136 raises the E-beam 9102 when fully retracted. This is accomplished by placement of the downward projection 9136 at a point where it cams upwardly on a proximal edge of the widened hole 9130 in the staple channel 9018. Referring now to FIG. 211, the laminate tapered firing bar 9094 also enhances operation of certain lockout features that may be incorporated into the staple channel 9018 by including a more proximal upward projection 9138 that is urged downwardly by the shaft frame 9070 during an initial portion of the firing travel. In particular, a lateral bar 9140 is defined between a pair of square apertures 9142 in the shaft frame 9070 (FIG. 204). A clip spring 9144 that encompasses the lateral bar 9140 downwardly urges a portion of the laminate tapered firing bar 9094 projecting distally out of the longitudinal firing bar slot 9092, which ensures certain advantageous lockout features are engaged when appropriate. This urging is more pronounced or confined solely to that portion of the firing travel when the upward projection 9138 contacts the clip spring 9144.

In FIGS. 207 and 208, the E-beam 9102 is retracted with the top pins 9110 thereof residing within an anvil pocket 9150 near the pivoting proximal end of the anvil 9022. A downwardly open vertical anvil slot 9152 (FIG. 203) laterally widens in the anvil 9022 into an anvil internal track 9154 that captures the top pins 9110 of the E-beam 9102 as they distally advance during firing, as depicted in FIGS. 210 and 211, affirmatively spacing the anvil 9022 from the staple channel 9018. Thus, with the E-beam 9102 retracted, the surgeon is able to repeatably open and close the staple applying assembly 9012 until satisfied with the placement and orientation of tissue captured therein for stapling and severing, yet the E-beam 9102 assists in proper positioning of tissue even for a staple applying assembly 9012 of reduced diameter and correspondingly reduced rigidity. In FIGS. 203, 204, 206, 207, 209, and 215, the staple applying assembly 9012 is shown with the replaceable staple cartridge 9020 that includes the wedge sled 9126. Longitudinally aligned and parallel plurality of downwardly open wedge slots 9202 (FIG. 209) receive respective wedges 9204 integral to the wedge sled 9126. In FIGS. 209-211, the wedge sled 9126 thus cams upwardly a plurality of staple drivers 9206 that are vertically slidable within staple driver recesses 9208. In this illustrative version, each staple driver 9206 includes two vertical prongs, each translating upwardly into a respective staple hole 9210, or cavity 9024, to upwardly force out and deform a staple 9023 resting thereupon against a staple forming surface 9214 (FIG. 211) of the anvil 9022. A central firing recess 9216 (FIG. 204) defined within the staple cartridge 9020 proximate to the staple channel 9018 allows the passage of the bottom, horizontal portion 9218 (FIG. 206) of the wedge sled 9126 as well as the middle pins 9112 of the E-beam 9102. Specifically, a staple cartridge tray 9220 (FIGS. 204, 209) attaches to and underlies a polymer staple cartridge body 9222 that has the staple driver recesses 9208, staple holes 9210, and central firing recess 9216 formed therein. As staples 9023 are thus formed to either side, the sharp cutting edge 9116 enters a vertical through slot 9230 passing through the longitudinal axis of the staple cartridge 9020, excepting only a most distal end thereof.

Firing the staple applying assembly 9012 begins as depicted in FIG. 211 with the two-piece knife and firing bar 9090 proximally drawn until the downward projection 9136 cams the middle guide 9120 on the E-beam 9102 upward and aft, allowing a new staple cartridge 9020 to be inserted into the staple channel 9018 when the anvil 9022 is open as depicted in FIGS. 203 and 207. In FIG. 212, the two-piece knife and firing bar 9090 has been distally advanced a small distance, allowing the downward projection 9136 to drop into the widened hole 9130 of the lower track 9132 under the urging of the clip spring 9144 against the upward projection 9138 of the laminate tapered firing bar 9094. The middle guide 9120 prevents further downward rotation by resting upon the stepped central member 9124 of the wedge sled 9126, thus maintaining the middle pin 9112 of the E-beam within the central firing recess 9216. In FIG. 213, the two-piece knife and firing bar 9090 has been distally fired, advancing the wedge sled 9126 to cause formation of staples 9023 while severing tissue 9242 clamped between the anvil 9022 and staple cartridge 9020 with the sharp cutting edge 9116. Thereafter, in FIG. 214, the two-piece knife and firing bar 9090 is retracted, leaving the wedge sled 9126 distally positioned. In FIG. 215, the middle pin 9112 is allowed to translate down into a lockout recess 9240 formed in the staple channel 9018 (also see FIGS. 208, 211). Thus, the operator would receive a tactile indication as the middle pin 9112 encounters the distal edge of the lockout recess 9240 when the wedge sled 9126 (not shown in FIG. 215) is not proximally positioned (i.e., missing staple cartridge 9020 or spent staple cartridge 9020). Similar surgical stapling instruments are disclosed in U.S. Pat. No. 7,380,696, which issued on Jun. 3, 2008, the entire disclosure of which is incorporated by reference herein.

In various embodiments, as described above, a staple cartridge can comprise a cartridge body including a plurality of staple cavities defined therein. The cartridge body can comprise a deck and a top deck surface wherein each staple cavity can define an opening in the deck surface. As also described above, a staple can be positioned within each staple cavity such that the staples are stored within the cartridge body until they are ejected therefrom. Prior to being ejected from the cartridge body, in various embodiments, the staples can be contained with the cartridge body such that the staples do not protrude above the deck surface. As the staples are positioned below the deck surface, in such embodiments, the possibility of the staples becoming damaged and/or prematurely contacting the targeted tissue can be reduced. In various circumstances, the staples can be moved between an unfired position in which they do not protrude from the cartridge body and a fired position in which they have emerged from the cartridge body and can contact an anvil positioned opposite the staple cartridge. In various embodiments, the anvil, and/or the forming pockets defined within the anvil, can be positioned a predetermined distance above the deck surface such that, as the staples are being deployed from the cartridge body, the staples are deformed to a predetermined formed height. In some circumstances, the thickness of the tissue captured between the anvil and the staple cartridge may vary and, as a result, thicker tissue may be captured within certain staples while thinner tissue may be captured within certain other staples. In either event, the clamping pressure, or force, applied to the tissue by the staples may vary from staple to staple or vary between a staple on one end of a staple row and a staple on the other end of the staple row, for example. In certain circumstances, the gap between the anvil and the staple cartridge deck can be controlled such that the staples apply a certain minimum clamping pressure within each staple. In some such circumstances, however, significant variation of the clamping pressure within different staples may still exist.

In various embodiments described herein, a staple cartridge can comprise means for compensating for the thickness of the tissue captured within the staples deployed from the staple cartridge. In various embodiments, referring to FIG. 216, a staple cartridge, such as staple cartridge 10000, for example, can include a rigid first portion, such as support portion 10010, for example, and a compressible second portion, such as tissue thickness compensator 10020, for example. In at least one embodiment, referring primarily to FIG. 218, the support portion 10010 can comprise a cartridge body, a top deck surface 10011, and a plurality of staple cavities 10012 wherein, similar to the above, each staple cavity 10012 can define an opening in the deck surface 10011. A staple 10030, for example, can be removably positioned in each staple cavity 10012. In at least one such embodiment, referring primarily to FIG. 245 and as described in greater detail below, each staple 10030 can comprise a base 10031 and one or more legs 10032 extending from the base 10031. Prior to the staples 10030 being deployed, as also described in greater detail below, the bases 10031 of the staples 10030 can be supported by staple drivers positioned within the support portion 10010 and, concurrently, the legs 10032 of the staples 10030 can be at least partially contained within the staple cavities 10012. In various embodiments, the staples 10030 can be deployed between an unfired position and a fired position such that the legs 10032 move through the tissue thickness compensator 10020, penetrate through a top surface of the tissue thickness compensator 10020, penetrate the tissue T, and contact an anvil positioned opposite the staple cartridge 10000. As the legs 10032 are deformed against the anvil, the legs 10032 of each staple 10030 can capture a portion of the tissue thickness compensator 10020 and a portion of the tissue T within each staple 10030 and apply a compressive force to the tissue. Further to the above, the legs 10032 of each staple 10030 can be deformed downwardly toward the base 10031 of the staple to form a staple entrapment area 10039 in which the tissue T and the tissue thickness compensator 10020 can be captured. In various circumstances, the staple entrapment area 10039 can be defined between the inner surfaces of the deformed legs 10032 and the inner surface of the base 10031. The size of the entrapment area for a staple can depend on several factors such as the length of the legs, the diameter of the legs, the width of the base, and/or the extent in which the legs are deformed, for example.

In previous embodiments, a surgeon was often required to select the appropriate staples having the appropriate staple height for the tissue being stapled. For example, a surgeon could select tall staples for use with thick tissue and short staples for use with thin tissue. In some circumstances, however, the tissue being stapled did not have a consistent thickness and, thus, some staples were unable to achieve the desired fired configuration. For example, FIG. 250 illustrates a tall staple used in thin tissue. Referring now to FIG. 251, when a tissue thickness compensator, such as tissue thickness compensator 10020, for example, is used with thin tissue, for example, the larger staple may be formed to a desired fired configuration.

Owing to the compressibility of the tissue thickness compensator, the tissue thickness compensator can compensate for the thickness of the tissue captured within each staple. More particularly, referring now to FIGS. 245 and 246, a tissue thickness compensator, such as tissue thickness compensator 10020, for example, can consume larger and/or smaller portions of the staple entrapment area 10039 of each staple 10030 depending on the thickness and/or type of tissue contained within the staple entrapment area 10039. For example, if thinner tissue T is captured within a staple 10030, the tissue thickness compensator 10020 can consume a larger portion of the staple entrapment area 10039 as compared to circumstances where thicker tissue T is captured within the staple 10030. Correspondingly, if thicker tissue T is captured within a staple 10030, the tissue thickness compensator 10020 can consume a smaller portion of the staple entrapment area 10039 as compared to the circumstances where thinner tissue T is captured within the staple 10030. In this way, the tissue thickness compensator can compensate for thinner tissue and/or thicker tissue and assure that a compressive pressure is applied to the tissue irrespective, or at least substantially irrespective, of the tissue thickness captured within the staples. In addition to the above, the tissue thickness compensator 10020 can compensate for different types, or compressibilities, of tissues captured within different staples 10030. Referring now to FIG. 246, the tissue thickness compensator 10020 can apply a compressive force to vascular tissue T which can include vessels V and, as a result, restrict the flow of blood through the less compressible vessels V while still applying a desired compressive pressure to the surrounding tissue T. In various circumstances, further to the above, the tissue thickness compensator 10020 can also compensate for malformed staples. Referring to FIG. 247, the malformation of various staples 10030 can result in larger staple entrapment areas 10039 being defined within such staples. Owing to the resiliency of the tissue thickness compensator 10020, referring now to FIG. 248, the tissue thickness compensator 10020 positioned within malformed staples 10030 may still apply a sufficient compressive pressure to the tissue T eventhough the staple entrapment areas 10039 defined within such malformed staples 10030 may be enlarged. In various circumstances, the tissue thickness compensator 10020 located intermediate adjacent staples 10030 can be biased against the tissue T by properly-formed staples 10030 surrounding a malformed staple 10030 and, as a result, apply a compressive pressure to the tissue surrounding and/or captured within the malformed staple 10030, for example. In various circumstances, a tissue thickness compensator can compensate for different tissue densities which can arise due to calcifications, fibrous areas, and/or tissue that has been previously stapled or treated, for example.

In various embodiments, a fixed, or unchangeable, tissue gap can be defined between the support portion and the anvil and, as a result, the staples may be deformed to a predetermined height regardless of the thickness of the tissue captured within the staples. When a tissue thickness compensator is used with these embodiments, the tissue thickness compensator can adapt to the tissue captured between the anvil and the support portion staple cartridge and, owing to the resiliency of the tissue thickness compensator, the tissue thickness compensator can apply an additional compressive pressure to the tissue. Referring now to FIGS. 252-257, a staple 10030 has been formed to a predefined height H. With regard to FIG. 252, a tissue thickness compensator has not been utilized and the tissue T consumes the entirety of the staple entrapment area 10039. With regard to FIG. 259, a portion of a tissue thickness compensator 10020 has been captured within the staple 10030, compressed the tissue T, and consumed at least a portion of the staple entrapment area 10039. Referring now to FIG. 254, thin tissue T has been captured within the staple 10030. In this embodiment, the compressed tissue T has a height of approximately 2/9H and the compressed tissue thickness compensator 10020 has a height of approximately 7/9H, for example. Referring now to FIG. 255, tissue T having an intermediate thickness has been captured within the staple 10030. In this embodiment, the compressed tissue T has a height of approximately 4/9H and the compressed tissue thickness compensator 10020 has a height of approximately 5/9H, for example. Referring now to FIG. 256, tissue T having an intermediate thickness has been captured within the staple 10030. In this embodiment, the compressed tissue T has a height of approximately 2/3H and the compressed tissue thickness compensator 10020 has a height of approximately 1/3H, for example. Referring now to FIG. 255, thick tissue T has been captured within the staple 10030. In this embodiment, the compressed tissue T has a height of approximately 8/9H and the compressed tissue thickness compensator 10020 has a height of approximately 1/9H, for example. In various circumstances, the tissue thickness compensator can comprise a compressed height which comprises approximately 10% of the staple entrapment height, approximately 20% of the staple entrapment height, approximately 30% of the staple entrapment height, approximately 40% of the staple entrapment height, approximately 50% of the staple entrapment height, approximately 60% of the staple entrapment height, approximately 70% of the staple entrapment height, approximately 80% of the staple entrapment height, and/or approximately 90% of the staple entrapment height, for example.

In various embodiments, the staples 10030 can comprise any suitable unformed height. In certain embodiments, the staples 10030 can comprise an unformed height between approximately 2 mm and approximately 4.8 mm, for example. The staples 10030 can comprise an unformed height of approximately 2.0 mm, approximately 2.5 mm, approximately 3.0 mm, approximately 3.4 mm, approximately 3.5 mm, approximately 3.8 mm, approximately 4.0 mm, approximately 4.1 mm, and/or approximately 4.8 mm, for example. In various embodiments, the height H to which the staples can be deformed can be dictated by the distance between the deck surface 10011 of the support portion 10010 and the opposing anvil. In at least one embodiment, the distance between the deck surface 10011 and the tissue-contacting surface of the anvil can be approximately 0.097", for example. The height H can also be dictated by the depth of the forming pockets defined within the anvil. In at least one embodiment, the forming pockets can have a depth measured from the tissue-contacting surface, for example. In various embodiments, as described in greater detail below, the staple cartridge 10000 can further comprise staple drivers which can lift the staples 10030 toward the anvil and, in at least one embodiment, lift, or "overdrive", the staples above the deck surface 10011. In such embodiments, the height H to which the staples 10030 are formed can also be dictated by the distance in which the staples 10030 are overdriven. In at least one such embodiment, the staples 10030 can be overdriven by approximately 0.028", for example, and can result in the staples 10030 being formed to a height of approximately 0.189", for example. In various embodiments, the staples 10030 can be formed to a height of approximately 0.8 mm, approximately 1.0 mm, approximately 1.5 mm, approximately 1.8 mm, approximately 2.0 mm, and/or approximately 2.25 mm, for example. In certain embodiments, the staples can be formed to a height between approximately 2.25 mm and approximately 3.0 mm, for example. Further to the above, the height of the staple entrapment area of a staple can be determined by the formed height of the staple and the width, or diameter, of the wire comprising the staple. In various embodiments, the height of the staple entrapment area 10039 of a staple 10030 can comprise the formed height H of the staple less two diameter widths of the wire. In certain embodiments, the staple wire can comprise a diameter of approximately 0.0089", for example. In various embodiments, the staple wire can comprise a diameter between approximately 0.0069" and approximately 0.0119", for example. In at least one exemplary embodiment, the formed height H of a staple 10030 can be approximately 0.189" and the staple wire diameter can be approximately 0.0089" resulting in a staple entrapment height of approximately 0.171", for example.

In various embodiments, further to the above, the tissue thickness compensator can comprise an uncompressed, or pre-deployed, height and can be configured to deform to one of a plurality of compressed heights. In certain embodiments, the tissue thickness compensator can comprise an uncompressed height of approximately 0.125", for example. In various embodiments, the tissue thickness compensator can comprise an uncompressed height of greater than or equal to approximately 0.080", for example. In at least one embodiment, the tissue thickness compensator can comprise an uncompressed, or pre-deployed, height which is greater than the unfired height of the staples. In at least one embodiment, the uncompressed, or pre-deployed, height of the tissue thickness compensator can be approximately 10% taller, approximately 20% taller, approximately 30% taller, approximately 40% taller, approximately 50% taller, approximately 60% taller, approximately 70% taller, approximately 80% taller, approximately 90% taller, and/or approximately 100% taller than the unfired height of the staples, for example. In at least one embodiment, the uncompressed, or pre-deployed, height of the tissue thickness compensator can be up to approximately 100% taller than the unfired height of the staples, for example. In certain embodiments, the uncompressed, or pre-deployed, height of the tissue thickness compensator can be over 100% taller than the unfired height of the staples, for example. In at least one embodiment, the tissue thickness compensator can comprise an uncompressed height which is equal to the unfired height of the staples. In at least one embodiment, the tissue thickness compensator can comprise an uncompressed height which is less than the unfired height of the staples. In at least one embodiment, the uncompressed, or pre-deployed, height of the thickness compensator can be approximately 10% shorter, approximately 20% shorter, approximately 30% shorter, approximately 40% shorter, approximately 50% shorter, approximately 60% shorter, approximately 70% shorter, approximately 80% shorter, and/or approximately 90% shorter than the unfired height of the staples, for example. In various embodiments, the compressible second portion can comprise an uncompressed height which is taller than an uncompressed height of the tissue T being stapled. In certain embodiments, the tissue thickness compensator can comprise an uncompressed height which is equal to an uncompressed height of the tissue T being stapled. In various embodiments, the tissue thickness compensator can comprise an uncompressed height which is shorter than an uncompressed height of the tissue T being stapled.

As described above, a tissue thickness compensator can be compressed within a plurality of formed staples regardless of whether thick tissue or thin tissue is captured within the staples. In at least one exemplary embodiment, the staples within a staple line, or row, can be deformed such that the staple entrapment area of each staple comprises a height of approximately 2.0 mm, for example, wherein the tissue T and the tissue thickness compensator can be compressed within this height. In certain circumstances, the tissue T can comprise a compressed height of approximately 1.75 mm within the staple entrapment area while the tissue thickness compensator can comprise a compressed height of approximately 0.25 mm within the staple entrapment area, thereby totaling the approximately 2.0 mm staple entrapment area height, for example. In certain circumstances, the tissue T can comprise a compressed height of approximately 1.50 mm within the staple entrapment area while the tissue thickness compensator can comprise a compressed height of approximately 0.50 mm within the staple entrapment area, thereby totaling the approximately 2.0 mm staple entrapment area height, for example. In certain circumstances, the tissue T can comprise a compressed height of approximately 1.25 mm within the staple entrapment area while the tissue thickness compensator can comprise a compressed height of approximately 0.75 mm within the staple entrapment area, thereby totaling the approximately 2.0 mm staple entrapment area height, for example. In certain circumstances, the tissue T can comprise a compressed height of approximately 1.0 mm within the staple entrapment area while the tissue thickness compensator can comprise a compressed height of approximately 1.0 mm within the staple entrapment area, thereby totaling the approximately 2.0 mm staple entrapment area height, for example. In certain circumstances, the tissue T can comprise a compressed height of approximately 0.75 mm within the staple entrapment area while the tissue thickness compensator can comprise a compressed height of approximately 1.25 mm within the staple entrapment area, thereby totaling the approximately 2.0 mm staple entrapment area height, for example. In certain circumstances, the tissue T can comprise a compressed height of approximately 1.50 mm within the staple entrapment area while the tissue thickness compensator can comprise a compressed height of approximately 0.50 mm within the staple entrapment area, thereby totaling the approximately 2.0 mm staple entrapment area height, for example. In certain circumstances, the tissue T can comprise a compressed height of approximately 0.25 mm within the staple entrapment area while the tissue thickness compensator can comprise a compressed height of approximately 1.75 mm within the staple entrapment area, thereby totaling the approximately 2.0 mm staple entrapment area height, for example.

In various embodiments, further to the above, the tissue thickness compensator can comprise an uncompressed height which is less than the fired height of the staples. In certain embodiments, the tissue thickness compensator can comprise an uncompressed height which is equal to the fired height of the staples. In certain other embodiments, the tissue thickness compensator can comprise an uncompressed height which is taller than the fired height of the staples. In at least one such embodiment, the uncompressed height of a tissue thickness compensator can comprise a thickness which is approximately 110% of the formed staple height, approximately 120% of the formed staple height, approximately 130% of the formed staple height, approximately 140% of the formed staple height, approximately 150% of the formed staple height, approximately 160% of the formed staple height, approximately 170% of the formed staple height, approximately 180% of the formed staple height, approximately 190% of the formed staple height, and/or approximately 200% of the formed staple height, for example. In certain embodiments, the tissue thickness compensator can comprise an uncompressed height which is more than twice the fired height of the staples. In various embodiments, the tissue thickness compensator can comprise a compressed height which is from approximately 85% to approximately 150% of the formed staple height, for example. In various embodiments, as described above, the tissue thickness compensator can be compressed between an uncompressed thickness and a compressed thickness. In certain embodiments, the compressed thickness of a tissue thickness compensator can be approximately 10% of its uncompressed thickness, approximately 20% of its uncompressed thickness, approximately 30% of its uncompressed thickness, approximately 40% of its uncompressed thickness, approximately 50% of its uncompressed thickness, approximately 60% of its uncompressed thickness, approximately 70% of its uncompressed thickness, approximately 80% of its uncompressed thickness, and/or approximately 90% of its uncompressed thickness, for example. In various embodiments, the uncompressed thickness of the tissue thickness compensator can be approximately two times, approximately ten times, approximately fifty times, and/or approximately one hundred times thicker than its compressed thickness, for example. In at least one embodiment, the compressed thickness of the tissue thickness compensator can be between approximately 60% and approximately 99% of its uncompressed thickness. In at least one embodiment, the uncompressed thickness of the tissue thickness compensator can be at least 50% thicker than its compressed thickness. In at least one embodiment, the uncompressed thickness of the tissue thickness compensator can be up to one hundred times thicker than its compressed thickness. In various embodiments, the compressible second portion can be elastic, or at least partially elastic, and can bias the tissue T against the deformed legs of the staples. In at least one such embodiment, the compressible second portion can resiliently expand between the tissue T and the base of the staple in order to push the tissue T against the legs of the staple. In certain embodiments, discussed in further detail below, the tissue thickness compensator can be positioned intermediate the tissue T and the deformed staple legs. In various circumstances, as a result of the above, the tissue thickness compensator can be configured to consume any gaps within the staple entrapment area.

In various embodiments, the tissue thickness compensator may comprise materials characterized by one or more of the following properties: biocompatible, bioabsorable, bioresorbable, biodurable, biodegradable, compressible, fluid absorbable, swellable, self-expandable, bioactive, medicament, pharmaceutically active, anti-adhesion, haemostatic, antibiotic, anti-microbial, anti-viral, nutritional, adhesive, permeable, hydrophilic and/or hydrophobic, for example. In various embodiments, a surgical instrument comprising an anvil and a staple cartridge may comprise a tissue thickness compensator associated with the anvil and/or staple cartridge comprising at least one of a haemostatic agent, such as fibrin and thrombin, an antibiotic, such as doxycpl, and medicament, such as matrix metalloproteinases (MMPs).

In various embodiments, the tissue thickness compensator may comprise synthetic and/or non-synthetic materials. The tissue thickness compensator may comprise a polymeric composition comprising one or more synthetic polymers and/or one or more non-synthetic polymers. The synthetic polymer may comprise a synthetic absorbable polymer and/or a synthetic non-absorbable polymer. In various embodiments, the polymeric composition may comprise a biocompatible foam, for example. The biocompatible foam may comprise a porous, open cell foam and/or a porous, closed cell foam, for example. The biocompatible foam may have a uniform pore morphology or may have a gradient pore morphology (i.e. small pores gradually increasing in size to large pores across the thickness of the foam in one direction). In various embodiments, the polymeric composition may comprise one or more of a porous scaffold, a porous matrix, a gel matrix, a hydrogel matrix, a solution matrix, a filamentous matrix, a tubular matrix, a composite matrix, a membranous matrix, a biostable polymer, and a biodegradable polymer, and combinations thereof. For example, the tissue thickness compensator may comprise a foam reinforced by a filamentous matrix or may comprise a foam having an additional hydrogel layer that expands in the presence of bodily fluids to further provide the compression on the tissue. In various embodiments, a tissue thickness compensator could also be comprised of a coating on a material and/or a second or third layer that expands in the presence of bodily fluids to further provide the compression on the tissue. Such a layer could be a hydrogel that could be a synthetic and/or naturally derived material and could be either biodurable and/or biodegradable, for example. In various embodiments, the tissue thickness compensator may comprise a microgel or a nanogel. The hydrogel may comprise carbohydrate-derived microgels and/or nanogels. In certain embodiments, a tissue thickness compensator may be reinforced with fibrous non-woven materials or fibrous mesh type elements, for example, that can provide additional flexibility, stiffness, and/or strength. In various embodiments, a tissue thickness compensator that has a porous morphology which exhibits a gradient structure such as, for example, small pores on one surface and larger pores on the other surface. Such morphology could be more optimal for tissue in-growth or haemostatic behavior. Further, the gradient could be also compositional with a varying bio-absorption profile. A short term absorption profile may be preferred to address hemostasis while a long term absorption profile may address better tissue healing without leakages.

Examples of non-synthetic materials include, but are not limited to, lyophilized polysaccharide, glycoprotein, bovine pericardium, collagen, gelatin, fibrin, fibrinogen, elastin, proteoglycan, keratin, albumin, hydroxyethyl cellulose, cellulose, oxidized cellulose, oxidized regenerated cellulose (ORC), hydroxypropyl cellulose, carboxyethyl cellulose, carboxymethylcellulose, chitan, chitosan, casein, alginate, and combinations thereof.

Examples of synthetic absorbable materials include, but are not limited to, poly(lactic acid) (PLA), poly(L-lactic acid) (PLLA), polycaprolactone (PCL), polyglycolic acid (PGA), poly(trimethylene carbonate) (TMC), polyethylene terephthalate (PET), polyhydroxyalkanoate (PHA), a copolymer of glycolide and ε-caprolactone (PGCL), a copolymer of glycolide and -trimethylene carbonate, poly(glycerol sebacate) (PGS), poly(dioxanone) (PDS), polyesters, poly (orthoesters), polyoxaesters, polyetheresters, polycarbonates, polyamide esters, polyanhydrides, polysaccharides, poly(ester-amides), tyrosine-based polyarylates, polyamines, tyrosine-based polyiminocarbonates, tyrosine-based polycarbonates, poly(D,L-lactide-urethane), poly(hydroxybutyrate), poly(B-hydroxybutyrate), poly(E-caprolactone), polyethyleneglycol (PEG), poly[bis (carboxylatophenoxy) phosphazene] poly(amino acids), pseudo-poly(amino acids), absorbable polyurethanes, poly (phosphazine), polyphosphazenes, polyalkyleneoxides, polyacrylamides, polyhydroxyethylmethylacrylate, polyvinylpyrrolidone, polyvinyl alcohols, poly(caprolactone), polyacrylic acid, polyacetate, polypropylene, aliphatic polyesters, glycerols, copoly(ether-esters), polyalkylene oxalates, polyamides, poly(iminocarbonates), polyalkylene oxalates, and combinations thereof. In various embodiments, the polyester is may be selected from the group consisting of polylactides, polyglycolides, trimethylene carbonates, polydioxanones, polycaprolactones, polybutesters, and combinations thereof.

In various embodiments, the synthetic absorbable polymer may comprise one or more of 90/10 poly(glycolide-L-lactide) copolymer, commercially available from Ethicon, Inc. under the trade designation VICRYL (polyglactic 910), polyglycolide, commercially available from American Cyanamid Co. under the trade designation DEXON, polydioxanone, commercially available from Ethicon, Inc. under the trade designation PDS, poly(glycolide-trimethylene carbonate) random block copolymer, commercially available from American Cyanamid Co. under the trade designation MAXON, 75/25 poly(glycolide-ε-caprolactone-poliglecaprolactone 25) copolymer, commercially available from Ethicon under the trade designation MONOCRYL, for example.

Examples of synthetic non-absorbable materials include, but are not limited to, polyurethane, polypropylene (PP), polyethylene (PE), polycarbonate, polyamides, such as nylon, polyvinylchloride (PVC), polymethylmetacrylate (PMMA), polystyrene (PS), polyester, polyetheretherketone (PEEK), polytetrafluoroethylene (PTFE), polytrifluorochloroethylene (PTFCE), polyvinylfluoride (PVF), fluorinated ethylene propylene (FEP), polyacetal, polysulfone, silicons, and combinations thereof. The synthetic non-absorbable polymers may include, but are not limited to, foamed elastomers and porous elastomers, such as, for example, silicone, polyisoprene, and rubber. In various embodiments, the synthetic polymers may comprise expanded polytetrafluoroethylene (ePTFE), commercially available from W. L. Gore & Associates, Inc. under the trade designation GORE-TEX Soft Tissue Patch and co-polyetherester urethane foam commercially available from Polyganics under the trade designation NASOPORE.

In various embodiments, the polymeric composition may comprise from approximately 50% to approximately 90% by weight of the polymeric composition of PLLA and approximately 50% to approximately 10% by weight of the polymeric composition of PCL, for example. In at least one embodiment, the polymeric composition may comprise approximately 70% by weight of PLLA and approximately 30% by weight of PCL, for example. In various embodiments, the polymeric composition may comprise from approximately 55% to approximately 85% by weight of the polymeric composition of PGA and 15% to 45% by weight of the polymeric composition of PCL, for example. In at least one embodiment, the polymeric composition may comprise approximately 65% by weight of PGA and approximately 35% by weight of PCL, for example. In various embodiments, the polymeric composition may comprise from approximately 90% to approximately 95% by weight of the polymeric composition of PGA and approximately 5% to approximately 10% by weight of the polymeric composition of PLA, for example.

In various embodiments, the synthetic absorbable polymer may comprise a bioabsorbable, biocompatible elastomeric copolymer. Suitable bioabsorbable, biocompatible elastomeric copolymers include but are not limited to copolymers of ε-caprolactone and glycolide (preferably having a mole ratio of ε-caprolactone to glycolide of from about 30:70 to about 70:30, preferably 35:65 to about 65:35, and more preferably 45:55 to 35:65); elastomeric copolymers of ε-caprolactone and lactide, including L-lactide, D-lactide blends thereof or lactic acid copolymers (preferably having a mole ratio of ε-caprolactone to lactide of from about 35:65 to about 65:35 and more preferably 45:55 to 30:70) elastomeric copolymers of p-dioxanone (1,4-dioxan-2-one) and lactide including L-lactide, D-lactide and lactic acid (preferably having a mole ratio of p-dioxanone to lactide of from about 40:60 to about 60:40); elastomeric copolymers of ε-caprolactone and p-dioxanone (preferably having a mole ratio of ε-caprolactone to p-dioxanone of from about 30:70 to about 70:30); elastomeric copolymers of p-dioxanone and trimethylene carbonate (preferably having a mole ratio of p-dioxanone to trimethylene carbonate of from about 30:70 to about 70:30); elastomeric copolymers of trimethylene carbonate and glycolide (preferably having a mole ratio of trimethylene carbonate to glycolide of from about 30:70 to about 70:30); elastomeric copolymer of trimethylene carbonate and lactide including L-lactide, D-lactide, blends thereof or lactic acid copolymers (preferably having a mole ratio of trimethylene carbonate to lactide of from about 30:70 to about 70:30) and blends thereof. In one embodiment, the elastomeric copolymer is a copolymer of glycolide and ε-caprolactone. In another embodiment, the elastomeric copolymer is a copolymer of lactide and ε-caprolactone.

The disclosures of U.S. Pat. No. 5,468,253, entitled ELASTOMERIC MEDICAL DEVICE, which issued on Nov. 21, 1995, and U.S. Pat. No. 6,325,810, entitled FOAM BUTTRESS FOR STAPLING APPARATUS, which issued on Dec. 4, 2001, are hereby incorporated by reference in their respective entireties.

In various embodiments, the tissue thickness compensator may comprise an emulsifier. Examples of emulsifiers may include, but are not limited to, water-soluble polymers, such as, polyvinyl alcohol (PVA), polyvinyl pyrrolidone (PVP), polyethylene glycol (PEG), polypropylene glycol (PPG), PLURONICS, TWEENS, polysaccharides and combinations thereof.

In various embodiments, the tissue thickness compensator may comprise a surfactant. Examples of surfactants may include, but are not limited to, polyacrylic acid, methalose, methyl cellulose, ethyl cellulose, propyl cellulose, hydroxy ethyl cellulose, carboxy methyl cellulose, polyoxyethylene cetyl ether, polyoxyethylene lauryl ether, polyoxyethylene octyl ether, polyoxyethylene octylphenyl ether, polyoxyethylene oleyl ether, polyoxyethylene sorbitan monolaurate, polyoxyethylene stearyl ether, polyoxyethylene nonylphenyl ether, dialkylphenoxy poly(ethyleneoxy) ethanol, and polyoxamers.

In various embodiments, the polymeric composition may comprise a pharmaceutically active agent. The polymeric composition may release a therapeutically effective amount of the pharmaceutically active agent. In various embodiments, the pharmaceutically active agent may be released as the polymeric composition is desorbed/absorbed. In various embodiments, the pharmaceutically active agent may be released into fluid, such as, for example, blood, passing over or through the polymeric composition. Examples of pharmaceutically active agents may include, but are not limited to, haemostatic agents and drugs, such as, for example, fibrin, thrombin, and oxidized regenerated cellulose (ORC); anti-inflammatory drugs, such as, for example, diclofenac, aspirin, naproxen, sulindac, and hydrocortisone; antibiotic and antimicrobial drug or agents, such as, for example, triclosan, ionic silver, ampicillin, gentamicin, polymyxin B, chloramphenicol; and anticancer agents, such as, for example, cisplatin, mitomycin, adriamycin.

In various embodiments, the polymeric composition may comprise a haemostatic material. The tissue thickness compensator may comprise haemostatic materials comprising poly(lactic acid), poly(glycolic acid), poly(hydroxybutyrate), poly(caprolactone), poly(dioxanone), polyalkyleneoxides, copoly(ether-esters), collagen, gelatin, thrombin, fibrin, fibrinogen, fibronectin, elastin, albumin, hemoglobin, ovalbumin, polysaccharides, hyaluronic acid, chondroitin sulfate, hydroxyethyl starch, hydroxyethyl cellulose, cellulose, oxidized cellulose, hydroxypropyl cellulose, carboxyethyl cellulose, carboxymethyl cellulose, chitan, chitosan, agarose, maltose, maltodextrin, alginate, clotting factors, methacrylate, polyurethanes, cyanoacrylates, platelet agonists, vasoconstrictors, alum, calcium, RGD peptides, proteins, protamine sulfate, ε-amino caproic acid, ferric sulfate, ferric subsulfates, ferric chloride, zinc, zinc chloride, aluminum chloride, aluminum sulfates, aluminum acetates, permanganates, tannins, bone wax, polyethylene glycols, fucans and combinations thereof. The tissue thickness compensator may be characterized by haemostatic properties.

The polymeric composition of a tissue thickness compensator may be characterized by percent porosity, pore size, and/or hardness, for example. In various embodiments, the polymeric composition may have a percent porosity from approximately 30% by volume to approximately 99% by volume, for example. In certain embodiments, the polymeric composition may have a percent porosity from approximately 60% by volume to approximately 98% by volume, for example. In various embodiments, the polymeric composition may have a percent porosity from approximately 85% by volume to approximately 97% by volume, for example. In at least one embodiment, the polymeric composition may comprise approximately 70% by weight of PLLA and approximately 30% by weight of PCL, for example, and can comprise approximately 90% porosity by volume, for example. In at least one such embodiment, as a result, the polymeric composition would comprise approximately 10% copolymer by volume. In at least one embodiment, the polymeric composition may comprise approximately 65% by weight of PGA and approximately 35% by weight of PCL, for example, and can have a percent porosity from approximately 93% by volume to approximately 95% by volume, for example. In various embodiments, the polymeric composition may comprise greater than 85% porosity by volume. The polymeric composition may have a pore size from approximately 5 micrometers to approximately 2000 micrometers, for example. In various embodiments, the polymeric composition may have a pore size between approximately 10 micrometers to approximately 100 micrometers, for example. In at least one such embodiment, the polymeric composition can comprise a copolymer of PGA and PCL, for example. In certain embodiments, the polymeric composition may have a pore size between approximately 100 micrometers to approximately 1000 micrometers, for example. In at least one such embodiment, the polymeric composition can comprise a copolymer of PLLA and PCL, for example.

According to certain aspects, the hardness of a polymeric composition may be expressed in terms of the Shore Hardness, which can defined as the resistance to permanent indentation of a material as determined with a durometer, such as a Shore Durometer. In order to assess the durometer value for a given material, a pressure is applied to the material with a durometer indenter foot in accordance with ASTM procedure D2240-00, entitled, "Standard Test Method for Rubber Property-Durometer Hardness", the entirety of which is incorporated herein by reference. The durometer indenter foot may be applied to the material for a sufficient period of time, such as 15 seconds, for example, wherein a reading is then taken from the appropriate scale. Depending on the type of scale being used, a reading of 0 can be obtained when the indenter foot completely penetrates the material, and a reading of 100 can be obtained when no penetration into the material occurs. This reading is dimensionless. In various embodiments, the durometer may be determined in accordance with any suitable scale, such as Type A and/or Type OO scales, for example, in accordance with ASTM D2240-00. In various embodiments, the polymeric composition of a tissue thickness compensator may have a Shore A hardness value from approximately 4 A to approximately 16 A, for example, which is approximately 45 OO to approximately 65 OO on the Shore OO range. In at least one such embodiment, the polymeric composition can comprise a PLLA/PCL copolymer or a PGA/PCL copolymer, for example. In various embodiments, the polymeric composition of a tissue thickness compensator may have a Shore A Hardness value of less than 15 A. In various embodiments, the polymeric composition of a tissue thickness compensator may have a Shore A Hardness value of less than 10 A. In various embodiments, the polymeric composition of a tissue thickness compensator may have a Shore A Hardness value of less than 5 A. In certain embodiments, the polymeric material may have a Shore OO composition value from approximately 35 OO to approximately 75 OO, for example.

In various embodiments, the polymeric composition may have at least two of the above-identified properties. In various embodiments, the polymeric composition may have at least three of the above-identified properties. The polymeric composition may have a porosity from 85% to 97% by volume, a pore size from 5 micrometers to 2000 micrometers, and a Shore A hardness value from 4 A to 16 A and Shore OO hardness value from 45 OO to 65 OO, for example. In at least one embodiment, the polymeric composition may comprise 70% by weight of the polymeric composition of PLLA and 30% by weight of the polymeric composition of PCL having a porosity of 90% by volume, a pore size from 100 micrometers to 1000 micrometers, and a Shore A hardness value from 4 A to 16 A and Shore OO hardness value from 45 OO to 65 OO, for example. In at least one embodiment, the polymeric composition may comprise 65% by weight of the polymeric composition of PGA and 35% by weight of the polymeric composition of PCL having a porosity from 93% to 95% by volume, a pore size from 10 micrometers to 100 micrometers, and a Shore A hardness value from 4 A to 16 A and Shore OO hardness value from 45 OO to 65 OO, for example.

In various embodiments, the tissue thickness compensator may comprise a material that expands. As discussed above, the tissue thickness compensator may comprise a compressed material that expands when uncompressed or deployed, for example. In various embodiments, the tissue thickness compensator may comprise a self-expanding material formed in situ. In various embodiments, the tissue thickness compensator may comprise at least one precursor selected to spontaneously crosslink when contacted with at least one of other precursor(s), water, and/or bodily fluids. Referring to FIG. 534, in various embodiments, a first precursor may contact one or more other precursors to form an expandable and/or swellable tissue thickness compensator. In various embodiments, the tissue thickness compensator may comprise a fluid-swellable composition, such as a water-swellable composition, for example. In various embodiments, the tissue thickness compensator may comprise a gel comprising water.

Referring to FIGS. 518A and B, for example, a tissue thickness compensator 70000 may comprise at least one hydrogel precursor 70010 selected to form a hydrogel in situ and/or in vivo to expand the tissue thickness compensator 70000. FIG. 518A illustrates a tissue thickness compensator 70000 comprising an encapsulation comprising a first hydrogel precursor 70010A and a second hydrogel precursor 70010B prior to expansion. In certain embodiments, as shown in FIG. 518A, the first hydrogel precursor 70010A and second hydrogel precursor 70010B may be physically separated from other in the same encapsulation. In certain embodiments, a first encapsulation may comprise the first hydrogel precursor 70010A and a second encapsulation may comprise the second hydrogel precursor 70010B. FIG. 518B illustrates the expansion of the thickness tissue compensator 70000 when the hydrogel is formed in situ and/or in vivo. As shown in FIG. 518B, the encapsulation may be ruptured, and the first hydrogel precursor 70010A may contact the second hydrogel precursor 70010B to form the hydrogel 70020. In certain embodiments, the hydrogel may comprise an expandable material. In certain embodiments, the hydrogel may expand up to 72 hours, for example.

In various embodiments, the tissue thickness compensator may comprise a biodegradable foam having an encapsulation comprising dry hydrogel particles or granules embedded therein. Without wishing to be bound to any particular theory, the encapsulations in the foam may be formed by contacting an aqueous solution of a hydrogel precursor and an organic solution of biocompatible materials to form the foam. As shown in FIG. 535, the aqueous solution and organic solution may form micelles. The aqueous solution and organic solution may be dried to encapsulate dry hydrogel particles or granules within the foam. For example, a hydrogel precursor, such as a hydrophilic polymer, may be dissolved in water to form a dispersion of micelles. The aqueous solution may contact an organic solution of dioxane comprising poly(glycolic acid) and polycaprolactone. The aqueous and organic solutions may be lyophilized to form a biodegradable foam having dry hydrogel particles or granules dispersed therein. Without wishing to be bound to any particular theory, it is believed that the micelles form the encapsulation having the dry hydrogel particles or granules dispersed within the foam structure. In certain embodiments, the encapsulation may be ruptured, and the dry hydrogel particles or granules may contact a fluid, such as a bodily fluid, and expand.

In various embodiments, the tissue thickness compensator may expand when contacted with an activator, such as a fluid, for example. Referring to FIG. 519, for example, a tissue thickness compensator 70050 may comprise a swellable material, such as a hydrogel, that expands when contacted with a fluid 70055, such as bodily fluids, saline, water and/or an activator, for example. Examples of bodily fluids may include, but are not limited to, blood, plasma, peritoneal fluid, cerebral spinal fluid, urine, lymph fluid, synovial fluid, vitreous fluid, saliva, gastrointestinal luminal contents, bile, and/or gas (e.g., $CO_2$). In certain embodiments, the tissue thickness compensator 70050 may expand when the tissue thickness compensator 70050 absorbs the fluid. In another example, the tissue thickness compensator 70050 may comprise a non-crosslinked hydrogel that expands when contacted with an activator 70055 comprising a cross-linking agent to form a crosslinked hydrogel. In various embodiments, the tissue thickness compensator may expand when contacted with an activator. In various embodiments, the tissue thickness compensator may expand or swell from contact up to 72 hours, such as from 24-72 hours, up to 24 hours, up to 48 hours, and up to 72 hours, for example, to provide continuously increasing pressure and/or compression to the tissue. As shown in FIG. 519, the initial thickness of the tissue thickness compensator 70050 may be less than an expanded thickness after the fluid 70055 contacts the tissue thickness compensator 70050.

Referring to FIGS. 516 and 517, in various embodiments, a staple cartridge 70100 may comprise a tissue thickness compensator 70105 and a plurality of staples 70110 each comprising staple legs 70112. As shown in FIG. 516, tissue thickness compensator 70105 may have an initial thickness or compressed height that is less than the fired height of the staples 70110. The tissue thickness compensator 70100 may be configured to expand in situ and/or in vivo when contacted with a fluid 70102, such as bodily fluids, saline, and/or an activator for example, to push the tissue T against the legs 70112 of the staple 70110. As shown in FIG. 517, the tissue thickness compensator 70100 may expand and/or swell when contacted with a fluid 70102. The tissue thickness compensator 70105 can compensate for the thickness of the tissue T captured within each staple 70110. As shown in FIG. 517, tissue thickness compensator 70105 may have an expanded thickness or an uncompressed height that is less than the fired height of the staples 70110.

In various embodiments, as described above, the tissue thickness compensator may comprise an initial thickness and an expanded thickness. In certain embodiments, the initial thickness of a tissue thickness compensator can be approximately 0.001% of its expanded thickness, approximately 0.01% of its expanded thickness, approximately 0.1% of its expanded thickness, approximately 1% of its expanded thickness, approximately 10% of its expanded thickness, approximately 20% of its expanded thickness, approximately 30% of its expanded thickness, approximately 40% of its expanded thickness, approximately 50% of its expanded thickness, approximately 60% of its expanded thickness, approximately 70% of its expanded thickness, approximately 80% of its expanded thickness, and/or approximately 90% of its expanded thickness, for example. In various embodiments, the expanded thickness of the tissue thickness compensator can be approximately two times, approximately five times, approximately ten times, approximately fifty times, approximately one hundred times, approximately two hundred times, approximately three hundred times, approximately four hundred times, approximately five hundred times, approximately six hundred times, approximately seven hundred times, approximately eight hundred times, approximately nine hundred times, and/or approximately one thousand times thicker than its initial thickness, for example. In various embodiments, the initial thickness of the tissue thickness compensator can be up to 1% its expanded thickness, up to 5% its expanded thickness, up to 10% its expanded thickness, and up to 50% its expanded thickness. In various embodiments, the expanded thickness of the tissue thickness compensator can be at least 50% thicker than its initial thickness, at least 100% thicker than its initial thickness, at least 300% thicker than its initial thickness, and at least 500% thicker than its initial thickness. As described above, in various circumstances, as a result of the above, the tissue thickness compensator can be configured to consume any gaps within the staple entrapment area.

As discussed above, in various embodiments, the tissue thickness compensator may comprise a hydrogel. In various embodiments, the hydrogel may comprise homopolymer hydrogels, copolymer hydrogels, multipolymer hydrogels, interpenetrating polymer hydrogels, and combinations thereof. In various embodiments, the hydrogel may comprise microgels, nanogels, and combinations thereof. The hydrogel may generally comprise a hydrophilic polymer network capable of absorbing and/or retaining fluids. In various embodiments, the hydrogel may comprise a non-crosslinked hydrogel, a crosslinked hydrogel, and combinations thereof. The hydrogel may comprise chemical crosslinks, physical crosslinks, hydrophobic segments and/or water insoluble segments. The hydrogel may be chemically crosslinked by polymerization, small-molecule crosslinking, and/or polymer-polymer crosslinking. The hydrogel may be physically crosslinked by ionic interactions, hydrophobic interactions, hydrogen bonding interactions, sterocomplexation, and/or supramolecular chemistry. The hydrogel may be substantially insoluble due to the crosslinks, hydrophobic segments and/or water insoluble segments, but be expandable and/or swellable due to absorbing and/or retaining fluids. In certain embodiments, the precursor may crosslink with endogenous materials and/or tissues.

In various embodiments, the hydrogel may comprise an environmentally sensitive hydrogel (ESH). The ESH may comprise materials having fluid-swelling properties that relate to environmental conditions. The environmental conditions may include, but are not limited to, the physical conditions, biological conditions, and/or chemical conditions at the surgical site. In various embodiments, the hydrogel may swell or shrink in response to temperature, pH, electric fields, ionic strength, enzymatic and/or chemical reactions, electrical and/or magnetic stimuli, and other physiological and environmental variables, for example. In various embodiments, the ESH may comprise multifunctional acrylates, hydroxyethylmethacrylate (HEMA), elastomeric acrylates, and related monomers.

In various embodiments, the tissue thickness compensator comprising a hydrogel may comprise at least one of the non-synthetic materials and synthetic materials described above. The hydrogel may comprise a synthetic hydrogel and/or a non-synthetic hydrogel. In various embodiments, the tissue thickness compensator may comprise a plurality of layers. The plurality of the layers may comprise porous layers and/or non-porous layers. For example, the tissue thickness compensator may comprise a non-porous layer and a porous layer. In another example, the tissue thickness compensator may comprise a porous layer intermediate a first non-porous layer and a second non-porous layer. In another example, the tissue thickness compensator may comprise a non-porous layer intermediate a first porous layer and a second porous layer. The non-porous layers and porous layers may be positioned in any order relative to the surfaces of the staple cartridge and/or anvil.

Examples of the non-synthetic material may include, but are not limited to, albumin, alginate, carbohydrate, casein, cellulose, chitin, chitosan, collagen, blood, dextran, elastin, fibrin, fibrinogen, gelatin, heparin, hyaluronic acid, keratin, protein, serum, and starch. The cellulose may comprise hydroxyethyl cellulose, oxidized cellulose, oxidized regenerated cellulose (ORC), hydroxypropyl cellulose, carboxyethyl cellulose, carboxymethylcellulose, and combinations thereof. The collagen may comprise bovine pericardium. The carbohydrate may comprise a polysaccharide, such as lyophilized polysaccharide. The protein may comprise glycoprotein, proteoglycan, and combinations thereof.

Examples of the synthetic material may include, but are not limited to, poly(lactic acid), poly(glycolic acid), poly (hydroxybutyrate), poly(phosphazine), polyesters, polyethylene glycols, polyethylene oxide, polyethylene oxide-co-polypropylene oxide, co-polyethylene oxide, polyalkyleneoxides, polyacrylamides, polyhydroxyethylmethylacrylate, poly(vinylpyrrolidone), polyvinyl alcohols, poly(caprolactone), poly(dioxanone), polyacrylic acid, polyacetate, polypropylene, aliphatic polyesters, glycerols, poly (amino acids), copoly(ether-esters), polyalkylene oxalates, polyamides, poly(iminocarbonates), polyoxaesters, polyorthoesters, polyphosphazenes and combinations thereof. In certain embodiments, the above non-synthetic materials may be synthetically prepared, e.g., synthetic hyaluronic acid, utilizing conventional methods.

In various embodiments, the hydrogel may be made from one or more hydrogel precursors. The precursor may comprise a monomer and/or a macromer. The hydrogel precursor may comprise an electrophile functional group and/or a nucleophile electrophile functional group. In general, electrophiles may react with nucleophiles to form a bond. The term "functional group" as used herein refers to electrophilic or nucleophilic groups capable of reacting with each other to form a bond. Examples of electrophilic functional groups may include, but are not limited to, N-hydroxysuccinimides ("NHS"), sulfosuccinimides, carbonyldiimidazole, sulfonyl chloride, aryl halides, sulfosuccinimidyl esters, N-hydroxysuccinimidyl esters, succinimidyl esters such as succinimidyl succinates and/or succinimidyl propionates, isocyanates, thiocyanates, carbodiimides, benzotriazole carbonates, epoxides, aldehydes, maleimides, imidoesters, combinations thereof, and the like. In at least one embodiment, the electrophilic functional group may comprise a succinimidyl ester. Examples of nucleophile functional groups may include, but are not limited to, $—NH_2$, —SH, —OH, $—PH_2$, and —CO—NH—$NH_2$.

In various embodiments, the hydrogel may be formed from a single precursor or multiple precursors. In certain embodiments, the hydrogel may be formed from a first precursor and a second precursor. The first hydrogel precursor and second hydrogel precursor may form a hydrogel in situ and/or in vivo upon contact. The hydrogel precursor may generally refer to a polymer, functional group, macromolecule, small molecule, and/or crosslinker that can take part in a reaction to form a hydrogel. The precursor may comprise a homogeneous solution, heterogeneous, or phase separated solution in a suitable solvent, such as water or a buffer, for example. The buffer may have a pH from about 8 to about 12, such as, about 8.2 to about 9, for example. Examples of buffers may include, but are not limited to borate buffers. In certain embodiments, the precursor(s) may be in an emulsion. In various embodiments, a first precursor may react with a second precursor to form a hydrogel. In various embodiments, the first precursor may spontaneously crosslink when contacted with the second precursor. In various embodiments, a first set of electrophilic functional groups on a first precursor may react with a second set of nucleophilic functional groups on a second precursor. When the precursors are mixed in an environment that permits reaction (e.g., as relating to pH, temperature, and/or solvent), the functional groups may react with each other to form covalent bonds. The precursors may become crosslinked when at least some of the precursors react with more than one other precursor.

In various embodiments, the tissue thickness compensator may comprise at least one monomer selected from the group consisting of 3-sulfopropyl acrylate potassium salt ("KSPA"), sodium acrylate ("NaA"), N-(tris(hydroxylmethyl)methyl)acrylamide ("tris acryl"), and 2-acrylamido-2-methyl-1-propane sulfonic acid (AMPS). The tissue thickness compensator may comprise a copolymer comprising two or more monomers selected from the group consisting of KSPA, NaA, tris acryl, AMPS. The tissue thickness compensator may comprise homopolymers derived from KSPA, NaA, trisacryl and AMPS. The tissue thickness compensator may comprise hydrophilicity modifying monomers copolymerizable therewith. The hydrophilicity modifying monomers may comprise methylmethacrylate, butylacrylate, cyclohexylacrylate, styrene, styrene sulphonic acid.

In various embodiments, the tissue thickness compensator may comprise a crosslinker. The crosslinker may comprise a low molecular weight di- or polyvinylic crosslinking agent, such as ethylenglycol diacrylate or dimethacrylate, di-, tri- or tetraethylen-glycol diacrylate or dimethacrylate, allyl (meth)acrylate, a $C_2$-$C_8$-alkylene diacrylate or dimethacrylate, divinyl ether, divinyl sulfone, di- and trivinylbenzene, trimethylolpropane triacrylate or trimethacrylate, pentaerythritol tetraacrylate or tetramethacrylate, bisphenol A diacrylate or dimethacrylate, methylene bisacrylamide or bismethacrylamide, ethylene bisacrylamide or ethylene bismethacrylamide, triallyl phthalate or diallyl phthalate. In at least one embodiment, the crosslinker may comprise N,N'-methylenebisacrylamide ("MBAA").

In various embodiments, the tissue thickness compensator may comprise at least one of acrylate and/or methacrylate functional hydrogels, biocompatible photoinitiator, alkylcyanoacrylates, isocyanate functional macromers, optionally comprising amine functional macromers, succinimidyl ester functional macromers, optionally comprising amine and/or sulfhydryl functional macromers, epoxy functional macromers, optionally comprising amine functional macromers, mixtures of proteins and/or polypeptides and aldehyde crosslinkers, Genipin, and water-soluble carbodiimides, anionic polysaccharides and polyvalent cations.

In various embodiments, the tissue thickness compensator may comprise unsaturated organic acid monomers, acrylic substituted alcohols, and/or acrylamides. In various embodiments, the tissue thickness compensator may comprise methacrylic acids, acrylic acids, glycerolacrylate, glycerolmethacryulate, 2-hydroxyethylmethacrylate, 2-hydroxyethylacrylate, 2-(dimethylaminoethyl) methacrylate, N-vinyl pyrrolidone, methacrylamide, and/or N,N-dimethylacrylamide poly(methacrylic acid).

In various embodiments, the tissue thickness compensator may comprise a reinforcement material. In various embodiments, the reinforcement material may comprise at least one of the non-synthetic materials and synthetic materials described above. In various embodiments, the reinforcement material may comprise collagen, gelatin, fibrin, fibrinogen, elastin, keratin, albumin, hydroxyethyl cellulose, cellulose, oxidized cellulose, hydroxypropyl cellulose, carboxyethyl cellulose, carboxymethylcellulose, chitan, chitosan, alginate, poly(lactic acid), poly(glycolic acid), poly(hydroxybutyrate), poly(phosphazine), polyesters, polyethylene glycols, polyalkyleneoxides, polyacrylamides, polyhydroxyethylmethylacrylate, polyvinylpyrrolidone, polyvinyl alcohols, poly(caprolactone), poly(dioxanone), polyacrylic acid, polyacetate, polycaprolactone, polypropylene, aliphatic polyesters, glycerols, poly(amino acids), copoly(ether-esters), polyalkylene oxalates, polyamides, poly(iminocarbonates), polyalkylene oxalates, polyoxaesters, polyorthoesters, polyphosphazenes and combinations thereof.

In various embodiments, the tissue thickness compensator may comprise a layer comprising the reinforcement material. In certain embodiments, a porous layer and/or a non-porous layer of a tissue thickness compensator may comprise the reinforcement material. For example, the porous layer may comprise the reinforcement material and the non-porous layer may not comprise the reinforcement material. In various embodiments, the reinforcement layer may comprise an inner layer intermediate a first non-porous layer and a second non-porous layer. In certain embodiments, the reinforcement layer may comprise an outer layer of the tissue thickness compensator. In certain embodiments, the reinforcement layer may comprise an exterior surface of the tissue thickness compensator.

In various embodiments, the reinforcement material may comprise meshes, monofilaments, multifilament braids, fibers, mats, felts, particles, and/or powders. In certain embodiments, the reinforcement material may be incorporated into a layer of the tissue thickness compensator. The reinforcement material may be incorporated into at least one of a non-porous layer and a porous layer. A mesh comprising the reinforcement material may be formed using conventional techniques, such as, for example, knitting, weaving, tatting, and/or knipling. In various embodiments, a plurality of reinforcement materials may be oriented in a random direction and/or a common direction. In certain embodiments, the common direction may be one of parallel to the staple line and perpendicular to the staple line, for example. For example, the monofilaments and/or multifilament braids may be oriented in a random direction and/or a common direction. The monofilaments and multifilament braids may be associated with the non-porous layer and/or the porous layer. In various embodiments, the tissue thickness compensator may comprise a plurality of reinforcement fibers oriented in a random direction within a non-porous layer. In various embodiments, the tissue thickness compensator may comprise a plurality of reinforcement fibers oriented in a common direction within a non-porous layer.

In various embodiments, referring to FIG. 528, an anvil 70300 may comprise a tissue thickness compensator 70305 comprising a first non-porous layer 70307 and a second non-porous layer 70309 sealingly enclosing a reinforcement layer 70310. In various embodiments, the reinforcement layer 70310 may comprise a hydrogel comprising ORC particles or fibers embedded therein, and the non-porous layers may comprise ORC. As shown in FIG. 528, the tissue thickness compensator 70305 may be configured to conform to the contour of the anvil 70300. The inner layer of the tissue thickness compensator 70305 may conform to the inner surface of the anvil 70300, which includes the forming pockets 70301.

The fibers may form a non-woven material, such as, for example, a mat and a felt. The fibers may have any suitable length, such as, for example from 0.1 mm to 100 mm and 0.4 mm to 50 mm. The reinforcement material may be ground to a powder. The powder may have a particle size from 10 micrometers to 1 cm, for example. The powder may be incorporated into the tissue thickness compensator.

In various embodiments, the tissue thickness compensator may be formed in situ. In various embodiments, the hydrogel may be formed in situ. The tissue thickness compensator may be formed in situ by covalent, ionic, and/or hydrophobic bonds. Physical (non-covalent) crosslinks may result from complexation, hydrogen bonding, desolvation, Van der Waals interactions, ionic bonding, and combinations thereof. Chemical (covalent) crosslinking may be accomplished by any of a number of mechanisms, including: free radical polymerization, condensation polymerization, anionic or cationic polymerization, step growth polymerization, electrophile-nucleophile reactions, and combinations thereof.

In various embodiments, in situ formation of the tissue thickness compensator may comprise reacting two or more precursors that are physically separated until contacted in situ and/or react to an environmental condition to react with each other to form the hydrogel. In situ polymerizable polymers may be prepared from precursor(s) that can be reacted to form a polymer at the surgical site. The tissue thickness compensator may be formed by crosslinking reactions of the precursor(s) in situ. In certain embodiments, the precursor may comprise an initiator capable of initiating a polymerization reaction for the formation of the in situ tissue thickness compensator. The tissue thickness compensator may comprise a precursor that can be activated at the time of application to create, in various embodiments, a crosslinked hydrogel. In situ formation of the tissue thickness compensator may comprise activating at least one precursor to form bonds to form the tissue thickness compensator. In various embodiments, activation may be achieved by changes in the physical conditions, biological conditions, and/or chemical conditions at the surgical site, including, but not limited to temperature, pH, electric fields, ionic strength, enzymatic and/or chemical reactions, electrical and/or magnetic stimuli, and other physiological and environmental variables. In various embodiments, the precursors may be contacted outside the body and introduced to the surgical site.

In various embodiments, the tissue thickness compensator may comprise one or more encapsulations, or cells, which can be configured to store at least one component therein. In certain embodiments, the encapsulation may be configured to store a hydrogel precursor therein. In certain embodiments, the encapsulation may be configured to store two components therein, for example. In certain embodiments, the encapsulation may be configured to store a first hydrogel precursor and a second hydrogel precursor therein. In certain embodiments, a first encapsulation may be configured to store a first hydrogel precursor therein and a second encapsulation may be configured to store a second hydrogel precursor therein. As described above, the encapsulations can be aligned, or at least substantially aligned, with the staple legs to puncture and/or otherwise rupture the encapsulations when the staple legs contact the encapsulation. In certain embodiments, the encapsulations may be compressed, crushed, collapsed, and/or otherwise ruptured when the staples are deployed. After the encapsulations have been ruptured, the component(s) stored therein can flow out of the encapsulation. The component stored therein may contact other components, layers of the tissue thickness compensator, and/or the tissue. In various embodiments, the other components may be flowing from the same or different encapsulations, provided in the layers of the tissue thickness compensator, and/or provided to the surgical site by the clinician. As a result of the above, the component(s) stored within the encapsulations can provide expansion and/or swelling of the tissue thickness compensator.

In various embodiments, the tissue thickness compensator may comprise a layer comprising the encapsulations. In various embodiments, the encapsulation may comprise a void, a pocket, a dome, a tube, and combinations thereof associated with the layer. In certain embodiments, the encapsulations may comprise voids in the layer. In at least one embodiment, the layer can comprise two layers that can be attached to one another wherein the encapsulations can be defined between the two layers. In certain embodiments, the encapsulations may comprise domes on the surface of the layer. For example, at least a portion of the encapsulations can be positioned within domes extending upwardly from the layer. In certain embodiments, the encapsulations may comprise pockets formed within the layer. In certain embodiments, a first portion of the encapsulations may comprise a dome and a second portion of the encapsulations may comprise a pocket. In certain embodiments, the encapsulations may comprise a tube embedded within the layer. In certain embodiments, the tube may comprise the non-synthetic materials and/or synthetic materials described herein, such as PLA. In at least one embodiment, the tissue thickness compensator may comprise a bioabsorable foam, such as ORC, comprising PLA tubes embedded therein, and the tube may encapsulate a hydrogel, for example. In certain embodiments, the encapsulations may comprise discrete cells that are unconnected to each other. In certain embodiments, one or more of the encapsulations can be in fluid communication with each other via one or more passageways, conduits, and/or channels, for example, extending through the layer.

The rate of release of a component from the encapsulation may be controlled by the thickness of the tissue thickness compensator, the composition of tissue thickness compensator, the size of the component, the hydrophilicity of the component, and/or the physical and/or chemical interactions among the component, the composition of the tissue thickness compensator, and/or the surgical instrument, for example. In various embodiments, the layer can comprise one or more thin sections or weakened portions, such as partial perforations, for example, which can facilitate the incision of the layer and the rupture of the encapsulations. In various embodiments, the partial perforations may not completely extend through a layer while, in certain embodiments, perforations may completely extend through the layer.

Referring to FIGS. 523 and 524, in various embodiments, a tissue thickness compensator 70150 may comprise an outer layer 70152A and an inner layer 70152B comprising encapsulations 70154. In certain embodiments, the encapsulation may comprise a first encapsulated component and a second encapsulated component. In certain embodiments, the encapsulations may independently comprise one of a first encapsulated component and a second encapsulated component. The first encapsulated component may be separated from the second encapsulated component. The outer layer 70152A may comprise a tissue-contacting surface. The inner layer 70152B may comprise an instrument-contacting surface. The instrument-contacting surface 70152B may be releasably attached to the anvil 70156. The outer layer 70152A may be attached to the inner layer 70152B to define a void between the outer layer 70152A and inner layer 70152B. As shown in FIG. 523, each encapsulation 70154 may comprise a dome on the instrument-contacting surface of the inner layer 70152B. The dome may comprise partial perforations to facilitate the incision of the layer by the staple legs and the rupture of the encapsulation. As shown in the FIG. 524, the anvil 70156 can comprise a plurality of forming pocket rows 70158 wherein the domes of the encapsulations 70154 may be aligned with the forming pocket 70158. The tissue-contacting surface may comprise a flat surface lacking domes. In certain embodiments, the tissue-contacting surface may comprise one or more encapsulations, such as encapsulations 70154, for example, extending therefrom.

In various embodiments, an anvil may comprise a tissue thickness compensator comprising an encapsulated component comprising at least one microsphere particle. In certain embodiments, the tissue thickness compensator may comprise an encapsulation comprising a first encapsulated component and a second encapsulated component. In certain embodiments, the tissue thickness compensator may comprise an encapsulation comprising a first microsphere particle and a second microsphere particle.

In various embodiments, referring to FIG. 525, a stapling apparatus may comprise an anvil 70180 and a staple cartridge (illustrated in other figures). The staples 70190 of a staple cartridge can be deformed by an anvil 70180 when the anvil 70180 is moved into a closed position and/or by a staple driver system 70192 which moves the staples 70190 toward the closed anvil 70180. The legs 70194 of the staples may contact the anvil 70180 such that the staples 70190 are at least partially deformed. The anvil 70180 may comprise a tissue thickness compensator 70182 comprising an outer layer 70183A, an inner layer 70183B. The tissue thickness compensator 70182 may comprise a first encapsulated component and a second encapsulated component. In certain embodiments, the encapsulations 210185 can be aligned, or at least substantially aligned, such that, when the staple legs 70194 are pushed through the tissue T and the outer layer 70183A, the staple legs 70194 can puncture and/or otherwise rupture the encapsulations 70185. As shown in FIG. 525, the staple 70190C is in its fully fired position, the staple 70190B is in the process of being fired, and the staple 70190A is in its unfired position. The legs of staples 70190C and 70190B have moved through the tissue T, the outer layer 70183A, and the inner layer 70183B of the tissue thickness compensator 70182, and have contacted an anvil 70180 positioned opposite the staple cartridge. After the encapsulations 70185 have been ruptured, the encapsulated components can flow out and contact each other, bodily fluids, and/or the tissue T, for example. The encapsulated components may react to form a reaction product such as a hydrogel, for example, to expand between the tissue T and the base of the staple and to push the tissue T against the legs of the staple. In various circumstances, as a result of the above, the tissue thickness compensator can be configured to consume any gaps within the staple entrapment area.

In various embodiments, the tissue thickness compensator may be suitable for use with a surgical instrument. As described above the tissue thickness compensator may be associated with the staple cartridge and/or the anvil. The tissue thickness compensator may be configured into any shape, size and/or dimension suitable to fit the staple cartridge and/or anvil. As described herein, the tissue thickness compensator may be releasably attached to the staple cartridge and/or anvil. The tissue thickness compensator may be attached to the staple cartridge and/or anvil in any mechanical and/or chemical manner capable of retaining the tissue thickness compensator in contact with the staple cartridge and/or anvil prior to and during the stapling process. The tissue thickness compensator may be removed or released from the staple cartridge and/or anvil after the staple penetrates the tissue thickness compensator. The tissue thickness compensator may be removed or released from the staple cartridge and/or anvil as the staple cartridge and/or anvil is moved away from the tissue thickness compensator.

Referring to FIGS. 520-522, stapling apparatus 70118 may comprise an anvil 70120 and a staple cartridge 70122 comprising a firing member 70124, a plurality of staples 70128, a knife edge 70129, and a tissue thickness compensator 70130. The tissue thickness compensator 70130 may comprise at least one encapsulated component. The encapsulated component may be ruptured when the tissue thickness compensator is compressed, stapled, and/or cut. Referring to FIG. 521, for example, the staples 70128 can be deployed between an unfired position and a fired position such that the staple legs move through the tissue thickness compensator 70130, penetrate through a bottom surface and a top surface of the tissue thickness compensator 70130, penetrate the tissue T, and contact an anvil 70120 positioned opposite the staple cartridge 70118. The encapsulated components may react with each other, a hydrophilic powder embedded or dispersed in the tissue thickness compensator, and/or bodily fluids to expand or swell the tissue thickness compensator 70130. As the legs are deformed against the anvil, the legs of each staple can capture a portion of the tissue thickness compensator 70130 and a portion of the tissue T within each staple 70128 and apply a compressive force to the tissue T. As shown in FIGS. 521 and 522, the tissue thickness compensator 70130 can compensate for the thickness of the tissue T captured within each staple 70128.

Referring to FIG. 526, a surgical instrument 70200 may comprise an anvil 70205 comprising an upper tissue thickness compensator 70210 and a staple cartridge 70215 comprising a lower tissue thickness compensator comprising an outer layer 70220 and an inner layer 70225. The upper tissue thickness compensator 70210 can be positioned on a first side of the targeted tissue and the lower tissue thickness compensator can be positioned on a second side of the tissue. In certain embodiments, the upper tissue thickness compensator 70210 may comprise ORC, the outer layer of the lower tissue thickness compensator may comprise a hydrogel having ORC particles embedded therein, and the inner layer of the lower tissue thickness compensator may comprise ORC, for example.

Referring to FIGS. 529-531, in various embodiments, a surgical instrument 70400 may comprise a staple cartridge 70405 and an anvil 70410. The staple cartridge 70405 may comprise a tissue thickness compensator 70415 including bioabsorbable foam. In various embodiments, the bioabsorbable foam can comprise an encapsulation which comprises an encapsulated component 70420. The bioabsorable foam may comprise ORC and the encapsulated component may comprise a medicament, for example. The tissue thickness compensator 70415 of the anvil 70410 may comprise an inner layer 70425 and an outer layer 70430. The inner layer 70425 may comprise a bioabsorbable foam, and the outer layer 70430 may comprise a hydrogel, optionally comprising reinforcement materials, for example. During an exemplary firing sequence, referring primarily to FIG. 530, a sled 70435 can first contact staple 70440A and begin to lift the staple upwardly. As the sled 70435 is advanced further distally, the sled 70435 can begin to lift staples 70440B-D, and any other subsequent staples, in a sequential order. The sled 70435 can drive the staples 70440 upwardly such that the legs of the staples contact the opposing anvil 70410 and are deformed to a desired shape. With regard to the firing sequence illustrated in FIG. 530, the staples 70440A-C have been moved into their fully fired positions, the staple 70440D is in the process of being fired, and the staple 70420E is still in its unfired position. The encapsulated component 70470 may be ruptured by the staple legs during the exemplary firing sequence. The encapsulated component 70420 may flow from the encapsulation around the staple legs to contact the tissue T. In various circumstances, additional compression of the tissue thickness compensator can squeeze additional medicament out of the encapsulation. In various embodiments, the medicament can immediately treat the tissue and can reduce bleeding from the tissue.

In various circumstances, a surgeon, or other clinician, may deliver a fluid to the tissue thickness compensator to manufacture a tissue thickness compensator comprising at least one medicament stored and/or absorbed therein. In various embodiments, a staple cartridge and/or anvil may comprise a port configured to provide access to the tissue thickness compensator. Referring to FIG. 532B, a staple cartridge 70500 may comprise a port 70505 at a distal end thereof, for example. The port 70505 may be configured to receive a needle 70510, such as a fenestrated needle shown in FIG. 532A. In at least one embodiment, the clinician may insert a needle 70510 through the port 70505 into the tissue thickness compensator 70515 to deliver the fluid to the tissue thickness compensator 70515. In various embodiments, the fluid may comprise a medicament and hydrogel precursor, for example. As described above, the fluid may be released from tissue thickness compensator to the tissue when the tissue thickness compensator is ruptured and/or compressed. For example, the medicament may be released from the tissue thickness compensator 70515 as the tissue thickness compensator 70515 biodegrades.

In various embodiments, referring now to FIG. 216, a staple cartridge, such as staple cartridge 10000, for example, can comprise a support portion 10010 and a compressible tissue thickness compensator 10020. Referring now to FIGS. 218-220, the support portion 10010 can comprise a deck surface 10011 and a plurality of staple cavities 10012 defined within the support portion 10010. Each staple cavity 10012 can be sized and configured to removably store a staple, such as a staple 10030, for example, therein. The staple cartridge 10000 can further comprise a plurality of staple drivers 10040 which can each be configured to support one or more staples 10030 within the staple cavities 10012 when the staples 10030 and the staple drivers 10040 are in their unfired positions. In at least one such embodiment, referring primarily to FIGS. 224 and 225, each staple driver 10040 can comprise one or more cradles, or troughs, 10041, for example, which can be configured to support the staples and limit relative movement between the staples 10030 and the staple drivers 10040. In various embodiments, referring again to FIG. 218, the staple cartridge 10000 can further comprise a staple-firing sled 10050 which can be moved from a proximal end 10001 to a distal end 10002 of the staple cartridge in order to sequentially lift the staple drivers 10040 and the staples 10030 from their unfired positions toward an anvil positioned opposite the staple cartridge 10000. In certain embodiments, referring primarily to FIGS. 218 and 220, each staple 10030 can comprise a base 10031 and one or more legs 10032 extending from the base 10031 wherein each staple can be at least one of substantially U-shaped and substantially V-shaped, for example. In at least one embodiment, the staples 10030 can be configured such that the tips of the staple legs 10032 are recessed with respect to the deck surface 10011 of the support portion 10010 when the staples 10030 are in their unfired positions. In at least one embodiment, the staples 10030 can be configured such that the tips of the staple legs 10032 are flush with respect to the deck surface 10011 of the support portion 10010 when the staples 10030 are in their unfired positions. In at least one embodiment, the staples 10030 can be configured such that the tips of the staple legs 10032, or at least some portion of the staple legs 10032, extend above the deck surface 10011 of the support portion 10010 when the staples 10030 are in their unfired positions. In such embodiments, the staple legs 10032 can extend into and can be embedded within the tissue thickness compensator 10020 when the staples 10030 are in their unfired positions. In at least one such embodiment, the staple legs 10032 can extend above the deck surface 10011 by approximately 0.075", for example. In various embodiments, the staple legs 10032 can extend above the deck surface 10011 by a distance between approximately 0.025" and approximately 0.125", for example. In certain embodiments, further to the above, the tissue thickness compensator 10020 can comprise an uncompressed thickness between approximately 0.08" and approximately 0.125", for example.

In use, further to the above and referring primarily to FIG. 233, an anvil, such as anvil, 10060, for example, can be moved into a closed position opposite the staple cartridge 10000. As described in greater detail below, the anvil 10060 can position tissue against the tissue thickness compensator 10020 and, in various embodiments, compress the tissue thickness compensator 10020 against the deck surface 10011 of the support portion 10010, for example. Once the anvil 10060 has been suitably positioned, the staples 10030 can be deployed, as also illustrated in FIG. 233. In various embodiments, as mentioned above, the staple-firing sled 10050 can be moved from the proximal end 10001 of the staple cartridge 10000 toward the distal end 10002, as illustrated in FIG. 234. As the sled 10050 is advanced, the sled 10050 can contact the staple drivers 10040 and lift the staple drivers 10040 upwardly within the staple cavities 10012. In at least one embodiment, the sled 10050 and the staple drivers 10040 can each comprise one or more ramps, or inclined surfaces, which can co-operate to move the staple drivers 10040 upwardly from their unfired positions. In at least one such embodiment, referring to FIGS. 221-225, each staple driver 10040 can comprise at least one inclined surface 10042 and the sled 10050 can comprise one or more inclined surfaces 10052 which can be configured such that the inclined surfaces 10052 can slide under the inclined surface 10042 as the sled 10050 is advanced distally within the staple cartridge. As the staple drivers 10040 are lifted upwardly within their respective staple cavities 10012, the staple drivers 10040 can lift the staples 10030 upwardly such that the staples 10030 can emerge from their staple cavities 10012 through openings in the staple deck 10011. During an exemplary firing sequence, referring primarily to FIGS. 227-229, the sled 10050 can first contact staple 10030*a* and begin to lift the staple 10030*a* upwardly. As the sled 10050 is advanced further distally, the sled 10050 can begin to lift staples 10030*b*, 10030*c*, 10030*d*, 10030*e*, and 10030*f*, and any other subsequent staples, in a sequential order. As illustrated in FIG. 229, the sled 10050 can drive the staples 10030 upwardly such that the legs 10032 of the staples contact the opposing anvil, are deformed to a desired shape, and ejected therefrom the support portion 10010. In various circumstances, the sled 10030 can move several staples upwardly at the same time as part of a firing sequence. With regard to the firing sequence illustrated in FIG. 229, the staples 10030*a* and 10030*b* have been moved into their fully fired positions and ejected from the support portion 10010, the staples 10030*c* and 10030*d* are in the process of being fired and are at least partially contained within the support portion 10010, and the staples 10030*e* and 10030*f* are still in their unfired positions.

As discussed above, and referring to FIG. 235, the staple legs 10032 of the staples 10030 can extend above the deck surface 10011 of the support portion 10010 when the staples 10030 are in their unfired positions. With further regard to this firing sequence illustrated in FIG. 229, the staples 10030*e* and 10030*f* are illustrated in their unfired position and their staple legs 10032 extend above the deck surface 10011 and into the tissue thickness compensator 10020. In various embodiments, the tips of the staple legs 10032, or any other portion of the staple legs 10032, may not protrude through a top tissue-contacting surface 10021 of the tissue thickness compensator 10020 when the staples 10030 are in their unfired positions. As the staples 10030 are moved from their unfired positions to their fired positions, as illustrated in FIG. 229, the tips of the staple legs can protrude through the tissue-contacting surface 10032. In various embodiments, the tips of the staple legs 10032 can comprise sharp tips which can incise and penetrate the tissue thickness compensator 10020. In certain embodiments, the tissue thickness compensator 10020 can comprise a plurality of apertures which can be configured to receive the staple legs 10032 and allow the staple legs 10032 to slide relative to the tissue thickness compensator 10020. In certain embodiments, the support portion 10010 can further comprise a plurality of guides 10013 extending from the deck surface 10011. The guides 10013 can be positioned adjacent to the staple cavity openings in the deck surface 10011 such that the staple legs 10032 can be at least partially supported by the guides 10013. In certain embodiments, a guide 10013 can be positioned at a proximal end and/or a distal end of a staple cavity opening. In various embodiments, a first guide 10013 can be positioned at a first end of each staple cavity opening and a second guide 10013 can be positioned at a second end of each staple cavity opening such that each first guide 10013 can support a first staple leg 10032 of a staple 10030 and each second guide 10013 can support a second staple leg 10032 of the staple. In at least one embodiment, referring to FIG. 235, each guide 10013 can comprise a groove or slot, such as groove 10016, for example, within which a staple leg 10032 can be slidably received. In various embodiments, each guide 10013 can comprise a cleat, protrusion, and/or spike that can extend from the deck surface 10011 and can extend into the tissue thickness compensator 10020. In at least one embodiment, as discussed in greater detail below, the cleats, protrusions, and/or spikes can reduce relative movement between the tissue thickness compensator 10020 and the support portion 10010. In certain embodiments, the tips of the staple legs 10032 may be positioned within the guides 10013 and may not extend above the top surfaces of the guides 10013 when the staples 10030 are in their unfired position. In at least such embodiment, the guides 10013 can define a guide height and the staples 10030 may not extend above this guide height when they are in their unfired position.

In various embodiments, a tissue thickness compensator, such as tissue thickness compensator 10020, for example, can be comprised of a single sheet of material. In at least one embodiment, a tissue thickness compensator can comprise a continuous sheet of material which can cover the entire top deck surface 10011 of the support portion 10010 or, alternatively, cover less than the entire deck surface 10011. In certain embodiments, the sheet of material can cover the staple cavity openings in the support portion 10010 while, in other embodiments, the sheet of material can comprise openings which can be aligned, or at least partially aligned, with the staple cavity openings. In various embodiments, a tissue thickness compensator can be comprised of multiple layers of material. In some embodiments, referring now to FIG. 217, a tissue thickness compensator can comprise a compressible core and a wrap surrounding the compressible core. In certain embodiments, a wrap 10022 can be configured to releasably hold the compressible core to the support portion 10010. In at least one such embodiment, the support portion 10010 can comprise one or more projections, such as projections 10014 (FIG. 220), for example, extending therefrom which can be received within one or more apertures and/or slots, such as apertures 10024, for example, defined in the wrap 10022. The projections 10014 and the apertures 10024 can be configured such that the projections 10014 can retain the wrap 10022 to the support portion 10010. In at least one embodiment, the ends of the projections 10014 can be deformed, such as by a heat-stake process, for example, in order to enlarge the ends of the projections 10014 and, as a result, limit the relative movement between the wrap 10022 and the support portion 10010. In at least one embodiment, the wrap 10022 can comprise one or more perforations 10025 which can facilitate the release of the wrap 10022 from the support portion 10010, as illustrated in FIG. 217. Referring now to FIG. 226, a tissue thickness compensator can comprise a wrap 10222 including a plurality of apertures 10223, wherein the apertures 10223 can be aligned, or at least partially aligned, with the staple cavity openings in the support portion 10010. In certain embodiments, the core of the tissue thickness compensator can also comprise apertures which are aligned, or at least partially aligned, with the apertures 10223 in the wrap 10222. In other embodiments, the core of the tissue thickness compensator can comprise a continuous body and can extend underneath the apertures 10223 such that the continuous body covers the staple cavity openings in the deck surface 10011.

In various embodiments, as described above, a tissue thickness compensator can comprise a wrap for releasably holding a compressible core to the support portion 10010. In at least one such embodiment, referring to FIG. 218, a staple cartridge can further comprise retainer clips 10026 which can be configured to inhibit the wrap, and the compressible core, from prematurely detaching from the support portion 10010. In various embodiments, each retainer clip 10026 can comprise apertures 10028 which can be configured to receive the projections 10014 extending from the support portion 10010 such that the retainer clips 10026 can be retained to the support portion 10010. In certain embodiments, the retainer clips 10026 can each comprise at least one pan portion 10027 which can extend underneath the support portion 10010 and can support and retain the staple drivers 10040 within the support portion 10010. In certain embodiments, as described above, a tissue thickness compensator can be removably attached to the support portion 10010 by the staples 10030. More particularly, as also described above, the legs of the staples 10030 can extend into the tissue thickness compensator 10020 when the staples 10030 are in their unfired position and, as a result, releasably hold the tissue thickness compensator 10020 to the support portion 10010. In at least one embodiment, the legs of the staples 10030 can be in contact with the sidewalls of their respective staple cavities 10012 wherein, owing to friction between the staple legs 10032 and the sidewalls, the staples 10030 and the tissue thickness compensator 10020 can be retained in position until the staples 10030 are deployed from the staple cartridge 10000. When the staples 10030 are deployed, the tissue thickness compensator 10020 can be captured within the staples 10030 and held against the stapled tissue T. When the anvil is thereafter moved into an open position to release the tissue T, the support portion 10010 can be moved away from the tissue thickness compensator 10020 which has been fastened to the tissue. In certain embodiments, an adhesive can be utilized to removably hold the tissue thickness compensator 10020 to the support portion 10010. In at least one embodiment, a two-part adhesive can be utilized wherein, in at least one embodiment, a first part of the adhesive can be placed on the deck surface 10011 and a second part of the adhesive can be placed on the tissue thickness compensator 10020 such that, when the tissue thickness compensator 10020 is placed against the deck surface 10011, the first part can contact the second part to active the adhesive and detachably bond the tissue thickness compensator 10020 to the support portion 10010. In various embodiments, any other suitable means could be used to detachably retain the tissue thickness compensator to the support portion of a staple cartridge.

In various embodiments, further to the above, the sled 10050 can be advanced from the proximal end 10001 to the distal end 10002 to fully deploy all of the staples 10030 contained within the staple cartridge 10000. In at least one embodiment, referring now to FIGS. 258-262, the sled 10050 can be advanced distally within a longitudinal cavity 10016 within the support portion 10010 by a firing member, or knife bar, 10052 of a surgical stapler. In use, the staple cartridge 10000 can be inserted into a staple cartridge channel in a jaw of the surgical stapler, such as staple cartridge channel 10070, for example, and the firing member 10052 can be advanced into contact with the sled 10050, as illustrated in FIG. 258. As the sled 10050 is advanced distally by the firing member 10052, the sled 10050 can contact the proximal-most staple driver, or drivers, 10040 and fire, or eject, the staples 10030 from the cartridge body 10010, as described above. As illustrated in FIG. 258, the firing member 10052 can further comprise a cutting edge 10053 which can be advanced distally through a knife slot in the support portion 10010 as the staples 10030 are being fired. In various embodiments, a corresponding knife slot can extend through the anvil positioned opposite the staple cartridge 10000 such that, in at least one embodiment, the cutting edge 10053 can extend between the anvil and the support portion 10010 and incise the tissue and the tissue thickness compensator positioned therebetween. In various circumstances, the sled 10050 can be advanced distally by the firing member 10052 until the sled 10050 reaches the distal end 10002 of the staple cartridge 10000, as illustrated in FIG. 260. At such point, the firing member 10052 can be retracted proximally. In some embodiments, the sled 10050 can be retracted proximally with the firing member 10052 but, in various embodiments, referring now to FIG. 261, the sled 10050 can be left behind in the distal end 10002 of the staple cartridge 10000 when the firing member 10052 is retracted. Once the firing member 10052 has been sufficiently retracted, the anvil can be re-opened, the tissue thickness compensator 10020 can be detached from the support portion 10010, and the remaining non-implanted portion of the expended staple cartridge 10000, including the support portion 10010, can be removed from the staple cartridge channel 10070.

After the expended staple cartridge 10000 has been removed from the staple cartridge channel, further to the above, a new staple cartridge 10000, or any other suitable staple cartridge, can be inserted into the staple cartridge channel 10070. In various embodiments, further to the above, the staple cartridge channel 10070, the firing member 10052, and/or the staple cartridge 10000 can comprise co-operating features which can prevent the firing member 10052 from being advanced distally a second, or subsequent, time without a new, or unfired, staple cartridge 10000 positioned in the staple cartridge channel 10070. More particularly, referring again to FIG. 258, as the firing member 10052 is advanced into contact with the sled 10050 and, when the sled 10050 is in its proximal unfired position, a support nose 10055 of the firing member 10052 can be positioned on and/or over a support ledge 10056 on the sled 10050 such that the firing member 10052 is held in a sufficient upward position to prevent a lock, or beam, 10054 extending from the firing member 10052 from dropping into a lock recess defined within the staple cartridge channel. As the lock 10054 will not drop into the lock recess, in such circumstances, the lock 10054 may not abut a distal sidewall 10057 of the lock recess as the firing member 10052 is advanced. As the firing member 10052 pushes the sled 10050 distally, the firing member 10052 can be supported in its upward firing position owing to the support nose 10055 resting on the support ledge 10056. When the firing member 10052 is retracted relative to the sled 10050, as discussed above and illustrated in FIG. 261, the firing member 10052 can drop downwardly from its upward position as the support nose 10055 is no longer resting on the support ledge 10056 of the sled 10050. In at least one such embodiment, the surgical staple can comprise a spring 10058, and/or any other suitable biasing element, which can be configured to bias the firing member 10052 into its downward position. Once the firing member 10052 has been completely retracted, as illustrated in FIG. 262, the firing member 10052 cannot be advanced distally through the spent staple cartridge 10000 once again. More particularly, the firing member 10052 can't be held in its upper position by the sled 10050 as the sled 10050, at this point in the operating sequence, has been left behind at the distal end 10002 of the staple cartridge 10000. Thus, as mentioned above, in the event that the firing member 10052 is advanced once again without replacing the staple cartridge, the lock beam 10054 will contact the sidewall 10057 of the lock recess which will prevent the firing member 10052 from being advanced distally into the staple cartridge 10000 once again. Stated another way, once the spent staple cartridge 10000 has been replaced with a new staple cartridge, the new staple cartridge will have a proximally-positioned sled 10050 which can hold the firing member 10052 in its upper position and allow the firing member 10052 to be advanced distally once again.

As described above, the sled 10050 can be configured to move the staple drivers 10040 between a first, unfired position and a second, fired position in order to eject staples 10030 from the support portion 10010. In various embodiments, the staple drivers 10040 can be contained within the staple cavities 10012 after the staples 10030 have been ejected from the support portion 10010. In certain embodiments, the support portion 10010 can comprise one or more retention features which can be configured to block the staple drivers 10040 from being ejected from, or falling out of, the staple cavities 10012. In various other embodiments, the sled 10050 can be configured to eject the staple drivers 10040 from the support portion 10010 with the staples 10030. In at least one such embodiment, the staple drivers 10040 can be comprised of a bioabsorbable and/or biocompatible material, such as Ultem, for example. In certain embodiments, the staple drivers can be attached to the staples 10030. In at least one such embodiment, a staple driver can be molded over and/or around the base of each staple 10030 such that the driver is integrally formed with the staple. U.S. patent application Ser. No. 11/541,123, entitled SURGICAL STAPLES HAVING COMPRESSIBLE OR CRUSHABLE MEMBERS FOR SECURING TISSUE THEREIN AND STAPLING INSTRUMENTS FOR DEPLOYING THE SAME, filed on Sep. 29, 2006, now U.S. Pat. No. 7,794,475, is hereby incorporated by reference in its entirety.

In various circumstances, further to the above, a compressible tissue thickness compensator can move, twist, and/or deflect relative to the underlying rigid support portion of a staple cartridge. In various embodiments, the support portion, and/or any other suitable portion of the staple cartridge, can comprise one or more features configured to limit relative movement between the tissue thickness compensator and the support portion. As described above, at least a portion of the staples 10030 can extend above the deck surface 10011 of the support portion 10010 wherein, in certain circumstances, referring now to FIGS. 263 and 264, lateral forces applied to a tissue thickness compensator 10120, for example, can be resisted by the staples 10030 and/or the cleats 10013 extending from the support portion 10010, for example. In various circumstances, the staples 10030 may tilt and/or bend within the staple cavities 10012 while resisting the lateral movement of the tissue thickness compensator 10120 wherein, in various embodiments, the staple cavities 10012 and the staples 10030 can be sized and configured to maintain the relative alignment between the legs 10032 of the staples 10030 and the forming pockets 10062 in the opposing anvil 10060 such that the staples 10000 are properly formed during the staple forming process. In various embodiments, the staples 10030 and/or the cleats 10013 can be configured to prevent or at least limit lateral distortion within the tissue thickness compensator 10020, as illustrated in FIG. 264. In at least one such embodiment, the staples 10030 and/or cleats 10013, for example, can be configured to stiffen, or limit the lateral and/or longitudinal movement of, a first, or tissue-contacting, surface 10021 of the tissue thickness compensator relative to a second, or bottom, surface 10029. In various embodiments, a staple cartridge, and/or a staple cartridge channel in which the staple cartridge is positioned, can comprise at least one distortion minimizing member which can extend upwardly to limit the lateral and/or longitudinal movement, or distortion, of a tissue thickness compensator. A wrap at least partially surrounding a tissue thickness compensator, as discussed above, may also prevent, or at least limit, the lateral and/or longitudinal movement, or distortion, of the tissue thickness compensator.

In various embodiments, referring again to FIGS. 263 and 264, a tissue thickness compensator, such as tissue thickness compensator 10120, for example, can comprise a core 10128 and a skin 10122. The skin 10122 and the compressible core 10128 can be comprised of different materials or, alternatively, of the same material. In either event, the skin 10122 can have a higher density than the core 10128. In circumstances where the skin 10122 comprises the top of the tissue thickness compensator 10120, the tips of the staple legs 10032 can be embedded in the skin 10122. In embodiments wherein a skin comprises the bottom of the tissue thickness compensator 10120, the staple legs 10032 can extend through the skin and into the core. In either event, the skin of the tissue thickness compensator can assist in holding the staple legs 10032 in alignment with the forming pockets 10062 of the anvil 10060. In various embodiments, the skin 10122 can comprise a density which is approximately 10% greater than the density of the core 10128, approximately 20% greater than the density of the core 10128, approximately 30% greater than the density of the core 10128, approximately 40% greater than the density of the core 10128, approximately 50% greater than the density of the core 10128, approximately 60% greater than the density of the core 10128, approximately 70% greater than the density of the core 10128, approximately 80% greater than the density of the core 10128, approximately 90% greater than the density of the core 10128, and/or approximately 100% greater than the density of the core 10128, for example. In various embodiments, the skin 10122 can comprise a density which is more than the density of the core 10128 and less than twice the density of the core 10128, for example. In various embodiments, the skin 10122 can comprise a density which is over twice the density of the core 10128, for example. In various embodiments, further to the above, the skin 10122 and the core 10128 can be formed, or manufactured, simultaneously. In at least one such embodiment, a fluid comprising any suitable material disclosed herein can be poured into a dish or mold and, while the fluid solidifies, the fluid can form a skin, or layer, which has a higher density than the remainder of the material. In various embodiments, multiple layers within a material can be formed by utilizing a process in which one or more subsequent layers of material are poured onto a previously cured layer. In certain embodiments, two or more layers can be bonded to each other with an adhesive, for example. In some embodiments, two or more layers can be attached to each other by one or more fasteners and/or one or more mechanical interlocking features, for example. In at least one such embodiment, adjacent layers can be connected together by one or more dovetail joints, for example. In certain embodiments, the skin can comprise a sealed surface which can prevent, or at least limit, the flow of fluid therethrough. In certain other embodiments, the skin can comprise an open cell porous structure, for example.

In various embodiments, further to the above, the skin can be cut off of the tissue thickness compensator. In at least one embodiment, the tissue thickness compensator can be cut from a larger block of material such that the tissue thickness compensator does not comprise a skin. In at least one such embodiment, the tissue thickness compensator can be comprised of a homogenous, or at least substantially homogeneous, material, comprising large pores, for example.

In various embodiments, a staple cartridge can comprise a plurality of staple cavities each containing a staple positioned therein wherein the staple cavities can be arranged in a plurality of rows, and wherein an anvil positioned opposite the staple cartridge can comprise a plurality of forming pockets which correspond to the staple cavities in the staple cartridge. Stated another way, the anvil can comprise a plurality of forming pocket rows wherein each forming pocket can be positioned opposite a staple cavity in the staple cartridge. In various embodiments, each forming pocket can comprise two forming cups configured to receive the staple legs 10032 of a staple 10030 wherein each forming cup is configured to receive a staple leg 10032 and form or curl the staple leg 10032 toward the other staple leg 10032, for example. In various circumstances, the legs 10032 may miss or not properly enter into the forming cups and, as a result, the staple legs 10032 may become malformed during the firing sequence. In various embodiments described herein, an anvil can comprise an array, or grid, of forming pockets which are each configured to receive and form a staple leg. In at least one such embodiment, the array of forming pockets can comprise a quantity of forming pockets that exceeds the quantity of staples contained within the staple cartridge. In at least one embodiment, a staple cartridge can comprise six longitudinal rows of staple cavities, for example, wherein the anvil can comprise six rows of forming pockets aligned with the six rows of staple cavities and, in addition, forming pockets positioned intermediate the rows of forming pockets. For example, on one side of the anvil, the anvil can comprise a first row of forming pockets which can be positioned over a first row of staple cavities, a second row of forming pockets which can be positioned over a second row of staple cavities that is adjacent to the first row of staple cavities, and, in addition, a row of forming pockets positioned intermediate the first row of forming pockets and the second row of forming pockets. In various embodiments, referring now to FIGS. 276-279, an anvil 10260 can comprise six rows of forming pockets 10261 which can be configured to be placed over six corresponding rows of staple cavities in the staple cartridge 10200. In at least one such embodiment, rows of intermediate forming pockets 10262 can be positioned intermediate and/or adjacent to the rows of forming pockets 10261. In certain embodiments, referring now to FIGS. 277, 278, and 280, each forming pocket 10261 and 10262 can comprise two forming cups, wherein each forming cup can comprise a distal portion 10263 which can be configured to form or curl a staple leg 10032 proximally and a proximal portion 10264 which can be configured to form or curl a staple leg 10032 distally. In various other circumstances, the staples 10030 can be formed in a variety of other ways. For example, a staple 10030 can be formed such that one leg 10032 is formed outwardly and the other leg 10032 is formed inwardly (FIG. 281), or such that both legs 10032 are formed outwardly (FIG. 282) depending on, one, which forming cups that the staple legs 10032 enter into and/or, two, whether the legs 10032 enter into the proximal portion 10263 or the distal portion 10064 of each forming cup, for example.

In various embodiments, further to the above, each forming pocket 10261 and/or forming pocket 10262 can comprise a triangular or diamond-like shape, for example. In at least one embodiment, each distal portion 10263 and/or each proximal portion 10264 of the forming pockets can comprise a triangular shape wherein, in at least one such embodiment, the triangular shapes of the distal portions 10263 and the proximal portions 10264 can be arranged such that they have vertices pointing in opposite directions. In certain embodiments, an anvil can comprise an array of substantially square forming pockets, for example. In at least one such embodiment, the forming surface of each square forming pocket can comprise an arcuate surface that extends between the sides of the square. In some embodiments, an anvil can comprise an array of circular or spherical dimples, for example. In various embodiments, further to the above, the forming pockets 10261 can be positioned along one or more lines and, similarly, the forming pockets 10262 can also be positioned along one or more lines. In various other embodiments, the forming pockets 10261 and/or the forming pockets 10262 can be arranged in one or more circular rows. In at least one such embodiment, the forming pockets 10261 can be arranged along a primary circumference and the forming pockets 10262 can be arranged along a different circumference. In various embodiments, the primary circumference and the different circumference can be concentric, or at least substantially concentric. In certain embodiments, the forming pockets 10262 can be arranged along an inner circumference positioned radially inwardly with respect to the primary circumference and/or an outer circumference positioned radially outwardly with respect to the primary circumference, for example. In various embodiments, the primary circumference can be defined by a primary diameter, the inner circumference can be defined by an inner diameter, and the outer circumference can be defined by an outer diameter. In at least one such embodiment, the inner diameter can be shorter than the primary diameter and the outer diameter can be longer than the primary diameter.

In various embodiments, as described above, an anvil can be moved from an open position to a closed position in order to compress tissue against the tissue thickness compensator of a staple cartridge, such as tissue thickness compensator 10020, for example. In various circumstances, the tissue thickness compensator can be positioned adjacent to the support portion of the staple cartridge prior to the tissue thickness compensator being positioned relative to the tissue. In certain embodiments, the tissue thickness compensator 10020 can be in a position in which it abuts the support portion 10018 prior to the anvil being moved into its closed position. In certain other embodiments, the tissue thickness compensator 10020 can be in a position in which a gap is present between the tissue thickness compensator 10020 and the support portion 10018. In at least one such embodiment, the anvil can displace the tissue and the tissue thickness compensator 10020 downwardly until the tissue thickness compensator 10020 abuts the support portion 10018 wherein, at such point, the anvil can be moved into is closed position and generate compression within the tissue. In the event that a surgeon is not satisfied with the positioning of the tissue between the anvil and the staple cartridge, the surgeon can open the anvil, adjust the position of the anvil and the staple cartridge, and close the anvil once again. Owing to such positioning and re-positioning of the staple cartridge relative to the tissue, in various circumstances, the distal end of the tissue thickness compensator 10020 may become dislodged from the support portion 10010, for example. In some such circumstances, the distal end of the tissue thickness compensator 10020 can contact the tissue and peel away from, or roll relative to, the support portion 10010. In various embodiments, as described in greater detail below, a staple cartridge can comprise one or more features configured to releasably retain a tissue thickness compensator to an underlying support portion of the staple cartridge.

In various embodiments, referring now to FIG. 265, a staple cartridge 10300 can comprise a support portion 10310, a tissue thickness compensator 10320 supported by the support portion 10310, and a distal end 10302 which includes a nose 10303 configured to releasably hold a distal end 10325 of the tissue thickness compensator 10320 in position. In at least one embodiment, the nose 10303 can comprise a slot 10305 configured to receive the distal end 10325 of the tissue thickness compensator 10320. In various embodiments, the distal end 10325 can be compressed, or wedged, within the slot 10305 such that the distal end 10325 can be held in place as the staple cartridge 10300 is positioned relative to the tissue. In at least one such embodiment, the slot 10305 can be oriented in a direction which is parallel, or at least substantially parallel, to the deck surface 10311 of the support portion 10310. In various embodiments, the slot 10305 can be horizontal with respect to the deck surface 10311. In various other embodiments, referring now to FIG. 266, a staple cartridge 10400 can comprise a support portion, a tissue thickness compensator 10420 supported by support portion, and a distal end 10402 which includes a nose 10403 configured to releasably hold the distal end 10425 of the tissue thickness compensator 10420 in position. In at least one embodiment, the distal end 10425 can comprise a projection extending therefrom and the nose 10403 can comprise a vertical slot 10405 configured to receive the projection of the distal end 10425. In various embodiments, the distal end 10425, and/or the projection extending therefrom, can be compressed, or wedged, within the slot 10405 such that the distal end 10425 can be held in place as the staple cartridge 10400 is positioned relative to the tissue. In certain embodiments, the tissue thickness compensator 10420 can comprise a slot, such as slot 10429, for example, which can be configured to receive at least a portion of the nose 10403 therein. In at least one embodiment, the slot 10405 can be oriented in a direction which is perpendicular, or at least substantially perpendicular, to the deck surface 10411 of the support portion. In various embodiments, referring now to FIG. 267, a staple cartridge 10500 can comprise a support portion, a tissue thickness compensator 10520 supported by the support portion, and a distal end 10502 which includes a nose configured to releasably hold the distal end 10525 of the tissue thickness compensator 10520 in position. In at least one embodiment, the nose can comprise a vertical slot 10505 configured to receive the distal end 10525 of the tissue thickness compensator 10520. In various embodiments, the distal end 10525 can be compressed, or wedged, within the slot 10505 such that the distal end 10525 can be held in place as the staple cartridge 10500 is positioned relative to the tissue.

In various embodiments, referring again to FIG. 265, the tissue thickness compensator 10320 can comprise a top surface 10324 which can be positioned above the top surface 10304 of the nose 10303. Another exemplary embodiment in which the top surface of a tissue thickness compensator is positioned above the nose of the staple cartridge is illustrated in FIG. 238, wherein the top surface 10721 of the tissue thickness compensator 10720 is positioned above the top surface 10004 of the nose 10003, for example. In use, referring once again to FIG. 265, tissue can slide over the top surface 10304 of the nose 10303 and, in some circumstance, the tissue can contact the distal end 10325 of the tissue thickness compensator 10320 and can apply a force to the tissue thickness compensator 10320 tending to peel the tissue thickness compensator 10320 away from the support portion 10310. In the embodiments described herein, this peel force can be resisted by the portion of the distal end 10325 wedged within the nose 10303. In any event, once the tissue has been suitably positioned relative to the staple cartridge 13000, an anvil can be rotated into a closed position to compress the tissue and the tissue thickness compensator 10320 against the support portion 10310. In at least one such embodiment, the anvil can be rotated into a position in which the anvil contacts the top surface 10304 of the nose 10303 and, as a result, the anvil can be prevented from rotating further. In various circumstances, owing to the top surface 10324 of the tissue thickness compensator 10320 being positioned above the top surface 10304 of the nose 10303, the top surface 10324 can be pushed downwardly toward the support portion 10310 as the anvil is being closed and, in some circumstances, the top surface 10324 can be pushed below the top surface 10304 of the nose 10303, for example. After the staples contained within the staple cartridge 10300 have been deployed and the tissue thickness compensator 10320 has been incised, as described herein, the support portion 10310 and the nose 10303 can be moved away from the tissue thickness compensator 10320 such that the distal end 10325 of the tissue thickness compensator 10320 can slide out of the slot 10305.

As described above, an anvil, such as anvil 10060, for example, can be rotated into a closed position in which the anvil 10060 contacts the top nose surface 10004 of a staple cartridge, such as staple cartridge 10000, for example. Once the anvil has reached its closed position, the amount in which a tissue thickness compensator, such as tissue thickness compensator 10020, for example, is compressed will depend on, among other things, the uncompressed thickness, or height, of the tissue thickness compensator and the thickness of the tissue. Referring now to FIGS. 236 and 237, a tissue thickness compensator 10920 can comprise a top surface which is flush, or at least substantially flush, with the top surface 10004 of the nose 10003. In such embodiments, the top surface of the tissue thickness compensator 10920 can be pushed below the top surface 10004 of the nose 10003. Referring now to FIGS. 241 and 242, a tissue thickness compensator, such as tissue thickness compensator 10820, for example, can comprise a top surface 10821 which is positioned below the top nose surface 10004 prior to the tissue thickness compensator 10820 being compressed by the tissue T and anvil 10060. In the circumstances where the tissue T is relatively thin, as illustrated in FIGS. 239 and 240, the tissue thickness compensator 10920 may undergo relatively little compression. Referring now to FIGS. 241 and 242, the tissue thickness compensator 10820 may undergo a larger compression when the tissue T is relatively thicker. In the circumstances where the tissue T has both thin sections and thicker sections, as illustrated in FIGS. 243 and 244, the tissue thickness compensator 10820 may be compressed a larger amount when it is positioned under the thicker tissue T and a lesser amount when it is positioned under the thinner tissue T, for example. In this way, as described above, the tissue thickness compensator can compensate for different tissue thicknesses.

In various embodiments, referring now to FIGS. 268-270, a surgical stapling instrument can comprise, one, a cartridge channel 16670 configured to receive a staple cartridge 16600 and, two, an anvil 16660 pivotably coupled to the cartridge channel 16670. The staple cartridge 16600 can comprise a support portion 16610 and a tissue thickness compensator 16620 wherein a distal end 16625 of the tissue thickness compensator 16620 can be releasably held to the support portion 16610 by a nose 16603 at the distal end 16602 of the staple cartridge 16600. In at least one embodiment, the nose 16603 can comprise a slot 16605 and can be comprised of a flexible material. In use, referring primarily to FIG. 269, the nose 16603 can be flexed downwardly in order to expand the opening of slot 16605. In certain embodiments, the nose 16603 can comprise notches or cut-outs 16606 which can be configured to permit the nose 16603 to flex downwardly. In any event, in various circumstances, the expanded opening of the slot 16605 can facilitate the insertion of the distal end 16625 of the tissue thickness compensator 16620 into the slot 16605. Once the tissue thickness compensator 16620 has been suitably positioned, the nose 16603 can be released and, owing to the resiliency of the material comprising the nose 16603, the nose 16603 can return, or at least substantially return, to its unflexed condition and trap the distal end 16625 of the tissue thickness compensator 16620 against the deck surface 16611, as illustrated in FIG. 270. In use, similar to the above, the distal end 16625 can be pulled out of the slot 16605 when the support portion 16610 is moved away from the stapled tissue. In various circumstances, the flexible nose 16603 can be configured to deflect as the tissue thickness compensator 16620 is detached from the support portion 16610. In various embodiments, referring again to FIG. 270, the tissue thickness compensator 16620 can comprise a top surface 16621 which is aligned, or at least substantially aligned, with a top surface 16604 of the nose 16603.

In various embodiments, referring to FIG. 271, a surgical stapling instrument can comprise, one, a channel 10770 configured to receive a staple cartridge 10700 and, two, an anvil 10760 rotatably coupled to the channel 10770. The staple cartridge 10700 can comprise a support portion 10710 and a tissue thickness compensator 10720. In various embodiments, the tissue thickness compensator 10720 can be held in position by a nose sock 10703 which can be slid over the support portion 10710. In at least one embodiment, referring primarily to FIG. 272, the nose sock 10703 can comprise one or more side slots 10707 which can be configured to removably receive one or more attachment rails extending along the support portion 10710, for example. In various embodiments, the tissue thickness compensator 10720 can be positioned intermediate the side slots 10707. In certain embodiments, the nose sock 10703 can further comprise a distal end 10702 and a cavity 10706 defined in the distal end 10702 wherein the cavity 10706 can also be configured to receive at least a portion of the support portion 10710, for example, therein. In use, the nose sock 10703 can be slid onto the support portion 10710 in a distal to proximal direction. In various embodiments, the tissue thickness compensator 10720 can be removably mounted to the nose sock 10703 such that, after staples have been fired through the tissue thickness compensator 10720, the tissue thickness compensator 10720 can detach from the nose sock 10703 as the support portion 10710 and the nose sock 10703 are moved away from the tissue thickness compensator 10720. In various embodiments, the top surface 10721 of the tissue thickness compensator 10720 can be positioned below the top surface 10704 of the nose 10703.

In various embodiments, referring now to FIGS. 273 and 274, a surgical stapling instrument can comprise, one, a staple cartridge channel 11070 configured to receive a staple cartridge 11000 and, two, an anvil 11060 rotatably coupled to the channel 11070. The staple cartridge 11000 can comprise a support portion 11010 and a tissue thickness compensator 11020. In various embodiments, the tissue thickness compensator 11020 can be held in position by a one or more longitudinal rails 11019 extending from the deck 11011 of the support portion 11010. In at least one embodiment, the longitudinal rails 11019 can be embedded within the tissue thickness compensator 11020. In certain embodiments, referring primarily to FIG. 274, the tissue thickness compensator 11020 can comprise a longitudinal recess 11029 which can be configured to receive the longitudinal rails 11019. In at least one such embodiment, the recess 11029 can be sized and configured to receive the rails 11019 in a press-fit arrangement, for example. Such features, further to the above, can be configured to prevent, or at least limit, relative lateral movement between the tissue thickness compensator 11020 and the support portion 11010 and, in addition, limit the pre-mature release of the tissue thickness compensator 11020 from the support portion 11010, for example. In various embodiments, referring now to FIG. 275, a surgical stapling instrument can comprise, one, a staple cartridge channel 11170 configured to receive a staple cartridge 11100 and, two, an anvil 11160 rotatably coupled to the channel 11170. The staple cartridge 11100 can comprise a support portion 11110 and a tissue thickness compensator 11120. In various embodiments, the tissue thickness compensator 11120 can be held in position by one or more longitudinal rows of spikes, or teeth, 11119 extending from the deck 11111 of the support portion 11110. In at least one embodiment, the longitudinal rows of spikes 11119 can be embedded within the tissue thickness compensator 11120.

With regard to the embodiment illustrated in FIG. 273, further to the above, the tissue thickness compensator 11020 of the staple cartridge 11000 can be progressively released from the support portion 11010 as the staples are ejected from the staple cavities 10012 defined therein. More particularly, further to the above, the staples positioned in the staple cavities 10012 can be ejected sequentially between the proximal end 11001 of the staple cartridge 11000 and the distal end 11002 of the staple cartridge 11000 such that, as the staples are being ejected, the staples can apply an upward biasing force to the tissue thickness compensator 11020 which acts to push the tissue thickness compensator 11020 off of the rails 11019. In such circumstances, the proximal end 11006 of the tissue thickness compensator 11020 can be released from the support portion 11010 as the staples are ejected from the proximal-most staple cavities 10012. The tissue thickness compensator 11020 can then be progressively released from the support portion 11010 as the staples are progressively ejected from the support portion 11010 between the proximal end 11001 and the distal end 11002 of the staple cartridge 11000. When the staples positioned within the distal-most staple cavities 10012 are ejected from the support portion 11010, the distal end 11007 of the tissue thickness compensator 11020 can be released from the support portion 11010. With regard to the embodiment illustrated in FIG. 275, the tissue thickness compensator 11120 can be progressively released from the spikes 1119 extending from the support portion 11110 as the staples are progressively ejected from the staple cartridge between the proximal end 11101 and the distal end 11102.

As discussed above, a tissue thickness compensator can be progressively released from the support portion of a staple cartridge as the staples are progressively ejected from the support portion and contact the tissue thickness compensator. In various embodiments, the legs of the staple, such as staple legs 10032, for example, may be able to pass through the tissue thickness compensator without releasing the tissue thickness compensator from the support portion. In such embodiments, the tissue thickness compensator may remain engaged with the support portion until the bases of the staples, such as bases 10031, contact the tissue thickness compensator and push it upwardly. In various embodiments, however, cleats and/or other retention features extending from the support portion, for example, may oppose the release of the tissue thickness compensator from the support portion. In certain embodiments, as described in greater detail below, a support portion can comprise retention features which can be configured to progressively release a tissue thickness compensator from the support portion as the staples are progressively fired from the staple cartridge. Referring now to FIG. 283, a staple cartridge, such as staple cartridge 11200, for example, can comprise a support portion 11210 including retention features 11213 which can be configured to releasably hold a tissue thickness compensator 11220 (FIG. 284) to the support portion 11210. In various embodiments, the retention features 11213 can be positioned at the ends of each staple cavity 11212, for example, wherein each retention feature 11213 can comprise a guide groove 11216 defined therein which is configured to slidably receive a staple leg 10032 of a staple 10030. In such embodiments, both the staple legs 10032 and the retention features 11213 can be configured to releasably retain the tissue thickness compensator 11220 to the support portion 11210. In use, referring now to FIG. 284, staple drivers 10040 contained within the support portion 11210 can be driven upwardly by a sled 10050, as described above, wherein the staple drivers 10040 can be configured to contact the retention features 11213, at least partially detach the retention features 11213 from the support portion 11210, and displace the retention features 11213 outwardly and away from the staples 10030 and the staple cavities 11212. When the retention features 11213 are detached from the support portion 11210 and/or displaced outwardly, as illustrated in FIG. 284, the retention features 11213 may no longer be able to retain the tissue thickness compensator 11220 to the support portion 11210 and, as a result, the tissue thickness compensator 11220 can be released from the support portion 11210. Similar to the above, the tissue thickness compensator 11220 can be progressively released from the support portion 11210 as the staples 10030 are progressively ejected from the staple cartridge toward an anvil, such as anvil 11260, for example. In various embodiments, the staple drivers 10040 may contact the retention features 11213 when the top surfaces of the staple drivers 10040 become co-planar, or at least substantially co-planar, with the deck surface 11211 of the support portion 11210, for example. In such embodiments, the tissue thickness compensator 11220 may be released from the support portion 11210 at the same time as and/or just before the staples 10030 are formed to their fully-formed, or fully-fired, configuration. In at least one such embodiment, referring primarily to FIG. 285, the drivers 10040 can be overdriven such that they are pushed above the deck surface 11211 to fully form the staples 10030 and, during the process of being overdriven, break the retention features 11213 away from the support portion 11210. In various embodiments, referring again to FIG. 284, the retention features 11213 may extend over, or overhang, into the staple cavities 11212 prior to being detached or displaced outwardly such that the drivers 10040 can contact the retention features 11213 just as the drivers 10040 reach the deck surface 11211. In any event, once the tissue thickness compensator 11220 has been released from the support portion 11210, referring now to FIG. 285, the support portion 11210 can be moved away from the implanted tissue thickness compensator 11220.

As described above, a compressible tissue thickness compensator of a staple cartridge can be progressively released from a support portion, or cartridge body, of the staple cartridge as the staples are fired, or deployed, from the staple cartridge. In various circumstances, such a release can comprise a progressive loosening of the tissue thickness compensator from the support portion wherein, in some circumstances, a complete detachment of the tissue thickness compensator from the support portion may not occur until the anvil is opened and the support portion is moved away from the implanted tissue thickness compensator. In various embodiments, referring now to FIG. 289, a staple cartridge, such as staple cartridge 11300, for example, can comprise a tissue thickness compensator 11320 which is releasably retained to a support portion 11310. In at least one embodiment, the support portion 11310 can comprise a plurality of retention members 11313 extending therefrom which are configured to releasably compress and hold the longitudinal sides of the tissue thickness compensator 11320 to the support portion 11310. In at least one such embodiment, each retention member 11313 can comprise an inwardly-facing channel or slot 11316 which can be configured to receive the longitudinal sides of the tissue thickness compensator 11320 therein. In various circumstances, a plurality of retention members 11313 can extend along a first longitudinal side of the support portion 11310 and a plurality of retention members 11313 can extend along a second longitudinal side of the support portion 11310 wherein, in certain circumstances, the retention members 11313 can be configured to prevent, or at least limit, relative lateral movement between the tissue thickness compensator 11320 and the support portion 11310 and, in addition, prevent, or at least limit, the premature release of the tissue thickness compensator 11320 from the support portion 11310. In various embodiments, the retention members 11313 can be integrally formed with the support portion 11310 and, in at least one embodiment, referring to FIG. 290, the retention members 11313 can be configured to detach, or at least partially detach, from the support portion 11310 in order to allow the tissue thickness compensator 11320 to detach from the support portion 11310, as illustrated in FIG. 291, for example. In certain embodiments, an anvil, such as anvil 11360, for example, can be configured to compress the tissue thickness compensator 11320 and, in response to pressure generated within the tissue thickness compensator 11320, the tissue thickness compensator 11320 can expand laterally to at least partially detach, or disengage, the retention members 11313 from the tissue thickness compensator 11320. In various embodiments, the advancement of a knife member, discussed above, through the anvil 11360 and the staple cartridge 11300 can deploy the staples contained therein and, simultaneously, squeeze the anvil 11360 and the staple cartridge 11300 closer to one another which can apply an added compressive pressure to the tissue thickness compensator 11320 and thereby cause the retention members 11313 to sequentially detach as the knife member passes through the staple cartridge 11300.

In various embodiments, referring now to FIGS. 292-294, a staple cartridge, such as staple cartridge 11400, for example, can comprise a tissue thickness compensator 11420 removably attached to a support portion 11410. In at least one embodiment, the staple cartridge 11400 can comprise one or more retainer bars 11413 which can be configured to hold the longitudinal sides of the tissue thickness compensator 11420 to the deck surface 11411. In at least one such embodiment, each retainer bar 11413 can comprise opposing arms 11418 which can define a channel 11416 therebetween. In such embodiments, one of the arms 11418 can be configured to extend over the tissue thickness compensator 11420 and the other arm 11418 can be configured to extend under a lip 11419 extending from the support portion 11410. Referring primarily to FIG. 292, the channel 11416 of each retainer bar 11413 can be sized and configured to apply a compressive force to the longitudinal sides of the tissue thickness compensator 11420 prior to the staple cartridge 11400 being used. During use, referring primarily to FIG. 293, the staple cartridge 11400 can be positioned within a staple cartridge channel and, once the staple cartridge 11400 has been suitably positioned, an anvil, such as anvil 11460, for example, can be moved into a position in which it can compress the tissue thickness compensator 11420. Similar to the above, the thickness tissue compensator 11420, when compressed, can expand laterally, or outwardly, and, as a result, detach the retainer bars 11413 from the staple cartridge 11400. In certain other embodiments, the closing of the anvil 11460 may not detach, or may not completely detach, the retainer bars 11413 from the staple cartridge. In at least one such embodiment, the advancement of a firing bar, described above, through the staple cartridge 11400 can deploy the staples 10030 from the support portion 11410 and, simultaneously, squeeze the anvil 11460 and the staple cartridge 11400 closer together to apply a compressive force to the tissue thickness compensator 11420 that is sufficient to cause the tissue thickness compensator 11420 to expand laterally and detach the retainer bars 11413 from the staple cartridge 11400. Once the retainer bars 11413 have been detached from the staple cartridge 11400, referring to FIG. 294, the support portion 11410 can be moved away from the implanted tissue thickness compensator 11420 and removed from the surgical site. In certain alternative embodiments, referring now to FIG. 295, a staple cartridge 11400' can comprise retainer bars 11413' which, similar to the above, can comprise arms 11418' extending therefrom. In at least one such embodiment, each of the arms 11418' can comprise a wedge-lock bevel 11417' which can be configured to releasably latch the retainer bars 11413' to the staple cartridge 11400'. More particularly, in at least one embodiment, the support portion 11410' of the staple cartridge 11400' can comprise undercuts 11419' which, in co-operation with the wedge-lock bevels 11417', can be configured to releasably retain the retainer bars 11413' to the staple cartridge 11400 and inhibit the tissue thickness compensator 11420 from being prematurely detached from the support portion 11410'. During use, similar to the above, the retainer bars 11413' can be detached from the staple cartridge 11400' when a sufficient compressive force is applied to the tissue thickness compensator 11420, for example.

In various circumstances, as described above and referring again to FIGS. 259 and 260, the sled 10050 of the staple cartridge 10000 and the firing member 10052 of a surgical stapling instrument can be moved from the proximal end 10001 of the staple cartridge 10000 to the distal end 10002 (FIG. 219) of the staple cartridge 10000 in order to deploy the staples 10030 from the support portion 10010. In at least one such circumstance, each staple 10030 can be moved from an unfired position to a fired position and ejected from the support portion 10010 to capture the entirety of the tissue thickness compensator 10020 against the tissue positioned between the anvil 10060 and the staple cartridge 10000. In certain circumstances, a surgeon may not need to fire all of the staples 10030 from the staple cartridge 10000 and the surgeon may stop the progression of the sled 10050 and the firing bar 10052 at a point located intermediate the proximal end 10001 and the distal end 10002 of the staple cartridge 10000. In such circumstances, the tissue thickness compensator 10020 may only be partially implanted to the tissue T and, in order to detach the unimplanted portion of the tissue thickness compensator 10020 from the support portion 10010, the surgeon can pull the support portion 10010 away from the partially implanted tissue thickness compensator 10020 such that the unimplanted portion peels or pulls off of the support portion 10010. While such embodiments are suitable in various circumstances, an improvement is illustrated in FIGS. 300-302 wherein a tissue thickness compensator, such as tissue thickness compensator 11520 of staple cartridge 11500, for example, can comprise a plurality of connected segments which can be configured to detach from one another. In at least one such embodiment, the tissue thickness compensator 11520 can comprise a first, or proximal-most, segment **11520*a*, a second segment 11520*b* removably connected to the first segment 11520*a*, a third segment 11520*c* removably connected to the second segment 11520*b*, a fourth segment 11520*d* removably connected to the third segment 11520*c*, and a fifth segment 11520*e* removably connected to the fourth segment 11520*d*, for example. In various embodiments, the tissue thickness compensator 11520 can comprise at least one thin section 11529 positioned intermediate any two adjacent segments 11520*a*-11520*e* which can be configured to define a predetermined rupture or separation point in which the tissue thickness compensator segments can separate from one another. In certain embodiments, a tissue thickness compensator can include any suitable arrangement of perforations, thin sections, and/or any other means for creating a separation point within the tissue thickness compensator. Referring primarily to FIG. 301, an anvil 11560 is illustrated in a closed position and the firing member 10052 is illustrated as having been partially advanced through the staple cartridge 11500 such that the staples 10030 underlying the first segment 11520*a*, the second segment 11520*b*, and the third segment 11520*c* have been fired to capture the tissue thickness compensator 11520 against the tissue T. In such a position, the firing member 10052 has not yet been advanced to deploy the staples 10030 underlying the fourth segment 11520*d* and the fifth segment 11520*e*, for example. Referring now to FIG. 302, the anvil 11560 has been moved into an open position and the support portion 11510 of the staple cartridge 11500 has been moved away from the portion of the tissue thickness compensator 11520 that has been implanted. As illustrated in FIG. 302, the thin section 11529 (FIG. 300) located intermediate the third segment 11520*c* and the fourth segment 11520*d* has allowed the unimplanted portion of the tissue thickness compensator 11520** to separate from the implanted portion.

In various embodiments, further to the above, a staple cartridge can comprise a plurality of fasteners configured to releasably hold a tissue thickness compensator to a support portion of the staple cartridge. In certain embodiments, the support portion can comprise a plurality of apertures defined in the deck surface, for example, wherein the fasteners can extend through the tissue thickness compensator and can be releasably retained in the support portion apertures. In use, the fasteners can be progressively released from the support portion as the staples are progressively ejected from the support portion. In at least one such embodiment, the fasteners can be implanted with the tissue thickness compensator and, in at least one embodiment, the fasteners can be comprised of at least one bioabsorbable material, for example. In certain embodiments, the fasteners can detach from the support portion after the tissue thickness compensator has been at least partially implanted and as the support portion is moved away from the implanted tissue thickness compensator. In various embodiments, referring now to FIGS. 323-325, a staple cartridge, such as staple cartridge 11600, for example, can comprise a tissue thickness compensator 11620 releasably mounted to a support portion 11610 by a plurality of fasteners 11613. Each fastener 11613 can comprise a first end 11618 embedded within and/or otherwise engaged with the tissue thickness compensator 11620, a second end 11618 engaged with the support portion 11610, and a connector 11616 which connects the first end 11618 to the second end 11618. In various embodiments, the fasteners 11613 can extend through a knife slot 11615 defined in the support portion 11610. In use, the firing member 10052, described above, can move a knife edge through the knife slot 11615 in the support portion 11610 and incise the fasteners 11613 in order to release the tissue thickness compensator 11620 from the support portion 11610. In at least one such embodiment, the firing bar 10052 can be advanced from a proximal end 11601 of the staple cartridge 11600 to a distal end 11602 of the staple cartridge 11600 in order to, one, advance the sled 10050 distally and progressively fire the staples 10030, as discussed above, and, two, progressively incise and/or break the fasteners 11613 to progressively release the tissue thickness compensator 11620 from the support portion 11610. In certain embodiments, similar to the above, the tissue thickness compensator 11620 can comprise a plurality of detachable segments 11620*a*-11620*e* which can each be held to support portion 11610 by one or more fasteners 11613, for example. In the event that the firing member 10052 is stopped intermediate the proximal end 11601 and the distal end 11602 of the staple cartridge 11600, as illustrated in FIG. 324, the fasteners 11613 can assist in holding the unimplanted portion of the tissue thickness compensator 11620 to the support portion 11610 after the anvil 11660 is opened and the support portion 11610 is moved away from the tissue T, as illustrated in FIG. 325. In various embodiments, further to the above, the cutting edge 10053 of the firing member 10052 can be configured to incise and/or break the fasteners 11613. In certain alternative embodiments, referring now to FIGS. 327 and 328, a staple-deploying sled, such as sled 11650, for example, can comprise a knife edge 11653 which can be configured to incise the connectors 11616 of the fasteners 11613 as the sled 11650 traverses the staple cartridge 11600. In at least one such embodiment, each connector 11616 can comprise a cylindrical member extending between the T-shaped ends 11618 of the fasteners 11613 wherein the knife edge 11653 can comprise a concave profile 11653 which can be configured to receive the cylindrical connector 11616, for example.

As discussed above, a staple cartridge can be loaded into a staple cartridge channel of a surgical stapling instrument. In various circumstances, a surgeon, or other clinician, may insert the staple cartridge into the staple cartridge channel by placing a downward force onto the staple cartridge to lock the staple cartridge in place. In some such circumstances, the clinician may place their thumb, for example, on the top surface of the staple cartridge to apply such a downward force. In various embodiments, the top surface of the staple cartridge may comprise the top surface of a tissue thickness compensator wherein, as described above, the tissue thickness compensator can be compressible and, in certain embodiments, the downward force applied to tissue thickness compensator can cause the tissue thickness compensator to compress to the point in which the clinician's thumb comes into contact with the tips of the staples stored within the support portion. In various embodiments, a staple cartridge applicator can be utilized to insert a staple cartridge into a staple cartridge channel which can be configured to prevent, or at least limit, the possibility of the clinician touching the staples in the staple cartridge. After the staple cartridge has been suitably positioned within the staple cartridge channel, as described in greater detail below, the applicator can be detached from the staple cartridge.

In certain embodiments, referring now to FIGS. 305 and 306, a staple cartridge applicator can comprise a rigid cover, such as cover 10080, for example, which can be attached to a staple cartridge 10000. Further to the above, the cover 10080 can be configured to prevent, or at least inhibit, a clinician's thumb, for example, from contacting the tips of the staples 10030 positioned within the staple cartridge 10000 when the staple cartridge 10000 is inserted into a staple cartridge channel. Referring now to FIGS. 307 and 308, the cover 10080 can extend over the top surface 10021, or at least a portion of the top surface 10021, of the tissue thickness compensator 10020 and can include, one, a bottom surface 10081 which can extend over and/or abut the tissue thickness compensator 10020 and, two, a top surface 10082 which can provide a pushing surface for the clinician to apply a downward force thereto, for example. In use, the clinician can grab a handle portion 10084 of the cover 10080, align the support portion 10010 of the staple cartridge 10000 with the staple cartridge channel, and at least partially insert the staple cartridge 10000 within the staple cartridge channel. Thereafter, the clinician can completely seat the staple cartridge 10000 in the staple cartridge channel by applying the downward force to the top surface 10082 of the cover 10880 which can, in various embodiments, transmit the downward force directly to the support portion 10010. In at least one such embodiment, the cover 10080 can comprise proximal supports 10087 which can extend downwardly and contact the deck surface 10011 of the support portion. In certain embodiments, the cover 10080 can further comprise a distal support portion 10083 which can be configured to abut the nose 10003. When a downward force is applied the cover 10080, the downward force can be transmitted through the proximal supports 10087 and/or the distal support portion 10083 without transmitting, or at least without substantially transmitting, the downward force to the support portion 10010 through the tissue thickness compensator 10020. In various circumstances, as a result of the above, the clinician may not directly contact the tissue thickness compensator 10020. Also as a result of the above, the cover 10080 may not compress, or at least substantially compress, the tissue thickness compensator 10020 as the staple cartridge 10000 is being inserted into the staple cartridge channel. In various embodiments, a cover can comprise any suitable number of supports which are configured to transmit a downward force to the support portion without transmitting, or at least substantially transmitting, the downward force through the tissue thickness compensator. In certain embodiments, the supports can extend around the distal end, the proximal end, and/or the longitudinal sides of the tissue thickness compensator. In some embodiments, the supports can extend through the tissue thickness compensator. In at least one such embodiment, the supports can extend through apertures within the tissue thickness compensator and abut the deck of the support portion. In certain embodiments, at least some of the supports may not be in contact with the deck before the downward force is applied to the cover; however, in various embodiments, the cover can be configured to flex, or move, downwardly until the supports contact the deck of the support portion. At such point, the downward flexure, or movement, of the cover can be impeded, or at least substantially impeded, from flexing further.

As described above, the cover 10080 can be attached to the staple cartridge 10000 and can be used to manipulate the position of the staple cartridge 10000. In various embodiments, the cover 10080 can comprise any suitable number of gripping members which can be configured to releasably hold the cover 10080 to the support portion 10010 of the staple cartridge 10000, for example. In at least one such embodiment, the cover 10080 can further comprise one or more retention members, such as latch arms 10088 and/or 10089, for example. In various embodiments, the latch arms 10089 can be configured to extend around the sides of the nose 10003 and engage the bottom surface 10009 (FIG. 306) of the nose 10003. Similarly, the latch arms 10088 can extend around the sides of lock projections 10008 extending from the support portion 10010 and engage the bottom surfaces of the lock projections 10008. These latch arms, in various embodiments, can be configured to position the cover 10080 over the zone or region in which the staples are stored within the support portion 10010. In any event, once the staple cartridge 10000 has been suitably positioned, the cover 10080 can be detached from the staple cartridge 10000. In at least one embodiment, the clinician can apply an upward lifting force to the handle 10084 in order to detach the distal end of the cover 10080 from the distal end 10002 of the staple cartridge 10000. In at least one such embodiment, the latch arms 10088 and 10089 can flex outwardly as the handle 10084 is lifted upwardly such that the latch arms 10088 and 10089 can flex around the lock projections 10008 and the nose 10003, respectively. Thereafter, the proximal end of the cover 10080 can be lifted away from the proximal end 10001 of the staple cartridge and the cover 10080 can be moved away from the staple cartridge 10000.

In certain embodiments, referring now to FIGS. 309 and 310, a staple cartridge applicator, such as staple cartridge applicator 10680, for example, can be configured to position an upper tissue thickness compensator, such as tissue thickness compensator 10690, for example, relative to an anvil in addition to positioning a staple cartridge, such as staple cartridge 10600, for example, within a staple cartridge channel. Similar to the above, the applicator 10680 can comprise latch arms 10688 which can be releasably engaged with lock projections 10608 extending from a support portion 10610 of the staple cartridge 10600 such that the applicator 10680 can be maintained in position over a tissue thickness compensator 10620 of the staple cartridge 10600. In various embodiments, the upper tissue thickness compensator 10690 can be removably attached to the staple cartridge applicator 10680 such that the anvil of a surgical instrument, such as anvil 10060, for example, can be closed onto the applicator 10680, engage the tissue thickness compensator 10690, and detach the tissue thickness compensator 10690 from the applicator 10680. In various embodiments, the tissue thickness compensator 10690 and/or the anvil 10060 can comprise one or more retention features which can be configured to releasably hold the tissue thickness compensator 10690 to the anvil 10060. In at least one such embodiment, the tissue thickness compensator 10690 can comprise a longitudinal rail 10695, for example, extending from the top surface 10691 of the tissue thickness compensator 10690 which can be received within a longitudinal knife slot 10065 defined within the anvil 10060. In various embodiments, the tissue thickness compensator 10690 and the longitudinal rail 10695 can be comprised of any suitable compressible material, such as those described in the this patent application, for example, wherein the longitudinal rail 10695 can be compressed and/or wedged within the knife slot 10065, for example. Once the anvil 10060 has been engaged with the tissue thickness compensator 10690, the anvil 10060 can be returned to an open position and, in such circumstances, the tissue thickness compensator 10690 can detach from the applicator 10680. Thereafter, the applicator 10680 can be detached from the staple cartridge 10600 such that the anvil 10060 and the staple cartridge 10600 can be positioned relative to the tissue that is to be stapled and/or incised. In use, a staple-deploying sled, such as sled 10050 (FIG. 236), for example, can be advanced distally through the staple cartridge 10600 by a firing member 10052 (FIG. 236), for example, in order to eject the staples from the staple cartridge 10060, as outlined above. As the staples are deformed, each staple can capture a portion of the tissue thickness compensator 10690 against the top surface of the tissue and a portion of the tissue thickness compensator 10620 against the bottom surface of the tissue. At the same time, the firing member 10052 can advance a knife edge 10053 (FIG. 236) through the tissue thickness compensator 10620 and/or the tissue thickness compensator 10690 wherein, in at least one embodiment, the knife edge 10053 can be advanced through the longitudinal rail 10695 in order to incise the rail 10695 and progressively detach the tissue thickness compensator 10690 from the anvil 10060. After the staples have been deployed, the anvil 10060 can be re-opened and moved away from the implanted tissue thickness compensator 10690 and, similarly, the support portion 10610 of the staple cartridge 10600 can be moved away from the implanted tissue thickness compensator 10620. In various embodiments, further to the above, the tissue thickness compensator 10620 and/or the tissue thickness compensator 10690 can comprise a plurality of detachable segments which can be configured to separate from one another in the event that only portions of the tissue thickness compensators 10620 and 10690 are implanted by the staples.

In various embodiments, further to the above, the applicator 10680 can comprise one or more retention features which can be configured to releasably hold the tissue thickness compensator 10690 to the applicator 10680. In at least one such embodiment, referring primarily to FIG. 310, the applicator 10680 can comprise a longitudinal retention rail 10685 which can be configured to be received in a longitudinal retention slot 10694 defined in the bottom surface 10692 of the tissue thickness compensator 10690 in a press-fit manner, for example. In various circumstances, the retention rail 10685 and the retention slot 10694 can be configured to retain the tissue thickness compensator 10690 to the applicator 10680 until a sufficient upward lifting force is applied to the tissue thickness compensator 10690 by the anvil 10060, as described above. In at least one such embodiment, the retention rail 10685 extending from the applicator 10680 can further comprise end stops 10686 positioned at the proximal and distal ends of the retention rail 10685 which can be configured to prevent, or at least limit, relative longitudinal movement between the tissue thickness compensator 10690 and the applicator 10680. In certain embodiments, referring again to FIG. 310, one or more adhesives, such as longitudinal adhesive strips 10693, for example, can be placed on the contact surface 10691 of the tissue thickness compensator 10690 such that, when the anvil 10060 contacts the tissue thickness compensator 10690, as described above, the adhesive can releasably attach the tissue thickness compensator 10690 to the anvil 10060. In various embodiments, one or more adhesives can be utilized in addition to or in lieu of the compressible retention features described above, for example. In certain embodiments, one or more adhesives can be utilized to releasably hold a tissue thickness compensator to a staple cartridge applicator. In at least one embodiment, referring now to FIG. 310A, the cover 10080, for example, can include one or more adhesive pads 12185 which can be configured to releasably retain an upper tissue thickness compensator, such as tissue thickness compensator 12190, for example, to the top surface 10082 of the cover 10080. In at least one such embodiment, similar to the embodiments described above, an anvil can be closed onto to the tissue thickness compensator 12190 to engage the longitudinal retention rail 12195 of the tissue thickness compensator 12190. In certain embodiments, a release mechanism can be positioned intermediate the tissue thickness compensator 12190 and the cover 10080 which can be utilized to break the adhesive bonds holding the tissue thickness compensator 12190 to the cover 10080 and detach the tissue thickness compensator 12190 from the cover 10080. In at least one embodiment, the release mechanism can comprise a pull tab 12196 and a loop 12197 wherein the loop 12197 can comprise first and second ends which are attached to the pull tab 12196. The loop 12197 can comprise a suture, for example, which can define a perimeter which circumscribes the adhesive pads 12185 such that, when the pull tab 12196 is pulled distally, the suture can slide between the tissue thickness compensator 12190 and the cover 10080 and contact the tissue pads 12185. In such circumstances, the suture can at least one of separate the adhesive pads 12185 from the tissue thickness compensator 12190, separate the adhesive pads 12185 from the cover 10080, and/or sever the adhesive pads 12185, for example.

In various embodiments, referring now to FIG. 311, a staple cartridge can comprise a support portion 10710, for example, which, similar to the above, can comprise a longitudinal knife slot 10715 extending therethrough. In at least one such embodiment, a staple cartridge applicator, such as applicator 10780, for example, can comprise a longitudinal retention and alignment member 10786 which can extend into the knife slot 10715 in the support portion 10710. In certain embodiments, the retention member 10786 can be configured to engage the sidewalls of the knife slot 10715 in a press-fit manner, for example, such that the applicator 10780 can be releasably retained to the support portion 10710. In various embodiments, although not illustrated, a first portion of a tissue thickness compensator can be positioned on a first side of the retention member 10786 and a second portion of the tissue thickness compensator can be positioned on an opposite, or second, side of the retention member 10786. Similar to the above, the first and second portions of the tissue thickness compensator can be mounted to the support portion 10710 of the staple cartridge via retention members 10013, for example. Also similar to the above, an upper tissue thickness compensator 10790 can be removably mounted to the applicator 10780 via a longitudinal retention member 10785 extending from the loading surface 10782 of the applicator 10780 wherein the retention member 10785 can be releasably press-fit into a longitudinal slot 10794 defined in the bottom surface 10792 of the tissue thickness compensator 10790, for example. In various embodiments, also similar to the above, the tissue thickness compensator 10790 can further comprise a longitudinal retention member 10795 extending from the top surface 10791 of the tissue thickness compensator 10790 which can be releasably retained in the longitudinal knife slot 10065 defined in the anvil 10060, for example. In at least one such embodiment, the longitudinal retention member 10795 can comprise a wedge-shaped cross-section comprising a top portion which is larger than a bottom portion, wherein the bottom portion can attach the retention member 10795 to the tissue thickness compensator 10790, for example.

In various embodiments, referring now to FIGS. 312 and 313, a staple cartridge 10800 comprising a support portion 10810 and a tissue thickness compensator 10820 can be loaded into a staple cartridge channel with a staple cartridge applicator 10880, for example. Similar to the above, the staple cartridge applicator 10880 can also be configured to position an upper tissue thickness compensator 10890, for example, relative to an anvil, such as anvil 10060, for example, such that, when the anvil 10060 is closed, the anvil 10060 can contact and engage the tissue thickness compensator 10890. In at least one embodiment, the tissue thickness compensator 10890 can comprise a plurality of retention legs 10895 extending from the top surface 10891 of the tissue thickness compensator 10890 which can be configured to be engage the anvil 10060 and releasably retain the tissue thickness compensator 10890 to the anvil 10060. In at least one such embodiment, the legs 10895 can be arranged in a longitudinal row wherein each leg 10895 can comprise at least one foot configured to enter into and engage the knife slot 10065 defined in the anvil 10060. In certain embodiments, some of the feet of legs 10895 can extend in one direction while other feet can extend in another direction. In at least one embodiment, some of the feet can extend in opposite directions. In any event, once the anvil 10060 has been engaged with the tissue thickness compensator 10890, referring now to FIGS. 313 and 314, the anvil 10060 can be reopened and the clinician can move the staple cartridge applicator 10880 away from the tissue thickness compensators 10820 and 10890. Thereafter, referring to FIG. 314A, the upper tissue thickness compensator 10890 can be positioned on a first side of the targeted tissue and the tissue thickness compensator 10820, which can comprise a lower tissue thickness compensator, can be positioned on a second side of the tissue. After the tissue thickness compensators 10820 and 10890 have been suitably positioned, referring now to FIG. 314B, a knife edge of a firing member, such as knife edge 10053, for example, can be advanced through the tissue and the tissue thickness compensators. In various embodiments, referring now to FIG. 318, a staple cartridge applicator, such as applicator 12280, for example, can comprise a tissue thickness compensator 12290 detachably mounted thereto which can be, similar to the above, inserted into a staple cartridge channel, as illustrated in FIG. 319, and engaged by the anvil 10060 when the anvil 10060 is moved into a closed position. In at least one such embodiment, the tissue thickness compensator 12290 can comprise a plurality of retention members 12295 extending upwardly from the top surface 12291 of the tissue thickness compensator 12290 wherein each retention member 12295 can comprise a plurality of flexible legs 12296 which can be configured to be inserted into the knife slot 10065 in the anvil 10060. Referring primarily to FIGS. 321 and 322, the flexible legs 12296 of each retention member 12295 can be separated by a gap 12298 such that, as the legs 12296 are inserted into the knife slot 10065, the legs 12296 can flex inwardly and then resiliently return outwardly once the enlarged feet of the flexible legs 12296 have passed through the knife slot 10065. In various embodiments, the enlarged feet of the flexible legs 12296 can flex behind opposing retention lips 12297 defined in the anvil 10060 and, as a result of the interaction of the legs 12296 and the lips 12297, the tissue thickness compensator 12290 can be retained to the anvil 10060. Thereafter, the staple cartridge applicator 12280 can be moved away from the tissue thickness compensator 12290, as illustrated in FIG. 320. In use, once the tissue thickness compensator 12290 has been implanted against the tissue by staples deployed from staple cartridge 10000, for example, the anvil 10060 can be re-opened and, as the anvil 10060 is moved away from the implanted tissue thickness compensator 12290, the legs 12296 of the retention members 12995 can flex inwardly such that they can be pulled out of the knife slot 10065.

In various embodiments, referring now to FIGS. 315 and 316, a tissue thickness compensator, such as tissue thickness compensator 11990, for example, can be loaded longitudinally into an anvil, such as anvil 11960, for example. More particularly, in at least one embodiment, the tissue thickness compensator 11990 can comprise one or more longitudinal rails 11995 which can be inserted into a distal opening in a knife slot 11965 of the anvil 11960 and then pushed proximally until the tissue thickness compensator 11990 has been properly seated in the anvil 11960. In at least one such embodiment, each rail 11995 can comprise a longitudinal retention foot 11996 which can be positioned behind a longitudinal retention lip 11997 which at least partially defines the knife slot 11965, for example. As illustrated in FIG. 316, the feet 11996 can extend in opposite directions in order to be positioned behind retention lips 11997 positioned on the opposite sides of the knife slot 11965. In various embodiments, a longitudinal gap 11998 can be defined between the rails 11995 which can be configured to permit the rails 11995 to flex inwardly toward one another when the tissue thickness compensator 11990 is detached from the anvil 11960. In certain embodiments, referring now to FIG. 317, a tissue thickness compensator, such as tissue thickness compensator 12090, for example, can comprise one or more lock arms 12098 which can extend around the sides of an anvil, such as anvil 12060, for example. In use, the lock arms 12098 can engage the anvil 12060 and releasably retain the tissue thickness compensator 12090 to the anvil 12060. In at least one such embodiment, the anvil 12060 can comprise one or more notches, or lock shoulders, 12097, for example, which can each be configured to receive a foot extending from a lock arm 12098. In use, the arms 12098 can flex outwardly and detach from the anvil 12060 when the anvil 12060 is moved away from the tissue thickness compensator 12090 after the tissue thickness compensator 12090 has been at least partially implanted.

As described above, a surgical stapling instrument can comprise a staple cartridge channel configured to receive a staple cartridge, an anvil rotatably coupled to the staple cartridge channel, and a firing member comprising a knife edge which is movable relative to the anvil and the staple cartridge channel. In use, a staple cartridge can be positioned within the staple cartridge channel and, after the staple cartridge has been at least partially expended, the staple cartridge can be removed from the staple cartridge channel and replaced with a new staple cartridge. In some such embodiments, the staple cartridge channel, the anvil, and/or the firing member of the surgical stapling instrument may be re-used with the replacement staple cartridge. In certain other embodiments, a staple cartridge may comprise a part of a disposable loading unit assembly which can include a staple cartridge channel, an anvil, and/or a firing member, for example, which can be replaced along with the staple cartridge as part of replacing the disposable loading unit assembly. Certain disposable loading unit assemblies are disclosed in U.S. patent application Ser. No. 12/031,817, entitled END EFFECTOR COUPLING ARRANGEMENTS FOR A SURGICAL CUTTING AND STAPLING INSTRUMENT, which was filed on Feb. 15, 2008, now U.S. Patent Application Publication No. 2009/0206131, the entire disclosure of which is incorporated by reference herein. Referring now to FIG. 370, a disposable loading unit, such as disposable loading unit 12500, for example, can comprise a support portion 12510, an anvil 12560 rotatably coupled to the support portion 12510, and an elongate shaft 12570 extending from the support portion 12510. Similar to the staple cartridges described herein, the support portion 12510 can comprise a plurality of staple cavities 10012 and a staple, such as a staple 10030, for example, positioned in each staple cavity 10012, for example. The disposable loading unit 12500 can further comprise a firing member 12552 which can be advanced distally in order to move the anvil 12560 from an open position, as illustrated in FIG. 370, to a closed position. In various embodiments, the disposable loading unit 12500 can further comprise a tissue thickness compensator 12520 positioned on and/or attached to the support portion 12510 wherein, when the anvil 12560 is in its closed position, the anvil 12560 can be positioned opposite the tissue thickness compensator 12520 and, in some embodiments, the anvil 12560 can at least partially compress the tissue thickness compensator 12520 when the anvil 12560 is in its closed position. In either event, the firing member 12552 can be advanced further in order to eject the staples from the support portion 12510. As the staples are ejected, the staples can be deformed by the anvil 12560 and trap at least a portion of the tissue thickness compensator 12520 therein. Thereafter, the firing member 12552 can be retracted proximally, the anvil 12560 can be re-opened, and the support portion 12510 can be moved away from the implanted tissue thickness compensator 12520.

In various embodiments, further to the above, the tissue thickness compensator 12520 can be detachably mounted to the support portion 12510. In at least one such embodiment, the support portion 12510 can comprise a longitudinal retention rail 12526 mounted to each side thereof wherein each rail 12526 can comprise one or more apertures 12528 which can be configured to receive at least a portion of the tissue thickness compensator 12520 therein. Once the tissue thickness compensator 12520 has been at least partially implanted, the tissue thickness compensator 12520 can pull out of the apertures 12528 as the support portion 12510 is moved away. In various embodiments, referring now to FIGS. 371-373, a disposable loading unit 12600 can comprise a support portion 12610, a tissue thickness compensator 12620 detachably mounted to the support portion 12610, and one or more retention rails 12626 which can be configured to extend under the tissue thickness compensator 12620 and mount the tissue thickness compensator 12620 to the support portion 12610. Each retention rail 12626 can comprise a plurality of retention hooks 12628, for example, which can be engaged to the support portion 12610 via retention slots 12614, for example, defined in the support portion 12610. In use, in at least one such embodiment, the tissue thickness compensator 12620 can be configured to detach from the retention rails 12626 after the tissue thickness compensator 12620 has been at least partially implanted and the support portion 12610 is moved away from the tissue thickness compensator 12620. In various embodiments, referring now to FIGS. 374-376, a disposable loading unit 12700 can comprise one or more retention rails 12726 which can each comprise a bottom bar 12725 which can extend under the tissue thickness compensator 12720 and a top bar 12727 which can extend over the top surface 12621 of the tissue thickness compensator 12620. In certain embodiments, the tissue thickness compensator 12620 can be at least partially compressed between the top bars 12727 and the bottom bars 12725 such that the retention rails 12726 can releasably hold the tissue thickness compensator 12620 relative to the support portion 12610. In at least one such embodiment, each retention rail 12726 can comprise one or more retention hooks 12728 which can be engaged with the support portion 12610 to retain the retention rails 12726 to the support portion 12610.

In various embodiments, referring now to FIGS. 377 and 378, a disposable loading unit 12800 can comprise a retention member 12822 which can be configured to mount a tissue thickness compensator 12620 to the support portion 12610. In at least one such embodiment, the retention member 12822 can comprise a sheet of material positioned against the deck surface 12611 of the support portion wherein the tissue thickness compensator 12620 can be attached to the sheet of material by at least one adhesive, for example. The retention member 12822 can further comprise a longitudinal retention rail 12825 configured to extend downwardly into a knife slot 12615 defined in the support portion 12610. In at least one such embodiment, the retention rail 12825 can be sized and configured such that it is compressed between the sidewalls of the knife slot 12615. In use, the firing member 12552 can comprise a knife edge which can pass through the knife slot 12615 as the firing member 12552 is advanced distally and transect the tissue thickness compensator 12620 and the retention rail 12825 longitudinally. Also, in use, the staples ejected from the support portion 12610 can penetrate the retention member 12822, the tissue thickness compensator 12820, and the tissue positioned between the tissue thickness compensator 12820 and the anvil 12560. In various embodiments, the retention member 12822 can be comprised of a biocompatible and/or bioabsorbable material. In certain embodiments, the retention member 12822 can be comprised of a sufficiently compressible material to comprise a tissue thickness compensator underlying the tissue thickness compensator 12620. In various embodiments, referring now to FIGS. 379-381, a disposable loading unit 12900 can comprise a loading assembly including a bottom portion 12922 which can be removably attached to the support portion 12610, a top portion 12990 which can be removably attached to the anvil 12560, and a flexible joint 12991 connecting the bottom portion 12922 and the top portion 12990. Similar to the above, a longitudinal retention rail 12825 can extend downwardly from the bottom portion 12922 and into the knife slot 12615 defined in the support portion 12610 such that the bottom portion 12922 can be releasably retained to the support portion 12610. Similarly, a longitudinal retention rail 12995 can extend upwardly from the top portion 12990 into a knife slot defined in the anvil 12560 such that the top portion 12990 can be releasably retained to the anvil 12560. As illustrated in FIGS. 380 and 381, a tissue thickness compensator 12620 can be mounted to the bottom portion 12922 of the loading assembly wherein, in order to position the tissue thickness compensator 12620 relative to the support portion 12610, a clinician could flex the top portion 12990 and the bottom portion 12922 toward one another, position the loading assembly between the anvil 12560 and the support portion 12610, and release the flexed loading assembly such that it can resiliently expand and bias the top portion 12990 against the anvil 12560 and the bottom portion 12922 against the support portion 12610. In at least one embodiment, referring now to FIGS. 382-384, the loading assembly can further comprise one or more latch hooks, such as latch hooks 12994, for example, extending therefrom which can be configured to releasably connect the top portion 12990 to the anvil 12560 and/or releasably connect the bottom portion 12922 to the support portion 12610.

In various embodiments, referring now to FIG. 385, a disposable loading unit 15900, for example, can comprise an anvil 15960 and a staple cartridge channel 15970 wherein the staple cartridge channel 15970 can rotate relative to the anvil 15960. In at least one such embodiment, the anvil 15960 may not be able to rotate. In certain embodiments, tissue can be positioned between the anvil 15960 and the staple cartridge channel 15970 and, thereafter, the staple cartridge channel 15970 can be rotated toward the tissue to clamp the tissue against the anvil. In at least one such embodiment, the disposable loading unit 15900 can further comprise a tissue thickness compensator 15920 which can be configured to contact the tissue.

As discussed above and referring to FIG. 332, a staple cartridge, such as staple cartridge 10000, for example, can comprise a support portion 10010 and a tissue thickness compensator 10020 wherein a plurality of staples 10030 can be at least partially stored in the support portion 10010 and can extend into the tissue thickness compensator 10020 when the staples 10030 are in their unfired position. In various embodiments, the tips of the staples 10030 do not protrude from the tissue thickness compensator 10020 when the staples 10030 are in their unfired positions. As the staples 10030 are moved from their unfired positions to their fired positions by the staple drivers 10040, as discussed above, the tips of the staples 10030 can penetrate through the tissue thickness compensator 10020 and/or penetrate through the upper layer, or skin, 10022. In certain alternative embodiments, the tips of the staples 10030 can protrude through the top surface of the tissue thickness compensator 10020 and/or skin 10022 when the staples 10030 are in their unfired position. In either event, the staples 10030, as they extend upwardly out of the support portion 10010 prior to being deployed, may tilt and/or deflect relative to the support portion, as also discussed above. In various embodiments, referring now to FIG. 329, a staple cartridge, such as staple cartridge 13000, for example, can comprise a plurality of guide members, or retainers, which can be configured to limit relative movement between the support portion 13010 of the staple cartridge 13000 and the tips of the staples positioned therein. Referring primarily to FIG. 330, the staple cartridge 13000 can comprise a tissue thickness compensator 13020 mounted to a support portion 13010 and, in addition, a plurality of pledgets 13022 attached to the top surface 13021 of the tissue thickness compensator 13020. In various embodiments, each pledget 13022 can comprise a plurality of apertures 13029 defined therein which can be configured to slidably receive and/or guide the legs 13022 of a staple 13030 therein. In addition to or in lieu of the apertures, a pledget can comprise any suitable opening such as a slot, guide, and/or groove, for example, which can be configured to slidably receive and/or guide the legs 13022. In certain embodiments, as illustrated in FIG. 330, the tips of the staple legs 13032 can be positioned within the apertures 13029 when the staples 13030 are in their unfired positions. In at least one such embodiment, the tips of the staple legs 13032 can protrude above the pledgets 13022 when the staples are in their unfired position. In certain other embodiments, the tips of the staple legs 13032 may be positioned just below the pledgets 13022 when the staples 13030 are in their unfired positions such that, when the staples 13030 are moved upwardly through the tissue thickness compensator 13020, the staple legs 13032 can enter into the apertures 13029 of the pledgets 13022 and slide therethrough. In any event, when the legs 13032 of the staples 13030 are positioned within the pledgets, the lateral and/or longitudinal movement of the staple legs 13032 can be limited without preventing the upward movement of the staple legs 13032 when the staples 13030 are deployed. When the staples 13030 are deployed, referring now to FIG. 331, the staple legs 13032 can slide upwardly through the pledgets 13022 to penetrate the tissue T, contact an anvil positioned opposite the staple cartridge 13030, and deform downwardly to capture the tissue T and the tissue thickness compensator 13030 therein.

In various embodiments, further to the above, the pledgets 13022 can be attached to the tissue thickness compensator 13020 utilizing at least one biocompatible and/or bioabsorbable adhesive, for example. In certain embodiments, the pledgets 13022, and/or a retention member extending from each pledget, can be at least partially embedded within the tissue thickness compensator 13020. In at least one such embodiment, the tissue thickness compensator 13020 can comprise pockets defined therein which are configured to at least partially receive a pledget 13022. In certain embodiments, the tissue thickness compensator 13020 can be integrally molded, or formed around, the pledgets 13022 during a molding manufacturing process. In various embodiments, the pledgets 13022 may comprise discrete retainers that can move independently of one another. In at least one embodiment, referring primarily to FIG. 330, each pledget 13022 can comprise interlocking and/or keyed features which can be configured to permit and, to a certain extent, limit relative lateral and longitudinal movement between the pledgets 13022. In at least one such embodiment, each pledget 13022 can comprise a projection 13026 and one or more recesses 13027, for example, wherein the projection 13026 of a first pledget 13022 can be positioned within and/or aligned with respect to the recesses of 13027 of adjacent second and third pledgets 13022. In various embodiments, gaps can be present between adjacent pledgets 13022 which can permit the pledgets 13022 to move or slide relative to one another until they contact an adjacent pledget 13022. In certain embodiments, the pledgets 13022 can be loosely interconnected. In various embodiments, the pledgets 13022 can be detachably connected to one another. In at least one such embodiment, the pledgets 13022 can be manufactured as a sheet of interconnected pledgets wherein, when a sufficient force is applied to the sheet, one or more of the pledgets 13022 can break away from the others. In certain embodiments, referring again to FIG. 329, a first sheet 13024 of pledgets 13022 can be positioned on a first side of a longitudinal slot 13025 and a second sheet 13024 of pledgets 13022 can be positioned on a second side of slot 13025. In at least one embodiment, further to the above, the longitudinal slot 13025 extending through the tissue thickness compensator 13020 can be configured to facilitate the passage of a knife edge of a firing member through the tissue thickness compensator 13020 and, as the firing member passes thereby, the firing member can apply a compressive force to the sheets 13024 and separate or singulate at least some of the pledgets 13022.

In various embodiments, the pledgets 13022 can be comprised of a biocompatible and/or bioabsorbable plastic, for example. In certain embodiments, the pledgets 13022 can be comprised of a solid material, a semi-solid material, and/or a flexible material, for example. In certain embodiments, the pledgets 13022 can be embedded within a tissue thickness compensator such that the pledgets 13022 move with the tissue thickness compensator. In at least one such embodiment, the pledgets 13022 can be sufficiently flexible such that they can flex with the top surface of the tissue thickness compensator. In certain embodiments, the pledgets 13022 can be configured to remain embedded in the tissue thickness compensator while, in certain other embodiments, the pledgets 13022 can be configured to pop out of, or detach from, the tissue thickness compensator. In various embodiments, the pledges 13022 can comprise a top surface which is flush with the top surface of the tissue thickness compensator. In certain embodiments, the top surfaces of the pledgets 13022 can be positioned above and/or below the top surface of the tissue thickness compensator. In various embodiments, the top surfaces of the pledgets 13022 can be disposed such that they are visible when viewing the top surface of the tissue thickness compensator while, in other embodiments, the top surfaces of the pledgets 13022 can be positioned below a layer of the tissue thickness compensator, for example. In certain embodiments, guide features can be molded into the top surface of a tissue thickness compensator, for example. In at least one such embodiment, the tissue thickness compensator may not comprise a composite material and may comprise a unitary piece of material, for example.

In various embodiments, referring now to FIG. 338, a staple cartridge can comprise a tissue thickness compensator 13620 and a skin, or top layer, 13621, for example. In at least one such embodiment, one or more pledgets, or retainers, 13622, for example, can be embedded in the skin 13621. In certain embodiments, each retainer 13622 can comprise one or more apertures 13629 defined therein which can be configured to receive the staple legs 13032 of staples 13030 therein when the staples 13030 are in their unfired position, as illustrated in FIG. 338. In use, further to the above, the staple legs 10032 can slide through the apertures 13629 when the staples 13030 are moved from their unfired position to their fired position until the bases 13031 of the staples 13030 contact the tissue thickness compensator 13620 and compress at least a portion of the tissue thickness compensator 13620 against the bottom surfaces of the pledgets 13622, for example. In various embodiments, referring now to FIG. 333, a staple cartridge can comprise a tissue thickness compensator 13120 and a skin, or top layer, 13122, for example. In at least one such embodiment, the tissue thickness compensator 13120 can comprise conical bumps, projections, and/or protrusions 13128, for example, which can extend upwardly from the top surface 13121 of the tissue thickness compensator 13120. The projections 13128 can be configured to receive and envelop the tips of the staple legs 13032 of the staples 13030 when the staples 13030 are in their unfired position, as illustrated in FIG. 333. The top layer 13122 can also comprise conical bumps, projections, and/or protrusions 13129 which can be aligned, or at least substantially aligned, with the projections 13128. In use, the staple legs 10032 can penetrate the projections 13128 and 13129 and emerge from the tissue thickness compensator 13120. In various embodiments, referring now to FIG. 337, a staple cartridge can comprise a tissue thickness compensator 13520 and a skin, or top layer, 13522, for example. In at least one such embodiment, the skin 13522 can comprise conical bumps, projections, and/or protrusions 13529, for example, which can extend upwardly from the top surface 13521 of the tissue thickness compensator 13520. Similar to the above, the projections 13529 can be configured to receive and envelop the tips of the staple legs 13032 of the staples 13030 when the staples 13030 are in their unfired position, as illustrated in FIG. 337. In use, the staple legs 10032 can penetrate the projections 13529 and emerge from the skin 13522.

In various embodiments, referring now to FIG. 334, a staple cartridge can comprise a tissue thickness compensator 13220 and a skin, or top layer, 13222, for example. In at least one such embodiment, the tissue thickness compensator 13220 can comprise conical dimples and/or recesses 13128, for example, which can extend downwardly into the top surface 13221 of the tissue thickness compensator 13220. In various embodiments, the tips of the staple legs 13032 can extend through the recesses 13128 when the staples 13030 are in their unfired position, as illustrated in FIG. 334. In at least one embodiment, the top layer 13222 can also comprise conical dimples and/or recesses 13229 which can be aligned, or at least substantially aligned, with the recesses 13228. In various embodiments, referring now to FIG. 335, a staple cartridge can comprise a tissue thickness compensator 13320 and a skin, or top layer, 13322, for example. In at least one such embodiment, the skin 13320 can comprise thick portions 13329 which can extend downwardly into the top surface 13321 of the tissue thickness compensator 13320. In various circumstances, the thick portions 13329 can be configured to receive at least a portion of the staple legs 13032 of the staples 13030 therein when the staples 13030 are in their unfired position, as illustrated in FIG. 335. In such embodiments, the thick portions 13329 can hold the staple legs 13032 in position such that the legs 13032 are aligned, or at least substantially aligned, with the staple-forming pockets of an anvil positioned opposite the tissue thickness compensator 13320. In various embodiments, referring now to FIG. 336, a staple cartridge can comprise a tissue thickness compensator 13420 and a skin, or top layer, 13422, for example. In at least one such embodiment, the skin 13422 can comprise thick portions 13429 which can extend upwardly from the top surface 13421 of the tissue thickness compensator 13420. In various circumstances, the thick portions 13429 can be configured to receive at least a portion of the staple legs 13032 of the staples 13030 therein when the staples 13030 are in their unfired position, as illustrated in FIG. 336. In such embodiments, the thick portions 13429 can hold the staple legs 13032 in position such that the legs 13032 are aligned, or at least substantially aligned, with the staple-forming pockets of an anvil positioned opposite the tissue thickness compensator 13420.

In various embodiments, referring now to FIGS. 339 and 340, a staple cartridge can comprise a tissue thickness compensator 13720 and a skin, or top layer, 13721, for example. In at least one such embodiment, the tissue thickness compensator 13720 can comprise pyramidal and/or stepped bumps, projections, and/or protrusions 13728, for example, which can extend upwardly from the top surface 13721 of the tissue thickness compensator 13720. The projections 13728 can be configured to receive and envelop the tips of the staple legs 13032 of the staples 13030 when the staples 13030 are in their unfired position, as illustrated in FIG. 340. Similarly, the top layer 13721 can comprise pyramidal and/or stepped bumps, projections, and/or protrusions 13729 which can be aligned, or at least substantially aligned, with the projections 13728. In various embodiments, the skin 13721 can further comprise one or more teeth 13727 extending upwardly from the projections 13729 which can be configured to engage tissue positioned against the top layer 13721 and prevent, or at least limit, relative lateral and/or longitudinal movement between the tissue, the top layer 13721, and/or the tips of the staple legs 13032. In use, the staple legs 13032 can penetrate the projections 13728 and 13729 and emerge from the tissue thickness compensator 13720 when the staples 13030 are moved from their unfired positions to their fired positions. In various embodiments, referring now to FIGS. 341 and 342, a staple cartridge can comprise a tissue thickness compensator 13820 and a skin, or top layer, 13821, for example. In at least one such embodiment, the tissue thickness compensator 13820 can comprise pyramidal and/or stepped bumps, projections, and/or protrusions 13828, for example, which can extend upwardly from the top surface 13821 of the tissue thickness compensator 13820. The projections 13828 can be configured to receive and envelop the tips of the staple legs 13032 of the staples 13030 when the staples 13030 are in their unfired position, as illustrated in FIG. 342. Similarly, the top layer 13821 can comprise pyramidal and/or stepped bumps, projections, and/or protrusions 13829 which can be aligned, or at least substantially aligned, with the projections 13828. In various embodiments, the top layer 13821 can further comprise one or more teeth 13827 extending downwardly into the tissue thickness compensator 13820 which can be configured to prevent, or at least limit, relative lateral and/or longitudinal movement between the top layer 13821 and the tissue thickness compensator 13820, for example. In use, the staple legs 10032 can penetrate the projections 13828 and 13829 and emerge from the tissue thickness compensator 13820 when the staples 13030 are moved from their unfired positions and their fired positions.

In various embodiments, referring now to FIG. 343, a staple cartridge can comprise a tissue thickness compensator, such as tissue thickness compensator 13920, for example, which can include ridges 13923 and valleys 13924 defined therein wherein, in at least one embodiment, the valleys 13924 can be defined between the ridges 13923. In various embodiments, each ridge 13923 can comprise the same height, substantially the same height, or different heights. Similarly, each valley 13924 can comprise the same depth, substantially the same depth, or different depths. In various embodiments, a plurality of staples 13030 can be at least partially stored within the tissue thickness compensator 13920 such that the tips of the staples 13030 can be positioned within the ridges 13923. In at least one such embodiment, the staple legs 13032 of the staples 13030 may not protrude from the tissue thickness compensator 13920 and/or a skin, or top layer, 13921 attached to the tissue thickness compensator 13920, for example, when the staples 13030 are stored in their unfired position. In various embodiments, the ridges 13923 and/or the valleys 13924 can extend laterally across the staple cartridge. In at least one such embodiment, the staple cartridge can comprise a longitudinal knife slot wherein the ridges 13923 and the valleys 13924 can extend in a direction which is transverse and/or perpendicular to the knife slot. In various circumstances, the ridges 13923 can be configured to hold the tips of the staple legs 13032 in position until the staples 13030 are moved from their unfired position into their fired position. In various embodiments, referring now to FIG. 344, a tissue thickness compensator, and/or a skin covering a tissue thickness compensator, can comprise longitudinal ridges and/or valleys. In at least one such embodiment, a tissue thickness compensator can comprise a top surface defined by ridges 14023 and valleys 14024, wherein the valleys

14024 can be defined between the ridges 14023, for example. In various embodiments, the tissue thickness compensator can comprise a skin 14021 which can include a plurality of apertures 14029 defined therein which can each be configured to receive a staple leg 13032. In certain embodiments, the apertures 14029 can be defined in the ridges 14023 wherein the tips of the staple legs 13032 may be positioned below the peaks 14028 of the ridges 14029, positioned flush with the peaks 14028, and/or positioned above the peaks 14028. In certain embodiments, in addition to or in lieu of the above, the apertures 14029 can be defined in the valleys 14024, for example. In certain embodiments, each aperture can be surrounded, or at least partially surrounded, by an embossment, for example, which can strengthen the skin and/or tissue thickness compensator surrounding the apertures. In any event, further to the above, the skin 14021 can be attached to a tissue thickness compensator in any suitable manner, including using at least one adhesive, for example.

As described above and referring again to FIG. 233, a surgical stapling instrument can comprise an anvil, such as anvil 10060, for example, which can be moved between an open position and a closed position in order to compress tissue T against the tissue thickness compensator 10020 of a staple cartridge 10000, for example. In various circumstances, the anvil 10060 can be rotated toward the staple cartridge 10000 until its downward movement is stopped by some portion of the staple cartridge 10000 and/or some portion of the channel in which the staple cartridge 10000 is positioned. In at least one such circumstance, the anvil 10060 can be rotated downwardly until its downward movement is resisted by the nose 10003 of the staple cartridge 10000 and/or the tissue T positioned intermediate the nose 10003 and the staple cartridge 10000. In some circumstances, the anvil 10060 may sufficiently compress the tissue thickness compensator 10020 to permit the tissue T to contact the tips of the staples 10030. In certain circumstances, depending on the thickness of the tissue T, the anvil 10060 may sufficiently compress the tissue thickness compensator 10020 such that the anvil 10060 comes into contact with the staples 10030 by the time the anvil 10060 has reached its fully closed position. Stated another way, in such circumstances, the anvil 10060 may deform the staples 10030 prior to the firing member 10052 being advanced into the staple cartridge 10000 to fire the staples 10030. Such circumstances may be acceptable in certain embodiments; however, referring now to FIGS. 358 and 359, other embodiments are envisioned in which a distal gap-setting element, such as element 10059, for example, can be utilized to limit the distance in which the anvil 10060 can be closed prior to the firing bar 10052 being advanced into the staple cartridge 10000. In various embodiments, the element 10059 can extend upwardly from the top surface 10021 of the tissue thickness compensator 10020 such that the downward movement of the anvil 10060 can be arrested as the tissue T is compressed against the element 10059 and a resistive force is generated therebetween. In use, as described above, the firing member 10052 can be advanced distally into the staple cartridge 10000 toward the distal end 10002 of the staple cartridge 10000 in order to eject the staples 10030 from the support portion 10010. Simultaneously, the firing member 10052 can engage the anvil 10060 and position the anvil 10060 a desired distance from the deck surface 10011 (FIG. 218) of the support portion 10010 over the staples 10030 being formed. In this way, the firing member 10052 can control the distance, or gap, between the tissue-contacting surface of the anvil 10060 and the deck surface 10011 at a particular location, wherein this particular location can be advanced distally as the firing member 10052 is advanced distally. In various circumstances, this gap distance may be shorter than the gap between the anvil 10060 and the deck surface 10011 being controlled or dictated by the distal gap-setting element 10059 at the distal end of the tissue thickness compensator 10020. In various embodiments, referring now to FIG. 359, the knife edge 10053 of the firing member 10052 can be configured to transect the distal gap-setting element 10059 when the firing member 10052 reaches the distal end of the tissue thickness compensator 10020 such that, after the element 10059 has been transected, the firing member 10052 can pull the anvil 10060 downwardly toward the support portion 10010 and close the gap to the desired gap height when firing the staples 10030 at the distal end of the staple cartridge 10000. In certain alternative embodiments, a distal gap-setting element can be configured to collapse as the firing member approaches the distal end of the staple cartridge. In at least one such embodiment, the distal gap-setting element can comprise a column which can provide resistance to the anvil as described above and then suddenly buckle once the buckling strength of the gap-setting element has been reached when the firing member approaches the distal end of the staple cartridge. In at least one embodiment, this buckling force can be approximately 10 lbf, for example. In certain embodiments, a gap setting element can be configured to drop downwardly into the deck of the support portion when a force exceeding a predetermined amount is applied to the gap setting element, for example. In certain other embodiments, the distal gap can be controlled by the nose of the staple cartridge. In at least one such embodiment, the downward movement of the anvil 10060 can be limited by the nose until the firing member has reached the distal end of the cartridge wherein, at such point, the compressive force applied to the nose can cause the nose to collapse. In certain embodiments, the nose can comprise a cavity defined by cavity walls which can allow the cavity to collapse once the compressive force applied thereto has exceed a predetermined force. In at least one such embodiment, the cavity can be defined by collapsible walls.

In various embodiments, as described above, an anvil, such as anvil 10060, for example, can be moved between an open position and a closed position in order to compress a tissue thickness compensator between the anvil and the support portion of a staple cartridge. In certain circumstances, referring now to FIGS. 360 and 361, the tissue thickness compensator of a staple cartridge, such as tissue thickness compensator 14120 of staple cartridge 14100, for example, may expand laterally and/or longitudinally when the tissue thickness compensator 14120 is compressed against a support portion 14110 of the staple cartridge 14100. In certain embodiments, the ends and/or sides of the tissue thickness compensator 14120 may not be constrained by the support portion 14110 and/or the anvil 10060 and, as a result, the tissue thickness compensator 14120 can expand in those directions without generating a compressive pressure, or at least an undesirable compressive pressure, within the tissue thickness compensator 14120. In such embodiments, a firing member, such as firing member 10052 (FIG. 236), for example, passing through the tissue thickness compensator 14120 may not be unduly impeded by an undesirable compressive pressure within the tissue thickness compensator 14120, for example. In certain other embodiments, referring again to FIG. 360, the distal end 14125 of the tissue thickness compensator 14120 may be constrained by the nose 14103 of the staple cartridge 14100, for example. In this particular embodiment, similar to the above, the distal end 14125 of the tissue thickness compensator 14120 may be constrained by the nose 14103 in order to reduce the possibility of the tissue thickness compensator 14120 from becoming prematurely detached from the support portion 14110. In any event, as a result of the above, a large internal pressure can be generated within the distal end 14125 which can impede the advancement of the firing member 10052, especially when the firing member 10052 reaches the distal end 14125. More particularly, in certain circumstances, the firing member 10052 can push, plow, and/or displace the tissue thickness compensator 14120 distally as it transects the tissue thickness compensator 14120 and, as a result, an even larger internal pressure can be created within the distal end 14125 of the tissue thickness compensator 14120. In order to at least partially dissipate this pressure within the tissue thickness compensator 14120, the nose 14103 can be comprised of a flexible material which can allow the nose 14103 to flex distally, for example, and create additional space for the tissue thickness compensator 14120. In certain embodiments, referring now to FIGS. 362 and 363, the nose of a staple cartridge can comprise a portion which can slide distally. More particularly, the nose 14203 of the staple cartridge 14200 can comprise a slidable portion 14204 which can be slidably connected to the nose 14203 such that, when the anvil 10060 is closed and/or the firing member 10052 is advanced into the distal end of the staple cartridge 14200, the slidable portion 14204 can slide distally and create additional room for the tissue thickness compensator 14200 and at least partially alleviate the internal pressure therein. In at least one embodiment, one of the nose 14203 and the slidable portion 14204 can comprise one or more rails and the other of the nose 14203 and the slidable portion 14204 can comprise one or more channels configured to slidably receive the rails therein. In at least one such embodiment, the channels and rails can be configured to co-operatively limit the movement of the slidable portion 14204 to a longitudinal distal path, for example.

In various circumstances, further to the above, certain staples, such as the distal-most staples within a staple cartridge, for example, can capture a larger portion of a tissue thickness compensator than the proximal staples within the staple cartridge. In such circumstances, as a result, a large clamping pressure can be applied to the tissue captured within the distal staples as compared to the proximal staples. These circumstances can arise when at least a portion of the tissue thickness compensator is shifted to and/or gathered at the distal end of the staple cartridge during use, as described above, eventhough the tissue thickness compensator may be comprised of a substantially homogenous material having a substantially constant thickness. In various circumstances, it may be desirable for certain staples to apply a higher clamping pressure to the tissue than other staples wherein, in various embodiments, a support portion and/or a tissue thickness compensator can be constructed and arranged to control which staples may apply the higher clamping pressure to the tissue and which staples may apply a lower clamping pressure to the tissue. Referring now to FIG. 364, a staple cartridge 14300 can comprise a support portion 14310 and, in addition, a tissue thickness compensator 14320 positioned on the deck surface 14311 of the support portion 14310. As compared to other embodiments disclosed in this application which comprise a support portion 14310 having a flat, or at least substantially flat, deck surface, the deck surface 14311 can be inclined and/or declined between the distal end 14305 and the proximal end 14306 of the support portion 14310. In at least one embodiment, the deck surface 14311 of the support portion 14310 can comprise a deck height at its distal end 14305 which is shorter than the deck height at its proximal end 14306. In at least one such embodiment, the staples 10030 at the distal end of the staple cartridge 14300 can extend above the deck surface 14311 a larger distance than the staples 10030 at the proximal end. In various alterative embodiments, the deck surface of a support portion can comprise a height at its distal end which is taller than its height at its proximal end. Referring again to FIG. 364, the tissue thickness compensator 14320 may comprise a thickness which is different along the longitudinal length thereof. In various embodiments, the tissue thickness compensator 14320 can comprise a thickness at its distal end 14325 which is thicker than its proximal end 14326, for example. In at least one such embodiment, the tissue thickness compensator 14322 can comprise a bottom surface 14322 which can be inclined or declined to match, or at least substantially match, the inclined or declined deck surface 14311 of the support portion 14310. As a result, the top, or tissue-contacting, surface 14321 of the tissue thickness compensator 14320 can comprise a flat, or at least substantially flat, surface upon which the tissue T can be positioned. In any event, as the tissue thickness compensator 14320 is thicker at its distal end 14325, the distal staples 10030 can capture a larger portion of the tissue thickness compensator 14320 therein than the proximal staples 10030 and, as a result, the distal staples 10030 can apply a larger compressive force to the tissue T, especially when the gap distance between the anvil 10060 and the deck surface 14311 is constant, or at least substantially constant, at the proximal and distal ends of the staple cartridge. In certain circumstances, however, the anvil 10060 may not reach a fully closed position and, as a result, the gap distance between the anvil 10060 and the deck surface 14311 may be larger at the distal end of the staple cartridge 14300 than the proximal end. In various circumstances, the distal staples 10030 may not be fully formed and, as a result, the distal staples 10030 may not apply the desired clamping pressure to the tissue T. In the embodiments where the tissue thickness compensator is thicker at the distal end of the staple cartridge, the tissue thickness compensator may compensate for the underforming of the staples and apply a sufficient pressure to the tissue T.

In various embodiments, referring now to FIG. 365, a staple cartridge, such as staple cartridge 14400, for example, can comprise a support portion 14410 and, in addition, a tissue thickness compensator 14420 positioned on the deck surface 14411 of the support portion 14410. Similar to the above, the deck surface 14411 can be inclined and/or declined such that, in at least one embodiment, the distal end 14405 of the support portion 14410 can have a deck height which is shorter than the deck height at the proximal end 14406, for example. In certain embodiments, the tissue thickness compensator 14420 can comprise a constant, or at least substantially constant, thickness along the length thereof and, as a result, the top, or tissue-contacting, surface 14421 of the tissue thickness compensator 14420 may parallel, or at least substantially parallel, the contour of the deck surface 14411. In various embodiments, the staples 10030 of the staple cartridge 14400 can be completely embedded within the tissue thickness compensator 14420 and the support portion 14410 when the staples 10030 are in their unfired position. In certain embodiments, the staples 10030 positioned at the proximal end of the staple cartridge 14400 may be completely embedded within the tissue thickness compensator 14420 and the support portion 14410 when the staples 10030 are in their unfired position whereas, due to the declined slope of the deck 14411 and top surface 14421, the tips of certain staples 10030, including the staples 10030 positioned at the distal end of the staple cartridge 14400, can protrude through the top surface 14421 of the tissue thickness compensator 14420 when the staples 10030 are in their unfired position.

In various embodiments, as described above, a tissue thickness compensator can be comprised of a single material wherein the entirety of the tissue thickness compensator can have the same, or at least substantially the same, material properties, such as density, stiffness, spring rate, durometer, and/or elasticity, for example, throughout. In various other embodiments, referring now to FIG. 368, a tissue thickness compensator, such as tissue thickness compensator 14520, for example, can comprise a plurality of materials or layers of materials. In at least one embodiment, the tissue thickness compensator 14520 can comprise a first, or central, layer 14520*a*, second, or intermediate, layers 14520*b* attached to the first layer 14520*a* on opposite sides thereof, and a third, or outer layer 14520*c* attached to each of the second layers 14520*b*. In certain embodiments, the intermediate layers 14520*b* can be attached to the central layer 14520*a* utilizing at least one adhesive and, similarly, the outer layers 14520*c* can be attached the second layers 14520 utilizing at least one adhesive. In addition to or in lieu of an adhesive, the layers 14520*a*-14520*c* can be held together by one or more interlocking features and/or fasteners, for example. In any event, the inner layer 14520*a* can be comprised of a first material having a first set of material properties, the intermediate layers 14520*b* can be comprised of a second material having a second set of material properties, and the outer layers 14520*c* can be comprised of a third material having a third set of material properties, for example. These sets of material properties can include density, stiffness, spring rate, durometer, and/or elasticity, for example. In certain embodiments, a staple cartridge can comprise six rows of staples 10030, for example, wherein a row of staples 10030 can be at least partially positioned in each of the outer layers 14520*c* and each of the inner layers 14520*b*, for example, and wherein two rows of staples 10030 can be at least partially positioned with the inner layer 14520*a*. In use, similar to the above, the staples 10030 can be ejected from the staple cartridge such that the staple legs 10032 of the staples 10030 penetrate the top surface 14521 of the tissue thickness compensator 14520, penetrate tissue positioned against the top surface 14521 by an anvil, and then contact the anvil such that the legs 10032 are deformed to capture the tissue thickness compensator 14520 and the tissue within the staples 10030. Also similar to the above, the tissue thickness compensator 14520 can be transected by a firing member as the firing member is advanced through the staple cartridge. In at least one such embodiment, the firing member can transect the inner layer 14520*a*, and the tissue, along a path defined by axis 14529, for example.

In various embodiments, further to the above, the rows of staples 10030 positioned within the inner layer 14520*a* can comprise the staple rows which are closest to the edges of the transected tissue. Correspondingly, the rows of staples 10030 positioned within the outer layers 14520*c* can comprise the staple rows which are furthest away from the edges of the transected tissue. In certain embodiments, the first material comprising the inner layer 14520*a* may comprise a density which is higher than the density of the second material comprising the intermediate layers 14520*b* and, similarly, the density of the second material may be higher than the density of the third material comprising the outer layers 14520*c*, for example. In various circumstances, as a result, larger compressive forces can be created within the staples 10030 positioned within the inner layer 14520*a* as compared to the compressive forces generated within the staples 10030 positioned within the intermediate layers 14520*b* and the outer layers 14520*c*. Similarly, larger compressive forces can be created within the staples 10030 positioned within the intermediate layers 14520*b* as compared to compressive forces created within the staples 10030 positioned within the outer layers 14520*c*, for example. In various alternative embodiments, the first material comprising the inner layer 14520*a* may comprise a density which is lower than the density of the second material comprising the intermediate layers 14520*b* and, similarly, the density of the second material may be lower than the density of the third material comprising the outer layers 14520*c*, for example. In various circumstances, as a result, larger compressive forces can be created within the staples 10030 positioned within the outer layers 14520*c* as compared to the compressive forces created within the staples 10030 positioned within the intermediate layers 14520*b* and the inner layer 14520*a*. Similarly, larger compressive forces can be created within the staples 10030 positioned within the intermediate layers 14520*b* as compared to the compressive forces created within the staples 10030 positioned within the inner layer 14520*a*, for example. In various other embodiments, any other suitable arrangement of layers, materials, and/or material properties could be utilized. In any event, in various embodiments, the layers 14520*a*-14520*c* of the tissue thickness compensator 14520 can be configured to remain attached to one another after they have been implanted. In certain other embodiments, the layers 14520*a*-14520*c* of the tissue thickness compensator 14520 can be configured to detach from one another after they have been implanted. In at least one such embodiment, the layers 14520*a*-14520*c* can be bonded together utilizing one or more bioabsorbable adhesives which can initially hold the layers together and then allow the layers to release from one another over time.

As described above, a tissue thickness compensator of a staple cartridge, such as tissue thickness compensator 14520, for example, can comprise a plurality of longitudinal layers. In various other embodiments, referring now to FIG. 369, a staple cartridge can comprise a tissue thickness compensator, such as tissue thickness compensator 14620, for example, which can comprise a plurality of horizontal layers. In at least one such embodiment, the tissue thickness compensator 14620 can comprise a first, or bottom, layer 14620*a*, a second, or intermediate, layer 14620*b* attached to the bottom layer 14620*a*, and a third, or top, layer 14620*c* attached to the intermediate layer 14620*b*. In various embodiments, the first layer 14620*a* can comprise a flat, or substantially flat, bottom surface 14626*a* and a triangular, or pyramidal, top surface 14625*a*, for example. In at least one such embodiment, the second layer 14620*b* can comprise a triangular, or pyramidal, bottom surface 14626*b* which can be configured to parallel and abut the top surface 14625*a* of the first layer 14620*a*. Similar to the above, the second layer 14620*b* can comprise a triangular, or pyramidal, top surface 14625*b* which can parallel and abut a bottom triangular, or pyramidal, bottom surface 14626*c* of the third layer 14620*c*, for example. In various embodiments, the top surface of the third layer 14626*c* can comprise a flat, or at least substantially flat, tissue-contacting surface 14621. Also similar to the above, the tissue thickness compensator 14620 can be configured to at least partially store six rows of staples, such as staples 10030, for example, therein wherein a firing member can transect the tissue thickness compensator 14620 between the two innermost staple rows along a path extending through axis 14629, for example. Similar to the above, each layer 14620*a*, 14620*b*, and 14620*c* can be comprised of a different material which can comprise different material properties and, as a result of the triangular, or pyramidal, configuration of the layers 14620*a*-14620*c*, the tissue thickness compensator 14620 can have different overall properties at various locations therewithin. For example, the outermost rows of staples 10030 may capture more of the third layer 14620*c* than the first layer 14620*a* therein whereas the innermost rows of staples 10030 may capture less of the third layer 14620*c* than the first layer 14620*a* and, as a result, the tissue thickness compensator 14620 may compress the tissue captured within the outermost staples 10030 differently than the tissue captured within the innermost staples 10030, for example, eventhough the tissue thickness compensator 14620 may have the same, or at least substantially the same, overall thickness thereacross.

In various embodiments, referring now to FIG. 286, a tissue thickness compensator of a staple cartridge, such as tissue thickness compensator 14720 of staple cartridge 14700, for example, can comprise voids, pockets, channels, and/or grooves, for example, defined therein which can vary the thickness of the tissue thickness compensator 14720. In at least one such embodiment, the tissue thickness compensator 14720 can be positioned against the deck surface 14711 of a support portion 14710 of the staple cartridge 14700 such that voids 14723 defined in the bottom surface 14722 of the tissue thickness compensator 14720 can overlie certain staple cavities 10012, but not others. In various embodiments, the voids 14723 can extend transversely to the knife slot 14715 of the support portion 14710, perpendicular to the knife slot 14715, and/or parallel to the knife slot 14715, for example. In certain embodiments, the voids 14723 can define a tread pattern in the bottom surface 14722 of the tissue thickness compensator 14720. In any event, when staples, such as staples 10030, for example, are deployed from the support portion 14710, referring now to FIGS. 287 and 288, certain staples 10030 can capture the tissue thickness compensator 14720 within a region containing a void 14723 while other staples 10030 can capture the tissue thickness compensator 14720 within a region positioned intermediate the voids 14723. In addition to or in lieu of the above, the tissue thickness compensator 14720 can comprise voids, pockets, channels, and/or grooves, for example, defined in the top, or tissue-contacting, surface 14721. In certain embodiments, referring now to FIGS. 366 and 367, a staple cartridge 14800 can comprise a tissue thickness compensator 14820 which can include a plurality of treads 14823 extending at least one of upwardly from a top surface 14821 of the tissue thickness compensator 14820, inwardly toward a central groove 14825, and/or distally toward the distal end of the staple cartridge 14800, for example. In at least one such embodiment, the treads 14823 can be separated by channels, slots, and/or grooves, such as channels 14824, for example. In various circumstances, as a result of the above, the overall thickness of the tissue thickness compensator can vary between staple rows and/or vary between the staples within a staple row. In certain circumstances, the treads, or thick portions, can be constructed and arranged such that they can flow in a desire direction, such as inwardly, for example, when the tissue thickness compensator is compressed.

In various embodiments, referring now to FIG. 303, a staple cartridge, such as staple cartridge 14900, for example, can comprise a support portion 14910 and, in addition, a tissue thickness compensator 14920 positioned against the support portion 14910. Similar to the above, the support portion 14910 can comprise staple drivers which can be lifted upwardly by a staple-deploying sled in order to lift staples, such as staples 10030, for example, at least partially positioned within the support portion 14910 toward an anvil, such as anvil 10060, for example, positioned opposite the staple cartridge 14900. In certain embodiments, the support portion 14910 can comprise six rows of staple cavities, such as two outer rows of staple cavities, two inner rows of staple cavities, and two intermediate rows of staple cavities positioned intermediate the inner rows and the outer rows, for example, wherein the anvil 10060 can comprise six rows of forming pockets 10062 aligned, or at least substantially aligned, with the staple cavities. In various embodiments, the inner rows of staple cavities can include staple drivers 14940*a* positioned therein, the intermediate rows of staple cavities can include staple drivers 14940*b* positioned therein, and the outer rows of staple cavities can include staple drivers 14940*c* positioned therein, wherein each of the staple drivers 14940*a* can include a cradle 14949*a* configured to support a staple 10030, wherein each of the staple drivers 14940*b* can include a cradle 14949*b* configured to support a staple 10030, and wherein each of the staple drivers 14940*c* can include a cradle 14949*c* configured to support a staple 10030. In their unfired positions, i.e., when the staple drivers 14940*a*-14940*c* are sitting on driver supports 14926 which extend underneath the support portion 14910, the cradles 14949*a* of the staple drivers 14940*a* can be positioned closer to the anvil 10060 than the cradles 14949*b* of the staple drivers 14940*b* and the cradles 14949*c* of the staple drivers 14940*c*. In such a position, a first forming distance can be defined between the cradles 14949*a* and the forming pockets 10062 positioned over the cradles 14949*a*, a second forming distance can be defined between the cradles 14949*b* and the forming pockets 10062 positioned over the cradles 14949*b*, and a third forming distance can be defined between the cradles 14949*c* and the forming pockets 10062 positioned over the cradles 14949*c*, wherein, in various embodiments, the first forming distance can be shorter than the second forming distance and the second forming distance can be shorter than the third forming distance, for example. When the staple drivers 14940*a*-14940*c* are moved from their unfired positions (FIG. 303) to their fired positions, each staple driver 14940*a*-14940*c* can be moved upwardly an equal, or an at least substantially equal, distance toward the anvil 10060 by the staple-deploying sled such that the first drivers 14940*a* drive their respective staples 10030 to a first formed height, the second drivers 14940*b* drive their respective staples 10030 to a second formed height, and the third drivers 14940*c* drive their respective staples 10030 to a third formed height, wherein the first formed height can be shorter than the second formed height and the second formed height can be shorter than the third formed height, for example. Various other embodiments are envisioned in which the first staple drivers 14940*a* are displaced upwardly a first distance, the second staple drivers 14940*b* are displaced upwardly a second distance, and the third staple drivers 14940*c* are displaced upwardly a third distance, wherein one or more of the first distance, the second distance, and the third distance can be different.

In various embodiments, referring again to FIG. 303, the deck surface 14911 of the support portion 14910 can vary in height with respect to the tissue-contacting surface 10061 of the anvil 10060. In certain embodiments, this height variation can occur laterally and, in at least one embodiment, the height of the deck surface 14911 surrounding the inner rows of staple cavities can be higher than the deck surface 14911 surrounding the outer rows of staple cavities, for example. In various embodiments, the bottom surface 14922 of the tissue thickness compensator 14920 can be configured to parallel, or at least substantially parallel, the deck surface 14911 of the support portion 14910. Further to the above, the tissue thickness compensator 14920 can also vary in thickness wherein, in at least one embodiment, the top, or tissue-contacting, surface 14921 of the tissue thickness compensator 14920 can slope inwardly from the outside or lateral edges thereof. In at least one such embodiment, as a result of the above, the tissue thickness compensator 14920 can be thinner in a region positioned over the inner rows of staple cavities and thicker in a region positioned over the outer rows of staple cavities, for example. In various embodiments, referring now to FIG. 304, the deck surface of a support portion 15010 can comprise a stepped deck surface, for example, wherein the highest steps of the stepped surface can surround the inner rows of staple cavities and the lowest steps of the stepped surface can surround the outer rows of staple cavities, for example. In at least one such embodiment, steps having an intermediate height can surround the intermediate rows of staple cavities. In certain embodiments, a tissue thickness compensator, such as tissue thickness compensator 15020, for example, can comprise a bottom surface which can parallel and abut the deck surface of the support portion 15010. In at least one embodiment, the top, or tissue-contacting, surface 15021 of the tissue thickness compensator can comprise an arcuate, parabolic, and/or curved surface, for example, which, in at least one such embodiment, can extend from a first lateral side of the tissue thickness compensator 15020 to a second lateral side of the tissue thickness compensator 15020 with an apex aligned, or at least substantially aligned, with the center of the staple cartridge 15000, for example. In various embodiments, referring now to FIG. 299, a staple cartridge 15300, for example, can comprise a support portion 15310, a plurality of staple drivers 15340 movably positioned within staple cavities defined in the support portion 15310, and a tissue thickness compensator 15320 positioned above the deck surface 15311 of the support portion 15310. The staple cartridge 15300 can further comprise one or more bottom pan portions 15326 which can be attached to the support portion 15310 and extend around the bottom of the support portion 15310 and support the drivers 15340, and staples 15330, in their unfired positions. As a staple-deploying sled is advanced through the staple cartridge, the sled can also be supported by the bottom pan portions 15326 as the sled lifts the staple drivers 15340 and the staples 15330 upwardly through the tissue thickness compensator 15320. In at least one embodiment, the tissue thickness compensator 15320 can comprise a first, or inner, portion **15322*a* positioned over an inner row of staple cavities, a second, or intermediate portion 15322*b* positioned over an intermediate row of staple cavities, and a third, or outer, portion 15322*c* positioned over a row of staple cavities, wherein the inner portion 15322*a* can be thicker than the intermediate portion 15322*b* and the intermediate portion 15322*b* can be thicker than the outer portion 15322*c*, for example. In at least one embodiment, the tissue thickness compensator 15320 can comprise longitudinal channels, for example, defined therein which can create the thinner portions 15322*b* and 15322*c* of the tissue thickness compensator 15320. In various alternative embodiments, the longitudinal channels can be defined in the top surface and/or the bottom surface of a tissue thickness compensator. In at least one embodiment, the top surface 15321 of the tissue thickness compensator 15320** can comprise a flat, or at least substantially flat, surface, for example.

In various embodiments, referring now to FIG. 296, a staple cartridge can comprise a tissue thickness compensator, such as tissue thickness compensator 15120, for example, which can comprise a plurality of portions having different thicknesses. In at least one embodiment, the tissue thickness compensator 15120 can comprise a first, or inner, portion **15122*a* which can have a first thickness, second, or intermediate, portions 15122*b* extending from the first portion 15122*b* which can each have a second thickness, and third, or outer, portions 15122*c* extending from the second portions 15122*b* which can each have a third thickness. In at least one such embodiment, the third thickness can be thicker than the second thickness and the second thickness can be thicker than the first thickness, for example, although any suitable thicknesses could be utilized in various other embodiments. In various embodiments, the portions 15122*a*-15122*c* of the tissue thickness compensator 15120 can comprise steps having different thickness. In at least one embodiment, similar to the above, a staple cartridge can comprise several rows of staples 10030 and a plurality of staple drivers having different heights which can deform the staples 10030 to different formed heights. Also similar to the above, the staple cartridge can comprise first staple drivers 15140*a* which can drive the staples 10030 supported thereon to a first formed height, second staple drivers 15140*b* which can drive the staples 10030 supported thereon to a second formed height, and third staple drivers which can drive the staples 10030 supported thereon to a third formed height, wherein the first formed height can be shorter than the second formed height and the second formed height can be shorter than the third formed height, for example. In various embodiments, as illustrated in FIG. 296, each staple 10030 can comprise the same, or substantially the same, unformed, or unfired, height. In certain other embodiments, referring now to FIG. 296A, the first drivers 15140*a*, the second drivers 15140*b*, and/or the third drivers 15140*c* can support staples having different unformed heights. In at least one such embodiment, the first staple drivers 15140*a* can support staples 15130*a* having a first unformed height, the second staple drivers 15140*b* can support staples 15130*b* having a second unformed height, and the third staple drivers 15140*c* can support staples 15130*c* having a third unformed height, wherein the first unformed height can be shorter than the second unformed height and the second unformed height can be shorter than the third unformed height, for example. In various embodiments, referring again to FIG. 296A, the tips of the staples 15130*a*, 15130*b*, and/or 15130*c* can lie, or at least substantially lie, in the same plane while, in other embodiments, the tips of the staples 15130*a*, 15130*b*, and/or 15130*c* may not lie in same plane. In certain embodiments, referring now to FIG. 297, a staple cartridge can include a tissue thickness compensator 15220 having a plurality of portions having different thickness which can be implanted against the tissue T by the staples 15130*a*, 15130*b*, and 15130*c*, as described above. In at least one embodiment, referring now to FIG. 298, the staples 15130*a*, 15130*b*, and/or 15130*c* can be deformed to different formed heights wherein the first staples 15130*a* can be formed to a first formed height, the second staples 15130*b* can be formed to a second formed height, and the third staples 15130*c* can be formed to a third formed height, and wherein the first formed height can be shorter than the second formed height and the second formed height can be shorter than the third formed height, for example. Other embodiments are envisioned in which the staples 15130***a*, 15130*b*, and 15130*c* can be formed to any suitable formed heights and/or any relative formed heights.

In various embodiments, as described above, the anvil of a surgical stapling instrument can be moved between an open position and a closed position. In such circumstances, the tissue-contacting surface of the anvil can be moved into its final, or forming, position as the anvil is moved into its closed position. Once the anvil is in its closed position, in certain embodiments, the tissue-contacting surface may no longer be adjustable. In certain other embodiments, referring now to FIG. 351, a surgical stapler, such as surgical stapler 15500, for example, can comprise an anvil channel 15560 and an adjustable tissue-contacting anvil adjustment plate 15561 positioned within the anvil channel 15560. In such embodiments, the anvil plate 15561 can be raised and/or lowered within the anvil channel 15560 in order to adjust the position of the tissue-contacting surface of the anvil plate 15561 relative to a staple cartridge positioned opposite the anvil plate 15561. In various embodiments, the surgical stapler 15500 can comprise an adjustment slide 15564 which, referring to FIGS. 356 and 357, can be slid intermediate the anvil channel 15560 and the anvil plate 15561 in order to control the distance between the anvil plate 15561 and the staple cartridge. In certain embodiments, referring again to FIGS. 351 and 352, the surgical stapler 15500 can further comprise an actuator 15562 coupled to the adjustment slide 15564 which can be slid proximally in order to slide the adjustment slide 15564 proximally and/or slid distally in order to slide the adjustment slide 15564 distally. In various embodiments, referring again to FIGS. 356 and 357, the actuator 15562 can be slid between two or more pre-defined positions in order to adjust the anvil plate 15561 between two or more positions, respectively. In at least one embodiment, such pre-defined positions can be demarcated on the surgical stapler 15500 as demarcations 15563 (FIG. 351), for example. In certain embodiments, referring to FIG. 357, the adjustment slide 15564 can comprise a plurality of support surfaces, such as first support surface 15565*a*, second support surface 15565*b*, and third support surface 15565*c*, for example, which can be aligned with a plurality of plate positioning surfaces, such as first positioning surface 15569*a*, second positioning surface 15569*b*, and third positioning surface 15569*c*, respectively, on the backside of the anvil plate 15561 in order to position the anvil plate 15561 in a first position. In order to position the anvil plate 15561 in a second position, the actuator 15562 and the slide 15564 can be slid proximally, for example, in order to realign the support surfaces 15565*a*-15565*c* of the slide 15564 relative to the positioning surfaces 15569*a*-15569*c* of the anvil plate 15561. More particularly, referring to FIG. 356, the slide 15564 can be slid distally such that the first support surface 15565*a* of the slide 15564 can be positioned behind the second positioning surface 15569*b* of the anvil plate 15561 and such that the second support surface 15565*b* of the slide 15564 can be positioned behind the third positioning surface 15569*c* of the anvil plate 15561 in order to move the anvil plate 15561 closer to the staple cartridge. When the anvil plate 15561 is moved from its first position to its second position, in such circumstances, the adjustable anvil plate 15561 can further compress the tissue T positioned between the anvil plate 15561 and the staple cartridge. In addition to the above, the formed height of the staples can be controlled by the position of the anvil plate 15561 relative to the staple cartridge as the forming pockets defined in the anvil plate 15561 will move closer to and/or further away from the staple cartridge when the anvil plate 15561 is adjusted. Although only two positions are discussed above, the slide 15564 can be slid into a suitable number of positions to move the anvil plate 15561 closer to and/or away from the staple cartridge. In any event, once the anvil plate 15561 has been suitably positioned, a staple-deploying sled 15550 can be slid distally within the staple cartridge in order to lift staple drivers 15540 and staples 15530 toward the anvil plate 15561 and staple the tissue T, as illustrated in FIG. 354. Similar surgical staplers are disclosed in U.S. patent application Ser. No. 13/036,647, entitled SURGICAL STAPLING INSTRUMENT, which was filed on Feb. 28, 2011, now U.S. Pat. No. 8,561,870, the entire disclosure of which is incorporated by reference herein.

In various embodiments, referring now to FIG. 353, a staple cartridge can be positioned within a staple cartridge channel 15570 of the surgical stapler 15500 which can comprise a tissue thickness compensator, such as tissue thickness compensator 15520, for example. When the anvil plate 15561 is moved toward the staple cartridge, as described above, the anvil plate 15561 can compress the tissue thickness compensator 15520 and/or the tissue T positioned intermediate the anvil plate 15561 and the tissue thickness compensator 15520. As the staples 15530 are deployed from the staple cartridge, referring to FIG. 355, the staples 15530 can compress and implant the tissue thickness compensator 15520 against the tissue T. In various embodiments, when the anvil plate 15561 is positioned against the slide 15564 and tissue has not yet been placed between the anvil plate 15561 and the tissue thickness compensator 15520, a gap can be defined between the anvil plate 15561 and the top surface 15521 of the tissue thickness compensator 15520 when the anvil plate 15561 is in a first position. When the anvil plate 15561 is moved into a second position, the anvil plate 15561 can contact the tissue thickness compensator 15520. In various alternative embodiments, when the anvil plate 15561 is positioned against the slide 15564 and tissue has not yet been placed between the anvil plate 15561 and the tissue thickness compensator 15520, a gap can be defined between the anvil plate 15561 and the top surface 15521 of the tissue thickness compensator 15520 when the anvil plate 15561 is in a first position and/or a second position. In at least one such embodiment, the anvil plate 15561 may not come into contact with the tissue thickness compensator 15520. In further alternative embodiments, when the anvil plate 15561 is positioned against the slide 15564 and tissue has not yet been placed between the anvil plate 15561 and the tissue thickness compensator 15520, the anvil plate 15561 can be in contact with the top surface 15521 of the tissue thickness compensator 15520 regardless of whether the anvil plate 15561 is in a first position and/or a second position, for example. Although only two positions for the anvil plate 15611 are described herein, the anvil plate 15611 may be positioned, or indexed, into any suitable number of positions.

In various embodiments, as a result of the above, a surgical stapling instrument can comprise means for adjusting the formed height of the staples which can, in various circumstance, compensate for different tissue thicknesses. In addition, the surgical stapling instrument can comprise other means for compensating for different tissue thicknesses and/or thickness variations within the tissue, for example. In at least one such embodiment, the anvil plate 15561 can be adjusted upwardly, or away, from the opposing staple cartridge to increase the formed, or fired, height of the staples. Correspondingly, the anvil plate 15561 can be adjusted downwardly, or toward, the opposing staple cartridge to decrease the formed, or fired, height of the staples. In various embodiments, the adjustment of the anvil plate 15561, for example, can adjust the gap between the forming pockets defined in the anvil plate 15561 and the fired height of the staple drivers or, more specifically, the fired height of the staple driver cradles, for example. Even with such a capacity to adjust the formed height of the staples to account for thicker and/or thinner tissue, for example, a tissue thickness compensator can also compensate for thicker and/or thinner tissue and/or compensate for thickness variations within the tissue, as described above. In such embodiments, a surgeon can be afforded with several compensation means within the same surgical stapling instrument.

As described above and illustrated in several embodiments, a surgical stapling instrument can utilize a staple cartridge having a linear arrangement of staple cavities and staples wherein a firing member can be advanced distally through the staple cartridge to deploy the staples from the staple cavities. In certain embodiments, a staple cartridge can comprise rows of staple cavities and staples which are curved. In at least one embodiment, referring now to FIGS. 345 and 346, a surgical stapling instrument, such as stapler 15600, for example, can comprise one or more circular or annular rows of staple cavities defined in a circular or annular support portion 15610. Such circular staple rows can comprise a circular row of inner staple cavities 15612 and a circular row of outer staple cavities 15613, for example. In at least one such embodiment, the circular rows of staple cavities can surround a circular or annular aperture 15615 defined in the stapler 15600 which can house a circular or annular knife movably positioned therein. In use, tissue can be positioned against the deck surface 15611 of the support portion 15610 and an anvil (not illustrated) can be assembled to the surgical stapler 15600 via an actuator extending through and/or positioned within the aperture 15615 such that, when the actuator is actuated, the anvil can be clamped toward the support portion 15610 and compress the tissue against the deck surface 15611. Once the tissue has been sufficiently compressed, the staples positioned within the staple cavities 15612 and 15613 can be ejected from the support portion 15610 and through the tissue such that the staples can contact the anvil and be sufficiently deformed to capture the tissue therein. As the staples are being fired and/or after the staples have been fired, the circular knife can be advanced to transect the tissue. Thereafter, the anvil can be moved away from the support portion 15610 and/or detached from the surgical stapler 15600 such that the anvil and the surgical stapler 15600 can be removed from the surgical site. Such surgical staplers 15600 and such surgical techniques, in various embodiments, can be utilized to join two portions of a large intestine, for example. In various circumstances, the circular staple lines may be configured to hold the portions of the large intestine together while the tissue heals and, at the same time, permit the portions of the large intestine to resiliently expand. Similar surgical stapling instruments and surgical techniques are disclosed in U.S. Pat. No. 5,285,945, entitled SURGICAL ANASTOMOSIS STAPLING INSTRUMENT, which issued on Feb. 15, 1994, the entire disclosure of which is incorporated by reference herein.

In various embodiments, further to the above, a tissue thickness compensator may be positioned against and/or attached to the support portion 15610 of the surgical stapler 15600, for example. In at least one embodiment, the tissue thickness compensator can be comprised of a circular or annular ring of material comprising an inner radius and an outer radius, for example. In certain circumstances, tissue can be positioned against this ring of material and, when the anvil is used to move the tissue toward the support portion 15610, the tissue thickness compensator can be compressed between the tissue and the deck surface 15611. During use, the staples can be fired through the tissue thickness compensator and the tissue such that the staples can contact the anvil and deform to their fired position to capture portions of the tissue and the tissue thickness compensator within the staples. In various circumstances, further to the above, the ring of material comprising the tissue thickness compensator must be sufficiently resilient to permit the portions of the large intestine surrounding the staple lines to expand. In various embodiments, referring again to FIGS. 345 and 346, a flexible tissue thickness compensator 15620 can comprise a circular or annular flexible inner ring 15624, for example, which, in at least one embodiment, can define a circular or annular aperture 15625. In certain embodiments, the inner ring 15624 may be configured such that it is not captured within staples deployed from the surgical stapler 15600; rather, in at least one embodiment, the inner ring 15624 may be positioned radially inwardly with respect to the inner row of staple cavities 15612. In at least one such embodiment, the tissue thickness compensator 15620 can comprise a plurality of tags, such as inner tags 15622 and outer tags 15623, for example, extending therefrom such that the tags can be at least partially captured within the staples as they are being deformed. More particularly, referring primarily to FIG. 345, each inner tag 15622 can comprise a head which is positioned over a staple cavity 15612 defined in the surgical stapler 15600 wherein the head can be attached to the inner ring 15624 by a neck 15626, for example, and, similarly, each outer tag 15623 can comprise a head which is positioned over a staple cavity 15613 defined in the surgical stapler 15600 wherein the head can be attached to the inner ring 15624 by a neck 15627, for example. In various embodiments, the heads of the inner tags 15622 and the outer tags 15623 can comprise any suitable shape, such as round, oval, and/or elliptical, for example. The necks 15626 and/or 15627 can also comprise any suitable shape wherein, in at least one embodiment, the necks 15627 connecting the heads of the outer tags 15623 to the inner ring 15624 can be configured to extend between adjacent inner staple cavities 15612 in the support portion 15610 such that the necks 15627 are not captured within the staples deployed from the inner staple cavities 15612.

In various embodiments, referring now to FIGS. 347 and 348, a flexible tissue thickness compensator 15720 can comprise a circular or annular flexible outer ring 15724, for example. In certain embodiments, the outer ring 15724 may be configured such that it is not captured within staples deployed from the surgical stapler 15600; rather, in at least one embodiment, the outer ring 15724 may be positioned radially outwardly with respect to the outer row of staple cavities 15613. In at least one such embodiment, the tissue thickness compensator 15720 can comprise a plurality of tags, such as inner tags 15622 and outer tags 15623, for example, extending therefrom such that the tags can be at least partially captured within the staples as they are being deformed. More particularly, referring primarily to FIG. 347, each inner tag 15622 can comprise a head which is positioned over a staple cavity 15612 defined in the surgical stapler 15600 wherein the head can be attached to the outer ring 15724 by a neck 15726, for example, and, similarly, each outer tag 15623 can comprise a head which is positioned over a staple cavity 15613 defined in the surgical stapler 15600 wherein the head can be attached to the outer ring 15724 by a neck 15727, for example. In various embodiments, the heads of the inner tags 15622 and the outer tags 15623 can comprise any suitable shape, such as round, oval, and/or elliptical, for example. The necks 15726 and/or 15727 can also comprise any suitable shape wherein, in at least one embodiment, the necks 15726 connecting the heads of the inner tags 15622 to the outer ring 15724 can be configured to extend between adjacent outer staple cavities 15613 such that the necks 15726 are not captured within the staples deployed from the outer staple cavities 15613. In certain alternative embodiments, a tissue thickness compensator can comprise a circular or annular flexible inner ring, a circular or annular flexible outer ring, and, in addition, a plurality of tags which can be connected to the inner ring and/or the outer ring. In at least one embodiment, certain tags can be connected to the inner ring and certain other tags can be connected to the outer ring. In certain embodiments, at least some of the tags can be connected to both the inner ring and the outer ring. In any event, further to the above, the inner ring 15624 of the tissue thickness compensator 15620, the outer ring 15724 of the tissue thickness compensator 15720, and/or any other suitable tissue thickness compensator, can be configured to resiliently expand and/or contract in order to accommodate the expansion and/or contraction of the tissue that it has been implanted against. Furthermore, although various embodiments are described herein as comprising circular or annular support rings, a tissue thickness compensator can comprise any suitably-shaped support structure for connecting the tags thereto. In various embodiments, further to the above, the circular knife advanced by the surgical stapler to cut the tissue captured between the anvil and the support portion can also cut the buttress material. In at least one such embodiment, the knife can separate the inner support ring from the tags by cutting the necks thereof, for example.

In various embodiments, further to the above, a tissue thickness compensator can comprise detachable and/or relatively movable positions which can be configured to allow the tissue thickness compensator to expand and/or contract in order to accommodate the movement of the tissue that it has been implanted against. Referring now to FIGS. 349 and 350, a circular or annular tissue thickness compensator 15820 can be positioned against and/or supported by the deck surface 15611 of the surgical stapler 15600 which can be held in an unexpanded position (FIG. 349) as it is being implanted against the tissue and, after the tissue thickness compensator 15820 has been implanted, the tissue thickness compensator 15820 can be configured to expand outwardly, as illustrated in FIG. 350. In various embodiments, the tissue thickness compensator 15820 can comprise a plurality of arcuate portions 15822 which can be connected together by an inner ring 15824, for example. In at least one embodiment, the arcuate portions 15822 can be separated from one another by seams 15828. In at least one other embodiment, the arcuate portions 15822 may be connected to one another wherein, in at least one such embodiment, an arrangement of perforations may permit the arcuate portions 15822 to separate from one another. In either event, in various embodiments, the arcuate portions 15822 can each comprise interlocking features, such as projections 15826 and notches 15823, for example, which can co-operate to limit relative movement between the arcuate portions 15822 prior to the tissue thickness compensator 15820 being implanted. Further to the above, each arcuate portion 15822 can be connected to the inner ring 15824 by one or more connectors 15827, for example, which can be configured to releasably hold the arcuate portions 15822 in position. After the staples, such as staples 10030, for example, stored within the support portion 15610 have been utilized to implant the tissue thickness compensator 15620 against the tissue, referring primarily to FIG. 350, the connectors 15827 can detach from the inner ring 15824 and allow the tissue thickness compensator 15820 to at least partially expand to accommodate movement within the underlying tissue. In various circumstances, all of the arcuate portions 15822 may detach from the inner ring 15824 while, in other circumstances, only some of the arcuate portions 15822 may detach from the inner ring 15824. In certain alternative embodiments, the arcuate portions 15822 can be connected by flexible sections which can permit the arcuate portions 15822 to move relative to each other but not detach from one another. In at least one such embodiment, the flexible sections may not receive staples therein and can be configured to stretch and/or contract to accommodate the relative movement of the arcuate portions 15822. In the embodiment illustrated in FIGS. 349 and 350, the tissue thickness compensator 15820 can comprise eight arcuate portions 15822, for example. In certain other embodiments, a tissue thickness compensator can comprise any suitable number of arcuate portions, such as two or more arcuate portions, for example.

Further to the above, a tissue thickness compensator 15620, 15720, and/or 15820, for example, can be configured to compensate for thicker and/or thinner tissue captured between the anvil and the support portion 15610 of the surgical instrument 15600. In various embodiments, similar to the above, the formed, or fired, height of the staples can be adjusted by moving the anvil toward and/or away from the support portion 15610. More particularly, the anvil can be moved closer to the support portion 15610 to decrease the formed height of the staples while, correspondingly, the anvil can be moved further away from the support portion 15610 to increase the formed height of the staples. In such embodiments, as a result, a surgeon can adjust the anvil away from the support portion 15610 to account for thick tissue and toward the support portion 15610 to account for thin tissue. In various other circumstances, the surgeon may decide not to adjust the anvil at all and rely on the tissue thickness compensator to account for the thinner and/or thicker tissue. In various embodiments, as a result, the surgical instrument 15600 can comprise at least two means for compensating for different tissue thicknesses and/or variations in the tissue thickness.

In various embodiments, as described above, a tissue thickness compensator can be attached to a support portion of a staple cartridge. In certain embodiments, the bottom surface of the tissue thickness compensator can comprise one of a layer of hooks or a layer of loops while a deck surface on the support portion can comprise the other one of the layer of hooks and the layer of loops. In at least one such embodiment, the hooks and the loops can be configured to engage one another and releasably retain the tissue thickness compensator to the support portion. In various embodiments, each hook can comprise an enlarged head extending from a neck, for example. In certain embodiments, a plurality of pads comprising the loops, for example, can be bonded to the bottom surface of the tissue thickness compensator while a plurality of pads comprising the hooks can be bonded to the deck surface of the support portion. In at least one embodiment, the support portion can comprise one or more apertures and/or recesses, for example, which can be configured to receive an insert therein comprising hooks and/or loops. In addition to or in lieu of the above, a tissue thickness compensator can be removably mounted to an anvil utilizing such hook and loop arrangements, for example. In various embodiments, the hooks and loops can comprise fibrous surfaces, for example.

In various embodiments, as described above, a staple cartridge can comprise a support portion and a tissue thickness compensator attached to the support portion. In certain embodiments, as also described above, the support portion can comprise a longitudinal slot configured to receive a cutting member therein and the tissue thickness compensator can comprise a retention member that can be retained in the longitudinal slot. In at least one embodiment, referring now to FIG. 386, a staple cartridge 16000 can comprise a support portion 16010 including a deck surface 16011 and a longitudinal slot 16015. The staple cartridge 16000 can further comprise a tissue thickness compensator 16020 positioned above the deck surface 16011. In various embodiments, the tissue thickness compensator 16020 can include a longitudinal retention member 16025 which extends downwardly into the longitudinal slot 16015. In at least one such embodiment, the retention member 16025 can be pressed into the slot 16015 such that the interaction between the retention member 16025 and the slot 16015 can resist relative movement between the support portion 16010 and the tissue thickness compensator 16020. In various embodiments, the body of the tissue thickness compensator 16020 can be comprised of a first material and the retention member 16025 can be comprised of a second, or different, material. In certain embodiments, the body of the tissue thickness compensator 16020 can be comprised of a material having a first durometer and the retention member 16025 can be comprised of a material having a second durometer, wherein the second durometer can be higher than the first durometer, for example. In use, in at least one embodiment, the staples 10030 can be pushed upwardly by staple drivers 10040 such that the tips of the staples 10030 can push through the body of the tissue thickness compensator 16020 and emerge from the tissue contacting surface 16021 and capture at least a portion of the tissue thickness compensator 16020 against the targeted tissue. In various embodiments, a cutting member passing through the slot 16015 can transect the retention member 16025 as the staples 10030 are being deployed. Once the tissue thickness compensator 16020 has been implanted, in various embodiments, the retention member 16025 can be pulled out of the slot 16015. In certain other embodiments, the body of the tissue thickness compensator 16020 can be configured to detach from the retention member 16025.

Referring now to FIGS. 387 and 389, a staple cartridge 17000 can comprise a support portion 17010 including a deck surface 17011 and a longitudinal slot 17015. The staple cartridge 17000 can further comprise a tissue thickness compensator 17020 positioned above the deck surface 17011. In various embodiments, the tissue thickness compensator 17020 can include a longitudinal retention member 17025 which extends downwardly into the longitudinal slot 17015. In at least one such embodiment, the retention member 17025 can be pressed into the slot 17015 such that the interaction between the retention member 17025 and the slot 17015 can resist relative movement between the support portion 17010 and the tissue thickness compensator 17020. In various embodiments, the retention member 17025 can extend through the entirety of the tissue thickness compensator 17020 to the top surface 17021 thereof wherein body portions 17024 of the tissue thickness compensator 17020 can be attached to opposite sides of the retention member 17025. In at least one such embodiment, the retention member 17025 can also be configured to resist the lateral deflection, for example, of the tissue thickness compensator 17020. In various embodiments, the body portions 17024 can be comprised of a first material and the retention member 17025 can be comprised of a second, or different, material. In certain embodiments, the body portions 17024 can be comprised of a material having a first durometer and the retention member 17025 can be comprised of a material having a second durometer, wherein the second durometer can be higher than the first durometer, for example. In various embodiments, further to the above, a cutting member passing through the slot 17015 can transect the retention member 17025 as the staples 10030 are being deployed. Once the tissue thickness compensator 17020 has been implanted, in various embodiments, the retention member 17025 can be pulled out of the slot 17015. In certain other embodiments, the body portions 17024 can be configured to detach from the retention member 17025.

Referring now to FIG. 388, a staple cartridge 18000 can comprise a support portion 18010 including a deck surface 18011 and a longitudinal slot 18015. The staple cartridge 18000 can further comprise a tissue thickness compensator 18020 positioned above the deck surface 18011. In various embodiments, the tissue thickness compensator 18020 can include a longitudinal retention member 18025 which extends downwardly into the longitudinal slot 18015. In at least one such embodiment, the retention member 18025 can be pressed into the slot 18015 such that the interaction between the retention member 18025 and the slot 18015 can resist relative movement between the support portion 18010 and the tissue thickness compensator 18020. In various embodiments, the retention member 18025 can extend through the entirety of the tissue thickness compensator 18020 to the top surface 18021 thereof wherein body portions 18024 of the tissue thickness compensator 18020 can be attached to opposite sides of the retention member 18025. In at least one embodiment, the retention member 18025 can comprise an enlarged portion 18026 which can be received in a cavity 18016 defined in the slot 18015. In at least one such embodiment, the enlarged portion 18026 can resist the withdrawal of the retention member 18025 from the slot 18015.

In various embodiments, the tissue thickness compensator may comprise an extrudable, a castable, and/or moldable composition comprising at least one of the synthetic and/or non-synthetic materials described herein. In various embodiments, the tissue thickness compensator may comprise a film or sheet comprising two or more layers. The tissue thickness compensator may be obtained using conventional methods, such as, for example, mixing, blending, compounding, spraying, wicking, solvent evaporating, dipping, brushing, vapor deposition, extruding, calendaring, casting, molding and the like. In extrusion, an opening may be in the form of a die comprising at least one opening to impart a shape to the emerging extrudate. In calendering, an opening may comprise a nip between two rolls. Conventional molding methods may include, but are not limited to, blow molding, injection molding, foam injection, compression molding, thermoforming, extrusion, foam extrusion, film blowing, calendaring, spinning, solvent welding, coating methods, such as dip coating and spin coating, solution casting and film casting, plastisol processing (including knife coating, roller coating and casting), and combinations thereof. In injection molding, an opening may comprise a nozzle and/or channels/runners and/or mold cavities and features. In compression molding, the composition may be positioned in a mold cavity, heated to a suitable temperature, and shaped by exposure to compression under relatively high pressure. In casting, the composition may comprise a liquid or slurry that may be poured or otherwise provided into, onto and/or around a mold or object to replicate features of the mold or object. After casting, the composition may be dried, cooled, and/or cured to form a solid.

In various embodiments, a method of manufacturing a tissue thickness compensator may generally comprise providing a tissue thickness compensator composition, liquifying the composition to make it flowable, and forming the composition in the molten, semi-molten, or plastic state into a layer and/or film having the desired thickness. Referring to FIG. 527A, a tissue thickness compensator may be manufactured by dissolving a hydrogel precursor in an aqueous solution, dispersing biocompatible particles and/or fibers therein, providing a mold having biocompatible particles therein, providing the solution into the mold, contacting an activator and the solution, and curing the solution to form the tissue thickness compensator comprising an outer layer comprise biocompatible particles and an inner layer comprising biocompatible particles embedded therein. A shown in FIG. 527A, a biocompatible layer 70250 may be provided in the bottom of a mold 70260, and an aqueous solution of a hydrogel precursor 70255 having biocompatible particles 70257 disposed therein may be provided to the mold 70260, and the aqueous solution may be cured to form a tissue thickness compensator having a first layer comprising a biocompatible material, such as ORC, for example, and a second layer comprising a hydrogel having biocompatible fibers, such as ORC fibers, disposed therein. The tissue thickness compensator may comprise a foam comprising an outer layer comprise biocompatible particles and an inner layer comprising biocompatible particles embedded therein. In at least one embodiment, a tissue thickness compensator may be manufactured by dissolving a sodium alginater in water, dispersing ORC particles therein, providing a mold having ORC particles therein, pouring the solution into the mold, spraying or infusing calcium chloride to contact the solution to initiate crosslinking of the sodium alginater, freeze drying the hydrogel to form the tissue thickness compensator comprising an outer layer comprising ORC and an inner layer comprising a hydrogel and ORC particles embedded therein.

Referring to FIG. 527B, in various embodiments, a method of manufacturing a trilayer tissue thickness compensator may generally comprise by dissolving a first hydrogel precursor in a first aqueous solution, dispersing biocompatible particles and/or fibers in the first aqueous solution, providing a mold 70260 having a first layer 70250 of biocompatible particles therein, providing the first aqueous solution into the mold, contacting an activator and the first aqueous solution, curing the first aqueous solution to form a second layer 70255, dissolving a second hydrogel precursor in a second aqueous solution, providing the second aqueous solution into the mold, curing the second aqueous solution to form a third layer 70265. In at least one embodiment, a trilayer tissue thickness compensator may be manufactured by dissolving a sodium alginater in water to form a first aqueous solution, dispersing ORC particles in the first aqueous solution, providing a mold having a first layer of ORC particles therein, pouring the first aqueous solution into the mold, spraying or infusing calcium chloride to contact the first aqueous solution to initiate crosslinking of the sodium alginater, freeze drying the first aqueous solution to form a second layer comprising a hydrogel having OCR particles embedded therein, dissolving a sodium alginater in water to form a second aqueous solution, pouring the second aqueous solution into the mold, spraying or infusing calcium chloride to contact the second aqueous solution to initiate crosslinking of the sodium alginater, freeze drying the second aqueous solution to form a third layer comprising a hydrogel.

In various embodiments, a method of manufacturing a tissue thickness compensator comprising at least one medicament stored and/or absorbed therein may generally comprise providing a tissue thickness compensator and contacting the tissue thickness compensator and the medicament to retain the medicament in the tissue thickness compensator. In at least one embodiment, a method of manufacturing a tissue thickness compensator comprising an antibacterial material may comprise providing a hydrogel, drying the hydrogel, swelling the hydrogel in an aqueous solution of silver nitrate, contacting the hydrogel and a solution of sodium chloride to form the tissue thickness compensator having antibacterial properties. The tissue thickness compensator may comprise silver dispersed therein.

Referring to FIG. 533, in various embodiments, a method for manufacturing a tissue thickness compensator may comprise co-extrusion and/or bonding. In various embodiments, the tissue thickness compensator 70550 may comprise a laminate comprising a first layer 70555 and a second layer 70560 sealingly enclosing an inner layer 70565 comprising a hydrogel, for example. The hydrogel may comprise a dry film, a dry foam, a powder, and/or granules, for example. The hydrogel may comprise super absorbent materials, such as, for example, polyvinylpyrrolidone, carboxy methycellulose, poly sulful propyl acrylate. The first and/or second layers may be made in-line by feeding raw materials of the first and second layers, respectively, into an extruder from a hopper, and thereafter supplying the first and second layers. The raw materials of the inner layer 70565 may be added to a hopper of an extruder. The raw materials can be dispersively mixed and compounded at an elevated temperature within the extruder. As the raw materials exit the die 70570 at an opening, the inner layer 70565 may be deposited onto a surface of the first layer 70555. In various embodiments, the tissue thickness compensator may comprise a foam, film, powder, and/or granule. The first and second layers 70555 and 70560 may be positioned in the face-to-face relationship. The second layer 70560 may be aligned with the first layer 70555 in a face-to-face relationship by a roller 70575. The first layer 70555 may adhere to the second layer 70560 wherein the first and second layers 70555, 70560 may physically entrap the inner layer 70565. The layers may be joined together under light pressure, under conventional calendar bonding processes, and/or through the use of adhesives, for example, to form the tissue thickness compensator 70550. In at least one embodiment, as shown in FIG. 407, the first and second layers 70555 and 70560 may be joined together through a rolling process utilizing a grooved roller 70580, for example. In various embodiments, as a result of the above, the inner layer 70565 may be contained and/or sealed by the first and second layers 70555 and 70560 which can collectively form an outer layer, or barrier. The outer layer may prevent or reduce moisture from contacting the inner layer 70565 until the outer layer is ruptured.

Referring to FIG. 390, an end effector 12 for a surgical instrument 10 (FIG. 1) can be configured to receive a fastener cartridge assembly, such as staple cartridge 20000, for example. As illustrated in FIG. 390, the staple cartridge 20000 can be configured to fit in a cartridge channel 20072 of a jaw 20070 of the end effector 12. In other embodiments, the staple cartridge 20000 can be integral to the end effector 12 such that the staple cartridge 20000 and the end effector 12 are formed as a single unit construction. The staple cartridge 20000 can comprise a first body portion, such as rigid support portion 20010, for example. The staple cartridge 20000 can also comprise a second body portion, such as a compressible portion or a tissue thickness compensator 20020, for example. In other embodiments, the tissue thickness compensator 20020 may not comprise an integral part of the staple cartridge 20000 but may be otherwise positioned relative to the end effector 12. For example, the tissue thickness compensator 20020 can be secured to an anvil 20060 of the end effector 12 or can be otherwise retained in the end effector 12. In at least one embodiment, referring to FIG. 407, the staple cartridge can further comprise retainer clips 20126 which can be configured to inhibit the tissue thickness compensator 20020 from prematurely detaching from the support portion 20010. The reader will appreciate that the tissue thickness compensators described herein can be installed in or otherwise engaged with a variety of end effectors and that such embodiments are within the scope of the present disclosure.

Similar to the tissue thickness compensators described herein, referring now to FIG. 407, the tissue thickness compensator 20020 can be released from or disengaged with the surgical end effector 12. For example, in some embodiments, the rigid support portion 20010 of the staple cartridge 20000 can remain engaged with the fastener cartridge channel 20072 of the end effector jaw 20070 while the tissue thickness compensator 20020 disengages from the rigid support portion 20010. In various embodiments, the tissue thickness compensator 20020 can release from the end effector 12 after staples 20030 (FIGS. 407-412) are deployed from staple cavities 20012 in the rigid support portion 2010, similar to various embodiments described herein. Staples 20030 can be fired from staple cavities 20012 such that the staples 20030 engage the tissue thickness compensator 20020. Also similar to various embodiments described herein, referring generally to FIGS. 392, 411 and 412, a staple 20030 can capture a portion of the tissue thickness compensator 20020 along with stapled tissue T. In some embodiments, the tissue thickness compensator 20020 can be deformable and the portion of the tissue thickness compensator 20020 that is captured within a fired staple 20030 can be compressed. Similar to the tissue thickness compensators described herein, the tissue thickness compensator 20020 can compensate for different thicknesses, compressibilities, and/or densities of tissue T captured within each staple 20030. Further, as also described herein, the tissue thickness compensator 20020 can compensate for gaps created by malformed staples 20030.

The tissue thickness compensator 20020 can be compressible between non-compressed height(s) and compressed height(s). Referring to FIG. 407, the tissue thickness compensator 20020 can have a top surface 20021 and a bottom surface 20022. The height of the tissue thickness compensator can be the distance between the top surface 20021 and the bottom surface 20022. In various embodiments, the non-compressed height of the tissue thickness compensator 20020 can be the distance between the top surface 20021 and the bottom surface 20022 when minimal or no force is applied to the tissue thickness compensator 20020, i.e., when the tissue thickness compensator 20020 is not compressed. The compressed height of the tissue thickness compensator 20020 can be the distance between the top surface 20021 and the bottom surface 20022 when a force is applied to the tissue thickness compensator 20020, such as when a fired staple 20030 captures a portion of the tissue thickness compensator 20020, for example. The tissue thickness compensator 20020 can have a distal end 20025 and a proximal end 20026. As illustrated in FIG. 407, the non-compressed height of the tissue thickness compensator 20020 can be uniform between the distal end 20025 and the proximal end 20026 of the tissue thickness compensator 20020. In other embodiments, the non-compressed height can vary between the distal end 20025 and the proximal end 20026. For example, the top surface 20021 and/or bottom surface 20022 of the tissue thickness compensator 20020 can be angled and/or stepped relative to the other such that the non-compressed height varies between the proximal end 20026 and the distal end 20025. In some embodiments, the non-compressed height of the tissue thickness compensator 20020 can be approximately 0.08 inches, for example. In other embodiments, the non-compressed height of the tissue thickness compensator 20020 can vary between approximately 0.025 inches and approximately 0.10 inches, for example.

As described in greater detail herein, the tissue thickness compensator 20020 can be compressed to different compressed heights between the proximal end 20026 and the distal end 20025 thereof. In other embodiments, the tissue thickness compensator 20020 can be uniformly compressed throughout the length thereof. The compressed height(s) of the tissue thickness compensator 20020 can depend on the geometry of the end effector 12, characteristics of the tissue thickness compensator 20020, the engaged tissue T and/or the staples 20030, for example. In various embodiments, the compressed height of the tissue thickness compensator 20020 can relate to the tissue gap in the end effector 12. In various embodiments, when the anvil 20060 is clamped towards the staple cartridge 20000, the tissue gap can be defined between a top deck surface 20011 (FIG. 407) of the staple cartridge 20000 and a tissue contacting surface 20061 (FIG. 390) of the anvil 20060, for example. The tissue gap can be approximately 0.025 inches or approximately 0.100 inches, for example. In some embodiments, the tissue gap can be approximately 0.750 millimeters or approximately 3.500 millimeters, for example. In various embodiments, the compressed height of the tissue thickness compensator 20020 can equal or substantially equal the tissue gap, for example. When tissue T is positioned within the tissue gap of the end effector 12, the compressed height of the tissue thickness compensator can be less in order to accommodate the tissue T. For example, where the tissue gap is approximately 0.750 millimeters, the compressed height of the tissue thickness compensator can be approximately 0.500 millimeters. In embodiments where the tissue gap is approximately 3.500 millimeters, the compressed height of the tissue thickness compensator 20020 can be approximately 2.5 mm, for example. Furthermore, the tissue thickness compensator 20020 can comprise a minimum compressed height. For example, the minimum compressed height of the tissue thickness compensator 20020 can be approximately 0.250 millimeters. In various embodiments, the tissue gap defined between the deck surface of the staple cartridge and the tissue contacting surface of the anvil can equal, or at least substantially equal, the uncompressed height of the tissue thickness compensator, for example.

Referring primarily to FIG. 391, the tissue thickness compensator 20020 can comprise a fibrous, nonwoven material 20080 including fibers 20082. In some embodiments, the tissue thickness compensator 20020 can comprise felt or a felt-like material. Fibers 20082 in the nonwoven material 20080 can be fastened together by any means known in the art, including, but not limited to, needle-punching, thermal bonding, hydro-entanglement, ultrasonic pattern bonding, chemical bonding, and meltblown bonding. Further, in various embodiments, layers of nonwoven material 20080 can be mechanically, thermally, or chemically fastened together to form the tissue thickness compensator 20020. As described in greater detail herein, the fibrous, nonwoven material 20080 can be compressible, which can enable compression of the tissue thickness compensator 20020. In various embodiments, the tissue thickness compensator 20020 can comprise a non-compressible portion as well. For example, the tissue thickness compensator 20020 can comprise a compressible nonwoven material 20080 and a non-compressible portion.

Still referring primarily to FIG. 391, the nonwoven material 20080 can comprise a plurality of fibers 20082. At least some of the fibers 20082 in the nonwoven material 20080 can be crimped fibers 20086. The crimped fibers 20086 can be, for example, crimped, twisted, coiled, bent, crippled, spiraled, curled, and/or bowed within the nonwoven material 20080. As described in greater detail herein, the crimped fibers 20086 can be formed in any suitable shape such that deformation of the crimped fibers 20086 generates a spring load or restoring force. In some embodiments, the crimped fibers 20086 can be heat-shaped to form a coiled or substantially coil-like shape. The crimped fibers 20086 can be formed from non-crimped fibers 20084. For example, non-crimped fibers 20084 can be wound around a heated mandrel to form a substantially coil-like shape.

In various embodiments, the tissue thickness compensator 20020 can comprise a homogeneous absorbable polymer matrix. The homogenous absorbable polymer matrix can comprise a foam, gel, and/or film, for example. Further, the plurality of fibers 20082 can be dispersed throughout the homogenous absorbable polymer matrix. At least some of the fibers 20082 in the homogenous absorbable polymer matrix can be crimped fibers 20086, for example. As described in greater detail herein, the homogeneous absorbable polymer matrix of the tissue thickness compensator 2002 can be compressible.

In various embodiments, referring to FIGS. 394 and 395, crimped fibers 20086 can be randomly dispersed throughout at least a portion of the nonwoven material 20080. For example, crimped fibers 20086 can be randomly dispersed throughout the nonwoven material 20080 such that a portion of the nonwoven material 20080 comprises more crimped fibers 20086 than other portions of the nonwoven material 20080. Further, the crimped fibers 20086 can congregate in fiber clusters **20085*a*, 20085*b*, 20085*c*, 20085*d* and 20085*e*, for example, in the nonwoven material 20080. The shape of the crimped fibers 20086 can cause entanglement of the fibers 20086 during manufacturing of the nonwoven material 20080; entanglement of the crimped fibers 20086 can, in turn, result in the formation of the fiber clusters 20085*a*, 20085*b*, 20085*c*, 20085*d* and 20085*e*. Additionally or alternatively, crimped fibers 20086 can be randomly oriented throughout the nonwoven material 20080. For example, referring to FIG. 391, a first crimped fiber 20086*a* can be oriented in a first direction, a second crimped fiber 20086*b* can be oriented in a second direction, and a third crimped fiber 20086*c*** can be oriented in a third direction.

In some embodiments, the crimped fibers 20086 can be systematically distributed and/or arranged throughout at least a portion of the nonwoven material 20080. For example, referring now to FIG. 396, crimped fibers 20186 can be positioned in an arrangement 20185, in which a plurality of crimped fibers **20186*a* are arranged in a first direction and another plurality of crimped fibers 20186*b* are arranged in a second direction. The crimped fibers 20186 can overlap such that they become entangled or interconnected with each other. In various embodiments, the crimped fibers 20186 can be systematically arranged such that a crimped fiber 20186*a* is substantially parallel to another crimped fiber 20186*a*. Still another crimped fiber 20186*b* can be substantially transverse to some crimped fibers 20186*a*. In various embodiments, crimped fibers 20186*a* can be substantially aligned with a first axis Y and crimped fibers 20186*b*** can be substantially aligned with a second axis X. In some embodiments the first axis Y can be perpendicular or substantially perpendicular to the second axis X, for example.

Referring primarily to FIG. 397, in various embodiments, crimped fibers 20286 can be arranged in an arrangement 20285. In some embodiments, each crimped fibers 20286 can comprise a longitudinal axis defined between a first end 20287 and a second end 20289 of the crimped fiber 20286. In some embodiments, the crimped fibers 20286 can be systematically distributed in the nonwoven material 20080 such that a first end 20287 of one crimped fiber 20286 is positioned adjacent to a second end 20289 of another crimped fiber 20286. In another embodiment, referring now to FIG. 398, a fiber arrangement 20385 can comprise a first crimped fiber **20386*a* oriented in a first direction, a second crimped fiber 20386*b* oriented in a second direction, and a third crimped fiber 20386*c* oriented in a third direction, for example. In various embodiments, a single pattern or arrangement of crimped fibers 20286 can be repeated throughout the nonwoven material 20080. In at least one embodiment, crimped fibers can be arranged in different patterns throughout the nonwoven material 20080. In still other embodiments, the nonwoven material 20080** can comprise at least one pattern of crimped fibers, as well as a plurality of randomly oriented and/or randomly distributed crimped fibers.

Referring again to FIG. 391, the plurality of fibers 20082 in the nonwoven material 20080 can comprise at least some non-crimped fibers 20084. The non-crimped fibers 20084 and crimped fibers 20086 in the nonwoven material 20080 can be entangled or interconnected. In one embodiment, the ratio of crimped fibers 20086 to non-crimped fibers 20084 can be approximately 25:1, for example. In another embodiment, the ratio of crimped fibers 20086 to non-crimped fibers 20084 can be approximately 1:25, for example. In other embodiments, the ratio of crimped fibers 20086 to non-crimped fibers 20084 can be approximately 1:1, for example. As described in greater detail herein, the number of crimped fibers 20086 per unit volume of nonwoven material 20080 can affect the restoring force generated by the nonwoven material 20080 when the nonwoven material 20080 has been deformed. As also described in greater detail herein, the restoring force generated by the nonwoven material 20080 can also depend on, for example, the material, shape, size, position and/or orientation of crimped and non-crimped fibers 20086, 20084 in the nonwoven material 20080.

In various embodiments, the fibers 20082 of the nonwoven material 20080 can comprise a polymeric composition. The polymeric composition of the fibers 20082 can comprise non-absorbable polymers, absorbable polymers, or combinations thereof. In some embodiments, the absorbable polymers can include bioabsorbable, biocompatible elastomeric polymers. Furthermore, the polymeric composition of the fibers 20082 can comprise synthetic polymers, non-synthetic polymers, or combinations thereof. Examples of synthetic polymers include, but are not limited to, polyglycolic acid (PGA), poly(lactic acid) (PLA), polycaprolactone (PCL), polydioxanone (PDO), and copolymers thereof. For example, the fibers 20082 can comprise a 90/10 poly(glycolide-L-lactide) copolymer, such as, for example, the copolymer commercially available from Ethicon, Inc. under the trade designation "VICRYL (polyglactic 910)." Examples of non-synthetic polymers include, but are not limited to, lyophilized polysaccharide, glycoprotein, elastin, proteoglycan, gelatin, collagen, and oxidized regenerated cellulose (ORC). In various embodiments, similar to the polymeric compositions in tissue thickness compensators described herein, the polymeric composition of the fibers 20082 can include varied amounts of absorbable polymers, non-absorbable polymers, synthetic polymers, and/or non-synthetic polymers, for example, by weight percentage.

In some embodiments, the crimped fibers 20086 of the nonwoven material 20080 can comprise a first polymeric composition and the non-crimped fibers 20084 of the nonwoven material 20080 can comprise a different polymeric composition. For example, the crimped fibers 20086 can comprise synthetic polymer(s), such as, for example, 90/10 poly(glycolide-L-lactide), while the non-crimped fibers 20084 can comprise non-synthetic polymer(s), such as, for example, oxidized regenerated cellulose. In other embodiments, the crimped fibers 20086 and the non-crimped fibers 20084 can comprise the same polymeric composition.

As described herein, crimped fibers 20086 and non-crimped fibers 20084 can be fastened together, for example, by needle-punching, thermal bonding, hydro-entanglement, ultrasonic pattern bonding, chemical bonding, and melt-blown bonding. In some embodiments, crimped fibers 20086 comprising synthetic polymers such as, for example, "VICRYL (polyglactic 910)", and non-crimped fibers 20084 comprising oxidized regenerated cellulose can be needle-punched together to form the nonwoven material 20080. In various embodiments, the nonwoven material 20080 can comprise approximately 5% to 50% crimped "VICRYL (polyglactic 910)" fibers 20086 by weight and approximately 5% to 50% non-crimped oxidized regenerated cellulose (ORC) fibers 20084 by weight, for example. When the nonwoven material 20080 contacts tissue T, the non-crimped ORC fibers 20084 can rapidly react with plasma in the tissue to form a gelatinous mass, for example. In various embodiments, the formation of the gelatinous ORC mass can be instantaneous or nearly instantaneous with the tissue contact. Further, after the formation of the gelatinous ORC mass, the crimped "VICRYL (polyglactic 910)" fibers 20086 can remain dispersed throughout the nonwoven material 20080. For example, the crimped fibers 20086 can be suspended in the gelatinous ORC mass. As the gelatinous ORC mass is bioabsorbed, the crimped "VICRYL (polyglactic 910)" fibers 20086 can exert a springback force on adjacent tissue, as described in greater detail herein. Further, the tissue can begin to heal around the "VICRYL (polyglactic 910)" fibers and/or the formed staples 30030, as also described in greater detail herein.

In at least one embodiment, referring primarily to FIGS. 407-410, the support portion 20010 of the staple cartridge 20000 can comprise a cartridge body 20017, a top deck surface 20011, and a plurality of staple cavities 20012. Similar to the embodiments described herein, each staple cavity 20012 can define an opening in the deck surface 20011. A staple 20030 can be removably positioned in a staple cavity 20012. In various embodiments, a single staple 20030 is disposed in each staple cavity 20012. In at least one embodiment, referring primarily to FIGS. 411 and 412 and similar to the staples described herein, each staple 20030 can comprise a base 20031 having a first end 20035 and a second end 20036. A staple leg 20032 can extend from the first end 20035 of the base 20031 and another staple leg 20032 can extend from the second end 20036 of the base 20031. Referring again to FIGS. 407-410, prior to the deployment of the staples 20030, the base 20031 of each staple 20030 can be supported by a staple driver 20040 positioned within the rigid support portion 20010 of the staple cartridge 20000. Also prior to deployment of the staples 20030, the legs 20032 of each staple 20030 can be at least partially contained within a staple cavity 20012.

In various embodiments, the staples 20030 can be deployed between an initial position and a fired position. For example, referring primarily to FIG. 410, staples 20030 can be in an initial position (staples 20030*e*, 20030*f*), a partially fired or intermediate position (staples 20030*c*, 20030*d*), or a fired position (staples 20030*a*, 20030*b*). A driver 20040 can motivate the staples between the initial position and the fired position. For example, the base 20031 of each staple 20030 can be supported by a driver 20040. The legs 20032 of a staple (staples 20030*e*, 20030*f* in FIG. 409, for example) can be positioned within a staple cavity 20012. As the firing member or staple-firing sled 20050 translates from the proximal end 20001 to the distal end 20002 of the staple cartridge 20000, an inclined surface 20051 on the sled 20050 can contact an inclined surface 20042 on a driver 20040 to deploy the staple 20030 positioned above to the contacted driver 20040. In various embodiments, the staples 20030 can be deployed between an initial position and a fired position such that the legs 20032 move through the nonwoven material 20080 of the tissue thickness compensator 20020, penetrate the top surface 20021 of the tissue thickness compensator 20020, penetrate tissue T, and contact an anvil 20060 (FIG. 390) positioned opposite the staple cartridge 20000 in the end effector 12. The staple legs 20032 can be deformed against the anvil 20060 and the legs 20032 of each staple 20030 can capture a portion of the nonwoven material 20080 and a portion of the tissue T.

In the fired configuration (FIGS. 411 and 412), each staple 20030 can apply a compressive force to the tissue T and to the tissue thickness compensator 20020 captured within the staple 20030. Referring primarily to FIGS. 409 and 410, the legs 20032 of each staple 20030 can be deformed downwardly toward the base 20031 of the staple 20030 to form a staple entrapment area 20039. The staple entrapment area 20039 can be the area in which the tissue T and the tissue thickness compensator 20020 can be captured by a fired staple 20030. In various circumstances, the staple entrapment area 20039 can be defined between the inner surfaces of the deformed legs 20032 and the inner surface of the base 20031 of a staple 20030. The size of the entrapment area 20039 for a staple 20030 can depend on several factors such as the length of the legs, the diameter of the legs, the width of the base, and/or the extent in which the legs are deformed, for example.

In various embodiments, when a nonwoven material 20080 is captured in a staple entrapment area 20039, the captured portion of the nonwoven material 20080 can be compressed. The compressed height of the nonwoven material 20080 captured in a staple entrapment area 20039 can vary within the staple cartridge 20000 depending on the tissue T in that same staple entrapment area 20039. For example, where the tissue T is thinner, the staple entrapment area 20039 may have more room for the nonwoven material 20080 and, as a result, the nonwoven material 20080 may not be as compressed as it would be if the tissue T were thicker. Where the tissue T is thicker, the nonwoven material 20080 can be compressed more to accommodate the thicker tissue T, for example. For example, referring to FIG. 411, the nonwoven material 20080 can be compressed to a first height in a first staple entrapment area 20039*a*, a second height in a second staple entrapment area 20039*b*, a third height in a third staple entrapment area 20039*c*, a fourth height in a fourth staple entrapment area 20039*d*, and a fifth height in a fifth staple entrapment area 20039*e*, for example. Similarly, as illustrated in FIG. 412, the nonwoven material 20080 can be compressed to a first height in the first staple entrapment area 20039*a*, a second height in the second staple entrapment area 20039*b*, a third height in the third staple entrapment area 20039*c*, and a fourth height in the fourth staple entrapment area 20039*d*. In other embodiments, the compressed height of the nonwoven material 20080 can be uniform throughout the staple cartridge 20010.

In various embodiments, an applied force can move the nonwoven material 20080 from an initial uncompressed configuration to a compressed configuration. Further, the nonwoven material 20080 can be resilient, such that, when compressed, the nonwoven material 20080 can generate a springback or restoring force. When deformed, the nonwoven material 20080 can seek to rebound from the compressed or deformed configuration. As the nonwoven material 20080 seeks to rebound, it can exert a springback or restoring force on the tissue also captured in the staple entrapment area 30039, as described in greater detail herein. When the applied force is subsequently removed, the restoring force can cause the nonwoven material to rebound from the compressed configuration. In various embodiments, the nonwoven material 20080 can rebound to the initial, uncompressed configuration or may rebound to a configuration substantially similar to the initial, uncompressed configuration. In various embodiments, the deformation of the nonwoven material 20080 can be elastic. In some embodiments, the deformation of the nonwoven material can be partially elastic and partially plastic.

When a portion of the nonwoven material 20080 is compressed in a staple entrapment area 20039, the crimped fibers 20086 in that portion of the nonwoven compensator 20039 can also be compressed or otherwise deformed. The amount a crimped fiber 20086 is deformed can correspond to the amount that the captured portion of the nonwoven material 20080 is compressed. For example, referring to FIG. 392, the nonwoven material 20080 can be captured by deployed staples 20030. Where the nonwoven material 20080 is more compressed by a deployed staple 20030, the average deformation of crimped fibers 20086 can be greater. Further, where the nonwoven material 20080 is less compressed by a deployed staple, the average deformation of crimped fibers 20086 can be smaller. Similarly, referring to FIGS. 411 and 412, in a staple entrapment area 20039*d* where the nonwoven material 20080 is more compressed, the crimped fibers 20086 in that staple entrapment area 20039*d* can be, on average, more deformed. Further, in a staple entrapment area 20039*a* where the nonwoven material 20080 is less compressed, the crimped fibers 20086 in that staple entrapment area 20039*a* can be, on average, less deformed.

The ability of the nonwoven material 20080 to rebound from the deformed configuration, i.e., the resiliency of the nonwoven material 20080, can be a function of the resiliency of the crimped fibers 20086 in the nonwoven material 20080. In various embodiments, the crimped fibers 20086 can deform elastically. In some embodiments, deformation of the crimped fibers 20086 can be partially elastic and partially plastic. In various embodiments, compression of each crimped fiber 20086 can cause the compressed crimped fibers 20086 to generate a springback or restoring force. For example, the compressed crimped fibers 20086 can generate a restoring force as the fibers 20086 seek to rebound from their compressed configuration. In various embodiments, the fibers 20086 can seek to return to their initial, uncompressed configuration or to a configuration substantially similar thereto. In some embodiments, the crimped fibers 20086 can seek to partially return to their initial configuration. In various embodiments, only a portion of the crimped fibers 20086 in the nonwoven material 20080 can be resilient. When a crimped fiber 20086 is comprised of a linear-elastic material, the restoring force of the compressed crimped fiber 20086 can be a function of the amount the crimped fiber 20086 is compressed and the spring rate of the crimped fiber 20086, for example. The spring rate of the crimped fiber 20086 can at least depend on the orientation, material, shape and/or size of the crimped fiber 20086, for example.

In various embodiments, the crimped fibers 20086 in the nonwoven material 20080 can comprise a uniform spring rate. In other embodiments, the spring rate of the crimped fibers 20086 in the nonwoven material 20080 can vary. When a crimped fiber 20086 having a large spring rate is greatly compressed, the crimped fiber 20086 can generate a large restoring force. When a crimped fiber 20086 having the same large spring rate is less compressed, the crimped fiber 20086 can generate a smaller restoring force. The aggregate of restoring forces generated by compressed crimped fibers 20086 in the nonwoven material 20080 can generate a combined restoring force throughout the nonwoven material 20080 of the tissue thickness compensator 20020. In various embodiments, the nonwoven material 20080 can exert the combined restoring force on tissue T captured within a fired staple 20030 with the compressed nonwoven material 20080.

Furthermore, the number of crimped fibers 20086 per unit volume of nonwoven material 20080 can affect the spring rate of the nonwoven material 20080. For example, the resiliency in a nonwoven material 20080 can be low when the number of crimped fibers 20086 per unit volume of nonwoven material 20080 is low, for example; the resiliency of the nonwoven material 20080 can be higher when the number of crimped fibers 20086 per unit volume of nonwoven material 20080 is higher, for example; and the resiliency of the nonwoven material 20080 can be higher still when the number of crimped fibers 20086 per unit volume of nonwoven material 20080 is even higher, for example. When the resiliency of the nonwoven material 20080 is low, such as when the number of crimped fibers 20086 per unit volume of nonwoven material 20080 is low, the combined restoring force exerted by the tissue thickness compensator 20020 on captured tissue T can also be low. When the resiliency of the nonwoven material 20080 is higher, such as when the number of crimped fibers 20086 per unit volume of nonwoven material 20080 is higher, the aggregate restoring force exerted by the tissue thickness compensator 20020 on captured tissue T can also be higher.

In various embodiments, referring primarily to FIG. 393, a nonwoven material 20080' of a tissue thickness compensator 20020' can comprise a therapeutic agent 20088, such as a medicament and/or pharmaceutically active agent, for example. In various embodiments, the nonwoven material 20080' can release a therapeutically effective amount of the therapeutic agent 20088. For example, the therapeutic agent 20088 can be released as the nonwoven material 20080' is absorbed. In various embodiments, the therapeutic agent 20088 can be released into fluid, such as blood, for example, passing over or through the nonwoven material 20080'. Examples of therapeutic agents 20088 can include, but are not limited to, haemostatic agents and drugs such as, for example, fibrin, thrombin, and/or oxidized regenerated cellulose (ORC); anti-inflammatory drugs such as, for example, diclofenac, aspirin, naproxen, sulindac, and/or hydrocortisone; antibiotic and antimicrobial drugs or agents such as, for example, triclosan, ionic silver, ampicillin, gentamicin, polymyxin B, and/or chloramphenicol; and anticancer agents such as, for example, cisplatin, mitomycin, and/or adriamycin. In various embodiments, the therapeutic agent 20088 can comprise a biologic, such as a stem cell, for example. In some embodiments, the fibers 20082 of the nonwoven material 20080' can comprise the therapeutic agent 20088. In other embodiments, the therapeutic agent 20088 can be added to the nonwoven material 20080' or otherwise integrated into the tissue thickness compensator 20020'.

In some embodiments, primarily referring to FIGS. 399-399B, a tissue thickness compensator 20520 for an end effector 12 (FIG. 390) can comprise a plurality of springs or coiled fibers 20586. Similar to the crimped fibers 20086 described herein, the coiled fibers 20586 can be, for example, crimped, twisted, coiled, bent, crippled, spiraled, curled, and/or bowed within the tissue thickness compensator 20520. In some embodiments, the coiled fibers 20586 can be wound around a mandrel to form a coiled or substantially coil-like shape. Similar to the embodiments described herein, the coiled fibers 20586 can be randomly oriented and/or randomly distributed throughout the tissue thickness compensator 20520. In other embodiments, the coiled fibers 20586 can be systematically arranged and/or uniformly distributed throughout the tissue thickness compensator 20520. For example, referring to FIG. 399, the coiled fibers 20586 can comprise a longitudinal axis between a first end 20587 and a second end 20589 of the coiled fiber 20586. The longitudinal axes of the coiled fibers 20520 in the tissue thickness compensator 20520 can be parallel or substantially parallel. In some embodiments, the first end 20587 of each coiled fiber 20520 can be positioned along a first longitudinal side 20523 of the tissue thickness compensator 20520 and the second end 20589 of each coiled fiber 20586 can be positioned along a second longitudinal side 20524 of the tissue thickness compensator 20520. In such an arrangement, the coiled fibers 20586 can laterally traverse the tissue thickness compensator. In other embodiments, the coiled fibers 20586 can longitudinally or diagonally traverse the tissue thickness compensator 20520.

In various embodiments, similar to the crimped fibers 20086 described herein, the coiled fibers 20586 can comprise a polymeric composition. The crimped fibers 20586 can be at least partially elastic such that deformation of the crimped fibers 20586 generates a restoring force. In some embodiments, the polymeric composition of the coiled fibers 20586 can comprise polycaprolactone (PCL), for example, such that the coiled fibers 20586 are not soluble in a chlorophyll solvent. Referring to FIG. 399A, the springs or coiled fibers 20520 can be retained in a compensation material 20580. In various embodiments, the compensation material 20580 can hold the coiled fibers 20586 in a loaded position such that the coiled fibers 20586 exert a spring load on, or within, the compensation material 20580. In certain embodiments, the compensation material 20580 can hold the coiled fibers 20586 in a neutral position where the coiled fibers 20586 are not exerting a spring load on, or within, the compensation material 20580. The compensation material 20580 can be bioabsorbable and, in some embodiments, can comprise a foam, such as, for example, polyglycolic acid (PGA) foam. Furthermore, the compensation material 20580 can be soluble in a chlorophyll solvent, for example. In some embodiments the tissue thickness compensator can comprise coiled fibers 20586 that comprise polycaprolactone (PCL) and compensation material 20580 that comprises polyglycolic acid (PGA) foam, for example, such that the coiled fibers 20520 are not soluble in a chlorophyll solvent while the compensation material 20580 is soluble in the chlorophyll solvent. In various embodiments, the compensation material 20580 can be at least partially elastic, such that compression of the compensation material 20580 generates a restoring force. Further, similar to the embodiments described herein, referring to FIG. 399B, the compensation material 20580 of the tissue thickness compensator 20520 can comprise a therapeutic agent 20588, such as stem cells, for example. The compensation material 20580 can release a therapeutically effective amount of the therapeutic agent 20588 as the compensation material 20580 is absorbed.

Similar to the tissue thickness compensator 20020 described herein, the tissue thickness compensator 20520 can be compressible. For example, as staples 20030 (FIGS. 407-410) are deployed from an initial position to a fired position, the staples 20030 can engage a portion of tissue thickness compensator 20520. In various embodiments, a staple 20030 can capture a portion of the tissue thickness compensator 20520 and adjacent tissue T. The staple 20030 can apply a compressive force to the captured portion of the tissue thickness compensator 20520 and tissue T such that the tissue thickness compensator 20520 is compressed from a non-compressed height to a compressed height. Similar to the embodiments described herein, compression of the tissue thickness compensator 20520 can result in a corresponding deformation of the coiled fibers 20586 therein. As described in greater detail herein, deformation of each coiled fiber 20586 can generate a restoring force that can depend on the resiliency of the coiled fiber, for example, the amount the coiled fiber 20586 is deformed and/or the spring rate of the coiled fiber 20586. The spring rate of the coiled fiber 20586 can at least depend on the orientation, material, shape and/or size of the coiled fiber 20586, for example. Deformation of the coiled fibers 20586 in the tissue thickness compensator 20520 can generate restoring forces throughout the tissue thickness compensator 20520. Similar to the embodiments described herein, the tissue thickness compensator 20520 can exert the aggregate restoring force generated by the deformed coiled fibers 20586 and/or the resilient compensation material 20586 on the captured tissue T in the fired staples 20030.

In some embodiments, primarily referring to FIGS. 400 and 401, a tissue thickness compensator 20620 for an end effector 12 can comprise a plurality of spring coils 20686. Similar to the crimped fibers 20086 and coiled fibers 20586 described herein, spring coils 20686 can be, for example, crimped, twisted, coiled, bent, crippled, spiraled, curled, and/or bowed within the tissue thickness compensator 20620. In various embodiments, similar to the fibers and coils described herein, the spring coils 20686 can comprise a polymeric composition. Further, the spring coils 20686 can be at least partially elastic such that deformation of the spring coils 20686 generates a restoring force. The spring coils 20686 can comprise a first end 20687, a second end 20689, and a longitudinal axis therebetween. Referring to FIG. 400, the first end 20686 of a spring coil 20686 can be positioned at or near a proximal end 20626 of the tissue thickness compensator and the second end 20689 of the same spring coil 20686 can be positioned at or near a distal end 20625 of the tissue thickness compensator 20620 such that the spring coil 20686 longitudinally traverses the tissue thickness compensator 20620, for example. In other embodiments, the coiled fibers 20686 can laterally or diagonally traverse the tissue thickness compensator 20620.

The tissue thickness compensator 20620 can comprise an outer film 20680 that at least partially surrounds at least one spring coil 20686. In various embodiments, referring to FIG. 400, the outer film 20680 can extend around the perimeter of multiple spring coils 20686 in the tissue thickness compensator 20620. In other embodiments, the outer film 20680 can completely encapsulate the spring coils 20686 or at least one spring coil 20686 in the tissue thickness compensator 20620. The outer film 20680 can retain the spring coils 20686 in the end effector 12. In various embodiments, the outer film 20680 can hold the spring coils 20686 in a loaded position such that the spring coils 20686 generate a spring load and exert a springback force on the outer film 20680. In other embodiments, the outer film 20680 can hold the spring coils 20686 in a neutral position. The tissue thickness compensator 20620 can also comprise a filling material 20624. In some embodiments, the filling material 20624 can be retained within and/or around the spring coils 20686 by the outer film 20680. In some embodiments, the filling material 20624 can comprise a therapeutic agent 20688, similar to the therapeutic agents described herein. Further, the filling material 20624 can support the spring coils 20686 within the tissue thickness compensator 20620. The filling material 20624 can be compressible and at least partially resilient, such that the filling material 20624 contributes to the springback or restoring force generated by the tissue thickness compensator 20620, as described in greater detail herein.

Similar to the tissue thickness compensators described herein, the tissue thickness compensator 20620 can be compressible. As staples 20030 (FIGS. 407-410) are deployed from an initial position to a fired position, in various embodiments, the staples 20030 can engage a portion of the tissue thickness compensator 20620. In various embodiments, each staple 20030 can capture a portion of the tissue thickness compensator 20620 along with adjacent tissue T. The staple 20030 can apply a compressive force to the captured portion of the tissue thickness compensator 20620 and the captured tissue T such that the tissue thickness compensator 20620 is compressed between a non-compressed height and a compressed height. Similar to the embodiments described herein, compression of the tissue thickness compensator 20620 can result in a corresponding deformation of the spring coils 20686 retained therein (FIG. 401). As described in greater detail herein, deformation of each spring coils 20686 can generate a restoring force that depends on the resiliency of the spring coil 20686, for example, the amount the spring coil 20686 is deformed and/or the spring rate of the spring coil 20686. The spring rate of a spring coil 20686 can at least depend on the material, shape and/or dimensions of the spring coil 20686, for example. Furthermore, depending on the resiliency of the filling material 20624 and the outer film 20680, compression of the filling material 20624 and/or the outer film 20680 can also generate restoring forces. The aggregate of restoring forces generated at least by the deformed spring coils 20686, the filling material 20624 and/or the outer film 20680 in the tissue thickness compensator 20620 can generate restoring forces throughout the tissue thickness compensator 20620. Similar to the embodiments described herein, the tissue thickness compensator 20620 can exert the aggregate restoring force generated by the deformed spring coils 20686 on the captured tissue T in a fired staple 20030.

In various embodiments, primarily referring to FIGS. 402-404, a tissue thickness compensator 20720 for an end effector 12 can comprise a plurality of spring coils 20786. Similar to the coiled fibers and springs described herein, spring coils 20786 can be, for example, crimped, twisted, coiled, bent, crippled, spiraled, curled, and/or bowed within the tissue thickness compensator 20720. The spring coils 20786 can be at least partially elastic such that deformation of the spring coils 20786 generates a restoring force. Further, the spring coils 20786 can comprise a first end 20787, a second end 20789, and a longitudinal axis therebetween. Referring primarily to FIG. 404, the first end 20787 of the spring coil 20786 can be positioned at or near a proximal end 20726 of the tissue thickness compensator 20720 and the second end 20789 of the spring coil 20786 can be positioned at or near a distal end 20725 of the tissue thickness compensator 20720 such that the spring coil 20786 longitudinally traverses the tissue thickness compensator 20720. In some embodiments, the spring coil 20786 can longitudinally extend in two parallel rows in the tissue thickness compensator 20720. The tissue thickness compensator 20720 can be positioned in an end effector 12 such that a sled 20050 (FIG. 390) or cutting element 20052 can translate along a slot 20015 between the parallel rows of spring coils 20786. In other embodiments, similar to various embodiments described herein, the spring coils 20786 can laterally or diagonally traverse the tissue thickness compensator 20720.

Referring again to FIG. 404, the spring coils 20786 can be retained or embedded in a compensation material 20780. The compensation material 20780 can be bioabsorbable and, in some embodiments, can comprise foam, such as, for example, polyglycolic acid (PGA) foam. In various embodiments, the compensation material 20780 can be resilient such that deformation of the compensation material 20780 generates a springback force. The compensation material 20780 can be soluble in a chlorophyll solvent, for example. In some embodiments, for example, the tissue thickness compensator can comprise spring coils 20786 that comprise polycaprolactone (PCL) and compensation material 20780 that comprises polyglycolic acid (PGA) foam such that the spring coils 20786 are not soluble in a chlorophyll solvent while the compensation material 20780 is soluble in a chlorophyll solvent, for example. The compensation material 20780 can be at least partially resilient such that deformation of the compensation material 20780 generates a spring load or restoring force.

In various embodiments, the tissue thickness compensator 20720 can comprise interwoven threads 20790, which can extend between parallel rows of spring coils 20786. For example, referring to FIG. 404, a first interwoven thread 20790 can diagonally traverse the two parallel rows of spring coils 20786 and a second interwoven thread 20790 can also diagonally traverse the two parallel rows of spring coils 20786. In some embodiments, the first and second interwoven threads 20790 can crisscross. In various embodiments, the interwoven threads 20790 can crisscross multiple times along the length of the tissue thickness compensator 20720. The interwoven threads 20790 can hold the spring coils 20786 in a loaded configuration such that the spring coils 20786 are held in a substantially flat position in the tissue thickness compensator 20720. In some embodiments, the interwoven threads 20790 that traverse the tissue thickness compensator 20720 can be directly attached to the spring coils 20786. In other embodiments, the interwoven threads 20790 can be coupled to the spring coils 20786 via a support 20792 that extends through each spring coil 20786 along the longitudinal axis thereof.

As described in greater detail herein, in various embodiments, a staple cartridge 20000 can comprise a slot 20015 configured to receive a translating sled 20050 comprising a cutting element 20052 (FIG. 390). As the sled 20050 translates along the slot 20015, the sled 20050 can eject staples 20030 from fastener cavities 20012 in the staple cartridge 20000 and the cutting element 20052 can simultaneously or nearly simultaneously sever tissue T. In various embodiments, referring again to FIG. 404, as the cutting element 20052 translates, it can also sever the interwoven threads 20790 that crisscross between the parallel rows of spring coils 20786 in the tissue thickness compensator 20720. As the interwoven threads 20790 are severed, each spring coil 20786 can be released from its loaded configuration such that each spring coil 20786 reverts from the loaded, substantially flat position to an expanded position in the tissue thickness compensator 20720. In various embodiments, when a spring coil 20786 is expanded, the compensation material 20780 surrounding the spring coil 20786 can also expand.

In various embodiments, as staples 20030 (FIGS. 407-410) are deployed from an initial position to a fired position, the staples 20030 can engage a portion of the tissue thickness compensator 20720 and the tissue thickness compensator 20720 can expand, or attempt to expand, within the staples 20030 and can apply a compressive force to the tissue T. In various embodiments, at least one staple 20030 can capture a portion of the tissue thickness compensator 20720, along with adjacent tissue T. The staple 20030 can apply a compressive force to the captured portion of the tissue thickness compensator 20720 and the captured tissue T, such that the tissue thickness compensator 20720 is compressed between a non-compressed height and a compressed height. Similar to the embodiments described herein, compression of the tissue thickness compensator 20720 can result in a corresponding deformation of the spring coils 20786 and compensation material 20780 retained therein. As described in greater detail herein, deformation of each spring coils 20786 can generate a restoring force that can depend on the resiliency of the spring coil, for example, the amount the spring coil 20786 is deformed and/or the spring rate of the spring coil 20786. The spring rate of a spring coil 20786 can at least depend on the orientation, material, shape and/or size of the spring coil 20786, for example. The aggregate of restoring forces generated by at least the deformed spring coils 20786 and/or the compensation material 30380 in the tissue thickness compensator 20720 can generate restoring forces throughout the tissue thickness compensator 20720. Similar to the embodiments described herein, the tissue thickness compensator 20720 can exert the aggregate restoring force generated by the deformed spring coils 20786 in the tissue thickness compensator 20720 on the captured tissue T and fired staples 20030.

In various embodiments, primarily referring to FIGS. 405 and 406, a tissue thickness compensator 20820 for a surgical end effector 12 can comprise a spring coil 20886. Similar to the fibers and coils described herein, spring coil 20886 can be, for example, crimped, twisted, coiled, bent, crippled, spiraled, curled, and/or bowed within the tissue thickness compensator 20820. The spring coil 20886 can comprise a polymeric composition and can be at least partially elastic, such that deformation of the spring coil 20886 generates a springback force. Further, the spring coil 20886 can comprise a first end 20887 and a second end 20889. Referring to FIG. 405, the first end 20887 can be positioned at or near a proximal end 20826 of the tissue thickness compensator 20820 and the second end 20889 can be positioned at or near a distal end 20825 of the tissue thickness compensator 20820. The spring coil 20886 can wind or meander from the proximal end 20825 to the distal end 20826 of the tissue thickness compensator 20820.

Referring again to FIG. 405, the spring coil 20886 can be retained or embedded in a compensation material 20880. The compensation material 20880 can be bioabsorbable and, in some embodiments, can comprise a foam, such as, for example, polyglycolic acid (PGA) foam. The compensation material 20880 can be soluble in a chlorophyll solvent, for example. In some embodiments, the tissue thickness compensator can comprise spring coils 20886 comprising polycaprolactone (PCL) and compensation material 20880 comprising polyglycolic acid (PGA) foam, for example, such that the spring coil 20886 is not soluble in a chlorophyll solvent while the compensation material 20880 is soluble in a chlorophyll solvent. The compensation material 20880 can be at least partially resilient such that deformation of the compensation material 20880 generates a spring load or restoring force.

Similar to tissue thickness compensators described herein, for example, the tissue thickness compensator 20820 can be compressible. Compression of the tissue thickness compensator 20820 can result in a deformation of at least a portion of the spring coil 20886 retained or embedded in the compensation material 20880 of the tissue thickness compensator 20820. As described in greater detail herein, deformation of the spring coil 20886 can generate restoring forces that can depend on the resiliency of the spring coil 20886, the amount the spring coil 20886 is deformed, and/or the spring rate of the spring coil 20886, for example. The aggregate of restoring forces generated by the deformed spring coil 20886 and/or deformed compensation material 20880 can generate restoring forces throughout the tissue thickness compensator 20820. The tissue thickness compensator 20820 can exert the aggregate restoring force on the captured tissue T in the fired staples 20030.

Referring now to FIG. 413, a surgical end effector 12 can comprise a tissue thickness compensator 30020 having at least one tubular element 30080. The tissue thickness compensator 30020 can be retained in the surgical end effector 12. As described in greater detail herein, a fastener in the end effector 12 can be deployed such that the fastener moves to a fired position and deforms at least a portion of the tubular element 30080 in the tissue thickness compensator 30020. The reader will appreciate that tissue thickness compensators comprising at least one tubular element as described herein can be installed in or otherwise engaged with a variety of surgical end effectors and that such embodiments are within the scope of the present disclosure.

In various embodiments, still referring to FIG. 413, the tissue thickness compensator 30020 can be positioned relative to the anvil 30060 of the end effector 12. In other embodiments, the tissue thickness compensator 30020 can be positioned relative to a fastener cartridge assembly, such as staple cartridge 30000, of the end effector 12. In various embodiments, the staple cartridge 30000 can be configured to fit in a cartridge channel 30072 of a jaw 30070 of the end effector 12. For example, the tissue thickness compensator 30020 can be releasably secured to the staple cartridge 30000. In at least one embodiment, the tubular element 30080 of the tissue thickness compensator 30020 can be positioned adjacent to a top deck surface 30011 of a rigid support portion 30010 of the staple cartridge 30000. In various embodiments, the tubular element 30080 can be secured to the top deck surface 30011 by an adhesive or by a wrap, similar to at least one of the wraps described herein (e.g., FIG. 218). In various embodiments, the tissue thickness compensator 30020 can be integral to an assembly comprises the staple cartridge 30000 such that the staple cartridge 30000 and the tissue thickness compensator 30020 are formed as a single unit construction. For example, the staple cartridge 30000 can comprise a first body portion, such as the rigid support portion 30010, and a second body portion, such as the tissue thickness compensator 30020, for example.

Referring to FIGS. 413-415, the tubular element 30080 in the tissue thickness compensator 30020 can comprise an elongate portion 30082 having at least one lumen 30084 that extends at least partially therethrough. Referring primarily to FIG. 415, the elongate portion 30082 of the tubular element 30080 can comprise woven or braided strands 30090, as described in greater detail herein. In other embodiments, the elongate portion 30082 can comprise a solid structure, such as a polymer extrusion, rather than woven strands 30090. The elongate portion 30082 of the tubular element 30080 can comprise a thickness. In various embodiments, the thickness of the elongate portion 30082 can be substantially uniform throughout the length and around the diameter thereof; in other embodiments, the thickness can vary. The elongate portion 30082 can be elongated such that the length of the elongate portion 30082 is greater than the diameter of the elongate portion 30082, for example. In various embodiments, the elongate portion can comprise a length of approximately 1.20 inches to approximately 2.60 inches and a diameter of approximately 0.10 inches to approximately 0.15 inches, for example. In some embodiments, the length of the tubular element 20080 can be approximately 1.40 inches, for example, and the diameter of the tubular element 20080 can be approximately 0.125 inches, for example. Furthermore, the elongate portion 30082 can define a substantially circular or elliptical cross-sectional shape, for example. In other embodiments, the cross-sectional shape can comprise a polygonal shape, such as, for example, a triangle, a hexagon and/or an octagon. Referring again to FIG. 413, the tubular element 30080 can comprise a first distal end 30083 and a second proximal end 30085. In various embodiments, the cross-sectional shape of the elongate portion 30082 can narrow at the first and/or second end 30083, 30085 wherein at least one end 30083, 30085 of the tubular element 30080 can be closed and/or sealed. In other embodiments, a lumen 30084 can continue through the distal ends 30083, 30085 of the tubular element 30080 such that the ends 30083, 30085 are open.

In various embodiments, the tubular element 30080 can comprise a single central lumen 30084 that extends at least partially through the elongate portion 30084. In some embodiments, the lumen 30084 can extend through the entire length of the elongate portion 30084. In still other embodiments, the tubular element 30080 can comprise multiple lumens 30084 extending therethrough. Lumens 30084 extending through the tubular element 30080 can be circular, semi-circular, wedge-shaped, and/or combinations thereof. In various embodiments, a tubular element 30080 can also comprise support webs that can form a modified "T" or "X" shape, for example, within the lumen 30084. In various embodiments, the dimensions, lumen(s), and/or support web(s) within the tubular element 30080 can define the cross-sectional shape of the tubular element 30080. The cross-sectional shape of the tubular element 30080 can be consistent throughout the length thereof or, in other embodiments, the cross-sectional shape of the tubular element 30080 can vary along the length thereof. As described in greater detail herein, the cross-sectional shape of the tubular element 30080 can affect the compressibility and resiliency of the tubular element 30080.

In various embodiments, the tubular element 30080 can comprise a vertical diameter and a horizontal diameter; the dimensions thereof can be selected depending on the arrangement of the tubular element 30080 in the end effector 12, the dimensions of the end effector 12, including the tissue gap of the end effector 12, and the expected geometry of the staple entrapment areas 30039. For example, the vertical diameter of the tubular element 30080 can relate to the expected height of a formed staple. In such embodiments, the vertical diameter of the tubular element 30080 can be selected such that the vertical diameter can be reduced approximately 5% to approximately 20% when the tubular element 30080 is captured within a formed staple 30030. For example, a tubular element 30080 having a vertical diameter of approximately 0.100 inches may be used for staples having an expected formed height of approximately 0.080 inches to approximately 0.095 inches. As a result, the vertical diameter of the tubular element 30080 can be reduced approximately 5% to approximately 20% when captured within the formed staple 30030 even when no tissue T is captured therein. When tissue T is captured within the formed staple 30030, the compression of the tubular element 30080 may be even greater. In some embodiments, the vertical diameter can be uniform throughout the length of the tubular element 30080 or, in other embodiments, the vertical diameter can vary along the length thereof.

In some embodiments, the horizontal diameter of the tubular element 30080 can be greater than, equal to, or less than the vertical diameter of the tubular element 30080 when the tubular element 30080 is in an undeformed or rebounded configuration. For example, referring to FIG. 414, the horizontal diameter can be approximately three times larger than the vertical diameter, for example. In some embodiments the horizontal diameter can be approximately 0.400 inches and the vertical diameter can be approximately 0.125 inches, for example. In other embodiments, referring now to FIG. 416, the horizontal diameter of a tubular element 31080 can be equal to or substantially equal to the vertical diameter of the tubular element 31080 when the tubular element 31080 is in an undeformed or rebounded configuration. In some embodiments the horizontal diameter can be approximately 0.125 inches and the vertical diameter can also be approximately 0.125 inches, for example. In various embodiments, the tubular element 30080 can comprise a vertical diameter of approximately 0.125 inches, a horizontal diameter of approximately 0.400 inches, and a length of approximately 1.400 inches. As described in greater detail herein, when a force A is applied to the tubular element 30080 and/or 31080, the tubular element can deform such that the cross-sectional geometry, including the horizontal and vertical diameters, can change.

Referring again to FIGS. 413-415, the tubular element 30080 in the tissue thickness compensator 30020 can be deformable. In various embodiments, the entire tubular element 30080 can be deformable. For example, the tubular element 30080 can be deformable from the proximal end 30083 to the distal end 30085 of the elongate portion 30082 and around the entire circumference thereof. In other embodiments, only a portion of the tubular element 30080 can be deformable. For example, in various embodiments, only an intermediate length of the elongate portion 30082 and/or only a portion of the circumference of the tubular element 30080 can be deformable.

When a compressive force is applied to a contact point on the elongate portion 30082 of the tubular element 30080, the contact point can shift, which can alter the cross-sectional dimensions of the tubular element 30080. For example, referring again to FIG. 414, the tubular element 30080 can comprise a top apex 30086 and a bottom apex 30088 on the elongate portion 30082. In the initial, undeformed configuration, the tubular element 30080 can comprise undeformed cross-sectional dimensions, including an undeformed vertical diameter between the top apex 30086 and the bottom apex 30088. When a compressive force A is applied to the top apex 30086, the tubular element 30080 can move to a deformed configuration. In the deformed configuration, the cross-sectional dimensions of the tube 30080 can be altered. For example, the tube 30086 can comprise a deformed vertical diameter between the top apex 30086 and the bottom apex 30088, which can be less than the undeformed vertical diameter. In some embodiments, referring to FIG. 416, the horizontal diameter of the deformed tube 30080 can be lengthened, for example, when the tubular element 30080 moves from an undeformed configuration to a deformed configuration. The deformed cross-sectional dimensions of the deformed tube 30080 can at least depend on the position, angular orientation, and/or magnitude of the applied force A. As described in greater detail herein, deformation of a tubular element 30080 can generate a springback or restoring force that can depend on the resiliency of the tubular element 30080.

Referring still to FIG. 414, the tubular element 30080 can generate a springback or restoring force when compressed. In such embodiments, as described herein, the tubular element 30080 can move from an initial undeformed configuration to a deformed configuration when a force A is applied to a contact point on the elongate portion 30082 of the tubular element 30080. When the applied force A is removed, the deformed tube 30080 can rebound from the deformed configuration. The deformed tube 30080 may rebound to the initial, undeformed configuration or may rebound to a configuration substantially similar to the initial, undeformed configuration. The ability of the tubular element 30080 to rebound from a deformed configuration relates to the resiliency of the tubular element 30080.

Referring again to FIG. 414, a tubular element 30080 can exert a springback or restoring force. The restoring force can be generated by the tubular element 30080 when an applied force A is exerted on the tubular element 30080, for example, by a staple 30030 (FIGS. 417 and 418), as described in greater detail herein. An applied force A can alter the cross-sectional dimensions of the tubular element 30080. Furthermore, in linear-elastic materials, the restoring force of each deformed portion of the tubular element 30080 can be a function of the deformed dimensions of the tubular element 30080 and the spring rate of that portion of the tubular element 30080. The spring rate of a tubular element 30080 can at least depend on the orientation, material, cross-sectional geometry and/or dimensions of the tubular element 30080, for example. In various embodiments, the tubular element 30080 in a tissue thickness compensator 30020 can comprise a uniform spring rate. In other embodiments, the spring rate can vary along the length and/or around the diameter of the tubular element 30080. When a portion of a tubular element 30080 having a first spring rate is greatly compressed, the tubular element 30080 can generate a large restoring force. When a portion of the tubular element 30080 having the same first spring rate is less compressed, the tubular element 30080 can generate a smaller restoring force.

Referring again to FIG. 413, the tubular element 30080 in the tissue thickness compensator 30020 can comprise a polymeric composition. In some embodiments, the elongate portion 30082 of the tubular element 30080 can comprise the polymeric composition. Further, in various embodiments, the polymeric composition can comprise an at least partially elastic material such that deformation of the tubular element 30080 generates a restoring force. The polymeric composition can comprise non-absorbable polymers, absorbable polymers, or combinations thereof, for example. Examples of synthetic polymers include, but are not limited to, polyglycolic acid (PGA), poly(lactic acid) (PLA), polycaprolactone (PCL), polydioxanone (PDO), and copolymers thereof. In some embodiments, the absorbable polymers can include bioabsorbable, biocompatible elastomeric polymers, for example. Furthermore, the polymeric composition of the tubular element 30080 can comprise synthetic polymers, non-synthetic polymers, or combinations thereof, for example. In various embodiments, similar to the polymeric compositions in embodiments described herein, the polymeric composition of the tubular element 30080 can include varied amounts of absorbable polymers, non-absorbable polymers, synthetic polymers, and/or non-synthetic polymers, for example, by weight percentage.

Referring to FIGS. 413 and 414, the tubular element 30080 can comprise a therapeutic agent 30098 such as a pharmaceutically active agent or medicament, for example. In various embodiments, the therapeutic agent 30098 can be retained in the lumen 30084 of the tubular element 30080. The elongate portion 30082 can encapsulate or partially encapsulate the therapeutic agent 30098. Additionally or alternatively, the polymeric composition of the elongate portion 30082 can comprise the therapeutic agent 30098. The tubular element 30080 can release a therapeutically effective amount of the therapeutic agent 30098. In various embodiments, the therapeutic agent 30098 can be released as the tubular element 30080 is absorbed. For example, the therapeutic agent 30098 can be released into fluid (such as blood) passing over or through the tubular element 30080. In still other embodiments, the therapeutic agent 30098 can be released when a staple 30030 (FIGS. 417 and 418) pierces the tubular element 30080 and/or when the cutting element 30052 on the staple-firing sled 30050 (FIG. 413) cuts a portion of the tubular element 30080, for example. Examples of therapeutic agents 30098 can include, but are not limited to, haemostatic agents and drugs such as, for example, fibrin, thrombin, and/or oxidized regenerated cellulose (ORC), anti-inflammatory drugs such as, for example, diclofenac, aspirin, naproxen, sulindac, and/or hydrocortisone, antibiotic and antimicrobial drugs or agents such as, for example, triclosan, ionic silver, ampicillin, gentamicin, polymyxin B, and/or chloramphenicol, anticancer agents such as, for example, cisplatin, mitomycin, and/or adriamycin, and/or biologics such as, for example, stem cells.

In various embodiments, referring again to FIGS. 413, 417 and 418, fasteners such as staples 30030, for example, can be deployed from a staple cartridge 30000 such that the staples 30030 engage a tissue thickness compensator 30020 and apply a force A to a tubular element 32080 therein. As described herein, application of a force A to the tubular element 30080 can cause deformation of the tubular element 30080. Similar to the end effectors 12 described herein, the rigid support portion 30010 of the staple cartridge 30000 can comprise a cartridge body 30017, a deck surface 30011, and a plurality of staple cavities 30012 therein. Each staple cavity 30012 can define an opening in the deck surface 30011 and a staple 30030 can be removably positioned in a staple cavity 30012 (FIG. 433). In at least one embodiment, referring primarily to FIGS. 417 and 418, each staple 30030 can comprise a base 30031 and two staple legs 30032 extending from the base 30031. Prior to the deployment of the staples 30030, the base 30031 of each staple 30030 can be supported by a staple driver 30040 (FIG. 433) positioned within the rigid support portion 30010 of the staple cartridge 30000. Also prior to the deployment of the staples 30030, the legs 30032 of each staple 30030 can be at least partially contained within the staple cavity 30012 (FIG. 433).

In various embodiments, as described in greater detail herein, the staples 30030 can be deployed between an initial position and a fired position. For example, a staple-firing sled 30050 can engage a driver 30040 (FIG. 433) to move at least one staple 30030 between the initial position and the fired position. In various embodiments, referring primarily to FIG. 417, the staple 30030 can be moved to a fired position, wherein the legs 30032 of the staple 30030 engage a tubular element 32080 of a tissue thickness compensator 32020, penetrate tissue T, and contact an anvil 30060 (FIG. 433) positioned opposite the staple cartridge 30000 in the surgical end effector 12. Staple forming pockets 30062 in the anvil 30060 can bend the staple legs 30032 such that the fired staple 30030 captures a portion of the tubular element 32080 and a portion of the tissue T in a staple entrapment area 30039. As described in greater detail herein, at least one staple leg 30032 can pierce the tubular element 32080 of the tissue thickness compensator 32020 when the staple 30030 moves between the initial position and the fired position. In other embodiments, the staple legs 30032 can move around the perimeter of the tubular element 32080 such that the staple legs 30032 avoid piercing the tubular element 32080. Similar to the fasteners described herein, the legs 30032 of each staple 30030 can be deformed downwardly toward the base 30031 of the staple 30030 to form a staple entrapment area 30039 therebetween. The staple entrapment area 30039 can be the area in which tissue T and a portion of the tissue thickness compensator 32020 can be captured by a fired staple 30030. In the fired position, each staple 30030 can apply a compressive force to the tissue T and to the tissue thickness compensator 32020 captured within the staple entrapment area 30039 of the staple 30030.

In various embodiments, referring still to FIG. 417, when the tubular element 32080 is captured in a staple entrapment area 30039, the captured portion of the tubular element 32080 can be deformed, as described herein. Furthermore, the tubular element 32080 can be deformed to different deformed configurations in different staple entrapment areas 30039 depending on, for example, the thickness, compressibility, and/or density of the tissue T captured in that same staple entrapment area 30039. In various embodiments, the tubular element 32080 in the tissue thickness compensator 32080 can extend longitudinally through successive staple entrapment areas 30039. In such an arrangement, the tubular element 32080 can be deformed to different deformed configurations in each staple entrapment area 30039 along a row of fired staples 30030. Referring now to FIG. 418, tubular elements 33080 in a tissue thickness compensator 33020 can be laterally arranged in the staple entrapment areas 30039 along a row of fired staples 30030. In various embodiments, the tubular elements 33080 can be retained by a flexible shell 33210. In such arrangements, the tubular elements 33080 and flexible shell 33210 can be deformed to different deformed configurations in each staple entrapment area 30039. For example, where the tissue T is thinner, the tubular elements 33080 can be compressed less and where the tissue T is thicker, the tubular elements 33080 can be compressed more to accommodate the thicker tissue T. In other embodiments, the deformed dimensions of the tubular elements 33080 can be uniform throughout the entire length and/or width of the tissue thickness compensator 33020.

Referring to FIGS. 419-421, in various embodiments, a tubular element 34080 in a tissue thickness compensator 34020 can comprise a plurality of strands 34090. Referring primarily to FIG. 419, in some embodiments, the strands 34090 can be woven or braided into a tubular lattice 34092 forming the tubular element 34080. The tubular lattice 34092 formed by the strands 34090 can be substantially hollow. The strands 34090 of the tubular element 34080 can be solid strands, tubular strands, and/or another other suitable shape. For example, referring to FIG. 420, a single strand 34090 of the tubular lattice 34092 can be a tube. In various embodiments, referring to FIG. 422, a strand 34090 can comprise at least one lumen 34094 extending therethrough. The number, geometry and/or dimensions(s) of the lumens 34094 can determine the cross-sectional shape of the strand 34090. For example, a strand 34090 can comprise circular lumen(s), semi-circular lumen(s), wedge-shaped lumen(s), and/or combinations thereof. In various embodiments, a strand 34090 can also comprise support webs 34096 that can form a modified "T" or "X" shape, for example. At least the diameter of the strand 34090, the lumen(s) extending therethrough, and the support web(s) can characterize the cross-sectional shape of a strand 34090. The cross-sectional shape of each strand 34090, as discussed in greater detail herein, can affect the springback or restoring force generated by the strand 34090 and the corresponding springback or restoring force generated by the tubular element 34080.

Referring to FIG. 423, a tubular lattice 34092 of strands 34090 can be deformable. In various embodiments, the tubular lattice 34092 can produce or contribute to the deformability and/or the resiliency of the tubular element 34080. For example, the strands 34090 of the tubular lattice 34092 can be woven together such that the strands 34090 are configured to slide and/or bend relative to each other. When a force is applied to the elongate portion 34082 of the tubular element 34080, the strands 34090 therein may slide and/or bend such that the tubular lattice 34092 moves to a deformed configuration. For example, referring still to FIG. 423, a staple 30030 can compress the tubular lattice 34092 and the tissue T captured in a staple entrapment area 34039 which can cause the strands 34090 of the tubular lattice 34092 to slide and/or bend relative to each other. A top apex 34086 of the tubular lattice 34092 can move towards a bottom apex 34088 of the tubular lattice 34092 when the tubular lattice 34092 is compressed to the deformed configuration in order to accommodate the captured tissue T in a staple entrapment area 30039. In various circumstances, the tubular lattice 34092 captured in a fired stapled 30030 will seek to regain its undeformed configuration and can apply a restoring force to the captured tissue T. Further, the portions of the tubular lattice 34092 positioned between staple entrapment areas 30039, i.e., not captured within a fired staple 30030, can also be deformed due to the deformation of adjacent portions of the tubular lattice 34092 that are within the staple entrapment areas 30039. Where the tubular lattice 34092 is deformed, the tubular lattice 34092 can seek to rebound or partially rebound from the deformed configuration. In various embodiments, portions of the tubular lattice 34092 can rebound to their initial configurations and other portions of the tubular lattice 34092 can only partially rebound and/or remain fully compressed.

Similar to the description of the tubular elements herein, each strand 34090 can also be deformable. Further, deformation of a strand 34090 can generate a restoring force that depends on the resiliency of each strand 34090. In some embodiments, referring primarily to FIGS. 420 and 421, each strand 34090 of a tubular lattice 34092 can be tubular. In other embodiments, each strand 34090 of a tubular lattice 34092 can be solid. In still other embodiments, the tubular lattice 30092 can comprise at least one tubular strand 34090, at least one solid strand 34090, at least one "X"- or "T"-shaped strand 34090, and/or a combination thereof.

In various embodiments, the strands 34090 in the tubular element 34080 can comprise a polymeric composition. The polymeric composition of a strand 34090 can comprise non-absorbable polymers, absorbable polymers, or combinations thereof. Examples of synthetic polymers include, but are not limited to, polyglycolic acid (PGA), poly(lactic acid) (PLA), polycaprolactone (PCL), polydioxanone (PDO), and copolymers thereof. In some embodiments, the absorbable polymers can include bioabsorbable, biocompatible elastomeric polymers, for example. Furthermore, the polymeric composition of the strand 34090 can comprise synthetic polymers, non-synthetic polymers, and/or combinations thereof. In various embodiments, similar to the polymeric compositions in embodiments described herein, the polymeric composition of the strand 34090 can include varied amounts of absorbable polymers, non-absorbable polymers, synthetic polymers, and/or non-synthetic polymers, for example, by weight percentage.

The strands 34090 in the tubular element 34080 can further comprise a therapeutic agent 34098 (FIG. 420) such as a pharmaceutically active agent or medicament, for example. In some embodiments, the strand 34090 can release a therapeutically effective amount of the therapeutic agent 34098. In various embodiments, the therapeutic agent 34098 can be released as the tubular strand 34090 is absorbed. For example, the therapeutic agent 30098 can be released into fluid, such as blood for example, passing over or through the strand 34090. In still other embodiments, the therapeutic agent 34098 can be released when a staple 30030 pierces the strand 34090 and/or when the cutting element 30052 on the staple-firing sled 30050 (FIG. 413) cuts a portion of the tubular lattice 34092, for example. Examples of therapeutic agents 34098 can include, but are not limited to, haemostatic agents and drugs such as, for example, fibrin, thrombin, and/or oxidized regenerated cellulose (ORC), anti-inflammatory drugs such as, for example, diclofenac, aspirin, naproxen, sulindac, and/or hydrocortisone, antibiotic and antimicrobial drugs or agents such as, for example, triclosan, ionic silver, ampicillin, gentamicin, polymyxin B, and/or chloramphenicol, anticancer agents such as, for example, cisplatin, mitomycin, and/or adriamycin; and/or biologics such as, for example, stem cells.

Referring to FIGS. 424 and 425, a tubular element 35080 can comprise multiple layers 35100 of strands 35090. In some embodiments, the tubular element 35080 can comprise multiple layers 35100 of tubular lattices 35092. Referring to FIG. 424, the tubular element 35080 can comprise a first layer **35100*a* and a second layer 35100*b* of strands 35090, for example. Referring now to FIG. 425, a tubular element 35180 of a tissue thickness compensator 35120 can comprise a third layer 35100*c* of strands 35090, for example. Furthermore, different layers 35100 in the tubular element 35180 can comprise different materials. In some embodiments, each layer 35100*a*, 35100*b*, 35100*c* can be bioabsorbable, wherein, in at least one embodiment, each layer 35100*a*, 35100*b*, 35100*c* can comprise a different polymeric composition. For example, the first layer 35100*a* can comprise a first polymeric composition; the second layer 35100*b* can comprise a second polymeric composition; and the third layer 35100*c* can comprise a third polymeric composition. In such embodiments, layers 35100*a*, 35100*b*, 35100*c* of the tubular element 35180 can be bioabsorbed at different rates. For example, the first layer 35100*a* can absorb quickly, the second layer 35100*b* can absorb slower than the first layer 35100*a*, and the third layer 35100*c* can absorb slower than the first layer 35100*a* and/or the second layer 35100*b*. In other embodiments, the first layer 35100*a* can absorb slowly, the second layer 35100*b* can absorb faster than the first layer 35100*a*, and the third layer 35100*c* can absorb faster than the first layer 35100*a* and/or the second layer 35100*b***.

Similar to strands 34090 described herein, the strands 35090 in the tubular element 35180 can comprise a medicament 35098. In various embodiments, referring again to FIG. 424, to control elusion or release of the medicament(s) 35098, the first layer **35100*a* of strands 35090 comprising a medicament 35098*a* can be bioabsorbed at a first rate and the second layer 35100*b* of strands 35090 comprising a medicament 30098*b* can be bioabsorbed at a second rate. For example, the first layer 35100*a* can absorb quickly to allow for a rapid initial release of the medicament 35098*a* and the second layer 35100*b* can absorb slower to allow controlled release of the medicament 30098*b*. The medicament 35098*a* in the strands 35090 of the first layer 30100*a* can be different than the medicament 35098*b* in the strands 35090 of the second layer 35100*b*. For example, the strands 35090 in the first layer 35100*a* can comprise oxidized regenerated cellulose (ORC) and the strands 35090 in the second layer 35100*b* can comprise a solution comprising hyaluronic acid. In such embodiments, initial absorption of the first layer 35100*a* can release oxidized regenerated cellulose to help control bleeding while subsequent absorption of the second layer 35100*b* can release a solution comprising hyaluronic acid to can help prevent the adhesion of tissue. In other embodiments, the layers 35100*a*, 35100*b* can comprise the same medicament 35098*a*, 35098*b*. For example, referring again to FIG. 425, strands 35090 in layers 35100*a*, 35100*b* and 35100*c* can comprise an anticancer agent, such as, for example, cisplatin. Furthermore, the first layer 35100*a* can absorb quickly to allow for a rapid initial release of cisplatin, the second layer 35100*b* can absorb slower to allow for a controlled release of cisplatin, and the third layer 35100*c*** can absorb slowest to allow for a more extended, controlled release of cisplatin.

In various embodiments, referring to FIGS. 426 and 427, a tissue thickness compensator 36020 can comprise an overmold material 36024. The overmold material 36024 can be formed outside a tubular element 36080, inside a tubular element 36080, or both inside and outside a tubular element 36080. In some embodiments, referring to FIG. 426, the overmold material 36024 can be coextruded both inside and outside the tubular element 36080 and, in at least one embodiment, the tubular element 36080 can comprise a tubular lattice 36092 of strands 36090. Similar to the polymeric composition described herein, the overmold material 36024 can comprise polyglycolic acid (PGA), poly(lactic acid) (PLA), and/or any other suitable, bioabsorbable and biocompatible elastomeric polymers, for example. Further, the overmold material 36024 can be non-porous such that the overmold material 36024 forms a fluid-impervious layer in the tubular element 36080. In various embodiments, the overmold material 36024 can define a lumen 36084 therethrough.

Further to the discussion above, the tubular element 36080 and/or the strands 36090 in a tubular lattice 36092 can comprise a therapeutic agent 36098. In some embodiments, referring still to FIGS. 426 and 427, a non-porous overmold material 36024 can contain the medicament 36098 within an inner lumen 36084*a*. Alternatively or additionally, the non-porous, overmold material 36024 can contain the medicament 36098 within an intermediate lumen 36084*b*, such as, for example, the intermediate lumen 36084*b* that contains the tubular lattice 36092 of medicament-comprising strands 36090. Similar to the above, the tubular element 36080 can be positioned relative to staple cavities 30012 and a cutting element 30052 in staple cartridge 30000 (FIG. 413). In several such embodiments, the deployment of the staples 30030 and/or the translation of the cutting element 30052 can be configured to pierce or rupture the non-porous, overmold material 36024 such that the medicament 36098 contained in at least one lumen 36084 of the tubular element 30080 can be released from the lumen 30084. In various embodiments, referring to FIG. 428, a tubular element 37080 can comprise a non-porous film 37110. The non-porous film 37110 can at least partially surround a tubular lattice 37092 or a first layer 37100*a* and a second layer 37100*b* of tubular lattices 30092 to provide a fluid-impervious cover similar to the overmold material 36024 described herein.

As described herein, a tubular element can comprise at least one of a bioabsorbable material, a therapeutic agent, a plurality of strands, a tubular lattice, layers of tubular lattices, an overmold material, a non-porous film, or combinations thereof. For example, referring to FIG. FIG. 429, a tubular element 38080 can comprise an overmold material 38024 and a plurality of strands 38090 positioned through a central lumen 38084 of the tubular element 38080. In some embodiments, the strands 38090 can comprise a therapeutic agent 38098. In other embodiments, for example, referring to FIG. 430, a tubular element 39080 can comprise an overmold material 39024 and a therapeutic agent 39098 positioned in a central lumen 39084 of the tubular element 39080, for example. In various embodiments, at least one of the tubular element 39080 and overmold material 39024 can comprise a fluidic therapeutic agent 39098.

In various embodiments, referring again primarily FIG. 413, the tubular element 30080 can be positioned relative to the rigid support portion 30010 of the staple cartridge 30000. The tubular element 30080 can be longitudinally positioned adjacent to the rigid support portion 30010. In some embodiments, the tubular element 30080 can be substantially parallel to or aligned with a longitudinal slot or cavity 30015 in the rigid support portion 30010. The tubular element 30080 can be aligned with the longitudinal slot 30015 such that a portion of the tubular element 30080 overlaps a portion of the longitudinal slot 30015. In such embodiments, a cutting element 30052 on the staple-firing sled 30050 can sever a portion of the tubular element 30080 as the cutting edge 30052 translates along the longitudinal slot 30015. In other embodiments, the tubular element 30080 can be longitudinally positioned on a first or second side of the longitudinal slot 30015. In still other embodiments, the tubular element 30080 can be positioned relative to the rigid support portion 30010 of the staple cartridge 30000 such that the tubular element 30080 laterally or diagonally traverses at least a portion of the rigid support portion 30010.

In various embodiments, referring to FIG. 431 for example, a tissue thickness compensator 40020 can comprise multiple tubular elements 40080. In some embodiments, the tubular elements 40080 can comprise different lengths, cross-sectional shapes, and/or materials, for example. Further, the tubular elements 40080 can be positioned relative to the rigid support portion 40010 of the staple cartridge 30000 such that the tubular axes of the tubular elements 40080 are parallel to each other. In some embodiments, the tubular axes of tubular elements 40080 can be longitudinally aligned such that a first tubular element 40080 is positioned within another tubular element 40080. In other embodiments, parallel tubular elements 40080 can longitudinally traverse the staple cartridge 30000, for example. In still other embodiments, parallel tubular elements 40080 can laterally or diagonally traverse the staple cartridge 30000. In various other embodiments, non-parallel tubular elements 40080 can be angularly-oriented relative to each other such that their tubular axes intersect and/or are not parallel to each other.

Referring to FIGS. 431-434, a tissue thickness compensator 40020 can have two tubular elements 40080; a first tubular element 40080*a* can be longitudinally positioned on a first side of the longitudinal slot 30015 in the rigid support portion 30010 and a second tubular element 40080*b* can be longitudinally positioned on a second side of the longitudinal slot 30015. Each tubular element 40080 can comprise a tubular lattice 40092 of strands 40090. In various embodiments, the staple cartridge 30000 can comprise a total of six rows of staple cavities 30012, wherein three rows of staple cavities 30012 are positioned on each side of the longitudinal slot 30015, for example. In such embodiments, the cutting edge 30052 on the translating staple-firing sled 30050 may not be required to sever a portion of the tubular element 40080.

Similarly, referring now to FIGS. 435-436, a tissue thickness compensator 41020 can comprise two tubular elements 41080*a*, 41080*b* longitudinally arranged in the staple cartridge 30000. Similar to the above, staples 30030 from three rows of staple cavities 30012 can engage one tubular element 41080*a* and staples 30030 from three different rows of staple cavities 30012 can engage another tubular element 41080*b*. In various embodiments, referring still to FIGS. 435-436, deployed staples 30030 can engage the tubular element 40080 at different locations across the cross-section of the tubular element 40080. As discussed herein, the springback resiliency and corresponding restoring force exerted by the tubular element 41080 can depend on the cross-sectional shape of the tubular element 41080, among other things. In some embodiments, a staple 30030 positioned in a staple entrapment area 30039 located at or near an arced portion of the tubular element 41080 can experience a greater restoring force than a staple 30030 in a staple entrapment area 30039 positioned near a non-arced portion. Similarly, a staple 30030 positioned in staple entrapment area 30039 in the non-arced portion of the tubular element 41080 can experience a lesser restoring force than the restoring force experienced by a staple 30030 positioned at or nearer to the arced portion of the tubular element 30080. In other words, the arced portions of a tubular element 41080 can have a greater spring rate than the non-arced portion of the tubular element 41080 owing to the possibility that a larger quantity of elastic material may be captured by the staples 30030 along such portions. In various embodiments, as a result, referring primarily to FIG. 436, the restoring force generated by the tissue thickness compensator 41020 can be greater near staples 30030*a* and 30030*c* and less near staple 30030*b* in tubular element 30080*a*. Correspondingly, the restoring force generated by the tissue thickness compensator 41020 can be greater near staples 30030*d* and 30030*f* than near staple 30030*e* in tubular element 30080*b*.

Referring again to FIGS. 431-434, in various embodiments, the cross-sectional geometries of strands 40090 comprising the tubular lattice 40092 can be selected in order to provide a desired springback resiliency and corresponding restoring force exerted by the tubular lattice 40092. For example, referring again to FIG. 432, strands 40090*a* positioned in arced portions of the tubular element 40080 can comprise X-shaped cross-sections, whereas strands 40090*b* positioned in non-arced portions of the tubular element 40080 can comprise tubular cross-sections. In some embodiments, strands 40090*a* and 40090*b* comprising different cross-sectional geometries can be woven together to form the tubular lattice 40092. In other embodiments, the strands 40090*a* and 40090*b* can be attached to one another with an adhesive, for example. Referring to FIGS. 433 and 434, the different cross-sectional geometries of strands 40090 in the tubular element 40080 can optimize the restoring force experienced in staple entrapment areas 30039 across the staple cartridge 30000. In some embodiments, specific cross-sectional geometries can be selected such that the springback constant in staple entrapment areas 30039 across the staple cartridge is substantially balanced or equal.

In some embodiments, referring to FIG. 437, the tubular elements 41080*a*, 41080*b* of a tissue thickness compensator 41120 can be fastened together by an adjoining portion 41126. Though the translating cutting element 30052 can be configured to pass between tubular elements 41080*a* and 41080*b*, the cutting element 30052 can be required to sever at least a portion of the adjoining portion 41126. In some embodiments, the adjoining portion 41126 can comprise a soft material, such as, for example, a foam or gel, which is easily severed by the translating cutting element 30052. In various embodiments, the adjoining portion 41026 can releasably secure the tissue thickness compensator 41120 to the surgical end effector 12. In at least one embodiment, the adjoining portion 41126 can be fixed to the top deck surface 30011 of the rigid support portion 30010 such that the adjoining portion 41126 remains retained in the surgical end effector 12 after the tubular elements 41080*a*, 41080*b* are released therefrom.

In various embodiments, referring to FIGS. 438-439, a tissue thickness compensator 42020 can comprise multiple tubular elements 42080 such that the number of tubular elements 42080 is the same as the number of rows of staple cavities 30012 in the staple cartridge 30000, for example. In at least one embodiment, the staple cartridge 30000 can comprise six rows of staple cavities 30012 and the tissue thickness compensator 42020 can comprise six tubular elements 42080. Each tubular element 42080 can be substantially aligned with a row of staple cavities 30012. When staples 30030 are ejected from a row of staple cavities 30012, each staple 30030 from that row can pierce the same tubular element 42080 (FIG. 439). In various embodiments, the deformation of one tube 42080 can have little or no impact on the deformation of an adjacent tube 42080. Accordingly, the tubular elements 42080 can exert a substantially discrete and customized springback force in staple entrapment areas 30039 across the width of the staple cartridge 30030. In some embodiments, where staples 30030 fired from multiple rows of staple cavities 30012 engage the same tubular element 35080 (FIG. 436), the deformation of the tubular element 35080 can be less customized. For example, the deformation of a tubular element 35080 in a staple entrapment area 30039 in a first row can impact the deformation of that tubular element 35080 in staple entrapment area 30039 in another row. In at least one embodiment, the translating cutting edge 30052 can avoid severing the tubular elements 42080. In other embodiments, referring to FIG. 440, a tissue thickness compensator 43020 can comprise more than six tubular elements 43080, such as, for example, seven tubular elements 44080. Further, the tubular elements 43080 can be symmetrically or non-symmetrically arranged in the end effector 12. When an odd number of tubular elements 43080 are longitudinally and symmetrically arranged in the end effector 12, the translating cutting element 30052 can be configured to sever the middle tubular element that overlies the longitudinal channel 30015.

In various embodiments, referring to FIG. 441, a tissue thickness compensator 44020 can comprise a central tubular element 44080*b* that is at least partially aligned with the longitudinal slot 30015 in the rigid support portion 33010 of the staple cartridge 30000. The tissue thickness compensator 44020 can further comprise at least one peripheral tubular element 44080*a*, 44080*c* located on a side of the longitudinal slot 30015. For example, the tissue thickness compensator 44020 can comprise three tubular elements 44080: a first peripheral tubular element 44080*a* can be longitudinally positioned on a first side of the longitudinal slot 30015 of the staple cartridge 30000, a central tubular element 44080*b* can be substantially positioned over and/or aligned with the longitudinal slot 30015, and a second peripheral tubular element 44080*c* can be longitudinally positioned on a second side of the longitudinal slot 30015. In some embodiments, the central tubular element 44080*b* can comprise a horizontal diameter that is substantially elongated relative to the vertical diameter. In various embodiments, the central tubular element 44080*b*, and/or any other tubular element, can overlap multiples rows of staple cavities 30012. Referring still to FIG. 441, the central tubular element 44080*b* can overlap four staple rows of staple cavities 30012 and each peripheral tubular element 44080*a*, 44080*c* can overlap a single row of staple cavities 30012, for example. In other embodiments, the central tubular element 44080*b* can overlap less than four rows of staple cavities 30012, such as, for example, two rows of staple cavities 30012, for example. Further, peripheral tubular elements 44080*a*, 44080*c* can overlap more than one row of staple cavities 30012, such as, for example, two rows of staple cavities 30012. Referring now to FIG. 442, a central tubular element 44180*b* of a tissue thickness compensator 44120 can comprise a therapeutic agent 44198 in a lumen 44184 of the central tubular element 44180*b*. In various embodiments, central tubular element 44180*b* and/or at least one peripheral tubular element 44080*a*, 44080*c* can comprise the therapeutic agent 44198 and/or any other suitable therapeutic agent.

In various embodiments, referring to FIG. 443, the tissue thickness compensator 44220 can comprise a shell 44224, which can be similar to overmold material 32024 described herein. In various embodiments, the shell 44224 retains multiple tubular elements 44080 in position in the end effector 12. The shell 44224 can be coextruded with the tubular elements 44080. In some embodiments, the tubular elements 44080 can comprise a tubular lattice 44092 of strands 44090. Similar to the polymeric compositions described in embodiments herein, the shell 44224 can comprise polyglycolic acid (PGA), poly(lactic acid) (PLA), and/or any other suitable bioabsorbable, biocompatible elastomeric polymers, for example. Further, the shell 44224 can be non-porous such that the shell 44224 forms a fluid-impervious layer in the tissue thickness compensator 44220, for example. Further to the discussion herein, the tubular element 44080 and/or the strands 44090 in the tubular lattice 44092 can comprise a therapeutic agent 44098. In some embodiments, the non-porous shell 44224 can contain the therapeutic agent 44098 within the tissue thickness compensator. As described herein, the tubular element 44080 can be positioned relative to staple cavities 30012 and a cutting element 30052 in staple cartridge 30000. In several such embodiments, deployment of the staples 30030 and/or translation of the cutting element 30052 can be configured to pierce or rupture the non-porous, shell 44224 such that the therapeutic agent 44198 contained therein can be released from the tissue thickness compensator 44020.

Referring to FIG. 444, a tissue thickness compensator 44320 can comprise a central tubular element 44380*b* comprising a tubular lattice 44392. The tubular lattice 44392 can have a non-woven portion or a gap 44381 that is substantially aligned with the longitudinal slot 30015 of the rigid support portion 30010. In such embodiments, a woven portion of the tubular lattice 44092 of the tubular element 44380*b* does not overlap the longitudinal slot 30015. Accordingly, the cutting element 30052 on the translating staple-fire sled 30052 can translate along the longitudinal slot 30015 without severing an overlapping a woven portion of the tubular lattice 44392. Though staples 30030*c* and 30030*d* positioned adjacent to the gap 44381 in tubular element 44380*b* may receive less support from the tubular lattice 44392 structure, in some embodiments, additional features can provide support for those staples 30030 and/or additional restoring force in the staple entrapment areas 30039 thereof. For example, as described in greater detail herein, additional tubular elements, support webbing, springs and/or buttressing material can be positioned at least one of inside and outside tubular element 44380*b* near gap 44381, for example.

Referring now to FIGS. 445-448, in various embodiments, a tissue thickness compensator 45020 can comprise multiple tubular elements 45080 that laterally traverse the staple cartridge 30000. The tubular elements 45080 can be positioned perpendicular to the rows of staple cavities 30012 and/or the longitudinal axis of the rigid support portion 30010 of the staple cartridge 30000. In some embodiments, referring to FIG. 445, the tubular elements 45080 can traverse the longitudinal slot 30015 in the staple cartridge 30000 such that the cutting element 30052 on the staple-firing sled 30050 is configured to sever the tubular elements 45080 as the staple-firing sled 30050 translates along the longitudinal slot 30015. In other embodiments, referring now to FIG. 446, the tissue thickness compensator 46020 can comprise two sets of laterally traversing tubular elements 46080. The first set of laterally traversing tubular elements 46080*a* can be positioned on a first side of the longitudinal slot 30015 and the second set of laterally traversing tubular elements 46080*b* can be positioned on a second side of the longitudinal slot 30015. In such an arrangement, the cutting element 30052 can be configured to pass between the two sets of tubular elements 46080 without severing a portion of the tubular elements 46080. In other embodiments, the cutting element 30052 can sever at least one tubular element 46080 that traverses the longitudinal slot 30015 while at least one other tubular element 46080 does not traverse the longitudinal slot 30015 and is not severed by the cutting element 30052.

As the tubular elements 45080 laterally traverse the staple cartridge 30000, referring to FIGS. 447 and 448, a staple 30030 can engage at least one tubular element 45080 in each staple entrapment area 30039. In such an arrangement, each tubular element 45080 can provide a discrete restoring force along the length of the staple cartridge 30000. For example, referring primarily to FIG. 448, the tubular elements 45080 positioned near the proximal end of the tissue thickness compensator 45020 where the tissue is thicker can be greatly compressed compared to the tubular elements 45080 positioned near to the distal end of the tissue thickness compensator 45020 where the tissue is thinner. As a result, the tubular elements 45080 positioned closer to the proximal end of the tissue thickness compensator 45020 can provide a greater restoring force than the restoring force that could be generated by the tubular elements 46080 positioned closer to the distal end of the tissue thickness compensator 45020. Further, referring still to FIG. 448, the deformation of one tube 45080 can have little or no impact on the deformation of an adjacent tube 45080. Accordingly, the tubular elements 45080 can exert a substantially discrete and customized springback force in staple entrapment areas 30039 along the length of the staple cartridge 30030. In some embodiments, where multiple staples 30030 fired from a single row of staple cavities 30012 engage the same tubular element 35080, the deformation of the tubular element 35080 can be less customized. For example, the deformation of a tubular element 35080 in one staple entrapment area 30039 can impact the deformation of that tubular element 35080 in another staple entrapment area 30039.

In still other embodiments, referring to FIGS. 449-454, tubular elements 47080 of the tissue thickness compensator 47020 can diagonally traverse the staple cartridge 30000. The tubular elements 47080 can traverse the longitudinal slot 30015 of the staple cartridge 30000 such that the cutting element 30052 on the staple-firing sled 30050 is configured to sever the diagonally traversing tubular elements 47080 as the staple-firing sled 30052 translates along the longitudinal slot 30015. In other embodiments, the tissue thickness compensator 47020 can comprise two sets of diagonally traversing tubular elements 47080. A first set of diagonally traversing tubular elements 47080 can be positioned on a first side of the longitudinal slot 30015 and a second set of diagonally traversing tubular elements 47080 can be positioned on a second side of the longitudinal slot 30015. In such an arrangement, the cutting element 30052 can pass between the two sets of tubular elements 47080 and may not sever any tubular element 47080.

Referring still to FIGS. 449-452, the diagonally traversing tubular elements 47080 can be positioned in the staple cartridge 30000 such that a gap is defined between the tubular elements 47080. A gap between adjacent tubular elements 47080 can provide space for horizontal expansion of the tubular elements 47080 when a compressive force is applied thereto, such as, for example, by tissue T captured within the staple entrapment area 30039 of the formed staple 30030. The tubular elements 47080 can be connected across a gap by a film or sheet of material 47024. The sheet of material can be positioned on at least one of the deck surface 30011 of the rigid support portion 30010 and/or the tissue contacting side of the tubular elements 47080.

In various embodiments, referring to FIGS. 453 and 454, at least one diagonally traversing tubular element 47080 can be positioned relative to the staple cavities 30012 in the staple cartridge 30000 such that the tubular element 47080 is positioned between the legs 30032 of the staples 30030 deployed from multiple rows of staple cavities 30012. As the staples 30030 are moved from the initial position to the fired position, as described in greater detail herein, the staple legs 30032 can remain positioned around the tubular element 47080. Further, the staples can be deformed such that the staple legs 30032 wrap around the perimeter of the tubular element 47080, for example. In such an arrangement, the staples 30030 can be configured to move to the fired or formed position without piercing the tubular element 47080. Movement of the staple legs 30032 around the tubular element 47080 could in some embodiments, prevent the inadvertent release of a therapeutic agent 47098 retained therein. The selected angular orientation of each tubular element 47080 relative to the longitudinal slot 30015 of the staple cartridge 30000 can depend on the position of the staple cavities 30012 in the staple cartridge 30000. For example, in some embodiments, the tubular elements 47080 can be positioned at an approximately forty-five (45) degree angle relative to the longitudinal slot 30015 of the staple cartridge 30000. In other embodiments, the tubular elements 47080 can be positioned at a fifteen (15) to seventy-five (75) degree angle relative to the longitudinal slot 30015 of the staple cartridge 30000, for example.

Similar to descriptions throughout the present disclosure, multiple tubular elements in a tissue thickness compensator can be connected by a binding agent, wrap, webbing, overmold, compensation material, and/or any other suitable connecting adhesive or structure, for example. In various embodiments, referring to FIGS. 455-457, a flexible shell 48024 may surround or encapsulate tubular elements 48080 in a tissue thickness compensator 48020. In various embodiments, the flexible shell 48024 can restrain the tubular elements 48080 in the end effector 12 and can hold each tubular element 48080 in position, such as, for example, in longitudinal alignment with a row of staple cavities 30012. In at least one embodiment, the tissue thickness compensator 48020 can comprise six tubular elements 48080, for example. In various embodiments, the flexible shell 48024 can be sufficiently deformable and resilient to restrain the tubular elements 48020 encased therein while permitting deformation and rebound of the tubular elements 48080. Further, in some embodiments, the flexible shell 48024 can tautly surround the tubular elements 48080 and can remain tautly engaged with the tubular elements 48080 as they deform and/or rebound.

Referring to FIG. 456, prior to the deployment of staples 30030, the anvil 30060 can be pivoted or rotated downwardly to compress the tissue thickness compensator 48020 and tissue T between the anvil 30060 and the staple cartridge 30000. Compression of the tissue thickness compensator 48020 can include a corresponding compression of the flexible shell 48024 and the tubular elements 48020 therein. As the tubular elements 48020 deform, the flexible shell 48024 can similarly deform. In various embodiments, the tubular elements 48020 can be uniformly compressed across the width of the staple cartridge 30000 and the flexible shell 48024 can experience a similarly uniform compression across the tubular elements 48080. Referring to FIG. 457, when the anvil 30060 is opened after the staples 30030 have been deployed from the staple cartridge 30000, the tubular elements 48080 can rebound or partially rebound from the compressed configurations (FIG. 456). In various embodiments, a tubular element 48080 can rebound such that the tubular element 48080 returns to its initial, undeformed configuration. In some embodiments, a tubular element 48080 can partially rebound such that the tubular element 48080 partially returns to its initial undeformed configuration. For example, the deformation of the tubular element 48080 can be partially elastic and partially plastic. As the tubular elements 48080 rebound, the flexible shell 48024 can remain tautly engaged with each tubular element 48080. The tubular elements 48080 and flexible shell 48024 can rebound to such a degree that the tubular elements 48080 and tissue T fill the staple entrapment areas 30039 while the tubular elements 48080 exert an appropriate restoring force on the tissue T therein. Referring to FIG. 458, in other embodiments, a tissue thickness compensator 48120 comprising six tubular elements 48180 retained in a flexible shell 48124 can be positioned on the anvil 30060 of the end effector 12, for example.

Referring to FIGS. 459-462, a tissue thickness compensator 49020 can comprise a tubular element 49080 longitudinally positioned along the longitudinal axis of the anvil 30060. In various embodiments, the tissue thickness compensator 49020 can be secured to the anvil 30060 of the end effector 12 by a compressible compensation material 49024. Further, the compressible compensation material 49024 can surround or encapsulate the tubular element 49080. Similar to the descriptions herein, the tubular element 49080 can comprise at least one therapeutic agent 49098 which may be released by the absorption of various components of the tissue thickness compensator 49020, the piercing of the tubular element 49080 by staples 30030 fired from the staple cartridge 30000, and/or by the cutting element 30052.

Referring to FIG. 460, a staple cartridge 30000 can comprise staples 30030 positioned in staple cavities 30012, wherein, prior to deployment of the staples 30030, the anvil 30060 and the tissue thickness compensator 49020 attached thereto can pivot toward the staple cartridge 30000 and compress tissue T captured therebetween. In some embodiments, the tubular element 49080 of the tissue thickness compensator 49020 can be uniformly deformed along the length of the staple cartridge 30000 by the pivoting anvil 30060 (FIG. 460). Referring to FIGS. 461 and 462, the staple-firing sled 30050 can translate along the longitudinal slot 30015 in the staple cartridge 30000 and engage each driver 30040 positioned beneath a staple 30030 in a staple cavity 30010, wherein each engaged driver 30040 can fire or eject the staple 30030 from the staple cavity 30012. When the anvil 30060 releases pressure on the tissue T and the tissue thickness compensator 49020, the tissue thickness compensator 49020, including the tubular element 49080 and the compressible compensation material 49024, can rebound or partially rebound from the compressed configurations (FIG. 460) to a rebounded configuration (FIGS. 461 and 462). The tubular element 49080 and compressible compensation material 49024 can rebound to such a degree that the tissue thickness compensator 49020 and tissue T fill the staple entrapment areas 30039 while the tissue thickness compensator 49020 exert an a restoring force on the captured tissue T.

In various embodiments, referring to FIGS. 463-465, two tissue thickness compensators **50020*a*, 50020*b* can be positioned in the end effector 12 of a surgical instrument. For example, a first tissue thickness compensator 50020*a* can be attached to the staple cartridge 30000 in the lower jaw 30070 and a second tissue thickness compensator 50020*b* can be attached to the anvil 30060. In at least one embodiment, the first tissue thickness compensator 50020*a* can comprise a plurality of tubular elements 50080 longitudinally arranged and retained in a first compensation material 50024*a*. At least one tubular element 50080 can comprise a therapeutic agent 50098, similar to the therapeutic agents described herein. The first compensation material 50024*a* can be deformable or substantially rigid. Further, in some embodiments, the first compensation material 50024*a* can hold the tubular elements 50080 in position relative to the staple channel 30000. For example, the first compensation material 50024*a* can hold each tubular element 50080 in longitudinal alignment with a row of staple cavities 30012. In at least one embodiment, the second tissue thickness compensator 50020***b* can comprise the first compensation material 50024*a*, a second compensation material 50024*b* and/or a third compensation material 50024*c*. The second and third compensation material 50024*b*, 50024*c* can be deformable or substantially rigid.

Similar to at least one embodiment described herein, the anvil 30060 can pivot and apply a compressive force to the tissue thickness compensators 50020*a*, 50020*b* and the tissue T between the anvil 30060 and the staple cartridge 30000. In some embodiments, neither the first tissue thickness compensators 50020*a* nor the second tissue thickness compensators 50020*b* can be compressible. In other embodiments, at least one component of the first tissue thickness compensators 50020*a* and/or the second tissue thickness compensators 50020*b* can be compressible. When the staples 30030 are fired from the staple cartridge 30000, referring now to FIGS. 464 and 465, each staple 30030 can pierce a tubular element 50080 retained in the first tissue thickness compensator 50020*a*. As shown in FIG. 464, the therapeutic agent 50098 retained in the tubular element 50080 can be released when a staple 30030 pierces the tubular element 50080. When released, the therapeutic agent 50098 can coat the staple legs 30032 and tissue T surrounding the fired staple 30030. In various embodiments, the staples 30030 can also pierce the second tissue thickness compensator 50020*b* when the staples 30030 are fired from the staple cartridge 30000.

Referring to FIGS. 466-469, a tissue thickness compensator 51020 can comprise at least one tubular element 51080 that laterally traverses the tissue thickness compensator 51020. For example, referring to FIG. 466, the tissue thickness compensator 51020 can be positioned relative to the staple cartridge 30000 such that a first end 51083 of the laterally traversing tubular element 51080 can be positioned near a first longitudinal side of the staple cartridge 30000 and a second end 51085 of the laterally traversing tubular element 51080 can be positioned near a second longitudinal side of the staple cartridge 30000. In various embodiments, the tubular element 51080 can comprise a capsule-like shape, for example. As illustrated in FIG. 467, the tubular element 51080 can be perforated between the first end 51083 and the second end 51085 and, in some embodiments, the tubular element 51080 can be perforated at or near the center 51087 of the tubular element 51080. The tubular element 51080 can comprise a polymeric composition, such as a bioabsorbable, biocompatible elastomeric polymer, for example. Further, referring again to FIG. 466, the tissue thickness compensator 51020 can comprise a plurality of laterally traversing tubular elements 51080. In at least one embodiment, thirteen tubular elements 51080 can be laterally arranged in the tissue thickness compensator 51020, for example.

Referring again to FIG. 466, the tissue thickness compensator 51020 can further comprise a compensation material 51024 that at least partially surrounds the tubular elements 51080. In various embodiments, the compensation material 51024 can comprise a bioabsorbable polymer, such as, for example, lyophilized polysaccharide, glycoprotein, elastin, proteoglycan, gelatin, collagen, and/or oxidized regenerated cellulose (ORC). The compensation material 51024 can hold the tubular elements 51080 in position in the tissue thickness compensator 51020. Further, the compensation material 51024 can be secured to the top deck surface 30011 of the rigid support portion 30010 of the staple cartridge 30000 such that the compensation material 51020 is securely positioned in the end effector 12. In some embodiments, the compensation material 51024 can comprise at least one medicament 51098.

Still referring to FIG. 466, laterally positioned tubular elements 51080 can be positioned relative to the translating cutting element 30052 such that the cutting element 30052 is configured to sever the tubular elements 51080. In various embodiments, the cutting element 30052 can sever the tubular elements 51080 at or near the perforation therein. When the tubular elements 51080 are severed in two halves, the severed portions of the tubular elements 51080 can be configured to swell or expand, as illustrated in FIG. 468. For example, in various embodiments, the tubular element 51080 can comprise a hydrophilic substance 51099 that can be released and/or exposed when the tubular element 51080 is severed. Furthermore, when the hydrophilic substance 51099 contacts bodily fluids in tissue T, the hydrophilic substance 51099 can attract the fluid, which can cause the tubular element 51080 to swell or expand. As the tubular element 51080 expands, the compensation material 51024 surrounding the tubular element 51080 can shift or adjust to accommodate the swollen tubular element 51080. For example, when the compensation material 51024 comprises gelatin, the gelatin can shift to accommodate the swollen tubular elements 51080. Referring now to FIG. 469, expansion of the tubular elements 51080 and shifting of the compensation material 51024 can cause a corresponding expansion of the tissue thickness compensator 51020.

Similar to other tissue thickness compensators discussed throughout the present disclosure, the tissue thickness compensator 51020 can be deformed or compressed by an applied force. Further, the tissue thickness compensator 51020 can be sufficiently resilient such that it produces a springback force when deformed by the applied force and can subsequently rebound or partially rebound when the applied force is removed. In various embodiments, when the tissue thickness compensator 51020 is captured in a staple entrapment area 30039, the staple 30030 can deform the tissue thickness compensator 51020. For example, the staple 30030 can deform the tubular elements 51080 and/or the compensation material 51024 of the tissue thickness compensator 51020 that are captured within the fired staple 30030. In various embodiments, non-captured portions of the tissue thickness compensator 51020 can also be deformed due to the deformation in the staple entrapment areas 30039. When deformed, the tissue thickness compensator 51020 can seek to rebound from the deformed configuration. In various embodiments, such a rebound may occur prior to the hydrophilic expansion of the tubular element 51080, simultaneously with the hydrophilic expansion of the tubular element 51080, and/or after the hydrophilic expansion of the tubular element 51080. As the tissue thickness compensator 51020 seeks to rebound, it can exert a restoring force on the tissue also captured in the staple entrapment area 30039, as described in greater detail herein.

In various embodiments, at least one of the tubular elements 51080 and/or the compensation material 51024 in the tissue thickness compensator 51020 can comprise a therapeutic agent 51098. When the tubular element 51080 that contains a therapeutic agent 51098 is severed, the therapeutic agent 51098 contained within the tubular elements 51080 can be released. Furthermore, when the compensation material 51024 comprises the therapeutic agent 51098, the therapeutic agent 51098 can be released as the bioabsorbable compensation material 51024 is absorbed. In various embodiments, the tissue thickness compensator 51020 can provide for a rapid initial release of the therapeutic agent 51098 followed by a controlled release of the therapeutic agent 51098. For example, the tissue thickness compensator 51020 can provide a rapid initial release of the therapeutic agent 51098 from the tubular elements 51080 to the tissue T along the cut line when the tubular elements 51080 comprising the therapeutic agent 51098 are severed. Further, as the bioabsorbable compensation material 51024 comprising the therapeutic agent 51098 is absorbed, the tissue thickness compensator 51020 can provide an extended, controlled release of the therapeutic agent 51098. In some embodiments, at least some of the therapeutic agent 51098 can remain in the tubular element 51080 for a short period of time before the therapeutic agent 51098 flows into the compensation material 51024. In other embodiments, at least some of the therapeutic agent 51098 can remain in the tubular element 51080 until the tubular element 51080 is absorbed. In various embodiments, the therapeutic agent 51098 released from the tubular element 51080 and the compensation material 51024 can be the same. In other embodiments, the tubular element 51080 and the compensation material 51024 can comprise different therapeutic agents or different combinations of therapeutic agents, for example.

Referring still to FIG. 469, in various embodiments, the end effector 12 can cut tissue T and fire staples 30030 into the severed tissue T nearly simultaneously or in quick succession. In such embodiments, a staple 30030 can be deployed into the tissue T immediately after the cutting element 30052 has severed the tubular element 51080 adjacent to the tissue T. In other words, the staples 30030 can engage the tissue thickness compensator 51020 immediately following or simultaneously with the swelling of the tubular element 51080 and the expansion of the tissue thickness compensator 51020. In various embodiments, the tissue thickness compensator 51020 can continue to grow or expand after the staples 30030 have been fired into the tissue T. In various embodiments, the staples 30030 can be configured to puncture the tubular elements 51080 when the staples 30030 are deployed. In such embodiments, therapeutic agents 51098 still retained in the severed tubular elements 51080 can be released from the tubular elements 51080 and, in some embodiments, can cover the legs 30031 of the fired staples 30030.

Referring to FIG. 470, the tissue thickness compensator 51020 can be manufactured by a molding technique, for example. In various embodiments, a frame, or a mold, 51120 can comprise a first longitudinal side 51122 and a second longitudinal side 51124. Each longitudinal side 51124 can comprise one or more notches 51130, which can each be configured to receive the first or second end 50183, 50185 of a tubular element 51080. In some embodiments, the first end 50183 of the tubular element 51080 can be positioned in a first notch 51130*a* on the first longitudinal side 51122 and the second end 50183 of the tubular element 51080 can be positioned in a second notch 51130*b* on the second longitudinal side 51124 such that the tubular element 51080 laterally traverses the frame 51120. In various embodiments, the notch 51180 can comprise a semi-circular groove, which can securely fit the first or second end 50183, 50185 of the tubular element 51080 therein. In various embodiments, the first notch 51130*a* can be positioned directly across from the second notch 51130*b* and the tubular element 51080 can be positioned perpendicular, or at least substantially perpendicular, to the longitudinal axis of the frame 51120. In other embodiments, the first notch 51130*a* can be offset from the second notch 51130*b* such that the tubular element 51080 is angularly positioned relative to the longitudinal axis of the frame 51120. In still other embodiments, at least one tubular element 51080 can be longitudinally positioned within the frame 51120 such that the tubular element extends between the lateral sides 51126, 51128 of the frame 51120. Further, at least one tubular element can be angularly positioned in the frame between two notches on the lateral sides 51126, 51128 of the frame and/or between a notch on a lateral side 51126 and a notch on a longitudinal side 51124, for example. In various embodiments, the frame 51120 can comprise a support ledge 51136, which can support the tubular elements 51080 positioned within the frame 51120.

In various embodiments, the frame 51120 can comprise notches 51130 to accommodate twelve tubular elements 51080, for example. In some embodiments, the frame notches 51130 can be filled with tubular elements 51080 while, in other embodiments, less than all of the notches 51130 may be filled. In various embodiments, at least one tubular element 51080 can be positioned in the frame 51120. In some embodiments, at least half the notches 51130 can receive tubular elements 51080. In at least one embodiment, once the tubular elements 51080 are positioned in the frame 51120, compensation material 51024 can be added to the frame 51120. The compensation material 51024 can be fluidic when added to the frame 51120. For example, in various embodiments, the compensation material 51024 can be poured into the frame 51120 and can flow around the tubular elements 51080 positioned therein. Referring to FIG. 471, the fluidic compensation material 51024 can flow around the tubular element 51080 supported by notches 51130 in the frame 51120. After the compensation material 51024 cures, or at least sufficiently cures, referring now to FIG. 472, the tissue thickness compensator 51020 comprising the compensation material 51024 and tubular elements 51080 can be removed from the frame 51120. In at least one embodiment, the tissue thickness compensator 51020 can be trimmed. For example, excess compensation material 51024 can be removed from the tissue thickness compensator 51020 such that the longitudinal sides of the compensation material are substantially planar. Furthermore, in some embodiments, referring to FIG. 473, the first and second ends 50183, 50185 of the tubular elements 51080 can be pressed together, or closed, to seal the tubular element 51080. In some embodiments, the ends can be closed before the tubular elements 51080 are placed in the frame 51120. In other embodiments, the trimming process may transect the ends 51083, 51085 and a heat stacking process can be used to seal and/or close the ends 51083, 51085 of the tubular elements 51080.

In various embodiments, referring again to FIG. 470, a stiffening pin 51127 can be positioned within each tubular element 51080. For example, the stiffening pin 51127 can extend through a longitudinal lumen of the tubular element 51080. In some embodiments, the stiffening pin 51127 can extend beyond each tubular element 51080 such that the stiffening pin 51127 can be positioned in notches 51130 in the frame 51120. In embodiments having stiffening pins 51127, the stiffening pins 51127 can support the tubular elements 51080 when the compensation material 51204 is poured into the frame 51120 and as the fluidic compensation material 51024 flows around the tubular elements 51080, for example. Once the compensation material 51024 cures, solidifies, and/or lyophilizes or sufficiently cures, solidifies, and/or lyophilizes the tissue thickness compensator 51020 can be removed from the frame 51120 and the stiffening pins 51127 can be removed from the longitudinal lumens of the tubular elements 51080. In some embodiments, the tubular elements 51080 can then be filled with medicaments, for example. Similar to at least one embodiment described herein, after the tubular elements 51080 are filled with medicaments, the tissue thickness compensator 51020, including the ends 51083, 51085 of the tubular elements 51080, for example, can be trimmed. In various embodiments, the tissue thickness compensator 51020 can be die cut, for example, and/or sealed by heat and/or pressure, for example.

As discussed herein, the tissue thickness compensator 52020 can comprise multiple tubular elements 51080. Referring now to FIG. 474, the tubular elements 51080 can comprise different material properties, dimensions and geometries. For example, a first tubular element 51080*a* can comprise a first thickness and a first material and a second tubular element 51080*b* can comprise a second thickness and a second material. In various embodiments, at least two tubular elements 51080 in the tissue thickness compensator 52020 can comprise the same material. In other embodiments, each tubular element 51080 in the tissue thickness compensator 5202 can comprise different materials. Similarly, in various embodiments, at least two tubular elements 51080 in the tissue thickness compensator 52020 can comprise the same geometry. In other embodiments, each tubular element 51080 in the tissue thickness compensator 52020 can comprise different geometries.

Referring now to FIGS. 537-540, a tissue thickness compensator 51220 can comprise at least one tubular element 51280 that laterally traverses the tissue thickness compensator 51220. In various embodiments, referring to FIG. 537, the tissue thickness compensator 51220 can be positioned relative to the anvil 30060 of the end effector 12. The tissue thickness compensator 51220 can be secured to a securing surface 30061 of the anvil 30060 of the end effector 12, for example. In various embodiments, referring primarily to FIG. 538, the tubular element 51280 can comprise a capsule-like shape, for example. The tubular element 51280 can comprise a polymeric composition, such as a bioabsorbable, biocompatible elastomeric polymer, for example.

Referring again to FIG. 537, the tissue thickness compensator 51220 can further comprise a compensation material 51224 that at least partially surrounds the tubular elements 51280. In various embodiments, the compensation material 51224 can comprise a bioabsorbable polymer, such as, for example, lyophilized polysaccharide, glycoprotein, elastin, proteoglycan, gelatin, collagen, and/or oxidized regenerated cellulose (ORC), for example. Similar to the above, the compensation material 51024 can hold the tubular elements 51280 in position in the tissue thickness compensator 51220. Further, the compensation material 51224 can be secured to the securing surface 30061 of the anvil 30060 such that the compensation material 51220 is securely positioned in the end effector 12. In some embodiments, the compensation material 51224 can comprise at least one medicant.

Still referring to FIG. 537, the laterally positioned tubular elements 51280 can be positioned relative to the cutting element 30252 on a translating sled 30250 such that the translatable cutting element 30252 is configured to sever the tubular elements 51280. In various embodiments, the cutting element 30252 can sever the tubular elements 51280 at or near the center of each tubular element 51280, for example. When the tubular elements 51280 are severed in two halves, the severed portions of the tubular elements 51280 can be configured to swell or expand, as illustrated in FIG. 537. Referring primarily to FIG. 539, in various embodiments, a tubular element 51280 can comprise a hydrophilic substance 51099 that can be released and/or exposed when the tubular element 51280 is severed. Furthermore, referring now to FIG. 540, when the hydrophilic substance 51099 contacts bodily fluids in the tissue T, the hydrophilic substance 51099 can attract the fluid, which can cause the tubular element 51280 to swell or expand. As the tubular element 51280 expands, the compensation material 51224 surrounding the tubular element 51280 can shift or adjust to accommodate the swollen tubular element 51280. For example, when the compensation material 51224 comprises gelatin, the gelatin can shift to accommodate the swollen tubular element 51280. Referring again to FIG. 537, expansion of the tubular elements 51280 and shifting of the compensation material 51224 can cause a corresponding expansion of the tissue thickness compensator 51220.

Similar to other tissue thickness compensators discussed throughout the present disclosure, the tissue thickness compensator 51220 can be deformed or compressed by an applied force. Further, the tissue thickness compensator 51220 can be sufficiently resilient such that it produces a springback force when deformed by the applied force and can subsequently rebound or partially rebound when the applied force is removed. In various embodiments, when the tissue thickness compensator 51220 is captured in a staple entrapment area 30039 (FIG. 417), the staple 30030 can deform the tissue thickness compensator 51220. For example, the staple 30030 can deform the tubular elements 51280 and/or the compensation material 51224 of the tissue thickness compensator 51220 captured within the fired staple 30030. In various embodiments, non-captured portions of the tissue thickness compensator 51220 can also be deformed due to the deformation in the staple entrapment areas 30039. When deformed, the tissue thickness compensator 51220 can seek to rebound from the deformed configuration. In various embodiments, such a rebound may occur prior to the hydrophilic expansion of the tubular element 51280, simultaneously with the hydrophilic expansion of the tubular element 51280, and/or after the hydrophilic expansion of the tubular element 51280. As the tissue thickness compensator 51220 seeks to rebound, it can exert a restoring force on the tissue also captured in the staple entrapment area 30039, as described in greater detail herein.

Referring to FIGS. 475-478, a tissue thickness compensator 52020 can comprise one or more tubular elements 52080 that laterally traverse the tissue thickness compensator 52020, similar to at least one tissue thickness compensator described herein. In various embodiments, the tissue thickness compensator 52020 can comprise multiple laterally traversing tubular elements 52080. The tissue thickness compensator 52020 can further comprise one or more sheets of material 52024 that hold or retain at least one tubular element 52080 in the tissue thickness compensator 52020. In various embodiments, the one or more sheets of material 52024 can be positioned above and/or below the tubular elements 52080 and can securely retain each tubular element 52080 in the tissue thickness compensator 52020. Referring primarily to FIG. 475, the tissue thickness compensator can comprise a first sheet of material 52024*a* and a second sheet of material 52024*b*. In various embodiments, the tubular elements 52080 can be positioned between the first and second sheets of material 52024*a*, 52024*b*. Further, referring still to FIG. 475, the sheet of material 52024*b* can be secured to the top deck surface 30011 of the rigid support portion of the staple cartridge 30000 such that the tissue thickness compensator 52020 is securely positioned in the end effector 12. In other embodiments, one or more of the sheets of material 52024 can be secured to the anvil 30060 or otherwise retained in the end effector 12.

In various embodiments, referring primarily to FIG. 476, the tissue thickness compensator 52020 can be porous and/or permeable. For example, the sheet of material 52024 can comprise a plurality of apertures 52026. In various embodiments, the apertures 52026 can be substantially circular. In at least one embodiment, the apertures 52036 can be visible in the sheet of material 52024. In other embodiments, the apertures 52036 can be microscopic. Referring still to FIG. 476, the tubular elements 52080 can comprise a plurality of apertures 52026, as well. In various embodiments, referring to FIG. 477, a tissue thickness compensator 52120 can comprise a sheet of material 52124 that comprises a plurality of non-circular apertures 52126. For example, the apertures 52126 can comprise a diamond and/or slotted shape. In various other embodiments, referring to FIG. 478, a tissue thickness compensator 52220 can comprise a tubular element 52280 that comprises a permeable tubular lattice 52292. In various embodiments, the sheet of material 52224 can comprise a bioabsorbable, biocompatible elastomeric polymer and can comprise a medicament, for example.

Similar to at least one embodiment described herein, at least one tubular element 52080 can be configured to swell or expand, as illustrated in FIGS. 479A-479D. For example, referring to FIG. 479A, the tubular elements 52080 can be positioned intermediate the first and second sheet of material 52024*a*, 52024*b* in the tissue thickness compensator 52020. When the tissue thickness compensator 52020 contacts tissue T, as illustrated in FIG. 479B, the tissue thickness compensator 52020 can expand. In various embodiments, for example, the tubular elements 52080 can comprise a hydrophilic substance 52099 that expands when exposed to fluid in and/or on the tissue T. Further, the sheet of material 52024 and tubular elements 52080 can be permeable, as described herein, such that fluid from the tissue T can permeate the tissue thickness compensator 52020 thereby allowing the fluid to contact the hydrophilic substance 52099 within the tubular elements 52080. As the tubular elements 52080 expand, the sheet of material 52024 surrounding the tubular elements 52080 can shift or adjust to accommodate the swollen tubular elements 52080. Similar to various tissue thickness compensators discussed throughout the present disclosure, the expanded tissue thickness compensator 52020 can be deformed or compressed by an applied force, such as, for example, a compressive force applied by fired staples, as illustrated in FIG. 479C. Further, the tissue thickness compensator 52020 can be sufficiently resilient such that it produces a springback force when deformed by the applied force and can subsequently rebound when the applied force is removed. Referring now to FIGS. 479D and 479E, the tissue thickness compensator 52020 can rebound to different configurations in different staple entrapment areas 30039 to appropriately accommodate the captured tissue T.

Referring to FIGS. 480-485, a tissue thickness compensator 53020 can comprise a plurality of vertically positioned tubular elements 53080. In various embodiments, each tubular element 53080 can comprise a tubular axis that is substantially perpendicular to the top deck surface 30011 of the rigid support portion 30010 of the staple cartridge 30000. Further, the first end of each tubular element 53080 can be positioned adjacent to the top deck surface 30011, for example. Similar to at least one embodiment described herein, the tubular elements 53080 can be deformable and may comprise an elastomeric polymer, for example. In various embodiments, as illustrated in FIG. 481, the tubular elements 53080 can be compressed when captured in a staple entrapment area 30039 with stapled tissue T. A tubular element 53080 can comprise an elastic material such that deformation of the tubular element 53080 generates a restoring force as the tubular element 53080 seeks to rebound from the deformed configuration. In some embodiments, deformation of the tubular element 53080 can be at least partially elastic and at least partially plastic. The tubular element 53080 can be configured to act as a spring under an applied force and, in various embodiments, can be configured not to buckle. In various embodiments, referring to FIG. 482, the tubular elements 53080 can be substantially cylindrical. In some embodiments, referring to FIG. 483, a tubular element 53180 can comprise a buckling region 53112. The tubular element 53180 can be configured to buckle or deform at the buckling region 53112 when a compressive force is applied thereto. The tubular element 53180 can deform elastically and/or plastically and then be designed to buckle suddenly at the buckling region 53112 under a preselected buckling force.

Referring primarily to FIG. 484, a first tubular element 53080 can be positioned at a first end of a staple cavity 30012 and another tubular element 53080 can be positioned at a second end of the staple cavity 30012. As illustrated in FIG. 482, the tubular element 53080 can comprise a lumen 53084 extending therethrough. Referring again to FIG. 481, when the staple 30030 is moved from the initial position to the fired position, each staple leg 30032 can be configured to pass through a lumen 53084 of each tubular element 53080. In various other embodiments, referring primarily to FIG. 485, vertically positioned tubular elements 54080 can be arranged in a tissue thickness compensator 54020 such that the tubular elements 54080 abut or contact each other. In other words, the tubular elements 54080 can be clustered or gathered together. In some embodiments, the tubular elements 54080 can be systematically arranged in the tissue thickness compensator 54020; however, in other embodiments, the tubular elements 54080 can be randomly arranged.

Referring again to FIGS. 480, 484, and 485, the tissue thickness compensator 53020 can also comprise a sheet of material 53024 that holds or retains the tubular elements 53080 in the tissue thickness compensator 53020. In various embodiments, the sheet of material 53024 can be positioned above and/or below the tubular elements 53080 and can securely retain each tubular element 53080 in the tissue thickness compensator 53020. In various embodiments, the tissue thickness compensator 53020 can comprise a first and a second sheet of material 53024. In various embodiments, the tubular elements 53080 can be positioned between the first and second sheets of material 53024. Further, the sheet of material 53024 can be secured to the top deck surface 30011 of the rigid support portion of the staple cartridge 30000 such that the tissue thickness compensator 53020 is securely positioned in the end effector 12. In other embodiments, a sheet of material 53024 can be secured to the anvil 30060 or otherwise retained in the end effector 12. Similar to at least one embodiment described herein, the sheet of material 53024 can be sufficiently deformable such that the sheet of material 53024 deforms as springs 55080 within the tissue thickness compensator are deformed.

Referring to FIGS. 486 and 487, a tissue thickness compensator 55020 can comprise at least one spring 55080 that is sufficiently resilient such that it is capable of producing a springback force when deformed. Referring primarily to FIG. 486, the tissue thickness compensator 55020 can comprise a plurality of springs 55080, such as, for example, three rows of springs 55080. The springs 55080 can be systematically and/or randomly arranged in the tissue thickness compensator 55020. In various embodiments, the springs 55080 can comprise an elastomeric polymer, for example. In some embodiments, the shape of the springs 55080 can allow for deformation thereof. In various embodiments, the springs 55080 can be deformed from an initial configuration to a deformed configuration. For example, when a portion of the tissue thickness compensator 55020 is captured in a staple entrapment area 30039, the springs 55080 in and/or around the staple entrapment area 30039 can be deformed. In various embodiments, the springs 55080 can buckle or collapse under a compressive force applied for a fired staple 30030 and the springs 55080 may generate a restoring force that is a function of the spring rate of the deformed spring 55080 and/or the amount the spring 55080 is deformed, for example. In some embodiments, the spring 55080 can act as a sponge under a compressive force applied by a fired staple 30030. Further, the spring 55080 can comprise a compensation material, as described in greater detail throughout the present disclosure.

The tissue thickness compensator 55020 can further comprise one or more sheets of material 55024 that hold or retain at least one spring 55080 in the tissue thickness compensator 55020. In various embodiments, the sheets of material 55024 can be positioned above and/or below the springs 55080 and can securely retain the springs 55080 in the tissue thickness compensator 55020. In at least one embodiment, the tissue thickness compensator 55020 can comprise a first sheet of material 55024*a* and a second sheet of material 55024*b*. In various embodiments, the tubular elements 52080 can be positioned between the first and second sheets of material 55024*a*, 55024*b*. Referring primarily to FIG. 487, in various embodiments, the tissue thickness compensator 55020 can further comprise a third sheet of material 55024*c* positioned adjacent to either the first or second sheet of material 55024*a*, 55024*b*. In various embodiments, at least one sheet of material 55024 can be secured to the top deck surface 30011 of the rigid support portion of the staple cartridge 30000, such that the tissue thickness compensator 55020 is securely positioned in the end effector 12. In other embodiments, at least one sheet of material 55024 can be secured to the anvil 30060 or otherwise retained in the end effector 12.

Referring now to FIG. 487, when a staple 30030 is fired from the staple cartridge 30000 (FIG. 485), the staple 30030 can engage the tissue thickness compensator 55020. In various embodiments, the fired staple 30030 can capture tissue T and a portion of the tissue thickness compensator 55020 in the staple entrapment area 30039. The springs 55080 can be deformable such that the tissue thickness compensator 55020 compresses when captured by a fired staple 30030. In some embodiments, the springs 55080 can be positioned between fired staples 30030 in the tissue thickness compensator 55020. In other embodiments, at least one spring 55080 can be captured within the staple entrapment area 30039.

Referring to FIG. 488, a tissue thickness compensator 60020 can comprise at least two compensation layers 60022. In various embodiments, the tissue thickness compensator 60020 can comprise a plurality of compensation layers 60022 which can be stacked on top of each other, positioned side-by-side, or a combination thereof. As described in greater detail herein, the compensation layers 60022 of the tissue thickness compensator 60020 can comprise different geometric and/or material properties, for example. Furthermore, as described in greater detail herein, pockets and/or channels can exist between adjacently stacked compensation layers 60022. For example, a tissue thickness compensator 62020 can comprise six compensation layers 62022*a*, 62022*b*, 62022*c*, 62022*d*, 62022*e*, 62022*f*, which can be adjacently stacked on top of each other (FIG. 503).

Referring to FIGS. 489, 490, and 492-497, a tissue thickness compensator can comprise a first compensation layer 60122*a* and a second compensation layer 60122*b*. In various embodiments, the first compensation layer 60122*a* can be adjacently stacked on top of the second compensation layer 60122*b*. In at least one embodiment, adjacently stacked compensation layers 60122 can be separated by a separation gap or pocket 60132. Referring primarily to FIG. 489, a tissue thickness compensator 60120 can also comprise at least one cantilever beam or support 60124 positioned between the first and second compensation layers 60122*a*, 60122*b*. In various embodiments, the support 60124 can be configured to position the first compensation layer 60122*a* relative to the second compensation layer 60122*b* such that compensation layers 60122 are separated by the separation gap 60132. As described in greater detail herein, deformation of the support 60124 and/or the compensation layers 60122*a*, 60122*b*, for example, can reduce the separation gap 60132.

The support beam of a tissue thickness compensator can comprise various geometries and dimensions. For example, the support beam can be a simple I-beam, a centered, single-bend support beam 60124 (FIG. 489), an off-centered, single-bend support beam 60224 (FIG. 490), an elliptical support beam 60324 (FIG. 492), a multi-bend support beam 60424 (FIG. 493), and/or a symmetrical, dual-cantilevered support beam 60524 (FIG. 494). Furthermore, referring now to FIGS. 489, 495, and 496, a support beam 60624 can be thinner than at least one compensation layer 60122 (FIG. 495), a support beam 60724 can be thicker than at least one compensation layer 60122 (FIG. 496), and/or a support beam 60124 can be substantially the same thickness as at least one compensation layer 60122 (FIG. 489), for example. The material, geometry and/or dimensions of the support beam 60124, for example, can affect the deformability and springback resiliency of the tissue thickness compensator 60120.

Referring still to FIG. 489, the compensation layers 60122 and support beam 60124 of the tissue thickness compensator 60120 can comprise different materials, such as, for example, structural material, biological material, and/or electrical material, for example. For example, in various embodiments, at least one compensation layer 60122 can comprise a polymeric composition. The polymeric composition can comprise an at least partially elastic material such that deformation of the compensation layer 60122 and/or the support beam 60124 can generate a springback force. The polymeric composition of the compensation layer 60122 can comprise non-absorbable polymers, absorbable polymers, or combinations thereof. In some embodiments, the absorbable polymers can include bioabsorbable, biocompatible elastomeric polymers, for example. Furthermore, the polymeric composition of the compensation layer 60122 can comprise synthetic polymers, non-synthetic polymers, or combinations thereof. Examples of synthetic polymers include, but are not limited to, polyglycolic acid (PGA), poly(lactic acid) (PLA), polycaprolactone (PCL), polydioxanone (PDO), and copolymers thereof. Examples of non-synthetic polymers include, but are not limited to, polysaccharides, glycoprotein, elastin, proteoglycan, gelatin, collagen, and oxidized regenerated cellulose (ORC). In various embodiments, similar to the polymeric compositions in embodiments described herein, the polymeric composition of the compensation layers 60122 can include varied amounts of absorbable polymers, non-absorbable polymers, synthetic polymers, and non-synthetic polymers, for example, by weight percentage. In various embodiments, each compensation layer 60022 in the tissue thickness compensator 60120 can comprise a different polymeric composition or, in various other embodiments, at least two compensation layers 60122 can comprise the same polymeric composition.

Referring again to FIG. 488, in various embodiments, at least one compensation layer 60022 can comprise a therapeutic agent 60098 such as a medicament or pharmaceutically active agent, for example. The compensation layer 60022 can release a therapeutically effective amount of the therapeutic agent 60098. In various embodiments, the therapeutic agent 60098 can be released as the compensation layer 60022 is absorbed. Examples of therapeutic agents 60098 can include, but are not limited to, haemostatic agents and drugs, such as, for example, fibrin, thrombin, and/or oxidized regenerated cellulose (ORC), anti-inflammatory drugs such as, for example, diclofenac, aspirin, naproxen, sulindac, and/or hydrocortisone antibiotic and antimicrobial drugs or agents such as, for example, triclosan, ionic silver, ampicillin, gentamicin, polymyxin B, and/or chloramphenicol, and/or anticancer agents such as, for example, cisplatin, mitomycin, and/or adriamycin. In some embodiments, the therapeutic agent 60098 can comprise a biologic, such as a stem cell, for example. In various embodiments, each compensation layer 60022 in a tissue thickness compensator 60020 can comprise a different therapeutic agent 60098 or, in various other embodiments, at least two compensation layers 60022 can comprise the same therapeutic agent 60098. In at least one embodiment, a compensation layer 60022 comprising a therapeutic agent 60098, such as a biologic, for example, can be encased between two structural compensation layers 60022 comprising a polymeric composition, such as, for example, polyglycolic acid (PGA) foam, for example. In various embodiments, a compensation layer 60022 can also comprise an electrically conductive material, such as, for example, copper.

In various embodiments, referring again to FIG. 503, the compensation layers 62022 in the tissue thickness compensator 62020 can have different geometries. When layers 62022 are adjacently positioned in the tissue thickness compensator 62020, the compensation layers 62022 can form at least one three-dimensional conduit 62032 between the layers 62022. For example, when a second compensation layer **62022*b* comprising a channel is positioned above a substantially flat third compensation layer 62022*c*, the channel and flat surface of the third compensation layer 62022*c* can define a three-dimensional conduit 62032*a* therebetween. Similarly, for example, when a fifth compensation layer 62022*e* comprising a channel is positioned below a fourth compensation layer 62022*d* comprising a corresponding channel, the channels can form a three-dimensional conduit 62032*b* defined by the channels in the adjacently stacked compensation layers 62022*d*, 62022*e*. In various embodiments, the conduits 62032 can direct therapeutic agents and/or bodily fluids as the fluids flow through the tissue thickness compensator 62020**.

In various embodiments, referring to FIG. 499, a tissue thickness compensator 61020 can comprise compensation layers 61022, such as layers **60122*a* and 21022*b*, configured to receive staples 30030 deployed from the staple cartridge 20000 (FIG. 498). As a staple 30030 is moved from an initial position to a fired position, the geometry of at least one compensation layer 61022 can guide the staple legs 30032 to the fired position. In various embodiments, at least one compensation layer 61022 can comprise apertures 61030 extending therethrough, wherein the apertures 61030 can be arranged to receive the staple legs 30032 of deployed staples 30030 when the staples 30030 are fired from the staple cartridge 20000 (FIG. 498), as described in greater detail herein. In various other embodiments, referring again to FIG. 503, staple legs 30032 can pierce through at least one compensation layer, such as compensation layer 62022*f*, for example, and can be received through apertures 62030 in at least one compensation layer, such as, for example, compensation layer 62022*a***.

Referring primarily to FIG. 499, the tissue thickness compensator 60120 can comprise at least one support tab 61026 on one of the compensation layers **61022*a*, 61022*b*. The support tab 61026 can protrude into the separation gap 61032 defined between adjacent compensation layers, such as the gap 61032 between the first compensation layer 61020*a* and second compensation layer 61020*b*. In various embodiments, the support tab 61026 can protrude from a longitudinal side of a first compensation layer 61022*a*. Further, the support tab 61026 can extend along the length of the longitudinal side or only along a portion thereof. In various embodiments, at least one support tab 61026 can protrude from two longitudinal sides of the compensation layer 61022*a*, 61022*b*. Further, adjacently positioned compensation layers 61022*a*, 61022*b* can comprise corresponding support tabs 60126, such that the support tab 60126 that extends from the first compensation layer 60122*a* can at least partially align with the support tab 60126 that extends from the second compensation layer 60122*b*. In at least one embodiment, referring again to FIG. 497, a tissue thickness compensator 60820 can comprise a limiter plate 60828 between adjacent compensation layers 60122*a*, 60122*b*. The limiter plate 60828 can be positioned in the gap 60132 defined between the first compensation layer 60122*a* and the second compensation layer 60122*b*, for example. As described in greater detail herein, support tab(s) 61026 and/or limiter plate(s) 60828 can control the deformation and/or deflection of a support 60124 and/or the compensation layers 60122*a*, 60122*b***.

As described herein, in various embodiments, the compensation layers 60022 of the tissue thickness compensator 60020 can comprise different materials, geometries and/or dimensions. Such tissue thickness compensators 60020 can be assembled by a variety of manufacturing techniques. Referring primarily to FIG. 488, the tissue thickness compensator 60022 can be manufactured by lithographic, stereolithographic (SLA), or silk screening processes. For example, a stereolithographic manufacturing process can create a tissue thickness compensator 60020 in which each compensation layer 60022 comprises different materials and/or geometric features. For example, an ultraviolet light in a stereolithography machine can draw the geometry of a first compensation layer 60022, such that the first compensation layer 60022 comprising a first material, geometry and/or dimensions is cured by the ultraviolet light. The ultraviolet light can subsequently draw the geometry of a second compensation layer 60022, such that the second compensation layer 60022 comprising a second material, geometry and/or dimensions is cured by the ultraviolet light. In various embodiments, a stereolithography machine can draw compensation layers 60022 on top of each other, side-by-side, or a combination thereof. Further, the compensation layers 60022 can be drawn such that pockets 60132 exist between adjacent compensation layers 60022. Because a stereolithography machine can create very thin layers having unique geometries, a tissue thickness compensator 60020 manufactured by a stereolithographic process can comprise a very complex three-dimensional geometry.

In various embodiments, referring to FIG. 498, the tissue thickness compensator 60920 can be positioned in the end effector 12 of a surgical instrument 10 (FIG. 1). The tissue thickness compensator 60920 can be positioned relative to the staple cartridge 20000 of the end effector 12. For example, the tissue thickness compensator 60920 can be releasably secured to the staple cartridge 20000. In at least one embodiment, at least one compensation layer 60922 of the tissue thickness compensator 60920 can be positioned adjacent to the top deck surface 20011 (FIG. 408) of the staple cartridge 20000. For example, a second compensation layer 60922*b* can be secured to the top deck surface 20011 by an adhesive or by a wrap, similar to at least one of the wraps described herein (FIG. 218). In various embodiments, the tissue thickness compensator 60920 can be integral to the staple cartridge 20000 such that the staple cartridge 20000 and the tissue thickness compensator 60920 are formed as a single unit construction. For example, the staple cartridge 20000 can comprise a first body portion, such as the rigid support portion 20010 (FIG. 408), and a second body portion, such the as tissue thickness compensator 60920.

Still referring to FIG. 498, the tissue thickness compensator 60920 can comprise a first compensator portion 60920*a* and a second compensator portion 60920*b*. The first compensator portion 60920*a* can be positioned on a first longitudinal side of the staple cartridge 20000 and the second compensator portion 60920*b* can be positioned on a second longitudinal side of the staple cartridge 20000. In various embodiments, when the tissue thickness compensator 60920 is positioned relative to the staple cartridge 20000, the longitudinal slot 20015 (FIG. 407) in the rigid support portion 20010 (FIG. 407) can extend between the first compensator portion 60920*a* and the second compensator portion 60920*b*. When the cutting element 20052 on the staple-firing sled 20050 (FIG. 407) translates through the end effector 12, the cutting element 20052 can pass through the longitudinal slot 20015 between the first compensator portion 60920*a* and the second compensator portion 60920*b* without severing a portion of the tissue thickness compensator 60920, for example. In other embodiments, the cutting element 20052 can be configured to sever a portion of the tissue thickness compensator 60920.

In various embodiments, referring now to FIG. 491, a tissue thickness compensator 63020 can be configured to fit in the end effector 12' of a circular surgical instrument. In various embodiments, the tissue thickness compensator 62030 can comprise a circular first compensation layer 63022*a* and a circular second compensation layer 63022*b*. The second compensation layer 63022*b* can be positioned on a circular top deck surface 20011' of a circular staple cartridge 20000', wherein the second compensation layer 63022*b* can comprise a geometry that corresponds to the geometry of the deck surface 20011'. For example, the deck surface 20011' can comprise a stepped portion and the second compensation layer 63022*b* can comprise a corresponding stepped portion. Similar to various embodiments described herein, the tissue thickness compensator can further comprise at least one support 63024 and/or support tabs 63026, for example, extending around the tissue thickness compensator 63020.

Referring again to FIG. 499, fired staples 30030 can be configured to engage the tissue thickness compensator 60920. As described throughout the present disclosure, a fired staple 30030 can capture a portion of the tissue thickness compensator 60920 and tissue T and apply a compressive force to the tissue thickness compensator 60920. Further, referring primarily to FIGS. 500-502, the tissue thickness compensator 60920 can be deformable. In various embodiments, as described herein, a first compensation layer 60920*a* can be separated from a second compensation layer 60920*b* by a separation gap 60932. Referring to FIG. 500, prior to compression of the tissue thickness compensator 60920, the gap 60932 can comprise a first distance. When a compressive force A is applied to the tissue thickness compensator 60920 and tissue T, for example, by a fired staple 30030 (FIG. 499), the support 60924 can be configured to deform. Referring now to FIG. 501, the single-bend support beam 60924 can bend under the compressive force A such that the separation gap 60932 between the first compensation layer 60920*a* and the second compensation layer 60920*b* is reduced to a second distance. Referring primarily to FIG. 502, the first and second compensation layers 60922*a*, 60922*b* can also deform under the compressive force A. In various embodiments, the support tabs 60926 can control deformation of the compensation layers 60920. For example, the support tabs 60926 can prevent excessive bending of the compensation layers 60920 by supporting the longitudinal sides of the compensation layer 60920 when they come into contact with one another. The support tabs 60926 can also be configured to bend or bow under the compressive force A. Additionally or alternatively, the limiter plate 60128 (FIG. 497) described in greater detail herein, can limit the deformation of the compensation layers 60920 when the compensation layers 60920 and/or support tabs 60926 contact the limiter plate 60128.

Furthermore, similar to various tissue thickness compensators described herein, tissue thickness compensator 60920 can generate a springback or restoring force when deformed. The restoring force generated by the deformed tissue thickness compensator can at least depend on the orientation, dimensions, material, and/or geometry of the tissue thickness compensator 60920, as well as the amount of the tissue thickness compensator 60920 that is deformed by the applied force. Furthermore, in various embodiments, at least a portion of the tissue thickness compensator 60920 can be resilient such that the tissue thickness compensator 60920 generates a spring load or restoring force when deformed by a fired staple 30030. In at least one embodiment, the support 60924 can comprise an elastic material and/or at least one compensation layer 60922 can comprise an elastic material such that the tissue thickness compensator 60920 is resilient.

In various embodiments, referring now to FIG. 504, an end effector of a surgical stapling instrument can comprise a first jaw and a second jaw, wherein at least one of the first jaw and the second jaw can be configured to be moved relative to the other. In certain embodiments, the end effector can comprise a first jaw including a staple cartridge channel 19070 and a second jaw including an anvil 19060, wherein the anvil 19060 can be pivoted toward and/or away from the staple cartridge channel 19070, for example. The staple cartridge channel 19070 can be configured to receive a staple cartridge 19000, for example, which, in at least one embodiment, can be removably retained within the staple cartridge channel 19070. In various embodiments, the staple cartridge 19000 can comprise a cartridge body 19010 and a tissue thickness compensator 19020 wherein, in at least one embodiment, the tissue thickness compensator 19020 can be removably attached to the cartridge body 19010. Similar to other embodiments described herein, referring now to FIG. 505, the cartridge body 19010 can comprise a plurality of staple cavities 19012 and a staple 19030 positioned within each staple cavity 19012. Also similar to other embodiments described herein, the staples 19030 can be supported by staple drivers 19040 positioned within the cartridge body 19010 wherein a sled and/or firing member, for example, can be advanced through the staple cartridge 19000 to lift the staple drivers 19040 upwardly within the staple cavities 19012, as illustrated in FIG. 506, and eject the staples 19030 from the staple cavities 19012.

In various embodiments, referring primarily to FIGS. 504 and 505, the tissue thickness compensator 19020 can comprise resilient members 19022 and a vessel 19024 encapsulating the resilient members 19022. In at least one embodiment, the vessel 19024 can be sealed and can define a cavity containing an inner atmosphere having a pressure which is different than the surrounding atmospheric pressure. In certain embodiments, the pressure of the inner atmosphere can be greater than the pressure of the surrounding atmosphere while, in other embodiments, the pressure of the inner atmosphere can be less than the pressure of the surrounding atmosphere. In the embodiments in which the vessel 19024 contains a pressure less than the pressure of the surrounding atmosphere, the sidewall of the vessel 19024 can enclose a vacuum. In such embodiments, the vacuum can cause the vessel 19024 to distort, collapse, and/or flatten wherein the resilient members 19022 positioned within the vessel 19024 can be resiliently compressed within the vessel 19024. When a vacuum is drawn on the vessel 19024, the resilient members 19022 can deflect or deform downwardly and can be held in position by the sidewalls of the vessel 19024 in a compressed, or vacuum-packed, state.

Resilient member 19022 and vessel 19024 are comprised of biocompatible materials. In various embodiments, resilient member 19022 and/or vessel 19024 can be comprised of bioabsorbable materials such as PLLA, PGA, and/or PCL, for example. In certain embodiments, resilient member 19022 can be comprised of a resilient material. Resilient member 19022 can also comprise structural resilience. For example, resilient member 19022 can be in the form of a hollow tube.

Further to the above, the tissue thickness compensator 19020 can be positioned against or adjacent to the deck surface 19011 of the cartridge body 19010. When the staples 19030 are at least partially fired, referring now to FIG. 506, the legs of the staples 19030 can puncture or rupture the vessel 19024. In certain embodiments, the vessel 19024 can comprise a central portion 19026 which can be positioned over a cutting slot 19016 of the cartridge body 19010 such that, when a cutting member 19080 is advanced to incise tissue T positioned between the staple cartridge 19000 and the anvil 19060, the cutting member 19080 can also incise the central portion 19026 of the vessel 19024 thereby puncturing or rupturing the vessel 19024. In either event, once the vessel 19024 has been ruptured, the inner atmosphere within the vessel 19024 can equalize with the atmosphere surrounding the tissue thickness compensator 19020 and allow the resilient members 19022 to resiliently expand to regain, or at least partially regain, their undistorted and/or unflattened configuration. In such circumstances, the resilient members 19022 can apply a biasing force to the tissue T captured within the deformed staples 19020. More specifically, after being deformed by the forming surfaces of pockets 19062 defined in the anvil 19060, the legs of the staples 19030 can capture tissue T and at least a portion of a resilient member 19022 within the staples 19030 such that, when the vessel 19024 ruptures, the tissue thickness compensator 19020 can compensate for the thickness of the tissue T captured within the staples 19030. For instance, when the tissue T captured within a staple 19030 is thinner, a resilient member 19022 captured within that staple 19030 can expand to fill gaps within the staple 19030 and apply a sufficient compression force to the tissue T. Correspondingly, when the tissue T captured within a staple 19030 is thicker, a resilient member 19022 captured within that staple 19030 can remain compressed to make room for the thicker tissue within the staple 19030 and, likewise, apply a sufficient compression force to the tissue T.

When the vessel 19024 is punctured, as outlined above, the resilient members 19022 can expand in an attempt to resiliently return to their original configuration. In certain circumstances, the portion of resilient members 19022 that have been captured within the staples 19030 may not be able to return to their original undistorted shape. In such circumstances, the resilient members 19022 can comprise a spring which can apply a compression force to the tissue T captured within the staples 19030. In various embodiments, a resilient member 19022 can emulate a linear spring wherein the compression force applied by the resilient member 19022 is linearly proportional to the amount, or distance, in which the resilient member 19022 remains deflected within the staple 19030. In certain other embodiments, a resilient member 19022 can emulate a non-linear spring wherein the compression force applied by the resilient member 19022 is not linearly proportional to the amount, or distance, in which the resilient member 19022 remains deflected within the staple 19030.

In various embodiments, referring primarily to FIGS. 507 and 508, a staple cartridge 19200 can comprise a tissue thickness compensator 19220 which can comprise one or more sealed vessels 19222 therein. In at least one embodiment, each of the vessels 19222 can be sealed and can contain an inner atmosphere. In certain embodiments, the pressure of the inner atmosphere within a sealed vessel 19222 can exceed atmospheric pressure while, in certain other embodiments, the pressure of the inner atmosphere within a sealed vessel 19222 can be below atmospheric pressure. In embodiments where the pressure of the inner atmosphere within a vessel 19222 is below atmospheric pressure, the vessel 19222 can be described as containing a vacuum. In various embodiments, one or more of the vessels 19222 can be wrapped or contained in an outer shroud, container, wrap, and/or film 19224, for example, wherein the tissue thickness compensator 19220 can be positioned above a deck surface 19011 of the cartridge body 19010. In certain embodiments, each vessel 19222 can be manufactured from a tube having a circular, or an at least substantially circular, cross-section, for example, having a closed end and an open end. A vacuum can be drawn on the open end of the tube and, when a sufficient vacuum has been reached within the tube, the open end can be closed and sealed. In at least one such embodiment, the tube can be comprised of a polymeric material, for example, wherein the open end of the tube can be heat staked in order to close and seal the same. In any event, the vacuum within each vessel 19222 can pull the sidewalls of the tube inwardly and resiliently distort and/or flatten the tube. The vessels 19222 are illustrated in an at least partially flattened state in FIG. 508.

When the staples 19030 are in their unfired position, as illustrated in FIG. 508, the tips of the staples 19030 can be positioned below the tissue thickness compensator 19220. In at least one such embodiment, the staples 19030 can be positioned within their respective staple cavities 19012 such that the staples 19030 do not contact the vessels 19222 until the staples 19030 are moved from the unfired positions, illustrated in FIG. 508, to their fired positions, illustrated in FIG. 509. In certain embodiments, the wrap 19224 of the tissue thickness compensator 19220 can protect the vessels 19220 from being prematurely punctured by the staples 19030. When the staples 19030 are at least partially fired, referring now to FIG. 509, the legs of the staples 19030 can puncture or rupture the vessels 19222. In such circumstances, the inner atmospheres within the vessels 19222 can equalize with the atmosphere surrounding the vessels 19222 and resiliently expand to regain, or at least partially regain, their undistorted and/or unflattened configuration. In such circumstances, the punctured vessels 19222 can apply a biasing force to the tissue captured within the deformed staples 19030. More specifically, after being deformed by the forming surfaces of pockets 19062 defined in the anvil 19060, the legs of the staples 19030 can capture tissue T and at least a portion of a vessel 19222 within the staples 19030 such that, when the vessels 19222 rupture, the vessels 19222 can compensate for the thickness of the tissue T captured within the staples 19030. For instance, when the tissue T captured within a staple 19030 is thinner, a vessel 19222 captured within that staple 19030 can expand to fill gaps within the staple 19030 and, concurrently, apply a sufficient compression force to the tissue T. Correspondingly, when the tissue T captured within a staple 19030 is thicker, a vessel 19222 captured within that staple 19030 can remain compressed to make room for the thicker tissue within the staple 19030 and, concurrently, apply a sufficient compression force to the tissue T.

When the vessels 19222 are punctured, as outlined above, the vessels 19222 can expand in an attempt to resiliently return to their original configuration. The portion of vessels 19222 that have captured within the staples 19030 may not be able to return to their original undistorted shape. In such circumstances, the vessel 19222 can comprise a spring which can apply a compression force to the tissue T captured within the staples 19030. In various embodiments, a vessel 19222 can emulate a linear spring wherein the compression force applied by the vessel 19222 is linearly proportional to the amount, or distance, in which the vessel 19222 remains deflected within the staple 19030. In certain other embodiments, a vessel 19222 can emulate a non-linear spring wherein the compression force applied by the vessel 19222 is not linearly proportional to the amount, or distance, in which the vessel 19222 remains deflected within the staple 19030. In various embodiments, the vessels 19222 can be hollow and, in at least one embodiment, empty when they are in their sealed configuration. In certain other embodiments, each of the vessels 19222 can define a cavity and can further include at least one medicament contained therein. In at least some embodiments, the vessels 19222 can be comprised of at least one medicament which can be released and/or bioabsorbed, for example.

In various embodiments, the vessels 19222 of the tissue thickness compensator 19220 can be arranged in any suitable manner. As illustrated in FIG. 507, the staple cavities 19012 defined in the cartridge body 19010, and the staples 19030 positioned in the staple cavities 19012, can be arranged in rows. In at least the illustrated embodiment, the staple cavities 19012 can be arranged in six longitudinal, linear rows, for example; however, any suitable arrangement of staple cavities 19012 could be utilized. As also illustrated in FIG. 507, the tissue thickness compensator 19220 can comprise six vessels 19222 wherein each of the vessels 19222 can be aligned with, or positioned over, a row of staple cavities 19012. In at least one embodiment, each of the staples 19030 within a row of staple cavities 19012 can be configured to puncture the same vessel 19222. In certain situations, some of the staple legs of the staples 19030 may not puncture the vessel 19222 positioned thereover; however, in embodiments where the vessel 19222 defines a continuous internal cavity, for example, the cavity can be sufficiently punctured by at least one of the staples 19030 in order to allow the pressure of the internal cavity atmosphere to equalize with the atmospheric pressure surrounding the vessel 19222. In various embodiments, referring now to FIG. 514, a tissue thickness compensator can comprise a vessel, such as vessel 19222', for example, which can extend in a direction which is transverse to a line of staples 19030. In at least one such embodiment, a vessel 19222' can extend across multiple staple rows. In certain embodiments, referring now to FIG. 515, a tissue thickness compensator 19220" can comprise a plurality of vessels 19222" which extend in a direction which is perpendicular, or at least substantially perpendicular, to a line of staples 19030. In at least one such embodiment, some of the vessels 19222" may be punctured by the staples 19030 while others may not be punctured by the staples 19030. In at least one embodiment, the vessels 19222" can extend across or through a cutting path in which a cutting member could transect and rupture the vessels 19222", for example.

In various embodiments, as described above, a tissue thickness compensator, such as tissue thickness compensator 19220, for example, can comprise a plurality of sealed vessels, such as vessels 19222, for example. As also described above, each of the sealed vessels 19222 can comprise a separate internal atmosphere. In certain embodiments, the vessels 19222 can have different internal pressures. In at least one embodiment, for example, a first vessel 19222 can comprise an internal vacuum having a first pressure and a second vessel 19222 can comprise an internal vacuum having a second, different pressure, for example. In at least one such embodiment, the amount of distortion or flattening of a vessel 19222 can be a function of the vacuum pressure of the internal atmosphere contained therein. For instance, a vessel 19222 having a greater vacuum can be distorted or flattened a greater amount as compared to a vessel 19222 having a smaller vacuum. In certain embodiments, the cavity of a vessel can be segmented into two or more separate, sealed cavities wherein each separate, sealed cavity can comprise a separate internal atmosphere. In at least one such embodiment, some of the staples within a staple row can be configured and arranged to puncture a first cavity defined in the vessel while other staples within the staple row can be configured and arranged to puncture a second cavity defined in the vessel, for example. In such embodiments, especially in embodiments in which the staples in a staple row are sequentially fired from one end of the staple row to the other, as described above, one of the cavities can remain intact and can maintain its internal atmosphere when another cavity is ruptured. In certain embodiments, the first cavity can have an inner atmosphere having a first vacuum pressure and the second cavity can have an inner atmosphere having a second, different vacuum pressure, for example. In various embodiments, a cavity that remains intact can maintain its inner pressure until the vessel is bioabsorbed thereby creating a timed pressure release.

In various embodiments, referring now to FIGS. 510 and 511, a tissue thickness compensator, such as tissue thickness compensator 19120, for example, can be attached to an anvil 19160. Similar to the above, the tissue thickness compensator 19120 can comprise a vessel 19124 and a plurality of resilient members 19122 positioned therein. Also similar to the above, the vessel 19124 can define a cavity containing an inner atmosphere having a pressure which is less than or greater than the pressure of the atmosphere surrounding the tissue thickness compensator 19120. In embodiments where the inner atmosphere within the vessel 19124 comprises a vacuum, the vessel 19124 and the resilient members 19122 positioned therein can be distorted, collapsed, and/or flattened by the difference in pressure between the vacuum in the vessel 19124 and the atmospheric pressure outside of the vessel 19124. In use, the anvil 19160 can be moved into a closed position in which it is positioned opposite a staple cartridge 19100 and in which a tissue engaging surface 19121 on the vessel 19124 can engage the tissue T positioned intermediate the tissue thickness compensator 19120 and a staple cartridge 19100. In use, the firing member 19080 can be advanced distally to fire the staples 19030, as described above, and, at the same time, incise the tissue T. In at least one embodiment, the tissue thickness compensator 19120 can further comprise an intermediate portion 19126 which can be aligned with a cutting slot defined in the anvil 19160 wherein, when the firing member 19080 is advanced distally through the tissue thickness compensator 19120, the firing member 19080 can puncture or rupture the vessel 19124. Also, similar to the above, the firing member 19080 can lift the staple drivers 19040 upwardly and fire the staples 19030 such that the staples 19030 can contact the anvil 19160 and be deformed into their deformed configuration, as illustrated in FIG. 512. When the staples 19030 are fired, the staples 19030 can pierce the tissue T and then pierce or rupture the vessel 19124 such that the resilient members 19122 positioned within the vessel 19124 can at least partially expand, as outlined above.

In various embodiments, further to the above, a tissue thickness compensator can be comprised of a biocompatible material. The biocompatible material, such as, a foam, may comprise tackifiers, surfactants, fillers, cross-linkers, pigments, dyes, antioxidants and other stabilizers and/or combinations thereof to provide desired properties to the material. In certain embodiments, a biocompatible foam may comprise a surfactant. The surfactant may be applied to the surface of the material and/or dispersed within the material. Without wishing to be bound to any particular theory, the surfactant applied to the biocompatible material may reduce the surface tension of the fluids contacting the material. For example, the surfactant may reduce the surface tension of water contacting the material to accelerate the penetration of water into the material. In various embodiments, the water may act as a catalyst. The surfactant may increase the hydrophilicity of the material.

In various embodiments, the surfactant may comprise an anionic surfactant, a cationic surfactant, and/or a non-ionic surfactant. Examples surfactants include, but are not limited to polyacrylic acid, methalose, methyl cellulose, ethyl cellulose, propyl cellulose, hydroxy ethyl cellulose, carboxy methyl cellulose, polyoxyethylene cetyl ether, polyoxyethylene lauryl ether, polyoxyethylene octyl ether, polyoxyethylene octylphenyl ether, polyoxyethylene oleyl ether, polyoxyethylene sorbitan monolaurate, polyoxyethylene stearyl ether, polyoxyethylene nonylphenyl ether, dialkylphenoxy poly(ethyleneoxy) ethanol, and polyoxamers, and combinations thereof. In at least one embodiment, the surfactant may comprise a copolymer of polyethylene glycol and polypropylene glycol. In at least one embodiment, the surfactant may comprise a phospholipid surfactant. The phospholipid surfactant may provide antibacterial stabilizing properties and/or disperse other materials in the biocompatible material. In various embodiments, the tissue thickness compensator may comprise at least one medicament. The tissue thickness compensator may comprise one or more of the natural materials, non-synthetic materials, and/or synthetic materials described herein. In certain embodiments, the tissue thickness compensator may comprise a biocompatible foam comprising gelatin, collagen, hyaluronic acid, oxidized regenerated cellulose, polyglycolic acid, polycaprolactone, polyactic acid, polydioxanone, polyhydroxyalkanoate, poliglecaprone, and combinations thereof. In certain embodiments, the tissue thickness compensator may comprise a film comprising the at least one medicament. In certain embodiments, the tissue thickness compensator may comprise a biodegradable film comprising the at least one medicament. In certain embodiments, the medicament may comprise a liquid, gel, and/or powder. In various embodiments, the medicaments may comprise anticancer agents, such as, for example, cisplatin, mitomycin, and/or adriamycin.

In various embodiments, the tissue thickness compensator may comprise a biodegradable material to provide controlled elution of the at least one medicament as the biodegradable material degrades. In various embodiments, the biodegradable material may degrade may decompose, or loses structural integrity, when the biodegradable material contacts an activator, such as, for example an activator fluid. In various embodiments, the activator fluid may comprise saline or any other electrolyte solution, for example. The biodegradable material may contact the activator fluid by conventional techniques, including, but not limited to spraying, dipping, and/or brushing. In use, for example, a surgeon may dip an end effector and/or a staple cartridge comprising the tissue thickness compensator comprising the at least one medicament into an activator fluid comprising a salt solution, such as sodium chloride, calcium chloride, and/or potassium chloride. The tissue thickness compensator may release the medicament as the tissue thickness compensator degrades. In certain embodiments, the elution of the medicament from the tissue thickness compensator may be characterized by a rapid initial elution rate and a slower sustained elution rate.

In various embodiments, a tissue thickness compensator, for example, can be comprised of a biocompatible material which may comprise an oxidizing agent. In various embodiments, the oxidizing agent may an organic peroxide and/or an inorganic peroxide. Examples of oxidizing agents may include, but are not limited to, hydrogen peroxide, urea peroxide, calcium peroxide, and magnesium peroxide, and sodium percarbonate. In various embodiments, the oxidizing agent may comprise peroxygen-based oxidizing agents and hypohalite-based oxidizing agents, such as, for example, hydrogen peroxide, hypochlorous acid, hypochlorites, hypocodites, and percarbonates. In various embodiments, the oxidizing agent may comprise alkali metal chlorites, hypochlorites and perborates, such as, for example, sodium chlorite, sodium hypochlorite and sodium perborate. In certain embodiments, the oxidizing agent may comprise vanadate. In certain embodiments, the oxidizing agent may comprise ascorbic acid. In certain embodiments, the oxidizing agent may comprise an active oxygen generator. In various embodiments, a tissue scaffold may comprise the biocompatible material comprising an oxidizing agent.

In various embodiments, the biocompatible material may comprise a liquid, gel, and/or powder. In certain embodiments, the oxidizing agent may comprise microparticles and/or nanoparticles, for example. For example, the oxidizing agent may be milled into microparticles and/or nanoparticles. In certain embodiments, the oxidizing agent may be incorporated into the biocompatible material by suspending the oxidizing agent in a polymer solution. In certain embodiments, the oxidizing agent may be incorporated into the biocompatible material during the lyophylization process. After lyophylization, the oxidizing agent may be attached to the cell walls of the biocompatible material to interact with the tissue upon contact. In various embodiments, the oxidizing agent may not be chemically bonded to the biocompatible material. In at least one embodiment, a percarbonate dry power may be embedded within a biocompatible foam to provide a prolonged biological effect by the slow release of oxygen. In at least one embodiment, a percarbonate dry power may be embedded within a polymeric fiber in a non-woven structure to provide a prolonged biological effect by the slow release of oxygen. In various embodiments, the biocompatible material may comprise an oxidizing agent and a medicament, such as, for example, doxycycline and ascorbic acid.

In various embodiments, the biocompatible material may comprise a rapid release oxidizing agent and/or a slower sustained release oxidizing agent. In certain embodiments, the elution of the oxidizing agent from the biocompatible material may be characterized by a rapid initial elution rate and a slower sustained elution rate. In various embodiments, the oxidizing agent may generate oxygen when the oxidizing agent contacts bodily fluid, such as, for example, water. Examples of bodily fluids may include, but are not limited to, blood, plasma, peritoneal fluid, cerebral spinal fluid, urine, lymph fluid, synovial fluid, vitreous fluid, saliva, gastrointestinal luminal contents, and/or bile. Without wishing to be bound to any particular theory, the oxidizing agent may reduce cell death, enhance tissue viability and/or maintain the mechanical strength of the tissue to tissue that may be damaged during cutting and/or stapling. In various embodiments, the biocompatible material may comprise at least one microparticle and/or nanoparticle. The biocompatible material may comprise one or more of the natural materials, non-synthetic materials, and synthetic materials described herein. In various embodiments, the biocompatible material may comprise particles having a mean diameter of about 10 nm to about 100 nm and/or about 10 □m to about 100 □m, such as, for example, 45-50 nm and/or 45-50 □m. In various embodiments, the biocompatible material may comprise biocompatible foam comprising at least one microparticle and/or nanoparticle embedded therein. The microparticle and/or nanoparticle may not be chemically bonded to the biocompatible material. The microparticle and/or nanoparticle may provide controlled release of the medicament. In certain embodiments, the microparticle and/or nanoparticle may comprise at least one medicament. In certain embodiments, the microparticle and/or nanoparticle may comprise a hemostatic agent, an anti-microbial agent, and/or an oxidizing agent, for example. In certain embodiments, the tissue thickness compensator may comprise a biocompatible foam comprising an hemostatic agent comprising oxidized regenerated cellulose, an anti-microbial agent comprising doxycline and/or Gentamicin, and/or an oxidizing agent comprising a percarbant. In various embodiments, the microparticle and/or nanoparticle may provide controlled release of the medicament up to three days, for example.

In various embodiments, the microparticle and/or nanoparticle may be embedded in the biocompatible material during a manufacturing process. For example, a biocompatible polymer, such as, for example, a PGA/PCL, may contact a solvent, such as, for example, dioxane to form a mixture. The biocompatible polymer may be ground to form particles. Dry particles, with or without ORC particles, may be contacted with the mixture to form a suspension. The suspension may be lyophilized to form a biocompatible foam comprising PGA/PCL having dry particles and/or ORC particles embedded therein.

In various embodiments, the tissue thickness compensators or layers disclosed herein can be comprised of an absorbable polymer, for example. In certain embodiments, a tissue thickness compensator can be comprised of foam, film, fibrous woven, fibrous non-woven PGA, PGA/PCL (Poly(glycolic acid-co-caprolactone)), PLA/PCL (Poly(lactic acid-co-polycaprolactone)), PLLA/PCL, PGA/TMC (Poly(glycolic acid-co-trimethylene carbonate)), PDS, PEPBO or other absorbable polyurethane, polyester, polycarbonate, Polyorthoesters, Polyanhydrides, Polyesteramides, and/or Polyoxaesters, for example. In various embodiments, a tissue thickness compensator can be comprised of PGA/PLA (Poly(glycolic acid-co-lactic acid)) and/or PDS/PLA (Poly(p-dioxanone-co-lactic acid)), for example. In various embodiments, a tissue thickness compensator can be comprised of an organic material, for example. In certain embodiments, a tissue thickness compensator can be comprised of Carboxymethyl Cellulose, Sodium Alginate, Cross-linked Hyaluronic Acid, and/or Oxidized regenerated cellulose, for example. In various embodiments, a tissue thickness compensator can comprise a durometer in the 3-7 Shore A (30-50 Shore OO) ranges with a maximum stiffness of 15 Shore A (65 Shore OO), for example. In certain embodiments, a tissue thickness compensator can undergo 40% compression under 3 lbf load, 60% compression under 6 lbf load, and/or 80% compression under 20 lbf load, for example. In certain embodiments, one or more gasses, such as air, nitrogen, carbon dioxide, and/or oxygen, for example, can be bubbled through and/or contained within the tissue thickness compensator. In at least one embodiment, a tissue thickness compensator can comprise beads therein which comprise between approximately 50% and approximately 75% of the material stiffness comprising the tissue thickness compensator.

In various embodiments, a tissue thickness compensator can comprise hyaluronic acid, nutrients, fibrin, thrombin, platelet rich plasma, Sulfasalazine (Azulfidine®–5ASA+Sulfapyridine diazo bond))–prodrug–colonic bacterial (Azoreductase), Mesalamine (5ASA with different prodrug configurations for delayed release), Asacol® (5ASA+Eudragit-S coated–pH>7 (coating dissolution)), Pentasa® (5ASA+ethylcellulose coated–time/pH dependent slow release), Mesasal® (5ASA+Eudragit-L coated–pH>6), Olsalazine (5ASA+5ASA–colonic bacterial (Azoreductase)), Balsalazide (5ASA+4Aminobenzoyl-B-alanine)–colonic bacterial (Azoreductase)), Granulated mesalamine, Lialda (delay and SR formulation of mesalamine), HMPL-004 (herbal mixture that may inhibit TNF-alpha, interleukin-1 beta, and nuclear-kappa B activation), CCX282-B (oral chemokine receptor antagonist that interferes with trafficking of T lymphocytes into the intestinal mucosa), Rifaximin (nonabsorbable broad-spectrum antibiotic), Infliximab, murine chymieric (monoclonal antibody directed against TNF-alpha-approved for reducing signs/symptoms and maintaining clinical remission in adult/pediatric patients with moderate/severe luminal and fistulizing Crohn's disease who have had inadequate response to conventional therapy), Adalimumab, Total Human IgG1 (anti-TNF-alpha monoclonal antibody—approved for reducing signs/symptoms of Crohn's disease, and for the induction and maintenance of clinical remission in adult patients with moderate/severe active Crohn's disease with inadequate response to conventional therapies, or who become intolerant to Infliximab), Certolizumab pegoll, humanized anti- TNF FAB' (monoclonal antibody fragment linked to polyethylene glycol—approved for reducing signs/symptoms of Crohn's disease and for the induction and maintenance of response in adult patients w/moderate/severe disease with inadequate response to conventional therapies), Natalizumab, First non-TNF-alpha inhibitor (biologic compound approved for Crohn's disease), Humanized monoclonal IgG4 antibody (directed against alpha-4 integrin—FDA approved for inducing and maintaining clinical response and remission in patients with moderate/severe disease with evidence of inflammation and who have had inadequate response to or are unable to tolerate conventional Crohn's therapies and inhibitors of TNF-alpha), concomitant Immunomodulators potentially given with Infliximab, Azathioprine 6-Mercaptopurine (purine synthesis inhibitor—prodrug), Methotrexate (binds dihydrofolate reductase (DHFR) enzyme that participates in tetrahydrofolate synthesis, inhibits all purine synthesis), Allopurinol and Thioprine therapy, PPI, H2 for acid suppression to protect the healing line, C-Diff—Flagyl, Vancomycin (fecal translocation treatment; probiotics; repopulation of normal endoluminal flora), and/or Rifaximin (treatment of bacterial overgrowth (notably hepatic encephalopathy); not absorbed in GI tract with action on intraluminal bacteria), for example.

As described herein, a tissue thickness compensator can compensate for variations in the thickness of tissue that is captured within the staples ejected from a staple cartridge and/or contained within a staple line, for example. Stated another way, certain staples within a staple line can capture thick portions of the tissue while other staples within the staple line can capture thin portions of the tissue. In such circumstances, the tissue thickness compensator can assume different heights or thicknesses within the staples and apply a compressive force to the tissue captured within the staples regardless of whether the captured tissue is thick or thin. In various embodiments, a tissue thickness compensator can compensate for variations in the hardness of the tissue. For instance, certain staples within a staple line can capture highly compressible portions of the tissue while other staples within the staple line can capture portions of the tissue which are less compressible. In such circumstances, the tissue thickness compensator can be configured to assume a smaller height within the staples that have captured tissue having a lower compressibility, or higher hardness, and, correspondingly, a larger height within the staples that have captured tissue having a higher compressibility, or lower hardness, for example. In any event, a tissue thickness compensator, regardless of whether it compensates for variations in tissue thickness and/or variations in tissue hardness, for example, can be referred to as a 'tissue compensator' and/or as a 'compensator', for example.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A staple cartridge, comprising:

a cartridge body, wherein a plurality of staple cavities are defined in said cartridge body;

a plurality of staples removably positioned in said staple cavities; and an absorbable tissue thickness compensator releasably secured to said cartridge body, wherein said absorbable tissue thickness compensator comprises:

a first zone comprising a tissue-supporting surface;

a second zone comprising a cartridge body contacting surface; and an intermediate zone positioned intermediate said first zone and said second zone, wherein said first zone comprises a first spring rate, wherein said second zone comprises a second spring rate greater than said first spring rate, and wherein said intermediate zone comprises a third spring rate less than said first spring rate.

2. A staple cartridge, comprising:

a cartridge body, wherein a plurality of staple cavities are defined in said cartridge body;

a plurality of staples removably positioned in said staple cavities; and an absorbable adjunct releasably secured to said cartridge body, wherein said absorbable adjunct comprises:

a first zone comprising a tissue-supporting surface, wherein said first zone comprises a first compressibility;

a second zone comprising a cartridge body contacting surface, wherein said second zone comprises a second compressibility that is less than said first compressibility; and an intermediate zone positioned between said first zone and said second zone, wherein said intermediate zone comprises a third compressibility greater than said first compressibility.

3. A staple cartridge, comprising:

a cartridge body, wherein a plurality of staple cavities are defined in said cartridge body;

a plurality of staples removably positioned in said staple cavities; and an absorbable adjunct releasably secured to said cartridge body, wherein said absorbable adjunct comprises:

a first zone comprising a tissue-supporting surface, wherein said first zone comprises a first compressive constant;

a second zone comprising a cartridge body contacting surface, wherein said second zone comprises a second compressive constant that is less than said first compressive constant; and an intermediate zone positioned between said first zone and said second zone, wherein said intermediate zone comprises a third compressive constant greater than said first compressive constant.

* * * * *